United States Patent [19]
Abdel-Meguid et al.

[11] Patent Number: 6,083,711
[45] Date of Patent: Jul. 4, 2000

[54] PROTEASES COMPOSITIONS CAPABLE OF BINDING TO SAID SITE, AND METHODS OF USE THEREOF

[75] Inventors: Sherin Salaheldin Abdel-Meguid, Exton; Xiayang Qiu, Audubon; Ward Whitlock Smith, Jr.; Cheryl Ann Janson, both of Bryn Mawr; Susan S. Hoog, Bala Cynwyd; Jeffrey Culp, Collegeville; Christine Marie Debouck, Wayne, all of Pa.

[73] Assignee: SmithKline Beecham Corporation, Philadelphia, Pa.

[21] Appl. No.: 08/853,755

[22] Filed: May 9, 1997

Related U.S. Application Data

[60] Provisional application No. 60/018,616, May 15, 1996, provisional application No. 60/022,470, Jul. 26, 1996, provisional application No. 60/024,416, Aug. 21, 1996, provisional application No. 60/030,901, Nov. 14, 1996, provisional application No. 60/035,973, Jan. 21, 1997, and provisional application No. 60/039,191, Feb. 27, 1997.

[51] Int. Cl.[7] .................................................. C12Q 1/37
[52] U.S. Cl. ............................ 435/23; 435/24; 435/212; 435/219
[58] Field of Search .................................... 435/212, 219, 435/23, 24; 536/23.2, 23.7, 23.72

[56] References Cited

PUBLICATIONS

Chen et al. "Structure of the human cytomegalovirus protease catalytic domain reveals a novel serine protease fold and catalytic triad" Cell 66, 835–843, Sep. 6, 1996.

Shieh et al. "Three–dimentional structure of human cytomegalovirus protease" Nature 383, 279–282, Sep. 19, 1996.

Hoog et al. "Active site cavity of herpesvirus protease revealed by crystal structure of herpes simplex virus protease/inhibitor complex" Biochemistry 36, 14023–14029, 1997.

Schmidt et al. "Dimerization and activation of the herpes simplex virus type 1 protease" J. Biol. Chem. 272, 7732–7735, Mar. 21, 1997.

Qui et al. "Unique fold and active site in cytomegalovirus" Nature 383, 275–279, Sep. 19, 1996.

Tong et al. "A new serine–protease fold revealed by crystal structure of human cytomegalovirus protease" Nature 383, 272–275, Sep. 19, 1996.

Qui et al. "Crystal structure of varicella–zoster virus protease" Proc. Natl. Acad. Sci. USA 94, 2874–2879, Apr. 1997.

*Primary Examiner*—Robert A. Wax
*Assistant Examiner*—Nashaat T. Nashed
*Attorney, Agent, or Firm*—Dara L. Dinner; Stephen Venetianer

[57] ABSTRACT

Novel herpes viral protease crystalline structures are identified which have an active site formed by the three amino acids Ser, His and His. Also disclosed are methods of identifying inhibitors of these proteases and/or active sites.

66 Claims, 449 Drawing Sheets

Figure 1

Herpes Proteases Sequence Alignment Based on Structures

```
                                                 B1                                              A1                                          B2
CMV                   MTMDEQQSQA VAPVYVGGFL ARYDQSPDEA ELLLPRDVVE HWLHAQGQGQ PSLSVALPLN    60
HHV6                             MSKWWGGFL  CVYGEEPSEE CLALPRDTVQ KEL---GSGN ----IPLPLN
EBV                          MVQ APSVYVCGFV ERPDAPPKDA CLHLDPLTVK SQLPLK---- ----KPLPLT
HSV1   MAADAPG DRMEEPLPDR AVPIYVAGFL ALYDSGDSGE -LALDPDTVR AALPPD---- ----NPLPIN
HSV2   MASAEMR ERLEAPLPDR AVPIYVAGFL ALYDSGDPGE -LALDPDTVR AALPPE---- ----NPLPIN
VZV            MAAEADEEN CEALYVAGYL ALY-SKDEGE -LNITPEIVR SALPPT---- ----SKIPIN

B3                                           A2                            B4                                                              A3
CMV    INHDDTAVVG HVAAMQSVRD GLFCLGCVTS PRFLEIVRRA SEKS--ELVSRG PVSPLQPDKV VEFLSGSYAG  130
HHV6   INHNEKATEG MVRGLFDLEH GLFCVAQIQS QTFMDIIRNI AGKS-KLITAGS VIEPLPPDPE IECLSSSFPG
EBV    VEHLPDAPVG SVFGLYQSRA GLFSAASITS GDFLSLLDSI YHDC--DIAQSQ RL-PLPREPK VEALHAWLPS
HSV1   VNHRAGCEVG RVLAVVDDPR GPFFVGLIAC VQLERVLETA ASAAIFERRGP- PLSRE--ERL LYLITNYLPS
HSV2   VNHRARCEVG RVLAVVNDPR GPFFVGLIAC VQLERVLETA ASAAIFERRGP- ALSRE--ERL LYLITNYLPS
VZV    IDHRKDCVVG EVIAIIEDIR GPFFLGIVRC PQLHAVLFEA AHSNFFGNRDSV -LSPL--ERA LYLVTNYLPS

B5                                       B6                                      B7                                     A4                                A5
CMV    LSLSSRRCDD VEAATSLSGS ETTPFKHVAL CSVGRRRGTL AVYGRDPEWV TQRFPDLTAA DRDGLRAQWQ   200
HHV6   LSLSSK---- VLQDENLDGK --PFFHHVSV CGVGRRPGTI AIFGREISWI LDRFSCISES EKRQVLEGVN
EBV    LSLASLHPD- -IPQTTADGG KLSFFDHVSI CALGRRRGTT AVYGTDLAWV LKHFSDLEPS IAAQIENDAN
HSV1   VSLATKRLGG EAHPDR---- --TLFAHVAL CAIGRRLGTI VTYDTGLDAA IAPFRHLSPA SREGARRLAA
HSV2   VSLSTKRRGD EVPPDR---- --TLFAHVAL CAIGRRLGTI VTYDTSLDAA IAPFRHLDPA TREGVRREAA
VZV    VSLSSKRLSP NEIPDG---- --NFFTHVAL CVVGRRVGTV VNYDCTPESS IEPFRVLSME SKARLLSLVK

A6                                               A7
CMV    RCGSTAVDAS GDP-FRSDSYG LLGNSVDALY IRERLPKLRYD KQLVGVTER ESYVKA        256
HHV6   VYSQGFDENL FS----ADLYD LLADSLDTSY IRKRFPKLQLD KQLCGLS-K CTYIKA
EBV    AAKRESGCPE DHP--LPLTK LIAKAIDAGF LRNRVETLRQD RGVANIPA- ESYLKA
HSV1   EAELALSGRT WAPGVEALTHT LLSTAVNNMM LRDRWSLVAER RRQAGIAGH -TYLQA
HSV2   EAELALAGRT WAPGVEALTHT LLSTAVNNMM LRDRWSLVAER RRQAGIAGH -TYLQA
VZV    DYAGLN--KV WKVSEDKLAKV LLSTAVNNML LRDRWDVVAKR RREAGIMGH -VYLQA
```

Figure 2A

| Atom | | No. | AA | | X | Y | Z | OCC | B-Factor |
|---|---|---|---|---|---|---|---|---|---|
| ATOM | N | 72 | LEU | A | 35.736 | 25.246 | 1.206 | 1.00 | 5.10 |
| ATOM | CA | 73 | LEU | A | 35.022 | 24.000 | 1.421 | 1.00 | 6.35 |
| ATOM | CB | 74 | LEU | A | 34.241 | 23.628 | 0.173 | 1.00 | 4.80 |
| ATOM | CG | 75 | LEU | A | 32.753 | 23.867 | 0.051 | 1.00 | 2.00 |
| ATOM | CD1 | 76 | LEU | A | 32.147 | 24.549 | 1.270 | 1.00 | 2.00 |
| ATOM | CD2 | 77 | LEU | A | 32.558 | 24.628 | -1.224 | 1.00 | 2.00 |
| ATOM | C | 78 | LEU | A | 36.089 | 22.929 | 1.732 | 1.00 | 8.64 |
| ATOM | O | 79 | LEU | A | 35.816 | 21.898 | 2.340 | 1.00 | 8.93 |
| ATOM | N | 151 | LEU | A | 38.679 | 12.044 | 3.012 | 1.00 | 26.85 |
| ATOM | CA | 152 | LEU | A | 38.221 | 13.442 | 2.935 | 1.00 | 20.79 |
| ATOM | CB | 153 | LEU | A | 38.298 | 14.040 | 4.341 | 1.00 | 19.20 |
| ATOM | CG | 154 | LEU | A | 37.385 | 13.373 | 5.387 | 1.00 | 19.62 |
| ATOM | CD1 | 155 | LEU | A | 37.541 | 14.052 | 6.749 | 1.00 | 14.44 |
| ATOM | CD2 | 156 | LEU | A | 35.921 | 13.404 | 4.918 | 1.00 | 12.06 |
| ATOM | C | 157 | LEU | A | 38.902 | 14.349 | 1.898 | 1.00 | 18.61 |
| ATOM | O | 158 | LEU | A | 38.318 | 15.277 | 1.372 | 1.00 | 19.33 |
| ATOM | N | 314 | ASP | A | 24.054 | 21.586 | 10.505 | 1.00 | 20.34 |
| ATOM | CA | 315 | ASP | A | 24.514 | 20.256 | 10.991 | 1.00 | 32.81 |
| ATOM | CB | 316 | ASP | A | 24.285 | 20.194 | 12.514 | 1.00 | 40.06 |
| ATOM | CG | 317 | ASP | A | 25.230 | 19.225 | 13.226 | 1.00 | 46.11 |
| ATOM | OD1 | 318 | ASP | A | 26.474 | 19.401 | 13.129 | 1.00 | 48.62 |
| ATOM | OD2 | 319 | ASP | A | 24.718 | 18.292 | 13.900 | 1.00 | 50.43 |
| ATOM | C | 320 | ASP | A | 23.866 | 19.032 | 10.254 | 1.00 | 36.61 |
| ATOM | O | 321 | ASP | A | 23.201 | 18.163 | 10.839 | 1.00 | 39.35 |
| ATOM | N | 322 | HIS | A | 24.053 | 19.024 | 8.937 | 1.00 | 41.05 |
| ATOM | CA | 323 | HIS | A | 23.564 | 17.952 | 8.013 | 1.00 | 47.22 |
| ATOM | CB | 324 | HIS | A | 24.547 | 16.770 | 7.982 | 1.00 | 47.84 |
| ATOM | CG | 325 | HIS | A | 25.792 | 17.052 | 7.195 | 1.00 | 49.75 |
| ATOM | CD2 | 326 | HIS | A | 25.965 | 17.423 | 5.907 | 1.00 | 51.27 |

Figure 2B

| Atom | | No. | AA | | No | X | Y | Z | OCC | B-Factor |
|---|---|---|---|---|---|---|---|---|---|---|
| ATOM | 327 | ND1 | HIS | A | 61 | 27.049 | 17.028 | 7.757 | 1.00 | 51.98 |
| ATOM | 328 | CE1 | HIS | A | 61 | 27.943 | 17.377 | 6.847 | 1.00 | 53.59 |
| ATOM | 329 | NE2 | HIS | A | 61 | 27.311 | 17.623 | 5.713 | 1.00 | 50.47 |
| ATOM | 330 | C | HIS | A | 61 | 22.126 | 17.445 | 8.142 | 1.00 | 49.08 |
| ATOM | 331 | O | HIS | A | 61 | 21.680 | 16.560 | 7.392 | 1.00 | 53.07 |
| ATOM | 782 | N | SER | A | 127 | 32.204 | 26.649 | 11.275 | 1.00 | 2.00 |
| ATOM | 783 | CA | SER | A | 127 | 32.669 | 25.783 | 10.146 | 1.00 | 2.00 |
| ATOM | 784 | CB | SER | A | 127 | 33.270 | 24.508 | 10.731 | 1.00 | 2.00 |
| ATOM | 785 | OG | SER | A | 127 | 34.258 | 24.800 | 11.690 | 1.00 | 2.49 |
| ATOM | 786 | C | SER | A | 127 | 31.674 | 25.377 | 9.036 | 1.00 | 2.00 |
| ATOM | 787 | O | SER | A | 127 | 30.463 | 25.486 | 9.164 | 1.00 | 2.00 |
| ATOM | 788 | N | VAL | A | 128 | 32.222 | 24.903 | 7.920 | 1.00 | 2.00 |
| ATOM | 789 | CA | VAL | A | 128 | 31.380 | 24.368 | 6.809 | 1.00 | 4.25 |
| ATOM | 790 | CB | VAL | A | 128 | 31.641 | 24.922 | 5.406 | 1.00 | 5.15 |
| ATOM | 791 | CG1 | VAL | A | 128 | 30.631 | 25.964 | 5.077 | 1.00 | 14.62 |
| ATOM | 792 | CG2 | VAL | A | 128 | 33.039 | 25.411 | 5.261 | 1.00 | 3.69 |
| ATOM | 793 | C | VAL | A | 128 | 31.775 | 22.937 | 6.678 | 1.00 | 5.33 |
| ATOM | 794 | O | VAL | A | 128 | 32.845 | 22.503 | 7.066 | 1.00 | 8.22 |
| ATOM | 795 | P1 | SEI | A | 129 | 31.695 | 17.762 | 7.461 | 1.00 | 8.79 |
| ATOM | 796 | O3 | SEI | A | 129 | 31.372 | 17.687 | 9.055 | 1.00 | 11.54 |
| ATOM | 797 | O4 | SEI | A | 129 | 31.616 | 16.285 | 6.832 | 1.00 | 7.78 |
| ATOM | 798 | O5 | SEI | A | 129 | 30.630 | 18.671 | 6.720 | 1.00 | 9.57 |
| ATOM | 799 | C5 | SEI | A | 129 | 30.226 | 17.113 | 9.752 | 1.00 | 10.71 |
| ATOM | 800 | C6 | SEI | A | 129 | 30.679 | 16.036 | 10.741 | 1.00 | 11.64 |
| ATOM | 801 | C7 | SEI | A | 129 | 29.405 | 18.197 | 10.462 | 1.00 | 2.00 |
| ATOM | 802 | C8 | SEI | A | 129 | 31.769 | 15.900 | 5.468 | 1.00 | 5.88 |
| ATOM | 803 | C9 | SEI | A | 129 | 30.614 | 14.989 | 5.035 | 1.00 | 10.05 |
| ATOM | 804 | C10 | SEI | A | 129 | 33.106 | 15.201 | 5.285 | 1.00 | 10.92 |
| ATOM | 805 | N | SEI | A | 129 | 30.916 | 22.193 | 6.024 | 1.00 | 7.00 |

Figure 2C

| Atom | No. | AA | | No. | X | Y | Z | OCC | B-Factor |
|---|---|---|---|---|---|---|---|---|---|
| ATOM | 806 | CA | SER | A | 129 | 31.186 | 20.804 | 5.818 | 1.00 | 4.93 |
| ATOM | 807 | C | SER | A | 129 | 30.516 | 20.458 | 4.534 | 1.00 | 3.57 |
| ATOM | 808 | O | SER | A | 129 | 29.305 | 20.529 | 4.410 | 1.00 | 5.86 |
| ATOM | 809 | CB | SER | A | 129 | 30.536 | 20.063 | 6.956 | 1.00 | 4.94 |
| ATOM | 810 | O2 | SER | A | 129 | 33.031 | 18.359 | 7.260 | 1.00 | 17.04 |
| ATOM | 811 | N | LEU | A | 130 | 31.332 | 20.138 | 3.541 | 1.00 | 4.70 |
| ATOM | 812 | CA | LEU | A | 130 | 30.814 | 19.774 | 2.219 | 1.00 | 6.09 |
| ATOM | 813 | CB | LEU | A | 130 | 31.825 | 20.095 | 1.127 | 1.00 | 8.94 |
| ATOM | 814 | CG | LEU | A | 130 | 31.491 | 19.566 | -0.273 | 1.00 | 2.00 |
| ATOM | 815 | CD1 | LEU | A | 130 | 30.306 | 20.309 | -0.854 | 1.00 | 2.00 |
| ATOM | 816 | CD2 | LEU | A | 130 | 32.720 | 19.745 | -1.157 | 1.00 | 4.46 |
| ATOM | 817 | C | LEU | A | 130 | 30.500 | 18.314 | 2.158 | 1.00 | 6.28 |
| ATOM | 818 | O | LEU | A | 130 | 31.293 | 17.487 | 2.554 | 1.00 | 12.07 |
| ATOM | 819 | N | SER | A | 131 | 29.320 | 17.984 | 1.669 | 1.00 | 8.28 |
| ATOM | 820 | CA | SER | A | 131 | 28.978 | 16.564 | 1.504 | 1.00 | 8.85 |
| ATOM | 821 | CB | SER | A | 131 | 27.618 | 16.283 | 2.096 | 1.00 | 5.12 |
| ATOM | 822 | OG | SER | A | 131 | 27.656 | 16.625 | 3.465 | 1.00 | 19.47 |
| ATOM | 823 | C | SER | A | 131 | 29.022 | 16.243 | -0.003 | 1.00 | 10.39 |
| ATOM | 824 | O | SER | A | 131 | 28.527 | 16.996 | -0.846 | 1.00 | 11.22 |
| ATOM | 825 | N | THR | A | 132 | 29.664 | 15.127 | -0.333 | 1.00 | 12.55 |
| ATOM | 826 | CA | THR | A | 132 | 29.790 | 14.670 | -1.728 | 1.00 | 16.62 |
| ATOM | 827 | CB | THR | A | 132 | 31.271 | 14.437 | -2.085 | 1.00 | 15.84 |
| ATOM | 828 | OG1 | THR | A | 132 | 31.893 | 13.713 | -1.019 | 1.00 | 16.85 |
| ATOM | 829 | CG2 | THR | A | 132 | 32.004 | 15.768 | -2.282 | 1.00 | 14.99 |
| ATOM | 830 | C | THR | A | 132 | 29.028 | 13.347 | -1.849 | 1.00 | 19.10 |
| ATOM | 831 | O | THR | A | 132 | 28.990 | 12.558 | -0.903 | 1.00 | 18.44 |
| ATOM | 893 | N | HIS | A | 148 | 25.733 | 19.031 | -0.862 | 1.00 | 12.59 |
| ATOM | 894 | CA | HIS | A | 148 | 25.300 | 20.234 | -0.089 | 1.00 | 10.63 |
| ATOM | 895 | CB | HIS | A | 148 | 23.987 | 19.958 | 0.619 | 1.00 | 10.37 |

Figure 2D

| Atom | | AA | | No. | X | Y | Z | OCC | B-Factor |
|---|---|---|---|---|---|---|---|---|---|
| ATOM | CG | HIS | A | 148 | 24.047 | 18.808 | 1.577 | 1.00 | 19.25 |
| ATOM | CD2 | HIS | A | 148 | 23.866 | 17.477 | 1.389 | 1.00 | 23.23 |
| ATOM | ND1 | HIS | A | 148 | 24.283 | 18.967 | 2.926 | 1.00 | 26.01 |
| ATOM | CE1 | HIS | A | 148 | 24.244 | 17.791 | 3.527 | 1.00 | 23.57 |
| ATOM | NE2 | HIS | A | 148 | 23.992 | 16.869 | 2.615 | 1.00 | 25.40 |
| ATOM | C | HIS | A | 148 | 26.358 | 20.634 | 0.949 | 1.00 | 12.85 |
| ATOM | O | HIS | A | 148 | 27.342 | 19.912 | 1.222 | 1.00 | 10.96 |
| ATOM | N | VAL | A | 149 | 26.145 | 21.803 | 1.547 | 1.00 | 9.18 |
| ATOM | CA | VAL | A | 149 | 27.067 | 22.274 | 2.595 | 1.00 | 7.72 |
| ATOM | CB | VAL | A | 149 | 27.780 | 23.596 | 2.229 | 1.00 | 9.50 |
| ATOM | CG1 | VAL | A | 149 | 28.036 | 23.637 | 0.751 | 1.00 | 11.54 |
| ATOM | CG2 | VAL | A | 149 | 27.012 | 24.800 | 2.695 | 1.00 | 11.06 |
| ATOM | C | VAL | A | 149 | 26.277 | 22.435 | 3.880 | 1.00 | 7.39 |
| ATOM | O | VAL | A | 149 | 25.120 | 22.861 | 3.904 | 1.00 | 6.80 |
| ATOM | N | ALA | A | 150 | 26.916 | 22.032 | 4.964 | 1.00 | 7.47 |
| ATOM | CA | ALA | A | 150 | 26.302 | 22.093 | 6.270 | 1.00 | 5.81 |
| ATOM | CB | ALA | A | 150 | 26.244 | 20.710 | 6.876 | 1.00 | 2.00 |
| ATOM | C | ALA | A | 150 | 27.130 | 23.017 | 7.142 | 1.00 | 5.80 |
| ATOM | O | ALA | A | 150 | 28.347 | 23.019 | 7.091 | 1.00 | 15.09 |
| ATOM | N | LEU | A | 151 | 26.443 | 23.901 | 7.853 | 1.00 | 5.33 |
| ATOM | CA | LEU | A | 151 | 27.083 | 24.817 | 8.800 | 1.00 | 3.39 |
| ATOM | CB | LEU | A | 151 | 26.157 | 25.991 | 9.072 | 1.00 | 5.70 |
| ATOM | CG | LEU | A | 151 | 26.241 | 27.301 | 8.296 | 1.00 | 7.34 |
| ATOM | CD1 | LEU | A | 151 | 26.854 | 27.107 | 6.939 | 1.00 | 3.41 |
| ATOM | CD2 | LEU | A | 151 | 24.841 | 27.925 | 8.241 | 1.00 | 4.66 |
| ATOM | C | LEU | A | 151 | 27.204 | 23.934 | 10.043 | 1.00 | 3.49 |
| ATOM | O | LEU | A | 151 | 26.316 | 23.128 | 10.340 | 1.00 | 2.65 |
| ATOM | N | CYS | A | 152 | 28.306 | 24.058 | 10.770 | 1.00 | 5.06 |
| ATOM | CA | CYS | A | 152 | 28.482 | 23.240 | 11.983 | 1.00 | 2.81 |

Figure 2E

| Atom | No. | | AA | No. | X | Y | Z | OCC | B-Factor |
|---|---|---|---|---|---|---|---|---|---|
| ATOM | 925 | CB | CYS | A 152 | 28.884 | 21.838 | 11.561 | 1.00 | 2.00 |
| ATOM | 926 | SG | CYS | A 152 | 30.351 | 21.833 | 10.545 | 1.00 | 12.33 |
| ATOM | 927 | C | CYS | A 152 | 29.525 | 23.887 | 12.880 | 1.00 | 3.00 |
| ATOM | 928 | O | CYS | A 152 | 30.084 | 24.917 | 12.574 | 1.00 | 6.88 |
| ATOM | 934 | N | ILE | A 154 | 32.449 | 22.278 | 14.209 | 1.00 | 3.33 |
| ATOM | 935 | CA | ILE | A 154 | 33.791 | 21.856 | 13.831 | 1.00 | 6.57 |
| ATOM | 936 | CB | ILE | A 154 | 34.519 | 21.214 | 15.065 | 1.00 | 13.23 |
| ATOM | 937 | CG2 | ILE | A 154 | 35.849 | 20.661 | 14.679 | 1.00 | 15.20 |
| ATOM | 938 | CG1 | ILE | A 154 | 34.742 | 22.247 | 16.184 | 1.00 | 17.08 |
| ATOM | 939 | CD1 | ILE | A 154 | 35.736 | 23.354 | 15.845 | 1.00 | 21.42 |
| ATOM | 940 | C | ILE | A 154 | 33.620 | 20.837 | 12.671 | 1.00 | 8.07 |
| ATOM | 941 | O | ILE | A 154 | 32.935 | 19.820 | 12.802 | 1.00 | 6.60 |
| ATOM | 942 | N | GLY | A 155 | 34.206 | 21.179 | 11.516 | 1.00 | 7.25 |
| ATOM | 943 | CA | GLY | A 155 | 34.138 | 20.338 | 10.335 | 1.00 | 8.29 |
| ATOM | 944 | C | GLY | A 155 | 35.202 | 19.269 | 10.364 | 1.00 | 9.30 |
| ATOM | 945 | O | GLY | A 155 | 36.071 | 19.289 | 11.239 | 1.00 | 11.83 |
| ATOM | 946 | N | ARG | A 156 | 35.176 | 18.363 | 9.393 | 1.00 | 8.85 |
| ATOM | 947 | CA | ARG | A 156 | 36.182 | 17.277 | 9.359 | 1.00 | 10.92 |
| ATOM | 948 | CB | ARG | A 156 | 35.496 | 15.967 | 8.996 | 1.00 | 17.70 |
| ATOM | 949 | CG | ARG | A 156 | 34.400 | 15.595 | 9.973 | 1.00 | 20.67 |
| ATOM | 950 | CD | ARG | A 156 | 34.337 | 14.120 | 10.205 | 1.00 | 29.56 |
| ATOM | 951 | NE | ARG | A 156 | 34.168 | 13.376 | 8.965 | 1.00 | 41.87 |
| ATOM | 952 | CZ | ARG | A 156 | 34.645 | 12.149 | 8.765 | 1.00 | 50.41 |
| ATOM | 953 | NH1 | ARG | A 156 | 34.438 | 11.536 | 7.603 | 1.00 | 51.55 |
| ATOM | 954 | NH2 | ARG | A 156 | 35.340 | 11.537 | 9.724 | 1.00 | 54.89 |
| ATOM | 955 | C | ARG | A 156 | 37.420 | 17.537 | 8.476 | 1.00 | 10.96 |
| ATOM | 956 | O | ARG | A 156 | 38.466 | 16.913 | 8.597 | 1.00 | 13.19 |
| ATOM | 957 | N | ARG | A 157 | 37.278 | 18.458 | 7.547 | 1.00 | 9.18 |
| ATOM | 958 | CA | ARG | A 157 | 38.395 | 18.809 | 6.689 | 1.00 | 7.21 |

Figure 2F

| Atom | | AA | No. | X | Y | Z | OCC | B-Factor |
|---|---|---|---|---|---|---|---|---|
| ATOM | 959 | CB | ARG A 157 | 37.889 | 19.001 | 5.268 | 1.00 | 3.14 |
| ATOM | 960 | CG | ARG A 157 | 37.587 | 17.685 | 4.570 | 1.00 | 5.26 |
| ATOM | 961 | CD | ARG A 157 | 37.501 | 17.781 | 3.034 | 1.00 | 5.80 |
| ATOM | 962 | NE | ARG A 157 | 36.109 | 17.989 | 2.665 | 1.00 | 9.28 |
| ATOM | 963 | CZ | ARG A 157 | 35.294 | 17.125 | 2.068 | 1.00 | 10.11 |
| ATOM | 964 | NH1 | ARG A 157 | 35.612 | 15.920 | 1.630 | 1.00 | 7.28 |
| ATOM | 965 | NH2 | ARG A 157 | 34.036 | 17.269 | 2.355 | 1.00 | 17.52 |
| ATOM | 966 | C | ARG A 157 | 39.054 | 20.074 | 7.280 | 1.00 | 9.04 |
| ATOM | 967 | O | ARG A 157 | 38.454 | 20.808 | 8.066 | 1.00 | 7.54 |
| ATOM | 3320 | OH2 | HOH WAT1 | 34.674 | 20.373 | 6.663 | 1.00 | 2.00 |
| ATOM | 3355 | OH2 | HOH WAT2 | 34.176 | 20.162 | 3.994 | 1.00 | 17.52 |

Figure 3A

| Residue | Atom | X | Y | Z | B |
|---|---|---|---|---|---|
| 27 LEU | N | 35.91 | 25.23 | 1.03 | 8.63 |
| 27 LEU | CA | 35.20 | 23.98 | 1.32 | 9.80 |
| 27 LEU | CB | 34.35 | 23.49 | 0.15 | 7.49 |
| 27 LEU | CG | 32.94 | 24.00 | -0.06 | 7.63 |
| 27 LEU | CD1 | 32.31 | 24.50 | 1.21 | 2.13 |
| 27 LEU | CD2 | 32.97 | 25.06 | -1.07 | 9.69 |
| 27 LEU | C | 36.25 | 22.93 | 1.61 | 9.77 |
| 27 LEU | O | 35.93 | 21.86 | 2.11 | 12.13 |
| 38 LEU | N | 38.77 | 12.21 | 3.00 | 25.79 |
| 38 LEU | CA | 38.44 | 13.62 | 2.95 | 22.29 |
| 38 LEU | CB | 38.81 | 14.28 | 4.28 | 21.83 |
| 38 LEU | CG | 37.90 | 13.88 | 5.44 | 22.40 |
| 38 LEU | CD1 | 36.48 | 13.63 | 4.92 | 18.69 |
| 38 LEU | CD2 | 38.44 | 12.61 | 6.10 | 24.95 |
| 38 LEU | C | 39.06 | 14.39 | 1.80 | 21.48 |
| 38 LEU | O | 38.38 | 15.13 | 1.08 | 19.95 |
| 60 ASP | N | 24.14 | 21.54 | 10.22 | 6.21 |
| 60 ASP | CA | 24.72 | 20.29 | 10.69 | 9.27 |
| 60 ASP | CB | 24.50 | 20.16 | 12.22 | 12.92 |
| 60 ASP | CG | 25.64 | 19.40 | 12.93 | 18.52 |
| 60 ASP | OD1 | 26.78 | 19.39 | 12.40 | 23.62 |
| 60 ASP | OD2 | 25.43 | 18.84 | 14.04 | 15.83 |
| 60 ASP | C | 24.21 | 19.05 | 9.96 | 10.71 |
| 60 ASP | O | 23.88 | 18.06 | 10.57 | 12.47 |
| 61 HIS | N | 24.13 | 19.11 | 8.64 | 12.79 |
| 61 HIS | CA | 23.68 | 17.98 | 7.81 | 14.32 |
| 61 HIS | C | 22.24 | 17.54 | 7.92 | 17.79 |
| 61 HIS | O | 21.85 | 16.59 | 7.25 | 20.60 |
| 61 HIS | CB | 24.59 | 16.76 | 7.96 | 10.25 |
| 61 HIS | CG | 26.00 | 17.01 | 7.52 | 12.30 |
| 61 HIS | ND1 | 26.39 | 17.08 | 6.21 | 13.19 |

Figure 3B

| Residue | Atom | X | Y | Z | B |
|---|---|---|---|---|---|
| 61 HIS | CD2 | 27.10 | 17.30 | 8.26 | 11.24 |
| 61 HIS | NE2 | 28.16 | 17.57 | 7.41 | 13.47 |
| 61 HIS | CE1 | 27.69 | 17.42 | 6.18 | 11.79 |
| 127 SER | N | 32.35 | 26.51 | 11.23 | 7.34 |
| 127 SER | CA | 32.78 | 25.64 | 10.14 | 7.69 |
| 127 SER | CB | 33.33 | 24.36 | 10.71 | 7.69 |
| 127 SER | OG | 34.45 | 24.61 | 11.53 | 12.66 |
| 127 SER | C | 31.75 | 25.27 | 9.10 | 7.85 |
| 127 SER | O | 30.58 | 25.48 | 9.30 | 11.85 |
| 128 VAL | N | 32.23 | 24.80 | 7.95 | 4.94 |
| 128 VAL | CA | 31.36 | 24.32 | 6.89 | 5.12 |
| 128 VAL | CB | 31.40 | 25.12 | 5.59 | 2.60 |
| 128 VAL | CG1 | 31.07 | 26.50 | 5.86 | 11.40 |
| 128 VAL | CG2 | 32.70 | 25.03 | 4.93 | 2.00 |
| 128 VAL | C | 31.84 | 22.93 | 6.62 | 7.19 |
| 128 VAL | O | 32.97 | 22.58 | 6.92 | 11.48 |
| 129 SER | N | 30.97 | 22.13 | 6.04 | 6.97 |
| 129 SER | CA | 31.32 | 20.78 | 5.73 | 7.38 |
| 129 SER | CB | 30.73 | 19.90 | 6.80 | 8.32 |
| 129 SER | OG | 31.11 | 18.56 | 6.62 | 14.12 |
| 129 SER | C | 30.68 | 20.52 | 4.37 | 9.06 |
| 129 SER | O | 29.51 | 20.77 | 4.20 | 11.11 |
| 130 LEU | N | 31.47 | 20.13 | 3.38 | 8.54 |
| 130 LEU | CA | 30.93 | 19.85 | 2.07 | 8.69 |
| 130 LEU | CB | 31.97 | 20.16 | 0.99 | 12.13 |
| 130 LEU | CG | 31.88 | 19.67 | -0.47 | 11.59 |
| 130 LEU | CD1 | 30.63 | 20.19 | -1.18 | 7.88 |
| 130 LEU | CD2 | 33.15 | 20.15 | -1.20 | 12.99 |
| 130 LEU | C | 30.56 | 18.41 | 1.96 | 7.67 |
| 130 LEU | O | 31.36 | 17.56 | 2.22 | 10.85 |
| 131 SER | N | 29.32 | 18.10 | 1.66 | 7.41 |

Figure 3C

| Residue | Atom | X | Y | Z | B |
|---|---|---|---|---|---|
| 131 SER | CA | 29.03 | 16.71 | 1.46 | 10.24 |
| 131 SER | CB | 27.65 | 16.35 | 1.96 | 12.02 |
| 131 SER | OG | 27.68 | 16.30 | 3.36 | 18.85 |
| 131 SER | C | 29.16 | 16.49 | -0.04 | 12.33 |
| 131 SER | O | 28.84 | 17.37 | -0.85 | 13.24 |
| 132 THR | N | 29.73 | 15.36 | -0.41 | 14.15 |
| 132 THR | CA | 29.89 | 14.98 | -1.80 | 15.87 |
| 132 THR | CB | 31.34 | 14.59 | -2.10 | 13.37 |
| 132 THR | OG1 | 31.80 | 13.73 | -1.08 | 12.74 |
| 132 THR | CG2 | 32.24 | 15.82 | -2.18 | 11.44 |
| 132 THR | C | 29.00 | 13.77 | -1.94 | 18.29 |
| 132 THR | O | 29.23 | 12.74 | -1.28 | 19.88 |
| 148 HIS | N | 25.72 | 18.90 | -0.80 | 8.71 |
| 148 HIS | CA | 25.34 | 20.14 | -0.15 | 8.60 |
| 148 HIS | C | 26.51 | 20.61 | 0.73 | 8.75 |
| 148 HIS | O | 27.57 | 20.01 | 0.73 | 9.64 |
| 148 HIS | CB | 24.11 | 19.91 | 0.72 | 7.49 |
| 148 HIS | CG | 24.35 | 18.95 | 1.85 | 10.55 |
| 148 HIS | ND1 | 24.75 | 19.32 | 3.11 | 14.28 |
| 148 HIS | CD2 | 24.25 | 17.60 | 1.89 | 13.72 |
| 148 HIS | NE2 | 24.59 | 17.13 | 3.17 | 10.96 |
| 148 HIS | CE1 | 24.88 | 18.20 | 3.87 | 11.30 |
| 149 VAL | N | 26.28 | 21.66 | 1.52 | 5.64 |
| 149 VAL | CA | 27.28 | 22.20 | 2.42 | 4.43 |
| 149 VAL | CB | 27.91 | 23.52 | 1.85 | 2.00 |
| 149 VAL | CG1 | 27.13 | 24.01 | 0.72 | 2.60 |
| 149 VAL | CG2 | 28.02 | 24.63 | 2.90 | 2.00 |
| 149 VAL | C | 26.66 | 22.41 | 3.81 | 5.08 |
| 149 VAL | O | 25.76 | 23.23 | 3.99 | 6.81 |
| 150 ALA | N | 27.07 | 21.63 | 4.79 | 4.31 |
| 150 ALA | CA | 26.54 | 21.77 | 6.12 | 4.19 |

Figure 3D

| Residue | Atom | X | Y | Z | B |
|---|---|---|---|---|---|
| 150 ALA | CB | 26.61 | 20.47 | 6.82 | 2.00 |
| 150 ALA | C | 27.27 | 22.85 | 6.92 | 6.21 |
| 150 ALA | O | 28.45 | 23.04 | 6.74 | 8.36 |
| 151 LEU | N | 26.52 | 23.64 | 7.70 | 8.89 |
| 151 LEU | CA | 27.04 | 24.68 | 8.59 | 8.16 |
| 151 LEU | CB | 25.96 | 25.72 | 8.87 | 6.76 |
| 151 LEU | CG | 26.17 | 27.20 | 8.57 | 13.35 |
| 151 LEU | CD1 | 26.80 | 27.33 | 7.16 | 14.96 |
| 151 LEU | CD2 | 24.86 | 28.01 | 8.69 | 2.52 |
| 151 LEU | C | 27.28 | 23.87 | 9.88 | 10.36 |
| 151 LEU | O | 26.40 | 23.13 | 10.32 | 11.10 |
| 152 CYS | N | 28.45 | 23.97 | 10.47 | 10.07 |
| 152 CYS | CA | 28.70 | 23.20 | 11.68 | 10.06 |
| 152 CYS | CB | 29.09 | 21.78 | 11.30 | 9.56 |
| 152 CYS | SG | 30.55 | 21.68 | 10.32 | 12.05 |
| 152 CYS | C | 29.70 | 23.84 | 12.62 | 10.73 |
| 152 CYS | O | 30.22 | 24.91 | 12.35 | 10.79 |
| 154 ILE | N | 32.67 | 22.27 | 14.19 | 13.17 |
| 154 ILE | CA | 34.04 | 21.91 | 13.84 | 14.44 |
| 154 ILE | CB | 34.76 | 21.20 | 15.06 | 16.21 |
| 154 ILE | CG2 | 35.94 | 20.37 | 14.62 | 16.07 |
| 154 ILE | CG1 | 35.25 | 22.26 | 16.04 | 18.38 |
| 154 ILE | CD1 | 36.24 | 23.28 | 15.42 | 19.24 |
| 154 ILE | C | 33.90 | 20.99 | 12.62 | 14.39 |
| 154 ILE | O | 33.23 | 19.97 | 12.69 | 13.58 |
| 155 GLY | N | 34.40 | 21.47 | 11.48 | 16.35 |
| 155 GLY | CA | 34.31 | 20.72 | 10.24 | 18.21 |
| 155 GLY | C | 35.41 | 19.67 | 10.20 | 20.38 |
| 155 GLY | O | 36.41 | 19.78 | 10.93 | 21.76 |
| 156 ARG | N | 35.26 | 18.69 | 9.32 | 20.77 |
| 156 ARG | CA | 36.24 | 17.61 | 9.21 | 21.11 |

Figure 3E

| Residue | Atom | X | Y | Z | B |
|---|---|---|---|---|---|
| 156 ARG | CB | 35.53 | 16.30 | 8.87 | 24.90 |
| 156 ARG | CG | 35.76 | 15.25 | 9.94 | 29.04 |
| 156 ARG | CD | 34.71 | 14.16 | 9.85 | 32.89 |
| 156 ARG | NE | 34.84 | 13.39 | 8.62 | 39.65 |
| 156 ARG | CZ | 34.67 | 12.06 | 8.54 | 43.91 |
| 156 ARG | NH1 | 34.81 | 11.44 | 7.34 | 44.98 |
| 156 ARG | NH2 | 34.32 | 11.35 | 9.63 | 42.89 |
| 156 ARG | C | 37.40 | 17.83 | 8.24 | 20.04 |
| 156 ARG | O | 38.31 | 17.01 | 8.18 | 22.30 |
| 157 ARG | N | 37.35 | 18.89 | 7.45 | 17.53 |
| 157 ARG | CA | 38.43 | 19.17 | 6.53 | 15.10 |
| 157 ARG | CB | 37.95 | 19.20 | 5.08 | 11.19 |
| 157 ARG | CG | 37.67 | 17.82 | 4.59 | 7.60 |
| 157 ARG | CD | 37.61 | 17.73 | 3.11 | 10.17 |
| 157 ARG | NE | 36.33 | 18.14 | 2.57 | 15.38 |
| 157 ARG | CZ | 35.39 | 17.30 | 2.14 | 17.80 |
| 157 ARG | NH1 | 35.56 | 15.99 | 2.20 | 14.74 |
| 157 ARG | NH2 | 34.30 | 17.77 | 1.53 | 18.94 |
| 157 ARG | C | 39.11 | 20.45 | 7.00 | 15.95 |
| 157 ARG | O | 38.48 | 21.29 | 7.67 | 15.82 |
| 321 WAT | OH2 | 34.16 | 20.32 | 7.14 | 15.58 |

Figure 4A

| | | | | | | | | | |
|---|---|---|---|---|---|---|---|---|---|
| ATOM | 1 | CB | ALA | A | 17 | 10.980 | 40.209 | 8.106 | 1.00 31.97 |
| ATOM | 2 | C | ALA | A | 17 | 13.480 | 40.173 | 8.007 | 1.00 27.25 |
| ATOM | 3 | O | ALA | A | 17 | 14.076 | 40.347 | 9.079 | 1.00 26.95 |
| ATOM | 4 | N | ALA | A | 17 | 12.141 | 41.223 | 6.151 | 1.00 26.54 |
| ATOM | 5 | CA | ALA | A | 17 | 12.217 | 40.962 | 7.529 | 1.00 28.53 |
| ATOM | 6 | N | ALA | A | 18 | 13.850 | 39.255 | 7.120 | 1.00 27.32 |
| ATOM | 7 | CA | ALA | A | 18 | 15.059 | 38.441 | 7.337 | 1.00 25.64 |
| ATOM | 8 | CB | ALA | A | 18 | 15.030 | 37.202 | 6.471 | 1.00 23.07 |
| ATOM | 9 | C | ALA | A | 18 | 16.260 | 39.306 | 6.980 | 1.00 22.24 |
| ATOM | 10 | O | ALA | A | 18 | 16.185 | 40.221 | 6.154 | 1.00 21.42 |
| ATOM | 11 | N | VAL | A | 19 | 17.343 | 39.069 | 7.711 | 1.00 22.87 |
| ATOM | 12 | CA | VAL | A | 19 | 18.635 | 39.758 | 7.485 | 1.00 16.87 |
| ATOM | 13 | CB | VAL | A | 19 | 19.447 | 39.903 | 8.801 | 1.00 17.31 |
| ATOM | 14 | CG1 | VAL | A | 19 | 20.873 | 40.382 | 8.529 | 1.00 16.47 |
| ATOM | 15 | CG2 | VAL | A | 19 | 18.773 | 40.870 | 9.711 | 1.00 17.73 |
| ATOM | 16 | C | VAL | A | 19 | 19.349 | 38.757 | 6.565 | 1.00 12.56 |
| ATOM | 17 | O | VAL | A | 19 | 19.512 | 37.578 | 6.888 | 1.00 13.32 |
| ATOM | 18 | N | PRO | A | 20 | 19.629 | 39.176 | 5.333 | 1.00 9.51 |
| ATOM | 19 | CD | PRO | A | 20 | 19.146 | 40.372 | 4.636 | 1.00 7.49 |
| ATOM | 20 | CA | PRO | A | 20 | 20.318 | 38.269 | 4.413 | 1.00 7.09 |
| ATOM | 21 | CB | PRO | A | 20 | 20.239 | 39.011 | 3.078 | 1.00 10.46 |
| ATOM | 22 | CG | PRO | A | 20 | 19.018 | 39.861 | 3.222 | 1.00 9.68 |
| ATOM | 23 | C | PRO | A | 20 | 21.742 | 38.196 | 4.897 | 1.00 6.66 |
| ATOM | 24 | O | PRO | A | 20 | 22.429 | 39.197 | 5.037 | 1.00 12.21 |
| ATOM | 25 | N | ILE | A | 21 | 22.183 | 36.996 | 5.191 | 1.00 6.42 |
| ATOM | 26 | CA | ILE | A | 21 | 23.537 | 36.791 | 5.683 | 1.00 6.75 |
| ATOM | 27 | CB | ILE | A | 21 | 23.481 | 35.922 | 6.984 | 1.00 9.36 |
| ATOM | 28 | CG2 | ILE | A | 21 | 24.860 | 35.410 | 7.387 | 1.00 8.42 |
| ATOM | 29 | CG1 | ILE | A | 21 | 22.848 | 36.713 | 8.126 | 1.00 7.06 |
| ATOM | 30 | CD1 | ILE | A | 21 | 22.600 | 35.873 | 9.373 | 1.00 9.87 |
| ATOM | 31 | C | ILE | A | 21 | 24.342 | 36.056 | 4.610 | 1.00 7.41 |
| ATOM | 32 | O | ILE | A | 21 | 23.852 | 35.129 | 3.976 | 1.00 7.22 |
| ATOM | 33 | N | TYR | A | 22 | 25.567 | 36.522 | 4.376 | 1.00 10.46 |
| ATOM | 34 | CA | TYR | A | 22 | 26.522 | 35.876 | 3.420 | 1.00 8.42 |
| ATOM | 35 | CB | TYR | A | 22 | 27.248 | 36.920 | 2.597 | 1.00 9.47 |
| ATOM | 36 | CG | TYR | A | 22 | 26.318 | 37.634 | 1.718 | 1.00 11.88 |
| ATOM | 37 | CD1 | TYR | A | 22 | 26.025 | 37.134 | 0.460 | 1.00 16.31 |
| ATOM | 38 | CE1 | TYR | A | 22 | 25.084 | 37.734 | -0.340 | 1.00 16.44 |
| ATOM | 39 | CD2 | TYR | A | 22 | 25.653 | 38.764 | 2.156 | 1.00 11.71 |
| ATOM | 40 | CE2 | TYR | A | 22 | 24.710 | 39.377 | 1.361 | 1.00 11.64 |
| ATOM | 41 | CZ | TYR | A | 22 | 24.431 | 38.851 | 0.119 | 1.00 16.41 |
| ATOM | 42 | OH | TYR | A | 22 | 23.476 | 39.422 | -0.671 | 1.00 24.08 |
| ATOM | 43 | C | TYR | A | 22 | 27.561 | 35.060 | 4.232 | 1.00 8.38 |
| ATOM | 44 | O | TYR | A | 22 | 28.061 | 35.486 | 5.281 | 1.00 6.96 |
| ATOM | 45 | N | VAL | A | 23 | 27.838 | 33.857 | 3.747 | 1.00 7.92 |
| ATOM | 46 | CA | VAL | A | 23 | 28.829 | 32.966 | 4.376 | 1.00 7.55 |
| ATOM | 47 | CB | VAL | A | 23 | 28.298 | 31.531 | 4.564 | 1.00 7.21 |
| ATOM | 48 | CG1 | VAL | A | 23 | 28.894 | 30.874 | 5.794 | 1.00 2.00 |
| ATOM | 49 | CG2 | VAL | A | 23 | 26.832 | 31.508 | 4.557 | 1.00 5.18 |
| ATOM | 50 | C | VAL | A | 23 | 29.868 | 32.854 | 3.260 | 1.00 8.10 |
| ATOM | 51 | O | VAL | A | 23 | 29.536 | 32.829 | 2.080 | 1.00 12.46 |

Figure 4B

| ATOM | 52 | N | ALA | A | 24 | 31.125 | 32.733 | 3.627 | 1.00 | 5.41 |
|---|---|---|---|---|---|---|---|---|---|---|
| ATOM | 53 | CA | ALA | A | 24 | 32.187 | 32.593 | 2.627 | 1.00 | 2.87 |
| ATOM | 54 | CB | ALA | A | 24 | 32.712 | 33.965 | 2.229 | 1.00 | 2.00 |
| ATOM | 55 | C | ALA | A | 24 | 33.250 | 31.799 | 3.351 | 1.00 | 6.88 |
| ATOM | 56 | O | ALA | A | 24 | 33.368 | 31.890 | 4.573 | 1.00 | 10.26 |
| ATOM | 57 | N | GLY | A | 25 | 33.970 | 30.952 | 2.622 | 1.00 | 7.52 |
| ATOM | 58 | CA | GLY | A | 25 | 35.015 | 30.159 | 3.234 | 1.00 | 2.00 |
| ATOM | 59 | C | GLY | A | 25 | 35.416 | 29.067 | 2.288 | 1.00 | 5.06 |
| ATOM | 60 | O | GLY | A | 25 | 34.807 | 28.898 | 1.236 | 1.00 | 8.24 |
| ATOM | 61 | N | PHE | A | 26 | 36.463 | 28.340 | 2.643 | 1.00 | 8.52 |
| ATOM | 62 | CA | PHE | A | 26 | 36.950 | 27.220 | 1.310 | 1.00 | 6.14 |
| ATOM | 63 | CB | PHE | A | 26 | 38.474 | 26.990 | 1.985 | 1.00 | 3.33 |
| ATOM | 64 | CG | PHE | A | 26 | 39.347 | 27.965 | 1.206 | 1.00 | 6.92 |
| ATOM | 65 | CD1 | PHE | A | 26 | 39.879 | 29.107 | 1.818 | 1.00 | 8.24 |
| ATOM | 66 | CD2 | PHE | A | 26 | 39.665 | 27.727 | -0.132 | 1.00 | 6.96 |
| ATOM | 67 | CE1 | PHE | A | 26 | 40.711 | 29.984 | 1.102 | 1.00 | 4.75 |
| ATOM | 68 | CE2 | PHE | A | 26 | 40.502 | 28.603 | -0.856 | 1.00 | 3.94 |
| ATOM | 69 | CZ | PHE | A | 26 | 41.021 | 29.725 | -0.239 | 1.00 | 2.00 |
| ATOM | 70 | C | PHE | A | 26 | 36.168 | 25.973 | 2.222 | 1.00 | 4.85 |
| ATOM | 71 | O | PHE | A | 26 | 35.893 | 25.704 | 3.398 | 1.00 | 3.88 |
| ATOM | 72 | N | LEU | A | 27 | 35.736 | 25.246 | 1.206 | 1.00 | 5.10 |
| ATOM | 73 | CA | LEU | A | 27 | 35.022 | 24.000 | 1.421 | 1.00 | 6.35 |
| ATOM | 74 | CB | LEU | A | 27 | 34.241 | 23.628 | 0.173 | 1.00 | 4.80 |
| ATOM | 75 | CG | LEU | A | 27 | 32.753 | 23.867 | 0.051 | 1.00 | 2.00 |
| ATOM | 76 | CD1 | LEU | A | 27 | 32.147 | 24.549 | 1.270 | 1.00 | 2.00 |
| ATOM | 77 | CD2 | LEU | A | 27 | 32.558 | 24.628 | -1.224 | 1.00 | 2.00 |
| ATOM | 78 | C | LEU | A | 27 | 36.089 | 22.929 | 1.732 | 1.00 | 8.64 |
| ATOM | 79 | O | LEU | A | 27 | 35.816 | 21.898 | 2.340 | 1.00 | 8.93 |
| ATOM | 80 | N | ALA | A | 28 | 37.308 | 23.191 | 1.258 | 1.00 | 9.18 |
| ATOM | 81 | CA | ALA | A | 28 | 38.464 | 22.295 | 1.443 | 1.00 | 6.84 |
| ATOM | 82 | CB | ALA | A | 28 | 38.247 | 21.026 | 0.660 | 1.00 | 8.67 |
| ATOM | 83 | C | ALA | A | 28 | 39.763 | 22.986 | 0.965 | 1.00 | 9.42 |
| ATOM | 84 | O | ALA | A | 28 | 39.751 | 23.869 | 0.111 | 1.00 | 10.30 |
| ATOM | 85 | N | LEU | A | 29 | 40.888 | 22.591 | 1.561 | 1.00 | 11.25 |
| ATOM | 86 | CA | LEU | A | 29 | 42.226 | 23.138 | 1.173 | 1.00 | 12.15 |
| ATOM | 87 | CB | LEU | A | 29 | 43.035 | 23.608 | 2.388 | 1.00 | 10.90 |
| ATOM | 88 | CG | LEU | A | 29 | 42.517 | 24.776 | 3.233 | 1.00 | 6.47 |
| ATOM | 89 | CD1 | LEU | A | 29 | 43.379 | 24.840 | 4.442 | 1.00 | 7.44 |
| ATOM | 90 | CD2 | LEU | A | 29 | 42.530 | 26.106 | 2.498 | 1.00 | 2.00 |
| ATOM | 91 | C | LEU | A | 29 | 42.912 | 21.952 | 0.486 | 1.00 | 12.45 |
| ATOM | 92 | O | LEU | A | 29 | 42.949 | 20.854 | 1.018 | 1.00 | 14.70 |
| ATOM | 93 | N | TYR | A | 30 | 43.431 | 22.201 | -0.714 | 1.00 | 15.16 |
| ATOM | 94 | CA | TYR | A | 30 | 44.080 | 21.186 | -1.553 | 1.00 | 17.04 |
| ATOM | 95 | CB | TYR | A | 30 | 44.473 | 21.823 | -2.867 | 1.00 | 12.21 |
| ATOM | 96 | CG | TYR | A | 30 | 43.306 | 22.048 | -3.780 | 1.00 | 12.98 |
| ATOM | 97 | CD1 | TYR | A | 30 | 42.289 | 21.099 | -3.881 | 1.00 | 3.60 |
| ATOM | 98 | CE1 | TYR | A | 30 | 41.240 | 21.308 | -4.746 | 1.00 | 4.61 |
| ATOM | 99 | CD2 | TYR | A | 30 | 43.227 | 23.203 | -4.571 | 1.00 | 7.48 |
| ATOM | 100 | CE2 | TYR | A | 30 | 42.180 | 23.409 | -5.429 | 1.00 | 2.00 |
| ATOM | 101 | CZ | TYR | A | 30 | 41.199 | 22.464 | -5.511 | 1.00 | 2.00 |
| ATOM | 102 | OH | TYR | A | 30 | 40.166 | 22.662 | -6.376 | 1.00 | 7.18 |
| ATOM | 103 | C | TYR | A | 30 | 45.239 | 20.315 | -1.021 | 1.00 | 23.99 |

Figure 4C

| ATOM | 104 | O | TYR | A | 30 | 45.216 | 19.081 | -1.157 | 1.00 | 35.15 |
|------|-----|-----|-----|---|----|--------|--------|--------|------|-------|
| ATOM | 105 | N | ASP | A | 31 | 46.284 | 20.906 | -0.466 | 1.00 | 16.90 |
| ATOM | 106 | CA | ASP | A | 31 | 47.369 | 20.015 | 0.028 | 1.00 | 21.03 |
| ATOM | 107 | CB | ASP | A | 31 | 48.678 | 20.216 | -0.769 | 1.00 | 24.41 |
| ATOM | 108 | CG | ASP | A | 31 | 48.693 | 19.462 | -2.114 | 1.00 | 27.07 |
| ATOM | 109 | OD1 | ASP | A | 31 | 48.911 | 20.097 | -3.178 | 1.00 | 33.82 |
| ATOM | 110 | OD2 | ASP | A | 31 | 48.517 | 18.225 | -2.118 | 1.00 | 27.94 |
| ATOM | 111 | C | ASP | A | 31 | 47.526 | 20.346 | 1.494 | 1.00 | 23.37 |
| ATOM | 112 | O | ASP | A | 31 | 48.559 | 20.829 | 1.955 | 1.00 | 26.14 |
| ATOM | 113 | N | SER | A | 32 | 46.439 | 20.089 | 2.223 | 1.00 | 22.26 |
| ATOM | 114 | CA | SER | A | 32 | 46.348 | 20.395 | 3.637 | 1.00 | 24.96 |
| ATOM | 115 | CB | SER | A | 32 | 44.953 | 20.963 | 4.013 | 1.00 | 23.87 |
| ATOM | 116 | OG | SER | A | 32 | 43.933 | 20.112 | 3.521 | 1.00 | 22.56 |
| ATOM | 117 | C | SER | A | 32 | 46.691 | 19.255 | 4.664 | 1.00 | 23.19 |
| ATOM | 118 | O | SER | A | 32 | 47.031 | 19.464 | 5.830 | 1.00 | 24.17 |
| ATOM | 119 | N | GLY | A | 33 | 46.560 | 18.034 | 4.172 | 1.00 | 21.42 |
| ATOM | 120 | CA | GLY | A | 33 | 46.845 | 16.892 | 4.999 | 1.00 | 17.05 |
| ATOM | 121 | C | GLY | A | 33 | 45.571 | 16.203 | 5.409 | 1.00 | 20.62 |
| ATOM | 122 | O | GLY | A | 33 | 45.594 | 15.459 | 6.377 | 1.00 | 24.68 |
| ATOM | 123 | N | ASP | A | 34 | 44.455 | 16.464 | 4.720 | 1.00 | 22.48 |
| ATOM | 124 | CA | ASP | A | 34 | 43.133 | 15.793 | 5.068 | 1.00 | 22.57 |
| ATOM | 125 | CB | ASP | A | 34 | 41.981 | 16.214 | 4.126 | 1.00 | 17.56 |
| ATOM | 126 | CG | ASP | A | 34 | 41.390 | 17.572 | 4.455 | 1.00 | 12.57 |
| ATOM | 127 | OD1 | ASP | A | 34 | 41.118 | 18.353 | 3.519 | 1.00 | 17.61 |
| ATOM | 128 | OD2 | ASP | A | 34 | 41.161 | 17.858 | 5.633 | 1.00 | 10.35 |
| ATOM | 129 | C | ASP | A | 34 | 43.359 | 14.276 | 4.937 | 1.00 | 24.91 |
| ATOM | 130 | O | ASP | A | 34 | 44.117 | 13.803 | 4.085 | 1.00 | 29.90 |
| ATOM | 131 | N | PRO | A | 35 | 42.703 | 13.490 | 5.795 | 1.00 | 25.20 |
| ATOM | 132 | CD | PRO | A | 35 | 41.853 | 13.864 | 6.936 | 1.00 | 26.67 |
| ATOM | 133 | CA | PRO | A | 35 | 42.879 | 12.038 | 5.716 | 1.00 | 26.21 |
| ATOM | 134 | CB | PRO | A | 35 | 41.850 | 11.527 | 6.707 | 1.00 | 26.43 |
| ATOM | 135 | CG | PRO | A | 35 | 41.881 | 12.607 | 7.768 | 1.00 | 28.24 |
| ATOM | 136 | C | PRO | A | 35 | 42.618 | 11.527 | 4.290 | 1.00 | 29.80 |
| ATOM | 137 | O | PRO | A | 35 | 42.139 | 12.248 | 3.420 | 1.00 | 29.68 |
| ATOM | 138 | N | GLY | A | 36 | 42.921 | 10.252 | 4.067 | 1.00 | 35.36 |
| ATOM | 139 | CA | GLY | A | 36 | 42.755 | 9.668 | 2.744 | 1.00 | 33.76 |
| ATOM | 140 | C | GLY | A | 36 | 41.429 | 9.970 | 2.100 | 1.00 | 34.27 |
| ATOM | 141 | O | GLY | A | 36 | 41.359 | 10.597 | 1.054 | 1.00 | 32.21 |
| ATOM | 142 | N | GLU | A | 37 | 40.369 | 9.560 | 2.778 | 1.00 | 36.66 |
| ATOM | 143 | CA | GLU | A | 37 | 38.991 | 9.746 | 2.289 | 1.00 | 37.10 |
| ATOM | 144 | CB | GLU | A | 37 | 38.037 | 9.040 | 3.274 | 1.00 | 48.49 |
| ATOM | 145 | CG | GLU | A | 37 | 36.527 | 9.343 | 3.059 | 1.00 | 55.75 |
| ATOM | 146 | CD | GLU | A | 37 | 35.613 | 8.655 | 4.068 | 1.00 | 57.77 |
| ATOM | 147 | OE1 | GLU | A | 37 | 35.672 | 8.990 | 5.277 | 1.00 | 59.61 |
| ATOM | 148 | OE2 | GLU | A | 37 | 34.823 | 7.787 | 3.635 | 1.00 | 60.72 |
| ATOM | 149 | C | GLU | A | 37 | 38.515 | 11.192 | 2.013 | 1.00 | 33.55 |
| ATOM | 150 | O | GLU | A | 37 | 37.959 | 11.515 | 0.969 | 1.00 | 37.68 |
| ATOM | 151 | N | LEU | A | 38 | 38.679 | 12.044 | 3.012 | 1.00 | 26.85 |
| ATOM | 152 | CA | LEU | A | 38 | 38.221 | 13.442 | 2.935 | 1.00 | 20.79 |
| ATOM | 153 | CB | LEU | A | 38 | 38.298 | 14.040 | 4.341 | 1.00 | 19.20 |
| ATOM | 154 | CG | LEU | A | 38 | 37.385 | 13.373 | 5.387 | 1.00 | 19.62 |
| ATOM | 155 | CD1 | LEU | A | 38 | 37.541 | 14.052 | 6.749 | 1.00 | 14.44 |

Figure 4D

| ATOM | 156 | CD2 | LEU | A | 38 | 35.921 | 13.404 | 4.918 | 1.00 | 12.06 |
|---|---|---|---|---|---|---|---|---|---|---|
| ATOM | 157 | C | LEU | A | 38 | 38.902 | 14.349 | 1.898 | 1.00 | 18.61 |
| ATOM | 158 | O | LEU | A | 38 | 38.318 | 15.277 | 1.372 | 1.00 | 19.33 |
| ATOM | 159 | N | ALA | A | 39 | 40.167 | 14.077 | 1.631 | 1.00 | 18.81 |
| ATOM | 160 | CA | ALA | A | 39 | 40.970 | 14.880 | 0.683 | 1.00 | 20.42 |
| ATOM | 161 | CB | ALA | A | 39 | 42.280 | 14.175 | 0.393 | 1.00 | 21.73 |
| ATOM | 162 | C | ALA | A | 39 | 40.269 | 15.208 | -0.632 | 1.00 | 21.36 |
| ATOM | 163 | O | ALA | A | 39 | 39.540 | 14.416 | -1.217 | 1.00 | 26.23 |
| ATOM | 164 | N | LEU | A | 40 | 40.547 | 16.408 | -1.118 | 1.00 | 20.60 |
| ATOM | 165 | CA | LEU | A | 40 | 39.977 | 16.891 | -2.390 | 1.00 | 17.27 |
| ATOM | 166 | CB | LEU | A | 40 | 38.922 | 17.964 | -2.130 | 1.00 | 21.23 |
| ATOM | 167 | CG | LEU | A | 40 | 37.489 | 17.482 | -1.898 | 1.00 | 20.88 |
| ATOM | 168 | CD1 | LEU | A | 40 | 36.603 | 18.647 | -1.462 | 1.00 | 21.76 |
| ATOM | 169 | CD2 | LEU | A | 40 | 36.960 | 16.857 | -3.167 | 1.00 | 15.74 |
| ATOM | 170 | C | LEU | A | 40 | 41.136 | 17.452 | -3.189 | 1.00 | 13.74 |
| ATOM | 171 | O | LEU | A | 40 | 42.063 | 18.035 | -2.644 | 1.00 | 14.61 |
| ATOM | 172 | N | ASP | A | 41 | 41.071 | 17.284 | -4.501 | 1.00 | 12.75 |
| ATOM | 173 | CA | ASP | A | 41 | 42.139 | 17.763 | -5.377 | 1.00 | 11.19 |
| ATOM | 174 | CB | ASP | A | 41 | 42.921 | 16.572 | -5.885 | 1.00 | 13.80 |
| ATOM | 175 | CG | ASP | A | 41 | 42.080 | 15.650 | -6.682 | 1.00 | 15.44 |
| ATOM | 176 | OD1 | ASP | A | 41 | 42.092 | 15.759 | -7.933 | 1.00 | 19.46 |
| ATOM | 177 | OD2 | ASP | A | 41 | 41.407 | 14.826 | -6.044 | 1.00 | 16.75 |
| ATOM | 178 | C | ASP | A | 41 | 41.600 | 18.629 | -6.517 | 1.00 | 8.12 |
| ATOM | 179 | O | ASP | A | 41 | 40.440 | 18.583 | -6.865 | 1.00 | 11.10 |
| ATOM | 180 | N | PRO | A | 42 | 42.486 | 19.394 | -7.169 | 1.00 | 9.16 |
| ATOM | 181 | CD | PRO | A | 42 | 43.932 | 19.509 | -6.923 | 1.00 | 2.03 |
| ATOM | 182 | CA | PRO | A | 42 | 42.101 | 20.283 | -8.266 | 1.00 | 6.51 |
| ATOM | 183 | CB | PRO | A | 42 | 43.436 | 20.806 | -8.751 | 1.00 | 2.00 |
| ATOM | 184 | CG | PRO | A | 42 | 44.224 | 20.841 | -7.562 | 1.00 | 2.00 |
| ATOM | 185 | C | PRO | A | 42 | 41.296 | 19.677 | -9.394 | 1.00 | 8.97 |
| ATOM | 186 | O | PRO | A | 42 | 40.256 | 20.180 | -9.796 | 1.00 | 8.38 |
| ATOM | 187 | N | ASP | A | 43 | 41.767 | 18.561 | -9.914 | 1.00 | 9.69 |
| ATOM | 188 | CA | ASP | A | 43 | 41.033 | 17.943 | -11.015 | 1.00 | 12.54 |
| ATOM | 189 | CB | ASP | A | 43 | 41.862 | 16.838 | -11.622 | 1.00 | 17.14 |
| ATOM | 190 | CG | ASP | A | 43 | 42.792 | 17.345 | -12.685 | 1.00 | 23.39 |
| ATOM | 191 | OD1 | ASP | A | 43 | 42.591 | 18.464 | -13.198 | 1.00 | 25.32 |
| ATOM | 192 | OD2 | ASP | A | 43 | 43.730 | 16.610 | -13.019 | 1.00 | 29.45 |
| ATOM | 193 | C | ASP | A | 43 | 39.627 | 17.457 | -10.650 | 1.00 | 11.48 |
| ATOM | 194 | O | ASP | A | 43 | 38.710 | 17.553 | -11.436 | 1.00 | 13.95 |
| ATOM | 195 | N | THR | A | 44 | 39.464 | 16.910 | -9.451 | 1.00 | 12.99 |
| ATOM | 196 | CA | THR | A | 44 | 38.132 | 16.450 | -9.012 | 1.00 | 12.32 |
| ATOM | 197 | CB | THR | A | 44 | 38.235 | 15.592 | -7.784 | 1.00 | 10.64 |
| ATOM | 198 | OG1 | THR | A | 44 | 39.153 | 14.540 | -8.072 | 1.00 | 4.70 |
| ATOM | 199 | CG2 | THR | A | 44 | 36.885 | 14.972 | -7.445 | 1.00 | 16.51 |
| ATOM | 200 | C | THR | A | 44 | 37.194 | 17.639 | -8.756 | 1.00 | 13.28 |
| ATOM | 201 | O | THR | A | 44 | 35.981 | 17.565 | -8.938 | 1.00 | 13.50 |
| ATOM | 202 | N | VAL | A | 45 | 37.768 | 18.764 | -8.352 | 1.00 | 7.49 |
| ATOM | 203 | CA | VAL | A | 45 | 36.919 | 19.905 | -8.134 | 1.00 | 7.31 |
| ATOM | 204 | CB | VAL | A | 45 | 37.571 | 20.941 | -7.270 | 1.00 | 5.44 |
| ATOM | 205 | CG1 | VAL | A | 45 | 36.684 | 22.165 | -7.172 | 1.00 | 3.80 |
| ATOM | 206 | CG2 | VAL | A | 45 | 37.772 | 20.364 | -5.888 | 1.00 | 8.22 |
| ATOM | 207 | C | VAL | A | 45 | 36.555 | 20.480 | -9.488 | 1.00 | 11.60 |

Figure 4E

| ATOM | 208 | O   | VAL | A | 45 | 35.413 | 20.840 | -9.756  | 1.00 | 19.59 |
| ---- | --- | --- | --- | - | -- | ------ | ------ | ------- | ---- | ----- |
| ATOM | 209 | N   | ARG | A | 46 | 37.529 | 20.488 | -10.380 | 1.00 | 11.14 |
| ATOM | 210 | CA  | ARG | A | 46 | 37.337 | 21.025 | -11.734 | 1.00 | 13.59 |
| ATOM | 211 | CB  | ARG | A | 46 | 38.594 | 20.804 | -12.562 | 1.00 | 19.57 |
| ATOM | 212 | CG  | ARG | A | 46 | 38.741 | 21.707 | -13.777 | 1.00 | 32.87 |
| ATOM | 213 | CD  | ARG | A | 46 | 39.159 | 23.150 | -13.381 | 1.00 | 51.39 |
| ATOM | 214 | NE  | ARG | A | 46 | 38.054 | 23.942 | -12.791 | 1.00 | 61.85 |
| ATOM | 215 | CZ  | ARG | A | 46 | 38.090 | 25.255 | -12.512 | 1.00 | 60.50 |
| ATOM | 216 | NH1 | ARG | A | 46 | 37.009 | 25.837 | -11.986 | 1.00 | 58.23 |
| ATOM | 217 | NH2 | ARG | A | 46 | 39.181 | 25.988 | -12.751 | 1.00 | 57.75 |
| ATOM | 218 | C   | ARG | A | 46 | 36.153 | 20.334 | -12.386 | 1.00 | 11.46 |
| ATOM | 219 | O   | ARG | A | 46 | 35.281 | 20.936 | -12.971 | 1.00 | 14.55 |
| ATOM | 220 | N   | ALA | A | 47 | 36.112 | 19.026 | -12.224 | 1.00 | 9.86  |
| ATOM | 221 | CA  | ALA | A | 47 | 35.048 | 18.202 | -12.812 | 1.00 | 9.60  |
| ATOM | 222 | CB  | ALA | A | 47 | 35.499 | 16.765 | -12.814 | 1.00 | 2.00  |
| ATOM | 223 | C   | ALA | A | 47 | 33.658 | 18.329 | -12.115 | 1.00 | 8.75  |
| ATOM | 224 | O   | ALA | A | 47 | 32.653 | 17.857 | -12.604 | 1.00 | 10.75 |
| ATOM | 225 | N   | ALA | A | 48 | 33.619 | 18.961 | -10.955 | 1.00 | 10.20 |
| ATOM | 226 | CA  | ALA | A | 48 | 32.363 | 19.098 | -10.221 | 1.00 | 8.04  |
| ATOM | 227 | CB  | ALA | A | 48 | 32.610 | 18.863 | -8.761  | 1.00 | 2.69  |
| ATOM | 228 | C   | ALA | A | 48 | 31.737 | 20.470 | -10.438 | 1.00 | 11.37 |
| ATOM | 229 | O   | ALA | A | 48 | 30.618 | 20.739 | -10.032 | 1.00 | 14.85 |
| ATOM | 230 | N   | LEU | A | 49 | 32.465 | 21.346 | -11.112 | 1.00 | 11.13 |
| ATOM | 231 | CA  | LEU | A | 49 | 31.979 | 22.703 | -11.330 | 1.00 | 11.79 |
| ATOM | 232 | CB  | LEU | A | 49 | 33.047 | 23.684 | -10.857 | 1.00 | 12.92 |
| ATOM | 233 | CG  | LEU | A | 49 | 33.663 | 23.406 | -9.481  | 1.00 | 15.46 |
| ATOM | 234 | CD1 | LEU | A | 49 | 34.707 | 24.462 | -9.188  | 1.00 | 9.31  |
| ATOM | 235 | CD2 | LEU | A | 49 | 32.595 | 23.352 | -8.384  | 1.00 | 10.40 |
| ATOM | 236 | C   | LEU | A | 49 | 31.571 | 22.981 | -12.780 | 1.00 | 19.21 |
| ATOM | 237 | O   | LEU | A | 49 | 32.261 | 22.618 | -13.723 | 1.00 | 19.07 |
| ATOM | 238 | N   | PRO | A | 50 | 30.412 | 23.635 | -12.978 | 1.00 | 23.72 |
| ATOM | 239 | CD  | PRO | A | 50 | 30.023 | 24.107 | -14.310 | 1.00 | 24.14 |
| ATOM | 240 | CA  | PRO | A | 50 | 29.454 | 24.124 | -11.978 | 1.00 | 23.03 |
| ATOM | 241 | CB  | PRO | A | 50 | 28.536 | 25.039 | -12.789 | 1.00 | 23.46 |
| ATOM | 242 | CG  | PRO | A | 50 | 29.352 | 25.399 | -13.972 | 1.00 | 27.62 |
| ATOM | 243 | C   | PRO | A | 50 | 28.652 | 22.958 | -11.459 | 1.00 | 18.14 |
| ATOM | 244 | O   | PRO | A | 50 | 28.526 | 21.931 | -12.109 | 1.00 | 18.10 |
| ATOM | 245 | N   | PRO | A | 51 | 28.099 | 23.104 | -10.254 | 1.00 | 18.73 |
| ATOM | 246 | CD  | PRO | A | 51 | 28.320 | 24.148 | -9.234  | 1.00 | 18.25 |
| ATOM | 247 | CA  | PRO | A | 51 | 27.313 | 21.994 | -9.723  | 1.00 | 20.17 |
| ATOM | 248 | CB  | PRO | A | 51 | 26.927 | 22.495 | -8.333  | 1.00 | 19.76 |
| ATOM | 249 | CG  | PRO | A | 51 | 28.104 | 23.388 | -7.961  | 1.00 | 19.37 |
| ATOM | 250 | C   | PRO | A | 51 | 26.083 | 21.738 | -10.613 | 1.00 | 18.98 |
| ATOM | 251 | O   | PRO | A | 51 | 25.473 | 22.650 | -11.142 | 1.00 | 17.43 |
| ATOM | 252 | N   | GLU | A | 52 | 25.769 | 20.469 | -10.825 | 1.00 | 20.72 |
| ATOM | 253 | CA  | GLU | A | 52 | 24.592 | 20.102 | -11.633 | 1.00 | 27.18 |
| ATOM | 254 | CB  | GLU | A | 52 | 24.444 | 18.587 | -11.623 | 1.00 | 30.68 |
| ATOM | 255 | CG  | GLU | A | 52 | 23.234 | 18.060 | -12.376 | 1.00 | 38.66 |
| ATOM | 256 | CD  | GLU | A | 52 | 23.353 | 18.247 | -13.863 | 1.00 | 43.25 |
| ATOM | 257 | OE1 | GLU | A | 52 | 22.803 | 19.243 | -14.377 | 1.00 | 47.66 |
| ATOM | 258 | OE2 | GLU | A | 52 | 23.997 | 17.396 | -14.514 | 1.00 | 47.58 |
| ATOM | 259 | C   | GLU | A | 52 | 23.342 | 20.798 | -11.011 | 1.00 | 28.46 |

Figure 4F

| ATOM | 260 | O | GLU | A | 52 | 22.564 | 21.519 | -11.646 | 1.00 | 25.49 |
|---|---|---|---|---|---|---|---|---|---|---|
| ATOM | 261 | N | ASN | A | 53 | 23.188 | 20.580 | -9.714 | 1.00 | 31.10 |
| ATOM | 262 | CA | ASN | A | 53 | 22.067 | 21.176 | -8.981 | 1.00 | 33.66 |
| ATOM | 263 | CB | ASN | A | 53 | 21.158 | 20.075 | -8.436 | 1.00 | 40.90 |
| ATOM | 264 | CG | ASN | A | 53 | 20.249 | 19.494 | -9.510 | 1.00 | 48.10 |
| ATOM | 265 | OD1 | ASN | A | 53 | 20.377 | 18.327 | -9.871 | 1.00 | 54.90 |
| ATOM | 266 | ND2 | ASN | A | 53 | 19.332 | 20.312 | -10.035 | 1.00 | 49.48 |
| ATOM | 267 | C | ASN | A | 53 | 22.564 | 22.109 | -7.878 | 1.00 | 29.61 |
| ATOM | 268 | O | ASN | A | 53 | 23.666 | 21.951 | -7.359 | 1.00 | 32.75 |
| ATOM | 269 | N | PRO | A | 54 | 21.752 | 23.122 | -7.527 | 1.00 | 26.65 |
| ATOM | 270 | CD | PRO | A | 54 | 20.408 | 23.409 | -8.062 | 1.00 | 30.19 |
| ATOM | 271 | CA | PRO | A | 54 | 22.097 | 24.095 | -6.491 | 1.00 | 22.46 |
| ATOM | 272 | CB | PRO | A | 54 | 20.815 | 24.914 | -6.345 | 1.00 | 29.07 |
| ATOM | 273 | CG | PRO | A | 54 | 20.239 | 24.878 | -7.731 | 1.00 | 33.83 |
| ATOM | 274 | C | PRO | A | 54 | 22.450 | 23.408 | -5.199 | 1.00 | 15.80 |
| ATOM | 275 | O | PRO | A | 54 | 21.956 | 22.341 | -4.858 | 1.00 | 14.86 |
| ATOM | 276 | N | LEU | A | 55 | 23.370 | 24.024 | -4.484 | 1.00 | 12.78 |
| ATOM | 277 | CA | LEU | A | 55 | 23.783 | 23.460 | -3.231 | 1.00 | 5.47 |
| ATOM | 278 | CB | LEU | A | 55 | 25.284 | 23.570 | -3.036 | 1.00 | 7.35 |
| ATOM | 279 | CG | LEU | A | 55 | 26.122 | 22.704 | -3.957 | 1.00 | 8.64 |
| ATOM | 280 | CD1 | LEU | A | 55 | 27.572 | 22.922 | -3.657 | 1.00 | 15.60 |
| ATOM | 281 | CD2 | LEU | A | 55 | 25.768 | 21.275 | -3.725 | 1.00 | 10.92 |
| ATOM | 282 | C | LEU | A | 55 | 23.060 | 24.199 | -2.157 | 1.00 | 5.03 |
| ATOM | 283 | O | LEU | A | 55 | 23.183 | 25.399 | -2.004 | 1.00 | 11.73 |
| ATOM | 284 | N | PRO | A | 56 | 22.155 | 23.512 | -1.485 | 1.00 | 4.24 |
| ATOM | 285 | CD | PRO | A | 56 | 21.635 | 22.179 | -1.824 | 1.00 | 2.00 |
| ATOM | 286 | CA | PRO | A | 56 | 21.394 | 24.111 | -0.394 | 1.00 | 3.54 |
| ATOM | 287 | CB | PRO | A | 56 | 20.343 | 23.050 | -0.122 | 1.00 | 4.57 |
| ATOM | 288 | CG | PRO | A | 56 | 21.025 | 21.780 | -0.547 | 1.00 | 2.00 |
| ATOM | 289 | C | PRO | A | 56 | 22.337 | 24.217 | 0.818 | 1.00 | 4.48 |
| ATOM | 290 | O | PRO | A | 56 | 23.371 | 23.542 | 0.675 | 1.00 | 6.64 |
| ATOM | 291 | N | ILE | A | 57 | 21.995 | 25.068 | 1.782 | 1.00 | 2.94 |
| ATOM | 292 | CA | ILE | A | 57 | 22.823 | 25.182 | 2.991 | 1.00 | 2.00 |
| ATOM | 293 | CB | ILE | A | 57 | 23.305 | 26.620 | 3.252 | 1.00 | 4.36 |
| ATOM | 294 | CG2 | ILE | A | 57 | 23.900 | 26.738 | 4.695 | 1.00 | 2.00 |
| ATOM | 295 | CG1 | ILE | A | 57 | 24.299 | 27.056 | 2.172 | 1.00 | 2.00 |
| ATOM | 296 | CD1 | ILE | A | 57 | 24.677 | 28.481 | 2.269 | 1.00 | 2.00 |
| ATOM | 297 | C | ILE | A | 57 | 21.926 | 24.775 | 4.139 | 1.00 | 4.15 |
| ATOM | 298 | O | ILE | A | 57 | 20.816 | 25.275 | 4.294 | 1.00 | 3.38 |
| ATOM | 299 | N | ASN | A | 58 | 22.372 | 23.796 | 4.906 | 1.00 | 4.69 |
| ATOM | 300 | CA | ASN | A | 58 | 21.591 | 23.377 | 6.049 | 1.00 | 7.45 |
| ATOM | 301 | CB | ASN | A | 58 | 20.933 | 22.038 | 5.793 | 1.00 | 11.69 |
| ATOM | 302 | CG | ASN | A | 58 | 21.882 | 21.008 | 5.311 | 1.00 | 15.54 |
| ATOM | 303 | OD1 | ASN | A | 58 | 22.949 | 20.827 | 5.869 | 1.00 | 22.74 |
| ATOM | 304 | ND2 | ASN | A | 58 | 21.480 | 20.277 | 4.285 | 1.00 | 24.85 |
| ATOM | 305 | C | ASN | A | 58 | 22.423 | 23.393 | 7.327 | 1.00 | 10.45 |
| ATOM | 306 | O | ASN | A | 58 | 23.607 | 23.670 | 7.298 | 1.00 | 9.69 |
| ATOM | 307 | N | VAL | A | 59 | 21.766 | 23.203 | 8.470 | 1.00 | 11.45 |
| ATOM | 308 | CA | VAL | A | 59 | 22.467 | 23.226 | 9.764 | 1.00 | 9.16 |
| ATOM | 309 | CB | VAL | A | 59 | 21.639 | 23.911 | 10.870 | 1.00 | 8.10 |
| ATOM | 310 | CG1 | VAL | A | 59 | 22.366 | 23.801 | 12.195 | 1.00 | 8.74 |
| ATOM | 311 | CG2 | VAL | A | 59 | 21.415 | 25.376 | 10.544 | 1.00 | 3.69 |

Figure 4G

| ATOM | 312 | C   | VAL | A | 59 | 22.786 | 21.821 | 10.211 | 1.00 | 13.11 |
|------|-----|-----|-----|---|----|--------|--------|--------|------|-------|
| ATOM | 313 | O   | VAL | A | 59 | 21.932 | 20.957 | 10.268 | 1.00 | 15.12 |
| ATOM | 314 | N   | ASP | A | 60 | 24.054 | 21.586 | 10.505 | 1.00 | 20.34 |
| ATOM | 315 | CA  | ASP | A | 60 | 24.514 | 20.256 | 10.991 | 1.00 | 32.81 |
| ATOM | 316 | CB  | ASP | A | 60 | 24.285 | 20.194 | 12.514 | 1.00 | 40.06 |
| ATOM | 317 | CG  | ASP | A | 60 | 25.230 | 19.225 | 13.226 | 1.00 | 46.11 |
| ATOM | 318 | OD1 | ASP | A | 60 | 26.474 | 19.401 | 13.129 | 1.00 | 48.62 |
| ATOM | 319 | OD2 | ASP | A | 60 | 24.718 | 18.292 | 13.900 | 1.00 | 50.43 |
| ATOM | 320 | C   | ASP | A | 60 | 23.866 | 19.032 | 10.254 | 1.00 | 36.61 |
| ATOM | 321 | O   | ASP | A | 60 | 23.201 | 18.163 | 10.839 | 1.00 | 39.35 |
| ATOM | 322 | N   | HIS | A | 61 | 24.053 | 19.024 | 8.937  | 1.00 | 41.05 |
| ATOM | 323 | CA  | HIS | A | 61 | 23.564 | 17.952 | 8.013  | 1.00 | 47.22 |
| ATOM | 324 | CB  | HIS | A | 61 | 24.547 | 16.770 | 7.982  | 1.00 | 47.84 |
| ATOM | 325 | CG  | HIS | A | 61 | 25.792 | 17.052 | 7.195  | 1.00 | 49.75 |
| ATOM | 326 | CD2 | HIS | A | 61 | 25.965 | 17.423 | 5.907  | 1.00 | 51.27 |
| ATOM | 327 | ND1 | HIS | A | 61 | 27.049 | 17.028 | 7.757  | 1.00 | 51.98 |
| ATOM | 328 | CE1 | HIS | A | 61 | 27.943 | 17.377 | 6.847  | 1.00 | 53.59 |
| ATOM | 329 | NE2 | HIS | A | 61 | 27.311 | 17.623 | 5.713  | 1.00 | 50.47 |
| ATOM | 330 | C   | HIS | A | 61 | 22.126 | 17.445 | 8.142  | 1.00 | 49.08 |
| ATOM | 331 | O   | HIS | A | 61 | 21.680 | 16.560 | 7.392  | 1.00 | 53.07 |
| ATOM | 332 | N   | ARG | A | 62 | 21.406 | 18.012 | 9.103  | 1.00 | 47.98 |
| ATOM | 333 | CA  | ARG | A | 62 | 20.002 | 17.686 | 9.322  | 1.00 | 45.13 |
| ATOM | 334 | CB  | ARG | A | 62 | 19.558 | 18.379 | 10.602 | 1.00 | 48.49 |
| ATOM | 335 | CG  | ARG | A | 62 | 19.694 | 17.540 | 11.869 | 1.00 | 56.34 |
| ATOM | 336 | CD  | ARG | A | 62 | 18.561 | 16.509 | 11.937 | 1.00 | 63.51 |
| ATOM | 337 | NE  | ARG | A | 62 | 17.279 | 17.081 | 11.504 | 1.00 | 67.20 |
| ATOM | 338 | CZ  | ARG | A | 62 | 16.272 | 17.389 | 12.317 | 1.00 | 67.07 |
| ATOM | 339 | NH1 | ARG | A | 62 | 16.383 | 17.174 | 13.628 | 1.00 | 67.89 |
| ATOM | 340 | NH2 | ARG | A | 62 | 15.162 | 17.928 | 11.815 | 1.00 | 65.00 |
| ATOM | 341 | C   | ARG | A | 62 | 19.353 | 18.305 | 8.061  | 1.00 | 42.93 |
| ATOM | 342 | O   | ARG | A | 62 | 19.083 | 19.513 | 8.001  | 1.00 | 42.60 |
| ATOM | 343 | N   | ALA | A | 63 | 19.193 | 17.481 | 7.023  | 1.00 | 40.84 |
| ATOM | 344 | CA  | ALA | A | 63 | 18.627 | 17.948 | 5.721  | 1.00 | 40.08 |
| ATOM | 345 | CB  | ALA | A | 63 | 18.606 | 16.822 | 4.702  | 1.00 | 36.71 |
| ATOM | 346 | C   | ALA | A | 63 | 17.250 | 18.651 | 5.785  | 1.00 | 42.68 |
| ATOM | 347 | O   | ALA | A | 63 | 16.783 | 19.234 | 4.812  | 1.00 | 42.31 |
| ATOM | 348 | N   | ARG | A | 64 | 16.588 | 18.554 | 6.938  | 1.00 | 44.53 |
| ATOM | 349 | CA  | ARG | A | 64 | 15.249 | 19.240 | 7.162  | 1.00 | 45.15 |
| ATOM | 350 | CB  | ARG | A | 64 | 14.541 | 18.716 | 8.425  | 1.00 | 52.01 |
| ATOM | 351 | CG  | ARG | A | 64 | 14.178 | 17.223 | 8.388  | 1.00 | 61.80 |
| ATOM | 352 | CD  | ARG | A | 64 | 12.681 | 17.016 | 8.169  | 1.00 | 68.05 |
| ATOM | 353 | NE  | ARG | A | 64 | 12.006 | 16.573 | 9.388  | 1.00 | 75.79 |
| ATOM | 354 | CZ  | ARG | A | 64 | 11.603 | 15.328 | 9.663  | 1.00 | 79.65 |
| ATOM | 355 | NH1 | ARG | A | 64 | 11.789 | 14.319 | 8.810  | 1.00 | 80.90 |
| ATOM | 356 | NH2 | ARG | A | 64 | 10.986 | 15.097 | 10.815 | 1.00 | 79.73 |
| ATOM | 357 | C   | ARG | A | 64 | 15.510 | 20.745 | 7.362  | 1.00 | 38.34 |
| ATOM | 358 | O   | ARG | A | 64 | 14.659 | 21.607 | 7.042  | 1.00 | 40.42 |
| ATOM | 359 | N   | CYS | A | 65 | 16.723 | 21.034 | 7.856  | 1.00 | 26.96 |
| ATOM | 360 | CA  | CYS | A | 65 | 17.169 | 22.412 | 8.179  | 1.00 | 20.44 |
| ATOM | 361 | CB  | CYS | A | 65 | 18.129 | 22.373 | 9.329  | 1.00 | 18.01 |
| ATOM | 362 | SG  | CYS | A | 65 | 17.322 | 22.682 | 10.775 | 1.00 | 22.41 |
| ATOM | 363 | C   | CYS | A | 65 | 17.789 | 23.225 | 7.090  | 1.00 | 15.86 |

Figure 4H

| ATOM | 364 | O   | CYS | A | 65 | 18.883 | 23.742 | 7.234  | 1.00 | 19.52 |
| ---- | --- | --- | --- | - | -- | ------ | ------ | ------ | ---- | ----- |
| ATOM | 365 | N   | GLU | A | 66 | 17.071 | 23.404 | 6.007  | 1.00 | 9.13  |
| ATOM | 366 | CA  | GLU | A | 66 | 17.605 | 24.185 | 4.953  | 1.00 | 5.50  |
| ATOM | 367 | CB  | GLU | A | 66 | 16.894 | 23.810 | 3.685  | 1.00 | 6.69  |
| ATOM | 368 | CG  | GLU | A | 66 | 17.515 | 24.418 | 2.501  | 1.00 | 13.05 |
| ATOM | 369 | CD  | GLU | A | 66 | 17.003 | 23.830 | 1.239  | 1.00 | 14.87 |
| ATOM | 370 | OE1 | GLU | A | 66 | 16.957 | 22.580 | 1.173  | 1.00 | 21.13 |
| ATOM | 371 | OE2 | GLU | A | 66 | 16.662 | 24.612 | 0.317  | 1.00 | 20.98 |
| ATOM | 372 | C   | GLU | A | 66 | 17.369 | 25.630 | 5.396  | 1.00 | 7.85  |
| ATOM | 373 | O   | GLU | A | 66 | 16.276 | 25.972 | 5.831  | 1.00 | 9.32  |
| ATOM | 374 | N   | VAL | A | 67 | 18.425 | 26.450 | 5.345  | 1.00 | 2.00  |
| ATOM | 375 | CA  | VAL | A | 67 | 18.338 | 27.862 | 5.760  | 1.00 | 2.00  |
| ATOM | 376 | CB  | VAL | A | 67 | 19.092 | 28.115 | 7.090  | 1.00 | 4.04  |
| ATOM | 377 | CG1 | VAL | A | 67 | 18.431 | 27.338 | 8.255  | 1.00 | 4.42  |
| ATOM | 378 | CG2 | VAL | A | 67 | 20.566 | 27.742 | 6.938  | 1.00 | 2.00  |
| ATOM | 379 | C   | VAL | A | 67 | 18.904 | 28.826 | 4.689  | 1.00 | 2.30  |
| ATOM | 380 | O   | VAL | A | 67 | 18.836 | 30.057 | 4.779  | 1.00 | 2.00  |
| ATOM | 381 | N   | GLY | A | 68 | 19.450 | 28.248 | 3.635  | 1.00 | 2.00  |
| ATOM | 382 | CA  | GLY | A | 68 | 20.025 | 29.075 | 2.597  | 1.00 | 2.48  |
| ATOM | 383 | C   | GLY | A | 68 | 20.409 | 28.329 | 1.331  | 1.00 | 5.80  |
| ATOM | 384 | O   | GLY | A | 68 | 20.007 | 27.176 | 1.121  | 1.00 | 5.04  |
| ATOM | 385 | N   | ARG | A | 69 | 21.206 | 28.992 | 0.497  | 1.00 | 4.71  |
| ATOM | 386 | CA  | ARG | A | 69 | 21.633 | 28.441 | -0.800 | 1.00 | 2.93  |
| ATOM | 387 | CB  | ARG | A | 69 | 20.607 | 28.868 | -1.840 | 1.00 | 5.96  |
| ATOM | 388 | CG  | ARG | A | 69 | 20.876 | 28.429 | -3.240 | 1.00 | 2.76  |
| ATOM | 389 | CD  | ARG | A | 69 | 20.782 | 26.944 | -3.325 | 1.00 | 12.84 |
| ATOM | 390 | NE  | ARG | A | 69 | 19.420 | 26.446 | -3.154 | 1.00 | 20.69 |
| ATOM | 391 | CZ  | ARG | A | 69 | 18.414 | 26.726 | -3.981 | 1.00 | 26.00 |
| ATOM | 392 | NH1 | ARG | A | 69 | 17.222 | 26.189 | -3.755 | 1.00 | 31.06 |
| ATOM | 393 | NH2 | ARG | A | 69 | 18.575 | 27.566 | -5.005 | 1.00 | 19.94 |
| ATOM | 394 | C   | ARG | A | 69 | 23.039 | 28.947 | -1.181 | 1.00 | 7.65  |
| ATOM | 395 | O   | ARG | A | 69 | 23.357 | 30.142 | -1.074 | 1.00 | 10.32 |
| ATOM | 396 | N   | VAL | A | 70 | 23.890 | 28.003 | -1.572 | 1.00 | 3.09  |
| ATOM | 397 | CA  | VAL | A | 70 | 25.255 | 28.293 | -2.032 | 1.00 | 4.52  |
| ATOM | 398 | CB  | VAL | A | 70 | 26.003 | 26.973 | -2.298 | 1.00 | 7.64  |
| ATOM | 399 | CG1 | VAL | A | 70 | 27.218 | 27.213 | -3.172 | 1.00 | 4.40  |
| ATOM | 400 | CG2 | VAL | A | 70 | 26.394 | 26.316 | -0.990 | 1.00 | 2.00  |
| ATOM | 401 | C   | VAL | A | 70 | 25.131 | 29.074 | -3.370 | 1.00 | 5.74  |
| ATOM | 402 | O   | VAL | A | 70 | 24.599 | 28.572 | -4.371 | 1.00 | 8.25  |
| ATOM | 403 | N   | LEU | A | 71 | 25.586 | 30.323 | -3.365 | 1.00 | 3.92  |
| ATOM | 404 | CA  | LEU | A | 71 | 25.536 | 31.164 | -4.598 | 1.00 | 4.53  |
| ATOM | 405 | CB  | LEU | A | 71 | 25.626 | 32.632 | -4.222 | 1.00 | 2.00  |
| ATOM | 406 | CG  | LEU | A | 71 | 24.540 | 33.220 | -3.364 | 1.00 | 2.00  |
| ATOM | 407 | CD1 | LEU | A | 71 | 24.895 | 34.632 | -3.013 | 1.00 | 2.00  |
| ATOM | 408 | CD2 | LEU | A | 71 | 23.235 | 33.127 | -4.095 | 1.00 | 3.70  |
| ATOM | 409 | C   | LEU | A | 71 | 26.640 | 30.834 | -5.654 | 1.00 | 9.13  |
| ATOM | 410 | O   | LEU | A | 71 | 26.368 | 30.776 | -6.879 | 1.00 | 9.84  |
| ATOM | 411 | N   | ALA | A | 72 | 27.886 | 30.666 | -5.188 | 1.00 | 6.69  |
| ATOM | 412 | CA  | ALA | A | 72 | 29.052 | 30.374 | -6.057 | 1.00 | 4.02  |
| ATOM | 413 | CB  | ALA | A | 72 | 29.666 | 31.650 | -6.519 | 1.00 | 3.51  |
| ATOM | 414 | C   | ALA | A | 72 | 30.126 | 29.535 | -5.401 | 1.00 | 4.92  |
| ATOM | 415 | O   | ALA | A | 72 | 30.435 | 29.665 | -4.233 | 1.00 | 11.03 |

Figure 4I

| ATOM | 416 | N   | VAL | A | 73 | 30.707 | 28.653 | -6.201 | 1.00 | 10.43 |
|------|-----|-----|-----|---|----|--------|--------|--------|------|-------|
| ATOM | 417 | CA  | VAL | A | 73 | 31.820 | 27.777 | -5.771 | 1.00 | 6.81  |
| ATOM | 418 | CB  | VAL | A | 73 | 31.430 | 26.308 | -5.804 | 1.00 | 2.00  |
| ATOM | 419 | CG1 | VAL | A | 73 | 32.555 | 25.455 | -5.236 | 1.00 | 2.00  |
| ATOM | 420 | CG2 | VAL | A | 73 | 30.189 | 26.099 | -5.002 | 1.00 | 5.59  |
| ATOM | 421 | C   | VAL | A | 73 | 32.883 | 28.024 | -6.848 | 1.00 | 8.19  |
| ATOM | 422 | O   | VAL | A | 73 | 32.647 | 27.820 | -8.022 | 1.00 | 11.49 |
| ATOM | 423 | N   | VAL | A | 74 | 34.024 | 28.575 | -6.461 | 1.00 | 9.12  |
| ATOM | 424 | CA  | VAL | A | 74 | 35.096 | 28.841 | -7.432 | 1.00 | 12.05 |
| ATOM | 425 | CB  | VAL | A | 74 | 35.448 | 30.326 | -7.505 | 1.00 | 14.05 |
| ATOM | 426 | CG1 | VAL | A | 74 | 36.561 | 30.545 | -8.508 | 1.00 | 24.53 |
| ATOM | 427 | CG2 | VAL | A | 74 | 34.247 | 31.120 | -7.923 | 1.00 | 18.08 |
| ATOM | 428 | C   | VAL | A | 74 | 36.347 | 28.070 | -7.028 | 1.00 | 15.85 |
| ATOM | 429 | O   | VAL | A | 74 | 36.768 | 28.042 | -5.872 | 1.00 | 20.53 |
| ATOM | 430 | N   | ASN | A | 75 | 36.950 | 27.410 | -8.005 | 1.00 | 18.46 |
| ATOM | 431 | CA  | ASN | A | 75 | 38.184 | 26.631 | -7.742 | 1.00 | 15.45 |
| ATOM | 432 | CB  | ASN | A | 75 | 38.390 | 25.617 | -8.861 | 1.00 | 13.02 |
| ATOM | 433 | CG  | ASN | A | 75 | 39.521 | 24.674 | -8.588 | 1.00 | 17.82 |
| ATOM | 434 | OD1 | ASN | A | 75 | 39.685 | 23.691 | -9.285 | 1.00 | 23.74 |
| ATOM | 435 | ND2 | ASN | A | 75 | 40.301 | 24.941 | -7.556 | 1.00 | 25.51 |
| ATOM | 436 | C   | ASN | A | 75 | 39.368 | 27.612 | -7.622 | 1.00 | 15.03 |
| ATOM | 437 | O   | ASN | A | 75 | 39.864 | 28.196 | -8.580 | 1.00 | 21.05 |
| ATOM | 438 | N   | ASP | A | 76 | 39.763 | 27.857 | -6.389 | 1.00 | 11.85 |
| ATOM | 439 | CA  | ASP | A | 76 | 40.876 | 28.758 | -6.129 | 1.00 | 7.24  |
| ATOM | 440 | CB  | ASP | A | 76 | 40.668 | 29.441 | -4.799 | 1.00 | 6.29  |
| ATOM | 441 | CG  | ASP | A | 76 | 41.737 | 30.428 | -4.504 | 1.00 | 5.01  |
| ATOM | 442 | OD1 | ASP | A | 76 | 42.770 | 30.070 | -3.923 | 1.00 | 13.20 |
| ATOM | 443 | OD2 | ASP | A | 76 | 41.582 | 31.575 | -4.905 | 1.00 | 6.55  |
| ATOM | 444 | C   | ASP | A | 76 | 42.117 | 27.891 | -6.031 | 1.00 | 11.98 |
| ATOM | 445 | O   | ASP | A | 76 | 42.051 | 26.707 | -5.724 | 1.00 | 14.65 |
| ATOM | 446 | N   | PRO | A | 77 | 43.286 | 28.467 | -6.428 | 1.00 | 12.34 |
| ATOM | 447 | CD  | PRO | A | 77 | 43.528 | 29.807 | -6.995 | 1.00 | 11.81 |
| ATOM | 448 | CA  | PRO | A | 77 | 44.536 | 27.705 | -6.402 | 1.00 | 12.16 |
| ATOM | 449 | CB  | PRO | A | 77 | 45.587 | 28.793 | -6.606 | 1.00 | 7.70  |
| ATOM | 450 | CG  | PRO | A | 77 | 44.942 | 29.716 | -7.505 | 1.00 | 4.35  |
| ATOM | 451 | C   | PRO | A | 77 | 44.754 | 26.967 | -5.057 | 1.00 | 8.68  |
| ATOM | 452 | O   | PRO | A | 77 | 45.498 | 26.013 | -4.963 | 1.00 | 13.91 |
| ATOM | 453 | N   | ARG | A | 78 | 44.080 | 27.430 | -4.019 | 1.00 | 6.30  |
| ATOM | 454 | CA  | ARG | A | 78 | 44.198 | 26.819 | -2.693 | 1.00 | 6.81  |
| ATOM | 455 | CB  | ARG | A | 78 | 44.216 | 27.920 | -1.654 | 1.00 | 10.10 |
| ATOM | 456 | CG  | ARG | A | 78 | 45.331 | 28.956 | -1.816 | 1.00 | 17.49 |
| ATOM | 457 | CD  | ARG | A | 78 | 45.291 | 29.994 | -0.688 | 1.00 | 18.69 |
| ATOM | 458 | NE  | ARG | A | 78 | 45.447 | 29.361 | 0.633  | 1.00 | 31.64 |
| ATOM | 459 | CZ  | ARG | A | 78 | 44.803 | 29.705 | 1.754  | 1.00 | 33.18 |
| ATOM | 460 | NH1 | ARG | A | 78 | 45.054 | 29.035 | 2.869  | 1.00 | 29.53 |
| ATOM | 461 | NH2 | ARG | A | 78 | 43.909 | 30.696 | 1.771  | 1.00 | 33.74 |
| ATOM | 462 | C   | ARG | A | 78 | 43.096 | 25.762 | -2.361 | 1.00 | 7.54  |
| ATOM | 463 | O   | ARG | A | 78 | 43.277 | 24.854 | -1.558 | 1.00 | 6.14  |
| ATOM | 464 | N   | GLY | A | 79 | 41.959 | 25.860 | -3.023 | 1.00 | 5.69  |
| ATOM | 465 | CA  | GLY | A | 79 | 40.890 | 24.922 | -2.748 | 1.00 | 4.76  |
| ATOM | 466 | C   | GLY | A | 79 | 39.569 | 25.503 | -3.201 | 1.00 | 2.72  |
| ATOM | 467 | O   | GLY | A | 79 | 39.493 | 26.685 | -3.550 | 1.00 | 5.32  |

Figure 4J

| ATOM | 468 | N   | PRO | A | 80 | 38.509 | 24.705 | -3.203 | 1.00 | 2.00  |
|------|-----|-----|-----|---|----|--------|--------|--------|------|-------|
| ATOM | 469 | CD  | PRO | A | 80 | 38.451 | 23.305 | -2.747 | 1.00 | 9.44  |
| ATOM | 470 | CA  | PRO | A | 80 | 37.195 | 25.181 | -3.626 | 1.00 | 2.00  |
| ATOM | 471 | CB  | PRO | A | 80 | 36.351 | 23.910 | -3.643 | 1.00 | 4.12  |
| ATOM | 472 | CG  | PRO | A | 80 | 36.937 | 23.081 | -2.554 | 1.00 | 7.73  |
| ATOM | 473 | C   | PRO | A | 80 | 36.671 | 26.145 | -2.591 | 1.00 | 5.31  |
| ATOM | 474 | O   | PRO | A | 80 | 36.447 | 25.789 | -1.433 | 1.00 | 4.34  |
| ATOM | 475 | N   | PHE | A | 81 | 36.478 | 27.382 | -3.028 | 1.00 | 2.00  |
| ATOM | 476 | CA  | PHE | A | 81 | 35.980 | 28.451 | -2.177 | 1.00 | 2.00  |
| ATOM | 477 | CB  | PHE | A | 81 | 36.820 | 29.678 | -2.460 | 1.00 | 2.00  |
| ATOM | 478 | CG  | PHE | A | 81 | 36.469 | 30.865 | -1.616 | 1.00 | 3.57  |
| ATOM | 479 | CD1 | PHE | A | 81 | 37.002 | 31.014 | -0.344 | 1.00 | 2.00  |
| ATOM | 480 | CD2 | PHE | A | 81 | 35.626 | 31.852 | -2.103 | 1.00 | 5.30  |
| ATOM | 481 | CE1 | PHE | A | 81 | 36.704 | 32.113 | 0.410  | 1.00 | 2.00  |
| ATOM | 482 | CE2 | PHE | A | 81 | 35.325 | 32.967 | -1.331 | 1.00 | 3.68  |
| ATOM | 483 | CZ  | PHE | A | 81 | 35.865 | 33.091 | -0.081 | 1.00 | 2.00  |
| ATOM | 484 | C   | PHE | A | 81 | 34.502 | 28.681 | -2.531 | 1.00 | 7.75  |
| ATOM | 485 | O   | PHE | A | 81 | 34.112 | 28.576 | -3.685 | 1.00 | 15.16 |
| ATOM | 486 | N   | PHE | A | 82 | 33.664 | 29.007 | -1.554 | 1.00 | 6.33  |
| ATOM | 487 | CA  | PHE | A | 82 | 32.242 | 29.232 | -1.873 | 1.00 | 4.82  |
| ATOM | 488 | CB  | PHE | A | 82 | 31.422 | 27.997 | -1.496 | 1.00 | 6.81  |
| ATOM | 489 | CG  | PHE | A | 82 | 30.867 | 28.042 | -0.102 | 1.00 | 4.39  |
| ATOM | 490 | CD1 | PHE | A | 82 | 31.695 | 27.858 | 1.007  | 1.00 | 8.36  |
| ATOM | 491 | CD2 | PHE | A | 82 | 29.521 | 28.326 | 0.113  | 1.00 | 6.71  |
| ATOM | 492 | CE1 | PHE | A | 82 | 31.184 | 27.967 | 2.313  | 1.00 | 2.00  |
| ATOM | 493 | CE2 | PHE | A | 82 | 29.003 | 28.437 | 1.416  | 1.00 | 2.00  |
| ATOM | 494 | CZ  | PHE | A | 82 | 29.826 | 28.261 | 2.506  | 1.00 | 2.00  |
| ATOM | 495 | C   | PHE | A | 82 | 31.658 | 30.467 | -1.186 | 1.00 | 6.36  |
| ATOM | 496 | O   | PHE | A | 82 | 32.196 | 31.009 | -0.222 | 1.00 | 10.33 |
| ATOM | 497 | N   | VAL | A | 83 | 30.528 | 30.916 | -1.711 | 1.00 | 4.44  |
| ATOM | 498 | CA  | VAL | A | 83 | 29.814 | 32.038 | -1.130 | 1.00 | 2.00  |
| ATOM | 499 | CB  | VAL | A | 83 | 30.015 | 33.276 | -1.924 | 1.00 | 3.99  |
| ATOM | 500 | CG1 | VAL | A | 83 | 29.023 | 34.322 | -1.503 | 1.00 | 2.78  |
| ATOM | 501 | CG2 | VAL | A | 83 | 31.425 | 33.791 | -1.678 | 1.00 | 13.68 |
| ATOM | 502 | C   | VAL | A | 83 | 28.341 | 31.663 | -1.106 | 1.00 | 3.33  |
| ATOM | 503 | O   | VAL | A | 83 | 27.759 | 31.273 | -2.111 | 1.00 | 2.00  |
| ATOM | 504 | N   | GLY | A | 84 | 27.756 | 31.739 | 0.089  | 1.00 | 5.01  |
| ATOM | 505 | CA  | GLY | A | 84 | 26.361 | 31.403 | 0.276  | 1.00 | 2.00  |
| ATOM | 506 | C   | GLY | A | 84 | 25.521 | 32.507 | 0.877  | 1.00 | 3.07  |
| ATOM | 507 | O   | GLY | A | 84 | 26.021 | 33.514 | 1.368  | 1.00 | 3.16  |
| ATOM | 508 | N   | LEU | A | 85 | 24.214 | 32.300 | 0.613  | 1.00 | 5.57  |
| ATOM | 509 | CA  | LEU | A | 85 | 23.225 | 33.244 | 1.345  | 1.00 | 6.55  |
| ATOM | 510 | CB  | LEU | A | 85 | 22.446 | 33.914 | 0.204  | 1.00 | 9.10  |
| ATOM | 511 | CG  | LEU | A | 85 | 21.273 | 34.832 | 0.602  | 1.00 | 13.82 |
| ATOM | 512 | CD1 | LEU | A | 85 | 21.742 | 36.213 | 1.049  | 1.00 | 10.07 |
| ATOM | 513 | CD2 | LEU | A | 85 | 20.340 | 34.954 | -0.574 | 1.00 | 15.04 |
| ATOM | 514 | C   | LEU | A | 85 | 22.261 | 32.507 | 2.284  | 1.00 | 4.79  |
| ATOM | 515 | O   | LEU | A | 85 | 21.641 | 31.512 | 1.946  | 1.00 | 3.64  |
| ATOM | 516 | N   | ILE | A | 86 | 22.079 | 33.084 | 3.454  | 1.00 | 5.27  |
| ATOM | 517 | CA  | ILE | A | 86 | 21.205 | 32.530 | 4.479  | 1.00 | 3.56  |
| ATOM | 518 | CB  | ILE | A | 86 | 22.028 | 32.326 | 5.749  | 1.00 | 2.77  |
| ATOM | 519 | CG2 | ILE | A | 86 | 21.167 | 31.976 | 6.944  | 1.00 | 2.00  |

Figure 4K

| | | | | | | | | | |
|---|---|---|---|---|---|---|---|---|---|
| ATOM | 520 | CG1 | ILE | A | 86 | 23.096 | 31.285 | 5.462 | 1.00 2.00 |
| ATOM | 521 | CD1 | ILE | A | 86 | 24.264 | 31.383 | 6.391 | 1.00 4.00 |
| ATOM | 522 | C | ILE | A | 86 | 20.123 | 33.590 | 4.702 | 1.00 4.40 |
| ATOM | 523 | O | ILE | A | 86 | 20.391 | 34.729 | 5.083 | 1.00 10.66 |
| ATOM | 524 | N | ALA | A | 87 | 18.895 | 33.243 | 4.364 | 1.00 2.00 |
| ATOM | 525 | CA | ALA | A | 87 | 17.769 | 34.182 | 4.546 | 1.00 2.63 |
| ATOM | 526 | CB | ALA | A | 87 | 17.195 | 34.573 | 3.209 | 1.00 2.00 |
| ATOM | 527 | C | ALA | A | 87 | 16.769 | 33.359 | 5.373 | 1.00 4.47 |
| ATOM | 528 | O | ALA | A | 87 | 15.911 | 32.647 | 4.852 | 1.00 8.98 |
| ATOM | 529 | N | CYS | A | 88 | 16.915 | 33.457 | 6.690 | 1.00 2.00 |
| ATOM | 530 | CA | CYS | A | 88 | 16.103 | 32.696 | 7.618 | 1.00 2.00 |
| ATOM | 531 | CB | CYS | A | 88 | 16.808 | 31.403 | 7.904 | 1.00 2.00 |
| ATOM | 532 | SG | CYS | A | 88 | 15.896 | 30.256 | 8.869 | 1.00 8.13 |
| ATOM | 533 | C | CYS | A | 88 | 15.933 | 33.490 | 8.887 | 1.00 8.16 |
| ATOM | 534 | O | CYS | A | 88 | 16.888 | 33.696 | 9.630 | 1.00 15.01 |
| ATOM | 535 | N | VAL | A | 89 | 14.686 | 33.892 | 9.151 | 1.00 9.38 |
| ATOM | 536 | CA | VAL | A | 89 | 14.304 | 34.687 | 10.324 | 1.00 5.40 |
| ATOM | 537 | CB | VAL | A | 89 | 13.011 | 35.449 | 10.038 | 1.00 10.95 |
| ATOM | 538 | CG1 | VAL | A | 89 | 11.818 | 34.490 | 9.938 | 1.00 17.11 |
| ATOM | 539 | CG2 | VAL | A | 89 | 12.776 | 36.474 | 11.101 | 1.00 18.15 |
| ATOM | 540 | C | VAL | A | 89 | 14.146 | 33.847 | 11.593 | 1.00 6.11 |
| ATOM | 541 | O | VAL | A | 89 | 14.405 | 34.285 | 12.704 | 1.00 7.14 |
| ATOM | 542 | N | GLN | A | 90 | 13.743 | 32.596 | 11.409 | 1.00 8.62 |
| ATOM | 543 | CA | GLN | A | 90 | 13.560 | 31.676 | 12.558 | 1.00 10.52 |
| ATOM | 544 | CB | GLN | A | 90 | 12.874 | 30.382 | 12.105 | 1.00 9.44 |
| ATOM | 545 | CG | GLN | A | 90 | 11.509 | 30.622 | 11.532 | 1.00 10.44 |
| ATOM | 546 | CD | GLN | A | 90 | 10.788 | 29.349 | 11.176 | 1.00 9.31 |
| ATOM | 547 | OE1 | GLN | A | 90 | 11.395 | 28.352 | 10.832 | 1.00 11.38 |
| ATOM | 548 | NE2 | GLN | A | 90 | 9.483 | 29.381 | 11.256 | 1.00 7.37 |
| ATOM | 549 | C | GLN | A | 90 | 14.912 | 31.386 | 13.225 | 1.00 10.11 |
| ATOM | 550 | O | GLN | A | 90 | 15.032 | 31.318 | 14.451 | 1.00 13.62 |
| ATOM | 551 | N | LEU | A | 91 | 15.912 | 31.162 | 12.378 | 1.00 8.00 |
| ATOM | 552 | CA | LEU | A | 91 | 17.302 | 30.911 | 12.807 | 1.00 8.35 |
| ATOM | 553 | CB | LEU | A | 91 | 18.165 | 30.723 | 11.572 | 1.00 11.36 |
| ATOM | 554 | CG | LEU | A | 91 | 19.674 | 30.578 | 11.747 | 1.00 11.77 |
| ATOM | 555 | CD1 | LEU | A | 91 | 19.995 | 29.420 | 12.673 | 1.00 12.66 |
| ATOM | 556 | CD2 | LEU | A | 91 | 20.305 | 30.390 | 10.389 | 1.00 7.29 |
| ATOM | 557 | C | LEU | A | 91 | 17.774 | 32.130 | 13.638 | 1.00 10.15 |
| ATOM | 558 | O | LEU | A | 91 | 18.449 | 31.984 | 14.644 | 1.00 6.95 |
| ATOM | 559 | N | GLU | A | 92 | 17.391 | 33.327 | 13.180 | 1.00 9.63 |
| ATOM | 560 | CA | GLU | A | 92 | 17.691 | 34.611 | 13.874 | 1.00 12.76 |
| ATOM | 561 | CB | GLU | A | 92 | 17.091 | 35.810 | 13.110 | 1.00 12.46 |
| ATOM | 562 | CG | GLU | A | 92 | 17.655 | 36.034 | 11.770 | 1.00 21.61 |
| ATOM | 563 | CD | GLU | A | 92 | 17.159 | 37.312 | 11.128 | 1.00 22.26 |
| ATOM | 564 | OE1 | GLU | A | 92 | 17.145 | 37.365 | 9.871 | 1.00 14.51 |
| ATOM | 565 | OE2 | GLU | A | 92 | 16.811 | 38.259 | 11.880 | 1.00 22.36 |
| ATOM | 566 | C | GLU | A | 92 | 17.113 | 34.600 | 15.273 | 1.00 14.56 |
| ATOM | 567 | O | GLU | A | 92 | 17.820 | 34.756 | 16.257 | 1.00 18.51 |
| ATOM | 568 | N | ARG | A | 93 | 15.789 | 34.447 | 15.340 | 1.00 16.39 |
| ATOM | 569 | CA | ARG | A | 93 | 15.034 | 34.420 | 16.618 | 1.00 11.28 |
| ATOM | 570 | CB | ARG | A | 93 | 13.555 | 34.263 | 16.325 | 1.00 19.47 |
| ATOM | 571 | CG | ARG | A | 93 | 13.043 | 35.267 | 15.317 | 1.00 33.53 |

Figure 4L

| ATOM | 572 | CD | ARG A | 93 | 13.303 | 36.728 | 15.717 | 1.00 | 45.19 |
|---|---|---|---|---|---|---|---|---|---|
| ATOM | 573 | NE | ARG A | 93 | 12.803 | 37.635 | 14.671 | 1.00 | 57.43 |
| ATOM | 574 | CZ | ARG A | 93 | 12.734 | 38.965 | 14.766 | 1.00 | 58.50 |
| ATOM | 575 | NH1 | ARG A | 93 | 12.254 | 39.681 | 13.744 | 1.00 | 55.89 |
| ATOM | 576 | NH2 | ARG A | 93 | 13.134 | 39.583 | 15.874 | 1.00 | 63.25 |
| ATOM | 577 | C | ARG A | 93 | 15.502 | 33.355 | 17.594 | 1.00 | 7.89 |
| ATOM | 578 | O | ARG A | 93 | 15.806 | 33.641 | 18.738 | 1.00 | 12.57 |
| ATOM | 579 | N | VAL A | 94 | 15.514 | 32.104 | 17.147 | 1.00 | 9.52 |
| ATOM | 580 | CA | VAL A | 94 | 15.980 | 30.944 | 17.982 | 1.00 | 9.28 |
| ATOM | 581 | CB | VAL A | 94 | 16.129 | 29.677 | 17.106 | 1.00 | 8.75 |
| ATOM | 582 | CG1 | VAL A | 94 | 16.944 | 28.652 | 17.794 | 1.00 | 3.33 |
| ATOM | 583 | CG2 | VAL A | 94 | 14.779 | 29.132 | 16.743 | 1.00 | 2.00 |
| ATOM | 584 | C | VAL A | 94 | 17.341 | 31.254 | 18.682 | 1.00 | 11.69 |
| ATOM | 585 | O | VAL A | 94 | 17.529 | 30.958 | 19.849 | 1.00 | 16.80 |
| ATOM | 586 | N | LEU A | 95 | 18.275 | 31.852 | 17.930 | 1.00 | 13.58 |
| ATOM | 587 | CA | LEU A | 95 | 19.654 | 32.266 | 18.403 | 1.00 | 9.12 |
| ATOM | 588 | CB | LEU A | 95 | 20.525 | 32.603 | 17.186 | 1.00 | 6.38 |
| ATOM | 589 | CG | LEU A | 95 | 21.859 | 31.898 | 16.895 | 1.00 | 10.10 |
| ATOM | 590 | CD1 | LEU A | 95 | 21.871 | 30.426 | 17.327 | 1.00 | 3.73 |
| ATOM | 591 | CD2 | LEU A | 95 | 22.163 | 32.031 | 15.409 | 1.00 | 2.00 |
| ATOM | 592 | C | LEU A | 95 | 19.563 | 33.499 | 19.352 | 1.00 | 13.12 |
| ATOM | 593 | O | LEU A | 95 | 20.104 | 33.521 | 20.446 | 1.00 | 13.37 |
| ATOM | 594 | N | GLU A | 96 | 18.887 | 34.539 | 18.873 | 1.00 | 13.34 |
| ATOM | 595 | CA | GLU A | 96 | 18.659 | 35.804 | 19.629 | 1.00 | 17.07 |
| ATOM | 596 | CB | GLU A | 96 | 17.734 | 36.757 | 18.853 | 1.00 | 19.22 |
| ATOM | 597 | CG | GLU A | 96 | 18.408 | 37.707 | 17.868 | 1.00 | 32.52 |
| ATOM | 598 | CD | GLU A | 96 | 17.406 | 38.554 | 17.059 | 1.00 | 38.30 |
| ATOM | 599 | OE1 | GLU A | 96 | 17.825 | 39.156 | 16.026 | 1.00 | 43.55 |
| ATOM | 600 | OE2 | GLU A | 96 | 16.205 | 38.612 | 17.448 | 1.00 | 37.03 |
| ATOM | 601 | C | GLU A | 96 | 18.035 | 35.572 | 21.013 | 1.00 | 19.12 |
| ATOM | 602 | O | GLU A | 96 | 18.311 | 36.270 | 21.987 | 1.00 | 22.88 |
| ATOM | 603 | N | THR A | 97 | 17.101 | 34.635 | 21.069 | 1.00 | 16.70 |
| ATOM | 604 | CA | THR A | 97 | 16.412 | 34.372 | 22.330 | 1.00 | 13.97 |
| ATOM | 605 | CB | THR A | 97 | 14.913 | 33.848 | 22.102 | 1.00 | 16.11 |
| ATOM | 606 | OG1 | THR A | 97 | 14.907 | 32.571 | 21.446 | 1.00 | 17.85 |
| ATOM | 607 | CG2 | THR A | 97 | 14.131 | 34.796 | 21.229 | 1.00 | 8.17 |
| ATOM | 608 | C | THR A | 97 | 17.220 | 33.430 | 23.234 | 1.00 | 14.30 |
| ATOM | 609 | O | THR A | 97 | 17.150 | 33.500 | 24.456 | 1.00 | 21.32 |
| ATOM | 610 | N | ALA A | 98 | 17.985 | 32.528 | 22.626 | 1.00 | 13.54 |
| ATOM | 611 | CA | ALA A | 98 | 18.795 | 31.570 | 23.418 | 1.00 | 11.87 |
| ATOM | 612 | CB | ALA A | 98 | 19.441 | 30.531 | 22.509 | 1.00 | 13.72 |
| ATOM | 613 | C | ALA A | 98 | 19.864 | 32.364 | 24.134 | 1.00 | 7.51 |
| ATOM | 614 | O | ALA A | 98 | 20.184 | 32.156 | 25.275 | 1.00 | 14.36 |
| ATOM | 615 | N | ALA A | 99 | 20.422 | 33.316 | 23.419 | 1.00 | 11.45 |
| ATOM | 616 | CA | ALA A | 99 | 21.467 | 34.153 | 23.964 | 1.00 | 15.58 |
| ATOM | 617 | CB | ALA A | 99 | 22.039 | 35.055 | 22.873 | 1.00 | 6.98 |
| ATOM | 618 | C | ALA A | 99 | 20.887 | 35.000 | 25.077 | 1.00 | 23.42 |
| ATOM | 619 | O | ALA A | 99 | 20.260 | 36.027 | 24.851 | 1.00 | 27.39 |
| ATOM | 620 | N | SER A | 100 | 21.074 | 34.551 | 26.308 | 1.00 | 32.15 |
| ATOM | 621 | CA | SER A | 100 | 20.618 | 35.352 | 27.493 | 1.00 | 39.64 |
| ATOM | 622 | CB | SER A | 100 | 20.268 | 34.422 | 28.668 | 1.00 | 43.91 |
| ATOM | 623 | OG | SER A | 100 | 19.189 | 33.539 | 28.344 | 1.00 | 42.68 |

Figure 4M

| ATOM | 624 | C | SER | A | 100 | 21.921 | 36.163 | 27.718 | 1.00 | 38.85 |
| --- | --- | --- | --- | --- | --- | --- | --- | --- | --- | --- |
| ATOM | 625 | O | SER | A | 100 | 22.580 | 36.190 | 28.753 | 1.00 | 34.35 |
| ATOM | 626 | N | ALA | A | 101 | 22.272 | 36.809 | 26.619 | 1.00 | 42.20 |
| ATOM | 627 | CA | ALA | A | 101 | 23.483 | 37.575 | 26.483 | 1.00 | 48.71 |
| ATOM | 628 | CB | ALA | A | 101 | 23.616 | 38.111 | 25.044 | 1.00 | 48.97 |
| ATOM | 629 | C | ALA | A | 101 | 23.751 | 38.676 | 27.480 | 1.00 | 52.91 |
| ATOM | 630 | O | ALA | A | 101 | 22.903 | 39.483 | 27.879 | 1.00 | 51.94 |
| ATOM | 631 | N | ALA | A | 102 | 25.000 | 38.637 | 27.910 | 1.00 | 56.37 |
| ATOM | 632 | CA | ALA | A | 102 | 25.550 | 39.612 | 28.800 | 1.00 | 59.62 |
| ATOM | 633 | CB | ALA | A | 102 | 26.570 | 38.960 | 29.679 | 1.00 | 61.10 |
| ATOM | 634 | C | ALA | A | 102 | 26.223 | 40.477 | 27.723 | 1.00 | 63.57 |
| ATOM | 635 | O | ALA | A | 102 | 25.807 | 41.600 | 27.410 | 1.00 | 66.92 |
| ATOM | 636 | N | ALA | A | 103 | 27.198 | 39.855 | 27.060 | 1.00 | 64.90 |
| ATOM | 637 | CA | ALA | A | 103 | 27.969 | 40.496 | 25.958 | 1.00 | 64.92 |
| ATOM | 638 | CB | ALA | A | 103 | 29.159 | 41.292 | 26.514 | 1.00 | 63.32 |
| ATOM | 639 | C | ALA | A | 103 | 28.456 | 39.397 | 24.981 | 1.00 | 64.15 |
| ATOM | 640 | O | ALA | A | 103 | 28.807 | 39.751 | 23.838 | 1.00 | 64.98 |
| ATOM | 641 | OT | ALA | A | 103 | 28.431 | 38.200 | 25.360 | 1.00 | 64.17 |
| ATOM | 642 | CB | LEU | A | 111 | 26.747 | 44.455 | 20.372 | 1.00 | 56.29 |
| ATOM | 643 | CG | LEU | A | 111 | 27.624 | 44.132 | 19.156 | 1.00 | 54.59 |
| ATOM | 644 | CD1 | LEU | A | 111 | 28.799 | 45.121 | 18.988 | 1.00 | 51.56 |
| ATOM | 645 | CD2 | LEU | A | 111 | 28.112 | 42.683 | 19.301 | 1.00 | 52.46 |
| ATOM | 646 | C | LEU | A | 111 | 25.766 | 46.776 | 19.890 | 1.00 | 58.98 |
| ATOM | 647 | O | LEU | A | 111 | 25.724 | 48.011 | 20.026 | 1.00 | 60.58 |
| ATOM | 648 | N | LEU | A | 111 | 25.687 | 45.879 | 22.111 | 1.00 | 60.93 |
| ATOM | 649 | CA | LEU | A | 111 | 26.541 | 45.892 | 20.888 | 1.00 | 59.20 |
| ATOM | 650 | N | SER | A | 112 | 25.096 | 46.141 | 18.932 | 1.00 | 55.16 |
| ATOM | 651 | CA | SER | A | 112 | 24.314 | 46.915 | 17.974 | 1.00 | 51.29 |
| ATOM | 652 | CB | SER | A | 112 | 25.164 | 47.301 | 16.768 | 1.00 | 53.00 |
| ATOM | 653 | OG | SER | A | 112 | 26.127 | 48.277 | 17.146 | 1.00 | 59.40 |
| ATOM | 654 | C | SER | A | 112 | 22.994 | 46.330 | 17.540 | 1.00 | 48.24 |
| ATOM | 655 | O | SER | A | 112 | 21.948 | 46.720 | 18.039 | 1.00 | 52.52 |
| ATOM | 656 | N | ARG | A | 113 | 23.032 | 45.323 | 16.678 | 1.00 | 43.61 |
| ATOM | 657 | CA | ARG | A | 113 | 21.765 | 44.782 | 16.147 | 1.00 | 40.68 |
| ATOM | 658 | CB | ARG | A | 113 | 21.251 | 45.872 | 15.247 | 1.00 | 46.02 |
| ATOM | 659 | CG | ARG | A | 113 | 22.407 | 46.709 | 14.618 | 1.00 | 53.20 |
| ATOM | 660 | CD | ARG | A | 113 | 22.013 | 47.317 | 13.295 | 1.00 | 68.22 |
| ATOM | 661 | NE | ARG | A | 113 | 20.629 | 47.807 | 13.317 | 1.00 | 78.52 |
| ATOM | 662 | CZ | ARG | A | 113 | 19.562 | 47.071 | 12.992 | 1.00 | 82.20 |
| ATOM | 663 | NH1 | ARG | A | 113 | 18.342 | 47.604 | 13.052 | 1.00 | 85.11 |
| ATOM | 664 | NH2 | ARG | A | 113 | 19.707 | 45.800 | 12.627 | 1.00 | 83.47 |
| ATOM | 665 | C | ARG | A | 113 | 21.936 | 43.443 | 15.397 | 1.00 | 39.97 |
| ATOM | 666 | O | ARG | A | 113 | 22.039 | 42.363 | 15.964 | 1.00 | 39.56 |
| ATOM | 667 | N | GLU | A | 114 | 21.934 | 43.524 | 14.075 | 1.00 | 37.09 |
| ATOM | 668 | CA | GLU | A | 114 | 22.175 | 42.332 | 13.265 | 1.00 | 34.54 |
| ATOM | 669 | CB | GLU | A | 114 | 21.901 | 42.632 | 11.786 | 1.00 | 38.06 |
| ATOM | 670 | CG | GLU | A | 114 | 22.674 | 43.797 | 11.194 | 1.00 | 44.41 |
| ATOM | 671 | CD | GLU | A | 114 | 21.784 | 44.832 | 10.494 | 1.00 | 46.14 |
| ATOM | 672 | OE1 | GLU | A | 114 | 20.608 | 44.533 | 10.181 | 1.00 | 43.86 |
| ATOM | 673 | OE2 | GLU | A | 114 | 22.270 | 45.963 | 10.261 | 1.00 | 50.76 |
| ATOM | 674 | C | GLU | A | 114 | 23.648 | 41.888 | 13.520 | 1.00 | 31.23 |
| ATOM | 675 | O | GLU | A | 114 | 24.063 | 40.781 | 13.208 | 1.00 | 32.58 |

Figure 4N

| ATOM | 676 | N | GLU | A | 115 | 24.433 | 42.784 | 14.112 | 1.00 | 24.68 |
| --- | --- | --- | --- | --- | --- | --- | --- | --- | --- | --- |
| ATOM | 677 | CA | GLU | A | 115 | 25.838 | 42.476 | 14.465 | 1.00 | 21.27 |
| ATOM | 678 | CB | GLU | A | 115 | 26.582 | 43.757 | 14.818 | 1.00 | 23.85 |
| ATOM | 679 | CG | GLU | A | 115 | 27.051 | 44.517 | 13.572 | 1.00 | 34.75 |
| ATOM | 680 | CD | GLU | A | 115 | 27.060 | 46.036 | 13.728 | 1.00 | 42.96 |
| ATOM | 681 | OE1 | GLU | A | 115 | 27.517 | 46.540 | 14.786 | 1.00 | 45.07 |
| ATOM | 682 | OE2 | GLU | A | 115 | 26.622 | 46.724 | 12.770 | 1.00 | 45.48 |
| ATOM | 683 | C | GLU | A | 115 | 25.815 | 41.468 | 15.617 | 1.00 | 18.01 |
| ATOM | 684 | O | GLU | A | 115 | 26.614 | 40.547 | 15.712 | 1.00 | 16.83 |
| ATOM | 685 | N | ARG | A | 116 | 24.819 | 41.629 | 16.476 | 1.00 | 17.08 |
| ATOM | 686 | CA | ARG | A | 116 | 24.616 | 40.713 | 17.602 | 1.00 | 13.12 |
| ATOM | 687 | CB | ARG | A | 116 | 23.423 | 41.200 | 18.420 | 1.00 | 23.37 |
| ATOM | 688 | CG | ARG | A | 116 | 23.715 | 41.525 | 19.891 | 1.00 | 40.43 |
| ATOM | 689 | CD | ARG | A | 116 | 23.791 | 40.244 | 20.790 | 1.00 | 50.89 |
| ATOM | 690 | NE | ARG | A | 116 | 24.307 | 40.566 | 22.119 | 1.00 | 51.56 |
| ATOM | 691 | CZ | ARG | A | 116 | 25.503 | 40.230 | 22.595 | 1.00 | 50.96 |
| ATOM | 692 | NH1 | ARG | A | 116 | 26.357 | 39.495 | 21.894 | 1.00 | 50.65 |
| ATOM | 693 | NH2 | ARG | A | 116 | 25.930 | 40.837 | 23.634 | 1.00 | 48.08 |
| ATOM | 694 | C | ARG | A | 116 | 24.330 | 39.344 | 16.948 | 1.00 | 9.40 |
| ATOM | 695 | O | ARG | A | 116 | 24.761 | 38.293 | 17.376 | 1.00 | 10.43 |
| ATOM | 696 | N | LEU | A | 117 | 23.592 | 39.388 | 15.853 | 1.00 | 8.24 |
| ATOM | 697 | CA | LEU | A | 117 | 23.256 | 38.181 | 15.130 | 1.00 | 5.12 |
| ATOM | 698 | CB | LEU | A | 117 | 22.198 | 38.486 | 14.082 | 1.00 | 11.72 |
| ATOM | 699 | CG | LEU | A | 117 | 21.910 | 37.396 | 13.046 | 1.00 | 14.16 |
| ATOM | 700 | CD1 | LEU | A | 117 | 21.610 | 36.054 | 13.696 | 1.00 | 11.49 |
| ATOM | 701 | CD2 | LEU | A | 117 | 20.762 | 37.846 | 12.186 | 1.00 | 17.08 |
| ATOM | 702 | C | LEU | A | 117 | 24.503 | 37.611 | 14.495 | 1.00 | 6.75 |
| ATOM | 703 | O | LEU | A | 117 | 24.755 | 36.403 | 14.538 | 1.00 | 10.82 |
| ATOM | 704 | N | LEU | A | 118 | 25.308 | 38.489 | 13.895 | 1.00 | 10.20 |
| ATOM | 705 | CA | LEU | A | 118 | 26.584 | 38.053 | 13.226 | 1.00 | 8.45 |
| ATOM | 706 | CB | LEU | A | 118 | 27.275 | 39.227 | 12.548 | 1.00 | 7.18 |
| ATOM | 707 | CG | LEU | A | 118 | 27.047 | 39.365 | 11.050 | 1.00 | 2.10 |
| ATOM | 708 | CD1 | LEU | A | 118 | 26.269 | 38.175 | 10.493 | 1.00 | 2.00 |
| ATOM | 709 | CD2 | LEU | A | 118 | 26.379 | 40.655 | 10.807 | 1.00 | 2.00 |
| ATOM | 710 | C | LEU | A | 118 | 27.517 | 37.406 | 14.234 | 1.00 | 7.43 |
| ATOM | 711 | O | LEU | A | 118 | 28.079 | 36.328 | 14.013 | 1.00 | 4.46 |
| ATOM | 712 | N | TYR | A | 119 | 27.601 | 38.060 | 15.388 | 1.00 | 5.07 |
| ATOM | 713 | CA | TYR | A | 119 | 28.443 | 37.599 | 16.496 | 1.00 | 11.79 |
| ATOM | 714 | CB | TYR | A | 119 | 28.461 | 38.650 | 17.626 | 1.00 | 14.97 |
| ATOM | 715 | CG | TYR | A | 119 | 29.115 | 38.152 | 18.895 | 1.00 | 20.96 |
| ATOM | 716 | CD1 | TYR | A | 119 | 28.408 | 37.339 | 19.734 | 1.00 | 26.44 |
| ATOM | 717 | CE1 | TYR | A | 119 | 28.995 | 36.828 | 20.938 | 1.00 | 30.15 |
| ATOM | 718 | CD2 | TYR | A | 119 | 30.441 | 38.452 | 19.184 | 1.00 | 25.49 |
| ATOM | 719 | CE2 | TYR | A | 119 | 31.048 | 37.949 | 20.338 | 1.00 | 31.21 |
| ATOM | 720 | CZ | TYR | A | 119 | 30.313 | 37.133 | 21.204 | 1.00 | 35.37 |
| ATOM | 721 | OH | TYR | A | 119 | 30.895 | 36.586 | 22.322 | 1.00 | 43.14 |
| ATOM | 722 | C | TYR | A | 119 | 27.960 | 36.227 | 16.991 | 1.00 | 10.78 |
| ATOM | 723 | O | TYR | A | 119 | 28.738 | 35.296 | 17.238 | 1.00 | 17.49 |
| ATOM | 724 | N | LEU | A | 120 | 26.645 | 36.102 | 17.119 | 1.00 | 10.50 |
| ATOM | 725 | CA | LEU | A | 120 | 26.017 | 34.833 | 17.584 | 1.00 | 7.62 |
| ATOM | 726 | CB | LEU | A | 120 | 24.540 | 35.090 | 17.381 | 1.00 | 7.13 |
| ATOM | 727 | CG | LEU | A | 120 | 23.932 | 34.993 | 19.283 | 1.00 | 9.79 |

Figure 4O

| ATOM | 728 | CD1 | LEU | A | 120 | 24.953 | 35.123 | 20.282 | 1.00 | 10.87 |
|---|---|---|---|---|---|---|---|---|---|---|
| ATOM | 729 | CD2 | LEU | A | 120 | 22.866 | 36.058 | 19.416 | 1.00 | 6.08 |
| ATOM | 730 | C | LEU | A | 120 | 26.197 | 33.666 | 16.592 | 1.00 | 5.17 |
| ATOM | 731 | O | LEU | A | 120 | 26.630 | 32.578 | 16.967 | 1.00 | 4.21 |
| ATOM | 732 | N | ILE | A | 121 | 25.911 | 33.890 | 15.306 | 1.00 | 6.28 |
| ATOM | 733 | CA | ILE | A | 121 | 26.046 | 32.758 | 14.333 | 1.00 | 4.47 |
| ATOM | 734 | CB | ILE | A | 121 | 25.227 | 32.973 | 13.005 | 1.00 | 4.54 |
| ATOM | 735 | CG2 | ILE | A | 121 | 25.844 | 34.013 | 12.150 | 1.00 | 2.00 |
| ATOM | 736 | CG1 | ILE | A | 121 | 25.179 | 31.673 | 12.203 | 1.00 | 5.33 |
| ATOM | 737 | CD1 | ILE | A | 121 | 24.105 | 31.640 | 11.167 | 1.00 | 2.00 |
| ATOM | 738 | C | ILE | A | 121 | 27.508 | 32.340 | 14.073 | 1.00 | 3.60 |
| ATOM | 739 | O | ILE | A | 121 | 27.831 | 31.150 | 14.057 | 1.00 | 5.52 |
| ATOM | 740 | N | THR | A | 122 | 28.401 | 33.329 | 13.965 | 1.00 | 2.00 |
| ATOM | 741 | CA | THR | A | 122 | 29.845 | 33.076 | 13.723 | 1.00 | 2.00 |
| ATOM | 742 | CB | THR | A | 122 | 30.641 | 34.347 | 13.741 | 1.00 | 2.00 |
| ATOM | 743 | OG1 | THR | A | 122 | 30.071 | 35.275 | 12.822 | 1.00 | 7.60 |
| ATOM | 744 | CG2 | THR | A | 122 | 32.064 | 34.055 | 13.321 | 1.00 | 5.83 |
| ATOM | 745 | C | THR | A | 122 | 30.520 | 32.170 | 14.742 | 1.00 | 2.73 |
| ATOM | 746 | O | THR | A | 122 | 31.240 | 31.224 | 14.415 | 1.00 | 6.41 |
| ATOM | 747 | N | ASN | A | 123 | 30.352 | 32.521 | 16.009 | 1.00 | 5.60 |
| ATOM | 748 | CA | ASN | A | 123 | 30.966 | 31.748 | 17.094 | 1.00 | 2.00 |
| ATOM | 749 | CB | ASN | A | 123 | 31.109 | 32.621 | 18.320 | 1.00 | 5.03 |
| ATOM | 750 | CG | ASN | A | 123 | 31.976 | 33.843 | 18.062 | 1.00 | 7.80 |
| ATOM | 751 | OD1 | ASN | A | 123 | 31.485 | 34.951 | 17.920 | 1.00 | 5.81 |
| ATOM | 752 | ND2 | ASN | A | 123 | 33.259 | 33.631 | 17.952 | 1.00 | 4.02 |
| ATOM | 753 | C | ASN | A | 123 | 30.266 | 30.443 | 17.415 | 1.00 | 4.01 |
| ATOM | 754 | O | ASN | A | 123 | 30.865 | 29.534 | 17.965 | 1.00 | 6.29 |
| ATOM | 755 | N | TYR | A | 124 | 28.982 | 30.342 | 17.089 | 1.00 | 2.98 |
| ATOM | 756 | CA | TYR | A | 124 | 28.238 | 29.070 | 17.342 | 1.00 | 3.33 |
| ATOM | 757 | CB | TYR | A | 124 | 26.721 | 29.293 | 17.531 | 1.00 | 2.24 |
| ATOM | 758 | CG | TYR | A | 124 | 26.043 | 28.123 | 18.215 | 1.00 | 3.71 |
| ATOM | 759 | CD1 | TYR | A | 124 | 26.249 | 27.882 | 19.575 | 1.00 | 6.66 |
| ATOM | 760 | CE1 | TYR | A | 124 | 25.678 | 26.797 | 20.214 | 1.00 | 3.17 |
| ATOM | 761 | CD2 | TYR | A | 124 | 25.232 | 27.230 | 17.510 | 1.00 | 4.38 |
| ATOM | 762 | CE2 | TYR | A | 124 | 24.651 | 26.140 | 18.148 | 1.00 | 2.75 |
| ATOM | 763 | CZ | TYR | A | 124 | 24.880 | 25.930 | 19.503 | 1.00 | 4.23 |
| ATOM | 764 | OH | TYR | A | 124 | 24.331 | 24.850 | 20.179 | 1.00 | 4.84 |
| ATOM | 765 | C | TYR | A | 124 | 28.468 | 28.114 | 16.166 | 1.00 | 2.60 |
| ATOM | 766 | O | TYR | A | 124 | 28.690 | 26.933 | 16.322 | 1.00 | 5.11 |
| ATOM | 767 | N | LEU | A | 125 | 28.368 | 28.656 | 14.964 | 1.00 | 4.89 |
| ATOM | 768 | CA | LEU | A | 125 | 28.552 | 27.858 | 13.757 | 1.00 | 9.24 |
| ATOM | 769 | CB | LEU | A | 125 | 27.240 | 27.849 | 12.972 | 1.00 | 6.85 |
| ATOM | 770 | CG | LEU | A | 125 | 26.063 | 27.110 | 13.626 | 1.00 | 2.89 |
| ATOM | 771 | CD1 | LEU | A | 125 | 24.860 | 27.277 | 12.737 | 1.00 | 2.00 |
| ATOM | 772 | CD2 | LEU | A | 125 | 26.361 | 25.631 | 13.854 | 1.00 | 2.00 |
| ATOM | 773 | C | LEU | A | 125 | 29.734 | 28.380 | 12.913 | 1.00 | 9.42 |
| ATOM | 774 | O | LEU | A | 125 | 29.572 | 28.868 | 11.804 | 1.00 | 8.71 |
| ATOM | 775 | N | PRO | A | 126 | 30.965 | 28.210 | 13.430 | 1.00 | 11.38 |
| ATOM | 776 | CD | PRO | A | 126 | 31.309 | 27.672 | 14.764 | 1.00 | 4.65 |
| ATOM | 777 | CA | PRO | A | 126 | 32.164 | 28.675 | 12.722 | 1.00 | 7.79 |
| ATOM | 778 | CB | PRO | A | 126 | 33.187 | 28.769 | 13.849 | 1.00 | 5.75 |
| ATOM | 779 | CG | PRO | A | 126 | 32.801 | 27.662 | 14.764 | 1.00 | 2.00 |

Figure 4P

| ATOM | 780 | C   | PRO A 126 | 32.704 | 27.870 | 11.495 | 1.00 | 7.74 |
|------|-----|-----|-----------|--------|--------|--------|------|------|
| ATOM | 781 | O   | PRO A 126 | 33.521 | 28.396 | 10.727 | 1.00 | 9.84 |
| ATOM | 782 | N   | SER A 127 | 32.204 | 26.649 | 11.275 | 1.00 | 2.00 |
| ATOM | 783 | CA  | SER A 127 | 32.669 | 25.783 | 10.146 | 1.00 | 2.00 |
| ATOM | 784 | CB  | SER A 127 | 33.270 | 24.508 | 10.731 | 1.00 | 2.00 |
| ATOM | 785 | OG  | SER A 127 | 34.258 | 24.800 | 11.690 | 1.00 | 2.49 |
| ATOM | 786 | C   | SER A 127 | 31.674 | 25.377 | 9.036  | 1.00 | 2.00 |
| ATOM | 787 | O   | SER A 127 | 30.463 | 25.486 | 9.164  | 1.00 | 2.00 |
| ATOM | 788 | N   | VAL A 128 | 32.222 | 24.903 | 7.920  | 1.00 | 2.00 |
| ATOM | 789 | CA  | VAL A 128 | 31.380 | 24.368 | 6.809  | 1.00 | 4.25 |
| ATOM | 790 | CB  | VAL A 128 | 31.641 | 24.922 | 5.406  | 1.00 | 5.15 |
| ATOM | 791 | CG1 | VAL A 128 | 30.631 | 25.964 | 5.077  | 1.00 | 14.62 |
| ATOM | 792 | CG2 | VAL A 128 | 33.039 | 25.411 | 5.261  | 1.00 | 3.69 |
| ATOM | 793 | C   | VAL A 128 | 31.775 | 22.937 | 6.678  | 1.00 | 5.33 |
| ATOM | 794 | O   | VAL A 128 | 32.845 | 22.503 | 7.066  | 1.00 | 8.22 |
| ATOM | 795 | P1  | SEI A 129 | 31.695 | 17.762 | 7.461  | 1.00 | 8.79 |
| ATOM | 796 | O3  | SEI A 129 | 31.372 | 17.687 | 9.055  | 1.00 | 11.54 |
| ATOM | 797 | O4  | SEI A 129 | 31.616 | 16.285 | 6.832  | 1.00 | 7.78 |
| ATOM | 798 | O5  | SEI A 129 | 30.630 | 18.671 | 6.720  | 1.00 | 9.57 |
| ATOM | 799 | C5  | SEI A 129 | 30.226 | 17.113 | 9.752  | 1.00 | 10.71 |
| ATOM | 800 | C6  | SEI A 129 | 30.679 | 16.036 | 10.741 | 1.00 | 11.64 |
| ATOM | 801 | C7  | SEI A 129 | 29.405 | 18.197 | 10.462 | 1.00 | 2.00 |
| ATOM | 802 | C8  | SEI A 129 | 31.769 | 15.900 | 5.468  | 1.00 | 5.88 |
| ATOM | 803 | C9  | SEI A 129 | 30.614 | 14.989 | 5.035  | 1.00 | 10.05 |
| ATOM | 804 | C10 | SEI A 129 | 33.106 | 15.201 | 5.285  | 1.00 | 10.92 |
| ATOM | 805 | N   | SEI A 129 | 30.916 | 22.193 | 6.024  | 1.00 | 7.00 |
| ATOM | 806 | CA  | SEI A 129 | 31.186 | 20.804 | 5.818  | 1.00 | 4.93 |
| ATOM | 807 | C   | SEI A 129 | 30.516 | 20.458 | 4.534  | 1.00 | 3.57 |
| ATOM | 808 | O   | SEI A 129 | 29.305 | 20.529 | 4.410  | 1.00 | 5.86 |
| ATOM | 809 | CB  | SEI A 129 | 30.536 | 20.063 | 6.956  | 1.00 | 4.94 |
| ATOM | 810 | O2  | SEI A 129 | 33.031 | 18.359 | 7.260  | 1.00 | 17.04 |
| ATOM | 811 | N   | LEU A 130 | 31.332 | 20.138 | 3.541  | 1.00 | 4.70 |
| ATOM | 812 | CA  | LEU A 130 | 30.814 | 19.774 | 2.219  | 1.00 | 6.09 |
| ATOM | 813 | CB  | LEU A 130 | 31.825 | 20.095 | 1.127  | 1.00 | 8.94 |
| ATOM | 814 | CG  | LEU A 130 | 31.491 | 19.566 | -0.273 | 1.00 | 2.00 |
| ATOM | 815 | CD1 | LEU A 130 | 30.306 | 20.309 | -0.854 | 1.00 | 2.00 |
| ATOM | 816 | CD2 | LEU A 130 | 32.720 | 19.745 | -1.157 | 1.00 | 4.46 |
| ATOM | 817 | C   | LEU A 130 | 30.500 | 18.314 | 2.158  | 1.00 | 6.28 |
| ATOM | 818 | O   | LEU A 130 | 31.293 | 17.487 | 2.554  | 1.00 | 12.07 |
| ATOM | 819 | N   | SER A 131 | 29.320 | 17.984 | 1.669  | 1.00 | 8.28 |
| ATOM | 820 | CA  | SER A 131 | 28.978 | 16.564 | 1.504  | 1.00 | 8.85 |
| ATOM | 821 | CB  | SER A 131 | 27.618 | 16.283 | 2.096  | 1.00 | 5.12 |
| ATOM | 822 | OG  | SER A 131 | 27.656 | 16.625 | 3.465  | 1.00 | 19.47 |
| ATOM | 823 | C   | SER A 131 | 29.022 | 16.243 | -0.003 | 1.00 | 10.39 |
| ATOM | 824 | O   | SER A 131 | 28.527 | 16.996 | -0.846 | 1.00 | 11.22 |
| ATOM | 825 | N   | THR A 132 | 29.664 | 15.127 | -0.333 | 1.00 | 12.55 |
| ATOM | 826 | CA  | THR A 132 | 29.790 | 14.670 | -1.728 | 1.00 | 16.62 |
| ATOM | 827 | CB  | THR A 132 | 31.271 | 14.437 | -2.085 | 1.00 | 15.84 |
| ATOM | 828 | OG1 | THR A 132 | 31.893 | 13.713 | -1.019 | 1.00 | 16.85 |
| ATOM | 829 | CG2 | THR A 132 | 32.004 | 15.768 | -2.282 | 1.00 | 14.99 |
| ATOM | 830 | C   | THR A 132 | 29.028 | 13.347 | -1.849 | 1.00 | 19.10 |
| ATOM | 831 | O   | THR A 132 | 28.990 | 12.558 | -0.903 | 1.00 | 18.44 |

Figure 4Q

| ATOM | 832 | N   | ALA | A | 133 | 28.363 | 13.150 | -2.992  | 1.00 | 24.92 |
| ---- | --- | --- | --- | - | --- | ------ | ------ | ------- | ---- | ----- |
| ATOM | 833 | CA  | ALA | A | 133 | 27.602 | 11.895 | -3.254  | 1.00 | 30.53 |
| ATOM | 834 | CB  | ALA | A | 133 | 26.599 | 12.110 | -4.378  | 1.00 | 28.49 |
| ATOM | 835 | C   | ALA | A | 133 | 28.612 | 10.768 | -3.625  | 1.00 | 35.62 |
| ATOM | 836 | O   | ALA | A | 133 | 28.611 | 9.704  | -2.964  | 1.00 | 42.46 |
| ATOM | 837 | OT  | ALA | A | 133 | 29.435 | 10.985 | -4.541  | 1.00 | 39.35 |
| ATOM | 838 | CB  | ALA | A | 141 | 34.850 | 13.048 | -10.291 | 1.00 | 40.89 |
| ATOM | 839 | C   | ALA | A | 141 | 32.972 | 13.033 | -12.027 | 1.00 | 36.57 |
| ATOM | 840 | O   | ALA | A | 141 | 33.249 | 12.981 | -13.225 | 1.00 | 35.01 |
| ATOM | 841 | N   | ALA | A | 141 | 34.375 | 11.021 | -11.658 | 1.00 | 39.81 |
| ATOM | 842 | CA  | ALA | A | 141 | 33.753 | 12.194 | -10.976 | 1.00 | 38.55 |
| ATOM | 843 | N   | ASP | A | 142 | 31.971 | 13.777 | -11.564 | 1.00 | 35.82 |
| ATOM | 844 | CA  | ASP | A | 142 | 31.137 | 14.620 | -12.475 | 1.00 | 37.99 |
| ATOM | 845 | CB  | ASP | A | 142 | 30.125 | 13.758 | -13.231 | 1.00 | 41.81 |
| ATOM | 846 | CG  | ASP | A | 142 | 28.984 | 13.256 | -12.345 | 1.00 | 46.15 |
| ATOM | 847 | OD1 | ASP | A | 142 | 27.863 | 13.801 | -12.478 | 1.00 | 53.97 |
| ATOM | 848 | OD2 | ASP | A | 142 | 29.195 | 12.310 | -11.547 | 1.00 | 46.27 |
| ATOM | 849 | C   | ASP | A | 142 | 30.433 | 15.767 | -11.713 | 1.00 | 36.58 |
| ATOM | 850 | O   | ASP | A | 142 | 30.523 | 15.872 | -10.493 | 1.00 | 38.92 |
| ATOM | 851 | N   | ARG | A | 143 | 29.686 | 16.588 | -12.451 | 1.00 | 34.69 |
| ATOM | 852 | CA  | ARG | A | 143 | 28.973 | 17.779 | -11.894 | 1.00 | 32.35 |
| ATOM | 853 | CB  | ARG | A | 143 | 28.284 | 18.540 | -13.030 | 1.00 | 32.68 |
| ATOM | 854 | CG  | ARG | A | 143 | 29.038 | 18.581 | -14.333 | 1.00 | 32.20 |
| ATOM | 855 | CD  | ARG | A | 143 | 29.532 | 19.965 | -14.668 | 1.00 | 39.13 |
| ATOM | 856 | NE  | ARG | A | 143 | 29.940 | 20.069 | -16.077 | 1.00 | 48.59 |
| ATOM | 857 | CZ  | ARG | A | 143 | 31.068 | 20.638 | -16.510 | 1.00 | 50.60 |
| ATOM | 858 | NH1 | ARG | A | 143 | 31.324 | 20.687 | -17.806 | 1.00 | 50.22 |
| ATOM | 859 | NH2 | ARG | A | 143 | 31.966 | 21.116 | -15.660 | 1.00 | 54.07 |
| ATOM | 860 | C   | ARG | A | 143 | 27.970 | 17.539 | -10.722 | 1.00 | 33.03 |
| ATOM | 861 | O   | ARG | A | 143 | 27.458 | 18.471 | -10.110 | 1.00 | 35.26 |
| ATOM | 862 | N   | THR | A | 144 | 27.688 | 16.279 | -10.415 | 1.00 | 31.99 |
| ATOM | 863 | CA  | THR | A | 144 | 26.751 | 15.942 | -9.304  | 1.00 | 29.49 |
| ATOM | 864 | CB  | THR | A | 144 | 25.807 | 14.787 | -9.716  | 1.00 | 31.98 |
| ATOM | 865 | OG1 | THR | A | 144 | 26.568 | 13.581 | -9.877  | 1.00 | 33.87 |
| ATOM | 866 | CG2 | THR | A | 144 | 25.110 | 15.099 | -11.040 | 1.00 | 35.59 |
| ATOM | 867 | C   | THR | A | 144 | 27.506 | 15.492 | -8.023  | 1.00 | 27.75 |
| ATOM | 868 | O   | THR | A | 144 | 26.920 | 14.959 | -7.075  | 1.00 | 30.96 |
| ATOM | 869 | N   | LEU | A | 145 | 28.823 | 15.680 | -8.021  | 1.00 | 22.66 |
| ATOM | 870 | CA  | LEU | A | 145 | 29.661 | 15.264 | -6.872  | 1.00 | 19.42 |
| ATOM | 871 | CB  | LEU | A | 145 | 31.138 | 15.419 | -7.230  | 1.00 | 14.05 |
| ATOM | 872 | CG  | LEU | A | 145 | 32.091 | 14.911 | -6.166  | 1.00 | 9.94  |
| ATOM | 873 | CD1 | LEU | A | 145 | 31.931 | 13.444 | -5.988  | 1.00 | 6.47  |
| ATOM | 874 | CD2 | LEU | A | 145 | 33.492 | 15.243 | -6.544  | 1.00 | 14.60 |
| ATOM | 875 | C   | LEU | A | 145 | 29.305 | 16.052 | -5.584  | 1.00 | 19.44 |
| ATOM | 876 | O   | LEU | A | 145 | 29.122 | 15.493 | -4.507  | 1.00 | 21.52 |
| ATOM | 877 | N   | PHE | A | 146 | 29.237 | 17.370 | -5.709  | 1.00 | 13.66 |
| ATOM | 878 | CA  | PHE | A | 146 | 28.890 | 18.214 | -4.566  | 1.00 | 13.40 |
| ATOM | 879 | CB  | PHE | A | 146 | 29.315 | 19.653 | -4.849  | 1.00 | 11.02 |
| ATOM | 880 | CG  | PHE | A | 146 | 30.800 | 19.839 | -4.893  | 1.00 | 4.61  |
| ATOM | 881 | CD1 | PHE | A | 146 | 31.338 | 21.086 | -5.053  | 1.00 | 4.68  |
| ATOM | 882 | CD2 | PHE | A | 146 | 31.647 | 18.760 | -4.774  | 1.00 | 4.07  |
| ATOM | 883 | CE1 | PHE | A | 146 | 32.699 | 21.250 | -5.094  | 1.00 | 6.69  |

Figure 4R

| ATOM | 884 | CE2 | PHE | A | 146 | 32.989 | 18.914 | -4.815 | 1.00 | 2.42 |
| --- | --- | --- | --- | --- | --- | --- | --- | --- | --- | --- |
| ATOM | 885 | CZ | PHE | A | 146 | 33.527 | 20.150 | -4.975 | 1.00 | 3.42 |
| ATOM | 886 | C | PHE | A | 146 | 27.387 | 18.112 | -4.267 | 1.00 | 14.49 |
| ATOM | 887 | O | PHE | A | 146 | 26.542 | 18.509 | -5.063 | 1.00 | 19.13 |
| ATOM | 888 | N | ALA | A | 147 | 27.074 | 17.547 | -3.101 | 1.00 | 13.64 |
| ATOM | 889 | CA | ALA | A | 147 | 25.671 | 17.346 | -2.640 | 1.00 | 10.83 |
| ATOM | 890 | CB | ALA | A | 147 | 25.614 | 16.168 | -1.715 | 1.00 | 9.08 |
| ATOM | 891 | C | ALA | A | 147 | 25.084 | 18.593 | -1.940 | 1.00 | 11.80 |
| ATOM | 892 | O | ALA | A | 147 | 24.067 | 19.126 | -2.341 | 1.00 | 15.54 |
| ATOM | 893 | N | HIS | A | 148 | 25.733 | 19.031 | -0.862 | 1.00 | 12.59 |
| ATOM | 894 | CA | HIS | A | 148 | 25.300 | 20.234 | -0.089 | 1.00 | 10.63 |
| ATOM | 895 | CB | HIS | A | 148 | 23.987 | 19.958 | 0.619 | 1.00 | 10.37 |
| ATOM | 896 | CG | HIS | A | 148 | 24.047 | 18.808 | 1.577 | 1.00 | 19.25 |
| ATOM | 897 | CD2 | HIS | A | 148 | 23.866 | 17.477 | 1.389 | 1.00 | 23.23 |
| ATOM | 898 | ND1 | HIS | A | 148 | 24.283 | 18.967 | 2.926 | 1.00 | 26.01 |
| ATOM | 899 | CE1 | HIS | A | 148 | 24.244 | 17.791 | 3.527 | 1.00 | 23.57 |
| ATOM | 900 | NE2 | HIS | A | 148 | 23.992 | 16.869 | 2.615 | 1.00 | 25.40 |
| ATOM | 901 | C | HIS | A | 148 | 26.358 | 20.634 | 0.949 | 1.00 | 12.85 |
| ATOM | 902 | O | HIS | A | 148 | 27.342 | 19.912 | 1.222 | 1.00 | 10.96 |
| ATOM | 903 | N | VAL | A | 149 | 26.145 | 21.803 | 1.547 | 1.00 | 9.18 |
| ATOM | 904 | CA | VAL | A | 149 | 27.067 | 22.274 | 2.595 | 1.00 | 7.72 |
| ATOM | 905 | CB | VAL | A | 149 | 27.780 | 23.596 | 2.229 | 1.00 | 9.50 |
| ATOM | 906 | CG1 | VAL | A | 149 | 28.036 | 23.637 | 0.751 | 1.00 | 11.54 |
| ATOM | 907 | CG2 | VAL | A | 149 | 27.012 | 24.800 | 2.695 | 1.00 | 11.06 |
| ATOM | 908 | C | VAL | A | 149 | 26.277 | 22.435 | 3.880 | 1.00 | 7.39 |
| ATOM | 909 | O | VAL | A | 149 | 25.120 | 22.861 | 3.904 | 1.00 | 6.80 |
| ATOM | 910 | N | ALA | A | 150 | 26.916 | 22.032 | 4.964 | 1.00 | 7.47 |
| ATOM | 911 | CA | ALA | A | 150 | 26.302 | 22.093 | 6.270 | 1.00 | 5.81 |
| ATOM | 912 | CB | ALA | A | 150 | 26.244 | 20.710 | 6.876 | 1.00 | 2.00 |
| ATOM | 913 | C | ALA | A | 150 | 27.130 | 23.017 | 7.142 | 1.00 | 5.80 |
| ATOM | 914 | O | ALA | A | 150 | 28.347 | 23.019 | 7.091 | 1.00 | 15.09 |
| ATOM | 915 | N | LEU | A | 151 | 26.443 | 23.901 | 7.853 | 1.00 | 5.33 |
| ATOM | 916 | CA | LEU | A | 151 | 27.083 | 24.817 | 8.800 | 1.00 | 3.39 |
| ATOM | 917 | CB | LEU | A | 151 | 26.157 | 25.991 | 9.072 | 1.00 | 5.70 |
| ATOM | 918 | CG | LEU | A | 151 | 26.241 | 27.301 | 8.296 | 1.00 | 7.34 |
| ATOM | 919 | CD1 | LEU | A | 151 | 26.854 | 27.107 | 6.939 | 1.00 | 3.41 |
| ATOM | 920 | CD2 | LEU | A | 151 | 24.841 | 27.925 | 8.241 | 1.00 | 4.66 |
| ATOM | 921 | C | LEU | A | 151 | 27.204 | 23.934 | 10.043 | 1.00 | 3.49 |
| ATOM | 922 | O | LEU | A | 151 | 26.316 | 23.128 | 10.340 | 1.00 | 2.65 |
| ATOM | 923 | N | CYS | A | 152 | 28.306 | 24.058 | 10.770 | 1.00 | 5.06 |
| ATOM | 924 | CA | CYS | A | 152 | 28.482 | 23.240 | 11.983 | 1.00 | 2.81 |
| ATOM | 925 | CB | CYS | A | 152 | 28.884 | 21.838 | 11.561 | 1.00 | 2.00 |
| ATOM | 926 | SG | CYS | A | 152 | 30.351 | 21.833 | 10.545 | 1.00 | 12.33 |
| ATOM | 927 | C | CYS | A | 152 | 29.525 | 23.887 | 12.880 | 1.00 | 3.00 |
| ATOM | 928 | O | CYS | A | 152 | 30.084 | 24.917 | 12.574 | 1.00 | 6.88 |
| ATOM | 929 | N | ALA | A | 153 | 29.777 | 23.273 | 14.019 | 1.00 | 5.62 |
| ATOM | 930 | CA | ALA | A | 153 | 30.765 | 23.806 | 14.978 | 1.00 | 5.99 |
| ATOM | 931 | CB | ALA | A | 153 | 30.505 | 23.247 | 16.345 | 1.00 | 3.64 |
| ATOM | 932 | C | ALA | A | 153 | 32.198 | 23.519 | 14.579 | 1.00 | 4.87 |
| ATOM | 933 | O | ALA | A | 153 | 33.069 | 24.366 | 14.631 | 1.00 | 8.95 |
| ATOM | 934 | N | ILE | A | 154 | 32.449 | 22.278 | 14.209 | 1.00 | 3.33 |
| ATOM | 935 | CA | ILE | A | 154 | 33.791 | 21.856 | 13.831 | 1.00 | 6.57 |

Figure 4S

| ATOM | 936 | CB  | ILE A 154 | 34.519 | 21.214 | 15.065 | 1.00 | 13.23 |
|------|-----|-----|-----------|--------|--------|--------|------|-------|
| ATOM | 937 | CG2 | ILE A 154 | 35.849 | 20.661 | 14.679 | 1.00 | 15.20 |
| ATOM | 938 | CG1 | ILE A 154 | 34.742 | 22.247 | 16.184 | 1.00 | 17.08 |
| ATOM | 939 | CD1 | ILE A 154 | 35.736 | 23.354 | 15.845 | 1.00 | 21.42 |
| ATOM | 940 | C   | ILE A 154 | 33.620 | 20.837 | 12.671 | 1.00 | 8.07  |
| ATOM | 941 | O   | ILE A 154 | 32.935 | 19.820 | 12.802 | 1.00 | 6.60  |
| ATOM | 942 | N   | GLY A 155 | 34.206 | 21.179 | 11.516 | 1.00 | 7.25  |
| ATOM | 943 | CA  | GLY A 155 | 34.138 | 20.338 | 10.335 | 1.00 | 8.29  |
| ATOM | 944 | C   | GLY A 155 | 35.202 | 19.269 | 10.364 | 1.00 | 9.30  |
| ATOM | 945 | O   | GLY A 155 | 36.071 | 19.289 | 11.239 | 1.00 | 11.83 |
| ATOM | 946 | N   | ARG A 156 | 35.176 | 18.363 | 9.393  | 1.00 | 8.85  |
| ATOM | 947 | CA  | ARG A 156 | 36.182 | 17.277 | 9.359  | 1.00 | 10.92 |
| ATOM | 948 | CB  | ARG A 156 | 35.496 | 15.967 | 8.996  | 1.00 | 17.70 |
| ATOM | 949 | CG  | ARG A 156 | 34.400 | 15.595 | 9.973  | 1.00 | 20.67 |
| ATOM | 950 | CD  | ARG A 156 | 34.337 | 14.120 | 10.205 | 1.00 | 29.56 |
| ATOM | 951 | NE  | ARG A 156 | 34.168 | 13.376 | 8.965  | 1.00 | 41.87 |
| ATOM | 952 | CZ  | ARG A 156 | 34.645 | 12.149 | 8.765  | 1.00 | 50.41 |
| ATOM | 953 | NH1 | ARG A 156 | 34.438 | 11.536 | 7.603  | 1.00 | 51.55 |
| ATOM | 954 | NH2 | ARG A 156 | 35.340 | 11.537 | 9.724  | 1.00 | 54.89 |
| ATOM | 955 | C   | ARG A 156 | 37.420 | 17.537 | 8.476  | 1.00 | 10.96 |
| ATOM | 956 | O   | ARG A 156 | 38.466 | 16.913 | 8.597  | 1.00 | 13.19 |
| ATOM | 957 | N   | ARG A 157 | 37.278 | 18.458 | 7.547  | 1.00 | 9.18  |
| ATOM | 958 | CA  | ARG A 157 | 38.395 | 18.809 | 6.689  | 1.00 | 7.21  |
| ATOM | 959 | CB  | ARG A 157 | 37.889 | 19.001 | 5.268  | 1.00 | 3.14  |
| ATOM | 960 | CG  | ARG A 157 | 37.587 | 17.685 | 4.570  | 1.00 | 5.26  |
| ATOM | 961 | CD  | ARG A 157 | 37.501 | 17.781 | 3.034  | 1.00 | 5.80  |
| ATOM | 962 | NE  | ARG A 157 | 36.109 | 17.989 | 2.665  | 1.00 | 9.28  |
| ATOM | 963 | CZ  | ARG A 157 | 35.294 | 17.125 | 2.068  | 1.00 | 10.11 |
| ATOM | 964 | NH1 | ARG A 157 | 35.612 | 15.920 | 1.630  | 1.00 | 7.28  |
| ATOM | 965 | NH2 | ARG A 157 | 34.036 | 17.269 | 2.355  | 1.00 | 17.52 |
| ATOM | 966 | C   | ARG A 157 | 39.054 | 20.074 | 7.280  | 1.00 | 9.04  |
| ATOM | 967 | O   | ARG A 157 | 38.454 | 20.808 | 8.066  | 1.00 | 7.54  |
| ATOM | 968 | N   | LEU A 158 | 40.319 | 20.283 | 6.932  | 1.00 | 6.31  |
| ATOM | 969 | CA  | LEU A 158 | 41.091 | 21.432 | 7.439  | 1.00 | 2.00  |
| ATOM | 970 | CB  | LEU A 158 | 42.568 | 21.158 | 7.234  | 1.00 | 2.00  |
| ATOM | 971 | CG  | LEU A 158 | 43.293 | 20.467 | 8.376  | 1.00 | 5.80  |
| ATOM | 972 | CD1 | LEU A 158 | 42.343 | 19.641 | 9.242  | 1.00 | 6.29  |
| ATOM | 973 | CD2 | LEU A 158 | 44.370 | 19.612 | 7.804  | 1.00 | 2.00  |
| ATOM | 974 | C   | LEU A 158 | 40.711 | 22.761 | 6.823  | 1.00 | 5.67  |
| ATOM | 975 | O   | LEU A 158 | 40.080 | 22.835 | 5.778  | 1.00 | 7.66  |
| ATOM | 976 | N   | GLY A 159 | 41.160 | 23.830 | 7.473  | 1.00 | 5.29  |
| ATOM | 977 | CA  | GLY A 159 | 40.894 | 25.173 | 7.002  | 1.00 | 6.28  |
| ATOM | 978 | C   | GLY A 159 | 39.459 | 25.541 | 6.686  | 1.00 | 8.92  |
| ATOM | 979 | O   | GLY A 159 | 39.219 | 26.610 | 6.096  | 1.00 | 12.32 |
| ATOM | 980 | N   | THR A 160 | 38.503 | 24.739 | 7.154  | 1.00 | 3.52  |
| ATOM | 981 | CA  | THR A 160 | 37.093 | 25.016 | 6.878  | 1.00 | 2.40  |
| ATOM | 982 | CB  | THR A 160 | 36.277 | 23.746 | 6.799  | 1.00 | 4.71  |
| ATOM | 983 | OG1 | THR A 160 | 36.602 | 22.888 | 7.903  | 1.00 | 2.00  |
| ATOM | 984 | CG2 | THR A 160 | 36.540 | 23.050 | 5.490  | 1.00 | 2.00  |
| ATOM | 985 | C   | THR A 160 | 36.412 | 25.949 | 7.837  | 1.00 | 4.22  |
| ATOM | 986 | O   | THR A 160 | 35.346 | 25.662 | 8.349  | 1.00 | 7.62  |
| ATOM | 987 | N   | ILE A 161 | 37.009 | 27.101 | 8.068  | 1.00 | 2.82  |

Figure 4T

| ATOM | 988 | CA | ILE A 161 | 36.397 | 28.064 | 8.963 | 1.00 | 3.28 |
|---|---|---|---|---|---|---|---|---|
| ATOM | 989 | CB | ILE A 161 | 37.437 | 28.672 | 9.857 | 1.00 | 2.00 |
| ATOM | 990 | CG2 | ILE A 161 | 36.878 | 29.842 | 10.580 | 1.00 | 2.00 |
| ATOM | 991 | CG1 | ILE A 161 | 37.919 | 27.623 | 10.853 | 1.00 | 2.99 |
| ATOM | 992 | CD1 | ILE A 161 | 36.891 | 27.160 | 11.792 | 1.00 | 2.00 |
| ATOM | 993 | C | ILE A 161 | 35.779 | 29.109 | 8.053 | 1.00 | 6.97 |
| ATOM | 994 | O | ILE A 161 | 36.444 | 29.599 | 7.133 | 1.00 | 9.59 |
| ATOM | 995 | N | VAL A 162 | 34.500 | 29.420 | 8.286 | 1.00 | 5.77 |
| ATOM | 996 | CA | VAL A 162 | 33.770 | 30.408 | 7.447 | 1.00 | 5.15 |
| ATOM | 997 | CB | VAL A 162 | 32.365 | 29.916 | 7.046 | 1.00 | 2.00 |
| ATOM | 998 | CG1 | VAL A 162 | 32.462 | 28.600 | 6.303 | 1.00 | 2.00 |
| ATOM | 999 | CG2 | VAL A 162 | 31.496 | 29.786 | 8.267 | 1.00 | 2.00 |
| ATOM | 1000 | C | VAL A 162 | 33.646 | 31.801 | 8.078 | 1.00 | 7.04 |
| ATOM | 1001 | O | VAL A 162 | 33.995 | 32.031 | 9.224 | 1.00 | 12.34 |
| ATOM | 1002 | N | THR A 163 | 33.154 | 32.733 | 7.265 | 1.00 | 10.55 |
| ATOM | 1003 | CA | THR A 163 | 32.935 | 34.153 | 7.619 | 1.00 | 5.79 |
| ATOM | 1004 | CB | THR A 163 | 33.805 | 35.069 | 6.743 | 1.00 | 2.00 |
| ATOM | 1005 | OG1 | THR A 163 | 35.168 | 34.996 | 7.158 | 1.00 | 10.28 |
| ATOM | 1006 | CG2 | THR A 163 | 33.376 | 36.457 | 6.870 | 1.00 | 9.64 |
| ATOM | 1007 | C | THR A 163 | 31.462 | 34.462 | 7.269 | 1.00 | 7.38 |
| ATOM | 1008 | O | THR A 163 | 30.920 | 33.997 | 6.268 | 1.00 | 9.26 |
| ATOM | 1009 | N | TYR A 164 | 30.828 | 35.273 | 8.104 | 1.00 | 6.43 |
| ATOM | 1010 | CA | TYR A 164 | 29.425 | 35.671 | 7.910 | 1.00 | 2.00 |
| ATOM | 1011 | CB | TYR A 164 | 28.555 | 35.167 | 9.057 | 1.00 | 5.35 |
| ATOM | 1012 | CG | TYR A 164 | 28.398 | 33.674 | 9.212 | 1.00 | 3.93 |
| ATOM | 1013 | CD1 | TYR A 164 | 29.240 | 32.945 | 10.051 | 1.00 | 10.71 |
| ATOM | 1014 | CE1 | TYR A 164 | 29.039 | 31.590 | 10.263 | 1.00 | 3.10 |
| ATOM | 1015 | CD2 | TYR A 164 | 27.365 | 33.003 | 8.587 | 1.00 | 2.00 |
| ATOM | 1016 | CE2 | TYR A 164 | 27.163 | 31.656 | 8.794 | 1.00 | 2.00 |
| ATOM | 1017 | CZ | TYR A 164 | 27.994 | 30.957 | 9.631 | 1.00 | 2.00 |
| ATOM | 1018 | OH | TYR A 164 | 27.757 | 29.617 | 9.848 | 1.00 | 7.05 |
| ATOM | 1019 | C | TYR A 164 | 29.350 | 37.181 | 7.918 | 1.00 | 2.77 |
| ATOM | 1020 | O | TYR A 164 | 29.950 | 37.836 | 8.750 | 1.00 | 5.86 |
| ATOM | 1021 | N | ASP A 165 | 28.603 | 37.754 | 6.991 | 1.00 | 3.90 |
| ATOM | 1022 | CA | ASP A 165 | 28.437 | 39.221 | 6.997 | 1.00 | 5.48 |
| ATOM | 1023 | CB | ASP A 165 | 29.675 | 39.950 | 6.514 | 1.00 | 6.87 |
| ATOM | 1024 | CG | ASP A 165 | 29.963 | 41.194 | 7.343 | 1.00 | 6.94 |
| ATOM | 1025 | OD1 | ASP A 165 | 29.217 | 42.183 | 7.246 | 1.00 | 10.37 |
| ATOM | 1026 | OD2 | ASP A 165 | 30.935 | 41.186 | 8.112 | 1.00 | 13.48 |
| ATOM | 1027 | C | ASP A 165 | 27.220 | 39.603 | 6.182 | 1.00 | 5.17 |
| ATOM | 1028 | O | ASP A 165 | 26.632 | 38.767 | 5.512 | 1.00 | 10.46 |
| ATOM | 1029 | N | THR A 166 | 26.805 | 40.860 | 6.288 | 1.00 | 2.54 |
| ATOM | 1030 | CA | THR A 166 | 25.605 | 41.331 | 5.564 | 1.00 | 8.12 |
| ATOM | 1031 | CB | THR A 166 | 24.839 | 42.392 | 6.361 | 1.00 | 8.39 |
| ATOM | 1032 | OG1 | THR A 166 | 25.734 | 43.462 | 6.710 | 1.00 | 7.48 |
| ATOM | 1033 | CG2 | THR A 166 | 24.245 | 41.778 | 7.612 | 1.00 | 3.71 |
| ATOM | 1034 | C | THR A 166 | 25.901 | 41.883 | 4.171 | 1.00 | 9.37 |
| ATOM | 1035 | O | THR A 166 | 25.077 | 42.532 | 3.532 | 1.00 | 11.11 |
| ATOM | 1036 | N | SER A 167 | 27.116 | 41.645 | 3.704 | 1.00 | 9.87 |
| ATOM | 1037 | CA | SER A 167 | 27.503 | 42.089 | 2.361 | 1.00 | 6.92 |
| ATOM | 1038 | CB | SER A 167 | 28.132 | 43.460 | 2.430 | 1.00 | 8.33 |
| ATOM | 1039 | OG | SER A 167 | 29.523 | 43.410 | 2.230 | 1.00 | 16.34 |

Figure 4U

| ATOM | 1040 | C   | SER | A | 167 | 28.468 | 41.029 | 1.885  | 1.00 | 8.44  |
|------|------|-----|-----|---|-----|--------|--------|--------|------|-------|
| ATOM | 1041 | O   | SER | A | 167 | 29.252 | 40.491 | 2.655  | 1.00 | 12.99 |
| ATOM | 1042 | N   | LEU | A | 168 | 28.379 | 40.676 | 0.611  | 1.00 | 8.80  |
| ATOM | 1043 | CA  | LEU | A | 168 | 29.280 | 39.636 | 0.069  | 1.00 | 10.94 |
| ATOM | 1044 | CB  | LEU | A | 168 | 28.897 | 39.309 | -1.370 | 1.00 | 5.14  |
| ATOM | 1045 | CG  | LEU | A | 168 | 29.694 | 38.235 | -2.092 | 1.00 | 3.65  |
| ATOM | 1046 | CD1 | LEU | A | 168 | 28.868 | 37.674 | -3.190 | 1.00 | 13.15 |
| ATOM | 1047 | CD2 | LEU | A | 168 | 30.944 | 38.825 | -2.696 | 1.00 | 16.58 |
| ATOM | 1048 | C   | LEU | A | 168 | 30.741 | 40.078 | 0.194  | 1.00 | 9.88  |
| ATOM | 1049 | O   | LEU | A | 168 | 31.588 | 39.384 | 0.724  | 1.00 | 15.05 |
| ATOM | 1050 | N   | ASP | A | 169 | 30.987 | 41.311 | -0.219 | 1.00 | 12.69 |
| ATOM | 1051 | CA  | ASP | A | 169 | 32.339 | 41.918 | -0.177 | 1.00 | 11.13 |
| ATOM | 1052 | CB  | ASP | A | 169 | 32.272 | 43.354 | -0.694 | 1.00 | 10.36 |
| ATOM | 1053 | CG  | ASP | A | 169 | 32.399 | 43.443 | -2.193 | 1.00 | 12.34 |
| ATOM | 1054 | OD1 | ASP | A | 169 | 32.686 | 44.547 | -2.701 | 1.00 | 19.74 |
| ATOM | 1055 | OD2 | ASP | A | 169 | 32.227 | 42.423 | -2.876 | 1.00 | 14.21 |
| ATOM | 1056 | C   | ASP | A | 169 | 32.948 | 41.873 | 1.225  | 1.00 | 10.65 |
| ATOM | 1057 | O   | ASP | A | 169 | 34.134 | 41.626 | 1.411  | 1.00 | 9.59  |
| ATOM | 1058 | N   | ALA | A | 170 | 32.095 | 42.098 | 2.221  | 1.00 | 10.94 |
| ATOM | 1059 | CA  | ALA | A | 170 | 32.530 | 42.107 | 3.633  | 1.00 | 7.86  |
| ATOM | 1060 | CB  | ALA | A | 170 | 31.515 | 42.782 | 4.477  | 1.00 | 12.83 |
| ATOM | 1061 | C   | ALA | A | 170 | 32.780 | 40.702 | 4.156  | 1.00 | 7.65  |
| ATOM | 1062 | O   | ALA | A | 170 | 33.551 | 40.492 | 5.081  | 1.00 | 10.44 |
| ATOM | 1063 | N   | ALA | A | 171 | 32.090 | 39.737 | 3.566  | 1.00 | 3.95  |
| ATOM | 1064 | CA  | ALA | A | 171 | 32.241 | 38.347 | 3.955  | 1.00 | 2.00  |
| ATOM | 1065 | CB  | ALA | A | 171 | 31.040 | 37.559 | 3.493  | 1.00 | 4.68  |
| ATOM | 1066 | C   | ALA | A | 171 | 33.536 | 37.766 | 3.354  | 1.00 | 5.20  |
| ATOM | 1067 | O   | ALA | A | 171 | 34.199 | 36.918 | 3.946  | 1.00 | 8.71  |
| ATOM | 1068 | N   | ILE | A | 172 | 33.904 | 38.215 | 2.158  | 1.00 | 4.62  |
| ATOM | 1069 | CA  | ILE | A | 172 | 35.138 | 37.689 | 1.538  | 1.00 | 7.44  |
| ATOM | 1070 | CB  | ILE | A | 172 | 35.016 | 37.510 | -0.014 | 1.00 | 7.03  |
| ATOM | 1071 | CG2 | ILE | A | 172 | 33.634 | 37.052 | -0.361 | 1.00 | 10.50 |
| ATOM | 1072 | CG1 | ILE | A | 172 | 35.273 | 38.802 | -0.780 | 1.00 | 5.94  |
| ATOM | 1073 | CD1 | ILE | A | 172 | 35.114 | 38.641 | -2.290 | 1.00 | 2.00  |
| ATOM | 1074 | C   | ILE | A | 172 | 36.432 | 38.434 | 1.909  | 1.00 | 6.82  |
| ATOM | 1075 | O   | ILE | A | 172 | 37.525 | 37.872 | 1.979  | 1.00 | 11.31 |
| ATOM | 1076 | N   | ALA | A | 173 | 36.296 | 39.685 | 2.326  | 1.00 | 6.16  |
| ATOM | 1077 | CA  | ALA | A | 173 | 37.472 | 40.531 | 2.709  | 1.00 | 5.51  |
| ATOM | 1078 | CB  | ALA | A | 173 | 37.022 | 41.903 | 3.147  | 1.00 | 7.11  |
| ATOM | 1079 | C   | ALA | A | 173 | 38.457 | 39.940 | 3.712  | 1.00 | 5.49  |
| ATOM | 1080 | O   | ALA | A | 173 | 39.651 | 40.219 | 3.693  | 1.00 | 10.38 |
| ATOM | 1081 | N   | PRO | A | 174 | 37.969 | 39.179 | 4.735  | 1.00 | 3.89  |
| ATOM | 1082 | CD  | PRO | A | 174 | 36.611 | 39.047 | 5.286  | 1.00 | 2.26  |
| ATOM | 1083 | CA  | PRO | A | 174 | 38.941 | 38.628 | 5.689  | 1.00 | 2.00  |
| ATOM | 1084 | CB  | PRO | A | 174 | 38.075 | 38.045 | 6.791  | 1.00 | 2.00  |
| ATOM | 1085 | CG  | PRO | A | 174 | 36.907 | 38.932 | 6.769  | 1.00 | 3.89  |
| ATOM | 1086 | C   | PRO | A | 174 | 39.786 | 37.536 | 5.074  | 1.00 | 2.00  |
| ATOM | 1087 | O   | PRO | A | 174 | 40.638 | 36.968 | 5.726  | 1.00 | 8.03  |
| ATOM | 1088 | N   | PHE | A | 175 | 39.487 | 37.172 | 3.835  | 1.00 | 2.90  |
| ATOM | 1089 | CA  | PHE | A | 175 | 40.278 | 36.139 | 3.159  | 1.00 | 6.14  |
| ATOM | 1090 | CB  | PHE | A | 175 | 39.376 | 35.292 | 2.295  | 1.00 | 6.27  |
| ATOM | 1091 | CG  | PHE | A | 175 | 38.504 | 34.388 | 3.084  | 1.00 | 4.47  |

Figure 4V

| ATOM | 1092 | CD1 | PHE | A | 175 | 38.954 | 33.114 | 3.433 | 1.00 | 2.00 |
|------|------|-----|-----|---|-----|--------|--------|-------|------|------|
| ATOM | 1093 | CD2 | PHE | A | 175 | 37.256 | 34.823 | 3.533 | 1.00 | 3.94 |
| ATOM | 1094 | CE1 | PHE | A | 175 | 38.186 | 32.287 | 4.216 | 1.00 | 2.00 |
| ATOM | 1095 | CE2 | PHE | A | 175 | 36.465 | 34.004 | 4.323 | 1.00 | 3.94 |
| ATOM | 1096 | CZ | PHE | A | 175 | 36.933 | 32.722 | 4.669 | 1.00 | 3.73 |
| ATOM | 1097 | C | PHE | A | 175 | 41.380 | 36.809 | 2.365 | 1.00 | 9.75 |
| ATOM | 1098 | O | PHE | A | 175 | 41.177 | 37.353 | 1.288 | 1.00 | 10.92 |
| ATOM | 1099 | N | ARG | A | 176 | 42.559 | 36.816 | 2.977 | 1.00 | 13.95 |
| ATOM | 1100 | CA | ARG | A | 176 | 43.751 | 37.439 | 2.400 | 1.00 | 12.43 |
| ATOM | 1101 | CB | ARG | A | 176 | 44.627 | 37.929 | 3.533 | 1.00 | 8.86 |
| ATOM | 1102 | CG | ARG | A | 176 | 43.912 | 38.821 | 4.513 | 1.00 | 9.09 |
| ATOM | 1103 | CD | ARG | A | 176 | 43.539 | 40.149 | 3.916 | 1.00 | 13.20 |
| ATOM | 1104 | NE | ARG | A | 176 | 42.418 | 40.731 | 4.644 | 1.00 | 17.45 |
| ATOM | 1105 | CZ | ARG | A | 176 | 42.535 | 41.620 | 5.624 | 1.00 | 16.50 |
| ATOM | 1106 | NH1 | ARG | A | 176 | 41.463 | 42.094 | 6.247 | 1.00 | 16.11 |
| ATOM | 1107 | NH2 | ARG | A | 176 | 43.718 | 42.063 | 5.960 | 1.00 | 12.86 |
| ATOM | 1108 | C | ARG | A | 176 | 44.543 | 36.532 | 1.441 | 1.00 | 18.03 |
| ATOM | 1109 | O | ARG | A | 176 | 45.286 | 36.994 | 0.587 | 1.00 | 21.73 |
| ATOM | 1110 | N | HIS | A | 177 | 44.426 | 35.221 | 1.595 | 1.00 | 21.39 |
| ATOM | 1111 | CA | HIS | A | 177 | 45.171 | 34.323 | 0.672 | 1.00 | 25.17 |
| ATOM | 1112 | CB | HIS | A | 177 | 45.790 | 33.156 | 1.429 | 1.00 | 33.05 |
| ATOM | 1113 | CG | HIS | A | 177 | 46.738 | 33.579 | 2.506 | 1.00 | 44.14 |
| ATOM | 1114 | CD2 | HIS | A | 177 | 47.160 | 32.935 | 3.623 | 1.00 | 48.92 |
| ATOM | 1115 | ND1 | HIS | A | 177 | 47.348 | 34.817 | 2.522 | 1.00 | 45.03 |
| ATOM | 1116 | CE1 | HIS | A | 177 | 48.098 | 34.923 | 3.601 | 1.00 | 47.09 |
| ATOM | 1117 | NE2 | HIS | A | 177 | 48.005 | 33.796 | 4.287 | 1.00 | 50.79 |
| ATOM | 1118 | C | HIS | A | 177 | 44.203 | 33.831 | -0.391 | 1.00 | 25.38 |
| ATOM | 1119 | O | HIS | A | 177 | 43.909 | 32.648 | -0.520 | 1.00 | 28.71 |
| ATOM | 1120 | N | LEU | A | 178 | 43.681 | 34.780 | -1.154 | 1.00 | 23.91 |
| ATOM | 1121 | CA | LEU | A | 178 | 42.701 | 34.468 | -2.211 | 1.00 | 22.54 |
| ATOM | 1122 | CB | LEU | A | 178 | 41.331 | 34.999 | -1.795 | 1.00 | 19.32 |
| ATOM | 1123 | CG | LEU | A | 178 | 40.121 | 34.072 | -1.941 | 1.00 | 17.09 |
| ATOM | 1124 | CD1 | LEU | A | 178 | 40.298 | 32.847 | -1.069 | 1.00 | 11.07 |
| ATOM | 1125 | CD2 | LEU | A | 178 | 38.874 | 34.820 | -1.536 | 1.00 | 9.82 |
| ATOM | 1126 | C | LEU | A | 178 | 43.127 | 35.049 | -3.570 | 1.00 | 23.94 |
| ATOM | 1127 | O | LEU | A | 178 | 43.453 | 36.226 | -3.731 | 1.00 | 29.67 |
| ATOM | 1128 | N | ASP | A | 179 | 43.163 | 34.178 | -4.562 | 1.00 | 21.90 |
| ATOM | 1129 | CA | ASP | A | 179 | 43.534 | 34.603 | -5.903 | 1.00 | 19.53 |
| ATOM | 1130 | CB | ASP | A | 179 | 43.448 | 33.410 | -6.835 | 1.00 | 20.21 |
| ATOM | 1131 | CG | ASP | A | 179 | 44.181 | 33.619 | -8.116 | 1.00 | 19.59 |
| ATOM | 1132 | OD1 | ASP | A | 179 | 43.783 | 34.499 | -8.900 | 1.00 | 16.37 |
| ATOM | 1133 | OD2 | ASP | A | 179 | 45.153 | 32.883 | -8.345 | 1.00 | 23.15 |
| ATOM | 1134 | C | ASP | A | 179 | 42.553 | 35.719 | -6.307 | 1.00 | 24.43 |
| ATOM | 1135 | O | ASP | A | 179 | 41.355 | 35.691 | -6.008 | 1.00 | 22.22 |
| ATOM | 1136 | N | PRO | A | 180 | 43.084 | 36.763 | -6.957 | 1.00 | 27.44 |
| ATOM | 1137 | CD | PRO | A | 180 | 44.521 | 36.981 | -7.209 | 1.00 | 26.55 |
| ATOM | 1138 | CA | PRO | A | 180 | 42.299 | 37.908 | -7.430 | 1.00 | 24.01 |
| ATOM | 1139 | CB | PRO | A | 180 | 43.327 | 38.702 | -8.202 | 1.00 | 24.07 |
| ATOM | 1140 | CG | PRO | A | 180 | 44.575 | 38.455 | -7.419 | 1.00 | 26.33 |
| ATOM | 1141 | C | PRO | A | 180 | 41.152 | 37.461 | -8.330 | 1.00 | 22.37 |
| ATOM | 1142 | O | PRO | A | 180 | 40.064 | 38.011 | -8.321 | 1.00 | 26.56 |
| ATOM | 1143 | N | ALA | A | 181 | 41.421 | 36.444 | -9.138 | 1.00 | 20.29 |

Figure 4W

| ATOM | 1144 | CA | ALA | A | 181 | 40.403 | 35.897 | -10.058 | 1.00 | 19.95 |
|------|------|------|------|---|-----|--------|--------|---------|------|-------|
| ATOM | 1145 | CB | ALA | A | 181 | 40.999 | 34.814 | -10.920 | 1.00 | 20.81 |
| ATOM | 1146 | C | ALA | A | 181 | 39.229 | 35.329 | -9.269 | 1.00 | 18.58 |
| ATOM | 1147 | O | ALA | A | 181 | 38.070 | 35.541 | -9.593 | 1.00 | 25.43 |
| ATOM | 1148 | N | THR | A | 182 | 39.538 | 34.601 | -8.208 | 1.00 | 14.88 |
| ATOM | 1149 | CA | THR | A | 182 | 38.484 | 34.012 | -7.376 | 1.00 | 14.96 |
| ATOM | 1150 | CB | THR | A | 182 | 39.067 | 33.282 | -6.138 | 1.00 | 12.63 |
| ATOM | 1151 | OG1 | THR | A | 182 | 40.015 | 32.324 | -6.638 | 1.00 | 4.87 |
| ATOM | 1152 | CG2 | THR | A | 182 | 37.961 | 32.559 | -5.423 | 1.00 | 7.24 |
| ATOM | 1153 | C | THR | A | 182 | 37.515 | 35.083 | -6.893 | 1.00 | 16.50 |
| ATOM | 1154 | O | THR | A | 182 | 36.296 | 34.960 | -7.015 | 1.00 | 16.74 |
| ATOM | 1155 | N | ARG | A | 183 | 38.083 | 36.171 | -6.337 | 1.00 | 15.79 |
| ATOM | 1156 | CA | ARG | A | 183 | 37.271 | 37.290 | -5.909 | 1.00 | 16.39 |
| ATOM | 1157 | CB | ARG | A | 183 | 38.162 | 38.392 | -5.392 | 1.00 | 13.25 |
| ATOM | 1158 | CG | ARG | A | 183 | 38.990 | 37.955 | -4.291 | 1.00 | 12.26 |
| ATOM | 1159 | CD | ARG | A | 183 | 39.787 | 39.094 | -3.834 | 1.00 | 25.61 |
| ATOM | 1160 | NE | ARG | A | 183 | 40.577 | 38.678 | -2.690 | 1.00 | 47.35 |
| ATOM | 1161 | CZ | ARG | A | 183 | 41.857 | 38.984 | -2.511 | 1.00 | 55.77 |
| ATOM | 1162 | NH1 | ARG | A | 183 | 42.493 | 38.548 | -1.424 | 1.00 | 58.95 |
| ATOM | 1163 | NH2 | ARG | A | 183 | 42.494 | 39.723 | -3.416 | 1.00 | 61.87 |
| ATOM | 1164 | C | ARG | A | 183 | 36.375 | 37.823 | -7.015 | 1.00 | 17.57 |
| ATOM | 1165 | O | ARG | A | 183 | 35.167 | 37.929 | -6.874 | 1.00 | 22.70 |
| ATOM | 1166 | N | GLU | A | 184 | 36.980 | 38.144 | -8.142 | 1.00 | 20.09 |
| ATOM | 1167 | CA | GLU | A | 184 | 36.204 | 38.694 | -9.272 | 1.00 | 26.95 |
| ATOM | 1168 | CB | GLU | A | 184 | 37.170 | 39.212 | -10.346 | 1.00 | 33.24 |
| ATOM | 1169 | CG | GLU | A | 184 | 36.588 | 40.359 | -11.193 | 1.00 | 46.75 |
| ATOM | 1170 | CD | GLU | A | 184 | 35.811 | 41.419 | -10.362 | 1.00 | 51.03 |
| ATOM | 1171 | OE1 | GLU | A | 184 | 36.437 | 42.126 | -9.535 | 1.00 | 47.53 |
| ATOM | 1172 | OE2 | GLU | A | 184 | 34.570 | 41.544 | -10.547 | 1.00 | 51.44 |
| ATOM | 1173 | C | GLU | A | 184 | 35.146 | 37.720 | -9.860 | 1.00 | 21.35 |
| ATOM | 1174 | O | GLU | A | 184 | 34.106 | 38.106 | -10.393 | 1.00 | 20.09 |
| ATOM | 1175 | N | GLY | A | 185 | 35.402 | 36.437 | -9.690 | 1.00 | 16.92 |
| ATOM | 1176 | CA | GLY | A | 185 | 34.488 | 35.450 | -10.216 | 1.00 | 15.65 |
| ATOM | 1177 | C | GLY | A | 185 | 33.372 | 35.135 | -9.256 | 1.00 | 14.47 |
| ATOM | 1178 | O | GLY | A | 185 | 32.233 | 34.941 | -9.653 | 1.00 | 12.70 |
| ATOM | 1179 | N | VAL | A | 186 | 33.695 | 35.127 | -7.974 | 1.00 | 15.32 |
| ATOM | 1180 | CA | VAL | A | 186 | 32.705 | 34.802 | -6.938 | 1.00 | 16.00 |
| ATOM | 1181 | CB | VAL | A | 186 | 33.391 | 34.447 | -5.609 | 1.00 | 14.82 |
| ATOM | 1182 | CG1 | VAL | A | 186 | 33.689 | 35.677 | -4.794 | 1.00 | 15.65 |
| ATOM | 1183 | CG2 | VAL | A | 186 | 32.558 | 33.483 | -4.874 | 1.00 | 13.63 |
| ATOM | 1184 | C | VAL | A | 186 | 31.690 | 35.929 | -6.756 | 1.00 | 15.03 |
| ATOM | 1185 | O | VAL | A | 186 | 30.565 | 35.732 | -6.307 | 1.00 | 13.19 |
| ATOM | 1186 | N | ARG | A | 187 | 32.118 | 37.132 | -7.117 | 1.00 | 14.81 |
| ATOM | 1187 | CA | ARG | A | 187 | 31.253 | 38.326 | -7.039 | 1.00 | 17.48 |
| ATOM | 1188 | CB | ARG | A | 187 | 32.085 | 39.592 | -7.084 | 1.00 | 12.71 |
| ATOM | 1189 | CG | ARG | A | 187 | 32.845 | 39.920 | -5.837 | 1.00 | 17.80 |
| ATOM | 1190 | CD | ARG | A | 187 | 33.473 | 41.298 | -5.983 | 1.00 | 16.35 |
| ATOM | 1191 | NE | ARG | A | 187 | 34.205 | 41.709 | -4.791 | 1.00 | 18.26 |
| ATOM | 1192 | CZ | ARG | A | 187 | 35.517 | 41.941 | -4.753 | 1.00 | 19.23 |
| ATOM | 1193 | NH1 | ARG | A | 187 | 36.091 | 42.308 | -3.616 | 1.00 | 18.29 |
| ATOM | 1194 | NH2 | ARG | A | 187 | 36.263 | 41.794 | -5.838 | 1.00 | 16.42 |
| ATOM | 1195 | C | ARG | A | 187 | 30.266 | 38.337 | -8.226 | 1.00 | 23.14 |

Figure 4X

| ATOM | 1196 | O | ARG | A | 187 | 29.100 | 38.725 | -8.118 | 1.00 | 26.11 |
|---|---|---|---|---|---|---|---|---|---|---|
| ATOM | 1197 | N | ARG | A | 188 | 30.787 | 37.940 | -9.383 | 1.00 | 23.78 |
| ATOM | 1198 | CA | ARG | A | 188 | 30.015 | 37.897 | -10.636 | 1.00 | 22.60 |
| ATOM | 1199 | CB | ARG | A | 188 | 30.970 | 37.659 | -11.809 | 1.00 | 27.05 |
| ATOM | 1200 | CG | ARG | A | 188 | 30.412 | 38.067 | -13.169 | 1.00 | 36.79 |
| ATOM | 1201 | CD | ARG | A | 188 | 30.536 | 36.945 | -14.192 | 1.00 | 42.25 |
| ATOM | 1202 | NE | ARG | A | 188 | 31.880 | 36.380 | -14.186 | 1.00 | 53.44 |
| ATOM | 1203 | CZ | ARG | A | 188 | 32.157 | 35.077 | -14.147 | 1.00 | 58.14 |
| ATOM | 1204 | NH1 | ARG | A | 188 | 33.424 | 34.675 | -14.135 | 1.00 | 62.47 |
| ATOM | 1205 | NH2 | ARG | A | 188 | 31.178 | 34.175 | -14.129 | 1.00 | 60.10 |
| ATOM | 1206 | C | ARG | A | 188 | 28.934 | 36.817 | -10.561 | 1.00 | 17.88 |
| ATOM | 1207 | O | ARG | A | 188 | 27.764 | 37.070 | -10.744 | 1.00 | 18.25 |
| ATOM | 1208 | N | GLU | A | 189 | 29.341 | 35.599 | -10.253 | 1.00 | 16.74 |
| ATOM | 1209 | CA | GLU | A | 189 | 28.384 | 34.507 | -10.154 | 1.00 | 16.68 |
| ATOM | 1210 | CB | GLU | A | 189 | 29.102 | 33.198 | -9.889 | 1.00 | 20.29 |
| ATOM | 1211 | CG | GLU | A | 189 | 30.013 | 32.735 | -11.008 | 1.00 | 30.56 |
| ATOM | 1212 | CD | GLU | A | 189 | 30.724 | 31.427 | -10.676 | 1.00 | 35.90 |
| ATOM | 1213 | OE1 | GLU | A | 189 | 31.854 | 31.221 | -11.186 | 1.00 | 36.83 |
| ATOM | 1214 | OE2 | GLU | A | 189 | 30.163 | 30.616 | -9.896 | 1.00 | 34.40 |
| ATOM | 1215 | C | GLU | A | 189 | 27.348 | 34.772 | -9.068 | 1.00 | 17.17 |
| ATOM | 1216 | O | GLU | A | 189 | 26.152 | 34.669 | -9.286 | 1.00 | 20.31 |
| ATOM | 1217 | N | ALA | A | 190 | 27.818 | 35.165 | -7.890 | 1.00 | 18.80 |
| ATOM | 1218 | CA | ALA | A | 190 | 26.915 | 35.420 | -6.730 | 1.00 | 17.03 |
| ATOM | 1219 | CB | ALA | A | 190 | 27.716 | 35.814 | -5.526 | 1.00 | 8.57 |
| ATOM | 1220 | C | ALA | A | 190 | 25.779 | 36.434 | -6.996 | 1.00 | 18.28 |
| ATOM | 1221 | O | ALA | A | 190 | 24.653 | 36.283 | -6.512 | 1.00 | 22.32 |
| ATOM | 1222 | N | ALA | A | 191 | 26.078 | 37.460 | -7.786 | 1.00 | 15.88 |
| ATOM | 1223 | CA | ALA | A | 191 | 25.068 | 38.496 | -8.136 | 1.00 | 17.67 |
| ATOM | 1224 | CB | ALA | A | 191 | 25.735 | 39.624 | -8.827 | 1.00 | 17.65 |
| ATOM | 1225 | C | ALA | A | 191 | 23.951 | 37.923 | -9.044 | 1.00 | 22.08 |
| ATOM | 1226 | O | ALA | A | 191 | 22.757 | 38.224 | -8.918 | 1.00 | 19.90 |
| ATOM | 1227 | N | GLU | A | 192 | 24.376 | 37.129 | -10.020 | 1.00 | 22.14 |
| ATOM | 1228 | CA | GLU | A | 192 | 23.431 | 36.504 | -10.935 | 1.00 | 24.00 |
| ATOM | 1229 | CB | GLU | A | 192 | 24.170 | 35.797 | -12.060 | 1.00 | 32.01 |
| ATOM | 1230 | CG | GLU | A | 192 | 24.990 | 36.720 | -12.955 | 1.00 | 43.84 |
| ATOM | 1231 | CD | GLU | A | 192 | 25.704 | 35.981 | -14.100 | 1.00 | 53.54 |
| ATOM | 1232 | OE1 | GLU | A | 192 | 25.543 | 34.735 | -14.237 | 1.00 | 54.40 |
| ATOM | 1233 | OE2 | GLU | A | 192 | 26.434 | 36.661 | -14.868 | 1.00 | 57.99 |
| ATOM | 1234 | C | GLU | A | 192 | 22.591 | 35.525 | -10.139 | 1.00 | 22.11 |
| ATOM | 1235 | O | GLU | A | 192 | 21.383 | 35.623 | -10.072 | 1.00 | 22.31 |
| ATOM | 1236 | N | ALA | A | 193 | 23.275 | 34.602 | -9.475 | 1.00 | 23.96 |
| ATOM | 1237 | CA | ALA | A | 193 | 22.627 | 33.558 | -8.647 | 1.00 | 21.81 |
| ATOM | 1238 | CB | ALA | A | 193 | 23.647 | 32.818 | -7.840 | 1.00 | 23.12 |
| ATOM | 1239 | C | ALA | A | 193 | 21.587 | 34.165 | -7.724 | 1.00 | 24.47 |
| ATOM | 1240 | O | ALA | A | 193 | 20.495 | 33.629 | -7.541 | 1.00 | 27.41 |
| ATOM | 1241 | N | GLU | A | 194 | 21.932 | 35.300 | -7.135 | 1.00 | 22.78 |
| ATOM | 1242 | CA | GLU | A | 194 | 20.998 | 35.976 | -6.241 | 1.00 | 26.02 |
| ATOM | 1243 | CB | GLU | A | 194 | 21.637 | 37.184 | -5.622 | 1.00 | 25.96 |
| ATOM | 1244 | CG | GLU | A | 194 | 22.436 | 36.883 | -4.434 | 1.00 | 27.36 |
| ATOM | 1245 | CD | GLU | A | 194 | 22.890 | 38.142 | -3.798 | 1.00 | 30.91 |
| ATOM | 1246 | OE1 | GLU | A | 194 | 24.048 | 38.553 | -4.057 | 1.00 | 31.62 |
| ATOM | 1247 | OE2 | GLU | A | 194 | 22.067 | 38.738 | -3.072 | 1.00 | 34.95 |

Figure 4Y

| ATOM | 1248 | C | GLU | A | 194 | 19.711 | 36.385 | -6.923 | 1.00 | 26.18 |
| --- | --- | --- | --- | --- | --- | --- | --- | --- | --- | --- |
| ATOM | 1249 | O | GLU | A | 194 | 18.640 | 36.351 | -6.343 | 1.00 | 28.88 |
| ATOM | 1250 | N | LEU | A | 195 | 19.838 | 36.835 | -8.161 | 1.00 | 28.13 |
| ATOM | 1251 | CA | LEU | A | 195 | 18.672 | 37.258 | -8.948 | 1.00 | 29.16 |
| ATOM | 1252 | CB | LEU | A | 195 | 19.115 | 37.635 | -10.348 | 1.00 | 32.65 |
| ATOM | 1253 | CG | LEU | A | 195 | 19.854 | 38.959 | -10.383 | 1.00 | 32.33 |
| ATOM | 1254 | CD1 | LEU | A | 195 | 20.238 | 39.320 | -11.794 | 1.00 | 29.08 |
| ATOM | 1255 | CD2 | LEU | A | 195 | 18.918 | 39.999 | -9.807 | 1.00 | 34.11 |
| ATOM | 1256 | C | LEU | A | 195 | 17.584 | 36.196 | -8.996 | 1.00 | 32.23 |
| ATOM | 1257 | O | LEU | A | 195 | 16.397 | 36.495 | -8.957 | 1.00 | 36.13 |
| ATOM | 1258 | N | ALA | A | 196 | 18.003 | 34.942 | -9.127 | 1.00 | 32.09 |
| ATOM | 1259 | CA | ALA | A | 196 | 17.049 | 33.827 | -9.159 | 1.00 | 37.21 |
| ATOM | 1260 | CB | ALA | A | 196 | 17.772 | 32.532 | -9.474 | 1.00 | 37.75 |
| ATOM | 1261 | C | ALA | A | 196 | 16.344 | 33.733 | -7.789 | 1.00 | 41.34 |
| ATOM | 1262 | O | ALA | A | 196 | 15.216 | 34.183 | -7.595 | 1.00 | 46.80 |
| ATOM | 1263 | N | LEU | A | 197 | 17.058 | 33.213 | -6.797 | 1.00 | 46.39 |
| ATOM | 1264 | CA | LEU | A | 197 | 16.463 | 33.054 | -5.441 | 1.00 | 48.16 |
| ATOM | 1265 | CB | LEU | A | 197 | 17.284 | 32.052 | -4.582 | 1.00 | 42.63 |
| ATOM | 1266 | CG | LEU | A | 197 | 18.689 | 32.259 | -4.007 | 1.00 | 40.14 |
| ATOM | 1267 | CD1 | LEU | A | 197 | 19.440 | 33.207 | -4.874 | 1.00 | 43.51 |
| ATOM | 1268 | CD2 | LEU | A | 197 | 18.638 | 32.798 | -2.592 | 1.00 | 43.15 |
| ATOM | 1269 | C | LEU | A | 197 | 16.277 | 34.401 | -4.750 | 1.00 | 48.97 |
| ATOM | 1270 | O | LEU | A | 197 | 16.339 | 34.526 | -3.526 | 1.00 | 54.40 |
| ATOM | 1271 | N | ALA | A | 198 | 16.035 | 35.427 | -5.558 | 1.00 | 48.46 |
| ATOM | 1272 | CA | ALA | A | 198 | 15.839 | 36.779 | -5.021 | 1.00 | 46.50 |
| ATOM | 1273 | CB | ALA | A | 198 | 15.861 | 37.815 | -6.127 | 1.00 | 51.57 |
| ATOM | 1274 | C | ALA | A | 198 | 14.495 | 36.750 | -4.361 | 1.00 | 41.42 |
| ATOM | 1275 | O | ALA | A | 198 | 13.485 | 36.388 | -4.944 | 1.00 | 39.01 |
| ATOM | 1276 | N | GLY | A | 199 | 14.522 | 37.050 | -3.075 | 1.00 | 40.95 |
| ATOM | 1277 | CA | GLY | A | 199 | 13.307 | 37.066 | -2.294 | 1.00 | 37.49 |
| ATOM | 1278 | C | GLY | A | 199 | 13.098 | 35.783 | -1.508 | 1.00 | 34.67 |
| ATOM | 1279 | O | GLY | A | 199 | 12.342 | 35.774 | -0.534 | 1.00 | 39.92 |
| ATOM | 1280 | N | ARG | A | 200 | 13.740 | 34.693 | -1.910 | 1.00 | 23.52 |
| ATOM | 1281 | CA | ARG | A | 200 | 13.547 | 33.463 | -1.170 | 1.00 | 15.36 |
| ATOM | 1282 | CB | ARG | A | 200 | 14.187 | 32.302 | -1.882 | 1.00 | 11.05 |
| ATOM | 1283 | CG | ARG | A | 200 | 13.206 | 31.227 | -2.159 | 1.00 | 14.32 |
| ATOM | 1284 | CD | ARG | A | 200 | 13.514 | 29.972 | -1.381 | 1.00 | 15.70 |
| ATOM | 1285 | NE | ARG | A | 200 | 13.964 | 28.919 | -2.284 | 1.00 | 21.84 |
| ATOM | 1286 | CZ | ARG | A | 200 | 14.077 | 27.641 | -1.945 | 1.00 | 26.11 |
| ATOM | 1287 | NH1 | ARG | A | 200 | 14.488 | 26.752 | -2.842 | 1.00 | 28.82 |
| ATOM | 1288 | NH2 | ARG | A | 200 | 13.800 | 27.251 | -0.707 | 1.00 | 27.00 |
| ATOM | 1289 | C | ARG | A | 200 | 14.066 | 33.566 | 0.259 | 1.00 | 17.46 |
| ATOM | 1290 | O | ARG | A | 200 | 15.121 | 34.141 | 0.560 | 1.00 | 16.43 |
| ATOM | 1291 | N | THR | A | 201 | 13.237 | 33.036 | 1.149 | 1.00 | 15.44 |
| ATOM | 1292 | CA | THR | A | 201 | 13.495 | 32.961 | 2.579 | 1.00 | 13.41 |
| ATOM | 1293 | CB | THR | A | 201 | 12.463 | 33.751 | 3.352 | 1.00 | 16.83 |
| ATOM | 1294 | OG1 | THR | A | 201 | 12.586 | 35.117 | 2.968 | 1.00 | 29.43 |
| ATOM | 1295 | CG2 | THR | A | 201 | 12.696 | 33.632 | 4.889 | 1.00 | 21.71 |
| ATOM | 1296 | C | THR | A | 201 | 13.251 | 31.505 | 2.872 | 1.00 | 13.79 |
| ATOM | 1297 | O | THR | A | 201 | 12.439 | 30.847 | 2.216 | 1.00 | 15.67 |
| ATOM | 1298 | N | TRP | A | 202 | 13.991 | 30.974 | 3.831 | 1.00 | 8.16 |
| ATOM | 1299 | CA | TRP | A | 202 | 13.807 | 29.592 | 4.212 | 1.00 | 3.30 |

Figure 4Z

| ATOM | 1300 | CB | TRP | A | 202 | 15.174 | 28.925 | 4.296 | 1.00 | 4.64 |
|---|---|---|---|---|---|---|---|---|---|---|
| ATOM | 1301 | CG | TRP | A | 202 | 15.771 | 28.616 | 2.922 | 1.00 | 4.90 |
| ATOM | 1302 | CD2 | TRP | A | 202 | 16.350 | 29.554 | 1.992 | 1.00 | 2.00 |
| ATOM | 1303 | CE2 | TRP | A | 202 | 16.708 | 28.829 | 0.835 | 1.00 | 2.00 |
| ATOM | 1304 | CE3 | TRP | A | 202 | 16.599 | 30.922 | 2.026 | 1.00 | 2.00 |
| ATOM | 1305 | CD1 | TRP | A | 202 | 15.821 | 27.389 | 2.306 | 1.00 | 2.00 |
| ATOM | 1306 | NE1 | TRP | A | 202 | 16.376 | 27.517 | 1.049 | 1.00 | 3.02 |
| ATOM | 1307 | CZ2 | TRP | A | 202 | 17.295 | 29.433 | -0.269 | 1.00 | 5.31 |
| ATOM | 1308 | CZ3 | TRP | A | 202 | 17.185 | 31.520 | 0.927 | 1.00 | 2.00 |
| ATOM | 1309 | CH2 | TRP | A | 202 | 17.525 | 30.780 | -0.205 | 1.00 | 2.00 |
| ATOM | 1310 | C | TRP | A | 202 | 13.065 | 29.639 | 5.538 | 1.00 | 3.53 |
| ATOM | 1311 | O | TRP | A | 202 | 13.029 | 30.653 | 6.208 | 1.00 | 9.14 |
| ATOM | 1312 | N | ALA | A | 203 | 12.376 | 28.567 | 5.880 | 1.00 | 5.19 |
| ATOM | 1313 | CA | ALA | A | 203 | 11.643 | 28.526 | 7.170 | 1.00 | 2.52 |
| ATOM | 1314 | CB | ALA | A | 203 | 10.311 | 29.159 | 7.025 | 1.00 | 3.82 |
| ATOM | 1315 | C | ALA | A | 203 | 11.501 | 27.061 | 7.568 | 1.00 | 6.65 |
| ATOM | 1316 | O | ALA | A | 203 | 10.440 | 26.446 | 7.473 | 1.00 | 8.95 |
| ATOM | 1317 | N | PRO | A | 204 | 12.608 | 26.469 | 8.041 | 1.00 | 9.57 |
| ATOM | 1318 | CD | PRO | A | 204 | 13.938 | 27.091 | 8.172 | 1.00 | 6.21 |
| ATOM | 1319 | CA | PRO | A | 204 | 12.651 | 25.062 | 8.455 | 1.00 | 8.75 |
| ATOM | 1320 | CB | PRO | A | 204 | 14.153 | 24.833 | 8.689 | 1.00 | 3.21 |
| ATOM | 1321 | CG | PRO | A | 204 | 14.642 | 26.156 | 9.094 | 1.00 | 3.99 |
| ATOM | 1322 | C | PRO | A | 204 | 11.763 | 24.635 | 9.647 | 1.00 | 8.59 |
| ATOM | 1323 | O | PRO | A | 204 | 11.392 | 23.465 | 9.781 | 1.00 | 12.31 |
| ATOM | 1324 | N | GLY | A | 205 | 11.395 | 25.608 | 10.482 | 1.00 | 8.27 |
| ATOM | 1325 | CA | GLY | A | 205 | 10.571 | 25.347 | 11.649 | 1.00 | 3.11 |
| ATOM | 1326 | C | GLY | A | 205 | 11.370 | 25.669 | 12.896 | 1.00 | 5.42 |
| ATOM | 1327 | O | GLY | A | 205 | 12.368 | 25.009 | 13.143 | 1.00 | 9.36 |
| ATOM | 1328 | N | VAL | A | 206 | 10.917 | 26.619 | 13.721 | 1.00 | 6.38 |
| ATOM | 1329 | CA | VAL | A | 206 | 11.685 | 27.008 | 14.914 | 1.00 | 6.22 |
| ATOM | 1330 | CB | VAL | A | 206 | 11.080 | 28.207 | 15.710 | 1.00 | 6.22 |
| ATOM | 1331 | CG1 | VAL | A | 206 | 10.724 | 29.351 | 14.784 | 1.00 | 2.24 |
| ATOM | 1332 | CG2 | VAL | A | 206 | 9.927 | 27.801 | 16.496 | 1.00 | 9.41 |
| ATOM | 1333 | C | VAL | A | 206 | 12.023 | 25.841 | 15.819 | 1.00 | 11.28 |
| ATOM | 1334 | O | VAL | A | 206 | 13.141 | 25.729 | 16.314 | 1.00 | 13.84 |
| ATOM | 1335 | N | GLU | A | 207 | 11.091 | 24.913 | 15.989 | 1.00 | 10.07 |
| ATOM | 1336 | CA | GLU | A | 207 | 11.417 | 23.764 | 16.847 | 1.00 | 13.64 |
| ATOM | 1337 | CB | GLU | A | 207 | 10.180 | 22.955 | 17.213 | 1.00 | 19.55 |
| ATOM | 1338 | CG | GLU | A | 207 | 9.265 | 23.633 | 18.231 | 1.00 | 27.99 |
| ATOM | 1339 | CD | GLU | A | 207 | 10.000 | 24.472 | 19.286 | 1.00 | 33.29 |
| ATOM | 1340 | OE1 | GLU | A | 207 | 11.063 | 24.067 | 19.806 | 1.00 | 35.11 |
| ATOM | 1341 | OE2 | GLU | A | 207 | 9.492 | 25.565 | 19.605 | 1.00 | 38.85 |
| ATOM | 1342 | C | GLU | A | 207 | 12.477 | 22.878 | 16.209 | 1.00 | 13.37 |
| ATOM | 1343 | O | GLU | A | 207 | 13.373 | 22.371 | 16.876 | 1.00 | 16.43 |
| ATOM | 1344 | N | ALA | A | 208 | 12.362 | 22.694 | 14.895 | 1.00 | 10.76 |
| ATOM | 1345 | CA | ALA | A | 208 | 13.336 | 21.884 | 14.132 | 1.00 | 7.80 |
| ATOM | 1346 | CB | ALA | A | 208 | 13.002 | 21.900 | 12.670 | 1.00 | 3.93 |
| ATOM | 1347 | C | ALA | A | 208 | 14.690 | 22.561 | 14.349 | 1.00 | 11.06 |
| ATOM | 1348 | O | ALA | A | 208 | 15.686 | 21.944 | 14.711 | 1.00 | 9.59 |
| ATOM | 1349 | N | LEU | A | 209 | 14.681 | 23.880 | 14.190 | 1.00 | 9.05 |
| ATOM | 1350 | CA | LEU | A | 209 | 15.889 | 24.673 | 14.358 | 1.00 | 7.77 |
| ATOM | 1351 | CB | LEU | A | 209 | 15.606 | 26.121 | 14.040 | 1.00 | 5.75 |

Figure 4AA

| | | | | | | | | | |
|---|---|---|---|---|---|---|---|---|---|
| ATOM | 1352 | CG | LEU | A | 209 | 15.872 | 26.381 | 12.570 | 1.00 5.74 |
| ATOM | 1353 | CD1 | LEU | A | 209 | 15.452 | 27.779 | 12.183 | 1.00 4.57 |
| ATOM | 1354 | CD2 | LEU | A | 209 | 17.336 | 26.151 | 12.332 | 1.00 4.67 |
| ATOM | 1355 | C | LEU | A | 209 | 16.428 | 24.550 | 15.774 | 1.00 8.89 |
| ATOM | 1356 | O | LEU | A | 209 | 17.611 | 24.337 | 16.014 | 1.00 10.17 |
| ATOM | 1357 | N | THR | A | 210 | 15.517 | 24.652 | 16.723 | 1.00 8.02 |
| ATOM | 1358 | CA | THR | A | 210 | 15.895 | 24.594 | 18.127 | 1.00 7.75 |
| ATOM | 1359 | CB | THR | A | 210 | 14.663 | 24.882 | 19.023 | 1.00 11.59 |
| ATOM | 1360 | OG1 | THR | A | 210 | 14.240 | 26.240 | 18.823 | 1.00 13.82 |
| ATOM | 1361 | CG2 | THR | A | 210 | 14.994 | 24.705 | 20.471 | 1.00 9.00 |
| ATOM | 1362 | C | THR | A | 210 | 16.537 | 23.243 | 18.462 | 1.00 7.25 |
| ATOM | 1363 | O | THR | A | 210 | 17.602 | 23.159 | 19.047 | 1.00 2.23 |
| ATOM | 1364 | N | HIS | A | 211 | 15.899 | 22.169 | 18.017 | 1.00 13.28 |
| ATOM | 1365 | CA | HIS | A | 211 | 16.410 | 20.814 | 18.306 | 1.00 14.39 |
| ATOM | 1366 | CB | HIS | A | 211 | 15.356 | 19.743 | 17.939 | 1.00 24.21 |
| ATOM | 1367 | CG | HIS | A | 211 | 14.163 | 19.719 | 18.861 | 1.00 32.10 |
| ATOM | 1368 | CD2 | HIS | A | 211 | 13.060 | 20.508 | 18.916 | 1.00 35.49 |
| ATOM | 1369 | ND1 | HIS | A | 211 | 14.028 | 18.810 | 19.891 | 1.00 36.32 |
| ATOM | 1370 | CE1 | HIS | A | 211 | 12.901 | 19.037 | 20.539 | 1.00 38.59 |
| ATOM | 1371 | NE2 | HIS | A | 211 | 12.295 | 20.061 | 19.968 | 1.00 39.12 |
| ATOM | 1372 | C | HIS | A | 211 | 17.749 | 20.577 | 17.621 | 1.00 12.30 |
| ATOM | 1373 | O | HIS | A | 211 | 18.697 | 20.066 | 18.224 | 1.00 17.25 |
| ATOM | 1374 | N | THR | A | 212 | 17.859 | 21.032 | 16.375 | 1.00 10.09 |
| ATOM | 1375 | CA | THR | A | 212 | 19.110 | 20.854 | 15.574 | 1.00 8.92 |
| ATOM | 1376 | CB | THR | A | 212 | 18.900 | 21.301 | 14.089 | 1.00 7.09 |
| ATOM | 1377 | OG1 | THR | A | 212 | 18.004 | 20.392 | 13.449 | 1.00 8.35 |
| ATOM | 1378 | CG2 | THR | A | 212 | 20.172 | 21.260 | 13.309 | 1.00 6.60 |
| ATOM | 1379 | C | THR | A | 212 | 20.352 | 21.537 | 16.219 | 1.00 9.02 |
| ATOM | 1380 | O | THR | A | 212 | 21.459 | 21.000 | 16.254 | 1.00 8.89 |
| ATOM | 1381 | N | LEU | A | 213 | 20.142 | 22.731 | 16.752 | 1.00 6.24 |
| ATOM | 1382 | CA | LEU | A | 213 | 21.203 | 23.459 | 17.414 | 1.00 2.00 |
| ATOM | 1383 | CB | LEU | A | 213 | 20.805 | 24.900 | 17.499 | 1.00 2.00 |
| ATOM | 1384 | CG | LEU | A | 213 | 20.712 | 25.597 | 16.140 | 1.00 2.00 |
| ATOM | 1385 | CD1 | LEU | A | 213 | 20.216 | 27.028 | 16.362 | 1.00 2.00 |
| ATOM | 1386 | CD2 | LEU | A | 213 | 22.055 | 25.630 | 15.448 | 1.00 2.00 |
| ATOM | 1387 | C | LEU | A | 213 | 21.574 | 22.854 | 18.802 | 1.00 6.60 |
| ATOM | 1388 | O | LEU | A | 213 | 22.729 | 22.862 | 19.238 | 1.00 8.97 |
| ATOM | 1389 | N | LEU | A | 214 | 20.597 | 22.267 | 19.480 | 1.00 7.27 |
| ATOM | 1390 | CA | LEU | A | 214 | 20.871 | 21.638 | 20.784 | 1.00 3.30 |
| ATOM | 1391 | CB | LEU | A | 214 | 19.593 | 21.107 | 21.396 | 1.00 6.48 |
| ATOM | 1392 | CG | LEU | A | 214 | 19.511 | 20.950 | 22.908 | 1.00 10.06 |
| ATOM | 1393 | CD1 | LEU | A | 214 | 18.657 | 19.758 | 23.193 | 1.00 10.04 |
| ATOM | 1394 | CD2 | LEU | A | 214 | 20.870 | 20.767 | 23.548 | 1.00 16.50 |
| ATOM | 1395 | C | LEU | A | 214 | 21.794 | 20.486 | 20.428 | 1.00 6.10 |
| ATOM | 1396 | O | LEU | A | 214 | 22.811 | 20.241 | 21.041 | 1.00 9.00 |
| ATOM | 1397 | N | SER | A | 215 | 21.401 | 19.760 | 19.393 | 1.00 9.89 |
| ATOM | 1398 | CA | SER | A | 215 | 22.193 | 18.594 | 18.867 | 1.00 10.91 |
| ATOM | 1399 | CB | SER | A | 215 | 21.475 | 18.029 | 17.639 | 1.00 12.69 |
| ATOM | 1400 | OG | SER | A | 215 | 22.031 | 16.804 | 17.213 | 1.00 12.85 |
| ATOM | 1401 | C | SER | A | 215 | 23.662 | 18.996 | 18.516 | 1.00 7.44 |
| ATOM | 1402 | O | SER | A | 215 | 24.631 | 18.285 | 18.772 | 1.00 4.85 |
| ATOM | 1403 | N | THR | A | 216 | 23.814 | 20.157 | 17.897 | 1.00 8.11 |

Figure 4BB

| ATOM | 1404 | CA | THR | A | 216 | 25.161 | 20.668 | 17.556 | 1.00 | 6.87 |
|---|---|---|---|---|---|---|---|---|---|---|
| ATOM | 1405 | CB | THR | A | 216 | 25.051 | 22.047 | 16.856 | 1.00 | 7.00 |
| ATOM | 1406 | OG1 | THR | A | 216 | 24.446 | 21.878 | 15.569 | 1.00 | 15.03 |
| ATOM | 1407 | CG2 | THR | A | 216 | 26.413 | 22.705 | 16.672 | 1.00 | 4.75 |
| ATOM | 1408 | C | THR | A | 216 | 26.007 | 20.800 | 18.869 | 1.00 | 13.37 |
| ATOM | 1409 | O | THR | A | 216 | 27.191 | 20.500 | 18.921 | 1.00 | 17.43 |
| ATOM | 1410 | N | ALA | A | 217 | 25.361 | 21.229 | 19.947 | 1.00 | 11.63 |
| ATOM | 1411 | CA | ALA | A | 217 | 26.035 | 21.391 | 21.237 | 1.00 | 6.33 |
| ATOM | 1412 | CB | ALA | A | 217 | 25.193 | 22.266 | 22.163 | 1.00 | 6.15 |
| ATOM | 1413 | C | ALA | A | 217 | 26.286 | 20.035 | 21.901 | 1.00 | 8.61 |
| ATOM | 1414 | O | ALA | A | 217 | 27.399 | 19.685 | 22.259 | 1.00 | 9.44 |
| ATOM | 1415 | N | VAL | A | 218 | 25.223 | 19.255 | 22.054 | 1.00 | 9.17 |
| ATOM | 1416 | CA | VAL | A | 218 | 25.338 | 17.961 | 22.734 | 1.00 | 8.52 |
| ATOM | 1417 | CB | VAL | A | 218 | 23.982 | 17.252 | 22.852 | 1.00 | 3.62 |
| ATOM | 1418 | CG1 | VAL | A | 218 | 24.189 | 15.816 | 23.241 | 1.00 | 2.00 |
| ATOM | 1419 | CG2 | VAL | A | 218 | 23.134 | 17.950 | 23.920 | 1.00 | 2.00 |
| ATOM | 1420 | C | VAL | A | 218 | 26.384 | 17.059 | 22.094 | 1.00 | 11.66 |
| ATOM | 1421 | O | VAL | A | 218 | 27.199 | 16.438 | 22.754 | 1.00 | 16.46 |
| ATOM | 1422 | N | ASN | A | 219 | 26.413 | 17.052 | 20.777 | 1.00 | 14.73 |
| ATOM | 1423 | CA | ASN | A | 219 | 27.377 | 16.202 | 20.051 | 1.00 | 15.26 |
| ATOM | 1424 | CB | ASN | A | 219 | 26.907 | 15.979 | 18.639 | 1.00 | 13.84 |
| ATOM | 1425 | CG | ASN | A | 219 | 25.812 | 15.002 | 18.559 | 1.00 | 16.76 |
| ATOM | 1426 | OD1 | ASN | A | 219 | 25.936 | 13.857 | 19.009 | 1.00 | 19.12 |
| ATOM | 1427 | ND2 | ASN | A | 219 | 24.700 | 15.437 | 17.990 | 1.00 | 29.15 |
| ATOM | 1428 | C | ASN | A | 219 | 28.838 | 16.686 | 20.051 | 1.00 | 15.41 |
| ATOM | 1429 | O | ASN | A | 219 | 29.753 | 15.985 | 19.628 | 1.00 | 10.84 |
| ATOM | 1430 | N | ASN | A | 220 | 29.047 | 17.917 | 20.484 | 1.00 | 15.22 |
| ATOM | 1431 | CA | ASN | A | 220 | 30.400 | 18.469 | 20.507 | 1.00 | 15.52 |
| ATOM | 1432 | CB | ASN | A | 220 | 30.474 | 19.727 | 19.646 | 1.00 | 18.98 |
| ATOM | 1433 | CG | ASN | A | 220 | 30.445 | 19.430 | 18.158 | 1.00 | 19.48 |
| ATOM | 1434 | OD1 | ASN | A | 220 | 31.489 | 19.182 | 17.541 | 1.00 | 18.11 |
| ATOM | 1435 | ND2 | ASN | A | 220 | 29.248 | 19.477 | 17.565 | 1.00 | 19.30 |
| ATOM | 1436 | C | ASN | A | 220 | 30.860 | 18.789 | 21.921 | 1.00 | 18.26 |
| ATOM | 1437 | O | ASN | A | 220 | 31.887 | 19.443 | 22.122 | 1.00 | 21.04 |
| ATOM | 1438 | N | MET | A | 221 | 30.104 | 18.312 | 22.908 | 1.00 | 20.02 |
| ATOM | 1439 | CA | MET | A | 221 | 30.424 | 18.590 | 24.340 | 1.00 | 18.92 |
| ATOM | 1440 | CB | MET | A | 221 | 29.282 | 18.146 | 25.246 | 1.00 | 14.70 |
| ATOM | 1441 | CG | MET | A | 221 | 29.066 | 16.672 | 25.254 | 1.00 | 7.03 |
| ATOM | 1442 | SD | MET | A | 221 | 27.847 | 16.303 | 26.412 | 1.00 | 15.09 |
| ATOM | 1443 | CE | MET | A | 221 | 27.200 | 14.801 | 25.301 | 1.00 | 5.24 |
| ATOM | 1444 | C | MET | A | 221 | 31.732 | 17.958 | 24.781 | 1.00 | 20.99 |
| ATOM | 1445 | O | MET | A | 221 | 32.515 | 18.529 | 25.517 | 1.00 | 21.94 |
| ATOM | 1446 | N | MET | A | 222 | 31.993 | 16.772 | 24.253 | 1.00 | 25.48 |
| ATOM | 1447 | CA | MET | A | 222 | 33.218 | 16.013 | 24.595 | 1.00 | 27.01 |
| ATOM | 1448 | CB | MET | A | 222 | 32.953 | 14.538 | 24.311 | 1.00 | 27.99 |
| ATOM | 1449 | CG | MET | A | 222 | 31.762 | 14.002 | 25.081 | 1.00 | 29.87 |
| ATOM | 1450 | SD | MET | A | 222 | 32.118 | 13.649 | 26.808 | 1.00 | 38.44 |
| ATOM | 1451 | CE | MET | A | 222 | 32.621 | 15.072 | 27.408 | 1.00 | 31.07 |
| ATOM | 1452 | C | MET | A | 222 | 34.518 | 16.505 | 23.925 | 1.00 | 26.90 |
| ATOM | 1453 | O | MET | A | 222 | 35.593 | 15.941 | 24.052 | 1.00 | 28.44 |
| ATOM | 1454 | N | LEU | A | 223 | 34.409 | 17.609 | 23.222 | 1.00 | 27.45 |
| ATOM | 1455 | CA | LEU | A | 223 | 35.564 | 18.156 | 22.539 | 1.00 | 24.63 |

Figure 4CC

| ATOM | 1456 | CB | LEU A 223 | 35.090 | 19.049 | 21.386 | 1.00 | 29.39 |
|---|---|---|---|---|---|---|---|---|
| ATOM | 1457 | CG | LEU A 223 | 35.847 | 19.121 | 20.049 | 1.00 | 24.93 |
| ATOM | 1458 | CD1 | LEU A 223 | 35.810 | 17.772 | 19.381 | 1.00 | 23.13 |
| ATOM | 1459 | CD2 | LEU A 223 | 35.188 | 20.151 | 19.127 | 1.00 | 28.48 |
| ATOM | 1460 | C | LEU A 223 | 36.375 | 18.937 | 23.567 | 1.00 | 27.48 |
| ATOM | 1461 | O | LEU A 223 | 35.886 | 19.790 | 24.309 | 1.00 | 23.71 |
| ATOM | 1462 | N | ARG A 224 | 37.638 | 18.563 | 23.667 | 1.00 | 34.72 |
| ATOM | 1463 | CA | ARG A 224 | 38.562 | 19.263 | 24.567 | 1.00 | 38.82 |
| ATOM | 1464 | CB | ARG A 224 | 39.765 | 18.382 | 24.849 | 1.00 | 43.75 |
| ATOM | 1465 | CG | ARG A 224 | 39.551 | 17.438 | 26.006 | 1.00 | 55.91 |
| ATOM | 1466 | CD | ARG A 224 | 39.000 | 18.223 | 27.190 | 1.00 | 65.77 |
| ATOM | 1467 | NE | ARG A 224 | 39.408 | 17.708 | 28.501 | 1.00 | 73.29 |
| ATOM | 1468 | CZ | ARG A 224 | 39.136 | 16.489 | 28.971 | 1.00 | 76.88 |
| ATOM | 1469 | NH1 | ARG A 224 | 39.569 | 16.154 | 30.189 | 1.00 | 76.89 |
| ATOM | 1470 | NH2 | ARG A 224 | 38.450 | 15.605 | 28.239 | 1.00 | 78.31 |
| ATOM | 1471 | C | ARG A 224 | 38.965 | 20.567 | 23.869 | 1.00 | 42.27 |
| ATOM | 1472 | O | ARG A 224 | 39.589 | 20.572 | 22.800 | 1.00 | 44.43 |
| ATOM | 1473 | N | ASP A 225 | 38.519 | 21.677 | 24.451 | 1.00 | 46.11 |
| ATOM | 1474 | CA | ASP A 225 | 38.803 | 23.044 | 23.902 | 1.00 | 49.33 |
| ATOM | 1475 | CB | ASP A 225 | 40.225 | 23.464 | 24.257 | 1.00 | 58.78 |
| ATOM | 1476 | CG | ASP A 225 | 40.542 | 24.890 | 23.805 | 1.00 | 66.98 |
| ATOM | 1477 | OD1 | ASP A 225 | 40.468 | 25.809 | 24.636 | 1.00 | 71.51 |
| ATOM | 1478 | OD2 | ASP A 225 | 40.856 | 25.114 | 22.619 | 1.00 | 73.88 |
| ATOM | 1479 | C | ASP A 225 | 38.614 | 23.170 | 22.371 | 1.00 | 48.68 |
| ATOM | 1480 | O | ASP A 225 | 39.552 | 23.149 | 21.620 | 1.00 | 51.27 |
| ATOM | 1481 | N | ARG A 226 | 37.419 | 23.413 | 21.885 | 1.00 | 41.79 |
| ATOM | 1482 | CA | ARG A 226 | 37.264 | 23.506 | 20.421 | 1.00 | 33.40 |
| ATOM | 1483 | CB | ARG A 226 | 35.786 | 23.442 | 20.030 | 1.00 | 36.65 |
| ATOM | 1484 | CG | ARG A 226 | 35.073 | 24.708 | 20.520 | 1.00 | 37.55 |
| ATOM | 1485 | CD | ARG A 226 | 33.573 | 24.698 | 20.287 | 1.00 | 37.46 |
| ATOM | 1486 | NE | ARG A 226 | 33.120 | 26.075 | 20.121 | 1.00 | 37.26 |
| ATOM | 1487 | CZ | ARG A 226 | 32.833 | 26.612 | 18.945 | 1.00 | 37.48 |
| ATOM | 1488 | NH1 | ARG A 226 | 32.461 | 27.877 | 18.878 | 1.00 | 37.93 |
| ATOM | 1489 | NH2 | ARG A 226 | 32.857 | 25.864 | 17.844 | 1.00 | 38.45 |
| ATOM | 1490 | C | ARG A 226 | 37.898 | 24.775 | 19.805 | 1.00 | 29.10 |
| ATOM | 1491 | O | ARG A 226 | 38.156 | 24.849 | 18.598 | 1.00 | 33.55 |
| ATOM | 1492 | N | TRP A 227 | 38.094 | 25.797 | 20.635 | 1.00 | 22.03 |
| ATOM | 1493 | CA | TRP A 227 | 38.656 | 27.091 | 20.166 | 1.00 | 21.39 |
| ATOM | 1494 | CB | TRP A 227 | 38.490 | 28.154 | 21.249 | 1.00 | 22.63 |
| ATOM | 1495 | CG | TRP A 227 | 37.077 | 28.584 | 21.461 | 1.00 | 24.25 |
| ATOM | 1496 | CD2 | TRP A 227 | 36.249 | 29.338 | 20.557 | 1.00 | 27.88 |
| ATOM | 1497 | CE2 | TRP A 227 | 34.975 | 29.468 | 21.165 | 1.00 | 31.02 |
| ATOM | 1498 | CE3 | TRP A 227 | 36.458 | 29.914 | 19.295 | 1.00 | 29.58 |
| ATOM | 1499 | CD1 | TRP A 227 | 36.297 | 28.311 | 22.549 | 1.00 | 26.56 |
| ATOM | 1500 | NE1 | TRP A 227 | 35.036 | 28.832 | 22.379 | 1.00 | 27.82 |
| ATOM | 1501 | CZ2 | TRP A 227 | 33.911 | 30.146 | 20.552 | 1.00 | 28.29 |
| ATOM | 1502 | CZ3 | TRP A 227 | 35.391 | 30.598 | 18.683 | 1.00 | 32.75 |
| ATOM | 1503 | CH2 | TRP A 227 | 34.138 | 30.703 | 19.316 | 1.00 | 31.24 |
| ATOM | 1504 | C | TRP A 227 | 40.113 | 27.048 | 19.660 | 1.00 | 23.70 |
| ATOM | 1505 | O | TRP A 227 | 40.606 | 27.960 | 18.977 | 1.00 | 27.60 |
| ATOM | 1506 | N | SER A 228 | 40.814 | 25.988 | 20.040 | 1.00 | 18.51 |
| ATOM | 1507 | CA | SER A 228 | 42.184 | 25.798 | 19.596 | 1.00 | 15.81 |

Figure 4DD

| | | | | | | | | | |
|---|---|---|---|---|---|---|---|---|---|
| ATOM | 1508 | CB | SER | A | 228 | 42.815 | 24.662 | 20.368 | 1.00 15.52 |
| ATOM | 1509 | OG | SER | A | 228 | 43.254 | 25.128 | 21.616 | 1.00 17.60 |
| ATOM | 1510 | C | SER | A | 228 | 42.101 | 25.458 | 18.119 | 1.00 14.79 |
| ATOM | 1511 | O | SER | A | 228 | 42.767 | 26.053 | 17.266 | 1.00 21.46 |
| ATOM | 1512 | N | LEU | A | 229 | 41.252 | 24.477 | 17.827 | 1.00 7.62 |
| ATOM | 1513 | CA | LEU | A | 229 | 41.047 | 24.042 | 16.448 | 1.00 7.17 |
| ATOM | 1514 | CB | LEU | A | 229 | 40.018 | 22.935 | 16.364 | 1.00 10.34 |
| ATOM | 1515 | CG | LEU | A | 229 | 40.194 | 21.741 | 17.280 | 1.00 20.72 |
| ATOM | 1516 | CD1 | LEU | A | 229 | 39.311 | 20.598 | 16.771 | 1.00 27.16 |
| ATOM | 1517 | CD2 | LEU | A | 229 | 41.658 | 21.326 | 17.305 | 1.00 27.96 |
| ATOM | 1518 | C | LEU | A | 229 | 40.585 | 25.224 | 15.621 | 1.00 7.22 |
| ATOM | 1519 | O | LEU | A | 229 | 41.089 | 25.499 | 14.537 | 1.00 8.55 |
| ATOM | 1520 | N | VAL | A | 230 | 39.619 | 25.959 | 16.159 | 1.00 5.89 |
| ATOM | 1521 | CA | VAL | A | 230 | 39.078 | 27.114 | 15.432 | 1.00 5.94 |
| ATOM | 1522 | CB | VAL | A | 230 | 37.922 | 27.795 | 16.232 | 1.00 4.89 |
| ATOM | 1523 | CG1 | VAL | A | 230 | 37.419 | 29.047 | 15.526 | 1.00 2.00 |
| ATOM | 1524 | CG2 | VAL | A | 230 | 36.773 | 26.806 | 16.398 | 1.00 4.47 |
| ATOM | 1525 | C | VAL | A | 230 | 40.224 | 28.090 | 15.072 | 1.00 6.40 |
| ATOM | 1526 | O | VAL | A | 230 | 40.438 | 28.506 | 13.922 | 1.00 9.66 |
| ATOM | 1527 | N | ALA | A | 231 | 41.052 | 28.344 | 16.064 | 1.00 7.60 |
| ATOM | 1528 | CA | ALA | A | 231 | 42.168 | 29.268 | 15.887 | 1.00 9.93 |
| ATOM | 1529 | CB | ALA | A | 231 | 42.872 | 29.443 | 17.201 | 1.00 8.04 |
| ATOM | 1530 | C | ALA | A | 231 | 43.128 | 28.732 | 14.827 | 1.00 11.60 |
| ATOM | 1531 | O | ALA | A | 231 | 43.551 | 29.400 | 13.884 | 1.00 13.10 |
| ATOM | 1532 | N | GLU | A | 232 | 43.399 | 27.448 | 14.957 | 1.00 10.99 |
| ATOM | 1533 | CA | GLU | A | 232 | 44.305 | 26.796 | 14.066 | 1.00 11.94 |
| ATOM | 1534 | CB | GLU | A | 232 | 44.569 | 25.399 | 14.581 | 1.00 13.60 |
| ATOM | 1535 | CG | GLU | A | 232 | 45.749 | 24.763 | 13.928 | 1.00 29.60 |
| ATOM | 1536 | CD | GLU | A | 232 | 45.731 | 23.252 | 14.019 | 1.00 35.18 |
| ATOM | 1537 | OE1 | GLU | A | 232 | 46.359 | 22.597 | 13.150 | 1.00 42.87 |
| ATOM | 1538 | OE2 | GLU | A | 232 | 45.085 | 22.719 | 14.949 | 1.00 33.58 |
| ATOM | 1539 | C | GLU | A | 232 | 43.796 | 26.788 | 12.623 | 1.00 13.86 |
| ATOM | 1540 | O | GLU | A | 232 | 44.517 | 27.157 | 11.679 | 1.00 20.91 |
| ATOM | 1541 | N | ARG | A | 233 | 42.522 | 26.440 | 12.456 | 1.00 13.11 |
| ATOM | 1542 | CA | ARG | A | 233 | 41.905 | 26.342 | 11.093 | 1.00 11.31 |
| ATOM | 1543 | CB | ARG | A | 233 | 40.726 | 25.380 | 11.138 | 1.00 12.40 |
| ATOM | 1544 | CG | ARG | A | 233 | 41.091 | 24.153 | 11.961 | 1.00 12.31 |
| ATOM | 1545 | CD | ARG | A | 233 | 40.903 | 22.852 | 11.256 | 1.00 13.86 |
| ATOM | 1546 | NE | ARG | A | 233 | 39.503 | 22.462 | 11.296 | 1.00 16.88 |
| ATOM | 1547 | CZ | ARG | A | 233 | 39.044 | 21.301 | 11.764 | 1.00 19.74 |
| ATOM | 1548 | NH1 | ARG | A | 233 | 37.736 | 21.049 | 11.757 | 1.00 17.79 |
| ATOM | 1549 | NH2 | ARG | A | 233 | 39.883 | 20.376 | 12.213 | 1.00 18.20 |
| ATOM | 1550 | C | ARG | A | 233 | 41.560 | 27.694 | 10.482 | 1.00 9.84 |
| ATOM | 1551 | O | ARG | A | 233 | 41.376 | 27.845 | 9.268 | 1.00 14.70 |
| ATOM | 1552 | N | ARG | A | 234 | 41.521 | 28.705 | 11.339 | 1.00 9.30 |
| ATOM | 1553 | CA | ARG | A | 234 | 41.297 | 30.079 | 10.885 | 1.00 8.94 |
| ATOM | 1554 | CB | ARG | A | 234 | 41.003 | 30.993 | 12.075 | 1.00 16.51 |
| ATOM | 1555 | CG | ARG | A | 234 | 41.011 | 32.462 | 11.684 | 1.00 25.37 |
| ATOM | 1556 | CD | ARG | A | 234 | 41.146 | 33.487 | 12.819 | 1.00 32.39 |
| ATOM | 1557 | NE | ARG | A | 234 | 41.213 | 34.830 | 12.225 | 1.00 44.51 |
| ATOM | 1558 | CZ | ARG | A | 234 | 40.612 | 35.934 | 12.683 | 1.00 46.54 |
| ATOM | 1559 | NH1 | ARG | A | 234 | 39.880 | 35.913 | 13.783 | 1.00 48.43 |

Figure 4EE

| | | | | | | | | |
|---|---|---|---|---|---|---|---|---|
| ATOM | 1560 | NH2 | ARG A 234 | 40.694 | 37.064 | 11.990 | 1.00 | 50.93 |
| ATOM | 1561 | C   | ARG A 234 | 42.615 | 30.513 | 10.199 | 1.00 | 11.94 |
| ATOM | 1562 | O   | ARG A 234 | 42.624 | 31.231 | 9.196  | 1.00 | 14.73 |
| ATOM | 1563 | N   | ARG A 235 | 43.739 | 30.106 | 10.804 | 1.00 | 12.37 |
| ATOM | 1564 | CA  | ARG A 235 | 45.114 | 30.426 | 10.286 | 1.00 | 16.31 |
| ATOM | 1565 | CB  | ARG A 235 | 46.170 | 30.059 | 11.313 | 1.00 | 23.21 |
| ATOM | 1566 | CG  | ARG A 235 | 46.045 | 30.880 | 12.594 | 1.00 | 34.61 |
| ATOM | 1567 | CD  | ARG A 235 | 47.263 | 30.750 | 13.491 | 1.00 | 37.31 |
| ATOM | 1568 | NE  | ARG A 235 | 47.521 | 29.350 | 13.824 | 1.00 | 43.60 |
| ATOM | 1569 | CZ  | ARG A 235 | 47.264 | 28.801 | 15.014 | 1.00 | 47.17 |
| ATOM | 1570 | NH1 | ARG A 235 | 47.535 | 27.511 | 15.221 | 1.00 | 45.31 |
| ATOM | 1571 | NH2 | ARG A 235 | 46.748 | 29.536 | 16.003 | 1.00 | 41.44 |
| ATOM | 1572 | C   | ARG A 235 | 45.404 | 29.739 | 8.969  | 1.00 | 15.83 |
| ATOM | 1573 | O   | ARG A 235 | 45.918 | 30.328 | 8.034  | 1.00 | 22.48 |
| ATOM | 1574 | N   | GLN A 236 | 45.058 | 28.460 | 8.906  | 1.00 | 14.95 |
| ATOM | 1575 | CA  | GLN A 236 | 45.211 | 27.650 | 7.652  | 1.00 | 11.72 |
| ATOM | 1576 | CB  | GLN A 236 | 44.718 | 26.211 | 7.886  | 1.00 | 11.77 |
| ATOM | 1577 | CG  | GLN A 236 | 45.357 | 25.449 | 9.055  | 1.00 | 15.53 |
| ATOM | 1578 | CD  | GLN A 236 | 44.614 | 24.163 | 9.391  | 1.00 | 16.00 |
| ATOM | 1579 | OE1 | GLN A 236 | 43.439 | 24.006 | 9.029  | 1.00 | 19.46 |
| ATOM | 1580 | NE2 | GLN A 236 | 45.278 | 23.252 | 10.114 | 1.00 | 10.57 |
| ATOM | 1581 | C   | GLN A 236 | 44.436 | 28.262 | 6.475  | 1.00 | 10.13 |
| ATOM | 1582 | O   | GLN A 236 | 44.815 | 28.101 | 5.324  | 1.00 | 15.63 |
| ATOM | 1583 | N   | ALA A 237 | 43.301 | 28.898 | 6.777  | 1.00 | 10.03 |
| ATOM | 1584 | CA  | ALA A 237 | 42.404 | 29.536 | 5.742  | 1.00 | 9.79  |
| ATOM | 1585 | CB  | ALA A 237 | 40.972 | 29.654 | 6.282  | 1.00 | 6.79  |
| ATOM | 1586 | C   | ALA A 237 | 42.890 | 30.911 | 5.264  | 1.00 | 10.12 |
| ATOM | 1587 | O   | ALA A 237 | 42.454 | 31.444 | 4.253  | 1.00 | 14.25 |
| ATOM | 1588 | N   | GLY A 238 | 43.813 | 31.491 | 6.024  | 1.00 | 10.29 |
| ATOM | 1589 | CA  | GLY A 238 | 44.340 | 32.789 | 5.674  | 1.00 | 4.75  |
| ATOM | 1590 | C   | GLY A 238 | 43.355 | 33.872 | 6.054  | 1.00 | 9.07  |
| ATOM | 1591 | O   | GLY A 238 | 43.334 | 34.929 | 5.424  | 1.00 | 8.04  |
| ATOM | 1592 | N   | ILE A 239 | 42.534 | 33.604 | 7.075  | 1.00 | 11.44 |
| ATOM | 1593 | CA  | ILE A 239 | 41.491 | 34.575 | 7.555  | 1.00 | 11.41 |
| ATOM | 1594 | CB  | ILE A 239 | 40.310 | 33.875 | 8.336  | 1.00 | 7.37  |
| ATOM | 1595 | CG2 | ILE A 239 | 39.322 | 34.874 | 8.830  | 1.00 | 4.21  |
| ATOM | 1596 | CG1 | ILE A 239 | 39.544 | 32.918 | 7.449  | 1.00 | 3.48  |
| ATOM | 1597 | CD1 | ILE A 239 | 38.562 | 32.125 | 8.208  | 1.00 | 3.45  |
| ATOM | 1598 | C   | ILE A 239 | 42.203 | 35.472 | 8.527  | 1.00 | 13.52 |
| ATOM | 1599 | O   | ILE A 239 | 42.912 | 35.017 | 9.436  | 1.00 | 12.69 |
| ATOM | 1600 | N   | ALA A 240 | 41.991 | 36.766 | 8.351  | 1.00 | 15.63 |
| ATOM | 1601 | CA  | ALA A 240 | 42.624 | 37.747 | 9.217  | 1.00 | 18.89 |
| ATOM | 1602 | CB  | ALA A 240 | 44.040 | 38.026 | 8.729  | 1.00 | 25.01 |
| ATOM | 1603 | C   | ALA A 240 | 41.834 | 39.029 | 9.231  | 1.00 | 24.53 |
| ATOM | 1604 | O   | ALA A 240 | 41.179 | 39.417 | 8.265  | 1.00 | 32.64 |
| ATOM | 1605 | N   | GLY A 241 | 41.890 | 39.706 | 10.363 | 1.00 | 26.12 |
| ATOM | 1606 | CA  | GLY A 241 | 41.196 | 40.962 | 10.462 | 1.00 | 28.34 |
| ATOM | 1607 | C   | GLY A 241 | 40.353 | 41.071 | 11.700 | 1.00 | 28.76 |
| ATOM | 1608 | O   | GLY A 241 | 40.482 | 40.318 | 12.648 | 1.00 | 23.53 |
| ATOM | 1609 | N   | HIS A 242 | 39.489 | 42.064 | 11.681 | 1.00 | 34.29 |
| ATOM | 1610 | CA  | HIS A 242 | 38.596 | 42.332 | 12.793 | 1.00 | 33.42 |
| ATOM | 1611 | CB  | HIS A 242 | 38.278 | 43.820 | 12.786 | 1.00 | 38.49 |

Figure 4FF

| | | | | | | | | | |
|---|---|---|---|---|---|---|---|---|---|
| ATOM | 1612 | CG | HIS | A | 242 | 38.080 | 44.396 | 14.146 | 1.00 42.30 |
| ATOM | 1613 | CD2 | HIS | A | 242 | 37.279 | 45.393 | 14.586 | 1.00 44.39 |
| ATOM | 1614 | ND1 | HIS | A | 242 | 38.763 | 43.939 | 15.251 | 1.00 46.23 |
| ATOM | 1615 | CE1 | HIS | A | 242 | 38.389 | 44.629 | 16.313 | 1.00 45.99 |
| ATOM | 1616 | NE2 | HIS | A | 242 | 37.489 | 45.517 | 15.936 | 1.00 46.42 |
| ATOM | 1617 | C | HIS | A | 242 | 37.353 | 41.479 | 12.565 | 1.00 31.34 |
| ATOM | 1618 | O | HIS | A | 242 | 36.288 | 41.957 | 12.177 | 1.00 31.77 |
| ATOM | 1619 | N | THR | A | 243 | 37.521 | 40.182 | 12.747 | 1.00 25.13 |
| ATOM | 1620 | CA | THR | A | 243 | 36.401 | 39.257 | 12.554 | 1.00 24.56 |
| ATOM | 1621 | CB | THR | A | 243 | 36.926 | 37.887 | 12.060 | 1.00 27.68 |
| ATOM | 1622 | OG1 | THR | A | 243 | 37.816 | 37.314 | 13.033 | 1.00 24.15 |
| ATOM | 1623 | CG2 | THR | A | 243 | 37.690 | 38.064 | 10.715 | 1.00 26.23 |
| ATOM | 1624 | C | THR | A | 243 | 35.561 | 39.124 | 13.854 | 1.00 21.74 |
| ATOM | 1625 | O | THR | A | 243 | 35.993 | 39.525 | 14.930 | 1.00 19.85 |
| ATOM | 1626 | N | TYR | A | 244 | 34.313 | 38.667 | 13.722 | 1.00 19.10 |
| ATOM | 1627 | CA | TYR | A | 244 | 33.427 | 38.457 | 14.913 | 1.00 15.57 |
| ATOM | 1628 | CB | TYR | A | 244 | 31.962 | 38.295 | 14.532 | 1.00 14.06 |
| ATOM | 1629 | CG | TYR | A | 244 | 31.306 | 39.493 | 13.925 | 1.00 4.92 |
| ATOM | 1630 | CD1 | TYR | A | 244 | 30.688 | 40.458 | 14.715 | 1.00 4.27 |
| ATOM | 1631 | CE1 | TYR | A | 244 | 30.045 | 41.530 | 14.143 | 1.00 2.00 |
| ATOM | 1632 | CD2 | TYR | A | 244 | 31.261 | 39.637 | 12.548 | 1.00 9.74 |
| ATOM | 1633 | CE2 | TYR | A | 244 | 30.623 | 40.695 | 11.965 | 1.00 7.59 |
| ATOM | 1634 | CZ | TYR | A | 244 | 30.015 | 41.636 | 12.773 | 1.00 8.21 |
| ATOM | 1635 | OH | TYR | A | 244 | 29.357 | 42.669 | 12.179 | 1.00 18.77 |
| ATOM | 1636 | C | TYR | A | 244 | 33.862 | 37.187 | 15.595 | 1.00 14.96 |
| ATOM | 1637 | O | TYR | A | 244 | 33.530 | 36.924 | 16.738 | 1.00 19.83 |
| ATOM | 1638 | N | LEU | A | 245 | 34.511 | 36.329 | 14.811 | 1.00 15.53 |
| ATOM | 1639 | CA | LEU | A | 245 | 35.010 | 35.042 | 15.318 | 1.00 16.41 |
| ATOM | 1640 | CB | LEU | A | 245 | 35.716 | 34.282 | 14.205 | 1.00 11.78 |
| ATOM | 1641 | CG | LEU | A | 245 | 36.292 | 32.945 | 14.654 | 1.00 8.82 |
| ATOM | 1642 | CD1 | LEU | A | 245 | 35.234 | 32.102 | 15.349 | 1.00 7.84 |
| ATOM | 1643 | CD2 | LEU | A | 245 | 36.844 | 32.242 | 13.469 | 1.00 7.03 |
| ATOM | 1644 | C | LEU | A | 245 | 35.954 | 35.381 | 16.444 | 1.00 17.28 |
| ATOM | 1645 | O | LEU | A | 245 | 36.966 | 36.034 | 16.252 | 1.00 24.50 |
| ATOM | 1646 | N | GLN | A | 246 | 35.628 | 34.889 | 17.624 | 1.00 20.92 |
| ATOM | 1647 | CA | GLN | A | 246 | 36.404 | 35.187 | 18.855 | 1.00 25.04 |
| ATOM | 1648 | CB | GLN | A | 246 | 35.435 | 35.118 | 20.045 | 1.00 26.22 |
| ATOM | 1649 | CG | GLN | A | 246 | 35.506 | 36.290 | 21.006 | 1.00 34.07 |
| ATOM | 1650 | CD | GLN | A | 246 | 35.105 | 37.623 | 20.379 | 1.00 38.80 |
| ATOM | 1651 | OE1 | GLN | A | 246 | 35.160 | 37.811 | 19.166 | 1.00 33.06 |
| ATOM | 1652 | NE2 | GLN | A | 246 | 34.701 | 38.559 | 21.222 | 1.00 45.90 |
| ATOM | 1653 | C | GLN | A | 246 | 37.642 | 34.285 | 19.055 | 1.00 26.29 |
| ATOM | 1654 | O | GLN | A | 246 | 38.038 | 33.946 | 20.157 | 1.00 29.79 |
| ATOM | 1655 | N | ALA | A | 247 | 38.291 | 33.955 | 17.949 | 1.00 28.45 |
| ATOM | 1656 | CA | ALA | A | 247 | 39.452 | 33.069 | 17.978 | 1.00 28.46 |
| ATOM | 1657 | CB | ALA | A | 247 | 38.989 | 31.631 | 17.932 | 1.00 30.30 |
| ATOM | 1658 | C | ALA | A | 247 | 40.328 | 33.364 | 16.773 | 1.00 32.68 |
| ATOM | 1659 | O | ALA | A | 247 | 41.454 | 32.823 | 16.705 | 1.00 38.87 |
| ATOM | 1660 | OT | ALA | A | 247 | 39.871 | 34.130 | 15.912 | 1.00 34.37 |
| ATOM | 1661 | CB | ALA | B | 17 | 7.914 | 5.748 | 31.702 | 1.00 42.04 |
| ATOM | 1662 | C | ALA | B | 17 | 10.186 | 5.934 | 32.769 | 1.00 36.44 |
| ATOM | 1663 | O | ALA | B | 17 | 11.186 | 5.814 | 32.063 | 1.00 36.04 |

Figure 4GG

| ATOM | 1664 | N   | ALA | B | 17 | 8.300  | 4.683  | 33.913 | 1.00 | 41.59 |
|------|------|-----|-----|---|----|--------|--------|--------|------|-------|
| ATOM | 1665 | CA  | ALA | B | 17 | 8.924  | 5.050  | 32.589 | 1.00 | 39.91 |
| ATOM | 1666 | N   | ALA | B | 18 | 10.112 | 6.843  | 33.731 | 1.00 | 31.29 |
| ATOM | 1667 | CA  | ALA | B | 18 | 11.248 | 7.701  | 34.016 | 1.00 | 27.61 |
| ATOM | 1668 | CB  | ALA | B | 18 | 10.834 | 8.828  | 34.910 | 1.00 | 24.69 |
| ATOM | 1669 | C   | ALA | B | 18 | 12.280 | 6.823  | 34.725 | 1.00 | 29.22 |
| ATOM | 1670 | O   | ALA | B | 18 | 11.948 | 5.839  | 35.399 | 1.00 | 33.49 |
| ATOM | 1671 | N   | VAL | B | 19 | 13.546 | 7.137  | 34.466 | 1.00 | 27.94 |
| ATOM | 1672 | CA  | VAL | B | 19 | 14.697 | 6.453  | 35.079 | 1.00 | 23.42 |
| ATOM | 1673 | CB  | VAL | B | 19 | 15.917 | 6.368  | 34.124 | 1.00 | 21.98 |
| ATOM | 1674 | CG1 | VAL | B | 19 | 17.180 | 6.063  | 34.899 | 1.00 | 22.99 |
| ATOM | 1675 | CG2 | VAL | B | 19 | 15.707 | 5.276  | 33.094 | 1.00 | 22.11 |
| ATOM | 1676 | C   | VAL | B | 19 | 15.041 | 7.441  | 36.171 | 1.00 | 23.75 |
| ATOM | 1677 | O   | VAL | B | 19 | 15.320 | 8.613  | 35.902 | 1.00 | 29.08 |
| ATOM | 1678 | N   | PRO | B | 20 | 14.897 | 7.017  | 37.439 | 1.00 | 24.40 |
| ATOM | 1679 | CD  | PRO | B | 20 | 14.336 | 5.738  | 37.907 | 1.00 | 20.63 |
| ATOM | 1680 | CA  | PRO | B | 20 | 15.210 | 7.897  | 38.572 | 1.00 | 16.99 |
| ATOM | 1681 | CB  | PRO | B | 20 | 14.681 | 7.118  | 39.773 | 1.00 | 17.30 |
| ATOM | 1682 | CG  | PRO | B | 20 | 13.659 | 6.171  | 39.176 | 1.00 | 22.30 |
| ATOM | 1683 | C   | PRO | B | 20 | 16.735 | 8.039  | 38.627 | 1.00 | 15.71 |
| ATOM | 1684 | O   | PRO | B | 20 | 17.501 | 7.083  | 38.650 | 1.00 | 21.58 |
| ATOM | 1685 | N   | ILE | B | 21 | 17.186 | 9.266  | 38.594 | 1.00 | 12.31 |
| ATOM | 1686 | CA  | ILE | B | 21 | 18.595 | 9.500  | 38.613 | 1.00 | 10.03 |
| ATOM | 1687 | CB  | ILE | B | 21 | 18.979 | 10.413 | 37.430 | 1.00 | 11.03 |
| ATOM | 1688 | CG2 | ILE | B | 21 | 20.393 | 10.889 | 37.540 | 1.00 | 13.92 |
| ATOM | 1689 | CG1 | ILE | B | 21 | 18.828 | 9.672  | 36.106 | 1.00 | 9.00  |
| ATOM | 1690 | CD1 | ILE | B | 21 | 18.934 | 10.589 | 34.911 | 1.00 | 7.24  |
| ATOM | 1691 | C   | ILE | B | 21 | 18.867 | 10.215 | 39.901 | 1.00 | 13.47 |
| ATOM | 1692 | O   | ILE | B | 21 | 18.120 | 11.101 | 40.315 | 1.00 | 19.72 |
| ATOM | 1693 | N   | TYR | B | 22 | 19.933 | 9.791  | 40.567 | 1.00 | 14.67 |
| ATOM | 1694 | CA  | TYR | B | 22 | 20.410 | 10.416 | 41.827 | 1.00 | 13.36 |
| ATOM | 1695 | CB  | TYR | B | 22 | 20.804 | 9.351  | 42.841 | 1.00 | 14.24 |
| ATOM | 1696 | CG  | TYR | B | 22 | 19.639 | 8.560  | 43.295 | 1.00 | 14.90 |
| ATOM | 1697 | CD1 | TYR | B | 22 | 18.899 | 8.958  | 44.407 | 1.00 | 19.97 |
| ATOM | 1698 | CE1 | TYR | B | 22 | 17.735 | 8.300  | 44.763 | 1.00 | 21.18 |
| ATOM | 1699 | CD2 | TYR | B | 22 | 19.203 | 7.482  | 42.564 | 1.00 | 13.21 |
| ATOM | 1700 | CE2 | TYR | B | 22 | 18.053 | 6.818  | 42.909 | 1.00 | 19.45 |
| ATOM | 1701 | CZ  | TYR | B | 22 | 17.317 | 7.231  | 44.003 | 1.00 | 19.77 |
| ATOM | 1702 | OH  | TYR | B | 22 | 16.148 | 6.579  | 44.303 | 1.00 | 24.12 |
| ATOM | 1703 | C   | TYR | B | 22 | 21.628 | 11.324 | 41.562 | 1.00 | 12.70 |
| ATOM | 1704 | O   | TYR | B | 22 | 22.625 | 10.918 | 40.965 | 1.00 | 9.15  |
| ATOM | 1705 | N   | VAL | B | 23 | 21.531 | 12.557 | 42.040 | 1.00 | 14.63 |
| ATOM | 1706 | CA  | VAL | B | 23 | 22.629 | 13.540 | 41.904 | 1.00 | 16.43 |
| ATOM | 1707 | CB  | VAL | B | 23 | 22.123 | 14.954 | 41.556 | 1.00 | 17.71 |
| ATOM | 1708 | CG1 | VAL | B | 23 | 23.072 | 15.636 | 40.554 | 1.00 | 15.98 |
| ATOM | 1709 | CG2 | VAL | B | 23 | 20.685 | 14.909 | 41.031 | 1.00 | 17.96 |
| ATOM | 1710 | C   | VAL | B | 23 | 23.207 | 13.671 | 43.305 | 1.00 | 16.17 |
| ATOM | 1711 | O   | VAL | B | 23 | 22.493 | 13.693 | 44.302 | 1.00 | 18.84 |
| ATOM | 1712 | N   | ALA | B | 24 | 24.511 | 13.850 | 43.374 | 1.00 | 15.31 |
| ATOM | 1713 | CA  | ALA | B | 24 | 25.196 | 14.016 | 44.676 | 1.00 | 14.89 |
| ATOM | 1714 | CB  | ALA | B | 24 | 25.689 | 12.667 | 45.201 | 1.00 | 12.44 |
| ATOM | 1715 | C   | ALA | B | 24 | 26.381 | 14.936 | 44.414 | 1.00 | 14.63 |

Figure 4HH

| ATOM | 1716 | O   | ALA | B | 24 | 26.930 | 14.969 | 43.308 | 1.00 | 15.05 |
|------|------|-----|-----|---|----|--------|--------|--------|------|-------|
| ATOM | 1717 | N   | GLY | B | 25 | 26.729 | 15.731 | 45.423 | 1.00 | 12.31 |
| ATOM | 1718 | CA  | GLY | B | 25 | 27.860 | 16.623 | 45.310 | 1.00 | 5.61  |
| ATOM | 1719 | C   | GLY | B | 25 | 27.865 | 17.640 | 46.411 | 1.00 | 5.51  |
| ATOM | 1720 | O   | GLY | B | 25 | 27.029 | 17.585 | 47.284 | 1.00 | 12.72 |
| ATOM | 1721 | N   | PHE | B | 26 | 28.854 | 18.518 | 46.416 | 1.00 | 6.35  |
| ATOM | 1722 | CA  | PHE | B | 26 | 28.940 | 19.590 | 47.405 | 1.00 | 7.67  |
| ATOM | 1723 | CB  | PHE | B | 26 | 30.389 | 19.864 | 47.792 | 1.00 | 9.57  |
| ATOM | 1724 | CG  | PHE | B | 26 | 30.949 | 18.878 | 48.767 | 1.00 | 13.16 |
| ATOM | 1725 | CD1 | PHE | B | 26 | 31.679 | 17.773 | 48.328 | 1.00 | 11.14 |
| ATOM | 1726 | CD2 | PHE | B | 26 | 30.731 | 19.039 | 50.134 | 1.00 | 11.34 |
| ATOM | 1727 | CE1 | PHE | B | 26 | 32.184 | 16.834 | 49.253 | 1.00 | 13.74 |
| ATOM | 1728 | CE2 | PHE | B | 26 | 31.230 | 18.110 | 51.061 | 1.00 | 7.30  |
| ATOM | 1729 | CZ  | PHE | B | 26 | 31.953 | 17.011 | 50.627 | 1.00 | 7.04  |
| ATOM | 1730 | C   | PHE | B | 26 | 28.298 | 20.843 | 46.770 | 1.00 | 9.17  |
| ATOM | 1731 | O   | PHE | B | 26 | 28.474 | 21.176 | 45.581 | 1.00 | 11.18 |
| ATOM | 1732 | N   | LEU | B | 27 | 27.440 | 21.467 | 47.559 | 1.00 | 5.05  |
| ATOM | 1733 | CA  | LEU | B | 27 | 26.750 | 22.682 | 47.145 | 1.00 | 4.57  |
| ATOM | 1734 | CB  | LEU | B | 27 | 25.548 | 22.902 | 48.065 | 1.00 | 8.98  |
| ATOM | 1735 | CG  | LEU | B | 27 | 24.093 | 22.598 | 47.642 | 1.00 | 9.54  |
| ATOM | 1736 | CD1 | LEU | B | 27 | 24.012 | 22.036 | 46.225 | 1.00 | 8.26  |
| ATOM | 1737 | CD2 | LEU | B | 27 | 23.453 | 21.669 | 48.614 | 1.00 | 3.57  |
| ATOM | 1738 | C   | LEU | B | 27 | 27.788 | 23.805 | 47.279 | 1.00 | 6.30  |
| ATOM | 1739 | O   | LEU | B | 27 | 27.705 | 24.847 | 46.651 | 1.00 | 9.86  |
| ATOM | 1740 | N   | ALA | B | 28 | 28.800 | 23.539 | 48.097 | 1.00 | 5.73  |
| ATOM | 1741 | CA  | ALA | B | 28 | 29.898 | 24.487 | 48.379 | 1.00 | 7.39  |
| ATOM | 1742 | CB  | ALA | B | 28 | 29.332 | 25.732 | 49.076 | 1.00 | 4.11  |
| ATOM | 1743 | C   | ALA | B | 28 | 30.983 | 23.851 | 49.219 | 1.00 | 12.09 |
| ATOM | 1744 | O   | ALA | B | 28 | 30.745 | 22.923 | 50.101 | 1.00 | 10.48 |
| ATOM | 1745 | N   | LEU | B | 29 | 32.218 | 24.297 | 49.141 | 1.00 | 15.20 |
| ATOM | 1746 | CA  | LEU | B | 29 | 33.331 | 23.837 | 49.999 | 1.00 | 17.93 |
| ATOM | 1747 | CB  | LEU | B | 29 | 34.550 | 23.538 | 49.145 | 1.00 | 17.09 |
| ATOM | 1748 | CG  | LEU | B | 29 | 34.431 | 22.363 | 48.194 | 1.00 | 12.85 |
| ATOM | 1749 | CD1 | LEU | B | 29 | 35.778 | 22.222 | 47.469 | 1.00 | 13.89 |
| ATOM | 1750 | CD2 | LEU | B | 29 | 34.087 | 21.108 | 48.956 | 1.00 | 7.88  |
| ATOM | 1751 | C   | LEU | B | 29 | 33.600 | 25.025 | 50.968 | 1.00 | 18.65 |
| ATOM | 1752 | O   | LEU | B | 29 | 33.623 | 26.197 | 50.554 | 1.00 | 20.18 |
| ATOM | 1753 | N   | TYR | B | 30 | 33.810 | 24.706 | 52.248 | 1.00 | 18.71 |
| ATOM | 1754 | CA  | TYR | B | 30 | 34.028 | 25.738 | 53.309 | 1.00 | 19.45 |
| ATOM | 1755 | CB  | TYR | B | 30 | 33.951 | 25.113 | 54.704 | 1.00 | 15.67 |
| ATOM | 1756 | CG  | TYR | B | 30 | 32.538 | 24.795 | 55.139 | 1.00 | 13.40 |
| ATOM | 1757 | CD1 | TYR | B | 30 | 31.514 | 25.724 | 54.983 | 1.00 | 8.00  |
| ATOM | 1758 | CE1 | TYR | B | 30 | 30.213 | 25.422 | 55.378 | 1.00 | 8.39  |
| ATOM | 1759 | CD2 | TYR | B | 30 | 32.223 | 23.554 | 55.700 | 1.00 | 15.68 |
| ATOM | 1760 | CE2 | TYR | B | 30 | 30.912 | 23.241 | 56.104 | 1.00 | 7.37  |
| ATOM | 1761 | CZ  | TYR | B | 30 | 29.925 | 24.184 | 55.938 | 1.00 | 5.65  |
| ATOM | 1762 | OH  | TYR | B | 30 | 28.657 | 23.910 | 56.351 | 1.00 | 8.42  |
| ATOM | 1763 | C   | TYR | B | 30 | 35.233 | 26.657 | 53.213 | 1.00 | 23.64 |
| ATOM | 1764 | O   | TYR | B | 30 | 35.094 | 27.881 | 53.294 | 1.00 | 31.45 |
| ATOM | 1765 | N   | ASP | B | 31 | 36.432 | 26.100 | 53.037 | 1.00 | 23.40 |
| ATOM | 1766 | CA  | ASP | B | 31 | 37.626 | 26.995 | 52.963 | 1.00 | 28.47 |
| ATOM | 1767 | CB  | ASP | B | 31 | 38.533 | 26.833 | 54.207 | 1.00 | 37.77 |

Figure 4II

| ATOM | 1768 | CG | ASP | B | 31 | 38.070 | 27.693 | 55.427 | 1.00 | 43.27 |
| --- | --- | --- | --- | --- | --- | --- | --- | --- | --- | --- |
| ATOM | 1769 | OD1 | ASP | B | 31 | 37.920 | 27.126 | 56.541 | 1.00 | 46.07 |
| ATOM | 1770 | OD2 | ASP | B | 31 | 37.900 | 28.933 | 55.286 | 1.00 | 41.65 |
| ATOM | 1771 | C | ASP | B | 31 | 38.386 | 26.745 | 51.641 | 1.00 | 27.15 |
| ATOM | 1772 | O | ASP | B | 31 | 39.570 | 26.399 | 51.588 | 1.00 | 30.69 |
| ATOM | 1773 | N | SER | B | 32 | 37.680 | 27.020 | 50.555 | 1.00 | 24.54 |
| ATOM | 1774 | CA | SER | B | 32 | 38.202 | 26.778 | 49.219 | 1.00 | 20.41 |
| ATOM | 1775 | CB | SER | B | 32 | 37.112 | 26.114 | 48.387 | 1.00 | 21.75 |
| ATOM | 1776 | OG | SER | B | 32 | 35.933 | 26.899 | 48.408 | 1.00 | 26.20 |
| ATOM | 1777 | C | SER | B | 32 | 38.758 | 27.974 | 48.497 | 1.00 | 20.84 |
| ATOM | 1778 | O | SER | B | 32 | 39.635 | 27.855 | 47.651 | 1.00 | 23.98 |
| ATOM | 1779 | N | GLY | B | 33 | 38.226 | 29.146 | 48.785 | 1.00 | 20.77 |
| ATOM | 1780 | CA | GLY | B | 33 | 38.705 | 30.318 | 48.081 | 1.00 | 16.03 |
| ATOM | 1781 | C | GLY | B | 33 | 37.617 | 30.952 | 47.236 | 1.00 | 19.69 |
| ATOM | 1782 | O | GLY | B | 33 | 37.920 | 31.559 | 46.217 | 1.00 | 19.90 |
| ATOM | 1783 | N | ASP | B | 34 | 36.351 | 30.791 | 47.642 | 1.00 | 22.84 |
| ATOM | 1784 | CA | ASP | B | 34 | 35.194 | 31.407 | 46.915 | 1.00 | 23.86 |
| ATOM | 1785 | CB | ASP | B | 34 | 33.849 | 30.858 | 47.437 | 1.00 | 20.39 |
| ATOM | 1786 | CG | ASP | B | 34 | 33.467 | 29.505 | 46.845 | 1.00 | 20.19 |
| ATOM | 1787 | OD1 | ASP | B | 34 | 32.923 | 28.659 | 47.594 | 1.00 | 19.43 |
| ATOM | 1788 | OD2 | ASP | B | 34 | 33.655 | 29.287 | 45.636 | 1.00 | 21.35 |
| ATOM | 1789 | C | ASP | B | 34 | 35.262 | 32.941 | 47.180 | 1.00 | 28.22 |
| ATOM | 1790 | O | ASP | B | 34 | 35.542 | 33.385 | 48.295 | 1.00 | 29.13 |
| ATOM | 1791 | N | PRO | B | 35 | 35.030 | 33.765 | 46.141 | 1.00 | 29.64 |
| ATOM | 1792 | CD | PRO | B | 35 | 34.740 | 33.415 | 44.737 | 1.00 | 34.16 |
| ATOM | 1793 | CA | PRO | B | 35 | 35.066 | 35.217 | 46.319 | 1.00 | 30.50 |
| ATOM | 1794 | CB | PRO | B | 35 | 34.454 | 35.724 | 45.021 | 1.00 | 33.09 |
| ATOM | 1795 | CG | PRO | B | 35 | 34.952 | 34.726 | 44.024 | 1.00 | 33.02 |
| ATOM | 1796 | C | PRO | B | 35 | 34.205 | 35.636 | 47.522 | 1.00 | 32.77 |
| ATOM | 1797 | O | PRO | B | 35 | 33.386 | 34.867 | 48.044 | 1.00 | 34.58 |
| ATOM | 1798 | N | GLY | B | 36 | 34.344 | 36.902 | 47.903 | 1.00 | 33.77 |
| ATOM | 1799 | CA | GLY | B | 36 | 33.596 | 37.424 | 49.035 | 1.00 | 35.99 |
| ATOM | 1800 | C | GLY | B | 36 | 32.138 | 37.010 | 49.117 | 1.00 | 36.20 |
| ATOM | 1801 | O | GLY | B | 36 | 31.723 | 36.316 | 50.042 | 1.00 | 35.68 |
| ATOM | 1802 | N | GLU | B | 37 | 31.369 | 37.434 | 48.126 | 1.00 | 37.95 |
| ATOM | 1803 | CA | GLU | B | 37 | 29.933 | 37.137 | 48.051 | 1.00 | 37.96 |
| ATOM | 1804 | CB | GLU | B | 37 | 29.401 | 37.840 | 46.796 | 1.00 | 45.40 |
| ATOM | 1805 | CG | GLU | B | 37 | 27.957 | 37.539 | 46.417 | 1.00 | 58.85 |
| ATOM | 1806 | CD | GLU | B | 37 | 27.524 | 38.252 | 45.126 | 1.00 | 65.53 |
| ATOM | 1807 | OE1 | GLU | B | 37 | 28.214 | 38.093 | 44.086 | 1.00 | 66.48 |
| ATOM | 1808 | OE2 | GLU | B | 37 | 26.494 | 38.977 | 45.156 | 1.00 | 69.68 |
| ATOM | 1809 | C | GLU | B | 37 | 29.537 | 35.621 | 48.101 | 1.00 | 35.52 |
| ATOM | 1810 | O | GLU | B | 37 | 28.801 | 35.172 | 48.976 | 1.00 | 40.65 |
| ATOM | 1811 | N | LEU | B | 38 | 30.091 | 34.821 | 47.198 | 1.00 | 28.34 |
| ATOM | 1812 | CA | LEU | B | 38 | 29.715 | 33.384 | 47.117 | 1.00 | 20.64 |
| ATOM | 1813 | CB | LEU | B | 38 | 30.289 | 32.807 | 45.842 | 1.00 | 19.87 |
| ATOM | 1814 | CG | LEU | B | 38 | 29.891 | 33.584 | 44.600 | 1.00 | 19.38 |
| ATOM | 1815 | CD1 | LEU | B | 38 | 30.515 | 32.915 | 43.399 | 1.00 | 21.32 |
| ATOM | 1816 | CD2 | LEU | B | 38 | 28.374 | 33.625 | 44.484 | 1.00 | 20.57 |
| ATOM | 1817 | C | LEU | B | 38 | 30.056 | 32.479 | 48.285 | 1.00 | 19.55 |
| ATOM | 1818 | O | LEU | B | 38 | 29.484 | 31.410 | 48.494 | 1.00 | 16.14 |
| ATOM | 1819 | N | ALA | B | 39 | 31.042 | 32.914 | 49.043 | 1.00 | 21.73 |

Figure 4JJ

| ATOM | 1820 | CA | ALA | B | 39 | 31.535 | 32.138 | 50.189 | 1.00 | 23.75 |
|---|---|---|---|---|---|---|---|---|---|---|
| ATOM | 1821 | CB | ALA | B | 39 | 32.594 | 32.925 | 50.916 | 1.00 | 23.17 |
| ATOM | 1822 | C | ALA | B | 39 | 30.470 | 31.681 | 51.173 | 1.00 | 22.95 |
| ATOM | 1823 | O | ALA | B | 39 | 29.624 | 32.445 | 51.621 | 1.00 | 30.93 |
| ATOM | 1824 | N | LEU | B | 40 | 30.565 | 30.412 | 51.543 | 1.00 | 21.62 |
| ATOM | 1825 | CA | LEU | B | 40 | 29.645 | 29.799 | 52.517 | 1.00 | 23.96 |
| ATOM | 1826 | CB | LEU | B | 40 | 28.877 | 28.665 | 51.836 | 1.00 | 24.40 |
| ATOM | 1827 | CG | LEU | B | 40 | 27.534 | 29.021 | 51.176 | 1.00 | 26.75 |
| ATOM | 1828 | CD1 | LEU | B | 40 | 26.934 | 27.779 | 50.575 | 1.00 | 24.00 |
| ATOM | 1829 | CD2 | LEU | B | 40 | 26.533 | 29.598 | 52.192 | 1.00 | 25.11 |
| ATOM | 1830 | C | LEU | B | 40 | 30.436 | 29.293 | 53.757 | 1.00 | 23.95 |
| ATOM | 1831 | O | LEU | B | 40 | 31.531 | 28.783 | 53.634 | 1.00 | 27.29 |
| ATOM | 1832 | N | ASP | B | 41 | 29.892 | 29.461 | 54.960 | 1.00 | 24.27 |
| ATOM | 1833 | CA | ASP | B | 41 | 30.598 | 28.978 | 56.171 | 1.00 | 20.70 |
| ATOM | 1834 | CB | ASP | B | 41 | 31.074 | 30.151 | 56.983 | 1.00 | 24.18 |
| ATOM | 1835 | CG | ASP | B | 41 | 29.959 | 31.045 | 57.375 | 1.00 | 28.70 |
| ATOM | 1836 | OD1 | ASP | B | 41 | 29.490 | 30.924 | 58.524 | 1.00 | 35.82 |
| ATOM | 1837 | OD2 | ASP | B | 41 | 29.542 | 31.857 | 56.522 | 1.00 | 38.93 |
| ATOM | 1838 | C | ASP | B | 41 | 29.698 | 28.043 | 56.993 | 1.00 | 22.49 |
| ATOM | 1839 | O | ASP | B | 41 | 28.474 | 28.092 | 56.891 | 1.00 | 23.03 |
| ATOM | 1840 | N | PRO | B | 42 | 30.309 | 27.223 | 57.884 | 1.00 | 22.42 |
| ATOM | 1841 | CD | PRO | B | 42 | 31.738 | 27.246 | 58.252 | 1.00 | 17.94 |
| ATOM | 1842 | CA | PRO | B | 42 | 29.605 | 26.256 | 58.729 | 1.00 | 18.37 |
| ATOM | 1843 | CB | PRO | B | 42 | 30.709 | 25.733 | 59.644 | 1.00 | 17.62 |
| ATOM | 1844 | CG | PRO | B | 42 | 31.930 | 25.875 | 58.836 | 1.00 | 12.63 |
| ATOM | 1845 | C | PRO | B | 42 | 28.448 | 26.783 | 59.529 | 1.00 | 20.50 |
| ATOM | 1846 | O | PRO | B | 42 | 27.405 | 26.160 | 59.612 | 1.00 | 26.91 |
| ATOM | 1847 | N | ASP | B | 43 | 28.613 | 27.952 | 60.125 | 1.00 | 22.41 |
| ATOM | 1848 | CA | ASP | B | 43 | 27.514 | 28.502 | 60.949 | 1.00 | 27.41 |
| ATOM | 1849 | CB | ASP | B | 43 | 28.013 | 29.678 | 61.782 | 1.00 | 29.40 |
| ATOM | 1850 | CG | ASP | B | 43 | 28.516 | 29.236 | 63.138 | 1.00 | 35.28 |
| ATOM | 1851 | OD1 | ASP | B | 43 | 27.886 | 28.323 | 63.733 | 1.00 | 37.31 |
| ATOM | 1852 | OD2 | ASP | B | 43 | 29.535 | 29.800 | 63.603 | 1.00 | 41.37 |
| ATOM | 1853 | C | ASP | B | 43 | 26.257 | 28.857 | 60.148 | 1.00 | 27.94 |
| ATOM | 1854 | O | ASP | B | 43 | 25.133 | 28.474 | 60.492 | 1.00 | 28.82 |
| ATOM | 1855 | N | THR | B | 44 | 26.469 | 29.558 | 59.038 | 1.00 | 26.47 |
| ATOM | 1856 | CA | THR | B | 44 | 25.357 | 29.936 | 58.151 | 1.00 | 24.65 |
| ATOM | 1857 | CB | THR | B | 44 | 25.863 | 30.714 | 56.935 | 1.00 | 27.18 |
| ATOM | 1858 | OG1 | THR | B | 44 | 26.592 | 31.867 | 57.374 | 1.00 | 33.19 |
| ATOM | 1859 | CG2 | THR | B | 44 | 24.699 | 31.168 | 56.084 | 1.00 | 29.04 |
| ATOM | 1860 | C | THR | B | 44 | 24.629 | 28.672 | 57.637 | 1.00 | 23.56 |
| ATOM | 1861 | O | THR | B | 44 | 23.412 | 28.632 | 57.505 | 1.00 | 26.17 |
| ATOM | 1862 | N | VAL | B | 45 | 25.397 | 27.632 | 57.342 | 1.00 | 18.56 |
| ATOM | 1863 | CA | VAL | B | 45 | 24.805 | 26.391 | 56.835 | 1.00 | 19.89 |
| ATOM | 1864 | CB | VAL | B | 45 | 25.882 | 25.472 | 56.271 | 1.00 | 21.82 |
| ATOM | 1865 | CG1 | VAL | B | 45 | 25.289 | 24.119 | 55.829 | 1.00 | 18.35 |
| ATOM | 1866 | CG2 | VAL | B | 45 | 26.575 | 26.185 | 55.120 | 1.00 | 18.96 |
| ATOM | 1867 | C | VAL | B | 45 | 24.044 | 25.702 | 57.948 | 1.00 | 22.56 |
| ATOM | 1868 | O | VAL | B | 45 | 22.943 | 25.166 | 57.756 | 1.00 | 22.28 |
| ATOM | 1869 | N | ARG | B | 46 | 24.634 | 25.768 | 59.140 | 1.00 | 24.52 |
| ATOM | 1870 | CA | ARG | B | 46 | 24.037 | 25.160 | 60.355 | 1.00 | 25.74 |
| ATOM | 1871 | CB | ARG | B | 46 | 24.914 | 25.485 | 61.587 | 1.00 | 29.95 |

Figure 4KK

| ATOM | 1872 | CG  | ARG | B | 46 | 24.762 | 24.524 | 62.309 | 1.00 | 39.07 |
| ATOM | 1873 | CD  | ARG | B | 46 | 25.326 | 23.065 | 62.570 | 1.00 | 50.64 |
| ATOM | 1874 | NE  | ARG | B | 46 | 24.547 | 22.250 | 61.617 | 1.00 | 57.51 |
| ATOM | 1875 | CZ  | ARG | B | 46 | 24.746 | 20.952 | 61.373 | 1.00 | 56.52 |
| ATOM | 1876 | NH1 | ARG | B | 46 | 23.981 | 20.315 | 60.480 | 1.00 | 56.75 |
| ATOM | 1877 | NH2 | ARG | B | 46 | 25.686 | 20.282 | 62.032 | 1.00 | 55.99 |
| ATOM | 1878 | C   | ARG | B | 46 | 22.598 | 25.720 | 60.515 | 1.00 | 24.14 |
| ATOM | 1879 | O   | ARG | B | 46 | 21.592 | 25.009 | 60.593 | 1.00 | 27.14 |
| ATOM | 1880 | N   | ALA | B | 47 | 22.531 | 27.037 | 60.466 | 1.00 | 17.85 |
| ATOM | 1881 | CA  | ALA | B | 47 | 21.270 | 27.766 | 60.603 | 1.00 | 19.04 |
| ATOM | 1882 | CB  | ALA | B | 47 | 21.551 | 29.253 | 60.647 | 1.00 | 18.30 |
| ATOM | 1883 | C   | ALA | B | 47 | 20.262 | 27.496 | 59.501 | 1.00 | 19.75 |
| ATOM | 1884 | O   | ALA | B | 47 | 19.072 | 27.650 | 59.701 | 1.00 | 26.03 |
| ATOM | 1885 | N   | ALA | B | 48 | 20.745 | 27.149 | 58.313 | 1.00 | 23.65 |
| ATOM | 1886 | CA  | ALA | B | 48 | 19.865 | 26.905 | 57.132 | 1.00 | 20.82 |
| ATOM | 1887 | CB  | ALA | B | 48 | 20.610 | 27.271 | 55.877 | 1.00 | 17.62 |
| ATOM | 1888 | C   | ALA | B | 48 | 19.301 | 25.473 | 57.005 | 1.00 | 23.83 |
| ATOM | 1889 | O   | ALA | B | 48 | 18.437 | 25.184 | 56.167 | 1.00 | 26.26 |
| ATOM | 1890 | N   | LEU | B | 49 | 19.777 | 24.575 | 57.859 | 1.00 | 24.28 |
| ATOM | 1891 | CA  | LEU | B | 49 | 19.336 | 23.172 | 57.792 | 1.00 | 25.26 |
| ATOM | 1892 | CB  | LEU | B | 49 | 20.565 | 22.268 | 57.684 | 1.00 | 24.55 |
| ATOM | 1893 | CG  | LEU | B | 49 | 21.621 | 22.694 | 56.563 | 1.00 | 23.31 |
| ATOM | 1894 | CD1 | LEU | B | 49 | 22.852 | 21.816 | 56.752 | 1.00 | 21.74 |
| ATOM | 1895 | CD2 | LEU | B | 49 | 21.031 | 22.660 | 55.276 | 1.00 | 19.41 |
| ATOM | 1896 | C   | LEU | B | 49 | 18.494 | 22.796 | 59.005 | 1.00 | 27.28 |
| ATOM | 1897 | O   | LEU | B | 49 | 18.781 | 23.232 | 60.115 | 1.00 | 28.03 |
| ATOM | 1898 | N   | PRO | B | 50 | 17.378 | 22.051 | 58.789 | 1.00 | 29.74 |
| ATOM | 1899 | CD  | PRO | B | 50 | 16.528 | 21.489 | 59.855 | 1.00 | 30.25 |
| ATOM | 1900 | CA  | PRO | B | 50 | 16.912 | 21.585 | 57.476 | 1.00 | 27.96 |
| ATOM | 1901 | CB  | PRO | B | 50 | 15.817 | 20.566 | 57.826 | 1.00 | 24.32 |
| ATOM | 1902 | CG  | PRO | B | 50 | 16.089 | 20.190 | 59.252 | 1.00 | 28.79 |
| ATOM | 1903 | C   | PRO | B | 50 | 16.287 | 22.775 | 56.731 | 1.00 | 25.57 |
| ATOM | 1904 | O   | PRO | B | 50 | 15.964 | 23.810 | 57.311 | 1.00 | 22.54 |
| ATOM | 1905 | N   | PRO | B | 51 | 16.157 | 22.650 | 55.405 | 1.00 | 29.98 |
| ATOM | 1906 | CD  | PRO | B | 51 | 16.621 | 21.587 | 54.490 | 1.00 | 30.02 |
| ATOM | 1907 | CA  | PRO | B | 51 | 15.560 | 23.759 | 54.659 | 1.00 | 30.08 |
| ATOM | 1908 | CB  | PRO | B | 51 | 15.657 | 23.284 | 53.207 | 1.00 | 29.23 |
| ATOM | 1909 | CG  | PRO | B | 51 | 16.826 | 22.344 | 53.217 | 1.00 | 27.99 |
| ATOM | 1910 | C   | PRO | B | 51 | 14.090 | 23.883 | 55.103 | 1.00 | 28.49 |
| ATOM | 1911 | O   | PRO | B | 51 | 13.410 | 22.890 | 55.392 | 1.00 | 24.66 |
| ATOM | 1912 | N   | GLU | B | 52 | 13.628 | 25.128 | 55.189 | 1.00 | 30.06 |
| ATOM | 1913 | CA  | GLU | B | 52 | 12.234 | 25.421 | 55.589 | 1.00 | 32.42 |
| ATOM | 1914 | CB  | GLU | B | 52 | 11.956 | 26.919 | 55.534 | 1.00 | 36.65 |
| ATOM | 1915 | CG  | GLU | B | 52 | 10.534 | 27.287 | 55.369 | 1.00 | 45.10 |
| ATOM | 1916 | CD  | GLU | B | 52 | 10.232 | 26.921 | 57.426 | 1.00 | 48.70 |
| ATOM | 1917 | OE1 | GLU | B | 52 | 9.896  | 25.738 | 57.705 | 1.00 | 48.23 |
| ATOM | 1918 | OE2 | GLU | B | 52 | 10.330 | 27.827 | 58.293 | 1.00 | 51.11 |
| ATOM | 1919 | C   | GLU | B | 52 | 11.325 | 24.679 | 54.636 | 1.00 | 31.01 |
| ATOM | 1920 | O   | GLU | B | 52 | 10.443 | 23.924 | 55.025 | 1.00 | 32.65 |
| ATOM | 1921 | N   | ASN | B | 53 | 11.592 | 24.884 | 53.352 | 1.00 | 33.12 |
| ATOM | 1922 | CA  | ASN | B | 53 | 10.824 | 24.222 | 52.380 | 1.00 | 34.05 |
| ATOM | 1923 | CB  | ASN | B | 53 | 10.056 | 25.273 | 51.489 | 1.00 | 40.45 |

Figure 4LL

| | | | | | | | | | |
|---|---|---|---|---|---|---|---|---|---|
| ATOM | 1924 | CG | ASN | B | 53 | 8.798 | 25.729 | 52.212 | 1.00 47.92 |
| ATOM | 1925 | OD1 | ASN | B | 53 | 8.737 | 26.855 | 52.716 | 1.00 51.57 |
| ATOM | 1926 | ND2 | ASN | B | 53 | 7.787 | 24.846 | 52.283 | 1.00 47.09 |
| ATOM | 1927 | C | ASN | B | 53 | 11.734 | 23.363 | 51.374 | 1.00 30.06 |
| ATOM | 1928 | O | ASN | B | 53 | 12.924 | 23.616 | 51.226 | 1.00 29.95 |
| ATOM | 1929 | N | PRO | B | 54 | 11.175 | 22.287 | 50.800 | 1.00 27.48 |
| ATOM | 1930 | CD | PRO | B | 54 | 9.757 | 21.907 | 50.877 | 1.00 29.87 |
| ATOM | 1931 | CA | PRO | B | 54 | 11.899 | 21.371 | 49.912 | 1.00 24.96 |
| ATOM | 1932 | CB | PRO | B | 54 | 10.774 | 20.588 | 49.244 | 1.00 26.24 |
| ATOM | 1933 | CG | PRO | B | 54 | 9.770 | 20.509 | 50.300 | 1.00 29.13 |
| ATOM | 1934 | C | PRO | B | 54 | 12.653 | 22.158 | 48.861 | 1.00 20.54 |
| ATOM | 1935 | O | PRO | B | 54 | 12.241 | 23.235 | 48.437 | 1.00 21.35 |
| ATOM | 1936 | N | LEU | B | 55 | 13.779 | 21.615 | 48.436 | 1.00 19.79 |
| ATOM | 1937 | CA | LEU | B | 55 | 14.563 | 22.315 | 47.407 | 1.00 17.15 |
| ATOM | 1938 | CB | LEU | B | 55 | 16.064 | 22.350 | 47.781 | 1.00 18.83 |
| ATOM | 1939 | CG | LEU | B | 55 | 16.558 | 23.207 | 48.963 | 1.00 14.00 |
| ATOM | 1940 | CD1 | LEU | B | 55 | 18.025 | 23.029 | 49.110 | 1.00 15.20 |
| ATOM | 1941 | CD2 | LEU | B | 55 | 16.277 | 24.667 | 48.746 | 1.00 12.68 |
| ATOM | 1942 | C | LEU | B | 55 | 14.299 | 21.641 | 46.046 | 1.00 12.16 |
| ATOM | 1943 | O | LEU | B | 55 | 14.511 | 20.442 | 45.838 | 1.00 15.08 |
| ATOM | 1944 | N | PRO | B | 56 | 13.675 | 22.390 | 45.142 | 1.00 7.04 |
| ATOM | 1945 | CD | PRO | B | 56 | 13.127 | 23.752 | 45.196 | 1.00 3.73 |
| ATOM | 1946 | CA | PRO | B | 56 | 13.426 | 21.767 | 43.853 | 1.00 10.23 |
| ATOM | 1947 | CB | PRO | B | 56 | 12.415 | 22.725 | 43.232 | 1.00 7.30 |
| ATOM | 1948 | CG | PRO | B | 56 | 12.859 | 24.046 | 43.760 | 1.00 5.82 |
| ATOM | 1949 | C | PRO | B | 56 | 14.771 | 21.812 | 43.090 | 1.00 11.89 |
| ATOM | 1950 | O | PRO | B | 56 | 15.706 | 22.550 | 43.446 | 1.00 8.62 |
| ATOM | 1951 | N | ILE | B | 57 | 14.898 | 20.968 | 42.077 | 1.00 13.53 |
| ATOM | 1952 | CA | ILE | B | 57 | 16.125 | 20.996 | 41.238 | 1.00 9.97 |
| ATOM | 1953 | CB | ILE | B | 57 | 16.791 | 19.630 | 41.091 | 1.00 5.65 |
| ATOM | 1954 | CG2 | ILE | B | 57 | 18.004 | 19.778 | 40.192 | 1.00 9.75 |
| ATOM | 1955 | CG1 | ILE | B | 57 | 17.274 | 19.121 | 42.441 | 1.00 4.70 |
| ATOM | 1956 | CD1 | ILE | B | 57 | 17.866 | 17.721 | 42.389 | 1.00 5.11 |
| ATOM | 1957 | C | ILE | B | 57 | 15.677 | 21.426 | 39.845 | 1.00 9.36 |
| ATOM | 1958 | O | ILE | B | 57 | 14.664 | 20.937 | 39.316 | 1.00 10.17 |
| ATOM | 1959 | N | ASN | B | 58 | 16.349 | 22.422 | 39.285 | 1.00 9.18 |
| ATOM | 1960 | CA | ASN | B | 58 | 15.979 | 22.813 | 37.919 | 1.00 9.79 |
| ATOM | 1961 | CB | ASN | B | 58 | 15.138 | 24.098 | 37.383 | 1.00 15.10 |
| ATOM | 1962 | CG | ASN | B | 58 | 15.657 | 25.182 | 38.786 | 1.00 21.46 |
| ATOM | 1963 | OD1 | ASN | B | 58 | 16.813 | 25.558 | 38.711 | 1.00 27.70 |
| ATOM | 1964 | ND2 | ASN | B | 58 | 14.773 | 25.741 | 39.611 | 1.00 23.05 |
| ATOM | 1965 | C | ASN | B | 58 | 17.193 | 22.882 | 37.029 | 1.00 7.41 |
| ATOM | 1966 | O | ASN | B | 58 | 18.297 | 22.619 | 37.452 | 1.00 8.49 |
| ATOM | 1967 | N | VAL | B | 59 | 16.965 | 23.052 | 35.738 | 1.00 10.81 |
| ATOM | 1968 | CA | VAL | B | 59 | 18.081 | 23.178 | 34.788 | 1.00 8.30 |
| ATOM | 1969 | CB | VAL | B | 59 | 17.776 | 22.591 | 33.427 | 1.00 6.35 |
| ATOM | 1970 | CG1 | VAL | B | 59 | 18.923 | 22.844 | 32.503 | 1.00 9.43 |
| ATOM | 1971 | CG2 | VAL | B | 59 | 17.543 | 21.118 | 33.532 | 1.00 11.08 |
| ATOM | 1972 | C | VAL | B | 59 | 18.377 | 24.662 | 34.586 | 1.00 14.22 |
| ATOM | 1973 | O | VAL | B | 59 | 17.490 | 25.489 | 34.378 | 1.00 14.62 |
| ATOM | 1974 | N | ASP | B | 60 | 19.653 | 24.994 | 34.744 | 1.00 22.05 |
| ATOM | 1975 | CA | ASP | B | 60 | 20.173 | 26.361 | 34.544 | 1.00 29.65 |

Figure 4MM

| ATOM | 1976 | CB | ASP | B | 60 | 20.522 | 26.502 | 33.054 | 1.00 | 36.44 |
|------|------|-----|-----|---|----|--------|--------|--------|------|-------|
| ATOM | 1977 | CG | ASP | B | 60 | 21.635 | 27.489 | 32.796 | 1.00 | 39.69 |
| ATOM | 1978 | OD1 | ASP | B | 60 | 22.698 | 27.401 | 33.449 | 1.00 | 42.99 |
| ATOM | 1979 | OD2 | ASP | B | 60 | 21.446 | 28.343 | 31.910 | 1.00 | 45.07 |
| ATOM | 1980 | C | ASP | B | 60 | 19.253 | 27.517 | 35.047 | 1.00 | 33.50 |
| ATOM | 1981 | O | ASP | B | 60 | 18.875 | 28.427 | 34.309 | 1.00 | 38.95 |
| ATOM | 1982 | N | HIS | B | 61 | 18.884 | 27.447 | 36.321 | 1.00 | 34.75 |
| ATOM | 1983 | CA | HIS | B | 61 | 18.051 | 28.492 | 36.991 | 1.00 | 42.36 |
| ATOM | 1984 | CB | HIS | B | 61 | 18.920 | 29.705 | 37.300 | 1.00 | 43.73 |
| ATOM | 1985 | CG | HIS | B | 61 | 19.841 | 29.482 | 38.452 | 1.00 | 50.34 |
| ATOM | 1986 | CD2 | HIS | B | 61 | 19.579 | 29.236 | 39.759 | 1.00 | 54.56 |
| ATOM | 1987 | ND1 | HIS | B | 61 | 21.210 | 29.409 | 38.317 | 1.00 | 51.49 |
| ATOM | 1988 | CE1 | HIS | B | 61 | 21.751 | 29.123 | 39.485 | 1.00 | 56.03 |
| ATOM | 1989 | NE2 | HIS | B | 61 | 20.784 | 29.014 | 40.379 | 1.00 | 56.93 |
| ATOM | 1990 | C | HIS | B | 61 | 16.709 | 28.940 | 36.390 | 1.00 | 46.16 |
| ATOM | 1991 | O | HIS | B | 61 | 15.989 | 29.790 | 36.949 | 1.00 | 46.73 |
| ATOM | 1992 | N | ARG | B | 62 | 16.393 | 28.373 | 35.229 | 1.00 | 48.44 |
| ATOM | 1993 | CA | ARG | B | 62 | 15.128 | 28.648 | 34.535 | 1.00 | 44.01 |
| ATOM | 1994 | CB | ARG | B | 62 | 15.220 | 28.078 | 33.142 | 1.00 | 49.05 |
| ATOM | 1995 | CG | ARG | B | 62 | 15.701 | 29.073 | 32.106 | 1.00 | 57.87 |
| ATOM | 1996 | CD | ARG | B | 62 | 14.543 | 30.004 | 31.734 | 1.00 | 65.09 |
| ATOM | 1997 | NE | ARG | B | 62 | 13.269 | 29.280 | 31.569 | 1.00 | 70.00 |
| ATOM | 1998 | CZ | ARG | B | 62 | 12.725 | 28.929 | 30.399 | 1.00 | 70.84 |
| ATOM | 1999 | NH1 | ARG | B | 62 | 13.323 | 29.232 | 29.248 | 1.00 | 73.75 |
| ATOM | 2000 | NH2 | ARG | B | 62 | 11.585 | 28.242 | 30.382 | 1.00 | 68.33 |
| ATOM | 2001 | C | ARG | B | 62 | 14.136 | 27.892 | 35.393 | 1.00 | 41.14 |
| ATOM | 2002 | O | ARG | B | 62 | 13.952 | 26.685 | 35.287 | 1.00 | 40.32 |
| ATOM | 2003 | N | ALA | B | 63 | 13.562 | 28.617 | 36.341 | 1.00 | 40.60 |
| ATOM | 2004 | CA | ALA | B | 63 | 12.598 | 28.026 | 37.299 | 1.00 | 37.84 |
| ATOM | 2005 | CB | ALA | B | 63 | 12.014 | 29.100 | 38.173 | 1.00 | 42.36 |
| ATOM | 2006 | C | ALA | B | 63 | 11.482 | 27.183 | 36.672 | 1.00 | 36.34 |
| ATOM | 2007 | O | ALA | B | 63 | 10.871 | 26.351 | 37.319 | 1.00 | 33.91 |
| ATOM | 2008 | N | ARG | B | 64 | 11.210 | 27.412 | 35.395 | 1.00 | 36.32 |
| ATOM | 2009 | CA | ARG | B | 64 | 10.171 | 26.624 | 34.711 | 1.00 | 37.08 |
| ATOM | 2010 | CB | ARG | B | 64 | 9.886 | 27.184 | 33.320 | 1.00 | 42.01 |
| ATOM | 2011 | CG | ARG | B | 64 | 9.199 | 28.527 | 33.337 | 1.00 | 54.78 |
| ATOM | 2012 | CD | ARG | B | 64 | 8.008 | 28.554 | 32.373 | 1.00 | 65.40 |
| ATOM | 2013 | NE | ARG | B | 64 | 7.263 | 29.806 | 32.507 | 1.00 | 75.40 |
| ATOM | 2014 | CZ | ARG | B | 64 | 7.000 | 30.689 | 31.539 | 1.00 | 76.53 |
| ATOM | 2015 | NH1 | ARG | B | 64 | 6.325 | 31.784 | 31.862 | 1.00 | 76.03 |
| ATOM | 2016 | NH2 | ARG | B | 64 | 7.366 | 30.498 | 30.273 | 1.00 | 77.64 |
| ATOM | 2017 | C | ARG | B | 64 | 10.574 | 25.157 | 34.602 | 1.00 | 33.67 |
| ATOM | 2018 | O | ARG | B | 64 | 9.753 | 24.243 | 34.608 | 1.00 | 37.87 |
| ATOM | 2019 | N | CYS | B | 65 | 11.876 | 24.933 | 34.536 | 1.00 | 29.33 |
| ATOM | 2020 | CA | CYS | B | 65 | 12.396 | 23.568 | 34.369 | 1.00 | 24.28 |
| ATOM | 2021 | CB | CYS | B | 65 | 13.633 | 23.582 | 33.511 | 1.00 | 21.75 |
| ATOM | 2022 | SG | CYS | B | 65 | 13.207 | 23.996 | 31.891 | 1.00 | 23.63 |
| ATOM | 2023 | C | CYS | B | 65 | 12.654 | 22.743 | 35.579 | 1.00 | 22.51 |
| ATOM | 2024 | O | CYS | B | 65 | 13.744 | 22.204 | 35.784 | 1.00 | 24.06 |
| ATOM | 2025 | N | GLU | B | 66 | 11.628 | 22.597 | 36.392 | 1.00 | 17.47 |
| ATOM | 2026 | CA | GLU | B | 66 | 11.791 | 21.768 | 37.557 | 1.00 | 12.75 |
| ATOM | 2027 | CB | GLU | B | 66 | 10.643 | 21.994 | 38.503 | 1.00 | 17.98 |

Figure 4NN

| ATOM | 2028 | CG  | GLU | B | 66 | 10.845 | 21.307 | 39.819 | 1.00 | 21.40 |
|------|------|-----|-----|---|----|--------|--------|--------|------|-------|
| ATOM | 2029 | CD  | GLU | B | 66 | 9.909  | 21.803 | 40.883 | 1.00 | 16.46 |
| ATOM | 2030 | OE1 | GLU | B | 66 | 9.787  | 23.031 | 41.030 | 1.00 | 19.74 |
| ATOM | 2031 | OE2 | GLU | B | 66 | 9.331  | 20.957 | 41.588 | 1.00 | 21.07 |
| ATOM | 2032 | C   | GLU | B | 66 | 11.814 | 20.338 | 37.006 | 1.00 | 12.59 |
| ATOM | 2033 | O   | GLU | B | 66 | 10.920 | 19.923 | 36.259 | 1.00 | 11.32 |
| ATOM | 2034 | N   | VAL | B | 67 | 12.888 | 19.616 | 37.338 | 1.00 | 8.95  |
| ATOM | 2035 | CA  | VAL | B | 67 | 13.083 | 18.216 | 36.883 | 1.00 | 3.32  |
| ATOM | 2036 | CB  | VAL | B | 67 | 14.267 | 18.100 | 35.885 | 1.00 | 8.56  |
| ATOM | 2037 | CG1 | VAL | B | 67 | 14.033 | 18.951 | 34.635 | 1.00 | 2.00  |
| ATOM | 2038 | CG2 | VAL | B | 67 | 15.561 | 18.506 | 36.565 | 1.00 | 2.00  |
| ATOM | 2039 | C   | VAL | B | 67 | 13.364 | 17.251 | 38.063 | 1.00 | 4.22  |
| ATOM | 2040 | O   | VAL | B | 67 | 13.470 | 16.032 | 37.898 | 1.00 | 5.26  |
| ATOM | 2041 | N   | GLY | B | 68 | 13.513 | 17.795 | 39.263 | 1.00 | 2.00  |
| ATOM | 2042 | CA  | GLY | B | 68 | 13.758 | 16.937 | 40.403 | 1.00 | 2.00  |
| ATOM | 2043 | C   | GLY | B | 68 | 13.611 | 17.600 | 41.750 | 1.00 | 4.97  |
| ATOM | 2044 | O   | GLY | B | 68 | 13.186 | 18.759 | 41.836 | 1.00 | 6.51  |
| ATOM | 2045 | N   | ARG | B | 69 | 14.023 | 16.874 | 42.789 | 1.00 | 5.96  |
| ATOM | 2046 | CA  | ARG | B | 69 | 13.901 | 17.365 | 44.160 | 1.00 | 11.64 |
| ATOM | 2047 | CB  | ARG | B | 69 | 12.568 | 16.892 | 44.746 | 1.00 | 12.82 |
| ATOM | 2048 | CG  | ARG | B | 69 | 12.335 | 17.260 | 46.204 | 1.00 | 16.69 |
| ATOM | 2049 | CD  | ARG | B | 69 | 12.028 | 18.729 | 46.379 | 1.00 | 19.84 |
| ATOM | 2050 | NE  | ARG | B | 69 | 10.802 | 19.122 | 45.698 | 1.00 | 22.42 |
| ATOM | 2051 | CZ  | ARG | B | 69 | 9.602  | 18.674 | 46.039 | 1.00 | 25.63 |
| ATOM | 2052 | NH1 | ARG | B | 69 | 8.530  | 19.094 | 45.380 | 1.00 | 28.55 |
| ATOM | 2053 | NH2 | ARG | B | 69 | 9.474  | 17.787 | 47.019 | 1.00 | 19.16 |
| ATOM | 2054 | C   | ARG | B | 69 | 15.056 | 16.876 | 45.014 | 1.00 | 13.29 |
| ATOM | 2055 | O   | ARG | B | 69 | 15.429 | 15.702 | 44.987 | 1.00 | 13.90 |
| ATOM | 2056 | N   | VAL | B | 70 | 15.633 | 17.833 | 45.740 | 1.00 | 12.54 |
| ATOM | 2057 | CA  | VAL | B | 70 | 16.750 | 17.628 | 46.705 | 1.00 | 12.50 |
| ATOM | 2058 | CB  | VAL | B | 70 | 17.296 | 18.999 | 47.162 | 1.00 | 7.84  |
| ATOM | 2059 | CG1 | VAL | B | 70 | 18.149 | 18.854 | 48.367 | 1.00 | 5.53  |
| ATOM | 2060 | CG2 | VAL | B | 70 | 18.058 | 19.662 | 46.021 | 1.00 | 9.22  |
| ATOM | 2061 | C   | VAL | B | 70 | 16.178 | 16.867 | 47.951 | 1.00 | 14.23 |
| ATOM | 2062 | O   | VAL | B | 70 | 15.295 | 17.340 | 48.668 | 1.00 | 16.82 |
| ATOM | 2063 | N   | LEU | B | 71 | 16.701 | 15.668 | 48.172 | 1.00 | 14.05 |
| ATOM | 2064 | CA  | LEU | B | 71 | 16.258 | 14.788 | 49.279 | 1.00 | 12.96 |
| ATOM | 2065 | CB  | LEU | B | 71 | 16.509 | 13.340 | 48.896 | 1.00 | 11.47 |
| ATOM | 2066 | CG  | LEU | B | 71 | 15.921 | 12.871 | 47.555 | 1.00 | 17.63 |
| ATOM | 2067 | CD1 | LEU | B | 71 | 16.274 | 11.394 | 47.305 | 1.00 | 19.17 |
| ATOM | 2068 | CD2 | LEU | B | 71 | 14.426 | 13.049 | 47.573 | 1.00 | 19.25 |
| ATOM | 2069 | C   | LEU | B | 71 | 16.905 | 15.087 | 50.644 | 1.00 | 14.49 |
| ATOM | 2070 | O   | LEU | B | 71 | 16.270 | 15.031 | 51.692 | 1.00 | 17.54 |
| ATOM | 2071 | N   | ALA | B | 72 | 18.205 | 15.358 | 50.615 | 1.00 | 14.25 |
| ATOM | 2072 | CA  | ALA | B | 72 | 18.983 | 15.648 | 51.835 | 1.00 | 9.02  |
| ATOM | 2073 | CB  | ALA | B | 72 | 19.533 | 14.373 | 52.408 | 1.00 | 6.95  |
| ATOM | 2074 | C   | ALA | B | 72 | 20.149 | 16.582 | 51.565 | 1.00 | 10.37 |
| ATOM | 2075 | O   | ALA | B | 72 | 20.841 | 16.534 | 50.559 | 1.00 | 14.80 |
| ATOM | 2076 | N   | VAL | B | 73 | 20.378 | 17.432 | 52.536 | 1.00 | 11.58 |
| ATOM | 2077 | CA  | VAL | B | 73 | 21.486 | 18.367 | 52.511 | 1.00 | 12.95 |
| ATOM | 2078 | CB  | VAL | B | 73 | 20.988 | 19.808 | 52.370 | 1.00 | 9.61  |
| ATOM | 2079 | CG1 | VAL | B | 73 | 22.170 | 20.765 | 52.334 | 1.00 | 4.74  |

Figure 4OO

| | | | | | | | | | |
|---|---|---|---|---|---|---|---|---|---|
| ATOM | 2080 | CG2 | VAL | B | 73 | 20.124 | 19.935 | 51.132 | 1.00 3.64 |
| ATOM | 2081 | C | VAL | B | 73 | 22.064 | 18.169 | 53.936 | 1.00 18.32 |
| ATOM | 2082 | O | VAL | B | 73 | 21.401 | 18.437 | 54.937 | 1.00 22.65 |
| ATOM | 2083 | N | VAL | B | 74 | 23.262 | 17.596 | 54.026 | 1.00 21.86 |
| ATOM | 2084 | CA | VAL | B | 74 | 23.948 | 17.375 | 55.341 | 1.00 18.90 |
| ATOM | 2085 | CB | VAL | B | 74 | 24.442 | 15.935 | 55.497 | 1.00 21.15 |
| ATOM | 2086 | CG1 | VAL | B | 74 | 25.246 | 15.811 | 56.788 | 1.00 25.84 |
| ATOM | 2087 | CG2 | VAL | B | 74 | 23.267 | 14.934 | 55.462 | 1.00 22.63 |
| ATOM | 2088 | C | VAL | B | 74 | 25.200 | 18.281 | 55.418 | 1.00 21.01 |
| ATOM | 2089 | O | VAL | B | 74 | 25.985 | 18.410 | 54.486 | 1.00 26.38 |
| ATOM | 2090 | N | ASN | B | 75 | 25.384 | 18.926 | 56.550 | 1.00 21.49 |
| ATOM | 2091 | CA | ASN | B | 75 | 26.554 | 19.791 | 56.728 | 1.00 21.46 |
| ATOM | 2092 | CB | ASN | B | 75 | 26.263 | 20.794 | 57.835 | 1.00 22.08 |
| ATOM | 2093 | CG | ASN | B | 75 | 27.355 | 21.817 | 58.007 | 1.00 24.47 |
| ATOM | 2094 | OD1 | ASN | B | 75 | 27.152 | 22.825 | 58.682 | 1.00 27.48 |
| ATOM | 2095 | ND2 | ASN | B | 75 | 28.520 | 21.580 | 57.409 | 1.00 24.10 |
| ATOM | 2096 | C | ASN | B | 75 | 27.779 | 18.909 | 57.060 | 1.00 26.34 |
| ATOM | 2097 | O | ASN | B | 75 | 27.976 | 18.461 | 58.193 | 1.00 34.33 |
| ATOM | 2098 | N | ASP | B | 76 | 28.569 | 18.613 | 56.030 | 1.00 25.27 |
| ATOM | 2099 | CA | ASP | B | 76 | 29.809 | 17.800 | 56.175 | 1.00 18.30 |
| ATOM | 2100 | CB | ASP | B | 76 | 30.186 | 17.176 | 54.815 | 1.00 19.72 |
| ATOM | 2101 | CG | ASP | B | 76 | 31.430 | 16.260 | 54.879 | 1.00 18.03 |
| ATOM | 2102 | OD1 | ASP | B | 76 | 32.568 | 16.762 | 54.802 | 1.00 20.83 |
| ATOM | 2103 | OD2 | ASP | B | 76 | 31.283 | 15.027 | 54.978 | 1.00 21.41 |
| ATOM | 2104 | C | ASP | B | 76 | 30.898 | 18.777 | 56.644 | 1.00 19.11 |
| ATOM | 2105 | O | ASP | B | 76 | 30.821 | 19.998 | 56.435 | 1.00 20.23 |
| ATOM | 2106 | N | PRO | B | 77 | 31.931 | 18.245 | 57.313 | 1.00 17.61 |
| ATOM | 2107 | CD | PRO | B | 77 | 32.017 | 16.869 | 57.841 | 1.00 15.76 |
| ATOM | 2108 | CA | PRO | B | 77 | 33.041 | 19.054 | 57.804 | 1.00 12.96 |
| ATOM | 2109 | CB | PRO | B | 77 | 34.045 | 18.003 | 58.217 | 1.00 14.74 |
| ATOM | 2110 | CG | PRO | B | 77 | 33.182 | 16.959 | 58.802 | 1.00 19.87 |
| ATOM | 2111 | C | PRO | B | 77 | 33.639 | 19.917 | 56.697 | 1.00 15.83 |
| ATOM | 2112 | O | PRO | B | 77 | 34.258 | 20.955 | 56.959 | 1.00 16.48 |
| ATOM | 2113 | N | ARG | B | 78 | 33.461 | 19.451 | 55.453 | 1.00 16.28 |
| ATOM | 2114 | CA | ARG | B | 78 | 34.011 | 20.129 | 54.221 | 1.00 15.16 |
| ATOM | 2115 | CB | ARG | B | 78 | 34.440 | 19.081 | 53.176 | 1.00 19.75 |
| ATOM | 2116 | CG | ARG | B | 78 | 35.498 | 18.054 | 53.674 | 1.00 27.41 |
| ATOM | 2117 | CD | ARG | B | 78 | 35.938 | 17.071 | 52.590 | 1.00 27.76 |
| ATOM | 2118 | NE | ARG | B | 78 | 36.547 | 17.759 | 51.445 | 1.00 34.10 |
| ATOM | 2119 | CZ | ARG | B | 78 | 36.347 | 17.430 | 50.169 | 1.00 35.08 |
| ATOM | 2120 | NH1 | ARG | B | 78 | 36.948 | 18.120 | 49.211 | 1.00 33.35 |
| ATOM | 2121 | NH2 | ARG | B | 78 | 35.557 | 16.410 | 49.844 | 1.00 35.93 |
| ATOM | 2122 | C | ARG | B | 78 | 33.101 | 21.161 | 53.565 | 1.00 12.35 |
| ATOM | 2123 | O | ARG | B | 78 | 33.578 | 22.095 | 52.943 | 1.00 15.66 |
| ATOM | 2124 | N | GLY | B | 79 | 31.789 | 20.964 | 53.677 | 1.00 10.86 |
| ATOM | 2125 | CA | GLY | B | 79 | 30.831 | 21.881 | 53.068 | 1.00 11.07 |
| ATOM | 2126 | C | GLY | B | 79 | 29.470 | 21.225 | 53.031 | 1.00 13.88 |
| ATOM | 2127 | O | GLY | B | 79 | 29.358 | 20.025 | 53.310 | 1.00 16.49 |
| ATOM | 2128 | N | PRO | B | 80 | 28.405 | 21.973 | 52.700 | 1.00 12.83 |
| ATOM | 2129 | CD | PRO | B | 80 | 28.428 | 23.394 | 52.305 | 1.00 11.83 |
| ATOM | 2130 | CA | PRO | B | 80 | 27.045 | 21.419 | 52.616 | 1.00 7.71 |
| ATOM | 2131 | CB | PRO | B | 80 | 26.201 | 22.639 | 52.336 | 1.00 8.81 |

Figure 4PP

| ATOM | 2132 | CG  | PRO B | 80 | 27.125 | 23.512 | 51.531 | 1.00 | 10.78 |
|------|------|-----|-------|----|--------|--------|--------|------|-------|
| ATOM | 2133 | C   | PRO B | 80 | 26.940 | 20.470 | 51.444 | 1.00 | 12.29 |
| ATOM | 2134 | O   | PRO B | 80 | 26.977 | 20.874 | 50.290 | 1.00 | 14.42 |
| ATOM | 2135 | N   | PHE B | 81 | 26.742 | 19.196 | 51.757 | 1.00 | 13.09 |
| ATOM | 2136 | CA  | PHE B | 81 | 26.626 | 18.109 | 50.747 | 1.00 | 13.43 |
| ATOM | 2137 | CB  | PHE B | 81 | 27.368 | 16.892 | 51.304 | 1.00 | 10.32 |
| ATOM | 2138 | CG  | PHE B | 81 | 27.441 | 15.719 | 50.368 | 1.00 | 10.20 |
| ATOM | 2139 | CD1 | PHE B | 81 | 28.426 | 15.654 | 49.388 | 1.00 | 11.18 |
| ATOM | 2140 | CD2 | PHE B | 81 | 26.573 | 14.636 | 50.518 | 1.00 | 9.80 |
| ATOM | 2141 | CE1 | PHE B | 81 | 28.550 | 14.519 | 48.571 | 1.00 | 12.48 |
| ATOM | 2142 | CE2 | PHE B | 81 | 26.688 | 13.500 | 49.708 | 1.00 | 6.35 |
| ATOM | 2143 | CZ  | PHE B | 81 | 27.677 | 13.439 | 48.737 | 1.00 | 8.16 |
| ATOM | 2144 | C   | PHE B | 81 | 25.128 | 17.814 | 50.489 | 1.00 | 15.88 |
| ATOM | 2145 | O   | PHE B | 81 | 24.280 | 17.997 | 51.361 | 1.00 | 21.18 |
| ATOM | 2146 | N   | PHE B | 82 | 24.788 | 17.370 | 49.282 | 1.00 | 14.59 |
| ATOM | 2147 | CA  | PHE B | 82 | 23.370 | 17.067 | 48.999 | 1.00 | 10.94 |
| ATOM | 2148 | CB  | PHE B | 82 | 22.674 | 18.267 | 48.369 | 1.00 | 12.56 |
| ATOM | 2149 | CG  | PHE B | 82 | 22.612 | 18.215 | 46.873 | 1.00 | 14.05 |
| ATOM | 2150 | CD1 | PHE B | 82 | 23.734 | 18.531 | 46.101 | 1.00 | 12.10 |
| ATOM | 2151 | CD2 | PHE B | 82 | 21.434 | 17.844 | 46.226 | 1.00 | 11.75 |
| ATOM | 2152 | CE1 | PHE B | 82 | 23.682 | 18.476 | 44.698 | 1.00 | 8.37 |
| ATOM | 2153 | CE2 | PHE B | 82 | 21.377 | 17.787 | 44.818 | 1.00 | 13.13 |
| ATOM | 2154 | CZ  | PHE B | 82 | 22.499 | 18.101 | 44.061 | 1.00 | 5.89 |
| ATOM | 2155 | C   | PHE B | 82 | 23.183 | 15.838 | 48.137 | 1.00 | 10.61 |
| ATOM | 2156 | O   | PHE B | 82 | 24.093 | 15.286 | 47.534 | 1.00 | 12.70 |
| ATOM | 2157 | N   | VAL B | 83 | 21.964 | 15.358 | 48.152 | 1.00 | 10.54 |
| ATOM | 2158 | CA  | VAL B | 83 | 21.608 | 14.212 | 47.342 | 1.00 | 14.69 |
| ATOM | 2159 | CB  | VAL B | 83 | 21.587 | 12.936 | 48.162 | 1.00 | 13.77 |
| ATOM | 2160 | CG1 | VAL B | 83 | 20.946 | 11.822 | 47.388 | 1.00 | 11.74 |
| ATOM | 2161 | CG2 | VAL B | 83 | 22.991 | 12.530 | 48.454 | 1.00 | 17.05 |
| ATOM | 2162 | C   | VAL B | 83 | 20.217 | 14.581 | 46.831 | 1.00 | 17.90 |
| ATOM | 2163 | O   | VAL B | 83 | 19.359 | 15.033 | 47.600 | 1.00 | 23.98 |
| ATOM | 2164 | N   | GLY B | 84 | 20.038 | 14.491 | 45.514 | 1.00 | 14.79 |
| ATOM | 2165 | CA  | GLY B | 84 | 18.769 | 14.825 | 44.901 | 1.00 | 11.59 |
| ATOM | 2166 | C   | GLY B | 84 | 18.288 | 13.725 | 43.991 | 1.00 | 11.44 |
| ATOM | 2167 | O   | GLY B | 84 | 19.056 | 12.814 | 43.659 | 1.00 | 17.85 |
| ATOM | 2168 | N   | LEU B | 85 | 17.038 | 13.839 | 43.549 | 1.00 | 10.95 |
| ATOM | 2169 | CA  | LEU B | 85 | 16.394 | 12.847 | 42.665 | 1.00 | 6.95 |
| ATOM | 2170 | CB  | LEU B | 85 | 15.241 | 12.189 | 43.400 | 1.00 | 11.44 |
| ATOM | 2171 | CG  | LEU B | 85 | 14.380 | 11.197 | 42.628 | 1.00 | 11.93 |
| ATOM | 2172 | CD1 | LEU B | 85 | 15.159 | 9.934  | 42.493 | 1.00 | 14.60 |
| ATOM | 2173 | CD2 | LEU B | 85 | 13.109 | 10.900 | 43.383 | 1.00 | 13.51 |
| ATOM | 2174 | C   | LEU B | 85 | 15.861 | 13.575 | 41.473 | 1.00 | 7.78 |
| ATOM | 2175 | O   | LEU B | 85 | 15.188 | 14.581 | 41.597 | 1.00 | 8.59 |
| ATOM | 2176 | N   | ILE B | 86 | 16.111 | 13.008 | 40.304 | 1.00 | 10.44 |
| ATOM | 2177 | CA  | ILE B | 86 | 15.648 | 13.557 | 39.027 | 1.00 | 6.43 |
| ATOM | 2178 | CB  | ILE B | 86 | 16.846 | 13.856 | 38.127 | 1.00 | 6.56 |
| ATOM | 2179 | CG2 | ILE B | 86 | 16.395 | 14.379 | 36.777 | 1.00 | 5.68 |
| ATOM | 2180 | CG1 | ILE B | 86 | 17.739 | 14.879 | 38.794 | 1.00 | 5.33 |
| ATOM | 2181 | CD1 | ILE B | 86 | 18.995 | 15.090 | 38.022 | 1.00 | 2.81 |
| ATOM | 2182 | C   | ILE B | 86 | 14.787 | 12.461 | 38.361 | 1.00 | 10.78 |
| ATOM | 2183 | O   | ILE B | 86 | 15.263 | 11.361 | 38.032 | 1.00 | 13.27 |

Figure 4QQ

| | | | | | | | | | |
|---|---|---|---|---|---|---|---|---|---|
| ATOM | 2184 | N | ALA | B | 87 | 13.502 | 12.760 | 38.194 | 1.00 9.91 |
| ATOM | 2185 | CA | ALA | B | 87 | 12.536 | 11.812 | 37.567 | 1.00 10.38 |
| ATOM | 2186 | CB | ALA | B | 87 | 11.536 | 11.331 | 38.600 | 1.00 14.06 |
| ATOM | 2187 | C | ALA | B | 87 | 11.820 | 12.610 | 36.484 | 1.00 13.06 |
| ATOM | 2188 | O | ALA | B | 87 | 10.779 | 13.224 | 36.703 | 1.00 15.63 |
| ATOM | 2189 | N | CYS | B | 88 | 12.402 | 12.607 | 35.293 | 1.00 13.93 |
| ATOM | 2190 | CA | CYS | B | 88 | 11.852 | 13.389 | 34.180 | 1.00 8.89 |
| ATOM | 2191 | CB | CYS | B | 88 | 12.505 | 14.754 | 34.209 | 1.00 2.00 |
| ATOM | 2192 | SG | CYS | B | 88 | 11.912 | 15.969 | 33.027 | 1.00 9.78 |
| ATOM | 2193 | C | CYS | B | 88 | 12.186 | 12.638 | 32.916 | 1.00 11.99 |
| ATOM | 2194 | O | CYS | B | 88 | 13.331 | 12.437 | 32.575 | 1.00 19.71 |
| ATOM | 2195 | N | VAL | B | 89 | 11.153 | 12.177 | 32.230 | 1.00 14.28 |
| ATOM | 2196 | CA | VAL | B | 89 | 11.328 | 11.417 | 30.995 | 1.00 10.90 |
| ATOM | 2197 | CB | VAL | B | 89 | 10.095 | 10.542 | 30.723 | 1.00 13.28 |
| ATOM | 2198 | CG1 | VAL | B | 89 | 8.908 | 11.408 | 30.329 | 1.00 16.79 |
| ATOM | 2199 | CG2 | VAL | B | 89 | 10.399 | 9.509 | 29.649 | 1.00 12.90 |
| ATOM | 2200 | C | VAL | B | 89 | 11.573 | 12.342 | 29.798 | 1.00 10.81 |
| ATOM | 2201 | O | VAL | B | 89 | 12.216 | 11.988 | 28.814 | 1.00 13.96 |
| ATOM | 2202 | N | GLN | B | 90 | 11.066 | 13.558 | 29.882 | 1.00 9.74 |
| ATOM | 2203 | CA | GLN | B | 90 | 11.258 | 14.514 | 28.762 | 1.00 12.71 |
| ATOM | 2204 | CB | GLN | B | 90 | 10.403 | 15.756 | 29.001 | 1.00 9.68 |
| ATOM | 2205 | CG | GLN | B | 90 | 8.934 | 15.394 | 29.138 | 1.00 16.94 |
| ATOM | 2206 | CD | GLN | B | 90 | 8.003 | 16.576 | 29.272 | 1.00 14.86 |
| ATOM | 2207 | OE1 | GLN | B | 90 | 8.310 | 17.554 | 29.950 | 1.00 18.44 |
| ATOM | 2208 | NE2 | GLN | B | 90 | 6.851 | 16.486 | 28.631 | 1.00 16.05 |
| ATOM | 2209 | C | GLN | B | 90 | 12.761 | 14.852 | 28.634 | 1.00 16.58 |
| ATOM | 2210 | O | GLN | B | 90 | 13.355 | 14.838 | 27.558 | 1.00 22.11 |
| ATOM | 2211 | N | LEU | B | 91 | 13.373 | 15.142 | 29.777 | 1.00 17.96 |
| ATOM | 2212 | CA | LEU | B | 91 | 14.820 | 15.468 | 29.847 | 1.00 16.95 |
| ATOM | 2213 | CB | LEU | B | 91 | 15.232 | 15.623 | 31.305 | 1.00 14.75 |
| ATOM | 2214 | CG | LEU | B | 91 | 16.687 | 15.866 | 31.647 | 1.00 9.95 |
| ATOM | 2215 | CD1 | LEU | B | 91 | 17.189 | 17.038 | 30.863 | 1.00 6.41 |
| ATOM | 2216 | CD2 | LEU | B | 91 | 16.768 | 16.137 | 33.124 | 1.00 9.30 |
| ATOM | 2217 | C | LEU | B | 91 | 15.585 | 14.330 | 29.167 | 1.00 16.51 |
| ATOM | 2218 | O | LEU | B | 91 | 16.450 | 14.552 | 28.320 | 1.00 22.78 |
| ATOM | 2219 | N | GLU | B | 92 | 15.206 | 13.101 | 29.512 | 1.00 14.86 |
| ATOM | 2220 | CA | GLU | B | 92 | 15.820 | 11.896 | 28.922 | 1.00 14.75 |
| ATOM | 2221 | CB | GLU | B | 92 | 15.166 | 10.624 | 29.432 | 1.00 15.36 |
| ATOM | 2222 | CG | GLU | B | 92 | 15.345 | 10.351 | 30.904 | 1.00 18.69 |
| ATOM | 2223 | CD | GLU | B | 92 | 14.586 | 9.114 | 31.342 | 1.00 23.90 |
| ATOM | 2224 | OE1 | GLU | B | 92 | 14.000 | 9.179 | 32.437 | 1.00 24.57 |
| ATOM | 2225 | OE2 | GLU | B | 92 | 14.557 | 8.098 | 30.592 | 1.00 25.95 |
| ATOM | 2226 | C | GLU | B | 92 | 15.714 | 11.914 | 27.400 | 1.00 18.59 |
| ATOM | 2227 | O | GLU | B | 92 | 16.712 | 11.826 | 26.703 | 1.00 24.00 |
| ATOM | 2228 | N | ARG | B | 93 | 14.490 | 12.027 | 26.885 | 1.00 18.28 |
| ATOM | 2229 | CA | ARG | B | 93 | 14.262 | 12.030 | 25.410 | 1.00 18.13 |
| ATOM | 2230 | CB | ARG | B | 93 | 12.767 | 12.036 | 25.076 | 1.00 24.10 |
| ATOM | 2231 | CG | ARG | B | 93 | 11.937 | 10.990 | 25.808 | 1.00 33.78 |
| ATOM | 2232 | CD | ARG | B | 93 | 12.345 | 9.557 | 25.486 | 1.00 43.31 |
| ATOM | 2233 | NE | ARG | B | 93 | 11.589 | 8.611 | 26.318 | 1.00 53.94 |
| ATOM | 2234 | CZ | ARG | B | 93 | 11.570 | 7.285 | 26.158 | 1.00 57.23 |
| ATOM | 2235 | NH1 | ARG | B | 93 | 10.848 | 6.530 | 26.986 | 1.00 53.37 |

Figure 4RR

| | | | | | | | | | |
|---|---|---|---|---|---|---|---|---|---|
| ATOM | 2236 | NH2 | ARG | B | 93 | 12.253 | 6.714 | 25.165 | 1.00 60.34 |
| ATOM | 2237 | C | ARG | B | 93 | 14.955 | 13.193 | 24.695 | 1.00 15.47 |
| ATOM | 2238 | O | ARG | B | 93 | 15.576 | 13.022 | 23.644 | 1.00 14.08 |
| ATOM | 2239 | N | VAL | B | 94 | 14.837 | 14.383 | 25.281 | 1.00 12.48 |
| ATOM | 2240 | CA | VAL | B | 94 | 15.451 | 15.600 | 24.715 | 1.00 13.20 |
| ATOM | 2241 | CB | VAL | B | 94 | 15.119 | 16.836 | 25.579 | 1.00 14.89 |
| ATOM | 2242 | CG1 | VAL | B | 94 | 16.033 | 18.001 | 25.219 | 1.00 11.53 |
| ATOM | 2243 | CG2 | VAL | B | 94 | 13.676 | 17.262 | 25.323 | 1.00 10.23 |
| ATOM | 2244 | C | VAL | B | 94 | 16.986 | 15.417 | 24.542 | 1.00 15.57 |
| ATOM | 2245 | O | VAL | B | 94 | 17.595 | 15.752 | 23.508 | 1.00 18.39 |
| ATOM | 2246 | N | LEU | B | 95 | 17.591 | 14.841 | 25.575 | 1.00 12.07 |
| ATOM | 2247 | CA | LEU | B | 95 | 19.037 | 14.542 | 25.593 | 1.00 10.59 |
| ATOM | 2248 | CB | LEU | B | 95 | 19.416 | 14.207 | 27.031 | 1.00 9.22 |
| ATOM | 2249 | CG | LEU | B | 95 | 20.509 | 14.994 | 27.749 | 1.00 13.75 |
| ATOM | 2250 | CD1 | LEU | B | 95 | 20.535 | 16.434 | 27.319 | 1.00 7.90 |
| ATOM | 2251 | CD2 | LEU | B | 95 | 20.291 | 14.877 | 29.247 | 1.00 9.99 |
| ATOM | 2252 | C | LEU | B | 95 | 19.388 | 13.354 | 24.613 | 1.00 13.40 |
| ATOM | 2253 | O | LEU | B | 95 | 20.270 | 13.430 | 23.755 | 1.00 10.88 |
| ATOM | 2254 | N | GLU | B | 96 | 18.661 | 12.252 | 24.768 | 1.00 13.38 |
| ATOM | 2255 | CA | GLU | B | 96 | 18.857 | 11.034 | 23.955 | 1.00 15.22 |
| ATOM | 2256 | CB | GLU | B | 96 | 17.811 | 9.973 | 24.312 | 1.00 24.43 |
| ATOM | 2257 | CG | GLU | B | 96 | 18.132 | 9.005 | 25.442 | 1.00 32.00 |
| ATOM | 2258 | CD | GLU | B | 96 | 16.951 | 8.078 | 25.783 | 1.00 38.78 |
| ATOM | 2259 | OE1 | GLU | B | 96 | 16.967 | 7.484 | 26.887 | 1.00 50.86 |
| ATOM | 2260 | OE2 | GLU | B | 96 | 16.005 | 7.935 | 24.969 | 1.00 38.36 |
| ATOM | 2261 | C | GLU | B | 96 | 18.750 | 11.326 | 22.470 | 1.00 15.80 |
| ATOM | 2262 | O | GLU | B | 96 | 19.446 | 10.735 | 21.638 | 1.00 19.07 |
| ATOM | 2263 | N | THR | B | 97 | 17.806 | 12.197 | 22.128 | 1.00 13.25 |
| ATOM | 2264 | CA | THR | B | 97 | 17.586 | 12.513 | 20.713 | 1.00 10.33 |
| ATOM | 2265 | CB | THR | B | 97 | 16.135 | 12.953 | 20.403 | 1.00 9.54 |
| ATOM | 2266 | OG1 | THR | B | 97 | 15.856 | 14.186 | 21.055 | 1.00 13.77 |
| ATOM | 2267 | CG2 | THR | B | 97 | 15.137 | 11.901 | 20.886 | 1.00 12.86 |
| ATOM | 2268 | C | THR | B | 97 | 18.553 | 13.531 | 20.196 | 1.00 10.29 |
| ATOM | 2269 | O | THR | B | 97 | 18.862 | 13.541 | 19.021 | 1.00 15.13 |
| ATOM | 2270 | N | ALA | B | 98 | 19.028 | 14.423 | 21.062 | 1.00 10.23 |
| ATOM | 2271 | CA | ALA | B | 98 | 20.006 | 15.437 | 20.591 | 1.00 9.69 |
| ATOM | 2272 | CB | ALA | B | 98 | 20.293 | 16.497 | 21.664 | 1.00 6.19 |
| ATOM | 2273 | C | ALA | B | 98 | 21.287 | 14.691 | 20.225 | 1.00 10.63 |
| ATOM | 2274 | O | ALA | B | 98 | 21.950 | 14.975 | 19.242 | 1.00 11.46 |
| ATOM | 2275 | N | ALA | B | 99 | 21.629 | 13.709 | 21.041 | 1.00 13.55 |
| ATOM | 2276 | CA | ALA | B | 99 | 22.837 | 12.940 | 20.802 | 1.00 17.54 |
| ATOM | 2277 | CB | ALA | B | 99 | 23.216 | 12.100 | 22.008 | 1.00 17.11 |
| ATOM | 2278 | C | ALA | B | 99 | 22.697 | 12.049 | 19.585 | 1.00 24.87 |
| ATOM | 2279 | O | ALA | B | 99 | 22.138 | 10.955 | 19.603 | 1.00 23.85 |
| ATOM | 2280 | N | SER | B | 100 | 23.271 | 12.550 | 18.502 | 1.00 35.12 |
| ATOM | 2281 | CA | SER | B | 100 | 23.369 | 11.828 | 17.208 | 1.00 41.56 |
| ATOM | 2282 | CB | SER | B | 100 | 23.480 | 12.835 | 16.055 | 1.00 44.46 |
| ATOM | 2283 | OG | SER | B | 100 | 22.410 | 13.783 | 16.065 | 1.00 48.22 |
| ATOM | 2284 | C | SER | B | 100 | 24.730 | 11.150 | 17.494 | 1.00 44.46 |
| ATOM | 2285 | O | SER | B | 100 | 25.722 | 11.263 | 16.767 | 1.00 42.45 |
| ATOM | 2286 | N | ALA | B | 101 | 24.733 | 10.497 | 18.655 | 1.00 50.25 |
| ATOM | 2287 | CA | ALA | B | 101 | 25.895 | 9.829 | 19.237 | 1.00 54.69 |

Figure 4SS

| ATOM | 2288 | CB | ALA | B | 101 | 25.552 | 9.300 | 20.649 | 1.00 | 53.60 |
| --- | --- | --- | --- | --- | --- | --- | --- | --- | --- | --- |
| ATOM | 2289 | C | ALA | B | 101 | 26.542 | 8.731 | 18.407 | 1.00 | 58.50 |
| ATOM | 2290 | O | ALA | B | 101 | 25.905 | 7.853 | 17.793 | 1.00 | 57.09 |
| ATOM | 2291 | N | ALA | B | 102 | 27.864 | 8.865 | 18.376 | 1.00 | 62.77 |
| ATOM | 2292 | CA | ALA | B | 102 | 28.768 | 7.919 | 17.722 | 1.00 | 66.11 |
| ATOM | 2293 | CB | ALA | B | 102 | 30.030 | 8.650 | 17.241 | 1.00 | 63.86 |
| ATOM | 2294 | C | ALA | B | 102 | 29.088 | 7.024 | 18.943 | 1.00 | 69.14 |
| ATOM | 2295 | O | ALA | B | 102 | 28.790 | 5.825 | 19.011 | 1.00 | 73.52 |
| ATOM | 2296 | N | ALA | B | 103 | 29.629 | 7.680 | 19.960 | 1.00 | 68.90 |
| ATOM | 2297 | CA | ALA | B | 103 | 29.976 | 7.015 | 21.222 | 1.00 | 69.10 |
| ATOM | 2298 | CB | ALA | B | 103 | 31.329 | 6.264 | 21.096 | 1.00 | 68.74 |
| ATOM | 2299 | C | ALA | B | 103 | 30.049 | 8.142 | 22.273 | 1.00 | 69.15 |
| ATOM | 2300 | O | ALA | B | 103 | 30.027 | 7.796 | 23.477 | 1.00 | 72.07 |
| ATOM | 2301 | OT | ALA | B | 103 | 30.051 | 9.341 | 21.870 | 1.00 | 63.18 |
| ATOM | 2302 | CB | ALA | B | 111 | 28.451 | 2.056 | 27.380 | 1.00 | 59.43 |
| ATOM | 2303 | C | ALA | B | 111 | 26.410 | 1.110 | 26.192 | 1.00 | 55.79 |
| ATOM | 2304 | O | ALA | B | 111 | 26.484 | 0.178 | 25.387 | 1.00 | 54.99 |
| ATOM | 2305 | N | ALA | B | 111 | 26.884 | 3.629 | 26.299 | 1.00 | 58.71 |
| ATOM | 2306 | CA | ALA | B | 111 | 27.463 | 2.259 | 26.220 | 1.00 | 57.49 |
| ATOM | 2307 | N | SER | B | 112 | 25.409 | 1.222 | 27.063 | 1.00 | 54.21 |
| ATOM | 2308 | CA | SER | B | 112 | 24.357 | 0.190 | 27.187 | 1.00 | 53.07 |
| ATOM | 2309 | CB | SER | B | 112 | 24.571 | -0.601 | 28.475 | 1.00 | 58.33 |
| ATOM | 2310 | OG | SER | B | 112 | 25.759 | -1.384 | 28.425 | 1.00 | 65.13 |
| ATOM | 2311 | C | SER | B | 112 | 22.910 | 0.636 | 27.121 | 1.00 | 49.91 |
| ATOM | 2312 | O | SER | B | 112 | 22.121 | 0.098 | 26.358 | 1.00 | 54.68 |
| ATOM | 2313 | N | ARG | B | 113 | 22.544 | 1.613 | 27.944 | 1.00 | 44.84 |
| ATOM | 2314 | CA | ARG | B | 113 | 21.124 | 2.055 | 27.986 | 1.00 | 43.03 |
| ATOM | 2315 | CB | ARG | B | 113 | 20.332 | 0.903 | 28.581 | 1.00 | 52.72 |
| ATOM | 2316 | CG | ARG | B | 113 | 21.173 | 0.043 | 29.575 | 1.00 | 63.19 |
| ATOM | 2317 | CD | ARG | B | 113 | 20.340 | -0.560 | 30.717 | 1.00 | 73.93 |
| ATOM | 2318 | NE | ARG | B | 113 | 19.096 | -1.183 | 30.253 | 1.00 | 79.97 |
| ATOM | 2319 | CZ | ARG | B | 113 | 17.913 | -0.573 | 30.244 | 1.00 | 81.34 |
| ATOM | 2320 | NH1 | ARG | B | 113 | 16.838 | -1.216 | 29.802 | 1.00 | 83.78 |
| ATOM | 2321 | NH2 | ARG | B | 113 | 17.807 | 0.682 | 30.670 | 1.00 | 82.16 |
| ATOM | 2322 | C | ARG | B | 113 | 20.944 | 3.340 | 28.799 | 1.00 | 39.66 |
| ATOM | 2323 | O | ARG | B | 113 | 21.194 | 4.445 | 28.347 | 1.00 | 39.63 |
| ATOM | 2324 | N | GLU | B | 114 | 20.497 | 3.182 | 30.037 | 1.00 | 38.77 |
| ATOM | 2325 | CA | GLU | B | 114 | 20.349 | 4.340 | 30.942 | 1.00 | 38.18 |
| ATOM | 2326 | CB | GLU | B | 114 | 19.572 | 3.946 | 32.198 | 1.00 | 40.24 |
| ATOM | 2327 | CG | GLU | B | 114 | 20.183 | 2.798 | 32.978 | 1.00 | 46.21 |
| ATOM | 2328 | CD | GLU | B | 114 | 19.173 | 1.710 | 33.339 | 1.00 | 53.55 |
| ATOM | 2329 | OE1 | GLU | B | 114 | 17.950 | 1.886 | 33.105 | 1.00 | 58.82 |
| ATOM | 2330 | OE2 | GLU | B | 114 | 19.610 | 0.663 | 33.863 | 1.00 | 57.09 |
| ATOM | 2331 | C | GLU | B | 114 | 21.784 | 4.824 | 31.269 | 1.00 | 34.03 |
| ATOM | 2332 | O | GLU | B | 114 | 22.022 | 5.888 | 31.825 | 1.00 | 34.98 |
| ATOM | 2333 | N | GLU | B | 115 | 22.754 | 3.994 | 30.921 | 1.00 | 26.68 |
| ATOM | 2334 | CA | GLU | B | 115 | 24.151 | 4.377 | 31.108 | 1.00 | 26.38 |
| ATOM | 2335 | CB | GLU | B | 115 | 25.049 | 3.167 | 30.861 | 1.00 | 29.70 |
| ATOM | 2336 | CG | GLU | B | 115 | 25.107 | 2.344 | 32.240 | 1.00 | 39.85 |
| ATOM | 2337 | CD | GLU | B | 115 | 25.270 | 0.851 | 31.992 | 1.00 | 47.81 |
| ATOM | 2338 | OE1 | GLU | B | 115 | 26.235 | 0.479 | 31.278 | 1.00 | 44.94 |
| ATOM | 2339 | OE2 | GLU | B | 115 | 24.436 | 0.055 | 32.520 | 1.00 | 50.33 |

Figure 4TT

| ATOM | 2340 | C   | GLU | B | 115 | 24.452 | 5.441  | 30.060 | 1.00 | 23.31 |
|------|------|-----|-----|---|-----|--------|--------|--------|------|-------|
| ATOM | 2341 | O   | GLU | B | 115 | 25.182 | 6.393  | 30.281 | 1.00 | 23.55 |
| ATOM | 2342 | N   | ARG | B | 116 | 23.849 | 5.281  | 28.892 | 1.00 | 21.14 |
| ATOM | 2343 | CA  | ARG | B | 116 | 24.038 | 6.287  | 27.839 | 1.00 | 20.64 |
| ATOM | 2344 | CB  | ARG | B | 116 | 23.265 | 5.943  | 26.563 | 1.00 | 22.82 |
| ATOM | 2345 | CG  | ARG | B | 116 | 24.133 | 5.471  | 25.379 | 1.00 | 36.84 |
| ATOM | 2346 | CD  | ARG | B | 116 | 24.145 | 6.427  | 24.114 | 1.00 | 48.10 |
| ATOM | 2347 | NE  | ARG | B | 116 | 25.173 | 7.478  | 24.130 | 1.00 | 46.21 |
| ATOM | 2348 | CZ  | ARG | B | 116 | 26.394 | 7.402  | 23.600 | 1.00 | 47.41 |
| ATOM | 2349 | NH1 | ARG | B | 116 | 27.194 | 8.432  | 23.736 | 1.00 | 51.35 |
| ATOM | 2350 | NH2 | ARG | B | 116 | 26.824 | 6.347  | 22.921 | 1.00 | 49.43 |
| ATOM | 2351 | C   | ARG | B | 116 | 23.478 | 7.560  | 28.468 | 1.00 | 19.84 |
| ATOM | 2352 | O   | ARG | B | 116 | 24.095 | 8.618  | 28.473 | 1.00 | 22.78 |
| ATOM | 2353 | N   | LEU | B | 117 | 22.297 | 7.430  | 29.057 | 1.00 | 17.65 |
| ATOM | 2354 | CA  | LEU | B | 117 | 21.652 | 8.589  | 29.686 | 1.00 | 14.89 |
| ATOM | 2355 | CB  | LEU | B | 117 | 20.301 | 8.154  | 30.269 | 1.00 | 16.14 |
| ATOM | 2356 | CG  | LEU | B | 117 | 19.548 | 9.053  | 31.252 | 1.00 | 13.05 |
| ATOM | 2357 | CD1 | LEU | B | 117 | 19.351 | 10.447 | 30.699 | 1.00 | 9.32  |
| ATOM | 2358 | CD2 | LEU | B | 117 | 18.222 | 8.408  | 31.528 | 1.00 | 14.86 |
| ATOM | 2359 | C   | LEU | B | 117 | 22.598 | 9.209  | 30.747 | 1.00 | 15.06 |
| ATOM | 2360 | O   | LEU | B | 117 | 22.827 | 10.420 | 30.797 | 1.00 | 16.67 |
| ATOM | 2361 | N   | LEU | B | 118 | 23.199 | 8.348  | 31.559 | 1.00 | 14.24 |
| ATOM | 2362 | CA  | LEU | B | 118 | 24.101 | 8.819  | 32.618 | 1.00 | 10.27 |
| ATOM | 2363 | CB  | LEU | B | 118 | 24.618 | 7.629  | 33.413 | 1.00 | 8.73  |
| ATOM | 2364 | CG  | LEU | B | 118 | 23.938 | 7.334  | 34.757 | 1.00 | 8.30  |
| ATOM | 2365 | CD1 | LEU | B | 118 | 22.884 | 8.393  | 35.069 | 1.00 | 9.57  |
| ATOM | 2366 | CD2 | LEU | B | 118 | 23.336 | 5.948  | 34.739 | 1.00 | 7.43  |
| ATOM | 2367 | C   | LEU | B | 118 | 25.242 | 9.592  | 31.980 | 1.00 | 11.84 |
| ATOM | 2368 | O   | LEU | B | 118 | 25.566 | 10.738 | 32.309 | 1.00 | 11.94 |
| ATOM | 2369 | N   | TYR | B | 119 | 25.809 | 8.954  | 30.978 | 1.00 | 11.03 |
| ATOM | 2370 | CA  | TYR | B | 119 | 26.925 | 9.533  | 30.237 | 1.00 | 14.62 |
| ATOM | 2371 | CB  | TYR | B | 119 | 27.317 | 8.573  | 29.134 | 1.00 | 17.95 |
| ATOM | 2372 | CG  | TYR | B | 119 | 28.343 | 9.171  | 28.232 | 1.00 | 29.23 |
| ATOM | 2373 | CD1 | TYR | B | 119 | 27.960 | 9.966  | 27.142 | 1.00 | 32.82 |
| ATOM | 2374 | CE1 | TYR | B | 119 | 28.905 | 10.542 | 26.298 | 1.00 | 39.16 |
| ATOM | 2375 | CD2 | TYR | B | 119 | 29.698 | 8.965  | 28.463 | 1.00 | 30.58 |
| ATOM | 2376 | CE2 | TYR | B | 119 | 30.656 | 9.534  | 27.626 | 1.00 | 39.63 |
| ATOM | 2377 | CZ  | TYR | B | 119 | 30.255 | 10.321 | 26.544 | 1.00 | 41.40 |
| ATOM | 2378 | OH  | TYR | B | 119 | 31.205 | 10.886 | 25.715 | 1.00 | 48.04 |
| ATOM | 2379 | C   | TYR | B | 119 | 26.625 | 10.941 | 29.667 | 1.00 | 12.82 |
| ATOM | 2380 | O   | TYR | B | 119 | 27.423 | 11.875 | 29.713 | 1.00 | 15.87 |
| ATOM | 2381 | N   | LEU | B | 120 | 25.453 | 11.062 | 29.083 | 1.00 | 10.54 |
| ATOM | 2382 | CA  | LEU | B | 120 | 25.010 | 12.329 | 28.499 | 1.00 | 9.76  |
| ATOM | 2383 | CB  | LEU | B | 120 | 23.736 | 12.067 | 27.585 | 1.00 | 9.66  |
| ATOM | 2384 | CG  | LEU | B | 120 | 23.730 | 12.114 | 26.155 | 1.00 | 7.96  |
| ATOM | 2385 | CD1 | LEU | B | 120 | 25.119 | 11.872 | 25.618 | 1.00 | 9.33  |
| ATOM | 2386 | CD2 | LEU | B | 120 | 22.727 | 11.087 | 25.603 | 1.00 | 5.94  |
| ATOM | 2387 | C   | LEU | B | 120 | 24.790 | 13.471 | 29.535 | 1.00 | 9.78  |
| ATOM | 2388 | O   | LEU | B | 120 | 25.348 | 14.561 | 29.453 | 1.00 | 12.23 |
| ATOM | 2389 | N   | ILE | B | 121 | 23.986 | 13.206 | 30.551 | 1.00 | 8.55  |
| ATOM | 2390 | CA  | ILE | B | 121 | 23.699 | 14.267 | 31.512 | 1.00 | 2.58  |
| ATOM | 2391 | CB  | ILE | B | 121 | 22.502 | 13.921 | 32.427 | 1.00 | 5.92  |

Figure 4UU

| ATOM | 2392 | CG2 | ILE | B | 121 | 22.923 | 12.978 | 33.566 | 1.00 | 4.29 |
| --- | --- | --- | --- | --- | --- | --- | --- | --- | --- | --- |
| ATOM | 2393 | CG1 | ILE | B | 121 | 21.897 | 15.213 | 32.968 | 1.00 | 5.94 |
| ATOM | 2394 | CD1 | ILE | B | 121 | 20.636 | 15.010 | 33.721 | 1.00 | 7.70 |
| ATOM | 2395 | C | ILE | B | 121 | 24.927 | 14.641 | 32.294 | 1.00 | 2.01 |
| ATOM | 2396 | O | ILE | B | 121 | 25.235 | 15.816 | 32.489 | 1.00 | 3.56 |
| ATOM | 2397 | N | THR | B | 122 | 25.699 | 13.633 | 32.677 | 1.00 | 7.14 |
| ATOM | 2398 | CA | THR | B | 122 | 26.937 | 13.890 | 33.461 | 1.00 | 6.03 |
| ATOM | 2399 | CB | THR | B | 122 | 27.757 | 12.625 | 33.724 | 1.00 | 2.00 |
| ATOM | 2400 | OG1 | THR | B | 122 | 26.933 | 11.632 | 34.307 | 1.00 | 2.00 |
| ATOM | 2401 | CG2 | THR | B | 122 | 28.846 | 12.928 | 34.723 | 1.00 | 2.65 |
| ATOM | 2402 | C | THR | B | 122 | 27.861 | 14.904 | 32.760 | 1.00 | 6.41 |
| ATOM | 2403 | O | THR | B | 122 | 28.281 | 15.908 | 33.327 | 1.00 | 9.16 |
| ATOM | 2404 | N | ASN | B | 123 | 28.133 | 14.663 | 31.485 | 1.00 | 9.14 |
| ATOM | 2405 | CA | ASN | B | 123 | 29.047 | 15.568 | 30.734 | 1.00 | 8.97 |
| ATOM | 2406 | CB | ASN | B | 123 | 29.724 | 14.817 | 29.596 | 1.00 | 11.34 |
| ATOM | 2407 | CG | ASN | B | 123 | 30.535 | 13.668 | 30.094 | 1.00 | 12.46 |
| ATOM | 2408 | OD1 | ASN | B | 123 | 30.200 | 12.504 | 29.858 | 1.00 | 14.50 |
| ATOM | 2409 | ND2 | ASN | B | 123 | 31.562 | 13.975 | 30.864 | 1.00 | 9.02 |
| ATOM | 2410 | C | ASN | B | 123 | 28.420 | 16.846 | 30.235 | 1.00 | 8.15 |
| ATOM | 2411 | O | ASN | B | 123 | 29.119 | 17.806 | 29.923 | 1.00 | 9.35 |
| ATOM | 2412 | N | TYR | B | 124 | 27.091 | 16.849 | 30.113 | 1.00 | 10.17 |
| ATOM | 2413 | CA | TYR | B | 124 | 26.386 | 18.070 | 29.652 | 1.00 | 5.76 |
| ATOM | 2414 | CB | TYR | B | 124 | 25.099 | 17.742 | 28.912 | 1.00 | 2.67 |
| ATOM | 2415 | CG | TYR | B | 124 | 24.617 | 18.911 | 28.060 | 1.00 | 5.33 |
| ATOM | 2416 | CD1 | TYR | B | 124 | 25.295 | 19.281 | 26.893 | 1.00 | 7.28 |
| ATOM | 2417 | CE1 | TYR | B | 124 | 24.905 | 20.398 | 26.147 | 1.00 | 8.26 |
| ATOM | 2418 | CD2 | TYR | B | 124 | 23.527 | 19.690 | 28.451 | 1.00 | 6.81 |
| ATOM | 2419 | CE2 | TYR | B | 124 | 23.130 | 20.823 | 27.711 | 1.00 | 8.31 |
| ATOM | 2420 | CZ | TYR | B | 124 | 23.821 | 21.165 | 26.566 | 1.00 | 7.58 |
| ATOM | 2421 | OH | TYR | B | 124 | 23.438 | 22.266 | 25.855 | 1.00 | 5.26 |
| ATOM | 2422 | C | TYR | B | 124 | 26.125 | 19.036 | 30.813 | 1.00 | 8.01 |
| ATOM | 2423 | O | TYR | B | 124 | 26.336 | 20.238 | 30.688 | 1.00 | 13.58 |
| ATOM | 2424 | N | LEU | B | 125 | 25.669 | 18.507 | 31.946 | 1.00 | 4.43 |
| ATOM | 2425 | CA | LEU | B | 125 | 25.399 | 19.345 | 33.142 | 1.00 | 7.35 |
| ATOM | 2426 | CB | LEU | B | 125 | 23.909 | 19.294 | 33.471 | 1.00 | 4.74 |
| ATOM | 2427 | CG | LEU | B | 125 | 22.920 | 19.822 | 32.432 | 1.00 | 4.85 |
| ATOM | 2428 | CD1 | LEU | B | 125 | 21.551 | 19.196 | 32.631 | 1.00 | 2.00 |
| ATOM | 2429 | CD2 | LEU | B | 125 | 22.863 | 21.326 | 32.472 | 1.00 | 2.81 |
| ATOM | 2430 | C | LEU | B | 125 | 26.250 | 18.775 | 34.306 | 1.00 | 8.86 |
| ATOM | 2431 | O | LEU | B | 125 | 25.761 | 18.107 | 35.203 | 1.00 | 16.80 |
| ATOM | 2432 | N | PRO | B | 126 | 27.549 | 19.045 | 34.298 | 1.00 | 8.94 |
| ATOM | 2433 | CD | PRO | B | 126 | 28.339 | 19.724 | 33.259 | 1.00 | 11.24 |
| ATOM | 2434 | CA | PRO | B | 126 | 28.414 | 18.529 | 35.353 | 1.00 | 7.93 |
| ATOM | 2435 | CB | PRO | B | 126 | 29.776 | 18.529 | 34.676 | 1.00 | 9.38 |
| ATOM | 2436 | CG | PRO | B | 126 | 29.723 | 19.774 | 33.872 | 1.00 | 8.61 |
| ATOM | 2437 | C | PRO | B | 126 | 28.444 | 19.283 | 36.684 | 1.00 | 8.73 |
| ATOM | 2438 | O | PRO | B | 126 | 28.940 | 18.765 | 37.672 | 1.00 | 15.99 |
| ATOM | 2439 | N | SER | B | 127 | 27.874 | 20.478 | 36.742 | 1.00 | 7.51 |
| ATOM | 2440 | CA | SER | B | 127 | 27.882 | 21.253 | 38.015 | 1.00 | 9.27 |
| ATOM | 2441 | CB | SER | B | 127 | 28.693 | 22.527 | 37.796 | 1.00 | 12.59 |
| ATOM | 2442 | OG | SER | B | 127 | 29.906 | 22.231 | 37.129 | 1.00 | 17.76 |
| ATOM | 2443 | C | SER | B | 127 | 26.520 | 21.609 | 38.660 | 1.00 | 11.04 |
| ATOM | 2444 | O | SER | B | 127 | 25.460 | 21.548 | 38.028 | 1.00 | 9.89 |

Figure 4VV

| ATOM | 2445 | N | VAL | B | 128 | 26.578 | 21.971 | 39.949 | 1.00 | 9.43 |
| --- | --- | --- | --- | --- | --- | --- | --- | --- | --- | --- |
| ATOM | 2446 | CA | VAL | B | 128 | 25.371 | 22.410 | 40.724 | 1.00 | 7.72 |
| ATOM | 2447 | CB | VAL | B | 128 | 25.120 | 21.722 | 42.112 | 1.00 | 7.63 |
| ATOM | 2448 | CG1 | VAL | B | 128 | 24.281 | 20.498 | 41.949 | 1.00 | 15.58 |
| ATOM | 2449 | CG2 | VAL | B | 128 | 26.391 | 21.435 | 42.850 | 1.00 | 2.00 |
| ATOM | 2450 | C | VAL | B | 128 | 25.607 | 23.849 | 41.052 | 1.00 | 5.88 |
| ATOM | 2451 | O | VAL | B | 128 | 26.729 | 24.334 | 41.076 | 1.00 | 6.74 |
| ATOM | 2452 | P1 | SEI | B | 129 | 25.519 | 29.079 | 40.400 | 1.00 | 14.99 |
| ATOM | 2453 | O3 | SEI | B | 129 | 25.766 | 29.247 | 38.832 | 1.00 | 11.58 |
| ATOM | 2454 | O4 | SEI | B | 129 | 25.075 | 30.510 | 40.988 | 1.00 | 14.48 |
| ATOM | 2455 | O5 | SEI | B | 129 | 24.304 | 28.037 | 40.705 | 1.00 | 8.14 |
| ATOM | 2456 | C5 | SEI | B | 129 | 24.906 | 29.836 | 37.866 | 1.00 | 20.86 |
| ATOM | 2457 | C6 | SEI | B | 129 | 25.585 | 31.039 | 37.220 | 1.00 | 19.82 |
| ATOM | 2458 | C7 | SEI | B | 129 | 24.473 | 28.793 | 36.826 | 1.00 | 23.22 |
| ATOM | 2459 | C8 | SEI | B | 129 | 24.682 | 30.827 | 42.313 | 1.00 | 9.79 |
| ATOM | 2460 | C9 | SEI | B | 129 | 23.385 | 31.636 | 42.292 | 1.00 | 12.60 |
| ATOM | 2461 | C10 | SEI | B | 129 | 25.813 | 31.584 | 42.978 | 1.00 | 13.43 |
| ATOM | 2462 | N | SEI | B | 129 | 24.523 | 24.505 | 41.414 | 1.00 | 3.64 |
| ATOM | 2463 | CA | SEI | B | 129 | 24.573 | 25.896 | 41.749 | 1.00 | 5.61 |
| ATOM | 2464 | C | SEI | B | 129 | 23.438 | 26.120 | 42.741 | 1.00 | 7.34 |
| ATOM | 2465 | O | SEI | B | 129 | 22.271 | 25.854 | 42.468 | 1.00 | 12.17 |
| ATOM | 2466 | CB | SEI | B | 129 | 24.351 | 26.648 | 40.458 | 1.00 | 2.00 |
| ATOM | 2467 | O2 | SEI | B | 129 | 26.762 | 28.599 | 41.046 | 1.00 | 14.25 |
| ATOM | 2468 | N | LEU | B | 130 | 23.807 | 26.510 | 43.952 | 1.00 | 4.55 |
| ATOM | 2469 | CA | LEU | B | 130 | 22.814 | 26.749 | 45.005 | 1.00 | 6.57 |
| ATOM | 2470 | CB | LEU | B | 130 | 23.325 | 26.339 | 46.377 | 1.00 | 10.22 |
| ATOM | 2471 | CG | LEU | B | 130 | 22.435 | 26.812 | 47.537 | 1.00 | 10.59 |
| ATOM | 2472 | CD1 | LEU | B | 130 | 21.219 | 25.911 | 47.708 | 1.00 | 6.47 |
| ATOM | 2473 | CD2 | LEU | B | 130 | 23.245 | 26.840 | 48.811 | 1.00 | 17.62 |
| ATOM | 2474 | C | LEU | B | 130 | 22.467 | 28.178 | 45.059 | 1.00 | 6.26 |
| ATOM | 2475 | O | LEU | B | 130 | 23.325 | 29.026 | 45.206 | 1.00 | 6.59 |
| ATOM | 2476 | N | SER | B | 131 | 21.183 | 28.465 | 44.924 | 1.00 | 11.26 |
| ATOM | 2477 | CA | SER | B | 131 | 20.728 | 29.862 | 45.027 | 1.00 | 13.28 |
| ATOM | 2478 | CB | SER | B | 131 | 19.569 | 30.160 | 44.082 | 1.00 | 13.17 |
| ATOM | 2479 | OG | SER | B | 131 | 20.000 | 30.148 | 42.743 | 1.00 | 17.83 |
| ATOM | 2480 | C | SER | B | 131 | 20.285 | 30.029 | 46.470 | 1.00 | 13.30 |
| ATOM | 2481 | O | SER | B | 131 | 19.729 | 29.103 | 47.082 | 1.00 | 14.83 |
| ATOM | 2482 | N | THR | B | 132 | 20.617 | 31.190 | 47.026 | 1.00 | 14.68 |
| ATOM | 2483 | CA | THR | B | 132 | 20.238 | 31.558 | 48.411 | 1.00 | 23.27 |
| ATOM | 2484 | CB | THR | B | 132 | 21.453 | 31.820 | 49.285 | 1.00 | 18.86 |
| ATOM | 2485 | OG1 | THR | B | 132 | 22.336 | 32.710 | 48.602 | 1.00 | 22.21 |
| ATOM | 2486 | CG2 | THR | B | 132 | 22.163 | 30.536 | 49.584 | 1.00 | 18.49 |
| ATOM | 2487 | C | THR | B | 132 | 19.441 | 32.871 | 48.316 | 1.00 | 30.52 |
| ATOM | 2488 | O | THR | B | 132 | 19.774 | 33.755 | 47.511 | 1.00 | 34.88 |
| ATOM | 2489 | N | ALA | B | 133 | 18.374 | 32.965 | 49.114 | 1.00 | 34.31 |
| ATOM | 2490 | CA | ALA | B | 133 | 17.491 | 34.164 | 49.141 | 1.00 | 37.83 |
| ATOM | 2491 | CB | ALA | B | 133 | 16.179 | 33.825 | 49.850 | 1.00 | 37.10 |
| ATOM | 2492 | C | ALA | B | 133 | 18.196 | 35.371 | 49.833 | 1.00 | 43.25 |
| ATOM | 2493 | O | ALA | B | 133 | 18.153 | 36.511 | 49.285 | 1.00 | 46.91 |
| ATOM | 2494 | OT | ALA | B | 133 | 18.801 | 35.145 | 50.910 | 1.00 | 47.08 |
| ATOM | 2495 | CB | ALA | B | 141 | 21.810 | 32.816 | 58.328 | 1.00 | 39.82 |
| ATOM | 2496 | C | ALA | B | 141 | 19.477 | 32.765 | 59.227 | 1.00 | 37.50 |

Figure 4WW

| ATOM | 2497 | O | ALA | B | 141 | 19.419 | 32.695 | 60.452 | 1.00 | 39.73 |
|---|---|---|---|---|---|---|---|---|---|---|
| ATOM | 2498 | N | ALA | B | 141 | 20.876 | 34.800 | 59.432 | 1.00 | 40.30 |
| ATOM | 2499 | CA | ALA | B | 141 | 20.552 | 33.638 | 58.556 | 1.00 | 39.18 |
| ATOM | 2500 | N | ASP | B | 142 | 18.619 | 32.131 | 58.418 | 1.00 | 35.54 |
| ATOM | 2501 | CA | ASP | B | 142 | 17.542 | 31.222 | 58.939 | 1.00 | 34.78 |
| ATOM | 2502 | CB | ASP | B | 142 | 16.287 | 32.015 | 59.305 | 1.00 | 40.40 |
| ATOM | 2503 | CG | ASP | B | 142 | 15.499 | 32.467 | 58.100 | 1.00 | 44.17 |
| ATOM | 2504 | OD1 | ASP | B | 142 | 14.584 | 31.714 | 57.722 | 1.00 | 48.60 |
| ATOM | 2505 | OD2 | ASP | B | 142 | 15.768 | 33.568 | 57.550 | 1.00 | 44.92 |
| ATOM | 2506 | C | ASP | B | 142 | 17.222 | 30.077 | 57.948 | 1.00 | 33.91 |
| ATOM | 2507 | O | ASP | B | 142 | 17.741 | 30.025 | 56.843 | 1.00 | 35.30 |
| ATOM | 2508 | N | ARG | B | 143 | 16.322 | 29.181 | 58.342 | 1.00 | 35.00 |
| ATOM | 2509 | CA | ARG | B | 143 | 15.948 | 27.979 | 57.500 | 1.00 | 35.88 |
| ATOM | 2510 | CB | ARG | B | 143 | 14.943 | 27.076 | 58.251 | 1.00 | 40.75 |
| ATOM | 2511 | CG | ARG | B | 143 | 15.146 | 26.968 | 59.772 | 1.00 | 45.82 |
| ATOM | 2512 | CD | ARG | B | 143 | 15.334 | 25.538 | 60.280 | 1.00 | 48.09 |
| ATOM | 2513 | NE | ARG | B | 143 | 15.437 | 25.548 | 61.745 | 1.00 | 60.16 |
| ATOM | 2514 | CZ | ARG | B | 143 | 16.474 | 25.095 | 62.465 | 1.00 | 63.46 |
| ATOM | 2515 | NH1 | ARG | B | 143 | 16.436 | 25.168 | 63.795 | 1.00 | 63.68 |
| ATOM | 2516 | NH2 | ARG | B | 143 | 17.546 | 24.571 | 61.878 | 1.00 | 63.18 |
| ATOM | 2517 | C | ARG | B | 143 | 15.434 | 28.240 | 56.053 | 1.00 | 33.76 |
| ATOM | 2518 | O | ARG | B | 143 | 15.241 | 27.323 | 55.253 | 1.00 | 32.56 |
| ATOM | 2519 | N | THR | B | 144 | 15.214 | 29.503 | 55.720 | 1.00 | 30.77 |
| ATOM | 2520 | CA | THR | B | 144 | 14.737 | 29.842 | 54.366 | 1.00 | 28.86 |
| ATOM | 2521 | CB | THR | B | 144 | 13.628 | 30.887 | 54.437 | 1.00 | 29.22 |
| ATOM | 2522 | OG1 | THR | B | 144 | 14.175 | 32.132 | 54.893 | 1.00 | 27.77 |
| ATOM | 2523 | CG2 | THR | B | 144 | 12.556 | 30.427 | 55.417 | 1.00 | 30.05 |
| ATOM | 2524 | C | THR | B | 144 | 15.866 | 30.389 | 53.475 | 1.00 | 26.69 |
| ATOM | 2525 | O | THR | B | 144 | 15.629 | 30.999 | 52.438 | 1.00 | 32.36 |
| ATOM | 2526 | N | LEU | B | 145 | 17.108 | 30.192 | 53.896 | 1.00 | 22.02 |
| ATOM | 2527 | CA | LEU | B | 145 | 18.258 | 30.708 | 53.109 | 1.00 | 20.99 |
| ATOM | 2528 | CB | LEU | B | 145 | 19.537 | 30.629 | 53.951 | 1.00 | 19.79 |
| ATOM | 2529 | CG | LEU | B | 145 | 20.848 | 31.126 | 53.345 | 1.00 | 15.95 |
| ATOM | 2530 | CD1 | LEU | B | 145 | 20.842 | 32.616 | 53.136 | 1.00 | 14.52 |
| ATOM | 2531 | CD2 | LEU | B | 145 | 21.947 | 30.753 | 54.277 | 1.00 | 18.00 |
| ATOM | 2532 | C | LEU | B | 145 | 18.430 | 29.993 | 51.739 | 1.00 | 19.73 |
| ATOM | 2533 | O | LEU | B | 145 | 18.560 | 30.611 | 50.701 | 1.00 | 22.38 |
| ATOM | 2534 | N | PHE | B | 146 | 18.431 | 28.670 | 51.758 | 1.00 | 17.81 |
| ATOM | 2535 | CA | PHE | B | 146 | 18.589 | 27.868 | 50.536 | 1.00 | 15.34 |
| ATOM | 2536 | CB | PHE | B | 146 | 18.991 | 26.436 | 50.905 | 1.00 | 13.39 |
| ATOM | 2537 | CG | PHE | B | 146 | 20.370 | 26.315 | 51.488 | 1.00 | 13.44 |
| ATOM | 2538 | CD1 | PHE | B | 146 | 20.870 | 25.072 | 51.871 | 1.00 | 14.63 |
| ATOM | 2539 | CD2 | PHE | B | 146 | 21.165 | 27.439 | 51.681 | 1.00 | 16.84 |
| ATOM | 2540 | CE1 | PHE | B | 146 | 22.135 | 24.953 | 52.447 | 1.00 | 10.15 |
| ATOM | 2541 | CE2 | PHE | B | 146 | 22.438 | 27.329 | 52.260 | 1.00 | 14.58 |
| ATOM | 2542 | CZ | PHE | B | 146 | 22.917 | 26.082 | 52.543 | 1.00 | 11.68 |
| ATOM | 2543 | C | PHE | B | 146 | 17.280 | 27.881 | 49.749 | 1.00 | 15.13 |
| ATOM | 2544 | O | PHE | B | 146 | 16.255 | 27.384 | 50.182 | 1.00 | 18.59 |
| ATOM | 2545 | N | ALA | B | 147 | 17.341 | 28.453 | 48.558 | 1.00 | 17.08 |
| ATOM | 2546 | CA | ALA | B | 147 | 16.154 | 28.562 | 47.642 | 1.00 | 18.51 |
| ATOM | 2547 | CB | ALA | B | 147 | 16.265 | 29.844 | 46.815 | 1.00 | 20.19 |
| ATOM | 2548 | C | ALA | B | 147 | 15.965 | 27.334 | 46.682 | 1.00 | 19.37 |

Figure 4XX

| | | | | | | | | | |
|---|---|---|---|---|---|---|---|---|---|
| ATOM | 2549 | O | ALA | B | 147 | 14.880 | 26.755 | 46.536 | 1.00 23.52 |
| ATOM | 2550 | N | HIS | B | 148 | 17.026 | 26.999 | 45.958 | 1.00 13.42 |
| ATOM | 2551 | CA | HIS | B | 148 | 16.974 | 25.862 | 45.037 | 1.00 10.50 |
| ATOM | 2552 | CB | HIS | B | 148 | 15.975 | 26.133 | 43.917 | 1.00 9.04 |
| ATOM | 2553 | CG | HIS | B | 148 | 16.284 | 27.361 | 43.115 | 1.00 13.85 |
| ATOM | 2554 | CD2 | HIS | B | 148 | 15.926 | 28.653 | 43.289 | 1.00 16.64 |
| ATOM | 2555 | ND1 | HIS | B | 148 | 17.061 | 27.329 | 41.973 | 1.00 22.27 |
| ATOM | 2556 | CE1 | HIS | B | 148 | 17.169 | 28.549 | 41.479 | 1.00 16.08 |
| ATOM | 2557 | NE2 | HIS | B | 148 | 16.488 | 29.371 | 42.257 | 1.00 20.15 |
| ATOM | 2558 | C | HIS | B | 148 | 18.364 | 25.626 | 44.474 | 1.00 11.93 |
| ATOM | 2559 | O | HIS | B | 148 | 19.283 | 26.423 | 44.672 | 1.00 12.97 |
| ATOM | 2560 | N | VAL | B | 149 | 18.505 | 24.497 | 43.787 | 1.00 11.22 |
| ATOM | 2561 | CA | VAL | B | 149 | 19.759 | 24.115 | 43.140 | 1.00 10.27 |
| ATOM | 2562 | CB | VAL | B | 149 | 20.396 | 22.811 | 43.717 | 1.00 11.51 |
| ATOM | 2563 | CG1 | VAL | B | 149 | 20.208 | 22.760 | 45.208 | 1.00 14.24 |
| ATOM | 2564 | CG2 | VAL | B | 149 | 19.851 | 21.566 | 43.072 | 1.00 11.24 |
| ATOM | 2565 | C | VAL | B | 149 | 19.460 | 23.942 | 41.663 | 1.00 11.83 |
| ATOM | 2566 | O | VAL | B | 149 | 18.419 | 23.426 | 41.222 | 1.00 13.37 |
| ATOM | 2567 | N | ALA | B | 150 | 20.406 | 24.434 | 40.885 | 1.00 12.95 |
| ATOM | 2568 | CA | ALA | B | 150 | 20.324 | 24.392 | 39.438 | 1.00 9.02 |
| ATOM | 2569 | CB | ALA | B | 150 | 20.402 | 25.795 | 38.904 | 1.00 11.66 |
| ATOM | 2570 | C | ALA | B | 150 | 21.482 | 23.565 | 38.871 | 1.00 8.97 |
| ATOM | 2571 | O | ALA | B | 150 | 22.632 | 23.709 | 39.275 | 1.00 12.77 |
| ATOM | 2572 | N | LEU | B | 151 | 21.150 | 22.626 | 37.995 | 1.00 7.32 |
| ATOM | 2573 | CA | LEU | B | 151 | 22.177 | 21.822 | 37.314 | 1.00 3.63 |
| ATOM | 2574 | CB | LEU | B | 151 | 21.561 | 20.574 | 36.701 | 1.00 8.28 |
| ATOM | 2575 | CG | LEU | B | 151 | 21.249 | 19.340 | 37.586 | 1.00 13.08 |
| ATOM | 2576 | CD1 | LEU | B | 151 | 21.148 | 19.677 | 39.058 | 1.00 10.08 |
| ATOM | 2577 | CD2 | LEU | B | 151 | 19.985 | 18.634 | 37.094 | 1.00 12.45 |
| ATOM | 2578 | C | LEU | B | 151 | 22.671 | 22.801 | 36.240 | 1.00 4.77 |
| ATOM | 2579 | O | LEU | B | 151 | 21.957 | 23.681 | 35.748 | 1.00 6.86 |
| ATOM | 2580 | N | CYS | B | 152 | 23.952 | 22.741 | 35.964 | 1.00 6.25 |
| ATOM | 2581 | CA | CYS | B | 152 | 24.513 | 23.639 | 34.967 | 1.00 6.17 |
| ATOM | 2582 | CB | CYS | B | 152 | 24.644 | 25.033 | 35.551 | 1.00 2.00 |
| ATOM | 2583 | SG | CYS | B | 152 | 25.638 | 25.054 | 37.012 | 1.00 17.14 |
| ATOM | 2584 | C | CYS | B | 152 | 25.855 | 23.079 | 34.512 | 1.00 5.89 |
| ATOM | 2585 | O | CYS | B | 152 | 26.315 | 22.044 | 34.989 | 1.00 8.57 |
| ATOM | 2586 | N | ALA | B | 153 | 26.434 | 23.747 | 33.522 | 1.00 5.41 |
| ATOM | 2587 | CA | ALA | B | 153 | 27.707 | 23.364 | 32.928 | 1.00 4.87 |
| ATOM | 2588 | CB | ALA | B | 153 | 27.887 | 24.108 | 31.626 | 1.00 2.96 |
| ATOM | 2589 | C | ALA | B | 153 | 28.880 | 23.682 | 33.856 | 1.00 9.92 |
| ATOM | 2590 | O | ALA | B | 153 | 29.752 | 22.864 | 34.138 | 1.00 11.99 |
| ATOM | 2591 | N | ILE | B | 154 | 28.901 | 24.921 | 34.312 | 1.00 8.95 |
| ATOM | 2592 | CA | ILE | B | 154 | 29.978 | 25.394 | 35.164 | 1.00 13.64 |
| ATOM | 2593 | CB | ILE | B | 154 | 31.059 | 26.154 | 34.275 | 1.00 20.80 |
| ATOM | 2594 | CG2 | ILE | B | 154 | 32.190 | 26.719 | 35.116 | 1.00 22.34 |
| ATOM | 2595 | CG1 | ILE | B | 154 | 31.695 | 25.205 | 33.247 | 1.00 22.54 |
| ATOM | 2596 | CD1 | ILE | B | 154 | 32.481 | 24.047 | 33.853 | 1.00 28.65 |
| ATOM | 2597 | C | ILE | B | 154 | 29.319 | 26.326 | 36.219 | 1.00 12.91 |
| ATOM | 2598 | O | ILE | B | 154 | 28.628 | 27.298 | 35.900 | 1.00 13.79 |
| ATOM | 2599 | N | GLY | B | 155 | 29.506 | 25.965 | 37.490 | 1.00 16.22 |
| ATOM | 2600 | CA | GLY | B | 155 | 28.950 | 26.726 | 38.611 | 1.00 14.51 |

Figure 4YY

| ATOM | 2601 | C | GLY | B | 155 | 29.881 | 27.842 | 39.041 | 1.00 | 11.98 |
|---|---|---|---|---|---|---|---|---|---|---|
| ATOM | 2602 | O | GLY | B | 155 | 30.999 | 27.908 | 38.594 | 1.00 | 14.71 |
| ATOM | 2603 | N | ARG | B | 156 | 29.455 | 28.716 | 39.926 | 1.00 | 13.56 |
| ATOM | 2604 | CA | ARG | B | 156 | 30.346 | 29.826 | 40.309 | 1.00 | 14.30 |
| ATOM | 2605 | CB | ARG | B | 156 | 29.531 | 31.107 | 40.414 | 1.00 | 14.73 |
| ATOM | 2606 | CG | ARG | B | 156 | 28.786 | 31.396 | 39.149 | 1.00 | 22.12 |
| ATOM | 2607 | CD | ARG | B | 156 | 28.610 | 32.866 | 38.948 | 1.00 | 35.28 |
| ATOM | 2608 | NE | ARG | B | 156 | 28.027 | 33.502 | 40.121 | 1.00 | 48.94 |
| ATOM | 2609 | CZ | ARG | B | 156 | 28.245 | 34.769 | 40.462 | 1.00 | 56.23 |
| ATOM | 2610 | NH1 | ARG | B | 156 | 27.668 | 35.266 | 41.553 | 1.00 | 60.17 |
| ATOM | 2611 | NH2 | ARG | B | 156 | 29.040 | 35.541 | 39.722 | 1.00 | 59.06 |
| ATOM | 2612 | C | ARG | B | 156 | 31.168 | 29.578 | 41.569 | 1.00 | 13.08 |
| ATOM | 2613 | O | ARG | B | 156 | 32.069 | 30.330 | 41.930 | 1.00 | 12.46 |
| ATOM | 2614 | N | ARG | B | 157 | 30.803 | 28.515 | 42.265 | 1.00 | 13.13 |
| ATOM | 2615 | CA | ARG | B | 157 | 31.485 | 28.148 | 43.496 | 1.00 | 11.72 |
| ATOM | 2616 | CB | ARG | B | 157 | 30.472 | 27.872 | 44.624 | 1.00 | 12.67 |
| ATOM | 2617 | CG | ARG | B | 157 | 29.704 | 29.114 | 45.117 | 1.00 | 9.87 |
| ATOM | 2618 | CD | ARG | B | 157 | 29.266 | 28.984 | 46.588 | 1.00 | 13.32 |
| ATOM | 2619 | NE | ARG | B | 157 | 27.818 | 28.843 | 46.786 | 1.00 | 20.09 |
| ATOM | 2620 | CZ | ARG | B | 157 | 26.946 | 29.855 | 46.884 | 1.00 | 19.55 |
| ATOM | 2621 | NH1 | ARG | B | 157 | 25.678 | 29.651 | 47.094 | 1.00 | 23.95 |
| ATOM | 2622 | NH2 | ARG | B | 157 | 27.291 | 31.084 | 46.652 | 1.00 | 23.51 |
| ATOM | 2623 | C | ARG | B | 157 | 32.337 | 26.930 | 43.173 | 1.00 | 10.92 |
| ATOM | 2624 | O | ARG | B | 157 | 32.011 | 26.103 | 42.321 | 1.00 | 6.72 |
| ATOM | 2625 | N | LEU | B | 158 | 33.465 | 26.851 | 43.865 | 1.00 | 10.73 |
| ATOM | 2626 | CA | LEU | B | 158 | 34.431 | 25.752 | 43.668 | 1.00 | 8.72 |
| ATOM | 2627 | CB | LEU | B | 158 | 35.741 | 26.081 | 44.379 | 1.00 | 10.73 |
| ATOM | 2628 | CG | LEU | B | 158 | 36.829 | 26.934 | 43.726 | 1.00 | 10.53 |
| ATOM | 2629 | CD1 | LEU | B | 158 | 36.305 | 27.648 | 42.506 | 1.00 | 10.03 |
| ATOM | 2630 | CD2 | LEU | B | 158 | 37.385 | 27.921 | 44.753 | 1.00 | 6.05 |
| ATOM | 2631 | C | LEU | B | 158 | 33.888 | 24.425 | 44.171 | 1.00 | 9.08 |
| ATOM | 2632 | O | LEU | B | 158 | 32.939 | 24.353 | 44.936 | 1.00 | 11.24 |
| ATOM | 2633 | N | GLY | B | 159 | 34.526 | 23.359 | 43.708 | 1.00 | 10.66 |
| ATOM | 2634 | CA | GLY | B | 159 | 34.160 | 22.016 | 44.108 | 1.00 | 7.71 |
| ATOM | 2635 | C | GLY | B | 159 | 32.758 | 21.581 | 43.779 | 1.00 | 8.04 |
| ATOM | 2636 | O | GLY | B | 159 | 32.347 | 20.492 | 44.164 | 1.00 | 10.92 |
| ATOM | 2637 | N | THR | B | 160 | 32.031 | 22.393 | 43.030 | 1.00 | 10.18 |
| ATOM | 2638 | CA | THR | B | 160 | 30.649 | 22.048 | 42.678 | 1.00 | 11.25 |
| ATOM | 2639 | CB | THR | B | 160 | 29.810 | 23.307 | 42.479 | 1.00 | 10.87 |
| ATOM | 2640 | OG1 | THR | B | 160 | 30.463 | 24.164 | 41.526 | 1.00 | 4.27 |
| ATOM | 2641 | CG2 | THR | B | 160 | 29.639 | 24.014 | 43.816 | 1.00 | 7.08 |
| ATOM | 2642 | C | THR | B | 160 | 30.513 | 21.159 | 41.436 | 1.00 | 11.94 |
| ATOM | 2643 | O | THR | B | 160 | 29.957 | 21.517 | 40.419 | 1.00 | 16.34 |
| ATOM | 2644 | N | ILE | B | 161 | 31.064 | 19.974 | 41.519 | 1.00 | 11.86 |
| ATOM | 2645 | CA | ILE | B | 161 | 30.943 | 19.036 | 40.424 | 1.00 | 11.50 |
| ATOM | 2646 | CB | ILE | B | 161 | 32.337 | 18.564 | 39.970 | 1.00 | 8.85 |
| ATOM | 2647 | CG2 | ILE | B | 161 | 32.231 | 17.379 | 39.003 | 1.00 | 10.76 |
| ATOM | 2648 | CG1 | ILE | B | 161 | 33.044 | 19.713 | 39.269 | 1.00 | 5.36 |
| ATOM | 2649 | CD1 | ILE | B | 161 | 32.336 | 20.177 | 38.021 | 1.00 | 6.51 |
| ATOM | 2650 | C | ILE | B | 161 | 30.100 | 17.911 | 41.069 | 1.00 | 16.51 |
| ATOM | 2651 | O | ILE | B | 161 | 30.333 | 17.461 | 42.202 | 1.00 | 18.10 |
| ATOM | 2652 | N | VAL | B | 162 | 29.055 | 17.506 | 40.369 | 1.00 | 16.97 |

Figure 4ZZ

| ATOM | 2653 | CA | VAL | B | 162 | 28.172 | 16.468 | 40.905 | 1.00 | 14.97 |
| --- | --- | --- | --- | --- | --- | --- | --- | --- | --- | --- |
| ATOM | 2654 | CB | VAL | B | 162 | 26.688 | 16.890 | 40.825 | 1.00 | 15.28 |
| ATOM | 2655 | CG1 | VAL | B | 162 | 26.508 | 18.215 | 41.512 | 1.00 | 12.92 |
| ATOM | 2656 | CG2 | VAL | B | 162 | 26.213 | 16.941 | 39.380 | 1.00 | 8.32 |
| ATOM | 2657 | C | VAL | B | 162 | 28.341 | 15.123 | 40.207 | 1.00 | 17.23 |
| ATOM | 2658 | O | VAL | B | 162 | 28.947 | 14.994 | 39.151 | 1.00 | 20.63 |
| ATOM | 2659 | N | THR | B | 163 | 27.742 | 14.112 | 40.822 | 1.00 | 18.18 |
| ATOM | 2660 | CA | THR | B | 163 | 27.756 | 12.734 | 40.317 | 1.00 | 15.19 |
| ATOM | 2661 | CB | THR | B | 163 | 28.394 | 11.777 | 41.385 | 1.00 | 15.60 |
| ATOM | 2662 | OG1 | THR | B | 163 | 29.773 | 12.123 | 41.592 | 1.00 | 12.70 |
| ATOM | 2663 | CG2 | THR | B | 163 | 28.327 | 10.333 | 40.952 | 1.00 | 16.80 |
| ATOM | 2664 | C | THR | B | 163 | 26.271 | 12.355 | 40.080 | 1.00 | 14.87 |
| ATOM | 2665 | O | THR | B | 163 | 25.345 | 12.800 | 40.770 | 1.00 | 19.32 |
| ATOM | 2666 | N | TYR | B | 164 | 26.054 | 11.557 | 39.051 | 1.00 | 9.64 |
| ATOM | 2667 | CA | TYR | B | 164 | 24.721 | 11.096 | 38.715 | 1.00 | 5.61 |
| ATOM | 2668 | CB | TYR | B | 164 | 24.367 | 11.578 | 37.321 | 1.00 | 7.77 |
| ATOM | 2669 | CG | TYR | B | 164 | 24.194 | 13.065 | 37.161 | 1.00 | 5.11 |
| ATOM | 2670 | CD1 | TYR | B | 164 | 25.215 | 13.849 | 36.673 | 1.00 | 6.64 |
| ATOM | 2671 | CE1 | TYR | B | 164 | 25.023 | 15.208 | 36.425 | 1.00 | 4.55 |
| ATOM | 2672 | CD2 | TYR | B | 164 | 22.975 | 13.669 | 37.409 | 1.00 | 3.93 |
| ATOM | 2673 | CE2 | TYR | B | 164 | 22.784 | 15.008 | 37.158 | 1.00 | 5.02 |
| ATOM | 2674 | CZ | TYR | B | 164 | 23.805 | 15.766 | 36.664 | 1.00 | 2.00 |
| ATOM | 2675 | OH | TYR | B | 164 | 23.580 | 17.068 | 36.352 | 1.00 | 2.00 |
| ATOM | 2676 | C | TYR | B | 164 | 24.740 | 9.561 | 38.718 | 1.00 | 10.82 |
| ATOM | 2677 | O | TYR | B | 164 | 25.729 | 8.939 | 38.349 | 1.00 | 13.25 |
| ATOM | 2678 | N | ASP | B | 165 | 23.662 | 8.937 | 39.173 | 1.00 | 12.08 |
| ATOM | 2679 | CA | ASP | B | 165 | 23.587 | 7.465 | 39.102 | 1.00 | 13.24 |
| ATOM | 2680 | CB | ASP | B | 165 | 24.603 | 6.802 | 40.026 | 1.00 | 16.40 |
| ATOM | 2681 | CG | ASP | B | 165 | 25.297 | 5.623 | 39.352 | 1.00 | 20.71 |
| ATOM | 2682 | OD1 | ASP | B | 165 | 24.624 | 4.621 | 39.032 | 1.00 | 22.41 |
| ATOM | 2683 | OD2 | ASP | B | 165 | 26.518 | 5.705 | 39.113 | 1.00 | 26.52 |
| ATOM | 2684 | C | ASP | B | 165 | 22.161 | 6.990 | 39.376 | 1.00 | 15.45 |
| ATOM | 2685 | O | ASP | B | 165 | 21.294 | 7.755 | 39.783 | 1.00 | 16.33 |
| ATOM | 2686 | N | THR | B | 166 | 21.898 | 5.722 | 39.080 | 1.00 | 16.15 |
| ATOM | 2687 | CA | THR | B | 166 | 20.543 | 5.138 | 39.293 | 1.00 | 18.39 |
| ATOM | 2688 | CB | THR | B | 166 | 20.300 | 4.018 | 38.329 | 1.00 | 15.26 |
| ATOM | 2689 | OG1 | THR | B | 166 | 21.350 | 3.072 | 38.496 | 1.00 | 16.28 |
| ATOM | 2690 | CG2 | THR | B | 166 | 20.330 | 4.531 | 36.901 | 1.00 | 14.97 |
| ATOM | 2691 | C | THR | B | 166 | 20.334 | 4.559 | 40.704 | 1.00 | 22.40 |
| ATOM | 2692 | O | THR | B | 166 | 19.372 | 3.843 | 40.965 | 1.00 | 27.49 |
| ATOM | 2693 | N | SER | B | 167 | 21.278 | 4.849 | 41.599 | 1.00 | 25.31 |
| ATOM | 2694 | CA | SER | B | 167 | 21.235 | 4.386 | 43.007 | 1.00 | 21.41 |
| ATOM | 2695 | CB | SER | B | 167 | 21.929 | 3.012 | 43.159 | 1.00 | 27.45 |
| ATOM | 2696 | OG | SER | B | 167 | 23.065 | 3.031 | 44.032 | 1.00 | 28.47 |
| ATOM | 2697 | C | SER | B | 167 | 21.944 | 5.471 | 43.804 | 1.00 | 21.42 |
| ATOM | 2698 | O | SER | B | 167 | 22.947 | 6.055 | 43.390 | 1.00 | 21.57 |
| ATOM | 2699 | N | LEU | B | 168 | 21.363 | 5.788 | 44.949 | 1.00 | 23.05 |
| ATOM | 2700 | CA | LEU | B | 168 | 21.920 | 6.819 | 45.863 | 1.00 | 22.96 |
| ATOM | 2701 | CB | LEU | B | 168 | 21.001 | 6.980 | 47.078 | 1.00 | 19.41 |
| ATOM | 2702 | CG | LEU | B | 168 | 21.393 | 7.936 | 48.192 | 1.00 | 14.69 |
| ATOM | 2703 | CD1 | LEU | B | 168 | 20.191 | 8.226 | 48.975 | 1.00 | 12.83 |
| ATOM | 2704 | CD2 | LEU | B | 168 | 22.443 | 7.346 | 49.093 | 1.00 | 23.19 |

Figure 4AAA

| ATOM | 2705 | C | LEU | B | 168 | 23.324 | 6.400 | 46.283 | 1.00 | 23.29 |
|---|---|---|---|---|---|---|---|---|---|---|
| ATOM | 2706 | O | LEU | B | 168 | 24.266 | 7.181 | 46.247 | 1.00 | 26.87 |
| ATOM | 2707 | N | ASP | B | 169 | 23.439 | 5.131 | 46.674 | 1.00 | 25.84 |
| ATOM | 2708 | CA | ASP | B | 169 | 24.725 | 4.536 | 47.112 | 1.00 | 25.99 |
| ATOM | 2709 | CB | ASP | B | 169 | 24.505 | 3.071 | 47.507 | 1.00 | 28.63 |
| ATOM | 2710 | CG | ASP | B | 169 | 24.140 | 2.916 | 48.992 | 1.00 | 34.54 |
| ATOM | 2711 | OD1 | ASP | B | 169 | 24.574 | 1.919 | 49.616 | 1.00 | 36.98 |
| ATOM | 2712 | OD2 | ASP | B | 169 | 23.441 | 3.801 | 49.514 | 1.00 | 33.74 |
| ATOM | 2713 | C | ASP | B | 169 | 25.807 | 4.680 | 46.045 | 1.00 | 25.28 |
| ATOM | 2714 | O | ASP | B | 169 | 26.968 | 4.998 | 46.322 | 1.00 | 27.41 |
| ATOM | 2715 | N | ALA | B | 170 | 25.380 | 4.513 | 44.796 | 1.00 | 26.04 |
| ATOM | 2716 | CA | ALA | B | 170 | 26.292 | 4.635 | 43.607 | 1.00 | 24.21 |
| ATOM | 2717 | CB | ALA | B | 170 | 25.596 | 4.072 | 42.355 | 1.00 | 22.04 |
| ATOM | 2718 | C | ALA | B | 170 | 26.715 | 6.111 | 43.353 | 1.00 | 20.70 |
| ATOM | 2719 | O | ALA | B | 170 | 27.846 | 6.435 | 42.980 | 1.00 | 21.57 |
| ATOM | 2720 | N | ALA | B | 171 | 25.754 | 6.996 | 43.575 | 1.00 | 16.12 |
| ATOM | 2721 | CA | ALA | B | 171 | 25.942 | 8.412 | 43.366 | 1.00 | 12.56 |
| ATOM | 2722 | CB | ALA | B | 171 | 24.589 | 9.105 | 43.365 | 1.00 | 11.02 |
| ATOM | 2723 | C | ALA | B | 171 | 26.888 | 9.045 | 44.394 | 1.00 | 16.48 |
| ATOM | 2724 | O | ALA | B | 171 | 27.554 | 10.042 | 44.125 | 1.00 | 20.58 |
| ATOM | 2725 | N | ILE | B | 172 | 26.936 | 8.482 | 45.598 | 1.00 | 19.83 |
| ATOM | 2726 | CA | ILE | B | 172 | 27.846 | 9.039 | 46.658 | 1.00 | 20.98 |
| ATOM | 2727 | CB | ILE | B | 172 | 27.134 | 9.158 | 48.043 | 1.00 | 25.13 |
| ATOM | 2728 | CG2 | ILE | B | 172 | 25.662 | 9.517 | 47.842 | 1.00 | 28.72 |
| ATOM | 2729 | CG1 | ILE | B | 172 | 27.243 | 7.856 | 48.849 | 1.00 | 27.28 |
| ATOM | 2730 | CD1 | ILE | B | 172 | 26.580 | 7.931 | 50.237 | 1.00 | 27.33 |
| ATOM | 2731 | C | ILE | B | 172 | 29.235 | 8.306 | 46.794 | 1.00 | 17.41 |
| ATOM | 2732 | O | ILE | B | 172 | 30.213 | 8.843 | 47.328 | 1.00 | 15.53 |
| ATOM | 2733 | N | ALA | B | 173 | 29.310 | 7.093 | 46.253 | 1.00 | 10.44 |
| ATOM | 2734 | CA | ALA | B | 173 | 30.558 | 6.298 | 46.235 | 1.00 | 12.32 |
| ATOM | 2735 | CB | ALA | B | 173 | 30.375 | 5.005 | 45.530 | 1.00 | 12.15 |
| ATOM | 2736 | C | ALA | B | 173 | 31.823 | 7.014 | 45.765 | 1.00 | 12.79 |
| ATOM | 2737 | O | ALA | B | 173 | 32.882 | 6.896 | 46.348 | 1.00 | 17.71 |
| ATOM | 2738 | N | PRO | B | 174 | 31.728 | 7.747 | 44.634 | 1.00 | 11.72 |
| ATOM | 2739 | CD | PRO | B | 174 | 30.618 | 7.960 | 43.690 | 1.00 | 5.96 |
| ATOM | 2740 | CA | PRO | B | 174 | 32.933 | 8.417 | 44.144 | 1.00 | 7.36 |
| ATOM | 2741 | CB | PRO | B | 174 | 32.442 | 9.117 | 42.882 | 1.00 | 5.91 |
| ATOM | 2742 | CG | PRO | B | 174 | 31.353 | 8.224 | 42.429 | 1.00 | 6.53 |
| ATOM | 2743 | C | PRO | B | 174 | 33.459 | 9.439 | 45.140 | 1.00 | 10.22 |
| ATOM | 2744 | O | PRO | B | 174 | 34.609 | 9.864 | 45.094 | 1.00 | 14.59 |
| ATOM | 2745 | N | PHE | B | 175 | 32.589 | 9.892 | 46.029 | 1.00 | 12.76 |
| ATOM | 2746 | CA | PHE | B | 175 | 33.022 | 10.890 | 47.035 | 1.00 | 18.32 |
| ATOM | 2747 | CB | PHE | B | 175 | 31.809 | 11.687 | 47.513 | 1.00 | 17.04 |
| ATOM | 2748 | CG | PHE | B | 175 | 31.260 | 12.618 | 46.466 | 1.00 | 11.91 |
| ATOM | 2749 | CD1 | PHE | B | 175 | 31.751 | 13.913 | 46.348 | 1.00 | 7.73 |
| ATOM | 2750 | CD2 | PHE | B | 175 | 30.290 | 12.182 | 45.571 | 1.00 | 8.77 |
| ATOM | 2751 | CE1 | PHE | B | 175 | 31.290 | 14.755 | 45.350 | 1.00 | 6.39 |
| ATOM | 2752 | CE2 | PHE | B | 175 | 29.821 | 13.011 | 44.572 | 1.00 | 2.00 |
| ATOM | 2753 | CZ | PHE | B | 175 | 30.318 | 14.298 | 44.457 | 1.00 | 6.14 |
| ATOM | 2754 | C | PHE | B | 175 | 33.822 | 10.264 | 48.211 | 1.00 | 23.77 |
| ATOM | 2755 | O | PHE | B | 175 | 33.298 | 9.785 | 49.216 | 1.00 | 24.51 |
| ATOM | 2756 | N | ARG | B | 176 | 35.139 | 10.307 | 48.056 | 1.00 | 29.90 |

Figure 4BBB

| ATOM | 2757 | CA | ARG B 176 | 36.091 | 9.732 | 49.053 | 1.00 | 31.16 |
| --- | --- | --- | --- | --- | --- | --- | --- | --- |
| ATOM | 2758 | CB | ARG B 176 | 37.381 | 9.362 | 48.299 | 1.00 | 32.42 |
| ATOM | 2759 | CG | ARG B 176 | 37.138 | 8.411 | 47.097 | 1.00 | 33.93 |
| ATOM | 2760 | CD | ARG B 176 | 36.568 | 7.051 | 47.572 | 1.00 | 36.16 |
| ATOM | 2761 | NE | ARG B 176 | 35.781 | 6.325 | 46.565 | 1.00 | 39.27 |
| ATOM | 2762 | CZ | ARG B 176 | 36.288 | 5.678 | 45.513 | 1.00 | 42.32 |
| ATOM | 2763 | NH1 | ARG B 176 | 35.475 | 5.046 | 44.660 | 1.00 | 39.59 |
| ATOM | 2764 | NH2 | ARG B 176 | 37.605 | 5.665 | 45.299 | 1.00 | 46.87 |
| ATOM | 2765 | C | ARG B 176 | 36.380 | 10.610 | 50.316 | 1.00 | 34.51 |
| ATOM | 2766 | O | ARG B 176 | 36.590 | 10.134 | 51.435 | 1.00 | 33.36 |
| ATOM | 2767 | N | HIS B 177 | 36.416 | 11.919 | 50.127 | 1.00 | 37.74 |
| ATOM | 2768 | CA | HIS B 177 | 36.685 | 12.816 | 51.289 | 1.00 | 41.97 |
| ATOM | 2769 | CB | HIS B 177 | 37.487 | 14.027 | 50.811 | 1.00 | 49.15 |
| ATOM | 2770 | CG | HIS B 177 | 38.742 | 13.662 | 50.070 | 1.00 | 57.94 |
| ATOM | 2771 | CD2 | HIS B 177 | 39.484 | 14.360 | 49.175 | 1.00 | 60.33 |
| ATOM | 2772 | ND1 | HIS B 177 | 39.362 | 12.433 | 50.204 | 1.00 | 60.45 |
| ATOM | 2773 | CE1 | HIS B 177 | 40.428 | 12.391 | 49.425 | 1.00 | 60.67 |
| ATOM | 2774 | NE2 | HIS B 177 | 40.525 | 13.546 | 48.790 | 1.00 | 62.60 |
| ATOM | 2775 | C | HIS B 177 | 35.338 | 13.217 | 51.928 | 1.00 | 41.22 |
| ATOM | 2776 | O | HIS B 177 | 34.963 | 14.399 | 52.037 | 1.00 | 39.27 |
| ATOM | 2777 | N | LEU B 178 | 34.608 | 12.186 | 52.350 | 1.00 | 35.75 |
| ATOM | 2778 | CA | LEU B 178 | 33.270 | 12.393 | 52.930 | 1.00 | 33.62 |
| ATOM | 2779 | CB | LEU B 178 | 32.214 | 11.781 | 52.009 | 1.00 | 25.56 |
| ATOM | 2780 | CG | LEU B 178 | 30.966 | 12.640 | 51.850 | 1.00 | 23.73 |
| ATOM | 2781 | CD1 | LEU B 178 | 31.352 | 13.996 | 51.246 | 1.00 | 17.64 |
| ATOM | 2782 | CD2 | LEU B 178 | 29.940 | 11.895 | 50.987 | 1.00 | 20.17 |
| ATOM | 2783 | C | LEU B 178 | 33.179 | 11.793 | 54.328 | 1.00 | 35.50 |
| ATOM | 2784 | O | LEU B 178 | 33.387 | 10.586 | 54.532 | 1.00 | 35.12 |
| ATOM | 2785 | N | ASP B 179 | 32.857 | 12.658 | 55.292 | 1.00 | 33.15 |
| ATOM | 2786 | CA | ASP B 179 | 32.739 | 12.228 | 56.702 | 1.00 | 34.50 |
| ATOM | 2787 | CB | ASP B 179 | 32.269 | 13.376 | 57.595 | 1.00 | 34.37 |
| ATOM | 2788 | CG | ASP B 179 | 32.556 | 13.119 | 59.069 | 1.00 | 35.10 |
| ATOM | 2789 | OD1 | ASP B 179 | 31.979 | 12.181 | 59.660 | 1.00 | 35.71 |
| ATOM | 2790 | OD2 | ASP B 179 | 33.383 | 13.857 | 59.645 | 1.00 | 40.00 |
| ATOM | 2791 | C | ASP B 179 | 31.769 | 11.054 | 56.789 | 1.00 | 34.54 |
| ATOM | 2792 | O | ASP B 179 | 30.656 | 11.083 | 56.272 | 1.00 | 39.56 |
| ATOM | 2793 | N | PRO B 180 | 32.197 | 9.981 | 57.450 | 1.00 | 33.13 |
| ATOM | 2794 | CD | PRO B 180 | 33.550 | 9.735 | 57.977 | 1.00 | 33.10 |
| ATOM | 2795 | CA | PRO B 180 | 31.354 | 8.796 | 57.597 | 1.00 | 32.32 |
| ATOM | 2796 | CB | PRO B 180 | 32.124 | 7.983 | 58.631 | 1.00 | 30.87 |
| ATOM | 2797 | CG | PRO B 180 | 33.540 | 8.234 | 58.191 | 1.00 | 33.69 |
| ATOM | 2798 | C | PRO B 180 | 29.913 | 9.112 | 58.041 | 1.00 | 29.22 |
| ATOM | 2799 | O | PRO B 180 | 28.943 | 8.490 | 57.611 | 1.00 | 30.25 |
| ATOM | 2800 | N | ALA B 181 | 29.798 | 10.116 | 58.902 | 1.00 | 28.96 |
| ATOM | 2801 | CA | ALA B 181 | 28.488 | 10.560 | 59.444 | 1.00 | 28.30 |
| ATOM | 2802 | CB | ALA B 181 | 28.708 | 11.633 | 60.515 | 1.00 | 26.43 |
| ATOM | 2803 | C | ALA B 181 | 27.589 | 11.098 | 58.310 | 1.00 | 27.73 |
| ATOM | 2804 | O | ALA B 181 | 26.377 | 10.834 | 58.221 | 1.00 | 27.98 |
| ATOM | 2805 | N | THR B 182 | 28.228 | 11.853 | 57.421 | 1.00 | 25.91 |
| ATOM | 2806 | CA | THR B 182 | 27.537 | 12.446 | 56.259 | 1.00 | 24.31 |
| ATOM | 2807 | CB | THR B 182 | 28.522 | 13.235 | 55.418 | 1.00 | 20.96 |
| ATOM | 2808 | OG1 | THR B 182 | 29.211 | 14.161 | 56.276 | 1.00 | 19.00 |

Figure 4CCC

| ATOM | 2809 | CG2 | THR | B | 182 | 27.798 | 13.969 | 54.301 | 1.00 | 23.44 |
|---|---|---|---|---|---|---|---|---|---|---|
| ATOM | 2810 | C | THR | B | 182 | 26.852 | 11.363 | 55.412 | 1.00 | 22.69 |
| ATOM | 2811 | O | THR | B | 182 | 25.696 | 11.487 | 55.037 | 1.00 | 22.40 |
| ATOM | 2812 | N | ARG | B | 183 | 27.562 | 10.262 | 55.186 | 1.00 | 26.27 |
| ATOM | 2813 | CA | ARG | B | 183 | 27.030 | 9.119 | 54.386 | 1.00 | 29.52 |
| ATOM | 2814 | CB | ARG | B | 183 | 28.121 | 8.077 | 54.186 | 1.00 | 31.20 |
| ATOM | 2815 | CG | ARG | B | 183 | 29.339 | 8.625 | 53.496 | 1.00 | 35.42 |
| ATOM | 2816 | CD | ARG | B | 183 | 30.325 | 7.532 | 53.188 | 1.00 | 42.02 |
| ATOM | 2817 | NE | ARG | B | 183 | 31.455 | 8.110 | 52.474 | 1.00 | 58.05 |
| ATOM | 2818 | CZ | ARG | B | 183 | 32.732 | 7.851 | 52.742 | 1.00 | 64.94 |
| ATOM | 2819 | NH1 | ARG | B | 183 | 33.687 | 8.450 | 52.030 | 1.00 | 66.47 |
| ATOM | 2820 | NH2 | ARG | B | 183 | 33.062 | 6.988 | 53.704 | 1.00 | 69.62 |
| ATOM | 2821 | C | ARG | B | 183 | 25.816 | 8.475 | 55.042 | 1.00 | 30.12 |
| ATOM | 2822 | O | ARG | B | 183 | 24.761 | 8.273 | 54.442 | 1.00 | 32.43 |
| ATOM | 2823 | N | GLU | B | 184 | 25.979 | 8.161 | 56.318 | 1.00 | 34.51 |
| ATOM | 2824 | CA | GLU | B | 184 | 24.897 | 7.522 | 57.088 | 1.00 | 36.84 |
| ATOM | 2825 | CB | GLU | B | 184 | 25.424 | 7.018 | 58.432 | 1.00 | 43.30 |
| ATOM | 2826 | CG | GLU | B | 184 | 24.648 | 5.819 | 58.974 | 1.00 | 51.76 |
| ATOM | 2827 | CD | GLU | B | 184 | 24.342 | 4.792 | 57.889 | 1.00 | 56.21 |
| ATOM | 2828 | OE1 | GLU | B | 184 | 25.268 | 4.048 | 57.473 | 1.00 | 56.43 |
| ATOM | 2829 | OE2 | GLU | B | 184 | 23.173 | 4.755 | 57.435 | 1.00 | 56.35 |
| ATOM | 2830 | C | GLU | B | 184 | 23.708 | 8.450 | 57.281 | 1.00 | 33.32 |
| ATOM | 2831 | O | GLU | B | 184 | 22.564 | 8.022 | 57.371 | 1.00 | 36.41 |
| ATOM | 2832 | N | GLY | B | 185 | 23.996 | 9.743 | 57.321 | 1.00 | 31.11 |
| ATOM | 2833 | CA | GLY | B | 185 | 22.950 | 10.729 | 57.490 | 1.00 | 31.01 |
| ATOM | 2834 | C | GLY | B | 185 | 22.205 | 11.002 | 56.200 | 1.00 | 33.72 |
| ATOM | 2835 | O | GLY | B | 185 | 20.963 | 11.023 | 56.177 | 1.00 | 36.44 |
| ATOM | 2836 | N | VAL | B | 186 | 22.957 | 11.151 | 55.109 | 1.00 | 33.46 |
| ATOM | 2837 | CA | VAL | B | 186 | 22.371 | 11.451 | 53.775 | 1.00 | 29.64 |
| ATOM | 2838 | CB | VAL | B | 186 | 23.440 | 11.923 | 52.765 | 1.00 | 26.92 |
| ATOM | 2839 | CG1 | VAL | B | 186 | 24.057 | 10.742 | 52.022 | 1.00 | 27.97 |
| ATOM | 2840 | CG2 | VAL | B | 186 | 22.842 | 12.923 | 51.838 | 1.00 | 20.39 |
| ATOM | 2841 | C | VAL | B | 186 | 21.570 | 10.275 | 53.216 | 1.00 | 29.46 |
| ATOM | 2842 | O | VAL | B | 186 | 20.660 | 10.441 | 52.416 | 1.00 | 34.31 |
| ATOM | 2843 | N | ARG | B | 187 | 21.923 | 9.070 | 53.642 | 1.00 | 30.13 |
| ATOM | 2844 | CA | ARG | B | 187 | 21.173 | 7.861 | 53.209 | 1.00 | 32.23 |
| ATOM | 2845 | CB | ARG | B | 187 | 21.953 | 6.591 | 53.527 | 1.00 | 32.62 |
| ATOM | 2846 | CG | ARG | B | 187 | 23.146 | 6.326 | 52.666 | 1.00 | 32.11 |
| ATOM | 2847 | CD | ARG | B | 187 | 23.584 | 4.890 | 52.872 | 1.00 | 34.27 |
| ATOM | 2848 | NE | ARG | B | 187 | 24.719 | 4.562 | 52.020 | 1.00 | 41.30 |
| ATOM | 2849 | CZ | ARG | B | 187 | 25.989 | 4.673 | 52.393 | 1.00 | 43.96 |
| ATOM | 2850 | NH1 | ARG | B | 187 | 26.955 | 4.363 | 51.531 | 1.00 | 48.28 |
| ATOM | 2851 | NH2 | ARG | B | 187 | 26.291 | 5.066 | 53.630 | 1.00 | 45.23 |
| ATOM | 2852 | C | ARG | B | 187 | 19.822 | 7.809 | 53.946 | 1.00 | 33.88 |
| ATOM | 2853 | O | ARG | B | 187 | 18.748 | 7.577 | 53.376 | 1.00 | 37.83 |
| ATOM | 2854 | N | ARG | B | 188 | 19.905 | 8.032 | 55.251 | 1.00 | 32.30 |
| ATOM | 2855 | CA | ARG | B | 188 | 18.718 | 7.988 | 56.126 | 1.00 | 35.39 |
| ATOM | 2856 | CB | ARG | B | 188 | 19.171 | 8.199 | 57.568 | 1.00 | 40.56 |
| ATOM | 2857 | CG | ARG | B | 188 | 18.186 | 7.720 | 58.609 | 1.00 | 48.63 |
| ATOM | 2858 | CD | ARG | B | 188 | 17.974 | 8.792 | 59.679 | 1.00 | 56.09 |
| ATOM | 2859 | NE | ARG | B | 188 | 19.232 | 9.377 | 60.152 | 1.00 | 59.40 |
| ATOM | 2860 | CZ | ARG | B | 188 | 19.466 | 10.687 | 60.237 | 1.00 | 62.01 |

Figure 4DDD

| ATOM | 2861 | NH1 | ARG | B | 188 | 20.641 | 11.115 | 60.677 | 1.00 | 62.48 |
|---|---|---|---|---|---|---|---|---|---|---|
| ATOM | 2862 | NH2 | ARG | B | 188 | 18.538 | 11.572 | 59.877 | 1.00 | 63.45 |
| ATOM | 2863 | C | ARG | B | 188 | 17.617 | 8.996 | 55.720 | 1.00 | 33.02 |
| ATOM | 2864 | O | ARG | B | 188 | 16.448 | 8.644 | 55.535 | 1.00 | 36.28 |
| ATOM | 2865 | N | GLU | B | 189 | 17.995 | 10.265 | 55.593 | 1.00 | 28.51 |
| ATOM | 2866 | CA | GLU | B | 189 | 17.003 | 11.300 | 55.189 | 1.00 | 27.26 |
| ATOM | 2867 | CB | GLU | B | 189 | 17.596 | 12.699 | 55.307 | 1.00 | 24.81 |
| ATOM | 2868 | CG | GLU | B | 189 | 18.099 | 13.014 | 56.696 | 1.00 | 37.35 |
| ATOM | 2869 | CD | GLU | B | 189 | 18.840 | 14.337 | 56.780 | 1.00 | 42.32 |
| ATOM | 2870 | OE1 | GLU | B | 189 | 19.800 | 14.436 | 57.588 | 1.00 | 46.04 |
| ATOM | 2871 | OE2 | GLU | B | 189 | 18.458 | 15.278 | 56.044 | 1.00 | 48.19 |
| ATOM | 2872 | C | GLU | B | 189 | 16.480 | 11.055 | 53.759 | 1.00 | 24.99 |
| ATOM | 2873 | O | GLU | B | 189 | 15.305 | 11.192 | 53.475 | 1.00 | 25.77 |
| ATOM | 2874 | N | ALA | B | 190 | 17.368 | 10.653 | 52.861 | 1.00 | 26.56 |
| ATOM | 2875 | CA | ALA | B | 190 | 16.978 | 10.402 | 51.457 | 1.00 | 26.33 |
| ATOM | 2876 | CB | ALA | B | 190 | 18.162 | 9.964 | 50.668 | 1.00 | 24.46 |
| ATOM | 2877 | C | ALA | B | 190 | 15.845 | 9.374 | 51.345 | 1.00 | 31.10 |
| ATOM | 2878 | O | ALA | B | 190 | 14.824 | 9.611 | 50.682 | 1.00 | 32.33 |
| ATOM | 2879 | N | ALA | B | 191 | 16.017 | 8.241 | 52.031 | 1.00 | 31.63 |
| ATOM | 2880 | CA | ALA | B | 191 | 14.990 | 7.150 | 52.034 | 1.00 | 32.05 |
| ATOM | 2881 | CB | ALA | B | 191 | 15.412 | 6.030 | 52.979 | 1.00 | 31.11 |
| ATOM | 2882 | C | ALA | B | 191 | 13.607 | 7.705 | 52.465 | 1.00 | 33.82 |
| ATOM | 2883 | O | ALA | B | 191 | 12.553 | 7.457 | 51.861 | 1.00 | 32.73 |
| ATOM | 2884 | N | GLU | B | 192 | 13.632 | 8.461 | 53.555 | 1.00 | 35.01 |
| ATOM | 2885 | CA | GLU | B | 192 | 12.398 | 9.081 | 54.086 | 1.00 | 36.08 |
| ATOM | 2886 | CB | GLU | B | 192 | 12.710 | 9.791 | 55.413 | 1.00 | 38.15 |
| ATOM | 2887 | CG | GLU | B | 192 | 13.329 | 8.870 | 56.477 | 1.00 | 46.52 |
| ATOM | 2888 | CD | GLU | B | 192 | 13.459 | 9.510 | 57.852 | 1.00 | 53.18 |
| ATOM | 2889 | OE1 | GLU | B | 192 | 13.162 | 10.726 | 58.015 | 1.00 | 56.34 |
| ATOM | 2890 | OE2 | GLU | B | 192 | 13.870 | 8.784 | 58.803 | 1.00 | 53.41 |
| ATOM | 2891 | C | GLU | B | 192 | 11.821 | 10.056 | 53.031 | 1.00 | 35.97 |
| ATOM | 2892 | O | GLU | B | 192 | 10.727 | 9.873 | 52.493 | 1.00 | 36.66 |
| ATOM | 2893 | N | ALA | B | 193 | 12.626 | 11.063 | 52.699 | 1.00 | 35.17 |
| ATOM | 2894 | CA | ALA | B | 193 | 12.263 | 12.112 | 51.712 | 1.00 | 33.28 |
| ATOM | 2895 | CB | ALA | B | 193 | 13.493 | 12.939 | 51.337 | 1.00 | 33.84 |
| ATOM | 2896 | C | ALA | B | 193 | 11.650 | 11.497 | 50.458 | 1.00 | 33.19 |
| ATOM | 2897 | O | ALA | B | 193 | 10.654 | 11.973 | 49.919 | 1.00 | 32.52 |
| ATOM | 2898 | N | GLU | B | 194 | 12.250 | 10.413 | 49.992 | 1.00 | 33.67 |
| ATOM | 2899 | CA | GLU | B | 194 | 11.716 | 9.747 | 48.785 | 1.00 | 38.31 |
| ATOM | 2900 | CB | GLU | B | 194 | 12.557 | 8.555 | 48.390 | 1.00 | 39.02 |
| ATOM | 2901 | CG | GLU | B | 194 | 13.656 | 8.905 | 47.458 | 1.00 | 40.74 |
| ATOM | 2902 | CD | GLU | B | 194 | 14.380 | 7.685 | 47.010 | 1.00 | 42.51 |
| ATOM | 2903 | OE1 | GLU | B | 194 | 15.358 | 7.298 | 47.698 | 1.00 | 49.63 |
| ATOM | 2904 | OE2 | GLU | B | 194 | 13.952 | 7.102 | 45.987 | 1.00 | 42.55 |
| ATOM | 2905 | C | GLU | B | 194 | 10.280 | 9.306 | 48.966 | 1.00 | 40.47 |
| ATOM | 2906 | O | GLU | B | 194 | 9.454 | 9.461 | 48.081 | 1.00 | 41.16 |
| ATOM | 2907 | N | LEU | B | 195 | 9.998 | 8.732 | 50.133 | 1.00 | 43.06 |
| ATOM | 2908 | CA | LEU | B | 195 | 8.634 | 8.257 | 50.457 | 1.00 | 43.16 |
| ATOM | 2909 | CB | LEU | B | 195 | 8.564 | 7.832 | 51.915 | 1.00 | 45.19 |
| ATOM | 2910 | CG | LEU | B | 195 | 9.332 | 6.543 | 52.171 | 1.00 | 46.09 |
| ATOM | 2911 | CD1 | LEU | B | 195 | 9.084 | 6.113 | 53.627 | 1.00 | 47.82 |
| ATOM | 2912 | CD2 | LEU | B | 195 | 8.858 | 5.471 | 51.175 | 1.00 | 45.78 |

Figure 4EEE

| | | | | | | | | | |
|---|---|---|---|---|---|---|---|---|---|
| ATOM | 2913 | C | LEU | B | 195 | 7.547 | 9.292 | 50.136 | 1.00 42.89 |
| ATOM | 2914 | O | LEU | B | 195 | 6.491 | 8.973 | 49.597 | 1.00 43.65 |
| ATOM | 2915 | N | ALA | B | 196 | 7.810 | 10.545 | 50.480 | 1.00 42.64 |
| ATOM | 2916 | CA | ALA | B | 196 | 6.841 | 11.620 | 50.178 | 1.00 45.75 |
| ATOM | 2917 | CB | ALA | B | 196 | 7.308 | 12.939 | 50.765 | 1.00 46.26 |
| ATOM | 2918 | C | ALA | B | 196 | 6.689 | 11.738 | 48.639 | 1.00 47.35 |
| ATOM | 2919 | O | ALA | B | 196 | 5.726 | 11.266 | 48.031 | 1.00 49.97 |
| ATOM | 2920 | N | LEU | B | 197 | 7.694 | 12.321 | 47.995 | 1.00 49.59 |
| ATOM | 2921 | CA | LEU | B | 197 | 7.652 | 12.488 | 46.507 | 1.00 49.86 |
| ATOM | 2922 | CB | LEU | B | 197 | 8.671 | 13.551 | 46.049 | 1.00 41.45 |
| ATOM | 2923 | CG | LEU | B | 197 | 10.184 | 13.367 | 46.069 | 1.00 36.93 |
| ATOM | 2924 | CD1 | LEU | B | 197 | 10.576 | 12.472 | 47.170 | 1.00 39.69 |
| ATOM | 2925 | CD2 | LEU | B | 197 | 10.671 | 12.783 | 44.772 | 1.00 42.85 |
| ATOM | 2926 | C | LEU | B | 197 | 7.842 | 11.151 | 45.762 | 1.00 51.45 |
| ATOM | 2927 | O | LEU | B | 197 | 8.374 | 11.073 | 44.650 | 1.00 51.60 |
| ATOM | 2928 | N | ALA | B | 198 | 7.380 | 10.087 | 46.410 | 1.00 54.22 |
| ATOM | 2929 | CA | ALA | B | 198 | 7.471 | 8.730 | 45.848 | 1.00 54.54 |
| ATOM | 2930 | CB | ALA | B | 198 | 7.104 | 7.677 | 46.896 | 1.00 59.15 |
| ATOM | 2931 | C | ALA | B | 198 | 6.512 | 8.652 | 44.683 | 1.00 52.43 |
| ATOM | 2932 | O | ALA | B | 198 | 5.288 | 8.850 | 44.799 | 1.00 50.03 |
| ATOM | 2933 | N | GLY | B | 199 | 7.115 | 8.387 | 43.530 | 1.00 48.06 |
| ATOM | 2934 | CA | GLY | B | 199 | 6.353 | 8.274 | 42.316 | 1.00 41.89 |
| ATOM | 2935 | C | GLY | B | 199 | 6.316 | 9.580 | 41.562 | 1.00 37.38 |
| ATOM | 2936 | O | GLY | B | 199 | 6.005 | 9.562 | 40.377 | 1.00 45.85 |
| ATOM | 2937 | N | ARG | B | 200 | 6.642 | 10.704 | 42.193 | 1.00 29.22 |
| ATOM | 2938 | CA | ARG | B | 200 | 6.570 | 11.970 | 41.450 | 1.00 21.98 |
| ATOM | 2939 | CB | ARG | B | 200 | 6.799 | 13.184 | 42.337 | 1.00 20.19 |
| ATOM | 2940 | CG | ARG | B | 200 | 5.767 | 14.246 | 42.102 | 1.00 15.60 |
| ATOM | 2941 | CD | ARG | B | 200 | 6.333 | 15.483 | 41.458 | 1.00 11.83 |
| ATOM | 2942 | NE | ARG | B | 200 | 6.486 | 16.523 | 42.466 | 1.00 12.71 |
| ATOM | 2943 | CZ | ARG | B | 200 | 6.444 | 17.824 | 42.217 | 1.00 10.13 |
| ATOM | 2944 | NH1 | ARG | B | 200 | 6.597 | 18.693 | 43.204 | 1.00 14.91 |
| ATOM | 2945 | NH2 | ARG | B | 200 | 6.250 | 18.261 | 40.991 | 1.00 7.08 |
| ATOM | 2946 | C | ARG | B | 200 | 7.535 | 11.962 | 40.236 | 1.00 21.16 |
| ATOM | 2947 | O | ARG | B | 200 | 8.650 | 11.439 | 40.371 | 1.00 22.67 |
| ATOM | 2948 | N | THR | B | 201 | 7.029 | 12.503 | 39.192 | 1.00 19.44 |
| ATOM | 2949 | CA | THR | B | 201 | 7.747 | 12.626 | 37.911 | 1.00 13.79 |
| ATOM | 2950 | CB | THR | B | 201 | 7.166 | 11.682 | 36.859 | 1.00 12.91 |
| ATOM | 2951 | OG1 | THR | B | 201 | 7.496 | 10.345 | 37.219 | 1.00 17.68 |
| ATOM | 2952 | CG2 | THR | B | 201 | 7.746 | 11.940 | 35.492 | 1.00 15.91 |
| ATOM | 2953 | C | THR | B | 201 | 7.457 | 14.034 | 37.492 | 1.00 13.45 |
| ATOM | 2954 | O | THR | B | 201 | 6.321 | 14.505 | 37.561 | 1.00 20.19 |
| ATOM | 2955 | N | TRP | B | 202 | 8.516 | 14.747 | 37.137 | 1.00 11.08 |
| ATOM | 2956 | CA | TRP | B | 202 | 8.389 | 16.136 | 36.713 | 1.00 8.56 |
| ATOM | 2957 | CB | TRP | B | 202 | 9.642 | 16.890 | 37.118 | 1.00 3.97 |
| ATOM | 2958 | CG | TRP | B | 202 | 9.663 | 17.164 | 38.589 | 1.00 2.00 |
| ATOM | 2959 | CD2 | TRP | B | 202 | 9.944 | 16.230 | 39.636 | 1.00 2.00 |
| ATOM | 2960 | CE2 | TRP | B | 202 | 9.879 | 16.933 | 40.849 | 1.00 2.00 |
| ATOM | 2961 | CE3 | TRP | B | 202 | 10.259 | 14.863 | 39.667 | 1.00 3.43 |
| ATOM | 2962 | CD1 | TRP | B | 202 | 9.439 | 18.365 | 39.194 | 1.00 2.00 |
| ATOM | 2963 | NE1 | TRP | B | 202 | 9.569 | 18.235 | 40.549 | 1.00 2.46 |
| ATOM | 2964 | CZ2 | TRP | B | 202 | 10.122 | 16.325 | 42.084 | 1.00 4.01 |

Figure 4FFF

| ATOM | 2965 | CZ3 | TRP | B | 202 | 10.507 | 14.249 | 40.902 | 1.00 | 2.00 |
|------|------|-----|-----|---|-----|--------|--------|--------|------|-------|
| ATOM | 2966 | CH2 | TRP | B | 202 | 10.435 | 14.985 | 42.090 | 1.00 | 4.43 |
| ATOM | 2967 | C   | TRP | B | 202 | 8.157  | 16.158 | 35.231 | 1.00 | 10.04 |
| ATOM | 2968 | O   | TRP | B | 202 | 8.578  | 15.259 | 34.514 | 1.00 | 17.59 |
| ATOM | 2969 | N   | ALA | B | 203 | 7.442  | 17.166 | 34.751 | 1.00 | 9.79 |
| ATOM | 2970 | CA  | ALA | B | 203 | 7.180  | 17.259 | 33.291 | 1.00 | 10.58 |
| ATOM | 2971 | CB  | ALA | B | 203 | 5.858  | 16.608 | 32.949 | 1.00 | 4.38 |
| ATOM | 2972 | C   | ALA | B | 203 | 7.152  | 18.723 | 32.897 | 1.00 | 12.21 |
| ATOM | 2973 | O   | ALA | B | 203 | 6.088  | 19.287 | 32.658 | 1.00 | 11.26 |
| ATOM | 2974 | N   | PRO | B | 204 | 8.342  | 19.367 | 32.826 | 1.00 | 14.59 |
| ATOM | 2975 | CD  | PRO | B | 204 | 9.688  | 18.823 | 33.120 | 1.00 | 13.48 |
| ATOM | 2976 | CA  | PRO | B | 204 | 8.420  | 20.786 | 32.461 | 1.00 | 12.52 |
| ATOM | 2977 | CB  | PRO | B | 204 | 9.909  | 21.109 | 32.631 | 1.00 | 9.22 |
| ATOM | 2978 | CG  | PRO | B | 204 | 10.600 | 19.790 | 32.411 | 1.00 | 8.43 |
| ATOM | 2979 | C   | PRO | B | 204 | 7.912  | 21.127 | 31.059 | 1.00 | 12.04 |
| ATOM | 2980 | O   | PRO | B | 204 | 7.394  | 22.208 | 30.816 | 1.00 | 14.10 |
| ATOM | 2981 | N   | GLY | B | 205 | 8.021  | 20.162 | 30.148 | 1.00 | 13.67 |
| ATOM | 2982 | CA  | GLY | B | 205 | 7.615  | 20.364 | 28.759 | 1.00 | 12.39 |
| ATOM | 2983 | C   | GLY | B | 205 | 8.844  | 20.287 | 27.861 | 1.00 | 13.93 |
| ATOM | 2984 | O   | GLY | B | 205 | 9.758  | 21.118 | 27.946 | 1.00 | 16.91 |
| ATOM | 2985 | N   | VAL | B | 206 | 8.857  | 19.329 | 26.951 | 1.00 | 14.06 |
| ATOM | 2986 | CA  | VAL | B | 206 | 10.023 | 19.142 | 26.085 | 1.00 | 16.16 |
| ATOM | 2987 | CB  | VAL | B | 206 | 9.819  | 17.974 | 25.082 | 1.00 | 18.67 |
| ATOM | 2988 | CG1 | VAL | B | 206 | 9.438  | 16.690 | 25.810 | 1.00 | 16.49 |
| ATOM | 2989 | CG2 | VAL | B | 206 | 8.776  | 18.327 | 24.083 | 1.00 | 25.86 |
| ATOM | 2990 | C   | VAL | B | 206 | 10.553 | 20.408 | 25.373 | 1.00 | 17.11 |
| ATOM | 2991 | O   | VAL | B | 206 | 11.756 | 20.577 | 25.185 | 1.00 | 21.06 |
| ATOM | 2992 | N   | GLU | B | 207 | 9.672  | 21.320 | 24.987 | 1.00 | 16.09 |
| ATOM | 2993 | CA  | GLU | B | 207 | 10.183 | 22.530 | 24.109 | 1.00 | 15.16 |
| ATOM | 2994 | CB  | GLU | B | 207 | 9.098  | 23.249 | 23.522 | 1.00 | 19.15 |
| ATOM | 2995 | CG  | GLU | B | 207 | 8.664  | 22.478 | 22.248 | 1.00 | 33.99 |
| ATOM | 2996 | CD  | GLU | B | 207 | 9.827  | 21.763 | 21.456 | 1.00 | 39.72 |
| ATOM | 2997 | OE1 | GLU | B | 207 | 11.010 | 22.219 | 21.462 | 1.00 | 38.31 |
| ATOM | 2998 | OE2 | GLU | B | 207 | 9.532  | 20.719 | 20.815 | 1.00 | 39.55 |
| ATOM | 2999 | C   | GLU | B | 207 | 10.874 | 23.446 | 25.282 | 1.00 | 15.92 |
| ATOM | 3000 | O   | GLU | B | 207 | 11.901 | 24.041 | 24.979 | 1.00 | 20.22 |
| ATOM | 3001 | N   | ALA | B | 208 | 10.328 | 23.520 | 26.493 | 1.00 | 12.61 |
| ATOM | 3002 | CA  | ALA | B | 208 | 10.930 | 24.347 | 27.559 | 1.00 | 10.29 |
| ATOM | 3003 | CB  | ALA | B | 208 | 10.117 | 24.238 | 28.796 | 1.00 | 6.64 |
| ATOM | 3004 | C   | ALA | B | 208 | 12.345 | 23.787 | 27.819 | 1.00 | 10.41 |
| ATOM | 3005 | O   | ALA | B | 208 | 13.343 | 24.498 | 27.911 | 1.00 | 11.42 |
| ATOM | 3006 | N   | LEU | B | 209 | 12.399 | 22.465 | 27.833 | 1.00 | 7.66 |
| ATOM | 3007 | CA  | LEU | B | 209 | 13.646 | 21.737 | 28.107 | 1.00 | 7.68 |
| ATOM | 3008 | CB  | LEU | B | 209 | 13.346 | 20.245 | 28.262 | 1.00 | 6.10 |
| ATOM | 3009 | CG  | LEU | B | 209 | 13.021 | 19.886 | 29.711 | 1.00 | 4.44 |
| ATOM | 3010 | CD1 | LEU | B | 209 | 12.557 | 18.493 | 29.829 | 1.00 | 8.65 |
| ATOM | 3011 | CD2 | LEU | B | 209 | 14.260 | 20.097 | 30.553 | 1.00 | 7.74 |
| ATOM | 3012 | C   | LEU | B | 209 | 14.591 | 21.990 | 26.947 | 1.00 | 6.98 |
| ATOM | 3013 | O   | LEU | B | 209 | 15.722 | 22.405 | 27.094 | 1.00 | 13.90 |
| ATOM | 3014 | N   | THR | B | 210 | 14.072 | 21.812 | 25.754 | 1.00 | 8.48 |
| ATOM | 3015 | CA  | THR | B | 210 | 14.864 | 22.006 | 24.572 | 1.00 | 6.92 |
| ATOM | 3016 | CB  | THR | B | 210 | 14.061 | 21.619 | 23.373 | 1.00 | 7.75 |

Figure 4GGG

| ATOM | 3017 | OG1 | THR | B | 210 | 13.822 | 20.205 | 23.429 | 1.00 | 12.79 |
|---|---|---|---|---|---|---|---|---|---|---|
| ATOM | 3018 | CG2 | THR | B | 210 | 14.816 | 21.909 | 22.119 | 1.00 | 12.68 |
| ATOM | 3019 | C | THR | B | 210 | 15.420 | 23.432 | 24.473 | 1.00 | 10.25 |
| ATOM | 3020 | O | THR | B | 210 | 16.585 | 23.651 | 24.189 | 1.00 | 11.37 |
| ATOM | 3021 | N | HIS | B | 211 | 14.602 | 24.415 | 24.805 | 1.00 | 14.19 |
| ATOM | 3022 | CA | HIS | B | 211 | 15.066 | 25.811 | 24.738 | 1.00 | 15.90 |
| ATOM | 3023 | CB | HIS | B | 211 | 13.892 | 26.778 | 24.729 | 1.00 | 25.74 |
| ATOM | 3024 | CG | HIS | B | 211 | 13.138 | 26.799 | 23.433 | 1.00 | 29.51 |
| ATOM | 3025 | CD2 | HIS | B | 211 | 12.182 | 25.975 | 22.943 | 1.00 | 30.79 |
| ATOM | 3026 | ND1 | HIS | B | 211 | 13.356 | 27.751 | 22.461 | 1.00 | 36.28 |
| ATOM | 3027 | CE1 | HIS | B | 211 | 12.569 | 27.515 | 21.425 | 1.00 | 35.36 |
| ATOM | 3028 | NE2 | HIS | B | 211 | 11.846 | 26.438 | 21.696 | 1.00 | 32.16 |
| ATOM | 3029 | C | HIS | B | 211 | 16.024 | 26.155 | 25.861 | 1.00 | 17.72 |
| ATOM | 3030 | O | HIS | B | 211 | 16.936 | 26.961 | 25.710 | 1.00 | 23.58 |
| ATOM | 3031 | N | THR | B | 212 | 15.809 | 25.551 | 27.017 | 1.00 | 14.16 |
| ATOM | 3032 | CA | THR | B | 212 | 16.695 | 25.813 | 28.151 | 1.00 | 9.70 |
| ATOM | 3033 | CB | THR | B | 212 | 16.078 | 25.261 | 29.446 | 1.00 | 6.36 |
| ATOM | 3034 | OG1 | THR | B | 212 | 14.850 | 25.950 | 29.685 | 1.00 | 14.95 |
| ATOM | 3035 | CG2 | THR | B | 212 | 16.966 | 25.492 | 30.620 | 1.00 | 2.59 |
| ATOM | 3036 | C | THR | B | 212 | 18.109 | 25.229 | 27.881 | 1.00 | 8.25 |
| ATOM | 3037 | O | THR | B | 212 | 19.124 | 25.903 | 27.990 | 1.00 | 11.25 |
| ATOM | 3038 | N | LEU | B | 213 | 18.160 | 23.996 | 27.424 | 1.00 | 2.00 |
| ATOM | 3039 | CA | LEU | B | 213 | 19.444 | 23.380 | 27.182 | 1.00 | 5.12 |
| ATOM | 3040 | CB | LEU | B | 213 | 19.208 | 21.886 | 26.953 | 1.00 | 7.48 |
| ATOM | 3041 | CG | LEU | B | 213 | 18.641 | 21.101 | 28.116 | 1.00 | 3.50 |
| ATOM | 3042 | CD1 | LEU | B | 213 | 18.444 | 19.656 | 27.796 | 1.00 | 2.00 |
| ATOM | 3043 | CD2 | LEU | B | 213 | 19.588 | 21.196 | 29.320 | 1.00 | 7.80 |
| ATOM | 3044 | C | LEU | B | 213 | 20.295 | 24.071 | 26.050 | 1.00 | 9.49 |
| ATOM | 3045 | O | LEU | B | 213 | 21.523 | 24.207 | 26.135 | 1.00 | 15.34 |
| ATOM | 3046 | N | LEU | B | 214 | 19.625 | 24.549 | 25.011 | 1.00 | 7.61 |
| ATOM | 3047 | CA | LEU | B | 214 | 20.329 | 25.240 | 23.919 | 1.00 | 6.52 |
| ATOM | 3048 | CB | LEU | B | 214 | 19.356 | 25.710 | 22.843 | 1.00 | 6.24 |
| ATOM | 3049 | CG | LEU | B | 214 | 19.844 | 26.048 | 21.408 | 1.00 | 14.41 |
| ATOM | 3050 | CD1 | LEU | B | 214 | 19.042 | 27.217 | 20.841 | 1.00 | 2.19 |
| ATOM | 3051 | CD2 | LEU | B | 214 | 21.324 | 26.373 | 21.311 | 1.00 | 6.72 |
| ATOM | 3052 | C | LEU | B | 214 | 20.969 | 26.460 | 24.572 | 1.00 | 6.49 |
| ATOM | 3053 | O | LEU | B | 214 | 22.113 | 26.807 | 24.343 | 1.00 | 9.44 |
| ATOM | 3054 | N | SER | B | 215 | 20.183 | 27.103 | 25.417 | 1.00 | 4.46 |
| ATOM | 3055 | CA | SER | B | 215 | 20.607 | 28.300 | 26.133 | 1.00 | 4.60 |
| ATOM | 3056 | CB | SER | B | 215 | 19.435 | 28.754 | 26.988 | 1.00 | 8.67 |
| ATOM | 3057 | OG | SER | B | 215 | 19.576 | 30.090 | 27.411 | 1.00 | 21.29 |
| ATOM | 3058 | C | SER | B | 215 | 21.873 | 28.006 | 26.971 | 1.00 | 5.38 |
| ATOM | 3059 | O | SER | B | 215 | 22.814 | 28.796 | 27.042 | 1.00 | 5.45 |
| ATOM | 3060 | N | THR | B | 216 | 21.886 | 26.841 | 27.599 | 1.00 | 5.40 |
| ATOM | 3061 | CA | THR | B | 216 | 23.004 | 26.425 | 28.419 | 1.00 | 3.99 |
| ATOM | 3062 | CB | THR | B | 216 | 22.749 | 25.037 | 28.987 | 1.00 | 3.17 |
| ATOM | 3063 | OG1 | THR | B | 216 | 21.762 | 25.144 | 30.010 | 1.00 | 9.54 |
| ATOM | 3064 | CG2 | THR | B | 216 | 24.041 | 24.422 | 29.551 | 1.00 | 8.72 |
| ATOM | 3065 | C | THR | B | 216 | 24.216 | 26.351 | 27.508 | 1.00 | 11.59 |
| ATOM | 3066 | O | THR | B | 216 | 25.346 | 26.678 | 27.876 | 1.00 | 16.65 |
| ATOM | 3067 | N | ALA | B | 217 | 23.959 | 25.926 | 26.285 | 1.00 | 5.14 |
| ATOM | 3068 | CA | ALA | B | 217 | 25.026 | 25.769 | 25.338 | 1.00 | 5.04 |

Figure 4HHH

| ATOM | 3069 | CB | ALA | B | 217 | 24.606 | 24.829 | 24.241 | 1.00 | 6.37 |
| --- | --- | --- | --- | --- | --- | --- | --- | --- | --- | --- |
| ATOM | 3070 | C | ALA | B | 217 | 25.493 | 27.087 | 24.767 | 1.00 | 7.04 |
| ATOM | 3071 | O | ALA | B | 217 | 26.696 | 27.355 | 24.692 | 1.00 | 16.59 |
| ATOM | 3072 | N | VAL | B | 218 | 24.546 | 27.944 | 24.401 | 1.00 | 3.51 |
| ATOM | 3073 | CA | VAL | B | 218 | 24.890 | 29.243 | 23.804 | 1.00 | 4.65 |
| ATOM | 3074 | CB | VAL | B | 218 | 23.670 | 29.923 | 23.183 | 1.00 | 2.00 |
| ATOM | 3075 | CG1 | VAL | B | 218 | 24.002 | 31.334 | 22.747 | 1.00 | 2.00 |
| ATOM | 3076 | CG2 | VAL | B | 218 | 23.229 | 29.145 | 21.992 | 1.00 | 2.00 |
| ATOM | 3077 | C | VAL | B | 218 | 25.594 | 30.198 | 24.753 | 1.00 | 12.31 |
| ATOM | 3078 | O | VAL | B | 218 | 26.563 | 30.877 | 24.412 | 1.00 | 20.14 |
| ATOM | 3079 | N | ASN | B | 219 | 25.131 | 30.231 | 26.004 | 1.00 | 15.35 |
| ATOM | 3080 | CA | ASN | B | 219 | 25.741 | 31.138 | 27.000 | 1.00 | 16.47 |
| ATOM | 3081 | CB | ASN | B | 219 | 24.752 | 31.342 | 28.135 | 1.00 | 19.66 |
| ATOM | 3082 | CG | ASN | B | 219 | 23.492 | 32.104 | 27.674 | 1.00 | 20.27 |
| ATOM | 3083 | OD1 | ASN | B | 219 | 23.576 | 33.243 | 27.216 | 1.00 | 25.47 |
| ATOM | 3084 | ND2 | ASN | B | 219 | 22.337 | 31.462 | 27.762 | 1.00 | 17.30 |
| ATOM | 3085 | C | ASN | B | 219 | 27.147 | 30.738 | 27.493 | 1.00 | 16.69 |
| ATOM | 3086 | O | ASN | B | 219 | 27.916 | 31.555 | 27.986 | 1.00 | 17.63 |
| ATOM | 3087 | N | ASN | B | 220 | 27.512 | 29.482 | 27.250 | 1.00 | 15.59 |
| ATOM | 3088 | CA | ASN | B | 220 | 28.830 | 28.977 | 27.657 | 1.00 | 14.92 |
| ATOM | 3089 | CB | ASN | B | 220 | 28.690 | 27.694 | 28.484 | 1.00 | 15.29 |
| ATOM | 3090 | CG | ASN | B | 220 | 28.099 | 27.947 | 29.866 | 1.00 | 22.56 |
| ATOM | 3091 | OD1 | ASN | B | 220 | 28.824 | 28.198 | 30.835 | 1.00 | 26.87 |
| ATOM | 3092 | ND2 | ASN | B | 220 | 26.771 | 27.881 | 29.964 | 1.00 | 24.43 |
| ATOM | 3093 | C | ASN | B | 220 | 29.739 | 28.722 | 26.452 | 1.00 | 18.94 |
| ATOM | 3094 | O | ASN | B | 220 | 30.792 | 28.088 | 26.572 | 1.00 | 22.85 |
| ATOM | 3095 | N | MET | B | 221 | 29.355 | 29.227 | 25.279 | 1.00 | 14.50 |
| ATOM | 3096 | CA | MET | B | 221 | 30.193 | 28.982 | 24.087 | 1.00 | 13.78 |
| ATOM | 3097 | CB | MET | B | 221 | 29.427 | 29.313 | 22.810 | 1.00 | 11.99 |
| ATOM | 3098 | CG | MET | B | 221 | 29.037 | 30.731 | 22.674 | 1.00 | 9.03 |
| ATOM | 3099 | SD | MET | B | 221 | 28.366 | 31.026 | 21.060 | 1.00 | 10.14 |
| ATOM | 3100 | CE | MET | B | 221 | 27.662 | 32.561 | 21.311 | 1.00 | 2.09 |
| ATOM | 3101 | C | MET | B | 221 | 31.576 | 29.678 | 24.118 | 1.00 | 17.08 |
| ATOM | 3102 | O | MET | B | 221 | 32.580 | 29.139 | 23.655 | 1.00 | 18.42 |
| ATOM | 3103 | N | MET | B | 222 | 31.628 | 30.840 | 24.765 | 1.00 | 20.70 |
| ATOM | 3104 | CA | MET | B | 222 | 32.886 | 31.624 | 24.876 | 1.00 | 22.27 |
| ATOM | 3105 | CB | MET | B | 222 | 32.527 | 33.097 | 25.032 | 1.00 | 19.96 |
| ATOM | 3106 | CG | MET | B | 222 | 31.477 | 33.582 | 24.027 | 1.00 | 24.93 |
| ATOM | 3107 | SD | MET | B | 222 | 32.024 | 34.076 | 22.357 | 1.00 | 29.51 |
| ATOM | 3108 | CE | MET | B | 222 | 32.973 | 32.716 | 21.853 | 1.00 | 25.54 |
| ATOM | 3109 | C | MET | B | 222 | 33.842 | 31.137 | 26.007 | 1.00 | 27.44 |
| ATOM | 3110 | O | MET | B | 222 | 34.908 | 31.704 | 26.280 | 1.00 | 31.13 |
| ATOM | 3111 | N | LEU | B | 223 | 33.456 | 30.038 | 26.641 | 1.00 | 27.43 |
| ATOM | 3112 | CA | LEU | B | 223 | 34.257 | 29.487 | 27.720 | 1.00 | 24.97 |
| ATOM | 3113 | CB | LEU | B | 223 | 33.440 | 28.513 | 28.566 | 1.00 | 26.13 |
| ATOM | 3114 | CG | LEU | B | 223 | 33.811 | 28.346 | 30.042 | 1.00 | 23.51 |
| ATOM | 3115 | CD1 | LEU | B | 223 | 33.609 | 29.678 | 30.724 | 1.00 | 28.75 |
| ATOM | 3116 | CD2 | LEU | B | 223 | 32.955 | 27.280 | 30.715 | 1.00 | 22.72 |
| ATOM | 3117 | C | LEU | B | 223 | 35.448 | 28.788 | 27.121 | 1.00 | 27.33 |
| ATOM | 3118 | O | LEU | B | 223 | 35.341 | 27.827 | 26.357 | 1.00 | 23.84 |
| ATOM | 3119 | N | ARG | B | 224 | 36.609 | 29.344 | 27.425 | 1.00 | 34.22 |
| ATOM | 3120 | CA | ARG | B | 224 | 37.845 | 28.738 | 26.976 | 1.00 | 40.95 |

Figure 4III

| ATOM | 3121 | CB | ARG | B | 224 | 38.983 | 29.746 | 27.045 | 1.00 | 46.49 |
| --- | --- | --- | --- | --- | --- | --- | --- | --- | --- | --- |
| ATOM | 3122 | CG | ARG | B | 224 | 39.074 | 30.637 | 25.822 | 1.00 | 53.01 |
| ATOM | 3123 | CD | ARG | B | 224 | 39.176 | 29.810 | 24.544 | 1.00 | 58.82 |
| ATOM | 3124 | NE | ARG | B | 224 | 40.036 | 30.419 | 23.526 | 1.00 | 69.78 |
| ATOM | 3125 | CZ | ARG | B | 224 | 39.894 | 31.654 | 23.033 | 1.00 | 76.79 |
| ATOM | 3126 | NH1 | ARG | B | 224 | 40.746 | 32.091 | 22.104 | 1.00 | 78.95 |
| ATOM | 3127 | NH2 | ARG | B | 224 | 38.916 | 32.461 | 23.461 | 1.00 | 79.33 |
| ATOM | 3128 | C | ARG | B | 224 | 38.118 | 27.461 | 27.819 | 1.00 | 42.37 |
| ATOM | 3129 | O | ARG | B | 224 | 38.254 | 27.433 | 29.059 | 1.00 | 38.17 |
| ATOM | 3130 | N | ASP | B | 225 | 38.057 | 26.371 | 27.073 | 1.00 | 47.50 |
| ATOM | 3131 | CA | ASP | B | 225 | 38.274 | 25.019 | 27.567 | 1.00 | 51.89 |
| ATOM | 3132 | CB | ASP | B | 225 | 39.711 | 24.843 | 28.082 | 1.00 | 62.81 |
| ATOM | 3133 | CG | ASP | B | 225 | 40.049 | 23.374 | 28.411 | 1.00 | 69.78 |
| ATOM | 3134 | OD1 | ASP | B | 225 | 40.534 | 22.610 | 27.532 | 1.00 | 74.02 |
| ATOM | 3135 | OD2 | ASP | B | 225 | 39.833 | 23.000 | 29.579 | 1.00 | 75.01 |
| ATOM | 3136 | C | ASP | B | 225 | 37.266 | 24.412 | 28.532 | 1.00 | 48.26 |
| ATOM | 3137 | O | ASP | B | 225 | 36.890 | 23.309 | 28.312 | 1.00 | 53.44 |
| ATOM | 3138 | N | ARG | B | 226 | 36.844 | 25.052 | 29.607 | 1.00 | 39.29 |
| ATOM | 3139 | CA | ARG | B | 226 | 35.833 | 24.398 | 30.518 | 1.00 | 32.22 |
| ATOM | 3140 | CB | ARG | B | 226 | 34.452 | 24.316 | 29.815 | 1.00 | 33.64 |
| ATOM | 3141 | CG | ARG | B | 226 | 33.913 | 22.906 | 29.587 | 1.00 | 37.13 |
| ATOM | 3142 | CD | ARG | B | 226 | 32.493 | 22.860 | 29.041 | 1.00 | 42.88 |
| ATOM | 3143 | NE | ARG | B | 226 | 32.013 | 21.472 | 29.006 | 1.00 | 47.99 |
| ATOM | 3144 | CZ | ARG | B | 226 | 31.133 | 20.957 | 29.862 | 1.00 | 47.44 |
| ATOM | 3145 | NH1 | ARG | B | 226 | 30.764 | 19.687 | 29.755 | 1.00 | 45.94 |
| ATOM | 3146 | NH2 | ARG | B | 226 | 30.608 | 21.715 | 30.817 | 1.00 | 49.68 |
| ATOM | 3147 | C | ARG | B | 226 | 36.216 | 23.024 | 31.181 | 1.00 | 27.95 |
| ATOM | 3148 | O | ARG | B | 226 | 36.083 | 22.863 | 32.390 | 1.00 | 30.12 |
| ATOM | 3149 | N | TRP | B | 227 | 36.677 | 22.039 | 30.408 | 1.00 | 22.65 |
| ATOM | 3150 | CA | TRP | B | 227 | 37.075 | 20.704 | 30.967 | 1.00 | 20.68 |
| ATOM | 3151 | CB | TRP | B | 227 | 37.407 | 19.742 | 29.838 | 1.00 | 22.64 |
| ATOM | 3152 | CG | TRP | B | 227 | 36.172 | 19.263 | 29.105 | 1.00 | 34.12 |
| ATOM | 3153 | CD2 | TRP | B | 227 | 35.111 | 18.443 | 29.636 | 1.00 | 37.55 |
| ATOM | 3154 | CE2 | TRP | B | 227 | 34.140 | 18.299 | 28.615 | 1.00 | 39.86 |
| ATOM | 3155 | CE3 | TRP | B | 227 | 34.888 | 17.816 | 30.874 | 1.00 | 38.79 |
| ATOM | 3156 | CD1 | TRP | B | 227 | 35.808 | 19.566 | 27.813 | 1.00 | 33.65 |
| ATOM | 3157 | NE1 | TRP | B | 227 | 34.591 | 18.992 | 27.518 | 1.00 | 38.20 |
| ATOM | 3158 | CZ2 | TRP | B | 227 | 32.964 | 17.560 | 28.796 | 1.00 | 37.32 |
| ATOM | 3159 | CZ3 | TRP | B | 227 | 33.716 | 17.075 | 31.050 | 1.00 | 40.79 |
| ATOM | 3160 | CH2 | TRP | B | 227 | 32.770 | 16.956 | 30.011 | 1.00 | 40.13 |
| ATOM | 3161 | C | TRP | B | 227 | 38.211 | 20.742 | 31.995 | 1.00 | 20.73 |
| ATOM | 3162 | O | TRP | B | 227 | 38.366 | 19.853 | 32.819 | 1.00 | 21.16 |
| ATOM | 3163 | N | SER | B | 228 | 39.025 | 21.787 | 31.913 | 1.00 | 20.31 |
| ATOM | 3164 | CA | SER | B | 228 | 40.142 | 22.013 | 32.854 | 1.00 | 18.99 |
| ATOM | 3165 | CB | SER | B | 228 | 40.950 | 23.234 | 32.453 | 1.00 | 22.66 |
| ATOM | 3166 | OG | SER | B | 228 | 42.107 | 22.866 | 31.738 | 1.00 | 28.00 |
| ATOM | 3167 | C | SER | B | 228 | 39.478 | 22.266 | 34.184 | 1.00 | 18.77 |
| ATOM | 3168 | O | SER | B | 228 | 39.691 | 21.548 | 35.154 | 1.00 | 18.92 |
| ATOM | 3169 | N | LEU | B | 229 | 38.637 | 23.304 | 34.198 | 1.00 | 16.88 |
| ATOM | 3170 | CA | LEU | B | 229 | 37.852 | 23.687 | 35.400 | 1.00 | 13.89 |
| ATOM | 3171 | CB | LEU | B | 229 | 36.824 | 24.756 | 35.072 | 1.00 | 14.91 |
| ATOM | 3172 | CG | LEU | B | 229 | 37.229 | 25.997 | 34.302 | 1.00 | 21.34 |

Figure 4JJJ

| ATOM | 3173 | CD1 | LEU | B | 229 | 36.120 | 27.021 | 34.437 | 1.00 | 25.98 |
| --- | --- | --- | --- | --- | --- | --- | --- | --- | --- | --- |
| ATOM | 3174 | CD2 | LEU | B | 229 | 38.512 | 26.562 | 34.875 | 1.00 | 29.24 |
| ATOM | 3175 | C | LEU | B | 229 | 37.111 | 22.441 | 35.927 | 1.00 | 14.13 |
| ATOM | 3176 | O | LEU | B | 229 | 37.150 | 22.121 | 37.110 | 1.00 | 13.46 |
| ATOM | 3177 | N | VAL | B | 230 | 36.442 | 21.718 | 35.031 | 1.00 | 9.92 |
| ATOM | 3178 | CA | VAL | B | 230 | 35.729 | 20.525 | 35.481 | 1.00 | 7.86 |
| ATOM | 3179 | CB | VAL | B | 230 | 34.940 | 19.839 | 34.335 | 1.00 | 11.57 |
| ATOM | 3180 | CG1 | VAL | B | 230 | 34.352 | 18.516 | 34.808 | 1.00 | 5.13 |
| ATOM | 3181 | CG2 | VAL | B | 230 | 33.790 | 20.772 | 33.848 | 1.00 | 6.65 |
| ATOM | 3182 | C | VAL | B | 230 | 36.728 | 19.579 | 36.171 | 1.00 | 12.20 |
| ATOM | 3183 | O | VAL | B | 230 | 36.501 | 19.140 | 37.290 | 1.00 | 14.24 |
| ATOM | 3184 | N | ALA | B | 231 | 37.903 | 19.388 | 35.569 | 1.00 | 15.27 |
| ATOM | 3185 | CA | ALA | B | 231 | 38.952 | 18.469 | 36.156 | 1.00 | 13.72 |
| ATOM | 3186 | CB | ALA | B | 231 | 40.104 | 18.308 | 35.205 | 1.00 | 9.89 |
| ATOM | 3187 | C | ALA | B | 231 | 39.470 | 18.991 | 37.514 | 1.00 | 16.18 |
| ATOM | 3188 | O | ALA | B | 231 | 39.624 | 18.273 | 38.520 | 1.00 | 15.14 |
| ATOM | 3189 | N | GLU | B | 232 | 39.696 | 20.291 | 37.553 | 1.00 | 13.86 |
| ATOM | 3190 | CA | GLU | B | 232 | 40.197 | 20.911 | 38.784 | 1.00 | 15.67 |
| ATOM | 3191 | CB | GLU | B | 232 | 40.500 | 22.380 | 38.549 | 1.00 | 19.66 |
| ATOM | 3192 | CG | GLU | B | 232 | 41.154 | 22.995 | 39.754 | 1.00 | 25.78 |
| ATOM | 3193 | CD | GLU | B | 232 | 41.277 | 24.485 | 39.680 | 1.00 | 28.08 |
| ATOM | 3194 | OE1 | GLU | B | 232 | 41.820 | 25.041 | 40.658 | 1.00 | 23.63 |
| ATOM | 3195 | OE2 | GLU | B | 232 | 40.831 | 25.091 | 38.675 | 1.00 | 31.14 |
| ATOM | 3196 | C | GLU | B | 232 | 39.213 | 20.779 | 39.947 | 1.00 | 16.23 |
| ATOM | 3197 | O | GLU | B | 232 | 39.541 | 20.350 | 41.062 | 1.00 | 16.02 |
| ATOM | 3198 | N | ARG | B | 233 | 37.969 | 21.149 | 39.651 | 1.00 | 16.55 |
| ATOM | 3199 | CA | ARG | B | 233 | 36.896 | 21.149 | 40.657 | 1.00 | 14.61 |
| ATOM | 3200 | CB | ARG | B | 233 | 35.764 | 22.059 | 40.171 | 1.00 | 13.34 |
| ATOM | 3201 | CG | ARG | B | 233 | 36.345 | 23.340 | 39.536 | 1.00 | 18.87 |
| ATOM | 3202 | CD | ARG | B | 233 | 35.810 | 24.645 | 40.059 | 1.00 | 18.26 |
| ATOM | 3203 | NE | ARG | B | 233 | 34.477 | 24.898 | 39.530 | 1.00 | 20.17 |
| ATOM | 3204 | CZ | ARG | B | 233 | 34.014 | 26.085 | 39.147 | 1.00 | 17.42 |
| ATOM | 3205 | NH1 | ARG | B | 233 | 32.774 | 26.170 | 38.700 | 1.00 | 24.17 |
| ATOM | 3206 | NH2 | ARG | B | 233 | 34.771 | 27.170 | 39.169 | 1.00 | 9.59 |
| ATOM | 3207 | C | ARG | B | 233 | 36.460 | 19.738 | 41.044 | 1.00 | 12.43 |
| ATOM | 3208 | O | ARG | B | 233 | 35.927 | 19.500 | 42.114 | 1.00 | 14.45 |
| ATOM | 3209 | N | ARG | B | 234 | 36.781 | 18.771 | 40.197 | 1.00 | 14.26 |
| ATOM | 3210 | CA | ARG | B | 234 | 36.459 | 17.364 | 40.512 | 1.00 | 14.00 |
| ATOM | 3211 | CB | ARG | B | 234 | 36.632 | 16.472 | 39.279 | 1.00 | 18.42 |
| ATOM | 3212 | CG | ARG | B | 234 | 36.450 | 14.996 | 39.588 | 1.00 | 28.86 |
| ATOM | 3213 | CD | ARG | B | 234 | 37.005 | 14.028 | 38.519 | 1.00 | 36.84 |
| ATOM | 3214 | NE | ARG | B | 234 | 36.946 | 12.647 | 39.026 | 1.00 | 48.13 |
| ATOM | 3215 | CZ | ARG | B | 234 | 36.742 | 11.543 | 38.297 | 1.00 | 50.91 |
| ATOM | 3216 | NH1 | ARG | B | 234 | 36.575 | 11.591 | 36.974 | 1.00 | 51.01 |
| ATOM | 3217 | NH2 | ARG | B | 234 | 36.639 | 10.371 | 38.930 | 1.00 | 50.86 |
| ATOM | 3218 | C | ARG | B | 234 | 37.459 | 16.962 | 41.615 | 1.00 | 16.26 |
| ATOM | 3219 | O | ARG | B | 234 | 37.148 | 16.256 | 42.579 | 1.00 | 16.51 |
| ATOM | 3220 | N | ARG | B | 235 | 38.688 | 17.446 | 41.456 | 1.00 | 16.61 |
| ATOM | 3221 | CA | ARG | B | 235 | 39.767 | 17.132 | 42.412 | 1.00 | 15.51 |
| ATOM | 3222 | CB | ARG | B | 235 | 41.110 | 17.596 | 41.847 | 1.00 | 18.01 |
| ATOM | 3223 | CG | ARG | B | 235 | 41.476 | 16.874 | 40.572 | 1.00 | 23.11 |
| ATOM | 3224 | CD | ARG | B | 235 | 42.908 | 17.130 | 40.183 | 1.00 | 24.44 |

Figure 4KKK

| ATOM | 3225 | NE | ARG B 235 | 43.176 | 18.548 | 39.996 | 1.00 | 27.92 |
|---|---|---|---|---|---|---|---|---|
| ATOM | 3226 | CZ | ARG B 235 | 43.327 | 19.115 | 38.806 | 1.00 | 30.65 |
| ATOM | 3227 | NH1 | ARG B 235 | 43.566 | 20.426 | 38.709 | 1.00 | 32.71 |
| ATOM | 3228 | NH2 | ARG B 235 | 43.237 | 18.367 | 37.714 | 1.00 | 30.30 |
| ATOM | 3229 | C | ARG B 235 | 39.455 | 17.766 | 43.761 | 1.00 | 13.89 |
| ATOM | 3230 | O | ARG B 235 | 39.495 | 17.128 | 44.818 | 1.00 | 12.23 |
| ATOM | 3231 | N | GLN B 236 | 39.108 | 19.046 | 43.700 | 1.00 | 12.23 |
| ATOM | 3232 | CA | GLN B 236 | 38.729 | 19.796 | 44.906 | 1.00 | 12.63 |
| ATOM | 3233 | CB | GLN B 236 | 38.224 | 21.183 | 44.512 | 1.00 | 9.38 |
| ATOM | 3234 | CG | GLN B 236 | 39.239 | 22.038 | 43.777 | 1.00 | 9.89 |
| ATOM | 3235 | CD | GLN B 236 | 38.610 | 23.300 | 43.205 | 1.00 | 17.93 |
| ATOM | 3236 | OE1 | GLN B 236 | 37.398 | 23.328 | 42.933 | 1.00 | 22.34 |
| ATOM | 3237 | NE2 | GLN B 236 | 39.415 | 24.355 | 43.024 | 1.00 | 14.90 |
| ATOM | 3238 | C | GLN B 236 | 37.640 | 19.013 | 45.706 | 1.00 | 15.34 |
| ATOM | 3239 | O | GLN B 236 | 37.746 | 18.830 | 46.907 | 1.00 | 19.99 |
| ATOM | 3240 | N | ALA B 237 | 36.606 | 18.529 | 45.008 | 1.00 | 16.40 |
| ATOM | 3241 | CA | ALA B 237 | 35.476 | 17.777 | 45.652 | 1.00 | 11.75 |
| ATOM | 3242 | CB | ALA B 237 | 34.334 | 17.576 | 44.675 | 1.00 | 10.37 |
| ATOM | 3243 | C | ALA B 237 | 35.893 | 16.440 | 46.200 | 1.00 | 14.32 |
| ATOM | 3244 | O | ALA B 237 | 35.192 | 15.810 | 46.994 | 1.00 | 16.97 |
| ATOM | 3245 | N | GLY B 238 | 37.041 | 15.972 | 45.725 | 1.00 | 15.04 |
| ATOM | 3246 | CA | GLY B 238 | 37.550 | 14.686 | 46.165 | 1.00 | 15.25 |
| ATOM | 3247 | C | GLY B 238 | 36.856 | 13.544 | 45.468 | 1.00 | 11.48 |
| ATOM | 3248 | O | GLY B 238 | 36.743 | 12.446 | 46.018 | 1.00 | 10.44 |
| ATOM | 3249 | N | ILE B 239 | 36.376 | 13.818 | 44.262 | 1.00 | 12.60 |
| ATOM | 3250 | CA | ILE B 239 | 35.681 | 12.791 | 43.455 | 1.00 | 20.05 |
| ATOM | 3251 | CB | ILE B 239 | 34.728 | 13.419 | 42.348 | 1.00 | 18.52 |
| ATOM | 3252 | CG2 | ILE B 239 | 34.030 | 12.323 | 41.541 | 1.00 | 15.35 |
| ATOM | 3253 | CG1 | ILE B 239 | 33.629 | 14.264 | 43.004 | 1.00 | 15.89 |
| ATOM | 3254 | CD1 | ILE B 239 | 32.833 | 15.116 | 42.060 | 1.00 | 14.48 |
| ATOM | 3255 | C | ILE B 239 | 36.765 | 11.933 | 42.789 | 1.00 | 22.58 |
| ATOM | 3256 | O | ILE B 239 | 37.733 | 12.422 | 42.182 | 1.00 | 24.58 |
| ATOM | 3257 | N | ALA B 240 | 36.618 | 10.629 | 42.972 | 1.00 | 25.46 |
| ATOM | 3258 | CA | ALA B 240 | 37.549 | 9.658 | 42.388 | 1.00 | 30.26 |
| ATOM | 3259 | CB | ALA B 240 | 38.709 | 9.371 | 43.348 | 1.00 | 28.80 |
| ATOM | 3260 | C | ALA B 240 | 36.745 | 8.387 | 42.113 | 1.00 | 34.31 |
| ATOM | 3261 | O | ALA B 240 | 35.791 | 8.054 | 42.807 | 1.00 | 37.19 |
| ATOM | 3262 | N | GLY B 241 | 37.092 | 7.707 | 41.031 | 1.00 | 39.62 |
| ATOM | 3263 | CA | GLY B 241 | 36.391 | 6.486 | 40.708 | 1.00 | 42.87 |
| ATOM | 3264 | C | GLY B 241 | 36.177 | 6.350 | 39.226 | 1.00 | 47.59 |
| ATOM | 3265 | O | GLY B 241 | 36.675 | 7.159 | 38.430 | 1.00 | 50.53 |
| ATOM | 3266 | N | HIS B 242 | 35.419 | 5.320 | 38.858 | 1.00 | 49.74 |
| ATOM | 3267 | CA | HIS B 242 | 35.116 | 5.023 | 37.432 | 1.00 | 50.10 |
| ATOM | 3268 | CB | HIS B 242 | 34.946 | 3.503 | 37.242 | 1.00 | 54.63 |
| ATOM | 3269 | CG | HIS B 242 | 35.399 | 2.997 | 35.903 | 1.00 | 58.41 |
| ATOM | 3270 | CD2 | HIS B 242 | 34.978 | 1.942 | 35.161 | 1.00 | 60.60 |
| ATOM | 3271 | ND1 | HIS B 242 | 36.398 | 3.606 | 35.166 | 1.00 | 59.16 |
| ATOM | 3272 | CE1 | HIS B 242 | 36.569 | 2.952 | 34.032 | 1.00 | 60.65 |
| ATOM | 3273 | NE2 | HIS B 242 | 35.719 | 1.939 | 34.003 | 1.00 | 61.38 |
| ATOM | 3274 | C | HIS B 242 | 33.841 | 5.805 | 37.067 | 1.00 | 48.10 |
| ATOM | 3275 | O | HIS B 242 | 32.748 | 5.257 | 36.827 | 1.00 | 47.23 |
| ATOM | 3276 | N | THR B 243 | 34.011 | 7.125 | 37.076 | 1.00 | 42.49 |

Figure 4LLL

| ATOM | 3277 | CA  | THR | B | 243 |         | 32.920 | 8.055  | 36.769  | 1.00 | 39.40 |
|------|------|-----|-----|---|-----|---------|--------|--------|---------|------|-------|
| ATOM | 3278 | CB  | THR | B | 243 |         | 33.208 | 9.434  | 37.428  | 1.00 | 38.53 |
| ATOM | 3279 | OG1 | THR | B | 243 |         | 34.370 | 10.023 | 36.825  | 1.00 | 40.09 |
| ATOM | 3280 | CG2 | THR | B | 243 |         | 33.458 | 9.269  | 38.932  | 1.00 | 32.41 |
| ATOM | 3281 | C   | THR | B | 243 |         | 32.703 | 8.201  | 35.220  | 1.00 | 38.08 |
| ATOM | 3282 | O   | THR | B | 243 |         | 33.596 | 7.930  | 34.405  | 1.00 | 41.50 |
| ATOM | 3283 | N   | TYR | B | 244 |         | 31.474 | 8.561  | 34.835  | 1.00 | 34.19 |
| ATOM | 3284 | CA  | TYR | B | 244 |         | 31.114 | 8.792  | 33.403  | 1.00 | 28.57 |
| ATOM | 3285 | CB  | TYR | B | 244 |         | 29.607 | 8.849  | 33.203  | 1.00 | 24.09 |
| ATOM | 3286 | CG  | TYR | B | 244 |         | 28.855 | 7.610  | 33.592  | 1.00 | 23.03 |
| ATOM | 3287 | CD1 | TYR | B | 244 |         | 28.553 | 6.623  | 32.645  | 1.00 | 22.91 |
| ATOM | 3288 | CE1 | TYR | B | 244 |         | 27.800 | 5.500  | 32.993  | 1.00 | 23.73 |
| ATOM | 3289 | CD2 | TYR | B | 244 |         | 28.397 | 7.446  | 34.895  | 1.00 | 23.90 |
| ATOM | 3290 | CE2 | TYR | B | 244 |         | 27.648 | 6.350  | 35.258  | 1.00 | 26.28 |
| ATOM | 3291 | CZ  | TYR | B | 244 |         | 27.340 | 5.381  | 34.314  | 1.00 | 28.03 |
| ATOM | 3292 | OH  | TYR | B | 244 |         | 26.506 | 4.354  | 34.713  | 1.00 | 29.78 |
| ATOM | 3293 | C   | TYR | B | 244 |         | 31.699 | 10.155 | 33.000  | 1.00 | 29.97 |
| ATOM | 3294 | O   | TYR | B | 244 |         | 31.805 | 10.506 | 31.824  | 1.00 | 31.34 |
| ATOM | 3295 | N   | LEU | B | 245 |         | 31.988 | 10.968 | 34.017  | 1.00 | 30.30 |
| ATOM | 3296 | CA  | LEU | B | 245 |         | 32.541 | 12.304 | 33.783  | 1.00 | 27.66 |
| ATOM | 3297 | CB  | LEU | B | 245 |         | 32.641 | 13.083 | 35.087  | 1.00 | 25.66 |
| ATOM | 3298 | CG  | LEU | B | 245 |         | 33.130 | 14.529 | 34.979  | 1.00 | 25.02 |
| ATOM | 3299 | CD1 | LEU | B | 245 |         | 32.264 | 15.339 | 34.026  | 1.00 | 19.31 |
| ATOM | 3300 | CD2 | LEU | B | 245 |         | 33.092 | 15.147 | 36.363  | 1.00 | 28.05 |
| ATOM | 3301 | C   | LEU | B | 245 |         | 33.892 | 12.117 | 33.118  | 1.00 | 28.22 |
| ATOM | 3302 | O   | LEU | B | 245 |         | 34.834 | 11.550 | 33.662  | 1.00 | 30.23 |
| ATOM | 3303 | N   | GLN | B | 246 |         | 33.915 | 12.536 | 31.861  | 1.00 | 31.69 |
| ATOM | 3304 | CA  | GLN | B | 246 |         | 35.091 | 12.457 | 30.995  | 1.00 | 34.87 |
| ATOM | 3305 | CB  | GLN | B | 246 |         | 34.621 | 12.506 | 29.542  | 1.00 | 39.92 |
| ATOM | 3306 | CG  | GLN | B | 246 |         | 35.053 | 11.300 | 28.699  | 1.00 | 48.51 |
| ATOM | 3307 | CD  | GLN | B | 246 |         | 34.428 | 9.952  | 29.137  | 1.00 | 52.57 |
| ATOM | 3308 | OE1 | GLN | B | 246 |         | 34.027 | 9.761  | 30.296  | 1.00 | 50.35 |
| ATOM | 3309 | NE2 | GLN | B | 246 |         | 34.369 | 9.006  | 28.199  | 1.00 | 53.23 |
| ATOM | 3310 | C   | GLN | B | 246 |         | 36.129 | 13.544 | 31.274  | 1.00 | 35.82 |
| ATOM | 3311 | O   | GLN | B | 246 |         | 36.701 | 14.126 | 30.353  | 1.00 | 36.69 |
| ATOM | 3312 | N   | ALA | B | 247 |         | 36.371 | 13.799 | 32.556  | 1.00 | 38.80 |
| ATOM | 3313 | CA  | ALA | B | 247 |         | 37.355 | 14.823 | 33.026  | 1.00 | 37.44 |
| ATOM | 3314 | CB  | ALA | B | 247 |         | 36.755 | 16.208 | 32.963  | 1.00 | 29.80 |
| ATOM | 3315 | C   | ALA | B | 247 |         | 37.753 | 14.489 | 34.484  | 1.00 | 40.26 |
| ATOM | 3316 | O   | ALA | B | 247 |         | 38.713 | 15.107 | 35.015  | 1.00 | 40.54 |
| ATOM | 3317 | OT  | ALA | B | 247 |         | 37.091 | 13.596 | 35.065  | 1.00 | 41.41 |
| ATOM | 3318 | OH2 | HOH |   | 301 |         | 18.449 | 35.278 | 8.129   | 1.00 | 19.95 |
| ATOM | 3319 | OH2 | HOH |   | 302 |         | 37.818 | 28.901 | 5.084   | 1.00 | 3.27  |
| ATOM | 3320 | OH2 | HOH |   | 303 | (WAT1)  | 34.674 | 20.373 | 6.663   | 1.00 | 2.00  |
| ATOM | 3321 | OH2 | HOH |   | 304 |         | 46.125 | 24.346 | -0.517  | 1.00 | 13.01 |
| ATOM | 3322 | OH2 | HOH |   | 305 |         | 41.359 | 16.832 | 8.198   | 1.00 | 18.56 |
| ATOM | 3323 | OH2 | HOH |   | 306 |         | 44.100 | 17.051 | -9.350  | 1.00 | 5.18  |
| ATOM | 3324 | OH2 | HOH |   | 307 |         | 42.313 | 21.456 | -12.650 | 1.00 | 11.94 |
| ATOM | 3325 | OH2 | HOH |   | 308 |         | 36.358 | 23.401 | 10.644  | 1.00 | 2.00  |
| ATOM | 3326 | OH2 | HOH |   | 309 |         | 40.912 | 41.317 | 1.744   | 1.00 | 2.00  |
| ATOM | 3327 | OH2 | HOH |   | 310 |         | 43.309 | 21.298 | 13.228  | 1.00 | 5.80  |
| ATOM | 3328 | OH2 | HOH |   | 311 |         | 32.775 | 26.065 | 47.247  | 1.00 | 14.47 |

Figure 4MMM

| | | | | | | | | |
|---|---|---|---|---|---|---|---|---|
| ATOM | 3329 | OH2 | HOH | 312 | 11.888 | 31.064 | 34.277 | 1.00 25.86 |
| ATOM | 3330 | OH2 | HOH | 313 | 17.048 | 17.129 | 18.493 | 1.00 37.94 |
| ATOM | 3331 | OH2 | HOH | 314 | 24.428 | 32.396 | 46.383 | 1.00 58.79 |
| ATOM | 3332 | OH2 | HOH | 315 | 31.373 | 23.719 | 38.933 | 1.00 2.00 |
| ATOM | 3333 | OH2 | HOH | 316 | 41.066 | 20.833 | 3.872 | 1.00 13.01 |
| ATOM | 3334 | OH2 | HOH | 317 | 46.600 | 26.549 | 2.017 | 1.00 21.57 |
| ATOM | 3335 | OH2 | HOH | 318 | 34.686 | 36.202 | 11.099 | 1.00 14.87 |
| ATOM | 3336 | OH2 | HOH | 319 | 32.258 | 44.358 | 9.093 | 1.00 32.69 |
| ATOM | 3337 | OH2 | HOH | 320 | 39.030 | 38.810 | -0.342 | 1.00 28.05 |
| ATOM | 3338 | OH2 | HOH | 321 | 29.475 | 27.753 | -9.404 | 1.00 22.51 |
| ATOM | 3339 | OH2 | HOH | 322 | 7.826 | 21.059 | 36.030 | 1.00 13.85 |
| ATOM | 3340 | OH2 | HOH | 323 | 28.328 | 10.413 | 36.904 | 1.00 30.16 |
| ATOM | 3341 | OH2 | HOH | 324 | 16.240 | 17.853 | 20.766 | 1.00 36.46 |
| ATOM | 3342 | OH2 | HOH | 325 | 42.574 | 38.857 | 13.044 | 1.00 22.19 |
| ATOM | 3343 | OH2 | HOH | 326 | 48.573 | 15.605 | -1.357 | 1.00 23.01 |
| ATOM | 3344 | OH2 | HOH | 327 | 32.819 | 14.796 | 1.418 | 1.00 16.33 |
| ATOM | 3345 | OH2 | HOH | 328 | 40.175 | 25.424 | 46.900 | 1.00 10.91 |
| ATOM | 3346 | OH2 | HOH | 329 | 15.148 | 19.561 | 50.208 | 1.00 26.50 |
| ATOM | 3347 | OH2 | HOH | 330 | 27.957 | 26.048 | 42.339 | 1.00 12.44 |
| ATOM | 3348 | OH2 | HOH | 331 | 31.360 | 18.049 | 44.986 | 1.00 26.88 |
| ATOM | 3349 | OH2 | HOH | 332 | 28.746 | 43.379 | 9.745 | 1.00 16.49 |
| ATOM | 3350 | OH2 | HOH | 333 | 10.142 | 9.048 | 42.214 | 1.00 39.64 |
| ATOM | 3351 | OH2 | HOH | 334 | 6.398 | 19.052 | 47.895 | 1.00 13.50 |
| ATOM | 3352 | OH2 | HOH | 335 | 28.631 | 20.733 | 14.380 | 1.00 19.89 |
| ATOM | 3353 | OH2 | HOH | 336 | 45.598 | 19.716 | 12.124 | 1.00 30.51 |
| ATOM | 3354 | OH2 | HOH | 337 | 27.454 | 27.168 | 33.433 | 1.00 23.75 |
| ATOM | 3355 | OH2 | HOH | 338(WAT2) | 34.176 | 20.162 | 3.994 | 1.00 17.52 |
| ATOM | 3356 | OH2 | HOH | 339 | 26.751 | 26.551 | 44.715 | 1.00 20.42 |
| ATOM | 3357 | OH2 | HOH | 340 | 41.339 | 18.284 | 0.754 | 1.00 18.66 |
| ATOM | 3358 | OH2 | HOH | 341 | 44.857 | 16.855 | 1.384 | 1.00 38.33 |
| ATOM | 3359 | OH2 | HOH | 342 | 12.938 | 20.618 | 9.465 | 1.00 33.17 |
| ATOM | 3360 | OH2 | HOH | 343 | 9.295 | 13.961 | 31.913 | 1.00 36.87 |

Figure 5A

Table of the orthogonal three dimensional coordinates in Ångstroms and B factors (Å²) for unliganded HSV2 protease.

| Residue | Atom | X | Y | Z | B |
|---|---|---|---|---|---|
| 17 | ARG CB | 11.93 | 41.78 | 7.48 | 23.77 |
| 17 | ARG C | 13.26 | 39.77 | 8.31 | 23.47 |
| 17 | ARG O | 13.71 | 39.95 | 9.46 | 22.93 |
| 17 | ARG N | 10.94 | 40.20 | 9.07 | 24.64 |
| 17 | ARG CA | 11.86 | 40.32 | 7.91 | 23.58 |
| 18 | ALA N | 13.87 | 39.03 | 7.38 | 22.79 |
| 18 | ALA CA | 15.18 | 38.40 | 7.54 | 20.95 |
| 18 | ALA CB | 15.22 | 37.13 | 6.74 | 18.87 |
| 18 | ALA C | 16.41 | 39.26 | 7.17 | 20.78 |
| 18 | ALA O | 16.33 | 40.18 | 6.31 | 22.23 |
| 19 | VAL N | 17.53 | 39.00 | 7.86 | 18.03 |
| 19 | VAL CA | 18.80 | 39.69 | 7.58 | 16.65 |
| 19 | VAL CB | 19.73 | 39.85 | 8.85 | 16.23 |
| 19 | VAL CG1 | 21.11 | 40.36 | 8.46 | 15.83 |
| 19 | VAL CG2 | 19.13 | 40.81 | 9.84 | 18.15 |
| 19 | VAL C | 19.49 | 38.71 | 6.64 | 15.42 |
| 19 | VAL O | 19.70 | 37.54 | 7.01 | 16.93 |
| 20 | PRO N | 19.71 | 39.10 | 5.37 | 11.17 |
| 20 | PRO CD | 19.26 | 40.27 | 4.61 | 9.27 |
| 20 | PRO CA | 20.38 | 38.14 | 4.50 | 9.38 |
| 20 | PRO CB | 20.23 | 38.75 | 3.12 | 8.45 |
| 20 | PRO CG | 19.07 | 39.67 | 3.25 | 9.42 |
| 20 | PRO C | 21.82 | 38.19 | 4.97 | 10.57 |
| 20 | PRO O | 22.39 | 39.28 | 5.19 | 10.82 |
| 21 | ILE N | 22.37 | 37.03 | 5.26 | 10.67 |
| 21 | ILE CA | 23.72 | 36.97 | 5.73 | 10.40 |
| 21 | ILE CB | 23.80 | 36.13 | 7.05 | 10.18 |
| 21 | ILE CG2 | 25.24 | 35.79 | 7.37 | 13.71 |

Figure 5B

| Residue | Atom | X | Y | Z | B |
|---|---|---|---|---|---|
| 21 ILE | CG1 | 23.20 | 36.87 | 8.24 | 7.05 |
| 21 ILE | CD1 | 22.98 | 35.95 | 9.42 | 6.43 |
| 21 ILE | C | 24.42 | 36.24 | 4.63 | 11.21 |
| 21 ILE | O | 23.84 | 35.35 | 4.04 | 11.11 |
| 22 TYR | N | 25.64 | 36.66 | 4.33 | 12.65 |
| 22 TYR | CA | 26.50 | 36.01 | 3.34 | 10.47 |
| 22 TYR | CB | 27.16 | 37.06 | 2.49 | 11.30 |
| 22 TYR | CG | 26.17 | 37.79 | 1.65 | 15.61 |
| 22 TYR | CD1 | 25.76 | 37.27 | 0.41 | 18.56 |
| 22 TYR | CE1 | 24.80 | 37.91 | -0.37 | 18.37 |
| 22 TYR | CD2 | 25.61 | 38.98 | 2.08 | 13.23 |
| 22 TYR | CE2 | 24.65 | 39.63 | 1.30 | 17.16 |
| 22 TYR | CZ | 24.26 | 39.09 | 0.09 | 17.86 |
| 22 TYR | OH | 23.30 | 39.73 | -0.65 | 22.48 |
| 22 TYR | C | 27.55 | 35.17 | 4.08 | 9.27 |
| 22 TYR | O | 28.02 | 35.58 | 5.14 | 7.45 |
| 23 VAL | N | 27.83 | 33.96 | 3.60 | 8.25 |
| 23 VAL | CA | 28.86 | 33.09 | 4.20 | 8.74 |
| 23 VAL | CB | 28.36 | 31.69 | 4.57 | 8.18 |
| 23 VAL | CG1 | 29.09 | 31.19 | 5.80 | 7.22 |
| 23 VAL | CG2 | 26.87 | 31.66 | 4.66 | 9.15 |
| 23 VAL | C | 29.90 | 32.81 | 3.14 | 9.69 |
| 23 VAL | O | 29.54 | 32.52 | 2.00 | 11.20 |
| 24 ALA | N | 31.17 | 32.85 | 3.51 | 9.13 |
| 24 ALA | CA | 32.27 | 32.58 | 2.58 | 5.59 |
| 24 ALA | CB | 32.84 | 33.85 | 2.06 | 2.62 |
| 24 ALA | C | 33.35 | 31.79 | 3.28 | 5.65 |
| 24 ALA | O | 33.48 | 31.81 | 4.51 | 2.99 |
| 25 GLY | N | 34.09 | 31.04 | 2.49 | 5.77 |
| 25 GLY | CA | 35.17 | 30.23 | 3.02 | 6.58 |

Figure 5C

| Residue | Atom | X | Y | Z | B |
|---|---|---|---|---|---|
| 25 GLY | C | 35.55 | 29.12 | 2.07 | 7.51 |
| 25 GLY | O | 34.90 | 28.91 | 1.05 | 7.61 |
| 26 PHE | N | 36.63 | 28.41 | 2.40 | 7.15 |
| 26 PHE | CA | 37.09 | 27.28 | 1.61 | 7.60 |
| 26 PHE | CB | 38.59 | 27.05 | 1.82 | 7.69 |
| 26 PHE | CG | 39.48 | 27.94 | 0.98 | 10.69 |
| 26 PHE | CD1 | 39.75 | 27.62 | -0.33 | 11.02 |
| 26 PHE | CD2 | 39.99 | 29.13 | 1.49 | 9.49 |
| 26 PHE | CE1 | 40.50 | 28.48 | -1.12 | 10.54 |
| 26 PHE | CE2 | 40.74 | 29.99 | 0.69 | 7.24 |
| 26 PHE | CZ | 40.98 | 29.66 | -0.61 | 6.87 |
| 26 PHE | C | 36.32 | 26.04 | 2.01 | 7.99 |
| 26 PHE | O | 36.05 | 25.84 | 3.20 | 7.09 |
| 27 LEU | N | 35.91 | 25.23 | 1.03 | 8.63 |
| 27 LEU | CA | 35.20 | 23.98 | 1.32 | 9.80 |
| 27 LEU | CB | 34.35 | 23.49 | 0.15 | 7.49 |
| 27 LEU | CG | 32.94 | 24.00 | -0.06 | 7.63 |
| 27 LEU | CD1 | 32.31 | 24.50 | 1.21 | 2.13 |
| 27 LEU | CD2 | 32.97 | 25.06 | -1.07 | 9.69 |
| 27 LEU | C | 36.25 | 22.93 | 1.61 | 9.77 |
| 27 LEU | O | 35.93 | 21.86 | 2.11 | 12.13 |
| 28 ALA | N | 37.48 | 23.24 | 1.23 | 9.85 |
| 28 ALA | CA | 38.65 | 22.39 | 1.43 | 9.80 |
| 28 ALA | CB | 38.52 | 21.12 | 0.63 | 8.55 |
| 28 ALA | C | 39.90 | 23.14 | 1.01 | 10.74 |
| 28 ALA | O | 39.85 | 24.19 | 0.39 | 11.52 |
| 29 LEU | N | 41.04 | 22.64 | 1.44 | 12.26 |
| 29 LEU | CA | 42.30 | 23.22 | 1.06 | 12.96 |
| 29 LEU | CB | 43.11 | 23.72 | 2.27 | 12.36 |
| 29 LEU | CG | 42.64 | 25.03 | 2.94 | 10.60 |

Figure 5D

| Residue | Atom | X | Y | Z | B |
|---|---|---|---|---|---|
| 29 LEU | CD1 | 43.35 | 25.24 | 4.24 | 13.63 |
| 29 LEU | CD2 | 42.88 | 26.20 | 2.05 | 8.28 |
| 29 LEU | C | 42.99 | 22.07 | 0.34 | 14.02 |
| 29 LEU | O | 42.90 | 20.92 | 0.75 | 12.85 |
| 30 TYR | N | 43.64 | 22.40 | -0.76 | 16.21 |
| 30 TYR | CA | 44.30 | 21.45 | -1.60 | 17.27 |
| 30 TYR | CB | 44.66 | 22.07 | -2.92 | 15.53 |
| 30 TYR | CG | 43.47 | 22.22 | -3.82 | 11.82 |
| 30 TYR | CD1 | 42.51 | 21.21 | -3.89 | 7.98 |
| 30 TYR | CE1 | 41.42 | 21.35 | -4.70 | 7.53 |
| 30 TYR | CD2 | 43.30 | 23.36 | -4.59 | 11.67 |
| 30 TYR | CE2 | 42.21 | 23.51 | -5.40 | 10.27 |
| 30 TYR | CZ | 41.29 | 22.51 | -5.45 | 8.26 |
| 30 TYR | OH | 40.24 | 22.70 | -6.28 | 11.33 |
| 30 TYR | C | 45.45 | 20.64 | -1.06 | 19.34 |
| 30 TYR | O | 45.46 | 19.42 | -1.26 | 23.88 |
| 31 ASP | N | 46.46 | 21.23 | -0.46 | 18.47 |
| 31 ASP | CA | 47.46 | 20.31 | 0.02 | 22.18 |
| 31 ASP | CB | 48.82 | 20.49 | -0.64 | 23.48 |
| 31 ASP | CG | 49.12 | 19.40 | -1.64 | 25.72 |
| 31 ASP | OD1 | 49.10 | 18.21 | -1.26 | 25.53 |
| 31 ASP | OD2 | 49.33 | 19.73 | -2.83 | 31.11 |
| 31 ASP | C | 47.57 | 20.27 | 1.50 | 24.40 |
| 31 ASP | O | 48.56 | 19.77 | 2.04 | 26.77 |
| 32 SER | N | 46.46 | 20.65 | 2.13 | 26.99 |
| 32 SER | CA | 46.27 | 20.72 | 3.60 | 27.07 |
| 32 SER | CB | 44.83 | 21.14 | 3.92 | 25.49 |
| 32 SER | OG | 43.90 | 20.27 | 3.27 | 21.44 |
| 32 SER | C | 46.67 | 19.50 | 4.47 | 25.58 |
| 32 SER | O | 47.21 | 19.66 | 5.57 | 26.01 |

Figure 5E

| Residue | Atom | X | Y | Z | B |
|---|---|---|---|---|---|
| 33 GLY | N | 46.42 | 18.30 | 3.98 | 22.89 |
| 33 GLY | CA | 46.81 | 17.14 | 4.77 | 21.93 |
| 33 GLY | C | 45.62 | 16.37 | 5.31 | 21.48 |
| 33 GLY | O | 45.69 | 15.71 | 6.35 | 20.64 |
| 34 ASP | N | 44.51 | 16.46 | 4.59 | 22.42 |
| 34 ASP | CA | 43.29 | 15.74 | 4.98 | 21.94 |
| 34 ASP | CB | 42.09 | 16.12 | 4.09 | 19.38 |
| 34 ASP | CG | 41.52 | 17.48 | 4.40 | 18.22 |
| 34 ASP | OD1 | 41.43 | 18.31 | 3.48 | 16.27 |
| 34 ASP | OD2 | 41.18 | 17.71 | 5.57 | 19.82 |
| 34 ASP | C | 43.54 | 14.26 | 4.80 | 22.11 |
| 34 ASP | O | 44.53 | 13.85 | 4.18 | 24.20 |
| 35 PRO | N | 42.70 | 13.44 | 5.41 | 21.82 |
| 35 PRO | CD | 41.86 | 13.79 | 6.56 | 24.22 |
| 35 PRO | CA | 42.83 | 11.99 | 5.29 | 22.07 |
| 35 PRO | CB | 41.78 | 11.50 | 6.27 | 22.82 |
| 35 PRO | CG | 41.87 | 12.52 | 7.35 | 24.27 |
| 35 PRO | C | 42.46 | 11.60 | 3.85 | 23.00 |
| 35 PRO | O | 41.77 | 12.34 | 3.15 | 22.94 |
| 36 GLY | N | 42.91 | 10.41 | 3.43 | 23.64 |
| 36 GLY | CA | 42.64 | 9.93 | 2.09 | 23.75 |
| 36 GLY | C | 41.24 | 10.26 | 1.64 | 24.43 |
| 36 GLY | O | 41.03 | 11.01 | 0.70 | 23.27 |
| 37 GLU | N | 40.29 | 9.73 | 2.38 | 27.39 |
| 37 GLU | CA | 38.87 | 9.94 | 2.11 | 29.09 |
| 37 GLU | CB | 38.02 | 9.32 | 3.25 | 32.88 |
| 37 GLU | CG | 36.48 | 9.58 | 3.18 | 36.03 |
| 37 GLU | CD | 35.63 | 8.54 | 3.98 | 37.16 |
| 37 GLU | OE1 | 35.51 | 8.66 | 5.25 | 36.25 |
| 37 GLU | OE2 | 35.11 | 7.61 | 3.30 | 36.95 |

Figure 5F

| Residue | Atom | X | Y | Z | B |
|---|---|---|---|---|---|
| 37 GLU | C | 38.55 | 11.43 | 1.94 | 29.01 |
| 37 GLU | O | 38.15 | 11.87 | 0.84 | 32.05 |
| 38 LEU | N | 38.77 | 12.21 | 3.00 | 25.79 |
| 38 LEU | CA | 38.44 | 13.62 | 2.95 | 22.29 |
| 38 LEU | CB | 38.81 | 14.28 | 4.28 | 21.83 |
| 38 LEU | CG | 37.90 | 13.88 | 5.44 | 22.40 |
| 38 LEU | CD1 | 36.48 | 13.63 | 4.92 | 18.69 |
| 38 LEU | CD2 | 38.44 | 12.61 | 6.10 | 24.95 |
| 38 LEU | C | 39.06 | 14.39 | 1.80 | 21.48 |
| 38 LEU | O | 38.38 | 15.13 | 1.08 | 19.95 |
| 39 ALA | N | 40.36 | 14.19 | 1.67 | 23.17 |
| 39 ALA | CA | 41.19 | 14.85 | 0.67 | 22.76 |
| 39 ALA | CB | 42.49 | 14.07 | 0.52 | 22.75 |
| 39 ALA | C | 40.50 | 15.06 | -0.69 | 22.96 |
| 39 ALA | O | 40.01 | 14.11 | -1.32 | 25.23 |
| 40 LEU | N | 40.50 | 16.30 | -1.17 | 20.76 |
| 40 LEU | CA | 39.87 | 16.63 | -2.43 | 17.48 |
| 40 LEU | CB | 38.65 | 17.52 | -2.12 | 16.13 |
| 40 LEU | CG | 37.44 | 17.70 | -3.04 | 11.75 |
| 40 LEU | CD1 | 36.92 | 16.41 | -3.53 | 7.63 |
| 40 LEU | CD2 | 36.40 | 18.45 | -2.26 | 12.64 |
| 40 LEU | C | 40.90 | 17.37 | -3.29 | 16.67 |
| 40 LEU | O | 41.38 | 18.43 | -2.90 | 19.63 |
| 41 ASP | N | 41.30 | 16.81 | -4.41 | 15.24 |
| 41 ASP | CA | 42.30 | 17.48 | -5.25 | 15.78 |
| 41 ASP | CB | 43.22 | 16.47 | -5.88 | 14.72 |
| 41 ASP | CG | 42.56 | 15.72 | -6.99 | 15.87 |
| 41 ASP | OD1 | 42.85 | 15.99 | -8.18 | 16.55 |
| 41 ASP | OD2 | 41.75 | 14.85 | -6.63 | 15.87 |
| 41 ASP | C | 41.64 | 18.36 | -6.33 | 16.91 |

Figure 5G

| Residue | Atom | X | Y | Z | B |
|---|---|---|---|---|---|
| 41 ASP | O | 40.43 | 18.28 | -6.55 | 16.56 |
| 42 PRO | N | 42.44 | 19.17 | -7.06 | 17.31 |
| 42 PRO | CD | 43.90 | 19.34 | -6.96 | 15.77 |
| 42 PRO | CA | 41.91 | 20.05 | -8.10 | 16.95 |
| 42 PRO | CB | 43.12 | 20.93 | -8.44 | 12.88 |
| 42 PRO | CG | 44.21 | 20.03 | -8.25 | 14.99 |
| 42 PRO | C | 41.22 | 19.46 | -9.33 | 17.30 |
| 42 PRO | O | 40.29 | 20.07 | -9.88 | 17.30 |
| 43 ASP | N | 41.64 | 18.29 | -9.78 | 18.14 |
| 43 ASP | CA | 40.98 | 17.71 | -10.95 | 18.82 |
| 43 ASP | CB | 41.89 | 16.70 | -11.63 | 17.15 |
| 43 ASP | CG | 42.74 | 17.34 | -12.71 | 15.78 |
| 43 ASP | OD1 | 43.04 | 18.55 | -12.65 | 15.07 |
| 43 ASP | OD2 | 43.07 | 16.64 | -13.66 | 19.23 |
| 43 ASP | C | 39.55 | 17.19 | -10.68 | 19.69 |
| 43 ASP | O | 38.66 | 17.27 | -11.53 | 20.59 |
| 44 THR | N | 39.33 | 16.70 | -9.47 | 18.93 |
| 44 THR | CA | 38.03 | 16.25 | -9.04 | 16.75 |
| 44 THR | CB | 38.17 | 15.58 | -7.68 | 19.05 |
| 44 THR | OG1 | 39.06 | 14.46 | -7.80 | 20.07 |
| 44 THR | CG2 | 36.83 | 15.17 | -7.11 | 18.19 |
| 44 THR | C | 37.11 | 17.46 | -8.90 | 15.66 |
| 44 THR | O | 35.95 | 17.37 | -9.25 | 17.63 |
| 45 VAL | N | 37.63 | 18.58 | -8.40 | 14.40 |
| 45 VAL | CA | 36.87 | 19.82 | -8.21 | 12.95 |
| 45 VAL | CB | 37.65 | 20.83 | -7.32 | 10.87 |
| 45 VAL | CG1 | 37.07 | 22.23 | -7.41 | 8.51 |
| 45 VAL | CG2 | 37.62 | 20.37 | -5.91 | 9.61 |
| 45 VAL | C | 36.46 | 20.46 | -9.55 | 14.62 |
| 45 VAL | O | 35.34 | 20.92 | -9.73 | 15.51 |

Figure 5H

| Residue | Atom | X | Y | Z | B |
|---|---|---|---|---|---|
| 46 ARG | N | 37.38 | 20.45 | -10.51 | 16.51 |
| 46 ARG | CA | 37.15 | 20.98 | -11.85 | 16.58 |
| 46 ARG | CB | 38.44 | 20.77 | -12.66 | 20.37 |
| 46 ARG | CG | 38.45 | 21.26 | -14.09 | 26.06 |
| 46 ARG | CD | 39.37 | 22.49 | -14.20 | 34.14 |
| 46 ARG | NE | 38.95 | 23.59 | -13.30 | 38.64 |
| 46 ARG | CZ | 39.39 | 24.85 | -13.38 | 40.55 |
| 46 ARG | NH1 | 38.92 | 25.76 | -12.51 | 40.97 |
| 46 ARG | NH2 | 40.32 | 25.22 | -14.30 | 41.02 |
| 46 ARG | C | 36.02 | 20.18 | -12.49 | 14.81 |
| 46 ARG | O | 35.16 | 20.73 | -13.13 | 13.14 |
| 47 ALA | N | 36.08 | 18.86 | -12.34 | 15.77 |
| 47 ALA | CA | 35.09 | 17.92 | -12.86 | 15.83 |
| 47 ALA | CB | 35.49 | 16.52 | -12.52 | 15.76 |
| 47 ALA | C | 33.69 | 18.19 | -12.32 | 16.84 |
| 47 ALA | O | 32.74 | 18.09 | -13.06 | 17.38 |
| 48 ALA | N | 33.56 | 18.52 | -11.04 | 17.21 |
| 48 ALA | CA | 32.28 | 18.82 | -10.41 | 17.52 |
| 48 ALA | CB | 32.33 | 18.41 | -8.95 | 17.33 |
| 48 ALA | C | 31.75 | 20.26 | -10.53 | 17.33 |
| 48 ALA | O | 30.70 | 20.57 | -10.03 | 16.52 |
| 49 LEU | N | 32.46 | 21.14 | -11.22 | 17.96 |
| 49 LEU | CA | 32.00 | 22.52 | -11.33 | 19.43 |
| 49 LEU | CB | 33.05 | 23.49 | -10.79 | 18.53 |
| 49 LEU | CG | 33.42 | 23.38 | -9.33 | 16.94 |
| 49 LEU | CD1 | 34.37 | 24.52 | -9.02 | 14.90 |
| 49 LEU | CD2 | 32.17 | 23.38 | -8.46 | 13.36 |
| 49 LEU | C | 31.70 | 22.93 | -12.76 | 21.68 |
| 49 LEU | O | 32.52 | 22.70 | -13.65 | 23.49 |
| 50 PRO | N | 30.56 | 23.63 | -12.99 | 22.44 |

Figure 5I

| Residue | Atom | X | Y | Z | B |
|---|---|---|---|---|---|
| 50 PRO | CD | 30.23 | 24.24 | -14.29 | 20.44 |
| 50 PRO | CA | 29.58 | 24.03 | -11.97 | 20.59 |
| 50 PRO | CB | 28.68 | 24.98 | -12.73 | 20.21 |
| 50 PRO | CG | 28.79 | 24.47 | -14.15 | 20.99 |
| 50 PRO | C | 28.82 | 22.83 | -11.46 | 20.00 |
| 50 PRO | O | 28.61 | 21.86 | -12.20 | 19.97 |
| 51 PRO | N | 28.41 | 22.86 | -10.18 | 18.40 |
| 51 PRO | CD | 28.46 | 23.88 | -9.13 | 17.89 |
| 51 PRO | CA | 27.67 | 21.69 | -9.71 | 18.78 |
| 51 PRO | CB | 27.52 | 21.96 | -8.23 | 16.82 |
| 51 PRO | CG | 27.42 | 23.42 | -8.19 | 16.19 |
| 51 PRO | C | 26.34 | 21.57 | -10.46 | 21.71 |
| 51 PRO | O | 25.66 | 22.57 | -10.79 | 21.62 |
| 52 GLU | N | 26.03 | 20.32 | -10.82 | 22.45 |
| 52 GLU | CA | 24.83 | 19.97 | -11.54 | 22.76 |
| 52 GLU | CB | 24.59 | 18.48 | -11.36 | 24.61 |
| 52 GLU | CG | 23.33 | 18.02 | -11.96 | 27.88 |
| 52 GLU | CD | 23.50 | 17.70 | -13.40 | 28.89 |
| 52 GLU | OE1 | 23.96 | 18.61 | -14.17 | 31.44 |
| 52 GLU | OE2 | 23.20 | 16.53 | -13.72 | 26.97 |
| 52 GLU | C | 23.59 | 20.73 | -11.05 | 22.81 |
| 52 GLU | O | 22.91 | 21.41 | -11.83 | 23.60 |
| 53 ASN | N | 23.30 | 20.58 | -9.77 | 20.97 |
| 53 ASN | CA | 22.16 | 21.23 | -9.18 | 20.23 |
| 53 ASN | CB | 21.16 | 20.19 | -8.71 | 23.40 |
| 53 ASN | CG | 20.72 | 19.28 | -9.82 | 28.64 |
| 53 ASN | OD1 | 21.10 | 18.10 | -9.84 | 35.51 |
| 53 ASN | ND2 | 19.96 | 19.81 | -10.78 | 28.10 |
| 53 ASN | C | 22.60 | 22.05 | -8.01 | 19.30 |
| 53 ASN | O | 23.48 | 21.64 | -7.27 | 21.50 |

Figure 5J

| Residue | Atom | X | Y | Z | B |
|---|---|---|---|---|---|
| 54 PRO | N | 21.94 | 23.19 | -7.77 | 18.19 |
| 54 PRO | CD | 20.70 | 23.57 | -8.46 | 19.95 |
| 54 PRO | CA | 22.20 | 24.13 | -6.68 | 16.41 |
| 54 PRO | CB | 20.89 | 24.88 | -6.54 | 18.57 |
| 54 PRO | CG | 19.87 | 23.98 | -7.31 | 19.87 |
| 54 PRO | C | 22.59 | 23.46 | -5.39 | 13.92 |
| 54 PRO | O | 22.23 | 22.33 | -5.12 | 11.63 |
| 55 LEU | N | 23.35 | 24.17 | -4.59 | 13.45 |
| 55 LEU | CA | 23.81 | 23.57 | -3.37 | 12.25 |
| 55 LEU | CB | 25.33 | 23.72 | -3.26 | 15.69 |
| 55 LEU | CG | 26.14 | 22.73 | -4.07 | 14.38 |
| 55 LEU | CD1 | 27.55 | 23.24 | -4.23 | 15.31 |
| 55 LEU | CD2 | 26.12 | 21.42 | -3.31 | 17.14 |
| 55 LEU | C | 23.13 | 24.14 | -2.16 | 10.90 |
| 55 LEU | O | 23.34 | 25.31 | -1.83 | 14.26 |
| 56 PRO | N | 22.28 | 23.34 | -1.50 | 8.09 |
| 56 PRO | CD | 21.86 | 21.96 | -1.78 | 8.27 |
| 56 PRO | CA | 21.62 | 23.86 | -0.31 | 7.83 |
| 56 PRO | CB | 20.55 | 22.82 | -0.05 | 6.41 |
| 56 PRO | CG | 21.21 | 21.55 | -0.50 | 5.90 |
| 56 PRO | C | 22.58 | 23.95 | 0.87 | 8.56 |
| 56 PRO | O | 23.55 | 23.20 | 0.98 | 6.85 |
| 57 ILE | N | 22.33 | 24.95 | 1.70 | 8.07 |
| 57 ILE | CA | 23.11 | 25.14 | 2.90 | 6.88 |
| 57 ILE | CB | 23.57 | 26.60 | 3.08 | 3.62 |
| 57 ILE | CG2 | 24.46 | 26.72 | 4.32 | 3.19 |
| 57 ILE | CG1 | 24.31 | 27.07 | 1.84 | 2.00 |
| 57 ILE | CD1 | 24.90 | 28.39 | 1.99 | 2.00 |
| 57 ILE | C | 22.15 | 24.77 | 4.04 | 7.47 |
| 57 ILE | O | 21.08 | 25.36 | 4.19 | 8.61 |

Figure 5K

| Residue | Atom | X | Y | Z | B |
|---|---|---|---|---|---|
| 58 ASN | N | 22.47 | 23.71 | 4.77 | 5.54 |
| 58 ASN | CA | 21.63 | 23.31 | 5.87 | 6.46 |
| 58 ASN | CB | 21.03 | 21.94 | 5.61 | 4.75 |
| 58 ASN | CG | 22.05 | 20.93 | 5.24 | 6.39 |
| 58 ASN | OD1 | 23.08 | 20.84 | 5.87 | 6.72 |
| 58 ASN | ND2 | 21.75 | 20.14 | 4.23 | 6.81 |
| 58 ASN | C | 22.44 | 23.32 | 7.18 | 8.53 |
| 58 ASN | O | 23.65 | 23.56 | 7.16 | 10.73 |
| 59 VAL | N | 21.78 | 23.13 | 8.32 | 5.59 |
| 59 VAL | CA | 22.48 | 23.13 | 9.58 | 3.21 |
| 59 VAL | CB | 21.70 | 23.87 | 10.69 | 2.76 |
| 59 VAL | CG1 | 22.40 | 23.70 | 12.01 | 2.00 |
| 59 VAL | CG2 | 21.61 | 25.35 | 10.37 | 2.00 |
| 59 VAL | C | 22.85 | 21.74 | 10.03 | 4.47 |
| 59 VAL | O | 22.02 | 20.86 | 10.09 | 4.87 |
| 60 ASP | N | 24.14 | 21.54 | 10.22 | 6.21 |
| 60 ASP | CA | 24.72 | 20.29 | 10.69 | 9.27 |
| 60 ASP | CB | 24.50 | 20.16 | 12.22 | 12.92 |
| 60 ASP | CG | 25.64 | 19.40 | 12.93 | 18.52 |
| 60 ASP | OD1 | 26.78 | 19.39 | 12.40 | 23.62 |
| 60 ASP | OD2 | 25.43 | 18.84 | 14.04 | 15.83 |
| 60 ASP | C | 24.21 | 19.05 | 9.96 | 10.71 |
| 60 ASP | O | 23.88 | 18.06 | 10.57 | 12.47 |
| 61 HIS | N | 24.13 | 19.11 | 8.64 | 12.79 |
| 61 HIS | CA | 23.68 | 17.98 | 7.81 | 14.32 |
| 61 HIS | C | 22.24 | 17.54 | 7.92 | 17.79 |
| 61 HIS | O | 21.85 | 16.59 | 7.25 | 20.60 |
| 61 HIS | CB | 24.59 | 16.76 | 7.96 | 10.25 |
| 61 HIS | CG | 26.00 | 17.01 | 7.52 | 12.30 |
| 61 HIS | ND1 | 26.39 | 17.08 | 6.21 | 13.19 |

Figure 5L

| Residue | Atom | X | Y | Z | B |
|---|---|---|---|---|---|
| 61 HIS | CD2 | 27.10 | 17.30 | 8.26 | 11.24 |
| 61 HIS | NE2 | 28.16 | 17.57 | 7.41 | 13.47 |
| 61 HIS | CE1 | 27.69 | 17.42 | 6.18 | 11.79 |
| 62 ARG | N | 21.44 | 18.20 | 8.76 | 18.10 |
| 62 ARG | CA | 20.03 | 17.86 | 8.88 | 17.04 |
| 62 ARG | CB | 19.45 | 18.45 | 10.16 | 21.61 |
| 62 ARG | CG | 18.73 | 17.42 | 11.06 | 28.55 |
| 62 ARG | CD | 17.22 | 17.21 | 10.64 | 35.65 |
| 62 ARG | NE | 16.32 | 18.30 | 11.07 | 37.04 |
| 62 ARG | CZ | 15.69 | 18.35 | 12.26 | 39.49 |
| 62 ARG | NH1 | 15.85 | 17.36 | 13.16 | 37.41 |
| 62 ARG | NH2 | 14.86 | 19.36 | 12.53 | 39.13 |
| 62 ARG | C | 19.32 | 18.45 | 7.68 | 15.19 |
| 62 ARG | O | 19.09 | 19.65 | 7.62 | 16.59 |
| 63 ALA | N | 19.06 | 17.61 | 6.69 | 14.69 |
| 63 ALA | CA | 18.39 | 18.02 | 5.45 | 16.12 |
| 63 ALA | CB | 18.05 | 16.81 | 4.61 | 14.80 |
| 63 ALA | C | 17.14 | 18.86 | 5.74 | 17.87 |
| 63 ALA | O | 16.92 | 19.85 | 5.05 | 19.17 |
| 64 ARG | N | 16.37 | 18.50 | 6.78 | 20.11 |
| 64 ARG | CA | 15.16 | 19.26 | 7.18 | 20.31 |
| 64 ARG | CB | 14.38 | 18.58 | 8.30 | 23.48 |
| 64 ARG | CG | 13.07 | 19.33 | 8.64 | 26.43 |
| 64 ARG | CD | 12.35 | 18.73 | 9.83 | 28.44 |
| 64 ARG | NE | 12.20 | 17.28 | 9.69 | 29.46 |
| 64 ARG | CZ | 12.46 | 16.41 | 10.66 | 32.40 |
| 64 ARG | NH1 | 12.88 | 16.85 | 11.85 | 34.22 |
| 64 ARG | NH2 | 12.25 | 15.10 | 10.46 | 32.33 |
| 64 ARG | C | 15.40 | 20.73 | 7.59 | 18.85 |
| 64 ARG | O | 14.45 | 21.52 | 7.53 | 19.05 |

Figure 5M

| Residue | Atom | X | Y | Z | B |
|---|---|---|---|---|---|
| 65 CYS | N | 16.61 | 21.06 | 8.10 | 16.40 |
| 65 CYS | CA | 16.93 | 22.44 | 8.46 | 14.24 |
| 65 CYS | CB | 17.78 | 22.57 | 9.72 | 11.24 |
| 65 CYS | SG | 17.17 | 21.76 | 11.09 | 19.10 |
| 65 CYS | C | 17.77 | 22.99 | 7.36 | 13.25 |
| 65 CYS | O | 18.96 | 22.93 | 7.45 | 17.07 |
| 66 GLU | N | 17.15 | 23.47 | 6.30 | 9.68 |
| 66 GLU | CA | 17.89 | 24.05 | 5.23 | 8.49 |
| 66 GLU | CB | 17.27 | 23.62 | 3.93 | 7.02 |
| 66 GLU | CG | 17.73 | 24.38 | 2.73 | 9.23 |
| 66 GLU | CD | 17.32 | 23.71 | 1.45 | 10.47 |
| 66 GLU | OE1 | 17.44 | 22.48 | 1.36 | 11.03 |
| 66 GLU | OE2 | 16.89 | 24.43 | 0.53 | 10.11 |
| 66 GLU | C | 17.66 | 25.50 | 5.47 | 9.58 |
| 66 GLU | O | 16.54 | 25.87 | 5.61 | 13.45 |
| 67 VAL | N | 18.71 | 26.31 | 5.54 | 9.57 |
| 67 VAL | CA | 18.57 | 27.74 | 5.81 | 5.68 |
| 67 VAL | CB | 19.30 | 28.16 | 7.10 | 8.71 |
| 67 VAL | CG1 | 18.71 | 27.45 | 8.32 | 7.38 |
| 67 VAL | CG2 | 20.81 | 27.87 | 6.98 | 5.47 |
| 67 VAL | C | 19.09 | 28.61 | 4.69 | 5.54 |
| 67 VAL | O | 19.09 | 29.82 | 4.82 | 4.42 |
| 68 GLY | N | 19.51 | 28.00 | 3.59 | 6.23 |
| 68 GLY | CA | 20.02 | 28.80 | 2.48 | 7.33 |
| 68 GLY | C | 20.49 | 28.11 | 1.22 | 9.75 |
| 68 GLY | O | 20.25 | 26.92 | 1.01 | 11.38 |
| 69 ARG | N | 21.25 | 28.85 | 0.43 | 9.67 |
| 69 ARG | CA | 21.73 | 28.37 | -0.85 | 9.65 |
| 69 ARG | CB | 20.75 | 28.95 | -1.89 | 13.32 |
| 69 ARG | CG | 21.10 | 28.85 | -3.38 | 17.79 |

Figure 5N

| Residue | Atom | X | Y | Z | B |
|---|---|---|---|---|---|
| 69 ARG | CD | 21.07 | 27.45 | -3.86 | 20.10 |
| 69 ARG | NE | 20.21 | 26.67 | -2.99 | 25.53 |
| 69 ARG | CZ | 18.90 | 26.54 | -3.13 | 28.17 |
| 69 ARG | NH1 | 18.23 | 25.78 | -2.23 | 29.80 |
| 69 ARG | NH2 | 18.26 | 27.11 | -4.16 | 26.46 |
| 69 ARG | C | 23.17 | 28.82 | -1.13 | 8.83 |
| 69 ARG | O | 23.56 | 29.93 | -0.74 | 10.07 |
| 70 VAL | N | 23.96 | 27.98 | -1.79 | 6.16 |
| 70 VAL | CA | 25.31 | 28.36 | -2.17 | 5.74 |
| 70 VAL | CB | 26.17 | 27.13 | -2.48 | 3.22 |
| 70 VAL | CG1 | 27.46 | 27.51 | -3.18 | 2.00 |
| 70 VAL | CG2 | 26.49 | 26.43 | -1.23 | 2.00 |
| 70 VAL | C | 25.20 | 29.22 | -3.45 | 7.31 |
| 70 VAL | O | 24.71 | 28.73 | -4.46 | 9.38 |
| 71 LEU | N | 25.57 | 30.50 | -3.40 | 7.30 |
| 71 LEU | CA | 25.54 | 31.38 | -4.58 | 7.19 |
| 71 LEU | CB | 25.67 | 32.83 | -4.15 | 5.22 |
| 71 LEU | CG | 24.62 | 33.30 | -3.17 | 5.66 |
| 71 LEU | CD1 | 24.80 | 34.76 | -2.88 | 2.00 |
| 71 LEU | CD2 | 23.25 | 33.04 | -3.76 | 10.02 |
| 71 LEU | C | 26.57 | 31.04 | -5.71 | 9.63 |
| 71 LEU | O | 26.20 | 30.98 | -6.89 | 11.03 |
| 72 ALA | N | 27.84 | 30.82 | -5.36 | 9.00 |
| 72 ALA | CA | 28.89 | 30.46 | -6.30 | 7.85 |
| 72 ALA | CB | 29.54 | 31.68 | -6.80 | 9.83 |
| 72 ALA | C | 29.95 | 29.57 | -5.63 | 9.95 |
| 72 ALA | O | 30.10 | 29.58 | -4.41 | 11.10 |
| 73 VAL | N | 30.62 | 28.74 | -6.42 | 11.11 |
| 73 VAL | CA | 31.71 | 27.87 | -5.93 | 12.90 |
| 73 VAL | CB | 31.37 | 26.34 | -5.96 | 12.82 |

Figure 5O

| Residue | Atom | X | Y | Z | B |
|---|---|---|---|---|---|
| 73 VAL | CG1 | 32.48 | 25.51 | -5.30 | 10.03 |
| 73 VAL | CG2 | 30.06 | 26.07 | -5.26 | 14.65 |
| 73 VAL | C | 32.78 | 28.16 | -6.97 | 13.82 |
| 73 VAL | O | 32.48 | 28.19 | -8.15 | 15.35 |
| 74 VAL | N | 34.00 | 28.47 | -6.53 | 13.95 |
| 74 VAL | CA | 35.07 | 28.80 | -7.46 | 15.06 |
| 74 VAL | CB | 35.41 | 30.29 | -7.33 | 15.62 |
| 74 VAL | CG1 | 36.72 | 30.58 | -8.04 | 18.50 |
| 74 VAL | CG2 | 34.31 | 31.14 | -7.90 | 13.45 |
| 74 VAL | C | 36.31 | 28.00 | -7.14 | 15.92 |
| 74 VAL | O | 36.66 | 27.87 | -5.97 | 18.48 |
| 75 ASN | N | 36.98 | 27.46 | -8.15 | 15.92 |
| 75 ASN | CA | 38.22 | 26.71 | -7.89 | 15.66 |
| 75 ASN | CB | 38.46 | 25.68 | -9.00 | 16.57 |
| 75 ASN | CG | 39.67 | 24.82 | -8.74 | 18.18 |
| 75 ASN | OD1 | 40.18 | 24.16 | -9.63 | 20.99 |
| 75 ASN | ND2 | 40.12 | 24.81 | -7.52 | 20.52 |
| 75 ASN | C | 39.41 | 27.67 | -7.77 | 14.23 |
| 75 ASN | O | 39.91 | 28.19 | -8.75 | 16.41 |
| 76 ASP | N | 39.79 | 27.99 | -6.56 | 13.61 |
| 76 ASP | CA | 40.91 | 28.87 | -6.33 | 13.15 |
| 76 ASP | CB | 40.66 | 29.63 | -5.04 | 15.03 |
| 76 ASP | CG | 41.88 | 30.35 | -4.50 | 15.79 |
| 76 ASP | OD1 | 42.60 | 29.74 | -3.69 | 17.48 |
| 76 ASP | OD2 | 42.11 | 31.54 | -4.82 | 13.72 |
| 76 ASP | C | 42.14 | 27.95 | -6.24 | 13.28 |
| 76 ASP | O | 42.02 | 26.80 | -5.83 | 15.73 |
| 77 PRO | N | 43.32 | 28.43 | -6.62 | 10.71 |
| 77 PRO | CD | 43.67 | 29.79 | -7.06 | 9.86 |

Figure 5P

| Residue | Atom | X | Y | Z | B |
|---|---|---|---|---|---|
| 77 PRO | CA | 44.52 | 27.60 | -6.56 | 10.08 |
| 77 PRO | CB | 45.61 | 28.61 | -6.79 | 8.87 |
| 77 PRO | CG | 44.98 | 29.58 | -7.67 | 7.64 |
| 77 PRO | C | 44.70 | 26.87 | -5.22 | 11.39 |
| 77 PRO | O | 45.34 | 25.83 | -5.16 | 10.85 |
| 78 ARG | N | 44.11 | 27.43 | -4.16 | 10.81 |
| 78 ARG | CA | 44.20 | 26.85 | -2.83 | 11.79 |
| 78 ARG | CB | 44.22 | 27.95 | -1.78 | 10.22 |
| 78 ARG | CG | 45.36 | 28.94 | -1.94 | 12.52 |
| 78 ARG | CD | 45.44 | 29.88 | -0.75 | 16.01 |
| 78 ARG | NE | 45.45 | 29.10 | 0.51 | 22.19 |
| 78 ARG | CZ | 45.12 | 29.57 | 1.72 | 21.40 |
| 78 ARG | NH1 | 45.17 | 28.76 | 2.77 | 21.39 |
| 78 ARG | NH2 | 44.75 | 30.83 | 1.92 | 21.43 |
| 78 ARG | C | 43.10 | 25.83 | -2.52 | 12.63 |
| 78 ARG | O | 43.29 | 24.93 | -1.69 | 12.90 |
| 79 GLY | N | 41.95 | 25.95 | -3.18 | 11.40 |
| 79 GLY | CA | 40.85 | 25.04 | -2.95 | 9.61 |
| 79 GLY | C | 39.57 | 25.69 | -3.39 | 8.97 |
| 79 GLY | O | 39.60 | 26.87 | -3.76 | 8.84 |
| 80 PRO | N | 38.44 | 24.95 | -3.41 | 8.44 |
| 80 PRO | CD | 38.32 | 23.52 | -3.09 | 9.93 |
| 80 PRO | CA | 37.13 | 25.49 | -3.82 | 8.23 |
| 80 PRO | CB | 36.28 | 24.23 | -3.91 | 7.99 |
| 80 PRO | CG | 36.85 | 23.35 | -2.92 | 8.18 |
| 80 PRO | C | 36.63 | 26.47 | -2.77 | 8.23 |
| 80 PRO | O | 36.51 | 26.15 | -1.60 | 10.20 |
| 81 PHE | N | 36.49 | 27.71 | -3.17 | 7.10 |
| 81 PHE | CA | 36.03 | 28.73 | -2.26 | 9.63 |
| 81 PHE | CB | 36.87 | 29.98 | -2.47 | 8.78 |

Figure 5Q

| Residue | Atom | X | Y | Z | B |
|---|---|---|---|---|---|
| 81 PHE | CG | 36.40 | 31.19 | -1.70 | 11.26 |
| 81 PHE | CD1 | 36.84 | 31.42 | -0.40 | 6.17 |
| 81 PHE | CD2 | 35.53 | 32.14 | -2.29 | 11.51 |
| 81 PHE | CE1 | 36.45 | 32.56 | 0.29 | 6.96 |
| 81 PHE | CE2 | 35.13 | 33.28 | -1.59 | 8.50 |
| 81 PHE | CZ | 35.60 | 33.49 | -0.30 | 7.53 |
| 81 PHE | C | 34.57 | 28.97 | -2.63 | 13.60 |
| 81 PHE | O | 34.24 | 29.13 | -3.82 | 15.81 |
| 82 PHE | N | 33.67 | 28.96 | -1.64 | 13.48 |
| 82 PHE | CA | 32.26 | 29.18 | -1.91 | 12.13 |
| 82 PHE | CB | 31.42 | 27.98 | -1.46 | 8.73 |
| 82 PHE | CG | 30.82 | 28.12 | -0.12 | 7.25 |
| 82 PHE | CD1 | 29.47 | 28.33 | 0.02 | 8.88 |
| 82 PHE | CD2 | 31.61 | 28.07 | 1.01 | 8.28 |
| 82 PHE | CE1 | 28.91 | 28.48 | 1.27 | 8.50 |
| 82 PHE | CE2 | 31.04 | 28.22 | 2.27 | 6.88 |
| 82 PHE | CZ | 29.70 | 28.43 | 2.40 | 4.53 |
| 82 PHE | C | 31.75 | 30.45 | -1.23 | 12.39 |
| 82 PHE | O | 32.44 | 31.07 | -0.42 | 16.47 |
| 83 VAL | N | 30.55 | 30.86 | -1.62 | 9.90 |
| 83 VAL | CA | 29.89 | 32.01 | -1.04 | 11.13 |
| 83 VAL | CB | 30.03 | 33.25 | -1.92 | 9.41 |
| 83 VAL | CG1 | 29.04 | 34.31 | -1.48 | 6.73 |
| 83 VAL | CG2 | 31.44 | 33.81 | -1.82 | 12.28 |
| 83 VAL | C | 28.43 | 31.62 | -0.97 | 12.70 |
| 83 VAL | O | 27.87 | 31.20 | -1.97 | 13.65 |
| 84 GLY | N | 27.81 | 31.72 | 0.21 | 10.38 |
| 84 GLY | CA | 26.41 | 31.35 | 0.33 | 8.03 |
| 84 GLY | C | 25.57 | 32.42 | 0.94 | 6.01 |

Figure 5R

| Residue | Atom | X | Y | Z | B |
|---|---|---|---|---|---|
| 84 GLY | O | 26.07 | 33.37 | 1.52 | 6.85 |
| 85 LEU | N | 24.27 | 32.29 | 0.78 | 5.76 |
| 85 LEU | CA | 23.30 | 33.23 | 1.34 | 8.07 |
| 85 LEU | CB | 22.43 | 33.82 | 0.24 | 7.19 |
| 85 LEU | CG | 21.35 | 34.78 | 0.70 | 7.85 |
| 85 LEU | CD1 | 21.89 | 36.19 | 0.89 | 6.18 |
| 85 LEU | CD2 | 20.24 | 34.76 | -0.35 | 11.21 |
| 85 LEU | C | 22.40 | 32.54 | 2.37 | 8.00 |
| 85 LEU | O | 21.99 | 31.41 | 2.19 | 6.96 |
| 86 ILE | N | 22.10 | 33.23 | 3.46 | 8.19 |
| 86 ILE | CA | 21.27 | 32.66 | 4.50 | 7.74 |
| 86 ILE | CB | 22.11 | 32.40 | 5.73 | 8.25 |
| 86 ILE | CG2 | 21.26 | 31.83 | 6.81 | 6.69 |
| 86 ILE | CG1 | 23.30 | 31.51 | 5.37 | 2.00 |
| 86 ILE | CD1 | 24.13 | 31.13 | 6.56 | 4.98 |
| 86 ILE | C | 20.15 | 33.62 | 4.85 | 8.36 |
| 86 ILE | O | 20.39 | 34.64 | 5.47 | 12.27 |
| 87 ALA | N | 18.94 | 33.36 | 4.37 | 8.37 |
| 87 ALA | CA | 17.80 | 34.23 | 4.67 | 9.29 |
| 87 ALA | CB | 17.16 | 34.76 | 3.39 | 5.71 |
| 87 ALA | C | 16.82 | 33.39 | 5.46 | 8.92 |
| 87 ALA | O | 16.08 | 32.59 | 4.89 | 9.22 |
| 88 CYS | N | 16.84 | 33.55 | 6.77 | 8.19 |
| 88 CYS | CA | 16.01 | 32.74 | 7.65 | 9.16 |
| 88 CYS | CB | 16.71 | 31.40 | 7.88 | 6.92 |
| 88 CYS | SG | 15.87 | 30.13 | 8.78 | 5.83 |
| 88 CYS | C | 15.89 | 33.51 | 8.95 | 11.52 |
| 88 CYS | O | 16.88 | 33.64 | 9.67 | 14.84 |
| 89 VAL | N | 14.72 | 34.05 | 9.25 | 13.03 |
| 89 VAL | CA | 14.52 | 34.79 | 10.48 | 11.73 |

Figure 5S

| Residue | Atom | X | Y | Z | B |
|---|---|---|---|---|---|
| 89 VAL | CB | 13.45 | 35.90 | 10.31 | 13.04 |
| 89 VAL | CG1 | 12.07 | 35.28 | 10.12 | 15.08 |
| 89 VAL | CG2 | 13.49 | 36.86 | 11.49 | 12.47 |
| 89 VAL | C | 14.26 | 33.88 | 11.68 | 11.56 |
| 89 VAL | O | 14.28 | 34.33 | 12.81 | 10.96 |
| 90 GLN | N | 14.04 | 32.59 | 11.43 | 11.77 |
| 90 GLN | CA | 13.85 | 31.61 | 12.51 | 12.33 |
| 90 GLN | CB | 13.14 | 30.36 | 12.03 | 10.30 |
| 90 GLN | CG | 11.67 | 30.55 | 11.89 | 13.90 |
| 90 GLN | CD | 11.00 | 29.31 | 11.36 | 17.26 |
| 90 GLN | OE1 | 11.68 | 28.34 | 11.01 | 17.86 |
| 90 GLN | NE2 | 9.67 | 29.31 | 11.31 | 14.90 |
| 90 GLN | C | 15.20 | 31.25 | 13.12 | 13.24 |
| 90 GLN | O | 15.34 | 31.18 | 14.33 | 14.62 |
| 91 LEU | N | 16.20 | 31.01 | 12.28 | 12.44 |
| 91 LEU | CA | 17.56 | 30.72 | 12.74 | 11.11 |
| 91 LEU | CB | 18.45 | 30.49 | 11.54 | 9.40 |
| 91 LEU | CG | 19.93 | 30.33 | 11.76 | 8.68 |
| 91 LEU | CD1 | 20.18 | 29.11 | 12.58 | 9.22 |
| 91 LEU | CD2 | 20.61 | 30.19 | 10.45 | 9.24 |
| 91 LEU | C | 18.01 | 31.98 | 13.47 | 11.99 |
| 91 LEU | O | 18.61 | 31.92 | 14.53 | 11.04 |
| 92 GLU | N | 17.66 | 33.11 | 12.91 | 12.25 |
| 92 GLU | CA | 18.02 | 34.37 | 13.51 | 14.20 |
| 92 GLU | CB | 17.63 | 35.50 | 12.56 | 19.07 |
| 92 GLU | CG | 17.52 | 36.89 | 13.19 | 21.54 |
| 92 GLU | CD | 16.97 | 37.88 | 12.19 | 23.75 |
| 92 GLU | OE1 | 17.21 | 37.67 | 10.96 | 19.07 |
| 92 GLU | OE2 | 16.29 | 38.85 | 12.66 | 24.68 |
| 92 GLU | C | 17.44 | 34.58 | 14.89 | 13.85 |

Figure 5T

| Residue | Atom | X | Y | Z | B |
|---|---|---|---|---|---|
| 92 GLU | O | 18.16 | 35.01 | 15.79 | 16.48 |
| 93 ARG | N | 16.16 | 34.28 | 15.09 | 13.91 |
| 93 ARG | CA | 15.51 | 34.47 | 16.39 | 11.99 |
| 93 ARG | CB | 13.98 | 34.51 | 16.24 | 15.54 |
| 93 ARG | CG | 13.44 | 35.55 | 15.26 | 20.43 |
| 93 ARG | CD | 13.70 | 37.04 | 15.62 | 27.76 |
| 93 ARG | NE | 13.09 | 37.90 | 14.59 | 33.37 |
| 93 ARG | CZ | 13.19 | 39.24 | 14.47 | 32.48 |
| 93 ARG | NH1 | 12.56 | 39.85 | 13.46 | 34.48 |
| 93 ARG | NH2 | 13.90 | 39.98 | 15.32 | 31.73 |
| 93 ARG | C | 15.89 | 33.42 | 17.45 | 9.12 |
| 93 ARG | O | 16.18 | 33.77 | 18.59 | 9.17 |
| 94 VAL | N | 15.89 | 32.16 | 17.05 | 6.89 |
| 94 VAL | CA | 16.24 | 31.05 | 17.93 | 7.02 |
| 94 VAL | CB | 16.48 | 29.77 | 17.13 | 5.90 |
| 94 VAL | CG1 | 17.00 | 28.67 | 18.01 | 5.97 |
| 94 VAL | CG2 | 15.22 | 29.34 | 16.50 | 10.65 |
| 94 VAL | C | 17.52 | 31.37 | 18.68 | 10.18 |
| 94 VAL | O | 17.59 | 31.16 | 19.90 | 11.82 |
| 95 LEU | N | 18.53 | 31.85 | 17.95 | 10.80 |
| 95 LEU | CA | 19.83 | 32.21 | 18.50 | 10.14 |
| 95 LEU | CB | 20.81 | 32.54 | 17.36 | 9.46 |
| 95 LEU | CG | 21.99 | 31.63 | 16.98 | 8.46 |
| 95 LEU | CD1 | 21.83 | 30.26 | 17.59 | 8.92 |
| 95 LEU | CD2 | 22.12 | 31.55 | 15.46 | 2.00 |
| 95 LEU | C | 19.66 | 33.41 | 19.42 | 11.97 |
| 95 LEU | O | 20.00 | 33.32 | 20.60 | 11.21 |
| 96 GLU | N | 19.11 | 34.52 | 18.91 | 14.36 |
| 96 GLU | CA | 18.92 | 35.74 | 19.71 | 16.50 |
| 96 GLU | CB | 18.11 | 36.80 | 18.97 | 18.80 |

Figure 5U

| Residue | Atom | X | Y | Z | B |
|---|---|---|---|---|---|
| 96 GLU | CG | 18.81 | 37.50 | 17.84 | 23.30 |
| 96 GLU | CD | 17.84 | 38.28 | 16.98 | 29.76 |
| 96 GLU | OE1 | 18.33 | 39.02 | 16.07 | 32.86 |
| 96 GLU | OE2 | 16.59 | 38.15 | 17.20 | 28.34 |
| 96 GLU | C | 18.22 | 35.49 | 21.03 | 16.75 |
| 96 GLU | O | 18.39 | 36.21 | 22.01 | 15.67 |
| 97 THR | N | 17.33 | 34.54 | 21.03 | 16.21 |
| 97 THR | CA | 16.68 | 34.27 | 22.27 | 19.53 |
| 97 THR | CB | 15.25 | 33.77 | 22.05 | 21.08 |
| 97 THR | OG1 | 15.26 | 32.62 | 21.20 | 21.77 |
| 97 THR | CG2 | 14.43 | 34.84 | 21.37 | 22.70 |
| 97 THR | C | 17.54 | 33.32 | 23.13 | 19.94 |
| 97 THR | O | 17.75 | 33.57 | 24.32 | 22.37 |
| 98 ALA | N | 18.09 | 32.27 | 22.50 | 18.83 |
| 98 ALA | CA | 18.91 | 31.28 | 23.19 | 14.28 |
| 98 ALA | CB | 19.60 | 30.40 | 22.19 | 13.42 |
| 98 ALA | C | 19.93 | 31.98 | 24.01 | 13.36 |
| 98 ALA | O | 20.08 | 31.72 | 25.19 | 14.87 |
| 99 ALA | N | 20.60 | 32.94 | 23.40 | 13.17 |
| 99 ALA | CA | 21.63 | 33.69 | 24.08 | 15.11 |
| 99 ALA | CB | 22.40 | 34.60 | 23.12 | 12.19 |
| 99 ALA | C | 20.97 | 34.51 | 25.10 | 18.62 |
| 99 ALA | O | 20.46 | 35.59 | 24.80 | 21.12 |
| 100 SER | N | 20.95 | 33.99 | 26.33 | 22.85 |
| 100 SER | CA | 20.41 | 34.73 | 27.48 | 26.09 |
| 100 SER | CB | 20.05 | 33.73 | 28.59 | 24.21 |
| 100 SER | OG | 19.10 | 32.79 | 28.11 | 22.05 |
| 100 SER | C | 21.66 | 35.63 | 27.83 | 26.19 |
| 100 SER | O | 22.04 | 35.88 | 29.00 | 23.67 |
| 101 ALA | N | 22.20 | 36.16 | 26.75 | 25.61 |

Figure 5V

| Residue | Atom | X | Y | Z | B |
|---|---|---|---|---|---|
| 101 ALA | CA | 23.37 | 36.94 | 26.73 | 28.22 |
| 101 ALA | CB | 23.54 | 37.60 | 25.37 | 28.74 |
| 101 ALA | C | 23.49 | 37.96 | 27.81 | 29.83 |
| 101 ALA | O | 22.76 | 38.98 | 27.82 | 30.02 |
| 102 ALA | N | 24.35 | 37.61 | 28.77 | 30.00 |
| 102 ALA | CA | 24.70 | 38.56 | 29.82 | 30.27 |
| 102 ALA | CB | 25.58 | 37.91 | 30.86 | 31.28 |
| 102 ALA | C | 25.57 | 39.33 | 28.83 | 29.14 |
| 102 ALA | O | 25.24 | 40.43 | 28.39 | 28.35 |
| 103 ILE | N | 26.44 | 38.53 | 28.25 | 29.66 |
| 103 ILE | CA | 27.37 | 38.98 | 27.25 | 33.49 |
| 103 ILE | CB | 28.76 | 39.19 | 27.89 | 33.70 |
| 103 ILE | C | 27.41 | 37.85 | 26.21 | 35.49 |
| 103 ILE | O | 28.33 | 37.87 | 25.33 | 36.26 |
| 103 ILE | OT | 26.56 | 36.91 | 26.34 | 36.09 |
| 113 ARG | CB | 23.51 | 46.04 | 17.34 | 18.99 |
| 113 ARG | CG | 24.59 | 47.13 | 17.30 | 20.59 |
| 113 ARG | CD | 25.59 | 47.03 | 18.47 | 25.46 |
| 113 ARG | NE | 26.33 | 45.76 | 18.47 | 29.74 |
| 113 ARG | CZ | 26.69 | 45.09 | 19.57 | 28.63 |
| 113 ARG | NH1 | 27.36 | 43.93 | 19.47 | 26.03 |
| 113 ARG | NH2 | 26.40 | 45.60 | 20.77 | 31.45 |
| 113 ARG | C | 22.24 | 44.52 | 15.77 | 20.25 |
| 113 ARG | O | 21.47 | 43.97 | 16.52 | 21.30 |
| 113 ARG | N | 21.85 | 47.03 | 15.77 | 22.12 |
| 113 ARG | CA | 22.77 | 45.91 | 16.00 | 19.32 |
| 114 GLU | N | 22.59 | 44.05 | 14.60 | 23.15 |
| 114 GLU | CA | 22.34 | 42.73 | 14.04 | 23.09 |
| 114 GLU | CB | 21.77 | 42.92 | 12.65 | 24.43 |
| 114 GLU | CG | 22.55 | 43.98 | 11.90 | 27.32 |
| 114 GLU | CD | 22.26 | 43.99 | 10.42 | 33.37 |

Figure 5W

| Residue | Atom | X | Y | Z | B |
|---|---|---|---|---|---|
| 114 GLU | OE1 | 21.80 | 42.94 | 9.89 | 35.72 |
| 114 GLU | OE2 | 22.51 | 45.06 | 9.79 | 34.77 |
| 114 GLU | C | 23.79 | 42.18 | 13.92 | 22.64 |
| 114 GLU | O | 24.08 | 41.27 | 13.15 | 20.26 |
| 115 GLU | N | 24.69 | 42.89 | 14.60 | 22.39 |
| 115 GLU | CA | 26.10 | 42.60 | 14.73 | 20.62 |
| 115 GLU | CB | 26.85 | 43.88 | 15.18 | 22.97 |
| 115 GLU | CG | 27.12 | 44.94 | 14.04 | 31.25 |
| 115 GLU | CD | 25.99 | 46.01 | 13.77 | 37.09 |
| 115 GLU | OE1 | 25.17 | 46.29 | 14.68 | 38.27 |
| 115 GLU | OE2 | 25.93 | 46.60 | 12.64 | 36.47 |
| 115 GLU | C | 26.07 | 41.52 | 15.82 | 18.19 |
| 115 GLU | O | 26.87 | 40.61 | 15.84 | 16.89 |
| 116 ARG | N | 25.06 | 41.59 | 16.67 | 18.07 |
| 116 ARG | CA | 24.84 | 40.62 | 17.73 | 17.02 |
| 116 ARG | CB | 23.68 | 41.05 | 18.62 | 19.38 |
| 116 ARG | CG | 24.02 | 41.10 | 20.15 | 29.57 |
| 116 ARG | CD | 24.12 | 39.70 | 20.92 | 30.71 |
| 116 ARG | NE | 24.52 | 39.92 | 22.32 | 32.10 |
| 116 ARG | CZ | 25.77 | 39.76 | 22.78 | 33.92 |
| 116 ARG | NH1 | 26.73 | 39.34 | 21.95 | 33.08 |
| 116 ARG | NH2 | 26.07 | 40.15 | 24.04 | 33.45 |
| 116 ARG | C | 24.49 | 39.31 | 17.06 | 14.36 |
| 116 ARG | O | 24.93 | 38.27 | 17.50 | 15.85 |
| 117 LEU | N | 23.67 | 39.39 | 16.02 | 12.55 |
| 117 LEU | CA | 23.27 | 38.20 | 15.27 | 11.60 |
| 117 LEU | CB | 22.25 | 38.55 | 14.17 | 10.36 |
| 117 LEU | CG | 21.97 | 37.39 | 13.20 | 11.78 |
| 117 LEU | CD1 | 21.28 | 36.26 | 13.94 | 10.40 |
| 117 LEU | CD2 | 21.18 | 37.83 | 11.95 | 9.62 |

Figure 5X

| Residue | Atom | X | Y | Z | B |
|---|---|---|---|---|---|
| 117 LEU | C | 24.51 | 37.57 | 14.63 | 12.59 |
| 117 LEU | O | 24.73 | 36.35 | 14.74 | 14.14 |
| 118 LEU | N | 25.32 | 38.40 | 13.97 | 10.04 |
| 118 LEU | CA | 26.52 | 37.92 | 13.34 | 8.44 |
| 118 LEU | CB | 27.17 | 39.06 | 12.59 | 6.10 |
| 118 LEU | CG | 26.92 | 39.21 | 11.11 | 4.04 |
| 118 LEU | CD1 | 26.22 | 38.02 | 10.54 | 2.00 |
| 118 LEU | CD2 | 26.22 | 40.51 | 10.86 | 2.00 |
| 118 LEU | C | 27.52 | 37.32 | 14.33 | 9.99 |
| 118 LEU | O | 28.18 | 36.33 | 14.04 | 11.91 |
| 119 TYR | N | 27.59 | 37.90 | 15.52 | 11.11 |
| 119 TYR | CA | 28.49 | 37.42 | 16.56 | 12.87 |
| 119 TYR | CB | 28.61 | 38.46 | 17.68 | 17.73 |
| 119 TYR | CG | 29.24 | 38.00 | 18.98 | 22.08 |
| 119 TYR | CD1 | 28.54 | 37.18 | 19.87 | 24.95 |
| 119 TYR | CE1 | 29.06 | 36.83 | 21.09 | 25.82 |
| 119 TYR | CD2 | 30.50 | 38.46 | 19.36 | 22.55 |
| 119 TYR | CE2 | 31.03 | 38.12 | 20.57 | 24.18 |
| 119 TYR | CZ | 30.30 | 37.31 | 21.43 | 27.76 |
| 119 TYR | OH | 30.77 | 37.00 | 22.69 | 36.13 |
| 119 TYR | C | 28.04 | 36.06 | 17.09 | 12.48 |
| 119 TYR | O | 28.88 | 35.20 | 17.37 | 14.79 |
| 120 LEU | N | 26.73 | 35.85 | 17.18 | 9.50 |
| 120 LEU | CA | 26.20 | 34.60 | 17.66 | 6.08 |
| 120 LEU | CB | 24.73 | 34.78 | 18.06 | 6.24 |
| 120 LEU | CG | 24.30 | 35.27 | 19.45 | 5.20 |
| 120 LEU | CD1 | 24.96 | 36.55 | 19.82 | 6.12 |
| 120 LEU | CD2 | 22.83 | 35.47 | 19.46 | 4.68 |
| 120 LEU | C | 26.36 | 33.45 | 16.66 | 4.31 |
| 120 LEU | O | 26.77 | 32.35 | 17.01 | 3.72 |

Figure 5Y

| Residue | Atom | X | Y | Z | B |
|---|---|---|---|---|---|
| 121 ILE | N | 26.06 | 33.73 | 15.39 | 2.53 |
| 121 ILE | CA | 26.16 | 32.69 | 14.37 | 3.35 |
| 121 ILE | CB | 25.36 | 33.09 | 13.09 | 3.10 |
| 121 ILE | CG2 | 25.98 | 34.28 | 12.42 | 3.81 |
| 121 ILE | CG1 | 25.33 | 31.95 | 12.07 | 3.74 |
| 121 ILE | CD1 | 24.37 | 30.88 | 12.38 | 8.68 |
| 121 ILE | C | 27.60 | 32.30 | 14.04 | 5.31 |
| 121 ILE | O | 27.89 | 31.12 | 13.86 | 5.15 |
| 122 THR | N | 28.52 | 33.28 | 14.05 | 5.85 |
| 122 THR | CA | 29.94 | 33.03 | 13.76 | 4.14 |
| 122 THR | CB | 30.72 | 34.30 | 13.73 | 3.64 |
| 122 THR | OG1 | 30.31 | 35.09 | 12.62 | 7.50 |
| 122 THR | CG2 | 32.19 | 33.99 | 13.61 | 2.50 |
| 122 THR | C | 30.64 | 32.10 | 14.72 | 5.58 |
| 122 THR | O | 31.31 | 31.16 | 14.31 | 5.86 |
| 123 ASN | N | 30.50 | 32.38 | 16.02 | 7.95 |
| 123 ASN | CA | 31.11 | 31.58 | 17.08 | 7.96 |
| 123 ASN | CB | 31.24 | 32.40 | 18.35 | 9.01 |
| 123 ASN | CG | 32.26 | 33.52 | 18.22 | 10.01 |
| 123 ASN | OD1 | 31.93 | 34.70 | 18.14 | 6.01 |
| 123 ASN | ND2 | 33.52 | 33.13 | 18.16 | 12.74 |
| 123 ASN | C | 30.40 | 30.27 | 17.34 | 8.91 |
| 123 ASN | O | 31.02 | 29.31 | 17.77 | 12.08 |
| 124 TYR | N | 29.10 | 30.21 | 17.07 | 9.22 |
| 124 TYR | CA | 28.35 | 28.97 | 17.27 | 9.33 |
| 124 TYR | CB | 26.83 | 29.25 | 17.42 | 6.09 |
| 124 TYR | CG | 26.10 | 28.12 | 18.13 | 2.89 |
| 124 TYR | CD1 | 26.21 | 27.98 | 19.51 | 2.00 |
| 124 TYR | CE1 | 25.65 | 26.90 | 20.16 | 2.00 |
| 124 TYR | CD2 | 25.41 | 27.15 | 17.43 | 2.96 |

Figure 5Z

| Residue | Atom | X | Y | Z | B |
|---|---|---|---|---|---|
| 124 TYR | CE2 | 24.85 | 26.06 | 18.08 | 2.00 |
| 124 TYR | CZ | 24.98 | 25.95 | 19.44 | 2.00 |
| 124 TYR | OH | 24.45 | 24.90 | 20.09 | 8.86 |
| 124 TYR | C | 28.65 | 27.97 | 16.13 | 8.61 |
| 124 TYR | O | 28.92 | 26.79 | 16.35 | 8.04 |
| 125 LEU | N | 28.61 | 28.45 | 14.91 | 9.47 |
| 125 LEU | CA | 28.87 | 27.57 | 13.78 | 10.58 |
| 125 LEU | CB | 27.57 | 27.34 | 13.02 | 12.80 |
| 125 LEU | CG | 26.38 | 26.77 | 13.80 | 8.87 |
| 125 LEU | CD1 | 25.14 | 27.30 | 13.12 | 10.24 |
| 125 LEU | CD2 | 26.40 | 25.25 | 13.86 | 6.51 |
| 125 LEU | C | 29.96 | 28.21 | 12.90 | 10.55 |
| 125 LEU | O | 29.67 | 28.87 | 11.88 | 7.34 |
| 126 PRO | N | 31.23 | 28.02 | 13.29 | 11.29 |
| 126 PRO | CD | 31.71 | 27.28 | 14.47 | 10.63 |
| 126 PRO | CA | 32.37 | 28.57 | 12.56 | 9.46 |
| 126 PRO | CB | 33.49 | 28.56 | 13.60 | 7.45 |
| 126 PRO | CG | 32.85 | 28.11 | 14.89 | 8.18 |
| 126 PRO | C | 32.81 | 27.76 | 11.35 | 9.95 |
| 126 PRO | O | 33.57 | 28.28 | 10.53 | 10.59 |
| 127 SER | N | 32.35 | 26.51 | 11.23 | 7.34 |
| 127 SER | CA | 32.78 | 25.64 | 10.14 | 7.69 |
| 127 SER | CB | 33.33 | 24.36 | 10.71 | 7.69 |
| 127 SER | OG | 34.45 | 24.61 | 11.53 | 12.66 |
| 127 SER | C | 31.75 | 25.27 | 9.10 | 7.85 |
| 127 SER | O | 30.58 | 25.48 | 9.30 | 11.85 |
| 128 VAL | N | 32.23 | 24.80 | 7.95 | 4.94 |
| 128 VAL | CA | 31.36 | 24.32 | 6.89 | 5.12 |
| 128 VAL | CB | 31.40 | 25.12 | 5.59 | 2.60 |
| 128 VAL | CG1 | 31.07 | 26.50 | 5.86 | 11.40 |

Figure 5AA

| Residue | Atom | X | Y | Z | B |
|---|---|---|---|---|---|
| 128 VAL | CG2 | 32.70 | 25.03 | 4.93 | 2.00 |
| 128 VAL | C | 31.84 | 22.93 | 6.62 | 7.19 |
| 128 VAL | O | 32.97 | 22.58 | 6.92 | 11.48 |
| 129 SER | N | 30.97 | 22.13 | 6.04 | 6.97 |
| 129 SER | CA | 31.32 | 20.78 | 5.73 | 7.38 |
| 129 SER | CB | 30.73 | 19.90 | 6.80 | 8.32 |
| 129 SER | OG | 31.11 | 18.56 | 6.62 | 14.12 |
| 129 SER | C | 30.68 | 20.52 | 4.37 | 9.06 |
| 129 SER | O | 29.51 | 20.77 | 4.20 | 11.11 |
| 130 LEU | N | 31.47 | 20.13 | 3.38 | 8.54 |
| 130 LEU | CA | 30.93 | 19.85 | 2.07 | 8.69 |
| 130 LEU | CB | 31.97 | 20.16 | 0.99 | 12.13 |
| 130 LEU | CG | 31.88 | 19.67 | -0.47 | 11.59 |
| 130 LEU | CD1 | 30.63 | 20.19 | -1.18 | 7.88 |
| 130 LEU | CD2 | 33.15 | 20.15 | -1.20 | 12.99 |
| 130 LEU | C | 30.56 | 18.41 | 1.96 | 7.67 |
| 130 LEU | O | 31.36 | 17.56 | 2.22 | 10.85 |
| 131 SER | N | 29.32 | 18.10 | 1.66 | 7.41 |
| 131 SER | CA | 29.03 | 16.71 | 1.46 | 10.24 |
| 131 SER | CB | 27.65 | 16.35 | 1.96 | 12.02 |
| 131 SER | OG | 27.68 | 16.30 | 3.36 | 18.85 |
| 131 SER | C | 29.16 | 16.49 | -0.04 | 12.33 |
| 131 SER | O | 28.84 | 17.37 | -0.85 | 13.24 |
| 132 THR | N | 29.73 | 15.36 | -0.41 | 14.15 |
| 132 THR | CA | 29.89 | 14.98 | -1.80 | 15.87 |
| 132 THR | CB | 31.34 | 14.59 | -2.10 | 13.37 |
| 132 THR | OG1 | 31.80 | 13.73 | -1.08 | 12.74 |
| 132 THR | CG2 | 32.24 | 15.82 | -2.18 | 11.44 |
| 132 THR | C | 29.00 | 13.77 | -1.94 | 18.29 |
| 132 THR | O | 29.23 | 12.74 | -1.28 | 19.88 |

Figure 5BB

| Residue | Atom | X | Y | Z | B |
|---|---|---|---|---|---|
| 133 LYS | N | 27.94 | 13.93 | -2.72 | 22.98 |
| 133 LYS | CA | 26.95 | 12.87 | -2.99 | 26.56 |
| 133 LYS | CB | 25.72 | 13.45 | -3.76 | 22.20 |
| 133 LYS | C | 27.51 | 11.62 | -3.73 | 27.59 |
| 133 LYS | O | 28.76 | 11.46 | -3.88 | 23.36 |
| 133 LYS | OT | 26.63 | 10.80 | -4.13 | 33.47 |
| 141 PRO | CB | 35.57 | 12.86 | -10.86 | 23.68 |
| 141 PRO | C | 33.22 | 13.47 | -11.76 | 26.20 |
| 141 PRO | O | 33.51 | 13.12 | -12.90 | 24.99 |
| 141 PRO | N | 33.44 | 11.63 | -10.15 | 31.18 |
| 141 PRO | CA | 34.01 | 12.96 | -10.54 | 28.79 |
| 142 ASP | N | 32.12 | 14.16 | -11.45 | 25.77 |
| 142 ASP | CA | 31.21 | 14.78 | -12.41 | 24.78 |
| 142 ASP | CB | 30.18 | 13.81 | -13.02 | 22.65 |
| 142 ASP | CG | 29.62 | 12.83 | -12.03 | 20.99 |
| 142 ASP | OD1 | 29.84 | 12.97 | -10.82 | 22.51 |
| 142 ASP | OD2 | 28.98 | 11.87 | -12.49 | 19.92 |
| 142 ASP | C | 30.52 | 15.89 | -11.63 | 24.33 |
| 142 ASP | O | 30.73 | 16.00 | -10.43 | 24.66 |
| 143 ARG | N | 29.65 | 16.66 | -12.28 | 23.24 |
| 143 ARG | CA | 29.00 | 17.79 | -11.63 | 22.71 |
| 143 ARG | CB | 28.28 | 18.61 | -12.67 | 21.47 |
| 143 ARG | CG | 29.03 | 18.65 | -13.97 | 21.99 |
| 143 ARG | CD | 28.92 | 19.99 | -14.54 | 28.60 |
| 143 ARG | NE | 29.52 | 20.08 | -15.87 | 33.70 |
| 143 ARG | CZ | 30.76 | 20.49 | -16.11 | 33.84 |
| 143 ARG | NH1 | 31.20 | 20.56 | -17.36 | 34.28 |
| 143 ARG | NH2 | 31.57 | 20.78 | -15.10 | 32.21 |
| 143 ARG | C | 28.10 | 17.42 | -10.43 | 24.76 |
| 143 ARG | O | 27.83 | 18.25 | -9.52 | 25.81 |

Figure 5CC

| Residue | Atom | X | Y | Z | B |
|---|---|---|---|---|---|
| 144 THR | N | 27.71 | 16.16 | -10.40 | 22.71 |
| 144 THR | CA | 26.88 | 15.60 | -9.34 | 21.04 |
| 144 THR | CB | 26.08 | 14.44 | -9.92 | 22.19 |
| 144 THR | OG1 | 26.90 | 13.73 | -10.86 | 25.50 |
| 144 THR | CG2 | 24.89 | 14.96 | -10.65 | 25.73 |
| 144 THR | C | 27.72 | 15.09 | -8.16 | 19.87 |
| 144 THR | O | 27.34 | 14.14 | -7.47 | 20.20 |
| 145 LEU | N | 28.88 | 15.69 | -7.96 | 19.59 |
| 145 LEU | CA | 29.74 | 15.22 | -6.88 | 17.69 |
| 145 LEU | CB | 31.22 | 15.48 | -7.22 | 15.20 |
| 145 LEU | CG | 32.22 | 15.05 | -6.15 | 16.04 |
| 145 LEU | CD1 | 32.20 | 13.56 | -5.96 | 14.53 |
| 145 LEU | CD2 | 33.59 | 15.53 | -6.50 | 13.03 |
| 145 LEU | C | 29.34 | 15.89 | -5.59 | 17.52 |
| 145 LEU | O | 29.11 | 15.23 | -4.61 | 20.75 |
| 146 PHE | N | 29.18 | 17.20 | -5.63 | 17.08 |
| 146 PHE | CA | 28.80 | 17.99 | -4.46 | 16.09 |
| 146 PHE | CB | 29.26 | 19.43 | -4.70 | 15.22 |
| 146 PHE | CG | 30.77 | 19.58 | -4.82 | 13.02 |
| 146 PHE | CD1 | 31.33 | 20.81 | -5.10 | 8.98 |
| 146 PHE | CD2 | 31.62 | 18.49 | -4.60 | 12.64 |
| 146 PHE | CE1 | 32.72 | 20.96 | -5.14 | 8.43 |
| 146 PHE | CE2 | 32.99 | 18.63 | -4.65 | 10.95 |
| 146 PHE | CZ | 33.55 | 19.87 | -4.92 | 8.47 |
| 146 PHE | C | 27.28 | 17.94 | -4.12 | 15.64 |
| 146 PHE | O | 26.45 | 18.43 | -4.89 | 17.26 |
| 147 ALA | N | 26.93 | 17.30 | -3.00 | 13.26 |
| 147 ALA | CA | 25.55 | 17.20 | -2.55 | 8.71 |
| 147 ALA | CB | 25.41 | 16.04 | -1.61 | 7.80 |
| 147 ALA | C | 25.10 | 18.50 | -1.89 | 8.81 |

Figure 5DD

| Residue | Atom | X | Y | Z | B |
|---|---|---|---|---|---|
| 147 ALA | O | 24.22 | 19.17 | -2.37 | 10.64 |
| 148 HIS | N | 25.72 | 18.90 | -0.80 | 8.71 |
| 148 HIS | CA | 25.34 | 20.14 | -0.15 | 8.60 |
| 148 HIS | C | 26.51 | 20.61 | 0.73 | 8.75 |
| 148 HIS | O | 27.57 | 20.01 | 0.73 | 9.64 |
| 148 HIS | CB | 24.11 | 19.91 | 0.72 | 7.49 |
| 148 HIS | CG | 24.35 | 18.95 | 1.85 | 10.55 |
| 148 HIS | ND1 | 24.75 | 19.32 | 3.11 | 14.28 |
| 148 HIS | CD2 | 24.25 | 17.60 | 1.89 | 13.72 |
| 148 HIS | NE2 | 24.59 | 17.13 | 3.17 | 10.96 |
| 148 HIS | CE1 | 24.88 | 18.20 | 3.87 | 11.30 |
| 149 VAL | N | 26.28 | 21.66 | 1.52 | 5.64 |
| 149 VAL | CA | 27.28 | 22.20 | 2.42 | 4.43 |
| 149 VAL | CB | 27.91 | 23.52 | 1.85 | 2.00 |
| 149 VAL | CG1 | 27.13 | 24.01 | 0.72 | 2.60 |
| 149 VAL | CG2 | 28.02 | 24.63 | 2.90 | 2.00 |
| 149 VAL | C | 26.66 | 22.41 | 3.81 | 5.08 |
| 149 VAL | O | 25.76 | 23.23 | 3.99 | 6.81 |
| 150 ALA | N | 27.07 | 21.63 | 4.79 | 4.31 |
| 150 ALA | CA | 26.54 | 21.77 | 6.12 | 4.19 |
| 150 ALA | CB | 26.61 | 20.47 | 6.82 | 2.00 |
| 150 ALA | C | 27.27 | 22.85 | 6.92 | 6.21 |
| 150 ALA | O | 28.45 | 23.04 | 6.74 | 8.36 |
| 151 LEU | N | 26.52 | 23.64 | 7.70 | 8.89 |
| 151 LEU | CA | 27.04 | 24.68 | 8.59 | 8.16 |
| 151 LEU | CB | 25.96 | 25.72 | 8.87 | 6.76 |
| 151 LEU | CG | 26.17 | 27.20 | 8.57 | 13.35 |
| 151 LEU | CD1 | 26.80 | 27.33 | 7.16 | 14.96 |
| 151 LEU | CD2 | 24.86 | 28.01 | 8.69 | 2.52 |
| 151 LEU | C | 27.28 | 23.87 | 9.88 | 10.36 |

Figure 5EE

| Residue | Atom | X | Y | Z | B |
|---|---|---|---|---|---|
| 151 LEU | O | 26.40 | 23.13 | 10.32 | 11.10 |
| 152 CYS | N | 28.45 | 23.97 | 10.47 | 10.07 |
| 152 CYS | CA | 28.70 | 23.20 | 11.68 | 10.06 |
| 152 CYS | CB | 29.09 | 21.78 | 11.30 | 9.56 |
| 152 CYS | SG | 30.55 | 21.68 | 10.32 | 12.05 |
| 152 CYS | C | 29.70 | 23.84 | 12.62 | 10.73 |
| 152 CYS | O | 30.22 | 24.91 | 12.35 | 10.79 |
| 153 ALA | N | 29.91 | 23.18 | 13.75 | 12.36 |
| 153 ALA | CA | 30.82 | 23.66 | 14.81 | 13.12 |
| 153 ALA | CB | 30.51 | 22.92 | 16.14 | 11.10 |
| 153 ALA | C | 32.29 | 23.51 | 14.48 | 12.28 |
| 153 ALA | O | 33.04 | 24.47 | 14.54 | 11.41 |
| 154 ILE | N | 32.67 | 22.27 | 14.19 | 13.17 |
| 154 ILE | CA | 34.04 | 21.91 | 13.84 | 14.44 |
| 154 ILE | CB | 34.76 | 21.20 | 15.06 | 16.21 |
| 154 ILE | CG2 | 35.94 | 20.37 | 14.62 | 16.07 |
| 154 ILE | CG1 | 35.25 | 22.26 | 16.04 | 18.38 |
| 154 ILE | CD1 | 36.24 | 23.28 | 15.42 | 19.24 |
| 154 ILE | C | 33.90 | 20.99 | 12.62 | 14.39 |
| 154 ILE | O | 33.23 | 19.97 | 12.69 | 13.58 |
| 155 GLY | N | 34.40 | 21.47 | 11.48 | 16.35 |
| 155 GLY | CA | 34.31 | 20.72 | 10.24 | 18.21 |
| 155 GLY | C | 35.41 | 19.67 | 10.20 | 20.38 |
| 155 GLY | O | 36.41 | 19.78 | 10.93 | 21.76 |
| 156 ARG | N | 35.26 | 18.69 | 9.32 | 20.77 |
| 156 ARG | CA | 36.24 | 17.61 | 9.21 | 21.11 |
| 156 ARG | CB | 35.53 | 16.30 | 8.87 | 24.90 |
| 156 ARG | CG | 35.76 | 15.25 | 9.94 | 29.04 |
| 156 ARG | CD | 34.71 | 14.16 | 9.85 | 32.89 |
| 156 ARG | NE | 34.84 | 13.39 | 8.62 | 39.65 |

Figure 5FF

| Residue | Atom | X | Y | Z | B |
|---|---|---|---|---|---|
| 156 ARG | CZ | 34.67 | 12.06 | 8.54 | 43.91 |
| 156 ARG | NH1 | 34.81 | 11.44 | 7.34 | 44.98 |
| 156 ARG | NH2 | 34.32 | 11.35 | 9.63 | 42.89 |
| 156 ARG | C | 37.40 | 17.83 | 8.24 | 20.04 |
| 156 ARG | O | 38.31 | 17.01 | 8.18 | 22.30 |
| 157 ARG | N | 37.35 | 18.89 | 7.45 | 17.53 |
| 157 ARG | CA | 38.43 | 19.17 | 6.53 | 15.10 |
| 157 ARG | CB | 37.95 | 19.20 | 5.08 | 11.19 |
| 157 ARG | CG | 37.67 | 17.82 | 4.59 | 7.60 |
| 157 ARG | CD | 37.61 | 17.73 | 3.11 | 10.17 |
| 157 ARG | NE | 36.33 | 18.14 | 2.57 | 15.38 |
| 157 ARG | CZ | 35.39 | 17.30 | 2.14 | 17.80 |
| 157 ARG | NH1 | 35.56 | 15.99 | 2.20 | 14.74 |
| 157 ARG | NH2 | 34.30 | 17.77 | 1.53 | 18.94 |
| 157 ARG | C | 39.11 | 20.45 | 7.00 | 15.95 |
| 157 ARG | O | 38.48 | 21.29 | 7.67 | 15.82 |
| 158 LEU | N | 40.43 | 20.54 | 6.74 | 13.11 |
| 158 LEU | CA | 41.25 | 21.66 | 7.17 | 10.75 |
| 158 LEU | CB | 42.75 | 21.33 | 7.01 | 10.39 |
| 158 LEU | CG | 43.57 | 20.34 | 7.89 | 8.24 |
| 158 LEU | CD1 | 43.12 | 20.23 | 9.32 | 5.72 |
| 158 LEU | CD2 | 43.54 | 19.00 | 7.28 | 9.04 |
| 158 LEU | C | 40.95 | 23.00 | 6.55 | 10.71 |
| 158 LEU | O | 40.52 | 23.10 | 5.41 | 12.41 |
| 159 GLY | N | 41.14 | 24.05 | 7.33 | 9.74 |
| 159 GLY | CA | 40.90 | 25.38 | 6.83 | 11.59 |
| 159 GLY | C | 39.47 | 25.78 | 6.54 | 13.36 |
| 159 GLY | O | 39.19 | 26.92 | 6.09 | 14.85 |
| 160 THR | N | 38.55 | 24.89 | 6.85 | 12.99 |
| 160 THR | CA | 37.14 | 25.15 | 6.59 | 11.29 |

Figure 5GG

| Residue | Atom | X | Y | Z | B |
|---|---|---|---|---|---|
| 160 THR | CB | 36.41 | 23.84 | 6.33 | 13.60 |
| 160 THR | OG1 | 36.60 | 22.95 | 7.45 | 13.94 |
| 160 THR | CG2 | 36.98 | 23.18 | 5.06 | 14.91 |
| 160 THR | C | 36.45 | 25.93 | 7.68 | 9.45 |
| 160 THR | O | 35.60 | 25.41 | 8.34 | 10.14 |
| 161 ILE | N | 36.92 | 27.14 | 7.94 | 10.38 |
| 161 ILE | CA | 36.32 | 28.03 | 8.91 | 8.13 |
| 161 ILE | CB | 37.33 | 28.54 | 9.92 | 2.00 |
| 161 ILE | CG2 | 36.76 | 29.64 | 10.75 | 3.52 |
| 161 ILE | CG1 | 37.70 | 27.39 | 10.86 | 3.90 |
| 161 ILE | CD1 | 36.64 | 26.97 | 11.81 | 2.00 |
| 161 ILE | C | 35.76 | 29.13 | 8.03 | 10.09 |
| 161 ILE | O | 36.38 | 29.46 | 6.99 | 10.40 |
| 162 VAL | N | 34.58 | 29.63 | 8.36 | 8.80 |
| 162 VAL | CA | 33.97 | 30.62 | 7.50 | 9.20 |
| 162 VAL | CB | 32.73 | 30.05 | 6.87 | 9.13 |
| 162 VAL | CG1 | 33.10 | 28.81 | 6.09 | 4.95 |
| 162 VAL | CG2 | 31.72 | 29.73 | 7.93 | 11.25 |
| 162 VAL | C | 33.68 | 31.99 | 8.06 | 11.53 |
| 162 VAL | O | 33.77 | 32.20 | 9.26 | 15.32 |
| 163 THR | N | 33.41 | 32.94 | 7.16 | 12.01 |
| 163 THR | CA | 33.10 | 34.32 | 7.52 | 10.38 |
| 163 THR | CB | 34.05 | 35.26 | 6.81 | 6.93 |
| 163 THR | OG1 | 35.37 | 34.99 | 7.25 | 6.33 |
| 163 THR | CG2 | 33.77 | 36.65 | 7.16 | 8.99 |
| 163 THR | C | 31.61 | 34.61 | 7.20 | 12.20 |
| 163 THR | O | 31.08 | 34.09 | 6.22 | 14.86 |
| 164 TYR | N | 30.91 | 35.31 | 8.10 | 10.65 |
| 164 TYR | CA | 29.49 | 35.65 | 7.94 | 6.92 |
| 164 TYR | CB | 28.59 | 35.17 | 9.10 | 5.68 |

Figure 5HH

| Residue | Atom | X | Y | Z | B |
|---|---|---|---|---|---|
| 164 TYR | CG | 28.47 | 33.67 | 9.33 | 5.70 |
| 164 TYR | CD1 | 29.46 | 32.96 | 10.03 | 9.47 |
| 164 TYR | CE1 | 29.36 | 31.57 | 10.24 | 9.65 |
| 164 TYR | CD2 | 27.38 | 32.97 | 8.85 | 4.93 |
| 164 TYR | CE2 | 27.25 | 31.59 | 9.04 | 4.75 |
| 164 TYR | CZ | 28.25 | 30.90 | 9.73 | 8.93 |
| 164 TYR | OH | 28.16 | 29.53 | 9.91 | 5.04 |
| 164 TYR | C | 29.45 | 37.14 | 7.99 | 6.97 |
| 164 TYR | O | 30.10 | 37.74 | 8.82 | 6.41 |
| 165 ASP | N | 28.63 | 37.72 | 7.13 | 9.42 |
| 165 ASP | CA | 28.46 | 39.14 | 7.07 | 7.63 |
| 165 ASP | CB | 29.69 | 39.78 | 6.52 | 8.26 |
| 165 ASP | CG | 30.01 | 41.06 | 7.23 | 13.00 |
| 165 ASP | OD1 | 29.23 | 42.02 | 7.14 | 11.86 |
| 165 ASP | OD2 | 31.08 | 41.10 | 7.88 | 18.63 |
| 165 ASP | C | 27.28 | 39.56 | 6.23 | 7.52 |
| 165 ASP | O | 26.80 | 38.82 | 5.39 | 6.42 |
| 166 THR | N | 26.83 | 40.78 | 6.46 | 7.08 |
| 166 THR | CA | 25.71 | 41.33 | 5.75 | 8.22 |
| 166 THR | CB | 25.04 | 42.46 | 6.57 | 8.96 |
| 166 THR | OG1 | 26.03 | 43.39 | 7.02 | 7.50 |
| 166 THR | CG2 | 24.31 | 41.90 | 7.76 | 7.28 |
| 166 THR | C | 26.18 | 41.89 | 4.41 | 9.77 |
| 166 THR | O | 25.66 | 42.87 | 3.94 | 14.12 |
| 167 SER | N | 27.16 | 41.27 | 3.78 | 10.31 |
| 167 SER | CA | 27.66 | 41.77 | 2.51 | 10.89 |
| 167 SER | CB | 28.41 | 43.07 | 2.73 | 7.08 |
| 167 SER | OG | 29.09 | 43.45 | 1.56 | 10.27 |
| 167 SER | C | 28.59 | 40.74 | 1.95 | 14.09 |
| 167 SER | O | 29.32 | 40.11 | 2.71 | 15.00 |

Figure 5II

| Residue | Atom | X | Y | Z | B |
|---|---|---|---|---|---|
| 168 LEU | N | 28.60 | 40.58 | 0.62 | 16.24 |
| 168 LEU | CA | 29.49 | 39.60 | -0.02 | 15.71 |
| 168 LEU | CB | 29.15 | 39.44 | -1.50 | 13.79 |
| 168 LEU | CG | 29.69 | 38.25 | -2.27 | 9.75 |
| 168 LEU | CD1 | 29.01 | 38.19 | -3.57 | 11.59 |
| 168 LEU | CD2 | 31.14 | 38.40 | -2.50 | 14.35 |
| 168 LEU | C | 30.93 | 40.03 | 0.13 | 15.86 |
| 168 LEU | O | 31.75 | 39.26 | 0.57 | 16.44 |
| 169 ASP | N | 31.20 | 41.29 | -0.19 | 17.47 |
| 169 ASP | CA | 32.53 | 41.86 | -0.09 | 18.64 |
| 169 ASP | CB | 32.52 | 43.26 | -0.65 | 19.99 |
| 169 ASP | CG | 31.78 | 43.34 | -1.94 | 22.71 |
| 169 ASP | OD1 | 30.59 | 43.72 | -1.88 | 31.45 |
| 169 ASP | OD2 | 32.32 | 42.94 | -2.99 | 19.11 |
| 169 ASP | C | 33.08 | 41.85 | 1.31 | 18.68 |
| 169 ASP | O | 34.27 | 41.66 | 1.50 | 22.89 |
| 170 ALA | N | 32.23 | 42.09 | 2.30 | 16.76 |
| 170 ALA | CA | 32.65 | 42.06 | 3.68 | 13.79 |
| 170 ALA | CB | 31.62 | 42.68 | 4.52 | 13.68 |
| 170 ALA | C | 32.88 | 40.61 | 4.10 | 11.53 |
| 170 ALA | O | 33.81 | 40.32 | 4.81 | 12.15 |
| 171 ALA | N | 32.04 | 39.70 | 3.62 | 9.82 |
| 171 ALA | CA | 32.15 | 38.28 | 3.95 | 9.28 |
| 171 ALA | CB | 30.97 | 37.52 | 3.38 | 2.67 |
| 171 ALA | C | 33.44 | 37.70 | 3.42 | 12.12 |
| 171 ALA | O | 34.04 | 36.84 | 4.06 | 12.36 |
| 172 ILE | N | 33.89 | 38.16 | 2.25 | 13.16 |
| 172 ILE | CA | 35.12 | 37.64 | 1.68 | 13.45 |
| 172 ILE | CB | 35.01 | 37.34 | 0.16 | 14.59 |
| 172 ILE | CG2 | 33.88 | 36.35 | -0.11 | 15.84 |

Figure 5JJ

| Residue | Atom | X | Y | Z | B |
|---|---|---|---|---|---|
| 172 ILE | CG1 | 34.84 | 38.60 | -0.67 | 12.70 |
| 172 ILE | CD1 | 35.00 | 38.32 | -2.17 | 8.60 |
| 172 ILE | C | 36.39 | 38.44 | 1.95 | 13.84 |
| 172 ILE | O | 37.49 | 37.93 | 1.76 | 11.09 |
| 173 ALA | N | 36.25 | 39.68 | 2.43 | 13.69 |
| 173 ALA | CA | 37.41 | 40.53 | 2.74 | 13.94 |
| 173 ALA | CB | 36.97 | 41.93 | 3.20 | 10.45 |
| 173 ALA | C | 38.46 | 39.94 | 3.73 | 13.56 |
| 173 ALA | O | 39.66 | 40.12 | 3.55 | 13.78 |
| 174 PRO | N | 38.03 | 39.25 | 4.79 | 11.86 |
| 174 PRO | CD | 36.74 | 39.08 | 5.47 | 12.92 |
| 174 PRO | CA | 39.08 | 38.75 | 5.64 | 11.43 |
| 174 PRO | CB | 38.34 | 38.39 | 6.92 | 11.43 |
| 174 PRO | CG | 37.09 | 38.01 | 6.46 | 12.49 |
| 174 PRO | C | 39.80 | 37.59 | 5.03 | 12.85 |
| 174 PRO | O | 40.57 | 36.92 | 5.72 | 15.52 |
| 175 PHE | N | 39.58 | 37.32 | 3.76 | 13.77 |
| 175 PHE | CA | 40.36 | 36.25 | 3.11 | 15.02 |
| 175 PHE | CB | 39.48 | 35.31 | 2.28 | 15.53 |
| 175 PHE | CG | 38.50 | 34.52 | 3.10 | 10.81 |
| 175 PHE | CD1 | 38.83 | 33.25 | 3.56 | 5.68 |
| 175 PHE | CD2 | 37.26 | 35.09 | 3.44 | 10.26 |
| 175 PHE | CE1 | 37.97 | 32.56 | 4.33 | 7.24 |
| 175 PHE | CE2 | 36.37 | 34.41 | 4.22 | 5.77 |
| 175 PHE | CZ | 36.71 | 33.14 | 4.67 | 9.10 |
| 175 PHE | C | 41.48 | 36.90 | 2.27 | 13.48 |
| 175 PHE | O | 41.25 | 37.38 | 1.17 | 13.84 |
| 176 ARG | N | 42.67 | 36.92 | 2.81 | 13.55 |
| 176 ARG | CA | 43.80 | 37.56 | 2.17 | 17.04 |
| 176 ARG | CB | 44.73 | 38.05 | 3.26 | 19.56 |

Figure 5KK

| Residue | Atom | X | Y | Z | B |
|---|---|---|---|---|---|
| 176 ARG | CG | 44.00 | 38.69 | 4.44 | 20.17 |
| 176 ARG | CD | 43.62 | 40.15 | 4.20 | 17.77 |
| 176 ARG | NE | 42.54 | 40.54 | 5.10 | 16.71 |
| 176 ARG | CZ | 42.40 | 41.73 | 5.65 | 16.08 |
| 176 ARG | NH1 | 41.38 | 41.98 | 6.45 | 18.13 |
| 176 ARG | NH2 | 43.26 | 42.68 | 5.42 | 18.59 |
| 176 ARG | C | 44.57 | 36.76 | 1.08 | 18.45 |
| 176 ARG | O | 45.12 | 37.33 | 0.12 | 17.41 |
| 177 HIS | N | 44.64 | 35.43 | 1.24 | 19.20 |
| 177 HIS | CA | 45.31 | 34.60 | 0.25 | 19.47 |
| 177 HIS | CB | 45.95 | 33.38 | 0.90 | 23.19 |
| 177 HIS | CG | 46.60 | 33.67 | 2.21 | 25.40 |
| 177 HIS | CD2 | 46.85 | 32.87 | 3.27 | 28.95 |
| 177 HIS | ND1 | 47.06 | 34.92 | 2.55 | 26.63 |
| 177 HIS | CE1 | 47.55 | 34.89 | 3.78 | 29.03 |
| 177 HIS | NE2 | 47.44 | 33.66 | 4.24 | 31.80 |
| 177 HIS | C | 44.21 | 34.13 | -0.66 | 18.10 |
| 177 HIS | O | 43.68 | 33.06 | -0.46 | 19.23 |
| 178 LEU | N | 43.80 | 34.95 | -1.61 | 17.55 |
| 178 LEU | CA | 42.74 | 34.54 | -2.51 | 16.48 |
| 178 LEU | CB | 41.42 | 35.15 | -2.05 | 13.16 |
| 178 LEU | CG | 40.15 | 34.33 | -2.15 | 11.21 |
| 178 LEU | CD1 | 40.42 | 33.03 | -1.48 | 12.21 |
| 178 LEU | CD2 | 39.03 | 35.04 | -1.46 | 11.79 |
| 178 LEU | C | 43.14 | 35.11 | -3.85 | 19.60 |
| 178 LEU | O | 43.65 | 36.24 | -3.94 | 23.82 |
| 179 ASP | N | 43.00 | 34.32 | -4.91 | 18.49 |
| 179 ASP | CA | 43.35 | 34.83 | -6.21 | 18.94 |
| 179 ASP | CB | 43.21 | 33.72 | -7.24 | 17.14 |
| 179 ASP | CG | 43.87 | 34.04 | -8.54 | 19.35 |

Figure 5LL

| Residue | Atom | X | Y | Z | B |
|---|---|---|---|---|---|
| 179 ASP | OD1 | 43.91 | 35.21 | -8.99 | 19.23 |
| 179 ASP | OD2 | 44.34 | 33.08 | -9.16 | 25.64 |
| 179 ASP | C | 42.41 | 35.99 | -6.56 | 20.51 |
| 179 ASP | O | 41.25 | 36.01 | -6.14 | 20.70 |
| 180 PRO | N | 42.93 | 37.03 | -7.23 | 22.33 |
| 180 PRO | CD | 44.34 | 37.44 | -7.40 | 21.14 |
| 180 PRO | CA | 42.01 | 38.13 | -7.58 | 22.11 |
| 180 PRO | CB | 42.91 | 39.08 | -8.35 | 21.42 |
| 180 PRO | CG | 44.22 | 38.93 | -7.60 | 23.42 |
| 180 PRO | C | 40.90 | 37.59 | -8.47 | 21.04 |
| 180 PRO | O | 39.75 | 38.01 | -8.38 | 22.35 |
| 181 ALA | N | 41.26 | 36.64 | -9.33 | 19.96 |
| 181 ALA | CA | 40.34 | 36.01 | -10.26 | 16.55 |
| 181 ALA | CB | 41.06 | 35.00 | -11.14 | 16.69 |
| 181 ALA | C | 39.25 | 35.33 | -9.46 | 17.10 |
| 181 ALA | O | 38.12 | 35.24 | -9.93 | 18.74 |
| 182 THR | N | 39.58 | 34.87 | -8.26 | 15.61 |
| 182 THR | CA | 38.58 | 34.21 | -7.43 | 14.74 |
| 182 THR | CB | 39.22 | 33.42 | -6.29 | 13.42 |
| 182 THR | OG1 | 40.19 | 32.53 | -6.83 | 12.41 |
| 182 THR | CG2 | 38.18 | 32.62 | -5.56 | 11.92 |
| 182 THR | C | 37.63 | 35.25 | -6.88 | 14.68 |
| 182 THR | O | 36.44 | 35.07 | -6.93 | 14.89 |
| 183 ARG | N | 38.17 | 36.36 | -6.41 | 13.14 |
| 183 ARG | CA | 37.34 | 37.44 | -5.91 | 14.88 |
| 183 ARG | CB | 38.22 | 38.62 | -5.50 | 14.78 |
| 183 ARG | CG | 38.77 | 38.50 | -4.13 | 14.46 |
| 183 ARG | CD | 40.14 | 38.98 | -4.07 | 20.35 |
| 183 ARG | NE | 40.91 | 38.18 | -3.12 | 29.90 |
| 183 ARG | CZ | 41.59 | 38.66 | -2.07 | 32.97 |

Figure 5MM

| Residue | Atom | X | Y | Z | B |
|---|---|---|---|---|---|
| 183 ARG | NH1 | 42.28 | 37.84 | -1.27 | 30.33 |
| 183 ARG | NH2 | 41.63 | 39.96 | -1.82 | 33.84 |
| 183 ARG | C | 36.32 | 37.88 | -6.97 | 17.05 |
| 183 ARG | O | 35.10 | 37.76 | -6.82 | 18.36 |
| 184 GLU | N | 36.82 | 38.36 | -8.09 | 19.71 |
| 184 GLU | CA | 35.94 | 38.82 | -9.14 | 23.15 |
| 184 GLU | CB | 36.76 | 39.63 | -10.16 | 26.44 |
| 184 GLU | CG | 37.22 | 41.00 | -9.56 | 30.83 |
| 184 GLU | CD | 36.11 | 42.11 | -9.63 | 30.38 |
| 184 GLU | OE1 | 35.60 | 42.59 | -8.60 | 26.77 |
| 184 GLU | OE2 | 35.76 | 42.49 | -10.77 | 35.03 |
| 184 GLU | C | 35.03 | 37.75 | -9.78 | 21.57 |
| 184 GLU | O | 33.93 | 38.05 | -10.25 | 20.27 |
| 185 GLY | N | 35.48 | 36.50 | -9.75 | 20.10 |
| 185 GLY | CA | 34.69 | 35.43 | -10.34 | 19.41 |
| 185 GLY | C | 33.49 | 35.10 | -9.48 | 18.47 |
| 185 GLY | O | 32.36 | 35.08 | -9.95 | 18.35 |
| 186 VAL | N | 33.75 | 34.88 | -8.21 | 19.84 |
| 186 VAL | CA | 32.72 | 34.55 | -7.24 | 19.69 |
| 186 VAL | CB | 33.37 | 34.12 | -5.91 | 21.04 |
| 186 VAL | CG1 | 33.57 | 35.33 | -5.00 | 20.42 |
| 186 VAL | CG2 | 32.57 | 32.99 | -5.25 | 20.27 |
| 186 VAL | C | 31.78 | 35.73 | -7.03 | 19.38 |
| 186 VAL | O | 30.69 | 35.57 | -6.49 | 20.08 |
| 187 ARG | N | 32.22 | 36.91 | -7.41 | 19.63 |
| 187 ARG | CA | 31.38 | 38.10 | -7.29 | 19.57 |
| 187 ARG | CB | 32.20 | 39.38 | -7.27 | 17.68 |
| 187 ARG | CG | 32.83 | 39.74 | -5.95 | 16.17 |
| 187 ARG | CD | 32.88 | 41.25 | -5.92 | 17.78 |
| 187 ARG | NE | 33.99 | 41.87 | -5.20 | 16.37 |

Figure 5NN

| Residue | Atom | X | Y | Z | B |
|---|---|---|---|---|---|
| 187 ARG | CZ | 35.27 | 41.69 | -5.49 | 15.62 |
| 187 ARG | NH1 | 36.21 | 42.30 | -4.80 | 12.01 |
| 187 ARG | NH2 | 35.60 | 40.84 | -6.44 | 16.94 |
| 187 ARG | C | 30.32 | 38.18 | -8.41 | 20.06 |
| 187 ARG | O | 29.24 | 38.71 | -8.20 | 22.75 |
| 188 ARG | N | 30.64 | 37.72 | -9.61 | 19.80 |
| 188 ARG | CA | 29.64 | 37.74 | -10.66 | 21.24 |
| 188 ARG | CB | 30.22 | 37.59 | -12.04 | 22.69 |
| 188 ARG | CG | 31.14 | 38.67 | -12.45 | 28.10 |
| 188 ARG | CD | 31.87 | 38.20 | -13.69 | 31.07 |
| 188 ARG | NE | 32.28 | 36.81 | -13.53 | 32.08 |
| 188 ARG | CZ | 31.71 | 35.78 | -14.17 | 32.73 |
| 188 ARG | NH1 | 32.14 | 34.53 | -13.96 | 29.41 |
| 188 ARG | NH2 | 30.70 | 36.03 | -15.03 | 34.51 |
| 188 ARG | C | 28.67 | 36.60 | -10.45 | 21.19 |
| 188 ARG | O | 27.47 | 36.86 | -10.39 | 24.79 |
| 189 GLU | N | 29.14 | 35.36 | -10.35 | 18.68 |
| 189 GLU | CA | 28.21 | 34.26 | -10.15 | 19.63 |
| 189 GLU | CB | 28.89 | 32.91 | -9.92 | 22.18 |
| 189 GLU | CG | 29.77 | 32.37 | -11.04 | 27.60 |
| 189 GLU | CD | 31.02 | 31.65 | -10.49 | 30.89 |
| 189 GLU | OE1 | 32.13 | 32.22 | -10.60 | 33.41 |
| 189 GLU | OE2 | 30.90 | 30.54 | -9.91 | 30.22 |
| 189 GLU | C | 27.27 | 34.52 | -8.98 | 18.60 |
| 189 GLU | O | 26.08 | 34.29 | -9.09 | 21.78 |
| 190 ALA | N | 27.79 | 35.06 | -7.89 | 17.44 |
| 190 ALA | CA | 26.96 | 35.35 | -6.71 | 16.93 |
| 190 ALA | CB | 27.81 | 35.93 | -5.62 | 15.50 |
| 190 ALA | C | 25.74 | 36.24 | -6.95 | 17.54 |
| 190 ALA | O | 24.67 | 35.98 | -6.41 | 16.72 |

Figure 5OO

| Residue | Atom | X | Y | Z | B |
|---|---|---|---|---|---|
| 191 ALA | N | 25.91 | 37.29 | -7.77 | 19.33 |
| 191 ALA | CA | 24.84 | 38.26 | -8.12 | 19.45 |
| 191 ALA | CB | 25.43 | 39.45 | -8.78 | 18.90 |
| 191 ALA | C | 23.79 | 37.65 | -9.03 | 19.65 |
| 191 ALA | O | 22.58 | 37.75 | -8.81 | 20.16 |
| 192 GLU | N | 24.27 | 37.01 | -10.07 | 20.37 |
| 192 GLU | CA | 23.40 | 36.35 | -11.01 | 22.48 |
| 192 GLU | CB | 24.21 | 35.64 | -12.05 | 25.16 |
| 192 GLU | CG | 25.14 | 36.54 | -12.76 | 33.62 |
| 192 GLU | CD | 25.82 | 35.84 | -13.91 | 41.14 |
| 192 GLU | OE1 | 26.84 | 36.41 | -14.39 | 47.35 |
| 192 GLU | OE2 | 25.34 | 34.73 | -14.35 | 41.85 |
| 192 GLU | C | 22.54 | 35.34 | -10.30 | 22.43 |
| 192 GLU | O | 21.36 | 35.21 | -10.61 | 23.12 |
| 193 ALA | N | 23.13 | 34.61 | -9.36 | 21.17 |
| 193 ALA | CA | 22.40 | 33.60 | -8.63 | 21.73 |
| 193 ALA | CB | 23.30 | 32.71 | -7.90 | 21.96 |
| 193 ALA | C | 21.42 | 34.24 | -7.68 | 23.53 |
| 193 ALA | O | 20.34 | 33.69 | -7.46 | 26.65 |
| 194 GLU | N | 21.74 | 35.40 | -7.13 | 23.26 |
| 194 GLU | CA | 20.80 | 36.02 | -6.21 | 22.79 |
| 194 GLU | CB | 21.38 | 37.27 | -5.59 | 22.73 |
| 194 GLU | CG | 22.50 | 36.97 | -4.72 | 24.60 |
| 194 GLU | CD | 22.71 | 38.07 | -3.75 | 29.85 |
| 194 GLU | OE1 | 23.31 | 39.09 | -4.14 | 32.69 |
| 194 GLU | OE2 | 22.27 | 37.91 | -2.58 | 34.29 |
| 194 GLU | C | 19.54 | 36.37 | -6.96 | 23.63 |
| 194 GLU | O | 18.43 | 36.33 | -6.41 | 25.04 |
| 195 LEU | N | 19.71 | 36.71 | -8.24 | 24.06 |
| 195 LEU | CA | 18.60 | 37.05 | -9.10 | 23.45 |

Figure 5PP

| Residue | Atom | X | Y | Z | B |
|---|---|---|---|---|---|
| 195 LEU | CB | 19.10 | 37.53 | -10.45 | 24.46 |
| 195 LEU | CG | 19.80 | 38.89 | -10.41 | 24.17 |
| 195 LEU | CD1 | 20.24 | 39.34 | -11.80 | 25.83 |
| 195 LEU | CD2 | 18.86 | 39.91 | -9.83 | 24.72 |
| 195 LEU | C | 17.61 | 35.88 | -9.24 | 23.50 |
| 195 LEU | O | 16.48 | 36.08 | -9.62 | 25.60 |
| 196 ALA | N | 18.05 | 34.66 | -8.98 | 23.27 |
| 196 ALA | CA | 17.11 | 33.55 | -9.05 | 23.63 |
| 196 ALA | CB | 17.82 | 32.23 | -9.30 | 24.34 |
| 196 ALA | C | 16.39 | 33.52 | -7.72 | 24.88 |
| 196 ALA | O | 15.17 | 33.51 | -7.70 | 29.50 |
| 197 LEU | N | 17.13 | 33.55 | -6.61 | 23.36 |
| 197 LEU | CA | 16.52 | 33.54 | -5.29 | 22.81 |
| 197 LEU | CB | 17.55 | 33.72 | -4.17 | 20.76 |
| 197 LEU | CG | 18.29 | 32.43 | -3.83 | 16.68 |
| 197 LEU | CD1 | 17.28 | 31.35 | -3.70 | 17.98 |
| 197 LEU | CD2 | 19.23 | 32.06 | -4.95 | 16.49 |
| 197 LEU | C | 15.41 | 34.59 | -5.20 | 24.66 |
| 197 LEU | O | 14.42 | 34.41 | -4.48 | 26.15 |
| 198 ALA | N | 15.60 | 35.71 | -5.88 | 23.99 |
| 198 ALA | CA | 14.57 | 36.73 | -5.91 | 24.22 |
| 198 ALA | CB | 13.48 | 36.28 | -6.85 | 24.94 |
| 198 ALA | C | 13.94 | 37.20 | -4.60 | 24.56 |
| 198 ALA | O | 13.04 | 38.04 | -4.61 | 26.75 |
| 199 GLY | N | 14.45 | 36.75 | -3.46 | 24.14 |
| 199 GLY | CA | 13.86 | 37.18 | -2.20 | 22.52 |
| 199 GLY | C | 13.29 | 35.97 | -1.50 | 21.30 |
| 199 GLY | O | 12.35 | 36.06 | -0.69 | 21.69 |
| 200 ARG | N | 13.82 | 34.81 | -1.87 | 18.31 |
| 200 ARG | CA | 13.40 | 33.56 | -1.29 | 15.04 |

Figure 5QQ

| Residue | Atom | X | Y | Z | B |
|---|---|---|---|---|---|
| 200 ARG | CB | 14.13 | 32.45 | -2.00 | 12.08 |
| 200 ARG | CG | 13.33 | 31.23 | -2.17 | 16.15 |
| 200 ARG | CD | 13.80 | 30.12 | -1.30 | 17.37 |
| 200 ARG | NE | 14.08 | 28.96 | -2.13 | 16.81 |
| 200 ARG | CZ | 14.00 | 27.71 | -1.72 | 17.20 |
| 200 ARG | NH1 | 14.27 | 26.73 | -2.55 | 19.87 |
| 200 ARG | NH2 | 13.66 | 27.46 | -0.46 | 19.95 |
| 200 ARG | C | 13.85 | 33.59 | 0.15 | 14.28 |
| 200 ARG | O | 14.75 | 34.33 | 0.50 | 15.36 |
| 201 THR | N | 13.25 | 32.78 | 0.99 | 13.05 |
| 201 THR | CA | 13.66 | 32.76 | 2.37 | 11.06 |
| 201 THR | CB | 12.87 | 33.75 | 3.14 | 12.97 |
| 201 THR | OG1 | 13.24 | 35.05 | 2.66 | 17.96 |
| 201 THR | CG2 | 13.14 | 33.64 | 4.67 | 14.46 |
| 201 THR | C | 13.41 | 31.38 | 2.86 | 9.58 |
| 201 THR | O | 12.58 | 30.66 | 2.31 | 13.25 |
| 202 TRP | N | 14.21 | 30.95 | 3.82 | 3.78 |
| 202 TRP | CA | 14.04 | 29.65 | 4.35 | 3.74 |
| 202 TRP | CB | 15.39 | 28.98 | 4.43 | 2.42 |
| 202 TRP | CG | 15.90 | 28.63 | 3.02 | 3.24 |
| 202 TRP | CD2 | 16.45 | 29.52 | 2.06 | 2.00 |
| 202 TRP | CE2 | 16.70 | 28.78 | 0.90 | 2.00 |
| 202 TRP | CE3 | 16.75 | 30.88 | 2.07 | 6.37 |
| 202 TRP | CD1 | 15.85 | 27.40 | 2.42 | 2.00 |
| 202 TRP | NE1 | 16.33 | 27.49 | 1.14 | 2.00 |
| 202 TRP | CZ2 | 17.23 | 29.35 | -0.24 | 2.00 |
| 202 TRP | CZ3 | 17.29 | 31.45 | 0.93 | 4.03 |
| 202 TRP | CH2 | 17.52 | 30.69 | -0.21 | 5.11 |
| 202 TRP | C | 13.29 | 29.73 | 5.65 | 5.38 |
| 202 TRP | O | 13.29 | 30.78 | 6.27 | 7.63 |

Figure 5RR

| Residue | Atom | X | Y | Z | B |
|---|---|---|---|---|---|
| 203 ALA | N | 12.51 | 28.70 | 5.95 | 5.73 |
| 203 ALA | CA | 11.71 | 28.64 | 7.18 | 6.91 |
| 203 ALA | CB | 10.37 | 29.27 | 6.96 | 2.00 |
| 203 ALA | C | 11.55 | 27.18 | 7.62 | 9.43 |
| 203 ALA | O | 10.45 | 26.63 | 7.70 | 11.74 |
| 204 PRO | N | 12.66 | 26.53 | 7.97 | 9.34 |
| 204 PRO | CD | 14.00 | 27.11 | 8.21 | 6.42 |
| 204 PRO | CA | 12.63 | 25.14 | 8.39 | 7.43 |
| 204 PRO | CB | 14.10 | 24.87 | 8.72 | 4.23 |
| 204 PRO | CG | 14.59 | 26.18 | 9.20 | 3.30 |
| 204 PRO | C | 11.71 | 24.83 | 9.57 | 8.06 |
| 204 PRO | O | 11.29 | 23.70 | 9.71 | 9.66 |
| 205 GLY | N | 11.45 | 25.81 | 10.45 | 9.18 |
| 205 GLY | CA | 10.61 | 25.63 | 11.63 | 9.18 |
| 205 GLY | C | 11.41 | 25.82 | 12.90 | 8.97 |
| 205 GLY | O | 12.38 | 25.10 | 13.10 | 9.01 |
| 206 VAL | N | 10.99 | 26.71 | 13.80 | 7.76 |
| 206 VAL | CA | 11.82 | 26.92 | 14.97 | 9.21 |
| 206 VAL | CB | 11.49 | 28.20 | 15.86 | 7.78 |
| 206 VAL | CG1 | 10.94 | 29.36 | 15.05 | 4.18 |
| 206 VAL | CG2 | 10.66 | 27.87 | 17.04 | 5.53 |
| 206 VAL | C | 12.14 | 25.71 | 15.81 | 11.82 |
| 206 VAL | O | 13.27 | 25.56 | 16.20 | 14.86 |
| 207 GLU | N | 11.23 | 24.79 | 16.05 | 13.45 |
| 207 GLU | CA | 11.65 | 23.65 | 16.87 | 16.00 |
| 207 GLU | CB | 10.46 | 22.93 | 17.53 | 20.19 |
| 207 GLU | CG | 9.67 | 23.76 | 18.59 | 26.38 |
| 207 GLU | CD | 10.54 | 24.73 | 19.45 | 30.51 |
| 207 GLU | OE1 | 11.35 | 24.27 | 20.29 | 29.04 |
| 207 GLU | OE2 | 10.39 | 25.97 | 19.31 | 32.60 |

Figure 5SS

| Residue | Atom | X | Y | Z | B |
|---|---|---|---|---|---|
| 207 GLU | C | 12.60 | 22.65 | 16.18 | 15.39 |
| 207 GLU | O | 13.30 | 21.91 | 16.87 | 15.80 |
| 208 ALA | N | 12.61 | 22.61 | 14.85 | 13.40 |
| 208 ALA | CA | 13.51 | 21.73 | 14.09 | 10.45 |
| 208 ALA | CB | 13.13 | 21.64 | 12.63 | 9.96 |
| 208 ALA | C | 14.87 | 22.38 | 14.23 | 10.25 |
| 208 ALA | O | 15.86 | 21.68 | 14.40 | 12.17 |
| 209 LEU | N | 14.90 | 23.72 | 14.16 | 8.37 |
| 209 LEU | CA | 16.14 | 24.50 | 14.32 | 7.08 |
| 209 LEU | CB | 15.92 | 25.99 | 14.07 | 2.00 |
| 209 LEU | CG | 15.89 | 26.40 | 12.61 | 2.00 |
| 209 LEU | CD1 | 15.68 | 27.88 | 12.43 | 2.00 |
| 209 LEU | CD2 | 17.20 | 26.00 | 12.02 | 6.01 |
| 209 LEU | C | 16.66 | 24.32 | 15.75 | 8.22 |
| 209 LEU | O | 17.79 | 23.95 | 15.96 | 9.00 |
| 210 THR | N | 15.79 | 24.58 | 16.72 | 9.20 |
| 210 THR | CA | 16.11 | 24.43 | 18.13 | 10.30 |
| 210 THR | CB | 14.85 | 24.69 | 18.97 | 11.52 |
| 210 THR | OG1 | 14.38 | 26.02 | 18.71 | 14.04 |
| 210 THR | CG2 | 15.15 | 24.57 | 20.43 | 12.38 |
| 210 THR | C | 16.65 | 23.02 | 18.42 | 11.22 |
| 210 THR | O | 17.66 | 22.86 | 19.07 | 11.57 |
| 211 HIS | N | 15.98 | 22.00 | 17.92 | 13.49 |
| 211 HIS | CA | 16.43 | 20.65 | 18.14 | 15.52 |
| 211 HIS | CB | 15.38 | 19.62 | 17.68 | 20.64 |
| 211 HIS | CG | 14.24 | 19.40 | 18.64 | 26.90 |
| 211 HIS | CD2 | 12.90 | 19.58 | 18.49 | 27.65 |
| 211 HIS | ND1 | 14.41 | 18.93 | 19.93 | 29.22 |
| 211 HIS | CE1 | 13.24 | 18.84 | 20.53 | 28.12 |
| 211 HIS | NE2 | 12.30 | 19.22 | 19.68 | 28.69 |

Figure 5TT

| Residue | Atom | X | Y | Z | B |
|---|---|---|---|---|---|
| 211 HIS | C | 17.77 | 20.39 | 17.47 | 16.33 |
| 211 HIS | O | 18.56 | 19.58 | 17.95 | 20.48 |
| 212 THR | N | 18.05 | 21.06 | 16.35 | 13.98 |
| 212 THR | CA | 19.32 | 20.84 | 15.65 | 11.93 |
| 212 THR | CB | 19.15 | 21.12 | 14.16 | 9.12 |
| 212 THR | OG1 | 18.02 | 20.38 | 13.70 | 8.08 |
| 212 THR | CG2 | 20.36 | 20.66 | 13.39 | 9.84 |
| 212 THR | C | 20.54 | 21.58 | 16.26 | 12.09 |
| 212 THR | O | 21.67 | 21.06 | 16.32 | 12.03 |
| 213 LEU | N | 20.31 | 22.80 | 16.74 | 10.65 |
| 213 LEU | CA | 21.32 | 23.57 | 17.38 | 9.64 |
| 213 LEU | CB | 20.81 | 24.98 | 17.55 | 6.93 |
| 213 LEU | CG | 20.72 | 25.73 | 16.22 | 6.38 |
| 213 LEU | CD1 | 20.09 | 27.11 | 16.40 | 5.81 |
| 213 LEU | CD2 | 22.10 | 25.88 | 15.62 | 4.84 |
| 213 LEU | C | 21.70 | 22.91 | 18.74 | 12.82 |
| 213 LEU | O | 22.88 | 22.87 | 19.11 | 12.94 |
| 214 LEU | N | 20.73 | 22.34 | 19.45 | 12.13 |
| 214 LEU | CA | 21.04 | 21.67 | 20.71 | 10.23 |
| 214 LEU | CB | 19.77 | 21.15 | 21.41 | 9.12 |
| 214 LEU | CG | 19.70 | 20.84 | 22.94 | 9.66 |
| 214 LEU | CD1 | 19.43 | 19.41 | 23.18 | 8.62 |
| 214 LEU | CD2 | 20.96 | 21.26 | 23.71 | 10.58 |
| 214 LEU | C | 21.97 | 20.51 | 20.37 | 11.45 |
| 214 LEU | O | 23.05 | 20.39 | 20.94 | 9.53 |
| 215 SER | N | 21.58 | 19.71 | 19.38 | 13.87 |
| 215 SER | CA | 22.34 | 18.52 | 18.93 | 12.55 |
| 215 SER | CB | 21.62 | 17.82 | 17.80 | 12.82 |
| 215 SER | OG | 22.33 | 16.68 | 17.38 | 11.94 |
| 215 SER | C | 23.79 | 18.82 | 18.54 | 10.44 |

Figure 5UU

| Residue | Atom | X | Y | Z | B |
|---|---|---|---|---|---|
| 215 SER | O | 24.65 | 17.93 | 18.59 | 7.88 |
| 216 THR | N | 24.04 | 20.04 | 18.10 | 9.57 |
| 216 THR | CA | 25.40 | 20.46 | 17.78 | 11.80 |
| 216 THR | CB | 25.38 | 21.81 | 17.13 | 10.37 |
| 216 THR | OG1 | 24.95 | 21.63 | 15.79 | 16.81 |
| 216 THR | CG2 | 26.72 | 22.46 | 17.14 | 8.20 |
| 216 THR | C | 26.17 | 20.53 | 19.11 | 13.58 |
| 216 THR | O | 27.18 | 19.86 | 19.29 | 15.60 |
| 217 ALA | N | 25.61 | 21.25 | 20.07 | 13.36 |
| 217 ALA | CA | 26.22 | 21.39 | 21.37 | 10.87 |
| 217 ALA | CB | 25.39 | 22.25 | 22.23 | 11.37 |
| 217 ALA | C | 26.39 | 20.05 | 22.04 | 10.76 |
| 217 ALA | O | 27.41 | 19.80 | 22.65 | 12.12 |
| 218 VAL | N | 25.39 | 19.19 | 21.94 | 11.01 |
| 218 VAL | CA | 25.50 | 17.91 | 22.61 | 10.40 |
| 218 VAL | CB | 24.15 | 17.17 | 22.73 | 7.87 |
| 218 VAL | CG1 | 24.38 | 15.75 | 23.14 | 2.00 |
| 218 VAL | CG2 | 23.30 | 17.83 | 23.77 | 9.41 |
| 218 VAL | C | 26.51 | 17.04 | 21.95 | 12.12 |
| 218 VAL | O | 27.44 | 16.59 | 22.59 | 13.85 |
| 219 ASN | N | 26.38 | 16.86 | 20.65 | 14.27 |
| 219 ASN | CA | 27.31 | 15.99 | 19.95 | 15.70 |
| 219 ASN | CB | 26.84 | 15.77 | 18.53 | 16.16 |
| 219 ASN | CG | 25.63 | 14.91 | 18.45 | 17.91 |
| 219 ASN | OD1 | 25.65 | 13.75 | 18.89 | 18.27 |
| 219 ASN | ND2 | 24.57 | 15.45 | 17.89 | 18.83 |
| 219 ASN | C | 28.76 | 16.45 | 19.98 | 15.95 |
| 219 ASN | O | 29.67 | 15.67 | 19.77 | 16.48 |
| 220 ASN | N | 28.97 | 17.70 | 20.36 | 16.79 |
| 220 ASN | CA | 30.31 | 18.24 | 20.38 | 18.70 |

Figure 5VV

| Residue | Atom | X | Y | Z | B |
|---|---|---|---|---|---|
| 220 ASN | CB | 30.38 | 19.53 | 19.54 | 21.43 |
| 220 ASN | CG | 30.40 | 19.26 | 18.06 | 23.36 |
| 220 ASN | OD1 | 31.38 | 18.73 | 17.56 | 25.24 |
| 220 ASN | ND2 | 29.32 | 19.61 | 17.36 | 22.89 |
| 220 ASN | C | 30.82 | 18.58 | 21.75 | 19.42 |
| 220 ASN | O | 31.87 | 19.23 | 21.85 | 20.88 |
| 221 MET | N | 30.09 | 18.16 | 22.80 | 19.08 |
| 221 MET | CA | 30.46 | 18.48 | 24.19 | 16.02 |
| 221 MET | CB | 29.34 | 18.12 | 25.18 | 11.71 |
| 221 MET | CG | 29.13 | 16.64 | 25.30 | 7.04 |
| 221 MET | SD | 27.78 | 16.27 | 26.31 | 12.68 |
| 221 MET | CE | 27.78 | 14.54 | 26.24 | 5.67 |
| 221 MET | C | 31.77 | 17.87 | 24.65 | 15.97 |
| 221 MET | O | 32.38 | 18.40 | 25.56 | 17.74 |
| 222 MET | N | 32.19 | 16.79 | 24.00 | 15.13 |
| 222 MET | CA | 33.43 | 16.08 | 24.33 | 15.50 |
| 222 MET | CB | 33.30 | 14.65 | 23.86 | 14.49 |
| 222 MET | CG | 32.34 | 13.93 | 24.74 | 13.32 |
| 222 MET | SD | 32.51 | 14.48 | 26.50 | 14.19 |
| 222 MET | CE | 32.06 | 12.88 | 27.24 | 8.26 |
| 222 MET | C | 34.78 | 16.69 | 23.90 | 17.78 |
| 222 MET | O | 35.85 | 16.39 | 24.46 | 17.28 |
| 223 LEU | N | 34.75 | 17.54 | 22.89 | 19.11 |
| 223 LEU | CA | 35.94 | 18.21 | 22.43 | 16.60 |
| 223 LEU | CB | 35.61 | 19.13 | 21.25 | 16.31 |
| 223 LEU | CG | 35.57 | 18.53 | 19.84 | 15.40 |
| 223 LEU | CD1 | 34.35 | 17.66 | 19.66 | 17.38 |
| 223 LEU | CD2 | 35.58 | 19.61 | 18.79 | 14.99 |
| 223 LEU | C | 36.60 | 19.01 | 23.56 | 18.12 |
| 223 LEU | O | 36.03 | 19.93 | 24.16 | 17.20 |

Figure 5WW

| Residue | Atom | X | Y | Z | B |
|---|---|---|---|---|---|
| 224 ARG | N | 37.78 | 18.54 | 23.91 | 22.06 |
| 224 ARG | CA | 38.64 | 19.19 | 24.90 | 24.12 |
| 224 ARG | CB | 39.73 | 18.20 | 25.29 | 23.20 |
| 224 ARG | CG | 39.12 | 16.87 | 25.81 | 28.37 |
| 224 ARG | CD | 38.67 | 16.97 | 27.29 | 29.88 |
| 224 ARG | NE | 37.37 | 16.38 | 27.72 | 31.45 |
| 224 ARG | CZ | 36.71 | 15.32 | 27.20 | 31.68 |
| 224 ARG | NH1 | 35.56 | 14.94 | 27.75 | 28.69 |
| 224 ARG | NH2 | 37.14 | 14.67 | 26.12 | 32.52 |
| 224 ARG | C | 39.12 | 20.36 | 24.02 | 25.20 |
| 224 ARG | O | 39.76 | 20.18 | 22.98 | 25.52 |
| 225 ASP | N | 38.62 | 21.54 | 24.36 | 26.60 |
| 225 ASP | CA | 38.82 | 22.77 | 23.58 | 27.04 |
| 225 ASP | CB | 39.87 | 23.73 | 24.12 | 29.55 |
| 225 ASP | CG | 39.45 | 25.20 | 23.94 | 32.91 |
| 225 ASP | OD1 | 38.28 | 25.44 | 23.55 | 32.59 |
| 225 ASP | OD2 | 40.27 | 26.11 | 24.21 | 36.97 |
| 225 ASP | C | 38.83 | 22.71 | 22.05 | 26.34 |
| 225 ASP | O | 39.69 | 22.11 | 21.40 | 24.27 |
| 226 ARG | N | 37.80 | 23.32 | 21.50 | 25.04 |
| 226 ARG | CA | 37.64 | 23.36 | 20.07 | 25.34 |
| 226 ARG | CB | 36.18 | 23.15 | 19.68 | 28.06 |
| 226 ARG | CG | 35.21 | 24.15 | 20.36 | 30.00 |
| 226 ARG | CD | 33.98 | 24.48 | 19.49 | 28.19 |
| 226 ARG | NE | 33.30 | 25.67 | 19.99 | 27.27 |
| 226 ARG | CZ | 32.73 | 26.59 | 19.23 | 25.17 |
| 226 ARG | NH1 | 32.16 | 27.64 | 19.79 | 25.45 |
| 226 ARG | NH2 | 32.73 | 26.46 | 17.91 | 26.06 |
| 226 ARG | C | 38.12 | 24.72 | 19.64 | 23.86 |
| 226 ARG | O | 38.23 | 24.98 | 18.43 | 23.14 |

Figure 5XX

| Residue | Atom | X | Y | Z | B |
|---|---|---|---|---|---|
| 227 TRP | N | 38.36 | 25.59 | 20.61 | 20.47 |
| 227 TRP | CA | 38.86 | 26.92 | 20.29 | 20.99 |
| 227 TRP | CB | 38.83 | 27.82 | 21.52 | 24.01 |
| 227 TRP | CG | 37.47 | 28.34 | 21.84 | 29.39 |
| 227 TRP | CD2 | 36.61 | 29.13 | 20.99 | 29.25 |
| 227 TRP | CE2 | 35.45 | 29.44 | 21.73 | 29.90 |
| 227 TRP | CE3 | 36.72 | 29.61 | 19.67 | 29.32 |
| 227 TRP | CD1 | 36.81 | 28.21 | 23.03 | 31.69 |
| 227 TRP | NE1 | 35.60 | 28.87 | 22.97 | 32.92 |
| 227 TRP | CZ2 | 34.41 | 30.21 | 21.21 | 29.51 |
| 227 TRP | CZ3 | 35.68 | 30.37 | 19.15 | 28.34 |
| 227 TRP | CH2 | 34.54 | 30.66 | 19.92 | 30.27 |
| 227 TRP | C | 40.28 | 26.88 | 19.70 | 21.14 |
| 227 TRP | O | 40.70 | 27.78 | 18.98 | 23.66 |
| 228 SER | N | 41.02 | 25.82 | 20.02 | 18.16 |
| 228 SER | CA | 42.35 | 25.67 | 19.51 | 15.93 |
| 228 SER | CB | 43.01 | 24.60 | 20.32 | 16.29 |
| 228 SER | OG | 42.49 | 24.70 | 21.62 | 19.84 |
| 228 SER | C | 42.25 | 25.29 | 18.02 | 17.85 |
| 228 SER | O | 42.97 | 25.85 | 17.17 | 20.25 |
| 229 LEU | N | 41.33 | 24.36 | 17.71 | 14.42 |
| 229 LEU | CA | 41.09 | 23.92 | 16.36 | 10.55 |
| 229 LEU | CB | 40.08 | 22.81 | 16.38 | 9.10 |
| 229 LEU | CG | 40.63 | 21.50 | 16.89 | 11.53 |
| 229 LEU | CD1 | 39.52 | 20.48 | 17.04 | 10.67 |
| 229 LEU | CD2 | 41.66 | 21.00 | 15.92 | 13.85 |
| 229 LEU | C | 40.52 | 25.09 | 15.57 | 11.38 |
| 229 LEU | O | 40.93 | 25.36 | 14.46 | 13.27 |
| 230 VAL | N | 39.59 | 25.80 | 16.15 | 11.63 |
| 230 VAL | CA | 39.03 | 26.94 | 15.44 | 10.61 |

Figure 5YY

| Residue | Atom | X | Y | Z | B |
|---|---|---|---|---|---|
| 230 VAL | CB | 37.97 | 27.70 | 16.30 | 7.94 |
| 230 VAL | CG1 | 37.50 | 28.94 | 15.62 | 2.00 |
| 230 VAL | CG2 | 36.80 | 26.80 | 16.56 | 6.47 |
| 230 VAL | C | 40.19 | 27.84 | 15.03 | 11.91 |
| 230 VAL | O | 40.41 | 28.04 | 13.83 | 14.51 |
| 231 ALA | N | 41.02 | 28.24 | 15.99 | 12.11 |
| 231 ALA | CA | 42.16 | 29.11 | 15.71 | 12.32 |
| 231 ALA | CB | 42.83 | 29.52 | 16.97 | 7.72 |
| 231 ALA | C | 43.19 | 28.58 | 14.70 | 13.21 |
| 231 ALA | O | 43.59 | 29.29 | 13.79 | 14.39 |
| 232 GLU | N | 43.59 | 27.33 | 14.85 | 13.83 |
| 232 GLU | CA | 44.56 | 26.72 | 13.95 | 12.96 |
| 232 GLU | CB | 44.93 | 25.34 | 14.50 | 11.20 |
| 232 GLU | CG | 45.60 | 24.47 | 13.51 | 19.11 |
| 232 GLU | CD | 45.15 | 23.00 | 13.59 | 25.85 |
| 232 GLU | OE1 | 45.99 | 22.16 | 14.01 | 27.20 |
| 232 GLU | OE2 | 43.98 | 22.67 | 13.21 | 25.73 |
| 232 GLU | C | 44.01 | 26.67 | 12.50 | 13.22 |
| 232 GLU | O | 44.78 | 26.81 | 11.53 | 14.62 |
| 233 ARG | N | 42.68 | 26.56 | 12.39 | 11.85 |
| 233 ARG | CA | 41.95 | 26.50 | 11.11 | 9.70 |
| 233 ARG | CB | 40.61 | 25.83 | 11.26 | 6.48 |
| 233 ARG | CG | 40.65 | 24.48 | 11.84 | 10.11 |
| 233 ARG | CD | 41.18 | 23.46 | 10.91 | 13.64 |
| 233 ARG | NE | 40.24 | 22.35 | 10.76 | 15.30 |
| 233 ARG | CZ | 39.98 | 21.45 | 11.70 | 14.92 |
| 233 ARG | NH1 | 39.12 | 20.46 | 11.47 | 14.87 |
| 233 ARG | NH2 | 40.59 | 21.53 | 12.88 | 19.60 |
| 233 ARG | C | 41.71 | 27.89 | 10.56 | 8.03 |
| 233 ARG | O | 41.72 | 28.07 | 9.36 | 9.31 |

Figure 5ZZ

| Residue | Atom | X | Y | Z | B |
|---|---|---|---|---|---|
| 234 ARG | N | 41.40 | 28.85 | 11.43 | 5.29 |
| 234 ARG | CA | 41.23 | 30.21 | 10.97 | 8.12 |
| 234 ARG | CB | 40.99 | 31.17 | 12.15 | 9.61 |
| 234 ARG | CG | 41.12 | 32.63 | 11.76 | 13.36 |
| 234 ARG | CD | 40.99 | 33.66 | 12.86 | 19.39 |
| 234 ARG | NE | 41.13 | 35.02 | 12.27 | 31.29 |
| 234 ARG | CZ | 40.78 | 36.20 | 12.83 | 34.64 |
| 234 ARG | NH1 | 40.22 | 36.27 | 14.06 | 34.94 |
| 234 ARG | NH2 | 41.11 | 37.34 | 12.19 | 33.68 |
| 234 ARG | C | 42.56 | 30.53 | 10.26 | 11.77 |
| 234 ARG | O | 42.58 | 31.07 | 9.15 | 14.61 |
| 235 ARG | N | 43.68 | 30.16 | 10.89 | 13.57 |
| 235 ARG | CA | 45.04 | 30.34 | 10.36 | 13.19 |
| 235 ARG | CB | 46.06 | 29.70 | 11.30 | 15.90 |
| 235 ARG | CG | 46.65 | 30.65 | 12.33 | 21.17 |
| 235 ARG | CD | 47.32 | 29.87 | 13.48 | 28.37 |
| 235 ARG | NE | 48.05 | 28.64 | 13.04 | 34.85 |
| 235 ARG | CZ | 48.35 | 27.59 | 13.84 | 35.90 |
| 235 ARG | NH1 | 49.03 | 26.54 | 13.34 | 33.53 |
| 235 ARG | NH2 | 47.99 | 27.57 | 15.13 | 33.79 |
| 235 ARG | C | 45.16 | 29.70 | 8.99 | 11.79 |
| 235 ARG | O | 45.43 | 30.38 | 8.01 | 10.49 |
| 236 GLN | N | 44.97 | 28.39 | 8.93 | 10.68 |
| 236 GLN | CA | 45.05 | 27.66 | 7.67 | 11.39 |
| 236 GLN | CB | 44.43 | 26.28 | 7.82 | 12.95 |
| 236 GLN | CG | 45.38 | 25.22 | 8.35 | 15.41 |
| 236 GLN | CD | 44.68 | 24.20 | 9.21 | 19.29 |
| 236 GLN | OE1 | 43.46 | 24.27 | 9.42 | 22.58 |
| 236 GLN | NE2 | 45.44 | 23.23 | 9.72 | 16.75 |
| 236 GLN | C | 44.41 | 28.41 | 6.51 | 11.05 |

Figure 5AAA

| Residue | Atom | X | Y | Z | B |
|---|---|---|---|---|---|
| 236 GLN | O | 45.10 | 28.82 | 5.61 | 12.47 |
| 237 ALA | N | 43.10 | 28.63 | 6.58 | 11.48 |
| 237 ALA | CA | 42.32 | 29.35 | 5.57 | 12.32 |
| 237 ALA | CB | 40.88 | 29.54 | 6.09 | 9.54 |
| 237 ALA | C | 42.97 | 30.72 | 5.19 | 13.34 |
| 237 ALA | O | 42.85 | 31.22 | 4.06 | 13.35 |
| 238 GLY | N | 43.65 | 31.32 | 6.14 | 12.66 |
| 238 GLY | CA | 44.29 | 32.59 | 5.88 | 11.36 |
| 238 GLY | C | 43.37 | 33.74 | 6.12 | 10.86 |
| 238 GLY | O | 43.43 | 34.72 | 5.38 | 12.92 |
| 239 ILE | N | 42.55 | 33.64 | 7.16 | 10.68 |
| 239 ILE | CA | 41.60 | 34.70 | 7.51 | 11.68 |
| 239 ILE | CB | 40.36 | 34.16 | 8.28 | 10.27 |
| 239 ILE | CG2 | 39.49 | 35.30 | 8.79 | 10.05 |
| 239 ILE | CG1 | 39.53 | 33.25 | 7.38 | 8.25 |
| 239 ILE | CD1 | 38.76 | 32.25 | 8.14 | 10.93 |
| 239 ILE | C | 42.33 | 35.70 | 8.38 | 14.80 |
| 239 ILE | O | 43.02 | 35.35 | 9.33 | 14.06 |
| 240 ALA | N | 42.24 | 36.96 | 8.00 | 17.15 |
| 240 ALA | CA | 42.88 | 38.00 | 8.75 | 20.17 |
| 240 ALA | CB | 43.68 | 38.87 | 7.81 | 22.58 |
| 240 ALA | C | 41.71 | 38.77 | 9.31 | 22.83 |
| 240 ALA | O | 40.68 | 38.19 | 9.62 | 26.27 |
| 241 GLY | N | 41.88 | 40.06 | 9.52 | 25.88 |
| 241 GLY | CA | 40.77 | 40.86 | 9.95 | 28.69 |
| 241 GLY | C | 40.33 | 40.95 | 11.39 | 29.43 |
| 241 GLY | O | 40.80 | 40.26 | 12.29 | 27.82 |
| 242 HIS | N | 39.40 | 41.89 | 11.56 | 31.35 |
| 242 HIS | CA | 38.73 | 42.29 | 12.79 | 30.69 |
| 242 HIS | CB | 38.60 | 43.82 | 12.72 | 32.80 |

Figure 5BBB

| Residue | Atom | X | Y | Z | B |
|---|---|---|---|---|---|
| 242 HIS | CG | 38.00 | 44.46 | 13.93 | 33.44 |
| 242 HIS | CD2 | 37.82 | 45.77 | 14.24 | 34.70 |
| 242 HIS | ND1 | 37.46 | 43.75 | 14.98 | 35.41 |
| 242 HIS | CE1 | 36.98 | 44.59 | 15.88 | 35.13 |
| 242 HIS | NE2 | 37.17 | 45.82 | 15.45 | 33.22 |
| 242 HIS | C | 37.34 | 41.58 | 12.68 | 30.07 |
| 242 HIS | O | 36.27 | 42.22 | 12.55 | 30.34 |
| 243 THR | N | 37.42 | 40.25 | 12.69 | 27.31 |
| 243 THR | CA | 36.29 | 39.35 | 12.60 | 26.00 |
| 243 THR | CB | 36.78 | 37.90 | 12.31 | 28.51 |
| 243 THR | OG1 | 37.38 | 37.37 | 13.51 | 30.37 |
| 243 THR | CG2 | 37.80 | 37.84 | 11.15 | 27.57 |
| 243 THR | C | 35.55 | 39.27 | 13.91 | 24.69 |
| 243 THR | O | 36.01 | 39.77 | 14.94 | 26.56 |
| 244 TYR | N | 34.38 | 38.63 | 13.86 | 22.67 |
| 244 TYR | CA | 33.53 | 38.43 | 15.03 | 19.67 |
| 244 TYR | CB | 32.07 | 38.16 | 14.60 | 12.48 |
| 244 TYR | CG | 31.38 | 39.31 | 13.93 | 4.66 |
| 244 TYR | CD1 | 31.42 | 39.46 | 12.55 | 7.44 |
| 244 TYR | CE1 | 30.78 | 40.51 | 11.91 | 4.93 |
| 244 TYR | CD2 | 30.68 | 40.23 | 14.67 | 5.71 |
| 244 TYR | CE2 | 30.04 | 41.29 | 14.07 | 7.76 |
| 244 TYR | CZ | 30.08 | 41.43 | 12.70 | 10.20 |
| 244 TYR | OH | 29.41 | 42.52 | 12.16 | 16.33 |
| 244 TYR | C | 34.05 | 37.21 | 15.81 | 20.03 |
| 244 TYR | O | 33.75 | 37.05 | 16.99 | 22.51 |
| 245 LEU | N | 34.85 | 36.38 | 15.15 | 18.64 |
| 245 LEU | CA | 35.35 | 35.15 | 15.74 | 17.77 |
| 245 LEU | CB | 35.90 | 34.29 | 14.60 | 13.77 |
| 245 LEU | CG | 36.22 | 32.85 | 14.88 | 12.70 |

Figure 5CCC

| Residue | Atom | X | Y | Z | B |
|---|---|---|---|---|---|
| 245 LEU | CD1 | 34.93 | 32.10 | 14.96 | 9.99 |
| 245 LEU | CD2 | 37.07 | 32.32 | 13.76 | 12.02 |
| 245 LEU | C | 36.39 | 35.37 | 16.84 | 18.62 |
| 245 LEU | O | 37.44 | 35.96 | 16.60 | 21.44 |
| 246 GLN | N | 36.11 | 34.90 | 18.05 | 18.72 |
| 246 GLN | CA | 37.04 | 35.09 | 19.17 | 20.51 |
| 246 GLN | CB | 36.28 | 35.10 | 20.51 | 20.38 |
| 246 GLN | CG | 34.94 | 35.80 | 20.50 | 21.11 |
| 246 GLN | CD | 35.00 | 37.32 | 20.62 | 19.51 |
| 246 GLN | OE1 | 34.89 | 37.85 | 21.71 | 19.14 |
| 246 GLN | NE2 | 35.11 | 38.02 | 19.48 | 13.60 |
| 246 GLN | C | 38.12 | 33.99 | 19.18 | 21.66 |
| 246 GLN | O | 38.33 | 33.30 | 20.20 | 23.64 |
| 247 ALA | N | 38.78 | 33.82 | 18.04 | 21.35 |
| 247 ALA | CA | 39.82 | 32.83 | 17.85 | 20.56 |
| 247 ALA | CB | 39.28 | 31.42 | 17.98 | 17.52 |
| 247 ALA | C | 40.31 | 33.09 | 16.43 | 23.39 |
| 247 ALA | O | 41.37 | 32.52 | 16.09 | 27.93 |
| 247 ALA | OT | 39.70 | 33.90 | 15.69 | 22.64 |
| 301 WAT | OH2 | 18.08 | 35.78 | 8.28 | 4.83 |
| 302 WAT | OH2 | 46.30 | 24.32 | -0.62 | 2.00 |
| 303 WAT | OH2 | 42.26 | 21.71 | -12.75 | 9.96 |
| 304 WAT | OH2 | 29.16 | 25.07 | 19.50 | 12.46 |
| 305 WAT | OH2 | 40.30 | 41.06 | 1.38 | 9.27 |
| 306 WAT | OH2 | 43.02 | 20.55 | 13.31 | 8.53 |
| 307 WAT | OH2 | 31.60 | 24.18 | 39.04 | 11.92 |
| 308 WAT | OH2 | 44.97 | 16.87 | 1.77 | 11.06 |
| 309 WAT | OH2 | 46.56 | 26.96 | 1.84 | 17.18 |
| 310 WAT | OH2 | 39.10 | 38.80 | -0.17 | 14.70 |
| 311 WAT | OH2 | 13.79 | 29.75 | -5.95 | 4.60 |

Figure 5DDD

| Residue | Atom | X | Y | Z | B |
|---|---|---|---|---|---|
| 312 WAT | OH2 | 19.29 | 20.32 | 2.86 | 17.45 |
| 313 WAT | OH2 | 38.55 | 38.56 | 16.92 | 9.84 |
| 314 WAT | OH2 | 40.37 | 25.41 | 46.65 | 9.57 |
| 315 WAT | OH2 | 28.73 | 43.64 | 9.47 | 8.54 |
| 316 WAT | OH2 | 28.63 | 20.63 | 14.19 | 7.23 |
| 317 WAT | OH2 | 36.01 | 35.30 | 23.39 | 21.88 |
| 318 WAT | OH2 | 29.89 | 36.21 | 28.21 | 20.83 |
| 319 WAT | OH2 | 46.03 | 18.98 | -4.95 | 19.25 |
| 320 WAT | OH2 | 43.26 | 18.57 | 1.32 | 11.00 |
| 321 WAT | OH2 | 34.16 | 20.32 | 7.14 | 15.58 |
| 322 WAT | OH2 | 39.89 | 14.13 | 37.97 | 20.48 |
| 323 WAT | OH2 | 40.43 | 21.05 | 3.53 | 26.12 |
| 324 WAT | OH2 | 38.65 | 17.74 | 12.52 | 22.99 |
| 325 WAT | OH2 | 13.54 | 17.29 | 5.31 | 22.94 |
| 326 WAT | OH2 | 20.17 | 15.73 | 2.01 | 29.37 |
| 327 WAT | OH2 | 3.49 | 7.49 | 39.34 | 20.46 |
| 328 WAT | OH2 | 31.98 | 14.24 | 1.64 | 26.83 |
| 329 WAT | OH2 | 5.50 | 12.64 | 32.21 | 27.11 |
| 330 WAT | OH2 | 5.64 | 16.70 | 45.62 | 11.34 |
| 331 WAT | OH2 | 28.48 | 17.59 | 11.13 | 39.80 |
| 332 WAT | OH2 | 14.11 | 16.60 | 15.62 | 25.28 |
| 333 WAT | OH2 | 8.97 | 13.57 | 32.58 | 29.38 |

Figure 6A

| Residue | Atom | X | Y | Z | B |
|---|---|---|---|---|---|
| 61 HIS | N | -12.45 | -4.14 | 6.98 | 30.00 |
| 61 HIS | CA | -13.09 | -5.29 | 7.68 | 30.00 |
| 61 HIS | CB | -13.58 | -6.34 | 6.67 | 30.00 |
| 61 HIS | CG | -14.61 | -5.80 | 5.72 | 30.00 |
| 61 HIS | CD2 | -14.77 | -4.58 | 5.17 | 30.00 |
| 61 HIS | ND1 | -15.59 | -6.59 | 5.17 | 30.00 |
| 61 HIS | CE1 | -16.31 | -5.88 | 4.32 | 30.00 |
| 61 HIS | NE2 | -15.84 | -4.65 | 4.30 | 30.00 |
| 61 HIS | C | -12.35 | -5.97 | 8.84 | 30.00 |
| 61 HIS | O | -12.85 | -6.93 | 9.45 | 30.00 |
| 129 SER | N | -17.57 | -0.53 | 1.82 | 30.00 |
| 129 SER | CA | -17.87 | -1.90 | 1.55 | 30.00 |
| 129 SER | CB | -16.59 | -2.67 | 1.72 | 30.00 |
| 129 SER | OG | -16.86 | -4.06 | 1.63 | 30.00 |
| 129 SER | C | -18.86 | -2.27 | 2.69 | 30.00 |
| 129 SER | O | -18.55 | -2.30 | 3.78 | 30.00 |
| 131 ALA | N | -21.18 | -4.82 | 4.64 | 30.00 |
| 131 ALA | CA | -21.24 | -6.27 | 4.85 | 30.00 |
| 131 ALA | CB | -20.27 | -6.70 | 5.94 | 30.00 |
| 131 ALA | C | -22.65 | -6.66 | 5.32 | 30.00 |
| 131 ALA | O | -23.26 | -5.92 | 6.11 | 30.00 |
| 148 HIS | N | -22.28 | -4.06 | 8.86 | 30.00 |
| 148 HIS | CA | -21.39 | -2.88 | 9.07 | 30.00 |
| 148 HIS | CB | -20.28 | -3.23 | 10.04 | 30.00 |
| 148 HIS | CG | -19.42 | -4.37 | 9.58 | 30.00 |
| 148 HIS | CD2 | -19.55 | -5.71 | 9.74 | 30.00 |
| 148 HIS | ND1 | -18.23 | -4.18 | 8.90 | 30.00 |
| 148 HIS | CE1 | -17.67 | -5.35 | 8.66 | 30.00 |
| 148 HIS | NE2 | -18.45 | -6.30 | 9.16 | 30.00 |
| 148 HIS | C | -20.78 | -2.41 | 7.74 | 30.00 |
| 148 HIS | O | -20.87 | -3.07 | 6.68 | 30.00 |

Figure 6B

| Residue | Atom | X | Y | Z | B |
|---|---|---|---|---|---|
| 152 CYS | N | -12.19 | 1.21 | 2.74 | 30.00 |
| 152 CYS | CA | -11.12 | 0.42 | 2.10 | 30.00 |
| 152 CYS | CB | -11.67 | -0.96 | 1.79 | 30.00 |
| 152 CYS | SG | -13.13 | -0.89 | 0.76 | 30.00 |
| 152 CYS | C | -10.63 | 1.13 | 0.86 | 30.00 |
| 152 CYS | O | -11.10 | 2.19 | 0.50 | 30.00 |
| 156 ARG | N | -15.93 | -4.07 | -3.57 | 30.00 |
| 156 ARG | CA | -16.32 | -5.09 | -4.56 | 30.00 |
| 156 ARG | CB | -16.44 | -6.44 | -3.87 | 30.00 |
| 156 ARG | CG | -15.72 | -6.48 | -2.54 | 30.00 |
| 156 ARG | CD | -16.10 | -7.68 | -1.74 | 30.00 |
| 156 ARG | NE | -15.93 | -8.92 | -2.48 | 30.00 |
| 156 ARG | CZ | -15.62 | -10.08 | -1.91 | 30.00 |
| 156 ARG | NH1 | -15.48 | -11.17 | -2.65 | 30.00 |
| 156 ARG | NH2 | -15.44 | -10.16 | -0.59 | 30.00 |
| 156 ARG | C | -17.57 | -4.76 | -5.40 | 30.00 |
| 156 ARG | O | -17.83 | -5.32 | -6.46 | 30.00 |
| 157 ARG | N | -18.38 | -3.86 | -4.89 | 30.00 |
| 157 ARG | CA | -19.57 | -3.45 | -5.62 | 30.00 |
| 157 ARG | CB | -20.72 | -3.30 | -4.65 | 30.00 |
| 157 ARG | CG | -21.29 | -4.64 | -4.20 | 30.00 |
| 157 ARG | CD | -22.70 | -4.56 | -3.58 | 30.00 |
| 157 ARG | NE | -22.57 | -4.44 | -2.14 | 30.00 |
| 157 ARG | CZ | -22.86 | -5.36 | -1.23 | 30.00 |
| 157 ARG | NH1 | -23.39 | -6.54 | -1.44 | 30.00 |
| 157 ARG | NH2 | -22.15 | -5.29 | -0.14 | 30.00 |
| 157 ARG | C | -19.22 | -2.14 | -6.37 | 30.00 |
| 157 ARG | O | -18.27 | -1.44 | -6.03 | 30.00 |

Figure 7A

Figure of the orthogonal three dimensional coordinates in Ångstroms and B factors ($Å^2$) for HSV1 protease.

| Residue | Atom | X | Y | Z | B |
|---|---|---|---|---|---|
| 15 ALA | CB | -3.94 | 13.47 | 22.28 | 30.00 |
| 15 ALA | C | -4.35 | 15.65 | 21.21 | 30.00 |
| 15 ALA | O | -3.99 | 16.48 | 22.06 | 30.00 |
| 15 ALA | N | -2.11 | 14.64 | 21.12 | 30.00 |
| 15 ALA | CA | -3.54 | 14.35 | 21.10 | 30.00 |
| 16 ALA | N | -5.16 | 15.44 | 20.95 | 30.00 |
| 16 ALA | CA | -6.27 | 15.84 | 21.83 | 30.00 |
| 16 ALA | CB | -5.75 | 16.59 | 23.05 | 30.00 |
| 16 ALA | C | -7.22 | 16.78 | 21.08 | 30.00 |
| 16 ALA | O | -6.71 | 17.71 | 20.41 | 30.00 |
| 17 ALA | N | -8.37 | 16.64 | 20.99 | 30.00 |
| 17 ALA | CA | -9.22 | 16.75 | 19.86 | 30.00 |
| 17 ALA | CB | -8.80 | 18.20 | 19.75 | 30.00 |
| 17 ALA | C | -9.63 | 16.02 | 18.57 | 30.00 |
| 17 ALA | O | -8.98 | 16.11 | 17.52 | 30.00 |
| 18 ALA | N | -10.39 | 14.93 | 18.74 | 30.00 |
| 18 ALA | CA | -10.65 | 14.73 | 17.19 | 30.00 |
| 18 ALA | CB | -11.47 | 13.48 | 17.45 | 30.00 |
| 18 ALA | C | -11.39 | 15.66 | 16.24 | 30.00 |
| 18 ALA | O | -12.13 | 16.57 | 16.66 | 30.00 |
| 19 VAL | N | -11.08 | 15.50 | 14.96 | 30.00 |
| 19 VAL | CA | -11.73 | 16.26 | 13.87 | 30.00 |
| 19 VAL | CB | -10.77 | 16.47 | 12.67 | 30.00 |
| 19 VAL | CG1 | -11.51 | 17.03 | 11.45 | 30.00 |
| 19 VAL | CG2 | -9.67 | 17.40 | 13.04 | 30.00 |
| 19 VAL | C | -12.85 | 15.30 | 13.46 | 30.00 |

Figure 7B

| Residue | Atom | X | Y | Z | B |
|---|---|---|---|---|---|
| 19 VAL | O | -12.62 | 14.14 | 13.13 | 30.00 |
| 20 PRO | N | -14.10 | 15.72 | 13.65 | 30.00 |
| 20 PRO | CD | -14.57 | 16.88 | 14.41 | 30.00 |
| 20 PRO | CA | -15.21 | 14.86 | 13.27 | 30.00 |
| 20 PRO | CB | -16.43 | 15.58 | 13.85 | 30.00 |
| 20 PRO | CG | -15.86 | 16.35 | 14.99 | 30.00 |
| 20 PRO | C | -15.25 | 14.87 | 11.76 | 30.00 |
| 20 PRO | O | -15.34 | 15.91 | 11.13 | 30.00 |
| 21 ILE | N | -15.42 | 13.51 | 11.16 | 30.00 |
| 21 ILE | CA | -15.27 | 13.49 | 9.71 | 30.00 |
| 21 ILE | CB | -13.91 | 12.80 | 9.34 | 30.00 |
| 21 ILE | CG2 | -14.13 | 11.53 | 8.51 | 30.00 |
| 21 ILE | CG1 | -12.99 | 13.77 | 8.60 | 30.00 |
| 21 ILE | CD1 | -11.60 | 13.22 | 8.35 | 30.00 |
| 21 ILE | C | -16.43 | 12.70 | 9.11 | 30.00 |
| 21 ILE | O | -16.83 | 11.65 | 9.61 | 30.00 |
| 22 TYR | N | -16.97 | 13.68 | 8.21 | 30.00 |
| 22 TYR | CA | -18.14 | 12.98 | 7.59 | 30.00 |
| 22 TYR | CB | -19.26 | 13.96 | 7.30 | 30.00 |
| 22 TYR | CG | -19.63 | 14.71 | 8.49 | 30.00 |
| 22 TYR | CD1 | -19.94 | 16.05 | 8.37 | 30.00 |
| 22 TYR | CE1 | -20.44 | 16.76 | 9.44 | 30.00 |
| 22 TYR | CD2 | -19.83 | 14.08 | 9.71 | 30.00 |
| 22 TYR | CE2 | -20.33 | 14.78 | 10.78 | 30.00 |
| 22 TYR | CZ | -20.64 | 16.12 | 10.64 | 30.00 |
| 22 TYR | OH | -21.16 | 16.82 | 11.68 | 30.00 |
| 22 TYR | C | -17.68 | 12.33 | 6.26 | 30.00 |
| 22 TYR | O | -16.91 | 12.91 | 5.47 | 30.00 |
| 23 VAL | N | -18.49 | 10.90 | 6.19 | 30.00 |

Figure 7C

| Residue | Atom | X | Y | Z | B |
|---|---|---|---|---|---|
| 23 VAL | CA | -18.25 | 10.08 | 4.99 | 30.00 |
| 23 VAL | CB | -17.91 | 8.62 | 5.33 | 30.00 |
| 23 VAL | CG1 | -16.97 | 8.01 | 4.31 | 30.00 |
| 23 VAL | CG2 | -17.41 | 8.50 | 6.71 | 30.00 |
| 23 VAL | C | -19.66 | 10.02 | 4.39 | 30.00 |
| 23 VAL | O | -20.65 | 9.97 | 5.11 | 30.00 |
| 24 ALA | N | -19.75 | 9.98 | 3.08 | 30.00 |
| 24 ALA | CA | -21.06 | 9.90 | 2.42 | 30.00 |
| 24 ALA | CB | -21.59 | 11.30 | 2.15 | 30.00 |
| 24 ALA | C | -20.75 | 9.18 | 1.13 | 30.00 |
| 24 ALA | O | -19.65 | 9.28 | 0.60 | 30.00 |
| 25 GLY | N | -21.70 | 8.37 | 0.66 | 30.00 |
| 25 GLY | CA | -21.49 | 7.65 | -0.58 | 30.00 |
| 25 GLY | C | -22.54 | 6.57 | -0.70 | 30.00 |
| 25 GLY | O | -23.32 | 6.36 | 0.23 | 30.00 |
| 26 PHE | N | -22.73 | 5.83 | -1.73 | 30.00 |
| 26 PHE | CA | -23.74 | 4.80 | -1.93 | 30.00 |
| 26 PHE | CB | -23.93 | 4.65 | -3.42 | 30.00 |
| 26 PHE | CG | -24.81 | 5.79 | -3.94 | 30.00 |
| 26 PHE | CD1 | -24.23 | 6.88 | -4.59 | 30.00 |
| 26 PHE | CD2 | -26.17 | 5.72 | -3.79 | 30.00 |
| 26 PHE | CE1 | -25.06 | 7.89 | -5.08 | 30.00 |
| 26 PHE | CE2 | -26.99 | 6.73 | -4.29 | 30.00 |
| 26 PHE | CZ | -26.41 | 7.83 | -4.94 | 30.00 |
| 26 PHE | C | -23.32 | 3.48 | -1.25 | 30.00 |
| 26 PHE | O | -22.13 | 3.10 | -1.28 | 30.00 |
| 27 LEU | N | -23.57 | 2.86 | -0.72 | 30.00 |
| 27 LEU | CA | -23.26 | 1.51 | -0.31 | 30.00 |
| 27 LEU | CB | -24.17 | 1.10 | 0.83 | 30.00 |

Figure 7D

| Residue | Atom | X | Y | Z | B |
|---|---|---|---|---|---|
| 27 LEU | CG | -23.69 | 1.06 | 2.27 | 30.00 |
| 27 LEU | CD1 | -23.37 | 2.44 | 2.84 | 30.00 |
| 27 LEU | CD2 | -24.75 | 0.33 | 3.02 | 30.00 |
| 27 LEU | C | -23.49 | 0.60 | -1.54 | 30.00 |
| 27 LEU | O | -22.96 | -0.50 | -1.65 | 30.00 |
| 28 ALA | N | -24.23 | 0.82 | -2.47 | 30.00 |
| 28 ALA | CA | -24.47 | -0.01 | -3.67 | 30.00 |
| 28 ALA | CB | -25.14 | -1.29 | -3.27 | 30.00 |
| 28 ALA | C | -25.36 | 0.76 | -4.68 | 30.00 |
| 28 ALA | O | -26.14 | 1.63 | -4.32 | 30.00 |
| 29 LEU | N | -25.14 | 0.44 | -5.97 | 30.00 |
| 29 LEU | CA | -26.00 | 1.15 | -6.96 | 30.00 |
| 29 LEU | CB | -25.20 | 1.58 | -8.20 | 30.00 |
| 29 LEU | CG | -23.97 | 2.49 | -8.02 | 30.00 |
| 29 LEU | CD1 | -24.47 | 3.89 | -8.07 | 30.00 |
| 29 LEU | CD2 | -23.22 | 2.25 | -6.72 | 30.00 |
| 29 LEU | C | -27.05 | 0.10 | -7.35 | 30.00 |
| 29 LEU | O | -26.73 | -1.03 | -7.68 | 30.00 |
| 30 TYR | N | -28.21 | 0.18 | -7.58 | 30.00 |
| 30 TYR | CA | -29.23 | -0.80 | -7.96 | 30.00 |
| 30 TYR | CB | -30.59 | -0.15 | -7.84 | 30.00 |
| 30 TYR | CG | -31.04 | 0.00 | -6.42 | 30.00 |
| 30 TYR | CD1 | -30.80 | -1.01 | -5.48 | 30.00 |
| 30 TYR | CE1 | -31.25 | -0.87 | -4.19 | 30.00 |
| 30 TYR | CD2 | -31.74 | 1.14 | -6.00 | 30.00 |
| 30 TYR | CE2 | -32.19 | 1.27 | -4.71 | 30.00 |
| 30 TYR | CZ | -31.94 | 0.27 | -3.82 | 30.00 |
| 30 TYR | OH | -32.39 | 0.40 | -2.54 | 30.00 |
| 30 TYR | C | -29.14 | -1.59 | -9.28 | 30.00 |

Figure 7E

| Residue | Atom | X | Y | Z | B |
|---|---|---|---|---|---|
| 30 TYR | O | -29.28 | -2.83 | -9.29 | 30.00 |
| 31 ASP | N | -28.98 | -0.93 | -10.42 | 30.00 |
| 31 ASP | CA | -28.90 | -1.75 | -11.66 | 30.00 |
| 31 ASP | CB | -30.09 | -1.48 | -12.60 | 30.00 |
| 31 ASP | CG | -31.37 | -2.24 | -12.19 | 30.00 |
| 31 ASP | OD1 | -32.44 | -1.60 | -11.99 | 30.00 |
| 31 ASP | OD2 | -31.33 | -3.49 | -12.10 | 30.00 |
| 31 ASP | C | -27.57 | -1.40 | -12.29 | 30.00 |
| 31 ASP | O | -27.49 | -0.85 | -13.39 | 30.00 |
| 32 SER | N | -26.52 | -1.72 | -11.54 | 30.00 |
| 32 SER | CA | -25.11 | -1.40 | -11.94 | 30.00 |
| 32 SER | CB | -24.31 | -0.92 | -10.71 | 30.00 |
| 32 SER | OG | -24.43 | -1.83 | -9.64 | 30.00 |
| 32 SER | C | -24.32 | -2.51 | -12.67 | 30.00 |
| 32 SER | O | -23.34 | -2.27 | -13.38 | 30.00 |
| 33 GLY | N | -24.76 | -3.74 | -12.45 | 30.00 |
| 33 GLY | CA | -24.09 | -4.86 | -13.07 | 30.00 |
| 33 GLY | C | -23.28 | -5.62 | -12.06 | 30.00 |
| 33 GLY | O | -22.39 | -6.35 | -12.46 | 30.00 |
| 34 ASP | N | -23.71 | -5.38 | -10.73 | 30.00 |
| 34 ASP | CA | -22.81 | -6.14 | -9.76 | 30.00 |
| 34 ASP | CB | -23.15 | -5.87 | -8.28 | 30.00 |
| 34 ASP | CG | -23.41 | -4.40 | -7.98 | 30.00 |
| 34 ASP | OD1 | -23.66 | -3.62 | -8.93 | 30.00 |
| 34 ASP | OD2 | -23.39 | -4.02 | -6.81 | 30.00 |
| 34 ASP | C | -23.00 | -7.64 | -10.05 | 30.00 |
| 34 ASP | O | -24.10 | -8.09 | -10.40 | 30.00 |
| 35 SER | N | -22.14 | -8.42 | -9.62 | 30.00 |
| 35 SER | CA | -22.07 | -9.88 | -9.87 | 30.00 |

Figure 7F

| Residue | Atom | X | Y | Z | B |
|---|---|---|---|---|---|
| 35 SER | CB | -20.80 | -10.44 | -9.22 | 30.00 |
| 35 SER | OG | -21.23 | -11.56 | -8.48 | 30.00 |
| 35 SER | C | -23.28 | -10.61 | -9.28 | 30.00 |
| 35 SER | O | -24.09 | -10.02 | -8.51 | 30.00 |
| 36 GLY | N | -23.70 | -11.73 | -9.47 | 30.00 |
| 36 GLY | CA | -24.89 | -12.34 | -8.89 | 30.00 |
| 36 GLY | C | -25.04 | -12.12 | -7.41 | 30.00 |
| 36 GLY | O | -25.99 | -11.51 | -6.95 | 30.00 |
| 37 GLU | N | -24.07 | -12.51 | -6.64 | 30.00 |
| 37 GLU | CA | -23.93 | -12.42 | -5.18 | 30.00 |
| 37 GLU | CB | -22.84 | -13.41 | -4.75 | 30.00 |
| 37 GLU | CG | -22.73 | -13.63 | -3.21 | 30.00 |
| 37 GLU | CD | -23.38 | -14.91 | -2.73 | 30.00 |
| 37 GLU | OE1 | -23.96 | -14.92 | -1.62 | 30.00 |
| 37 GLU | OE2 | -23.32 | -15.91 | -3.48 | 30.00 |
| 37 GLU | C | -23.67 | -11.02 | -4.56 | 30.00 |
| 37 GLU | O | -24.32 | -10.58 | -3.61 | 30.00 |
| 38 LEU | N | -23.20 | -10.28 | -4.85 | 30.00 |
| 38 LEU | CA | -23.10 | -8.86 | -4.46 | 30.00 |
| 38 LEU | CB | -21.80 | -8.30 | -5.04 | 30.00 |
| 38 LEU | CG | -20.54 | -8.55 | -4.19 | 30.00 |
| 38 LEU | CD1 | -20.92 | -9.02 | -2.79 | 30.00 |
| 38 LEU | CD2 | -19.61 | -9.56 | -4.88 | 30.00 |
| 38 LEU | C | -24.30 | -7.95 | -4.78 | 30.00 |
| 38 LEU | O | -24.58 | -6.99 | -4.09 | 30.00 |
| 39 ALA | N | -24.99 | -8.10 | -5.82 | 30.00 |
| 39 ALA | CA | -26.14 | -7.26 | -6.20 | 30.00 |
| 39 ALA | CB | -26.88 | -7.89 | -7.37 | 30.00 |
| 39 ALA | C | -27.13 | -6.99 | -5.07 | 30.00 |

Figure 7G

| Residue | Atom | X | Y | Z | B |
|---|---|---|---|---|---|
| 39 ALA | O | -27.44 | -7.83 | -4.23 | 30.00 |
| 40 LEU | N | -27.69 | -5.88 | -5.02 | 30.00 |
| 40 LEU | CA | -28.65 | -5.45 | -4.00 | 30.00 |
| 40 LEU | CB | -28.07 | -4.29 | -3.19 | 30.00 |
| 40 LEU | CG | -27.45 | -4.63 | -1.83 | 30.00 |
| 40 LEU | CD1 | -26.29 | -3.67 | -1.51 | 30.00 |
| 40 LEU | CD2 | -28.51 | -4.56 | -0.76 | 30.00 |
| 40 LEU | C | -29.90 | -5.03 | -4.75 | 30.00 |
| 40 LEU | O | -29.85 | -4.48 | -5.84 | 30.00 |
| 41 ASP | N | -31.10 | -4.72 | -4.25 | 30.00 |
| 41 ASP | CA | -32.26 | -4.39 | -5.09 | 30.00 |
| 41 ASP | CB | -32.83 | -5.67 | -5.67 | 30.00 |
| 41 ASP | CG | -32.63 | -6.82 | -4.76 | 30.00 |
| 41 ASP | OD1 | -33.63 | -7.49 | -4.46 | 30.00 |
| 41 ASP | OD2 | -31.47 | -7.03 | -4.36 | 30.00 |
| 41 ASP | C | -33.31 | -3.57 | -4.33 | 30.00 |
| 41 ASP | O | -33.35 | -3.56 | -3.12 | 30.00 |
| 42 PRO | N | -33.98 | -2.73 | -4.64 | 30.00 |
| 42 PRO | CD | -34.24 | -2.52 | -6.07 | 30.00 |
| 42 PRO | CA | -34.86 | -1.88 | -3.84 | 30.00 |
| 42 PRO | CB | -35.77 | -1.27 | -4.90 | 30.00 |
| 42 PRO | CG | -34.93 | -1.18 | -6.04 | 30.00 |
| 42 PRO | C | -35.65 | -2.54 | -2.74 | 30.00 |
| 42 PRO | O | -35.66 | -2.10 | -1.59 | 30.00 |
| 43 ASP | N | -36.49 | -3.44 | -3.10 | 30.00 |
| 43 ASP | CA | -37.09 | -4.30 | -2.07 | 30.00 |
| 43 ASP | CB | -37.91 | -5.36 | -2.72 | 30.00 |
| 43 ASP | CG | -38.97 | -4.78 | -3.62 | 30.00 |
| 43 ASP | OD1 | -39.44 | -3.64 | -3.38 | 30.00 |

Figure 7H

| Residue | Atom | X | Y | Z | B |
|---|---|---|---|---|---|
| 43 ASP | OD2 | -39.34 | -5.47 | -4.56 | 30.00 |
| 43 ASP | C | -36.10 | -4.90 | -1.07 | 30.00 |
| 43 ASP | O | -36.40 | -5.03 | 0.10 | 30.00 |
| 44 THR | N | -35.16 | -5.37 | -1.04 | 30.00 |
| 44 THR | CA | -34.25 | -5.88 | -0.01 | 30.00 |
| 44 THR | CB | -33.30 | -6.88 | -0.61 | 30.00 |
| 44 THR | OG1 | -33.56 | -8.11 | 0.04 | 30.00 |
| 44 THR | CG2 | -31.84 | -6.49 | -0.34 | 30.00 |
| 44 THR | C | -33.47 | -4.73 | 0.66 | 30.00 |
| 44 THR | O | -33.11 | -4.78 | 1.83 | 30.00 |
| 45 VAL | N | -33.47 | -3.66 | 0.15 | 30.00 |
| 45 VAL | CA | -32.95 | -2.57 | 0.94 | 30.00 |
| 45 VAL | CB | -32.35 | -1.49 | 0.10 | 30.00 |
| 45 VAL | CG1 | -33.00 | -0.16 | 0.42 | 30.00 |
| 45 VAL | CG2 | -30.88 | -1.40 | 0.39 | 30.00 |
| 45 VAL | C | -34.09 | -2.03 | 1.78 | 30.00 |
| 45 VAL | O | -33.95 | -1.74 | 2.97 | 30.00 |
| 46 ARG | N | -35.27 | -1.97 | 1.18 | 30.00 |
| 46 ARG | CA | -36.46 | -1.46 | 1.86 | 30.00 |
| 46 ARG | CB | -37.68 | -1.61 | 0.95 | 30.00 |
| 46 ARG | CG | -38.95 | -0.93 | 1.45 | 30.00 |
| 46 ARG | CD | -38.82 | 0.62 | 1.44 | 30.00 |
| 46 ARG | NE | -37.98 | 1.15 | 2.54 | 30.00 |
| 46 ARG | CZ | -37.83 | 2.44 | 2.87 | 30.00 |
| 46 ARG | NH1 | -37.05 | 2.76 | 3.90 | 30.00 |
| 46 ARG | NH2 | -38.46 | 3.40 | 2.19 | 30.00 |
| 46 ARG | C | -36.68 | -2.22 | 3.15 | 30.00 |
| 46 ARG | O | -36.92 | -1.68 | 4.21 | 30.00 |
| 47 ALA | N | -36.53 | -3.53 | 3.06 | 30.00 |

Figure 7I

| Residue | Atom | X | Y | Z | B |
|---|---|---|---|---|---|
| 47 ALA | CA | -36.72 | -4.42 | 4.21 | 30.00 |
| 47 ALA | CB | -36.90 | -5.83 | 3.70 | 30.00 |
| 47 ALA | C | -35.59 | -4.37 | 5.27 | 30.00 |
| 47 ALA | O | -35.71 | -4.91 | 6.36 | 30.00 |
| 48 ALA | N | -34.48 | -3.73 | 4.95 | 30.00 |
| 48 ALA | CA | -33.35 | -3.67 | 5.88 | 30.00 |
| 48 ALA | CB | -32.07 | -3.88 | 5.13 | 30.00 |
| 48 ALA | C | -33.32 | -2.34 | 6.62 | 30.00 |
| 48 ALA | O | -32.55 | -2.13 | 7.55 | 30.00 |
| 49 LEU | N | -34.00 | -1.44 | 6.23 | 30.00 |
| 49 LEU | CA | -34.13 | -0.13 | 6.85 | 30.00 |
| 49 LEU | CB | -34.20 | 0.93 | 5.74 | 30.00 |
| 49 LEU | CG | -32.85 | 1.45 | 5.22 | 30.00 |
| 49 LEU | CD1 | -31.95 | 0.27 | 4.91 | 30.00 |
| 49 LEU | CD2 | -33.03 | 2.37 | 4.00 | 30.00 |
| 49 LEU | C | -35.33 | -0.01 | 7.79 | 30.00 |
| 49 LEU | O | -36.43 | -0.46 | 7.49 | 30.00 |
| 50 PRO | N | -35.21 | 0.72 | 8.93 | 30.00 |
| 50 PRO | CD | -36.32 | 1.15 | 9.78 | 30.00 |
| 50 PRO | CA | -33.93 | 1.16 | 9.51 | 30.00 |
| 50 PRO | CB | -34.37 | 2.00 | 10.71 | 30.00 |
| 50 PRO | CG | -35.75 | 2.40 | 10.37 | 30.00 |
| 50 PRO | C | -33.19 | -0.05 | 10.02 | 30.00 |
| 50 PRO | O | -33.77 | -1.09 | 10.30 | 30.00 |
| 51 PRO | N | -31.86 | 0.07 | 10.13 | 30.00 |
| 51 PRO | CD | -30.97 | 1.13 | 9.63 | 30.00 |
| 51 PRO | CA | -31.11 | -1.08 | 10.61 | 30.00 |
| 51 PRO | CB | -29.66 | -0.59 | 10.52 | 30.00 |
| 51 PRO | CG | -29.71 | 0.37 | 9.35 | 30.00 |

Figure 7J

| Residue | Atom | X | Y | Z | B |
|---|---|---|---|---|---|
| 51 PRO | C | -31.52 | -1.42 | 12.06 | 30.00 |
| 51 PRO | O | -31.80 | -0.55 | 12.86 | 30.00 |
| 52 ASP | N | -31.64 | -2.67 | 12.33 | 30.00 |
| 52 ASP | CA | -31.97 | -3.14 | 13.66 | 30.00 |
| 52 ASP | CB | -31.91 | -4.64 | 13.83 | 30.00 |
| 52 ASP | CG | -30.69 | -5.08 | 14.67 | 30.00 |
| 52 ASP | OD1 | -29.91 | -5.96 | 14.24 | 30.00 |
| 52 ASP | OD2 | -30.54 | -4.51 | 15.77 | 30.00 |
| 52 ASP | C | -30.99 | -2.61 | 14.69 | 30.00 |
| 52 ASP | O | -31.28 | -1.86 | 15.70 | 30.00 |
| 53 ASN | N | -29.69 | -2.75 | 14.39 | 30.00 |
| 53 ASN | CA | -28.61 | -2.21 | 15.22 | 30.00 |
| 53 ASN | CB | -27.80 | -3.36 | 15.82 | 30.00 |
| 53 ASN | CG | -28.50 | -4.01 | 17.00 | 30.00 |
| 53 ASN | OD1 | -28.90 | -5.17 | 16.94 | 30.00 |
| 53 ASN | ND2 | -28.67 | -3.25 | 18.09 | 30.00 |
| 53 ASN | C | -27.73 | -1.24 | 14.43 | 30.00 |
| 53 ASN | O | -27.63 | -1.33 | 13.21 | 30.00 |
| 54 PRO | N | -27.11 | -0.28 | 15.13 | 30.00 |
| 54 PRO | CD | -27.15 | -0.08 | 16.59 | 30.00 |
| 54 PRO | CA | -26.25 | 0.72 | 14.51 | 30.00 |
| 54 PRO | CB | -25.66 | 1.47 | 15.71 | 30.00 |
| 54 PRO | CG | -26.76 | 1.38 | 16.73 | 30.00 |
| 54 PRO | C | -25.16 | 0.07 | 13.69 | 30.00 |
| 54 PRO | O | -24.69 | -1.02 | 13.97 | 30.00 |
| 55 LEU | N | -24.80 | 0.75 | 12.62 | 30.00 |
| 55 LEU | CA | -23.78 | 0.22 | 11.77 | 30.00 |
| 55 LEU | CB | -24.11 | 0.42 | 10.30 | 30.00 |
| 55 LEU | CG | -25.51 | 0.00 | 9.89 | 30.00 |

Figure 7K

| Residue | Atom | X | Y | Z | B |
|---------|------|-----|------|------|-------|
| 55 LEU | CD1 | -25.88 | 0.69 | 8.61 | 30.00 |
| 55 LEU | CD2 | -25.53 | -1.47 | 9.70 | 30.00 |
| 55 LEU | C | -22.51 | 0.92 | 12.12 | 30.00 |
| 55 LEU | O | -22.39 | 2.13 | 12.02 | 30.00 |
| 56 PRO | N | -21.57 | 0.19 | 12.69 | 30.00 |
| 56 PRO | CD | -21.73 | -1.18 | 13.22 | 30.00 |
| 56 PRO | CA | -20.28 | 0.75 | 13.06 | 30.00 |
| 56 PRO | CB | -19.68 | -0.37 | 13.89 | 30.00 |
| 56 PRO | CG | -20.33 | -1.60 | 13.32 | 30.00 |
| 56 PRO | C | -19.47 | 0.92 | 11.77 | 30.00 |
| 56 PRO | O | -19.78 | 0.31 | 10.74 | 30.00 |
| 57 ILE | N | -18.43 | 1.76 | 11.81 | 30.00 |
| 57 ILE | CA | -17.58 | 1.93 | 10.62 | 30.00 |
| 57 ILE | CB | -17.48 | 3.40 | 10.17 | 30.00 |
| 57 ILE | CG2 | -16.33 | 3.57 | 9.12 | 30.00 |
| 57 ILE | CG1 | -18.84 | 3.89 | 9.64 | 30.00 |
| 57 ILE | CD1 | -18.86 | 5.33 | 9.33 | 30.00 |
| 57 ILE | C | -16.20 | 1.48 | 11.04 | 30.00 |
| 57 ILE | O | -15.67 | 1.92 | 12.06 | 30.00 |
| 58 ASN | N | -15.65 | 0.54 | 10.30 | 30.00 |
| 58 ASN | CA | -14.31 | 0.08 | 10.61 | 30.00 |
| 58 ASN | CB | -14.34 | -1.30 | 11.24 | 30.00 |
| 58 ASN | CG | -15.14 | -2.27 | 10.45 | 30.00 |
| 58 ASN | OD1 | -15.41 | -2.06 | 9.29 | 30.00 |
| 58 ASN | ND2 | -15.47 | -3.39 | 11.08 | 30.00 |
| 58 ASN | C | -13.40 | 0.16 | 9.39 | 30.00 |
| 58 ASN | O | -13.83 | 0.51 | 8.31 | 30.00 |
| 59 VAL | N | -12.10 | -0.06 | 9.60 | 30.00 |
| 59 VAL | CA | -11.13 | 0.02 | 8.50 | 30.00 |

Figure 7L

| Residue | Atom | X | Y | Z | B |
|---|---|---|---|---|---|
| 59 VAL | CB | -9.80 | 0.66 | 8.94 | 30.00 |
| 59 VAL | CG1 | -8.68 | -0.36 | 8.84 | 30.00 |
| 59 VAL | CG2 | -9.46 | 1.85 | 8.06 | 30.00 |
| 59 VAL | C | -10.84 | -1.36 | 7.96 | 30.00 |
| 59 VAL | O | -10.50 | -2.28 | 8.69 | 30.00 |
| 60 ASP | N | -11.00 | -1.52 | 6.66 | 30.00 |
| 60 ASP | CA | -10.72 | -2.81 | 5.98 | 30.00 |
| 60 ASP | CB | -9.21 | -2.88 | 5.67 | 30.00 |
| 60 ASP | CG | -8.78 | -4.21 | 5.06 | 30.00 |
| 60 ASP | OD1 | -9.01 | -4.42 | 3.83 | 30.00 |
| 60 ASP | OD2 | -8.20 | -5.04 | 5.80 | 30.00 |
| 60 ASP | C | -11.21 | -4.08 | 6.77 | 30.00 |
| 60 ASP | O | -10.44 | -4.98 | 7.14 | 30.00 |
| 61 HIS | N | -12.45 | -4.14 | 6.98 | 30.00 |
| 61 HIS | CA | -13.09 | -5.29 | 7.68 | 30.00 |
| 61 HIS | CB | -13.58 | -6.34 | 6.67 | 30.00 |
| 61 HIS | CG | -14.61 | -5.80 | 5.72 | 30.00 |
| 61 HIS | CD2 | -14.77 | -4.58 | 5.17 | 30.00 |
| 61 HIS | ND1 | -15.59 | -6.59 | 5.17 | 30.00 |
| 61 HIS | CE1 | -16.31 | -5.88 | 4.32 | 30.00 |
| 61 HIS | NE2 | -15.84 | -4.65 | 4.30 | 30.00 |
| 61 HIS | C | -12.35 | -5.97 | 8.84 | 30.00 |
| 61 HIS | O | -12.85 | -6.93 | 9.45 | 30.00 |
| 62 ARG | N | -11.45 | -5.26 | 9.41 | 30.00 |
| 62 ARG | CA | -10.77 | -5.67 | 10.63 | 30.00 |
| 62 ARG | CB | -9.40 | -4.99 | 10.64 | 30.00 |
| 62 ARG | CG | -8.40 | -5.55 | 9.64 | 30.00 |
| 62 ARG | CD | -8.02 | -6.99 | 10.03 | 30.00 |
| 62 ARG | NE | -7.41 | -7.05 | 11.36 | 30.00 |

Figure 7M

| Residue | Atom | X | Y | Z | B |
|---|---|---:|---:|---:|---:|
| 62 ARG | CZ | -6.11 | -7.26 | 11.59 | 30.00 |
| 62 ARG | NH1 | -5.28 | -7.45 | 10.57 | 30.00 |
| 62 ARG | NH2 | -5.66 | -7.28 | 12.84 | 30.00 |
| 62 ARG | C | -11.72 | -5.10 | 11.71 | 30.00 |
| 62 ARG | O | -11.66 | -3.91 | 12.06 | 30.00 |
| 63 ALA | N | -12.65 | -5.94 | 12.17 | 30.00 |
| 63 ALA | CA | -13.67 | -5.52 | 13.18 | 30.00 |
| 63 ALA | CB | -14.63 | -6.65 | 13.48 | 30.00 |
| 63 ALA | C | -13.13 | -4.90 | 14.48 | 30.00 |
| 63 ALA | O | -13.87 | -4.36 | 15.29 | 30.00 |
| 64 GLY | N | -11.80 | -5.03 | 14.74 | 30.00 |
| 64 GLY | CA | -11.16 | -4.41 | 15.87 | 30.00 |
| 64 GLY | C | -11.01 | -2.93 | 15.71 | 30.00 |
| 64 GLY | O | -11.01 | -2.10 | 16.66 | 30.00 |
| 65 CYS | N | -10.97 | -2.54 | 14.41 | 30.00 |
| 65 CYS | CA | -10.80 | -1.13 | 13.96 | 30.00 |
| 65 CYS | CB | -10.05 | -1.10 | 12.66 | 30.00 |
| 65 CYS | SG | -8.41 | -0.83 | 12.94 | 30.00 |
| 65 CYS | C | -12.03 | -0.29 | 13.80 | 30.00 |
| 65 CYS | O | -12.26 | 0.29 | 12.76 | 30.00 |
| 66 GLU | N | -12.83 | -0.02 | 14.72 | 30.00 |
| 66 GLU | CA | -14.08 | 0.65 | 14.67 | 30.00 |
| 66 GLU | CB | -14.86 | 0.23 | 15.88 | 30.00 |
| 66 GLU | CG | -16.24 | 0.71 | 15.83 | 30.00 |
| 66 GLU | CD | -17.02 | 0.26 | 17.00 | 30.00 |
| 66 GLU | OE1 | -16.95 | -0.95 | 17.33 | 30.00 |
| 66 GLU | OE2 | -17.71 | 1.11 | 17.59 | 30.00 |
| 66 GLU | C | -13.70 | 2.13 | 14.62 | 30.00 |
| 66 GLU | O | -12.85 | 2.58 | 15.40 | 30.00 |

Figure 7N

| Residue | Atom | X | Y | Z | B |
|---|---|---:|---:|---:|---:|
| 67 VAL | N | -13.84 | 2.95 | 14.01 | 30.00 |
| 67 VAL | CA | -13.40 | 4.36 | 14.03 | 30.00 |
| 67 VAL | CB | -12.41 | 4.67 | 12.88 | 30.00 |
| 67 VAL | CG1 | -11.69 | 3.38 | 12.41 | 30.00 |
| 67 VAL | CG2 | -13.14 | 5.34 | 11.72 | 30.00 |
| 67 VAL | C | -14.59 | 5.34 | 13.93 | 30.00 |
| 67 VAL | O | -14.46 | 6.57 | 14.03 | 30.00 |
| 68 GLY | N | -15.78 | 4.79 | 13.74 | 30.00 |
| 68 GLY | CA | -16.94 | 5.64 | 13.61 | 30.00 |
| 68 GLY | C | -18.27 | 4.91 | 13.65 | 30.00 |
| 68 GLY | O | -18.34 | 3.73 | 14.03 | 30.00 |
| 69 ARG | N | -19.32 | 5.62 | 13.23 | 30.00 |
| 69 ARG | CA | -20.69 | 5.08 | 13.24 | 30.00 |
| 69 ARG | CB | -21.30 | 5.44 | 14.59 | 30.00 |
| 69 ARG | CG | -22.72 | 5.00 | 14.79 | 30.00 |
| 69 ARG | CD | -22.78 | 3.52 | 14.82 | 30.00 |
| 69 ARG | NE | -22.16 | 2.94 | 16.01 | 30.00 |
| 69 ARG | CZ | -22.59 | 3.15 | 17.25 | 30.00 |
| 69 ARG | NH1 | -21.97 | 2.54 | 18.26 | 30.00 |
| 69 ARG | NH2 | -23.59 | 3.98 | 17.50 | 30.00 |
| 69 ARG | C | -21.52 | 5.67 | 12.09 | 30.00 |
| 69 ARG | O | -21.52 | 6.88 | 11.82 | 30.00 |
| 70 VAL | N | -22.20 | 4.78 | 11.37 | 30.00 |
| 70 VAL | CA | -23.09 | 5.14 | 10.27 | 30.00 |
| 70 VAL | CB | -23.62 | 3.87 | 9.58 | 30.00 |
| 70 VAL | CG1 | -24.86 | 4.18 | 8.76 | 30.00 |
| 70 VAL | CG2 | -22.54 | 3.25 | 8.72 | 30.00 |
| 70 VAL | C | -24.30 | 5.91 | 10.89 | 30.00 |
| 70 VAL | O | -25.06 | 5.36 | 11.70 | 30.00 |

Figure 7O

| Residue | Atom | X | Y | Z | B |
|---|---|---|---|---|---|
| 71 LEU | N | -24.43 | 7.18 | 10.54 | 30.00 |
| 71 LEU | CA | -25.56 | 8.01 | 11.06 | 30.00 |
| 71 LEU | CB | -25.22 | 9.48 | 10.94 | 30.00 |
| 71 LEU | CG | -24.36 | 10.11 | 11.99 | 30.00 |
| 71 LEU | CD1 | -23.36 | 9.11 | 12.48 | 30.00 |
| 71 LEU | CD2 | -23.72 | 11.34 | 11.44 | 30.00 |
| 71 LEU | C | -26.95 | 7.73 | 10.37 | 30.00 |
| 71 LEU | O | -28.00 | 7.65 | 11.04 | 30.00 |
| 72 ALA | N | -27.07 | 7.71 | 9.08 | 30.00 |
| 72 ALA | CA | -28.21 | 7.52 | 8.18 | 30.00 |
| 72 ALA | CB | -28.67 | 8.84 | 7.64 | 30.00 |
| 72 ALA | C | -27.92 | 6.60 | 7.01 | 30.00 |
| 72 ALA | O | -26.86 | 6.58 | 6.42 | 30.00 |
| 73 VAL | N | -28.88 | 5.80 | 6.62 | 30.00 |
| 73 VAL | CA | -28.88 | 5.00 | 5.38 | 30.00 |
| 73 VAL | CB | -28.79 | 3.51 | 5.66 | 30.00 |
| 73 VAL | CG1 | -28.66 | 2.73 | 4.36 | 30.00 |
| 73 VAL | CG2 | -27.61 | 3.23 | 6.54 | 30.00 |
| 73 VAL | C | -30.25 | 5.30 | 4.77 | 30.00 |
| 73 VAL | O | -31.27 | 5.07 | 5.38 | 30.00 |
| 74 VAL | N | -30.27 | 5.92 | 3.55 | 30.00 |
| 74 VAL | CA | -31.56 | 6.30 | 3.00 | 30.00 |
| 74 VAL | CB | -31.60 | 7.78 | 2.65 | 30.00 |
| 74 VAL | CG1 | -32.95 | 8.12 | 2.08 | 30.00 |
| 74 VAL | CG2 | -31.35 | 8.62 | 3.87 | 30.00 |
| 74 VAL | C | -31.84 | 5.48 | 1.74 | 30.00 |
| 74 VAL | O | -30.99 | 5.31 | 0.85 | 30.00 |
| 75 ASP | N | -32.72 | 4.94 | 1.33 | 30.00 |
| 75 ASP | CA | -32.92 | 4.24 | 0.08 | 30.00 |

Figure 7P

| Residue | Atom | X | Y | Z | B |
|---|---|---|---|---|---|
| 75 ASP | CB | -34.07 | 3.26 | 0.08 | 30.00 |
| 75 ASP | CG | -35.35 | 3.87 | -0.53 | 30.00 |
| 75 ASP | OD1 | -35.40 | 4.16 | -1.75 | 30.00 |
| 75 ASP | OD2 | -36.31 | 4.04 | 0.24 | 30.00 |
| 75 ASP | C | -33.26 | 5.20 | -1.05 | 30.00 |
| 75 ASP | O | -34.28 | 5.88 | -1.16 | 30.00 |
| 76 ASP | N | -32.19 | 5.56 | -1.85 | 30.00 |
| 76 ASP | CA | -32.32 | 6.53 | -2.92 | 30.00 |
| 76 ASP | CB | -30.99 | 7.21 | -3.15 | 30.00 |
| 76 ASP | CG | -31.14 | 8.53 | -3.80 | 30.00 |
| 76 ASP | OD1 | -32.27 | 9.05 | -3.91 | 30.00 |
| 76 ASP | OD2 | -30.13 | 9.10 | -4.18 | 30.00 |
| 76 ASP | C | -32.72 | 5.74 | -4.16 | 30.00 |
| 76 ASP | O | -32.37 | 4.55 | -4.29 | 30.00 |
| 77 PRO | N | -33.44 | 6.38 | -5.10 | 30.00 |
| 77 PRO | CD | -34.03 | 7.73 | -5.05 | 30.00 |
| 77 PRO | CA | -33.85 | 5.70 | -6.32 | 30.00 |
| 77 PRO | CB | -34.39 | 6.84 | -7.17 | 30.00 |
| 77 PRO | CG | -35.00 | 7.72 | -6.20 | 30.00 |
| 77 PRO | C | -32.68 | 4.99 | -7.04 | 30.00 |
| 77 PRO | O | -32.86 | 4.08 | -7.82 | 30.00 |
| 78 ARG | N | -31.46 | 5.42 | -6.73 | 30.00 |
| 78 ARG | CA | -30.27 | 4.82 | -7.34 | 30.00 |
| 78 ARG | CB | -29.29 | 5.93 | -7.65 | 30.00 |
| 78 ARG | CG | -29.81 | 7.03 | -8.57 | 30.00 |
| 78 ARG | CD | -28.72 | 8.08 | -8.86 | 30.00 |
| 78 ARG | NE | -27.54 | 7.46 | -9.50 | 30.00 |
| 78 ARG | CZ | -26.27 | 7.78 | -9.27 | 30.00 |
| 78 ARG | NH1 | -25.31 | 7.13 | -9.93 | 30.00 |

Figure 7Q

| Residue | Atom | X | Y | Z | B |
|---|---|---|---|---|---|
| 78 ARG | NH2 | -25.93 | 8.71 | -8.37 | 30.00 |
| 78 ARG | C | -29.59 | 3.70 | -6.48 | 30.00 |
| 78 ARG | O | -28.91 | 2.81 | -6.99 | 30.00 |
| 79 GLY | N | -29.82 | 3.73 | -5.18 | 30.00 |
| 79 GLY | CA | -29.20 | 2.73 | -4.33 | 30.00 |
| 79 GLY | C | -29.17 | 3.22 | -2.91 | 30.00 |
| 79 GLY | O | -29.45 | 4.39 | -2.64 | 30.00 |
| 80 PRO | N | -28.81 | 2.36 | -1.96 | 30.00 |
| 80 PRO | CD | -28.38 | 0.96 | -2.15 | 30.00 |
| 80 PRO | CA | -28.75 | 2.75 | -0.56 | 30.00 |
| 80 PRO | CB | -28.49 | 1.43 | 0.16 | 30.00 |
| 80 PRO | CG | -27.68 | 0.65 | -0.81 | 30.00 |
| 80 PRO | C | -27.59 | 3.69 | -0.36 | 30.00 |
| 80 PRO | O | -26.43 | 3.33 | -0.57 | 30.00 |
| 81 PHE | N | -27.92 | 4.90 | 0.02 | 30.00 |
| 81 PHE | CA | -26.95 | 5.96 | 0.30 | 30.00 |
| 81 PHE | CB | -27.46 | 7.23 | -0.34 | 30.00 |
| 81 PHE | CG | -26.34 | 8.26 | -0.42 | 30.00 |
| 81 PHE | CD1 | -26.60 | 9.51 | -0.97 | 30.00 |
| 81 PHE | CD2 | -25.10 | 7.94 | 0.05 | 30.00 |
| 81 PHE | CE1 | -25.55 | 10.44 | -1.01 | 30.00 |
| 81 PHE | CE2 | -24.07 | 8.87 | 0.01 | 30.00 |
| 81 PHE | CZ | -24.32 | 10.14 | -0.53 | 30.00 |
| 81 PHE | C | -26.73 | 6.11 | 1.81 | 30.00 |
| 81 PHE | O | -27.70 | 5.95 | 2.56 | 30.00 |
| 82 PHE | N | -25.51 | 6.37 | 2.30 | 30.00 |
| 82 PHE | CA | -25.35 | 6.50 | 3.75 | 30.00 |
| 82 PHE | CB | -24.74 | 5.22 | 4.25 | 30.00 |
| 82 PHE | CG | -23.22 | 5.28 | 4.13 | 30.00 |

Figure 7R

| Residue | Atom | X | Y | Z | B |
|---|---|---|---|---|---|
| 82 PHE | CD1 | -22.48 | 4.10 | 4.12 | 30.00 |
| 82 PHE | CD2 | -22.60 | 6.49 | 4.01 | 30.00 |
| 82 PHE | CE1 | -21.09 | 4.19 | 3.98 | 30.00 |
| 82 PHE | CE2 | -21.23 | 6.57 | 3.86 | 30.00 |
| 82 PHE | CZ | -20.47 | 5.39 | 3.85 | 30.00 |
| 82 PHE | C | -24.49 | 7.73 | 4.08 | 30.00 |
| 82 PHE | O | -23.75 | 8.29 | 3.30 | 30.00 |
| 83 VAL | N | -24.58 | 8.09 | 5.37 | 30.00 |
| 83 VAL | CA | -23.77 | 9.17 | 5.91 | 30.00 |
| 83 VAL | CB | -24.57 | 10.41 | 6.07 | 30.00 |
| 83 VAL | CG1 | -23.82 | 11.39 | 6.92 | 30.00 |
| 83 VAL | CG2 | -24.82 | 11.01 | 4.70 | 30.00 |
| 83 VAL | C | -23.25 | 8.70 | 7.26 | 30.00 |
| 83 VAL | O | -23.99 | 8.27 | 8.13 | 30.00 |
| 84 GLY | N | -21.92 | 8.75 | 7.40 | 30.00 |
| 84 GLY | CA | -21.27 | 8.34 | 8.62 | 30.00 |
| 84 GLY | C | -20.40 | 9.39 | 9.27 | 30.00 |
| 84 GLY | O | -20.10 | 10.43 | 8.69 | 30.00 |
| 85 LEU | N | -19.80 | 9.19 | 10.33 | 30.00 |
| 85 LEU | CA | -19.06 | 10.04 | 11.27 | 30.00 |
| 85 LEU | CB | -20.00 | 10.54 | 12.38 | 30.00 |
| 85 LEU | CG | -19.83 | 12.01 | 12.82 | 30.00 |
| 85 LEU | CD1 | -18.67 | 12.22 | 13.79 | 30.00 |
| 85 LEU | CD2 | -19.63 | 12.86 | 11.59 | 30.00 |
| 85 LEU | C | -17.89 | 9.27 | 11.87 | 30.00 |
| 85 LEU | O | -18.04 | 8.19 | 12.42 | 30.00 |
| 86 ILE | N | -16.79 | 9.78 | 11.64 | 30.00 |
| 86 ILE | CA | -15.53 | 9.18 | 12.07 | 30.00 |
| 86 ILE | CB | -14.63 | 9.04 | 10.85 | 30.00 |

Figure 7S

| Residue | Atom | X | Y | Z | B |
|---|---|---|---|---|---|
| 86 ILE | CG2 | -13.21 | 8.65 | 11.22 | 30.00 |
| 86 ILE | CG1 | -15.28 | 8.06 | 9.88 | 30.00 |
| 86 ILE | CD1 | -14.81 | 8.24 | 8.47 | 30.00 |
| 86 ILE | C | -14.94 | 10.17 | 13.07 | 30.00 |
| 86 ILE | O | -14.65 | 11.33 | 12.75 | 30.00 |
| 87 ALA | N | -14.83 | 9.75 | 14.31 | 30.00 |
| 87 ALA | CA | -14.26 | 10.62 | 15.36 | 30.00 |
| 87 ALA | CB | -15.31 | 10.96 | 16.38 | 30.00 |
| 87 ALA | C | -13.15 | 9.75 | 15.96 | 30.00 |
| 87 ALA | O | -13.35 | 8.98 | 16.90 | 30.00 |
| 88 CYS | N | -12.03 | 9.67 | 15.53 | 30.00 |
| 88 CYS | CA | -10.79 | 8.98 | 15.81 | 30.00 |
| 88 CYS | CB | -10.71 | 7.77 | 14.93 | 30.00 |
| 88 CYS | SG | -9.21 | 6.86 | 15.04 | 30.00 |
| 88 CYS | C | -9.63 | 9.91 | 15.52 | 30.00 |
| 88 CYS | O | -9.37 | 10.26 | 14.37 | 30.00 |
| 89 VAL | N | -8.92 | 10.28 | 16.53 | 30.00 |
| 89 VAL | CA | -7.60 | 10.92 | 16.48 | 30.00 |
| 89 VAL | CB | -7.43 | 11.79 | 17.71 | 30.00 |
| 89 VAL | CG1 | -7.34 | 10.94 | 18.99 | 30.00 |
| 89 VAL | CG2 | -6.22 | 12.64 | 17.53 | 30.00 |
| 89 VAL | C | -6.45 | 9.91 | 16.38 | 30.00 |
| 89 VAL | O | -5.41 | 10.16 | 15.78 | 30.00 |
| 90 GLN | N | -6.48 | 8.80 | 16.66 | 30.00 |
| 90 GLN | CA | -5.36 | 7.87 | 16.41 | 30.00 |
| 90 GLN | CB | -5.54 | 6.58 | 17.23 | 30.00 |
| 90 GLN | CG | -5.90 | 6.86 | 18.66 | 30.00 |
| 90 GLN | CD | -6.38 | 5.63 | 19.39 | 30.00 |
| 90 GLN | OE1 | -5.74 | 4.60 | 19.38 | 30.00 |

Figure 7T

| Residue | Atom | X | Y | Z | B |
|---|---|---|---|---|---|
| 90 GLN | NE2 | -7.52 | 5.74 | 20.02 | 30.00 |
| 90 GLN | C | -5.25 | 7.56 | 14.91 | 30.00 |
| 90 GLN | O | -4.17 | 7.48 | 14.33 | 30.00 |
| 91 LEU | N | -6.49 | 7.40 | 14.26 | 30.00 |
| 91 LEU | CA | -6.45 | 7.38 | 12.78 | 30.00 |
| 91 LEU | CB | -7.85 | 7.13 | 12.28 | 30.00 |
| 91 LEU | CG | -8.16 | 7.42 | 10.81 | 30.00 |
| 91 LEU | CD1 | -8.78 | 6.21 | 10.14 | 30.00 |
| 91 LEU | CD2 | -9.06 | 8.62 | 10.75 | 30.00 |
| 91 LEU | C | -5.90 | 8.76 | 12.31 | 30.00 |
| 91 LEU | O | -5.12 | 8.84 | 11.37 | 30.00 |
| 92 GLU | N | -6.04 | 9.82 | 12.69 | 30.00 |
| 92 GLU | CA | -5.47 | 11.12 | 12.24 | 30.00 |
| 92 GLU | CB | -5.94 | 12.28 | 13.13 | 30.00 |
| 92 GLU | CG | -7.00 | 13.13 | 12.51 | 30.00 |
| 92 GLU | CD | -7.00 | 14.55 | 13.05 | 30.00 |
| 92 GLU | OE1 | -8.01 | 14.92 | 13.71 | 30.00 |
| 92 GLU | OE2 | -6.02 | 15.29 | 12.78 | 30.00 |
| 92 GLU | C | -3.96 | 11.09 | 12.30 | 30.00 |
| 92 GLU | O | -3.28 | 11.29 | 11.31 | 30.00 |
| 93 ARG | N | -3.44 | 10.86 | 13.51 | 30.00 |
| 93 ARG | CA | -1.99 | 10.79 | 13.77 | 30.00 |
| 93 ARG | CB | -1.75 | 10.54 | 15.25 | 30.00 |
| 93 ARG | CG | -1.15 | 11.73 | 15.96 | 30.00 |
| 93 ARG | CD | -2.06 | 12.97 | 15.97 | 30.00 |
| 93 ARG | NE | -1.83 | 13.75 | 17.20 | 30.00 |
| 93 ARG | CZ | -2.34 | 14.96 | 17.45 | 30.00 |
| 93 ARG | NH1 | -2.05 | 15.57 | 18.61 | 30.00 |
| 93 ARG | NH2 | -3.13 | 15.56 | 16.57 | 30.00 |

Figure 7U

| Residue | Atom | X | Y | Z | B |
|---|---|---:|---:|---:|---:|
| 93 ARG | C | -1.25 | 9.77 | 12.93 | 30.00 |
| 93 ARG | O | -0.27 | 10.08 | 12.27 | 30.00 |
| 94 VAL | N | -1.73 | 8.57 | 12.87 | 30.00 |
| 94 VAL | CA | -1.10 | 7.44 | 12.13 | 30.00 |
| 94 VAL | CB | -1.84 | 6.11 | 12.44 | 30.00 |
| 94 VAL | CG1 | -1.51 | 5.08 | 11.45 | 30.00 |
| 94 VAL | CG2 | -1.51 | 5.64 | 13.83 | 30.00 |
| 94 VAL | C | -1.11 | 7.70 | 10.59 | 30.00 |
| 94 VAL | O | -0.13 | 7.48 | 9.91 | 30.00 |
| 95 LEU | N | -2.03 | 8.16 | 10.10 | 30.00 |
| 95 LEU | CA | -1.95 | 8.81 | 8.73 | 30.00 |
| 95 LEU | CB | -3.32 | 9.37 | 8.34 | 30.00 |
| 95 LEU | CG | -4.45 | 8.51 | 7.74 | 30.00 |
| 95 LEU | CD1 | -5.01 | 9.07 | 6.42 | 30.00 |
| 95 LEU | CD2 | -3.92 | 7.09 | 7.55 | 30.00 |
| 95 LEU | C | -0.88 | 9.94 | 8.73 | 30.00 |
| 95 LEU | O | -0.01 | 10.01 | 7.89 | 30.00 |
| 96 GLU | N | -1.20 | 11.17 | 9.39 | 30.00 |
| 96 GLU | CA | -0.39 | 12.42 | 9.42 | 30.00 |
| 96 GLU | CB | -0.79 | 13.31 | 10.61 | 30.00 |
| 96 GLU | CG | -2.07 | 14.12 | 10.46 | 30.00 |
| 96 GLU | CD | -1.87 | 15.63 | 10.67 | 30.00 |
| 96 GLU | OE1 | -2.70 | 16.25 | 11.39 | 30.00 |
| 96 GLU | OE2 | -0.88 | 16.19 | 10.13 | 30.00 |
| 96 GLU | C | 1.12 | 12.16 | 9.52 | 30.00 |
| 96 GLU | O | 1.95 | 12.88 | 8.96 | 30.00 |
| 97 THR | N | 1.58 | 11.16 | 10.05 | 30.00 |
| 97 THR | CA | 2.95 | 10.85 | 10.42 | 30.00 |
| 97 THR | CB | 3.08 | 10.38 | 11.96 | 30.00 |

Figure 7V

| Residue | Atom | X | Y | Z | B |
|---|---|---|---|---|---|
| 97 THR | OG1 | 3.73 | 9.09 | 12.05 | 30.00 |
| 97 THR | CG2 | 1.72 | 10.24 | 12.60 | 30.00 |
| 97 THR | C | 3.60 | 9.83 | 9.46 | 30.00 |
| 97 THR | O | 4.80 | 9.83 | 9.23 | 30.00 |
| 98 ALA | N | 2.61 | 9.14 | 8.82 | 30.00 |
| 98 ALA | CA | 3.06 | 8.24 | 7.73 | 30.00 |
| 98 ALA | CB | 1.97 | 7.23 | 7.38 | 30.00 |
| 98 ALA | C | 3.38 | 9.10 | 6.53 | 30.00 |
| 98 ALA | O | 4.33 | 8.92 | 5.83 | 30.00 |
| 99 ALA | N | 2.52 | 10.08 | 6.31 | 30.00 |
| 99 ALA | CA | 2.69 | 10.98 | 5.20 | 30.00 |
| 99 ALA | CB | 1.48 | 11.91 | 5.09 | 30.00 |
| 99 ALA | C | 3.94 | 11.80 | 5.41 | 30.00 |
| 99 ALA | O | 3.96 | 12.79 | 6.13 | 30.00 |
| 100 SER | N | 5.01 | 11.57 | 4.38 | 30.00 |
| 100 SER | CA | 6.31 | 12.16 | 4.85 | 30.00 |
| 100 SER | CB | 7.29 | 11.04 | 5.23 | 30.00 |
| 100 SER | OG | 6.80 | 10.24 | 6.31 | 30.00 |
| 100 SER | C | 6.63 | 13.02 | 3.69 | 30.00 |
| 100 SER | O | 7.73 | 12.73 | 2.90 | 30.00 |
| 101 ALA | N | 5.73 | 13.72 | 3.16 | 30.00 |
| 101 ALA | CA | 5.75 | 14.49 | 1.94 | 30.00 |
| 101 ALA | CB | 4.44 | 15.26 | 1.77 | 30.00 |
| 101 ALA | C | 6.93 | 15.39 | 1.68 | 30.00 |
| 101 ALA | O | 7.46 | 16.12 | 2.53 | 30.00 |
| 111 ALA | N | -0.35 | 22.93 | 2.59 | 30.00 |
| 111 ALA | CA | -1.80 | 22.98 | 2.21 | 30.00 |
| 111 ALA | CB | -2.37 | 21.55 | 2.11 | 30.00 |
| 111 ALA | C | -2.45 | 23.81 | 3.33 | 30.00 |

Figure 7W

| Residue | Atom | X | Y | Z | B |
|---|---|---|---|---|---|
| 111 ALA | O | -2.29 | 25.04 | 3.40 | 30.00 |
| 112 SER | N | -3.13 | 23.13 | 4.25 | 30.00 |
| 112 SER | CA | -3.75 | 23.84 | 5.36 | 30.00 |
| 112 SER | CB | -5.17 | 24.27 | 5.01 | 30.00 |
| 112 SER | OG | -5.13 | 25.30 | 4.03 | 30.00 |
| 112 SER | C | -3.71 | 23.17 | 6.72 | 30.00 |
| 112 SER | O | -2.88 | 23.50 | 7.55 | 30.00 |
| 113 ARG | N | -4.54 | 22.16 | 6.92 | 30.00 |
| 113 ARG | CA | -4.61 | 21.54 | 8.25 | 30.00 |
| 113 ARG | CB | -5.27 | 22.59 | 9.11 | 30.00 |
| 113 ARG | CG | -6.24 | 23.49 | 8.30 | 30.00 |
| 113 ARG | CD | -7.34 | 24.06 | 9.16 | 30.00 |
| 113 ARG | NE | -6.84 | 24.47 | 10.48 | 30.00 |
| 113 ARG | CZ | -6.78 | 23.66 | 11.54 | 30.00 |
| 113 ARG | NH1 | -6.30 | 24.12 | 12.70 | 30.00 |
| 113 ARG | NH2 | -7.19 | 22.40 | 11.46 | 30.00 |
| 113 ARG | C | -5.39 | 20.21 | 8.27 | 30.00 |
| 113 ARG | O | -4.91 | 19.14 | 7.92 | 30.00 |
| 114 GLU | N | -6.63 | 20.28 | 8.74 | 30.00 |
| 114 GLU | CA | -7.49 | 19.10 | 8.72 | 30.00 |
| 114 GLU | CB | -8.78 | 19.37 | 9.50 | 30.00 |
| 114 GLU | CG | -8.70 | 20.45 | 10.56 | 30.00 |
| 114 GLU | CD | -9.85 | 21.46 | 10.51 | 30.00 |
| 114 GLU | OE1 | -11.04 | 21.05 | 10.53 | 30.00 |
| 114 GLU | OE2 | -9.57 | 22.67 | 10.44 | 30.00 |
| 114 GLU | C | -7.77 | 18.75 | 7.22 | 30.00 |
| 114 GLU | O | -8.22 | 17.66 | 6.88 | 30.00 |
| 115 GLU | N | -7.45 | 19.88 | 6.38 | 30.00 |
| 115 GLU | CA | -7.54 | 19.49 | 4.96 | 30.00 |

Figure 7X

| Residue | Atom | X | Y | Z | B |
|---|---|---|---|---|---|
| 115 GLU | CB | -7.57 | 20.74 | 4.08 | 30.00 |
| 115 GLU | CG | -6.19 | 21.06 | 3.51 | 30.00 |
| 115 GLU | CD | -6.17 | 22.26 | 2.57 | 30.00 |
| 115 GLU | OE1 | -5.39 | 22.25 | 1.59 | 30.00 |
| 115 GLU | OE2 | -6.97 | 23.20 | 2.80 | 30.00 |
| 115 GLU | C | -6.35 | 18.58 | 4.66 | 30.00 |
| 115 GLU | O | -6.43 | 17.61 | 3.91 | 30.00 |
| 116 ARG | N | -5.40 | 18.59 | 5.09 | 30.00 |
| 116 ARG | CA | -4.29 | 17.67 | 4.84 | 30.00 |
| 116 ARG | CB | -3.10 | 18.09 | 5.70 | 30.00 |
| 116 ARG | CG | -1.93 | 17.09 | 5.76 | 30.00 |
| 116 ARG | CD | -0.53 | 17.79 | 5.75 | 30.00 |
| 116 ARG | NE | -0.05 | 17.96 | 4.38 | 30.00 |
| 116 ARG | CZ | 0.96 | 17.29 | 3.82 | 30.00 |
| 116 ARG | NH1 | 1.68 | 16.41 | 4.50 | 30.00 |
| 116 ARG | NH2 | 1.09 | 17.34 | 2.51 | 30.00 |
| 116 ARG | C | -4.82 | 16.28 | 5.25 | 30.00 |
| 116 ARG | O | -4.58 | 15.26 | 4.63 | 30.00 |
| 117 LEU | N | -5.59 | 16.27 | 6.32 | 30.00 |
| 117 LEU | CA | -6.17 | 15.04 | 6.81 | 30.00 |
| 117 LEU | CB | -6.78 | 15.27 | 8.18 | 30.00 |
| 117 LEU | CG | -7.67 | 14.15 | 8.74 | 30.00 |
| 117 LEU | CD1 | -6.97 | 12.80 | 8.72 | 30.00 |
| 117 LEU | CD2 | -8.08 | 14.53 | 10.14 | 30.00 |
| 117 LEU | C | -7.20 | 14.54 | 5.83 | 30.00 |
| 117 LEU | O | -7.26 | 13.35 | 5.50 | 30.00 |
| 118 LEU | N | -8.03 | 15.46 | 5.33 | 30.00 |
| 118 LEU | CA | -9.11 | 15.10 | 4.34 | 30.00 |
| 118 LEU | CB | -9.96 | 16.30 | 4.00 | 30.00 |

Figure 7Y

| Residue | Atom | X | Y | Z | B |
|---|---|---|---|---|---|
| 118 LEU | CG | -11.29 | 16.41 | 4.74 | 30.00 |
| 118 LEU | CD1 | -11.56 | 15.18 | 5.59 | 30.00 |
| 118 LEU | CD2 | -11.27 | 17.66 | 5.53 | 30.00 |
| 118 LEU | C | -8.49 | 14.52 | 3.08 | 30.00 |
| 118 LEU | O | -8.90 | 13.47 | 2.57 | 30.00 |
| 119 TYR | N | -7.29 | 15.04 | 2.80 | 30.00 |
| 119 TYR | CA | -6.59 | 14.64 | 1.58 | 30.00 |
| 119 TYR | CB | -5.67 | 15.78 | 1.09 | 30.00 |
| 119 TYR | CG | -4.59 | 15.32 | 0.15 | 30.00 |
| 119 TYR | CD1 | -4.63 | 15.66 | -1.21 | 30.00 |
| 119 TYR | CE1 | -3.63 | 15.29 | -2.08 | 30.00 |
| 119 TYR | CD2 | -3.51 | 14.57 | 0.63 | 30.00 |
| 119 TYR | CE2 | -2.50 | 14.18 | -0.24 | 30.00 |
| 119 TYR | CZ | -2.57 | 14.55 | -1.59 | 30.00 |
| 119 TYR | OH | -1.56 | 14.22 | -2.46 | 30.00 |
| 119 TYR | C | -5.82 | 13.34 | 1.83 | 30.00 |
| 119 TYR | O | -5.84 | 12.40 | 1.03 | 30.00 |
| 120 LEU | N | -5.50 | 13.19 | 2.83 | 30.00 |
| 120 LEU | CA | -4.86 | 11.88 | 3.18 | 30.00 |
| 120 LEU | CB | -4.07 | 12.05 | 4.47 | 30.00 |
| 120 LEU | CG | -2.57 | 12.37 | 4.51 | 30.00 |
| 120 LEU | CD1 | -1.70 | 11.14 | 4.50 | 30.00 |
| 120 LEU | CD2 | -2.25 | 13.27 | 3.34 | 30.00 |
| 120 LEU | C | -5.87 | 10.72 | 3.28 | 30.00 |
| 120 LEU | O | -5.68 | 9.66 | 2.68 | 30.00 |
| 121 ILE | N | -6.91 | 10.75 | 3.95 | 30.00 |
| 121 ILE | CA | -7.98 | 9.72 | 4.07 | 30.00 |
| 121 ILE | CB | -8.79 | 9.85 | 5.41 | 30.00 |
| 121 ILE | CG2 | -9.51 | 11.15 | 5.51 | 30.00 |

Figure 7Z

| Residue | Atom | X | Y | Z | B |
|---|---|---|---|---|---|
| 121 ILE | CG1 | -9.83 | 8.74 | 5.47 | 30.00 |
| 121 ILE | CD1 | -10.35 | 8.51 | 6.84 | 30.00 |
| 121 ILE | C | -8.90 | 9.61 | 2.82 | 30.00 |
| 121 ILE | O | -9.20 | 8.51 | 2.35 | 30.00 |
| 122 THR | N | -9.10 | 10.50 | 2.10 | 30.00 |
| 122 THR | CA | -9.83 | 10.33 | 0.82 | 30.00 |
| 122 THR | CB | -10.07 | 11.65 | 0.14 | 30.00 |
| 122 THR | OG1 | -10.72 | 12.53 | 1.05 | 30.00 |
| 122 THR | CG2 | -10.96 | 11.44 | -1.06 | 30.00 |
| 122 THR | C | -9.12 | 9.48 | -0.22 | 30.00 |
| 122 THR | O | -9.69 | 8.57 | -0.84 | 30.00 |
| 123 ASN | N | -7.87 | 9.83 | -0.48 | 30.00 |
| 123 ASN | CA | -7.07 | 9.10 | -1.48 | 30.00 |
| 123 ASN | CB | -5.96 | 9.99 | -1.98 | 30.00 |
| 123 ASN | CG | -6.48 | 11.26 | -2.63 | 30.00 |
| 123 ASN | OD1 | -6.43 | 12.34 | -2.05 | 30.00 |
| 123 ASN | ND2 | -7.03 | 11.13 | -3.81 | 30.00 |
| 123 ASN | C | -6.54 | 7.76 | -1.01 | 30.00 |
| 123 ASN | O | -6.25 | 6.89 | -1.81 | 30.00 |
| 124 PHE | N | -6.37 | 7.56 | 0.36 | 30.00 |
| 124 PHE | CA | -5.94 | 6.25 | 0.83 | 30.00 |
| 124 PHE | CB | -5.24 | 6.45 | 2.16 | 30.00 |
| 124 PHE | CG | -4.44 | 5.20 | 2.52 | 30.00 |
| 124 PHE | CD1 | -5.10 | 4.04 | 2.87 | 30.00 |
| 124 PHE | CD2 | -3.07 | 5.24 | 2.48 | 30.00 |
| 124 PHE | CE1 | -4.34 | 2.90 | 3.17 | 30.00 |
| 124 PHE | CE2 | -2.33 | 4.12 | 2.78 | 30.00 |
| 124 PHE | CZ | -2.98 | 2.93 | 3.12 | 30.00 |
| 124 PHE | C | -7.14 | 5.30 | 0.95 | 30.00 |

Figure 7AA

| Residue | Atom | X | Y | Z | B |
|---|---|---|---|---|---|
| 124 PHE | O | -7.07 | 4.15 | 0.63 | 30.00 |
| 125 LEU | N | -8.08 | 5.73 | 1.56 | 30.00 |
| 125 LEU | CA | -9.32 | 4.99 | 1.69 | 30.00 |
| 125 LEU | CB | -9.77 | 5.01 | 3.15 | 30.00 |
| 125 LEU | CG | -8.88 | 4.23 | 4.14 | 30.00 |
| 125 LEU | CD1 | -9.27 | 2.78 | 4.09 | 30.00 |
| 125 LEU | CD2 | -7.39 | 4.39 | 3.83 | 30.00 |
| 125 LEU | C | -10.41 | 5.55 | 0.74 | 30.00 |
| 125 LEU | O | -11.43 | 6.09 | 1.17 | 30.00 |
| 126 PRO | N | -10.55 | 5.54 | -0.42 | 30.00 |
| 126 PRO | CD | -9.43 | 5.04 | -1.24 | 30.00 |
| 126 PRO | CA | -11.63 | 6.07 | -1.27 | 30.00 |
| 126 PRO | CB | -10.92 | 6.24 | -2.62 | 30.00 |
| 126 PRO | CG | -9.94 | 5.12 | -2.64 | 30.00 |
| 126 PRO | C | -12.97 | 5.29 | -1.41 | 30.00 |
| 126 PRO | O | -13.97 | 5.86 | -1.87 | 30.00 |
| 127 SER | N | -13.02 | 4.04 | -0.93 | 30.00 |
| 127 SER | CA | -14.26 | 3.19 | -1.03 | 30.00 |
| 127 SER | CB | -13.93 | 1.96 | -1.87 | 30.00 |
| 127 SER | OG | -13.37 | 2.32 | -3.11 | 30.00 |
| 127 SER | C | -14.96 | 2.72 | 0.26 | 30.00 |
| 127 SER | O | -14.42 | 2.75 | 1.36 | 30.00 |
| 128 VAL | N | -16.20 | 2.27 | 0.10 | 30.00 |
| 128 VAL | CA | -16.96 | 1.68 | 1.24 | 30.00 |
| 128 VAL | CB | -18.36 | 2.23 | 1.51 | 30.00 |
| 128 VAL | CG1 | -18.31 | 3.21 | 2.64 | 30.00 |
| 128 VAL | CG2 | -18.97 | 2.80 | 0.28 | 30.00 |
| 128 VAL | C | -17.24 | 0.27 | 0.83 | 30.00 |
| 128 VAL | O | -17.25 | -0.10 | -0.33 | 30.00 |

Figure 7BB

| Residue | Atom | X | Y | Z | B |
|---|---|---|---|---|---|
| 129 SER | N | -17.57 | -0.53 | 1.82 | 30.00 |
| 129 SER | CA | -17.87 | -1.90 | 1.55 | 30.00 |
| 129 SER | CB | -16.59 | -2.67 | 1.72 | 30.00 |
| 129 SER | OG | -16.86 | -4.06 | 1.63 | 30.00 |
| 129 SER | C | -18.86 | -2.27 | 2.69 | 30.00 |
| 129 SER | O | -18.55 | -2.30 | 3.78 | 30.00 |
| 130 LEU | N | -19.99 | -2.64 | 2.45 | 30.00 |
| 130 LEU | CA | -21.21 | -2.90 | 3.21 | 30.00 |
| 130 LEU | CB | -22.45 | -2.72 | 2.32 | 30.00 |
| 130 LEU | CG | -23.71 | -2.26 | 3.04 | 30.00 |
| 130 LEU | CD1 | -24.41 | -1.17 | 2.24 | 30.00 |
| 130 LEU | CD2 | -24.61 | -3.49 | 3.20 | 30.00 |
| 130 LEU | C | -21.18 | -4.29 | 3.74 | 30.00 |
| 130 LEU | O | -20.88 | -5.24 | 3.03 | 30.00 |
| 131 ALA | N | -21.18 | -4.82 | 4.64 | 30.00 |
| 131 ALA | CA | -21.24 | -6.27 | 4.85 | 30.00 |
| 131 ALA | CB | -20.27 | -6.70 | 5.94 | 30.00 |
| 131 ALA | C | -22.65 | -6.66 | 5.32 | 30.00 |
| 131 ALA | O | -23.26 | -5.92 | 6.11 | 30.00 |
| 132 THR | N | -23.19 | -7.71 | 4.76 | 30.00 |
| 132 THR | CA | -24.55 | -8.17 | 5.09 | 30.00 |
| 132 THR | CB | -25.40 | -8.32 | 3.81 | 30.00 |
| 132 THR | OG1 | -24.63 | -8.99 | 2.82 | 30.00 |
| 132 THR | CG2 | -25.82 | -6.95 | 3.28 | 30.00 |
| 132 THR | C | -24.42 | -9.54 | 5.77 | 30.00 |
| 132 THR | O | -23.53 | -10.32 | 5.43 | 30.00 |
| 133 ALA | N | -25.27 | -9.79 | 6.77 | 30.00 |
| 133 ALA | CA | -25.27 | -11.09 | 7.50 | 30.00 |
| 133 ALA | CB | -25.97 | -10.95 | 8.84 | 30.00 |

Figure 7CC

| Residue | Atom | X | Y | Z | B |
|---|---|---|---|---|---|
| 133 ALA | C | -25.98 | -12.16 | 6.62 | 30.00 |
| 133 ALA | O | -25.37 | -13.21 | 6.33 | 30.00 |
| 144 THR | N | -31.96 | -6.77 | 10.16 | 30.00 |
| 144 THR | CA | -30.60 | -7.15 | 10.63 | 30.00 |
| 144 THR | CB | -30.68 | -8.37 | 11.59 | 30.00 |
| 144 THR | OG1 | -31.10 | -9.53 | 10.86 | 30.00 |
| 144 THR | CG2 | -31.67 | -8.11 | 12.71 | 30.00 |
| 144 THR | C | -29.66 | -7.54 | 9.45 | 30.00 |
| 144 THR | O | -28.58 | -8.11 | 9.64 | 30.00 |
| 145 LEU | N | -30.11 | -7.28 | 8.23 | 30.00 |
| 145 LEU | CA | -29.33 | -7.63 | 7.03 | 30.00 |
| 145 LEU | CB | -30.17 | -7.39 | 5.77 | 30.00 |
| 145 LEU | CG | -29.51 | -7.83 | 4.48 | 30.00 |
| 145 LEU | CD1 | -29.30 | -9.30 | 4.48 | 30.00 |
| 145 LEU | CD2 | -30.34 | -7.42 | 3.32 | 30.00 |
| 145 LEU | C | -28.05 | -6.49 | 6.64 | 30.00 |
| 145 LEU | O | -26.92 | -7.42 | 6.73 | 30.00 |
| 146 PHE | N | -28.09 | -5.22 | 7.07 | 30.00 |
| 146 PHE | CA | -26.85 | -4.45 | 7.20 | 30.00 |
| 146 PHE | CB | -27.23 | -2.99 | 7.26 | 30.00 |
| 146 PHE | CG | -27.87 | -2.56 | 5.95 | 30.00 |
| 146 PHE | CD1 | -28.29 | -1.25 | 5.78 | 30.00 |
| 146 PHE | CD2 | -28.02 | -3.47 | 4.94 | 30.00 |
| 146 PHE | CE1 | -28.85 | -0.88 | 4.55 | 30.00 |
| 146 PHE | CE2 | -28.57 | -3.10 | 3.73 | 30.00 |
| 146 PHE | CZ | -28.99 | -1.78 | 3.54 | 30.00 |
| 146 PHE | C | -26.06 | -4.91 | 8.43 | 30.00 |
| 146 PHE | O | -26.50 | -4.77 | 9.56 | 30.00 |
| 147 ALA | N | -24.89 | -5.47 | 8.17 | 30.00 |

Figure 7DD

| Residue | Atom | X | Y | Z | B |
|---|---|---|---|---|---|
| 147 ALA | CA  | -23.95 | -5.76 | 9.43  | 30.00 |
| 147 ALA | CB  | -23.08 | -6.93 | 9.09  | 30.00 |
| 147 ALA | C   | -23.08 | -4.55 | 9.81  | 30.00 |
| 147 ALA | O   | -23.10 | -4.08 | 10.93 | 30.00 |
| 148 HIS | N   | -22.28 | -4.06 | 8.86  | 30.00 |
| 148 HIS | CA  | -21.39 | -2.88 | 9.07  | 30.00 |
| 148 HIS | CB  | -20.28 | -3.23 | 10.04 | 30.00 |
| 148 HIS | CG  | -19.42 | -4.37 | 9.58  | 30.00 |
| 148 HIS | CD2 | -19.55 | -5.71 | 9.74  | 30.00 |
| 148 HIS | ND1 | -18.23 | -4.18 | 8.90  | 30.00 |
| 148 HIS | CE1 | -17.67 | -5.35 | 8.66  | 30.00 |
| 148 HIS | NE2 | -18.45 | -6.30 | 9.16  | 30.00 |
| 148 HIS | C   | -20.78 | -2.41 | 7.74  | 30.00 |
| 148 HIS | O   | -20.87 | -3.07 | 6.68  | 30.00 |
| 149 VAL | N   | -20.13 | -1.25 | 7.81  | 30.00 |
| 149 VAL | CA  | -19.46 | -0.71 | 6.61  | 30.00 |
| 149 VAL | CB  | -20.03 | 0.65  | 6.15  | 30.00 |
| 149 VAL | CG1 | -21.50 | 0.69  | 6.42  | 30.00 |
| 149 VAL | CG2 | -19.31 | 1.80  | 6.78  | 30.00 |
| 149 VAL | C   | -17.98 | -0.59 | 6.92  | 30.00 |
| 149 VAL | O   | -17.55 | -0.23 | 8.02  | 30.00 |
| 150 ALA | N   | -17.18 | -0.94 | 5.92  | 30.00 |
| 150 ALA | CA  | -15.75 | -0.91 | 6.05  | 30.00 |
| 150 ALA | CB  | -15.18 | -2.29 | 5.81  | 30.00 |
| 150 ALA | C   | -15.20 | 0.07  | 5.03  | 30.00 |
| 150 ALA | O   | -15.67 | 0.15  | 3.90  | 30.00 |
| 151 LEU | N   | -14.29 | 0.92  | 5.48  | 30.00 |
| 151 LEU | CA  | -13.61 | 1.88  | 4.61  | 30.00 |
| 151 LEU | CB  | -13.02 | 3.00  | 5.45  | 30.00 |

Figure 7EE

| Residue | Atom | X | Y | Z | B |
|---|---|---|---|---|---|
| 151 LEU | CG | -13.76 | 4.30 | 5.72 | 30.00 |
| 151 LEU | CD1 | -12.81 | 5.47 | 5.79 | 30.00 |
| 151 LEU | CD2 | -14.84 | 4.47 | 4.65 | 30.00 |
| 151 LEU | C | -12.49 | 1.01 | 4.01 | 30.00 |
| 151 LEU | O | -11.92 | 0.16 | 4.69 | 30.00 |
| 152 CYS | N | -12.19 | 1.21 | 2.74 | 30.00 |
| 152 CYS | CA | -11.12 | 0.42 | 2.10 | 30.00 |
| 152 CYS | CB | -11.67 | -0.96 | 1.79 | 30.00 |
| 152 CYS | SG | -13.13 | -0.89 | 0.76 | 30.00 |
| 152 CYS | C | -10.63 | 1.13 | 0.86 | 30.00 |
| 152 CYS | O | -11.10 | 2.19 | 0.50 | 30.00 |
| 153 ALA | N | -9.66 | 0.54 | 0.19 | 30.00 |
| 153 ALA | CA | -9.09 | 1.15 | -1.03 | 30.00 |
| 153 ALA | CB | -7.72 | 0.58 | -1.30 | 30.00 |
| 153 ALA | C | -9.96 | 0.94 | -2.26 | 30.00 |
| 153 ALA | O | -10.20 | 1.84 | -3.04 | 30.00 |
| 154 ILE | N | -10.41 | -0.28 | -2.44 | 30.00 |
| 154 ILE | CA | -11.24 | -0.63 | -3.59 | 30.00 |
| 154 ILE | CB | -10.34 | -1.21 | -4.74 | 30.00 |
| 154 ILE | CG2 | -11.16 | -1.69 | -5.88 | 30.00 |
| 154 ILE | CG1 | -9.35 | -0.16 | -5.27 | 30.00 |
| 154 ILE | CD1 | -10.00 | 1.00 | -6.02 | 30.00 |
| 154 ILE | C | -12.28 | -1.66 | -3.09 | 30.00 |
| 154 ILE | O | -11.93 | -2.72 | -2.56 | 30.00 |
| 155 GLY | N | -13.56 | -1.30 | -3.22 | 30.00 |
| 155 GLY | CA | -14.66 | -2.15 | -2.80 | 30.00 |
| 155 GLY | C | -15.01 | -3.15 | -3.87 | 30.00 |
| 155 GLY | O | -14.49 | -3.07 | -4.99 | 30.00 |
| 156 ARG | N | -15.93 | -4.07 | -3.57 | 30.00 |

Figure 7FF

| Residue | Atom | X | Y | Z | B |
|---|---|---|---|---|---|
| 156 ARG | CA | -16.32 | -5.09 | -4.56 | 30.00 |
| 156 ARG | CB | -16.44 | -6.44 | -3.87 | 30.00 |
| 156 ARG | CG | -15.72 | -6.48 | -2.54 | 30.00 |
| 156 ARG | CD | -16.10 | -7.68 | -1.74 | 30.00 |
| 156 ARG | NE | -15.93 | -8.92 | -2.48 | 30.00 |
| 156 ARG | CZ | -15.62 | -10.08 | -1.91 | 30.00 |
| 156 ARG | NH1 | -15.48 | -11.17 | -2.65 | 30.00 |
| 156 ARG | NH2 | -15.44 | -10.16 | -0.59 | 30.00 |
| 156 ARG | C | -17.57 | -4.76 | -5.40 | 30.00 |
| 156 ARG | O | -17.83 | -5.32 | -6.46 | 30.00 |
| 157 ARG | N | -18.38 | -3.86 | -4.89 | 30.00 |
| 157 ARG | CA | -19.57 | -3.45 | -5.62 | 30.00 |
| 157 ARG | CB | -20.72 | -3.30 | -4.65 | 30.00 |
| 157 ARG | CG | -21.29 | -4.64 | -4.20 | 30.00 |
| 157 ARG | CD | -22.70 | -4.56 | -3.58 | 30.00 |
| 157 ARG | NE | -22.57 | -4.44 | -2.14 | 30.00 |
| 157 ARG | CZ | -22.86 | -5.36 | -1.23 | 30.00 |
| 157 ARG | NH1 | -23.39 | -6.54 | -1.44 | 30.00 |
| 157 ARG | NH2 | -22.15 | -5.29 | -0.14 | 30.00 |
| 157 ARG | C | -19.22 | -2.14 | -6.37 | 30.00 |
| 157 ARG | O | -18.27 | -1.44 | -6.03 | 30.00 |
| 158 LEU | N | -19.98 | -1.85 | -7.42 | 30.00 |
| 158 LEU | CA | -19.76 | -0.66 | -8.25 | 30.00 |
| 158 LEU | CB | -20.46 | -0.84 | -9.58 | 30.00 |
| 158 LEU | CG | -19.65 | -1.48 | -10.69 | 30.00 |
| 158 LEU | CD1 | -18.52 | -2.35 | -10.15 | 30.00 |
| 158 LEU | CD2 | -20.57 | -2.27 | -11.56 | 30.00 |
| 158 LEU | C | -20.19 | 0.64 | -7.60 | 30.00 |
| 158 LEU | O | -20.95 | 0.67 | -6.64 | 30.00 |

Figure 7GG

| Residue | Atom | X | Y | Z | B |
|---|---|---|---|---|---|
| 159 GLY | N | -19.72 | 1.74 | -8.18 | 30.00 |
| 159 GLY | CA | -20.05 | 3.06 | -7.69 | 30.00 |
| 159 GLY | C | -19.85 | 3.34 | -6.21 | 30.00 |
| 159 GLY | O | -20.30 | 4.38 | -5.72 | 30.00 |
| 160 THR | N | -19.09 | 2.48 | -5.53 | 30.00 |
| 160 THR | CA | -18.86 | 2.67 | -4.09 | 30.00 |
| 160 THR | CB | -18.67 | 1.35 | -3.38 | 30.00 |
| 160 THR | OG1 | -17.75 | 0.53 | -4.12 | 30.00 |
| 160 THR | CG2 | -20.01 | 0.66 | -3.21 | 30.00 |
| 160 THR | C | -17.71 | 3.57 | -3.73 | 30.00 |
| 160 THR | O | -16.87 | 3.22 | -2.93 | 30.00 |
| 161 ILE | N | -17.68 | 4.76 | -4.30 | 30.00 |
| 161 ILE | CA | -16.62 | 5.69 | -3.98 | 30.00 |
| 161 ILE | CB | -16.13 | 6.37 | -5.22 | 30.00 |
| 161 ILE | CG2 | -16.35 | 7.83 | -5.13 | 30.00 |
| 161 ILE | CG1 | -14.65 | 6.06 | -5.41 | 30.00 |
| 161 ILE | CD1 | -13.78 | 6.61 | -4.37 | 30.00 |
| 161 ILE | C | -17.25 | 6.69 | -3.02 | 30.00 |
| 161 ILE | O | -18.34 | 7.21 | -3.30 | 30.00 |
| 162 VAL | N | -16.59 | 6.92 | -1.89 | 30.00 |
| 162 VAL | CA | -17.11 | 7.86 | -0.85 | 30.00 |
| 162 VAL | CB | -17.01 | 7.27 | 0.57 | 30.00 |
| 162 VAL | CG1 | -17.75 | 5.96 | 0.66 | 30.00 |
| 162 VAL | CG2 | -15.56 | 7.10 | 0.96 | 30.00 |
| 162 VAL | C | -16.45 | 9.24 | -0.87 | 30.00 |
| 162 VAL | O | -15.50 | 9.50 | -1.58 | 30.00 |
| 163 THR | N | -17.04 | 10.13 | -0.07 | 30.00 |
| 163 THR | CA | -16.61 | 11.54 | 0.10 | 30.00 |
| 163 THR | CB | -17.72 | 12.50 | -0.36 | 30.00 |

Figure 7HH

| Residue | Atom | X | Y | Z | B |
|---|---|---|---|---|---|
| 163 THR | OG1 | -17.80 | 12.52 | -1.79 | 30.00 |
| 163 THR | CG2 | -17.43 | 13.86 | 0.08 | 30.00 |
| 163 THR | C | -16.43 | 11.76 | 1.61 | 30.00 |
| 163 THR | O | -17.18 | 11.25 | 2.44 | 30.00 |
| 164 TYR | N | -15.40 | 12.49 | 1.97 | 30.00 |
| 164 TYR | CA | -15.10 | 12.87 | 3.35 | 30.00 |
| 164 TYR | CB | -13.76 | 12.30 | 3.74 | 30.00 |
| 164 TYR | CG | -13.75 | 10.79 | 3.68 | 30.00 |
| 164 TYR | CD1 | -14.55 | 10.17 | 2.76 | 30.00 |
| 164 TYR | CE1 | -14.53 | 8.79 | 2.70 | 30.00 |
| 164 TYR | CD2 | -12.94 | 10.09 | 4.54 | 30.00 |
| 164 TYR | CE2 | -12.92 | 8.72 | 4.50 | 30.00 |
| 164 TYR | CZ | -13.72 | 8.07 | 3.58 | 30.00 |
| 164 TYR | OH | -13.76 | 6.68 | 3.59 | 30.00 |
| 164 TYR | C | -15.05 | 14.38 | 3.57 | 30.00 |
| 164 TYR | O | -14.46 | 15.05 | 2.72 | 30.00 |
| 165 ASP | N | -15.66 | 14.87 | 4.59 | 30.00 |
| 165 ASP | CA | -15.57 | 16.32 | 4.83 | 30.00 |
| 165 ASP | CB | -16.45 | 17.12 | 3.88 | 30.00 |
| 165 ASP | CG | -15.75 | 18.39 | 3.40 | 30.00 |
| 165 ASP | OD1 | -15.57 | 19.33 | 4.19 | 30.00 |
| 165 ASP | OD2 | -15.37 | 18.45 | 2.22 | 30.00 |
| 165 ASP | C | -15.91 | 16.62 | 6.27 | 30.00 |
| 165 ASP | O | -16.35 | 15.74 | 7.00 | 30.00 |
| 166 THR | N | -15.66 | 17.85 | 6.70 | 30.00 |
| 166 THR | CA | -15.91 | 18.24 | 8.10 | 30.00 |
| 166 THR | CB | -14.89 | 19.26 | 8.61 | 30.00 |
| 166 THR | OG1 | -14.86 | 20.39 | 7.71 | 30.00 |
| 166 THR | CG2 | -13.52 | 18.62 | 8.70 | 30.00 |

Figure 7II

| Residue | Atom | X | Y | Z | B |
|---|---|---|---|---|---|
| 166 THR | C | -17.32 | 18.80 | 8.34 | 30.00 |
| 166 THR | O | -17.63 | 19.39 | 9.37 | 30.00 |
| 167 GLY | N | -18.15 | 18.67 | 7.38 | 30.00 |
| 167 GLY | CA | -19.54 | 19.03 | 7.44 | 30.00 |
| 167 GLY | C | -20.42 | 18.10 | 6.67 | 30.00 |
| 167 GLY | O | -19.91 | 17.60 | 5.64 | 30.00 |
| 168 LEU | N | -21.53 | 17.72 | 7.17 | 30.00 |
| 168 LEU | CA | -22.36 | 16.73 | 6.45 | 30.00 |
| 168 LEU | CB | -23.59 | 16.37 | 7.29 | 30.00 |
| 168 LEU | CG | -24.08 | 14.93 | 7.24 | 30.00 |
| 168 LEU | CD1 | -25.13 | 14.81 | 6.20 | 30.00 |
| 168 LEU | CD2 | -22.95 | 14.00 | 6.88 | 30.00 |
| 168 LEU | C | -22.74 | 17.26 | 5.07 | 30.00 |
| 168 LEU | O | -22.55 | 16.62 | 4.05 | 30.00 |
| 169 ASP | N | -23.20 | 18.50 | 5.05 | 30.00 |
| 169 ASP | CA | -23.62 | 19.19 | 3.81 | 30.00 |
| 169 ASP | CB | -24.06 | 20.61 | 4.14 | 30.00 |
| 169 ASP | CG | -25.51 | 20.70 | 4.54 | 30.00 |
| 169 ASP | OD1 | -26.07 | 21.82 | 4.51 | 30.00 |
| 169 ASP | OD2 | -26.11 | 19.67 | 4.88 | 30.00 |
| 169 ASP | C | -22.51 | 19.20 | 2.75 | 30.00 |
| 169 ASP | O | -22.75 | 19.02 | 1.56 | 30.00 |
| 170 ALA | N | -21.28 | 19.38 | 3.22 | 30.00 |
| 170 ALA | CA | -20.11 | 19.42 | 2.33 | 30.00 |
| 170 ALA | CB | -18.95 | 20.04 | 3.03 | 30.00 |
| 170 ALA | C | -19.72 | 18.04 | 1.83 | 30.00 |
| 170 ALA | O | -19.12 | 17.89 | 0.77 | 30.00 |
| 171 ALA | N | -20.05 | 17.03 | 2.62 | 30.00 |
| 171 ALA | CA | -19.75 | 15.65 | 2.26 | 30.00 |

Figure 7JJ

| Residue | Atom | X | Y | Z | B |
|---|---|---|---|---|---|
| 171 ALA | CB | -19.78 | 14.79 | 3.50 | 30.00 |
| 171 ALA | C | -20.77 | 15.15 | 1.22 | 30.00 |
| 171 ALA | O | -20.46 | 14.35 | 0.34 | 30.00 |
| 172 ILE | N | -22.02 | 15.61 | 1.32 | 30.00 |
| 172 ILE | CA | -23.03 | 15.15 | 0.34 | 30.00 |
| 172 ILE | CB | -24.45 | 14.96 | 0.98 | 30.00 |
| 172 ILE | CG2 | -25.14 | 13.81 | 0.32 | 30.00 |
| 172 ILE | CG1 | -24.39 | 14.65 | 2.47 | 30.00 |
| 172 ILE | CD1 | -25.76 | 14.42 | 3.09 | 30.00 |
| 172 ILE | C | -23.12 | 15.98 | -0.95 | 30.00 |
| 172 ILE | O | -23.53 | 15.49 | -2.00 | 30.00 |
| 173 ALA | N | -22.66 | 17.23 | -0.90 | 30.00 |
| 173 ALA | CA | -22.70 | 18.14 | -2.08 | 30.00 |
| 173 ALA | CB | -22.11 | 19.49 | -1.72 | 30.00 |
| 173 ALA | C | -22.08 | 17.62 | -3.39 | 30.00 |
| 173 ALA | O | -22.53 | 17.97 | -4.48 | 30.00 |
| 174 PRO | N | -20.98 | 16.84 | -3.32 | 30.00 |
| 174 PRO | CD | -20.00 | 16.63 | -2.25 | 30.00 |
| 174 PRO | CA | -20.43 | 16.36 | -4.59 | 30.00 |
| 174 PRO | CB | -19.11 | 15.73 | -4.20 | 30.00 |
| 174 PRO | CG | -18.71 | 16.55 | -3.05 | 30.00 |
| 174 PRO | C | -21.32 | 15.32 | -5.24 | 30.00 |
| 174 PRO | O | -21.00 | 14.81 | -6.30 | 30.00 |
| 175 PHE | N | -22.38 | 14.92 | -4.56 | 30.00 |
| 175 PHE | CA | -23.30 | 13.94 | -5.12 | 30.00 |
| 175 PHE | CB | -23.81 | 13.03 | -4.03 | 30.00 |
| 175 PHE | CG | -22.78 | 12.08 | -3.54 | 30.00 |
| 175 PHE | CD1 | -22.63 | 10.84 | -4.16 | 30.00 |
| 175 PHE | CD2 | -21.93 | 12.44 | -2.50 | 30.00 |

Figure 7KK

| Residue | Atom | X | Y | Z | B |
|---|---|---|---|---|---|
| 175 PHE | CE1 | -21.64 | 9.97 | -3.76 | 30.00 |
| 175 PHE | CE2 | -20.92 | 11.58 | -2.08 | 30.00 |
| 175 PHE | CZ | -20.78 | 10.33 | -2.72 | 30.00 |
| 175 PHE | C | -24.42 | 14.67 | -5.84 | 30.00 |
| 175 PHE | O | -25.35 | 15.19 | -5.25 | 30.00 |
| 176 ARG | N | -24.25 | 14.75 | -7.16 | 30.00 |
| 176 ARG | CA | -25.19 | 15.44 | -8.04 | 30.00 |
| 176 ARG | CB | -24.43 | 15.99 | -9.22 | 30.00 |
| 176 ARG | CG | -23.25 | 16.85 | -8.83 | 30.00 |
| 176 ARG | CD | -23.66 | 18.14 | -8.20 | 30.00 |
| 176 ARG | NE | -22.59 | 18.66 | -7.37 | 30.00 |
| 176 ARG | CZ | -21.69 | 19.57 | -7.76 | 30.00 |
| 176 ARG | NH1 | -20.73 | 19.98 | -6.94 | 30.00 |
| 176 ARG | NH2 | -21.78 | 20.08 | -8.96 | 30.00 |
| 176 ARG | C | -26.38 | 14.57 | -8.50 | 30.00 |
| 176 ARG | O | -27.43 | 15.07 | -8.88 | 30.00 |
| 177 HIS | N | -26.21 | 13.26 | -8.53 | 30.00 |
| 177 HIS | CA | -27.35 | 12.40 | -8.96 | 30.00 |
| 177 HIS | CB | -26.87 | 11.28 | -9.87 | 30.00 |
| 177 HIS | CG | -26.18 | 11.77 | -11.11 | 30.00 |
| 177 HIS | CD2 | -25.28 | 11.16 | -11.92 | 30.00 |
| 177 HIS | ND1 | -26.36 | 13.04 | -11.61 | 30.00 |
| 177 HIS | CE1 | -25.60 | 13.20 | -12.68 | 30.00 |
| 177 HIS | NE2 | -24.94 | 12.08 | -12.89 | 30.00 |
| 177 HIS | C | -28.02 | 11.84 | -7.71 | 30.00 |
| 177 HIS | O | -28.05 | 10.64 | -7.47 | 30.00 |
| 178 LEU | N | -28.54 | 12.75 | -6.91 | 30.00 |
| 178 LEU | CA | -29.20 | 12.37 | -5.64 | 30.00 |
| 178 LEU | CB | -28.33 | 12.82 | -4.47 | 30.00 |

Figure 7LL

| Residue | Atom | X | Y | Z | B |
|---|---|---|---|---|---|
| 178 LEU | CG | -28.06 | 11.82 | -3.34 | 30.00 |
| 178 LEU | CD1 | -27.32 | 10.62 | -3.88 | 30.00 |
| 178 LEU | CD2 | -27.24 | 12.49 | -2.27 | 30.00 |
| 178 LEU | C | -30.61 | 12.96 | -5.54 | 30.00 |
| 178 LEU | O | -30.86 | 14.16 | -5.72 | 30.00 |
| 179 SER | N | -31.53 | 12.06 | -5.32 | 30.00 |
| 179 SER | CA | -32.92 | 12.54 | -5.14 | 30.00 |
| 179 SER | CB | -33.82 | 11.34 | -4.79 | 30.00 |
| 179 SER | OG | -35.07 | 11.91 | -4.43 | 30.00 |
| 179 SER | C | -33.03 | 13.57 | -4.00 | 30.00 |
| 179 SER | O | -32.28 | 13.48 | -3.00 | 30.00 |
| 180 PRO | N | -33.76 | 14.64 | -4.22 | 30.00 |
| 180 PRO | CD | -34.48 | 14.95 | -5.47 | 30.00 |
| 180 PRO | CA | -33.91 | 15.73 | -3.26 | 30.00 |
| 180 PRO | CB | -34.98 | 16.58 | -3.91 | 30.00 |
| 180 PRO | CG | -34.68 | 16.42 | -5.36 | 30.00 |
| 180 PRO | C | -34.37 | 15.21 | -1.90 | 30.00 |
| 180 PRO | O | -33.98 | 15.70 | -0.85 | 30.00 |
| 181 ALA | N | -35.23 | 14.21 | -1.93 | 30.00 |
| 181 ALA | CA | -35.75 | 13.59 | -0.70 | 30.00 |
| 181 ALA | CB | -36.78 | 12.54 | -1.02 | 30.00 |
| 181 ALA | C | -34.61 | 12.96 | 0.10 | 30.00 |
| 181 ALA | O | -34.52 | 13.10 | 1.31 | 30.00 |
| 182 SER | N | -33.68 | 12.50 | -0.57 | 30.00 |
| 182 SER | CA | -32.63 | 11.68 | 0.07 | 30.00 |
| 182 SER | CB | -31.78 | 11.01 | -1.02 | 30.00 |
| 182 SER | OG | -30.49 | 10.84 | -0.44 | 30.00 |
| 182 SER | C | -31.69 | 12.51 | 0.96 | 30.00 |
| 182 SER | O | -31.43 | 12.16 | 2.10 | 30.00 |

Figure 7MM

| Residue | Atom | X | Y | Z | B |
|---|---|---|---|---|---|
| 183 ARG | N | -31.50 | 13.75 | 0.23 | 30.00 |
| 183 ARG | CA | -30.76 | 14.82 | 0.89 | 30.00 |
| 183 ARG | CB | -30.57 | 15.98 | -0.06 | 30.00 |
| 183 ARG | CG | -29.34 | 15.87 | -0.82 | 30.00 |
| 183 ARG | CD | -29.53 | 16.56 | -2.10 | 30.00 |
| 183 ARG | NE | -29.90 | 17.94 | -1.83 | 30.00 |
| 183 ARG | CZ | -29.40 | 18.98 | -2.48 | 30.00 |
| 183 ARG | NH1 | -29.80 | 20.21 | -2.16 | 30.00 |
| 183 ARG | NH2 | -28.50 | 18.80 | -3.44 | 30.00 |
| 183 ARG | C | -31.48 | 15.29 | 2.14 | 30.00 |
| 183 ARG | O | -30.93 | 15.32 | 3.23 | 30.00 |
| 184 GLU | N | -32.74 | 15.64 | 1.98 | 30.00 |
| 184 GLU | CA | -33.53 | 16.13 | 3.13 | 30.00 |
| 184 GLU | CB | -34.86 | 16.70 | 2.63 | 30.00 |
| 184 GLU | CG | -35.68 | 17.41 | 3.73 | 30.00 |
| 184 GLU | CD | -35.24 | 18.89 | 3.97 | 30.00 |
| 184 GLU | OE1 | -34.03 | 19.13 | 4.23 | 30.00 |
| 184 GLU | OE2 | -36.10 | 19.80 | 3.90 | 30.00 |
| 184 GLU | C | -33.73 | 15.09 | 4.27 | 30.00 |
| 184 GLU | O | -33.87 | 15.41 | 5.45 | 30.00 |
| 185 GLY | N | -33.67 | 13.83 | 3.89 | 30.00 |
| 185 GLY | CA | -33.87 | 12.78 | 4.87 | 30.00 |
| 185 GLY | C | -32.58 | 12.41 | 5.57 | 30.00 |
| 185 GLY | O | -32.57 | 12.14 | 6.76 | 30.00 |
| 186 ALA | N | -31.48 | 12.44 | 4.83 | 30.00 |
| 186 ALA | CA | -30.18 | 12.04 | 5.37 | 30.00 |
| 186 ALA | CB | -29.19 | 11.86 | 4.31 | 30.00 |
| 186 ALA | C | -29.66 | 13.12 | 6.32 | 30.00 |
| 186 ALA | O | -28.84 | 12.86 | 7.21 | 30.00 |

Figure 7NN

| Residue | Atom | X | Y | Z | B |
|---|---|---|---|---|---|
| 187 ARG | N | -30.12 | 14.34 | 6.12 | 30.00 |
| 187 ARG | CA | -29.73 | 15.48 | 6.98 | 30.00 |
| 187 ARG | CB | -30.04 | 16.80 | 6.29 | 30.00 |
| 187 ARG | CG | -29.13 | 17.18 | 5.17 | 30.00 |
| 187 ARG | CD | -29.47 | 18.59 | 4.71 | 30.00 |
| 187 ARG | NE | -28.59 | 19.06 | 3.64 | 30.00 |
| 187 ARG | CZ | -29.01 | 19.37 | 2.41 | 30.00 |
| 187 ARG | NH1 | -28.13 | 19.78 | 1.51 | 30.00 |
| 187 ARG | NH2 | -30.29 | 19.26 | 2.08 | 30.00 |
| 187 ARG | C | -30.50 | 15.42 | 8.31 | 30.00 |
| 187 ARG | O | -30.00 | 15.74 | 9.39 | 30.00 |
| 188 ARG | N | -31.78 | 15.05 | 8.20 | 30.00 |
| 188 ARG | CA | -32.69 | 14.95 | 9.35 | 30.00 |
| 188 ARG | CB | -34.12 | 14.76 | 8.85 | 30.00 |
| 188 ARG | CG | -35.20 | 15.12 | 9.87 | 30.00 |
| 188 ARG | CD | -36.22 | 14.00 | 10.04 | 30.00 |
| 188 ARG | NE | -36.68 | 13.52 | 8.74 | 30.00 |
| 188 ARG | CZ | -36.76 | 12.23 | 8.39 | 30.00 |
| 188 ARG | NH1 | -37.19 | 11.91 | 7.17 | 30.00 |
| 188 ARG | NH2 | -36.41 | 11.28 | 9.25 | 30.00 |
| 188 ARG | C | -32.26 | 13.80 | 10.28 | 30.00 |
| 188 ARG | O | -32.02 | 13.98 | 11.45 | 30.00 |
| 189 LEU | N | -32.09 | 12.61 | 9.73 | 30.00 |
| 189 LEU | CA | -31.73 | 11.47 | 10.54 | 30.00 |
| 189 LEU | CB | -31.74 | 10.19 | 9.64 | 30.00 |
| 189 LEU | CG | -32.07 | 8.79 | 10.13 | 30.00 |
| 189 LEU | CD1 | -30.97 | 7.78 | 9.86 | 30.00 |
| 189 LEU | CD2 | -32.41 | 8.89 | 11.58 | 30.00 |
| 189 LEU | C | -30.34 | 11.71 | 11.11 | 30.00 |

Figure 7OO

| Residue | Atom | X | Y | Z | B |
|---|---|---|---|---|---|
| 189 LEU | O | -30.13 | 11.50 | 12.31 | 30.00 |
| 190 ALA | N | -29.39 | 12.11 | 10.30 | 30.00 |
| 190 ALA | CA | -27.98 | 12.32 | 10.76 | 30.00 |
| 190 ALA | CB | -27.12 | 12.77 | 9.62 | 30.00 |
| 190 ALA | C | -27.83 | 13.26 | 11.98 | 30.00 |
| 190 ALA | O | -26.99 | 13.04 | 12.86 | 30.00 |
| 191 ALA | N | -28.66 | 14.29 | 12.03 | 30.00 |
| 191 ALA | CA | -28.63 | 15.27 | 13.16 | 30.00 |
| 191 ALA | CB | -29.49 | 16.43 | 12.84 | 30.00 |
| 191 ALA | C | -29.10 | 14.62 | 14.49 | 30.00 |
| 191 ALA | O | -28.57 | 14.85 | 15.58 | 30.00 |
| 192 GLU | N | -30.17 | 13.84 | 14.38 | 30.00 |
| 192 GLU | CA | -30.71 | 13.15 | 15.54 | 30.00 |
| 192 GLU | CB | -32.03 | 12.48 | 15.19 | 30.00 |
| 192 GLU | CG | -33.14 | 13.45 | 14.79 | 30.00 |
| 192 GLU | CD | -34.48 | 12.74 | 14.47 | 30.00 |
| 192 GLU | OE1 | -34.56 | 11.49 | 14.60 | 30.00 |
| 192 GLU | OE2 | -35.44 | 13.46 | 14.09 | 30.00 |
| 192 GLU | C | -29.69 | 12.13 | 15.99 | 30.00 |
| 192 GLU | O | -29.21 | 12.16 | 17.11 | 30.00 |
| 193 ALA | N | -29.32 | 11.26 | 15.07 | 30.00 |
| 193 ALA | CA | -28.33 | 10.18 | 15.33 | 30.00 |
| 193 ALA | CB | -27.93 | 9.51 | 14.05 | 30.00 |
| 193 ALA | C | -27.09 | 10.73 | 16.02 | 30.00 |
| 193 ALA | O | -26.55 | 10.13 | 16.95 | 30.00 |
| 194 GLU | N | -26.65 | 11.89 | 15.56 | 30.00 |
| 194 GLU | CA | -25.48 | 12.52 | 16.17 | 30.00 |
| 194 GLU | CB | -25.10 | 13.77 | 15.43 | 30.00 |
| 194 GLU | CG | -24.26 | 13.53 | 14.25 | 30.00 |

Figure 7PP

| Residue | Atom | X | Y | Z | B |
|---|---|---|---|---|---|
| 194 GLU | CD | -23.81 | 14.81 | 13.68 | 30.00 |
| 194 GLU | OE1 | -24.44 | 15.29 | 12.71 | 30.00 |
| 194 GLU | OE2 | -22.83 | 15.37 | 14.24 | 30.00 |
| 194 GLU | C | -25.67 | 12.84 | 17.63 | 30.00 |
| 194 GLU | O | -24.75 | 12.75 | 18.43 | 30.00 |
| 195 LEU | N | -26.87 | 13.29 | 17.97 | 30.00 |
| 195 LEU | CA | -27.20 | 13.63 | 19.36 | 30.00 |
| 195 LEU | CB | -28.66 | 14.02 | 19.45 | 30.00 |
| 195 LEU | CG | -28.93 | 15.39 | 18.85 | 30.00 |
| 195 LEU | CD1 | -30.38 | 15.76 | 19.00 | 30.00 |
| 195 LEU | CD2 | -28.05 | 16.38 | 19.59 | 30.00 |
| 195 LEU | C | -26.88 | 12.51 | 20.33 | 30.00 |
| 195 LEU | O | -26.43 | 12.73 | 21.45 | 30.00 |
| 196 ALA | N | -27.16 | 11.28 | 19.91 | 30.00 |
| 196 ALA | CA | -26.88 | 10.11 | 20.74 | 30.00 |
| 196 ALA | CB | -27.44 | 8.86 | 20.10 | 30.00 |
| 196 ALA | C | -25.35 | 9.98 | 20.93 | 30.00 |
| 196 ALA | O | -24.78 | 10.36 | 21.94 | 30.00 |
| 197 LEU | N | -24.68 | 9.51 | 19.88 | 30.00 |
| 197 LEU | CA | -23.20 | 9.33 | 19.96 | 30.00 |
| 197 LEU | CB | -22.69 | 8.39 | 18.84 | 30.00 |
| 197 LEU | CG | -22.63 | 8.69 | 17.34 | 30.00 |
| 197 LEU | CD1 | -23.69 | 9.67 | 16.99 | 30.00 |
| 197 LEU | CD2 | -21.28 | 9.23 | 16.93 | 30.00 |
| 197 LEU | C | -22.47 | 10.67 | 19.98 | 30.00 |
| 197 LEU | O | -21.34 | 10.81 | 19.51 | 30.00 |
| 198 SER | N | -23.19 | 11.66 | 20.51 | 30.00 |
| 198 SER | CA | -22.53 | 12.98 | 20.64 | 30.00 |
| 198 SER | CB | -23.57 | 14.03 | 21.05 | 30.00 |

Figure 7QQ

| Residue | Atom | X | Y | Z | B |
|---|---|---|---|---|---|
| 198 SER | OG | -22.90 | 14.87 | 21.98 | 30.00 |
| 198 SER | C | -21.41 | 12.96 | 21.68 | 30.00 |
| 198 SER | O | -21.66 | 12.48 | 22.78 | 30.00 |
| 199 GLY | N | -20.26 | 13.22 | 21.20 | 30.00 |
| 199 GLY | CA | -19.11 | 13.17 | 22.08 | 30.00 |
| 199 GLY | C | -18.31 | 11.88 | 21.92 | 30.00 |
| 199 GLY | O | -17.14 | 11.84 | 22.29 | 30.00 |
| 200 ARG | N | -18.92 | 10.83 | 21.39 | 30.00 |
| 200 ARG | CA | -18.18 | 9.60 | 21.25 | 30.00 |
| 200 ARG | CB | -19.08 | 8.47 | 20.82 | 30.00 |
| 200 ARG | CG | -18.32 | 7.22 | 20.59 | 30.00 |
| 200 ARG | CD | -19.19 | 6.00 | 20.73 | 30.00 |
| 200 ARG | NE | -18.40 | 4.87 | 21.18 | 30.00 |
| 200 ARG | CZ | -18.81 | 3.61 | 21.18 | 30.00 |
| 200 ARG | NH1 | -18.01 | 2.64 | 21.60 | 30.00 |
| 200 ARG | NH2 | -20.04 | 3.31 | 20.76 | 30.00 |
| 200 ARG | C | -17.02 | 9.74 | 20.27 | 30.00 |
| 200 ARG | O | -17.09 | 10.38 | 19.22 | 30.00 |
| 201 THR | N | -15.90 | 9.17 | 20.71 | 30.00 |
| 201 THR | CA | -14.65 | 9.12 | 19.97 | 30.00 |
| 201 THR | CB | -13.56 | 9.86 | 20.72 | 30.00 |
| 201 THR | OG1 | -13.94 | 11.22 | 20.82 | 30.00 |
| 201 THR | CG2 | -12.20 | 9.77 | 19.96 | 30.00 |
| 201 THR | C | -14.31 | 7.66 | 20.01 | 30.00 |
| 201 THR | O | -14.65 | 6.95 | 20.96 | 30.00 |
| 202 TRP | N | -13.67 | 7.18 | 18.95 | 30.00 |
| 202 TRP | CA | -13.27 | 5.79 | 18.91 | 30.00 |
| 202 TRP | CB | -13.67 | 5.21 | 17.56 | 30.00 |
| 202 TRP | CG | -15.19 | 5.16 | 17.37 | 30.00 |

Figure 7RR

| Residue | Atom | X | Y | Z | B |
|---|---|---|---|---|---|
| 202 TRP | CD2 | -16.07 | 6.26 | 17.09 | 30.00 |
| 202 TRP | CE2 | -17.39 | 5.75 | 17.05 | 30.00 |
| 202 TRP | CE3 | -15.88 | 7.62 | 16.87 | 30.00 |
| 202 TRP | CD1 | -15.99 | 4.04 | 17.46 | 30.00 |
| 202 TRP | NE1 | -17.31 | 4.40 | 17.29 | 30.00 |
| 202 TRP | CZ2 | -18.49 | 6.55 | 16.81 | 30.00 |
| 202 TRP | CZ3 | -16.99 | 8.41 | 16.62 | 30.00 |
| 202 TRP | CH2 | -18.27 | 7.88 | 16.60 | 30.00 |
| 202 TRP | C | -11.77 | 5.81 | 19.15 | 30.00 |
| 202 TRP | O | -11.11 | 6.82 | 19.02 | 30.00 |
| 203 ALA | N | -11.22 | 4.70 | 19.61 | 30.00 |
| 203 ALA | CA | -9.76 | 4.62 | 19.85 | 30.00 |
| 203 ALA | CB | -9.43 | 5.17 | 21.19 | 30.00 |
| 203 ALA | C | -9.36 | 3.16 | 19.76 | 30.00 |
| 203 ALA | O | -9.09 | 2.48 | 20.75 | 30.00 |
| 204 PRO | N | -9.30 | 2.64 | 18.53 | 30.00 |
| 204 PRO | CD | -9.63 | 3.34 | 17.27 | 30.00 |
| 204 PRO | CA | -8.95 | 1.24 | 18.26 | 30.00 |
| 204 PRO | CB | -9.25 | 1.10 | 16.76 | 30.00 |
| 204 PRO | CG | -9.02 | 2.46 | 16.24 | 30.00 |
| 204 PRO | C | -7.53 | 0.77 | 18.65 | 30.00 |
| 204 PRO | O | -7.29 | -0.42 | 18.88 | 30.00 |
| 205 GLY | N | -6.61 | 1.72 | 18.77 | 30.00 |
| 205 GLY | CA | -5.23 | 1.42 | 19.12 | 30.00 |
| 205 GLY | C | -4.33 | 1.80 | 17.96 | 30.00 |
| 205 GLY | O | -4.45 | 1.21 | 16.90 | 30.00 |
| 206 VAL | N | -3.39 | 2.73 | 18.16 | 30.00 |
| 206 VAL | CA | -2.53 | 3.18 | 17.05 | 30.00 |
| 206 VAL | CB | -1.56 | 4.34 | 17.42 | 30.00 |

Figure 7SS

| Residue | Atom | X | Y | Z | B |
|---|---|---|---|---|---|
| 206 VAL | CG1 | -0.15 | 3.83 | 17.65 | 30.00 |
| 206 VAL | CG2 | -1.56 | 5.38 | 16.40 | 30.00 |
| 206 VAL | C | -1.81 | 2.04 | 16.35 | 30.00 |
| 206 VAL | O | -1.73 | 2.00 | 15.13 | 30.00 |
| 207 GLU | N | -1.34 | 1.06 | 17.11 | 30.00 |
| 207 GLU | CA | -0.66 | -0.06 | 16.44 | 30.00 |
| 207 GLU | CB | 0.10 | -0.94 | 17.42 | 30.00 |
| 207 GLU | CG | 1.38 | -0.31 | 17.97 | 30.00 |
| 207 GLU | CD | 2.12 | 0.58 | 16.97 | 30.00 |
| 207 GLU | OE1 | 2.24 | 0.24 | 15.77 | 30.00 |
| 207 GLU | OE2 | 2.61 | 1.64 | 17.40 | 30.00 |
| 207 GLU | C | -1.64 | -0.89 | 15.61 | 30.00 |
| 207 GLU | O | -1.33 | -1.33 | 14.51 | 30.00 |
| 208 ALA | N | -2.84 | -1.09 | 16.16 | 30.00 |
| 208 ALA | CA | -3.90 | -1.84 | 15.47 | 30.00 |
| 208 ALA | CB | -5.16 | -1.86 | 16.29 | 30.00 |
| 208 ALA | C | -4.15 | -1.08 | 14.16 | 30.00 |
| 208 ALA | O | -4.16 | -1.64 | 13.07 | 30.00 |
| 209 LEU | N | -4.28 | 0.23 | 14.31 | 30.00 |
| 209 LEU | CA | -4.52 | 1.10 | 13.16 | 30.00 |
| 209 LEU | CB | -4.71 | 2.52 | 13.63 | 30.00 |
| 209 LEU | CG | -6.18 | 2.79 | 13.90 | 30.00 |
| 209 LEU | CD1 | -6.38 | 4.15 | 14.51 | 30.00 |
| 209 LEU | CD2 | -6.91 | 2.64 | 12.60 | 30.00 |
| 209 LEU | C | -3.39 | 1.02 | 12.16 | 30.00 |
| 209 LEU | O | -3.57 | 0.88 | 10.96 | 30.00 |
| 210 THR | N | -2.18 | 1.07 | 12.70 | 30.00 |
| 210 THR | CA | -0.99 | 1.05 | 11.85 | 30.00 |
| 210 THR | CB | 0.27 | 1.27 | 12.72 | 30.00 |

Figure 7TT

| Residue | Atom | X | Y | Z | B |
|---|---|---|---|---|---|
| 210 THR | OG1 | 0.25 | 2.60 | 13.26 | 30.00 |
| 210 THR | CG2 | 1.52 | 1.13 | 11.90 | 30.00 |
| 210 THR | C | -0.92 | -0.26 | 11.05 | 30.00 |
| 210 THR | O | -0.74 | -0.27 | 9.85 | 30.00 |
| 211 HIS | N | -1.13 | -1.37 | 11.74 | 30.00 |
| 211 HIS | CA | -1.05 | -2.69 | 11.08 | 30.00 |
| 211 HIS | CB | -1.05 | -3.83 | 12.13 | 30.00 |
| 211 HIS | CG | -0.99 | -5.21 | 11.53 | 30.00 |
| 211 HIS | CD2 | -1.96 | -5.99 | 10.99 | 30.00 |
| 211 HIS | ND1 | 0.17 | -5.95 | 11.46 | 30.00 |
| 211 HIS | CE1 | -0.08 | -7.12 | 10.91 | 30.00 |
| 211 HIS | NE2 | -1.36 | -7.17 | 10.62 | 30.00 |
| 211 HIS | C | -2.16 | -2.85 | 10.05 | 30.00 |
| 211 HIS | O | -1.93 | -3.30 | 8.92 | 30.00 |
| 212 THR | N | -3.36 | -2.40 | 10.40 | 30.00 |
| 212 THR | CA | -4.55 | -2.51 | 9.50 | 30.00 |
| 212 THR | CB | -5.87 | -2.09 | 10.23 | 30.00 |
| 212 THR | OG1 | -6.17 | -3.05 | 11.24 | 30.00 |
| 212 THR | CG2 | -7.04 | -2.06 | 9.31 | 30.00 |
| 212 THR | C | -4.36 | -1.75 | 8.15 | 30.00 |
| 212 THR | O | -4.72 | -2.21 | 7.07 | 30.00 |
| 213 LEU | N | -3.77 | -0.56 | 8.24 | 30.00 |
| 213 LEU | CA | -3.51 | 0.24 | 7.06 | 30.00 |
| 213 LEU | CB | -3.27 | 1.65 | 7.49 | 30.00 |
| 213 LEU | CG | -4.51 | 2.33 | 8.09 | 30.00 |
| 213 LEU | CD1 | -4.11 | 3.73 | 8.56 | 30.00 |
| 213 LEU | CD2 | -5.62 | 2.44 | 7.07 | 30.00 |
| 213 LEU | C | -2.34 | -0.33 | 6.20 | 30.00 |
| 213 LEU | O | -2.33 | -0.25 | 4.97 | 30.00 |

Figure 7UU

| Residue | Atom | X | Y | Z | B |
|---|---|---|---|---|---|
| 214 LEU | N | -1.38 | -0.97 | 6.84 | 30.00 |
| 214 LEU | CA | -0.26 | -1.57 | 6.10 | 30.00 |
| 214 LEU | CB | 0.75 | -2.18 | 7.05 | 30.00 |
| 214 LEU | CG | 2.20 | -2.33 | 6.60 | 30.00 |
| 214 LEU | CD1 | 2.74 | -3.56 | 7.23 | 30.00 |
| 214 LEU | CD2 | 2.33 | -2.42 | 5.09 | 30.00 |
| 214 LEU | C | -0.92 | -2.67 | 5.29 | 30.00 |
| 214 LEU | O | -0.70 | -2.85 | 4.11 | 30.00 |
| 215 SER | N | -1.77 | -3.43 | 5.97 | 30.00 |
| 215 SER | CA | -2.55 | -4.55 | 5.34 | 30.00 |
| 215 SER | CB | -3.46 | -5.17 | 6.40 | 30.00 |
| 215 SER | OG | -3.71 | -6.53 | 6.16 | 30.00 |
| 215 SER | C | -3.38 | -4.06 | 4.11 | 30.00 |
| 215 SER | O | -3.49 | -4.71 | 3.07 | 30.00 |
| 216 THR | N | -4.00 | -2.90 | 4.25 | 30.00 |
| 216 THR | CA | -4.78 | -2.31 | 3.14 | 30.00 |
| 216 THR | CB | -5.38 | -0.94 | 3.56 | 30.00 |
| 216 THR | OG1 | -6.38 | -1.16 | 4.56 | 30.00 |
| 216 THR | CG2 | -6.01 | -0.21 | 2.39 | 30.00 |
| 216 THR | C | -3.84 | -2.11 | 1.90 | 30.00 |
| 216 THR | O | -4.20 | -2.34 | 0.75 | 30.00 |
| 217 ALA | N | -2.60 | -1.72 | 2.16 | 30.00 |
| 217 ALA | CA | -1.62 | -1.50 | 1.09 | 30.00 |
| 217 ALA | CB | -0.45 | -0.67 | 1.61 | 30.00 |
| 217 ALA | C | -1.10 | -2.83 | 0.55 | 30.00 |
| 217 ALA | O | -1.15 | -3.11 | -0.64 | 30.00 |
| 218 VAL | N | -0.60 | -3.68 | 1.44 | 30.00 |
| 218 VAL | CA | -0.02 | -4.95 | 1.02 | 30.00 |
| 218 VAL | CB | 0.55 | -5.74 | 2.21 | 30.00 |

Figure 7VV

| Residue | Atom | X | Y | Z | B |
|---|---|---|---|---|---|
| 218 VAL | CG1 | 0.83 | -7.16 | 1.79 | 30.00 |
| 218 VAL | CG2 | 1.86 | -5.09 | 2.67 | 30.00 |
| 218 VAL | C | -0.99 | -5.80 | 0.21 | 30.00 |
| 218 VAL | O | -0.66 | -6.36 | -0.82 | 30.00 |
| 219 ASN | N | -2.23 | -5.81 | 0.63 | 30.00 |
| 219 ASN | CA | -3.25 | -6.61 | -0.07 | 30.00 |
| 219 ASN | CB | -4.43 | -6.87 | 0.84 | 30.00 |
| 219 ASN | CG | -4.14 | -7.91 | 1.84 | 30.00 |
| 219 ASN | OD1 | -3.77 | -9.04 | 1.50 | 30.00 |
| 219 ASN | ND2 | -4.28 | -7.55 | 3.10 | 30.00 |
| 219 ASN | C | -3.76 | -6.04 | -1.41 | 30.00 |
| 219 ASN | O | -4.48 | -6.68 | -2.16 | 30.00 |
| 220 ASN | N | -3.41 | -4.79 | -1.68 | 30.00 |
| 220 ASN | CA | -3.85 | -4.16 | -2.92 | 30.00 |
| 220 ASN | CB | -4.66 | -2.90 | -2.62 | 30.00 |
| 220 ASN | CG | -6.05 | -3.21 | -2.10 | 30.00 |
| 220 ASN | OD1 | -7.00 | -3.40 | -2.88 | 30.00 |
| 220 ASN | ND2 | -6.20 | -3.25 | -0.77 | 30.00 |
| 220 ASN | C | -2.67 | -3.80 | -3.82 | 30.00 |
| 220 ASN | O | -2.83 | -3.08 | -4.81 | 30.00 |
| 221 MET | N | -1.49 | -4.31 | -3.48 | 30.00 |
| 221 MET | CA | -0.25 | -4.00 | -4.26 | 30.00 |
| 221 MET | CB | 0.98 | -4.51 | -3.53 | 30.00 |
| 221 MET | CG | 1.05 | -5.99 | -3.42 | 30.00 |
| 221 MET | SD | 2.55 | -6.42 | -2.70 | 30.00 |
| 221 MET | CE | 2.18 | -7.97 | -1.97 | 30.00 |
| 221 MET | C | -0.30 | -4.55 | -5.68 | 30.00 |
| 221 MET | O | 0.13 | -3.93 | -6.63 | 30.00 |
| 222 MET | N | -0.90 | -5.72 | -5.81 | 30.00 |

Figure 7WW

| Residue | Atom | X | Y | Z | B |
|---|---|---|---|---|---|
| 222 MET | CA | -1.01 | -6.40 | -7.12 | 30.00 |
| 222 MET | CB | -1.21 | -7.89 | -6.86 | 30.00 |
| 222 MET | CG | -0.08 | -8.49 | -6.04 | 30.00 |
| 222 MET | SD | 1.41 | -8.81 | -7.00 | 30.00 |
| 222 MET | CE | 1.82 | -7.35 | -7.59 | 30.00 |
| 222 MET | C | -2.08 | -5.84 | -8.08 | 30.00 |
| 222 MET | O | -2.34 | -6.33 | -9.16 | 30.00 |
| 223 LEU | N | -2.69 | -4.75 | -7.67 | 30.00 |
| 223 LEU | CA | -3.72 | -4.14 | -8.48 | 30.00 |
| 223 LEU | CB | -4.63 | -3.28 | -7.58 | 30.00 |
| 223 LEU | CG | -6.03 | -3.76 | -7.16 | 30.00 |
| 223 LEU | CD1 | -6.98 | -3.60 | -8.31 | 30.00 |
| 223 LEU | CD2 | -5.99 | -5.23 | -6.75 | 30.00 |
| 223 LEU | C | -3.03 | -3.30 | -9.55 | 30.00 |
| 223 LEU | O | -2.15 | -2.47 | -9.29 | 30.00 |
| 224 ARG | N | -3.37 | -3.60 | -10.79 | 30.00 |
| 224 ARG | CA | -2.84 | -2.83 | -11.92 | 30.00 |
| 224 ARG | CB | -3.00 | -3.64 | -13.20 | 30.00 |
| 224 ARG | CG | -2.15 | -4.88 | -13.22 | 30.00 |
| 224 ARG | CD | -0.72 | -4.52 | -12.84 | 30.00 |
| 224 ARG | NE | 0.30 | -5.34 | -13.48 | 30.00 |
| 224 ARG | CZ | 0.43 | -6.66 | -13.35 | 30.00 |
| 224 ARG | NH1 | 1.42 | -7.28 | -13.99 | 30.00 |
| 224 ARG | NH2 | -0.42 | -7.37 | -12.60 | 30.00 |
| 224 ARG | C | -3.62 | -1.51 | -11.98 | 30.00 |
| 224 ARG | O | -4.83 | -1.48 | -12.19 | 30.00 |
| 225 ASP | N | -2.90 | -0.43 | -11.70 | 30.00 |
| 225 ASP | CA | -3.50 | 0.95 | -11.69 | 30.00 |
| 225 ASP | CB | -3.65 | 1.46 | -13.12 | 30.00 |

Figure 7XX

| Residue | Atom | X | Y | Z | B |
|---|---|---|---|---|---|
| 225 ASP | CG | -3.92 | 2.96 | -13.18 | 30.00 |
| 225 ASP | OD1 | -3.84 | 3.62 | -12.13 | 30.00 |
| 225 ASP | OD2 | -4.24 | 3.50 | -14.26 | 30.00 |
| 225 ASP | C | -4.87 | 1.05 | -10.98 | 30.00 |
| 225 ASP | O | -5.90 | 1.08 | -11.60 | 30.00 |
| 226 ARG | N | -4.91 | 1.22 | -9.67 | 30.00 |
| 226 ARG | CA | -6.23 | 1.29 | -9.02 | 30.00 |
| 226 ARG | CB | -6.03 | 1.13 | -7.52 | 30.00 |
| 226 ARG | CG | -4.69 | 1.68 | -7.09 | 30.00 |
| 226 ARG | CD | -4.23 | 1.22 | -5.72 | 30.00 |
| 226 ARG | NE | -4.53 | 2.27 | -4.75 | 30.00 |
| 226 ARG | CZ | -5.55 | 2.22 | -3.91 | 30.00 |
| 226 ARG | NH1 | -5.77 | 3.23 | -3.09 | 30.00 |
| 226 ARG | NH2 | -6.32 | 1.13 | -3.86 | 30.00 |
| 226 ARG | C | -7.01 | 2.59 | -9.32 | 30.00 |
| 226 ARG | O | -8.23 | 2.67 | -9.14 | 30.00 |
| 227 TRP | N | -6.28 | 3.63 | -9.73 | 30.00 |
| 227 TRP | CA | -6.90 | 4.95 | -10.02 | 30.00 |
| 227 TRP | CB | -5.81 | 6.01 | -10.17 | 30.00 |
| 227 TRP | CG | -5.62 | 6.85 | -8.96 | 30.00 |
| 227 TRP | CD2 | -5.41 | 6.41 | -7.61 | 30.00 |
| 227 TRP | CE2 | -5.23 | 7.56 | -6.80 | 30.00 |
| 227 TRP | CE3 | -5.36 | 5.14 | -7.00 | 30.00 |
| 227 TRP | CD1 | -5.57 | 8.22 | -8.91 | 30.00 |
| 227 TRP | NE1 | -5.33 | 8.65 | -7.63 | 30.00 |
| 227 TRP | CZ2 | -5.00 | 7.49 | -5.42 | 30.00 |
| 227 TRP | CZ3 | -5.13 | 5.08 | -5.61 | 30.00 |
| 227 TRP | CH2 | -4.95 | 6.25 | -4.85 | 30.00 |
| 227 TRP | C | -7.88 | 4.99 | -11.21 | 30.00 |

Figure 7YY

| Residue | Atom | X | Y | Z | B |
|---|---|---|---|---|---|
| 227 TRP | O | -8.68 | 5.92 | -11.38 | 30.00 |
| 228 SER | N | -7.78 | 3.98 | -12.06 | 30.00 |
| 228 SER | CA | -8.67 | 3.87 | -13.20 | 30.00 |
| 228 SER | CB | -8.18 | 2.78 | -14.13 | 30.00 |
| 228 SER | OG | -7.15 | 3.28 | -14.94 | 30.00 |
| 228 SER | C | -10.03 | 3.51 | -12.64 | 30.00 |
| 228 SER | O | -11.05 | 4.14 | -12.93 | 30.00 |
| 229 LEU | N | -10.02 | 2.48 | -11.80 | 30.00 |
| 229 LEU | CA | -11.25 | 2.02 | -11.16 | 30.00 |
| 229 LEU | CB | -10.99 | 0.85 | -10.23 | 30.00 |
| 229 LEU | CG | -10.21 | -0.32 | -10.79 | 30.00 |
| 229 LEU | CD1 | -10.40 | -1.52 | -9.85 | 30.00 |
| 229 LEU | CD2 | -10.70 | -0.65 | -12.19 | 30.00 |
| 229 LEU | C | -11.86 | 3.17 | -10.37 | 30.00 |
| 229 LEU | O | -13.04 | 3.46 | -10.45 | 30.00 |
| 230 VAL | N | -11.01 | 3.85 | -9.61 | 30.00 |
| 230 VAL | CA | -11.49 | 4.96 | -8.78 | 30.00 |
| 230 VAL | CB | -10.33 | 5.57 | -7.93 | 30.00 |
| 230 VAL | CG1 | -10.80 | 6.79 | -7.14 | 30.00 |
| 230 VAL | CG2 | -9.79 | 4.52 | -6.97 | 30.00 |
| 230 VAL | C | -12.21 | 6.00 | -9.67 | 30.00 |
| 230 VAL | O | -13.36 | 6.42 | -9.45 | 30.00 |
| 231 ALA | N | -11.56 | 6.31 | -10.77 | 30.00 |
| 231 ALA | CA | -12.10 | 7.30 | -11.70 | 30.00 |
| 231 ALA | CB | -11.11 | 7.53 | -12.80 | 30.00 |
| 231 ALA | C | -13.43 | 6.82 | -12.27 | 30.00 |
| 231 ALA | O | -14.45 | 7.50 | -12.30 | 30.00 |
| 232 GLU | N | -13.42 | 5.55 | -12.64 | 30.00 |
| 232 GLU | CA | -14.58 | 4.95 | -13.22 | 30.00 |

Figure 7ZZ

| Residue | Atom | X | Y | Z | B |
|---|---|---|---|---|---|
| 232 GLU | CB | -14.20 | 3.57 | -13.73 | 30.00 |
| 232 GLU | CG | -15.10 | 3.11 | -14.82 | 30.00 |
| 232 GLU | CD | -14.76 | 1.72 | -15.32 | 30.00 |
| 232 GLU | OE1 | -15.38 | 0.74 | -14.83 | 30.00 |
| 232 GLU | OE2 | -13.86 | 1.59 | -16.18 | 30.00 |
| 232 GLU | C | -15.92 | 4.63 | -12.26 | 30.00 |
| 232 GLU | O | -16.89 | 5.30 | -12.58 | 30.00 |
| 233 ARG | N | -15.48 | 4.47 | -11.02 | 30.00 |
| 233 ARG | CA | -16.55 | 4.32 | -9.97 | 30.00 |
| 233 ARG | CB | -16.11 | 3.29 | -8.95 | 30.00 |
| 233 ARG | CG | -15.92 | 1.94 | -9.62 | 30.00 |
| 233 ARG | CD | -14.70 | 1.20 | -9.19 | 30.00 |
| 233 ARG | NE | -14.85 | -0.22 | -9.46 | 30.00 |
| 233 ARG | CZ | -14.72 | -1.19 | -8.56 | 30.00 |
| 233 ARG | NH1 | -14.89 | -2.46 | -8.93 | 30.00 |
| 233 ARG | NH2 | -14.39 | -0.91 | -7.31 | 30.00 |
| 233 ARG | C | -16.98 | 5.65 | -9.36 | 30.00 |
| 233 ARG | O | -18.05 | 5.78 | -8.76 | 30.00 |
| 234 ARG | N | -16.76 | 6.50 | -9.75 | 30.00 |
| 234 ARG | CA | -16.48 | 8.02 | -9.11 | 30.00 |
| 234 ARG | CB | -15.25 | 8.92 | -9.19 | 30.00 |
| 234 ARG | CG | -15.60 | 10.38 | -8.97 | 30.00 |
| 234 ARG | CD | -14.57 | 11.42 | -9.43 | 30.00 |
| 234 ARG | NE | -15.13 | 12.76 | -9.21 | 30.00 |
| 234 ARG | CZ | -14.48 | 13.83 | -8.74 | 30.00 |
| 234 ARG | NH1 | -13.20 | 13.78 | -8.43 | 30.00 |
| 234 ARG | NH2 | -15.14 | 14.96 | -8.51 | 30.00 |
| 234 ARG | C | -17.57 | 8.52 | -10.08 | 30.00 |
| 234 ARG | O | -18.51 | 9.23 | -9.70 | 30.00 |

Figure 7AAA

| Residue | Atom | X | Y | Z | B |
|---|---|---|---|---|---|
| 235 ARG | N | -17.40 | 8.19 | -11.37 | 30.00 |
| 235 ARG | CA | -18.36 | 8.59 | -12.46 | 30.00 |
| 235 ARG | CB | -17.76 | 8.29 | -13.82 | 30.00 |
| 235 ARG | CG | -16.50 | 9.12 | -14.10 | 30.00 |
| 235 ARG | CD | -16.08 | 9.07 | -15.56 | 30.00 |
| 235 ARG | NE | -15.88 | 7.69 | -16.00 | 30.00 |
| 235 ARG | CZ | -14.68 | 7.14 | -16.20 | 30.00 |
| 235 ARG | NH1 | -14.60 | 5.87 | -16.60 | 30.00 |
| 235 ARG | NH2 | -13.57 | 7.85 | -16.01 | 30.00 |
| 235 ARG | C | -19.70 | 7.91 | -12.32 | 30.00 |
| 235 ARG | O | -20.75 | 8.52 | -12.44 | 30.00 |
| 236 GLN | N | -19.66 | 6.61 | -12.05 | 30.00 |
| 236 GLN | CA | -20.89 | 5.80 | -11.81 | 30.00 |
| 236 GLN | CB | -20.53 | 4.34 | -11.51 | 30.00 |
| 236 GLN | CG | -19.31 | 3.77 | -12.26 | 30.00 |
| 236 GLN | CD | -19.28 | 2.25 | -12.26 | 30.00 |
| 236 GLN | OE1 | -18.36 | 1.64 | -12.82 | 30.00 |
| 236 GLN | NE2 | -20.29 | 1.62 | -11.65 | 30.00 |
| 236 GLN | C | -21.73 | 6.36 | -10.64 | 30.00 |
| 236 GLN | O | -22.94 | 6.21 | -10.61 | 30.00 |
| 237 ALA | N | -21.04 | 6.92 | -9.64 | 30.00 |
| 237 ALA | CA | -21.70 | 7.50 | -8.40 | 30.00 |
| 237 ALA | CB | -20.70 | 7.53 | -7.24 | 30.00 |
| 237 ALA | C | -22.30 | 8.89 | -8.61 | 30.00 |
| 237 ALA | O | -23.09 | 9.39 | -7.82 | 30.00 |
| 238 GLY | N | -21.89 | 9.54 | -9.70 | 30.00 |
| 238 GLY | CA | -22.39 | 10.86 | -10.00 | 30.00 |
| 238 GLY | C | -21.68 | 11.89 | -9.14 | 30.00 |
| 238 GLY | O | -22.25 | 12.93 | -8.84 | 30.00 |

Figure 7BBB

| Residue | Atom | X | Y | Z | B |
|---|---|---|---|---|---|
| 239 ILE | N | -20.44 | 11.58 | -8.74 | 30.00 |
| 239 ILE | CA | -19.61 | 12.49 | -7.87 | 30.00 |
| 239 ILE | CB | -18.48 | 11.72 | -7.08 | 30.00 |
| 239 ILE | CG2 | -17.66 | 12.66 | -6.26 | 30.00 |
| 239 ILE | CG1 | -19.07 | 10.71 | -6.11 | 30.00 |
| 239 ILE | CD1 | -18.02 | 9.87 | -5.50 | 30.00 |
| 239 ILE | C | -18.94 | 13.43 | -8.82 | 30.00 |
| 239 ILE | O | -18.33 | 13.03 | -9.83 | 30.00 |
| 240 ALA | N | -19.01 | 14.71 | -8.48 | 30.00 |
| 240 ALA | CA | -18.40 | 15.73 | -9.31 | 30.00 |
| 240 ALA | CB | -19.35 | 16.10 | -10.46 | 30.00 |
| 240 ALA | C | -18.10 | 16.97 | -8.50 | 30.00 |
| 240 ALA | O | -18.78 | 17.31 | -7.53 | 30.00 |
| 241 GLY | N | -17.05 | 17.66 | -8.91 | 30.00 |
| 241 GLY | CA | -16.70 | 18.87 | -8.21 | 30.00 |
| 241 GLY | C | -15.25 | 18.93 | -7.84 | 30.00 |
| 241 GLY | O | -14.41 | 18.20 | -8.34 | 30.00 |
| 242 HIS | N | -14.95 | 19.87 | -6.97 | 30.00 |
| 242 HIS | CA | -13.60 | 20.10 | -6.50 | 30.00 |
| 242 HIS | CB | -13.47 | 21.56 | -6.11 | 30.00 |
| 242 HIS | CG | -12.12 | 22.14 | -6.36 | 30.00 |
| 242 HIS | CD2 | -11.42 | 23.09 | -5.70 | 30.00 |
| 242 HIS | ND1 | -11.33 | 21.73 | -7.41 | 30.00 |
| 242 HIS | CE1 | -10.19 | 22.41 | -7.38 | 30.00 |
| 242 HIS | NE2 | -10.22 | 23.23 | -6.36 | 30.00 |
| 242 HIS | C | -13.39 | 19.17 | -5.31 | 30.00 |
| 242 HIS | O | -13.38 | 19.57 | -4.15 | 30.00 |
| 243 THR | N | -13.30 | 17.88 | -5.61 | 30.00 |
| 243 THR | CA | -13.11 | 16.89 | -4.55 | 30.00 |

Figure 7CCC

| Residue | Atom | X | Y | Z | B |
|---|---|---|---|---|---|
| 243 THR | CB | -13.77 | 15.55 | -4.95 | 30.00 |
| 243 THR | OG1 | -15.02 | 15.80 | -5.62 | 30.00 |
| 243 THR | CG2 | -14.03 | 14.69 | -3.69 | 30.00 |
| 243 THR | C | -11.60 | 16.72 | -4.22 | 30.00 |
| 243 THR | O | -10.73 | 17.15 | -4.97 | 30.00 |
| 244 TYR | N | -11.30 | 16.18 | -3.03 | 30.00 |
| 244 TYR | CA | -9.88 | 15.93 | -2.62 | 30.00 |
| 244 TYR | CB | -9.73 | 15.68 | -1.13 | 30.00 |
| 244 TYR | CG | -10.06 | 16.83 | -0.23 | 30.00 |
| 244 TYR | CD1 | -9.57 | 16.89 | 1.07 | 30.00 |
| 244 TYR | CE1 | -9.92 | 17.93 | 1.90 | 30.00 |
| 244 TYR | CD2 | -10.90 | 17.83 | -0.68 | 30.00 |
| 244 TYR | CE2 | -11.26 | 18.87 | 0.14 | 30.00 |
| 244 TYR | CZ | -10.77 | 18.90 | 1.43 | 30.00 |
| 244 TYR | OH | -11.15 | 19.93 | 2.24 | 30.00 |
| 244 TYR | C | -9.40 | 14.70 | -3.34 | 30.00 |
| 244 TYR | O | -8.22 | 14.42 | -3.44 | 30.00 |
| 245 LEU | N | -10.37 | 13.87 | -3.73 | 30.00 |
| 245 LEU | CA | -10.09 | 12.62 | -4.45 | 30.00 |
| 245 LEU | CB | -11.38 | 11.90 | -4.78 | 30.00 |
| 245 LEU | CG | -11.18 | 10.60 | -5.55 | 30.00 |
| 245 LEU | CD1 | -10.17 | 9.70 | -4.85 | 30.00 |
| 245 LEU | CD2 | -12.49 | 9.92 | -5.70 | 30.00 |
| 245 LEU | C | -9.35 | 13.03 | -5.70 | 30.00 |
| 245 LEU | O | -9.87 | 13.74 | -6.55 | 30.00 |
| 246 GLN | N | -8.14 | 12.53 | -5.84 | 30.00 |
| 246 GLN | CA | -7.25 | 12.88 | -6.97 | 30.00 |
| 246 GLN | CB | -5.80 | 12.76 | -6.48 | 30.00 |
| 246 GLN | CG | -5.04 | 14.07 | -6.37 | 30.00 |

Figure 7DDD

| Residue | Atom | X | Y | Z | B |
|---|---|---|---|---|---|
| 246 GLN | CD | -5.89 | 15.30 | -6.68 | 30.00 |
| 246 GLN | OE1 | -5.60 | 16.42 | -6.26 | 30.00 |
| 246 GLN | NE2 | -6.96 | 15.09 | -7.42 | 30.00 |
| 246 GLN | C | -7.50 | 12.06 | -8.25 | 30.00 |
| 246 GLN | O | -6.59 | 11.75 | -9.03 | 30.00 |
| 247 ALA | N | -8.76 | 11.76 | -8.50 | 30.00 |
| 247 ALA | CA | -9.15 | 10.95 | -9.65 | 30.00 |
| 247 ALA | CB | -9.05 | 9.48 | -9.29 | 30.00 |
| 247 ALA | C | -10.58 | 11.28 | -10.04 | 30.00 |
| 247 ALA | O | -11.04 | 10.81 | -11.10 | 30.00 |
| 247 ALA | OT | -11.22 | 12.01 | -9.27 | 30.00 |

Figure 8A

| Atom 1 | Atom 2 | Distance | Atom 1 | Atom 2 | Distance |
|---|---|---|---|---|---|
| 129 N | 128 C | 1.311 | 129 N | 128 O | 2.215 |
| 129 N | 128 CA | 2.359 | 129 N | 128 CB | 2.891 |
| 129 N | 150 O | 2.902 | 129 N | 130 N | 3.249 |
| 129 N | 128 N | 3.556 | 129 N | 128 CG1 | 3.899 |
| 129 N | 128 CG2 | 3.930 | 129 N | 150 C | 4.033 |
| 129 N | 150 N | 4.141 | 129 N | 300 OH2 | 4.223 |
| 129 N | 301 OH2 | 4.344 | 129 N | 127 C | 4.448 |
| 129 N | 130 CA | 4.510 | 129 N | 152 SG | 4.570 |
| 129 N | 127 O | 4.573 | 129 N | 150 CA | 4.622 |
| 129 N | 150 CB | 4.975 | 129 N | 149 C | 5.116 |
| 129 N | 149 CB | 5.120 | 129 N | 151 N | 5.126 |
| 129 N | 149 CA | 5.155 | 129 N | 130 CB | 5.405 |
| 129 N | 151 CA | 5.411 | 129 N | 27 CD1 | 5.447 |
| 129 N | 130 C | 5.492 | 129 N | 155 CA | 5.693 |
| 129 N | 61 CE1 | 5.719 | 129 N | 152 N | 5.729 |
| 129 N | 127 CA | 5.740 | 129 N | 151 C | 5.742 |
| 129 N | 127 CB | 5.749 | 129 N | 149 CG2 | 5.756 |
| 129 N | 61 NE2 | 5.828 | 129 N | 130 O | 5.858 |
| 129 N | 152 CB | 5.908 | 129 N | 27 O | 6.138 |
| 129 N | 149 CG1 | 6.179 | 129 N | 149 O | 6.208 |
| 129 N | 131 N | 6.263 | 129 N | 151 O | 6.377 |
| 129 N | 148 O | 6.406 | 129 N | 27 CA | 6.428 |
| 129 N | 151 CD1 | 6.441 | 129 N | 27 CG | 6.469 |
| 129 N | 155 N | 6.481 | 129 N | 152 CA | 6.521 |
| 129 N | 149 N | 6.555 | 129 N | 156 N | 6.645 |
| 129 N | 61 ND1 | 6.681 | 129 N | 27 C | 6.762 |
| 129 N | 155 C | 6.764 | 129 N | 151 CB | 6.810 |
| 129 N | 130 CG | 6.847 | 129 N | 61 CD2 | 6.875 |
| 129 N | 27 CB | 6.882 | 129 N | 157 NH2 | 6.887 |
| 129 N | 131 OG | 6.941 | 129 N | 148 C | 6.997 |
| 129 N | 127 N | 7.007 | 129 N | 127 OG | 7.076 |
| 129 N | 152 O | 7.143 | 129 N | 130 CD1 | 7.157 |
| 129 N | 152 C | 7.198 | 129 N | 151 CG | 7.288 |
| 129 N | 154 C | 7.303 | 129 N | 61 CG | 7.352 |
| 129 N | 154 O | 7.459 | 129 N | 27 N | 7.468 |
| 129 N | 131 CA | 7.475 | 129 N | 157 NE | 7.478 |
| 129 N | 157 N | 7.533 | 129 N | 157 CB | 7.706 |
| 129 N | 157 CZ | 7.778 | 129 N | 130 CD2 | 7.798 |
| 129 N | 27 CD2 | 7.821 | 129 N | 131 CB | 7.825 |
| 129 N | 155 O | 7.887 | 129 N | 157 O | 7.932 |
| 129 N | 156 CA | 7.938 | 129 N | 148 ND1 | 8.000 |
| 129 N | 61 N | 8.102 | 129 N | 157 CG | 8.181 |
| 129 N | 60 N | 8.218 | 129 N | 157 CA | 8.235 |
| 129 N | 156 CB | 8.281 | 129 N | 154 CA | 8.326 |
| 129 N | 154 N | 8.327 | 129 N | 60 CA | 8.331 |
| 129 N | 156 C | 8.365 | 129 N | 148 CE1 | 8.374 |

Figure 8B

| Atom 1 | Atom 2 | Distance | Atom 1 | Atom 2 | Distance |
|---|---|---|---|---|---|
| 129 N | 156 CG | 8.442 | 129 N | 157 CD | 8.471 |
| 129 N | 157 C | 8.503 | 129 N | 148 CA | 8.529 |
| 129 N | 61 CB | 8.591 | 129 N | 151 CD2 | 8.642 |
| 129 N | 131 C | 8.679 | 129 N | 61 CA | 8.718 |
| 129 N | 60 C | 8.808 | 129 N | 60 OD1 | 8.832 |
| 129 N | 148 CG | 8.855 | 129 N | 131 O | 8.939 |
| 129 N | 157 NH1 | 8.984 | 129 N | 148 CB | 9.068 |
| 129 N | 148 N | 9.181 | 129 N | 148 NE2 | 9.376 |
| 129 N | 60 CB | 9.492 | 129 N | 156 O | 9.565 |
| 129 N | 132 N | 9.587 | 129 N | 60 CG | 9.644 |
| 129 N | 148 CD2 | 9.666 | 129 N | 156 CD | 9.714 |
| 129 N | 154 CB | 9.781 | 129 N | 156 NE | 9.846 |
| 129 N | 60 O | 9.947 | 129 N | 154 CG2 | 10.079 |
| 129 N | 38 CD2 | 10.174 | 129 N | 61 C | 10.212 |
| 129 N | 38 CD1 | 10.521 | 129 N | 132 CG2 | 10.557 |
| 129 N | 60 OD2 | 10.755 | 129 N | 154 CG1 | 10.857 |
| 129 N | 132 CA | 10.861 | 129 N | 61 O | 10.904 |
| 129 N | 38 CG | 10.956 | 129 N | 154 CD1 | 11.002 |
| 129 N | 156 CZ | 11.059 | 129 N | 132 OG1 | 11.066 |
| 129 N | 38 CB | 11.126 | 129 N | 38 O | 11.147 |
| 129 N | 132 CB | 11.227 | 129 N | 156 NH2 | 11.334 |
| 129 N | 38 CA | 11.810 | 129 N | 38 C | 11.929 |
| 129 N | 132 C | 11.992 | 129 CA | 128 C | 2.374 |
| 129 CA | 130 N | 2.377 | 129 CA | 128 O | 2.683 |
| 129 CA | 301 OH2 | 3.560 | 129 CA | 300 OH2 | 3.614 |
| 129 CA | 128 CA | 3.704 | 129 CA | 130 CA | 3.762 |
| 129 CA | 150 O | 3.819 | 129 CA | 128 CB | 4.163 |
| 129 CA | 130 C | 4.480 | 129 CA | 150 N | 4.525 |
| 129 CA | 130 O | 4.654 | 129 CA | 128 N | 4.722 |
| 129 CA | 130 CB | 4.788 | 129 CA | 150 C | 4.807 |
| 129 CA | 61 CE1 | 4.829 | 129 CA | 152 SG | 4.909 |
| 129 CA | 128 CG2 | 4.997 | 129 CA | 61 NE2 | 5.014 |
| 129 CA | 150 CB | 5.055 | 129 CA | 150 CA | 5.071 |
| 129 CA | 128 CG1 | 5.243 | 129 CA | 131 N | 5.353 |
| 129 CA | 155 CA | 5.416 | 129 CA | 149 CA | 5.433 |
| 129 CA | 149 C | 5.524 | 129 CA | 127 C | 5.613 |
| 129 CA | 149 CB | 5.682 | 129 CA | 157 NH2 | 5.711 |
| 129 CA | 127 O | 5.801 | 129 CA | 156 N | 5.887 |
| 129 CA | 27 O | 5.894 | 129 CA | 61 ND1 | 5.927 |
| 129 CA | 131 OG | 5.955 | 129 CA | 27 CD1 | 5.969 |
| 129 CA | 151 N | 6.019 | 129 CA | 148 O | 6.058 |
| 129 CA | 61 CD2 | 6.221 | 129 CA | 130 CG | 6.223 |
| 129 CA | 155 C | 6.257 | 129 CA | 152 CB | 6.273 |
| 129 CA | 131 CA | 6.439 | 129 CA | 155 N | 6.459 |
| 129 CA | 151 CA | 6.468 | 129 CA | 157 NE | 6.488 |
| 129 CA | 127 CB | 6.496 | 129 CA | 149 CG2 | 6.569 |

Figure 8C

| Atom 1 | Atom 2 | Distance | Atom 1 | Atom 2 | Distance |
|---|---|---|---|---|---|
| 129 CA | 152 N | 6.588 | 129 CA | 151 C | 6.596 |
| 129 CA | 149 CG1 | 6.605 | 129 CA | 27 CA | 6.653 |
| 129 CA | 157 CZ | 6.668 | 129 CA | 149 N | 6.683 |
| 129 CA | 149 O | 6.685 | 129 CA | 61 CG | 6.713 |
| 129 CA | 27 CG | 6.715 | 129 CA | 27 C | 6.727 |
| 129 CA | 130 CD1 | 6.748 | 129 CA | 157 N | 6.753 |
| 129 CA | 127 CA | 6.762 | 129 CA | 131 CB | 6.857 |
| 129 CA | 148 C | 6.859 | 129 CA | 157 CB | 6.963 |
| 129 CA | 27 CB | 7.013 | 129 CA | 151 O | 7.040 |
| 129 CA | 156 CA | 7.066 | 129 CA | 152 CA | 7.159 |
| 129 CA | 156 CB | 7.216 | 129 CA | 130 CD2 | 7.220 |
| 129 CA | 157 CG | 7.229 | 129 CA | 154 O | 7.266 |
| 129 CA | 154 C | 7.272 | 129 CA | 156 CG | 7.398 |
| 129 CA | 155 O | 7.453 | 129 CA | 156 C | 7.522 |
| 129 CA | 157 CA | 7.530 | 129 CA | 157 CD | 7.534 |
| 129 CA | 157 O | 7.608 | 129 CA | 131 C | 7.706 |
| 129 CA | 148 ND1 | 7.706 | 129 CA | 151 CD1 | 7.730 |
| 129 CA | 127 OG | 7.739 | 129 CA | 157 NH1 | 7.809 |
| 129 CA | 27 N | 7.855 | 129 CA | 152 C | 7.883 |
| 129 CA | 148 CE1 | 7.907 | 129 CA | 151 CB | 7.924 |
| 129 CA | 152 O | 7.986 | 129 CA | 61 N | 7.986 |
| 129 CA | 157 C | 8.036 | 129 CA | 127 N | 8.061 |
| 129 CA | 61 CB | 8.064 | 129 CA | 131 O | 8.123 |
| 129 CA | 27 CD2 | 8.130 | 129 CA | 148 CA | 8.359 |
| 129 CA | 61 CA | 8.429 | 129 CA | 60 CA | 8.460 |
| 129 CA | 154 CA | 8.491 | 129 CA | 132 N | 8.508 |
| 129 CA | 151 CG | 8.533 | 129 CA | 148 CG | 8.540 |
| 129 CA | 60 N | 8.570 | 129 CA | 156 CD | 8.594 |
| 129 CA | 156 NE | 8.600 | 129 CA | 154 N | 8.612 |
| 129 CA | 156 O | 8.710 | 129 CA | 60 C | 8.740 |
| 129 CA | 148 NE2 | 8.803 | 129 CA | 148 N | 8.804 |
| 129 CA | 60 OD1 | 8.811 | 129 CA | 38 CD2 | 8.831 |
| 129 CA | 148 CB | 8.920 | 129 CA | 148 CD2 | 9.180 |
| 129 CA | 38 CD1 | 9.319 | 129 CA | 132 CG2 | 9.573 |
| 129 CA | 60 CG | 9.635 | 129 CA | 60 CB | 9.635 |
| 129 CA | 38 CG | 9.687 | 129 CA | 156 CZ | 9.775 |
| 129 CA | 60 O | 9.795 | 129 CA | 132 CA | 9.825 |
| 129 CA | 154 CB | 9.837 | 129 CA | 151 CD2 | 9.841 |
| 129 CA | 132 OG1 | 9.875 | 129 CA | 38 CB | 9.925 |
| 129 CA | 61 C | 9.938 | 129 CA | 156 NH2 | 9.982 |
| 129 CA | 154 CG2 | 10.014 | 129 CA | 38 O | 10.059 |
| 129 CA | 132 CB | 10.149 | 129 CA | 61 O | 10.529 |
| 129 CA | 38 CA | 10.583 | 129 CA | 60 OD2 | 10.652 |
| 129 CA | 38 C | 10.796 | 129 CA | 132 O | 10.863 |
| 129 CA | 156 NH1 | 10.881 | 129 CA | 132 C | 10.911 |
| 129 CA | 154 CG1 | 11.054 | 129 CA | 154 CD1 | 11.303 |

Figure 8D

| Atom 1 | Atom 2 | Distance | Atom 1 | Atom 2 | Distance |
|---|---|---|---|---|---|
| 129 CA | 38 N | 11.864 | 129 C | 130 N | 1.324 |
| 129 C | 130 CA | 2.432 | 129 C | 130 C | 3.200 |
| 129 C | 128 C | 3.511 | 129 C | 130 O | 3.653 |
| 129 C | 130 CB | 3.668 | 129 C | 301 OH2 | 3.711 |
| 129 C | 150 N | 3.953 | 129 C | 131 N | 3.970 |
| 129 C | 128 O | 4.002 | 129 C | 150 O | 4.219 |
| 129 C | 149 CA | 4.353 | 129 C | 61 NE2 | 4.438 |
| 129 C | 128 CA | 4.606 | 129 C | 148 O | 4.620 |
| 129 C | 61 CE1 | 4.633 | 129 C | 300 OH2 | 4.672 |
| 129 C | 128 CB | 4.685 | 129 C | 149 C | 4.723 |
| 129 C | 149 CB | 4.759 | 129 C | 150 CA | 4.842 |
| 129 C | 150 CB | 4.879 | 129 C | 131 OG | 4.900 |
| 129 C | 150 C | 4.982 | 129 C | 130 CG | 4.985 |
| 129 C | 131 CA | 5.168 | 129 C | 157 NH2 | 5.225 |
| 129 C | 130 CD1 | 5.394 | 129 C | 149 N | 5.463 |
| 129 C | 27 CD1 | 5.482 | 129 C | 148 C | 5.493 |
| 129 C | 149 CG1 | 5.529 | 129 C | 128 CG1 | 5.535 |
| 129 C | 128 CG2 | 5.606 | 129 C | 131 CB | 5.637 |
| 129 C | 61 CD2 | 5.640 | 129 C | 128 N | 5.842 |
| 129 C | 61 ND1 | 5.846 | 129 C | 149 CG2 | 5.875 |
| 129 C | 27 O | 5.915 | 129 C | 149 O | 5.940 |
| 129 C | 27 CG | 6.060 | 129 C | 130 CD2 | 6.144 |
| 129 C | 152 SG | 6.169 | 129 C | 151 N | 6.282 |
| 129 C | 157 CZ | 6.326 | 129 C | 131 C | 6.371 |
| 129 C | 157 NE | 6.393 | 129 C | 61 CG | 6.403 |
| 129 C | 27 CA | 6.522 | 129 C | 27 CB | 6.554 |
| 129 C | 148 ND1 | 6.607 | 129 C | 131 O | 6.700 |
| 129 C | 27 C | 6.709 | 129 C | 127 C | 6.768 |
| 129 C | 127 O | 6.836 | 129 C | 155 CA | 6.840 |
| 129 C | 148 CE1 | 6.889 | 129 C | 148 CA | 6.974 |
| 129 C | 151 CA | 6.999 | 129 C | 156 N | 7.050 |
| 129 C | 132 N | 7.269 | 129 C | 148 CG | 7.302 |
| 129 C | 151 C | 7.308 | 129 C | 152 CB | 7.345 |
| 129 C | 148 N | 7.351 | 129 C | 27 CD2 | 7.397 |
| 129 C | 157 NH1 | 7.416 | 129 C | 152 N | 7.532 |
| 129 C | 157 CB | 7.551 | 129 C | 155 C | 7.573 |
| 129 C | 157 CG | 7.595 | 129 C | 157 CD | 7.629 |
| 129 C | 148 CB | 7.629 | 129 C | 151 O | 7.647 |
| 129 C | 157 N | 7.668 | 129 C | 148 NE2 | 7.689 |
| 129 C | 61 CB | 7.818 | 129 C | 27 N | 7.826 |
| 129 C | 127 CB | 7.899 | 129 C | 155 N | 7.930 |
| 129 C | 148 CD2 | 7.937 | 129 C | 61 N | 7.951 |
| 129 C | 151 CD1 | 7.962 | 129 C | 127 CA | 8.030 |
| 129 C | 156 CB | 8.055 | 129 C | 156 CA | 8.093 |
| 129 C | 61 CA | 8.168 | 129 C | 152 CA | 8.207 |
| 129 C | 156 CG | 8.265 | 129 C | 157 CA | 8.333 |

Figure 8E

| Atom 1 | Atom 2 | Distance | Atom 1 | Atom 2 | Distance |
|---|---|---|---|---|---|
| 129 C | 151 CB | 8.379 | 129 C | 132 CG2 | 8.406 |
| 129 C | 156 C | 8.469 | 129 C | 132 CA | 8.559 |
| 129 C | 154 O | 8.638 | 129 C | 157 O | 8.695 |
| 129 C | 154 C | 8.717 | 129 C | 155 O | 8.785 |
| 129 C | 60 CA | 8.818 | 129 C | 132 OG1 | 8.844 |
| 129 C | 60 N | 8.870 | 129 C | 60 C | 8.886 |
| 129 C | 38 CD2 | 8.894 | 129 C | 151 CG | 8.903 |
| 129 C | 157 C | 8.977 | 129 C | 132 CB | 8.980 |
| 129 C | 152 C | 9.078 | 129 C | 156 NE | 9.117 |
| 129 C | 127 OG | 9.169 | 129 C | 152 O | 9.204 |
| 129 C | 127 N | 9.307 | 129 C | 156 CD | 9.324 |
| 129 C | 60 OD1 | 9.557 | 129 C | 156 O | 9.606 |
| 129 C | 61 C | 9.617 | 129 C | 132 C | 9.671 |
| 129 C | 132 O | 9.711 | 129 C | 38 CD1 | 9.761 |
| 129 C | 38 O | 9.885 | 129 C | 38 CG | 9.905 |
| 129 C | 60 O | 9.926 | 129 C | 154 CA | 9.956 |
| 129 C | 154 N | 10.032 | 129 C | 61 O | 10.072 |
| 129 C | 151 CD2 | 10.085 | 129 C | 38 CB | 10.089 |
| 129 C | 60 CB | 10.129 | 129 C | 156 CZ | 10.197 |
| 129 C | 156 NH2 | 10.217 | 129 C | 60 CG | 10.247 |
| 129 C | 38 CA | 10.543 | 129 C | 38 C | 10.704 |
| 129 C | 60 OD2 | 11.226 | 129 C | 154 CB | 11.291 |
| 129 C | 156 NH1 | 11.392 | 129 C | 154 CG2 | 11.463 |
| 129 C | 38 N | 11.821 | 129 O | 130 N | 2.240 |
| 129 O | 130 CA | 2.765 | 129 O | 150 N | 2.876 |
| 129 O | 149 CA | 3.368 | 129 O | 130 C | 3.377 |
| 129 O | 149 C | 3.617 | 129 O | 131 N | 3.740 |
| 129 O | 61 NE2 | 3.757 | 129 O | 150 O | 3.782 |
| 129 O | 148 O | 3.794 | 129 O | 150 CA | 3.863 |
| 129 O | 150 CB | 3.935 | 129 O | 149 CB | 4.061 |
| 129 O | 130 O | 4.080 | 129 O | 128 C | 4.129 |
| 129 O | 130 CB | 4.162 | 129 O | 61 CE1 | 4.210 |
| 129 O | 150 C | 4.288 | 129 O | 131 OG | 4.342 |
| 129 O | 149 N | 4.450 | 129 O | 148 C | 4.546 |
| 129 O | 61 CD2 | 4.800 | 129 O | 149 O | 4.817 |
| 129 O | 128 O | 4.847 | 129 O | 301 OH2 | 4.903 |
| 129 O | 131 CA | 4.926 | 129 O | 149 CG1 | 4.965 |
| 129 O | 128 CA | 4.980 | 129 O | 128 CB | 5.074 |
| 129 O | 131 CB | 5.121 | 129 O | 149 CG2 | 5.142 |
| 129 O | 130 CG | 5.257 | 129 O | 61 ND1 | 5.343 |
| 129 O | 130 CD1 | 5.363 | 129 O | 148 ND1 | 5.464 |
| 129 O | 151 N | 5.605 | 129 O | 128 CG1 | 5.635 |
| 129 O | 61 CG | 5.673 | 129 O | 148 CE1 | 5.821 |
| 129 O | 300 OH2 | 5.825 | 129 O | 27 CD1 | 5.839 |
| 129 O | 148 CA | 6.030 | 129 O | 157 NH2 | 6.102 |
| 129 O | 131 C | 6.158 | 129 O | 128 CG2 | 6.205 |

Figure 8F

| Atom 1 | Atom 2 | Distance | Atom 1 | Atom 2 | Distance |
|---|---|---|---|---|---|
| 129 O | 148 CG | 6.215 | 129 O | 128 N | 6.322 |
| 129 O | 152 SG | 6.359 | 129 O | 131 O | 6.380 |
| 129 O | 27 CG | 6.483 | 129 O | 151 CA | 6.526 |
| 129 O | 148 N | 6.542 | 129 O | 148 CB | 6.556 |
| 129 O | 130 CD2 | 6.578 | 129 O | 148 NE2 | 6.696 |
| 129 O | 151 C | 6.910 | 129 O | 148 CD2 | 6.929 |
| 129 O | 127 O | 6.966 | 129 O | 27 O | 6.969 |
| 129 O | 61 CB | 7.037 | 129 O | 61 N | 7.095 |
| 129 O | 127 C | 7.108 | 129 O | 151 O | 7.131 |
| 129 O | 132 N | 7.198 | 129 O | 27 CB | 7.206 |
| 129 O | 61 CA | 7.252 | 129 O | 157 CZ | 7.276 |
| 129 O | 152 CB | 7.282 | 129 O | 27 CA | 7.326 |
| 129 O | 152 N | 7.342 | 129 O | 151 CD1 | 7.461 |
| 129 O | 157 NE | 7.470 | 129 O | 155 CA | 7.649 |
| 129 O | 27 C | 7.678 | 129 O | 27 CD2 | 7.690 |
| 129 O | 151 CB | 7.841 | 129 O | 156 N | 7.999 |
| 129 O | 152 CA | 8.085 | 129 O | 60 N | 8.114 |
| 129 O | 60 C | 8.122 | 129 O | 60 CA | 8.145 |
| 129 O | 157 NH1 | 8.292 | 129 O | 151 CG | 8.388 |
| 129 O | 127 CB | 8.456 | 129 O | 155 C | 8.474 |
| 129 O | 127 CA | 8.475 | 129 O | 132 CA | 8.500 |
| 129 O | 27 N | 8.596 | 129 O | 132 CG2 | 8.645 |
| 129 O | 155 N | 8.657 | 129 O | 61 C | 8.659 |
| 129 O | 157 CD | 8.753 | 129 O | 157 CG | 8.758 |
| 129 O | 157 CB | 8.761 | 129 O | 157 N | 8.815 |
| 129 O | 156 CB | 8.954 | 129 O | 156 CG | 9.014 |
| 129 O | 156 CA | 9.075 | 129 O | 132 OG1 | 9.090 |
| 129 O | 61 O | 9.099 | 129 O | 152 C | 9.115 |
| 129 O | 132 CB | 9.119 | 129 O | 154 O | 9.171 |
| 129 O | 60 O | 9.175 | 129 O | 60 OD1 | 9.237 |
| 129 O | 152 O | 9.302 | 129 O | 154 C | 9.325 |
| 129 O | 151 CD2 | 9.450 | 129 O | 157 CA | 9.528 |
| 129 O | 132 C | 9.531 | 129 O | 60 CB | 9.539 |
| 129 O | 156 C | 9.557 | 129 O | 132 O | 9.585 |
| 129 O | 127 N | 9.643 | 129 O | 155 O | 9.693 |
| 129 O | 38 CD2 | 9.736 | 129 O | 156 NE | 9.775 |
| 129 O | 127 OG | 9.787 | 129 O | 60 CG | 9.799 |
| 129 O | 157 O | 9.857 | 129 O | 156 CD | 9.999 |
| 129 O | 157 C | 10.173 | 129 O | 154 N | 10.438 |
| 129 O | 154 CA | 10.519 | 129 O | 156 O | 10.702 |
| 129 O | 38 CD1 | 10.736 | 129 O | 60 OD2 | 10.775 |
| 129 O | 156 NH2 | 10.835 | 129 O | 38 CG | 10.838 |
| 129 O | 156 CZ | 10.849 | 129 O | 38 O | 10.865 |
| 129 O | 38 CB | 11.090 | 129 O | 38 CA | 11.485 |
| 129 O | 38 C | 11.687 | 129 O | 154 CB | 11.882 |
| 129 CB | 128 C | 3.142 | 129 CB | 128 O | 3.361 |

Figure 8G

| Atom 1 | Atom 2 | Distance | Atom 1 | Atom 2 | Distance |
|---|---|---|---|---|---|
| 129 CB | 130 N | 3.507 | 129 CB | 150 O | 3.681 |
| 129 CB | 61 CE1 | 3.735 | 129 CB | 152 SG | 4.007 |
| 129 CB | 300 OH2 | 4.159 | 129 CB | 61 NE2 | 4.230 |
| 129 CB | 150 CB | 4.342 | 129 CB | 128 CA | 4.389 |
| 129 CB | 150 C | 4.513 | 129 CB | 150 N | 4.577 |
| 129 CB | 61 ND1 | 4.692 | 129 CB | 301 OH2 | 4.693 |
| 129 CB | 150 CA | 4.745 | 129 CB | 130 CA | 4.754 |
| 129 CB | 155 CA | 4.947 | 129 CB | 130 C | 5.107 |
| 129 CB | 130 O | 5.155 | 129 CB | 152 CB | 5.205 |
| 129 CB | 128 N | 5.215 | 129 CB | 128 CB | 5.218 |
| 129 CB | 61 CD2 | 5.382 | 129 CB | 156 N | 5.510 |
| 129 CB | 61 CG | 5.624 | 129 CB | 151 N | 5.682 |
| 129 CB | 131 OG | 5.683 | 129 CB | 149 C | 5.764 |
| 129 CB | 131 N | 5.810 | 129 CB | 127 C | 5.819 |
| 129 CB | 155 C | 5.832 | 129 CB | 127 O | 5.856 |
| 129 CB | 152 N | 5.957 | 129 CB | 155 N | 5.959 |
| 129 CB | 151 C | 5.968 | 129 CB | 130 CB | 5.970 |
| 129 CB | 149 CA | 5.994 | 129 CB | 128 CG2 | 6.143 |
| 129 CB | 151 CA | 6.158 | 129 CB | 128 CG1 | 6.194 |
| 129 CB | 151 O | 6.218 | 129 CB | 152 CA | 6.291 |
| 129 CB | 154 O | 6.324 | 129 CB | 157 NH2 | 6.420 |
| 129 CB | 127 CB | 6.441 | 129 CB | 149 CB | 6.513 |
| 129 CB | 154 C | 6.540 | 129 CB | 148 O | 6.565 |
| 129 CB | 156 CG | 6.633 | 129 CB | 131 CA | 6.662 |
| 129 CB | 156 CA | 6.739 | 129 CB | 156 CB | 6.749 |
| 129 CB | 131 CB | 6.813 | 129 CB | 149 O | 6.817 |
| 129 CB | 61 N | 6.859 | 129 CB | 127 CA | 6.888 |
| 129 CB | 61 CB | 6.911 | 129 CB | 157 N | 6.955 |
| 129 CB | 155 O | 7.041 | 129 CB | 152 C | 7.124 |
| 129 CB | 149 N | 7.181 | 129 CB | 27 O | 7.249 |
| 129 CB | 60 CA | 7.252 | 129 CB | 149 CG2 | 7.281 |
| 129 CB | 130 CG | 7.308 | 129 CB | 157 NE | 7.333 |
| 129 CB | 148 C | 7.339 | 129 CB | 61 CA | 7.361 |
| 129 CB | 27 CD1 | 7.419 | 129 CB | 60 OD1 | 7.420 |
| 129 CB | 157 CZ | 7.427 | 129 CB | 152 O | 7.439 |
| 129 CB | 156 C | 7.488 | 129 CB | 60 C | 7.512 |
| 129 CB | 148 CE1 | 7.517 | 129 CB | 148 ND1 | 7.519 |
| 129 CB | 60 N | 7.545 | 129 CB | 149 CG1 | 7.584 |
| 129 CB | 157 CB | 7.619 | 129 CB | 127 OG | 7.662 |
| 129 CB | 151 CB | 7.668 | 129 CB | 156 CD | 7.767 |
| 129 CB | 157 CG | 7.814 | 129 CB | 154 CA | 7.816 |
| 129 CB | 130 CD1 | 7.817 | 129 CB | 154 N | 7.821 |
| 129 CB | 156 NE | 7.870 | 129 CB | 151 CD1 | 7.948 |
| 129 CB | 157 CA | 7.963 | 129 CB | 157 O | 8.030 |
| 129 CB | 127 N | 8.051 | 129 CB | 131 C | 8.082 |
| 129 CB | 27 CA | 8.140 | 129 CB | 27 C | 8.144 |

Figure 8H

| Atom 1 | Atom 2 | Distance | Atom 1 | Atom 2 | Distance |
|---|---|---|---|---|---|
| 129 CB | 27 CG | 8.188 | 129 CB | 60 CG | 8.257 |
| 129 CB | 157 CD | 8.312 | 129 CB | 60 CB | 8.367 |
| 129 CB | 130 CD2 | 8.407 | 129 CB | 157 NH1 | 8.444 |
| 129 CB | 148 NE2 | 8.478 | 129 CB | 27 CB | 8.511 |
| 129 CB | 60 O | 8.514 | 129 CB | 148 CG | 8.521 |
| 129 CB | 151 CG | 8.522 | 129 CB | 157 C | 8.524 |
| 129 CB | 131 O | 8.620 | 129 CB | 156 O | 8.689 |
| 129 CB | 148 CA | 8.779 | 129 CB | 38 CD2 | 8.803 |
| 129 CB | 132 N | 8.846 | 129 CB | 61 C | 8.888 |
| 129 CB | 148 CD2 | 9.064 | 129 CB | 156 CZ | 9.099 |
| 129 CB | 154 CB | 9.107 | 129 CB | 148 CB | 9.113 |
| 129 CB | 60 OD2 | 9.231 | 129 CB | 38 CD1 | 9.233 |
| 129 CB | 148 N | 9.233 | 129 CB | 27 N | 9.325 |
| 129 CB | 154 CG2 | 9.394 | 129 CB | 156 NH2 | 9.399 |
| 129 CB | 61 O | 9.534 | 129 CB | 27 CD2 | 9.583 |
| 129 CB | 38 CG | 9.702 | 129 CB | 151 CD2 | 9.793 |
| 129 CB | 38 CB | 10.167 | 129 CB | 156 NH1 | 10.170 |
| 129 CB | 132 CA | 10.250 | 129 CB | 132 OG1 | 10.284 |
| 129 CB | 132 CG2 | 10.292 | 129 CB | 154 CG1 | 10.374 |
| 129 CB | 132 CB | 10.674 | 129 CB | 38 O | 10.707 |
| 129 CB | 154 CD1 | 10.812 | 129 CB | 38 CA | 10.912 |
| 129 CB | 132 O | 10.976 | 129 CB | 132 C | 11.176 |
| 129 CB | 38 C | 11.323 | 129 OG | 61 CE1 | 2.985 |
| 129 OG | 130 N | 3.571 | 129 OG | 61 NE2 | 3.623 |
| 129 OG | 61 ND1 | 4.074 | 129 OG | 130 O | 4.381 |
| 129 OG | 300 OH2 | 4.388 | 129 OG | 128 C | 4.417 |
| 129 OG | 128 O | 4.440 | 129 OG | 130 C | 4.578 |
| 129 OG | 130 CA | 4.638 | 129 OG | 301 OH2 | 4.714 |
| 129 OG | 150 CB | 4.840 | 129 OG | 131 OG | 4.860 |
| 129 OG | 61 CD2 | 4.897 | 129 OG | 150 O | 4.925 |
| 129 OG | 152 SG | 4.971 | 129 OG | 61 CG | 5.124 |
| 129 OG | 131 N | 5.263 | 129 OG | 156 N | 5.282 |
| 129 OG | 155 CA | 5.306 | 129 OG | 150 N | 5.308 |
| 129 OG | 150 CA | 5.536 | 129 OG | 150 C | 5.597 |
| 129 OG | 157 NH2 | 5.711 | 129 OG | 128 CA | 5.747 |
| 129 OG | 156 CG | 5.853 | 129 OG | 131 CA | 5.863 |
| 129 OG | 155 C | 5.877 | 129 OG | 130 CB | 5.894 |
| 129 OG | 131 CB | 6.013 | 129 OG | 156 CB | 6.014 |
| 129 OG | 152 CB | 6.043 | 129 OG | 156 CA | 6.303 |
| 129 OG | 149 C | 6.418 | 129 OG | 128 CB | 6.467 |
| 129 OG | 155 N | 6.487 | 129 OG | 61 CB | 6.497 |
| 129 OG | 148 O | 6.525 | 129 OG | 149 CA | 6.534 |
| 129 OG | 128 N | 6.543 | 129 OG | 154 O | 6.605 |
| 129 OG | 157 N | 6.702 | 129 OG | 156 NE | 6.752 |
| 129 OG | 157 CZ | 6.766 | 129 OG | 151 N | 6.795 |
| 129 OG | 156 CD | 6.827 | 129 OG | 157 NE | 6.850 |

Figure 8I

| Atom 1 | Atom 2 | Distance | Atom 1 | Atom 2 | Distance |
|---|---|---|---|---|---|
| 129 OG | 61 N | 6.950 | 129 OG | 154 C | 7.003 |
| 129 OG | 155 O | 7.100 | 129 OG | 130 CG | 7.102 |
| 129 OG | 156 C | 7.104 | 129 OG | 151 C | 7.105 |
| 129 OG | 152 N | 7.130 | 129 OG | 127 C | 7.171 |
| 129 OG | 151 O | 7.182 | 129 OG | 148 CE1 | 7.194 |
| 129 OG | 61 CA | 7.220 | 129 OG | 127 O | 7.243 |
| 129 OG | 149 CB | 7.249 | 129 OG | 152 CA | 7.293 |
| 129 OG | 128 CG2 | 7.305 | 129 OG | 131 C | 7.327 |
| 129 OG | 157 CG | 7.348 | 129 OG | 151 CA | 7.395 |
| 129 OG | 148 ND1 | 7.400 | 129 OG | 157 CB | 7.410 |
| 129 OG | 148 C | 7.443 | 129 OG | 149 O | 7.473 |
| 129 OG | 128 CG1 | 7.476 | 129 OG | 27 O | 7.516 |
| 129 OG | 149 N | 7.529 | 129 OG | 127 CB | 7.558 |
| 129 OG | 60 CA | 7.627 | 129 OG | 157 NH1 | 7.635 |
| 129 OG | 60 C | 7.640 | 129 OG | 60 OD1 | 7.674 |
| 129 OG | 38 CD2 | 7.680 | 129 OG | 130 CD1 | 7.756 |
| 129 OG | 157 CA | 7.766 | 129 OG | 157 CD | 7.848 |
| 129 OG | 156 CZ | 7.927 | 129 OG | 132 N | 7.952 |
| 129 OG | 148 NE2 | 8.010 | 129 OG | 131 O | 8.029 |
| 129 OG | 60 N | 8.128 | 129 OG | 156 NH2 | 8.135 |
| 129 OG | 152 C | 8.147 | 129 OG | 127 CA | 8.153 |
| 129 OG | 27 CD1 | 8.158 | 129 OG | 149 CG2 | 8.177 |
| 129 OG | 149 CG1 | 8.186 | 129 OG | 130 CD2 | 8.220 |
| 129 OG | 157 O | 8.222 | 129 OG | 156 O | 8.247 |
| 129 OG | 38 CD1 | 8.312 | 129 OG | 148 CG | 8.355 |
| 129 OG | 154 CA | 8.409 | 129 OG | 60 CG | 8.473 |
| 129 OG | 154 N | 8.509 | 129 OG | 60 O | 8.509 |
| 129 OG | 27 C | 8.533 | 129 OG | 157 C | 8.558 |
| 129 OG | 152 O | 8.578 | 129 OG | 127 OG | 8.685 |
| 129 OG | 38 CG | 8.688 | 129 OG | 148 CD2 | 8.695 |
| 129 OG | 27 CA | 8.704 | 129 OG | 61 C | 8.709 |
| 129 OG | 27 CG | 8.716 | 129 OG | 60 CB | 8.727 |
| 129 OG | 148 CA | 8.787 | 129 OG | 151 CB | 8.895 |
| 129 OG | 27 CB | 8.971 | 129 OG | 148 N | 9.033 |
| 129 OG | 156 NH1 | 9.061 | 129 OG | 148 CB | 9.111 |
| 129 OG | 61 O | 9.220 | 129 OG | 151 CD1 | 9.245 |
| 129 OG | 38 CB | 9.268 | 129 OG | 132 OG1 | 9.277 |
| 129 OG | 60 OD2 | 9.309 | 129 OG | 127 N | 9.321 |
| 129 OG | 132 CA | 9.386 | 129 OG | 154 CB | 9.551 |
| 129 OG | 132 CG2 | 9.557 | 129 OG | 154 CG2 | 9.724 |
| 129 OG | 132 CB | 9.791 | 129 OG | 151 CG | 9.810 |
| 129 OG | 132 O | 9.908 | 129 OG | 38 O | 9.961 |
| 129 OG | 38 CA | 9.965 | 129 OG | 27 N | 9.985 |
| 129 OG | 27 CD2 | 10.115 | 129 OG | 132 C | 10.215 |
| 129 OG | 38 C | 10.504 | 129 OG | 154 CG1 | 10.921 |
| 129 OG | 151 CD2 | 11.021 | 129 OG | 38 N | 11.065 |

Figure 8J

| Atom 1 | Atom 2 | Distance | Atom 1 | Atom 2 | Distance |
|---|---|---|---|---|---|
| 129 OG | 154 CD1 | 11.458 | 129 P1 | 61 CE1 | 3.821 |
| 129 P1 | 156 N | 4.026 | 129 P1 | 300 OH2 | 4.041 |
| 129 P1 | 156 CG | 4.281 | 129 P1 | 156 CB | 4.476 |
| 129 P1 | 155 CA | 4.568 | 129 P1 | 130 N | 4.598 |
| 129 P1 | 61 ND1 | 4.712 | 129 P1 | 61 NE2 | 4.721 |
| 129 P1 | 155 C | 4.796 | 129 P1 | 301 OH2 | 4.892 |
| 129 P1 | 128 O | 4.895 | 129 P1 | 156 CA | 4.896 |
| 129 P1 | 130 O | 4.931 | 129 P1 | 128 C | 5.235 |
| 129 P1 | 156 NE | 5.255 | 129 P1 | 156 CD | 5.271 |
| 129 P1 | 152 SG | 5.281 | 129 P1 | 130 C | 5.464 |
| 129 P1 | 157 N | 5.627 | 129 P1 | 157 NH2 | 5.639 |
| 129 P1 | 130 CA | 5.683 | 129 P1 | 131 OG | 5.794 |
| 129 P1 | 156 C | 5.818 | 129 P1 | 154 O | 5.856 |
| 129 P1 | 155 N | 5.868 | 129 P1 | 61 CD2 | 5.946 |
| 129 P1 | 61 CG | 5.951 | 129 P1 | 155 O | 5.980 |
| 129 P1 | 150 CB | 6.225 | 129 P1 | 150 O | 6.244 |
| 129 P1 | 131 N | 6.264 | 129 P1 | 154 C | 6.349 |
| 129 P1 | 152 CB | 6.428 | 129 P1 | 156 CZ | 6.474 |
| 129 P1 | 157 CZ | 6.515 | 129 P1 | 157 NE | 6.522 |
| 129 P1 | 157 CG | 6.564 | 129 P1 | 38 CD2 | 6.582 |
| 129 P1 | 128 CA | 6.645 | 129 P1 | 131 CA | 6.656 |
| 129 P1 | 157 CB | 6.687 | 129 P1 | 130 CB | 6.752 |
| 129 P1 | 156 NH2 | 6.805 | 129 P1 | 157 CA | 6.826 |
| 129 P1 | 150 N | 6.878 | 129 P1 | 131 CB | 6.898 |
| 129 P1 | 156 O | 6.919 | 129 P1 | 38 CD1 | 6.961 |
| 129 P1 | 150 C | 6.968 | 129 P1 | 150 CA | 7.018 |
| 129 P1 | 128 N | 7.175 | 129 P1 | 61 CB | 7.235 |
| 129 P1 | 157 NH1 | 7.262 | 129 P1 | 157 CD | 7.301 |
| 129 P1 | 157 O | 7.439 | 129 P1 | 128 CB | 7.449 |
| 129 P1 | 38 CG | 7.480 | 129 P1 | 156 NH1 | 7.561 |
| 129 P1 | 127 CB | 7.661 | 129 P1 | 157 C | 7.716 |
| 129 P1 | 27 O | 7.767 | 129 P1 | 127 C | 7.776 |
| 129 P1 | 152 CA | 7.796 | 129 P1 | 154 CA | 7.857 |
| 129 P1 | 60 OD1 | 7.879 | 129 P1 | 152 N | 7.879 |
| 129 P1 | 61 N | 7.885 | 129 P1 | 148 O | 7.905 |
| 129 P1 | 130 CG | 7.944 | 129 P1 | 149 C | 8.001 |
| 129 P1 | 127 O | 8.005 | 129 P1 | 151 C | 8.058 |
| 129 P1 | 128 CG2 | 8.072 | 129 P1 | 131 C | 8.072 |
| 129 P1 | 151 N | 8.088 | 129 P1 | 149 CA | 8.090 |
| 129 P1 | 151 O | 8.125 | 129 P1 | 61 CA | 8.152 |
| 129 P1 | 154 N | 8.154 | 129 P1 | 38 CB | 8.197 |
| 129 P1 | 60 CA | 8.381 | 129 P1 | 60 C | 8.408 |
| 129 P1 | 148 CE1 | 8.425 | 129 P1 | 152 C | 8.461 |
| 129 P1 | 132 N | 8.474 | 129 P1 | 127 CA | 8.514 |
| 129 P1 | 151 CA | 8.534 | 129 P1 | 127 OG | 8.602 |
| 129 P1 | 128 CG1 | 8.608 | 129 P1 | 149 CB | 8.760 |

Figure 8K

| Atom 1 | Atom 2 | Distance | Atom 1 | Atom 2 | Distance |
|---|---|---|---|---|---|
| 129 P1 | 148 ND1 | 8.772 | 129 P1 | 60 CG | 8.784 |
| 129 P1 | 130 CD1 | 8.807 | 129 P1 | 154 CB | 8.815 |
| 129 P1 | 154 CG2 | 8.819 | 129 P1 | 27 C | 8.879 |
| 129 P1 | 148 C | 8.895 | 129 P1 | 130 CD2 | 8.902 |
| 129 P1 | 131 O | 8.923 | 129 P1 | 152 O | 8.941 |
| 129 P1 | 38 CA | 9.042 | 129 P1 | 149 O | 9.048 |
| 129 P1 | 149 N | 9.061 | 129 P1 | 60 N | 9.070 |
| 129 P1 | 148 NE2 | 9.144 | 129 P1 | 60 O | 9.149 |
| 129 P1 | 27 CD1 | 9.198 | 129 P1 | 60 CB | 9.293 |
| 129 P1 | 27 CA | 9.299 | 129 P1 | 38 O | 9.334 |
| 129 P1 | 132 OG1 | 9.399 | 129 P1 | 60 OD2 | 9.509 |
| 129 P1 | 61 C | 9.598 | 129 P1 | 149 CG1 | 9.639 |
| 129 P1 | 27 CG | 9.659 | 129 P1 | 127 N | 9.685 |
| 129 P1 | 27 CB | 9.696 | 129 P1 | 149 CG2 | 9.705 |
| 129 P1 | 148 CG | 9.706 | 129 P1 | 38 C | 9.723 |
| 129 P1 | 132 CA | 9.881 | 129 P1 | 148 CD2 | 9.911 |
| 129 P1 | 132 CG2 | 9.949 | 129 P1 | 151 CB | 10.049 |
| 129 P1 | 38 N | 10.063 | 129 P1 | 61 O | 10.087 |
| 129 P1 | 132 CB | 10.118 | 129 P1 | 148 CA | 10.198 |
| 129 P1 | 132 O | 10.216 | 129 P1 | 154 CG1 | 10.271 |
| 129 P1 | 148 N | 10.316 | 129 P1 | 151 CD1 | 10.537 |
| 129 P1 | 148 CB | 10.538 | 129 P1 | 27 N | 10.558 |
| 129 P1 | 132 C | 10.643 | 129 P1 | 154 CD1 | 10.859 |
| 129 P1 | 151 CG | 11.019 | 129 P1 | 27 CD2 | 11.105 |
| 129 O3 | 156 CG | 3.793 | 129 O3 | 156 N | 3.878 |
| 129 O3 | 155 CA | 4.039 | 129 O3 | 61 CE1 | 4.090 |
| 129 O3 | 155 C | 4.345 | 129 O3 | 156 CB | 4.469 |
| 129 O3 | 152 SG | 4.522 | 129 O3 | 61 ND1 | 4.562 |
| 129 O3 | 154 O | 4.585 | 129 O3 | 156 CD | 4.779 |
| 129 O3 | 156 CA | 4.837 | 129 O3 | 300 OH2 | 4.883 |
| 129 O3 | 155 N | 5.127 | 129 O3 | 156 NE | 5.139 |
| 129 O3 | 61 NE2 | 5.260 | 129 O3 | 154 C | 5.296 |
| 129 O3 | 128 O | 5.415 | 129 O3 | 155 O | 5.423 |
| 129 O3 | 152 CB | 5.450 | 129 O3 | 128 C | 5.777 |
| 129 O3 | 61 CG | 5.917 | 129 O3 | 130 N | 6.035 |
| 129 O3 | 156 C | 6.077 | 129 O3 | 157 N | 6.144 |
| 129 O3 | 61 CD2 | 6.262 | 129 O3 | 301 OH2 | 6.293 |
| 129 O3 | 150 CB | 6.340 | 129 O3 | 150 O | 6.438 |
| 129 O3 | 156 CZ | 6.439 | 129 O3 | 130 O | 6.505 |
| 129 O3 | 60 OD1 | 6.598 | 129 O3 | 154 CA | 6.785 |
| 129 O3 | 131 OG | 6.796 | 129 O3 | 152 CA | 6.910 |
| 129 O3 | 61 CB | 6.970 | 129 O3 | 130 C | 6.981 |
| 129 O3 | 154 N | 6.985 | 129 O3 | 156 NH2 | 7.024 |
| 129 O3 | 128 CA | 7.048 | 129 O3 | 150 C | 7.076 |
| 129 O3 | 156 O | 7.151 | 129 O3 | 130 CA | 7.170 |
| 129 O3 | 157 NH2 | 7.223 | 129 O3 | 150 CA | 7.272 |

Figure 8L

| Atom 1 | Atom 2 | Distance | Atom 1 | Atom 2 | Distance |
|---|---|---|---|---|---|
| 129 O3 | 127 CB | 7.276 | 129 O3 | 152 N | 7.276 |
| 129 O3 | 156 NH1 | 7.349 | 129 O3 | 128 N | 7.354 |
| 129 O3 | 61 N | 7.442 | 129 O3 | 150 N | 7.448 |
| 129 O3 | 38 CD2 | 7.493 | 129 O3 | 157 CA | 7.495 |
| 129 O3 | 152 C | 7.516 | 129 O3 | 38 CD1 | 7.523 |
| 129 O3 | 151 O | 7.538 | 129 O3 | 151 C | 7.575 |
| 129 O3 | 60 CA | 7.575 | 129 O3 | 60 CG | 7.582 |
| 129 O3 | 154 CB | 7.645 | 129 O3 | 157 CB | 7.651 |
| 129 O3 | 157 CG | 7.664 | 129 O3 | 131 N | 7.672 |
| 129 O3 | 127 C | 7.696 | 129 O3 | 60 C | 7.719 |
| 129 O3 | 154 CG2 | 7.779 | 129 O3 | 157 O | 7.802 |
| 129 O3 | 127 O | 7.853 | 129 O3 | 61 CA | 7.882 |
| 129 O3 | 157 NE | 7.960 | 129 O3 | 131 CA | 8.001 |
| 129 O3 | 151 N | 8.022 | 129 O3 | 131 CB | 8.031 |
| 129 O3 | 157 CZ | 8.032 | 129 O3 | 128 CB | 8.108 |
| 129 O3 | 127 OG | 8.116 | 129 O3 | 152 O | 8.144 |
| 129 O3 | 157 C | 8.238 | 129 O3 | 60 OD2 | 8.253 |
| 129 O3 | 38 CG | 8.260 | 129 O3 | 127 CA | 8.272 |
| 129 O3 | 60 CB | 8.275 | 129 O3 | 130 CB | 8.299 |
| 129 O3 | 151 CA | 8.324 | 129 O3 | 60 O | 8.377 |
| 129 O3 | 60 N | 8.418 | 129 O3 | 157 CD | 8.592 |
| 129 O3 | 149 C | 8.677 | 129 O3 | 157 NH1 | 8.731 |
| 129 O3 | 128 CG2 | 8.766 | 129 O3 | 149 CA | 9.017 |
| 129 O3 | 148 CE1 | 9.022 | 129 O3 | 148 O | 9.086 |
| 129 O3 | 27 O | 9.087 | 129 O3 | 154 CG1 | 9.109 |
| 129 O3 | 38 CB | 9.137 | 129 O3 | 128 CG1 | 9.214 |
| 129 O3 | 127 N | 9.270 | 129 O3 | 61 C | 9.294 |
| 129 O3 | 148 ND1 | 9.458 | 129 O3 | 131 C | 9.469 |
| 129 O3 | 130 CG | 9.516 | 129 O3 | 149 O | 9.612 |
| 129 O3 | 149 CB | 9.717 | 129 O3 | 151 CB | 9.806 |
| 129 O3 | 148 NE2 | 9.830 | 129 O3 | 154 CD1 | 9.862 |
| 129 O3 | 132 N | 9.880 | 129 O3 | 61 O | 9.898 |
| 129 O3 | 148 C | 9.977 | 129 O3 | 149 N | 10.032 |
| 129 O3 | 38 CA | 10.119 | 129 O3 | 27 C | 10.167 |
| 129 O3 | 130 CD1 | 10.306 | 129 O3 | 131 O | 10.325 |
| 129 O3 | 27 CD1 | 10.407 | 129 O3 | 149 CG2 | 10.491 |
| 129 O3 | 130 CD2 | 10.504 | 129 O3 | 148 CG | 10.528 |
| 129 O3 | 27 CA | 10.558 | 129 O3 | 38 O | 10.635 |
| 129 O3 | 151 CD1 | 10.659 | 129 O3 | 148 CD2 | 10.731 |
| 129 O3 | 149 CG1 | 10.746 | 129 O3 | 132 OG1 | 10.842 |
| 129 O3 | 38 C | 10.911 | 129 O3 | 151 CG | 10.924 |
| 129 O3 | 27 CG | 11.008 | 129 O3 | 38 N | 11.034 |
| 129 O3 | 27 CB | 11.065 | 129 O3 | 148 CA | 11.269 |
| 129 O3 | 132 CA | 11.309 | 129 O3 | 148 CB | 11.440 |
| 129 O3 | 132 O | 11.452 | 129 O3 | 148 N | 11.488 |
| 129 O3 | 132 CG2 | 11.516 | 129 O3 | 132 CB | 11.605 |

Figure 8M

| Atom 1 | Atom 2 | Distance | Atom 1 | Atom 2 | Distance |
|---|---|---|---|---|---|
| 129 O3 | 27 N | 11.739 | 129 O3 | 132 C | 11.968 |
| 129 O4 | 61 CE1 | 3.831 | 129 O4 | 156 CG | 4.254 |
| 129 O4 | 156 NE | 4.418 | 129 O4 | 156 CB | 4.454 |
| 129 O4 | 130 O | 4.456 | 129 O4 | 61 NE2 | 4.644 |
| 129 O4 | 61 ND1 | 4.718 | 129 O4 | 156 CD | 4.845 |
| 129 O4 | 156 N | 4.853 | 129 O4 | 130 N | 5.075 |
| 129 O4 | 300 OH2 | 5.108 | 129 O4 | 157 NH2 | 5.184 |
| 129 O4 | 131 OG | 5.209 | 129 O4 | 130 C | 5.216 |
| 129 O4 | 156 CA | 5.312 | 129 O4 | 301 OH2 | 5.444 |
| 129 O4 | 156 CZ | 5.479 | 129 O4 | 38 CD2 | 5.523 |
| 129 O4 | 156 NH2 | 5.578 | 129 O4 | 61 CD2 | 5.838 |
| 129 O4 | 130 CA | 5.839 | 129 O4 | 155 C | 5.852 |
| 129 O4 | 61 CG | 5.885 | 129 O4 | 131 N | 5.901 |
| 129 O4 | 155 CA | 5.921 | 129 O4 | 131 CA | 5.951 |
| 129 O4 | 157 CZ | 6.077 | 129 O4 | 157 N | 6.107 |
| 129 O4 | 156 C | 6.160 | 129 O4 | 131 CB | 6.198 |
| 129 O4 | 38 CD1 | 6.333 | 129 O4 | 128 O | 6.343 |
| 129 O4 | 157 NE | 6.361 | 129 O4 | 157 CG | 6.537 |
| 129 O4 | 157 NH1 | 6.570 | 129 O4 | 38 CG | 6.622 |
| 129 O4 | 128 C | 6.656 | 129 O4 | 156 NH1 | 6.692 |
| 129 O4 | 152 SG | 6.795 | 129 O4 | 130 CB | 6.864 |
| 129 O4 | 155 O | 6.949 | 129 O4 | 150 CB | 6.960 |
| 129 O4 | 157 CB | 7.013 | 129 O4 | 154 O | 7.062 |
| 129 O4 | 156 O | 7.102 | 129 O4 | 157 CD | 7.162 |
| 129 O4 | 61 CB | 7.178 | 129 O4 | 157 CA | 7.235 |
| 129 O4 | 155 N | 7.253 | 129 O4 | 131 C | 7.311 |
| 129 O4 | 38 CB | 7.477 | 129 O4 | 150 O | 7.490 |
| 129 O4 | 132 N | 7.516 | 129 O4 | 150 N | 7.655 |
| 129 O4 | 154 C | 7.670 | 129 O4 | 152 CB | 7.789 |
| 129 O4 | 130 CG | 7.827 | 129 O4 | 150 CA | 7.892 |
| 129 O4 | 148 O | 7.931 | 129 O4 | 128 CA | 8.086 |
| 129 O4 | 150 C | 8.096 | 129 O4 | 38 CA | 8.180 |
| 129 O4 | 148 CE1 | 8.218 | 129 O4 | 132 OG1 | 8.266 |
| 129 O4 | 157 O | 8.291 | 129 O4 | 131 O | 8.306 |
| 129 O4 | 61 CA | 8.307 | 129 O4 | 61 N | 8.314 |
| 129 O4 | 27 O | 8.327 | 129 O4 | 157 C | 8.360 |
| 129 O4 | 149 CA | 8.632 | 129 O4 | 149 C | 8.663 |
| 129 O4 | 38 O | 8.704 | 129 O4 | 60 OD1 | 8.707 |
| 129 O4 | 128 N | 8.708 | 129 O4 | 148 ND1 | 8.730 |
| 129 O4 | 148 NE2 | 8.732 | 129 O4 | 128 CB | 8.754 |
| 129 O4 | 130 CD1 | 8.774 | 129 O4 | 130 CD2 | 8.776 |
| 129 O4 | 132 CA | 8.901 | 129 O4 | 60 C | 8.905 |
| 129 O4 | 132 O | 8.979 | 129 O4 | 148 C | 9.009 |
| 129 O4 | 38 C | 9.010 | 129 O4 | 38 N | 9.081 |
| 129 O4 | 132 CB | 9.113 | 129 O4 | 132 CG2 | 9.137 |
| 129 O4 | 60 CA | 9.138 | 129 O4 | 152 CA | 9.204 |

Figure 8N

| Atom 1 | Atom 2 | Distance | Atom 1 | Atom 2 | Distance |
|---|---|---|---|---|---|
| 129 O4 | 154 CA | 9.206 | 129 O4 | 127 CB | 9.250 |
| 129 O4 | 151 N | 9.263 | 129 O4 | 152 N | 9.321 |
| 129 O4 | 151 O | 9.339 | 129 O4 | 127 C | 9.355 |
| 129 O4 | 128 CG2 | 9.369 | 129 O4 | 151 C | 9.396 |
| 129 O4 | 149 N | 9.397 | 129 O4 | 149 CB | 9.453 |
| 129 O4 | 27 C | 9.496 | 129 O4 | 60 CG | 9.502 |
| 129 O4 | 60 O | 9.507 | 129 O4 | 132 C | 9.523 |
| 129 O4 | 154 N | 9.540 | 129 O4 | 148 CD2 | 9.545 |
| 129 O4 | 148 CG | 9.553 | 129 O4 | 127 O | 9.562 |
| 129 O4 | 61 C | 9.650 | 129 O4 | 149 O | 9.696 |
| 129 O4 | 151 CA | 9.859 | 129 O4 | 128 CG1 | 9.886 |
| 129 O4 | 154 CG2 | 9.932 | 129 O4 | 152 C | 9.937 |
| 129 O4 | 60 N | 9.938 | 129 O4 | 61 O | 9.955 |
| 129 O4 | 27 CD1 | 9.975 | 129 O4 | 27 CA | 10.020 |
| 129 O4 | 154 CB | 10.025 | 129 O4 | 60 CB | 10.065 |
| 129 O4 | 148 N | 10.067 | 129 O4 | 60 OD2 | 10.078 |
| 129 O4 | 127 CA | 10.114 | 129 O4 | 127 OG | 10.153 |
| 129 O4 | 148 CA | 10.168 | 129 O4 | 149 CG1 | 10.190 |
| 129 O4 | 27 CG | 10.235 | 129 O4 | 27 CB | 10.255 |
| 129 O4 | 152 O | 10.480 | 129 O4 | 148 CB | 10.502 |
| 129 O4 | 149 CG2 | 10.527 | 129 O4 | 127 N | 11.292 |
| 129 O4 | 27 N | 11.355 | 129 O4 | 151 CB | 11.358 |
| 129 O4 | 154 CG1 | 11.523 | 129 O4 | 27 CD2 | 11.636 |
| 129 O4 | 151 CD1 | 11.823 | 129 O5 | 300 OH2 | 2.667 |
| 129 O5 | 156 N | 3.025 | 129 O5 | 155 CA | 3.821 |
| 129 O5 | 156 CB | 3.849 | 129 O5 | 155 C | 3.896 |
| 129 O5 | 301 OH2 | 3.902 | 129 O5 | 156 CA | 3.938 |
| 129 O5 | 156 CG | 4.108 | 129 O5 | 128 O | 4.153 |
| 129 O5 | 157 N | 4.258 | 129 O5 | 130 N | 4.459 |
| 129 O5 | 156 C | 4.627 | 129 O5 | 128 C | 4.783 |
| 129 O5 | 130 O | 5.092 | 129 O5 | 155 O | 5.093 |
| 129 O5 | 157 NH2 | 5.124 | 129 O5 | 61 CE1 | 5.198 |
| 129 O5 | 155 N | 5.239 | 129 O5 | 157 CB | 5.290 |
| 129 O5 | 156 CD | 5.325 | 129 O5 | 157 CG | 5.334 |
| 129 O5 | 156 NE | 5.388 | 129 O5 | 157 CA | 5.413 |
| 129 O5 | 152 SG | 5.481 | 129 O5 | 157 NE | 5.543 |
| 129 O5 | 130 CA | 5.686 | 129 O5 | 130 C | 5.696 |
| 129 O5 | 154 O | 5.732 | 129 O5 | 156 O | 5.781 |
| 129 O5 | 157 CZ | 5.796 | 129 O5 | 61 NE2 | 5.970 |
| 129 O5 | 154 C | 5.981 | 129 O5 | 157 O | 6.005 |
| 129 O5 | 61 ND1 | 6.148 | 129 O5 | 157 CD | 6.178 |
| 129 O5 | 38 CD2 | 6.196 | 129 O5 | 128 CA | 6.248 |
| 129 O5 | 38 CD1 | 6.257 | 129 O5 | 157 C | 6.263 |
| 129 O5 | 130 CB | 6.487 | 129 O5 | 156 CZ | 6.591 |
| 129 O5 | 150 O | 6.609 | 129 O5 | 128 N | 6.627 |
| 129 O5 | 157 NH1 | 6.656 | 129 O5 | 27 O | 6.670 |

Figure 8O

| Atom 1 | Atom 2 | Distance | Atom 1 | Atom 2 | Distance |
|---|---|---|---|---|---|
| 129 O5 | 131 N | 6.721 | 129 O5 | 131 OG | 6.804 |
| 129 O5 | 38 CG | 6.880 | 129 O5 | 152 CB | 6.914 |
| 129 O5 | 128 CB | 6.960 | 129 O5 | 156 NH2 | 6.975 |
| 129 O5 | 127 CB | 7.065 | 129 O5 | 150 CB | 7.193 |
| 129 O5 | 61 CD2 | 7.255 | 129 O5 | 131 CA | 7.265 |
| 129 O5 | 128 CG2 | 7.330 | 129 O5 | 61 CG | 7.356 |
| 129 O5 | 127 C | 7.365 | 129 O5 | 38 CB | 7.411 |
| 129 O5 | 154 CA | 7.482 | 129 O5 | 150 N | 7.493 |
| 129 O5 | 150 C | 7.519 | 129 O5 | 156 NH1 | 7.612 |
| 129 O5 | 150 CA | 7.759 | 129 O5 | 131 CB | 7.763 |
| 129 O5 | 130 CG | 7.783 | 129 O5 | 27 C | 7.797 |
| 129 O5 | 127 O | 7.812 | 129 O5 | 127 OG | 7.913 |
| 129 O5 | 127 CA | 7.973 | 129 O5 | 154 N | 7.999 |
| 129 O5 | 152 CA | 8.174 | 129 O5 | 152 N | 8.193 |
| 129 O5 | 154 CG2 | 8.264 | 129 O5 | 128 CG1 | 8.268 |
| 129 O5 | 38 CA | 8.356 | 129 O5 | 27 CA | 8.359 |
| 129 O5 | 148 O | 8.440 | 129 O5 | 154 CB | 8.443 |
| 129 O5 | 38 O | 8.493 | 129 O5 | 149 CA | 8.523 |
| 129 O5 | 151 C | 8.531 | 129 O5 | 130 CD2 | 8.536 |
| 129 O5 | 131 C | 8.562 | 129 O5 | 149 C | 8.582 |
| 129 O5 | 152 C | 8.628 | 129 O5 | 151 N | 8.629 |
| 129 O5 | 27 CD1 | 8.659 | 129 O5 | 61 CB | 8.662 |
| 129 O5 | 130 CD1 | 8.779 | 129 O5 | 151 O | 8.793 |
| 129 O5 | 60 OD1 | 8.862 | 129 O5 | 38 C | 8.905 |
| 129 O5 | 132 N | 8.913 | 129 O5 | 151 CA | 8.913 |
| 129 O5 | 27 CB | 8.914 | 129 O5 | 152 O | 8.941 |
| 129 O5 | 149 CB | 8.961 | 129 O5 | 27 CG | 9.076 |
| 129 O5 | 61 N | 9.158 | 129 O5 | 127 N | 9.249 |
| 129 O5 | 131 O | 9.372 | 129 O5 | 148 C | 9.462 |
| 129 O5 | 38 N | 9.477 | 129 O5 | 60 CA | 9.490 |
| 129 O5 | 61 CA | 9.506 | 129 O5 | 27 N | 9.560 |
| 129 O5 | 132 OG1 | 9.561 | 129 O5 | 148 CE1 | 9.564 |
| 129 O5 | 149 N | 9.587 | 129 O5 | 60 C | 9.665 |
| 129 O5 | 149 O | 9.701 | 129 O5 | 149 CG1 | 9.755 |
| 129 O5 | 148 ND1 | 9.781 | 129 O5 | 60 CG | 9.859 |
| 129 O5 | 154 CG1 | 9.884 | 129 O5 | 149 CG2 | 9.927 |
| 129 O5 | 132 CG2 | 9.940 | 129 O5 | 60 N | 10.076 |
| 129 O5 | 132 CA | 10.242 | 129 O5 | 148 NE2 | 10.271 |
| 129 O5 | 132 CB | 10.286 | 129 O5 | 154 CD1 | 10.295 |
| 129 O5 | 60 CB | 10.367 | 129 O5 | 151 CB | 10.430 |
| 129 O5 | 60 O | 10.463 | 129 O5 | 27 CD2 | 10.559 |
| 129 O5 | 60 OD2 | 10.640 | 129 O5 | 148 CG | 10.640 |
| 129 O5 | 151 CD1 | 10.713 | 129 O5 | 132 O | 10.799 |
| 129 O5 | 148 CA | 10.830 | 129 O5 | 148 CD2 | 10.920 |
| 129 O5 | 148 N | 10.940 | 129 O5 | 61 C | 10.978 |
| 129 O5 | 132 C | 11.141 | 129 O5 | 151 CG | 11.275 |

Figure 8P

| Atom 1 | Atom 2 | Distance | Atom 1 | Atom 2 | Distance |
|---|---|---|---|---|---|
| 129 O5 | 148 CB | 11.334 | 129 O5 | 61 O | 11.493 |
| 129 C5 | 61 CE1 | 3.704 | 129 C5 | 61 ND1 | 3.752 |
| 129 C5 | 156 CG | 4.447 | 129 C5 | 152 SG | 4.788 |
| 129 C5 | 154 O | 4.895 | 129 C5 | 61 NE2 | 5.007 |
| 129 C5 | 155 CA | 5.103 | 129 C5 | 156 CD | 5.105 |
| 129 C5 | 156 N | 5.117 | 129 C5 | 61 CG | 5.119 |
| 129 C5 | 152 CB | 5.235 | 129 C5 | 156 CB | 5.446 |
| 129 C5 | 155 C | 5.457 | 129 C5 | 156 NE | 5.488 |
| 129 C5 | 60 OD1 | 5.543 | 129 C5 | 61 CD2 | 5.748 |
| 129 C5 | 154 C | 5.823 | 129 C5 | 155 N | 5.957 |
| 129 C5 | 61 CB | 5.959 | 129 C5 | 156 CA | 5.971 |
| 129 C5 | 150 CB | 6.089 | 129 C5 | 300 OH2 | 6.321 |
| 129 C5 | 155 O | 6.411 | 129 C5 | 60 CG | 6.441 |
| 129 C5 | 61 N | 6.514 | 129 C5 | 128 O | 6.567 |
| 129 C5 | 60 CA | 6.637 | 129 C5 | 60 C | 6.662 |
| 129 C5 | 156 CZ | 6.719 | 129 C5 | 150 O | 6.745 |
| 129 C5 | 152 CA | 6.749 | 129 C5 | 128 C | 6.765 |
| 129 C5 | 131 OG | 6.809 | 129 C5 | 61 CA | 6.937 |
| 129 C5 | 60 OD2 | 6.996 | 129 C5 | 130 N | 6.997 |
| 129 C5 | 150 C | 7.160 | 129 C5 | 154 N | 7.175 |
| 129 C5 | 60 O | 7.186 | 129 C5 | 151 O | 7.198 |
| 129 C5 | 154 CA | 7.200 | 129 C5 | 150 CA | 7.234 |
| 129 C5 | 60 CB | 7.241 | 129 C5 | 152 N | 7.277 |
| 129 C5 | 130 O | 7.286 | 129 C5 | 156 NH2 | 7.311 |
| 129 C5 | 156 C | 7.317 | 129 C5 | 151 C | 7.466 |
| 129 C5 | 152 C | 7.494 | 129 C5 | 157 N | 7.509 |
| 129 C5 | 156 NH1 | 7.566 | 129 C5 | 301 OH2 | 7.619 |
| 129 C5 | 150 N | 7.621 | 129 C5 | 60 N | 7.660 |
| 129 C5 | 130 C | 7.693 | 129 C5 | 128 CA | 7.913 |
| 129 C5 | 154 CB | 7.967 | 129 C5 | 151 N | 8.000 |
| 129 C5 | 130 CA | 8.011 | 129 C5 | 127 CB | 8.056 |
| 129 C5 | 131 CB | 8.130 | 129 C5 | 131 N | 8.180 |
| 129 C5 | 128 N | 8.248 | 129 C5 | 61 C | 8.265 |
| 129 C5 | 154 CG2 | 8.275 | 129 C5 | 152 O | 8.300 |
| 129 C5 | 157 NH2 | 8.322 | 129 C5 | 156 O | 8.323 |
| 129 C5 | 38 CD2 | 8.340 | 129 C5 | 131 CA | 8.360 |
| 129 C5 | 151 CA | 8.374 | 129 C5 | 127 O | 8.397 |
| 129 C5 | 127 C | 8.420 | 129 C5 | 38 CD1 | 8.479 |
| 129 C5 | 148 CE1 | 8.660 | 129 C5 | 149 C | 8.855 |
| 129 C5 | 61 O | 8.883 | 129 C5 | 157 CA | 8.887 |
| 129 C5 | 127 OG | 8.894 | 129 C5 | 127 CA | 9.016 |
| 129 C5 | 157 CG | 9.020 | 129 C5 | 128 CB | 9.048 |
| 129 C5 | 157 CB | 9.077 | 129 C5 | 157 O | 9.176 |
| 129 C5 | 38 CG | 9.181 | 129 C5 | 157 CZ | 9.204 |
| 129 C5 | 148 ND1 | 9.238 | 129 C5 | 157 NE | 9.252 |
| 129 C5 | 130 CB | 9.265 | 129 C5 | 149 CA | 9.372 |

Figure 8Q

| Atom 1 | Atom 2 | Distance | Atom 1 | Atom 2 | Distance |
|---|---|---|---|---|---|
| 129 C5 | 154 CG1 | 9.387 | 129 C5 | 148 O | 9.429 |
| 129 C5 | 148 NE2 | 9.480 | 129 C5 | 157 C | 9.634 |
| 129 C5 | 149 O | 9.660 | 129 C5 | 151 CB | 9.789 |
| 129 C5 | 157 NH1 | 9.818 | 129 C5 | 128 CG2 | 9.846 |
| 129 C5 | 127 N | 9.857 | 129 C5 | 131 C | 9.868 |
| 129 C5 | 157 CD | 9.924 | 129 C5 | 128 CG1 | 10.018 |
| 129 C5 | 38 CB | 10.192 | 129 C5 | 149 CB | 10.228 |
| 129 C5 | 148 C | 10.240 | 129 C5 | 132 N | 10.294 |
| 129 C5 | 149 N | 10.295 | 129 C5 | 154 CD1 | 10.317 |
| 129 C5 | 148 CG | 10.387 | 129 C5 | 130 CG | 10.398 |
| 129 C5 | 27 O | 10.444 | 129 C5 | 148 CD2 | 10.513 |
| 129 C5 | 131 O | 10.734 | 129 C5 | 151 CD1 | 10.916 |
| 129 C5 | 149 CG2 | 10.919 | 129 C5 | 151 CG | 11.036 |
| 129 C5 | 130 CD1 | 11.077 | 129 C5 | 38 CA | 11.130 |
| 129 C5 | 149 CG1 | 11.330 | 129 C5 | 132 OG1 | 11.417 |
| 129 C5 | 148 CB | 11.421 | 129 C5 | 148 CA | 11.439 |
| 129 C5 | 27 CD1 | 11.442 | 129 C5 | 130 CD2 | 11.496 |
| 129 C5 | 27 C | 11.512 | 129 C5 | 132 O | 11.654 |
| 129 C5 | 148 N | 11.685 | 129 C5 | 132 CA | 11.746 |
| 129 C5 | 38 O | 11.793 | 129 C5 | 27 CA | 11.825 |
| 129 C5 | 38 N | 11.940 | 129 C6 | 156 CG | 3.825 |
| 129 C6 | 156 CD | 4.164 | 129 C6 | 156 NE | 4.733 |
| 129 C6 | 61 ND1 | 4.802 | 129 C6 | 154 O | 4.864 |
| 129 C6 | 61 CE1 | 4.944 | 129 C6 | 156 CB | 5.124 |
| 129 C6 | 156 N | 5.239 | 129 C6 | 155 CA | 5.536 |
| 129 C6 | 155 C | 5.573 | 129 C6 | 156 CA | 5.808 |
| 129 C6 | 152 SG | 5.810 | 129 C6 | 60 OD1 | 5.892 |
| 129 C6 | 156 CZ | 5.894 | 129 C6 | 154 C | 5.953 |
| 129 C6 | 61 CG | 6.123 | 129 C6 | 152 CB | 6.129 |
| 129 C6 | 61 NE2 | 6.256 | 129 C6 | 155 N | 6.285 |
| 129 C6 | 155 O | 6.317 | 129 C6 | 156 NH1 | 6.557 |
| 129 C6 | 156 NH2 | 6.650 | 129 C6 | 61 CB | 6.764 |
| 129 C6 | 60 CG | 6.785 | 129 C6 | 61 CD2 | 6.892 |
| 129 C6 | 60 OD2 | 7.114 | 129 C6 | 300 OH2 | 7.169 |
| 129 C6 | 156 C | 7.267 | 129 C6 | 154 CA | 7.288 |
| 129 C6 | 154 N | 7.357 | 129 C6 | 60 C | 7.459 |
| 129 C6 | 60 CA | 7.476 | 129 C6 | 61 N | 7.489 |
| 129 C6 | 150 CB | 7.514 | 129 C6 | 152 CA | 7.633 |
| 129 C6 | 157 N | 7.721 | 129 C6 | 128 O | 7.747 |
| 129 C6 | 154 CB | 7.763 | 129 C6 | 60 O | 7.775 |
| 129 C6 | 60 CB | 7.831 | 129 C6 | 61 CA | 7.857 |
| 129 C6 | 131 OG | 7.900 | 129 C6 | 154 CG2 | 7.978 |
| 129 C6 | 128 C | 8.083 | 129 C6 | 156 O | 8.125 |
| 129 C6 | 38 CD1 | 8.183 | 129 C6 | 150 O | 8.218 |
| 129 C6 | 152 C | 8.219 | 129 C6 | 38 CD2 | 8.265 |
| 129 C6 | 130 N | 8.312 | 129 C6 | 151 O | 8.336 |

Figure 8R

| Atom 1 | Atom 2 | Distance | Atom 1 | Atom 2 | Distance |
|---|---|---|---|---|---|
| 129 C6 | 130 O | 8.337 | 129 C6 | 152 N | 8.366 |
| 129 C6 | 150 C | 8.619 | 129 C6 | 60 N | 8.646 |
| 129 C6 | 301 OH2 | 8.647 | 129 C6 | 151 C | 8.657 |
| 129 C6 | 150 CA | 8.708 | 129 C6 | 127 CB | 8.860 |
| 129 C6 | 130 C | 8.881 | 129 C6 | 38 CG | 8.985 |
| 129 C6 | 61 C | 9.049 | 129 C6 | 152 O | 9.088 |
| 129 C6 | 157 NH2 | 9.116 | 129 C6 | 150 N | 9.137 |
| 129 C6 | 157 CA | 9.146 | 129 C6 | 131 CB | 9.173 |
| 129 C6 | 154 CG1 | 9.205 | 129 C6 | 128 CA | 9.239 |
| 129 C6 | 130 CA | 9.306 | 129 C6 | 131 N | 9.377 |
| 129 C6 | 151 N | 9.388 | 129 C6 | 131 CA | 9.406 |
| 129 C6 | 157 CG | 9.408 | 129 C6 | 128 N | 9.432 |
| 129 C6 | 157 O | 9.507 | 129 C6 | 127 OG | 9.514 |
| 129 C6 | 157 CB | 9.525 | 129 C6 | 127 C | 9.547 |
| 129 C6 | 127 O | 9.583 | 129 C6 | 61 O | 9.616 |
| 129 C6 | 151 CA | 9.685 | 129 C6 | 148 CE1 | 9.825 |
| 129 C6 | 157 CZ | 9.884 | 129 C6 | 157 C | 9.921 |
| 129 C6 | 157 NE | 9.925 | 129 C6 | 127 CA | 9.966 |
| 129 C6 | 38 CB | 10.148 | 129 C6 | 154 CD1 | 10.257 |
| 129 C6 | 157 NH1 | 10.361 | 129 C6 | 149 C | 10.363 |
| 129 C6 | 128 CB | 10.409 | 129 C6 | 157 CD | 10.439 |
| 129 C6 | 130 CB | 10.498 | 129 C6 | 148 ND1 | 10.515 |
| 129 C6 | 148 NE2 | 10.556 | 129 C6 | 127 N | 10.736 |
| 129 C6 | 148 O | 10.806 | 129 C6 | 131 C | 10.872 |
| 129 C6 | 149 CA | 10.877 | 129 C6 | 151 CB | 11.060 |
| 129 C6 | 128 CG2 | 11.113 | 129 C6 | 149 O | 11.145 |
| 129 C6 | 132 N | 11.157 | 129 C6 | 38 CA | 11.160 |
| 129 C6 | 128 CG1 | 11.430 | 129 C6 | 27 O | 11.460 |
| 129 C6 | 130 CG | 11.594 | 129 C6 | 148 CG | 11.646 |
| 129 C6 | 148 C | 11.648 | 129 C6 | 148 CD2 | 11.659 |
| 129 C6 | 149 CB | 11.748 | 129 C6 | 149 N | 11.762 |
| 129 C6 | 38 N | 11.818 | 129 C6 | 131 O | 11.823 |
| 129 C7 | 152 SG | 3.758 | 129 C7 | 61 ND1 | 3.773 |
| 129 C7 | 152 CB | 3.840 | 129 C7 | 61 CE1 | 3.985 |
| 129 C7 | 60 OD1 | 4.142 | 129 C7 | 154 O | 4.535 |
| 129 C7 | 61 CG | 5.004 | 129 C7 | 60 CG | 5.111 |
| 129 C7 | 155 CA | 5.197 | 129 C7 | 61 NE2 | 5.222 |
| 129 C7 | 60 CA | 5.334 | 129 C7 | 152 CA | 5.348 |
| 129 C7 | 150 CB | 5.402 | 129 C7 | 154 C | 5.442 |
| 129 C7 | 60 C | 5.606 | 129 C7 | 61 N | 5.627 |
| 129 C7 | 61 CB | 5.638 | 129 C7 | 156 CG | 5.653 |
| 129 C7 | 155 N | 5.750 | 129 C7 | 61 CD2 | 5.760 |
| 129 C7 | 60 OD2 | 5.814 | 129 C7 | 151 O | 5.820 |
| 129 C7 | 60 CB | 5.867 | 129 C7 | 156 N | 5.871 |
| 129 C7 | 155 C | 5.896 | 129 C7 | 152 N | 5.972 |
| 129 C7 | 150 O | 5.979 | 129 C7 | 151 C | 6.159 |

Figure 8S

| Atom 1 | Atom 2 | Distance | Atom 1 | Atom 2 | Distance |
|---|---|---|---|---|---|
| 129 C7 | 152 C | 6.184 | 129 C7 | 60 O | 6.215 |
| 129 C7 | 150 C | 6.280 | 129 C7 | 154 N | 6.321 |
| 129 C7 | 60 N | 6.334 | 129 C7 | 61 CA | 6.339 |
| 129 C7 | 156 CD | 6.404 | 129 C7 | 128 O | 6.474 |
| 129 C7 | 150 CA | 6.511 | 129 C7 | 128 C | 6.512 |
| 129 C7 | 154 CA | 6.632 | 129 C7 | 156 CB | 6.650 |
| 129 C7 | 155 O | 6.799 | 129 C7 | 300 OH2 | 6.850 |
| 129 C7 | 156 CA | 6.927 | 129 C7 | 151 N | 6.937 |
| 129 C7 | 156 NE | 6.940 | 129 C7 | 152 O | 7.077 |
| 129 C7 | 150 N | 7.151 | 129 C7 | 151 CA | 7.210 |
| 129 C7 | 131 OG | 7.382 | 129 C7 | 127 CB | 7.405 |
| 129 C7 | 128 CA | 7.438 | 129 C7 | 130 N | 7.442 |
| 129 C7 | 127 O | 7.479 | 129 C7 | 154 CB | 7.513 |
| 129 C7 | 127 C | 7.664 | 129 C7 | 61 C | 7.677 |
| 129 C7 | 128 N | 7.706 | 129 C7 | 154 CG2 | 8.086 |
| 129 C7 | 130 O | 8.161 | 129 C7 | 156 CZ | 8.180 |
| 129 C7 | 127 CA | 8.265 | 129 C7 | 301 OH2 | 8.274 |
| 129 C7 | 156 C | 8.283 | 129 C7 | 127 OG | 8.286 |
| 129 C7 | 130 C | 8.377 | 129 C7 | 157 N | 8.399 |
| 129 C7 | 149 C | 8.431 | 129 C7 | 61 O | 8.472 |
| 129 C7 | 130 CA | 8.510 | 129 C7 | 151 CB | 8.558 |
| 129 C7 | 148 CE1 | 8.655 | 129 C7 | 128 CB | 8.706 |
| 129 C7 | 131 CB | 8.766 | 129 C7 | 131 N | 8.796 |
| 129 C7 | 154 CG1 | 8.811 | 129 C7 | 156 NH2 | 8.824 |
| 129 C7 | 127 N | 8.941 | 129 C7 | 156 NH1 | 8.951 |
| 129 C7 | 131 CA | 9.115 | 129 C7 | 149 O | 9.117 |
| 129 C7 | 148 ND1 | 9.144 | 129 C7 | 149 CA | 9.164 |
| 129 C7 | 156 O | 9.340 | 129 C7 | 157 NH2 | 9.383 |
| 129 C7 | 128 CG1 | 9.531 | 129 C7 | 128 CG2 | 9.608 |
| 129 C7 | 148 O | 9.622 | 129 C7 | 148 NE2 | 9.625 |
| 129 C7 | 157 O | 9.718 | 129 C7 | 157 CA | 9.769 |
| 129 C7 | 154 CD1 | 9.781 | 129 C7 | 38 CD2 | 9.806 |
| 129 C7 | 130 CB | 9.829 | 129 C7 | 38 CD1 | 9.857 |
| 129 C7 | 151 CG | 9.879 | 129 C7 | 151 CD1 | 9.915 |
| 129 C7 | 149 CB | 9.979 | 129 C7 | 157 CB | 9.980 |
| 129 C7 | 157 CG | 10.096 | 129 C7 | 149 N | 10.155 |
| 129 C7 | 148 C | 10.282 | 129 C7 | 157 NE | 10.285 |
| 129 C7 | 157 CZ | 10.309 | 129 C7 | 157 C | 10.332 |
| 129 C7 | 148 CG | 10.394 | 129 C7 | 149 CG2 | 10.472 |
| 129 C7 | 38 CG | 10.616 | 129 C7 | 131 C | 10.653 |
| 129 C7 | 148 CD2 | 10.654 | 129 C7 | 151 CD2 | 10.973 |
| 129 C7 | 27 O | 10.990 | 129 C7 | 157 CD | 10.995 |
| 129 C7 | 130 CG | 11.021 | 129 C7 | 157 NH1 | 11.032 |
| 129 C7 | 149 CG1 | 11.215 | 129 C7 | 132 N | 11.226 |
| 129 C7 | 148 CB | 11.373 | 129 C7 | 131 O | 11.405 |
| 129 C7 | 148 CA | 11.504 | 129 C7 | 27 CD1 | 11.505 |

Figure 8T

| Atom 1 | Atom 2 | Distance | Atom 1 | Atom 2 | Distance |
|---|---|---|---|---|---|
| 129 C7 | 130 CD1 | 11.547 | 129 C7 | 38 CB | 11.568 |
| 129 C7 | 148 N | 11.934 | 129 C7 | 27 C | 11.970 |
| 129 C8 | 130 O | 3.353 | 129 C8 | 157 NH2 | 4.087 |
| 129 C8 | 130 C | 4.289 | 129 C8 | 61 CE1 | 4.327 |
| 129 C8 | 131 OG | 4.632 | 129 C8 | 130 N | 4.677 |
| 129 C8 | 61 NE2 | 4.786 | 129 C8 | 38 CD2 | 4.875 |
| 129 C8 | 131 CA | 4.893 | 129 C8 | 156 NE | 4.934 |
| 129 C8 | 131 N | 4.978 | 129 C8 | 157 CZ | 5.048 |
| 129 C8 | 301 OH2 | 5.112 | 129 C8 | 156 CB | 5.132 |
| 129 C8 | 130 CA | 5.146 | 129 C8 | 156 CG | 5.226 |
| 129 C8 | 131 CB | 5.362 | 129 C8 | 61 ND1 | 5.366 |
| 129 C8 | 157 NH1 | 5.431 | 129 C8 | 300 OH2 | 5.466 |
| 129 C8 | 156 NH2 | 5.542 | 129 C8 | 157 NE | 5.573 |
| 129 C8 | 156 CD | 5.675 | 129 C8 | 156 N | 5.751 |
| 129 C8 | 156 CZ | 5.763 | 129 C8 | 61 CD2 | 6.017 |
| 129 C8 | 130 CB | 6.037 | 129 C8 | 156 CA | 6.042 |
| 129 C8 | 131 C | 6.132 | 129 C8 | 157 CG | 6.151 |
| 129 C8 | 38 CG | 6.159 | 129 C8 | 38 CD1 | 6.195 |
| 129 C8 | 132 N | 6.220 | 129 C8 | 61 CG | 6.327 |
| 129 C8 | 157 N | 6.419 | 129 C8 | 157 CD | 6.505 |
| 129 C8 | 156 C | 6.607 | 129 C8 | 130 CG | 6.818 |
| 129 C8 | 132 OG1 | 6.847 | 129 C8 | 155 C | 6.863 |
| 129 C8 | 157 CB | 6.864 | 129 C8 | 128 O | 6.878 |
| 129 C8 | 38 CB | 6.882 | 129 C8 | 155 CA | 7.000 |
| 129 C8 | 156 NH1 | 7.064 | 129 C8 | 128 C | 7.140 |
| 129 C8 | 131 O | 7.182 | 129 C8 | 148 O | 7.330 |
| 129 C8 | 157 CA | 7.339 | 129 C8 | 38 CA | 7.355 |
| 129 C8 | 150 CB | 7.460 | 129 C8 | 156 O | 7.461 |
| 129 C8 | 132 CA | 7.565 | 129 C8 | 61 CB | 7.697 |
| 129 C8 | 132 CB | 7.710 | 129 C8 | 132 O | 7.713 |
| 129 C8 | 130 CD2 | 7.719 | 129 C8 | 38 O | 7.750 |
| 129 C8 | 132 CG2 | 7.755 | 129 C8 | 150 N | 7.836 |
| 129 C8 | 130 CD1 | 7.846 | 129 C8 | 27 O | 7.883 |
| 129 C8 | 152 SG | 7.937 | 129 C8 | 155 O | 7.956 |
| 129 C8 | 148 CE1 | 7.998 | 129 C8 | 150 O | 8.064 |
| 129 C8 | 38 C | 8.125 | 129 C8 | 132 C | 8.220 |
| 129 C8 | 38 N | 8.285 | 129 C8 | 150 CA | 8.300 |
| 129 C8 | 148 NE2 | 8.340 | 129 C8 | 155 N | 8.390 |
| 129 C8 | 154 O | 8.397 | 129 C8 | 149 CA | 8.426 |
| 129 C8 | 148 ND1 | 8.480 | 129 C8 | 148 C | 8.492 |
| 129 C8 | 128 CA | 8.582 | 129 C8 | 157 C | 8.589 |
| 129 C8 | 150 C | 8.659 | 129 C8 | 149 C | 8.683 |
| 129 C8 | 157 O | 8.691 | 129 C8 | 61 CA | 8.833 |
| 129 C8 | 154 C | 8.927 | 129 C8 | 152 CB | 8.984 |
| 129 C8 | 61 N | 9.019 | 129 C8 | 128 CB | 9.023 |
| 129 C8 | 148 CD2 | 9.033 | 129 C8 | 149 N | 9.047 |

Figure 8U

| Atom 1 | Atom 2 | Distance | Atom 1 | Atom 2 | Distance |
|---|---|---|---|---|---|
| 129 C8 | 27 C | 9.057 | 129 C8 | 148 CG | 9.123 |
| 129 C8 | 149 CB | 9.254 | 129 C8 | 148 N | 9.290 |
| 129 C8 | 128 N | 9.342 | 129 C8 | 148 CA | 9.567 |
| 129 C8 | 128 CG2 | 9.598 | 129 C8 | 27 CD1 | 9.621 |
| 129 C8 | 27 CA | 9.622 | 129 C8 | 27 CG | 9.684 |
| 129 C8 | 27 CB | 9.689 | 129 C8 | 149 O | 9.752 |
| 129 C8 | 60 C | 9.755 | 129 C8 | 149 CG1 | 9.800 |
| 129 C8 | 151 N | 9.903 | 129 C8 | 60 OD1 | 9.950 |
| 129 C8 | 148 CB | 10.027 | 129 C8 | 60 CA | 10.105 |
| 129 C8 | 61 C | 10.126 | 129 C8 | 127 C | 10.127 |
| 129 C8 | 128 CG1 | 10.136 | 129 C8 | 127 CB | 10.201 |
| 129 C8 | 151 O | 10.282 | 129 C8 | 61 O | 10.292 |
| 129 C8 | 151 C | 10.311 | 129 C8 | 152 N | 10.328 |
| 129 C8 | 152 CA | 10.350 | 129 C8 | 127 O | 10.357 |
| 129 C8 | 60 O | 10.362 | 129 C8 | 154 CA | 10.464 |
| 129 C8 | 149 CG2 | 10.466 | 129 C8 | 151 CA | 10.610 |
| 129 C8 | 60 CG | 10.677 | 129 C8 | 60 N | 10.827 |
| 129 C8 | 154 N | 10.842 | 129 C8 | 127 CA | 10.971 |
| 129 C8 | 27 N | 11.011 | 129 C8 | 27 CD2 | 11.027 |
| 129 C8 | 152 C | 11.125 | 129 C8 | 60 CB | 11.140 |
| 129 C8 | 127 OG | 11.141 | 129 C8 | 154 CG2 | 11.143 |
| 129 C8 | 60 OD2 | 11.249 | 129 C8 | 154 CB | 11.309 |
| 129 C8 | 152 O | 11.604 | 129 C9 | 130 O | 3.586 |
| 129 C9 | 131 OG | 3.727 | 129 C9 | 61 CE1 | 4.015 |
| 129 C9 | 131 CA | 4.198 | 129 C9 | 61 NE2 | 4.279 |
| 129 C9 | 131 CB | 4.392 | 129 C9 | 130 C | 4.399 |
| 129 C9 | 131 N | 4.688 | 129 C9 | 157 NH2 | 4.908 |
| 129 C9 | 61 ND1 | 4.928 | 129 C9 | 61 CD2 | 5.320 |
| 129 C9 | 130 N | 5.410 | 129 C9 | 131 C | 5.431 |
| 129 C9 | 132 N | 5.453 | 129 C9 | 156 NE | 5.538 |
| 129 C9 | 38 CD2 | 5.539 | 129 C9 | 130 CA | 5.556 |
| 129 C9 | 61 CG | 5.672 | 129 C9 | 156 NH2 | 5.756 |
| 129 C9 | 157 CZ | 5.938 | 129 C9 | 157 NH1 | 6.119 |
| 129 C9 | 156 CZ | 6.183 | 129 C9 | 156 CG | 6.252 |
| 129 C9 | 132 OG1 | 6.318 | 129 C9 | 156 CB | 6.362 |
| 129 C9 | 301 OH2 | 6.366 | 129 C9 | 156 CD | 6.430 |
| 129 C9 | 130 CB | 6.543 | 129 C9 | 131 O | 6.555 |
| 129 C9 | 132 O | 6.619 | 129 C9 | 157 NE | 6.694 |
| 129 C9 | 132 CA | 6.821 | 129 C9 | 300 OH2 | 6.937 |
| 129 C9 | 38 CG | 6.970 | 129 C9 | 61 CB | 6.976 |
| 129 C9 | 148 O | 7.035 | 129 C9 | 130 CG | 7.064 |
| 129 C9 | 148 CE1 | 7.121 | 129 C9 | 156 N | 7.154 |
| 129 C9 | 132 CB | 7.172 | 129 C9 | 38 CD1 | 7.197 |
| 129 C9 | 132 C | 7.253 | 129 C9 | 148 NE2 | 7.297 |
| 129 C9 | 156 CA | 7.412 | 129 C9 | 150 CB | 7.431 |
| 129 C9 | 132 CG2 | 7.488 | 129 C9 | 157 CG | 7.490 |

Figure 8V

| Atom 1 | Atom 2 | Distance | Atom 1 | Atom 2 | Distance |
|---|---|---|---|---|---|
| 129 C9 | 156 NH1 | 7.499 | 129 C9 | 157 CD | 7.696 |
| 129 C9 | 148 ND1 | 7.769 | 129 C9 | 38 CB | 7.773 |
| 129 C9 | 157 N | 7.921 | 129 C9 | 130 CD1 | 7.943 |
| 129 C9 | 150 N | 7.955 | 129 C9 | 156 C | 8.040 |
| 129 C9 | 38 CA | 8.042 | 129 C9 | 148 CD2 | 8.064 |
| 129 C9 | 130 CD2 | 8.087 | 129 C9 | 128 O | 8.097 |
| 129 C9 | 148 C | 8.166 | 129 C9 | 128 C | 8.199 |
| 129 C9 | 61 CA | 8.207 | 129 C9 | 155 C | 8.232 |
| 129 C9 | 157 CB | 8.311 | 129 C9 | 155 CA | 8.314 |
| 129 C9 | 148 CG | 8.347 | 129 C9 | 150 CA | 8.402 |
| 129 C9 | 149 CA | 8.462 | 129 C9 | 38 O | 8.536 |
| 129 C9 | 150 O | 8.594 | 129 C9 | 61 N | 8.635 |
| 129 C9 | 148 N | 8.657 | 129 C9 | 149 C | 8.695 |
| 129 C9 | 152 SG | 8.791 | 129 C9 | 38 N | 8.821 |
| 129 C9 | 157 CA | 8.824 | 129 C9 | 156 O | 8.834 |
| 129 C9 | 149 N | 8.864 | 129 C9 | 38 C | 8.884 |
| 129 C9 | 150 C | 9.002 | 129 C9 | 148 CA | 9.056 |
| 129 C9 | 27 O | 9.059 | 129 C9 | 155 O | 9.314 |
| 129 C9 | 61 C | 9.367 | 129 C9 | 61 O | 9.373 |
| 129 C9 | 148 CB | 9.387 | 129 C9 | 154 O | 9.437 |
| 129 C9 | 60 C | 9.440 | 129 C9 | 149 CB | 9.486 |
| 129 C9 | 128 CA | 9.576 | 129 C9 | 152 CB | 9.617 |
| 129 C9 | 155 N | 9.655 | 129 C9 | 149 O | 9.666 |
| 129 C9 | 60 O | 9.935 | 129 C9 | 149 CG1 | 9.989 |
| 129 C9 | 128 CB | 9.993 | 129 C9 | 60 CA | 10.021 |
| 129 C9 | 154 C | 10.077 | 129 C9 | 60 OD1 | 10.106 |
| 129 C9 | 157 C | 10.106 | 129 C9 | 27 C | 10.195 |
| 129 C9 | 157 O | 10.223 | 129 C9 | 151 N | 10.236 |
| 129 C9 | 27 CD1 | 10.388 | 129 C9 | 27 CG | 10.403 |
| 129 C9 | 128 N | 10.450 | 129 C9 | 27 CB | 10.557 |
| 129 C9 | 151 O | 10.624 | 129 C9 | 27 CA | 10.663 |
| 129 C9 | 60 CG | 10.678 | 129 C9 | 128 CG2 | 10.703 |
| 129 C9 | 149 CG2 | 10.711 | 129 C9 | 60 N | 10.792 |
| 129 C9 | 151 C | 10.804 | 129 C9 | 128 CG1 | 10.976 |
| 129 C9 | 152 N | 10.976 | 129 C9 | 152 CA | 10.995 |
| 129 C9 | 60 CB | 11.095 | 129 C9 | 151 CA | 11.101 |
| 129 C9 | 60 OD2 | 11.148 | 129 C9 | 127 C | 11.182 |
| 129 C9 | 127 O | 11.281 | 129 C9 | 127 CB | 11.407 |
| 129 C9 | 154 CA | 11.603 | 129 C9 | 27 CD2 | 11.656 |
| 129 C9 | 154 N | 11.860 | 129 C9 | 152 C | 11.913 |
| 129 C10 | 38 CD2 | 3.359 | 129 C10 | 157 NH2 | 3.705 |
| 129 C10 | 130 O | 3.997 | 129 C10 | 156 NE | 4.242 |
| 129 C10 | 157 CZ | 4.340 | 129 C10 | 156 CB | 4.479 |
| 129 C10 | 157 NH1 | 4.489 | 129 C10 | 156 NH2 | 4.536 |
| 129 C10 | 38 CG | 4.654 | 129 C10 | 38 CD1 | 4.809 |
| 129 C10 | 157 NE | 4.863 | 129 C10 | 156 CZ | 4.878 |

Figure 8W

| Atom 1 | Atom 2 | Distance | Atom 1 | Atom 2 | Distance |
|---|---|---|---|---|---|
| 129 C10 | 156 CG | 4.880 | 129 C10 | 130 C | 5.125 |
| 129 C10 | 157 CG | 5.172 | 129 C10 | 156 CD | 5.186 |
| 129 C10 | 301 OH2 | 5.236 | 129 C10 | 38 CB | 5.403 |
| 129 C10 | 156 CA | 5.510 | 129 C10 | 130 N | 5.529 |
| 129 C10 | 157 CD | 5.570 | 129 C10 | 300 OH2 | 5.577 |
| 129 C10 | 156 N | 5.581 | 129 C10 | 157 N | 5.755 |
| 129 C10 | 131 CA | 5.762 | 129 C10 | 61 CE1 | 5.817 |
| 129 C10 | 156 C | 5.851 | 129 C10 | 38 CA | 5.897 |
| 129 C10 | 131 OG | 5.920 | 129 C10 | 131 N | 5.930 |
| 129 C10 | 130 CA | 5.964 | 129 C10 | 157 CB | 6.108 |
| 129 C10 | 156 NH1 | 6.174 | 129 C10 | 61 NE2 | 6.296 |
| 129 C10 | 131 CB | 6.439 | 129 C10 | 38 O | 6.518 |
| 129 C10 | 156 O | 6.529 | 129 C10 | 130 CB | 6.549 |
| 129 C10 | 157 CA | 6.554 | 129 C10 | 132 N | 6.589 |
| 129 C10 | 132 OG1 | 6.590 | 129 C10 | 131 C | 6.763 |
| 129 C10 | 38 C | 6.766 | 129 C10 | 61 ND1 | 6.793 |
| 129 C10 | 38 N | 6.796 | 129 C10 | 155 C | 6.836 |
| 129 C10 | 130 CG | 7.249 | 129 C10 | 155 CA | 7.277 |
| 129 C10 | 61 CD2 | 7.505 | 129 C10 | 128 O | 7.520 |
| 129 C10 | 132 CB | 7.634 | 129 C10 | 132 CG2 | 7.668 |
| 129 C10 | 132 CA | 7.776 | 129 C10 | 61 CG | 7.783 |
| 129 C10 | 27 O | 7.802 | 129 C10 | 155 O | 7.807 |
| 129 C10 | 131 O | 7.860 | 129 C10 | 132 O | 7.889 |
| 129 C10 | 130 CD2 | 7.892 | 129 C10 | 157 C | 7.943 |
| 129 C10 | 128 C | 7.972 | 129 C10 | 157 O | 8.232 |
| 129 C10 | 132 C | 8.424 | 129 C10 | 130 CD1 | 8.463 |
| 129 C10 | 148 O | 8.481 | 129 C10 | 155 N | 8.705 |
| 129 C10 | 154 O | 8.824 | 129 C10 | 152 SG | 8.902 |
| 129 C10 | 150 CB | 8.943 | 129 C10 | 27 C | 9.013 |
| 129 C10 | 61 CB | 9.111 | 129 C10 | 150 N | 9.224 |
| 129 C10 | 154 C | 9.305 | 129 C10 | 150 O | 9.329 |
| 129 C10 | 148 CE1 | 9.399 | 129 C10 | 128 CA | 9.451 |
| 129 C10 | 148 NE2 | 9.643 | 129 C10 | 149 CA | 9.681 |
| 129 C10 | 148 C | 9.688 | 129 C10 | 150 CA | 9.735 |
| 129 C10 | 27 CA | 9.799 | 129 C10 | 128 CB | 9.831 |
| 129 C10 | 148 ND1 | 9.879 | 129 C10 | 27 CB | 9.922 |
| 129 C10 | 150 C | 10.013 | 129 C10 | 149 C | 10.047 |
| 129 C10 | 152 CB | 10.063 | 129 C10 | 128 N | 10.092 |
| 129 C10 | 27 CG | 10.130 | 129 C10 | 128 CG2 | 10.210 |
| 129 C10 | 27 CD1 | 10.219 | 129 C10 | 148 CD2 | 10.283 |
| 129 C10 | 149 N | 10.297 | 129 C10 | 61 CA | 10.299 |
| 129 C10 | 148 N | 10.336 | 129 C10 | 149 CB | 10.401 |
| 129 C10 | 148 CG | 10.433 | 129 C10 | 61 N | 10.484 |
| 129 C10 | 148 CA | 10.731 | 129 C10 | 127 CB | 10.784 |
| 129 C10 | 149 CG1 | 10.836 | 129 C10 | 154 CA | 10.853 |
| 129 C10 | 127 C | 10.939 | 129 C10 | 128 CG1 | 11.046 |

Figure 8X

| Atom 1 | Atom 2 | Distance | Atom 1 | Atom 2 | Distance |
|---|---|---|---|---|---|
| 129 C10 | 60 OD1 | 11.098 | 129 C10 | 149 O | 11.152 |
| 129 C10 | 27 N | 11.156 | 129 C10 | 60 C | 11.169 |
| 129 C10 | 154 CG2 | 11.206 | 129 C10 | 151 N | 11.255 |
| 129 C10 | 148 CB | 11.295 | 129 C10 | 127 O | 11.306 |
| 129 C10 | 154 N | 11.408 | 129 C10 | 152 CA | 11.439 |
| 129 C10 | 27 CD2 | 11.469 | 129 C10 | 152 N | 11.471 |
| 129 C10 | 60 CA | 11.487 | 129 C10 | 151 C | 11.565 |
| 129 C10 | 61 C | 11.566 | 129 C10 | 154 CB | 11.567 |
| 129 C10 | 127 OG | 11.597 | 129 C10 | 151 O | 11.597 |
| 129 C10 | 127 CA | 11.653 | 129 C10 | 149 CG2 | 11.662 |
| 129 C10 | 61 O | 11.698 | 129 C10 | 60 O | 11.736 |
| 129 C10 | 151 CA | 11.878 | 129 C10 | 60 CG | 11.886 |

Figure 9A

| Atom 1 | Atom 2 | Distance | Atom 1 | Atom 2 | Distance |
|---|---|---|---|---|---|
| 129 N | 128 C   | 1.313 | 129 N | 128 O   | 2.229 |
| 129 N | 128 CA  | 2.384 | 129 N | 128 CB  | 3.053 |
| 129 N | 130 N   | 3.368 | 129 N | 128 N   | 3.513 |
| 129 N | 128 CG2 | 3.559 | 129 N | 321 OH2 | 3.837 |
| 129 N | 152 SG  | 4.323 | 129 N | 128 CG1 | 4.378 |
| 129 N | 130 CA  | 4.579 | 129 N | 152 N   | 5.419 |
| 129 N | 130 CB  | 5.512 | 129 N | 61 NE2  | 5.531 |
| 129 N | 130 C   | 5.542 | 129 N | 27 CD1  | 5.545 |
| 129 N | 152 CB  | 5.593 | 129 N | 61 CE1  | 5.741 |
| 129 N | 130 O   | 5.971 | 129 N | 152 CA  | 6.168 |
| 129 N | 131 N   | 6.179 | 129 N | 27 O    | 6.333 |
| 129 N | 156 N   | 6.399 | 129 N | 61 CD2  | 6.575 |
| 129 N | 27 CA   | 6.610 | 129 N | 148 O   | 6.652 |
| 129 N | 27 CG   | 6.673 | 129 N | 61 ND1  | 6.819 |
| 129 N | 152 C   | 6.917 | 129 N | 27 CB   | 6.923 |
| 129 N | 27 C    | 6.934 | 129 N | 152 O   | 6.936 |
| 129 N | 130 CG  | 7.019 | 129 N | 148 C   | 7.098 |
| 129 N | 157 NH2 | 7.106 | 129 N | 131 OG  | 7.208 |
| 129 N | 157 N   | 7.293 | 129 N | 61 CG   | 7.293 |
| 129 N | 131 CA  | 7.356 | 129 N | 148 ND1 | 7.428 |
| 129 N | 130 CD1 | 7.482 | 129 N | 157 NE  | 7.533 |
| 129 N | 148 CE1 | 7.567 | 129 N | 157 CZ  | 7.625 |
| 129 N | 156 CA  | 7.631 | 129 N | 157 CB  | 7.633 |
| 129 N | 27 N    | 7.688 | 129 N | 157 O   | 7.730 |
| 129 N | 130 CD2 | 7.812 | 129 N | 131 CB  | 7.817 |
| 129 N | 61 N    | 7.918 | 129 N | 156 CB  | 7.929 |
| 129 N | 27 CD2  | 7.952 | 129 N | 156 C   | 8.043 |
| 129 N | 157 CA  | 8.045 | 129 N | 157 CG  | 8.099 |

Figure 9B

| Atom 1 | Atom 2 | Distance | Atom 1 | Atom 2 | Distance |
|---|---|---|---|---|---|
| 129 N | 157 C | 8.370 | 129 N | 148 CG | 8.456 |
| 129 N | 131 C | 8.489 | 129 N | 157 CD | 8.490 |
| 129 N | 61 CB | 8.557 | 129 N | 61 CA | 8.571 |
| 129 N | 157 NH1 | 8.577 | 129 N | 148 CA | 8.599 |
| 129 N | 148 NE2 | 8.600 | 129 N | 131 O | 8.638 |
| 129 N | 148 CB | 8.960 | 129 N | 148 CD2 | 9.109 |
| 129 N | 156 O | 9.204 | 129 N | 148 N | 9.209 |
| 129 N | 156 CG | 9.248 | 129 N | 156 CD | 9.593 |
| 129 N | 156 NE | 9.904 | 129 N | 61 C | 10.040 |
| 129 N | 61 O | 10.738 | 129 N | 156 CZ | 11.017 |
| 129 N | 156 NH1 | 11.432 | 129 N | 156 NH2 | 11.852 |
| 129 CA | 128 C | 2.383 | 129 CA | 130 N | 2.442 |
| 129 CA | 128 O | 2.714 | 129 CA | 321 OH2 | 3.213 |
| 129 CA | 128 CA | 3.727 | 129 CA | 130 CA | 3.795 |
| 129 CA | 128 CB | 4.338 | 129 CA | 130 C | 4.521 |
| 129 CA | 128 CG2 | 4.540 | 129 CA | 128 N | 4.679 |
| 129 CA | 152 SG | 4.741 | 129 CA | 130 O | 4.764 |
| 129 CA | 61 NE2 | 4.812 | 129 CA | 130 CB | 4.821 |
| 129 CA | 61 CE1 | 4.969 | 129 CA | 131 N | 5.268 |
| 129 CA | 156 N | 5.726 | 129 CA | 128 CG1 | 5.727 |
| 129 CA | 27 CD1 | 5.933 | 129 CA | 27 O | 5.957 |
| 129 CA | 157 NH2 | 5.968 | 129 CA | 61 CD2 | 6.029 |
| 129 CA | 152 CB | 6.080 | 129 CA | 61 ND1 | 6.182 |
| 129 CA | 131 OG | 6.238 | 129 CA | 148 O | 6.293 |
| 129 CA | 130 CG | 6.321 | 129 CA | 131 CA | 6.326 |
| 129 CA | 152 N | 6.394 | 129 CA | 157 CZ | 6.452 |
| 129 CA | 157 NE | 6.489 | 129 CA | 157 N | 6.552 |
| 129 CA | 27 CA | 6.693 | 129 CA | 27 C | 6.769 |

Figure 9C

| Atom 1 | Atom 2 | Distance | Atom 1 | Atom 2 | Distance |
|---|---|---|---|---|---|
| 129 CA | 61 CG | 6.769 | 129 CA | 156 CA | 6.812 |
| 129 CA | 27 CG | 6.812 | 129 CA | 157 CB | 6.850 |
| 129 CA | 131 CB | 6.879 | 129 CA | 27 CB | 6.898 |
| 129 CA | 156 CB | 6.912 | 129 CA | 152 CA | 6.934 |
| 129 CA | 148 C | 6.936 | 129 CA | 130 CD1 | 6.964 |
| 129 CA | 157 CG | 7.101 | 129 CA | 148 CE1 | 7.184 |
| 129 CA | 130 CD2 | 7.187 | 129 CA | 156 C | 7.213 |
| 129 CA | 148 ND1 | 7.221 | 129 CA | 157 NH1 | 7.310 |
| 129 CA | 157 CA | 7.340 | 129 CA | 157 O | 7.435 |
| 129 CA | 157 CD | 7.469 | 129 CA | 131 C | 7.507 |
| 129 CA | 152 C | 7.713 | 129 CA | 131 O | 7.809 |
| 129 CA | 152 O | 7.881 | 129 CA | 157 C | 7.905 |
| 129 CA | 27 N | 7.931 | 129 CA | 61 N | 7.937 |
| 129 CA | 148 NE2 | 8.073 | 129 CA | 61 CB | 8.151 |
| 129 CA | 148 CG | 8.183 | 129 CA | 27 CD2 | 8.203 |
| 129 CA | 156 CG | 8.254 | 129 CA | 156 O | 8.317 |
| 129 CA | 61 CA | 8.397 | 129 CA | 148 CA | 8.406 |
| 129 CA | 156 CD | 8.508 | 129 CA | 148 CD2 | 8.653 |
| 129 CA | 156 NE | 8.688 | 129 CA | 148 N | 8.803 |
| 129 CA | 148 CB | 8.819 | 129 CA | 156 CZ | 9.760 |
| 129 CA | 61 C | 9.887 | 129 CA | 156 NH1 | 10.103 |
| 129 CA | 61 O | 10.466 | 129 CA | 156 NH2 | 10.648 |
| 129 CB | 128 C | 3.238 | 129 CB | 321 OH2 | 3.477 |
| 129 CB | 128 O | 3.494 | 129 CB | 130 N | 3.511 |
| 129 CB | 61 NE2 | 3.522 | 129 CB | 152 SG | 3.945 |
| 129 CB | 61 CE1 | 3.969 | 129 CB | 128 CA | 4.473 |
| 129 CB | 61 CD2 | 4.694 | 129 CB | 130 CA | 4.740 |
| 129 CB | 130 C | 5.074 | 129 CB | 152 CB | 5.139 |

Figure 9D

| Atom 1 | Atom 2 | Distance | Atom 1 | Atom 2 | Distance |
|--------|--------|----------|--------|--------|----------|
| 129 CB | 130 O   | 5.184 | 129 CB | 61 ND1  | 5.204 |
| 129 CB | 128 N   | 5.255 | 129 CB | 156 N   | 5.317 |
| 129 CB | 128 CB  | 5.405 | 129 CB | 61 CG   | 5.592 |
| 129 CB | 131 N   | 5.629 | 129 CB | 128 CG2 | 5.814 |
| 129 CB | 131 OG  | 5.835 | 129 CB | 152 N   | 5.936 |
| 129 CB | 130 CB  | 5.951 | 129 CB | 152 CA  | 6.226 |
| 129 CB | 156 CB  | 6.348 | 129 CB | 156 CA  | 6.431 |
| 129 CB | 131 CA  | 6.449 | 129 CB | 128 CG1 | 6.683 |
| 129 CB | 157 NH2 | 6.716 | 129 CB | 157 N   | 6.727 |
| 129 CB | 131 CB  | 6.748 | 129 CB | 148 CE1 | 6.763 |
| 129 CB | 148 O   | 6.845 | 129 CB | 61 N    | 6.897 |
| 129 CB | 61 CB   | 6.989 | 129 CB | 148 ND1 | 7.051 |
| 129 CB | 157 CZ  | 7.089 | 129 CB | 152 C   | 7.103 |
| 129 CB | 156 C   | 7.129 | 129 CB | 157 NE  | 7.241 |
| 129 CB | 27 O    | 7.275 | 129 CB | 130 CG  | 7.368 |
| 129 CB | 61 CA   | 7.372 | 129 CB | 27 CD1  | 7.416 |
| 129 CB | 148 C   | 7.428 | 129 CB | 157 CB  | 7.458 |
| 129 CB | 152 O   | 7.494 | 129 CB | 156 CG  | 7.533 |
| 129 CB | 157 CG  | 7.575 | 129 CB | 156 CD  | 7.617 |
| 129 CB | 148 NE2 | 7.651 | 129 CB | 157 NH1 | 7.733 |
| 129 CB | 157 CA  | 7.743 | 129 CB | 131 C   | 7.804 |
| 129 CB | 156 NE  | 7.910 | 129 CB | 157 O   | 7.920 |
| 129 CB | 130 CD1 | 7.987 | 129 CB | 157 CD  | 8.107 |
| 129 CB | 148 CG  | 8.133 | 129 CB | 27 C    | 8.160 |
| 129 CB | 27 CA   | 8.176 | 129 CB | 156 O   | 8.230 |
| 129 CB | 131 O   | 8.273 | 129 CB | 27 CG   | 8.293 |
| 129 CB | 130 CD2 | 8.359 | 129 CB | 27 CB   | 8.382 |
| 129 CB | 157 C   | 8.405 | 129 CB | 148 CD2 | 8.453 |

Figure 9E

| Atom 1 | Atom 2 | Distance | Atom 1 | Atom 2 | Distance |
|---|---|---|---|---|---|
| 129 CB | 148 CA | 8.800 | 129 CB | 61 C | 8.881 |
| 129 CB | 156 CZ | 8.941 | 129 CB | 148 CB | 8.990 |
| 129 CB | 148 N | 9.160 | 129 CB | 156 NH1 | 9.403 |
| 129 CB | 27 N | 9.413 | 129 CB | 61 O | 9.484 |
| 129 CB | 27 CD2 | 9.684 | 129 CB | 156 NH2 | 9.697 |
| 129 OG | 61 NE2 | 3.211 | 129 OG | 321 OH2 | 3.564 |
| 129 OG | 130 N | 3.619 | 129 OG | 61 CE1 | 3.630 |
| 129 OG | 128 C | 4.434 | 129 OG | 128 O | 4.438 |
| 129 OG | 61 CD2 | 4.510 | 129 OG | 130 O | 4.520 |
| 129 OG | 130 C | 4.700 | 129 OG | 130 CA | 4.737 |
| 129 OG | 152 SG | 4.869 | 129 OG | 156 N | 4.951 |
| 129 OG | 61 ND1 | 4.957 | 129 OG | 131 OG | 5.240 |
| 129 OG | 131 N | 5.294 | 129 OG | 61 CG | 5.418 |
| 129 OG | 156 CB | 5.456 | 129 OG | 128 CA | 5.777 |
| 129 OG | 156 CA | 5.824 | 129 OG | 131 CA | 5.863 |
| 129 OG | 130 CB | 5.918 | 129 OG | 152 CB | 6.023 |
| 129 OG | 157 NH2 | 6.062 | 129 OG | 131 CB | 6.210 |
| 129 OG | 157 N | 6.306 | 129 OG | 157 CZ | 6.328 |
| 129 OG | 128 N | 6.479 | 129 OG | 156 CD | 6.538 |
| 129 OG | 156 C | 6.538 | 129 OG | 156 CG | 6.606 |
| 129 OG | 157 NE | 6.627 | 129 OG | 128 CB | 6.647 |
| 129 OG | 156 NE | 6.684 | 129 OG | 157 NH1 | 6.781 |
| 129 OG | 148 CE1 | 6.821 | 129 OG | 128 CG2 | 6.880 |
| 129 OG | 61 CB | 6.892 | 129 OG | 157 CG | 6.909 |
| 129 OG | 148 O | 7.020 | 129 OG | 157 CB | 7.045 |
| 129 OG | 152 N | 7.152 | 129 OG | 130 CG | 7.220 |
| 129 OG | 131 C | 7.241 | 129 OG | 152 CA | 7.271 |
| 129 OG | 61 N | 7.286 | 129 OG | 148 ND1 | 7.301 |

Figure 9F

| Atom 1 | Atom 2 | Distance | Atom 1 | Atom 2 | Distance |
|---|---|---|---|---|---|
| 129 OG | 157 CA | 7.352 | 129 OG | 27 O | 7.382 |
| 129 OG | 157 CD | 7.440 | 129 OG | 148 NE2 | 7.511 |
| 129 OG | 156 O | 7.533 | 129 OG | 61 CA | 7.542 |
| 129 OG | 156 CZ | 7.656 | 129 OG | 148 C | 7.748 |
| 129 OG | 131 O | 7.892 | 129 OG | 157 O | 7.929 |
| 129 OG | 128 CG1 | 7.981 | 129 OG | 130 CD1 | 7.982 |
| 129 OG | 156 NH1 | 8.055 | 129 OG | 152 C | 8.115 |
| 129 OG | 27 CD1 | 8.126 | 129 OG | 130 CD2 | 8.232 |
| 129 OG | 157 C | 8.236 | 129 OG | 148 CG | 8.282 |
| 129 OG | 148 CD2 | 8.389 | 129 OG | 27 C | 8.403 |
| 129 OG | 156 NH2 | 8.453 | 129 OG | 152 O | 8.599 |
| 129 OG | 27 CA | 8.623 | 129 OG | 27 CB | 8.757 |
| 129 OG | 27 CG | 8.806 | 129 OG | 61 C | 9.020 |
| 129 OG | 148 CA | 9.033 | 129 OG | 148 N | 9.176 |
| 129 OG | 148 CB | 9.252 | 129 OG | 61 O | 9.484 |
| 129 OG | 27 N | 9.941 | 129 OG | 27 CD2 | 10.246 |
| 129 C | 130 N | 1.326 | 129 C | 130 CA | 2.411 |
| 129 C | 130 C | 3.213 | 129 C | 128 C | 3.490 |
| 129 C | 130 CB | 3.635 | 129 C | 130 O | 3.724 |
| 129 C | 131 N | 3.885 | 129 C | 128 O | 3.993 |
| 129 C | 321 OH2 | 4.454 | 129 C | 128 CA | 4.611 |
| 129 C | 61 CE1 | 4.678 | 129 C | 128 CB | 4.808 |
| 129 C | 148 O | 4.818 | 129 C | 61 NE2 | 4.933 |
| 129 C | 128 CG2 | 4.974 | 129 C | 130 CG | 5.058 |
| 129 C | 131 CA | 5.072 | 129 C | 131 OG | 5.277 |
| 129 C | 27 CD1 | 5.335 | 129 C | 157 NH2 | 5.362 |
| 129 C | 148 C | 5.539 | 129 C | 130 CD1 | 5.558 |
| 129 C | 131 CB | 5.695 | 129 C | 128 N | 5.785 |

Figure 9G

| Atom 1 | Atom 2 | Distance | Atom 1 | Atom 2 | Distance |
|---|---|---|---|---|---|
| 129 C | 61 ND1 | 5.801 | 129 C | 27 O | 5.865 |
| 129 C | 152 SG | 6.060 | 129 C | 27 CG | 6.064 |
| 129 C | 130 CD2 | 6.097 | 129 C | 157 CZ | 6.127 |
| 129 C | 131 C | 6.168 | 129 C | 128 CG1 | 6.177 |
| 129 C | 148 ND1 | 6.186 | 129 C | 61 CD2 | 6.194 |
| 129 C | 148 CE1 | 6.273 | 129 C | 27 CB | 6.327 |
| 129 C | 131 O | 6.367 | 129 C | 157 NE | 6.390 |
| 129 C | 27 CA | 6.461 | 129 C | 61 CG | 6.655 |
| 129 C | 27 C | 6.660 | 129 C | 156 N | 6.982 |
| 129 C | 148 CG | 6.997 | 129 C | 157 NH1 | 7.004 |
| 129 C | 148 CA | 7.009 | 129 C | 148 NE2 | 7.079 |
| 129 C | 152 CB | 7.217 | 129 C | 148 N | 7.349 |
| 129 C | 152 N | 7.356 | 129 C | 157 CB | 7.421 |
| 129 C | 27 CD2 | 7.449 | 129 C | 157 CG | 7.493 |
| 129 C | 148 CD2 | 7.493 | 129 C | 157 N | 7.522 |
| 129 C | 148 CB | 7.544 | 129 C | 157 CD | 7.576 |
| 129 C | 27 N | 7.785 | 129 C | 156 CB | 7.850 |
| 129 C | 156 CA | 7.920 | 129 C | 61 N | 7.951 |
| 129 C | 61 CB | 8.011 | 129 C | 152 CA | 8.029 |
| 129 C | 157 CA | 8.158 | 129 C | 156 C | 8.206 |
| 129 C | 61 CA | 8.206 | 129 C | 157 O | 8.497 |
| 129 C | 157 C | 8.829 | 129 C | 152 C | 8.946 |
| 129 C | 152 O | 9.119 | 129 C | 156 CG | 9.199 |
| 129 C | 156 O | 9.221 | 129 C | 156 NE | 9.287 |
| 129 C | 156 CD | 9.312 | 129 C | 61 C | 9.634 |
| 129 C | 61 O | 10.088 | 129 C | 156 CZ | 10.241 |
| 129 C | 156 NH1 | 10.408 | 129 C | 156 NH2 | 11.188 |
| 129 O | 130 N | 2.224 | 129 O | 130 CA | 2.723 |

Figure 9H

| Atom 1 | Atom 2 | Distance | Atom 1 | Atom 2 | Distance |
|---|---|---|---|---|---|
| 129 O | 130 C | 3.426 | 129 O | 131 N | 3.695 |
| 129 O | 128 C | 3.990 | 129 O | 148 O | 4.045 |
| 129 O | 130 CB | 4.093 | 129 O | 130 O | 4.206 |
| 129 O | 61 CE1 | 4.301 | 129 O | 148 C | 4.586 |
| 129 O | 61 NE2 | 4.732 | 129 O | 128 O | 4.758 |
| 129 O | 128 CA | 4.824 | 129 O | 131 OG | 4.902 |
| 129 O | 131 CA | 4.923 | 129 O | 128 CB | 4.938 |
| 129 O | 148 ND1 | 5.094 | 129 O | 61 ND1 | 5.235 |
| 129 O | 131 CB | 5.297 | 129 O | 148 CE1 | 5.306 |
| 129 O | 130 CG | 5.351 | 129 O | 128 CG2 | 5.375 |
| 129 O | 130 CD1 | 5.522 | 129 O | 321 OH2 | 5.529 |
| 129 O | 27 CD1 | 5.540 | 129 O | 61 CD2 | 5.862 |
| 129 O | 148 CG | 5.954 | 129 O | 131 C | 6.037 |
| 129 O | 148 CA | 6.055 | 129 O | 131 O | 6.122 |
| 129 O | 61 CG | 6.130 | 129 O | 128 N | 6.135 |
| 129 O | 128 CG1 | 6.169 | 129 O | 148 NE2 | 6.209 |
| 129 O | 157 NH2 | 6.258 | 129 O | 152 SG | 6.273 |
| 129 O | 27 CG | 6.346 | 129 O | 148 CB | 6.478 |
| 129 O | 130 CD2 | 6.537 | 129 O | 148 N | 6.546 |
| 129 O | 148 CD2 | 6.565 | 129 O | 27 O | 6.839 |
| 129 O | 27 CB | 6.870 | 129 O | 152 N | 7.121 |
| 129 O | 157 CZ | 7.139 | 129 O | 27 CA | 7.146 |
| 129 O | 61 N | 7.172 | 129 O | 152 CB | 7.181 |
| 129 O | 61 CB | 7.379 | 129 O | 61 CA | 7.403 |
| 129 O | 157 NE | 7.496 | 129 O | 27 C | 7.534 |
| 129 O | 27 CD2 | 7.629 | 129 O | 152 CA | 7.902 |
| 129 O | 157 NH1 | 7.972 | 129 O | 156 N | 7.976 |
| 129 O | 27 N | 8.418 | 129 O | 157 CB | 8.636 |

Figure 9I

| Atom 1 | Atom 2 | Distance | Atom 1 | Atom 2 | Distance |
|--------|--------|----------|--------|--------|----------|
| 129 O | 157 CG | 8.689 | 129 O | 157 N | 8.697 |
| 129 O | 157 CD | 8.727 | 129 O | 61 C | 8.783 |
| 129 O | 156 CB | 8.843 | 129 O | 152 C | 8.964 |
| 129 O | 156 CA | 8.968 | 129 O | 152 O | 9.169 |
| 129 O | 61 O | 9.242 | 129 O | 156 C | 9.344 |
| 129 O | 157 CA | 9.365 | 129 O | 157 O | 9.632 |
| 129 O | 157 C | 10.010 | 129 O | 156 NE | 10.127 |
| 129 O | 156 CG | 10.130 | 129 O | 156 CD | 10.137 |
| 129 O | 156 O | 10.370 | 129 O | 156 CZ | 11.020 |
| 129 O | 156 NH1 | 11.186 | 129 O | 156 NH2 | 11.901 |

Figure 10A

| Atom 1 | Atom 2 | Dist. | Atom 1 | Atom 2 | Dist. | Atom 1 | Atom 2 | Dist. |
|---|---|---|---|---|---|---|---|---|
| 61CA | 148CE1 | 4.683 | 61CB | 148CE1 | 4.657 | 61CG | 148CE1 | 4.271 |
| 61CG | 129OG | 4.982 | 61CD2 | 129OG | 4.142 | 61CD2 | 129CB | 4.339 |
| 61CD2 | 148CE1 | 4.601 | 61CD2 | 129O | 4.620 | 61ND1 | 148CE1 | 4.255 |
| 61ND1 | 129OG | 4.534 | 61ND1 | 131CB | 4.746 | 61ND1 | 148NE2 | 4.920 |
| 61CE1 | 129OG | 3.291 | 61CE1 | 129CB | 4.134 | 61CE1 | 129O | 4.249 |
| 61CE1 | 131CB | 4.357 | 61CE1 | 148CE1 | 4.581 | 61CE1 | 129C | 4.708 |
| 61CE1 | 131CA | 4.974 | 61CE1 | 131N | 4.990 | 61NE2 | 129OG | 2.922 |
| 61NE2 | 129CB | 3.336 | 61NE2 | 129O | 3.621 | 61NE2 | 129C | 4.171 |
| 61NE2 | 129CA | 4.389 | 61NE2 | 148CE1 | 4.781 | 129N | 152SG | 4.570 |
| 129CA | 61NE2 | 4.389 | 129CA | 152SG | 4.909 | 129CB | 61NE2 | 3.336 |
| 129CB | 152SG | 4.005 | 129CB | 61CE1 | 4.134 | 129CB | 61CD2 | 4.339 |
| 129OG | 61NE2 | 2.922 | 129OG | 61CE1 | 3.291 | 129OG | 61CD2 | 4.142 |
| 129OG | 61ND1 | 4.534 | 129OG | 156CG | 4.962 | 129OG | 152SG | 4.970 |
| 129OG | 61CG | 4.982 | 129C | 131N | 3.961 | 129C | 61NE2 | 4.171 |
| 129C | 148O | 4.545 | 129C | 61CE1 | 4.708 | 129O | 61NE2 | 3.621 |
| 129O | 131N | 3.740 | 129O | 148O | 3.795 | 129O | 61CE1 | 4.249 |
| 129O | 148C | 4.547 | 129O | 61CD2 | 4.620 | 129O | 131CA | 4.908 |
| 131N | 148O | 2.713 | 131N | 129O | 3.740 | 131N | 148C | 3.953 |
| 131N | 129C | 3.961 | 131N | 148N | 4.427 | 131N | 148CA | 4.842 |
| 131N | 157NH2 | 4.894 | 131N | 61CE1 | 4.990 | 131CA | 148O | 3.706 |
| 131CA | 148N | 4.689 | 131CA | 148C | 4.843 | 131CA | 129O | 4.908 |
| 131CA | 61CE1 | 4.974 | 131CB | 148NE2 | 3.715 | 131CB | 148O | 3.761 |
| 131CB | 148CD2 | 3.987 | 131CB | 148CE1 | 3.997 | 131CB | 61CE1 | 4.357 |
| 131CB | 148ND1 | 4.391 | 131CB | 148CG | 4.407 | 131CB | 148N | 4.420 |
| 131CB | 148C | 4.685 | 131CB | 61ND1 | 4.746 | 131C | 148O | 4.240 |
| 131C | 148N | 4.409 | 131O | 148N | 3.456 | 131O | 148O | 3.765 |
| 131O | 148C | 4.599 | 131O | 148CA | 4.633 | 148N | 131O | 3.456 |
| 148N | 131C | 4.409 | 148N | 131CB | 4.420 | 148N | 131N | 4.427 |
| 148N | 131CA | 4.689 | 148CA | 131O | 4.633 | 148CA | 131N | 4.842 |
| 148CG | 131CB | 4.407 | 148CD2 | 131CB | 3.987 | 148ND1 | 131CB | 4.391 |
| 148CE1 | 131CB | 3.997 | 148CE1 | 61ND1 | 4.255 | 148CE1 | 61CG | 4.271 |

Figure 10B

| Atom 1 | Atom 2 | Dist. | Atom 1 | Atom 2 | Dist. | Atom 1 | Atom 2 | Dist. |
|---|---|---|---|---|---|---|---|---|
| 148CE1 | 61CE1 | 4.581 | 148CE1 | 61CD2 | 4.601 | 148CE1 | 61CB | 4.657 |
| 148CE1 | 61CA | 4.683 | 148CE1 | 61NE2 | 4.781 | 148NE2 | 131CB | 3.715 |
| 148NE2 | 61ND1 | 4.920 | 148C | 131N | 3.953 | 148C | 129O | 4.547 |
| 148C | 131O | 4.599 | 148C | 131CB | 4.685 | 148C | 131CA | 4.843 |
| 148O | 131N | 2.713 | 148O | 131CA | 3.706 | 148O | 131CB | 3.761 |
| 148O | 131O | 3.765 | 148O | 129O | 3.795 | 148O | 131C | 4.240 |
| 148O | 129C | 4.545 | 152SG | 129CB | 4.005 | 152SG | 129N | 4.570 |
| 152SG | 129CA | 4.909 | 152SG | 129OG | 4.970 | 156N | 157N | 2.799 |
| 156N | 157CA | 4.227 | 156N | 157O | 4.299 | 156N | 157C | 4.735 |
| 156N | 157CB | 4.979 | 156CA | 157N | 2.426 | 156CA | 157CA | 3.792 |
| 156CA | 157O | 4.393 | 156CA | 157C | 4.516 | 156CA | 157CB | 4.758 |
| 156CB | 157N | 3.389 | 156CB | 157CA | 4.669 | 156CG | 157N | 4.416 |
| 156CG | 129OG | 4.962 | 156C | 157N | 1.316 | 156C | 157CA | 2.399 |
| 156C | 157C | 3.245 | 156C | 157O | 3.454 | 156C | 157CB | 3.557 |
| 156C | 157CG | 3.912 | 156O | 157N | 2.214 | 156O | 157CA | 2.690 |
| 156O | 157C | 3.474 | 156O | 157O | 3.931 | 156O | 157CB | 3.972 |
| 156O | 157CG | 4.193 | 157N | 156C | 1.316 | 157N | 156O | 2.214 |
| 157N | 156CA | 2.426 | 157N | 156N | 2.799 | 157N | 156CB | 3.389 |
| 157N | 156CG | 4.416 | 157CA | 156C | 2.399 | 157CA | 156O | 2.690 |
| 157CA | 156CA | 3.792 | 157CA | 156N | 4.227 | 157CA | 156CB | 4.669 |
| 157CB | 156C | 3.557 | 157CB | 156O | 3.972 | 157CB | 156CA | 4.758 |
| 157CB | 156N | 4.979 | 157CG | 156C | 3.912 | 157CG | 156O | 4.193 |
| 157NH2 | 131N | 4.894 | 157C | 156C | 3.245 | 157C | 156O | 3.474 |
| 157C | 156CA | 4.516 | 157C | 156N | 4.735 | 157O | 156C | 3.454 |
| 157O | 156O | 3.931 | 157O | 156N | 4.299 | 157O | 156CA | 4.393 |

Figure 11A

| Atom 1 | Atom 2 | Atom 3 | Angle | Atom 1 | Atom 2 | Atom 3 | Angle |
|---|---|---|---|---|---|---|---|
| 128 C  | 129 N | 128 O   | 27.78  | 128 C  | 129 N | 128 CA  | 35.07  |
| 128 C  | 129 N | 128 CB  | 53.60  | 128 C  | 129 N | 130 N   | 131.02 |
| 128 C  | 129 N | 128 N   | 20.09  | 128 C  | 129 N | 128 CG1 | 67.65  |
| 128 C  | 129 N | 128 CG2 | 43.80  | 128 C  | 129 N | 300 OH2 | 65.57  |
| 128 C  | 129 N | 301 OH2 | 90.41  | 128 C  | 129 N | 130 CA  | 137.76 |
| 128 C  | 129 N | 152 SG  | 68.42  | 128 C  | 129 N | 130 CB  | 124.22 |
| 128 C  | 129 N | 27 CD1  | 92.40  | 128 C  | 129 N | 130 C   | 143.31 |
| 128 C  | 129 N | 61 CE1  | 138.31 | 128 C  | 129 N | 152 N   | 72.55  |
| 128 C  | 129 N | 61 NE2  | 151.25 | 128 C  | 129 N | 130 O   | 135.18 |
| 128 C  | 129 N | 152 CB  | 77.98  | 128 O  | 129 N | 128 CA  | 62.79  |
| 128 O  | 129 N | 128 CB  | 75.52  | 128 O  | 129 N | 130 N   | 109.67 |
| 128 O  | 129 N | 128 N   | 47.34  | 128 O  | 129 N | 128 CG1 | 92.42  |
| 128 O  | 129 N | 128 CG2 | 60.40  | 128 O  | 129 N | 300 OH2 | 38.19  |
| 128 O  | 129 N | 301 OH2 | 68.39  | 128 O  | 129 N | 130 CA  | 119.47 |
| 128 O  | 129 N | 152 SG  | 69.72  | 128 O  | 129 N | 130 CB  | 109.53 |
| 128 O  | 129 N | 27 CD1  | 98.81  | 128 O  | 129 N | 130 C   | 119.76 |
| 128 O  | 129 N | 61 CE1  | 120.22 | 128 O  | 129 N | 152 N   | 87.80  |
| 128 O  | 129 N | 61 NE2  | 132.37 | 128 O  | 129 N | 130 O   | 109.59 |
| 128 O  | 129 N | 152 CB  | 82.37  | 128 CA | 129 N | 128 CB  | 31.92  |
| 128 CA | 129 N | 130 N   | 144.31 | 128 CA | 129 N | 128 N   | 17.71  |
| 128 CA | 129 N | 128 CG1 | 37.17  | 128 CA | 129 N | 128 CG2 | 37.17  |
| 128 CA | 129 N | 300 OH2 | 99.90  | 128 CA | 129 N | 301 OH2 | 116.05 |
| 128 CA | 129 N | 130 CA  | 141.26 | 128 CA | 129 N | 152 SG  | 76.56  |
| 128 CA | 129 N | 130 CB  | 128.79 | 128 CA | 129 N | 27 CD1  | 81.21  |
| 128 CA | 129 N | 130 C   | 154.23 | 128 CA | 129 N | 61 CE1  | 146.19 |
| 128 CA | 129 N | 152 N   | 60.89  | 128 CA | 129 N | 61 NE2  | 149.59 |
| 128 CA | 129 N | 130 O   | 157.70 | 128 CA | 129 N | 152 CB  | 79.10  |
| 128 CB | 129 N | 130 N   | 113.66 | 128 CB | 129 N | 128 N   | 45.76  |
| 128 CB | 129 N | 128 CG1 | 18.75  | 128 CB | 129 N | 128 CG2 | 18.18  |

Figure 11B

| Atom 1 | Atom 2 | Atom 3 | Angle | Atom 1 | Atom 2 | Atom 3 | Angle |
|---|---|---|---|---|---|---|---|
| 128 CB | 129 N | 300 OH2 | 102.48 | 128 CB | 129 N | 301 OH2 | 98.82 |
| 128 CB | 129 N | 130 CA | 109.37 | 128 CB | 129 N | 152 SG | 108.47 |
| 128 CB | 129 N | 130 CB | 97.50 | 128 CB | 129 N | 27 CD1 | 49.33 |
| 128 CB | 129 N | 130 C | 122.36 | 128 CB | 129 N | 61 CE1 | 162.96 |
| 128 CB | 129 N | 152 N | 89.08 | 128 CB | 129 N | 61 NE2 | 152.10 |
| 128 CB | 129 N | 130 O | 127.99 | 128 CB | 129 N | 152 CB | 110.07 |
| 130 N | 129 N | 128 N | 147.37 | 130 N | 129 N | 128 CG1 | 115.80 |
| 130 N | 129 N | 128 CG2 | 107.47 | 130 N | 129 N | 300 OH2 | 74.30 |
| 130 N | 129 N | 301 OH2 | 41.52 | 130 N | 129 N | 130 CA | 11.22 |
| 130 N | 129 N | 152 SG | 136.22 | 130 N | 129 N | 130 CB | 16.40 |
| 130 N | 129 N | 27 CD1 | 65.01 | 130 N | 129 N | 130 C | 12.93 |
| 130 N | 129 N | 61 CE1 | 69.16 | 130 N | 129 N | 152 N | 153.81 |
| 130 N | 129 N | 61 NE2 | 62.79 | 130 N | 129 N | 130 O | 14.40 |
| 130 N | 129 N | 152 CB | 136.24 | 128 N | 129 N | 128 CG1 | 54.48 |
| 128 N | 129 N | 128 CG2 | 44.02 | 128 N | 129 N | 300 OH2 | 85.46 |
| 128 N | 129 N | 301 OH2 | 109.26 | 128 N | 129 N | 130 CA | 150.10 |
| 128 N | 129 N | 152 SG | 65.04 | 128 N | 129 N | 130 CB | 135.82 |
| 128 N | 129 N | 27 CD1 | 93.01 | 128 N | 129 N | 130 C | 160.29 |
| 128 N | 129 N | 61 CE1 | 139.12 | 128 N | 129 N | 152 N | 58.50 |
| 128 N | 129 N | 61 NE2 | 148.56 | 128 N | 129 N | 130 O | 154.73 |
| 128 N | 129 N | 152 CB | 70.88 | 128 CG1 | 129 N | 128 CG2 | 36.88 |
| 128 CG1 | 129 N | 300 OH2 | 121.22 | 128 CG1 | 129 N | 301 OH2 | 113.17 |
| 128 CG1 | 129 N | 130 CA | 108.19 | 128 CG1 | 129 N | 152 SG | 107.90 |
| 128 CG1 | 129 N | 130 CB | 99.65 | 128 CG1 | 129 N | 27 CD1 | 52.13 |
| 128 CG1 | 129 N | 130 C | 120.44 | 128 CG1 | 129 N | 61 CE1 | 144.24 |
| 128 CG1 | 129 N | 152 N | 81.54 | 128 CG1 | 129 N | 61 NE2 | 134.44 |
| 128 CG1 | 129 N | 130 O | 129.62 | 128 CG1 | 129 N | 152 CB | 105.10 |
| 128 CG2 | 129 N | 300 OH2 | 84.35 | 128 CG2 | 129 N | 301 OH2 | 83.51 |
| 128 CG2 | 129 N | 130 CA | 106.72 | 128 CG2 | 129 N | 152 SG | 108.86 |

Figure 11C

| Atom 1 | Atom 2 | Atom 3 | Angle | Atom 1 | Atom 2 | Atom 3 | Angle |
|---|---|---|---|---|---|---|---|
| 128 CG2 | 129 N | 130 CB | 92.93 | 128 CG2 | 129 N | 27 CD1 | 49.78 |
| 128 CG2 | 129 N | 130 C | 118.86 | 128 CG2 | 129 N | 61 CE1 | 176.63 |
| 128 CG2 | 129 N | 152 N | 98.06 | 128 CG2 | 129 N | 61 NE2 | 164.94 |
| 128 CG2 | 129 N | 130 O | 120.53 | 128 CG2 | 129 N | 152 CB | 114.63 |
| 300 OH2 | 129 N | 301 OH2 | 37.04 | 300 OH2 | 129 N | 130 CA | 85.23 |
| 300 OH2 | 129 N | 152 SG | 85.78 | 300 OH2 | 129 N | 130 CB | 79.65 |
| 300 OH2 | 129 N | 27 CD1 | 96.74 | 300 OH2 | 129 N | 130 C | 82.52 |
| 300 OH2 | 129 N | 61 CE1 | 94.48 | 300 OH2 | 129 N | 152 N | 114.85 |
| 300 OH2 | 129 N | 61 NE2 | 102.75 | 300 OH2 | 129 N | 130 O | 71.73 |
| 300 OH2 | 129 N | 152 CB | 97.96 | 301 OH2 | 129 N | 130 CA | 51.10 |
| 301 OH2 | 129 N | 152 SG | 121.22 | 301 OH2 | 129 N | 130 CB | 43.03 |
| 301 OH2 | 129 N | 27 CD1 | 67.96 | 301 OH2 | 129 N | 130 C | 52.98 |
| 301 OH2 | 129 N | 61 CE1 | 93.65 | 301 OH2 | 129 N | 152 N | 151.80 |
| 301 OH2 | 129 N | 61 NE2 | 94.17 | 301 OH2 | 129 N | 130 O | 45.53 |
| 301 OH2 | 129 N | 152 CB | 131.91 | 130 CA | 129 N | 152 SG | 142.15 |
| 130 CA | 129 N | 130 CB | 14.34 | 130 CA | 129 N | 27 CD1 | 60.05 |
| 130 CA | 129 N | 130 C | 12.99 | 130 CA | 129 N | 61 CE1 | 70.00 |
| 130 CA | 129 N | 152 N | 149.69 | 130 CA | 129 N | 61 NE2 | 61.34 |
| 130 CA | 129 N | 130 O | 21.72 | 130 CA | 129 N | 152 CB | 138.64 |
| 152 SG | 129 N | 130 CB | 152.45 | 152 SG | 129 N | 27 CD1 | 157.72 |
| 152 SG | 129 N | 130 C | 129.15 | 152 SG | 129 N | 61 CE1 | 74.16 |
| 152 SG | 129 N | 152 N | 31.77 | 152 SG | 129 N | 61 NE2 | 85.11 |
| 152 SG | 129 N | 130 O | 122.05 | 152 SG | 129 N | 152 CB | 13.04 |
| 130 CB | 129 N | 27 CD1 | 48.62 | 130 CB | 129 N | 130 C | 25.95 |
| 130 CB | 129 N | 61 CE1 | 83.74 | 130 CB | 129 N | 152 N | 162.50 |
| 130 CB | 129 N | 61 NE2 | 75.60 | 130 CB | 129 N | 130 O | 30.77 |
| 130 CB | 129 N | 152 CB | 152.09 | 27 CD1 | 129 N | 130 C | 73.04 |
| 27 CD1 | 129 N | 61 CE1 | 127.40 | 27 CD1 | 129 N | 152 N | 133.24 |
| 27 CD1 | 129 N | 61 NE2 | 115.61 | 27 CD1 | 129 N | 130 O | 79.39 |

Figure 11D

| Atom 1 | Atom 2 | Atom 3 | Angle | Atom 1 | Atom 2 | Atom 3 | Angle |
|---|---|---|---|---|---|---|---|
| 27 CD1 | 129 N | 152 CB | 157.15 | 130 C | 129 N | 61 CE1 | 57.80 |
| 130 C | 129 N | 152 N | 141.13 | 130 C | 129 N | 61 NE2 | 50.34 |
| 130 C | 129 N | 130 O | 11.69 | 130 C | 129 N | 152 CB | 126.24 |
| 61 CE1 | 129 N | 152 N | 85.31 | 61 CE1 | 129 N | 61 NE2 | 13.10 |
| 61 CE1 | 129 N | 130 O | 56.11 | 61 CE1 | 129 N | 152 CB | 68.65 |
| 152 N | 129 N | 61 NE2 | 91.02 | 152 N | 129 N | 130 O | 141.41 |
| 152 N | 129 N | 152 CB | 24.01 | 61 NE2 | 129 N | 130 O | 51.58 |
| 61 NE2 | 129 N | 152 CB | 77.90 | 130 O | 129 N | 152 CB | 121.94 |
| 128 C | 129 CA | 130 N | 125.69 | 128 C | 129 CA | 128 O | 27.01 |
| 128 C | 129 CA | 301 OH2 | 98.02 | 128 C | 129 CA | 300 OH2 | 77.47 |
| 128 C | 129 CA | 128 CA | 13.00 | 128 C | 129 CA | 130 CA | 128.11 |
| 128 C | 129 CA | 128 CB | 28.37 | 128 C | 129 CA | 130 C | 146.45 |
| 128 C | 129 CA | 130 O | 152.69 | 128 C | 129 CA | 128 N | 5.31 |
| 128 C | 129 CA | 130 CB | 117.06 | 128 C | 129 CA | 61 CE1 | 136.63 |
| 128 C | 129 CA | 152 SG | 60.33 | 128 C | 129 CA | 128 CG2 | 28.36 |
| 128 C | 129 CA | 61 NE2 | 140.27 | 128 C | 129 CA | 128 CG1 | 36.20 |
| 128 C | 129 CA | 131 N | 147.20 | 128 C | 129 CA | 157 NH2 | 130.71 |
| 128 C | 129 CA | 156 N | 89.11 | 128 C | 129 CA | 27 O | 81.50 |
| 128 C | 129 CA | 61 ND1 | 128.82 | 128 C | 129 CA | 131 OG | 157.02 |
| 128 C | 129 CA | 27 CD1 | 70.88 | 130 N | 129 CA | 128 O | 125.80 |
| 130 N | 129 CA | 301 OH2 | 53.64 | 130 N | 129 CA | 300 OH2 | 97.55 |
| 130 N | 129 CA | 128 CA | 121.50 | 130 N | 129 CA | 130 CA | 9.21 |
| 130 N | 129 CA | 128 CB | 100.10 | 130 N | 129 CA | 130 C | 21.73 |
| 130 N | 129 CA | 130 O | 29.22 | 130 N | 129 CA | 128 N | 131.00 |
| 130 N | 129 CA | 130 CB | 8.71 | 130 N | 129 CA | 61 CE1 | 92.68 |
| 130 N | 129 CA | 152 SG | 172.57 | 130 N | 129 CA | 128 CG2 | 97.39 |
| 130 N | 129 CA | 61 NE2 | 81.36 | 130 N | 129 CA | 128 CG1 | 98.43 |
| 130 N | 129 CA | 131 N | 29.69 | 130 N | 129 CA | 157 NH2 | 38.28 |
| 130 N | 129 CA | 156 N | 115.10 | 130 N | 129 CA | 27 O | 55.83 |

Figure 11E

| Atom 1 | Atom 2 | Atom 3 | Angle | Atom 1 | Atom 2 | Atom 3 | Angle |
|---|---|---|---|---|---|---|---|
| 130 N   | 129 CA | 61 ND1  | 100.25 | 130 N   | 129 CA | 131 OG  | 57.41 |
| 130 N   | 129 CA | 27 CD1  | 55.65  | 128 O   | 129 CA | 301 OH2 | 80.40 |
| 128 O   | 129 CA | 300 OH2 | 50.94  | 128 O   | 129 CA | 128 CA  | 39.99 |
| 128 O   | 129 CA | 130 CA  | 132.82 | 128 O   | 129 CA | 128 CB  | 49.62 |
| 128 O   | 129 CA | 130 C   | 145.78 | 128 O   | 129 CA | 130 O   | 139.75 |
| 128 O   | 129 CA | 128 N   | 26.80  | 128 O   | 129 CA | 130 CB  | 117.84 |
| 128 O   | 129 CA | 61 CE1  | 139.97 | 128 O   | 129 CA | 152 SG  | 61.62 |
| 128 O   | 129 CA | 128 CG2 | 40.41  | 128 O   | 129 CA | 61 NE2  | 152.81 |
| 128 O   | 129 CA | 128 CG1 | 60.51  | 128 O   | 129 CA | 131 N   | 155.49 |
| 128 O   | 129 CA | 157 NH2 | 111.44 | 128 O   | 129 CA | 156 N   | 63.96 |
| 128 O   | 129 CA | 27 O    | 70.79  | 128 O   | 129 CA | 61 ND1  | 133.08 |
| 128 O   | 129 CA | 131 OG  | 174.20 | 128 O   | 129 CA | 27 CD1  | 81.81 |
| 301 OH2 | 129 CA | 300 OH2 | 44.61  | 301 OH2 | 129 CA | 128 CA  | 105.46 |
| 301 OH2 | 129 CA | 130 CA  | 62.85  | 301 OH2 | 129 CA | 128 CB  | 92.06 |
| 301 OH2 | 129 CA | 130 C   | 67.04  | 301 OH2 | 129 CA | 130 O   | 59.54 |
| 301 OH2 | 129 CA | 128 N   | 101.56 | 301 OH2 | 129 CA | 130 CB  | 50.15 |
| 301 OH2 | 129 CA | 61 CE1  | 123.03 | 301 OH2 | 129 CA | 152 SG  | 132.37 |
| 301 OH2 | 129 CA | 128 CG2 | 78.34  | 301 OH2 | 129 CA | 61 NE2  | 121.58 |
| 301 OH2 | 129 CA | 128 CG1 | 101.18 | 301 OH2 | 129 CA | 131 N   | 78.51 |
| 301 OH2 | 129 CA | 157 NH2 | 32.72  | 301 OH2 | 129 CA | 156 N   | 70.57 |
| 301 OH2 | 129 CA | 27 O    | 21.79  | 301 OH2 | 129 CA | 61 ND1  | 129.71 |
| 301 OH2 | 129 CA | 131 OG  | 99.72  | 301 OH2 | 129 CA | 27 CD1  | 65.65 |
| 300 OH2 | 129 CA | 128 CA  | 90.09  | 300 OH2 | 129 CA | 130 CA  | 106.66 |
| 300 OH2 | 129 CA | 128 CB  | 92.04  | 300 OH2 | 129 CA | 130 C   | 105.83 |
| 300 OH2 | 129 CA | 130 O   | 93.27  | 300 OH2 | 129 CA | 128 N   | 77.74 |
| 300 OH2 | 129 CA | 130 CB  | 94.75  | 300 OH2 | 129 CA | 61 CE1  | 120.91 |
| 300 OH2 | 129 CA | 152 SG  | 87.94  | 300 OH2 | 129 CA | 128 CG2 | 77.18 |
| 300 OH2 | 129 CA | 61 NE2  | 132.46 | 300 OH2 | 129 CA | 128 CG1 | 104.62 |
| 300 OH2 | 129 CA | 131 N   | 117.07 | 300 OH2 | 129 CA | 157 NH2 | 65.58 |

Figure 11F

| Atom 1 | Atom 2 | Atom 3 | Angle | Atom 1 | Atom 2 | Atom 3 | Angle |
|---|---|---|---|---|---|---|---|
| 300 OH2 | 129 CA | 156 N | 32.29 | 300 OH2 | 129 CA | 27 O | 53.27 |
| 300 OH2 | 129 CA | 61 ND1 | 121.41 | 300 OH2 | 129 CA | 131 OG | 125.51 |
| 300 OH2 | 129 CA | 27 CD1 | 95.60 | 128 CA | 129 CA | 130 CA | 121.64 |
| 128 CA | 129 CA | 128 CB | 21.44 | 128 CA | 129 CA | 130 C | 139.59 |
| 128 CA | 129 CA | 130 O | 150.69 | 128 CA | 129 CA | 128 N | 15.01 |
| 128 CA | 129 CA | 130 CB | 113.43 | 128 CA | 129 CA | 61 CE1 | 131.37 |
| 128 CA | 129 CA | 152 SG | 63.23 | 128 CA | 129 CA | 128 CG2 | 28.76 |
| 128 CA | 129 CA | 61 NE2 | 131.02 | 128 CA | 129 CA | 128 CG1 | 25.36 |
| 128 CA | 129 CA | 131 N | 137.09 | 128 CA | 129 CA | 157 NH2 | 137.03 |
| 128 CA | 129 CA | 156 N | 101.59 | 128 CA | 129 CA | 27 O | 86.45 |
| 128 CA | 129 CA | 61 ND1 | 124.18 | 128 CA | 129 CA | 131 OG | 144.28 |
| 128 CA | 129 CA | 27 CD1 | 65.91 | 130 CA | 129 CA | 128 CB | 100.77 |
| 130 CA | 129 CA | 130 C | 18.37 | 130 CA | 129 CA | 130 O | 30.26 |
| 130 CA | 129 CA | 128 N | 133.26 | 130 CA | 129 CA | 130 CB | 15.25 |
| 130 CA | 129 CA | 61 CE1 | 86.73 | 130 CA | 129 CA | 152 SG | 164.09 |
| 130 CA | 129 CA | 128 CG2 | 100.52 | 130 CA | 129 CA | 61 NE2 | 74.32 |
| 130 CA | 129 CA | 128 CG1 | 97.11 | 130 CA | 129 CA | 131 N | 23.02 |
| 130 CA | 129 CA | 157 NH2 | 45.55 | 130 CA | 129 CA | 156 N | 122.31 |
| 130 CA | 129 CA | 27 O | 64.16 | 130 CA | 129 CA | 61 ND1 | 93.98 |
| 130 CA | 129 CA | 131 OG | 51.03 | 130 CA | 129 CA | 27 CD1 | 57.24 |
| 128 CB | 129 CA | 130 C | 119.05 | 128 CB | 129 CA | 130 O | 129.25 |
| 128 CB | 129 CA | 128 N | 33.01 | 128 CB | 129 CA | 130 CB | 92.00 |
| 128 CB | 129 CA | 61 CE1 | 142.78 | 128 CB | 129 CA | 152 SG | 84.64 |
| 128 CB | 129 CA | 128 CG2 | 15.54 | 128 CB | 129 CA | 61 NE2 | 135.21 |
| 128 CB | 129 CA | 128 CG1 | 12.58 | 128 CB | 129 CA | 131 N | 118.84 |
| 128 CB | 129 CA | 157 NH2 | 119.85 | 128 CB | 129 CA | 156 N | 113.35 |
| 128 CB | 129 CA | 27 O | 70.86 | 128 CB | 129 CA | 61 ND1 | 137.61 |
| 128 CB | 129 CA | 131 OG | 136.03 | 128 CB | 129 CA | 27 CD1 | 44.48 |
| 130 C | 129 CA | 130 O | 15.09 | 130 C | 129 CA | 128 N | 151.62 |

Figure 11G

| Atom 1 | Atom 2 | Atom 3 | Angle | Atom 1 | Atom 2 | Atom 3 | Angle |
|---|---|---|---|---|---|---|---|
| 130 C | 129 CA | 130 CB | 30.40 | 130 C | 129 CA | 61 CE1 | 71.14 |
| 130 C | 129 CA | 152 SG | 151.30 | 130 C | 129 CA | 128 CG2 | 118.57 |
| 130 C | 129 CA | 61 NE2 | 60.78 | 130 C | 129 CA | 128 CG1 | 114.54 |
| 130 C | 129 CA | 131 N | 11.59 | 130 C | 129 CA | 157 NH2 | 40.26 |
| 130 C | 129 CA | 156 N | 111.69 | 130 C | 129 CA | 27 O | 75.02 |
| 130 C | 129 CA | 61 ND1 | 78.83 | 130 C | 129 CA | 131 OG | 36.51 |
| 130 C | 129 CA | 27 CD1 | 75.57 | 130 O | 129 CA | 128 N | 157.77 |
| 130 O | 129 CA | 130 CB | 37.27 | 130 O | 129 CA | 61 CE1 | 70.08 |
| 130 O | 129 CA | 152 SG | 145.95 | 130 O | 129 CA | 128 CG2 | 124.77 |
| 130 O | 129 CA | 61 NE2 | 63.32 | 130 O | 129 CA | 128 CG1 | 127.20 |
| 130 O | 129 CA | 131 N | 24.36 | 130 O | 129 CA | 157 NH2 | 28.62 |
| 130 O | 129 CA | 156 N | 96.60 | 130 O | 129 CA | 27 O | 72.57 |
| 130 O | 129 CA | 61 ND1 | 77.97 | 130 O | 129 CA | 131 OG | 40.22 |
| 130 O | 129 CA | 27 CD1 | 84.78 | 128 N | 129 CA | 130 CB | 122.37 |
| 128 N | 129 CA | 61 CE1 | 131.96 | 128 N | 129 CA | 152 SG | 55.02 |
| 128 N | 129 CA | 128 CG2 | 33.67 | 128 N | 129 CA | 61 NE2 | 136.85 |
| 128 N | 129 CA | 128 CG1 | 39.79 | 128 N | 129 CA | 131 N | 151.51 |
| 128 N | 129 CA | 157 NH2 | 134.26 | 128 N | 129 CA | 156 N | 86.62 |
| 128 N | 129 CA | 27 O | 85.93 | 128 N | 129 CA | 61 ND1 | 124.09 |
| 128 N | 129 CA | 131 OG | 156.23 | 128 N | 129 CA | 27 CD1 | 76.06 |
| 130 CB | 129 CA | 61 CE1 | 101.15 | 130 CB | 129 CA | 152 SG | 175.78 |
| 130 CB | 129 CA | 128 CG2 | 88.73 | 130 CB | 129 CA | 61 NE2 | 89.34 |
| 130 CB | 129 CA | 128 CG1 | 91.22 | 130 CB | 129 CA | 131 N | 37.71 |
| 130 CB | 129 CA | 157 NH2 | 41.19 | 130 CB | 129 CA | 156 N | 116.31 |
| 130 CB | 129 CA | 27 O | 49.04 | 130 CB | 129 CA | 61 ND1 | 108.63 |
| 130 CB | 129 CA | 131 OG | 65.67 | 130 CB | 129 CA | 27 CD1 | 47.53 |
| 61 CE1 | 129 CA | 152 SG | 80.17 | 61 CE1 | 129 CA | 128 CG2 | 157.98 |
| 61 CE1 | 129 CA | 61 NE2 | 15.28 | 61 CE1 | 129 CA | 128 CG1 | 131.11 |
| 61 CE1 | 129 CA | 131 N | 63.71 | 61 CE1 | 129 CA | 157 NH2 | 91.44 |

Figure 11H

| Atom 1 | Atom 2 | Atom 3 | Angle | Atom 1 | Atom 2 | Atom 3 | Angle |
|---|---|---|---|---|---|---|---|
| 61 CE1 | 129 CA | 156 N | 91.80 | 61 CE1 | 129 CA | 27 O | 141.74 |
| 61 CE1 | 129 CA | 61 ND1 | 7.90 | 61 CE1 | 129 CA | 131 OG | 35.72 |
| 61 CE1 | 129 CA | 27 CD1 | 135.69 | 152 SG | 129 CA | 128 CG2 | 88.69 |
| 152 SG | 129 CA | 61 NE2 | 91.25 | 152 SG | 129 CA | 128 CG1 | 84.94 |
| 152 SG | 129 CA | 131 N | 142.89 | 152 SG | 129 CA | 157 NH2 | 143.00 |
| 152 SG | 129 CA | 156 N | 67.51 | 152 SG | 129 CA | 27 O | 131.52 |
| 152 SG | 129 CA | 61 ND1 | 72.53 | 152 SG | 129 CA | 131 OG | 115.26 |
| 152 SG | 129 CA | 27 CD1 | 129.01 | 128 CG2 | 129 CA | 61 NE2 | 150.34 |
| 128 CG2 | 129 CA | 128 CG1 | 27.86 | 128 CG2 | 129 CA | 131 N | 121.91 |
| 128 CG2 | 129 CA | 157 NH2 | 108.55 | 128 CG2 | 129 CA | 156 N | 101.46 |
| 128 CG2 | 129 CA | 27 O | 58.11 | 128 CG2 | 129 CA | 61 ND1 | 151.95 |
| 128 CG2 | 129 CA | 131 OG | 145.36 | 128 CG2 | 129 CA | 27 CD1 | 43.69 |
| 61 NE2 | 129 CA | 128 CG1 | 122.66 | 61 NE2 | 129 CA | 131 N | 51.69 |
| 61 NE2 | 129 CA | 157 NH2 | 88.87 | 61 NE2 | 129 CA | 156 N | 105.87 |
| 61 NE2 | 129 CA | 27 O | 135.44 | 61 NE2 | 129 CA | 61 ND1 | 20.52 |
| 61 NE2 | 129 CA | 131 OG | 24.28 | 61 NE2 | 129 CA | 27 CD1 | 120.42 |
| 128 CG1 | 129 CA | 131 N | 111.84 | 128 CG1 | 129 CA | 157 NH2 | 125.19 |
| 128 CG1 | 129 CA | 156 N | 124.45 | 128 CG1 | 129 CA | 27 O | 79.45 |
| 128 CG1 | 129 CA | 61 ND1 | 126.82 | 128 CG1 | 129 CA | 131 OG | 124.90 |
| 128 CG1 | 129 CA | 27 CD1 | 44.91 | 131 N | 129 CA | 157 NH2 | 51.52 |
| 131 N | 129 CA | 156 N | 119.25 | 131 N | 129 CA | 27 O | 85.09 |
| 131 N | 129 CA | 61 ND1 | 71.01 | 131 N | 129 CA | 131 OG | 28.03 |
| 131 N | 129 CA | 27 CD1 | 78.23 | 149 CA | 129 CA | 61 ND1 | 80.64 |
| 157 NH2 | 129 CA | 156 N | 76.91 | 157 NH2 | 129 CA | 27 O | 50.58 |
| 157 NH2 | 129 CA | 61 ND1 | 98.77 | 157 NH2 | 129 CA | 131 OG | 67.78 |
| 157 NH2 | 129 CA | 27 CD1 | 81.14 | 156 N | 129 CA | 27 O | 84.43 |
| 156 N | 129 CA | 61 ND1 | 90.58 | 156 N | 129 CA | 131 OG | 110.53 |
| 156 N | 129 CA | 27 CD1 | 127.86 | 27 O | 129 CA | 61 ND1 | 149.29 |
| 27 O | 129 CA | 131 OG | 111.28 | 27 O | 129 CA | 27 CD1 | 46.17 |

Figure 11I

| Atom 1 | Atom 2 | Atom 3 | Angle | Atom 1 | Atom 2 | Atom 3 | Angle |
|---|---|---|---|---|---|---|---|
| 61 ND1 | 129 CA | 131 OG | 42.99 | 61 ND1 | 129 CA | 27 CD1 | 139.57 |
| 131 OG | 129 CA | 27 CD1 | 103.57 | 130 N | 129 C | 130 CA | 31.03 |
| 130 N | 129 C | 130 C | 44.35 | 130 N | 129 C | 128 C | 114.04 |
| 130 N | 129 C | 130 O | 42.82 | 130 N | 129 C | 130 CB | 19.91 |
| 130 N | 129 C | 301 OH2 | 42.62 | 130 N | 129 C | 131 N | 59.62 |
| 130 N | 129 C | 128 O | 103.83 | 130 N | 129 C | 61 NE2 | 119.34 |
| 130 N | 129 C | 128 CA | 117.36 | 130 N | 129 C | 148 O | 81.79 |
| 130 N | 129 C | 61 CE1 | 123.79 | 130 N | 129 C | 300 OH2 | 77.83 |
| 130 N | 129 C | 128 CB | 102.79 | 130 N | 129 C | 131 OG | 90.42 |
| 130 N | 129 C | 130 CG | 27.54 | 130 N | 129 C | 131 CA | 64.03 |
| 130 N | 129 C | 157 NH2 | 28.97 | 130 N | 129 C | 130 CD1 | 42.98 |
| 130 N | 129 C | 27 CD1 | 63.27 | 130 N | 129 C | 148 C | 89.12 |
| 130 N | 129 C | 128 CG1 | 107.50 | 130 N | 129 C | 128 CG2 | 91.90 |
| 130 N | 129 C | 131 CB | 79.27 | 130 N | 129 C | 61 CD2 | 123.37 |
| 130 N | 129 C | 128 N | 115.99 | 130 N | 129 C | 61 ND1 | 129.60 |
| 130 N | 129 C | 27 O | 39.51 | 130 CA | 129 C | 130 C | 26.56 |
| 130 CA | 129 C | 128 C | 137.39 | 130 CA | 129 C | 130 O | 39.60 |
| 130 CA | 129 C | 130 CB | 17.13 | 130 CA | 129 C | 301 OH2 | 73.65 |
| 130 CA | 129 C | 131 N | 34.38 | 130 CA | 129 C | 128 O | 132.43 |
| 130 CA | 129 C | 61 NE2 | 99.29 | 130 CA | 129 C | 128 CA | 133.32 |
| 130 CA | 129 C | 148 O | 50.83 | 130 CA | 129 C | 61 CE1 | 110.86 |
| 130 CA | 129 C | 300 OH2 | 108.66 | 130 CA | 129 C | 128 CB | 114.56 |
| 130 CA | 129 C | 131 OG | 69.13 | 130 CA | 129 C | 130 CG | 7.26 |
| 130 CA | 129 C | 131 CA | 42.82 | 130 CA | 129 C | 157 NH2 | 49.39 |
| 130 CA | 129 C | 130 CD1 | 17.50 | 130 CA | 129 C | 27 CD1 | 66.85 |
| 130 CA | 129 C | 148 C | 58.69 | 130 CA | 129 C | 128 CG1 | 111.76 |
| 130 CA | 129 C | 128 CG2 | 108.48 | 130 CA | 129 C | 131 CB | 56.14 |
| 130 CA | 129 C | 61 CD2 | 100.32 | 130 CA | 129 C | 128 N | 136.88 |
| 130 CA | 129 C | 61 ND1 | 115.62 | 130 CA | 129 C | 27 O | 66.79 |

Figure 11J

| Atom 1 | Atom 2 | Atom 3 | Angle | Atom 1 | Atom 2 | Atom 3 | Angle |
|---|---|---|---|---|---|---|---|
| 130 C | 129 C | 128 C | 158.17 | 130 C | 129 C | 130 O | 18.93 |
| 130 C | 129 C | 130 CB | 41.05 | 130 C | 129 C | 301 OH2 | 81.01 |
| 130 C | 129 C | 131 N | 17.29 | 130 C | 129 C | 128 O | 144.59 |
| 130 C | 129 C | 61 NE2 | 76.44 | 130 C | 129 C | 128 CA | 159.47 |
| 130 C | 129 C | 148 O | 52.05 | 130 C | 129 C | 61 CE1 | 85.54 |
| 130 C | 129 C | 300 OH2 | 109.33 | 130 C | 129 C | 128 CB | 141.05 |
| 130 C | 129 C | 131 OG | 46.45 | 130 C | 129 C | 130 CG | 33.42 |
| 130 C | 129 C | 131 CA | 19.68 | 130 C | 129 C | 157 NH2 | 44.37 |
| 130 C | 129 C | 130 CD1 | 40.52 | 130 C | 129 C | 27 CD1 | 93.41 |
| 130 C | 129 C | 148 C | 62.15 | 130 C | 129 C | 128 CG1 | 137.68 |
| 130 C | 129 C | 128 CG2 | 133.67 | 130 C | 129 C | 131 CB | 34.92 |
| 130 C | 129 C | 61 CD2 | 79.40 | 130 C | 129 C | 128 N | 160.30 |
| 130 C | 129 C | 61 ND1 | 90.76 | 130 C | 129 C | 27 O | 83.83 |
| 128 C | 129 C | 130 O | 145.98 | 128 C | 129 C | 130 CB | 120.61 |
| 128 C | 129 C | 301 OH2 | 77.98 | 128 C | 129 C | 131 N | 171.40 |
| 128 C | 129 C | 128 O | 17.11 | 128 C | 129 C | 61 NE2 | 123.21 |
| 128 C | 129 C | 128 CA | 14.44 | 128 C | 129 C | 148 O | 140.12 |
| 128 C | 129 C | 61 CE1 | 111.33 | 128 C | 129 C | 300 OH2 | 54.23 |
| 128 C | 129 C | 128 CB | 29.26 | 128 C | 129 C | 131 OG | 153.47 |
| 128 C | 129 C | 130 CG | 130.17 | 128 C | 129 C | 131 CA | 175.37 |
| 128 C | 129 C | 157 NH2 | 116.37 | 128 C | 129 C | 130 CD1 | 130.04 |
| 128 C | 129 C | 27 CD1 | 74.34 | 128 C | 129 C | 148 C | 130.33 |
| 128 C | 129 C | 128 CG1 | 39.65 | 128 C | 129 C | 128 CG2 | 30.19 |
| 128 C | 129 C | 131 CB | 166.26 | 128 C | 129 C | 61 CD2 | 121.36 |
| 128 C | 129 C | 128 N | 5.25 | 128 C | 129 C | 61 ND1 | 106.87 |
| 128 C | 129 C | 27 O | 74.53 | 130 O | 129 C | 130 CB | 48.72 |
| 130 O | 129 C | 301 OH2 | 69.31 | 130 O | 129 C | 131 N | 33.52 |
| 130 O | 129 C | 128 O | 129.39 | 130 O | 129 C | 61 NE2 | 77.19 |
| 130 O | 129 C | 128 CA | 156.66 | 130 O | 129 C | 148 O | 70.22 |

Figure 11K

| Atom 1 | Atom 2 | Atom 3 | Angle | Atom 1 | Atom 2 | Atom 3 | Angle |
|---|---|---|---|---|---|---|---|
| 130 O | 129 C | 61 CE1 | 81.26 | 130 O | 129 C | 300 OH2 | 92.47 |
| 130 O | 129 C | 128 CB | 145.53 | 130 O | 129 C | 131 OG | 50.94 |
| 130 O | 129 C | 130 CG | 44.80 | 130 O | 129 C | 131 CA | 29.88 |
| 130 O | 129 C | 157 NH2 | 30.07 | 130 O | 129 C | 130 CD1 | 56.26 |
| 130 O | 129 C | 27 CD1 | 102.76 | 130 O | 129 C | 148 C | 80.40 |
| 130 O | 129 C | 128 CG1 | 149.06 | 130 O | 129 C | 128 CG2 | 133.87 |
| 130 O | 129 C | 131 CB | 43.34 | 130 O | 129 C | 61 CD2 | 82.31 |
| 130 O | 129 C | 128 N | 150.53 | 130 O | 129 C | 61 ND1 | 87.02 |
| 130 O | 129 C | 27 O | 78.84 | 130 CB | 129 C | 301 OH2 | 60.34 |
| 130 CB | 129 C | 131 N | 51.35 | 130 CB | 129 C | 128 O | 115.50 |
| 130 CB | 129 C | 61 NE2 | 116.18 | 130 CB | 129 C | 128 CA | 118.42 |
| 130 CB | 129 C | 148 O | 64.37 | 130 CB | 129 C | 61 CE1 | 126.60 |
| 130 CB | 129 C | 300 OH2 | 95.98 | 130 CB | 129 C | 128 CB | 100.46 |
| 130 CB | 129 C | 131 OG | 85.88 | 130 CB | 129 C | 130 CG | 10.52 |
| 130 CB | 129 C | 131 CA | 59.14 | 130 CB | 129 C | 157 NH2 | 46.52 |
| 130 CB | 129 C | 130 CD1 | 23.55 | 130 CB | 129 C | 27 CD1 | 54.17 |
| 130 CB | 129 C | 148 C | 70.54 | 130 CB | 129 C | 128 CG1 | 100.49 |
| 130 CB | 129 C | 128 CG2 | 92.71 | 130 CB | 129 C | 131 CB | 73.05 |
| 130 CB | 129 C | 61 CD2 | 117.44 | 130 CB | 129 C | 128 N | 120.63 |
| 130 CB | 129 C | 61 ND1 | 131.74 | 130 CB | 129 C | 27 O | 50.20 |
| 301 OH2 | 129 C | 131 N | 98.20 | 301 OH2 | 129 C | 128 O | 63.83 |
| 301 OH2 | 129 C | 61 NE2 | 134.42 | 301 OH2 | 129 C | 128 CA | 87.40 |
| 301 OH2 | 129 C | 148 O | 124.32 | 301 OH2 | 129 C | 61 CE1 | 124.57 |
| 301 OH2 | 129 C | 300 OH2 | 35.64 | 301 OH2 | 129 C | 128 CB | 82.32 |
| 301 OH2 | 129 C | 131 OG | 118.78 | 301 OH2 | 129 C | 130 CG | 69.67 |
| 301 OH2 | 129 C | 131 CA | 98.52 | 301 OH2 | 129 C | 157 NH2 | 39.32 |
| 301 OH2 | 129 C | 130 CD1 | 83.74 | 301 OH2 | 129 C | 27 CD1 | 71.31 |
| 301 OH2 | 129 C | 148 C | 130.85 | 301 OH2 | 129 C | 128 CG1 | 94.19 |
| 301 OH2 | 129 C | 128 CG2 | 69.24 | 301 OH2 | 129 C | 131 CB | 112.65 |

Figure 11L

| Atom 1 | Atom 2 | Atom 3 | Angle | Atom 1 | Atom 2 | Atom 3 | Angle |
|---|---|---|---|---|---|---|---|
| 301 OH2 | 129 C | 61 CD2 | 142.03 | 301 OH2 | 129 C | 128 N | 81.78 |
| 301 OH2 | 129 C | 61 ND1 | 128.19 | 301 OH2 | 129 C | 27 O | 23.32 |
| 131 N | 129 C | 128 O | 161.88 | 131 N | 129 C | 61 NE2 | 64.91 |
| 131 N | 129 C | 128 CA | 160.40 | 131 N | 129 C | 148 O | 37.05 |
| 131 N | 129 C | 61 CE1 | 77.21 | 131 N | 129 C | 300 OH2 | 125.87 |
| 131 N | 129 C | 128 CB | 143.16 | 131 N | 129 C | 131 OG | 34.84 |
| 131 N | 129 C | 130 CG | 41.55 | 131 N | 129 C | 131 CA | 10.79 |
| 131 N | 129 C | 157 NH2 | 61.43 | 131 N | 129 C | 130 CD1 | 41.43 |
| 131 N | 129 C | 27 CD1 | 97.18 | 131 N | 129 C | 148 C | 47.21 |
| 131 N | 129 C | 128 CG1 | 134.19 | 131 N | 129 C | 128 CG2 | 141.24 |
| 131 N | 129 C | 131 CB | 21.78 | 131 N | 129 C | 61 CD2 | 66.25 |
| 131 N | 129 C | 128 N | 168.62 | 131 N | 129 C | 61 ND1 | 81.58 |
| 131 N | 129 C | 27 O | 98.87 | 128 O | 129 C | 61 NE2 | 125.36 |
| 128 O | 129 C | 128 CA | 31.18 | 128 O | 129 C | 148 O | 156.02 |
| 128 O | 129 C | 61 CE1 | 110.32 | 128 O | 129 C | 300 OH2 | 37.16 |
| 128 O | 129 C | 128 CB | 41.91 | 128 O | 129 C | 131 OG | 151.33 |
| 128 O | 129 C | 130 CG | 125.98 | 128 O | 129 C | 131 CA | 158.30 |
| 128 O | 129 C | 157 NH2 | 100.59 | 128 O | 129 C | 130 CD1 | 131.96 |
| 128 O | 129 C | 27 CD1 | 79.76 | 128 O | 129 C | 148 C | 146.82 |
| 128 O | 129 C | 128 CG1 | 54.37 | 128 O | 129 C | 128 CG2 | 37.30 |
| 128 O | 129 C | 131 CB | 162.05 | 128 O | 129 C | 61 CD2 | 126.20 |
| 128 O | 129 C | 128 N | 22.28 | 128 O | 129 C | 61 ND1 | 107.23 |
| 128 O | 129 C | 27 O | 65.71 | 61 NE2 | 129 C | 128 CA | 123.13 |
| 61 NE2 | 129 C | 148 O | 67.59 | 61 NE2 | 129 C | 61 CE1 | 16.57 |
| 61 NE2 | 129 C | 300 OH2 | 120.67 | 61 NE2 | 129 C | 128 CB | 137.09 |
| 61 NE2 | 129 C | 131 OG | 30.33 | 61 NE2 | 129 C | 130 CG | 106.45 |
| 61 NE2 | 129 C | 131 CA | 57.28 | 61 NE2 | 129 C | 157 NH2 | 101.97 |
| 61 NE2 | 129 C | 130 CD1 | 102.68 | 61 NE2 | 129 C | 27 CD1 | 148.17 |
| 61 NE2 | 129 C | 148 C | 69.34 | 61 NE2 | 129 C | 128 CG1 | 128.64 |

Figure 11M

| Atom 1 | Atom 2 | Atom 3 | Angle | Atom 1 | Atom 2 | Atom 3 | Angle |
|---|---|---|---|---|---|---|---|
| 61 NE2 | 129 C | 128 CG2 | 148.74 | 61 NE2 | 129 C | 131 CB | 43.15 |
| 61 NE2 | 129 C | 61 CD2 | 7.65 | 61 NE2 | 129 C | 128 N | 122.88 |
| 61 NE2 | 129 C | 61 ND1 | 18.29 | 61 NE2 | 129 C | 27 O | 154.32 |
| 128 CA | 129 C | 148 O | 125.68 | 128 CA | 129 C | 61 CE1 | 114.97 |
| 128 CA | 129 C | 300 OH2 | 67.87 | 128 CA | 129 C | 128 CB | 18.95 |
| 128 CA | 129 C | 131 OG | 151.80 | 128 CA | 129 C | 130 CG | 126.26 |
| 128 CA | 129 C | 131 CA | 170.11 | 128 CA | 129 C | 157 NH2 | 126.71 |
| 128 CA | 129 C | 130 CD1 | 121.61 | 128 CA | 129 C | 27 CD1 | 66.72 |
| 128 CA | 129 C | 148 C | 115.92 | 128 CA | 129 C | 128 CG1 | 26.22 |
| 128 CA | 129 C | 128 CG2 | 26.02 | 128 CA | 129 C | 131 CB | 159.86 |
| 128 CA | 129 C | 61 CD2 | 119.20 | 128 CA | 129 C | 128 N | 9.24 |
| 128 CA | 129 C | 61 ND1 | 109.69 | 128 CA | 129 C | 27 O | 78.95 |
| 148 O | 129 C | 61 CE1 | 84.13 | 148 O | 129 C | 300 OH2 | 159.40 |
| 148 O | 129 C | 128 CB | 114.25 | 148 O | 129 C | 131 OG | 49.48 |
| 148 O | 129 C | 130 CG | 54.69 | 148 O | 129 C | 131 CA | 44.46 |
| 148 O | 129 C | 157 NH2 | 95.27 | 148 O | 129 C | 130 CD1 | 41.74 |
| 148 O | 129 C | 27 CD1 | 82.28 | 148 O | 129 C | 148 C | 10.19 |
| 148 O | 129 C | 128 CG1 | 101.66 | 148 O | 129 C | 128 CG2 | 120.43 |
| 148 O | 129 C | 131 CB | 41.34 | 148 O | 129 C | 61 CD2 | 63.68 |
| 148 O | 129 C | 128 N | 134.90 | 148 O | 129 C | 61 ND1 | 85.33 |
| 148 O | 129 C | 27 O | 112.25 | 61 CE1 | 129 C | 300 OH2 | 104.76 |
| 61 CE1 | 129 C | 128 CB | 132.38 | 61 CE1 | 129 C | 131 OG | 42.66 |
| 61 CE1 | 129 C | 130 CG | 118.11 | 61 CE1 | 129 C | 131 CA | 68.06 |
| 61 CE1 | 129 C | 157 NH2 | 100.17 | 61 CE1 | 129 C | 130 CD1 | 117.31 |
| 61 CE1 | 129 C | 27 CD1 | 163.49 | 61 CE1 | 129 C | 148 C | 85.80 |
| 61 CE1 | 129 C | 128 CG1 | 128.63 | 61 CE1 | 129 C | 128 CG2 | 140.60 |
| 61 CE1 | 129 C | 131 CB | 55.79 | 61 CE1 | 129 C | 61 CD2 | 21.94 |
| 61 CE1 | 129 C | 128 N | 112.26 | 61 CE1 | 129 C | 61 ND1 | 5.81 |
| 61 CE1 | 129 C | 27 O | 147.66 | 300 OH2 | 129 C | 128 CB | 73.67 |

Figure 11N

| Atom 1 | Atom 2 | Atom 3 | Angle | Atom 1 | Atom 2 | Atom 3 | Angle |
|---|---|---|---|---|---|---|---|
| 300 OH2 | 129 C | 131 OG | 127.21 | 300 OH2 | 129 C | 130 CG | 105.20 |
| 300 OH2 | 129 C | 131 CA | 121.23 | 300 OH2 | 129 C | 157 NH2 | 65.15 |
| 300 OH2 | 129 C | 130 CD1 | 119.30 | 300 OH2 | 129 C | 27 CD1 | 91.15 |
| 300 OH2 | 129 C | 148 C | 166.33 | 300 OH2 | 129 C | 128 CG1 | 87.40 |
| 300 OH2 | 129 C | 128 CG2 | 63.67 | 300 OH2 | 129 C | 131 CB | 129.90 |
| 300 OH2 | 129 C | 61 CD2 | 126.69 | 300 OH2 | 129 C | 128 N | 59.32 |
| 300 OH2 | 129 C | 61 ND1 | 105.42 | 300 OH2 | 129 C | 27 O | 51.39 |
| 128 CB | 129 C | 131 OG | 157.80 | 128 CB | 129 C | 130 CG | 107.63 |
| 128 CB | 129 C | 131 CA | 153.95 | 128 CB | 129 C | 157 NH2 | 119.83 |
| 128 CB | 129 C | 130 CD1 | 102.79 | 128 CB | 129 C | 27 CD1 | 47.80 |
| 128 CB | 129 C | 148 C | 105.81 | 128 CB | 129 C | 128 CG1 | 13.78 |
| 128 CB | 129 C | 128 CG2 | 13.10 | 128 CB | 129 C | 131 CB | 155.44 |
| 128 CB | 129 C | 61 CD2 | 131.38 | 128 CB | 129 C | 128 N | 25.47 |
| 128 CB | 129 C | 61 ND1 | 126.78 | 128 CB | 129 C | 27 O | 67.78 |
| 131 OG | 129 C | 130 CG | 76.34 | 131 OG | 129 C | 131 CA | 27.01 |
| 131 OG | 129 C | 157 NH2 | 79.91 | 131 OG | 129 C | 130 CD1 | 74.80 |
| 131 OG | 129 C | 27 CD1 | 128.86 | 131 OG | 129 C | 148 C | 56.01 |
| 131 OG | 129 C | 128 CG1 | 144.27 | 131 OG | 129 C | 128 CG2 | 169.11 |
| 131 OG | 129 C | 131 CB | 13.16 | 131 OG | 129 C | 61 CD2 | 33.00 |
| 131 OG | 129 C | 128 N | 153.12 | 131 OG | 129 C | 61 ND1 | 46.79 |
| 131 OG | 129 C | 27 O | 129.24 | 130 CG | 129 C | 131 CA | 50.07 |
| 130 CG | 129 C | 157 NH2 | 49.98 | 130 CG | 129 C | 130 CD1 | 16.17 |
| 130 CG | 129 C | 27 CD1 | 60.07 | 130 CG | 129 C | 148 C | 61.60 |
| 130 CG | 129 C | 128 CG1 | 105.57 | 130 CG | 129 C | 128 CG2 | 101.25 |
| 130 CG | 129 C | 131 CB | 63.33 | 130 CG | 129 C | 61 CD2 | 107.24 |
| 130 CG | 129 C | 128 N | 129.62 | 130 CG | 129 C | 61 ND1 | 122.87 |
| 130 CG | 129 C | 27 O | 60.70 | 131 CA | 129 C | 157 NH2 | 59.75 |
| 131 CA | 129 C | 130 CD1 | 51.84 | 131 CA | 129 C | 27 CD1 | 107.57 |
| 131 CA | 129 C | 148 C | 54.29 | 131 CA | 129 C | 128 CG1 | 144.43 |

Figure 11O

| Atom 1 | Atom 2 | Atom 3 | Angle | Atom 1 | Atom 2 | Atom 3 | Angle |
|---|---|---|---|---|---|---|---|
| 131 CA | 129 C | 128 CG2 | 151.13 | 131 CA | 129 C | 131 CB | 15.28 |
| 131 CA | 129 C | 61 CD2 | 59.81 | 131 CA | 129 C | 128 N | 179.34 |
| 131 CA | 129 C | 61 ND1 | 72.82 | 131 CA | 129 C | 27 O | 103.46 |
| 157 NH2 | 129 C | 130 CD1 | 65.98 | 157 NH2 | 129 C | 27 CD1 | 90.38 |
| 157 NH2 | 129 C | 148 C | 104.90 | 157 NH2 | 129 C | 128 CG1 | 129.35 |
| 157 NH2 | 129 C | 128 CG2 | 106.87 | 157 NH2 | 129 C | 131 CB | 73.38 |
| 157 NH2 | 129 C | 61 CD2 | 108.47 | 157 NH2 | 129 C | 128 N | 120.62 |
| 157 NH2 | 129 C | 61 ND1 | 105.75 | 157 NH2 | 129 C | 27 O | 52.43 |
| 130 CD1 | 129 C | 27 CD1 | 55.76 | 130 CD1 | 129 C | 148 C | 47.11 |
| 130 CD1 | 129 C | 128 CG1 | 97.25 | 130 CD1 | 129 C | 128 CG2 | 99.87 |
| 130 CD1 | 129 C | 131 CB | 61.81 | 130 CD1 | 129 C | 61 CD2 | 101.36 |
| 130 CD1 | 129 C | 128 N | 127.67 | 130 CD1 | 129 C | 61 ND1 | 120.76 |
| 130 CD1 | 129 C | 27 O | 70.80 | 27 CD1 | 129 C | 148 C | 79.20 |
| 27 CD1 | 129 C | 128 CG1 | 46.34 | 27 CD1 | 129 C | 128 CG2 | 44.27 |
| 27 CD1 | 129 C | 131 CB | 116.63 | 27 CD1 | 129 C | 61 CD2 | 141.87 |
| 27 CD1 | 129 C | 128 N | 71.96 | 27 CD1 | 129 C | 61 ND1 | 160.49 |
| 27 CD1 | 129 C | 27 O | 47.99 | 148 C | 129 C | 128 CG1 | 92.74 |
| 148 C | 129 C | 128 CG2 | 113.38 | 148 C | 129 C | 131 CB | 49.63 |
| 148 C | 129 C | 61 CD2 | 64.24 | 148 C | 129 C | 128 N | 125.09 |
| 148 C | 129 C | 61 ND1 | 85.97 | 148 C | 129 C | 27 O | 115.37 |
| 128 CG1 | 129 C | 128 CG2 | 25.68 | 128 CG1 | 129 C | 131 CB | 142.19 |
| 128 CG1 | 129 C | 61 CD2 | 121.89 | 128 CG1 | 129 C | 128 N | 34.92 |
| 128 CG1 | 129 C | 61 ND1 | 122.82 | 128 CG1 | 129 C | 27 O | 77.02 |
| 128 CG2 | 129 C | 131 CB | 160.37 | 128 CG2 | 129 C | 61 CD2 | 143.80 |
| 128 CG2 | 129 C | 128 N | 28.50 | 128 CG2 | 129 C | 61 ND1 | 135.54 |
| 128 CG2 | 129 C | 27 O | 55.23 | 131 CB | 129 C | 61 CD2 | 44.92 |
| 131 CB | 129 C | 128 N | 164.64 | 131 CB | 129 C | 61 ND1 | 59.93 |
| 131 CB | 129 C | 27 O | 118.74 | 61 CD2 | 129 C | 128 N | 120.26 |
| 61 CD2 | 129 C | 61 ND1 | 21.79 | 61 CD2 | 129 C | 27 O | 160.83 |

Figure 11P

| Atom 1 | Atom 2 | Atom 3 | Angle | Atom 1 | Atom 2 | Atom 3 | Angle |
|---|---|---|---|---|---|---|---|
| 128 N   | 129 C | 61 ND1  | 107.46 | 128 N  | 129 C | 27 O     | 76.58  |
| 61 ND1  | 129 C | 27 O    | 151.51 | 130 N  | 129 O | 130 CA   | 31.92  |
| 130 N   | 129 O | 130 C   | 46.12  | 130 N  | 129 O | 131 N    | 66.02  |
| 130 N   | 129 O | 61 NE2  | 118.69 | 130 N  | 129 O | 148 O    | 96.55  |
| 130 N   | 129 O | 130 O   | 41.64  | 130 N  | 129 O | 128 C    | 76.90  |
| 130 N   | 129 O | 130 CB  | 29.28  | 130 N  | 129 O | 61 CE1   | 112.75 |
| 130 N   | 129 O | 131 OG  | 95.89  | 130 N  | 129 O | 148 C    | 107.17 |
| 130 N   | 129 O | 61 CD2  | 129.64 | 130 N  | 129 O | 128 O    | 67.81  |
| 130 N   | 129 O | 301 OH2 | 19.06  | 130 N  | 129 O | 131 CA   | 72.00  |
| 130 N   | 129 O | 128 CA  | 86.79  | 130 N  | 129 O | 128 CB   | 79.07  |
| 130 N   | 129 O | 131 CB  | 88.76  | 130 N  | 129 O | 130 CG   | 41.07  |
| 130 N   | 129 O | 61 ND1  | 120.73 | 130 N  | 129 O | 130 CD1  | 56.16  |
| 130 N   | 129 O | 148 ND1 | 132.58 | 130 N  | 129 O | 128 CG1  | 90.05  |
| 130 N   | 129 O | 61 CG   | 130.10 | 130 N  | 129 O | 148 CE1  | 130.24 |
| 130 N   | 129 O | 300 OH2 | 46.46  | 130 N  | 129 O | 27 CD1   | 58.05  |
| 130 CA  | 129 O | 130 C   | 25.78  | 130 CA | 129 O | 131 N    | 39.77  |
| 130 CA  | 129 O | 61 NE2  | 110.68 | 130 CA | 129 O | 148 O    | 64.67  |
| 130 CA  | 129 O | 130 O   | 33.92  | 130 CA | 129 O | 128 C    | 105.56 |
| 130 CA  | 129 O | 130 CB  | 10.28  | 130 CA | 129 O | 61 CE1   | 115.51 |
| 130 CA  | 129 O | 131 OG  | 77.83  | 130 CA | 129 O | 148 C    | 75.92  |
| 130 CA  | 129 O | 61 CD2  | 116.75 | 130 CA | 129 O | 128 O    | 98.44  |
| 130 CA  | 129 O | 301 OH2 | 50.97  | 130 CA | 129 O | 131 CA   | 49.39  |
| 130 CA  | 129 O | 128 CA  | 111.40 | 130 CA | 129 O | 128 CB   | 98.09  |
| 130 CA  | 129 O | 131 CB  | 66.13  | 130 CA | 129 O | 130 CG   | 10.68  |
| 130 CA  | 129 O | 61 ND1  | 123.22 | 130 CA | 129 O | 130 CD1  | 27.04  |
| 130 CA  | 129 O | 148 ND1 | 102.02 | 130 CA | 129 O | 128 CG1  | 103.22 |
| 130 CA  | 129 O | 61 CG   | 124.02 | 130 CA | 129 O | 148 CE1  | 103.04 |
| 130 CA  | 129 O | 300 OH2 | 78.25  | 130 CA | 129 O | 27 CD1   | 59.76  |
| 130 C   | 129 O | 131 N   | 20.56  | 130 C  | 129 O | 61 NE2   | 84.94  |

Figure 11Q

| Atom 1 | Atom 2 | Atom 3 | Angle | Atom 1 | Atom 2 | Atom 3 | Angle |
|---|---|---|---|---|---|---|---|
| 130 C | 129 O | 148 O | 61.06 | 130 C | 129 O | 130 O | 15.29 |
| 130 C | 129 O | 128 C | 122.50 | 130 C | 129 O | 130 CB | 36.03 |
| 130 C | 129 O | 61 CE1 | 90.54 | 130 C | 129 O | 131 OG | 53.09 |
| 130 C | 129 O | 148 C | 74.74 | 130 C | 129 O | 61 CD2 | 91.71 |
| 130 C | 129 O | 128 O | 111.97 | 130 C | 129 O | 301 OH2 | 62.80 |
| 130 C | 129 O | 131 CA | 26.14 | 130 C | 129 O | 128 CA | 132.80 |
| 130 C | 129 O | 128 CB | 122.40 | 130 C | 129 O | 131 CB | 43.24 |
| 130 C | 129 O | 130 CG | 30.55 | 130 C | 129 O | 61 ND1 | 97.90 |
| 130 C | 129 O | 130 CD1 | 41.63 | 130 C | 129 O | 148 ND1 | 87.51 |
| 130 C | 129 O | 128 CG1 | 128.93 | 130 C | 129 O | 61 CG | 98.30 |
| 130 C | 129 O | 148 CE1 | 84.14 | 130 C | 129 O | 300 OH2 | 85.09 |
| 130 C | 129 O | 27 CD1 | 85.46 | 131 N | 129 O | 61 NE2 | 74.34 |
| 131 N | 129 O | 148 O | 43.59 | 131 N | 129 O | 130 O | 32.60 |
| 131 N | 129 O | 128 C | 142.86 | 131 N | 129 O | 130 CB | 49.34 |
| 131 N | 129 O | 61 CE1 | 85.19 | 131 N | 129 O | 131 OG | 39.67 |
| 131 N | 129 O | 148 C | 57.34 | 131 N | 129 O | 61 CD2 | 77.95 |
| 131 N | 129 O | 128 O | 132.52 | 131 N | 129 O | 301 OH2 | 83.28 |
| 131 N | 129 O | 131 CA | 11.61 | 131 N | 129 O | 128 CA | 151.15 |
| 131 N | 129 O | 128 CB | 136.98 | 131 N | 129 O | 131 CB | 26.64 |
| 131 N | 129 O | 130 CG | 38.83 | 131 N | 129 O | 61 ND1 | 90.86 |
| 131 N | 129 O | 130 CD1 | 41.59 | 131 N | 129 O | 148 ND1 | 67.05 |
| 131 N | 129 O | 128 CG1 | 137.92 | 131 N | 129 O | 61 CG | 86.86 |
| 131 N | 129 O | 148 CE1 | 64.68 | 131 N | 129 O | 300 OH2 | 105.17 |
| 131 N | 129 O | 27 CD1 | 94.15 | 61 NE2 | 129 O | 148 O | 83.76 |
| 61 NE2 | 129 O | 130 O | 80.78 | 61 NE2 | 129 O | 128 C | 125.31 |
| 61 NE2 | 129 O | 130 CB | 120.95 | 61 NE2 | 129 O | 61 CE1 | 17.95 |
| 61 NE2 | 129 O | 131 OG | 34.77 | 61 NE2 | 129 O | 148 C | 86.45 |
| 61 NE2 | 129 O | 61 CD2 | 12.11 | 61 NE2 | 129 O | 128 O | 120.84 |
| 61 NE2 | 129 O | 301 OH2 | 119.92 | 61 NE2 | 129 O | 131 CA | 63.06 |

Figure 11R

| Atom 1 | Atom 2 | Atom 3 | Angle | Atom 1 | Atom 2 | Atom 3 | Angle |
|---|---|---|---|---|---|---|---|
| 61 NE2 | 129 O | 128 CA | 130.56 | 61 NE2 | 129 O | 128 CB | 147.76 |
| 61 NE2 | 129 O | 131 CB | 48.75 | 61 NE2 | 129 O | 130 CG | 112.83 |
| 61 NE2 | 129 O | 61 ND1 | 18.56 | 61 NE2 | 129 O | 130 CD1 | 114.07 |
| 61 NE2 | 129 O | 148 ND1 | 52.08 | 61 NE2 | 129 O | 128 CG1 | 146.09 |
| 61 NE2 | 129 O | 61 CG | 13.39 | 61 NE2 | 129 O | 148 CE1 | 39.43 |
| 61 NE2 | 129 O | 300 OH2 | 109.53 | 61 NE2 | 129 O | 27 CD1 | 167.74 |
| 148 O | 129 O | 130 O | 75.45 | 148 O | 129 O | 128 C | 149.99 |
| 148 O | 129 O | 130 CB | 68.50 | 148 O | 129 O | 61 CE1 | 101.39 |
| 148 O | 129 O | 131 OG | 58.31 | 148 O | 129 O | 148 C | 13.80 |
| 148 O | 129 O | 61 CD2 | 78.29 | 148 O | 129 O | 128 O | 154.77 |
| 148 O | 129 O | 301 OH2 | 115.51 | 148 O | 129 O | 131 CA | 48.65 |
| 148 O | 129 O | 128 CA | 138.21 | 148 O | 129 O | 128 CB | 122.94 |
| 148 O | 129 O | 131 CB | 46.79 | 148 O | 129 O | 130 CG | 55.74 |
| 148 O | 129 O | 61 ND1 | 101.63 | 148 O | 129 O | 130 CD1 | 42.71 |
| 148 O | 129 O | 148 ND1 | 41.41 | 148 O | 129 O | 128 CG1 | 112.21 |
| 148 O | 129 O | 61 CG | 89.57 | 148 O | 129 O | 148 CE1 | 49.18 |
| 148 O | 129 O | 300 OH2 | 142.90 | 148 O | 129 O | 27 CD1 | 84.94 |
| 130 O | 129 O | 128 C | 113.15 | 130 O | 129 O | 130 CB | 42.97 |
| 130 O | 129 O | 61 CE1 | 82.12 | 130 O | 129 O | 131 OG | 54.25 |
| 130 O | 129 O | 148 C | 89.24 | 130 O | 129 O | 61 CD2 | 89.93 |
| 130 O | 129 O | 128 O | 101.36 | 130 O | 129 O | 301 OH2 | 54.65 |
| 130 O | 129 O | 131 CA | 33.29 | 130 O | 129 O | 128 CA | 126.21 |
| 130 O | 129 O | 128 CB | 120.68 | 130 O | 129 O | 131 CB | 48.47 |
| 130 O | 129 O | 130 CG | 41.90 | 130 O | 129 O | 61 ND1 | 90.14 |
| 130 O | 129 O | 130 CD1 | 55.39 | 130 O | 129 O | 148 ND1 | 96.39 |
| 130 O | 129 O | 128 CG1 | 131.16 | 130 O | 129 O | 61 CG | 93.91 |
| 130 O | 129 O | 148 CE1 | 90.23 | 130 O | 129 O | 300 OH2 | 72.96 |
| 130 O | 129 O | 27 CD1 | 91.80 | 128 C | 129 O | 130 CB | 97.59 |
| 128 C | 129 O | 61 CE1 | 108.18 | 128 C | 129 O | 131 OG | 150.60 |

Figure 11S

| Atom 1 | Atom 2 | Atom 3 | Angle | Atom 1 | Atom 2 | Atom 3 | Angle |
|---|---|---|---|---|---|---|---|
| 128 C | 129 O | 148 C | 142.41 | 128 C | 129 O | 61 CD2 | 128.48 |
| 128 C | 129 O | 128 O | 12.64 | 128 C | 129 O | 301 OH2 | 59.72 |
| 128 C | 129 O | 131 CA | 146.43 | 128 C | 129 O | 128 CA | 15.50 |
| 128 C | 129 O | 128 CB | 27.35 | 128 C | 129 O | 131 CB | 158.26 |
| 128 C | 129 O | 130 CG | 110.33 | 128 C | 129 O | 61 ND1 | 106.89 |
| 128 C | 129 O | 130 CD1 | 116.84 | 128 C | 129 O | 148 ND1 | 149.96 |
| 128 C | 129 O | 128 CG1 | 39.77 | 128 C | 129 O | 61 CG | 117.27 |
| 128 C | 129 O | 148 CE1 | 151.38 | 128 C | 129 O | 300 OH2 | 41.54 |
| 128 C | 129 O | 27 CD1 | 66.59 | 130 CB | 129 O | 61 CE1 | 125.06 |
| 130 CB | 129 O | 131 OG | 87.97 | 130 CB | 129 O | 148 C | 78.13 |
| 130 CB | 129 O | 61 CD2 | 126.87 | 130 CB | 129 O | 128 O | 91.86 |
| 130 CB | 129 O | 301 OH2 | 47.44 | 130 CB | 129 O | 131 CA | 59.40 |
| 130 CB | 129 O | 128 CA | 102.01 | 130 CB | 129 O | 128 CB | 88.07 |
| 130 CB | 129 O | 131 CB | 75.91 | 130 CB | 129 O | 130 CG | 13.16 |
| 130 CB | 129 O | 61 ND1 | 132.97 | 130 CB | 129 O | 130 CD1 | 26.91 |
| 130 CB | 129 O | 148 ND1 | 108.21 | 130 CB | 129 O | 128 CG1 | 92.95 |
| 130 CB | 129 O | 61 CG | 134.30 | 130 CB | 129 O | 148 CE1 | 110.96 |
| 130 CB | 129 O | 300 OH2 | 75.18 | 130 CB | 129 O | 27 CD1 | 49.67 |
| 61 CE1 | 129 O | 131 OG | 47.94 | 61 CE1 | 129 O | 148 C | 104.39 |
| 61 CE1 | 129 O | 61 CD2 | 27.14 | 61 CE1 | 129 O | 128 O | 102.94 |
| 61 CE1 | 129 O | 301 OH2 | 108.32 | 61 CE1 | 129 O | 131 CA | 73.59 |
| 61 CE1 | 129 O | 128 CA | 115.65 | 61 CE1 | 129 O | 128 CB | 133.11 |
| 61 CE1 | 129 O | 131 CB | 62.25 | 61 CE1 | 129 O | 130 CG | 120.87 |
| 61 CE1 | 129 O | 61 ND1 | 8.26 | 61 CE1 | 129 O | 130 CD1 | 126.72 |
| 61 CE1 | 129 O | 148 ND1 | 69.27 | 61 CE1 | 129 O | 128 CG1 | 136.86 |
| 61 CE1 | 129 O | 61 CG | 19.41 | 61 CE1 | 129 O | 148 CE1 | 56.95 |
| 61 CE1 | 129 O | 300 OH2 | 93.11 | 61 CE1 | 129 O | 27 CD1 | 169.74 |
| 131 OG | 129 O | 148 C | 66.99 | 131 OG | 129 O | 61 CD2 | 38.92 |
| 131 OG | 129 O | 128 O | 139.72 | 131 OG | 129 O | 301 OH2 | 106.95 |

Figure 11T

| Atom 1 | Atom 2 | Atom 3 | Angle | Atom 1 | Atom 2 | Atom 3 | Angle |
|---|---|---|---|---|---|---|---|
| 131 OG | 129 O | 131 CA | 28.69 | 131 OG | 129 O | 128 CA | 162.98 |
| 131 OG | 129 O | 128 CB | 174.85 | 131 OG | 129 O | 131 CB | 14.34 |
| 131 OG | 129 O | 130 CG | 78.43 | 131 OG | 129 O | 61 ND1 | 52.19 |
| 131 OG | 129 O | 130 CD1 | 79.66 | 131 OG | 129 O | 148 ND1 | 48.31 |
| 131 OG | 129 O | 128 CG1 | 169.27 | 131 OG | 129 O | 61 CG | 47.21 |
| 131 OG | 129 O | 148 CE1 | 38.19 | 131 OG | 129 O | 300 OH2 | 114.22 |
| 131 OG | 129 O | 27 CD1 | 133.38 | 148 C | 129 O | 61 CD2 | 78.56 |
| 148 C | 129 O | 128 O | 151.78 | 148 C | 129 O | 301 OH2 | 125.52 |
| 148 C | 129 O | 131 CA | 61.75 | 148 C | 129 O | 128 CA | 128.24 |
| 148 C | 129 O | 128 CB | 115.32 | 148 C | 129 O | 131 CB | 57.44 |
| 148 C | 129 O | 130 CG | 66.15 | 148 C | 129 O | 61 ND1 | 102.62 |
| 148 C | 129 O | 130 CD1 | 51.29 | 148 C | 129 O | 148 ND1 | 37.29 |
| 148 C | 129 O | 128 CG1 | 102.73 | 148 C | 129 O | 61 CG | 89.23 |
| 148 C | 129 O | 148 CE1 | 48.09 | 148 C | 129 O | 300 OH2 | 153.18 |
| 148 C | 129 O | 27 CD1 | 83.69 | 61 CD2 | 129 O | 128 O | 126.93 |
| 61 CD2 | 129 O | 301 OH2 | 132.02 | 61 CD2 | 129 O | 131 CA | 67.49 |
| 61 CD2 | 129 O | 128 CA | 129.67 | 61 CD2 | 129 O | 128 CB | 145.00 |
| 61 CD2 | 129 O | 131 CB | 51.35 | 61 CD2 | 129 O | 130 CG | 116.67 |
| 61 CD2 | 129 O | 61 ND1 | 24.07 | 61 CD2 | 129 O | 130 CD1 | 114.18 |
| 61 CD2 | 129 O | 148 ND1 | 42.30 | 61 CD2 | 129 O | 128 CG1 | 138.67 |
| 61 CD2 | 129 O | 61 CG | 11.34 | 61 CD2 | 129 O | 148 CE1 | 30.48 |
| 61 CD2 | 129 O | 300 OH2 | 120.22 | 61 CD2 | 129 O | 27 CD1 | 162.14 |
| 128 O | 129 O | 301 OH2 | 49.54 | 128 O | 129 O | 131 CA | 134.39 |
| 128 O | 129 O | 128 CA | 28.06 | 128 O | 129 O | 128 CB | 37.20 |
| 128 O | 129 O | 131 CB | 145.69 | 128 O | 129 O | 130 CG | 105.01 |
| 128 O | 129 O | 61 ND1 | 103.41 | 128 O | 129 O | 130 CD1 | 114.72 |
| 128 O | 129 O | 148 ND1 | 159.49 | 128 O | 129 O | 128 CG1 | 50.96 |
| 128 O | 129 O | 61 CG | 115.66 | 128 O | 129 O | 148 CE1 | 155.49 |
| 128 O | 129 O | 300 OH2 | 29.01 | 128 O | 129 O | 27 CD1 | 70.04 |

Figure 11U

| Atom 1 | Atom 2 | Atom 3 | Angle | Atom 1 | Atom 2 | Atom 3 | Angle |
|---|---|---|---|---|---|---|---|
| 301 OH2 | 129 O | 131 CA | 87.46 | 301 OH2 | 129 O | 128 CA | 71.61 |
| 301 OH2 | 129 O | 128 CB | 67.92 | 301 OH2 | 129 O | 131 CB | 103.12 |
| 301 OH2 | 129 O | 130 CG | 59.84 | 301 OH2 | 129 O | 61 ND1 | 115.06 |
| 301 OH2 | 129 O | 130 CD1 | 74.23 | 301 OH2 | 129 O | 148 ND1 | 150.31 |
| 301 OH2 | 129 O | 128 CG1 | 81.28 | 301 OH2 | 129 O | 61 CG | 127.66 |
| 301 OH2 | 129 O | 148 CE1 | 144.66 | 301 OH2 | 129 O | 300 OH2 | 27.74 |
| 301 OH2 | 129 O | 27 CD1 | 61.47 | 131 CA | 129 O | 128 CA | 158.78 |
| 131 CA | 129 O | 128 CB | 147.47 | 131 CA | 129 O | 131 CB | 17.14 |
| 131 CA | 129 O | 130 CG | 49.83 | 131 CA | 129 O | 61 ND1 | 79.29 |
| 131 CA | 129 O | 130 CD1 | 53.17 | 131 CA | 129 O | 148 ND1 | 63.18 |
| 131 CA | 129 O | 128 CG1 | 149.52 | 131 CA | 129 O | 61 CG | 75.83 |
| 131 CA | 129 O | 148 CE1 | 58.29 | 131 CA | 129 O | 300 OH2 | 105.54 |
| 131 CA | 129 O | 27 CD1 | 105.62 | 128 CA | 129 O | 128 CB | 17.49 |
| 128 CA | 129 O | 131 CB | 173.75 | 128 CA | 129 O | 130 CG | 113.39 |
| 128 CA | 129 O | 61 ND1 | 112.28 | 128 CA | 129 O | 130 CD1 | 115.26 |
| 128 CA | 129 O | 148 ND1 | 137.23 | 128 CA | 129 O | 128 CG1 | 26.00 |
| 128 CA | 129 O | 61 CG | 119.60 | 128 CA | 129 O | 148 CE1 | 142.93 |
| 128 CA | 129 O | 300 OH2 | 56.64 | 128 CA | 129 O | 27 CD1 | 61.68 |
| 128 CB | 129 O | 131 CB | 163.36 | 128 CB | 129 O | 130 CG | 98.16 |
| 128 CB | 129 O | 61 ND1 | 129.69 | 128 CB | 129 O | 130 CD1 | 98.17 |
| 128 CB | 129 O | 148 ND1 | 136.37 | 128 CB | 129 O | 128 CG1 | 14.81 |
| 128 CB | 129 O | 61 CG | 136.00 | 128 CB | 129 O | 148 CE1 | 146.84 |
| 128 CB | 129 O | 300 OH2 | 61.50 | 128 CB | 129 O | 27 CD1 | 44.39 |
| 131 CB | 129 O | 130 CG | 65.34 | 131 CB | 129 O | 61 ND1 | 66.47 |
| 131 CB | 129 O | 130 CD1 | 65.43 | 131 CB | 129 O | 148 ND1 | 48.52 |
| 131 CB | 129 O | 128 CG1 | 158.56 | 131 CB | 129 O | 61 CG | 60.64 |
| 131 CB | 129 O | 148 CE1 | 41.85 | 131 CB | 129 O | 300 OH2 | 117.15 |
| 131 CB | 129 O | 27 CD1 | 119.22 | 130 CG | 129 O | 61 ND1 | 127.86 |
| 130 CG | 129 O | 130 CD1 | 16.36 | 130 CG | 129 O | 148 ND1 | 95.05 |

Figure 11V

| Atom 1 | Atom 2 | Atom 3 | Angle | Atom 1 | Atom 2 | Atom 3 | Angle |
|---|---|---|---|---|---|---|---|
| 130 CG | 129 O | 128 CG1 | 100.61 | 130 CG | 129 O | 61 CG | 125.63 |
| 130 CG | 129 O | 148 CE1 | 98.07 | 130 CG | 129 O | 300 OH2 | 87.50 |
| 130 CG | 129 O | 27 CD1 | 56.26 | 61 ND1 | 129 O | 130 CD1 | 131.84 |
| 61 ND1 | 129 O | 148 ND1 | 66.10 | 61 ND1 | 129 O | 128 CG1 | 131.09 |
| 61 ND1 | 129 O | 61 CG | 13.95 | 61 ND1 | 129 O | 148 CE1 | 54.54 |
| 61 ND1 | 129 O | 300 OH2 | 97.43 | 61 ND1 | 129 O | 27 CD1 | 173.42 |
| 130 CD1 | 129 O | 148 ND1 | 83.88 | 130 CD1 | 129 O | 128 CG1 | 96.41 |
| 130 CD1 | 129 O | 61 CG | 124.92 | 130 CD1 | 129 O | 148 CE1 | 89.66 |
| 130 CD1 | 129 O | 300 OH2 | 101.92 | 130 CD1 | 129 O | 27 CD1 | 53.81 |
| 148 ND1 | 129 O | 128 CG1 | 121.62 | 148 ND1 | 129 O | 61 CG | 52.34 |
| 148 ND1 | 129 O | 148 CE1 | 12.95 | 148 ND1 | 129 O | 300 OH2 | 160.82 |
| 148 ND1 | 129 O | 27 CD1 | 119.87 | 128 CG1 | 129 O | 61 CG | 132.75 |
| 128 CG1 | 129 O | 148 CE1 | 132.56 | 128 CG1 | 129 O | 300 OH2 | 76.28 |
| 128 CG1 | 129 O | 27 CD1 | 44.35 | 61 CG | 129 O | 148 CE1 | 41.23 |
| 61 CG | 129 O | 300 OH2 | 111.38 | 61 CG | 129 O | 27 CD1 | 170.85 |
| 148 CE1 | 129 O | 300 OH2 | 147.94 | 148 CE1 | 129 O | 27 CD1 | 131.71 |
| 300 OH2 | 129 O | 27 CD1 | 77.16 | 128 C | 129 CB | 128 O | 21.26 |
| 128 C | 129 CB | 130 N | 78.75 | 128 C | 129 CB | 61 CE1 | 158.28 |
| 128 C | 129 CB | 152 SG | 72.13 | 128 C | 129 CB | 300 OH2 | 62.18 |
| 128 C | 129 CB | 61 NE2 | 143.34 | 128 C | 129 CB | 128 CA | 12.60 |
| 128 C | 129 CB | 61 ND1 | 154.13 | 128 C | 129 CB | 301 OH2 | 67.63 |
| 128 C | 129 CB | 130 CA | 86.83 | 128 C | 129 CB | 130 C | 103.49 |
| 128 C | 129 CB | 130 O | 108.89 | 128 C | 129 CB | 152 CB | 83.75 |
| 128 C | 129 CB | 128 N | 16.24 | 128 C | 129 CB | 128 CB | 15.97 |
| 128 C | 129 CB | 61 CD2 | 140.03 | 128 C | 129 CB | 156 N | 89.39 |
| 128 C | 129 CB | 61 CG | 145.70 | 128 C | 129 CB | 131 OG | 134.35 |
| 128 C | 129 CB | 131 N | 109.25 | 128 C | 129 CB | 152 N | 65.83 |
| 128 C | 129 CB | 130 CB | 79.86 | 128 O | 129 CB | 130 N | 81.98 |
| 128 O | 129 CB | 61 CE1 | 179.39 | 128 O | 129 CB | 152 SG | 71.44 |

Figure 11W

| Atom 1 | Atom 2 | Atom 3 | Angle | Atom 1 | Atom 2 | Atom 3 | Angle |
|---|---|---|---|---|---|---|---|
| 128 O | 129 CB | 300 OH2 | 42.67 | 128 O | 129 CB | 61 NE2 | 162.18 |
| 128 O | 129 CB | 128 CA | 32.55 | 128 O | 129 CB | 61 ND1 | 167.04 |
| 128 O | 129 CB | 301 OH2 | 58.17 | 128 O | 129 CB | 130 CA | 92.11 |
| 128 O | 129 CB | 130 C | 106.53 | 128 O | 129 CB | 130 O | 106.85 |
| 128 O | 129 CB | 152 CB | 86.64 | 128 O | 129 CB | 128 N | 25.60 |
| 128 O | 129 CB | 128 CB | 35.75 | 128 O | 129 CB | 61 CD2 | 161.09 |
| 128 O | 129 CB | 156 N | 68.34 | 128 O | 129 CB | 61 CG | 165.19 |
| 128 O | 129 CB | 131 OG | 143.85 | 128 O | 129 CB | 131 N | 115.69 |
| 128 O | 129 CB | 152 N | 75.48 | 128 O | 129 CB | 130 CB | 83.10 |
| 130 N | 129 CB | 61 CE1 | 98.32 | 130 N | 129 CB | 152 SG | 150.85 |
| 130 N | 129 CB | 300 OH2 | 72.80 | 130 N | 129 CB | 61 NE2 | 84.22 |
| 130 N | 129 CB | 128 CA | 84.43 | 130 N | 129 CB | 61 ND1 | 110.43 |
| 130 N | 129 CB | 301 OH2 | 37.74 | 130 N | 129 CB | 130 CA | 10.85 |
| 130 N | 129 CB | 130 C | 25.08 | 130 N | 129 CB | 130 O | 31.37 |
| 130 N | 129 CB | 152 CB | 157.85 | 130 N | 129 CB | 128 N | 94.97 |
| 130 N | 129 CB | 128 CB | 69.07 | 130 N | 129 CB | 61 CD2 | 90.78 |
| 130 N | 129 CB | 156 N | 104.26 | 130 N | 129 CB | 61 CG | 104.14 |
| 130 N | 129 CB | 131 OG | 61.97 | 130 N | 129 CB | 131 N | 33.82 |
| 130 N | 129 CB | 152 N | 133.95 | 130 N | 129 CB | 130 CB | 1.13 |
| 61 CE1 | 129 CB | 152 SG | 108.16 | 61 CE1 | 129 CB | 300 OH2 | 137.92 |
| 61 CE1 | 129 CB | 61 NE2 | 17.73 | 61 CE1 | 129 CB | 128 CA | 146.91 |
| 61 CE1 | 129 CB | 61 ND1 | 12.53 | 61 CE1 | 129 CB | 301 OH2 | 122.36 |
| 61 CE1 | 129 CB | 130 CA | 88.15 | 61 CE1 | 129 CB | 130 C | 73.82 |
| 61 CE1 | 129 CB | 130 O | 73.61 | 61 CE1 | 129 CB | 152 CB | 92.90 |
| 61 CE1 | 129 CB | 128 N | 153.80 | 61 CE1 | 129 CB | 128 CB | 143.90 |
| 61 CE1 | 129 CB | 61 CD2 | 18.54 | 61 CE1 | 129 CB | 156 N | 112.06 |
| 61 CE1 | 129 CB | 61 CG | 14.21 | 61 CE1 | 129 CB | 131 OG | 36.42 |
| 61 CE1 | 129 CB | 131 N | 64.58 | 61 CE1 | 129 CB | 152 N | 103.95 |
| 61 CE1 | 129 CB | 130 CB | 97.20 | 152 SG | 129 CB | 300 OH2 | 94.36 |

Figure 11X

| Atom 1 | Atom 2 | Atom 3 | Angle | Atom 1 | Atom 2 | Atom 3 | Angle |
|---|---|---|---|---|---|---|---|
| 152 SG | 129 CB | 61 NE2 | 118.86 | 152 SG | 129 CB | 128 CA | 66.76 |
| 152 SG | 129 CB | 61 ND1 | 95.64 | 152 SG | 129 CB | 301 OH2 | 126.29 |
| 152 SG | 129 CB | 130 CA | 157.27 | 152 SG | 129 CB | 130 C | 173.08 |
| 152 SG | 129 CB | 130 O | 172.92 | 152 SG | 129 CB | 152 CB | 16.65 |
| 152 SG | 129 CB | 128 N | 55.90 | 152 SG | 129 CB | 128 CB | 82.22 |
| 152 SG | 129 CB | 61 CD2 | 110.60 | 152 SG | 129 CB | 156 N | 77.22 |
| 152 SG | 129 CB | 61 CG | 99.17 | 152 SG | 129 CB | 131 OG | 142.57 |
| 152 SG | 129 CB | 131 N | 164.52 | 152 SG | 129 CB | 152 N | 27.47 |
| 152 SG | 129 CB | 130 CB | 151.94 | 300 OH2 | 129 CB | 61 NE2 | 141.32 |
| 300 OH2 | 129 CB | 128 CA | 74.53 | 300 OH2 | 129 CB | 61 ND1 | 143.09 |
| 300 OH2 | 129 CB | 301 OH2 | 35.18 | 300 OH2 | 129 CB | 130 CA | 82.90 |
| 300 OH2 | 129 CB | 130 C | 88.09 | 300 OH2 | 129 CB | 130 O | 80.29 |
| 300 OH2 | 129 CB | 152 CB | 110.64 | 300 OH2 | 129 CB | 128 N | 67.80 |
| 300 OH2 | 129 CB | 128 CB | 72.49 | 300 OH2 | 129 CB | 61 CD2 | 150.21 |
| 300 OH2 | 129 CB | 156 N | 38.42 | 300 OH2 | 129 CB | 61 CG | 151.89 |
| 300 OH2 | 129 CB | 131 OG | 120.40 | 300 OH2 | 129 CB | 131 N | 99.85 |
| 300 OH2 | 129 CB | 152 N | 111.55 | 300 OH2 | 129 CB | 130 CB | 73.52 |
| 61 NE2 | 129 CB | 128 CA | 134.62 | 61 NE2 | 129 CB | 61 ND1 | 27.20 |
| 61 NE2 | 129 CB | 301 OH2 | 114.70 | 61 NE2 | 129 CB | 130 CA | 73.54 |
| 61 NE2 | 129 CB | 130 C | 61.38 | 61 NE2 | 129 CB | 130 O | 64.72 |
| 61 NE2 | 129 CB | 152 CB | 102.39 | 61 NE2 | 129 CB | 128 N | 146.72 |
| 61 NE2 | 129 CB | 128 CB | 127.67 | 61 NE2 | 129 CB | 61 CD2 | 9.04 |
| 61 NE2 | 129 CB | 156 N | 126.43 | 61 NE2 | 129 CB | 61 CG | 20.07 |
| 61 NE2 | 129 CB | 131 OG | 23.71 | 61 NE2 | 129 CB | 131 N | 50.70 |
| 61 NE2 | 129 CB | 152 N | 106.83 | 61 NE2 | 129 CB | 130 CB | 83.15 |
| 128 CA | 129 CB | 61 ND1 | 141.54 | 128 CA | 129 CB | 301 OH2 | 79.00 |
| 128 CA | 129 CB | 130 CA | 90.88 | 128 CA | 129 CB | 130 C | 107.82 |
| 128 CA | 129 CB | 130 O | 115.68 | 128 CA | 129 CB | 152 CB | 75.88 |
| 128 CA | 129 CB | 128 N | 14.93 | 128 CA | 129 CB | 128 CB | 15.46 |

Figure 11Y

| Atom 1 | Atom 2 | Atom 3 | Angle | Atom 1 | Atom 2 | Atom 3 | Angle |
|---|---|---|---|---|---|---|---|
| 128 CA | 129 CB | 61 CD2 | 129.64 | 128 CA | 129 CB | 156 N | 98.95 |
| 128 CA | 129 CB | 61 CG | 133.53 | 128 CA | 129 CB | 131 OG | 132.09 |
| 128 CA | 129 CB | 131 N | 111.16 | 128 CA | 129 CB | 152 N | 55.63 |
| 128 CA | 129 CB | 130 CB | 85.45 | 61 ND1 | 129 CB | 301 OH2 | 134.25 |
| 61 ND1 | 129 CB | 130 CA | 100.04 | 61 ND1 | 129 CB | 130 C | 86.20 |
| 61 ND1 | 129 CB | 130 O | 86.09 | 61 ND1 | 129 CB | 152 CB | 80.41 |
| 61 ND1 | 129 CB | 128 N | 144.00 | 61 ND1 | 129 CB | 128 CB | 144.13 |
| 61 ND1 | 129 CB | 61 CD2 | 23.75 | 61 ND1 | 129 CB | 156 N | 110.53 |
| 61 ND1 | 129 CB | 61 CG | 11.33 | 61 ND1 | 129 CB | 131 OG | 48.47 |
| 61 ND1 | 129 CB | 131 N | 76.61 | 61 ND1 | 129 CB | 152 N | 92.64 |
| 61 ND1 | 129 CB | 130 CB | 109.32 | 301 OH2 | 129 CB | 130 CA | 47.72 |
| 301 OH2 | 129 CB | 130 C | 54.55 | 301 OH2 | 129 CB | 130 O | 50.06 |
| 301 OH2 | 129 CB | 152 CB | 142.88 | 301 OH2 | 129 CB | 128 N | 81.17 |
| 301 OH2 | 129 CB | 128 CB | 68.22 | 301 OH2 | 129 CB | 61 CD2 | 123.10 |
| 301 OH2 | 129 CB | 156 N | 68.45 | 301 OH2 | 129 CB | 61 CG | 133.81 |
| 301 OH2 | 129 CB | 131 OG | 91.04 | 301 OH2 | 129 CB | 131 N | 66.16 |
| 301 OH2 | 129 CB | 152 N | 132.86 | 301 OH2 | 129 CB | 130 CB | 38.41 |
| 130 CA | 129 CB | 130 C | 16.95 | 130 CA | 129 CB | 130 O | 27.17 |
| 130 CA | 129 CB | 152 CB | 157.06 | 130 CA | 129 CB | 128 N | 102.82 |
| 130 CA | 129 CB | 128 CB | 75.43 | 130 CA | 129 CB | 61 CD2 | 79.96 |
| 130 CA | 129 CB | 156 N | 111.90 | 130 CA | 129 CB | 61 CG | 93.38 |
| 130 CA | 129 CB | 131 OG | 51.74 | 130 CA | 129 CB | 131 N | 23.61 |
| 130 CA | 129 CB | 152 N | 134.48 | 130 CA | 129 CB | 130 CB | 9.87 |
| 130 C | 129 CB | 130 O | 13.56 | 130 C | 129 CB | 152 CB | 161.05 |
| 130 C | 129 CB | 128 N | 119.60 | 130 C | 129 CB | 128 CB | 92.38 |
| 130 C | 129 CB | 61 CD2 | 69.08 | 130 C | 129 CB | 156 N | 108.42 |
| 130 C | 129 CB | 61 CG | 81.40 | 130 C | 129 CB | 131 OG | 38.01 |
| 130 C | 129 CB | 131 N | 11.76 | 130 C | 129 CB | 152 N | 145.96 |
| 130 C | 129 CB | 130 CB | 23.95 | 130 O | 129 CB | 152 CB | 166.51 |

Figure 11Z

| Atom 1 | Atom 2 | Atom 3 | Angle | Atom 1 | Atom 2 | Atom 3 | Angle |
|---|---|---|---|---|---|---|---|
| 130 O | 129 CB | 128 N | 125.03 | 130 O | 129 CB | 128 CB | 100.40 |
| 130 O | 129 CB | 61 CD2 | 73.34 | 130 O | 129 CB | 156 N | 95.74 |
| 130 O | 129 CB | 61 CG | 83.84 | 130 O | 129 CB | 131 OG | 41.22 |
| 130 O | 129 CB | 131 N | 22.34 | 130 O | 129 CB | 152 N | 159.50 |
| 130 O | 129 CB | 130 CB | 30.39 | 152 CB | 129 CB | 128 N | 67.82 |
| 152 CB | 129 CB | 128 CB | 90.71 | 152 CB | 129 CB | 61 CD2 | 94.01 |
| 152 CB | 129 CB | 156 N | 88.92 | 152 CB | 129 CB | 61 CG | 82.95 |
| 152 CB | 129 CB | 131 OG | 126.08 | 152 CB | 129 CB | 131 N | 149.40 |
| 152 CB | 129 CB | 152 N | 23.91 | 152 CB | 129 CB | 130 CB | 158.54 |
| 128 N | 129 CB | 128 CB | 28.64 | 128 N | 129 CB | 61 CD2 | 139.98 |
| 128 N | 129 CB | 156 N | 86.12 | 128 N | 129 CB | 61 CG | 139.61 |
| 128 N | 129 CB | 131 OG | 147.02 | 128 N | 129 CB | 131 N | 124.62 |
| 128 N | 129 CB | 152 N | 51.70 | 128 N | 129 CB | 130 CB | 96.07 |
| 128 CB | 129 CB | 61 CD2 | 125.36 | 128 CB | 129 CB | 156 N | 103.91 |
| 128 CB | 129 CB | 61 CG | 133.60 | 128 CB | 129 CB | 131 OG | 119.22 |
| 128 CB | 129 CB | 131 N | 96.16 | 128 CB | 129 CB | 152 N | 69.20 |
| 128 CB | 129 CB | 130 CB | 70.09 | 61 CD2 | 129 CB | 156 N | 130.54 |
| 61 CD2 | 129 CB | 61 CG | 13.87 | 61 CD2 | 129 CB | 131 OG | 32.14 |
| 61 CD2 | 129 CB | 131 N | 57.95 | 61 CD2 | 129 CB | 152 N | 97.80 |
| 61 CD2 | 129 CB | 130 CB | 89.76 | 156 N | 129 CB | 61 CG | 121.76 |
| 156 N | 129 CB | 131 OG | 120.78 | 156 N | 129 CB | 131 N | 117.94 |
| 156 N | 129 CB | 152 N | 103.82 | 156 N | 129 CB | 130 CB | 104.59 |
| 61 CG | 129 CB | 131 OG | 43.51 | 61 CG | 129 CB | 131 N | 70.76 |
| 61 CG | 129 CB | 152 N | 90.92 | 61 CG | 129 CB | 130 CB | 103.09 |
| 131 OG | 129 CB | 131 N | 28.17 | 131 OG | 129 CB | 152 N | 127.54 |
| 131 OG | 129 CB | 130 CB | 60.85 | 131 N | 129 CB | 152 N | 138.10 |
| 131 N | 129 CB | 130 CB | 32.71 | 152 N | 129 CB | 130 CB | 134.62 |
| 61 CE1 | 129 OG | 130 N | 113.14 | 61 CE1 | 129 OG | 61 NE2 | 20.27 |
| 61 CE1 | 129 OG | 61 ND1 | 12.36 | 61 CE1 | 129 OG | 130 O | 93.42 |

Figure 11AA

| Atom 1 | Atom 2 | Atom 3 | Angle | Atom 1 | Atom 2 | Atom 3 | Angle |
|---|---|---|---|---|---|---|---|
| 61 CE1 | 129 OG | 300 OH2 | 176.66 | 61 CE1 | 129 OG | 128 C | 130.71 |
| 61 CE1 | 129 OG | 128 O | 145.08 | 61 CE1 | 129 OG | 130 C | 89.02 |
| 61 CE1 | 129 OG | 130 CA | 100.37 | 61 CE1 | 129 OG | 301 OH2 | 147.01 |
| 61 CE1 | 129 OG | 131 OG | 45.19 | 61 CE1 | 129 OG | 61 CD2 | 16.07 |
| 61 CE1 | 129 OG | 152 SG | 101.09 | 61 CE1 | 129 OG | 61 CG | 7.75 |
| 61 CE1 | 129 OG | 131 N | 76.12 | 61 CE1 | 129 OG | 156 N | 136.70 |
| 61 CE1 | 129 OG | 157 NH2 | 117.58 | 61 CE1 | 129 OG | 128 CA | 123.12 |
| 61 CE1 | 129 OG | 156 CG | 109.17 | 61 CE1 | 129 OG | 131 CA | 68.19 |
| 61 CE1 | 129 OG | 130 CB | 109.12 | 130 N | 129 OG | 61 NE2 | 92.95 |
| 130 N | 129 OG | 61 ND1 | 124.41 | 130 N | 129 OG | 130 O | 40.07 |
| 130 N | 129 OG | 300 OH2 | 69.38 | 130 N | 129 OG | 128 C | 62.86 |
| 130 N | 129 OG | 128 O | 67.46 | 130 N | 129 OG | 130 C | 31.85 |
| 130 N | 129 OG | 130 CA | 14.20 | 130 N | 129 OG | 301 OH2 | 37.58 |
| 130 N | 129 OG | 131 OG | 72.37 | 130 N | 129 OG | 61 CD2 | 98.29 |
| 130 N | 129 OG | 152 SG | 115.76 | 130 N | 129 OG | 61 CG | 113.45 |
| 130 N | 129 OG | 131 N | 41.26 | 130 N | 129 OG | 156 N | 107.78 |
| 130 N | 129 OG | 157 NH2 | 45.83 | 130 N | 129 OG | 128 CA | 65.22 |
| 130 N | 129 OG | 156 CG | 125.75 | 130 N | 129 OG | 131 CA | 53.93 |
| 130 N | 129 OG | 130 CB | 10.29 | 61 NE2 | 129 OG | 61 ND1 | 31.69 |
| 61 NE2 | 129 OG | 130 O | 78.24 | 61 NE2 | 129 OG | 300 OH2 | 162.32 |
| 61 NE2 | 129 OG | 128 C | 120.93 | 61 NE2 | 129 OG | 128 O | 136.74 |
| 61 NE2 | 129 OG | 130 C | 70.99 | 61 NE2 | 129 OG | 130 CA | 80.51 |
| 61 NE2 | 129 OG | 301 OH2 | 128.29 | 61 NE2 | 129 OG | 131 OG | 29.73 |
| 61 NE2 | 129 OG | 61 CD2 | 7.04 | 61 NE2 | 129 OG | 152 SG | 110.27 |
| 61 NE2 | 129 OG | 61 CG | 21.48 | 61 NE2 | 129 OG | 131 N | 57.82 |
| 61 NE2 | 129 OG | 156 N | 155.80 | 61 NE2 | 129 OG | 157 NH2 | 105.24 |
| 61 NE2 | 129 OG | 128 CA | 114.23 | 61 NE2 | 129 OG | 156 CG | 126.34 |
| 61 NE2 | 129 OG | 131 CA | 52.46 | 61 NE2 | 129 OG | 130 CB | 89.53 |
| 61 ND1 | 129 OG | 130 O | 105.44 | 61 ND1 | 129 OG | 300 OH2 | 165.87 |

Figure 11BB

| Atom 1 | Atom 2 | Atom 3 | Angle | Atom 1 | Atom 2 | Atom 3 | Angle |
|---|---|---|---|---|---|---|---|
| 61 ND1 | 129 OG | 128 C | 128.28 | 61 ND1 | 129 OG | 128 O | 140.06 |
| 61 ND1 | 129 OG | 130 C | 101.38 | 61 ND1 | 129 OG | 130 CA | 112.20 |
| 61 ND1 | 129 OG | 301 OH2 | 159.37 | 61 ND1 | 129 OG | 131 OG | 57.52 |
| 61 ND1 | 129 OG | 61 CD2 | 26.13 | 61 ND1 | 129 OG | 152 SG | 90.64 |
| 61 ND1 | 129 OG | 61 CG | 11.21 | 61 ND1 | 129 OG | 131 N | 88.45 |
| 61 ND1 | 129 OG | 156 N | 127.16 | 61 ND1 | 129 OG | 157 NH2 | 128.31 |
| 61 ND1 | 129 OG | 128 CA | 120.69 | 61 ND1 | 129 OG | 156 CG | 102.28 |
| 61 ND1 | 129 OG | 131 CA | 80.44 | 61 ND1 | 129 OG | 130 CB | 121.15 |
| 130 O | 129 OG | 300 OH2 | 87.31 | 130 O | 129 OG | 128 C | 102.28 |
| 130 O | 129 OG | 128 O | 103.40 | 130 O | 129 OG | 130 C | 15.35 |
| 130 O | 129 OG | 130 CA | 30.16 | 130 O | 129 OG | 301 OH2 | 54.68 |
| 130 O | 129 OG | 131 OG | 48.86 | 130 O | 129 OG | 61 CD2 | 85.27 |
| 130 O | 129 OG | 152 SG | 155.79 | 130 O | 129 OG | 61 CG | 98.37 |
| 130 O | 129 OG | 131 N | 24.48 | 130 O | 129 OG | 156 N | 109.59 |
| 130 O | 129 OG | 157 NH2 | 27.96 | 130 O | 129 OG | 128 CA | 105.24 |
| 130 O | 129 OG | 156 CG | 106.81 | 130 O | 129 OG | 131 CA | 25.80 |
| 130 O | 129 OG | 130 CB | 29.80 | 300 OH2 | 129 OG | 128 C | 52.14 |
| 300 OH2 | 129 OG | 128 O | 37.46 | 300 OH2 | 129 OG | 130 C | 92.51 |
| 300 OH2 | 129 OG | 130 CA | 81.88 | 300 OH2 | 129 OG | 301 OH2 | 34.58 |
| 300 OH2 | 129 OG | 131 OG | 135.94 | 300 OH2 | 129 OG | 61 CD2 | 167.07 |
| 300 OH2 | 129 OG | 152 SG | 79.33 | 300 OH2 | 129 OG | 61 CG | 173.70 |
| 300 OH2 | 129 OG | 131 N | 105.53 | 300 OH2 | 129 OG | 156 N | 40.19 |
| 300 OH2 | 129 OG | 157 NH2 | 62.35 | 300 OH2 | 129 OG | 128 CA | 59.69 |
| 300 OH2 | 129 OG | 156 CG | 67.52 | 300 OH2 | 129 OG | 131 CA | 112.81 |
| 300 OH2 | 129 OG | 130 CB | 72.97 | 128 C | 129 OG | 128 O | 15.81 |
| 128 C | 129 OG | 130 C | 94.21 | 128 C | 129 OG | 130 CA | 75.58 |
| 128 C | 129 OG | 301 OH2 | 59.62 | 128 C | 129 OG | 131 OG | 123.97 |
| 128 C | 129 OG | 61 CD2 | 119.43 | 128 C | 129 OG | 152 SG | 53.66 |
| 128 C | 129 OG | 61 CG | 123.41 | 128 C | 129 OG | 131 N | 100.46 |

Figure 11CC

| Atom 1 | Atom 2 | Atom 3 | Angle | Atom 1 | Atom 2 | Atom 3 | Angle |
|---|---|---|---|---|---|---|---|
| 128 C | 129 OG | 156 N | 80.68 | 128 C | 129 OG | 157 NH2 | 94.32 |
| 128 C | 129 OG | 128 CA | 7.65 | 128 C | 129 OG | 156 CG | 110.24 |
| 128 C | 129 OG | 131 CA | 114.32 | 128 C | 129 OG | 130 CB | 72.85 |
| 128 O | 129 OG | 130 C | 99.16 | 128 O | 129 OG | 130 CA | 81.41 |
| 128 O | 129 OG | 301 OH2 | 52.90 | 128 O | 129 OG | 131 OG | 136.12 |
| 128 O | 129 OG | 61 CD2 | 135.08 | 128 O | 129 OG | 152 SG | 54.48 |
| 128 O | 129 OG | 61 CG | 137.44 | 128 O | 129 OG | 131 N | 108.16 |
| 128 O | 129 OG | 156 N | 65.26 | 128 O | 129 OG | 157 NH2 | 88.50 |
| 128 O | 129 OG | 128 CA | 22.79 | 128 O | 129 OG | 156 CG | 95.10 |
| 128 O | 129 OG | 131 CA | 121.34 | 128 O | 129 OG | 130 CB | 76.37 |
| 130 C | 129 OG | 130 CA | 18.65 | 130 C | 129 OG | 301 OH2 | 57.99 |
| 130 C | 129 OG | 131 OG | 44.14 | 130 C | 129 OG | 61 CD2 | 77.74 |
| 130 C | 129 OG | 152 SG | 144.58 | 130 C | 129 OG | 61 CG | 92.33 |
| 130 C | 129 OG | 131 N | 13.18 | 130 C | 129 OG | 156 N | 121.63 |
| 130 C | 129 OG | 157 NH2 | 40.20 | 130 C | 129 OG | 128 CA | 95.54 |
| 130 C | 129 OG | 156 CG | 122.10 | 130 C | 129 OG | 131 CA | 22.69 |
| 130 C | 129 OG | 130 CB | 22.92 | 130 CA | 129 OG | 301 OH2 | 48.23 |
| 130 CA | 129 OG | 131 OG | 58.29 | 130 CA | 129 OG | 61 CD2 | 86.40 |
| 130 CA | 129 OG | 152 SG | 126.71 | 130 CA | 129 OG | 61 CG | 101.68 |
| 130 CA | 129 OG | 131 N | 27.06 | 130 CA | 129 OG | 156 N | 118.10 |
| 130 CA | 129 OG | 157 NH2 | 45.01 | 130 CA | 129 OG | 128 CA | 76.95 |
| 130 CA | 129 OG | 156 CG | 129.72 | 130 CA | 129 OG | 131 CA | 39.94 |
| 130 CA | 129 OG | 130 CB | 9.44 | 301 OH2 | 129 OG | 131 OG | 101.90 |
| 301 OH2 | 129 OG | 61 CD2 | 134.52 | 301 OH2 | 129 OG | 152 SG | 106.62 |
| 301 OH2 | 129 OG | 61 CG | 149.73 | 301 OH2 | 129 OG | 131 N | 70.96 |
| 301 OH2 | 129 OG | 156 N | 70.36 | 301 OH2 | 129 OG | 157 NH2 | 35.63 |
| 301 OH2 | 129 OG | 128 CA | 66.25 | 301 OH2 | 129 OG | 156 CG | 90.18 |
| 301 OH2 | 129 OG | 131 CA | 79.12 | 301 OH2 | 129 OG | 130 CB | 38.96 |
| 131 OG | 129 OG | 61 CD2 | 36.75 | 131 OG | 129 OG | 152 SG | 138.48 |

Figure 11DD

| Atom 1 | Atom 2 | Atom 3 | Angle | Atom 1 | Atom 2 | Atom 3 | Angle |
|---|---|---|---|---|---|---|---|
| 131 OG | 129 OG | 61 CG | 49.56 | 131 OG | 129 OG | 131 N | 31.80 |
| 131 OG | 129 OG | 156 N | 147.23 | 131 OG | 129 OG | 157 NH2 | 75.51 |
| 131 OG | 129 OG | 128 CA | 120.50 | 131 OG | 129 OG | 156 CG | 123.03 |
| 131 OG | 129 OG | 131 CA | 23.15 | 131 OG | 129 OG | 130 CB | 65.81 |
| 61 CD2 | 129 OG | 152 SG | 103.66 | 61 CD2 | 129 OG | 61 CG | 15.28 |
| 61 CD2 | 129 OG | 131 N | 64.55 | 61 CD2 | 129 OG | 156 N | 152.74 |
| 61 CD2 | 129 OG | 157 NH2 | 112.26 | 61 CD2 | 129 OG | 128 CA | 112.30 |
| 61 CD2 | 129 OG | 156 CG | 124.89 | 61 CD2 | 129 OG | 131 CA | 59.49 |
| 61 CD2 | 129 OG | 130 CB | 95.58 | 152 SG | 129 OG | 61 CG | 94.40 |
| 152 SG | 129 OG | 131 N | 143.85 | 152 SG | 129 OG | 156 N | 72.30 |
| 152 SG | 129 OG | 157 NH2 | 141.06 | 152 SG | 129 OG | 128 CA | 50.56 |
| 152 SG | 129 OG | 156 CG | 86.71 | 152 SG | 129 OG | 131 CA | 153.82 |
| 152 SG | 129 OG | 130 CB | 126.01 | 61 CG | 129 OG | 131 N | 79.20 |
| 61 CG | 129 OG | 156 N | 138.35 | 61 CG | 129 OG | 157 NH2 | 123.80 |
| 61 CG | 129 OG | 128 CA | 115.78 | 61 CG | 129 OG | 156 CG | 113.00 |
| 61 CG | 129 OG | 131 CA | 72.71 | 61 CG | 129 OG | 130 CB | 110.83 |
| 131 N | 129 OG | 156 N | 133.82 | 131 N | 129 OG | 157 NH2 | 51.90 |
| 131 N | 129 OG | 128 CA | 100.18 | 131 N | 129 OG | 156 CG | 128.70 |
| 131 N | 129 OG | 131 CA | 13.88 | 131 N | 129 OG | 130 CB | 34.03 |
| 156 N | 129 OG | 157 NH2 | 81.92 | 156 N | 129 OG | 128 CA | 86.42 |
| 156 N | 129 OG | 156 CG | 29.98 | 156 N | 129 OG | 131 CA | 132.20 |
| 156 N | 129 OG | 130 CB | 108.66 | 157 NH2 | 129 OG | 128 CA | 100.22 |
| 157 NH2 | 129 OG | 156 CG | 84.94 | 157 NH2 | 129 OG | 131 CA | 53.12 |
| 157 NH2 | 129 OG | 130 CB | 38.10 | 128 CA | 129 OG | 156 CG | 115.36 |
| 128 CA | 129 OG | 131 CA | 114.01 | 128 CA | 129 OG | 130 CB | 75.45 |
| 156 CG | 129 OG | 131 CA | 119.15 | 156 CG | 129 OG | 130 CB | 121.60 |
| 131 CA | 129 OG | 130 CB | 45.55 | 61 CE1 | 129 P1 | 156 N | 160.22 |
| 61 CE1 | 129 P1 | 300 OH2 | 139.22 | 61 CE1 | 129 P1 | 156 CG | 131.59 |
| 61 CE1 | 129 P1 | 156 CB | 148.07 | 61 CE1 | 129 P1 | 130 N | 80.66 |

Figure 11EE

| Atom 1 | Atom 2 | Atom 3 | Angle | Atom 1 | Atom 2 | Atom 3 | Angle |
|---|---|---|---|---|---|---|---|
| 61 CE1 | 129 P1 | 61 ND1 | 13.22 | 61 CE1 | 129 P1 | 61 NE2 | 13.08 |
| 61 CE1 | 129 P1 | 301 OH2 | 115.69 | 61 CE1 | 129 P1 | 128 O | 108.39 |
| 61 CE1 | 129 P1 | 156 CA | 162.21 | 61 CE1 | 129 P1 | 130 O | 75.79 |
| 61 CE1 | 129 P1 | 128 C | 95.20 | 61 CE1 | 129 P1 | 156 NE | 115.09 |
| 61 CE1 | 129 P1 | 156 CD | 120.41 | 61 CE1 | 129 P1 | 152 SG | 85.51 |
| 61 CE1 | 129 P1 | 130 C | 68.87 | 61 CE1 | 129 P1 | 157 N | 171.54 |
| 61 CE1 | 129 P1 | 157 NH2 | 104.68 | 61 CE1 | 129 P1 | 130 CA | 74.65 |
| 61 CE1 | 129 P1 | 131 OG | 35.42 | 61 CE1 | 129 P1 | 156 C | 171.97 |
| 61 CE1 | 129 P1 | 61 CD2 | 6.38 | 61 CE1 | 129 P1 | 61 CG | 6.75 |
| 156 N | 129 P1 | 300 OH2 | 50.28 | 156 N | 129 P1 | 156 CG | 41.20 |
| 156 N | 129 P1 | 156 CB | 32.96 | 156 N | 129 P1 | 130 N | 113.58 |
| 156 N | 129 P1 | 61 ND1 | 147.71 | 156 N | 129 P1 | 61 NE2 | 169.99 |
| 156 N | 129 P1 | 301 OH2 | 80.11 | 156 N | 129 P1 | 128 O | 71.99 |
| 156 N | 129 P1 | 156 CA | 15.51 | 156 N | 129 P1 | 130 O | 123.79 |
| 156 N | 129 P1 | 128 C | 84.89 | 156 N | 129 P1 | 156 NE | 65.19 |
| 156 N | 129 P1 | 156 CD | 54.54 | 156 N | 129 P1 | 152 SG | 79.90 |
| 156 N | 129 P1 | 130 C | 129.77 | 156 N | 129 P1 | 157 N | 27.92 |
| 156 N | 129 P1 | 157 NH2 | 95.08 | 156 N | 129 P1 | 130 CA | 121.58 |
| 156 N | 129 P1 | 131 OG | 164.33 | 156 N | 129 P1 | 156 C | 21.78 |
| 156 N | 129 P1 | 61 CD2 | 165.23 | 156 N | 129 P1 | 61 CG | 153.74 |
| 300 OH2 | 129 P1 | 156 CG | 88.69 | 300 OH2 | 129 P1 | 156 CB | 72.59 |
| 300 OH2 | 129 P1 | 130 N | 63.63 | 300 OH2 | 129 P1 | 61 ND1 | 147.11 |
| 300 OH2 | 129 P1 | 61 NE2 | 129.07 | 300 OH2 | 129 P1 | 301 OH2 | 33.82 |
| 300 OH2 | 129 P1 | 128 O | 35.39 | 300 OH2 | 129 P1 | 156 CA | 57.64 |
| 300 OH2 | 129 P1 | 130 O | 84.24 | 300 OH2 | 129 P1 | 128 C | 47.18 |
| 300 OH2 | 129 P1 | 156 NE | 104.41 | 300 OH2 | 129 P1 | 156 CD | 100.36 |
| 300 OH2 | 129 P1 | 152 SG | 78.74 | 300 OH2 | 129 P1 | 130 C | 84.51 |
| 300 OH2 | 129 P1 | 157 N | 36.07 | 300 OH2 | 129 P1 | 157 NH2 | 64.64 |
| 300 OH2 | 129 P1 | 130 CA | 72.75 | 300 OH2 | 129 P1 | 131 OG | 120.30 |

Figure 11FF

| Atom 1 | Atom 2 | Atom 3 | Angle | Atom 1 | Atom 2 | Atom 3 | Angle |
|---|---|---|---|---|---|---|---|
| 300 OH2 | 129 P1 | 156 C | 48.25 | 300 OH2 | 129 P1 | 61 CD2 | 134.07 |
| 300 OH2 | 129 P1 | 61 CG | 143.08 | 156 CG | 129 P1 | 156 CB | 19.77 |
| 156 CG | 129 P1 | 130 N | 144.26 | 156 CG | 129 P1 | 61 ND1 | 120.48 |
| 156 CG | 129 P1 | 61 NE2 | 142.11 | 156 CG | 129 P1 | 301 OH2 | 110.10 |
| 156 CG | 129 P1 | 128 O | 112.89 | 156 CG | 129 P1 | 156 CA | 31.05 |
| 156 CG | 129 P1 | 130 O | 127.40 | 156 CG | 129 P1 | 128 C | 125.34 |
| 156 CG | 129 P1 | 156 NE | 27.40 | 156 CG | 129 P1 | 156 CD | 13.55 |
| 156 CG | 129 P1 | 152 SG | 102.02 | 156 CG | 129 P1 | 130 C | 139.37 |
| 156 CG | 129 P1 | 157 N | 55.01 | 156 CG | 129 P1 | 157 NH2 | 102.99 |
| 156 CG | 129 P1 | 130 CA | 144.93 | 156 CG | 129 P1 | 131 OG | 138.24 |
| 156 CG | 129 P1 | 156 C | 41.95 | 156 CG | 129 P1 | 61 CD2 | 137.18 |
| 156 CG | 129 P1 | 61 CG | 126.35 | 156 CB | 129 P1 | 130 N | 124.51 |
| 156 CB | 129 P1 | 61 ND1 | 138.88 | 156 CB | 129 P1 | 61 NE2 | 154.67 |
| 156 CB | 129 P1 | 301 OH2 | 90.51 | 156 CB | 129 P1 | 128 O | 102.50 |
| 156 CB | 129 P1 | 156 CA | 17.99 | 156 CB | 129 P1 | 130 O | 112.83 |
| 156 CB | 129 P1 | 128 C | 115.77 | 156 CB | 129 P1 | 156 NE | 33.62 |
| 156 CB | 129 P1 | 156 CD | 28.17 | 156 CB | 129 P1 | 152 SG | 108.97 |
| 156 CB | 129 P1 | 130 C | 123.99 | 156 CB | 129 P1 | 157 N | 37.02 |
| 156 CB | 129 P1 | 157 NH2 | 85.57 | 156 CB | 129 P1 | 130 CA | 126.15 |
| 156 CB | 129 P1 | 131 OG | 138.57 | 156 CB | 129 P1 | 156 C | 24.35 |
| 156 CB | 129 P1 | 61 CD2 | 152.28 | 156 CB | 129 P1 | 61 CG | 144.10 |
| 130 N | 129 P1 | 61 ND1 | 93.23 | 130 N | 129 P1 | 61 NE2 | 68.06 |
| 130 N | 129 P1 | 301 OH2 | 35.15 | 130 N | 129 P1 | 128 O | 56.58 |
| 130 N | 129 P1 | 156 CA | 116.98 | 130 N | 129 P1 | 130 O | 34.31 |
| 130 N | 129 P1 | 128 C | 50.42 | 130 N | 129 P1 | 156 NE | 135.42 |
| 130 N | 129 P1 | 156 CD | 147.20 | 130 N | 129 P1 | 152 SG | 94.56 |
| 130 N | 129 P1 | 130 C | 26.26 | 130 N | 129 P1 | 157 N | 91.57 |
| 130 N | 129 P1 | 157 NH2 | 46.05 | 130 N | 129 P1 | 130 CA | 11.07 |
| 130 N | 129 P1 | 131 OG | 57.22 | 130 N | 129 P1 | 156 C | 104.25 |

Figure 11GG

| Atom 1 | Atom 2 | Atom 3 | Angle | Atom 1 | Atom 2 | Atom 3 | Angle |
|---|---|---|---|---|---|---|---|
| 130 N   | 129 P1 | 61 CD2  | 74.38  | 130 N   | 129 P1 | 61 CG   | 86.87  |
| 61 ND1  | 129 P1 | 61 NE2  | 26.30  | 61 ND1  | 129 P1 | 301 OH2 | 128.39 |
| 61 ND1  | 129 P1 | 128 O   | 112.81 | 61 ND1  | 129 P1 | 156 CA  | 149.74 |
| 61 ND1  | 129 P1 | 130 O   | 88.49  | 61 ND1  | 129 P1 | 128 C   | 100.28 |
| 61 ND1  | 129 P1 | 156 NE  | 108.42 | 61 ND1  | 129 P1 | 156 CD  | 110.72 |
| 61 ND1  | 129 P1 | 152 SG  | 80.36  | 61 ND1  | 129 P1 | 130 C   | 82.02  |
| 61 ND1  | 129 P1 | 157 N   | 175.14 | 61 ND1  | 129 P1 | 157 NH2 | 116.92 |
| 61 ND1  | 129 P1 | 130 CA  | 87.73  | 61 ND1  | 129 P1 | 131 OG  | 47.60  |
| 61 ND1  | 129 P1 | 156 C   | 162.35 | 61 ND1  | 129 P1 | 61 CD2  | 19.55  |
| 61 ND1  | 129 P1 | 61 CG   | 6.53   | 61 NE2  | 129 P1 | 301 OH2 | 102.88 |
| 61 NE2  | 129 P1 | 128 O   | 102.52 | 61 NE2  | 129 P1 | 156 CA  | 172.55 |
| 61 NE2  | 129 P1 | 130 O   | 63.53  | 61 NE2  | 129 P1 | 128 C   | 89.31  |
| 61 NE2  | 129 P1 | 156 NE  | 121.23 | 61 NE2  | 129 P1 | 156 CD  | 129.64 |
| 61 NE2  | 129 P1 | 152 SG  | 90.16  | 61 NE2  | 129 P1 | 130 C   | 55.98  |
| 61 NE2  | 129 P1 | 157 N   | 158.51 | 61 NE2  | 129 P1 | 157 NH2 | 92.73  |
| 61 NE2  | 129 P1 | 130 CA  | 61.64  | 61 NE2  | 129 P1 | 131 OG  | 24.73  |
| 61 NE2  | 129 P1 | 156 C   | 167.68 | 61 NE2  | 129 P1 | 61 CD2  | 6.76   |
| 61 NE2  | 129 P1 | 61 CG   | 19.79  | 301 OH2 | 129 P1 | 128 O   | 49.34  |
| 301 OH2 | 129 P1 | 156 CA  | 81.85  | 301 OH2 | 129 P1 | 130 O   | 50.46  |
| 301 OH2 | 129 P1 | 128 C   | 53.22  | 301 OH2 | 129 P1 | 156 NE  | 111.93 |
| 301 OH2 | 129 P1 | 156 CD  | 116.98 | 301 OH2 | 129 P1 | 152 SG  | 99.48  |
| 301 OH2 | 129 P1 | 130 C   | 51.22  | 301 OH2 | 129 P1 | 157 N   | 56.42  |
| 301 OH2 | 129 P1 | 157 NH2 | 35.96  | 301 OH2 | 129 P1 | 130 CA  | 41.53  |
| 301 OH2 | 129 P1 | 131 OG  | 87.77  | 301 OH2 | 129 P1 | 156 C   | 69.12  |
| 301 OH2 | 129 P1 | 61 CD2  | 109.36 | 301 OH2 | 129 P1 | 61 CG   | 121.99 |
| 128 O   | 129 P1 | 156 CA  | 84.93  | 128 O   | 129 P1 | 130 O   | 89.58  |
| 128 O   | 129 P1 | 128 C   | 13.28  | 128 O   | 129 P1 | 156 NE  | 136.12 |
| 128 O   | 129 P1 | 156 CD  | 126.41 | 128 O   | 129 P1 | 152 SG  | 50.23  |
| 128 O   | 129 P1 | 130 C   | 82.84  | 128 O   | 129 P1 | 157 N   | 69.40  |

Figure 11HH

| Atom 1 | Atom 2 | Atom 3 | Angle | Atom 1 | Atom 2 | Atom 3 | Angle |
|---|---|---|---|---|---|---|---|
| 128 O | 129 P1 | 157 NH2 | 85.06 | 128 O | 129 P1 | 130 CA | 67.62 |
| 128 O | 129 P1 | 131 OG | 107.36 | 128 O | 129 P1 | 156 C | 79.64 |
| 128 O | 129 P1 | 61 CD2 | 105.11 | 128 O | 129 P1 | 61 CG | 110.19 |
| 156 CA | 129 P1 | 130 O | 117.05 | 156 CA | 129 P1 | 128 C | 98.15 |
| 156 CA | 129 P1 | 156 NE | 51.33 | 156 CA | 129 P1 | 156 CD | 43.15 |
| 156 CA | 129 P1 | 152 SG | 94.77 | 156 CA | 129 P1 | 130 C | 125.91 |
| 156 CA | 129 P1 | 157 N | 25.43 | 156 CA | 129 P1 | 157 NH2 | 87.81 |
| 156 CA | 129 P1 | 130 CA | 122.31 | 156 CA | 129 P1 | 131 OG | 152.46 |
| 156 CA | 129 P1 | 156 C | 13.29 | 156 CA | 129 P1 | 61 CD2 | 168.17 |
| 156 CA | 129 P1 | 61 CG | 156.15 | 130 O | 129 P1 | 128 C | 84.69 |
| 130 O | 129 P1 | 156 NE | 106.06 | 130 O | 129 P1 | 156 CD | 121.37 |
| 130 O | 129 P1 | 152 SG | 127.11 | 130 O | 129 P1 | 130 C | 12.04 |
| 130 O | 129 P1 | 157 N | 95.90 | 130 O | 129 P1 | 157 NH2 | 29.29 |
| 130 O | 129 P1 | 130 CA | 24.39 | 130 O | 129 P1 | 131 OG | 41.06 |
| 130 O | 129 P1 | 156 C | 104.57 | 130 O | 129 P1 | 61 CD2 | 70.02 |
| 130 O | 129 P1 | 61 CG | 82.42 | 128 C | 129 P1 | 156 NE | 149.39 |
| 128 C | 129 P1 | 156 CD | 138.89 | 128 C | 129 P1 | 152 SG | 47.87 |
| 128 C | 129 P1 | 130 C | 76.02 | 128 C | 129 P1 | 157 N | 82.23 |
| 128 C | 129 P1 | 157 NH2 | 86.83 | 128 C | 129 P1 | 130 CA | 60.96 |
| 128 C | 129 P1 | 131 OG | 95.83 | 128 C | 129 P1 | 156 C | 92.82 |
| 128 C | 129 P1 | 61 CD2 | 91.83 | 128 C | 129 P1 | 61 CG | 97.26 |
| 156 NE | 129 P1 | 156 CD | 15.91 | 156 NE | 129 P1 | 152 SG | 126.59 |
| 156 NE | 129 P1 | 130 C | 117.71 | 156 NE | 129 P1 | 157 N | 68.39 |
| 156 NE | 129 P1 | 157 NH2 | 89.47 | 156 NE | 129 P1 | 130 CA | 129.22 |
| 156 NE | 129 P1 | 131 OG | 111.20 | 156 NE | 129 P1 | 156 C | 56.96 |
| 156 NE | 129 P1 | 61 CD2 | 118.74 | 156 NE | 129 P1 | 61 CG | 112.34 |
| 156 CD | 129 P1 | 152 SG | 110.86 | 156 CD | 129 P1 | 130 C | 133.22 |
| 156 CD | 129 P1 | 157 N | 65.17 | 156 CD | 129 P1 | 157 NH2 | 101.71 |
| 156 CD | 129 P1 | 130 CA | 143.37 | 156 CD | 129 P1 | 131 OG | 124.95 |

Figure 11II

| Atom 1 | Atom 2 | Atom 3 | Angle | Atom 1 | Atom 2 | Atom 3 | Angle |
|---|---|---|---|---|---|---|---|
| 156 CD | 129 P1 | 156 C | 52.36 | 156 CD | 129 P1 | 61 CD2 | 125.43 |
| 156 CD | 129 P1 | 61 CG | 115.98 | 152 SG | 129 P1 | 130 C | 115.68 |
| 152 SG | 129 P1 | 157 N | 98.52 | 152 SG | 129 P1 | 157 NH2 | 134.57 |
| 152 SG | 129 P1 | 130 CA | 103.08 | 152 SG | 129 P1 | 131 OG | 112.13 |
| 152 SG | 129 P1 | 156 C | 100.27 | 152 SG | 129 P1 | 61 CD2 | 87.21 |
| 152 SG | 129 P1 | 61 CG | 82.29 | 130 C | 129 P1 | 157 N | 102.67 |
| 130 C | 129 P1 | 157 NH2 | 38.81 | 130 C | 129 P1 | 130 CA | 15.24 |
| 130 C | 129 P1 | 131 OG | 36.68 | 130 C | 129 P1 | 156 C | 112.86 |
| 130 C | 129 P1 | 61 CD2 | 62.70 | 130 C | 129 P1 | 61 CG | 75.62 |
| 157 N | 129 P1 | 157 NH2 | 67.21 | 157 N | 129 P1 | 130 CA | 97.13 |
| 157 N | 129 P1 | 131 OG | 136.58 | 157 N | 129 P1 | 156 C | 13.06 |
| 157 N | 129 P1 | 61 CD2 | 165.26 | 157 N | 129 P1 | 61 CG | 178.29 |
| 157 NH2 | 129 P1 | 130 CA | 42.28 | 157 NH2 | 129 P1 | 131 OG | 69.37 |
| 157 NH2 | 129 P1 | 156 C | 75.29 | 157 NH2 | 129 P1 | 61 CD2 | 99.12 |
| 157 NH2 | 129 P1 | 61 CG | 111.15 | 130 CA | 129 P1 | 131 OG | 47.57 |
| 130 CA | 129 P1 | 156 C | 109.09 | 130 CA | 129 P1 | 61 CD2 | 68.27 |
| 130 CA | 129 P1 | 61 CG | 81.21 | 131 OG | 129 P1 | 156 C | 142.99 |
| 131 OG | 129 P1 | 61 CD2 | 30.35 | 131 OG | 129 P1 | 61 CG | 41.79 |
| 156 C | 129 P1 | 61 CD2 | 172.50 | 156 C | 129 P1 | 61 CG | 168.26 |
| 61 CD2 | 129 P1 | 61 CG | 13.04 | 156 CG | 129 O3 | 156 N | 44.94 |
| 156 CG | 129 O3 | 61 CE1 | 139.30 | 156 CG | 129 O3 | 156 CB | 18.96 |
| 156 CG | 129 O3 | 152 SG | 127.31 | 156 CG | 129 O3 | 61 ND1 | 138.22 |
| 156 CG | 129 O3 | 156 CD | 15.17 | 156 CG | 129 O3 | 156 CA | 31.17 |
| 156 CG | 129 O3 | 300 OH2 | 83.24 | 156 CG | 129 O3 | 156 NE | 26.79 |
| 156 CG | 129 O3 | 61 NE2 | 139.77 | 156 CG | 129 O3 | 128 O | 111.24 |
| 156 CG | 129 O3 | 152 CB | 132.32 | 156 CG | 129 O3 | 128 C | 123.04 |
| 156 CG | 129 O3 | 61 CG | 140.34 | 156 N | 129 O3 | 61 CE1 | 151.94 |
| 156 N | 129 O3 | 156 CB | 33.19 | 156 N | 129 O3 | 152 SG | 91.89 |
| 156 N | 129 O3 | 61 ND1 | 168.38 | 156 N | 129 O3 | 156 CD | 60.05 |

Figure 11JJ

| Atom 1 | Atom 2 | Atom 3 | Angle | Atom 1 | Atom 2 | Atom 3 | Angle |
|---|---|---|---|---|---|---|---|
| 156 N   | 129 O3 | 156 CA  | 14.97  | 156 N   | 129 O3 | 300 OH2 | 44.24  |
| 156 N   | 129 O3 | 156 NE  | 67.31  | 156 N   | 129 O3 | 61 NE2  | 144.55 |
| 156 N   | 129 O3 | 128 O   | 67.05  | 156 N   | 129 O3 | 152 CB  | 105.96 |
| 156 N   | 129 O3 | 128 C   | 78.99  | 156 N   | 129 O3 | 61 CG   | 166.21 |
| 61 CE1  | 129 O3 | 156 CB  | 137.50 | 61 CE1  | 129 O3 | 152 SG  | 93.33  |
| 61 CE1  | 129 O3 | 61 ND1  | 16.45  | 61 CE1  | 129 O3 | 156 CD  | 126.40 |
| 61 CE1  | 129 O3 | 156 CA  | 149.44 | 61 CE1  | 129 O3 | 300 OH2 | 110.12 |
| 61 CE1  | 129 O3 | 156 NE  | 112.52 | 61 CE1  | 129 O3 | 61 NE2  | 7.61   |
| 61 CE1  | 129 O3 | 128 O   | 95.57  | 61 CE1  | 129 O3 | 152 CB  | 85.59  |
| 61 CE1  | 129 O3 | 128 C   | 84.56  | 61 CE1  | 129 O3 | 61 CG   | 14.39  |
| 156 CB  | 129 O3 | 152 SG  | 124.45 | 156 CB  | 129 O3 | 61 ND1  | 144.61 |
| 156 CB  | 129 O3 | 156 CD  | 31.06  | 156 CB  | 129 O3 | 156 CA  | 18.30  |
| 156 CB  | 129 O3 | 300 OH2 | 65.25  | 156 CB  | 129 O3 | 156 NE  | 34.39  |
| 156 CB  | 129 O3 | 61 NE2  | 134.37 | 156 CB  | 129 O3 | 128 O   | 94.96  |
| 156 CB  | 129 O3 | 152 CB  | 136.12 | 156 CB  | 129 O3 | 128 C   | 106.26 |
| 156 CB  | 129 O3 | 61 CG   | 145.58 | 152 SG  | 129 O3 | 61 ND1  | 90.69  |
| 152 SG  | 129 O3 | 156 CD  | 138.18 | 152 SG  | 129 O3 | 156 CA  | 106.35 |
| 152 SG  | 129 O3 | 300 OH2 | 79.03  | 152 SG  | 129 O3 | 156 NE  | 153.86 |
| 152 SG  | 129 O3 | 61 NE2  | 92.64  | 152 SG  | 129 O3 | 128 O   | 50.74  |
| 152 SG  | 129 O3 | 152 CB  | 17.66  | 152 SG  | 129 O3 | 128 C   | 47.01  |
| 152 SG  | 129 O3 | 61 CG   | 89.37  | 61 ND1  | 129 O3 | 156 CD  | 123.27 |
| 61 ND1  | 129 O3 | 156 CA  | 161.45 | 61 ND1  | 129 O3 | 300 OH2 | 125.51 |
| 61 ND1  | 129 O3 | 156 NE  | 112.92 | 61 ND1  | 129 O3 | 61 NE2  | 23.91  |
| 61 ND1  | 129 O3 | 128 O   | 106.37 | 61 ND1  | 129 O3 | 152 CB  | 78.93  |
| 61 ND1  | 129 O3 | 128 C   | 94.60  | 61 ND1  | 129 O3 | 61 CG   | 2.75   |
| 156 CD  | 129 O3 | 156 CA  | 45.96  | 156 CD  | 129 O3 | 300 OH2 | 96.27  |
| 156 CD  | 129 O3 | 156 NE  | 16.37  | 156 CD  | 129 O3 | 61 NE2  | 128.52 |
| 156 CD  | 129 O3 | 128 O   | 125.70 | 156 CD  | 129 O3 | 152 CB  | 137.84 |
| 156 CD  | 129 O3 | 128 C   | 137.24 | 156 CD  | 129 O3 | 61 CG   | 125.50 |

Figure 11KK

| Atom 1 | Atom 2 | Atom 3 | Angle | Atom 1 | Atom 2 | Atom 3 | Angle |
|---|---|---|---|---|---|---|---|
| 156 CA | 129 O3 | 300 OH2 | 53.48 | 156 CA | 129 O3 | 156 NE | 52.34 |
| 156 CA | 129 O3 | 61 NE2 | 143.76 | 156 CA | 129 O3 | 128 O | 80.08 |
| 156 CA | 129 O3 | 152 CB | 119.32 | 156 CA | 129 O3 | 128 C | 91.92 |
| 156 CA | 129 O3 | 61 CG | 161.54 | 300 OH2 | 129 O3 | 156 NE | 94.88 |
| 300 OH2 | 129 O3 | 61 NE2 | 102.55 | 300 OH2 | 129 O3 | 128 O | 31.42 |
| 300 OH2 | 129 O3 | 152 CB | 96.59 | 300 OH2 | 129 O3 | 128 C | 41.52 |
| 300 OH2 | 129 O3 | 61 CG | 122.87 | 156 NE | 129 O3 | 61 NE2 | 113.49 |
| 156 NE | 129 O3 | 128 O | 126.27 | 156 NE | 129 O3 | 152 CB | 153.58 |
| 156 NE | 129 O3 | 128 C | 135.82 | 156 NE | 129 O3 | 61 CG | 114.68 |
| 61 NE2 | 129 O3 | 128 O | 89.27 | 61 NE2 | 129 O3 | 152 CB | 87.07 |
| 61 NE2 | 129 O3 | 128 C | 78.66 | 61 NE2 | 129 O3 | 61 CG | 21.67 |
| 128 O | 129 O3 | 152 CB | 67.40 | 128 O | 129 O3 | 128 C | 11.94 |
| 128 O | 129 O3 | 61 CG | 103.68 | 152 CB | 129 O3 | 128 C | 61.88 |
| 152 CB | 129 O3 | 61 CG | 78.21 | 128 C | 129 O3 | 61 CG | 91.94 |
| 61 CE1 | 129 O4 | 156 CG | 132.12 | 61 CE1 | 129 O4 | 156 NE | 137.68 |
| 61 CE1 | 129 O4 | 156 CB | 148.60 | 61 CE1 | 129 O4 | 130 O | 81.80 |
| 61 CE1 | 129 O4 | 61 NE2 | 14.19 | 61 CE1 | 129 O4 | 61 ND1 | 13.26 |
| 61 CE1 | 129 O4 | 156 CD | 131.53 | 61 CE1 | 129 O4 | 156 N | 125.39 |
| 61 CE1 | 129 O4 | 130 N | 74.49 | 61 CE1 | 129 O4 | 300 OH2 | 110.23 |
| 61 CE1 | 129 O4 | 157 NH2 | 113.37 | 61 CE1 | 129 O4 | 131 OG | 41.87 |
| 61 CE1 | 129 O4 | 130 C | 71.79 | 61 CE1 | 129 O4 | 156 CA | 140.25 |
| 61 CE1 | 129 O4 | 301 OH2 | 104.47 | 61 CE1 | 129 O4 | 156 CZ | 138.05 |
| 61 CE1 | 129 O4 | 156 NH2 | 136.64 | 61 CE1 | 129 O4 | 61 CD2 | 10.66 |
| 61 CE1 | 129 O4 | 130 CA | 72.61 | 61 CE1 | 129 O4 | 61 CG | 9.64 |
| 61 CE1 | 129 O4 | 131 N | 63.15 | 61 CE1 | 129 O4 | 131 CA | 64.24 |
| 156 CG | 129 O4 | 156 NE | 32.73 | 156 CG | 129 O4 | 156 CB | 19.87 |
| 156 CG | 129 O4 | 130 O | 143.15 | 156 CG | 129 O4 | 61 NE2 | 146.23 |
| 156 CG | 129 O4 | 61 ND1 | 120.94 | 156 CG | 129 O4 | 156 CD | 17.40 |
| 156 CG | 129 O4 | 156 N | 36.83 | 156 CG | 129 O4 | 130 N | 129.68 |

Figure 11LL

| Atom 1 | Atom 2 | Atom 3 | Angle | Atom 1 | Atom 2 | Atom 3 | Angle |
|---|---|---|---|---|---|---|---|
| 156 CG | 129 O4 | 300 OH2 | 76.26 | 156 CG | 129 O4 | 157 NH2 | 111.29 |
| 156 CG | 129 O4 | 131 OG | 170.23 | 156 CG | 129 O4 | 130 C | 149.87 |
| 156 CG | 129 O4 | 156 CA | 27.93 | 156 CG | 129 O4 | 301 OH2 | 101.11 |
| 156 CG | 129 O4 | 156 CZ | 41.85 | 156 CG | 129 O4 | 156 NH2 | 55.16 |
| 156 CG | 129 O4 | 61 CD2 | 141.46 | 156 CG | 129 O4 | 130 CA | 140.37 |
| 156 CG | 129 O4 | 61 CG | 128.56 | 156 CG | 129 O4 | 131 N | 161.36 |
| 156 CG | 129 O4 | 131 CA | 163.48 | 156 NE | 129 O4 | 156 CB | 38.31 |
| 156 NE | 129 O4 | 130 O | 133.07 | 156 NE | 129 O4 | 61 NE2 | 147.28 |
| 156 NE | 129 O4 | 61 ND1 | 124.62 | 156 NE | 129 O4 | 156 CD | 17.31 |
| 156 NE | 129 O4 | 156 N | 66.64 | 156 NE | 129 O4 | 130 N | 147.68 |
| 156 NE | 129 O4 | 300 OH2 | 101.37 | 156 NE | 129 O4 | 157 NH2 | 105.79 |
| 156 NE | 129 O4 | 131 OG | 142.56 | 156 NE | 129 O4 | 130 C | 144.30 |
| 156 NE | 129 O4 | 156 CA | 52.91 | 156 NE | 129 O4 | 301 OH2 | 116.66 |
| 156 NE | 129 O4 | 156 CZ | 9.39 | 156 NE | 129 O4 | 156 NH2 | 23.15 |
| 156 NE | 129 O4 | 61 CD2 | 139.81 | 156 NE | 129 O4 | 130 CA | 148.64 |
| 156 NE | 129 O4 | 61 CG | 128.88 | 156 NE | 129 O4 | 131 N | 146.78 |
| 156 NE | 129 O4 | 131 CA | 135.96 | 156 CB | 129 O4 | 130 O | 123.28 |
| 156 CB | 129 O4 | 61 NE2 | 160.92 | 156 CB | 129 O4 | 61 ND1 | 139.39 |
| 156 CB | 129 O4 | 156 CD | 30.75 | 156 CB | 129 O4 | 156 N | 30.14 |
| 156 CB | 129 O4 | 130 N | 114.70 | 156 CB | 129 O4 | 300 OH2 | 63.37 |
| 156 CB | 129 O4 | 157 NH2 | 91.51 | 156 CB | 129 O4 | 131 OG | 168.78 |
| 156 CB | 129 O4 | 130 C | 130.50 | 156 CB | 129 O4 | 156 CA | 14.87 |
| 156 CB | 129 O4 | 301 OH2 | 83.94 | 156 CB | 129 O4 | 156 CZ | 45.01 |
| 156 CB | 129 O4 | 156 NH2 | 55.34 | 156 CB | 129 O4 | 61 CD2 | 159.09 |
| 156 CB | 129 O4 | 130 CA | 123.10 | 156 CB | 129 O4 | 61 CG | 147.30 |
| 156 CB | 129 O4 | 131 N | 141.68 | 156 CB | 129 O4 | 131 CA | 145.51 |
| 130 O | 129 O4 | 61 NE2 | 67.89 | 130 O | 129 O4 | 61 ND1 | 94.34 |
| 130 O | 129 O4 | 156 CD | 146.08 | 130 O | 129 O4 | 156 N | 116.38 |
| 130 O | 129 O4 | 130 N | 33.74 | 130 O | 129 O4 | 300 OH2 | 78.21 |

Figure 11MM

| Atom 1 | Atom 2 | Atom 3 | Angle | Atom 1 | Atom 2 | Atom 3 | Angle |
|---|---|---|---|---|---|---|---|
| 130 O | 129 O4 | 157 NH2 | 32.14 | 130 O | 129 O4 | 131 OG | 46.10 |
| 130 O | 129 O4 | 130 C | 11.23 | 130 O | 129 O4 | 156 CA | 117.93 |
| 130 O | 129 O4 | 301 OH2 | 48.80 | 130 O | 129 O4 | 156 CZ | 125.63 |
| 130 O | 129 O4 | 156 NH2 | 113.52 | 130 O | 129 O4 | 61 CD2 | 74.05 |
| 130 O | 129 O4 | 130 CA | 21.60 | 130 O | 129 O4 | 61 CG | 87.27 |
| 130 O | 129 O4 | 131 N | 18.90 | 130 O | 129 O4 | 131 CA | 25.27 |
| 61 NE2 | 129 O4 | 61 ND1 | 26.48 | 61 NE2 | 129 O4 | 156 CD | 144.80 |
| 61 NE2 | 129 O4 | 156 N | 133.13 | 61 NE2 | 129 O4 | 130 N | 64.73 |
| 61 NE2 | 129 O4 | 300 OH2 | 108.43 | 61 NE2 | 129 O4 | 157 NH2 | 99.78 |
| 61 NE2 | 129 O4 | 131 OG | 28.47 | 61 NE2 | 129 O4 | 130 C | 58.24 |
| 61 NE2 | 129 O4 | 156 CA | 149.03 | 61 NE2 | 129 O4 | 301 OH2 | 96.03 |
| 61 NE2 | 129 O4 | 156 CZ | 144.58 | 61 NE2 | 129 O4 | 156 NH2 | 138.38 |
| 61 NE2 | 129 O4 | 61 CD2 | 7.52 | 61 NE2 | 129 O4 | 130 CA | 60.67 |
| 61 NE2 | 129 O4 | 61 CG | 19.98 | 61 NE2 | 129 O4 | 131 N | 49.12 |
| 61 NE2 | 129 O4 | 131 CA | 50.21 | 61 ND1 | 129 O4 | 156 CD | 118.52 |
| 61 ND1 | 129 O4 | 156 N | 122.62 | 61 ND1 | 129 O4 | 130 N | 87.34 |
| 61 ND1 | 129 O4 | 300 OH2 | 117.38 | 61 ND1 | 129 O4 | 157 NH2 | 126.25 |
| 61 ND1 | 129 O4 | 131 OG | 51.74 | 61 ND1 | 129 O4 | 130 C | 84.68 |
| 61 ND1 | 129 O4 | 156 CA | 135.18 | 61 ND1 | 129 O4 | 301 OH2 | 116.44 |
| 61 ND1 | 129 O4 | 156 CZ | 125.79 | 61 ND1 | 129 O4 | 156 NH2 | 126.63 |
| 61 ND1 | 129 O4 | 61 CD2 | 20.54 | 61 ND1 | 129 O4 | 130 CA | 85.87 |
| 61 ND1 | 129 O4 | 61 CG | 7.97 | 61 ND1 | 129 O4 | 131 N | 75.50 |
| 61 ND1 | 129 O4 | 131 CA | 74.89 | 156 CD | 129 O4 | 156 N | 53.98 |
| 156 CD | 129 O4 | 130 N | 145.31 | 156 CD | 129 O4 | 300 OH2 | 92.55 |
| 156 CD | 129 O4 | 157 NH2 | 115.09 | 156 CD | 129 O4 | 131 OG | 154.98 |
| 156 CD | 129 O4 | 130 C | 156.62 | 156 CD | 129 O4 | 156 CA | 43.08 |
| 156 CD | 129 O4 | 301 OH2 | 114.65 | 156 CD | 129 O4 | 156 CZ | 26.67 |
| 156 CD | 129 O4 | 156 NH2 | 40.45 | 156 CD | 129 O4 | 61 CD2 | 137.82 |
| 156 CD | 129 O4 | 130 CA | 153.42 | 156 CD | 129 O4 | 61 CG | 124.83 |

Figure 11NN

| Atom 1 | Atom 2 | Atom 3 | Angle | Atom 1 | Atom 2 | Atom 3 | Angle |
|---|---|---|---|---|---|---|---|
| 156 CD | 129 O4 | 131 N | 163.04 | 156 CD | 129 O4 | 131 CA | 153.27 |
| 156 N | 129 O4 | 130 N | 93.33 | 156 N | 129 O4 | 300 OH2 | 40.15 |
| 156 N | 129 O4 | 157 NH2 | 91.84 | 156 N | 129 O4 | 131 OG | 150.56 |
| 156 N | 129 O4 | 130 C | 117.60 | 156 N | 129 O4 | 156 CA | 15.94 |
| 156 N | 129 O4 | 301 OH2 | 67.99 | 156 N | 129 O4 | 156 CZ | 74.42 |
| 156 N | 129 O4 | 156 NH2 | 85.44 | 156 N | 129 O4 | 61 CD2 | 135.25 |
| 156 N | 129 O4 | 130 CA | 105.18 | 156 N | 129 O4 | 61 CG | 129.62 |
| 156 N | 129 O4 | 131 N | 128.60 | 156 N | 129 O4 | 131 CA | 141.03 |
| 130 N | 129 O4 | 300 OH2 | 53.44 | 130 N | 129 O4 | 157 NH2 | 47.30 |
| 130 N | 129 O4 | 131 OG | 59.26 | 130 N | 129 O4 | 130 C | 27.34 |
| 130 N | 129 O4 | 156 CA | 102.39 | 130 N | 129 O4 | 301 OH2 | 31.53 |
| 130 N | 129 O4 | 156 CZ | 146.38 | 130 N | 129 O4 | 156 NH2 | 139.84 |
| 130 N | 129 O4 | 61 CD2 | 72.25 | 130 N | 129 O4 | 130 CA | 13.20 |
| 130 N | 129 O4 | 61 CG | 83.44 | 130 N | 129 O4 | 131 N | 36.12 |
| 130 N | 129 O4 | 131 CA | 50.15 | 300 OH2 | 129 O4 | 157 NH2 | 62.62 |
| 300 OH2 | 129 O4 | 131 OG | 112.42 | 300 OH2 | 129 O4 | 130 C | 77.71 |
| 300 OH2 | 129 O4 | 156 CA | 49.58 | 300 OH2 | 129 O4 | 301 OH2 | 29.69 |
| 300 OH2 | 129 O4 | 156 CZ | 106.55 | 300 OH2 | 129 O4 | 156 NH2 | 112.53 |
| 300 OH2 | 129 O4 | 61 CD2 | 114.72 | 300 OH2 | 129 O4 | 130 CA | 65.04 |
| 300 OH2 | 129 O4 | 61 CG | 119.35 | 300 OH2 | 129 O4 | 131 N | 88.49 |
| 300 OH2 | 129 O4 | 131 CA | 101.43 | 157 NH2 | 129 O4 | 131 OG | 77.53 |
| 157 NH2 | 129 O4 | 130 C | 41.59 | 157 NH2 | 129 O4 | 156 CA | 88.51 |
| 157 NH2 | 129 O4 | 301 OH2 | 36.39 | 157 NH2 | 129 O4 | 156 CZ | 100.95 |
| 157 NH2 | 129 O4 | 156 NH2 | 92.57 | 157 NH2 | 129 O4 | 61 CD2 | 106.14 |
| 157 NH2 | 129 O4 | 130 CA | 42.97 | 157 NH2 | 129 O4 | 61 CG | 119.37 |
| 157 NH2 | 129 O4 | 131 N | 51.04 | 157 NH2 | 129 O4 | 131 CA | 54.89 |
| 131 OG | 129 O4 | 130 C | 39.89 | 131 OG | 129 O4 | 156 CA | 161.57 |
| 131 OG | 129 O4 | 301 OH2 | 88.51 | 131 OG | 129 O4 | 156 CZ | 134.24 |
| 131 OG | 129 O4 | 156 NH2 | 121.97 | 131 OG | 129 O4 | 61 CD2 | 31.69 |

Figure 11OO

| Atom 1 | Atom 2 | Atom 3 | Angle | Atom 1 | Atom 2 | Atom 3 | Angle |
|---|---|---|---|---|---|---|---|
| 131 OG | 129 O4 | 130 CA | 49.15 | 131 OG | 129 O4 | 61 CG | 43.87 |
| 131 OG | 129 O4 | 131 N | 28.33 | 131 OG | 129 O4 | 131 CA | 23.27 |
| 130 C | 129 O4 | 156 CA | 122.51 | 130 C | 129 O4 | 301 OH2 | 49.95 |
| 130 C | 129 O4 | 156 CZ | 136.72 | 130 C | 129 O4 | 156 NH2 | 124.28 |
| 130 C | 129 O4 | 61 CD2 | 64.86 | 130 C | 129 O4 | 130 CA | 14.14 |
| 130 C | 129 O4 | 61 CG | 78.04 | 130 C | 129 O4 | 131 N | 11.67 |
| 130 C | 129 O4 | 131 CA | 23.76 | 156 CA | 129 O4 | 301 OH2 | 73.18 |
| 156 CA | 129 O4 | 156 CZ | 59.86 | 156 CA | 129 O4 | 156 NH2 | 70.03 |
| 156 CA | 129 O4 | 61 CD2 | 150.57 | 156 CA | 129 O4 | 130 CA | 112.47 |
| 156 CA | 129 O4 | 61 CG | 142.84 | 156 CA | 129 O4 | 131 N | 134.17 |
| 156 CA | 129 O4 | 131 CA | 142.94 | 301 OH2 | 129 O4 | 156 CZ | 117.48 |
| 301 OH2 | 129 O4 | 156 NH2 | 116.13 | 301 OH2 | 129 O4 | 61 CD2 | 103.52 |
| 301 OH2 | 129 O4 | 130 CA | 39.40 | 301 OH2 | 129 O4 | 61 CG | 113.87 |
| 301 OH2 | 129 O4 | 131 N | 61.43 | 301 OH2 | 129 O4 | 131 CA | 73.05 |
| 156 CZ | 129 O4 | 156 NH2 | 13.78 | 156 CZ | 129 O4 | 61 CD2 | 137.58 |
| 156 CZ | 129 O4 | 130 CA | 143.67 | 156 CZ | 129 O4 | 61 CG | 128.59 |
| 156 CZ | 129 O4 | 131 N | 137.83 | 156 CZ | 129 O4 | 131 CA | 126.60 |
| 156 NH2 | 129 O4 | 61 CD2 | 132.66 | 156 NH2 | 129 O4 | 130 CA | 133.42 |
| 156 NH2 | 129 O4 | 61 CG | 127.09 | 156 NH2 | 129 O4 | 131 N | 124.26 |
| 156 NH2 | 129 O4 | 131 CA | 112.82 | 61 CD2 | 129 O4 | 130 CA | 68.00 |
| 61 CD2 | 129 O4 | 61 CG | 13.22 | 61 CD2 | 129 O4 | 131 N | 55.15 |
| 61 CD2 | 129 O4 | 131 CA | 54.56 | 130 CA | 129 O4 | 61 CG | 80.49 |
| 130 CA | 129 O4 | 131 N | 23.54 | 130 CA | 129 O4 | 131 CA | 37.24 |
| 61 CG | 129 O4 | 131 N | 68.36 | 61 CG | 129 O4 | 131 CA | 67.07 |
| 131 N | 129 O4 | 131 CA | 14.24 | 300 OH2 | 129 O5 | 156 N | 73.74 |
| 300 OH2 | 129 O5 | 156 CB | 100.13 | 300 OH2 | 129 O5 | 301 OH2 | 44.20 |
| 300 OH2 | 129 O5 | 156 CA | 80.43 | 300 OH2 | 129 O5 | 156 CG | 116.78 |
| 300 OH2 | 129 O5 | 128 O | 42.55 | 300 OH2 | 129 O5 | 157 N | 51.91 |
| 300 OH2 | 129 O5 | 130 N | 75.33 | 300 OH2 | 129 O5 | 156 C | 66.97 |

Figure 11PP

| Atom 1 | Atom 2 | Atom 3 | Angle | Atom 1 | Atom 2 | Atom 3 | Angle |
|---|---|---|---|---|---|---|---|
| 300 OH2 | 129 O5 | 128 C | 53.95 | 300 OH2 | 129 O5 | 130 O | 97.63 |
| 300 OH2 | 129 O5 | 157 NH2 | 79.96 | 300 OH2 | 129 O5 | 61 CE1 | 136.71 |
| 300 OH2 | 129 O5 | 157 CB | 42.13 | 300 OH2 | 129 O5 | 156 CD | 125.03 |
| 300 OH2 | 129 O5 | 157 CG | 57.07 | 300 OH2 | 129 O5 | 156 NE | 129.74 |
| 300 OH2 | 129 O5 | 157 CA | 45.83 | 300 OH2 | 129 O5 | 152 SG | 87.51 |
| 300 OH2 | 129 O5 | 157 NE | 61.51 | 300 OH2 | 129 O5 | 130 CA | 81.60 |
| 300 OH2 | 129 O5 | 130 C | 94.55 | 300 OH2 | 129 O5 | 156 O | 70.21 |
| 300 OH2 | 129 O5 | 157 CZ | 73.74 | 300 OH2 | 129 O5 | 61 NE2 | 128.70 |
| 156 N | 129 O5 | 156 CB | 39.52 | 156 N | 129 O5 | 301 OH2 | 112.43 |
| 156 N | 129 O5 | 156 CA | 19.45 | 156 N | 129 O5 | 156 CG | 45.47 |
| 156 N | 129 O5 | 128 O | 93.63 | 156 N | 129 O5 | 157 N | 40.99 |
| 156 N | 129 O5 | 130 N | 149.06 | 156 N | 129 O5 | 156 C | 30.96 |
| 156 N | 129 O5 | 128 C | 105.71 | 156 N | 129 O5 | 130 O | 153.38 |
| 156 N | 129 O5 | 157 NH2 | 122.43 | 156 N | 129 O5 | 61 CE1 | 138.61 |
| 156 N | 129 O5 | 157 CB | 67.31 | 156 N | 129 O5 | 156 CD | 55.74 |
| 156 N | 129 O5 | 157 CG | 75.53 | 156 N | 129 O5 | 156 NE | 68.19 |
| 156 N | 129 O5 | 157 CA | 51.07 | 156 N | 129 O5 | 152 SG | 85.59 |
| 156 N | 129 O5 | 157 NE | 101.00 | 156 N | 129 O5 | 130 CA | 154.34 |
| 156 N | 129 O5 | 130 C | 161.23 | 156 N | 129 O5 | 156 O | 33.97 |
| 156 N | 129 O5 | 157 CZ | 110.79 | 156 N | 129 O5 | 61 NE2 | 149.55 |
| 156 CB | 129 O5 | 301 OH2 | 118.47 | 156 CB | 129 O5 | 156 CA | 22.53 |
| 156 CB | 129 O5 | 156 CG | 21.64 | 156 CB | 129 O5 | 128 O | 132.06 |
| 156 CB | 129 O5 | 157 N | 49.09 | 156 CB | 129 O5 | 130 N | 150.25 |
| 156 CB | 129 O5 | 156 C | 33.24 | 156 CB | 129 O5 | 128 C | 144.89 |
| 156 CB | 129 O5 | 130 O | 121.94 | 156 CB | 129 O5 | 157 NH2 | 100.01 |
| 156 CB | 129 O5 | 61 CE1 | 123.05 | 156 CB | 129 O5 | 157 CB | 69.94 |
| 156 CB | 129 O5 | 156 CD | 25.66 | 156 CB | 129 O5 | 157 CG | 66.53 |
| 156 CB | 129 O5 | 156 NE | 31.49 | 156 CB | 129 O5 | 157 CA | 57.62 |
| 156 CB | 129 O5 | 152 SG | 115.90 | 156 CB | 129 O5 | 157 NE | 88.66 |

Figure 11QQ

| Atom 1 | Atom 2 | Atom 3 | Angle | Atom 1 | Atom 2 | Atom 3 | Angle |
|---|---|---|---|---|---|---|---|
| 156 CB | 129 O5 | 130 CA | 143.54 | 156 CB | 129 O5 | 130 C | 133.13 |
| 156 CB | 129 O5 | 156 O | 30.46 | 156 CB | 129 O5 | 157 CZ | 91.23 |
| 156 CB | 129 O5 | 61 NE2 | 130.83 | 301 OH2 | 129 O5 | 156 CA | 109.76 |
| 301 OH2 | 129 O5 | 156 CG | 139.98 | 301 OH2 | 129 O5 | 128 O | 60.85 |
| 301 OH2 | 129 O5 | 157 N | 75.70 | 301 OH2 | 129 O5 | 130 N | 39.59 |
| 301 OH2 | 129 O5 | 156 C | 91.36 | 301 OH2 | 129 O5 | 128 C | 62.16 |
| 301 OH2 | 129 O5 | 130 O | 53.54 | 301 OH2 | 129 O5 | 157 NH2 | 40.50 |
| 301 OH2 | 129 O5 | 61 CE1 | 107.94 | 301 OH2 | 129 O5 | 157 CB | 50.16 |
| 301 OH2 | 129 O5 | 156 CD | 139.36 | 301 OH2 | 129 O5 | 157 CG | 52.09 |
| 301 OH2 | 129 O5 | 156 NE | 129.06 | 301 OH2 | 129 O5 | 157 CA | 65.32 |
| 301 OH2 | 129 O5 | 152 SG | 110.63 | 301 OH2 | 129 O5 | 157 NE | 34.33 |
| 301 OH2 | 129 O5 | 130 CA | 42.05 | 301 OH2 | 129 O5 | 130 C | 52.00 |
| 301 OH2 | 129 O5 | 156 O | 91.90 | 301 OH2 | 129 O5 | 157 CZ | 40.02 |
| 301 OH2 | 129 O5 | 61 NE2 | 96.96 | 156 CA | 129 O5 | 156 CG | 36.53 |
| 156 CA | 129 O5 | 128 O | 109.55 | 156 CA | 129 O5 | 157 N | 34.12 |
| 156 CA | 129 O5 | 130 N | 149.21 | 156 CA | 129 O5 | 156 C | 18.59 |
| 156 CA | 129 O5 | 128 C | 122.54 | 156 CA | 129 O5 | 130 O | 135.95 |
| 156 CA | 129 O5 | 157 NH2 | 107.15 | 156 CA | 129 O5 | 61 CE1 | 140.69 |
| 156 CA | 129 O5 | 157 CB | 59.93 | 156 CA | 129 O5 | 156 CD | 44.78 |
| 156 CA | 129 O5 | 157 CG | 63.28 | 156 CA | 129 O5 | 156 NE | 53.73 |
| 156 CA | 129 O5 | 157 CA | 44.44 | 156 CA | 129 O5 | 152 SG | 104.23 |
| 156 CA | 129 O5 | 157 NE | 88.79 | 156 CA | 129 O5 | 130 CA | 148.53 |
| 156 CA | 129 O5 | 130 C | 146.20 | 156 CA | 129 O5 | 156 O | 19.20 |
| 156 CA | 129 O5 | 157 CZ | 96.11 | 156 CA | 129 O5 | 61 NE2 | 150.57 |
| 156 CG | 129 O5 | 128 O | 135.81 | 156 CG | 129 O5 | 157 N | 68.82 |
| 156 CG | 129 O5 | 130 N | 161.15 | 156 CG | 129 O5 | 156 C | 52.47 |
| 156 CG | 129 O5 | 128 C | 144.27 | 156 CG | 129 O5 | 130 O | 127.52 |
| 156 CG | 129 O5 | 157 NH2 | 115.08 | 156 CG | 129 O5 | 61 CE1 | 104.57 |
| 156 CG | 129 O5 | 157 CB | 91.39 | 156 CG | 129 O5 | 156 CD | 10.66 |

Figure 11RR

| Atom 1 | Atom 2 | Atom 3 | Angle | Atom 1 | Atom 2 | Atom 3 | Angle |
|---|---|---|---|---|---|---|---|
| 156 CG | 129 O5 | 157 CG | 87.90 | 156 CG | 129 O5 | 156 NE | 25.64 |
| 156 CG | 129 O5 | 157 CA | 78.19 | 156 CG | 129 O5 | 152 SG | 101.15 |
| 156 CG | 129 O5 | 157 NE | 108.51 | 156 CG | 129 O5 | 130 CA | 152.00 |
| 156 CG | 129 O5 | 130 C | 137.26 | 156 CG | 129 O5 | 156 O | 50.63 |
| 156 CG | 129 O5 | 157 CZ | 108.56 | 156 CG | 129 O5 | 61 NE2 | 114.05 |
| 128 O | 129 O5 | 157 N | 91.41 | 128 O | 129 O5 | 130 N | 62.99 |
| 128 O | 129 O5 | 156 C | 103.41 | 128 O | 129 O5 | 128 C | 13.44 |
| 128 O | 129 O5 | 130 O | 96.46 | 128 O | 129 O5 | 157 NH2 | 100.16 |
| 128 O | 129 O5 | 61 CE1 | 98.11 | 128 O | 129 O5 | 157 CB | 84.40 |
| 128 O | 129 O5 | 156 CD | 146.23 | 128 O | 129 O5 | 157 CG | 98.09 |
| 128 O | 129 O5 | 156 NE | 161.28 | 128 O | 129 O5 | 157 CA | 87.50 |
| 128 O | 129 O5 | 152 SG | 51.22 | 128 O | 129 O5 | 157 NE | 93.02 |
| 128 O | 129 O5 | 130 CA | 72.12 | 128 O | 129 O5 | 130 C | 86.92 |
| 128 O | 129 O5 | 156 O | 107.60 | 128 O | 129 O5 | 157 CZ | 100.84 |
| 128 O | 129 O5 | 61 NE2 | 93.91 | 157 N | 129 O5 | 130 N | 115.28 |
| 157 N | 129 O5 | 156 C | 16.35 | 157 N | 129 O5 | 128 C | 104.36 |
| 157 N | 129 O5 | 130 O | 114.00 | 157 N | 129 O5 | 157 NH2 | 82.75 |
| 157 N | 129 O5 | 61 CE1 | 170.41 | 157 N | 129 O5 | 157 CB | 26.68 |
| 157 N | 129 O5 | 156 CD | 74.72 | 157 N | 129 O5 | 157 CG | 35.40 |
| 157 N | 129 O5 | 156 NE | 77.85 | 157 N | 129 O5 | 157 CA | 10.51 |
| 157 N | 129 O5 | 152 SG | 115.63 | 157 N | 129 O5 | 157 NE | 60.23 |
| 157 N | 129 O5 | 130 CA | 116.29 | 157 N | 129 O5 | 130 C | 120.26 |
| 157 N | 129 O5 | 156 O | 18.63 | 157 N | 129 O5 | 157 CZ | 71.08 |
| 157 N | 129 O5 | 61 NE2 | 167.38 | 130 N | 129 O5 | 156 C | 130.64 |
| 130 N | 129 O5 | 128 C | 54.31 | 130 N | 129 O5 | 130 O | 33.64 |
| 130 N | 129 O5 | 157 NH2 | 50.30 | 130 N | 129 O5 | 61 CE1 | 68.67 |
| 130 N | 129 O5 | 157 CB | 89.28 | 130 N | 129 O5 | 156 CD | 150.75 |
| 130 N | 129 O5 | 157 CG | 87.43 | 130 N | 129 O5 | 156 NE | 135.51 |
| 130 N | 129 O5 | 157 CA | 104.85 | 130 N | 129 O5 | 152 SG | 93.48 |

Figure 11SS

| Atom 1 | Atom 2 | Atom 3 | Angle | Atom 1 | Atom 2 | Atom 3 | Angle |
|---|---|---|---|---|---|---|---|
| 130 N | 129 O5 | 157 NE | 63.06 | 130 N | 129 O5 | 130 CA | 9.14 |
| 130 N | 129 O5 | 130 C | 24.04 | 130 N | 129 O5 | 156 O | 130.61 |
| 130 N | 129 O5 | 157 CZ | 59.12 | 130 N | 129 O5 | 61 NE2 | 57.87 |
| 156 C | 129 O5 | 128 C | 116.81 | 156 C | 129 O5 | 130 O | 122.42 |
| 156 C | 129 O5 | 157 NH2 | 91.59 | 156 C | 129 O5 | 61 CE1 | 156.28 |
| 156 C | 129 O5 | 157 CB | 41.37 | 156 C | 129 O5 | 156 CD | 58.71 |
| 156 C | 129 O5 | 157 CG | 45.57 | 156 C | 129 O5 | 156 NE | 63.41 |
| 156 C | 129 O5 | 157 CA | 26.20 | 156 C | 129 O5 | 152 SG | 114.75 |
| 156 C | 129 O5 | 157 NE | 71.29 | 156 C | 129 O5 | 130 CA | 130.32 |
| 156 C | 129 O5 | 130 C | 130.96 | 156 C | 129 O5 | 156 O | 4.55 |
| 156 C | 129 O5 | 157 CZ | 80.05 | 156 C | 129 O5 | 61 NE2 | 162.69 |
| 128 C | 129 O5 | 130 O | 87.81 | 128 C | 129 O5 | 157 NH2 | 97.97 |
| 128 C | 129 O5 | 61 CE1 | 85.07 | 128 C | 129 O5 | 157 CB | 94.55 |
| 128 C | 129 O5 | 156 CD | 153.35 | 128 C | 129 O5 | 157 CG | 106.50 |
| 128 C | 129 O5 | 156 NE | 168.29 | 128 C | 129 O5 | 157 CA | 99.66 |
| 128 C | 129 O5 | 152 SG | 48.53 | 128 C | 129 O5 | 157 NE | 96.26 |
| 128 C | 129 O5 | 130 CA | 63.36 | 128 C | 129 O5 | 130 C | 77.41 |
| 128 C | 129 O5 | 156 O | 120.96 | 128 C | 129 O5 | 157 CZ | 101.39 |
| 128 C | 129 O5 | 61 NE2 | 80.49 | 130 O | 129 O5 | 157 NH2 | 31.33 |
| 130 O | 129 O5 | 61 CE1 | 63.91 | 130 O | 129 O5 | 157 CB | 89.21 |
| 130 O | 129 O5 | 156 CD | 117.30 | 130 O | 129 O5 | 157 CG | 78.69 |
| 130 O | 129 O5 | 156 NE | 101.90 | 130 O | 129 O5 | 157 CA | 104.77 |
| 130 O | 129 O5 | 152 SG | 119.71 | 130 O | 129 O5 | 157 NE | 53.99 |
| 130 O | 129 O5 | 130 CA | 24.50 | 130 O | 129 O5 | 130 C | 11.20 |
| 130 O | 129 O5 | 156 O | 119.46 | 130 O | 129 O5 | 157 CZ | 43.03 |
| 130 O | 129 O5 | 61 NE2 | 54.02 | 157 NH2 | 129 O5 | 61 CE1 | 94.35 |
| 157 NH2 | 129 O5 | 157 CB | 59.02 | 157 NH2 | 129 O5 | 156 CD | 108.18 |
| 157 NH2 | 129 O5 | 157 CG | 47.38 | 157 NH2 | 129 O5 | 156 NE | 93.71 |
| 157 NH2 | 129 O5 | 157 CA | 73.88 | 157 NH2 | 129 O5 | 152 SG | 143.56 |

Figure 11TT

| Atom 1 | Atom 2 | Atom 3 | Angle | Atom 1 | Atom 2 | Atom 3 | Angle |
|---|---|---|---|---|---|---|---|
| 157 NH2 | 129 O5 | 157 NE | 23.57 | 157 NH2 | 129 O5 | 130 CA | 44.01 |
| 157 NH2 | 129 O5 | 130 C | 39.47 | 157 NH2 | 129 O5 | 156 O | 89.07 |
| 157 NH2 | 129 O5 | 157 CZ | 11.70 | 157 NH2 | 129 O5 | 61 NE2 | 85.05 |
| 61 CE1 | 129 O5 | 157 CB | 153.12 | 61 CE1 | 129 O5 | 156 CD | 97.67 |
| 61 CE1 | 129 O5 | 157 CG | 140.55 | 61 CE1 | 129 O5 | 156 NE | 93.27 |
| 61 CE1 | 129 O5 | 157 CA | 167.75 | 61 CE1 | 129 O5 | 152 SG | 71.87 |
| 61 CE1 | 129 O5 | 157 NE | 117.72 | 61 CE1 | 129 O5 | 130 CA | 66.10 |
| 61 CE1 | 129 O5 | 130 C | 59.49 | 61 CE1 | 129 O5 | 156 O | 153.05 |
| 61 CE1 | 129 O5 | 157 CZ | 105.72 | 61 CE1 | 129 O5 | 61 NE2 | 11.05 |
| 157 CB | 129 O5 | 156 CD | 94.57 | 157 CB | 129 O5 | 157 CG | 16.44 |
| 157 CB | 129 O5 | 156 NE | 92.15 | 157 CB | 129 O5 | 157 CA | 16.28 |
| 157 CB | 129 O5 | 152 SG | 126.72 | 157 CB | 129 O5 | 157 NE | 35.50 |
| 157 CB | 129 O5 | 130 CA | 89.66 | 157 CB | 129 O5 | 130 C | 94.12 |
| 157 CB | 129 O5 | 156 O | 41.75 | 157 CB | 129 O5 | 157 CZ | 47.93 |
| 157 CB | 129 O5 | 61 NE2 | 142.86 | 156 CD | 129 O5 | 157 CG | 88.22 |
| 156 CD | 129 O5 | 156 NE | 15.61 | 156 CD | 129 O5 | 157 CA | 83.20 |
| 156 CD | 129 O5 | 152 SG | 107.03 | 156 CD | 129 O5 | 157 NE | 105.61 |
| 156 CD | 129 O5 | 130 CA | 141.64 | 156 CD | 129 O5 | 130 C | 126.74 |
| 156 CD | 129 O5 | 156 O | 56.11 | 156 CD | 129 O5 | 157 CZ | 103.31 |
| 156 CD | 129 O5 | 61 NE2 | 106.27 | 157 CG | 129 O5 | 156 NE | 82.09 |
| 157 CG | 129 O5 | 157 CA | 27.23 | 157 CG | 129 O5 | 152 SG | 143.13 |
| 157 CG | 129 O5 | 157 NE | 25.72 | 157 CG | 129 O5 | 130 CA | 85.26 |
| 157 CG | 129 O5 | 130 C | 85.81 | 157 CG | 129 O5 | 156 O | 44.10 |
| 157 CG | 129 O5 | 157 CZ | 35.69 | 157 CG | 129 O5 | 61 NE2 | 132.23 |
| 156 NE | 129 O5 | 157 CA | 84.33 | 156 NE | 129 O5 | 152 SG | 119.98 |
| 156 NE | 129 O5 | 157 NE | 94.78 | 156 NE | 129 O5 | 130 CA | 126.36 |
| 156 NE | 129 O5 | 130 C | 111.71 | 156 NE | 129 O5 | 156 O | 59.81 |
| 156 NE | 129 O5 | 157 CZ | 90.23 | 156 NE | 129 O5 | 61 NE2 | 99.80 |
| 157 CA | 129 O5 | 152 SG | 119.67 | 157 CA | 129 O5 | 157 NE | 50.78 |

Figure 11UU

| Atom 1 | Atom 2 | Atom 3 | Angle | Atom 1 | Atom 2 | Atom 3 | Angle |
|---|---|---|---|---|---|---|---|
| 157 CA | 129 O5 | 130 CA | 105.80 | 157 CA | 129 O5 | 130 C | 110.28 |
| 157 CA | 129 O5 | 156 O | 27.56 | 157 CA | 129 O5 | 157 CZ | 62.37 |
| 157 CA | 129 O5 | 61 NE2 | 158.78 | 152 SG | 129 O5 | 157 NE | 144.17 |
| 152 SG | 129 O5 | 130 CA | 100.55 | 152 SG | 129 O5 | 130 C | 108.94 |
| 152 SG | 129 O5 | 156 O | 118.66 | 152 SG | 129 O5 | 157 CZ | 149.62 |
| 152 SG | 129 O5 | 61 NE2 | 76.41 | 157 NE | 129 O5 | 130 CA | 59.89 |
| 157 NE | 129 O5 | 130 C | 60.25 | 157 NE | 129 O5 | 156 O | 69.68 |
| 157 NE | 129 O5 | 157 CZ | 13.22 | 157 NE | 129 O5 | 61 NE2 | 108.00 |
| 130 CA | 129 O5 | 130 C | 15.09 | 130 CA | 129 O5 | 156 O | 129.34 |
| 130 CA | 129 O5 | 157 CZ | 53.93 | 130 CA | 129 O5 | 61 NE2 | 55.06 |
| 130 C | 129 O5 | 156 O | 128.54 | 130 C | 129 O5 | 157 CZ | 50.92 |
| 130 C | 129 O5 | 61 NE2 | 48.79 | 156 O | 129 O5 | 157 CZ | 77.69 |
| 156 O | 129 O5 | 61 NE2 | 158.40 | 157 CZ | 129 O5 | 61 NE2 | 96.65 |
| 61 CE1 | 129 C5 | 61 ND1 | 20.43 | 61 CE1 | 129 C5 | 156 CG | 129.94 |
| 61 CE1 | 129 C5 | 152 SG | 94.34 | 61 CE1 | 129 C5 | 61 NE2 | 2.93 |
| 61 CE1 | 129 C5 | 156 CD | 127.42 | 61 CE1 | 129 C5 | 156 N | 121.58 |
| 61 CE1 | 129 C5 | 61 CG | 22.36 | 61 CE1 | 129 C5 | 152 CB | 92.78 |
| 61 CE1 | 129 C5 | 156 CB | 120.17 | 61 CE1 | 129 C5 | 156 NE | 112.25 |
| 61 CE1 | 129 C5 | 61 CD2 | 9.81 | 61 CE1 | 129 C5 | 61 CB | 35.28 |
| 61 CE1 | 129 C5 | 156 CA | 124.14 | 61 ND1 | 129 C5 | 156 CG | 144.44 |
| 61 ND1 | 129 C5 | 152 SG | 97.61 | 61 ND1 | 129 C5 | 61 NE2 | 23.16 |
| 61 ND1 | 129 C5 | 156 CD | 135.70 | 61 ND1 | 129 C5 | 156 N | 141.93 |
| 61 ND1 | 129 C5 | 61 CG | 2.23 | 61 ND1 | 129 C5 | 152 CB | 89.25 |
| 61 ND1 | 129 C5 | 156 CB | 137.80 | 61 ND1 | 129 C5 | 156 NE | 121.09 |
| 61 ND1 | 129 C5 | 61 CD2 | 10.86 | 61 ND1 | 129 C5 | 61 CB | 14.93 |
| 61 ND1 | 129 C5 | 156 CA | 144.11 | 156 CG | 129 C5 | 152 SG | 107.69 |
| 156 CG | 129 C5 | 61 NE2 | 128.42 | 156 CG | 129 C5 | 156 CD | 16.19 |
| 156 CG | 129 C5 | 156 N | 34.82 | 156 CG | 129 C5 | 61 CG | 146.49 |
| 156 CG | 129 C5 | 152 CB | 122.12 | 156 CG | 129 C5 | 156 CB | 13.29 |

Figure 11VV

| Atom 1 | Atom 2 | Atom 3 | Angle | Atom 1 | Atom 2 | Atom 3 | Angle |
|---|---|---|---|---|---|---|---|
| 156 CG | 129 C5 | 156 NE | 25.92 | 156 CG | 129 C5 | 61 CD2 | 138.39 |
| 156 CG | 129 C5 | 61 CB | 152.84 | 156 CG | 129 C5 | 156 CA | 22.55 |
| 152 SG | 129 C5 | 61 NE2 | 92.77 | 152 SG | 129 C5 | 156 CD | 122.85 |
| 152 SG | 129 C5 | 156 N | 75.27 | 152 SG | 129 C5 | 61 CG | 96.72 |
| 152 SG | 129 C5 | 152 CB | 19.87 | 152 SG | 129 C5 | 156 CB | 101.85 |
| 152 SG | 129 C5 | 156 NE | 132.56 | 152 SG | 129 C5 | 61 CD2 | 94.41 |
| 152 SG | 129 C5 | 61 CB | 97.51 | 152 SG | 129 C5 | 156 CA | 87.58 |
| 61 NE2 | 129 C5 | 156 CD | 126.88 | 61 NE2 | 129 C5 | 156 N | 118.79 |
| 61 NE2 | 129 C5 | 61 CG | 25.04 | 61 NE2 | 129 C5 | 152 CB | 92.14 |
| 61 NE2 | 129 C5 | 156 CB | 118.21 | 61 NE2 | 129 C5 | 156 NE | 111.82 |
| 61 NE2 | 129 C5 | 61 CD2 | 12.40 | 61 NE2 | 129 C5 | 61 CB | 37.94 |
| 61 NE2 | 129 C5 | 156 CA | 121.65 | 156 CD | 129 C5 | 156 N | 51.01 |
| 156 CD | 129 C5 | 61 CG | 137.29 | 156 CD | 129 C5 | 152 CB | 134.84 |
| 156 CD | 129 C5 | 156 CB | 27.10 | 156 CD | 129 C5 | 156 NE | 15.25 |
| 156 CD | 129 C5 | 61 CD2 | 133.47 | 156 CD | 129 C5 | 61 CB | 139.47 |
| 156 CD | 129 C5 | 156 CA | 38.64 | 156 N | 129 C5 | 61 CG | 143.67 |
| 156 N | 129 C5 | 152 CB | 92.97 | 156 N | 129 C5 | 156 CB | 26.59 |
| 156 N | 129 C5 | 156 NE | 57.43 | 156 N | 129 C5 | 61 CD2 | 131.07 |
| 156 N | 129 C5 | 61 CB | 156.21 | 156 N | 129 C5 | 156 CA | 12.57 |
| 61 CG | 129 C5 | 152 CB | 87.78 | 61 CG | 129 C5 | 156 CB | 140.02 |
| 61 CG | 129 C5 | 156 NE | 122.84 | 61 CG | 129 C5 | 61 CD2 | 12.66 |
| 61 CG | 129 C5 | 61 CB | 12.92 | 61 CG | 129 C5 | 156 CA | 146.24 |
| 152 CB | 129 C5 | 156 CB | 119.09 | 152 CB | 129 C5 | 156 NE | 148.04 |
| 152 CB | 129 C5 | 61 CD2 | 89.55 | 152 CB | 129 C5 | 61 CB | 84.84 |
| 152 CB | 129 C5 | 156 CA | 104.70 | 156 CB | 129 C5 | 156 NE | 30.88 |
| 156 CB | 129 C5 | 61 CD2 | 129.49 | 156 CB | 129 C5 | 61 CB | 150.33 |
| 156 CB | 129 C5 | 156 CA | 14.41 | 156 NE | 129 C5 | 61 CD2 | 118.24 |
| 156 NE | 129 C5 | 61 CB | 127.06 | 156 NE | 129 C5 | 156 CA | 45.00 |
| 61 CD2 | 129 C5 | 61 CB | 25.54 | 61 CD2 | 129 C5 | 156 CA | 133.94 |

Figure 11WW

| Atom 1 | Atom 2 | Atom 3 | Angle | Atom 1 | Atom 2 | Atom 3 | Angle |
|---|---|---|---|---|---|---|---|
| 61 CB | 129 C5 | 156 CA | 158.86 | 156 CG | 129 C6 | 156 CD | 21.02 |
| 156 CG | 129 C6 | 156 NE | 31.00 | 156 CG | 129 C6 | 61 ND1 | 129.40 |
| 156 CG | 129 C6 | 61 CE1 | 114.32 | 156 CG | 129 C6 | 156 CB | 10.11 |
| 156 CG | 129 C6 | 156 N | 33.35 | 156 CG | 129 C6 | 156 CA | 19.12 |
| 156 CG | 129 C6 | 152 SG | 99.39 | 156 CG | 129 C6 | 156 CZ | 37.07 |
| 156 CD | 129 C6 | 156 NE | 17.37 | 156 CD | 129 C6 | 61 ND1 | 132.80 |
| 156 CD | 129 C6 | 61 CE1 | 120.65 | 156 CD | 129 C6 | 156 CB | 28.86 |
| 156 CD | 129 C6 | 156 N | 54.37 | 156 CD | 129 C6 | 156 CA | 40.14 |
| 156 CD | 129 C6 | 152 SG | 120.30 | 156 CD | 129 C6 | 156 CZ | 20.33 |
| 156 NE | 129 C6 | 61 ND1 | 116.13 | 156 NE | 129 C6 | 61 CE1 | 105.36 |
| 156 NE | 129 C6 | 156 CB | 34.06 | 156 NE | 129 C6 | 156 N | 61.34 |
| 156 NE | 129 C6 | 156 CA | 48.12 | 156 NE | 129 C6 | 152 SG | 126.14 |
| 156 NE | 129 C6 | 156 CZ | 7.08 | 61 ND1 | 129 C6 | 61 CE1 | 15.51 |
| 61 ND1 | 129 C6 | 156 CB | 120.13 | 61 ND1 | 129 C6 | 156 N | 113.41 |
| 61 ND1 | 129 C6 | 156 CA | 121.62 | 61 ND1 | 129 C6 | 152 SG | 74.35 |
| 61 ND1 | 129 C6 | 156 CZ | 115.90 | 61 CE1 | 129 C6 | 156 CB | 104.82 |
| 61 CE1 | 129 C6 | 156 N | 98.74 | 61 CE1 | 129 C6 | 156 CA | 106.20 |
| 61 CE1 | 129 C6 | 152 SG | 70.83 | 61 CE1 | 129 C6 | 156 CZ | 106.70 |
| 156 CB | 129 C6 | 156 N | 27.32 | 156 CB | 129 C6 | 156 CA | 14.33 |
| 156 CB | 129 C6 | 152 SG | 93.16 | 156 CB | 129 C6 | 156 CZ | 40.92 |
| 156 N | 129 C6 | 156 CA | 14.24 | 156 N | 129 C6 | 152 SG | 66.21 |
| 156 N | 129 C6 | 156 CZ | 68.24 | 156 CA | 129 C6 | 152 SG | 80.34 |
| 156 CA | 129 C6 | 156 CZ | 54.81 | 152 SG | 129 C6 | 156 CZ | 133.22 |
| 152 SG | 129 C7 | 61 ND1 | 118.21 | 152 SG | 129 C7 | 152 CB | 27.14 |
| 152 SG | 129 C7 | 61 CE1 | 108.14 | 152 SG | 129 C7 | 61 CG | 114.67 |
| 152 SG | 129 C7 | 61 NE2 | 103.13 | 152 SG | 129 C7 | 152 CA | 28.92 |
| 152 SG | 129 C7 | 61 N | 95.92 | 152 SG | 129 C7 | 61 CB | 118.12 |
| 152 SG | 129 C7 | 156 CG | 102.99 | 152 SG | 129 C7 | 61 CD2 | 107.32 |
| 152 SG | 129 C7 | 156 N | 74.29 | 152 SG | 129 C7 | 152 N | 25.24 |

Figure 11XX

| Atom 1 | Atom 2 | Atom 3 | Angle | Atom 1 | Atom 2 | Atom 3 | Angle |
|---|---|---|---|---|---|---|---|
| 61 ND1 | 129 C7 | 152 CB | 114.46 | 61 ND1 | 129 C7 | 61 CE1 | 19.39 |
| 61 ND1 | 129 C7 | 61 CG | 8.14 | 61 ND1 | 129 C7 | 61 NE2 | 20.53 |
| 61 ND1 | 129 C7 | 152 CA | 112.84 | 61 ND1 | 129 C7 | 61 N | 42.02 |
| 61 ND1 | 129 C7 | 61 CB | 21.26 | 61 ND1 | 129 C7 | 156 CG | 110.33 |
| 61 ND1 | 129 C7 | 61 CD2 | 11.04 | 61 ND1 | 129 C7 | 156 N | 119.48 |
| 61 ND1 | 129 C7 | 152 N | 103.06 | 152 CB | 129 C7 | 61 CE1 | 113.88 |
| 152 CB | 129 C7 | 61 CG | 107.80 | 152 CB | 129 C7 | 61 NE2 | 108.05 |
| 152 CB | 129 C7 | 152 CA | 2.13 | 152 CB | 129 C7 | 61 N | 78.98 |
| 152 CB | 129 C7 | 61 CB | 104.41 | 152 CB | 129 C7 | 156 CG | 125.54 |
| 152 CB | 129 C7 | 61 CD2 | 105.81 | 152 CB | 129 C7 | 156 N | 99.13 |
| 152 CB | 129 C7 | 152 N | 13.89 | 61 CE1 | 129 C7 | 61 CG | 25.26 |
| 61 CE1 | 129 C7 | 61 NE2 | 5.83 | 61 CE1 | 129 C7 | 152 CA | 112.87 |
| 61 CE1 | 129 C7 | 61 N | 55.62 | 61 CE1 | 129 C7 | 61 CB | 39.89 |
| 61 CE1 | 129 C7 | 156 CG | 98.69 | 61 CE1 | 129 C7 | 61 CD2 | 15.39 |
| 61 CE1 | 129 C7 | 156 N | 101.61 | 61 CE1 | 129 C7 | 152 N | 100.43 |
| 61 CG | 129 C7 | 61 NE2 | 24.70 | 61 CG | 129 C7 | 152 CA | 106.06 |
| 61 CG | 129 C7 | 61 N | 33.88 | 61 CG | 129 C7 | 61 CB | 14.70 |
| 61 CG | 129 C7 | 156 CG | 118.44 | 61 CG | 129 C7 | 61 CD2 | 11.97 |
| 61 CG | 129 C7 | 156 N | 126.67 | 61 CG | 129 C7 | 152 N | 97.19 |
| 61 NE2 | 129 C7 | 152 CA | 107.03 | 61 NE2 | 129 C7 | 61 N | 52.28 |
| 61 NE2 | 129 C7 | 61 CB | 39.34 | 61 NE2 | 129 C7 | 156 CG | 103.01 |
| 61 NE2 | 129 C7 | 61 CD2 | 13.25 | 61 NE2 | 129 C7 | 156 N | 103.39 |
| 61 NE2 | 129 C7 | 152 N | 94.63 | 152 CA | 129 C7 | 61 N | 76.95 |
| 152 CA | 129 C7 | 61 CB | 102.41 | 152 CA | 129 C7 | 156 CG | 127.67 |
| 152 CA | 129 C7 | 61 CD2 | 104.38 | 152 CA | 129 C7 | 156 N | 101.23 |
| 152 CA | 129 C7 | 152 N | 13.57 | 61 N | 129 C7 | 61 CB | 25.61 |
| 61 N | 129 C7 | 156 CG | 152.22 | 61 N | 129 C7 | 61 CD2 | 40.29 |
| 61 N | 129 C7 | 156 N | 151.82 | 61 N | 129 C7 | 152 N | 72.22 |
| 61 CB | 129 C7 | 156 CG | 127.37 | 61 CB | 129 C7 | 61 CD2 | 26.30 |

Figure 11YY

| Atom 1 | Atom 2 | Atom 3 | Angle | Atom 1 | Atom 2 | Atom 3 | Angle |
|---|---|---|---|---|---|---|---|
| 61 CB | 129 C7 | 156 N | 140.71 | 61 CB | 129 C7 | 152 N | 96.45 |
| 156 CG | 129 C7 | 61 CD2 | 113.43 | 156 CG | 129 C7 | 156 N | 29.41 |
| 156 CG | 129 C7 | 152 N | 128.23 | 61 CD2 | 129 C7 | 156 N | 116.54 |
| 61 CD2 | 129 C7 | 152 N | 93.59 | 156 N | 129 C7 | 152 N | 99.35 |
| 130 O | 129 C8 | 157 NH2 | 42.10 | 130 O | 129 C8 | 130 C | 11.65 |
| 130 O | 129 C8 | 61 CE1 | 89.41 | 130 O | 129 C8 | 131 OG | 54.82 |
| 130 O | 129 C8 | 130 N | 36.80 | 130 O | 129 C8 | 61 NE2 | 75.02 |
| 130 O | 129 C8 | 131 CA | 31.85 | 130 O | 129 C8 | 156 NE | 158.00 |
| 130 O | 129 C8 | 131 N | 21.31 | 130 O | 129 C8 | 157 CZ | 53.05 |
| 130 O | 129 C8 | 301 OH2 | 54.65 | 130 O | 129 C8 | 156 CB | 133.98 |
| 130 O | 129 C8 | 130 CA | 21.28 | 130 O | 129 C8 | 156 CG | 148.05 |
| 130 O | 129 C8 | 131 CB | 46.33 | 130 O | 129 C8 | 61 ND1 | 98.41 |
| 130 O | 129 C8 | 157 NH1 | 58.97 | 130 O | 129 C8 | 300 OH2 | 82.99 |
| 130 O | 129 C8 | 156 NH2 | 140.90 | 130 O | 129 C8 | 157 NE | 59.73 |
| 130 O | 129 C8 | 156 CD | 159.80 | 130 O | 129 C8 | 156 N | 118.33 |
| 130 O | 129 C8 | 156 CZ | 151.21 | 157 NH2 | 129 C8 | 130 C | 52.25 |
| 157 NH2 | 129 C8 | 61 CE1 | 128.23 | 157 NH2 | 129 C8 | 131 OG | 96.35 |
| 157 NH2 | 129 C8 | 130 N | 55.55 | 157 NH2 | 129 C8 | 61 NE2 | 115.78 |
| 157 NH2 | 129 C8 | 131 CA | 69.75 | 157 NH2 | 129 C8 | 156 NE | 116.20 |
| 157 NH2 | 129 C8 | 131 N | 63.34 | 157 NH2 | 129 C8 | 157 CZ | 11.03 |
| 157 NH2 | 129 C8 | 301 OH2 | 40.53 | 157 NH2 | 129 C8 | 156 CB | 96.69 |
| 157 NH2 | 129 C8 | 130 CA | 50.93 | 157 NH2 | 129 C8 | 156 CG | 113.40 |
| 157 NH2 | 129 C8 | 131 CB | 85.78 | 157 NH2 | 129 C8 | 61 ND1 | 137.93 |
| 157 NH2 | 129 C8 | 157 NH1 | 21.27 | 157 NH2 | 129 C8 | 300 OH2 | 66.28 |
| 157 NH2 | 129 C8 | 156 NH2 | 106.87 | 157 NH2 | 129 C8 | 157 NE | 19.85 |
| 157 NH2 | 129 C8 | 156 CD | 119.35 | 157 NH2 | 129 C8 | 156 N | 92.75 |
| 157 NH2 | 129 C8 | 156 CZ | 112.15 | 130 C | 129 C8 | 61 CE1 | 78.00 |
| 130 C | 129 C8 | 131 OG | 46.79 | 130 C | 129 C8 | 130 N | 31.15 |
| 130 C | 129 C8 | 61 NE2 | 63.96 | 130 C | 129 C8 | 131 CA | 29.50 |

Figure 11ZZ

| Atom 1 | Atom 2 | Atom 3 | Angle | Atom 1 | Atom 2 | Atom 3 | Angle |
|---|---|---|---|---|---|---|---|
| 130 C | 129 C8 | 156 NE | 168.13 | 130 C | 129 C8 | 131 N | 13.99 |
| 130 C | 129 C8 | 157 CZ | 63.28 | 130 C | 129 C8 | 301 OH2 | 56.47 |
| 130 C | 129 C8 | 156 CB | 137.57 | 130 C | 129 C8 | 130 CA | 14.98 |
| 130 C | 129 C8 | 156 CG | 147.91 | 130 C | 129 C8 | 131 CB | 41.00 |
| 130 C | 129 C8 | 61 ND1 | 87.16 | 130 C | 129 C8 | 157 NH1 | 70.25 |
| 130 C | 129 C8 | 300 OH2 | 82.27 | 130 C | 129 C8 | 156 NH2 | 151.99 |
| 130 C | 129 C8 | 157 NE | 68.37 | 130 C | 129 C8 | 156 CD | 162.70 |
| 130 C | 129 C8 | 156 N | 117.45 | 130 C | 129 C8 | 156 CZ | 162.86 |
| 61 CE1 | 129 C8 | 131 OG | 45.51 | 61 CE1 | 129 C8 | 130 N | 74.89 |
| 61 CE1 | 129 C8 | 61 NE2 | 15.65 | 61 CE1 | 129 C8 | 131 CA | 72.99 |
| 61 CE1 | 129 C8 | 156 NE | 112.25 | 61 CE1 | 129 C8 | 131 N | 70.44 |
| 61 CE1 | 129 C8 | 157 CZ | 138.52 | 61 CE1 | 129 C8 | 301 OH2 | 102.92 |
| 61 CE1 | 129 C8 | 156 CB | 114.75 | 61 CE1 | 129 C8 | 130 CA | 77.29 |
| 61 CE1 | 129 C8 | 156 CG | 100.97 | 61 CE1 | 129 C8 | 131 CB | 59.43 |
| 61 CE1 | 129 C8 | 61 ND1 | 9.75 | 61 CE1 | 129 C8 | 157 NH1 | 148.17 |
| 61 CE1 | 129 C8 | 300 OH2 | 96.94 | 61 CE1 | 129 C8 | 156 NH2 | 124.87 |
| 61 CE1 | 129 C8 | 157 NE | 136.13 | 61 CE1 | 129 C8 | 156 CD | 103.95 |
| 61 CE1 | 129 C8 | 156 N | 99.21 | 61 CE1 | 129 C8 | 156 CZ | 118.76 |
| 131 OG | 129 C8 | 130 N | 66.23 | 131 OG | 129 C8 | 61 NE2 | 30.53 |
| 131 OG | 129 C8 | 131 CA | 28.59 | 131 OG | 129 C8 | 156 NE | 144.90 |
| 131 OG | 129 C8 | 131 N | 33.64 | 131 OG | 129 C8 | 157 CZ | 106.91 |
| 131 OG | 129 C8 | 301 OH2 | 99.37 | 131 OG | 129 C8 | 156 CB | 160.06 |
| 131 OG | 129 C8 | 130 CA | 56.23 | 131 OG | 129 C8 | 156 CG | 145.99 |
| 131 OG | 129 C8 | 131 CB | 13.92 | 131 OG | 129 C8 | 61 ND1 | 50.99 |
| 131 OG | 129 C8 | 157 NH1 | 108.79 | 131 OG | 129 C8 | 300 OH2 | 115.99 |
| 131 OG | 129 C8 | 156 NH2 | 135.83 | 131 OG | 129 C8 | 157 NE | 114.54 |
| 131 OG | 129 C8 | 156 CD | 144.28 | 131 OG | 129 C8 | 156 N | 138.94 |
| 131 OG | 129 C8 | 156 CZ | 142.41 | 130 N | 129 C8 | 61 NE2 | 66.90 |
| 130 N | 129 C8 | 131 CA | 59.33 | 130 N | 129 C8 | 156 NE | 143.23 |

Figure 11AAA

| Atom 1 | Atom 2 | Atom 3 | Angle | Atom 1 | Atom 2 | Atom 3 | Angle |
|---|---|---|---|---|---|---|---|
| 130 N | 129 C8 | 131 N | 42.27 | 130 N | 129 C8 | 157 CZ | 64.39 |
| 130 N | 129 C8 | 301 OH2 | 33.85 | 130 N | 129 C8 | 156 CB | 109.84 |
| 130 N | 129 C8 | 130 CA | 16.28 | 130 N | 129 C8 | 156 CG | 117.08 |
| 130 N | 129 C8 | 131 CB | 66.65 | 130 N | 129 C8 | 61 ND1 | 84.43 |
| 130 N | 129 C8 | 157 NH1 | 76.80 | 130 N | 129 C8 | 300 OH2 | 52.99 |
| 130 N | 129 C8 | 156 NH2 | 156.53 | 130 N | 129 C8 | 157 NE | 61.69 |
| 130 N | 129 C8 | 156 CD | 132.12 | 130 N | 129 C8 | 156 N | 87.04 |
| 130 N | 129 C8 | 156 CZ | 150.73 | 61 NE2 | 129 C8 | 131 CA | 57.40 |
| 61 NE2 | 129 C8 | 156 NE | 126.93 | 61 NE2 | 129 C8 | 131 N | 55.24 |
| 61 NE2 | 129 C8 | 157 CZ | 126.69 | 61 NE2 | 129 C8 | 301 OH2 | 98.80 |
| 61 NE2 | 129 C8 | 156 CB | 129.54 | 61 NE2 | 129 C8 | 130 CA | 65.68 |
| 61 NE2 | 129 C8 | 156 CG | 116.48 | 61 NE2 | 129 C8 | 131 CB | 44.37 |
| 61 NE2 | 129 C8 | 61 ND1 | 23.52 | 61 NE2 | 129 C8 | 157 NH1 | 133.94 |
| 61 NE2 | 129 C8 | 300 OH2 | 100.90 | 61 NE2 | 129 C8 | 156 NH2 | 135.42 |
| 61 NE2 | 129 C8 | 157 NE | 128.04 | 61 NE2 | 129 C8 | 156 CD | 119.46 |
| 61 NE2 | 129 C8 | 156 N | 111.26 | 61 NE2 | 129 C8 | 156 CZ | 132.07 |
| 131 CA | 129 C8 | 156 NE | 157.03 | 131 CA | 129 C8 | 131 N | 17.10 |
| 131 CA | 129 C8 | 157 CZ | 79.62 | 131 CA | 129 C8 | 301 OH2 | 85.52 |
| 131 CA | 129 C8 | 156 CB | 165.76 | 131 CA | 129 C8 | 130 CA | 43.98 |
| 131 CA | 129 C8 | 156 CG | 173.42 | 131 CA | 129 C8 | 131 CB | 16.11 |
| 131 CA | 129 C8 | 61 ND1 | 79.36 | 131 CA | 129 C8 | 157 NH1 | 80.25 |
| 131 CA | 129 C8 | 300 OH2 | 111.67 | 131 CA | 129 C8 | 156 NH2 | 133.90 |
| 131 CA | 129 C8 | 157 NE | 89.20 | 131 CA | 129 C8 | 156 CD | 167.65 |
| 131 CA | 129 C8 | 156 N | 146.37 | 131 CA | 129 C8 | 156 CZ | 146.76 |
| 156 NE | 129 C8 | 131 N | 173.82 | 156 NE | 129 C8 | 157 CZ | 105.18 |
| 156 NE | 129 C8 | 301 OH2 | 113.70 | 156 NE | 129 C8 | 156 CB | 33.55 |
| 156 NE | 129 C8 | 130 CA | 157.34 | 156 NE | 129 C8 | 156 CG | 27.70 |
| 156 NE | 129 C8 | 131 CB | 149.15 | 156 NE | 129 C8 | 61 ND1 | 103.47 |
| 156 NE | 129 C8 | 157 NH1 | 99.13 | 156 NE | 129 C8 | 300 OH2 | 90.31 |

Figure 11BBB

| Atom 1 | Atom 2 | Atom 3 | Angle | Atom 1 | Atom 2 | Atom 3 | Angle |
|---|---|---|---|---|---|---|---|
| 156 NE | 129 C8 | 156 NH2 | 24.54 | 156 NE | 129 C8 | 157 NE | 99.76 |
| 156 NE | 129 C8 | 156 CD | 13.61 | 156 NE | 129 C8 | 156 N | 56.46 |
| 156 NE | 129 C8 | 156 CZ | 11.22 | 131 N | 129 C8 | 157 CZ | 74.22 |
| 131 N | 129 C8 | 301 OH2 | 70.28 | 131 N | 129 C8 | 156 CB | 151.23 |
| 131 N | 129 C8 | 130 CA | 27.31 | 131 N | 129 C8 | 156 CG | 158.45 |
| 131 N | 129 C8 | 131 CB | 27.01 | 131 N | 129 C8 | 61 ND1 | 78.74 |
| 131 N | 129 C8 | 157 NH1 | 78.89 | 131 N | 129 C8 | 300 OH2 | 94.92 |
| 131 N | 129 C8 | 156 NH2 | 149.38 | 131 N | 129 C8 | 157 NE | 80.94 |
| 131 N | 129 C8 | 156 CD | 172.37 | 131 N | 129 C8 | 156 N | 129.27 |
| 131 N | 129 C8 | 156 CZ | 162.70 | 157 CZ | 129 C8 | 301 OH2 | 43.51 |
| 157 CZ | 129 C8 | 156 CB | 87.29 | 157 CZ | 129 C8 | 130 CA | 61.43 |
| 157 CZ | 129 C8 | 156 CG | 104.08 | 157 CZ | 129 C8 | 131 CB | 95.73 |
| 157 CZ | 129 C8 | 61 ND1 | 148.27 | 157 CZ | 129 C8 | 157 NH1 | 13.87 |
| 157 CZ | 129 C8 | 300 OH2 | 65.01 | 157 CZ | 129 C8 | 156 NH2 | 96.56 |
| 157 CZ | 129 C8 | 157 NE | 13.22 | 157 CZ | 129 C8 | 156 CD | 108.81 |
| 157 CZ | 129 C8 | 156 N | 86.68 | 157 CZ | 129 C8 | 156 CZ | 101.23 |
| 301 OH2 | 129 C8 | 156 CB | 81.11 | 301 OH2 | 129 C8 | 130 CA | 43.75 |
| 301 OH2 | 129 C8 | 156 CG | 93.45 | 301 OH2 | 129 C8 | 131 CB | 97.10 |
| 301 OH2 | 129 C8 | 61 ND1 | 111.21 | 301 OH2 | 129 C8 | 157 NH1 | 57.32 |
| 301 OH2 | 129 C8 | 300 OH2 | 29.60 | 301 OH2 | 129 C8 | 156 NH2 | 122.74 |
| 301 OH2 | 129 C8 | 157 NE | 34.49 | 301 OH2 | 129 C8 | 156 CD | 106.82 |
| 301 OH2 | 129 C8 | 156 N | 63.95 | 301 OH2 | 129 C8 | 156 CZ | 118.21 |
| 156 CB | 129 C8 | 130 CA | 124.00 | 156 CB | 129 C8 | 156 CG | 16.79 |
| 156 CB | 129 C8 | 131 CB | 173.50 | 156 CB | 129 C8 | 61 ND1 | 110.05 |
| 156 CB | 129 C8 | 157 NH1 | 88.39 | 156 CB | 129 C8 | 300 OH2 | 56.85 |
| 156 CB | 129 C8 | 156 NH2 | 52.83 | 156 CB | 129 C8 | 157 NE | 77.01 |
| 156 CB | 129 C8 | 156 CD | 26.07 | 156 CB | 129 C8 | 156 N | 25.21 |
| 156 CB | 129 C8 | 156 CZ | 41.65 | 130 CA | 129 C8 | 156 CG | 132.98 |
| 130 CA | 129 C8 | 131 CB | 53.51 | 130 CA | 129 C8 | 61 ND1 | 87.00 |

Figure 11CCC

| Atom 1 | Atom 2 | Atom 3 | Angle | Atom 1 | Atom 2 | Atom 3 | Angle |
|---|---|---|---|---|---|---|---|
| 130 CA | 129 C8 | 157 NH1 | 71.49 | 130 CA | 129 C8 | 300 OH2 | 67.70 |
| 130 CA | 129 C8 | 156 NH2 | 157.72 | 130 CA | 129 C8 | 157 NE | 62.93 |
| 130 CA | 129 C8 | 156 CD | 147.93 | 130 CA | 129 C8 | 156 N | 102.62 |
| 130 CA | 129 C8 | 156 CZ | 160.73 | 156 CG | 129 C8 | 131 CB | 159.40 |
| 156 CG | 129 C8 | 61 ND1 | 95.01 | 156 CG | 129 C8 | 157 NH1 | 104.67 |
| 156 CG | 129 C8 | 300 OH2 | 65.91 | 156 CG | 129 C8 | 156 NH2 | 51.66 |
| 156 CG | 129 C8 | 157 NE | 93.64 | 156 CG | 129 C8 | 156 CD | 15.05 |
| 156 CG | 129 C8 | 156 N | 30.51 | 156 CG | 129 C8 | 156 CZ | 38.52 |
| 131 CB | 129 C8 | 61 ND1 | 64.67 | 131 CB | 129 C8 | 157 NH1 | 95.92 |
| 131 CB | 129 C8 | 300 OH2 | 119.37 | 131 CB | 129 C8 | 156 NH2 | 132.16 |
| 131 CB | 129 C8 | 157 NE | 105.06 | 131 CB | 129 C8 | 156 CD | 153.85 |
| 131 CB | 129 C8 | 156 N | 149.00 | 131 CB | 129 C8 | 156 CZ | 142.44 |
| 61 ND1 | 129 C8 | 157 NH1 | 157.38 | 61 ND1 | 129 C8 | 300 OH2 | 101.66 |
| 61 ND1 | 129 C8 | 156 NH2 | 115.13 | 61 ND1 | 129 C8 | 157 NE | 145.17 |
| 61 ND1 | 129 C8 | 156 CD | 96.19 | 61 ND1 | 129 C8 | 156 N | 98.04 |
| 61 ND1 | 129 C8 | 156 CZ | 109.38 | 157 NH1 | 129 C8 | 300 OH2 | 77.03 |
| 157 NH1 | 129 C8 | 156 NH2 | 86.24 | 157 NH1 | 129 C8 | 157 NE | 24.80 |
| 157 NH1 | 129 C8 | 156 CD | 105.72 | 157 NH1 | 129 C8 | 156 N | 93.53 |
| 157 NH1 | 129 C8 | 156 CZ | 93.07 | 300 OH2 | 129 C8 | 156 NH2 | 107.72 |
| 300 OH2 | 129 C8 | 157 NE | 52.36 | 300 OH2 | 129 C8 | 156 CD | 80.44 |
| 300 OH2 | 129 C8 | 156 N | 35.47 | 300 OH2 | 129 C8 | 156 CZ | 98.19 |
| 156 NH2 | 129 C8 | 157 NE | 96.54 | 156 NH2 | 129 C8 | 156 CD | 38.15 |
| 156 NH2 | 129 C8 | 156 N | 77.83 | 156 NH2 | 129 C8 | 156 CZ | 13.33 |
| 157 NE | 129 C8 | 156 CD | 100.67 | 157 NE | 129 C8 | 156 N | 73.82 |
| 157 NE | 129 C8 | 156 CZ | 98.22 | 156 CD | 129 C8 | 156 N | 45.31 |
| 156 CD | 129 C8 | 156 CZ | 24.83 | 156 N | 129 C8 | 156 CZ | 65.97 |
| 130 O | 129 C9 | 131 OG | 63.44 | 130 O | 129 C9 | 61 CE1 | 91.36 |
| 130 O | 129 C9 | 131 CA | 39.69 | 130 O | 129 C9 | 61 NE2 | 80.02 |
| 130 O | 129 C9 | 131 CB | 57.37 | 130 O | 129 C9 | 130 C | 13.01 |

Figure 11DDD

| Atom 1 | Atom 2 | Atom 3 | Angle | Atom 1 | Atom 2 | Atom 3 | Angle |
|---|---|---|---|---|---|---|---|
| 130 O | 129 C9 | 131 N | 27.17 | 130 O | 129 C9 | 157 NH2 | 33.54 |
| 130 O | 129 C9 | 61 ND1 | 103.34 | 130 O | 129 C9 | 61 CD2 | 87.71 |
| 130 O | 129 C9 | 130 N | 28.42 | 130 O | 129 C9 | 131 C | 41.65 |
| 130 O | 129 C9 | 156 NE | 124.91 | 130 O | 129 C9 | 130 CA | 16.74 |
| 130 O | 129 C9 | 61 CG | 99.84 | 130 O | 129 C9 | 156 NH2 | 126.93 |
| 130 O | 129 C9 | 157 CZ | 41.80 | 131 OG | 129 C9 | 61 CE1 | 53.20 |
| 131 OG | 129 C9 | 131 CA | 34.08 | 131 OG | 129 C9 | 61 NE2 | 35.30 |
| 131 OG | 129 C9 | 131 CB | 17.70 | 131 OG | 129 C9 | 130 C | 51.09 |
| 131 OG | 129 C9 | 131 N | 36.67 | 131 OG | 129 C9 | 157 NH2 | 96.85 |
| 131 OG | 129 C9 | 61 ND1 | 58.46 | 131 OG | 129 C9 | 61 CD2 | 34.37 |
| 131 OG | 129 C9 | 130 N | 64.60 | 131 OG | 129 C9 | 131 C | 43.54 |
| 131 OG | 129 C9 | 156 NE | 159.39 | 131 OG | 129 C9 | 130 CA | 55.73 |
| 131 OG | 129 C9 | 61 CG | 47.62 | 131 OG | 129 C9 | 156 NH2 | 168.07 |
| 131 OG | 129 C9 | 157 CZ | 104.90 | 61 CE1 | 129 C9 | 131 CA | 84.09 |
| 61 CE1 | 129 C9 | 61 NE2 | 17.97 | 61 CE1 | 129 C9 | 131 CB | 70.90 |
| 61 CE1 | 129 C9 | 130 C | 80.11 | 61 CE1 | 129 C9 | 131 N | 76.13 |
| 61 CE1 | 129 C9 | 157 NH2 | 115.71 | 61 CE1 | 129 C9 | 61 ND1 | 12.36 |
| 61 CE1 | 129 C9 | 61 CD2 | 21.94 | 61 CE1 | 129 C9 | 130 N | 69.31 |
| 61 CE1 | 129 C9 | 131 C | 94.95 | 61 CE1 | 129 C9 | 156 NE | 106.25 |
| 61 CE1 | 129 C9 | 130 CA | 74.95 | 61 CE1 | 129 C9 | 61 CG | 17.50 |
| 61 CE1 | 129 C9 | 156 NH2 | 126.68 | 61 CE1 | 129 C9 | 157 CZ | 122.39 |
| 131 CA | 129 C9 | 61 NE2 | 66.51 | 131 CA | 129 C9 | 131 CB | 20.08 |
| 131 CA | 129 C9 | 130 C | 32.45 | 131 CA | 129 C9 | 131 N | 17.97 |
| 131 CA | 129 C9 | 157 NH2 | 68.79 | 131 CA | 129 C9 | 61 ND1 | 91.57 |
| 131 CA | 129 C9 | 61 CD2 | 68.01 | 131 CA | 129 C9 | 130 N | 57.47 |
| 131 CA | 129 C9 | 131 C | 11.13 | 131 CA | 129 C9 | 156 NE | 162.96 |
| 131 CA | 129 C9 | 130 CA | 42.66 | 131 CA | 129 C9 | 61 CG | 81.51 |
| 131 CA | 129 C9 | 156 NH2 | 149.22 | 131 CA | 129 C9 | 157 CZ | 75.64 |
| 61 NE2 | 129 C9 | 131 CB | 52.98 | 61 NE2 | 129 C9 | 130 C | 67.54 |

Figure 11EEE

| Atom 1 | Atom 2 | Atom 3 | Angle | Atom 1 | Atom 2 | Atom 3 | Angle |
|---|---|---|---|---|---|---|---|
| 61 NE2 | 129 C9 | 131 N | 60.47 | 61 NE2 | 129 C9 | 157 NH2 | 109.79 |
| 61 NE2 | 129 C9 | 61 ND1 | 25.74 | 61 NE2 | 129 C9 | 61 CD2 | 10.80 |
| 61 NE2 | 129 C9 | 130 N | 63.90 | 61 NE2 | 129 C9 | 131 C | 77.20 |
| 61 NE2 | 129 C9 | 156 NE | 124.21 | 61 NE2 | 129 C9 | 130 CA | 65.02 |
| 61 NE2 | 129 C9 | 61 CG | 19.87 | 61 NE2 | 129 C9 | 156 NH2 | 144.23 |
| 61 NE2 | 129 C9 | 157 CZ | 117.77 | 131 CB | 129 C9 | 130 C | 47.29 |
| 131 CB | 129 C9 | 131 N | 31.00 | 131 CB | 129 C9 | 157 NH2 | 88.47 |
| 131 CB | 129 C9 | 61 ND1 | 75.76 | 131 CB | 129 C9 | 61 CD2 | 51.59 |
| 131 CB | 129 C9 | 130 N | 67.99 | 131 CB | 129 C9 | 131 C | 27.27 |
| 131 CB | 129 C9 | 156 NE | 176.71 | 131 CB | 129 C9 | 130 CA | 55.35 |
| 131 CB | 129 C9 | 61 CG | 64.38 | 131 CB | 129 C9 | 156 NH2 | 158.19 |
| 131 CB | 129 C9 | 157 CZ | 95.59 | 130 C | 129 C9 | 131 N | 16.29 |
| 130 C | 129 C9 | 157 NH2 | 46.35 | 130 C | 129 C9 | 61 ND1 | 91.70 |
| 130 C | 129 C9 | 61 CD2 | 74.84 | 130 C | 129 C9 | 130 N | 26.26 |
| 130 C | 129 C9 | 131 C | 37.90 | 130 C | 129 C9 | 156 NE | 134.51 |
| 130 C | 129 C9 | 130 CA | 10.98 | 130 C | 129 C9 | 61 CG | 87.24 |
| 130 C | 129 C9 | 156 NH2 | 139.69 | 130 C | 129 C9 | 157 CZ | 54.68 |
| 131 N | 129 C9 | 157 NH2 | 60.24 | 131 N | 129 C9 | 61 ND1 | 86.13 |
| 131 N | 129 C9 | 61 CD2 | 65.42 | 131 N | 129 C9 | 130 N | 39.66 |
| 131 N | 129 C9 | 131 C | 26.54 | 131 N | 129 C9 | 156 NE | 150.77 |
| 131 N | 129 C9 | 130 CA | 25.27 | 131 N | 129 C9 | 61 CG | 78.82 |
| 131 N | 129 C9 | 156 NH2 | 152.50 | 131 N | 129 C9 | 157 CZ | 68.23 |
| 157 NH2 | 129 C9 | 61 ND1 | 127.86 | 157 NH2 | 129 C9 | 61 CD2 | 119.09 |
| 157 NH2 | 129 C9 | 130 N | 46.72 | 157 NH2 | 129 C9 | 131 C | 65.83 |
| 157 NH2 | 129 C9 | 156 NE | 94.33 | 157 NH2 | 129 C9 | 130 CA | 45.42 |
| 157 NH2 | 129 C9 | 61 CG | 129.16 | 157 NH2 | 129 C9 | 156 NH2 | 93.40 |
| 157 NH2 | 129 C9 | 157 CZ | 8.40 | 61 ND1 | 129 C9 | 61 CD2 | 24.18 |
| 61 ND1 | 129 C9 | 130 N | 81.64 | 61 ND1 | 129 C9 | 131 C | 101.82 |
| 61 ND1 | 129 C9 | 156 NE | 101.12 | 61 ND1 | 129 C9 | 130 CA | 87.11 |

Figure 11FFF

| Atom 1 | Atom 2 | Atom 3 | Angle | Atom 1 | Atom 2 | Atom 3 | Angle |
|---|---|---|---|---|---|---|---|
| 61 ND1 | 129 C9 | 61 CG | 12.58 | 61 ND1 | 129 C9 | 156 NH2 | 118.84 |
| 61 ND1 | 129 C9 | 157 CZ | 134.21 | 61 CD2 | 129 C9 | 130 N | 74.08 |
| 61 CD2 | 129 C9 | 131 C | 77.89 | 61 CD2 | 129 C9 | 156 NE | 125.29 |
| 61 CD2 | 129 C9 | 130 CA | 73.76 | 61 CD2 | 129 C9 | 61 CG | 13.63 |
| 61 CD2 | 129 C9 | 156 NH2 | 141.43 | 61 CD2 | 129 C9 | 157 CZ | 127.30 |
| 130 N | 129 C9 | 131 C | 64.08 | 130 N | 129 C9 | 156 NE | 112.83 |
| 130 N | 129 C9 | 130 CA | 15.29 | 130 N | 129 C9 | 61 CG | 82.63 |
| 130 N | 129 C9 | 156 NH2 | 127.30 | 130 N | 129 C9 | 157 CZ | 54.20 |
| 131 C | 129 C9 | 156 NE | 156.02 | 131 C | 129 C9 | 130 CA | 48.81 |
| 131 C | 129 C9 | 61 CG | 91.14 | 131 C | 129 C9 | 156 NH2 | 138.34 |
| 131 C | 129 C9 | 157 CZ | 71.61 | 156 NE | 129 C9 | 130 CA | 125.97 |
| 156 NE | 129 C9 | 61 CG | 112.42 | 156 NE | 129 C9 | 156 NH2 | 23.45 |
| 156 NE | 129 C9 | 157 CZ | 87.33 | 130 CA | 129 C9 | 61 CG | 84.85 |
| 130 CA | 129 C9 | 156 NH2 | 135.96 | 130 CA | 129 C9 | 157 CZ | 53.75 |
| 61 CG | 129 C9 | 156 NH2 | 127.81 | 61 CG | 129 C9 | 157 CZ | 136.83 |
| 156 NH2 | 129 C9 | 157 CZ | 85.13 | 157 NH2 | 129 C10 | 130 O | 41.76 |
| 157 NH2 | 129 C10 | 156 NE | 149.70 | 157 NH2 | 129 C10 | 157 CZ | 16.24 |
| 157 NH2 | 129 C10 | 156 CB | 115.22 | 157 NH2 | 129 C10 | 157 NH1 | 29.16 |
| 157 NH2 | 129 C10 | 156 NH2 | 141.40 | 157 NH2 | 129 C10 | 157 NE | 25.73 |
| 157 NH2 | 129 C10 | 156 CZ | 146.55 | 157 NH2 | 129 C10 | 156 CG | 130.43 |
| 157 NH2 | 129 C10 | 130 C | 46.05 | 157 NH2 | 129 C10 | 157 CG | 53.51 |
| 157 NH2 | 129 C10 | 156 CD | 143.84 | 157 NH2 | 129 C10 | 301 OH2 | 39.20 |
| 157 NH2 | 129 C10 | 156 CA | 103.56 | 157 NH2 | 129 C10 | 130 N | 48.13 |
| 157 NH2 | 129 C10 | 157 CD | 39.12 | 157 NH2 | 129 C10 | 300 OH2 | 66.88 |
| 157 NH2 | 129 C10 | 156 N | 99.96 | 157 NH2 | 129 C10 | 157 N | 79.24 |
| 157 NH2 | 129 C10 | 131 CA | 61.88 | 157 NH2 | 129 C10 | 61 CE1 | 103.08 |
| 157 NH2 | 129 C10 | 156 C | 91.36 | 157 NH2 | 129 C10 | 131 OG | 81.58 |
| 157 NH2 | 129 C10 | 131 N | 54.26 | 157 NH2 | 129 C10 | 130 CA | 42.43 |
| 130 O | 129 C10 | 156 NE | 162.23 | 130 O | 129 C10 | 157 CZ | 57.91 |

Figure 11GGG

| Atom 1 | Atom 2 | Atom 3 | Angle | Atom 1 | Atom 2 | Atom 3 | Angle |
|---|---|---|---|---|---|---|---|
| 130 O | 129 C10 | 156 CB | 135.27 | 130 O | 129 C10 | 157 NH1 | 66.76 |
| 130 O | 129 C10 | 156 NH2 | 160.81 | 130 O | 129 C10 | 157 NE | 65.43 |
| 130 O | 129 C10 | 156 CZ | 171.31 | 130 O | 129 C10 | 156 CG | 136.94 |
| 130 O | 129 C10 | 130 C | 5.62 | 130 O | 129 C10 | 157 CG | 91.37 |
| 130 O | 129 C10 | 156 CD | 151.08 | 130 O | 129 C10 | 301 OH2 | 51.85 |
| 130 O | 129 C10 | 156 CA | 122.88 | 130 O | 129 C10 | 130 N | 29.31 |
| 130 O | 129 C10 | 157 CD | 79.46 | 130 O | 129 C10 | 300 OH2 | 76.46 |
| 130 O | 129 C10 | 156 N | 110.31 | 130 O | 129 C10 | 157 N | 105.89 |
| 130 O | 129 C10 | 131 CA | 24.66 | 130 O | 129 C10 | 61 CE1 | 64.32 |
| 130 O | 129 C10 | 156 C | 118.60 | 130 O | 129 C10 | 131 OG | 40.06 |
| 130 O | 129 C10 | 131 N | 12.86 | 130 O | 129 C10 | 130 CA | 15.35 |
| 156 NE | 129 C10 | 157 CZ | 135.03 | 156 NE | 129 C10 | 156 CB | 38.88 |
| 156 NE | 129 C10 | 157 NH1 | 129.45 | 156 NE | 129 C10 | 156 NH2 | 30.21 |
| 156 NE | 129 C10 | 157 NE | 124.01 | 156 NE | 129 C10 | 156 CZ | 14.78 |
| 156 NE | 129 C10 | 156 CG | 30.12 | 156 NE | 129 C10 | 130 C | 156.61 |
| 156 NE | 129 C10 | 157 CG | 96.30 | 156 NE | 129 C10 | 156 CD | 13.58 |
| 156 NE | 129 C10 | 301 OH2 | 124.77 | 156 NE | 129 C10 | 156 CA | 51.78 |
| 156 NE | 129 C10 | 130 N | 137.57 | 156 NE | 129 C10 | 157 CD | 110.63 |
| 156 NE | 129 C10 | 300 OH2 | 96.57 | 156 NE | 129 C10 | 156 N | 60.83 |
| 156 NE | 129 C10 | 157 N | 73.81 | 156 NE | 129 C10 | 131 CA | 148.23 |
| 156 NE | 129 C10 | 61 CE1 | 98.63 | 156 NE | 129 C10 | 156 C | 60.95 |
| 156 NE | 129 C10 | 131 OG | 126.90 | 156 NE | 129 C10 | 131 N | 152.95 |
| 156 NE | 129 C10 | 130 CA | 150.69 | 157 CZ | 129 C10 | 156 CB | 105.63 |
| 157 CZ | 129 C10 | 157 NH1 | 17.11 | 157 CZ | 129 C10 | 156 NH2 | 126.09 |
| 157 CZ | 129 C10 | 157 NE | 15.28 | 157 CZ | 129 C10 | 156 CZ | 130.33 |
| 157 CZ | 129 C10 | 156 CG | 122.88 | 157 CZ | 129 C10 | 130 C | 62.29 |
| 157 CZ | 129 C10 | 157 CG | 41.24 | 157 CZ | 129 C10 | 156 CD | 132.55 |
| 157 CZ | 129 C10 | 301 OH2 | 45.12 | 157 CZ | 129 C10 | 156 CA | 95.71 |
| 157 CZ | 129 C10 | 130 N | 62.10 | 157 CZ | 129 C10 | 157 CD | 25.52 |

Figure 11HHH

| Atom 1 | Atom 2 | Atom 3 | Angle | Atom 1 | Atom 2 | Atom 3 | Angle |
|---|---|---|---|---|---|---|---|
| 157 CZ | 129 C10 | 300 OH2 | 68.31 | 157 CZ | 129 C10 | 156 N | 96.18 |
| 157 CZ | 129 C10 | 157 N | 71.04 | 157 CZ | 129 C10 | 131 CA | 76.70 |
| 157 CZ | 129 C10 | 61 CE1 | 118.73 | 157 CZ | 129 C10 | 156 C | 81.70 |
| 157 CZ | 129 C10 | 131 OG | 97.45 | 157 CZ | 129 C10 | 131 N | 70.24 |
| 157 CZ | 129 C10 | 130 CA | 58.19 | 156 CB | 129 C10 | 157 NH1 | 110.45 |
| 156 CB | 129 C10 | 156 NH2 | 63.78 | 156 CB | 129 C10 | 157 NE | 91.08 |
| 156 CB | 129 C10 | 156 CZ | 49.28 | 156 CB | 129 C10 | 156 CG | 17.98 |
| 156 CB | 129 C10 | 130 C | 132.31 | 156 CB | 129 C10 | 157 CG | 64.56 |
| 156 CB | 129 C10 | 156 CD | 28.73 | 156 CB | 129 C10 | 301 OH2 | 86.18 |
| 156 CB | 129 C10 | 156 CA | 12.96 | 156 CB | 129 C10 | 130 N | 106.26 |
| 156 CB | 129 C10 | 157 CD | 80.49 | 156 CB | 129 C10 | 300 OH2 | 59.13 |
| 156 CB | 129 C10 | 156 N | 25.28 | 156 CB | 129 C10 | 157 N | 36.01 |
| 156 CB | 129 C10 | 131 CA | 152.31 | 156 CB | 129 C10 | 61 CE1 | 100.79 |
| 156 CB | 129 C10 | 156 C | 24.06 | 156 CB | 129 C10 | 131 OG | 134.81 |
| 156 CB | 129 C10 | 131 N | 139.97 | 156 CB | 129 C10 | 130 CA | 120.00 |
| 157 NH1 | 129 C10 | 156 NH2 | 112.43 | 157 NH1 | 129 C10 | 157 NE | 28.96 |
| 157 NH1 | 129 C10 | 156 CZ | 120.33 | 157 NH1 | 129 C10 | 156 CG | 128.42 |
| 157 NH1 | 129 C10 | 130 C | 71.94 | 157 NH1 | 129 C10 | 157 CG | 47.71 |
| 157 NH1 | 129 C10 | 156 CD | 132.34 | 157 NH1 | 129 C10 | 301 OH2 | 62.21 |
| 157 NH1 | 129 C10 | 156 CA | 103.30 | 157 NH1 | 129 C10 | 130 N | 77.26 |
| 157 NH1 | 129 C10 | 157 CD | 32.51 | 157 NH1 | 129 C10 | 300 OH2 | 84.03 |
| 157 NH1 | 129 C10 | 156 N | 107.56 | 157 NH1 | 129 C10 | 157 N | 79.92 |
| 157 NH1 | 129 C10 | 131 CA | 80.09 | 157 NH1 | 129 C10 | 61 CE1 | 130.86 |
| 157 NH1 | 129 C10 | 156 C | 88.21 | 157 NH1 | 129 C10 | 131 OG | 103.01 |
| 157 NH1 | 129 C10 | 131 N | 77.58 | 157 NH1 | 129 C10 | 130 CA | 70.93 |
| 156 NH2 | 129 C10 | 157 NE | 123.87 | 156 NH2 | 129 C10 | 156 CZ | 15.71 |
| 156 NH2 | 129 C10 | 156 CG | 59.77 | 156 NH2 | 129 C10 | 130 C | 162.13 |
| 156 NH2 | 129 C10 | 157 CG | 101.80 | 156 NH2 | 129 C10 | 156 CD | 43.70 |
| 156 NH2 | 129 C10 | 301 OH2 | 146.26 | 156 NH2 | 129 C10 | 156 CA | 76.29 |

Figure 11 III

| Atom 1 | Atom 2 | Atom 3 | Angle | Atom 1 | Atom 2 | Atom 3 | Angle |
|---|---|---|---|---|---|---|---|
| 156 NH2 | 129 C10 | 130 N | 167.66 | 156 NH2 | 129 C10 | 157 CD | 110.43 |
| 156 NH2 | 129 C10 | 300 OH2 | 122.72 | 156 NH2 | 129 C10 | 156 N | 88.44 |
| 156 NH2 | 129 C10 | 157 N | 92.51 | 156 NH2 | 129 C10 | 131 CA | 137.44 |
| 156 NH2 | 129 C10 | 61 CE1 | 115.18 | 156 NH2 | 129 C10 | 156 C | 80.08 |
| 156 NH2 | 129 C10 | 131 OG | 128.43 | 156 NH2 | 129 C10 | 131 N | 151.42 |
| 156 NH2 | 129 C10 | 130 CA | 174.26 | 157 NE | 129 C10 | 156 CZ | 123.25 |
| 157 NE | 129 C10 | 156 CG | 107.92 | 157 NE | 129 C10 | 130 C | 68.73 |
| 157 NE | 129 C10 | 157 CG | 27.80 | 157 NE | 129 C10 | 156 CD | 118.96 |
| 157 NE | 129 C10 | 301 OH2 | 36.68 | 157 NE | 129 C10 | 156 CA | 80.66 |
| 157 NE | 129 C10 | 130 N | 61.08 | 157 NE | 129 C10 | 157 CD | 14.03 |
| 157 NE | 129 C10 | 300 OH2 | 55.11 | 157 NE | 129 C10 | 156 N | 80.96 |
| 157 NE | 129 C10 | 157 N | 55.93 | 157 NE | 129 C10 | 131 CA | 87.33 |
| 157 NE | 129 C10 | 61 CE1 | 118.58 | 157 NE | 129 C10 | 156 C | 67.04 |
| 157 NE | 129 C10 | 131 OG | 105.37 | 157 NE | 129 C10 | 131 N | 78.28 |
| 157 NE | 129 C10 | 130 CA | 61.38 | 156 CZ | 129 C10 | 156 CG | 44.06 |
| 156 CZ | 129 C10 | 130 C | 167.37 | 156 CZ | 129 C10 | 157 CG | 97.23 |
| 156 CZ | 129 C10 | 156 CD | 28.09 | 156 CZ | 129 C10 | 301 OH2 | 134.77 |
| 156 CZ | 129 C10 | 156 CA | 62.12 | 156 CZ | 129 C10 | 130 N | 152.26 |
| 156 CZ | 129 C10 | 157 CD | 109.22 | 156 CZ | 129 C10 | 300 OH2 | 108.38 |
| 156 CZ | 129 C10 | 156 N | 73.29 | 156 CZ | 129 C10 | 157 N | 81.09 |
| 156 CZ | 129 C10 | 131 CA | 147.37 | 156 CZ | 129 C10 | 61 CE1 | 108.81 |
| 156 CZ | 129 C10 | 156 C | 68.18 | 156 CZ | 129 C10 | 131 OG | 131.32 |
| 156 CZ | 129 C10 | 131 N | 158.46 | 156 CZ | 129 C10 | 130 CA | 165.42 |
| 156 CG | 129 C10 | 130 C | 132.23 | 156 CG | 129 C10 | 157 CG | 82.21 |
| 156 CG | 129 C10 | 156 CD | 16.73 | 156 CG | 129 C10 | 301 OH2 | 96.10 |
| 156 CG | 129 C10 | 156 CA | 27.29 | 156 CG | 129 C10 | 130 N | 108.43 |
| 156 CG | 129 C10 | 157 CD | 98.15 | 156 CG | 129 C10 | 300 OH2 | 67.25 |
| 156 CG | 129 C10 | 156 N | 31.66 | 156 CG | 129 C10 | 157 N | 52.02 |
| 156 CG | 129 C10 | 131 CA | 143.26 | 156 CG | 129 C10 | 61 CE1 | 86.97 |

Figure 11 JJJ

| Atom 1 | Atom 2 | Atom 3 | Angle | Atom 1 | Atom 2 | Atom 3 | Angle |
|---|---|---|---|---|---|---|---|
| 156 CG | 129 C10 | 156 C | 41.27 | 156 CG | 129 C10 | 131 OG | 121.33 |
| 156 CG | 129 C10 | 131 N | 135.84 | 156 CG | 129 C10 | 130 CA | 122.28 |
| 130 C | 129 C10 | 157 CG | 93.71 | 130 C | 129 C10 | 156 CD | 145.72 |
| 130 C | 129 C10 | 301 OH2 | 51.54 | 130 C | 129 C10 | 156 CA | 120.41 |
| 130 C | 129 C10 | 130 N | 26.09 | 130 C | 129 C10 | 157 CD | 82.74 |
| 130 C | 129 C10 | 300 OH2 | 74.37 | 130 C | 129 C10 | 156 N | 107.08 |
| 130 C | 129 C10 | 157 N | 105.36 | 130 C | 129 C10 | 131 CA | 24.69 |
| 130 C | 129 C10 | 61 CE1 | 59.01 | 130 C | 129 C10 | 156 C | 117.73 |
| 130 C | 129 C10 | 131 OG | 36.68 | 130 C | 129 C10 | 131 N | 10.88 |
| 130 C | 129 C10 | 130 CA | 12.85 | 157 CG | 129 C10 | 156 CD | 91.48 |
| 157 CG | 129 C10 | 301 OH2 | 48.25 | 157 CG | 129 C10 | 156 CA | 55.79 |
| 157 CG | 129 C10 | 130 N | 78.79 | 157 CG | 129 C10 | 157 CD | 15.94 |
| 157 CG | 129 C10 | 300 OH2 | 49.12 | 157 CG | 129 C10 | 156 N | 60.57 |
| 157 CG | 129 C10 | 157 N | 32.31 | 157 CG | 129 C10 | 131 CA | 114.61 |
| 157 CG | 129 C10 | 61 CE1 | 128.79 | 157 CG | 129 C10 | 156 C | 41.00 |
| 157 CG | 129 C10 | 131 OG | 129.76 | 157 CG | 129 C10 | 131 N | 104.10 |
| 157 CG | 129 C10 | 130 CA | 83.90 | 156 CD | 129 C10 | 301 OH2 | 112.53 |
| 156 CD | 129 C10 | 156 CA | 40.96 | 156 CD | 129 C10 | 130 N | 124.18 |
| 156 CD | 129 C10 | 157 CD | 107.03 | 156 CD | 129 C10 | 300 OH2 | 83.82 |
| 156 CD | 129 C10 | 156 N | 48.08 | 156 CD | 129 C10 | 157 N | 64.74 |
| 156 CD | 129 C10 | 131 CA | 147.34 | 156 CD | 129 C10 | 61 CE1 | 91.94 |
| 156 CD | 129 C10 | 156 C | 52.49 | 156 CD | 129 C10 | 131 OG | 124.07 |
| 156 CD | 129 C10 | 131 N | 145.89 | 156 CD | 129 C10 | 130 CA | 137.64 |
| 301 OH2 | 129 C10 | 156 CA | 73.22 | 301 OH2 | 129 C10 | 130 N | 30.88 |
| 301 OH2 | 129 C10 | 157 CD | 45.62 | 301 OH2 | 129 C10 | 300 OH2 | 28.95 |
| 301 OH2 | 129 C10 | 156 N | 64.48 | 301 OH2 | 129 C10 | 157 N | 54.04 |
| 301 OH2 | 129 C10 | 131 CA | 76.14 | 301 OH2 | 129 C10 | 61 CE1 | 83.86 |
| 301 OH2 | 129 C10 | 156 C | 66.78 | 301 OH2 | 129 C10 | 131 OG | 83.36 |
| 301 OH2 | 129 C10 | 131 N | 62.32 | 301 OH2 | 129 C10 | 130 CA | 39.23 |

Figure 11 KKK

| Atom 1 | Atom 2 | Atom 3 | Angle | Atom 1 | Atom 2 | Atom 3 | Angle |
|---|---|---|---|---|---|---|---|
| 156 CA | 129 C10 | 130 N | 94.35 | 156 CA | 129 C10 | 157 CD | 71.57 |
| 156 CA | 129 C10 | 300 OH2 | 46.46 | 156 CA | 129 C10 | 156 N | 15.33 |
| 156 CA | 129 C10 | 157 N | 24.73 | 156 CA | 129 C10 | 131 CA | 142.75 |
| 156 CA | 129 C10 | 61 CE1 | 98.98 | 156 CA | 129 C10 | 156 C | 15.22 |
| 156 CA | 129 C10 | 131 OG | 130.58 | 156 CA | 129 C10 | 131 N | 129.08 |
| 156 CA | 129 C10 | 130 CA | 107.81 | 130 N | 129 C10 | 157 CD | 73.28 |
| 130 N | 129 C10 | 300 OH2 | 48.70 | 130 N | 129 C10 | 156 N | 81.10 |
| 130 N | 129 C10 | 157 N | 81.45 | 130 N | 129 C10 | 131 CA | 49.60 |
| 130 N | 129 C10 | 61 CE1 | 57.71 | 130 N | 129 C10 | 156 C | 92.99 |
| 130 N | 129 C10 | 131 OG | 52.61 | 130 N | 129 C10 | 131 N | 35.27 |
| 130 N | 129 C10 | 130 CA | 14.01 | 157 CD | 129 C10 | 300 OH2 | 56.55 |
| 157 CD | 129 C10 | 156 N | 75.09 | 157 CD | 129 C10 | 157 N | 47.54 |
| 157 CD | 129 C10 | 131 CA | 100.99 | 157 CD | 129 C10 | 61 CE1 | 129.46 |
| 157 CD | 129 C10 | 156 C | 56.91 | 157 CD | 129 C10 | 131 OG | 119.39 |
| 157 CD | 129 C10 | 131 N | 92.30 | 157 CD | 129 C10 | 130 CA | 74.96 |
| 300 OH2 | 129 C10 | 156 N | 35.77 | 300 OH2 | 129 C10 | 157 N | 34.36 |
| 300 OH2 | 129 C10 | 131 CA | 98.29 | 300 OH2 | 129 C10 | 61 CE1 | 80.57 |
| 300 OH2 | 129 C10 | 156 C | 44.60 | 300 OH2 | 129 C10 | 131 OG | 96.41 |
| 300 OH2 | 129 C10 | 131 N | 83.97 | 300 OH2 | 129 C10 | 130 CA | 61.58 |
| 156 N | 129 C10 | 157 N | 28.54 | 156 N | 129 C10 | 131 CA | 127.93 |
| 156 N | 129 C10 | 61 CE1 | 85.38 | 156 N | 129 C10 | 156 C | 25.75 |
| 156 N | 129 C10 | 131 OG | 115.55 | 156 N | 129 C10 | 131 N | 114.82 |
| 156 N | 129 C10 | 130 CA | 94.97 | 157 N | 129 C10 | 131 CA | 130.05 |
| 157 N | 129 C10 | 61 CE1 | 109.04 | 157 N | 129 C10 | 156 C | 12.98 |
| 157 N | 129 C10 | 131 OG | 130.70 | 157 N | 129 C10 | 131 N | 115.92 |
| 157 N | 129 C10 | 130 CA | 92.69 | 131 CA | 129 C10 | 61 CE1 | 56.75 |
| 131 CA | 129 C10 | 156 C | 142.34 | 131 CA | 129 C10 | 131 OG | 23.31 |
| 131 CA | 129 C10 | 131 N | 14.35 | 131 CA | 129 C10 | 130 CA | 37.42 |
| 61 CE1 | 129 C10 | 156 C | 111.01 | 61 CE1 | 129 C10 | 131 OG | 34.45 |

Figure 11 LLL

| Atom 1 | Atom 2 | Atom 3 | Angle | Atom 1 | Atom 2 | Atom 3 | Angle |
|---|---|---|---|---|---|---|---|
| 61 CE1 | 129 C10 | 131 N | 54.64 | 61 CE1 | 129 C10 | 130 CA | 60.66 |
| 156 C | 129 C10 | 131 OG | 138.61 | 156 C | 129 C10 | 131 N | 128.02 |
| 156 C | 129 C10 | 130 CA | 104.93 | 131 OG | 129 C10 | 131 N | 27.34 |
| 131 OG | 129 C10 | 130 CA | 45.86 | 131 N | 129 C10 | 130 CA | 23.23 |

Figure 12A

| Atom 1 | Atom 2 | Atom 3 | Angle | Atom 1 | Atom 2 | Atom 3 | Angle |
|---|---|---|---|---|---|---|---|
| 128 C   | 129 N | 129 CA  | 120.79 | 128 C   | 129 N | 128 O   | 27.54 |
| 128 C   | 129 N | 129 C   | 144.53 | 128 C   | 129 N | 129 CB  | 120.04 |
| 128 C   | 129 N | 128 CA  | 34.33  | 128 C   | 129 N | 129 O   | 163.28 |
| 128 C   | 129 N | 128 CB  | 51.26  | 128 C   | 129 N | 130 N   | 127.69 |
| 128 C   | 129 N | 128 N   | 20.30  | 128 C   | 129 N | 128 CG2 | 46.96 |
| 128 C   | 129 N | 129 OG  | 120.46 | 128 C   | 129 N | 321 OH2 | 67.29 |
| 128 C   | 129 N | 152 SG  | 72.21  | 128 C   | 129 N | 128 CG1 | 52.53 |
| 128 C   | 129 N | 130 CA  | 133.61 | 128 C   | 129 N | 152 N   | 74.93 |
| 129 CA  | 129 N | 128 O   | 93.25  | 129 CA  | 129 N | 129 C   | 38.96 |
| 129 CA  | 129 N | 129 CB  | 37.48  | 129 CA  | 129 N | 128 CA  | 155.12 |
| 129 CA  | 129 N | 129 O   | 60.71  | 129 CA  | 129 N | 128 CB  | 148.96 |
| 129 CA  | 129 N | 130 N   | 39.47  | 129 CA  | 129 N | 128 N   | 138.58 |
| 129 CA  | 129 N | 128 CG2 | 125.62 | 129 CA  | 129 N | 129 OG  | 25.11 |
| 129 CA  | 129 N | 321 OH2 | 54.02  | 129 CA  | 129 N | 152 SG  | 98.20 |
| 129 CA  | 129 N | 128 CG1 | 158.20 | 129 CA  | 129 N | 130 CA  | 48.82 |
| 129 CA  | 129 N | 152 N   | 127.86 | 128 O   | 129 N | 129 C   | 122.01 |
| 128 O   | 129 N | 129 CB  | 98.73  | 128 O   | 129 N | 128 CA  | 61.87 |
| 128 O   | 129 N | 129 O   | 148.34 | 128 O   | 129 N | 128 CB  | 74.70 |
| 128 O   | 129 N | 130 N   | 107.34 | 128 O   | 129 N | 128 N   | 46.59 |
| 128 O   | 129 N | 128 CG2 | 61.54  | 128 O   | 129 N | 129 OG  | 95.73 |
| 128 O   | 129 N | 321 OH2 | 40.06  | 128 O   | 129 N | 152 SG  | 73.56 |
| 128 O   | 129 N | 128 CG1 | 78.13  | 128 O   | 129 N | 130 CA  | 116.77 |
| 128 O   | 129 N | 152 N   | 91.39  | 129 C   | 129 N | 129 CB  | 64.49 |
| 129 C   | 129 N | 128 CA  | 155.27 | 129 C   | 129 N | 129 O   | 26.53 |
| 129 C   | 129 N | 128 CB  | 125.78 | 129 C   | 129 N | 130 N   | 17.05 |
| 129 C   | 129 N | 128 N   | 162.70 | 129 C   | 129 N | 128 CG2 | 113.45 |
| 129 C   | 129 N | 129 OG  | 55.95  | 129 C   | 129 N | 321 OH2 | 88.92 |
| 129 C   | 129 N | 152 SG  | 128.56 | 129 C   | 129 N | 128 CG1 | 131.44 |
| 129 C   | 129 N | 130 CA  | 15.50  | 129 C   | 129 N | 152 N   | 139.63 |
| 129 CB  | 129 N | 128 CA  | 140.15 | 129 CB  | 129 N | 129 O   | 72.14 |
| 129 CB  | 129 N | 128 CB  | 169.60 | 129 CB  | 129 N | 130 N   | 73.09 |
| 129 CB  | 129 N | 128 N   | 125.29 | 129 CB  | 129 N | 128 CG2 | 156.56 |
| 129 CB  | 129 N | 129 OG  | 12.50  | 129 CB  | 129 N | 321 OH2 | 63.01 |
| 129 CB  | 129 N | 152 SG  | 64.73  | 129 CB  | 129 N | 128 CG1 | 162.91 |
| 129 CB  | 129 N | 130 CA  | 79.04  | 129 CB  | 129 N | 152 N   | 90.53 |
| 128 CA  | 129 N | 129 O   | 142.14 | 128 CA  | 129 N | 128 CB  | 29.52 |
| 128 CA  | 129 N | 130 N   | 143.57 | 128 CA  | 129 N | 128 N   | 17.97 |
| 128 CA  | 129 N | 128 CG2 | 44.08  | 128 CA  | 129 N | 129 OG  | 147.55 |
| 128 CA  | 129 N | 321 OH2 | 101.36 | 128 CA  | 129 N | 152 SG  | 76.07 |
| 128 CA  | 129 N | 128 CG1 | 24.72  | 128 CA  | 129 N | 130 CA  | 140.21 |
| 128 CA  | 129 N | 152 N   | 58.11  | 129 O   | 129 N | 128 CB  | 117.66 |
| 129 O   | 129 N | 130 N   | 41.16  | 129 O   | 129 N | 128 N   | 160.10 |
| 129 O   | 129 N | 128 CG2 | 117.27 | 129 O   | 129 N | 129 OG  | 68.68 |

Figure 12B

| Atom 1 | Atom 2 | Atom 3 | Angle | Atom 1 | Atom 2 | Atom 3 | Angle |
|---|---|---|---|---|---|---|---|
| 129 O | 129 N | 321 OH2 | 114.01 | 129 O | 129 N | 152 SG | 124.51 |
| 129 O | 129 N | 128 CG1 | 118.99 | 129 O | 129 N | 130 CA | 32.68 |
| 129 O | 129 N | 152 N | 118.35 | 128 CB | 129 N | 130 N | 116.32 |
| 128 CB | 129 N | 128 N | 44.43 | 128 CB | 129 N | 128 CG2 | 23.99 |
| 128 CB | 129 N | 129 OG | 169.67 | 128 CB | 129 N | 321 OH2 | 112.84 |
| 128 CB | 129 N | 152 SG | 105.29 | 128 CB | 129 N | 128 CG1 | 9.24 |
| 128 CB | 129 N | 130 CA | 111.03 | 128 CB | 129 N | 152 N | 81.70 |
| 130 N | 129 N | 128 N | 145.82 | 130 N | 129 N | 128 CG2 | 99.56 |
| 130 N | 129 N | 129 OG | 62.24 | 130 N | 129 N | 321 OH2 | 79.71 |
| 130 N | 129 N | 152 SG | 137.22 | 130 N | 129 N | 128 CG1 | 123.96 |
| 130 N | 129 N | 130 CA | 11.53 | 130 N | 129 N | 152 N | 156.54 |
| 128 N | 129 N | 128 CG2 | 51.30 | 128 N | 129 N | 129 OG | 130.50 |
| 128 N | 129 N | 321 OH2 | 84.63 | 128 N | 129 N | 152 SG | 65.04 |
| 128 N | 129 N | 128 CG1 | 41.72 | 128 N | 129 N | 130 CA | 148.38 |
| 128 N | 129 N | 152 N | 57.61 | 128 CG2 | 129 N | 129 OG | 146.71 |
| 128 CG2 | 129 N | 321 OH2 | 94.01 | 128 CG2 | 129 N | 152 SG | 116.23 |
| 128 CG2 | 129 N | 128 CG1 | 32.95 | 128 CG2 | 129 N | 130 CA | 98.00 |
| 128 CG2 | 129 N | 152 N | 101.82 | 129 OG | 129 N | 321 OH2 | 57.00 |
| 129 OG | 129 N | 152 SG | 75.03 | 129 OG | 129 N | 128 CG1 | 172.22 |
| 129 OG | 129 N | 130 CA | 69.44 | 129 OG | 129 N | 152 N | 102.77 |
| 321 OH2 | 129 N | 152 SG | 75.36 | 321 OH2 | 129 N | 128 CG1 | 117.66 |
| 321 OH2 | 129 N | 130 CA | 91.20 | 321 OH2 | 129 N | 152 N | 108.16 |
| 152 SG | 129 N | 128 CG1 | 98.46 | 152 SG | 129 N | 130 CA | 143.66 |
| 152 SG | 129 N | 152 N | 34.95 | 128 CG1 | 129 N | 130 CA | 117.52 |
| 128 CG1 | 129 N | 152 N | 72.87 | 130 CA | 129 N | 152 N | 151.01 |
| 129 N | 129 CA | 129 CB | 107.57 | 129 N | 129 CA | 129 C | 104.87 |
| 129 N | 129 CA | 129 O | 87.62 | 129 N | 129 CA | 128 C | 28.26 |
| 129 N | 129 CA | 129 OG | 140.32 | 129 N | 129 CA | 130 N | 118.72 |
| 129 N | 129 CA | 128 O | 55.09 | 129 N | 129 CA | 321 OH2 | 104.92 |
| 129 N | 129 CA | 128 CA | 15.61 | 129 N | 129 CA | 130 CA | 114.75 |
| 129 N | 129 CA | 128 CB | 21.28 | 129 N | 129 CA | 130 C | 129.70 |
| 129 N | 129 CA | 128 CG2 | 39.58 | 129 N | 129 CA | 128 N | 29.78 |
| 129 N | 129 CA | 152 SG | 64.48 | 129 N | 129 CA | 130 O | 143.45 |
| 129 N | 129 CA | 61 NE2 | 113.16 | 129 N | 129 CA | 130 CB | 111.76 |
| 129 N | 129 CA | 61 CE1 | 116.08 | 129 N | 129 CA | 131 N | 123.98 |
| 129 CB | 129 CA | 129 C | 111.81 | 129 CB | 129 CA | 129 O | 99.15 |
| 129 CB | 129 CA | 128 C | 110.33 | 129 CB | 129 CA | 129 OG | 32.88 |
| 129 CB | 129 CA | 130 N | 123.38 | 129 CB | 129 CA | 128 O | 108.07 |
| 129 CB | 129 CA | 321 OH2 | 86.88 | 129 CB | 129 CA | 128 CA | 109.80 |
| 129 CB | 129 CA | 130 CA | 120.13 | 129 CB | 129 CA | 128 CB | 128.03 |
| 129 CB | 129 CA | 130 C | 102.69 | 129 CB | 129 CA | 128 CG2 | 142.36 |
| 129 CB | 129 CA | 128 N | 103.98 | 129 CB | 129 CA | 152 SG | 50.11 |
| 129 CB | 129 CA | 130 O | 97.48 | 129 CB | 129 CA | 61 NE2 | 26.48 |
| 129 CB | 129 CA | 130 CB | 132.53 | 129 CB | 129 CA | 61 CE1 | 41.74 |

Figure 12C

| Atom 1 | Atom 2 | Atom 3 | Angle | Atom 1 | Atom 2 | Atom 3 | Angle |
|---|---|---|---|---|---|---|---|
| 129 CB | 129 CA | 131 N | 95.92 | 129 C | 129 CA | 129 O | 26.49 |
| 129 C | 129 CA | 128 C | 125.36 | 129 C | 129 CA | 129 OG | 97.82 |
| 129 C | 129 CA | 130 N | 28.62 | 129 C | 129 CA | 128 O | 139.49 |
| 129 C | 129 CA | 321 OH2 | 137.54 | 129 C | 129 CA | 128 CA | 116.52 |
| 129 C | 129 CA | 130 CA | 19.07 | 129 C | 129 CA | 128 CB | 98.68 |
| 129 C | 129 CA | 130 C | 25.23 | 129 C | 129 CA | 128 CG2 | 97.56 |
| 129 C | 129 CA | 128 N | 130.67 | 129 C | 129 CA | 152 SG | 145.98 |
| 129 C | 129 CA | 130 O | 39.70 | 129 C | 129 CA | 61 NE2 | 85.55 |
| 129 C | 129 CA | 130 CB | 32.65 | 129 C | 129 CA | 61 CE1 | 70.21 |
| 129 C | 129 CA | 131 N | 20.79 | 129 O | 129 CA | 128 C | 114.21 |
| 129 O | 129 CA | 129 OG | 99.73 | 129 O | 129 CA | 130 N | 55.04 |
| 129 O | 129 CA | 128 O | 138.69 | 129 O | 129 CA | 321 OH2 | 163.86 |
| 129 O | 129 CA | 128 CA | 102.32 | 129 O | 129 CA | 130 CA | 45.51 |
| 129 O | 129 CA | 128 CB | 89.86 | 129 O | 129 CA | 130 C | 48.08 |
| 129 O | 129 CA | 128 CG2 | 97.10 | 129 O | 129 CA | 128 N | 117.21 |
| 129 O | 129 CA | 152 SG | 120.07 | 129 O | 129 CA | 130 O | 61.95 |
| 129 O | 129 CA | 61 NE2 | 73.75 | 129 O | 129 CA | 130 CB | 58.00 |
| 129 O | 129 CA | 61 CE1 | 59.90 | 129 O | 129 CA | 131 N | 37.87 |
| 128 C | 129 CA | 129 OG | 135.56 | 128 C | 129 CA | 130 N | 126.00 |
| 128 C | 129 CA | 128 O | 26.83 | 128 C | 129 CA | 321 OH2 | 76.99 |
| 128 C | 129 CA | 128 CA | 12.65 | 128 C | 129 CA | 130 CA | 127.11 |
| 128 C | 129 CA | 128 CB | 26.70 | 128 C | 129 CA | 130 C | 145.28 |
| 128 C | 129 CA | 128 CG2 | 32.34 | 128 C | 129 CA | 128 N | 6.42 |
| 128 C | 129 CA | 152 SG | 60.24 | 128 C | 129 CA | 130 O | 152.05 |
| 128 C | 129 CA | 61 NE2 | 127.94 | 128 C | 129 CA | 130 CB | 116.95 |
| 128 C | 129 CA | 61 CE1 | 137.23 | 128 C | 129 CA | 131 N | 146.15 |
| 129 OG | 129 CA | 130 N | 96.55 | 129 OG | 129 CA | 128 O | 120.02 |
| 129 OG | 129 CA | 321 OH2 | 77.24 | 129 OG | 129 CA | 128 CA | 139.71 |
| 129 OG | 129 CA | 130 CA | 97.04 | 129 OG | 129 CA | 128 CB | 159.61 |
| 129 OG | 129 CA | 130 C | 79.01 | 129 OG | 129 CA | 128 CG2 | 163.15 |
| 129 OG | 129 CA | 128 N | 129.39 | 129 OG | 129 CA | 152 SG | 78.47 |
| 129 OG | 129 CA | 130 O | 69.43 | 129 OG | 129 CA | 61 NE2 | 36.42 |
| 129 OG | 129 CA | 130 CB | 104.96 | 129 OG | 129 CA | 61 CE1 | 43.65 |
| 129 OG | 129 CA | 131 N | 77.43 | 130 N | 129 CA | 128 O | 124.27 |
| 130 N | 129 CA | 321 OH2 | 109.20 | 130 N | 129 CA | 128 CA | 123.71 |
| 130 N | 129 CA | 130 CA | 9.56 | 130 N | 129 CA | 128 CB | 103.67 |
| 130 N | 129 CA | 130 C | 21.19 | 130 N | 129 CA | 128 CG2 | 93.66 |
| 130 N | 129 CA | 128 N | 132.41 | 130 N | 129 CA | 152 SG | 172.64 |
| 130 N | 129 CA | 130 O | 27.13 | 130 N | 129 CA | 61 NE2 | 101.36 |
| 130 N | 129 CA | 130 CB | 9.16 | 130 N | 129 CA | 61 CE1 | 87.30 |
| 130 N | 129 CA | 131 N | 31.16 | 128 O | 129 CA | 321 OH2 | 50.51 |
| 128 O | 129 CA | 128 CA | 39.48 | 128 O | 129 CA | 130 CA | 130.46 |
| 128 O | 129 CA | 128 CB | 48.88 | 128 O | 129 CA | 130 C | 144.77 |
| 128 O | 129 CA | 128 CG2 | 43.40 | 128 O | 129 CA | 128 N | 26.59 |

Figure 12D

| Atom 1 | Atom 2 | Atom 3 | Angle | Atom 1 | Atom 2 | Atom 3 | Angle |
|---|---|---|---|---|---|---|---|
| 128 O | 129 CA | 152 SG | 63.10 | 128 O | 129 CA | 130 O | 139.99 |
| 128 O | 129 CA | 61 NE2 | 133.39 | 128 O | 129 CA | 130 CB | 115.79 |
| 128 O | 129 CA | 61 CE1 | 148.23 | 128 O | 129 CA | 131 N | 155.14 |
| 321 OH2 | 129 CA | 128 CA | 89.51 | 321 OH2 | 129 CA | 130 CA | 118.66 |
| 321 OH2 | 129 CA | 128 CB | 98.23 | 321 OH2 | 129 CA | 130 C | 116.07 |
| 321 OH2 | 129 CA | 128 CG2 | 86.77 | 321 OH2 | 129 CA | 128 N | 75.21 |
| 321 OH2 | 129 CA | 152 SG | 75.21 | 321 OH2 | 129 CA | 130 O | 102.56 |
| 321 OH2 | 129 CA | 61 NE2 | 109.32 | 321 OH2 | 129 CA | 130 CB | 107.08 |
| 321 OH2 | 129 CA | 61 CE1 | 120.52 | 321 OH2 | 129 CA | 131 N | 126.96 |
| 128 CA | 129 CA | 130 CA | 122.36 | 128 CA | 129 CA | 128 CB | 20.07 |
| 128 CA | 129 CA | 130 C | 139.61 | 128 CA | 129 CA | 128 CG2 | 33.12 |
| 128 CA | 129 CA | 128 N | 14.98 | 128 CA | 129 CA | 152 SG | 61.32 |
| 128 CA | 129 CA | 130 O | 150.79 | 128 CA | 129 CA | 61 NE2 | 122.18 |
| 128 CA | 129 CA | 130 CB | 115.31 | 128 CA | 129 CA | 61 CE1 | 128.42 |
| 128 CA | 129 CA | 131 N | 136.87 | 130 CA | 129 CA | 128 CB | 102.46 |
| 130 CA | 129 CA | 130 C | 18.18 | 130 CA | 129 CA | 128 CG2 | 95.25 |
| 130 CA | 129 CA | 128 N | 133.43 | 130 CA | 129 CA | 152 SG | 164.43 |
| 130 CA | 129 CA | 130 O | 29.00 | 130 CA | 129 CA | 61 NE2 | 96.05 |
| 130 CA | 129 CA | 130 CB | 15.28 | 130 CA | 129 CA | 61 CE1 | 81.29 |
| 130 CA | 129 CA | 131 N | 24.72 | 128 CB | 129 CA | 130 C | 120.10 |
| 128 CB | 129 CA | 128 CG2 | 18.76 | 128 CB | 129 CA | 128 N | 32.16 |
| 128 CB | 129 CA | 152 SG | 81.15 | 128 CB | 129 CA | 130 O | 130.72 |
| 128 CB | 129 CA | 61 NE2 | 133.74 | 128 CB | 129 CA | 130 CB | 95.39 |
| 128 CB | 129 CA | 61 CE1 | 133.86 | 128 CB | 129 CA | 131 N | 119.46 |
| 130 C | 129 CA | 128 CG2 | 113.38 | 130 C | 129 CA | 128 N | 151.57 |
| 130 C | 129 CA | 152 SG | 151.58 | 130 C | 129 CA | 130 O | 14.51 |
| 130 C | 129 CA | 61 NE2 | 80.19 | 130 C | 129 CA | 130 CB | 30.24 |
| 130 C | 129 CA | 61 CE1 | 66.35 | 130 C | 129 CA | 131 N | 12.63 |
| 128 CG2 | 129 CA | 128 N | 38.75 | 128 CG2 | 129 CA | 152 SG | 92.47 |
| 128 CG2 | 129 CA | 130 O | 120.11 | 128 CG2 | 129 CA | 61 NE2 | 152.50 |
| 128 CG2 | 129 CA | 130 CB | 84.63 | 128 CG2 | 129 CA | 61 CE1 | 150.72 |
| 128 CG2 | 129 CA | 131 N | 117.22 | 128 N | 129 CA | 152 SG | 53.87 |
| 128 N | 129 CA | 130 O | 158.21 | 128 N | 129 CA | 61 NE2 | 122.39 |
| 128 N | 129 CA | 130 CB | 123.35 | 128 N | 129 CA | 61 CE1 | 132.74 |
| 128 N | 129 CA | 131 N | 151.36 | 152 SG | 129 CA | 130 O | 147.35 |
| 152 SG | 129 CA | 61 NE2 | 71.40 | 152 SG | 129 CA | 130 CB | 176.16 |
| 152 SG | 129 CA | 61 CE1 | 85.36 | 152 SG | 129 CA | 131 N | 141.50 |
| 130 O | 129 CA | 61 NE2 | 79.09 | 130 O | 129 CA | 130 CB | 35.78 |
| 130 O | 129 CA | 61 CE1 | 67.48 | 130 O | 129 CA | 131 N | 24.46 |
| 61 NE2 | 129 CA | 130 CB | 110.27 | 61 NE2 | 129 CA | 61 CE1 | 15.34 |
| 61 NE2 | 129 CA | 131 N | 71.34 | 130 CB | 129 CA | 61 CE1 | 95.93 |
| 130 CB | 129 CA | 131 N | 39.40 | 61 CE1 | 129 CA | 131 N | 56.62 |
| 129 OG | 129 CB | 129 CA | 111.19 | 129 OG | 129 CB | 129 N | 146.00 |
| 129 OG | 129 CB | 129 C | 96.69 | 129 OG | 129 CB | 129 O | 105.98 |

Figure 12E

| Atom 1 | Atom 2 | Atom 3 | Angle | Atom 1 | Atom 2 | Atom 3 | Angle |
|---|---|---|---|---|---|---|---|
| 129 OG | 129 CB | 128 C | 142.68 | 129 OG | 129 CB | 321 OH2 | 82.02 |
| 129 OG | 129 CB | 128 O | 124.31 | 129 OG | 129 CB | 130 N | 83.03 |
| 129 OG | 129 CB | 61 NE2 | 65.74 | 129 OG | 129 CB | 152 SG | 124.02 |
| 129 OG | 129 CB | 61 CE1 | 65.92 | 129 OG | 129 CB | 128 CA | 155.37 |
| 129 OG | 129 CB | 61 CD2 | 73.86 | 129 OG | 129 CB | 130 CA | 81.35 |
| 129 OG | 129 CB | 130 C | 66.70 | 129 OG | 129 CB | 152 CB | 123.31 |
| 129 OG | 129 CB | 130 O | 54.67 | 129 OG | 129 CB | 61 ND1 | 72.12 |
| 129 OG | 129 CB | 128 N | 147.39 | 129 OG | 129 CB | 156 N | 67.44 |
| 129 OG | 129 CB | 128 CB | 149.20 | 129 CA | 129 CB | 129 N | 34.95 |
| 129 CA | 129 CB | 129 C | 34.15 | 129 CA | 129 CB | 129 O | 51.04 |
| 129 CA | 129 CB | 128 C | 43.64 | 129 CA | 129 CB | 321 OH2 | 67.33 |
| 129 CA | 129 CB | 128 O | 47.59 | 129 CA | 129 CB | 130 N | 35.50 |
| 129 CA | 129 CB | 61 NE2 | 142.46 | 129 CA | 129 CB | 152 SG | 112.75 |
| 129 CA | 129 CB | 61 CE1 | 123.54 | 129 CA | 129 CB | 128 CA | 51.62 |
| 129 CA | 129 CB | 61 CD2 | 147.70 | 129 CA | 129 CB | 130 CA | 43.82 |
| 129 CA | 129 CB | 130 C | 60.38 | 129 CA | 129 CB | 152 CB | 122.06 |
| 129 CA | 129 CB | 130 O | 65.67 | 129 CA | 129 CB | 61 ND1 | 124.07 |
| 129 CA | 129 CB | 128 N | 59.77 | 129 CA | 129 CB | 156 N | 97.93 |
| 129 CA | 129 CB | 128 CB | 39.21 | 129 N | 129 CB | 129 C | 57.02 |
| 129 N | 129 CB | 129 O | 59.18 | 129 N | 129 CB | 128 C | 20.56 |
| 129 N | 129 CB | 321 OH2 | 79.51 | 129 N | 129 CB | 128 O | 39.09 |
| 129 N | 129 CB | 130 N | 66.61 | 129 N | 129 CB | 61 NE2 | 138.67 |
| 129 N | 129 CB | 152 SG | 82.30 | 129 N | 129 CB | 61 CE1 | 127.89 |
| 129 N | 129 CB | 128 CA | 19.97 | 129 N | 129 CB | 61 CD2 | 134.29 |
| 129 N | 129 CB | 130 CA | 71.51 | 129 N | 129 CB | 130 C | 88.42 |
| 129 N | 129 CB | 152 CB | 88.20 | 129 N | 129 CB | 130 O | 97.34 |
| 129 N | 129 CB | 61 ND1 | 123.89 | 129 N | 129 CB | 128 N | 33.07 |
| 129 N | 129 CB | 156 N | 106.20 | 129 N | 129 CB | 128 CB | 5.85 |
| 129 C | 129 CB | 129 O | 23.30 | 129 C | 129 CB | 128 C | 73.51 |
| 129 C | 129 CB | 321 OH2 | 94.70 | 129 C | 129 CB | 128 O | 81.55 |
| 129 C | 129 CB | 130 N | 16.89 | 129 C | 129 CB | 61 NE2 | 108.50 |
| 129 C | 129 CB | 152 SG | 138.53 | 129 C | 129 CB | 61 CE1 | 89.48 |
| 129 C | 129 CB | 128 CA | 76.97 | 129 C | 129 CB | 61 CD2 | 115.12 |
| 129 C | 129 CB | 130 CA | 15.35 | 129 C | 129 CB | 130 C | 31.52 |
| 129 C | 129 CB | 152 CB | 138.56 | 129 C | 129 CB | 130 O | 42.13 |
| 129 C | 129 CB | 61 ND1 | 90.57 | 129 C | 129 CB | 128 N | 89.00 |
| 129 C | 129 CB | 156 N | 122.00 | 129 C | 129 CB | 128 CB | 62.81 |
| 129 O | 129 CB | 128 C | 79.32 | 129 O | 129 CB | 321 OH2 | 116.77 |
| 129 O | 129 CB | 128 O | 93.75 | 129 O | 129 CB | 130 N | 38.94 |
| 129 O | 129 CB | 61 NE2 | 92.53 | 129 O | 129 CB | 152 SG | 128.38 |
| 129 O | 129 CB | 61 CE1 | 74.69 | 129 O | 129 CB | 128 CA | 77.58 |
| 129 O | 129 CB | 61 CD2 | 96.66 | 129 O | 129 CB | 130 CA | 32.31 |
| 129 O | 129 CB | 130 C | 40.96 | 129 O | 129 CB | 152 CB | 121.40 |
| 129 O | 129 CB | 130 O | 54.24 | 129 O | 129 CB | 61 ND1 | 73.82 |

Figure 12F

| Atom 1 | Atom 2 | Atom 3 | Angle | Atom 1 | Atom 2 | Atom 3 | Angle |
|---|---|---|---|---|---|---|---|
| 129 O   | 129 CB | 128 N   | 91.78  | 129 O   | 129 CB | 156 N   | 145.25 |
| 129 O   | 129 CB | 128 CB  | 64.74  | 128 C   | 129 CB | 321 OH2 | 63.58  |
| 128 C   | 129 CB | 128 O   | 20.52  | 128 C   | 129 CB | 130 N   | 79.02  |
| 128 C   | 129 CB | 61 NE2  | 151.57 | 128 C   | 129 CB | 152 SG  | 69.13  |
| 128 C   | 129 CB | 61 CE1  | 146.86 | 128 C   | 129 CB | 128 CA  | 12.72  |
| 128 C   | 129 CB | 61 CD2  | 143.18 | 128 C   | 129 CB | 130 CA  | 86.34  |
| 128 C   | 129 CB | 130 C   | 103.38 | 128 C   | 129 CB | 152 CB  | 79.39  |
| 128 C   | 129 CB | 130 O   | 109.26 | 128 C   | 129 CB | 61 ND1  | 141.82 |
| 128 C   | 129 CB | 128 N   | 16.15  | 128 C   | 129 CB | 156 N   | 87.06  |
| 128 C   | 129 CB | 128 CB  | 15.85  | 321 OH2 | 129 CB | 128 O   | 43.24  |
| 321 OH2 | 129 CB | 130 N   | 83.01  | 321 OH2 | 129 CB | 61 NE2  | 141.72 |
| 321 OH2 | 129 CB | 152 SG  | 84.51  | 321 OH2 | 129 CB | 61 CE1  | 147.94 |
| 321 OH2 | 129 CB | 128 CA  | 74.92  | 321 OH2 | 129 CB | 61 CD2  | 143.18 |
| 321 OH2 | 129 CB | 130 CA  | 93.24  | 321 OH2 | 129 CB | 130 C   | 99.30  |
| 321 OH2 | 129 CB | 152 CB  | 100.66 | 321 OH2 | 129 CB | 130 O   | 91.14  |
| 321 OH2 | 129 CB | 61 ND1  | 154.04 | 321 OH2 | 129 CB | 128 N   | 65.48  |
| 321 OH2 | 129 CB | 156 N   | 30.68  | 321 OH2 | 129 CB | 128 CB  | 77.45  |
| 128 O   | 129 CB | 130 N   | 81.21  | 128 O   | 129 CB | 61 NE2  | 165.75 |
| 128 O   | 129 CB | 152 SG  | 69.68  | 128 O   | 129 CB | 61 CE1  | 166.98 |
| 128 O   | 129 CB | 128 CA  | 31.77  | 128 O   | 129 CB | 61 CD2  | 155.34 |
| 128 O   | 129 CB | 130 CA  | 90.78  | 128 O   | 129 CB | 130 C   | 106.20 |
| 128 O   | 129 CB | 152 CB  | 83.87  | 128 O   | 129 CB | 130 O   | 107.32 |
| 128 O   | 129 CB | 61 ND1  | 162.34 | 128 O   | 129 CB | 128 N   | 25.03  |
| 128 O   | 129 CB | 156 N   | 67.18  | 128 O   | 129 CB | 128 CB  | 35.57  |
| 130 N   | 129 CB | 61 NE2  | 111.40 | 130 N   | 129 CB | 152 SG  | 148.09 |
| 130 N   | 129 CB | 61 CE1  | 92.94  | 130 N   | 129 CB | 128 CA  | 85.64  |
| 130 N   | 129 CB | 61 CD2  | 120.18 | 130 N   | 129 CB | 130 CA  | 10.69  |
| 130 N   | 129 CB | 130 C   | 25.14  | 130 N   | 129 CB | 152 CB  | 153.62 |
| 130 N   | 129 CB | 130 O   | 30.86  | 130 N   | 129 CB | 61 ND1  | 95.78  |
| 130 N   | 129 CB | 128 N   | 95.17  | 130 N   | 129 CB | 156 N   | 107.25 |
| 130 N   | 129 CB | 128 CB  | 71.96  | 61 NE2  | 129 CB | 152 SG  | 96.45  |
| 61 NE2  | 129 CB | 61 CE1  | 19.04  | 61 NE2  | 129 CB | 128 CA  | 138.89 |
| 61 NE2  | 129 CB | 61 CD2  | 10.42  | 61 NE2  | 129 CB | 130 CA  | 101.30 |
| 61 NE2  | 129 CB | 130 C   | 86.85  | 61 NE2  | 129 CB | 152 CB  | 81.94  |
| 61 NE2  | 129 CB | 130 O   | 86.71  | 61 NE2  | 129 CB | 61 ND1  | 18.71  |
| 61 NE2  | 129 CB | 128 N   | 141.98 | 61 NE2  | 129 CB | 156 N   | 113.07 |
| 61 NE2  | 129 CB | 128 CB  | 140.16 | 152 SG  | 129 CB | 61 CE1  | 112.63 |
| 152 SG  | 129 CB | 128 CA  | 62.74  | 152 SG  | 129 CB | 61 CD2  | 86.40  |
| 152 SG  | 129 CB | 130 CA  | 153.66 | 152 SG  | 129 CB | 130 C   | 169.18 |
| 152 SG  | 129 CB | 152 CB  | 16.42  | 152 SG  | 129 CB | 130 O   | 175.63 |
| 152 SG  | 129 CB | 61 ND1  | 107.92 | 152 SG  | 129 CB | 128 N   | 52.98  |
| 152 SG  | 129 CB | 156 N   | 73.73  | 152 SG  | 129 CB | 128 CB  | 76.71  |
| 61 CE1  | 129 CB | 128 CA  | 136.69 | 61 CE1  | 129 CB | 61 CD2  | 27.27  |
| 61 CE1  | 129 CB | 130 CA  | 82.61  | 61 CE1  | 129 CB | 130 C   | 69.07  |

Figure 12G

| Atom 1 | Atom 2 | Atom 3 | Angle | Atom 1 | Atom 2 | Atom 3 | Angle |
|---|---|---|---|---|---|---|---|
| 61 CE1 | 129 CB | 152 CB | 96.91 | 61 CE1 | 129 CB | 130 O | 71.04 |
| 61 CE1 | 129 CB | 61 ND1 | 6.48 | 61 CE1 | 129 CB | 128 N | 146.49 |
| 61 CE1 | 129 CB | 156 N | 125.82 | 61 CE1 | 129 CB | 128 CB | 131.48 |
| 128 CA | 129 CB | 61 CD2 | 130.52 | 128 CA | 129 CB | 130 CA | 91.29 |
| 128 CA | 129 CB | 130 C | 108.29 | 128 CA | 129 CB | 152 CB | 70.44 |
| 128 CA | 129 CB | 130 O | 116.51 | 128 CA | 129 CB | 61 ND1 | 130.96 |
| 128 CA | 129 CB | 128 N | 14.42 | 128 CA | 129 CB | 156 N | 95.45 |
| 128 CA | 129 CB | 128 CB | 14.16 | 61 CD2 | 129 CB | 130 CA | 109.75 |
| 61 CD2 | 129 CB | 130 C | 96.23 | 61 CD2 | 129 CB | 152 CB | 71.62 |
| 61 CD2 | 129 CB | 130 O | 96.89 | 61 CD2 | 129 CB | 61 ND1 | 24.75 |
| 61 CD2 | 129 CB | 128 N | 131.97 | 61 CD2 | 129 CB | 156 N | 112.75 |
| 61 CD2 | 129 CB | 128 CB | 134.43 | 130 CA | 129 CB | 130 C | 17.11 |
| 130 CA | 129 CB | 152 CB | 152.93 | 130 CA | 129 CB | 130 O | 26.79 |
| 130 CA | 129 CB | 61 ND1 | 85.22 | 130 CA | 129 CB | 128 N | 102.32 |
| 130 CA | 129 CB | 156 N | 115.76 | 130 CA | 129 CB | 128 CB | 77.19 |
| 130 C | 129 CB | 152 CB | 158.79 | 130 C | 129 CB | 130 O | 13.35 |
| 130 C | 129 CB | 61 ND1 | 72.80 | 130 C | 129 CB | 128 N | 119.41 |
| 130 C | 129 CB | 156 N | 114.47 | 130 C | 129 CB | 128 CB | 94.15 |
| 152 CB | 129 CB | 130 O | 167.73 | 152 CB | 129 CB | 61 ND1 | 91.89 |
| 152 CB | 129 CB | 128 N | 63.82 | 152 CB | 129 CB | 156 N | 86.55 |
| 152 CB | 129 CB | 128 CB | 83.27 | 130 O | 129 CB | 61 ND1 | 75.93 |
| 130 O | 129 CB | 128 N | 125.32 | 130 O | 129 CB | 156 N | 102.27 |
| 130 O | 129 CB | 128 CB | 102.78 | 61 ND1 | 129 CB | 128 N | 140.14 |
| 61 ND1 | 129 CB | 156 N | 129.82 | 61 ND1 | 129 CB | 128 CB | 126.97 |
| 128 N | 129 CB | 156 N | 82.30 | 128 N | 129 CB | 128 CB | 27.29 |
| 156 N | 129 CB | 128 CB | 102.67 | 129 CB | 129 OG | 129 CA | 35.93 |
| 129 CB | 129 OG | 129 C | 55.83 | 129 CB | 129 OG | 61 NE2 | 90.82 |
| 129 CB | 129 OG | 321 OH2 | 75.06 | 129 CB | 129 OG | 130 N | 74.36 |
| 129 CB | 129 OG | 129 N | 21.50 | 129 CB | 129 OG | 61 CE1 | 93.44 |
| 129 CB | 129 OG | 129 O | 52.38 | 129 CB | 129 OG | 128 C | 26.27 |
| 129 CB | 129 OG | 128 O | 40.57 | 129 CB | 129 OG | 61 CD2 | 88.78 |
| 129 CB | 129 OG | 130 O | 110.68 | 129 CB | 129 OG | 130 C | 97.40 |
| 129 CB | 129 OG | 130 CA | 81.64 | 129 CB | 129 OG | 152 SG | 42.18 |
| 129 CB | 129 OG | 156 N | 97.41 | 129 CB | 129 OG | 61 ND1 | 92.27 |
| 129 CB | 129 OG | 131 OG | 108.36 | 129 CB | 129 OG | 131 N | 96.58 |
| 129 CB | 129 OG | 61 CG | 89.83 | 129 CB | 129 OG | 156 CB | 124.06 |
| 129 CA | 129 OG | 129 C | 29.94 | 129 CA | 129 OG | 61 NE2 | 117.15 |
| 129 CA | 129 OG | 321 OH2 | 61.56 | 129 CA | 129 OG | 130 N | 42.09 |
| 129 CA | 129 OG | 129 N | 14.57 | 129 CA | 129 OG | 61 CE1 | 109.11 |
| 129 CA | 129 OG | 129 O | 39.75 | 129 CA | 129 OG | 128 C | 22.10 |
| 129 CA | 129 OG | 128 O | 31.97 | 129 CA | 129 OG | 61 CD2 | 118.07 |
| 129 CA | 129 OG | 130 O | 80.66 | 129 CA | 129 OG | 130 C | 70.81 |
| 129 CA | 129 OG | 130 CA | 52.67 | 129 CA | 129 OG | 152 SG | 72.56 |
| 129 CA | 129 OG | 156 N | 95.97 | 129 CA | 129 OG | 61 ND1 | 109.21 |

Figure 12H

| Atom 1 | Atom 2 | Atom 3 | Angle | Atom 1 | Atom 2 | Atom 3 | Angle |
|---|---|---|---|---|---|---|---|
| 129 CA | 129 OG | 131 OG | 102.95 | 129 CA | 129 OG | 131 N | 76.22 |
| 129 CA | 129 OG | 61 CG | 114.16 | 129 CA | 129 OG | 156 CB | 117.71 |
| 129 C | 129 OG | 61 NE2 | 104.72 | 129 C | 129 OG | 321 OH2 | 84.76 |
| 129 C | 129 OG | 130 N | 20.59 | 129 C | 129 OG | 129 N | 39.91 |
| 129 C | 129 OG | 61 CE1 | 88.98 | 129 C | 129 OG | 129 O | 17.97 |
| 129 C | 129 OG | 128 C | 51.69 | 129 C | 129 OG | 128 O | 61.32 |
| 129 C | 129 OG | 61 CD2 | 109.15 | 129 C | 129 OG | 130 O | 54.94 |
| 129 C | 129 OG | 130 C | 42.62 | 129 C | 129 OG | 130 CA | 25.81 |
| 129 C | 129 OG | 152 SG | 97.67 | 129 C | 129 OG | 156 N | 120.43 |
| 129 C | 129 OG | 61 ND1 | 89.98 | 129 C | 129 OG | 131 OG | 74.01 |
| 129 C | 129 OG | 131 N | 46.38 | 129 C | 129 OG | 61 CG | 100.28 |
| 129 C | 129 OG | 156 CB | 133.74 | 61 NE2 | 129 OG | 321 OH2 | 154.78 |
| 61 NE2 | 129 OG | 130 N | 116.43 | 61 NE2 | 129 OG | 129 N | 107.95 |
| 61 NE2 | 129 OG | 61 CE1 | 21.03 | 61 NE2 | 129 OG | 129 O | 86.93 |
| 61 NE2 | 129 OG | 128 C | 117.08 | 61 NE2 | 129 OG | 128 O | 130.38 |
| 61 NE2 | 129 OG | 61 CD2 | 7.25 | 61 NE2 | 129 OG | 130 O | 102.81 |
| 61 NE2 | 129 OG | 130 C | 97.21 | 61 NE2 | 129 OG | 130 CA | 106.55 |
| 61 NE2 | 129 OG | 152 SG | 84.61 | 61 NE2 | 129 OG | 156 N | 130.20 |
| 61 NE2 | 129 OG | 61 ND1 | 18.93 | 61 NE2 | 129 OG | 131 OG | 54.38 |
| 61 NE2 | 129 OG | 131 N | 83.84 | 61 NE2 | 129 OG | 61 CG | 4.84 |
| 61 NE2 | 129 OG | 156 CB | 121.14 | 321 OH2 | 129 OG | 130 N | 80.29 |
| 321 OH2 | 129 OG | 129 N | 64.54 | 321 OH2 | 129 OG | 61 CE1 | 168.50 |
| 321 OH2 | 129 OG | 129 O | 100.02 | 321 OH2 | 129 OG | 128 C | 51.19 |
| 321 OH2 | 129 OG | 128 O | 35.36 | 321 OH2 | 129 OG | 61 CD2 | 147.83 |
| 321 OH2 | 129 OG | 130 O | 101.72 | 321 OH2 | 129 OG | 130 C | 105.14 |
| 321 OH2 | 129 OG | 130 CA | 92.19 | 321 OH2 | 129 OG | 152 SG | 70.85 |
| 321 OH2 | 129 OG | 156 N | 35.71 | 321 OH2 | 129 OG | 61 ND1 | 167.13 |
| 321 OH2 | 129 OG | 131 OG | 149.82 | 321 OH2 | 129 OG | 131 N | 117.98 |
| 321 OH2 | 129 OG | 61 CG | 157.83 | 321 OH2 | 129 OG | 156 CB | 56.48 |
| 130 N | 129 OG | 129 N | 55.44 | 130 N | 129 OG | 61 CE1 | 97.07 |
| 130 N | 129 OG | 129 O | 35.62 | 130 N | 129 OG | 128 C | 63.58 |
| 130 N | 129 OG | 128 O | 68.05 | 130 N | 129 OG | 61 CD2 | 122.40 |
| 130 N | 129 OG | 130 O | 38.58 | 130 N | 129 OG | 130 C | 30.31 |
| 130 N | 129 OG | 130 CA | 12.71 | 130 N | 129 OG | 152 SG | 114.46 |
| 130 N | 129 OG | 156 N | 113.09 | 130 N | 129 OG | 61 ND1 | 98.69 |
| 130 N | 129 OG | 131 OG | 72.27 | 130 N | 129 OG | 131 N | 39.83 |
| 130 N | 129 OG | 61 CG | 111.60 | 130 N | 129 OG | 156 CB | 117.88 |
| 129 N | 129 OG | 61 CE1 | 104.69 | 129 N | 129 OG | 129 O | 43.83 |
| 129 N | 129 OG | 128 C | 14.79 | 129 N | 129 OG | 128 O | 29.99 |
| 129 N | 129 OG | 61 CD2 | 107.41 | 129 N | 129 OG | 130 O | 93.68 |
| 129 N | 129 OG | 130 C | 82.43 | 129 N | 129 OG | 130 CA | 64.85 |
| 129 N | 129 OG | 152 SG | 59.05 | 129 N | 129 OG | 156 N | 95.31 |
| 129 N | 129 OG | 61 ND1 | 104.21 | 129 N | 129 OG | 131 OG | 107.44 |
| 129 N | 129 OG | 131 N | 85.58 | 129 N | 129 OG | 61 CG | 105.86 |

Figure 12I

| Atom 1 | Atom 2 | Atom 3 | Angle | Atom 1 | Atom 2 | Atom 3 | Angle |
|---|---|---|---|---|---|---|---|
| 129 N | 129 OG | 156 CB | 120.37 | 61 CE1 | 129 OG | 129 O | 72.40 |
| 61 CE1 | 129 OG | 128 C | 117.60 | 61 CE1 | 129 OG | 128 O | 133.34 |
| 61 CE1 | 129 OG | 61 CD2 | 28.22 | 61 CE1 | 129 OG | 130 O | 82.37 |
| 61 CE1 | 129 OG | 130 C | 76.18 | 61 CE1 | 129 OG | 130 CA | 86.28 |
| 61 CE1 | 129 OG | 152 SG | 100.55 | 61 CE1 | 129 OG | 156 N | 149.69 |
| 61 CE1 | 129 OG | 61 ND1 | 2.32 | 61 CE1 | 129 OG | 131 OG | 34.33 |
| 61 CE1 | 129 OG | 131 N | 62.81 | 61 CE1 | 129 OG | 61 CG | 16.53 |
| 61 CE1 | 129 OG | 156 CB | 133.17 | 129 O | 129 OG | 128 C | 58.18 |
| 129 O | 129 OG | 128 O | 71.30 | 129 O | 129 OG | 61 CD2 | 91.19 |
| 129 O | 129 OG | 130 O | 60.86 | 129 O | 129 OG | 130 C | 46.38 |
| 129 O | 129 OG | 130 CA | 34.94 | 129 O | 129 OG | 152 SG | 93.71 |
| 129 O | 129 OG | 156 N | 135.41 | 129 O | 129 OG | 61 ND1 | 73.15 |
| 129 O | 129 OG | 131 OG | 64.02 | 129 O | 129 OG | 131 N | 44.23 |
| 129 O | 129 OG | 61 CG | 82.58 | 129 O | 129 OG | 156 CB | 151.70 |
| 128 C | 129 OG | 128 O | 15.88 | 128 C | 129 OG | 61 CD2 | 114.91 |
| 128 C | 129 OG | 130 O | 102.00 | 128 C | 129 OG | 130 C | 92.86 |
| 128 C | 129 OG | 130 CA | 74.67 | 128 C | 129 OG | 152 SG | 52.26 |
| 128 C | 129 OG | 156 N | 80.57 | 128 C | 129 OG | 61 ND1 | 116.80 |
| 128 C | 129 OG | 131 OG | 122.09 | 128 C | 129 OG | 131 N | 98.07 |
| 128 C | 129 OG | 61 CG | 115.95 | 128 C | 129 OG | 156 CB | 106.01 |
| 128 O | 129 OG | 61 CD2 | 126.88 | 128 O | 129 OG | 130 O | 104.05 |
| 128 O | 129 OG | 130 C | 98.37 | 128 O | 129 OG | 130 CA | 80.42 |
| 128 O | 129 OG | 152 SG | 54.32 | 128 O | 129 OG | 156 N | 65.62 |
| 128 O | 129 OG | 61 ND1 | 132.44 | 128 O | 129 OG | 131 OG | 134.92 |
| 128 O | 129 OG | 131 N | 106.49 | 128 O | 129 OG | 61 CG | 130.05 |
| 128 O | 129 OG | 156 CB | 90.40 | 61 CD2 | 129 OG | 130 O | 110.03 |
| 61 CD2 | 129 OG | 130 C | 104.38 | 61 CD2 | 129 OG | 130 CA | 113.11 |
| 61 CD2 | 129 OG | 152 SG | 78.47 | 61 CD2 | 129 OG | 156 N | 123.65 |
| 61 CD2 | 129 OG | 61 ND1 | 26.07 | 61 CD2 | 129 OG | 131 OG | 61.60 |
| 61 CD2 | 129 OG | 131 N | 90.99 | 61 CD2 | 129 OG | 61 CG | 11.75 |
| 61 CD2 | 129 OG | 156 CB | 117.10 | 130 O | 129 OG | 130 C | 14.76 |
| 130 O | 129 OG | 130 CA | 29.15 | 130 O | 129 OG | 152 SG | 152.55 |
| 130 O | 129 OG | 156 N | 119.30 | 130 O | 129 OG | 61 ND1 | 84.66 |
| 130 O | 129 OG | 131 OG | 48.43 | 130 O | 129 OG | 131 N | 24.07 |
| 130 O | 129 OG | 61 CG | 98.74 | 130 O | 129 OG | 156 CB | 105.34 |
| 130 C | 129 OG | 130 CA | 18.25 | 130 C | 129 OG | 152 SG | 139.56 |
| 130 C | 129 OG | 156 N | 129.77 | 130 C | 129 OG | 61 ND1 | 78.31 |
| 130 C | 129 OG | 131 OG | 44.98 | 130 C | 129 OG | 131 N | 13.41 |
| 130 C | 129 OG | 61 CG | 92.64 | 130 C | 129 OG | 156 CB | 119.41 |
| 130 CA | 129 OG | 152 SG | 123.41 | 130 CA | 129 OG | 156 N | 123.22 |
| 130 CA | 129 OG | 61 ND1 | 88.09 | 130 CA | 129 OG | 131 OG | 59.70 |
| 130 CA | 129 OG | 131 N | 27.14 | 130 CA | 129 OG | 61 CG | 101.72 |
| 130 CA | 129 OG | 156 CB | 122.70 | 152 SG | 129 OG | 156 N | 70.43 |
| 152 SG | 129 OG | 61 ND1 | 98.33 | 152 SG | 129 OG | 131 OG | 132.25 |

Figure 12J

| Atom 1 | Atom 2 | Atom 3 | Angle | Atom 1 | Atom 2 | Atom 3 | Angle |
|---|---|---|---|---|---|---|---|
| 152 SG | 129 OG | 131 N | 136.81 | 152 SG | 129 OG | 61 CG | 87.05 |
| 152 SG | 129 OG | 156 CB | 92.58 | 156 N | 129 OG | 61 ND1 | 148.19 |
| 156 N | 129 OG | 131 OG | 154.03 | 156 N | 129 OG | 131 N | 142.72 |
| 156 N | 129 OG | 61 CG | 135.04 | 156 N | 129 OG | 156 CB | 26.68 |
| 61 ND1 | 129 OG | 131 OG | 36.65 | 61 ND1 | 129 OG | 131 N | 64.93 |
| 61 ND1 | 129 OG | 61 CG | 14.34 | 61 ND1 | 129 OG | 156 CB | 132.96 |
| 131 OG | 129 OG | 131 N | 32.77 | 131 OG | 129 OG | 61 CG | 50.41 |
| 131 OG | 129 OG | 156 CB | 127.55 | 131 N | 129 OG | 61 CG | 79.24 |
| 131 N | 129 OG | 156 CB | 128.62 | 61 CG | 129 OG | 156 CB | 125.31 |
| 129 O | 129 C | 130 N | 122.05 | 129 O | 129 C | 129 CA | 119.64 |
| 129 O | 129 C | 129 N | 94.39 | 129 O | 129 C | 130 CA | 91.21 |
| 129 O | 129 C | 129 CB | 101.89 | 129 O | 129 C | 129 OG | 112.10 |
| 129 O | 129 C | 130 C | 89.57 | 129 O | 129 C | 128 C | 105.50 |
| 129 O | 129 C | 130 CB | 103.44 | 129 O | 129 C | 130 O | 105.04 |
| 129 O | 129 C | 131 N | 72.04 | 129 O | 129 C | 128 O | 122.50 |
| 129 O | 129 C | 321 OH2 | 148.65 | 129 O | 129 C | 128 CA | 92.75 |
| 129 O | 129 C | 61 CE1 | 64.66 | 129 O | 129 C | 128 CB | 88.97 |
| 129 O | 129 C | 148 O | 44.70 | 129 O | 129 C | 61 NE2 | 73.43 |
| 129 O | 129 C | 128 CG2 | 102.76 | 129 O | 129 C | 130 CG | 97.32 |
| 129 O | 129 C | 131 CA | 76.07 | 129 O | 129 C | 131 OG | 65.61 |
| 129 O | 129 C | 27 CD1 | 93.30 | 129 O | 129 C | 157 NH2 | 133.24 |
| 130 N | 129 C | 129 CA | 118.07 | 130 N | 129 C | 129 N | 131.85 |
| 130 N | 129 C | 130 CA | 30.98 | 130 N | 129 C | 129 CB | 129.70 |
| 130 N | 129 C | 129 OG | 106.28 | 130 N | 129 C | 130 C | 42.69 |
| 130 N | 129 C | 128 C | 119.41 | 130 N | 129 C | 130 CB | 20.77 |
| 130 N | 129 C | 130 O | 39.01 | 130 N | 129 C | 131 N | 59.98 |
| 130 N | 129 C | 128 O | 106.95 | 130 N | 129 C | 321 OH2 | 89.28 |
| 130 N | 129 C | 128 CA | 124.58 | 130 N | 129 C | 61 CE1 | 118.22 |
| 130 N | 129 C | 128 CB | 112.67 | 130 N | 129 C | 148 O | 77.75 |
| 130 N | 129 C | 61 NE2 | 125.86 | 130 N | 129 C | 128 CG2 | 96.51 |
| 130 N | 129 C | 130 CG | 25.11 | 130 N | 129 C | 131 CA | 62.61 |
| 130 N | 129 C | 131 OG | 87.55 | 130 N | 129 C | 27 CD1 | 66.30 |
| 130 N | 129 C | 157 NH2 | 18.25 | 129 CA | 129 C | 129 N | 36.18 |
| 129 CA | 129 C | 130 CA | 149.05 | 129 CA | 129 C | 129 CB | 34.04 |
| 129 CA | 129 C | 129 OG | 52.24 | 129 CA | 129 C | 130 C | 143.15 |
| 129 CA | 129 C | 128 C | 33.84 | 129 CA | 129 C | 130 CB | 134.31 |
| 129 CA | 129 C | 130 O | 125.18 | 129 CA | 129 C | 131 N | 151.23 |
| 129 CA | 129 C | 128 O | 26.20 | 129 CA | 129 C | 321 OH2 | 29.14 |
| 129 CA | 129 C | 128 CA | 46.33 | 129 CA | 129 C | 61 CE1 | 92.00 |
| 129 CA | 129 C | 128 CB | 63.12 | 129 CA | 129 C | 148 O | 164.17 |
| 129 CA | 129 C | 61 NE2 | 76.57 | 129 CA | 129 C | 128 CG2 | 64.81 |
| 129 CA | 129 C | 130 CG | 141.70 | 129 CA | 129 C | 131 CA | 141.03 |
| 129 CA | 129 C | 131 OG | 123.06 | 129 CA | 129 C | 27 CD1 | 105.83 |
| 129 CA | 129 C | 157 NH2 | 106.21 | 129 N | 129 C | 130 CA | 149.50 |

Figure 12K

| Atom 1 | Atom 2 | Atom 3 | Angle | Atom 1 | Atom 2 | Atom 3 | Angle |
|---|---|---|---|---|---|---|---|
| 129 N  | 129 C | 129 CB  | 58.49  | 129 N  | 129 C | 129 OG  | 84.14 |
| 129 N  | 129 C | 130 C   | 174.51 | 129 N  | 129 C | 128 C   | 12.62 |
| 129 N  | 129 C | 130 CB  | 133.57 | 129 N  | 129 C | 130 O   | 159.81 |
| 129 N  | 129 C | 131 N   | 166.36 | 129 N  | 129 C | 128 O   | 28.26 |
| 129 N  | 129 C | 321 OH2 | 59.46  | 129 N  | 129 C | 128 CA  | 12.49 |
| 129 N  | 129 C | 61 CE1  | 104.89 | 129 N  | 129 C | 128 CB  | 31.01 |
| 129 N  | 129 C | 148 O   | 133.83 | 129 N  | 129 C | 61 NE2  | 92.00 |
| 129 N  | 129 C | 128 CG2 | 41.03  | 129 N  | 129 C | 130 CG  | 140.46 |
| 129 N  | 129 C | 131 CA  | 165.35 | 129 N  | 129 C | 131 OG  | 139.14 |
| 129 N  | 129 C | 27 CD1  | 82.69  | 129 N  | 129 C | 157 NH2 | 130.53 |
| 130 CA | 129 C | 129 CB  | 148.63 | 130 CA | 129 C | 129 OG  | 121.17 |
| 130 CA | 129 C | 130 C   | 26.26  | 130 CA | 129 C | 128 C   | 140.61 |
| 130 CA | 129 C | 130 CB  | 17.88  | 130 CA | 129 C | 130 O   | 37.70 |
| 130 CA | 129 C | 131 N   | 36.42  | 130 CA | 129 C | 128 O   | 134.02 |
| 130 CA | 129 C | 321 OH2 | 120.12 | 130 CA | 129 C | 128 CA  | 137.41 |
| 130 CA | 129 C | 61 CE1  | 104.60 | 130 CA | 129 C | 128 CB  | 119.45 |
| 130 CA | 129 C | 148 O   | 46.77  | 130 CA | 129 C | 61 NE2  | 118.29 |
| 130 CA | 129 C | 128 CG2 | 108.53 | 130 CA | 129 C | 130 CG  | 9.92 |
| 130 CA | 129 C | 131 CA  | 43.61  | 130 CA | 129 C | 131 OG  | 69.75 |
| 130 CA | 129 C | 27 CD1  | 67.05  | 130 CA | 129 C | 157 NH2 | 44.16 |
| 129 CB | 129 C | 129 OG  | 27.48  | 129 CB | 129 C | 130 C   | 124.35 |
| 129 CB | 129 C | 128 C   | 62.82  | 129 CB | 129 C | 130 CB  | 150.37 |
| 129 CB | 129 C | 130 O   | 110.95 | 129 CB | 129 C | 131 N   | 121.78 |
| 129 CB | 129 C | 128 O   | 59.95  | 129 CB | 129 C | 321 OH2 | 51.08 |
| 129 CB | 129 C | 128 CA  | 70.95  | 129 CB | 129 C | 61 CE1  | 58.03 |
| 129 CB | 129 C | 128 CB  | 89.48  | 129 CB | 129 C | 148 O   | 135.70 |
| 129 CB | 129 C | 61 NE2  | 42.61  | 129 CB | 129 C | 128 CG2 | 96.32 |
| 129 CB | 129 C | 130 CG  | 151.73 | 129 CB | 129 C | 131 CA  | 112.01 |
| 129 CB | 129 C | 131 OG  | 89.75  | 129 CB | 129 C | 27 CD1  | 138.93 |
| 129 CB | 129 C | 157 NH2 | 111.87 | 129 OG | 129 C | 130 C   | 97.91 |
| 129 OG | 129 C | 128 C   | 85.60  | 129 OG | 129 C | 130 CB  | 125.42 |
| 129 OG | 129 C | 130 O   | 83.53  | 129 OG | 129 C | 131 N   | 99.41 |
| 129 OG | 129 C | 128 O   | 77.17  | 129 OG | 129 C | 321 OH2 | 52.83 |
| 129 OG | 129 C | 128 CA  | 96.22  | 129 OG | 129 C | 61 CE1  | 50.88 |
| 129 OG | 129 C | 128 CB  | 114.38 | 129 OG | 129 C | 148 O   | 125.73 |
| 129 OG | 129 C | 61 NE2  | 39.02  | 129 OG | 129 C | 128 CG2 | 116.72 |
| 129 OG | 129 C | 130 CG  | 124.87 | 129 OG | 129 C | 131 CA  | 89.15 |
| 129 OG | 129 C | 131 OG  | 72.66  | 129 OG | 129 C | 27 CD1  | 152.16 |
| 129 OG | 129 C | 157 NH2 | 88.05  | 130 C  | 129 C | 128 C   | 162.05 |
| 130 C  | 129 C | 130 CB  | 41.42  | 130 C  | 129 C | 130 O   | 18.01 |
| 130 C  | 129 C | 131 N   | 18.27  | 130 C  | 129 C | 128 O   | 147.28 |
| 130 C  | 129 C | 321 OH2 | 117.87 | 130 C  | 129 C | 128 CA  | 163.63 |
| 130 C  | 129 C | 61 CE1  | 80.24  | 130 C  | 129 C | 128 CB  | 145.61 |
| 130 C  | 129 C | 148 O   | 48.45  | 130 C  | 129 C | 61 NE2  | 92.77 |

Figure 12L

| Atom 1 | Atom 2 | Atom 3 | Angle | Atom 1 | Atom 2 | Atom 3 | Angle |
|---|---|---|---|---|---|---|---|
| 130 C | 129 C | 128 CG2 | 134.23 | 130 C | 129 C | 130 CG | 34.83 |
| 130 C | 129 C | 131 CA | 20.13 | 130 C | 129 C | 131 OG | 46.22 |
| 130 C | 129 C | 27 CD1 | 93.31 | 130 C | 129 C | 157 NH2 | 44.77 |
| 128 C | 129 C | 130 CB | 123.32 | 128 C | 129 C | 130 O | 149.46 |
| 128 C | 129 C | 131 N | 174.93 | 128 C | 129 C | 128 O | 17.21 |
| 128 C | 129 C | 321 OH2 | 51.24 | 128 C | 129 C | 128 CA | 14.19 |
| 128 C | 129 C | 61 CE1 | 114.79 | 128 C | 129 C | 128 CB | 29.29 |
| 128 C | 129 C | 148 O | 140.66 | 128 C | 129 C | 61 NE2 | 100.76 |
| 128 C | 129 C | 128 CG2 | 33.62 | 128 C | 129 C | 130 CG | 130.87 |
| 128 C | 129 C | 131 CA | 174.74 | 128 C | 129 C | 131 OG | 149.64 |
| 128 C | 129 C | 27 CD1 | 76.43 | 128 C | 129 C | 157 NH2 | 118.22 |
| 130 CB | 129 C | 130 O | 47.15 | 130 CB | 129 C | 131 N | 54.09 |
| 130 CB | 129 C | 128 O | 116.23 | 130 CB | 129 C | 321 OH2 | 107.26 |
| 130 CB | 129 C | 128 CA | 122.53 | 130 CB | 129 C | 61 CE1 | 121.52 |
| 130 CB | 129 C | 128 CB | 106.04 | 130 CB | 129 C | 148 O | 61.13 |
| 130 CB | 129 C | 61 NE2 | 134.03 | 130 CB | 129 C | 128 CG2 | 92.86 |
| 130 CB | 129 C | 130 CG | 8.06 | 130 CB | 129 C | 131 CA | 60.49 |
| 130 CB | 129 C | 131 OG | 86.90 | 130 CB | 129 C | 27 CD1 | 54.16 |
| 130 CB | 129 C | 157 NH2 | 38.51 | 130 O | 129 C | 131 N | 33.24 |
| 130 O | 129 C | 128 O | 132.41 | 130 O | 129 C | 321 OH2 | 100.38 |
| 130 O | 129 C | 128 CA | 160.95 | 130 O | 129 C | 61 CE1 | 79.25 |
| 130 O | 129 C | 128 CB | 151.59 | 130 O | 129 C | 148 O | 66.19 |
| 130 O | 129 C | 61 NE2 | 88.41 | 130 O | 129 C | 128 CG2 | 135.46 |
| 130 O | 129 C | 130 CG | 43.16 | 130 O | 129 C | 131 CA | 29.52 |
| 130 O | 129 C | 131 OG | 50.02 | 130 O | 129 C | 27 CD1 | 101.28 |
| 130 O | 129 C | 157 NH2 | 33.12 | 131 N | 129 C | 128 O | 165.39 |
| 131 N | 129 C | 321 OH2 | 132.77 | 131 N | 129 C | 128 CA | 161.39 |
| 131 N | 129 C | 61 CE1 | 68.47 | 131 N | 129 C | 128 CB | 145.65 |
| 131 N | 129 C | 148 O | 34.84 | 131 N | 129 C | 61 NE2 | 82.90 |
| 131 N | 129 C | 128 CG2 | 141.90 | 131 N | 129 C | 130 CG | 46.31 |
| 131 N | 129 C | 131 CA | 10.26 | 131 N | 129 C | 131 OG | 33.71 |
| 131 N | 129 C | 27 CD1 | 99.15 | 131 N | 129 C | 157 NH2 | 62.99 |
| 128 O | 129 C | 321 OH2 | 34.87 | 128 O | 129 C | 128 CA | 31.00 |
| 128 O | 129 C | 61 CE1 | 117.33 | 128 O | 129 C | 128 CB | 42.38 |
| 128 O | 129 C | 148 O | 155.18 | 128 O | 129 C | 61 NE2 | 102.00 |
| 128 O | 129 C | 128 CG2 | 39.59 | 128 O | 129 C | 130 CG | 124.29 |
| 128 O | 129 C | 131 CA | 159.99 | 128 O | 129 C | 131 OG | 149.21 |
| 128 O | 129 C | 27 CD1 | 79.64 | 128 O | 129 C | 157 NH2 | 102.52 |
| 321 OH2 | 129 C | 128 CA | 65.42 | 321 OH2 | 129 C | 61 CE1 | 103.19 |
| 321 OH2 | 129 C | 128 CB | 76.75 | 321 OH2 | 129 C | 148 O | 166.01 |
| 321 OH2 | 129 C | 61 NE2 | 89.41 | 321 OH2 | 129 C | 128 CG2 | 69.83 |
| 321 OH2 | 129 C | 130 CG | 113.82 | 321 OH2 | 129 C | 131 CA | 125.23 |
| 321 OH2 | 129 C | 131 OG | 121.79 | 321 OH2 | 129 C | 27 CD1 | 99.47 |
| 321 OH2 | 129 C | 157 NH2 | 77.18 | 128 CA | 129 C | 61 CE1 | 115.33 |

Figure 12M

| Atom 1 | Atom 2 | Atom 3 | Angle | Atom 1 | Atom 2 | Atom 3 | Angle |
|---|---|---|---|---|---|---|---|
| 128 CA | 129 C | 128 CB | 18.53 | 128 CA | 129 C | 148 O | 126.57 |
| 128 CA | 129 C | 61 NE2 | 103.43 | 128 CA | 129 C | 128 CG2 | 29.70 |
| 128 CA | 129 C | 130 CG | 128.85 | 128 CA | 129 C | 131 CA | 168.77 |
| 128 CA | 129 C | 131 OG | 147.85 | 128 CA | 129 C | 27 CD1 | 70.39 |
| 128 CA | 129 C | 157 NH2 | 127.90 | 61 CE1 | 129 C | 128 CB | 129.11 |
| 61 CE1 | 129 C | 148 O | 78.89 | 61 CE1 | 129 C | 61 NE2 | 15.43 |
| 61 CE1 | 129 C | 128 CG2 | 144.82 | 61 CE1 | 129 C | 130 CG | 114.27 |
| 61 CE1 | 129 C | 131 CA | 61.10 | 61 CE1 | 129 C | 131 OG | 34.86 |
| 61 CE1 | 129 C | 27 CD1 | 156.87 | 61 CE1 | 129 C | 157 NH2 | 107.32 |
| 128 CB | 129 C | 148 O | 112.95 | 128 CB | 129 C | 61 NE2 | 119.56 |
| 128 CB | 129 C | 128 CG2 | 17.06 | 128 CB | 129 C | 130 CG | 111.56 |
| 128 CB | 129 C | 131 CA | 155.75 | 128 CB | 129 C | 131 OG | 153.81 |
| 128 CB | 129 C | 27 CD1 | 52.51 | 128 CB | 129 C | 157 NH2 | 121.62 |
| 148 O | 129 C | 61 NE2 | 93.93 | 148 O | 129 C | 128 CG2 | 116.42 |
| 148 O | 129 C | 130 CG | 53.97 | 148 O | 129 C | 131 CA | 43.54 |
| 148 O | 129 C | 131 OG | 53.23 | 148 O | 129 C | 27 CD1 | 80.26 |
| 148 O | 129 C | 157 NH2 | 88.96 | 61 NE2 | 129 C | 128 CG2 | 133.00 |
| 61 NE2 | 129 C | 130 CG | 127.54 | 61 NE2 | 129 C | 131 CA | 74.74 |
| 61 NE2 | 129 C | 131 OG | 49.21 | 61 NE2 | 129 C | 27 CD1 | 165.36 |
| 61 NE2 | 129 C | 157 NH2 | 111.37 | 128 CG2 | 129 C | 130 CG | 99.46 |
| 128 CG2 | 129 C | 131 CA | 151.39 | 128 CG2 | 129 C | 131 OG | 167.88 |
| 128 CG2 | 129 C | 27 CD1 | 42.81 | 128 CG2 | 129 C | 157 NH2 | 104.56 |
| 130 CG | 129 C | 131 CA | 53.18 | 130 CG | 129 C | 131 OG | 79.47 |
| 130 CG | 129 C | 27 CD1 | 59.09 | 130 CG | 129 C | 157 NH2 | 41.21 |
| 131 CA | 129 C | 131 OG | 26.43 | 131 CA | 129 C | 27 CD1 | 108.62 |
| 131 CA | 129 C | 157 NH2 | 61.95 | 131 OG | 129 C | 27 CD1 | 131.08 |
| 131 OG | 129 C | 157 NH2 | 82.70 | 27 CD1 | 129 C | 157 NH2 | 82.12 |
| 129 C | 129 O | 130 N | 30.35 | 129 C | 129 O | 129 CA | 33.87 |
| 129 C | 129 O | 129 N | 59.08 | 129 C | 129 O | 130 CA | 62.27 |
| 129 C | 129 O | 129 CB | 54.82 | 129 C | 129 O | 130 C | 69.65 |
| 129 C | 129 O | 129 OG | 49.93 | 129 C | 129 O | 131 N | 89.72 |
| 129 C | 129 O | 128 C | 57.43 | 129 C | 129 O | 148 O | 123.10 |
| 129 C | 129 O | 130 CB | 59.77 | 129 C | 129 O | 130 O | 58.75 |
| 129 C | 129 O | 61 CE1 | 100.53 | 129 C | 129 O | 148 C | 137.13 |
| 129 C | 129 O | 61 NE2 | 92.31 | 129 C | 129 O | 128 O | 45.06 |
| 129 C | 129 O | 128 CA | 72.67 | 129 C | 129 O | 131 OG | 101.33 |
| 129 C | 129 O | 131 CA | 90.06 | 129 C | 129 O | 128 CB | 76.78 |
| 129 C | 129 O | 148 ND1 | 151.06 | 129 C | 129 O | 61 ND1 | 112.00 |
| 129 C | 129 O | 131 CB | 103.03 | 129 C | 129 O | 148 CE1 | 138.86 |
| 129 C | 129 O | 130 CG | 69.65 | 129 C | 129 O | 128 CG2 | 64.49 |
| 130 N | 129 O | 129 CA | 64.13 | 130 N | 129 O | 129 N | 85.39 |
| 130 N | 129 O | 130 CA | 32.00 | 130 N | 129 O | 129 CB | 82.83 |
| 130 N | 129 O | 130 C | 44.51 | 130 N | 129 O | 129 OG | 71.39 |
| 130 N | 129 O | 131 N | 65.15 | 130 N | 129 O | 128 C | 82.26 |

Figure 12N

| Atom 1 | Atom 2 | Atom 3 | Angle | Atom 1 | Atom 2 | Atom 3 | Angle |
|---|---|---|---|---|---|---|---|
| 130 N | 129 O | 148 O | 93.03 | 130 N | 129 O | 130 CB | 30.20 |
| 130 N | 129 O | 130 O | 38.28 | 130 N | 129 O | 61 CE1 | 108.49 |
| 130 N | 129 O | 148 C | 106.82 | 130 N | 129 O | 61 NE2 | 107.74 |
| 130 N | 129 O | 128 O | 71.27 | 130 N | 129 O | 128 CA | 94.63 |
| 130 N | 129 O | 131 OG | 90.09 | 130 N | 129 O | 131 CA | 68.90 |
| 130 N | 129 O | 128 CB | 91.19 | 130 N | 129 O | 148 ND1 | 131.56 |
| 130 N | 129 O | 61 ND1 | 117.45 | 130 N | 129 O | 131 CB | 84.84 |
| 130 N | 129 O | 148 CE1 | 127.33 | 130 N | 129 O | 130 CG | 39.45 |
| 130 N | 129 O | 128 CG2 | 75.85 | 129 CA | 129 O | 129 N | 31.67 |
| 129 CA | 129 O | 130 CA | 96.12 | 129 CA | 129 O | 129 CB | 29.81 |
| 129 CA | 129 O | 130 C | 100.96 | 129 CA | 129 O | 129 OG | 40.52 |
| 129 CA | 129 O | 131 N | 118.95 | 129 CA | 129 O | 128 C | 33.00 |
| 129 CA | 129 O | 148 O | 156.88 | 129 CA | 129 O | 130 CB | 92.60 |
| 129 CA | 129 O | 130 O | 88.24 | 129 CA | 129 O | 61 CE1 | 91.63 |
| 129 CA | 129 O | 148 C | 170.88 | 129 CA | 129 O | 61 NE2 | 77.52 |
| 129 CA | 129 O | 128 O | 22.12 | 129 CA | 129 O | 128 CA | 49.00 |
| 129 CA | 129 O | 131 OG | 113.50 | 129 CA | 129 O | 131 CA | 115.84 |
| 129 CA | 129 O | 128 CB | 61.46 | 129 CA | 129 O | 148 ND1 | 148.47 |
| 129 CA | 129 O | 61 ND1 | 102.07 | 129 CA | 129 O | 131 CB | 122.93 |
| 129 CA | 129 O | 148 CE1 | 135.17 | 129 CA | 129 O | 130 CG | 103.01 |
| 129 CA | 129 O | 128 CG2 | 56.96 | 129 N | 129 O | 130 CA | 114.74 |
| 129 N | 129 O | 129 CB | 48.68 | 129 N | 129 O | 130 C | 128.60 |
| 129 N | 129 O | 129 OG | 67.49 | 129 N | 129 O | 131 N | 148.77 |
| 129 N | 129 O | 128 C | 5.43 | 129 N | 129 O | 148 O | 159.15 |
| 129 N | 129 O | 130 CB | 106.36 | 129 N | 129 O | 130 O | 117.61 |
| 129 N | 129 O | 61 CE1 | 107.68 | 129 N | 129 O | 148 C | 151.98 |
| 129 N | 129 O | 61 NE2 | 91.86 | 129 N | 129 O | 128 O | 14.24 |
| 129 N | 129 O | 128 CA | 17.66 | 129 N | 129 O | 131 OG | 140.56 |
| 129 N | 129 O | 131 CA | 147.34 | 129 N | 129 O | 128 CB | 33.20 |
| 129 N | 129 O | 148 ND1 | 142.23 | 129 N | 129 O | 61 ND1 | 114.34 |
| 129 N | 129 O | 131 CB | 153.27 | 129 N | 129 O | 148 CE1 | 138.98 |
| 129 N | 129 O | 130 CG | 117.16 | 129 N | 129 O | 128 CG2 | 36.05 |
| 130 CA | 129 O | 129 CB | 111.50 | 130 CA | 129 O | 130 C | 24.98 |
| 130 CA | 129 O | 129 OG | 94.87 | 130 CA | 129 O | 131 N | 40.78 |
| 130 CA | 129 O | 128 C | 110.63 | 130 CA | 129 O | 148 O | 61.05 |
| 130 CA | 129 O | 130 CB | 11.79 | 130 CA | 129 O | 130 O | 31.00 |
| 130 CA | 129 O | 61 CE1 | 108.61 | 130 CA | 129 O | 148 C | 74.86 |
| 130 CA | 129 O | 61 NE2 | 116.78 | 130 CA | 129 O | 128 O | 101.31 |
| 130 CA | 129 O | 128 CA | 119.02 | 130 CA | 129 O | 131 OG | 75.71 |
| 130 CA | 129 O | 131 CA | 48.35 | 130 CA | 129 O | 128 CB | 108.49 |
| 130 CA | 129 O | 148 ND1 | 103.00 | 130 CA | 129 O | 61 ND1 | 111.87 |
| 130 CA | 129 O | 131 CB | 64.47 | 130 CA | 129 O | 148 CE1 | 104.06 |
| 130 CA | 129 O | 130 CG | 10.27 | 130 CA | 129 O | 128 CG2 | 93.66 |
| 129 CB | 129 O | 130 C | 103.90 | 129 CB | 129 O | 129 OG | 21.65 |

Figure 12O

| Atom 1 | Atom 2 | Atom 3 | Angle | Atom 1 | Atom 2 | Atom 3 | Angle |
|---|---|---|---|---|---|---|---|
| 129 CB | 129 O | 131 N | 113.82 | 129 CB | 129 O | 128 C | 52.87 |
| 129 CB | 129 O | 148 O | 151.76 | 129 CB | 129 O | 130 CB | 112.97 |
| 129 CB | 129 O | 130 O | 90.28 | 129 CB | 129 O | 61 CE1 | 62.88 |
| 129 CB | 129 O | 148 C | 155.41 | 129 CB | 129 O | 61 NE2 | 48.03 |
| 129 CB | 129 O | 128 O | 47.12 | 129 CB | 129 O | 128 CA | 64.90 |
| 129 CB | 129 O | 131 OG | 91.88 | 129 CB | 129 O | 131 CA | 106.28 |
| 129 CB | 129 O | 128 CB | 81.83 | 129 CB | 129 O | 148 ND1 | 118.69 |
| 129 CB | 129 O | 61 ND1 | 72.68 | 129 CB | 129 O | 131 CB | 105.34 |
| 129 CB | 129 O | 148 CE1 | 105.50 | 129 CB | 129 O | 130 CG | 121.05 |
| 129 CB | 129 O | 128 CG2 | 82.65 | 130 C | 129 O | 129 OG | 83.13 |
| 130 C | 129 O | 131 N | 20.72 | 130 C | 129 O | 128 C | 126.24 |
| 130 C | 129 O | 148 O | 56.99 | 130 C | 129 O | 130 CB | 36.76 |
| 130 C | 129 O | 130 O | 13.74 | 130 C | 129 O | 61 CE1 | 83.91 |
| 130 C | 129 O | 148 C | 71.44 | 130 C | 129 O | 61 NE2 | 93.63 |
| 130 C | 129 O | 128 O | 114.40 | 130 C | 129 O | 128 CA | 139.10 |
| 130 C | 129 O | 131 OG | 51.17 | 130 C | 129 O | 131 CA | 25.19 |
| 130 C | 129 O | 128 CB | 132.37 | 130 C | 129 O | 148 ND1 | 87.12 |
| 130 C | 129 O | 61 ND1 | 86.91 | 130 C | 129 O | 131 CB | 41.68 |
| 130 C | 129 O | 148 CE1 | 83.81 | 130 C | 129 O | 130 CG | 31.86 |
| 130 C | 129 O | 128 CG2 | 117.00 | 129 OG | 129 O | 131 N | 92.19 |
| 129 OG | 129 O | 128 C | 70.77 | 129 OG | 129 O | 148 O | 131.52 |
| 129 OG | 129 O | 130 CB | 99.52 | 129 OG | 129 O | 130 O | 69.82 |
| 129 OG | 129 O | 61 CE1 | 53.56 | 129 OG | 129 O | 148 C | 139.99 |
| 129 OG | 129 O | 61 NE2 | 42.66 | 129 OG | 129 O | 128 O | 62.06 |
| 129 OG | 129 O | 128 CA | 84.73 | 129 OG | 129 O | 131 OG | 73.94 |
| 129 OG | 129 O | 131 CA | 84.90 | 129 OG | 129 O | 128 CB | 100.33 |
| 129 OG | 129 O | 148 ND1 | 112.13 | 129 OG | 129 O | 61 ND1 | 64.97 |
| 129 OG | 129 O | 131 CB | 85.82 | 129 OG | 129 O | 148 CE1 | 97.46 |
| 129 OG | 129 O | 130 CG | 105.07 | 129 OG | 129 O | 128 CG2 | 97.47 |
| 131 N | 129 O | 128 C | 146.86 | 131 N | 129 O | 148 O | 41.37 |
| 131 N | 129 O | 130 CB | 51.90 | 131 N | 129 O | 130 O | 31.20 |
| 131 N | 129 O | 61 CE1 | 74.46 | 131 N | 129 O | 148 C | 54.71 |
| 131 N | 129 O | 61 NE2 | 87.77 | 131 N | 129 O | 128 O | 134.75 |
| 131 N | 129 O | 128 CA | 159.35 | 131 N | 129 O | 131 OG | 37.22 |
| 131 N | 129 O | 131 CA | 9.83 | 131 N | 129 O | 128 CB | 148.16 |
| 131 N | 129 O | 148 ND1 | 66.43 | 131 N | 129 O | 61 ND1 | 73.93 |
| 131 N | 129 O | 131 CB | 23.97 | 131 N | 129 O | 148 CE1 | 64.07 |
| 131 N | 129 O | 130 CG | 43.35 | 131 N | 129 O | 128 CG2 | 134.19 |
| 128 C | 129 O | 148 O | 154.38 | 128 C | 129 O | 130 CB | 101.77 |
| 128 C | 129 O | 130 O | 116.18 | 128 C | 129 O | 61 CE1 | 112.86 |
| 128 C | 129 O | 148 C | 149.18 | 128 C | 129 O | 61 NE2 | 97.03 |
| 128 C | 129 O | 128 O | 12.59 | 128 C | 129 O | 128 CA | 16.27 |
| 128 C | 129 O | 131 OG | 144.52 | 128 C | 129 O | 131 CA | 147.12 |
| 128 C | 129 O | 128 CB | 29.56 | 128 C | 129 O | 148 ND1 | 145.97 |

Figure 12P

| Atom 1 | Atom 2 | Atom 3 | Angle | Atom 1 | Atom 2 | Atom 3 | Angle |
|---|---|---|---|---|---|---|---|
| 128 C   | 129 O | 61 ND1  | 119.73 | 128 C   | 129 O | 131 CB  | 155.87 |
| 128 C   | 129 O | 148 CE1 | 144.01 | 128 C   | 129 O | 130 CG  | 112.45 |
| 128 C   | 129 O | 128 CG2 | 30.91  | 148 O   | 129 O | 130 CB  | 65.75  |
| 148 O   | 129 O | 130 O   | 70.32  | 148 O   | 129 O | 61 CE1  | 92.56  |
| 148 O   | 129 O | 148 C   | 14.61  | 148 O   | 129 O | 61 NE2  | 108.34 |
| 148 O   | 129 O | 128 O   | 155.67 | 148 O   | 129 O | 128 CA  | 143.33 |
| 148 O   | 129 O | 131 OG  | 60.10  | 148 O   | 129 O | 131 CA  | 47.14  |
| 148 O   | 129 O | 128 CB  | 126.30 | 148 O   | 129 O | 148 ND1 | 46.78  |
| 148 O   | 129 O | 61 ND1  | 84.83  | 148 O   | 129 O | 131 CB  | 46.42  |
| 148 O   | 129 O | 148 CE1 | 55.64  | 148 O   | 129 O | 130 CG  | 54.94  |
| 148 O   | 129 O | 128 CG2 | 123.54 | 130 CB  | 129 O | 130 O   | 41.54  |
| 130 CB  | 129 O | 61 CE1  | 120.07 | 130 CB  | 129 O | 148 C   | 78.29  |
| 130 CB  | 129 O | 61 NE2  | 127.05 | 130 CB  | 129 O | 128 O   | 93.83  |
| 130 CB  | 129 O | 128 CA  | 108.42 | 130 CB  | 129 O | 131 OG  | 87.45  |
| 130 CB  | 129 O | 131 CA  | 59.90  | 130 CB  | 129 O | 128 CB  | 96.91  |
| 130 CB  | 129 O | 148 ND1 | 110.71 | 130 CB  | 129 O | 61 ND1  | 123.66 |
| 130 CB  | 129 O | 131 CB  | 75.80  | 130 CB  | 129 O | 148 CE1 | 113.86 |
| 130 CB  | 129 O | 130 CG  | 11.00  | 130 CB  | 129 O | 128 CG2 | 82.32  |
| 130 O   | 129 O | 61 CE1  | 78.95  | 130 O   | 129 O | 148 C   | 84.60  |
| 130 O   | 129 O | 61 NE2  | 85.81  | 130 O   | 129 O | 128 O   | 103.78 |
| 130 O   | 129 O | 128 CA  | 130.97 | 130 O   | 129 O | 131 OG  | 52.22  |
| 130 O   | 129 O | 131 CA  | 31.78  | 130 O   | 129 O | 128 CB  | 129.45 |
| 130 O   | 129 O | 148 ND1 | 95.34  | 130 O   | 129 O | 61 ND1  | 84.44  |
| 130 O   | 129 O | 131 CB  | 46.88  | 130 O   | 129 O | 148 CE1 | 89.14  |
| 130 O   | 129 O | 130 CG  | 40.26  | 130 O   | 129 O | 128 CG2 | 114.05 |
| 61 CE1  | 129 O | 148 C   | 92.53  | 61 CE1  | 129 O | 61 NE2  | 15.83  |
| 61 CE1  | 129 O | 128 O   | 109.78 | 61 CE1  | 129 O | 128 CA  | 118.54 |
| 61 CE1  | 129 O | 131 OG  | 37.82  | 61 CE1  | 129 O | 131 CA  | 64.76  |
| 61 CE1  | 129 O | 128 CB  | 135.90 | 61 CE1  | 129 O | 148 ND1 | 58.66  |
| 61 CE1  | 129 O | 61 ND1  | 11.58  | 61 CE1  | 129 O | 131 CB  | 52.85  |
| 61 CE1  | 129 O | 148 CE1 | 44.12  | 61 CE1  | 129 O | 130 CG  | 115.48 |
| 61 CE1  | 129 O | 128 CG2 | 143.74 | 148 C   | 129 O | 61 NE2  | 107.50 |
| 148 C   | 129 O | 128 O   | 157.19 | 148 C   | 129 O | 128 CA  | 134.35 |
| 148 C   | 129 O | 131 OG  | 66.06  | 148 C   | 129 O | 131 CA  | 59.12  |
| 148 C   | 129 O | 128 CB  | 119.65 | 148 C   | 129 O | 148 ND1 | 38.53  |
| 148 C   | 129 O | 61 ND1  | 82.88  | 148 C   | 129 O | 131 CB  | 54.64  |
| 148 C   | 129 O | 148 CE1 | 50.53  | 148 C   | 129 O | 130 CG  | 67.86  |
| 148 C   | 129 O | 128 CG2 | 121.35 | 61 NE2  | 129 O | 128 O   | 94.38  |
| 61 NE2  | 129 O | 128 CA  | 103.28 | 61 NE2  | 129 O | 131 OG  | 52.49  |
| 61 NE2  | 129 O | 131 CA  | 77.94  | 61 NE2  | 129 O | 128 CB  | 121.00 |
| 61 NE2  | 129 O | 148 ND1 | 71.54  | 61 NE2  | 129 O | 61 ND1  | 24.65  |
| 61 NE2  | 129 O | 131 CB  | 67.71  | 61 NE2  | 129 O | 148 CE1 | 57.65  |
| 61 NE2  | 129 O | 130 CG  | 125.35 | 61 NE2  | 129 O | 128 CG2 | 127.91 |
| 128 O   | 129 O | 128 CA  | 28.69  | 128 O   | 129 O | 131 OG  | 135.60 |

Figure 12Q

| Atom 1 | Atom 2 | Atom 3 | Angle | Atom 1 | Atom 2 | Atom 3 | Angle |
|---|---|---|---|---|---|---|---|
| 128 O   | 129 O | 131 CA  | 134.53 | 128 O   | 129 O | 128 CB  | 39.38 |
| 128 O   | 129 O | 148 ND1 | 155.45 | 128 O   | 129 O | 61 ND1  | 118.67 |
| 128 O   | 129 O | 131 CB  | 144.43 | 128 O   | 129 O | 148 CE1 | 148.64 |
| 128 O   | 129 O | 130 CG  | 104.81 | 128 O   | 129 O | 128 CG2 | 35.86 |
| 128 CA  | 129 O | 131 OG  | 155.40 | 128 CA  | 129 O | 131 CA  | 162.69 |
| 128 CA  | 129 O | 128 CB  | 17.97  | 128 CA  | 129 O | 148 ND1 | 133.46 |
| 128 CA  | 129 O | 61 ND1  | 122.22 | 128 CA  | 129 O | 131 CB  | 170.17 |
| 128 CA  | 129 O | 148 CE1 | 136.57 | 128 CA  | 129 O | 130 CG  | 117.95 |
| 128 CA  | 129 O | 128 CG2 | 27.49  | 131 OG  | 129 O | 131 CA  | 27.97 |
| 131 OG  | 129 O | 128 CB  | 173.37 | 131 OG  | 129 O | 148 ND1 | 49.75 |
| 131 OG  | 129 O | 61 ND1  | 36.82  | 131 OG  | 129 O | 131 CB  | 15.23 |
| 131 OG  | 129 O | 148 CE1 | 38.90  | 131 OG  | 129 O | 130 CG  | 80.14 |
| 131 OG  | 129 O | 128 CG2 | 165.42 | 131 CA  | 129 O | 128 CB  | 156.81 |
| 131 CA  | 129 O | 148 ND1 | 63.60  | 131 CA  | 129 O | 61 ND1  | 64.79 |
| 131 CA  | 129 O | 131 CB  | 16.50  | 131 CA  | 129 O | 148 CE1 | 58.76 |
| 131 CA  | 129 O | 130 CG  | 52.18  | 131 CA  | 129 O | 128 CG2 | 141.88 |
| 128 CB  | 129 O | 148 ND1 | 132.06 | 128 CB  | 129 O | 61 ND1  | 137.85 |
| 128 CB  | 129 O | 131 CB  | 171.25 | 128 CB  | 129 O | 148 CE1 | 141.13 |
| 128 CB  | 129 O | 130 CG  | 104.86 | 128 CB  | 129 O | 128 CG2 | 15.55 |
| 148 ND1 | 129 O | 61 ND1  | 47.49  | 148 ND1 | 129 O | 131 CB  | 48.98 |
| 148 ND1 | 129 O | 148 CE1 | 14.72  | 148 ND1 | 129 O | 130 CG  | 99.73 |
| 148 ND1 | 129 O | 128 CG2 | 144.22 | 61 ND1  | 129 O | 131 CB  | 50.53 |
| 61 ND1  | 129 O | 148 CE1 | 33.20  | 61 ND1  | 129 O | 130 CG  | 116.95 |
| 61 ND1  | 129 O | 128 CG2 | 149.41 | 131 CB  | 129 O | 148 CE1 | 42.54 |
| 131 CB  | 129 O | 130 CG  | 67.27  | 131 CB  | 129 O | 128 CG2 | 158.12 |
| 148 CE1 | 129 O | 130 CG  | 103.40 | 148 CE1 | 129 O | 128 CG2 | 155.68 |
| 130 CG  | 129 O | 128 CG2 | 91.07  |         |       |         |       |

Figure 13A

| Atom 1 | Atom 2 | Atom 3 | Angle | Atom 1 | Atom 2 | Atom 3 | Angle |
| --- | --- | --- | --- | --- | --- | --- | --- |
| 129OG | 61CD2 | 129CB | 19.02 | 129OG | 61CD2 | 129O | 43.06 |
| 129CB | 61CD2 | 129O | 37.16 | 148CE1 | 61CD2 | 129O | 78.30 |
| 148CE1 | 61ND1 | 131CB | 52.38 | 148CE1 | 61ND1 | 148NE2 | 14.31 |
| 129OG | 61ND1 | 131CB | 82.11 | 131CB | 61ND1 | 148NE2 | 45.16 |
| 129OG | 61CE1 | 129CB | 17.72 | 129OG | 61CE1 | 129O | 49.00 |
| 129OG | 61CE1 | 129C | 37.16 | 129OG | 61CE1 | 131CA | 87.97 |
| 129OG | 61CE1 | 131N | 76.81 | 129CB | 61CE1 | 129O | 39.96 |
| 129CB | 61CE1 | 129C | 32.01 | 129CB | 61CE1 | 131CA | 93.51 |
| 129CB | 61CE1 | 131N | 79.08 | 129O | 61CE1 | 131CB | 74.23 |
| 129O | 61CE1 | 148CE1 | 82.40 | 129O | 61CE1 | 129C | 13.37 |
| 129O | 61CE1 | 131CA | 63.73 | 129O | 61CE1 | 131N | 46.91 |
| 131CB | 61CE1 | 148CE1 | 53.06 | 131CB | 61CE1 | 129C | 77.45 |
| 131CB | 61CE1 | 131CA | 17.24 | 131CB | 61CE1 | 131N | 29.58 |
| 148CE1 | 61CE1 | 129C | 94.62 | 148CE1 | 61CE1 | 131CA | 67.27 |
| 148CE1 | 61CE1 | 131N | 68.05 | 129C | 61CE1 | 131CA | 63.93 |
| 129C | 61CE1 | 131N | 48.10 | 131CA | 61CE1 | 131N | 16.86 |
| 129OG | 61NE2 | 129CB | 25.02 | 129OG | 61NE2 | 129O | 58.32 |
| 129OG | 61NE2 | 129C | 43.65 | 129OG | 61NE2 | 129CA | 30.38 |
| 129CB | 61NE2 | 129O | 48.45 | 129CB | 61NE2 | 129C | 36.82 |
| 129CB | 61NE2 | 129CA | 16.19 | 129O | 61NE2 | 129C | 14.73 |
| 129O | 61NE2 | 129CA | 32.61 | 129O | 61NE2 | 148CE1 | 86.57 |
| 129C | 61NE2 | 129CA | 20.67 | 129C | 61NE2 | 148CE1 | 99.19 |
| 61NE2 | 129CA | 152SG | 77.41 | 61NE2 | 129CB | 61CE1 | 16.25 |
| 61NE2 | 129CB | 61CD2 | 14.16 | 152SG | 129CB | 61CD2 | 91.44 |
| 61CE1 | 129CB | 61CD2 | 29.75 | 61NE2 | 129OG | 61CE1 | 23.54 |
| 61NE2 | 129OG | 61CD2 | 10.38 | 61NE2 | 129OG | 61ND1 | 22.43 |
| 61NE2 | 129OG | 152SG | 91.43 | 61NE2 | 129OG | 61CG | 11.68 |
| 61CE1 | 129OG | 61CD2 | 31.62 | 61CE1 | 129OG | 61ND1 | 6.87 |
| 61CE1 | 129OG | 61CG | 20.09 | 61CD2 | 129OG | 61ND1 | 28.57 |
| 61CD2 | 129OG | 152SG | 81.45 | 61CD2 | 129OG | 61CG | 13.41 |
| 61ND1 | 129OG | 61CG | 15.68 | 156CG | 129OG | 152SG | 89.53 |
| 152SG | 129OG | 61CG | 91.59 | 131N | 129C | 61NE2 | 82.32 |
| 131N | 129C | 148O | 36.39 | 131N | 129C | 61CE1 | 69.68 |
| 61NE2 | 129C | 148O | 83.14 | 61NE2 | 129C | 61CE1 | 15.62 |
| 148O | 129C | 61CE1 | 78.52 | 61NE2 | 129O | 131N | 93.33 |
| 61NE2 | 129O | 61CE1 | 16.99 | 61NE2 | 129O | 61CD2 | 13.22 |
| 61NE2 | 129O | 131CA | 81.79 | 131N | 129O | 148O | 42.21 |
| 131N | 129O | 61CE1 | 77.02 | 131N | 129O | 148C | 55.96 |
| 131N | 129O | 131CA | 11.75 | 148O | 129O | 61CE1 | 93.27 |
| 148O | 129O | 148C | 13.81 | 148O | 129O | 61CD2 | 99.88 |
| 148O | 129O | 131CA | 48.34 | 61CE1 | 129O | 148C | 97.42 |
| 61CE1 | 129O | 61CD2 | 28.11 | 61CE1 | 129O | 131CA | 65.34 |
| 148C | 129O | 61CD2 | 97.33 | 148C | 129O | 131CA | 61.48 |
| 61CD2 | 129O | 131CA | 89.15 | 148O | 131N | 129O | 69.99 |

Figure 13B

| Atom 1 | Atom 2 | Atom 3 | Angle | Atom 1 | Atom 2 | Atom 3 | Angle |
|---|---|---|---|---|---|---|---|
| 148O | 131N | 148C | 2.84 | 148O | 131N | 129C | 83.60 |
| 148O | 131N | 148N | 36.71 | 148O | 131N | 148CA | 19.19 |
| 148O | 131N | 61CE1 | 94.32 | 129O | 131N | 148C | 72.41 |
| 129O | 131N | 129C | 16.68 | 129O | 131N | 148CA | 88.32 |
| 129O | 131N | 157NH2 | 88.88 | 129O | 131N | 61CE1 | 56.08 |
| 148C | 131N | 129C | 86.23 | 148C | 131N | 148N | 34.08 |
| 148C | 131N | 148CA | 16.44 | 148C | 131N | 61CE1 | 94.65 |
| 129C | 131N | 157NH2 | 72.38 | 129C | 131N | 61CE1 | 62.21 |
| 148N | 131N | 148CA | 17.83 | 157NH2 | 131N | 61CE1 | 96.41 |
| 148O | 131CA | 148N | 36.27 | 148O | 131CA | 148C | 7.03 |
| 148O | 131CA | 129O | 49.93 | 148O | 131CA | 61CE1 | 83.50 |
| 148N | 131CA | 148C | 30.32 | 148N | 131CA | 129O | 85.91 |
| 148C | 131CA | 129O | 55.59 | 148C | 131CA | 61CE1 | 84.67 |
| 129O | 131CA | 61CE1 | 50.93 | 148NE2 | 131CB | 148O | 78.60 |
| 148NE2 | 131CB | 148CD2 | 20.18 | 148NE2 | 131CB | 148CE1 | 19.26 |
| 148NE2 | 131CB | 61CE1 | 81.78 | 148NE2 | 131CB | 148ND1 | 29.14 |
| 148NE2 | 131CB | 148CG | 29.92 | 148NE2 | 131CB | 148N | 65.64 |
| 148NE2 | 131CB | 148C | 67.71 | 148NE2 | 131CB | 61ND1 | 69.90 |
| 148O | 131CB | 148CD2 | 66.42 | 148O | 131CB | 148CE1 | 69.14 |
| 148O | 131CB | 61CE1 | 92.06 | 148O | 131CB | 148ND1 | 52.14 |
| 148O | 131CB | 148CG | 49.88 | 148O | 131CB | 148N | 38.61 |
| 148O | 131CB | 148C | 11.51 | 148O | 131CB | 61ND1 | 99.72 |
| 148CD2 | 131CB | 148CE1 | 31.89 | 148CD2 | 131CB | 61CE1 | 98.25 |
| 148CD2 | 131CB | 148ND1 | 29.69 | 148CD2 | 131CB | 148CG | 17.70 |
| 148CD2 | 131CB | 148N | 46.03 | 148CD2 | 131CB | 148C | 54.91 |
| 148CD2 | 131CB | 61ND1 | 88.41 | 148CE1 | 131CB | 61CE1 | 66.36 |
| 148CE1 | 131CB | 148ND1 | 17.33 | 148CE1 | 131CB | 148CG | 29.95 |
| 148CE1 | 131CB | 148N | 69.27 | 148CE1 | 131CB | 148C | 60.00 |
| 148CE1 | 131CB | 61ND1 | 57.48 | 61CE1 | 131CB | 148ND1 | 73.80 |
| 61CE1 | 131CB | 148CG | 91.81 | 61CE1 | 131CB | 148C | 93.93 |
| 61CE1 | 131CB | 61ND1 | 16.02 | 148ND1 | 131CB | 148CG | 18.02 |
| 148ND1 | 131CB | 148N | 54.81 | 148ND1 | 131CB | 148C | 42.69 |
| 148ND1 | 131CB | 61ND1 | 68.89 | 148CG | 131CB | 148N | 39.36 |
| 148CG | 131CB | 148C | 38.54 | 148CG | 131CB | 61ND1 | 86.14 |
| 148N | 131CB | 148C | 31.66 | 148C | 131CB | 61ND1 | 98.62 |
| 148O | 131C | 148N | 37.37 | 148N | 131O | 148O | 44.95 |
| 148N | 131O | 148C | 32.33 | 148N | 131O | 148CA | 13.20 |
| 148O | 131O | 148C | 12.85 | 148O | 131O | 148CA | 31.80 |
| 148C | 131O | 148CA | 19.13 | 131O | 148N | 131C | 11.83 |
| 131O | 148N | 131CB | 44.24 | 131O | 148N | 131N | 38.86 |
| 131O | 148N | 131CA | 29.72 | 131C | 148N | 131CB | 32.41 |
| 131C | 148N | 131N | 32.25 | 131C | 148N | 131CA | 19.13 |
| 131CB | 148N | 131N | 32.34 | 131CB | 148N | 131CA | 18.99 |
| 131N | 148N | 131CA | 18.15 | 131O | 148CA | 131N | 34.00 |

Figure 13C

| Atom 1 | Atom 2 | Atom 3 | Angle | Atom 1 | Atom 2 | Atom 3 | Angle |
|---|---|---|---|---|---|---|---|
| 131CB | 148CE1 | 61ND1 | 70.14 | 131CB | 148CE1 | 61CG | 87.74 |
| 131CB | 148CE1 | 61CE1 | 60.59 | 131CB | 148CE1 | 61CD2 | 87.10 |
| 131CB | 148CE1 | 61NE2 | 71.26 | 61ND1 | 148CE1 | 61CG | 18.52 |
| 61ND1 | 148CE1 | 61CE1 | 16.74 | 61ND1 | 148CE1 | 61CD2 | 28.08 |
| 61ND1 | 148CE1 | 61CB | 32.50 | 61ND1 | 148CE1 | 61CA | 49.71 |
| 61ND1 | 148CE1 | 61NE2 | 26.67 | 61CG | 148CE1 | 61CE1 | 28.54 |
| 61CG | 148CE1 | 61CD2 | 17.02 | 61CG | 148CE1 | 61CB | 18.75 |
| 61CG | 148CE1 | 61CA | 32.50 | 61CG | 148CE1 | 61NE2 | 27.41 |
| 61CE1 | 148CE1 | 61CD2 | 27.52 | 61CE1 | 148CE1 | 61CB | 46.34 |
| 61CE1 | 148CE1 | 61CA | 60.86 | 61CE1 | 148CE1 | 61NE2 | 16.00 |
| 61CD2 | 148CE1 | 61CB | 32.66 | 61CD2 | 148CE1 | 61CA | 39.09 |
| 61CD2 | 148CE1 | 61NE2 | 16.68 | 61CB | 148CE1 | 61CA | 18.92 |
| 61CB | 148CE1 | 61NE2 | 45.92 | 61CA | 148CE1 | 61NE2 | 55.42 |
| 131CB | 148NE2 | 61ND1 | 64.94 | 131N | 148C | 129O | 51.62 |
| 131N | 148C | 131O | 36.94 | 131N | 148C | 131CB | 31.72 |
| 131N | 148C | 131CA | 15.22 | 129O | 148C | 131O | 88.46 |
| 129O | 148C | 131CB | 68.45 | 129O | 148C | 131CA | 62.93 |
| 131O | 148C | 131CB | 38.96 | 131O | 148C | 131CA | 29.36 |
| 131CB | 148C | 131CA | 18.33 | 131N | 148O | 131CA | 19.47 |
| 131N | 148O | 131CB | 40.86 | 131N | 148O | 131O | 47.43 |
| 131N | 148O | 129O | 67.80 | 131N | 148O | 131C | 32.92 |
| 131N | 148O | 129C | 60.01 | 131CA | 148O | 131CB | 23.57 |
| 131CA | 148O | 131O | 37.54 | 131CA | 148O | 129O | 81.73 |
| 131CA | 148O | 131C | 20.95 | 131CA | 148O | 129C | 76.15 |
| 131CB | 148O | 131O | 48.60 | 131CB | 148O | 129O | 86.85 |
| 131CB | 148O | 131C | 35.24 | 131CB | 148O | 129C | 85.69 |
| 131O | 148O | 131C | 16.59 | 129O | 148O | 129C | 11.83 |
| 131C | 148O | 129C | 92.92 | 129CB | 152SG | 129N | 31.00 |
| 129CB | 152SG | 129CA | 15.62 | 129CB | 152SG | 129OG | 13.31 |
| 129N | 152SG | 129CA | 16.86 | 129N | 152SG | 129OG | 44.10 |
| 129CA | 152SG | 129OG | 27.89 | 157N | 156N | 157CA | 4.31 |
| 157N | 156N | 157O | 37.33 | 157N | 156N | 157C | 22.91 |
| 157N | 156N | 157CB | 16.22 | 157CA | 156N | 157O | 33.09 |
| 157CA | 156N | 157C | 18.77 | 157CA | 156N | 157CB | 16.57 |
| 157O | 156N | 157C | 14.65 | 157O | 156N | 157CB | 41.91 |
| 157C | 156N | 157CB | 30.44 | 157N | 156CA | 157CA | 9.28 |
| 157N | 156CA | 157O | 32.35 | 157N | 156CA | 157C | 21.11 |
| 157N | 156CA | 157CB | 10.98 | 157CA | 156CA | 157O | 33.51 |
| 157CA | 156CA | 157C | 18.98 | 157CA | 156CA | 157CB | 15.89 |
| 157O | 156CA | 157C | 15.80 | 157O | 156CA | 157CB | 43.10 |
| 157C | 156CA | 157CB | 31.92 | 157N | 156CB | 157CA | 9.84 |
| 157N | 156CG | 129OG | 91.04 | 157N | 156C | 157CA | 31.55 |
| 157N | 156C | 157C | 41.25 | 157N | 156C | 157O | 44.51 |
| 157N | 156C | 157CB | 24.42 | 157N | 156C | 157CG | 43.37 |

Figure 13D

| Atom 1 | Atom 2 | Atom 3 | Angle | Atom 1 | Atom 2 | Atom 3 | Angle |
|---|---|---|---|---|---|---|---|
| 157CA | 156C | 157C | 26.80 | 157CA | 156C | 157O | 44.67 |
| 157CA | 156C | 157CB | 19.42 | 157CA | 156C | 157CG | 38.68 |
| 157C | 156C | 157O | 20.88 | 157C | 156C | 157CB | 43.93 |
| 157C | 156C | 157CG | 65.27 | 157O | 156C | 157CB | 57.59 |
| 157O | 156C | 157CG | 80.41 | 157CB | 156C | 157CG | 22.87 |
| 157N | 156O | 157CA | 32.63 | 157N | 156O | 157C | 43.65 |
| 157N | 156O | 157O | 40.81 | 157N | 156O | 157CB | 32.60 |
| 157N | 156O | 157CG | 45.85 | 157CA | 156O | 157C | 25.15 |
| 157CA | 156O | 157O | 37.46 | 157CA | 156O | 157CB | 14.38 |
| 157CA | 156O | 157CG | 35.30 | 157C | 156O | 157O | 17.80 |
| 157C | 156O | 157CB | 39.53 | 157C | 156O | 157CG | 60.29 |
| 157O | 156O | 157CB | 50.62 | 157O | 156O | 157CG | 71.80 |
| 157CB | 156O | 157CG | 21.25 | 156C | 157N | 156O | 28.15 |
| 156C | 157N | 156CA | 34.99 | 156C | 157N | 156N | 65.94 |
| 156C | 157N | 156CB | 40.62 | 156C | 157N | 156CG | 55.08 |
| 156O | 157N | 156CA | 63.13 | 156O | 157N | 156N | 93.80 |
| 156O | 157N | 156CB | 64.30 | 156O | 157N | 156CG | 80.42 |
| 156CA | 157N | 156N | 31.91 | 156CA | 157N | 156CB | 23.76 |
| 156CA | 157N | 156CG | 27.51 | 156N | 157N | 156CB | 45.42 |
| 156N | 157N | 156CG | 34.38 | 156CB | 157N | 156CG | 16.54 |
| 156C | 157CA | 156O | 27.04 | 156C | 157CA | 156CA | 12.72 |
| 156C | 157CA | 156N | 32.74 | 156C | 157CA | 156CB | 19.54 |
| 156O | 157CA | 156CA | 39.76 | 156O | 157CA | 156N | 59.49 |
| 156O | 157CA | 156CB | 40.29 | 156CA | 157CA | 156N | 20.36 |
| 156CA | 157CA | 156CB | 17.01 | 156N | 157CA | 156CB | 31.47 |
| 156C | 157CB | 156O | 17.61 | 156C | 157CB | 156CA | 13.56 |
| 156C | 157CB | 156N | 29.34 | 156O | 157CB | 156CA | 30.75 |
| 156O | 157CB | 156N | 46.94 | 156CA | 157CB | 156N | 17.30 |
| 156C | 157CG | 156O | 16.90 | 156C | 157C | 156O | 20.61 |
| 156C | 157C | 156CA | 13.16 | 156C | 157C | 156N | 30.83 |
| 156O | 157C | 156CA | 32.27 | 156O | 157C | 156N | 50.49 |
| 156CA | 157C | 156N | 18.22 | 156C | 157O | 156O | 17.58 |
| 156C | 157O | 156N | 36.58 | 156C | 157O | 156CA | 18.11 |
| 156O | 157O | 156N | 52.93 | 156O | 157O | 156CA | 33.44 |
| 156N | 157O | 156CA | 19.58 | | | | |

Figure 14

| | Phi<br>$C_{n-1}-N_n-C_{An}-C$ | Psi<br>$N-CA-C-N_{n+1}$ | Omega 1<br>$CA_{n-1}-C_{n-1}-N_n-CA_n$ | Omega 2<br>$CA_n-C_n-N_{n+1}-CA_{n+1}$ | Chi1<br>N-CA-CB-CG | Chi2<br>CA-CD-CG-XD |
|---|---|---|---|---|---|---|
| Ser129 | -150.1 | 113.4 | 179.3 | 179.9 | 172.9 | |
| His148 | -170.5 | 170.8 | 179.1 | 178.0 | 59.3 | 95.0 |
| His61 | 46.4 | -0.4 | 178.5 | 177.3 | -75.0 | 118.9 |

Figure 15

| | Phi $C_{n-1}-N_n-C_{An}-C$ | Psi $N-CA-C-N_{n+1}$ | Omega 1 $CA_{n-1}-C_{n-1}-N_n-CA_n$ | Omega 2 $CA_n-C_n-N_{n+1}-CA_{n+1}$ | Chi1 $N-CA-CB-CG$ | Chi2 $CA-CD-CG-XD$ |
|---|---|---|---|---|---|---|
| Ser129 | -140.4 | 123.5 | 179.7 | 179.6 | -175.8 | |
| His148 | -159.5 | -173.0 | 178.9 | 179.0 | 63.6 | 91.6 |
| His61 | 67.4 | 0.6 | 179.0 | 178.0 | -62.0 | -75.9 |

Figure 16

| | Phi $C_{n-1}-N_n-C_{An}-C$ | Psi $N-CA-C-N_{n+1}$ | Omega 1 $CA_{n-1}-C_{n-1}-N_n-CA_n$ | Omega 2 $CA_n-C_n-N_{n+1}-CA_{n+1}$ | Chi1 $N-CA-CB-CG$ | Chi2 $CA-CD-CG-XD$ |
|---|---|---|---|---|---|---|
| Ser129 | -151.5 | 119.5 | 179.3 | -170.5 | 172.9 | |
| His61 | 36.3 | 22.0 | 178.5 | 171.9 | -61.0 | -150.1 |
| His148 | -170.5 | 170.8 | 179.1 | 177.9 | 59.3 | 95.0 |

Figure 17A

| CRYST1 | 58.7 | 58.7 | 131.0 | 90.00 | 90.00 | 90.00 | 90.00 | P4₃22 | | |
|---|---|---|---|---|---|---|---|---|---|---|
| | | Residue | | | | | | | | |
| Atom | | AA | No. | X | Y | Z | | Occup'y | B Factor |
| ATOM | 1 | N | HIS | 63 | 32.880001 | 14.629000 | 8.245000 | 1.00 | 37.16 |
| ATOM | 2 | Cα | HIS | 63 | 33.591000 | 14.522000 | 6.961000 | 1.00 | 37.70 |
| ATOM | 3 | Cβ | HIS | 63 | 32.750000 | 13.848000 | 5.900000 | 1.00 | 33.47 |
| ATOM | 4 | Cγ | HIS | 63 | 32.007000 | 12.649000 | 6.383000 | 1.00 | 33.87 |
| ATOM | 5 | Cδ2 | HIS | 63 | 30.681000 | 12.452000 | 6.569000 | 1.00 | 33.18 |
| ATOM | 6 | Nδ1 | HIS | 63 | 32.612999 | 11.434000 | 6.615000 | 1.00 | 32.84 |
| ATOM | 7 | Cε1 | HIS | 63 | 31.691000 | 10.534000 | 6.904000 | 1.00 | 34.18 |
| ATOM | 8 | Nε2 | HIS | 63 | 30.510000 | 11.128000 | 6.886000 | 1.00 | 35.62 |
| ATOM | 9 | C | HIS | 63 | 34.087002 | 15.815000 | 6.320000 | 1.00 | 39.66 |
| ATOM | 10 | O | HIS | 63 | 34.634998 | 15.758000 | 5.226000 | 1.00 | 45.41 |
| ATOM | 11 | N | ASP | 65 | 36.516998 | 18.048000 | 5.389000 | 1.00 | 43.05 |
| ATOM | 12 | Cα | ASP | 65 | 37.967999 | 17.917000 | 5.469000 | 1.00 | 44.01 |

Figure 17B

| Atom | | Residue AA | No. | X | Y | Z | Occup'y | B Factor |
|---|---|---|---|---|---|---|---|---|
| ATOM | 13 | Cβ | ASP | 65 | 38.580002 | 17.417999 | 4.172000 | 1.00 | 48.74 |
| ATOM | 14 | Cγ | ASP | 65 | 38.945999 | 15.933000 | 4.246000 | 1.00 | 59.43 |
| ATOM | 15 | Oδ1 | ASP | 65 | 39.431999 | 15.451000 | 5.316000 | 1.00 | 61.90 |
| ATOM | 16 | Oδ2 | ASP | 65 | 38.706001 | 15.214000 | 3.244000 | 1.00 | 69.17 |
| ATOM | 17 | C | ASP | 65 | 38.757999 | 19.056000 | 6.036000 | 1.00 | 43.54 |
| ATOM | 18 | O | ASP | 65 | 39.959000 | 18.917000 | 6.271000 | 1.00 | 44.62 |
| ATOM | 19 | N | SER | 132 | 31.841000 | 7.353000 | 11.712000 | 1.00 | 33.66 |
| ATOM | 20 | Cα | SER | 132 | 31.664000 | 7.028000 | 10.296000 | 1.00 | 36.58 |
| ATOM | 21 | Cβ | SER | 132 | 30.868999 | 8.143000 | 9.624000 | 1.00 | 42.29 |
| ATOM | 22 | Oγ | SER | 132 | 30.243999 | 7.722000 | 8.425000 | 1.00 | 52.62 |
| ATOM | 23 | C | SER | 132 | 33.043999 | 6.951000 | 9.712000 | 1.00 | 33.26 |
| ATOM | 24 | O | SER | 132 | 33.858002 | 7.819000 | 9.936000 | 1.00 | 36.06 |
| ATOM | 25 | N | SER | 134 | 35.426998 | 6.727000 | 6.434000 | 1.00 | 43.43 |

Figure 17C

| Atom | | Residue AA | No. | X | Y | Z | Occup'y | B Factor |
|---|---|---|---|---|---|---|---|---|
| ATOM | 26 | Cα | SER | 134 | 35.398998 | 7.060000 | 5.004000 | 1.00 | 45.24 |
| ATOM | 27 | Cβ | SER | 134 | 35.264000 | 8.566000 | 4.788000 | 1.00 | 45.50 |
| ATOM | 28 | Oγ | SER | 134 | 36.527000 | 9.208000 | 4.914000 | 1.00 | 47.60 |
| ATOM | 29 | C | SER | 134 | 36.659000 | 6.527000 | 4.298000 | 1.00 | 46.95 |
| ATOM | 30 | O | SER | 134 | 37.787998 | 6.762000 | 4.753000 | 1.00 | 44.83 |
| ATOM | 31 | N | HIS | 157 | 39.505001 | 8.498000 | 6.198000 | 1.00 | 39.55 |
| ATOM | 32 | Cα | HIS | 157 | 39.470001 | 9.159000 | 7.516000 | 1.00 | 37.74 |
| ATOM | 33 | Cβ | HIS | 157 | 39.282001 | 10.681000 | 7.348000 | 1.00 | 36.93 |
| ATOM | 34 | Cγ | HIS | 157 | 37.972000 | 11.068000 | 6.714000 | 1.00 | 37.30 |
| ATOM | 35 | Cδ2 | HIS | 157 | 36.688999 | 10.772000 | 7.049000 | 1.00 | 34.05 |
| ATOM | 36 | Nδ1 | HIS | 157 | 37.898998 | 11.835000 | 5.574000 | 1.00 | 36.80 |
| ATOM | 37 | Cε1 | HIS | 157 | 36.636002 | 11.989000 | 5.228000 | 1.00 | 32.40 |
| ATOM | 38 | Nε2 | HIS | 157 | 35.882999 | 11.352000 | 6.105000 | 1.00 | 30.28 |

Figure 17D

| Atom | | Residue AA | No. | X | Y | Z | Occup'y | B Factor |
|---|---|---|---|---|---|---|---|---|
| ATOM | 39 | C | HIS | 157 | 38.316002 | 8.662000 | 8.365000 | 1.00 | 36.07 |
| ATOM | 40 | O | HIS | 157 | 37.532001 | 7.827000 | 7.909000 | 1.00 | 38.95 |
| ATOM | 41 | N | CYS | 161 | 29.908001 | 12.239000 | 13.796000 | 1.00 | 23.63 |
| ATOM | 42 | Cα | CYS | 161 | 28.625999 | 12.628000 | 13.235000 | 1.00 | 26.97 |
| ATOM | 43 | Cβ | CYS | 161 | 28.229000 | 11.594000 | 12.179000 | 1.00 | 30.92 |
| ATOM | 44 | Sγ | CYS | 161 | 29.539000 | 10.997000 | 11.202000 | 1.00 | 37.06 |
| ATOM | 45 | C | CYS | 161 | 27.500999 | 12.689000 | 14.261000 | 1.00 | 26.94 |
| ATOM | 46 | O | CYS | 161 | 27.638000 | 12.164000 | 15.366000 | 1.00 | 31.09 |
| ATOM | 47 | N | ARG | 165 | 25.921000 | 5.944000 | 10.186000 | 1.00 | 38.28 |
| ATOM | 48 | Cα | ARG | 165 | 24.966999 | 5.345000 | 9.241000 | 1.00 | 41.26 |
| ATOM | 49 | Cβ | ARG | 165 | 25.389999 | 5.613000 | 7.786000 | 1.00 | 42.30 |
| ATOM | 50 | C | ARG | 165 | 24.823999 | 3.847000 | 9.510000 | 1.00 | 42.27 |
| ATOM | 51 | O | ARG | 165 | 23.714001 | 3.300000 | 9.536000 | 1.00 | 46.30 |

Figure 17E

| Atom | | Residue AA | No. | X | Y | Z | Occup'y | B Factor |
|---|---|---|---|---|---|---|---|---|
| ATOM 52 | N | ARG | 166 | 25.959000 | 3.176000 | 9.654000 | 1.00 | 42.55 |
| ATOM 53 | Cα | ARG | 166 | 25.969999 | 1.760000 | 9.964000 | 1.00 | 42.91 |
| ATOM 54 | Cβ | ARG | 166 | 27.375000 | 1.214000 | 9.766000 | 1.00 | 47.77 |
| ATOM 55 | Cγ | ARG | 166 | 27.632999 | 0.619000 | 8.402000 | 1.00 | 54.62 |
| ATOM 56 | Cδ | ARG | 166 | 29.046000 | 0.078000 | 8.317000 | 1.00 | 60.07 |
| ATOM 57 | Nε | ARG | 166 | 30.000000 | 1.185000 | 8.308000 | 1.00 | 66.48 |
| ATOM 58 | Cζ | ARG | 166 | 30.875000 | 1.403000 | 7.318000 | 1.00 | 72.12 |
| ATOM 59 | NH1 | ARG | 166 | 31.709000 | 2.447000 | 7.369000 | 1.00 | 73.13 |
| ATOM 60 | NH2 | ARG | 166 | 30.945000 | 0.557000 | 6.277000 | 1.00 | 75.29 |
| ATOM 61 | C | ARG | 166 | 25.583000 | 1.743000 | 11.440000 | 1.00 | 42.23 |
| ATOM 62 | O | ARG | 166 | 25.955999 | 2.643000 | 12.192000 | 1.00 | 42.86 |
| ATOM 63 | O | H₂O | 336 | 31.416000 | 3.648000 | 9.731000 | 1.00 | 29.21 |
| ATOM 64 | ORGN | | | 0.000000 | 0.000000 | 0.000000 | 0.000000 | |

Figure 18A

| ATOM 1 | ATOM 2 | DISTANCE BETWEEN (°A) | ATOM 1 | ATOM 2 | DISTANCE BETWEEN (°A) |
|---|---|---|---|---|---|
| 63 N | 157 Nε2 | 4.8 | 63 Cε1 | 132 O | 4.5 |
| 63 Cα | 157 Nε2 | 4.0 | 63 Cε1 | 132 C | 4.8 |
| 63 Cα | 157 Cε1 | 4.3 | 63 Cε1 | 161 Sγ | 4.9 |
| 63 Cα | 65 N | 4.8 | | | |
| 63 Cα | 157 Cδ2 | 4.9 | 63 Nε2 | 32 Oγ | 3.3 |
| 63 Cß | 157 Nε2 | 4.1 | 63 Nε2 | 132 Cß | 4.6 |
| 63 Cß | 157 Cε1 | 4.4 | 63 Nε2 | 161 Sγ | 4.4 |
| 63 Cγ | 157 Nε2 | 4.0 | 63 C | 65 N | 3.4 |
| 63 Cγ | 157 Cε1 | 4.7 | 63 C | 65 Cα | 4.5 |
| 63 Cδ2 | 132 Oγ | 4.5 | 63 C | 157 Cε1 | 4.7 |
| 63 Nδ1 | 157 Nε2 | 3.2 | 63 C | 157 Nε2 | 4.8 |
| 63 Nδ1 | 157 Cγ2 | 4.2 | 63 O | 65 N | 2.9 |
| 63 Nδ1 | 157 Cε1 | 4.2 | 63 O | 65 Cα | 4.0 |
| 63 Nδ1 | 134 Cß | 4.3 | 63 O | 157 Cε1 | 4.3 |
| 63 Nδ1 | 132 Oγ | 4.2 | 63 O | 65 Cß | 4.4 |
| | | | 63 O | 65 Cγ | 4.4 |
| 63 Nδ1 | 134 Oγ | 4.8 | 63 O | 65 Oδ2 | 4.7 |
| 63 Cε1 | 132 Oγ | 3.0 | 63 O | 157 Nε2 | 4.7 |
| 63 Cε1 | 132 Cß | 4.4 | 63 O | 65 Oδ1 | 4.7 |
| 63 Cε1 | 157 Nε2 | 4.3 | 65 Cγ | 157 Nδ1 | 4.4 |
| 63 Cε1 | 134 Cß | 4.6 | 65 Cγ | 157 Cε1 | 4.8 |

Figure 18B

| ATOM 1 | ATOM 2 | DISTANCE BETWEEN (°A) | ATOM 1 | ATOM 2 | DISTANCE BETWEEN (°A) |
|---|---|---|---|---|---|
| 65 Oδ1 | 157 Nδ1 | 3.9 | 65 Oδ1 | 157 Cε1 | 4.4 |
| 65 Oδ1 | 157 Cγ | 4.7 | 65 Oδ2 | 157 Nδ1 | 4.2 |
| 65 Oδ2 | 157 Cε1 | 4.5 | 132 N | 336 O | 4.2 |
| 132 N | 161 Sγ | 4.3 | 132 Cα | 336 O | 3.2 |
| 132 Cα | 161 Sγ | 4.8 | 132 Cß | 161 Sγ | 4.2 |
|  |  |  | 132 Cß | 165 N | 4.9 |
| 132 Cß | 336 O | 3.8 | 132 Oγ | 161 Sγ | 3.6 |
| 132 C | 336 O | 3.6 | 132 C | 134 N | 4.1 |
|  |  |  | 132 O | 134 N | 4.0 |
| 132 O | 157 O | 4.4 |  |  |  |
| 132 O | 336 O | 4.8 | 134 N | 157 O | 2.8 |
| 134 N | 157 C | 4.0 | 134 N | 157 Cδ2 | 4.4 |
| 134 N | 157 N | 4.5 | 134 N | 157 Nε2 | 4.6 |
| 134 N | 157 Cα | 4.9 | 134 Cα | 157 O | 3.7 |
| 134 Cα | 157 Cδ2 | 4.5 | 134 Cα | 157 Nε2 | 4.5 |
| 134 Cα | 157 N | 4.5 | 134 Cα | 157 C | 4.8 |
| 134 Cß | 157 Nε2 | 3.1 | 134 Cß | 157 Cδ2 | 3.5 |
| 134 Cß | 157 Cε1 | 3.6 | 134 Cß | 157 O | 3.9 |
| 134 Cß | 157 Cγ | 4.1 | 134 Cß | 157 Nδ1 | 4.2 |
| 134 Cß | 157 N | 4.5 | 134 Cß | 157 C | 4.7 |
| 134 Oγ | 157 Nε2 | 2.6 | 134 Oγ | 157 Cδ2 | 2.7 |

Figure 18C

| ATOM 1 | ATOM 2 | DISTANCE BETWEEN (°A) | ATOM 1 | ATOM 2 | DISTANCE BETWEEN (°A) |
|---|---|---|---|---|---|
| 134 Oγ | 157 Cε1 | 2.8 | 134 Oγ | 157 Cγ | 3.0 |
| 134 Oγ | 157 Nδ1 | 3.0 | 134 Oγ | 157 N | 3.3 |
| 134 Oγ | 157 O | 3.3 | 134 Oγ | 157 C | 3.8 |
| 134 Oγ | 157 Cα | 3.9 | 134 Oγ | 157 Cß | 3.9 |
| 134 C | 157 O | 3.9 | 134 C | 157 N | 4.0 |
| 134 C | 157 C | 4.9 | 134 O | 157 N | 2.9 |
| 134 O | 157 O | 3.3 | 134 O | 157 Cα | 4.1 |
| 134 O | 157 C | 4.2 | 134 O | 157 Cγ | 4.8 |
| 134 O | 157 Cδ2 | 4.8 | | | |
| 165 Cα | 166 N | 2.4 | 165 Cα | 166 Cα | 3.8 |
| 165 Cα | 166 O | 4.1 | 165 Cα | 166 C | 4.3 |
| 165 Cα | 166 Cß | 4.8 | 165 Cß | 166 N | 3.1 |
| 165 Cß | 166 Cα | 4.5 | 165 C | 166 N | 1.3 |
| 165 C | 166 Cα | 2.4 | 165 C | 166 C | 3.0 |
| 165 C | 166 O | 3.2 | 165 C | 166 Cß | 3.7 |
| 165 C | 166 Cγ | 4.4 | 165 O | 166 N | 2.3 |
| 165 O | 166 Cα | 2.8 | 165 O | 166 C | 3.1 |
| 165 O | 166 O | 3.5 | 165 O | 166 Cß | 4.2 |
| 165 O | 166 Cγ | 4.9 | 166 Cß | 336 O | 4.8 |
| 166 Cδ | 336 O | 4.5 | 166 Nε | 336 O | 3.2 |
| 166 CZ | 336 O | 3.3 | 166 NH1 | 336 O | 2.7 |
| 166 NH2 | 336 O | 4.7 | | | |

Figure 19A

| ATOM 1 | MIDDLE ATOM | ATOM 3 | ANGLE ° |
| --- | --- | --- | --- |
| 63Cε1 | 63Nδ1 | 157Nε2 | 134 |
| 63Cγ | 63Nδ1 | 157Nε2 | 118 |
| 63Nε2 | 63Nδ1 | 157Nε2 | 168 |
| 63Cδ2 | 63Nδ1 | 157Nε2 | 155 |
| 63Cß | 63Nδ1 | 157Nε2 | 80 |
| 63Cα | 63Nδ1 | 157Nε2 | 70 |
| 63Nδ1 | 63Cε1 | 132Oγ | 146 |
| 63Nδ1 | 63Cε1 | 132Cß | 147 |
| 63Nε2 | 63Cε1 | 132Oγ | 89 |
| 63Nε2 | 63Cε1 | 132Cß | 93 |
| 63Cδ2 | 63Cε1 | 132Oγ | 123 |
| 63Cδ2 | 63Cε1 | 132Cß | 127 |
| 63Cγ | 63Cε1 | 132Oγ | 149 |
| 63Cγ | 63Cε1 | 132Cß | 154 |
| 132Oγ | 63Cε1 | 132Cß | 5 |
| 63Cß | 63Cε1 | 132Cß | 158 |
| 63Cε1 | 63Nε2 | 132Oγ | 67 |
| 63Cδ2 | 63Nε2 | 132Oγ | 153 |
| 63Nδ1 | 63Nε2 | 132Oγ | 98 |
| 63Cγ | 63Nε2 | 132Oγ | 130 |

Figure 19B

| ATOM 1 | MIDDLE ATOM | ATOM 3 | ANGLE ° |
|---|---|---|---|
| 63Cβ | 63Nε2 | 132Oγ | 136 |
| 63Cα | 63C | 65N | 153 |
| 63Cβ | 63C | 65N | 152 |
| 63N | 63C | 65N | 146 |
| 63C | 63O | 65N | 103 |
| 63C | 63O | 65Cα | 108 |
| 63Cα | 63O | 65N | 130 |
| 63Cα | 63O | 65Cα | 128 |
| 63Cβ | 63O | 65N | 162 |
| 63Cβ | 63O | 65Cα | 159 |
| 65N | 63O | 65Cα | 18 |
| 63N | 63O | 65Cα | 121 |
| 65Cα | 65N | 63O | 125 |
| 65Cα | 65N | 63C | 130 |
| 65Cβ | 65N | 63O | 108 |
| 65Cβ | 65N | 63C | 124 |
| 65C | 65N | 63O | 152 |
| 65C | 65N | 63C | 146 |
| 63O | 65N | 63C | 20 |
| 65Cγ | 65N | 63C | 101 |
| 65N | 65CA | 63O | 38 |

Figure 19C

| ATOM 1 | MIDDLE ATOM | ATOM 3 | ANGLE ° |
| --- | --- | --- | --- |
| 65C | 65Cα | 63O | 152 |
| 65Cβ | 65Cα | 63O | 96 |
| 65O | 65Cα | 63O | 164 |
| 65Cγ | 65Cα | 63O | 83 |
| 65Oδ1 | 65Cα | 63O | 86 |
| 65Oδ2 | 65Cα | 63O | 76 |
| 65Cγ | 65Oδ1 | 157Nδ1 | 107 |
| 65Oδ2 | 65Oδ1 | 157Nδ1 | 83 |
| 65Cβ | 65Oδ1 | 157Nδ1 | 131 |
| 65Cα | 65Oδ1 | 157Nδ1 | 129 |
| 65O | 65Oδ1 | 157Nδ1 | 160 |
| 65C | 65Oδ1 | 157Nδ1 | 146 |
| 65N | 65Oδ1 | 157Nδ1 | 110 |
| 132Oγ | 132Cβ | 63Cε1 | 11 |
| 132Cα | 132Cβ | 63Cε1 | 111 |
| 132N | 132Cβ | 63Cε1 | 112 |
| 132C | 132Cβ | 63Cε1 | 83 |
| 132O | 132Cβ | 63Cε1 | 71 |
| 132Cβ | 132Oγ | 63Cε1 | 164 |
| 132Cβ | 132Oγ | 63Nε2 | 163 |
| 132Cα | 132Oγ | 63Cε1 | 139 |

Figure 19D

| ATOM 1 | MIDDLE ATOM | ATOM 3 | ANGLE ° |
|---|---|---|---|
| 132Cα | 132Oγ | 63Nε2 | 162 |
| 132C | 132Oγ | 63Cε1 | 109 |
| 132C | 132Oγ | 63Nε2 | 133 |
| 63Cε1 | 132Oγ | 63Nε2 | 24 |
| 132N | 132Oγ | 63Nε2 | 148 |
| 157Cγ | 157Nδ1 | 65Oδ1 | 119 |
| 157Nε2 | 157Nδ1 | 65Oδ1 | 125 |
| 157Cδ2 | 157Nδ1 | 65Oδ1 | 131 |
| 157Cβ | 157Nδ1 | 65Oδ1 | 102 |
| 157Cα | 157Nδ1 | 65Oδ1 | 121 |
| 157N | 157Nδ1 | 65Oδ1 | 130 |
| 157Cε1 | 157Nε2 | 63Nδ1 | 128 |
| 157Cδ2 | 157Nε2 | 63Nδ1 | 126 |
| 157Nδ1 | 157Nε2 | 63Nδ1 | 161 |
| 157Cγ | 157Nε2 | 63Nδ1 | 160 |

Figure 20

| | Phi $C_{n-1}-N_n-C_{An}-C$ | Psi $N-CA-C-N_{n+1}$ | Omega 1 $CA_{n-1}-C_{n-1}-N_n-CA_n$ | Omega 2 $CA_n-C_n-N_{n+1}-CA_{n+1}$ | Chi1 $N-CA-CB-CG$ | Chi2 $CA-CD-CG-XD$ |
|---|---|---|---|---|---|---|
| Ser132 | -152 | 133 | 176 | -176 | 86 | — |
| His63 | 68 | -4 | -180 | 179 | -47 | -71 |
| His157 | 177 | 180 | -178 | 177 | 64 | -123 |
| Asp65 | -66 | -7 | -178 | 177 | -102 | -33 |

Figure 21A

| | | | | | | | | |
|---|---|---|---|---|---|---|---|---|
| CRYST1 | 58.7 | | 58.7 | 131.0 | 90.00 | 90.00 | 90.00 | P4322 |
| SCALE1 | | 0.01703 | 0.00000 | 0.00000 | | 0.00000 | | |
| SCALE2 | | 0.00000 | 0.01703 | 0.00000 | | 0.00000 | | |
| SCALE3 | | 0.00000 | 0.00000 | 0.00763 | | 0.00000 | | |
| ATOM | 1 | CB | GLU | 9 | 41.534 | 21.636 | 33.140 | 1.00 62.86 |
| ATOM | 4 | N | GLU | 9 | 42.716 | 22.008 | 30.930 | 1.00 62.91 |
| ATOM | 5 | CA | GLU | 9 | 41.969 | 21.019 | 31.798 | 1.00 63.33 |
| ATOM | 2 | C | GLU | 9 | 40.771 | 20.456 | 31.058 | 1.00 61.56 |
| ATOM | 3 | O | GLU | 9 | 40.829 | 19.324 | 30.627 | 1.00 62.88 |
| ATOM | 1 | CB | GLU | 9 | 41.534 | 21.636 | 33.140 | 1.00 62.86 |
| ATOM | 6 | N | ALA | 10 | 39.681 | 21.220 | 30.958 | 1.00 61.86 |
| ATOM | 7 | CA | ALA | 10 | 38.494 | 20.780 | 30.215 | 1.00 60.47 |
| ATOM | 9 | C | ALA | 10 | 38.939 | 20.765 | 28.752 | 1.00 60.20 |
| ATOM | 10 | O | ALA | 10 | 38.451 | 20.001 | 27.919 | 1.00 57.60 |
| ATOM | 8 | CB | ALA | 10 | 37.360 | 21.760 | 30.419 | 1.00 61.05 |
| ATOM | 11 | N | VAL | 11 | 39.861 | 21.668 | 28.448 | 1.00 60.59 |
| ATOM | 12 | CA | VAL | 11 | 40.454 | 21.740 | 27.121 | 1.00 61.51 |
| ATOM | 16 | C | VAL | 11 | 41.763 | 20.883 | 27.198 | 1.00 61.40 |
| ATOM | 17 | O | VAL | 11 | 42.895 | 21.400 | 27.320 | 1.00 65.52 |
| ATOM | 13 | CB | VAL | 11 | 40.674 | 23.242 | 26.691 | 1.00 62.09 |
| ATOM | 14 | CG1 | VAL | 11 | 41.642 | 23.342 | 25.496 | 1.00 61.02 |
| ATOM | 15 | CG2 | VAL | 11 | 39.311 | 23.891 | 26.339 | 1.00 53.35 |
| ATOM | 18 | N | ALA | 12 | 41.556 | 19.570 | 27.275 | 1.00 54.83 |
| ATOM | 19 | CA | ALA | 12 | 42.612 | 18.580 | 27.366 | 1.00 49.08 |
| ATOM | 21 | C | ALA | 12 | 42.120 | 17.568 | 26.386 | 1.00 45.83 |
| ATOM | 22 | O | ALA | 12 | 40.960 | 17.604 | 26.052 | 1.00 50.77 |
| ATOM | 20 | CB | ALA | 12 | 42.626 | 17.994 | 28.738 | 1.00 50.51 |
| ATOM | 23 | N | PRO | 13 | 42.934 | 16.581 | 25.996 | 1.00 42.62 |
| ATOM | 25 | CA | PRO | 13 | 42.385 | 15.631 | 25.020 | 1.00 38.99 |
| ATOM | 28 | C | PRO | 13 | 41.130 | 14.905 | 25.460 | 1.00 32.92 |
| ATOM | 29 | O | PRO | 13 | 40.847 | 14.770 | 26.649 | 1.00 35.39 |
| ATOM | 26 | CB | PRO | 13 | 43.542 | 14.642 | 24.782 | 1.00 41.06 |
| ATOM | 27 | CG | PRO | 13 | 44.740 | 15.396 | 25.178 | 1.00 43.00 |
| ATOM | 24 | CD | PRO | 13 | 44.266 | 16.145 | 26.423 | 1.00 44.44 |
| ATOM | 30 | N | VAL | 14 | 40.350 | 14.519 | 24.473 | 1.00 25.41 |
| ATOM | 31 | CA | VAL | 14 | 39.142 | 13.783 | 24.696 | 1.00 25.42 |
| ATOM | 35 | C | VAL | 14 | 39.339 | 12.569 | 23.782 | 1.00 26.70 |
| ATOM | 36 | O | VAL | 14 | 39.695 | 12.730 | 22.621 | 1.00 28.81 |
| ATOM | 32 | CB | VAL | 14 | 37.894 | 14.577 | 24.212 | 1.00 24.85 |
| ATOM | 33 | CG1 | VAL | 14 | 36.626 | 13.806 | 24.489 | 1.00 27.96 |
| ATOM | 34 | CG2 | VAL | 14 | 37.830 | 15.921 | 24.846 | 1.00 23.28 |
| ATOM | 37 | N | TYR | 15 | 39.277 | 11.368 | 24.335 | 1.00 22.49 |
| ATOM | 38 | CA | TYR | 15 | 39.378 | 10.173 | 23.541 | 1.00 18.63 |
| ATOM | 47 | C | TYR | 15 | 37.954 | 9.771 | 23.256 | 1.00 18.44 |
| ATOM | 48 | O | TYR | 15 | 37.058 | 10.063 | 24.033 | 1.00 20.57 |
| ATOM | 39 | CB | TYR | 15 | 40.080 | 9.085 | 24.306 | 1.00 21.59 |
| ATOM | 40 | CG | TYR | 15 | 41.542 | 9.405 | 24.478 | 1.00 27.13 |
| ATOM | 41 | CD1 | TYR | 15 | 41.963 | 10.367 | 25.402 | 1.00 26.70 |

Figure 21B

| ATOM | 43 | CD2 | TYR | 15 | 42.515 | 8.744 | 23.703 | 1.00 | 29.84 |
|---|---|---|---|---|---|---|---|---|---|
| ATOM | 42 | CE1 | TYR | 15 | 43.298 | 10.666 | 25.553 | 1.00 | 26.64 |
| ATOM | 44 | CE2 | TYR | 15 | 43.843 | 9.027 | 23.845 | 1.00 | 28.52 |
| ATOM | 45 | CZ | TYR | 15 | 44.227 | 9.990 | 24.771 | 1.00 | 34.44 |
| ATOM | 46 | OH | TYR | 15 | 45.567 | 10.264 | 24.905 | 1.00 | 46.06 |
| ATOM | 49 | N | VAL | 16 | 37.732 | 9.203 | 22.080 | 1.00 | 20.53 |
| ATOM | 50 | CA | VAL | 16 | 36.414 | 8.756 | 21.649 | 1.00 | 17.84 |
| ATOM | 54 | C | VAL | 16 | 36.641 | 7.332 | 21.202 | 1.00 | 18.98 |
| ATOM | 55 | O | VAL | 16 | 37.738 | 7.005 | 20.763 | 1.00 | 20.12 |
| ATOM | 51 | CB | VAL | 16 | 35.810 | 9.664 | 20.532 | 1.00 | 15.49 |
| ATOM | 52 | CG1 | VAL | 16 | 36.785 | 9.863 | 19.365 | 1.00 | 12.77 |
| ATOM | 53 | CG2 | VAL | 16 | 34.516 | 9.079 | 20.057 | 1.00 | 14.93 |
| ATOM | 56 | N | GLY | 17 | 35.666 | 6.447 | 21.398 | 1.00 | 19.44 |
| ATOM | 57 | CA | GLY | 17 | 35.897 | 5.069 | 21.006 | 1.00 | 14.35 |
| ATOM | 58 | C | GLY | 17 | 34.610 | 4.512 | 20.533 | 1.00 | 16.22 |
| ATOM | 59 | O | GLY | 17 | 33.562 | 5.031 | 20.868 | 1.00 | 18.87 |
| ATOM | 60 | N | GLY | 18 | 34.669 | 3.500 | 19.693 | 1.00 | 18.00 |
| ATOM | 61 | CA | GLY | 18 | 33.436 | 2.941 | 19.230 | 1.00 | 16.95 |
| ATOM | 62 | C | GLY | 18 | 33.640 | 2.066 | 18.039 | 1.00 | 19.29 |
| ATOM | 63 | O | GLY | 18 | 34.723 | 1.998 | 17.490 | 1.00 | 20.24 |
| ATOM | 64 | N | PHE | 19 | 32.564 | 1.417 | 17.636 | 1.00 | 22.41 |
| ATOM | 65 | CA | PHE | 19 | 32.586 | 0.545 | 16.504 | 1.00 | 27.48 |
| ATOM | 73 | C | PHE | 19 | 32.296 | 1.338 | 15.238 | 1.00 | 29.03 |
| ATOM | 74 | O | PHE | 19 | 31.310 | 2.084 | 15.168 | 1.00 | 28.29 |
| ATOM | 66 | CB | PHE | 19 | 31.546 | -0.587 | 16.696 | 1.00 | 32.20 |
| ATOM | 67 | CG | PHE | 19 | 31.959 | -1.632 | 17.741 | 1.00 | 38.36 |
| ATOM | 68 | CD1 | PHE | 19 | 31.758 | -1.398 | 19.105 | 1.00 | 35.34 |
| ATOM | 69 | CD2 | PHE | 19 | 32.627 | -2.812 | 17.356 | 1.00 | 36.45 |
| ATOM | 70 | CE1 | PHE | 19 | 32.219 | -2.302 | 20.041 | 1.00 | 34.55 |
| ATOM | 71 | CE2 | PHE | 19 | 33.093 | -3.731 | 18.297 | 1.00 | 33.01 |
| ATOM | 72 | CZ | PHE | 19 | 32.895 | -3.479 | 19.631 | 1.00 | 37.50 |
| ATOM | 75 | N | LEU | 20 | 33.196 | 1.196 | 14.266 | 1.00 | 30.89 |
| ATOM | 76 | CA | LEU | 20 | 33.072 | 1.812 | 12.942 | 1.00 | 32.67 |
| ATOM | 81 | C | LEU | 20 | 32.215 | 0.912 | 12.037 | 1.00 | 34.96 |
| ATOM | 82 | O | LEU | 20 | 31.651 | 1.377 | 11.031 | 1.00 | 31.94 |
| ATOM | 77 | CB | LEU | 20 | 34.435 | 1.915 | 12.279 | 1.00 | 33.81 |
| ATOM | 78 | CG | LEU | 20 | 35.361 | 2.921 | 12.913 | 1.00 | 34.20 |
| ATOM | 79 | CD1 | LEU | 20 | 36.708 | 2.830 | 12.254 | 1.00 | 36.26 |
| ATOM | 80 | CD2 | LEU | 20 | 34.756 | 4.270 | 12.701 | 1.00 | 34.94 |
| ATOM | 83 | N | ALA | 21 | 32.146 | -0.374 | 12.400 | 1.00 | 35.25 |
| ATOM | 84 | CA | ALA | 21 | 31.410 | -1.366 | 11.627 | 1.00 | 35.19 |
| ATOM | 86 | C | ALA | 21 | 31.222 | -2.658 | 12.385 | 1.00 | 35.36 |
| ATOM | 87 | O | ALA | 21 | 32.124 | -3.155 | 13.038 | 1.00 | 35.57 |
| ATOM | 85 | CB | ALA | 21 | 32.166 | -1.667 | 10.323 | 1.00 | 36.73 |
| ATOM | 88 | N | ARG | 22 | 30.051 | -3.230 | 12.240 | 1.00 | 37.54 |
| ATOM | 89 | CA | ARG | 22 | 29.744 | -4.481 | 12.881 | 1.00 | 42.49 |
| ATOM | 97 | C | ARG | 22 | 29.800 | -5.638 | 11.909 | 1.00 | 43.79 |
| ATOM | 98 | O | ARG | 22 | 29.916 | -5.466 | 10.705 | 1.00 | 47.98 |
| ATOM | 90 | CB | ARG | 22 | 28.338 | -4.417 | 13.461 | 1.00 | 46.25 |
| ATOM | 91 | CG | ARG | 22 | 28.258 | -3.651 | 14.759 | 1.00 | 49.18 |
| ATOM | 92 | CD | ARG | 22 | 28.025 | -4.622 | 15.889 | 1.00 | 50.35 |
| ATOM | 93 | NE | ARG | 22 | 28.767 | -4.220 | 17.069 | 1.00 | 47.50 |
| ATOM | 94 | CZ | ARG | 22 | 28.661 | -4.817 | 18.243 | 1.00 | 43.85 |
| ATOM | 95 | NH1 | ARG | 22 | 27.852 | -5.850 | 18.385 | 1.00 | 43.35 |

Figure 21C

| ATOM | 96 | NH2 | ARG | 22 | 29.377 | -4.381 | 19.267 | 1.00 | 48.14 |
|---|---|---|---|---|---|---|---|---|---|
| ATOM | 99 | N | TYR | 23 | 29.841 | -6.824 | 12.480 | 1.00 | 45.08 |
| ATOM | 100 | CA | TYR | 23 | 29.810 | -8.085 | 11.765 | 1.00 | 43.13 |
| ATOM | 109 | C | TYR | 23 | 28.553 | -8.677 | 12.448 | 1.00 | 51.17 |
| ATOM | 110 | O | TYR | 23 | 28.269 | -9.862 | 12.384 | 1.00 | 51.37 |
| ATOM | 101 | CB | TYR | 23 | 31.083 | -8.871 | 12.084 | 1.00 | 33.90 |
| ATOM | 102 | CG | TYR | 23 | 32.396 | -8.126 | 11.774 | 1.00 | 28.23 |
| ATOM | 103 | CD1 | TYR | 23 | 32.413 | -6.989 | 11.001 | 1.00 | 28.88 |
| ATOM | 105 | CD2 | TYR | 23 | 33.617 | -8.560 | 12.284 | 1.00 | 31.62 |
| ATOM | 104 | CE1 | TYR | 23 | 33.609 | -6.297 | 10.744 | 1.00 | 28.45 |
| ATOM | 106 | CE2 | TYR | 23 | 34.828 | -7.870 | 12.033 | 1.00 | 26.20 |
| ATOM | 107 | CZ | TYR | 23 | 34.808 | -6.738 | 11.272 | 1.00 | 26.64 |
| ATOM | 108 | OH | TYR | 23 | 35.955 | -5.981 | 11.093 | 1.00 | 29.32 |
| ATOM | 111 | N | ASP | 24 | 27.851 | -7.762 | 13.130 | 1.00 | 58.25 |
| ATOM | 112 | CA | ASP | 24 | 26.614 | -7.886 | 13.918 | 1.00 | 63.11 |
| ATOM | 117 | C | ASP | 24 | 26.435 | -8.359 | 15.386 | 1.00 | 63.57 |
| ATOM | 118 | O | ASP | 24 | 25.267 | -8.531 | 15.810 | 1.00 | 63.99 |
| ATOM | 113 | CB | ASP | 24 | 25.442 | -8.280 | 13.038 | 1.00 | 61.93 |
| ATOM | 114 | CG | ASP | 24 | 24.707 | -7.048 | 12.545 | 1.00 | 64.79 |
| ATOM | 115 | OD1 | ASP | 24 | 24.278 | -6.214 | 13.412 | 1.00 | 65.40 |
| ATOM | 116 | OD2 | ASP | 24 | 24.642 | -6.866 | 11.307 | 1.00 | 63.98 |
| ATOM | 123 | N | ALA | 56 | 47.806 | 7.903 | 12.460 | 1.00 | 59.91 |
| ATOM | 124 | CA | ALA | 56 | 46.875 | 7.183 | 11.545 | 1.00 | 58.34 |
| ATOM | 121 | C | ALA | 56 | 45.851 | 8.180 | 11.008 | 1.00 | 55.13 |
| ATOM | 122 | O | ALA | 56 | 46.087 | 9.389 | 11.060 | 1.00 | 55.11 |
| ATOM | 120 | CB | ALA | 56 | 46.172 | 6.018 | 12.291 | 1.00 | 58.09 |
| ATOM | 125 | N | LEU | 57 | 44.745 | 7.649 | 10.483 | 1.00 | 51.20 |
| ATOM | 126 | CA | LEU | 57 | 43.641 | 8.405 | 9.919 | 1.00 | 43.58 |
| ATOM | 131 | C | LEU | 57 | 43.284 | 9.682 | 10.678 | 1.00 | 44.00 |
| ATOM | 132 | O | LEU | 57 | 43.308 | 9.706 | 11.912 | 1.00 | 39.30 |
| ATOM | 127 | CB | LEU | 57 | 42.409 | 7.514 | 9.863 | 1.00 | 41.84 |
| ATOM | 128 | CG | LEU | 57 | 42.544 | 6.214 | 9.086 | 1.00 | 38.95 |
| ATOM | 129 | CD1 | LEU | 57 | 41.181 | 5.670 | 8.644 | 1.00 | 36.90 |
| ATOM | 130 | CD2 | LEU | 57 | 43.363 | 6.560 | 7.902 | 1.00 | 35.63 |
| ATOM | 133 | N | PRO | 58 | 43.002 | 10.778 | 9.940 | 1.00 | 43.35 |
| ATOM | 135 | CA | PRO | 58 | 42.646 | 12.015 | 10.617 | 1.00 | 40.99 |
| ATOM | 138 | C | PRO | 58 | 41.187 | 11.849 | 11.033 | 1.00 | 39.53 |
| ATOM | 139 | O | PRO | 58 | 40.395 | 11.143 | 10.392 | 1.00 | 37.00 |
| ATOM | 136 | CB | PRO | 58 | 42.808 | 13.062 | 9.516 | 1.00 | 40.54 |
| ATOM | 137 | CG | PRO | 58 | 42.298 | 12.347 | 8.350 | 1.00 | 39.45 |
| ATOM | 134 | CD | PRO | 58 | 42.912 | 10.958 | 8.477 | 1.00 | 42.41 |
| ATOM | 140 | N | LEU | 59 | 40.884 | 12.419 | 12.181 | 1.00 | 37.87 |
| ATOM | 141 | CA | LEU | 59 | 39.565 | 12.373 | 12.748 | 1.00 | 34.28 |
| ATOM | 146 | C | LEU | 59 | 39.054 | 13.731 | 12.336 | 1.00 | 30.93 |
| ATOM | 147 | O | LEU | 59 | 39.756 | 14.741 | 12.489 | 1.00 | 34.98 |
| ATOM | 142 | CB | LEU | 59 | 39.670 | 12.338 | 14.293 | 1.00 | 32.87 |
| ATOM | 143 | CG | LEU | 59 | 39.170 | 11.239 | 15.237 | 1.00 | 28.44 |
| ATOM | 144 | CD1 | LEU | 59 | 39.064 | 11.797 | 16.680 | 1.00 | 28.76 |
| ATOM | 145 | CD2 | LEU | 59 | 37.828 | 10.763 | 14.787 | 1.00 | 26.44 |
| ATOM | 148 | N | ASN | 60 | 37.887 | 13.774 | 11.740 | 1.00 | 29.17 |
| ATOM | 149 | CA | ASN | 60 | 37.328 | 15.059 | 11.422 | 1.00 | 31.43 |
| ATOM | 154 | C | ASN | 60 | 35.868 | 15.099 | 11.806 | 1.00 | 29.73 |
| ATOM | 155 | O | ASN | 60 | 35.281 | 14.081 | 12.205 | 1.00 | 30.65 |
| ATOM | 150 | CB | ASN | 60 | 37.535 | 15.437 | 9.959 | 1.00 | 31.90 |

Figure 21D

| ATOM | 151 | CG | ASN | 60 | 36.819 | 14.540 | 9.016 | 1.00 | 28.44 |
|---|---|---|---|---|---|---|---|---|---|
| ATOM | 152 | OD1 | ASN | 60 | 35.633 | 14.283 | 9.153 | 1.00 | 31.36 |
| ATOM | 153 | ND2 | ASN | 60 | 37.534 | 14.091 | 8.003 | 1.00 | 35.05 |
| ATOM | 156 | N | ILE | 61 | 35.295 | 16.281 | 11.678 | 1.00 | 26.50 |
| ATOM | 157 | CA | ILE | 61 | 33.908 | 16.483 | 12.017 | 1.00 | 31.39 |
| ATOM | 162 | C | ILE | 61 | 33.008 | 16.414 | 10.755 | 1.00 | 32.16 |
| ATOM | 163 | O | ILE | 61 | 33.238 | 17.096 | 9.772 | 1.00 | 34.15 |
| ATOM | 158 | CB | ILE | 61 | 33.695 | 17.843 | 12.810 | 1.00 | 27.75 |
| ATOM | 160 | CG1 | ILE | 61 | 34.467 | 17.856 | 14.134 | 1.00 | 17.65 |
| ATOM | 159 | CG2 | ILE | 61 | 32.244 | 18.075 | 13.075 | 1.00 | 25.73 |
| ATOM | 161 | CD1 | ILE | 61 | 34.057 | 16.786 | 15.063 | 1.00 | 19.49 |
| ATOM | 164 | N | ASN | 62 | 32.068 | 15.482 | 10.778 | 1.00 | 34.30 |
| ATOM | 165 | CA | ASN | 62 | 31.110 | 15.305 | 9.727 | 1.00 | 36.14 |
| ATOM | 170 | C | ASN | 62 | 31.724 | 15.247 | 8.327 | 1.00 | 38.20 |
| ATOM | 171 | O | ASN | 62 | 31.133 | 15.735 | 7.353 | 1.00 | 40.25 |
| ATOM | 166 | CB | ASN | 62 | 30.084 | 16.424 | 9.855 | 1.00 | 41.53 |
| ATOM | 167 | CG | ASN | 62 | 28.668 | 15.915 | 9.839 | 1.00 | 50.38 |
| ATOM | 168 | OD1 | ASN | 62 | 27.901 | 16.093 | 10.807 | 1.00 | 53.37 |
| ATOM | 169 | ND2 | ASN | 62 | 28.295 | 15.283 | 8.734 | 1.00 | 52.09 |
| ATOM | 172 | N | HIS | 63 | 32.904 | 14.647 | 8.212 | 1.00 | 37.80 |
| ATOM | 173 | CA | HIS | 63 | 33.585 | 14.536 | 6.920 | 1.00 | 38.53 |
| ATOM | 174 | C | HIS | 63 | 34.089 | 15.835 | 6.297 | 1.00 | 40.67 |
| ATOM | 175 | O | HIS | 63 | 34.665 | 15.795 | 5.217 | 1.00 | 46.88 |
| ATOM | 176 | CB | HIS | 63 | 32.692 | 13.894 | 5.883 | 1.00 | 33.48 |
| ATOM | 177 | CG | HIS | 63 | 32.012 | 12.655 | 6.360 | 1.00 | 34.46 |
| ATOM | 178 | ND1 | HIS | 63 | 32.650 | 11.463 | 6.594 | 1.00 | 32.89 |
| ATOM | 179 | CD2 | HIS | 63 | 30.684 | 12.410 | 6.543 | 1.00 | 33.18 |
| ATOM | 181 | CE1 | HIS | 63 | 31.716 | 10.546 | 6.885 | 1.00 | 32.87 |
| ATOM | 180 | NE2 | HIS | 63 | 30.502 | 11.073 | 6.870 | 1.00 | 35.51 |
| ATOM | 182 | N | ASP | 64 | 33.824 | 16.981 | 6.904 | 1.00 | 38.28 |
| ATOM | 183 | CA | ASP | 64 | 34.302 | 18.233 | 6.359 | 1.00 | 36.79 |
| ATOM | 188 | C | ASP | 64 | 35.792 | 18.139 | 6.510 | 1.00 | 40.50 |
| ATOM | 189 | O | ASP | 64 | 36.266 | 18.264 | 7.625 | 1.00 | 41.47 |
| ATOM | 184 | CB | ASP | 64 | 33.819 | 19.371 | 7.229 | 1.00 | 39.15 |
| ATOM | 185 | CG | ASP | 64 | 34.280 | 20.729 | 6.740 | 1.00 | 45.12 |
| ATOM | 186 | OD1 | ASP | 64 | 35.289 | 20.832 | 5.997 | 1.00 | 47.63 |
| ATOM | 187 | OD2 | ASP | 64 | 33.616 | 21.727 | 7.130 | 1.00 | 52.05 |
| ATOM | 190 | N | ASP | 65 | 36.539 | 18.046 | 5.407 | 1.00 | 42.46 |
| ATOM | 191 | CA | ASP | 65 | 37.992 | 17.914 | 5.497 | 1.00 | 43.12 |
| ATOM | 196 | C | ASP | 65 | 38.781 | 19.063 | 6.051 | 1.00 | 42.62 |
| ATOM | 197 | O | ASP | 65 | 39.992 | 18.935 | 6.265 | 1.00 | 43.71 |
| ATOM | 192 | CB | ASP | 65 | 38.616 | 17.402 | 4.209 | 1.00 | 46.43 |
| ATOM | 193 | CG | ASP | 65 | 38.980 | 15.918 | 4.294 | 1.00 | 58.98 |
| ATOM | 194 | OD1 | ASP | 65 | 39.355 | 15.409 | 5.390 | 1.00 | 62.06 |
| ATOM | 195 | OD2 | ASP | 65 | 38.867 | 15.231 | 3.256 | 1.00 | 67.86 |
| ATOM | 198 | N | THR | 66 | 38.112 | 20.183 | 6.303 | 1.00 | 41.56 |
| ATOM | 199 | CA | THR | 66 | 38.793 | 21.333 | 6.900 | 1.00 | 40.94 |
| ATOM | 203 | C | THR | 66 | 38.621 | 21.342 | 8.441 | 1.00 | 39.77 |
| ATOM | 204 | O | THR | 66 | 39.348 | 22.049 | 9.154 | 1.00 | 41.93 |
| ATOM | 200 | CB | THR | 66 | 38.283 | 22.658 | 6.289 | 1.00 | 43.33 |
| ATOM | 201 | OG1 | THR | 66 | 37.049 | 23.050 | 6.909 | 1.00 | 47.53 |
| ATOM | 202 | CG2 | THR | 66 | 38.039 | 22.477 | 4.801 | 1.00 | 39.24 |
| ATOM | 205 | N | ALA | 67 | 37.673 | 20.522 | 8.925 | 1.00 | 34.31 |
| ATOM | 206 | CA | ALA | 67 | 37.306 | 20.377 | 10.332 | 1.00 | 25.72 |

Figure 21E

| ATOM | 208 | C   | ALA | 67 | 38.006 | 19.185 | 10.954 | 1.00 | 27.24 |
|------|-----|-----|-----|----|--------|--------|--------|------|-------|
| ATOM | 209 | O   | ALA | 67 | 37.352 | 18.359 | 11.559 | 1.00 | 28.36 |
| ATOM | 207 | CB  | ALA | 67 | 35.819 | 20.168 | 10.426 | 1.00 | 18.91 |
| ATOM | 210 | N   | VAL | 68 | 39.312 | 19.045 | 10.772 | 1.00 | 27.63 |
| ATOM | 211 | CA  | VAL | 68 | 40.008 | 17.902 | 11.341 | 1.00 | 27.26 |
| ATOM | 215 | C   | VAL | 68 | 40.308 | 18.224 | 12.773 | 1.00 | 28.89 |
| ATOM | 216 | O   | VAL | 68 | 40.919 | 19.237 | 13.076 | 1.00 | 28.74 |
| ATOM | 212 | CB  | VAL | 68 | 41.239 | 17.566 | 10.550 | 1.00 | 26.97 |
| ATOM | 213 | CG1 | VAL | 68 | 42.171 | 16.655 | 11.343 | 1.00 | 23.43 |
| ATOM | 214 | CG2 | VAL | 68 | 40.778 | 16.883 | 9.269  | 1.00 | 22.68 |
| ATOM | 217 | N   | VAL | 69 | 39.863 | 17.351 | 13.665 | 1.00 | 29.30 |
| ATOM | 218 | CA  | VAL | 69 | 39.999 | 17.623 | 15.083 | 1.00 | 27.08 |
| ATOM | 222 | C   | VAL | 69 | 40.970 | 16.778 | 15.843 | 1.00 | 27.21 |
| ATOM | 223 | O   | VAL | 69 | 41.182 | 17.025 | 17.020 | 1.00 | 27.27 |
| ATOM | 219 | CB  | VAL | 69 | 38.637 | 17.547 | 15.765 | 1.00 | 26.23 |
| ATOM | 220 | CG1 | VAL | 69 | 37.617 | 18.423 | 14.998 | 1.00 | 24.62 |
| ATOM | 221 | CG2 | VAL | 69 | 38.168 | 16.117 | 15.812 | 1.00 | 24.71 |
| ATOM | 224 | N   | GLY | 70 | 41.574 | 15.813 | 15.160 | 1.00 | 25.43 |
| ATOM | 225 | CA  | GLY | 70 | 42.537 | 14.934 | 15.784 | 1.00 | 26.47 |
| ATOM | 226 | C   | GLY | 70 | 42.859 | 13.756 | 14.883 | 1.00 | 29.60 |
| ATOM | 227 | O   | GLY | 70 | 42.546 | 13.779 | 13.694 | 1.00 | 32.40 |
| ATOM | 228 | N   | HIS | 71 | 43.355 | 12.677 | 15.475 | 1.00 | 29.41 |
| ATOM | 229 | CA  | HIS | 71 | 43.770 | 11.490 | 14.740 | 1.00 | 28.39 |
| ATOM | 236 | C   | HIS | 71 | 43.259 | 10.230 | 15.432 | 1.00 | 29.26 |
| ATOM | 237 | O   | HIS | 71 | 42.832 | 10.275 | 16.566 | 1.00 | 32.50 |
| ATOM | 230 | CB  | HIS | 71 | 45.280 | 11.442 | 14.786 | 1.00 | 31.71 |
| ATOM | 231 | CG  | HIS | 71 | 45.818 | 11.420 | 16.188 | 1.00 | 36.79 |
| ATOM | 233 | ND1 | HIS | 71 | 45.936 | 12.563 | 16.953 | 1.00 | 39.46 |
| ATOM | 232 | CD2 | HIS | 71 | 46.206 | 10.396 | 16.979 | 1.00 | 40.16 |
| ATOM | 234 | CE1 | HIS | 71 | 46.378 | 12.240 | 18.155 | 1.00 | 45.55 |
| ATOM | 235 | NE2 | HIS | 71 | 46.550 | 10.931 | 18.201 | 1.00 | 44.70 |
| ATOM | 238 | N   | VAL | 72 | 43.368 | 9.097  | 14.762 | 1.00 | 30.12 |
| ATOM | 239 | CA  | VAL | 72 | 42.964 | 7.819  | 15.302 | 1.00 | 27.63 |
| ATOM | 243 | C   | VAL | 72 | 44.211 | 7.228  | 15.906 | 1.00 | 31.61 |
| ATOM | 244 | O   | VAL | 72 | 45.226 | 7.100  | 15.218 | 1.00 | 35.21 |
| ATOM | 240 | CB  | VAL | 72 | 42.524 | 6.905  | 14.206 | 1.00 | 25.86 |
| ATOM | 241 | CG1 | VAL | 72 | 42.140 | 5.564  | 14.755 | 1.00 | 26.21 |
| ATOM | 242 | CG2 | VAL | 72 | 41.387 | 7.541  | 13.450 | 1.00 | 28.96 |
| ATOM | 245 | N   | ALA | 73 | 44.134 | 6.908  | 17.199 | 1.00 | 31.08 |
| ATOM | 246 | CA  | ALA | 73 | 45.236 | 6.329  | 17.966 | 1.00 | 31.72 |
| ATOM | 248 | C   | ALA | 73 | 45.424 | 4.802  | 17.790 | 1.00 | 31.44 |
| ATOM | 249 | O   | ALA | 73 | 46.555 | 4.322  | 17.828 | 1.00 | 35.11 |
| ATOM | 247 | CB  | ALA | 73 | 45.061 | 6.657  | 19.451 | 1.00 | 23.78 |
| ATOM | 250 | N   | ALA | 74 | 44.325 | 4.069  | 17.600 | 1.00 | 28.56 |
| ATOM | 251 | CA  | ALA | 74 | 44.327 | 2.621  | 17.467 | 1.00 | 25.12 |
| ATOM | 253 | C   | ALA | 74 | 43.077 | 2.149  | 16.749 | 1.00 | 27.57 |
| ATOM | 254 | O   | ALA | 74 | 42.078 | 2.844  | 16.705 | 1.00 | 33.33 |
| ATOM | 252 | CB  | ALA | 74 | 44.359 | 2.009  | 18.806 | 1.00 | 22.03 |
| ATOM | 255 | N   | MET | 75 | 43.137 | 0.955  | 16.195 | 1.00 | 27.43 |
| ATOM | 256 | CA  | MET | 75 | 42.032 | 0.350  | 15.465 | 1.00 | 30.16 |
| ATOM | 261 | C   | MET | 75 | 42.200 | -1.132 | 15.734 | 1.00 | 31.88 |
| ATOM | 262 | O   | MET | 75 | 43.309 | -1.564 | 16.048 | 1.00 | 38.15 |
| ATOM | 257 | CB  | MET | 75 | 42.137 | 0.620  | 13.972 | 1.00 | 31.38 |
| ATOM | 258 | CG  | MET | 75 | 41.463 | 1.885  | 13.478 | 1.00 | 34.40 |

Figure 21F

| | | | | | | | | | |
|---|---|---|---|---|---|---|---|---|---|
| ATOM | 259 | SD | MET | 75 | 40.518 | 1.487 | 11.975 | 1.00 | 44.35 |
| ATOM | 260 | CE | MET | 75 | 40.613 | 2.988 | 11.127 | 1.00 | 45.26 |
| ATOM | 263 | N | GLN | 76 | 41.134 | -1.911 | 15.647 | 1.00 | 30.46 |
| ATOM | 264 | CA | GLN | 76 | 41.232 | -3.320 | 15.949 | 1.00 | 33.80 |
| ATOM | 270 | C | GLN | 76 | 40.013 | -4.010 | 15.501 | 1.00 | 36.87 |
| ATOM | 271 | O | GLN | 76 | 38.928 | -3.575 | 15.871 | 1.00 | 36.72 |
| ATOM | 265 | CB | GLN | 76 | 41.247 | -3.535 | 17.461 | 1.00 | 35.06 |
| ATOM | 266 | CG | GLN | 76 | 42.572 | -3.388 | 18.123 | 1.00 | 38.58 |
| ATOM | 267 | CD | GLN | 76 | 43.245 | -4.710 | 18.319 | 1.00 | 44.71 |
| ATOM | 268 | OE1 | GLN | 76 | 42.645 | -5.648 | 18.850 | 1.00 | 47.69 |
| ATOM | 269 | NE2 | GLN | 76 | 44.494 | -4.815 | 17.870 | 1.00 | 49.16 |
| ATOM | 272 | N | SER | 77 | 40.158 | -5.100 | 14.747 | 1.00 | 42.23 |
| ATOM | 273 | CA | SER | 77 | 38.970 | -5.873 | 14.356 | 1.00 | 46.68 |
| ATOM | 276 | C | SER | 77 | 38.752 | -6.793 | 15.532 | 1.00 | 48.65 |
| ATOM | 277 | O | SER | 77 | 39.582 | -7.622 | 15.876 | 1.00 | 53.74 |
| ATOM | 274 | CB | SER | 77 | 39.144 | -6.714 | 13.070 | 1.00 | 50.01 |
| ATOM | 275 | OG | SER | 77 | 37.898 | -7.259 | 12.608 | 1.00 | 45.65 |
| ATOM | 278 | N | VAL | 78 | 37.747 | -6.446 | 16.284 | 1.00 | 50.11 |
| ATOM | 279 | CA | VAL | 78 | 37.348 | -7.206 | 17.421 | 1.00 | 49.45 |
| ATOM | 283 | C | VAL | 78 | 36.405 | -8.256 | 16.781 | 1.00 | 51.72 |
| ATOM | 284 | O | VAL | 78 | 35.999 | -8.122 | 15.618 | 1.00 | 54.42 |
| ATOM | 280 | CB | VAL | 78 | 36.661 | -6.225 | 18.365 | 1.00 | 49.01 |
| ATOM | 281 | CG1 | VAL | 78 | 35.336 | -6.760 | 18.923 | 1.00 | 49.51 |
| ATOM | 282 | CG2 | VAL | 78 | 37.647 | -5.805 | 19.403 | 1.00 | 48.72 |
| ATOM | 285 | N | ARG | 79 | 36.070 | -9.305 | 17.508 | 1.00 | 49.34 |
| ATOM | 286 | CA | ARG | 79 | 35.206 | -10.325 | 16.948 | 1.00 | 50.82 |
| ATOM | 289 | C | ARG | 79 | 33.859 | -9.834 | 16.411 | 1.00 | 48.32 |
| ATOM | 290 | O | ARG | 79 | 33.346 | -10.394 | 15.419 | 1.00 | 48.68 |
| ATOM | 287 | CB | ARG | 79 | 34.988 | -11.436 | 17.970 | 1.00 | 55.34 |
| ATOM | 288 | CG | ARG | 79 | 34.603 | -10.892 | 19.226 | 1.00 | 64.21 |
| ATOM | 291 | N | ASP | 80 | 33.285 | -8.826 | 17.080 | 1.00 | 42.03 |
| ATOM | 292 | CA | ASP | 80 | 31.985 | -8.266 | 16.700 | 1.00 | 35.98 |
| ATOM | 297 | C | ASP | 80 | 32.025 | -7.108 | 15.713 | 1.00 | 33.25 |
| ATOM | 298 | O | ASP | 80 | 30.967 | -6.626 | 15.287 | 1.00 | 28.18 |
| ATOM | 293 | CB | ASP | 80 | 31.267 | -7.762 | 17.920 | 1.00 | 39.29 |
| ATOM | 294 | CG | ASP | 80 | 30.521 | -8.820 | 18.618 | 1.00 | 44.58 |
| ATOM | 295 | OD1 | ASP | 80 | 29.645 | -9.409 | 17.977 | 1.00 | 44.97 |
| ATOM | 296 | OD2 | ASP | 80 | 30.787 | -9.041 | 19.825 | 1.00 | 53.61 |
| ATOM | 299 | N | GLY | 81 | 33.221 | -6.611 | 15.411 | 1.00 | 28.25 |
| ATOM | 300 | CA | GLY | 81 | 33.323 | -5.504 | 14.485 | 1.00 | 24.48 |
| ATOM | 301 | C | GLY | 81 | 34.685 | -4.857 | 14.471 | 1.00 | 24.50 |
| ATOM | 302 | O | GLY | 81 | 35.671 | -5.398 | 14.951 | 1.00 | 26.60 |
| ATOM | 303 | N | LEU | 82 | 34.767 | -3.672 | 13.925 | 1.00 | 24.01 |
| ATOM | 304 | CA | LEU | 82 | 36.056 | -3.040 | 13.885 | 1.00 | 28.02 |
| ATOM | 309 | C | LEU | 82 | 35.941 | -1.861 | 14.785 | 1.00 | 30.82 |
| ATOM | 310 | O | LEU | 82 | 35.154 | -0.944 | 14.555 | 1.00 | 35.51 |
| ATOM | 305 | CB | LEU | 82 | 36.409 | -2.661 | 12.459 | 1.00 | 27.07 |
| ATOM | 306 | CG | LEU | 82 | 37.223 | -1.417 | 12.186 | 1.00 | 24.56 |
| ATOM | 307 | CD1 | LEU | 82 | 38.730 | -1.657 | 12.349 | 1.00 | 19.11 |
| ATOM | 308 | CD2 | LEU | 82 | 36.823 | -1.057 | 10.741 | 1.00 | 21.38 |
| ATOM | 311 | N | PHE | 83 | 36.606 | -2.006 | 15.911 | 1.00 | 32.41 |
| ATOM | 312 | CA | PHE | 83 | 36.640 | -1.012 | 16.959 | 1.00 | 29.23 |
| ATOM | 320 | C | PHE | 83 | 37.720 | 0.060 | 16.697 | 1.00 | 30.66 |
| ATOM | 321 | O | PHE | 83 | 38.838 | -0.251 | 16.328 | 1.00 | 34.10 |

Figure 21G

| ATOM | 313 | CB  | PHE | 83 | 36.869 | -1.732 | 18.297 | 1.00 | 24.26 |
| ATOM | 314 | CG  | PHE | 83 | 36.705 | -0.861 | 19.459 | 1.00 | 19.69 |
| ATOM | 315 | CD1 | PHE | 83 | 35.439 | -0.645 | 19.996 | 1.00 | 24.66 |
| ATOM | 316 | CD2 | PHE | 83 | 37.785 | -0.193 | 19.983 | 1.00 | 17.19 |
| ATOM | 317 | CE1 | PHE | 83 | 35.260 |  0.237 | 21.056 | 1.00 | 23.22 |
| ATOM | 318 | CE2 | PHE | 83 | 37.626 |  0.684 | 21.027 | 1.00 | 21.02 |
| ATOM | 319 | CZ  | PHE | 83 | 36.363 |  0.903 | 21.565 | 1.00 | 25.05 |
| ATOM | 322 | N   | CYS | 84 | 37.397 |  1.316 | 16.949 | 1.00 | 31.52 |
| ATOM | 323 | CA  | CYS | 84 | 38.326 |  2.398 | 16.725 | 1.00 | 32.29 |
| ATOM | 326 | C   | CYS | 84 | 38.381 |  3.256 | 17.967 | 1.00 | 31.97 |
| ATOM | 327 | O   | CYS | 84 | 37.351 |  3.485 | 18.598 | 1.00 | 34.84 |
| ATOM | 324 | CB  | CYS | 84 | 37.804 |  3.230 | 15.542 | 1.00 | 37.31 |
| ATOM | 325 | SG  | CYS | 84 | 38.364 |  4.960 | 15.396 | 1.00 | 40.75 |
| ATOM | 328 | N   | LEU | 85 | 39.568 |  3.695 | 18.351 | 1.00 | 28.35 |
| ATOM | 329 | CA  | LEU | 85 | 39.695 |  4.584 | 19.491 | 1.00 | 29.63 |
| ATOM | 334 | C   | LEU | 85 | 40.407 |  5.763 | 18.897 | 1.00 | 31.03 |
| ATOM | 335 | O   | LEU | 85 | 41.477 |  5.580 | 18.326 | 1.00 | 33.68 |
| ATOM | 330 | CB  | LEU | 85 | 40.579 |  3.986 | 20.572 | 1.00 | 33.66 |
| ATOM | 331 | CG  | LEU | 85 | 41.167 |  4.969 | 21.577 | 1.00 | 33.78 |
| ATOM | 332 | CD1 | LEU | 85 | 40.107 |  5.579 | 22.470 | 1.00 | 39.41 |
| ATOM | 333 | CD2 | LEU | 85 | 42.107 |  4.201 | 22.416 | 1.00 | 39.36 |
| ATOM | 336 | N   | GLY | 86 | 39.794 |  6.944 | 18.978 | 1.00 | 28.95 |
| ATOM | 337 | CA  | GLY | 86 | 40.367 |  8.166 | 18.435 | 1.00 | 24.27 |
| ATOM | 338 | C   | GLY | 86 | 40.800 |  9.198 | 19.473 | 1.00 | 22.24 |
| ATOM | 339 | O   | GLY | 86 | 40.508 |  9.093 | 20.657 | 1.00 | 21.56 |
| ATOM | 340 | N   | CYS | 87 | 41.483 | 10.230 | 19.033 | 1.00 | 21.98 |
| ATOM | 341 | CA  | CYS | 87 | 41.929 | 11.226 | 19.966 | 1.00 | 26.67 |
| ATOM | 344 | C   | CYS | 87 | 41.635 | 12.611 | 19.412 | 1.00 | 31.30 |
| ATOM | 345 | O   | CYS | 87 | 42.197 | 13.020 | 18.395 | 1.00 | 34.32 |
| ATOM | 342 | CB  | CYS | 87 | 43.424 | 11.079 | 20.251 | 1.00 | 24.73 |
| ATOM | 343 | SG  | CYS | 87 | 43.947 | 12.153 | 21.635 | 1.00 | 48.28 |
| ATOM | 346 | N   | VAL | 88 | 40.719 | 13.320 | 20.065 | 1.00 | 34.34 |
| ATOM | 347 | CA  | VAL | 88 | 40.372 | 14.665 | 19.672 | 1.00 | 32.23 |
| ATOM | 351 | C   | VAL | 88 | 41.411 | 15.564 | 20.367 | 1.00 | 33.80 |
| ATOM | 352 | O   | VAL | 88 | 41.443 | 15.643 | 21.585 | 1.00 | 35.25 |
| ATOM | 348 | CB  | VAL | 88 | 38.938 | 14.996 | 20.090 | 1.00 | 28.12 |
| ATOM | 349 | CG1 | VAL | 88 | 38.673 | 16.482 | 19.820 | 1.00 | 25.49 |
| ATOM | 350 | CG2 | VAL | 88 | 37.943 | 14.080 | 19.324 | 1.00 | 16.62 |
| ATOM | 353 | N   | THR | 89 | 42.318 | 16.149 | 19.584 | 1.00 | 33.79 |
| ATOM | 354 | CA  | THR | 89 | 43.390 | 16.972 | 20.124 | 1.00 | 33.14 |
| ATOM | 358 | C   | THR | 89 | 43.458 | 18.424 | 19.711 | 1.00 | 32.49 |
| ATOM | 359 | O   | THR | 89 | 44.239 | 19.152 | 20.289 | 1.00 | 33.05 |
| ATOM | 355 | CB  | THR | 89 | 44.780 | 16.363 | 19.823 | 1.00 | 35.08 |
| ATOM | 356 | OG1 | THR | 89 | 44.885 | 16.070 | 18.424 | 1.00 | 35.69 |
| ATOM | 357 | CG2 | THR | 89 | 45.009 | 15.072 | 20.648 | 1.00 | 36.62 |
| ATOM | 360 | N   | SER | 90 | 42.649 | 18.857 | 18.742 | 1.00 | 31.80 |
| ATOM | 361 | CA  | SER | 90 | 42.674 | 20.239 | 18.276 | 1.00 | 27.06 |
| ATOM | 364 | C   | SER | 90 | 42.263 | 21.289 | 19.312 | 1.00 | 28.01 |
| ATOM | 365 | O   | SER | 90 | 41.084 | 21.405 | 19.640 | 1.00 | 30.53 |
| ATOM | 362 | CB  | SER | 90 | 41.769 | 20.375 | 17.083 | 1.00 | 24.45 |
| ATOM | 363 | OG  | SER | 90 | 41.487 | 21.744 | 16.873 | 1.00 | 22.16 |
| ATOM | 366 | N   | PRO | 91 | 43.200 | 22.154 | 19.748 | 1.00 | 30.63 |
| ATOM | 368 | CA  | PRO | 91 | 42.806 | 23.158 | 20.748 | 1.00 | 29.38 |
| ATOM | 371 | C   | PRO | 91 | 41.789 | 24.184 | 20.273 | 1.00 | 30.13 |

Figure 21H

| | | | | | | | | | |
|---|---|---|---|---|---|---|---|---|---|
| ATOM | 372 | O | PRO | 91 | 41.055 | 24.746 | 21.112 | 1.00 | 31.90 |
| ATOM | 369 | CB | PRO | 91 | 44.136 | 23.790 | 21.161 | 1.00 | 28.63 |
| ATOM | 370 | CG | PRO | 91 | 45.019 | 23.604 | 19.960 | 1.00 | 27.74 |
| ATOM | 367 | CD | PRO | 91 | 44.647 | 22.232 | 19.450 | 1.00 | 30.89 |
| ATOM | 373 | N | ARG | 92 | 41.746 | 24.426 | 18.948 | 1.00 | 29.72 |
| ATOM | 374 | CA | ARG | 92 | 40.793 | 25.388 | 18.357 | 1.00 | 30.28 |
| ATOM | 382 | C | ARG | 92 | 39.422 | 24.813 | 18.474 | 1.00 | 26.46 |
| ATOM | 383 | O | ARG | 92 | 38.500 | 25.516 | 18.754 | 1.00 | 28.07 |
| ATOM | 375 | CB | ARG | 92 | 41.072 | 25.701 | 16.875 | 1.00 | 35.94 |
| ATOM | 376 | CG | ARG | 92 | 42.156 | 26.784 | 16.654 | 1.00 | 46.08 |
| ATOM | 377 | CD | ARG | 92 | 42.221 | 27.323 | 15.218 | 1.00 | 51.31 |
| ATOM | 378 | NE | ARG | 92 | 41.126 | 28.254 | 14.928 | 1.00 | 59.30 |
| ATOM | 379 | CZ | ARG | 92 | 40.071 | 27.975 | 14.151 | 1.00 | 63.79 |
| ATOM | 380 | NH1 | ARG | 92 | 39.974 | 26.779 | 13.573 | 1.00 | 65.29 |
| ATOM | 381 | NH2 | ARG | 92 | 39.106 | 28.885 | 13.941 | 1.00 | 60.53 |
| ATOM | 384 | N | PHE | 93 | 39.318 | 23.506 | 18.291 | 1.00 | 26.43 |
| ATOM | 385 | CA | PHE | 93 | 38.063 | 22.800 | 18.377 | 1.00 | 24.08 |
| ATOM | 393 | C | PHE | 93 | 37.615 | 22.748 | 19.812 | 1.00 | 26.54 |
| ATOM | 394 | O | PHE | 93 | 36.517 | 23.197 | 20.133 | 1.00 | 30.25 |
| ATOM | 386 | CB | PHE | 93 | 38.216 | 21.375 | 17.845 | 1.00 | 24.37 |
| ATOM | 387 | CG | PHE | 93 | 36.950 | 20.569 | 17.886 | 1.00 | 23.16 |
| ATOM | 388 | CD1 | PHE | 93 | 35.801 | 21.031 | 17.290 | 1.00 | 18.00 |
| ATOM | 389 | CD2 | PHE | 93 | 36.917 | 19.337 | 18.520 | 1.00 | 22.53 |
| ATOM | 390 | CE1 | PHE | 93 | 34.646 | 20.274 | 17.327 | 1.00 | 21.51 |
| ATOM | 391 | CE2 | PHE | 93 | 35.747 | 18.578 | 18.555 | 1.00 | 24.70 |
| ATOM | 392 | CZ | PHE | 93 | 34.618 | 19.047 | 17.955 | 1.00 | 20.70 |
| ATOM | 395 | N | LEU | 94 | 38.468 | 22.230 | 20.689 | 1.00 | 28.43 |
| ATOM | 396 | CA | LEU | 94 | 38.122 | 22.120 | 22.111 | 1.00 | 30.42 |
| ATOM | 401 | C | LEU | 94 | 37.648 | 23.446 | 22.718 | 1.00 | 31.64 |
| ATOM | 402 | O | LEU | 94 | 36.784 | 23.450 | 23.605 | 1.00 | 32.40 |
| ATOM | 397 | CB | LEU | 94 | 39.293 | 21.518 | 22.901 | 1.00 | 32.97 |
| ATOM | 398 | CG | LEU | 94 | 39.625 | 20.141 | 22.323 | 1.00 | 30.59 |
| ATOM | 399 | CD1 | LEU | 94 | 40.883 | 19.552 | 22.918 | 1.00 | 28.68 |
| ATOM | 400 | CD2 | LEU | 94 | 38.404 | 19.239 | 22.514 | 1.00 | 28.08 |
| ATOM | 403 | N | GLU | 95 | 38.148 | 24.568 | 22.186 | 1.00 | 31.10 |
| ATOM | 404 | CA | GLU | 95 | 37.751 | 25.887 | 22.666 | 1.00 | 29.37 |
| ATOM | 410 | C | GLU | 95 | 36.415 | 26.373 | 22.069 | 1.00 | 28.17 |
| ATOM | 411 | O | GLU | 95 | 35.689 | 27.175 | 22.674 | 1.00 | 30.64 |
| ATOM | 405 | CB | GLU | 95 | 38.882 | 26.890 | 22.431 | 1.00 | 31.01 |
| ATOM | 406 | CG | GLU | 95 | 38.583 | 28.321 | 22.898 | 1.00 | 35.53 |
| ATOM | 407 | CD | GLU | 95 | 38.293 | 28.450 | 24.401 | 1.00 | 39.93 |
| ATOM | 408 | OE1 | GLU | 95 | 38.606 | 27.509 | 25.180 | 1.00 | 40.14 |
| ATOM | 409 | OE2 | GLU | 95 | 37.756 | 29.521 | 24.805 | 1.00 | 41.17 |
| ATOM | 412 | N | ILE | 96 | 36.095 | 25.917 | 20.868 | 1.00 | 24.90 |
| ATOM | 413 | CA | ILE | 96 | 34.841 | 26.295 | 20.251 | 1.00 | 21.92 |
| ATOM | 418 | C | ILE | 96 | 33.860 | 25.605 | 21.175 | 1.00 | 22.41 |
| ATOM | 419 | O | ILE | 96 | 32.961 | 26.243 | 21.702 | 1.00 | 24.87 |
| ATOM | 414 | CB | ILE | 96 | 34.653 | 25.663 | 18.822 | 1.00 | 20.49 |
| ATOM | 416 | CG1 | ILE | 96 | 35.710 | 26.127 | 17.819 | 1.00 | 17.09 |
| ATOM | 415 | CG2 | ILE | 96 | 33.303 | 25.995 | 18.266 | 1.00 | 16.58 |
| ATOM | 417 | CD1 | ILE | 96 | 35.603 | 27.514 | 17.437 | 1.00 | 16.51 |
| ATOM | 420 | N | VAL | 97 | 34.124 | 24.315 | 21.435 | 1.00 | 25.93 |
| ATOM | 421 | CA | VAL | 97 | 33.296 | 23.401 | 22.259 | 1.00 | 24.81 |
| ATOM | 425 | C | VAL | 97 | 33.099 | 23.764 | 23.722 | 1.00 | 24.82 |

Figure 21I

| | | | | | | | | | |
|---|---|---|---|---|---|---|---|---|---|
| ATOM | 426 | O | VAL | 97 | 32.004 | 23.616 | 24.258 | 1.00 | 24.18 |
| ATOM | 422 | CB | VAL | 97 | 33.814 | 21.934 | 22.180 | 1.00 | 22.94 |
| ATOM | 423 | CG1 | VAL | 97 | 33.030 | 21.053 | 23.180 | 1.00 | 24.88 |
| ATOM | 424 | CG2 | VAL | 97 | 33.629 | 21.408 | 20.770 | 1.00 | 11.21 |
| ATOM | 427 | N | ARG | 98 | 34.182 | 24.151 | 24.380 | 1.00 | 24.78 |
| ATOM | 428 | CA | ARG | 98 | 34.128 | 24.566 | 25.766 | 1.00 | 25.00 |
| ATOM | 436 | C | ARG | 98 | 33.222 | 25.783 | 25.945 | 1.00 | 24.90 |
| ATOM | 437 | O | ARG | 98 | 32.390 | 25.831 | 26.836 | 1.00 | 27.48 |
| ATOM | 429 | CB | ARG | 98 | 35.513 | 24.908 | 26.216 | 1.00 | 24.67 |
| ATOM | 430 | CG | ARG | 98 | 35.642 | 24.954 | 27.674 | 1.00 | 30.94 |
| ATOM | 431 | CD | ARG | 98 | 36.587 | 26.059 | 28.036 | 1.00 | 40.09 |
| ATOM | 432 | NE | ARG | 98 | 35.865 | 27.299 | 28.292 | 1.00 | 45.08 |
| ATOM | 433 | CZ | ARG | 98 | 36.326 | 28.500 | 27.970 | 1.00 | 46.47 |
| ATOM | 434 | NH1 | ARG | 98 | 37.502 | 28.616 | 27.359 | 1.00 | 45.05 |
| ATOM | 435 | NH2 | ARG | 98 | 35.600 | 29.576 | 28.247 | 1.00 | 46.19 |
| ATOM | 438 | N | ARG | 99 | 33.388 | 26.768 | 25.080 | 1.00 | 26.59 |
| ATOM | 439 | CA | ARG | 99 | 32.581 | 27.974 | 25.115 | 1.00 | 25.39 |
| ATOM | 447 | C | ARG | 99 | 31.137 | 27.637 | 24.814 | 1.00 | 26.34 |
| ATOM | 448 | O | ARG | 99 | 30.254 | 28.226 | 25.373 | 1.00 | 29.98 |
| ATOM | 440 | CB | ARG | 99 | 33.052 | 28.968 | 24.067 | 1.00 | 24.52 |
| ATOM | 441 | CG | ARG | 99 | 34.402 | 29.547 | 24.250 | 1.00 | 26.43 |
| ATOM | 442 | CD | ARG | 99 | 34.233 | 31.068 | 24.120 | 1.00 | 44.08 |
| ATOM | 443 | NE | ARG | 99 | 35.510 | 31.764 | 24.079 | 1.00 | 54.56 |
| ATOM | 444 | CZ | ARG | 99 | 36.330 | 31.766 | 23.024 | 1.00 | 63.35 |
| ATOM | 445 | NH1 | ARG | 99 | 35.978 | 31.185 | 21.865 | 1.00 | 66.14 |
| ATOM | 446 | NH2 | ARG | 99 | 37.495 | 32.405 | 23.101 | 1.00 | 65.49 |
| ATOM | 449 | N | ALA | 100 | 30.892 | 26.685 | 23.922 | 1.00 | 27.99 |
| ATOM | 450 | CA | ALA | 100 | 29.522 | 26.331 | 23.562 | 1.00 | 24.77 |
| ATOM | 452 | C | ALA | 100 | 28.801 | 25.587 | 24.662 | 1.00 | 25.30 |
| ATOM | 453 | O | ALA | 100 | 27.678 | 25.920 | 25.012 | 1.00 | 23.06 |
| ATOM | 451 | CB | ALA | 100 | 29.517 | 25.537 | 22.317 | 1.00 | 30.83 |
| ATOM | 454 | N | SER | 101 | 29.454 | 24.561 | 25.190 | 1.00 | 25.97 |
| ATOM | 455 | CA | SER | 101 | 28.929 | 23.745 | 26.290 | 1.00 | 26.37 |
| ATOM | 458 | C | SER | 101 | 28.422 | 24.590 | 27.453 | 1.00 | 26.29 |
| ATOM | 459 | O | SER | 101 | 27.470 | 24.217 | 28.123 | 1.00 | 26.57 |
| ATOM | 456 | CB | SER | 101 | 30.036 | 22.860 | 26.808 | 1.00 | 22.89 |
| ATOM | 457 | OG | SER | 101 | 31.081 | 23.690 | 27.274 | 1.00 | 33.20 |
| ATOM | 460 | N | GLU | 102 | 29.068 | 25.727 | 27.676 | 1.00 | 27.99 |
| ATOM | 461 | CA | GLU | 102 | 28.683 | 26.645 | 28.739 | 1.00 | 31.99 |
| ATOM | 467 | C | GLU | 102 | 27.291 | 27.253 | 28.565 | 1.00 | 33.82 |
| ATOM | 468 | O | GLU | 102 | 26.715 | 27.794 | 29.508 | 1.00 | 34.90 |
| ATOM | 462 | CB | GLU | 102 | 29.724 | 27.746 | 28.868 | 1.00 | 37.00 |
| ATOM | 463 | CG | GLU | 102 | 30.912 | 27.375 | 29.771 | 1.00 | 46.44 |
| ATOM | 464 | CD | GLU | 102 | 31.984 | 28.469 | 29.817 | 1.00 | 56.16 |
| ATOM | 465 | OE1 | GLU | 102 | 31.632 | 29.690 | 29.843 | 1.00 | 59.34 |
| ATOM | 466 | OE2 | GLU | 102 | 33.184 | 28.096 | 29.823 | 1.00 | 61.81 |
| ATOM | 469 | N | LYS | 103 | 26.747 | 27.161 | 27.357 | 1.00 | 34.52 |
| ATOM | 470 | CA | LYS | 103 | 25.415 | 27.670 | 27.063 | 1.00 | 29.61 |
| ATOM | 476 | C | LYS | 103 | 24.451 | 26.519 | 26.791 | 1.00 | 28.42 |
| ATOM | 477 | O | LYS | 103 | 23.349 | 26.726 | 26.298 | 1.00 | 31.71 |
| ATOM | 471 | CB | LYS | 103 | 25.477 | 28.566 | 25.834 | 1.00 | 32.12 |
| ATOM | 472 | CG | LYS | 103 | 26.549 | 29.591 | 25.948 | 1.00 | 34.88 |
| ATOM | 473 | CD | LYS | 103 | 26.152 | 30.615 | 26.953 | 1.00 | 35.23 |
| ATOM | 474 | CE | LYS | 103 | 24.836 | 31.229 | 26.511 | 1.00 | 41.33 |

Figure 21J

| ATOM | 475 | NZ | LYS | 103 | 24.480 | 32.498 | 27.258 | 1.00 | 46.16 |
|---|---|---|---|---|---|---|---|---|---|
| ATOM | 478 | N | SER | 104 | 24.849 | 25.297 | 27.086 | 1.00 | 27.63 |
| ATOM | 479 | CA | SER | 104 | 23.959 | 24.201 | 26.824 | 1.00 | 28.05 |
| ATOM | 482 | C | SER | 104 | 23.211 | 23.788 | 28.069 | 1.00 | 33.45 |
| ATOM | 483 | O | SER | 104 | 23.812 | 23.562 | 29.120 | 1.00 | 37.03 |
| ATOM | 480 | CB | SER | 104 | 24.714 | 23.001 | 26.291 | 1.00 | 23.58 |
| ATOM | 481 | OG | SER | 104 | 23.791 | 21.958 | 26.049 | 1.00 | 19.53 |
| ATOM | 484 | N | GLU | 105 | 21.899 | 23.632 | 27.935 | 1.00 | 34.63 |
| ATOM | 485 | CA | GLU | 105 | 21.071 | 23.207 | 29.041 | 1.00 | 32.71 |
| ATOM | 491 | C | GLU | 105 | 21.307 | 21.744 | 29.247 | 1.00 | 31.79 |
| ATOM | 492 | O | GLU | 105 | 21.475 | 21.275 | 30.364 | 1.00 | 33.10 |
| ATOM | 486 | CB | GLU | 105 | 19.629 | 23.421 | 28.696 | 1.00 | 38.95 |
| ATOM | 487 | CG | GLU | 105 | 18.768 | 23.600 | 29.892 | 1.00 | 54.82 |
| ATOM | 488 | CD | GLU | 105 | 17.332 | 23.295 | 29.578 | 1.00 | 61.77 |
| ATOM | 489 | OE1 | GLU | 105 | 16.845 | 23.846 | 28.549 | 1.00 | 64.22 |
| ATOM | 490 | OE2 | GLU | 105 | 16.717 | 22.490 | 30.343 | 1.00 | 62.11 |
| ATOM | 493 | N | LEU | 106 | 21.371 | 21.011 | 28.149 | 1.00 | 29.89 |
| ATOM | 494 | CA | LEU | 106 | 21.597 | 19.586 | 28.261 | 1.00 | 29.47 |
| ATOM | 499 | C | LEU | 106 | 22.871 | 19.338 | 29.047 | 1.00 | 29.92 |
| ATOM | 500 | O | LEU | 106 | 22.864 | 18.576 | 29.995 | 1.00 | 32.83 |
| ATOM | 495 | CB | LEU | 106 | 21.700 | 18.940 | 26.881 | 1.00 | 29.36 |
| ATOM | 496 | CG | LEU | 106 | 22.014 | 17.438 | 26.834 | 1.00 | 30.11 |
| ATOM | 497 | CD1 | LEU | 106 | 20.724 | 16.658 | 27.088 | 1.00 | 34.79 |
| ATOM | 498 | CD2 | LEU | 106 | 22.655 | 17.040 | 25.487 | 1.00 | 28.82 |
| ATOM | 501 | N | VAL | 107 | 23.956 | 20.002 | 28.643 | 1.00 | 33.22 |
| ATOM | 502 | CA | VAL | 107 | 25.273 | 19.866 | 29.285 | 1.00 | 32.61 |
| ATOM | 506 | C | VAL | 107 | 25.260 | 20.293 | 30.764 | 1.00 | 35.86 |
| ATOM | 507 | O | VAL | 107 | 25.968 | 19.704 | 31.585 | 1.00 | 35.65 |
| ATOM | 503 | CB | VAL | 107 | 26.353 | 20.692 | 28.552 | 1.00 | 26.05 |
| ATOM | 504 | CG1 | VAL | 107 | 27.542 | 20.895 | 29.465 | 1.00 | 20.60 |
| ATOM | 505 | CG2 | VAL | 107 | 26.748 | 20.013 | 27.269 | 1.00 | 22.79 |
| ATOM | 508 | N | SER | 108 | 24.451 | 21.306 | 31.083 | 1.00 | 36.37 |
| ATOM | 509 | CA | SER | 108 | 24.336 | 21.808 | 32.439 | 1.00 | 37.26 |
| ATOM | 512 | C | SER | 108 | 23.612 | 20.862 | 33.377 | 1.00 | 35.98 |
| ATOM | 513 | O | SER | 108 | 23.861 | 20.897 | 34.555 | 1.00 | 38.67 |
| ATOM | 510 | CB | SER | 108 | 23.760 | 23.224 | 32.447 | 1.00 | 39.50 |
| ATOM | 511 | OG | SER | 108 | 24.648 | 24.081 | 31.701 | 1.00 | 49.13 |
| ATOM | 514 | N | ARG | 109 | 22.744 | 20.000 | 32.868 | 1.00 | 36.47 |
| ATOM | 515 | CA | ARG | 109 | 22.093 | 19.015 | 33.723 | 1.00 | 35.04 |
| ATOM | 523 | C | ARG | 109 | 23.129 | 17.948 | 34.150 | 1.00 | 35.68 |
| ATOM | 524 | O | ARG | 109 | 22.852 | 17.151 | 35.045 | 1.00 | 36.71 |
| ATOM | 516 | CB | ARG | 109 | 20.993 | 18.294 | 32.970 | 1.00 | 38.35 |
| ATOM | 517 | CG | ARG | 109 | 19.761 | 19.083 | 32.730 | 1.00 | 50.79 |
| ATOM | 518 | CD | ARG | 109 | 18.743 | 18.290 | 31.877 | 1.00 | 58.60 |
| ATOM | 519 | NE | ARG | 109 | 17.542 | 19.093 | 31.677 | 1.00 | 61.15 |
| ATOM | 520 | CZ | ARG | 109 | 16.771 | 19.512 | 32.683 | 1.00 | 64.92 |
| ATOM | 521 | NH1 | ARG | 109 | 17.077 | 19.178 | 33.945 | 1.00 | 61.63 |
| ATOM | 522 | NH2 | ARG | 109 | 15.719 | 20.303 | 32.444 | 1.00 | 66.50 |
| ATOM | 525 | N | GLY | 110 | 24.272 | 17.878 | 33.451 | 1.00 | 32.19 |
| ATOM | 526 | CA | GLY | 110 | 25.318 | 16.920 | 33.780 | 1.00 | 24.13 |
| ATOM | 527 | C | GLY | 110 | 24.970 | 15.456 | 33.563 | 1.00 | 26.01 |
| ATOM | 528 | O | GLY | 110 | 23.931 | 15.149 | 32.973 | 1.00 | 29.54 |
| ATOM | 529 | N | PRO | 111 | 25.827 | 14.524 | 34.036 | 1.00 | 24.15 |
| ATOM | 531 | CA | PRO | 111 | 25.726 | 13.077 | 33.956 | 1.00 | 24.37 |

Figure 21K

| ATOM | 534 | C   | PRO | 111 | 24.721 | 12.557 | 34.946 | 1.00 | 33.63 |
|------|-----|-----|-----|-----|--------|--------|--------|------|-------|
| ATOM | 535 | O   | PRO | 111 | 24.270 | 13.302 | 35.813 | 1.00 | 34.08 |
| ATOM | 532 | CB  | PRO | 111 | 27.102 | 12.620 | 34.398 | 1.00 | 21.65 |
| ATOM | 533 | CG  | PRO | 111 | 27.936 | 13.798 | 34.342 | 1.00 | 24.20 |
| ATOM | 530 | CD  | PRO | 111 | 27.045 | 14.868 | 34.761 | 1.00 | 22.63 |
| ATOM | 536 | N   | VAL | 112 | 24.530 | 11.232 | 34.925 | 1.00 | 42.68 |
| ATOM | 537 | CA  | VAL | 112 | 23.567 | 10.569 | 35.794 | 1.00 | 49.61 |
| ATOM | 541 | C   | VAL | 112 | 23.782 | 10.487 | 37.266 | 1.00 | 51.99 |
| ATOM | 542 | O   | VAL | 112 | 22.921 | 10.961 | 38.013 | 1.00 | 56.60 |
| ATOM | 538 | CB  | VAL | 112 | 23.211 | 9.115  | 35.393 | 1.00 | 53.14 |
| ATOM | 539 | CG1 | VAL | 112 | 22.457 | 9.090  | 34.072 | 1.00 | 56.14 |
| ATOM | 540 | CG2 | VAL | 112 | 24.461 | 8.209  | 35.431 | 1.00 | 56.78 |
| ATOM | 543 | N   | SER | 113 | 24.843 | 9.841  | 37.724 | 1.00 | 50.45 |
| ATOM | 544 | CA  | SER | 113 | 24.890 | 9.737  | 39.161 | 1.00 | 56.14 |
| ATOM | 547 | C   | SER | 113 | 26.187 | 9.891  | 39.864 | 1.00 | 56.87 |
| ATOM | 548 | O   | SER | 113 | 26.360 | 10.882 | 40.575 | 1.00 | 62.69 |
| ATOM | 545 | CB  | SER | 113 | 24.137 | 8.496  | 39.660 | 1.00 | 58.65 |
| ATOM | 546 | OG  | SER | 113 | 22.966 | 8.848  | 40.388 | 1.00 | 63.80 |
| ATOM | 549 | N   | PRO | 114 | 27.067 | 8.883  | 39.809 | 1.00 | 51.53 |
| ATOM | 551 | CA  | PRO | 114 | 28.311 | 9.156  | 40.539 | 1.00 | 46.33 |
| ATOM | 554 | C   | PRO | 114 | 29.374 | 9.770  | 39.640 | 1.00 | 42.61 |
| ATOM | 555 | O   | PRO | 114 | 30.429 | 10.140 | 40.133 | 1.00 | 43.75 |
| ATOM | 552 | CB  | PRO | 114 | 28.737 | 7.775  | 41.040 | 1.00 | 46.79 |
| ATOM | 553 | CG  | PRO | 114 | 27.463 | 6.925  | 40.912 | 1.00 | 48.56 |
| ATOM | 550 | CD  | PRO | 114 | 26.879 | 7.436  | 39.637 | 1.00 | 49.67 |
| ATOM | 556 | N   | LEU | 115 | 29.087 | 9.854  | 38.332 | 1.00 | 39.27 |
| ATOM | 557 | CA  | LEU | 115 | 30.011 | 10.410 | 37.327 | 1.00 | 34.32 |
| ATOM | 562 | C   | LEU | 115 | 30.277 | 11.905 | 37.407 | 1.00 | 33.66 |
| ATOM | 563 | O   | LEU | 115 | 29.359 | 12.718 | 37.563 | 1.00 | 34.73 |
| ATOM | 558 | CB  | LEU | 115 | 29.506 | 10.127 | 35.928 | 1.00 | 34.23 |
| ATOM | 559 | CG  | LEU | 115 | 29.644 | 8.789  | 35.224 | 1.00 | 35.32 |
| ATOM | 560 | CD1 | LEU | 115 | 29.081 | 8.998  | 33.854 | 1.00 | 42.43 |
| ATOM | 561 | CD2 | LEU | 115 | 31.081 | 8.349  | 35.070 | 1.00 | 37.40 |
| ATOM | 564 | N   | GLN | 116 | 31.526 | 12.280 | 37.185 | 1.00 | 33.52 |
| ATOM | 565 | CA  | GLN | 116 | 31.879 | 13.681 | 37.251 | 1.00 | 35.48 |
| ATOM | 571 | C   | GLN | 116 | 31.537 | 14.466 | 36.017 | 1.00 | 33.45 |
| ATOM | 572 | O   | GLN | 116 | 31.712 | 14.014 | 34.903 | 1.00 | 27.20 |
| ATOM | 566 | CB  | GLN | 116 | 33.358 | 13.860 | 37.588 | 1.00 | 44.39 |
| ATOM | 567 | CG  | GLN | 116 | 33.613 | 13.519 | 39.058 | 1.00 | 55.49 |
| ATOM | 568 | CD  | GLN | 116 | 34.925 | 14.025 | 39.615 | 1.00 | 61.22 |
| ATOM | 569 | OE1 | GLN | 116 | 35.991 | 13.915 | 38.973 | 1.00 | 66.18 |
| ATOM | 570 | NE2 | GLN | 116 | 34.867 | 14.565 | 40.833 | 1.00 | 58.06 |
| ATOM | 573 | N   | PRO | 117 | 30.986 | 15.650 | 36.210 | 1.00 | 33.36 |
| ATOM | 575 | CA  | PRO | 117 | 30.610 | 16.530 | 35.118 | 1.00 | 35.10 |
| ATOM | 578 | C   | PRO | 117 | 31.812 | 16.869 | 34.290 | 1.00 | 33.92 |
| ATOM | 579 | O   | PRO | 117 | 32.863 | 17.135 | 34.831 | 1.00 | 39.00 |
| ATOM | 576 | CB  | PRO | 117 | 30.118 | 17.752 | 35.852 | 1.00 | 31.85 |
| ATOM | 577 | CG  | PRO | 117 | 29.403 | 17.130 | 36.955 | 1.00 | 38.23 |
| ATOM | 574 | CD  | PRO | 117 | 30.370 | 16.093 | 37.454 | 1.00 | 35.43 |
| ATOM | 580 | N   | ASP | 118 | 31.675 | 16.773 | 32.976 | 1.00 | 34.87 |
| ATOM | 581 | CA  | ASP | 118 | 32.745 | 17.109 | 32.048 | 1.00 | 31.79 |
| ATOM | 586 | C   | ASP | 118 | 32.011 | 17.810 | 30.934 | 1.00 | 29.11 |
| ATOM | 587 | O   | ASP | 118 | 31.477 | 17.163 | 30.058 | 1.00 | 32.62 |
| ATOM | 582 | CB  | ASP | 118 | 33.445 | 15.852 | 31.534 | 1.00 | 27.53 |

Figure 21L

| ATOM | 583 | CG | ASP | 118 | 34.835 | 16.144 | 30.937 | 1.00 | 29.42 |
|------|-----|-----|-----|-----|--------|--------|--------|------|-------|
| ATOM | 584 | OD1 | ASP | 118 | 35.038 | 17.178 | 30.258 | 1.00 | 29.54 |
| ATOM | 585 | OD2 | ASP | 118 | 35.730 | 15.301 | 31.120 | 1.00 | 30.32 |
| ATOM | 588 | N | LYS | 119 | 31.855 | 19.118 | 31.066 | 1.00 | 26.70 |
| ATOM | 589 | CA | LYS | 119 | 31.143 | 19.911 | 30.077 | 1.00 | 27.57 |
| ATOM | 595 | C | LYS | 119 | 31.510 | 19.643 | 28.619 | 1.00 | 25.98 |
| ATOM | 596 | O | LYS | 119 | 30.631 | 19.455 | 27.795 | 1.00 | 27.96 |
| ATOM | 590 | CB | LYS | 119 | 31.306 | 21.384 | 30.379 | 1.00 | 30.48 |
| ATOM | 591 | CG | LYS | 119 | 30.348 | 21.887 | 31.415 | 1.00 | 41.34 |
| ATOM | 592 | CD | LYS | 119 | 30.650 | 23.345 | 31.784 | 1.00 | 46.39 |
| ATOM | 593 | CE | LYS | 119 | 29.436 | 24.017 | 32.460 | 1.00 | 54.46 |
| ATOM | 594 | NZ | LYS | 119 | 28.938 | 23.380 | 33.740 | 1.00 | 57.23 |
| ATOM | 597 | N | VAL | 120 | 32.800 | 19.632 | 28.301 | 1.00 | 22.59 |
| ATOM | 598 | CA | VAL | 120 | 33.259 | 19.376 | 26.944 | 1.00 | 16.79 |
| ATOM | 602 | C | VAL | 120 | 32.995 | 17.921 | 26.532 | 1.00 | 20.68 |
| ATOM | 603 | O | VAL | 120 | 32.563 | 17.666 | 25.414 | 1.00 | 24.32 |
| ATOM | 599 | CB | VAL | 120 | 34.757 | 19.651 | 26.813 | 1.00 | 15.66 |
| ATOM | 600 | CG1 | VAL | 120 | 35.210 | 19.423 | 25.386 | 1.00 | 14.04 |
| ATOM | 601 | CG2 | VAL | 120 | 35.066 | 21.054 | 27.256 | 1.00 | 12.50 |
| ATOM | 604 | N | VAL | 121 | 33.249 | 16.962 | 27.425 | 1.00 | 20.59 |
| ATOM | 605 | CA | VAL | 121 | 33.023 | 15.559 | 27.099 | 1.00 | 15.94 |
| ATOM | 609 | C | VAL | 121 | 31.541 | 15.290 | 26.866 | 1.00 | 23.12 |
| ATOM | 610 | O | VAL | 121 | 31.175 | 14.388 | 26.091 | 1.00 | 27.04 |
| ATOM | 606 | CB | VAL | 121 | 33.604 | 14.614 | 28.176 | 1.00 | 13.62 |
| ATOM | 607 | CG1 | VAL | 121 | 33.111 | 13.206 | 28.002 | 1.00 | 16.87 |
| ATOM | 608 | CG2 | VAL | 121 | 35.104 | 14.588 | 28.115 | 1.00 | 12.10 |
| ATOM | 611 | N | GLU | 122 | 30.691 | 16.147 | 27.430 | 1.00 | 22.34 |
| ATOM | 612 | CA | GLU | 122 | 29.258 | 15.969 | 27.316 | 1.00 | 17.82 |
| ATOM | 618 | C | GLU | 122 | 28.692 | 16.753 | 26.182 | 1.00 | 20.51 |
| ATOM | 619 | O | GLU | 122 | 27.624 | 16.445 | 25.660 | 1.00 | 20.42 |
| ATOM | 613 | CB | GLU | 122 | 28.574 | 16.361 | 28.598 | 1.00 | 21.95 |
| ATOM | 614 | CG | GLU | 122 | 28.841 | 15.460 | 29.765 | 1.00 | 27.87 |
| ATOM | 615 | CD | GLU | 122 | 28.146 | 15.985 | 31.001 | 1.00 | 36.96 |
| ATOM | 616 | OE1 | GLU | 122 | 26.893 | 15.854 | 31.101 | 1.00 | 31.07 |
| ATOM | 617 | OE2 | GLU | 122 | 28.850 | 16.586 | 31.843 | 1.00 | 39.15 |
| ATOM | 620 | N | PHE | 123 | 29.345 | 17.830 | 25.823 | 1.00 | 19.09 |
| ATOM | 621 | CA | PHE | 123 | 28.819 | 18.535 | 24.680 | 1.00 | 19.82 |
| ATOM | 629 | C | PHE | 123 | 29.111 | 17.634 | 23.484 | 1.00 | 19.97 |
| ATOM | 630 | O | PHE | 123 | 28.271 | 17.430 | 22.625 | 1.00 | 20.96 |
| ATOM | 622 | CB | PHE | 123 | 29.518 | 19.857 | 24.495 | 1.00 | 20.90 |
| ATOM | 623 | CG | PHE | 123 | 29.026 | 20.604 | 23.355 | 1.00 | 18.92 |
| ATOM | 624 | CD1 | PHE | 123 | 27.909 | 21.400 | 23.482 | 1.00 | 18.73 |
| ATOM | 625 | CD2 | PHE | 123 | 29.661 | 20.511 | 22.139 | 1.00 | 22.28 |
| ATOM | 626 | CE1 | PHE | 123 | 27.429 | 22.103 | 22.398 | 1.00 | 22.70 |
| ATOM | 627 | CE2 | PHE | 123 | 29.183 | 21.213 | 21.048 | 1.00 | 24.76 |
| ATOM | 628 | CZ | PHE | 123 | 28.069 | 22.010 | 21.178 | 1.00 | 19.92 |
| ATOM | 631 | N | LEU | 124 | 30.312 | 17.069 | 23.448 | 1.00 | 21.40 |
| ATOM | 632 | CA | LEU | 124 | 30.688 | 16.176 | 22.365 | 1.00 | 17.35 |
| ATOM | 637 | C | LEU | 124 | 29.731 | 15.001 | 22.304 | 1.00 | 17.32 |
| ATOM | 638 | O | LEU | 124 | 29.092 | 14.816 | 21.289 | 1.00 | 21.33 |
| ATOM | 633 | CB | LEU | 124 | 32.111 | 15.695 | 22.547 | 1.00 | 17.34 |
| ATOM | 634 | CG | LEU | 124 | 33.165 | 16.769 | 22.368 | 1.00 | 19.10 |
| ATOM | 635 | CD1 | LEU | 124 | 34.533 | 16.195 | 22.690 | 1.00 | 23.46 |
| ATOM | 636 | CD2 | LEU | 124 | 33.124 | 17.265 | 20.940 | 1.00 | 21.60 |

Figure 21M

| | | | | | | | | | |
|---|---|---|---|---|---|---|---|---|---|
| ATOM | 639 | N | SER | 125 | 29.514 | 14.303 | 23.422 | 1.00 | 19.23 |
| ATOM | 640 | CA | SER | 125 | 28.614 | 13.135 | 23.444 | 1.00 | 19.37 |
| ATOM | 643 | C | SER | 125 | 27.198 | 13.399 | 22.963 | 1.00 | 20.02 |
| ATOM | 644 | O | SER | 125 | 26.555 | 12.511 | 22.453 | 1.00 | 26.02 |
| ATOM | 641 | CB | SER | 125 | 28.564 | 12.477 | 24.831 | 1.00 | 15.49 |
| ATOM | 642 | OG | SER | 125 | 29.862 | 12.341 | 25.357 | 1.00 | 17.39 |
| ATOM | 645 | N | GLY | 126 | 26.685 | 14.587 | 23.186 | 1.00 | 22.04 |
| ATOM | 646 | CA | GLY | 126 | 25.346 | 14.897 | 22.748 | 1.00 | 22.04 |
| ATOM | 647 | C | GLY | 126 | 25.311 | 15.508 | 21.354 | 1.00 | 26.13 |
| ATOM | 648 | O | GLY | 126 | 24.225 | 15.563 | 20.761 | 1.00 | 30.84 |
| ATOM | 649 | N | SER | 127 | 26.444 | 16.034 | 20.867 | 1.00 | 23.79 |
| ATOM | 650 | CA | SER | 127 | 26.525 | 16.611 | 19.513 | 1.00 | 25.27 |
| ATOM | 653 | C | SER | 127 | 26.940 | 15.600 | 18.457 | 1.00 | 25.87 |
| ATOM | 654 | O | SER | 127 | 26.228 | 15.412 | 17.478 | 1.00 | 29.17 |
| ATOM | 651 | CB | SER | 127 | 27.536 | 17.731 | 19.434 | 1.00 | 19.35 |
| ATOM | 652 | OG | SER | 127 | 27.123 | 18.782 | 20.249 | 1.00 | 34.49 |
| ATOM | 655 | N | TYR | 128 | 28.109 | 14.992 | 18.653 | 1.00 | 17.70 |
| ATOM | 656 | CA | TYR | 128 | 28.687 | 14.042 | 17.725 | 1.00 | 16.14 |
| ATOM | 665 | C | TYR | 128 | 28.584 | 12.627 | 18.236 | 1.00 | 16.55 |
| ATOM | 666 | O | TYR | 128 | 29.593 | 11.963 | 18.448 | 1.00 | 19.42 |
| ATOM | 657 | CB | TYR | 128 | 30.151 | 14.425 | 17.497 | 1.00 | 13.00 |
| ATOM | 658 | CG | TYR | 128 | 30.260 | 15.848 | 17.059 | 1.00 | 10.30 |
| ATOM | 659 | CD1 | TYR | 128 | 29.527 | 16.303 | 15.979 | 1.00 | 12.91 |
| ATOM | 661 | CD2 | TYR | 128 | 30.973 | 16.763 | 17.803 | 1.00 | 14.08 |
| ATOM | 660 | CE1 | TYR | 128 | 29.484 | 17.631 | 15.672 | 1.00 | 17.29 |
| ATOM | 662 | CE2 | TYR | 128 | 30.945 | 18.103 | 17.511 | 1.00 | 16.38 |
| ATOM | 663 | CZ | TYR | 128 | 30.186 | 18.541 | 16.440 | 1.00 | 20.39 |
| ATOM | 664 | OH | TYR | 128 | 30.098 | 19.905 | 16.162 | 1.00 | 22.10 |
| ATOM | 667 | N | ALA | 129 | 27.371 | 12.118 | 18.261 | 1.00 | 11.21 |
| ATOM | 668 | CA | ALA | 129 | 27.108 | 10.806 | 18.820 | 1.00 | 14.30 |
| ATOM | 670 | C | ALA | 129 | 27.356 | 9.563 | 18.033 | 1.00 | 15.80 |
| ATOM | 671 | O | ALA | 129 | 26.860 | 8.510 | 18.419 | 1.00 | 15.01 |
| ATOM | 669 | CB | ALA | 129 | 25.685 | 10.769 | 19.310 | 1.00 | 13.72 |
| ATOM | 672 | N | GLY | 130 | 28.004 | 9.660 | 16.885 | 1.00 | 21.28 |
| ATOM | 673 | CA | GLY | 130 | 28.225 | 8.453 | 16.091 | 1.00 | 22.57 |
| ATOM | 674 | C | GLY | 130 | 29.478 | 8.536 | 15.252 | 1.00 | 21.76 |
| ATOM | 675 | O | GLY | 130 | 29.926 | 9.616 | 14.966 | 1.00 | 25.44 |
| ATOM | 676 | N | LEU | 131 | 30.051 | 7.416 | 14.865 | 1.00 | 22.99 |
| ATOM | 677 | CA | LEU | 131 | 31.246 | 7.417 | 14.042 | 1.00 | 26.31 |
| ATOM | 682 | C | LEU | 131 | 30.994 | 6.854 | 12.641 | 1.00 | 29.53 |
| ATOM | 683 | O | LEU | 131 | 30.034 | 6.085 | 12.406 | 1.00 | 26.35 |
| ATOM | 678 | CB | LEU | 131 | 32.346 | 6.580 | 14.714 | 1.00 | 20.02 |
| ATOM | 679 | CG | LEU | 131 | 32.891 | 7.044 | 16.055 | 1.00 | 20.16 |
| ATOM | 680 | CD1 | LEU | 131 | 33.596 | 5.914 | 16.648 | 1.00 | 16.69 |
| ATOM | 681 | CD2 | LEU | 131 | 33.839 | 8.224 | 15.937 | 1.00 | 18.57 |
| ATOM | 684 | N | SER | 132 | 31.789 | 7.324 | 11.685 | 1.00 | 31.91 |
| ATOM | 685 | CA | SER | 132 | 31.684 | 6.775 | 10.342 | 1.00 | 35.56 |
| ATOM | 688 | C | SER | 132 | 32.998 | 6.895 | 9.665 | 1.00 | 30.11 |
| ATOM | 689 | O | SER | 132 | 33.732 | 7.815 | 9.895 | 1.00 | 33.36 |
| ATOM | 686 | CB | SER | 132 | 30.507 | 7.294 | 9.522 | 1.00 | 40.11 |
| ATOM | 687 | OG | SER | 132 | 30.763 | 8.505 | 8.839 | 1.00 | 48.47 |
| ATOM | 690 | N | LEU | 133 | 33.377 | 5.799 | 9.063 | 1.00 | 35.05 |
| ATOM | 691 | CA | LEU | 133 | 34.657 | 5.623 | 8.399 | 1.00 | 35.32 |
| ATOM | 696 | C | LEU | 133 | 34.518 | 5.939 | 6.938 | 1.00 | 40.82 |

Figure 21N

| | | | | | | | | | |
|---|---|---|---|---|---|---|---|---|---|
| ATOM | 697 | O | LEU | 133 | 33.563 | 5.480 | 6.310 | 1.00 | 44.46 |
| ATOM | 692 | CB | LEU | 133 | 35.005 | 4.158 | 8.562 | 1.00 | 26.30 |
| ATOM | 693 | CG | LEU | 133 | 36.158 | 3.559 | 7.859 | 1.00 | 19.38 |
| ATOM | 694 | CD1 | LEU | 133 | 37.423 | 4.183 | 8.304 | 1.00 | 26.92 |
| ATOM | 695 | CD2 | LEU | 133 | 36.143 | 2.131 | 8.217 | 1.00 | 25.27 |
| ATOM | 698 | N | SER | 134 | 35.438 | 6.734 | 6.395 | 1.00 | 44.63 |
| ATOM | 699 | CA | SER | 134 | 35.414 | 7.089 | 4.971 | 1.00 | 45.92 |
| ATOM | 702 | C | SER | 134 | 36.666 | 6.529 | 4.271 | 1.00 | 47.21 |
| ATOM | 703 | O | SER | 134 | 37.802 | 6.751 | 4.720 | 1.00 | 44.61 |
| ATOM | 700 | CB | SER | 134 | 35.326 | 8.598 | 4.795 | 1.00 | 45.63 |
| ATOM | 701 | OG | SER | 134 | 36.609 | 9.183 | 4.988 | 1.00 | 47.82 |
| ATOM | 704 | N | SER | 135 | 36.451 | 5.756 | 3.209 | 1.00 | 49.21 |
| ATOM | 705 | CA | SER | 135 | 37.548 | 5.179 | 2.467 | 1.00 | 51.54 |
| ATOM | 708 | C | SER | 135 | 37.797 | 5.987 | 1.220 | 1.00 | 53.51 |
| ATOM | 709 | O | SER | 135 | 37.042 | 6.906 | 0.907 | 1.00 | 54.49 |
| ATOM | 706 | CB | SER | 135 | 37.225 | 3.744 | 2.104 | 1.00 | 52.24 |
| ATOM | 707 | OG | SER | 135 | 37.043 | 2.974 | 3.275 | 1.00 | 62.08 |
| ATOM | 710 | N | ARG | 136 | 38.873 | 5.665 | 0.516 | 1.00 | 55.26 |
| ATOM | 711 | CA | ARG | 136 | 39.191 | 6.373 | -0.710 | 1.00 | 56.10 |
| ATOM | 714 | C | ARG | 136 | 38.326 | 5.886 | -1.904 | 1.00 | 59.66 |
| ATOM | 715 | O | ARG | 136 | 37.840 | 4.744 | -1.914 | 1.00 | 61.20 |
| ATOM | 712 | CB | ARG | 136 | 40.681 | 6.217 | -0.998 | 1.00 | 55.37 |
| ATOM | 713 | CG | ARG | 136 | 41.445 | 6.949 | -0.063 | 1.00 | 51.86 |
| ATOM | 716 | N | ARG | 137 | 38.080 | 6.785 | -2.865 | 1.00 | 61.93 |
| ATOM | 717 | CA | ARG | 137 | 37.315 | 6.488 | -4.090 | 1.00 | 60.62 |
| ATOM | 719 | C | ARG | 137 | 38.106 | 7.023 | -5.321 | 1.00 | 61.32 |
| ATOM | 720 | O | ARG | 137 | 38.993 | 7.886 | -5.178 | 1.00 | 60.21 |
| ATOM | 718 | CB | ARG | 137 | 35.913 | 7.129 | -4.020 | 1.00 | 60.06 |
| ATOM | 721 | N | CYS | 138 | 37.849 | 6.460 | -6.505 | 1.00 | 62.66 |
| ATOM | 722 | CA | CYS | 138 | 38.523 | 6.910 | -7.739 | 1.00 | 63.23 |
| ATOM | 725 | C | CYS | 138 | 37.849 | 8.192 | -8.210 | 1.00 | 62.65 |
| ATOM | 726 | O | CYS | 138 | 38.416 | 8.969 | -8.974 | 1.00 | 61.75 |
| ATOM | 723 | CB | CYS | 138 | 38.414 | 5.853 | -8.829 | 1.00 | 62.56 |
| ATOM | 724 | SG | CYS | 138 | 37.074 | 4.671 | -8.542 | 1.00 | 69.15 |
| ATOM | 727 | N | ASP | 139 | 36.638 | 8.393 | -7.695 | 1.00 | 62.87 |
| ATOM | 728 | CA | ASP | 139 | 35.800 | 9.554 | -7.968 | 1.00 | 60.63 |
| ATOM | 733 | C | ASP | 139 | 36.354 | 10.873 | -7.344 | 1.00 | 60.68 |
| ATOM | 734 | O | ASP | 139 | 36.365 | 11.921 | -7.996 | 1.00 | 61.62 |
| ATOM | 729 | CB | ASP | 139 | 34.394 | 9.247 | -7.389 | 1.00 | 59.02 |
| ATOM | 730 | CG | ASP | 139 | 33.267 | 10.106 | -8.015 | 1.00 | 64.92 |
| ATOM | 731 | OD1 | ASP | 139 | 33.541 | 11.238 | -8.500 | 1.00 | 67.71 |
| ATOM | 732 | OD2 | ASP | 139 | 32.078 | 9.653 | -8.013 | 1.00 | 68.40 |
| ATOM | 735 | N | ASP | 140 | 36.881 | 10.798 | -6.120 | 1.00 | 59.87 |
| ATOM | 736 | CA | ASP | 140 | 37.326 | 11.986 | -5.381 | 1.00 | 59.86 |
| ATOM | 738 | C | ASP | 140 | 38.554 | 12.865 | -5.756 | 1.00 | 59.66 |
| ATOM | 739 | O | ASP | 140 | 39.593 | 12.383 | -6.241 | 1.00 | 61.53 |
| ATOM | 737 | CB | ASP | 140 | 37.304 | 11.676 | -3.888 | 1.00 | 60.15 |
| ATOM | 740 | N | VAL | 141 | 38.401 | 14.169 | -5.499 | 1.00 | 58.35 |
| ATOM | 741 | CA | VAL | 141 | 39.413 | 15.202 | -5.788 | 1.00 | 60.08 |
| ATOM | 745 | C | VAL | 141 | 40.702 | 14.983 | -4.989 | 1.00 | 62.62 |
| ATOM | 746 | O | VAL | 141 | 40.638 | 14.650 | -3.802 | 1.00 | 67.89 |
| ATOM | 742 | CB | VAL | 141 | 38.853 | 16.621 | -5.417 | 1.00 | 59.22 |
| ATOM | 743 | CG1 | VAL | 141 | 39.882 | 17.695 | -5.689 | 1.00 | 55.88 |
| ATOM | 744 | CG2 | VAL | 141 | 37.561 | 16.900 | -6.168 | 1.00 | 57.15 |

Figure 21O

| ATOM | 747 | N | GLU | 142 | 41.868 | 15.220 | -5.582 | 1.00 | 61.91 |
| --- | --- | --- | --- | --- | --- | --- | --- | --- | --- |
| ATOM | 748 | CA | GLU | 142 | 43.106 | 15.032 | -4.815 | 1.00 | 60.70 |
| ATOM | 750 | C | GLU | 142 | 44.159 | 16.169 | -4.993 | 1.00 | 62.01 |
| ATOM | 751 | O | GLU | 142 | 44.385 | 16.613 | -6.147 | 1.00 | 64.58 |
| ATOM | 749 | CB | GLU | 142 | 43.698 | 13.657 | -5.121 | 1.00 | 61.45 |
| ATOM | 756 | N | PRO | 154 | 39.096 | 0.505 | 5.789 | 1.00 | 59.89 |
| ATOM | 757 | CA | PRO | 154 | 39.598 | 1.565 | 6.749 | 1.00 | 64.46 |
| ATOM | 754 | C | PRO | 154 | 40.569 | 2.451 | 5.968 | 1.00 | 65.07 |
| ATOM | 755 | O | PRO | 154 | 41.741 | 2.063 | 5.878 | 1.00 | 69.33 |
| ATOM | 753 | CB | PRO | 154 | 40.354 | 0.888 | 7.938 | 1.00 | 59.84 |
| ATOM | 758 | N | PHE | 155 | 40.159 | 3.636 | 5.468 | 1.00 | 62.65 |
| ATOM | 759 | CA | PHE | 155 | 41.101 | 4.423 | 4.614 | 1.00 | 58.28 |
| ATOM | 761 | C | PHE | 155 | 41.211 | 5.936 | 4.677 | 1.00 | 53.77 |
| ATOM | 762 | O | PHE | 155 | 42.109 | 6.472 | 5.289 | 1.00 | 54.45 |
| ATOM | 760 | CB | PHE | 155 | 40.956 | 3.984 | 3.105 | 1.00 | 59.87 |
| ATOM | 763 | N | LYS | 156 | 40.317 | 6.635 | 4.012 | 1.00 | 49.59 |
| ATOM | 764 | CA | LYS | 156 | 40.409 | 8.071 | 3.960 | 1.00 | 45.31 |
| ATOM | 770 | C | LYS | 156 | 40.452 | 8.808 | 5.294 | 1.00 | 41.39 |
| ATOM | 771 | O | LYS | 156 | 41.325 | 9.654 | 5.500 | 1.00 | 41.85 |
| ATOM | 765 | CB | LYS | 156 | 39.319 | 8.619 | 3.037 | 1.00 | 47.60 |
| ATOM | 766 | CG | LYS | 156 | 39.648 | 9.918 | 2.354 | 1.00 | 46.63 |
| ATOM | 767 | CD | LYS | 156 | 38.385 | 10.634 | 1.945 | 1.00 | 45.66 |
| ATOM | 768 | CE | LYS | 156 | 37.593 | 9.760 | 1.025 | 1.00 | 48.31 |
| ATOM | 769 | NZ | LYS | 156 | 36.171 | 10.159 | 1.042 | 1.00 | 56.75 |
| ATOM | 772 | N | HIS | 157 | 39.546 | 8.501 | 6.209 | 1.00 | 38.72 |
| ATOM | 773 | CA | HIS | 157 | 39.519 | 9.209 | 7.509 | 1.00 | 37.81 |
| ATOM | 774 | C | HIS | 157 | 38.351 | 8.715 | 8.340 | 1.00 | 36.09 |
| ATOM | 775 | O | HIS | 157 | 37.580 | 7.867 | 7.857 | 1.00 | 38.87 |
| ATOM | 776 | CB | HIS | 157 | 39.330 | 10.731 | 7.318 | 1.00 | 37.59 |
| ATOM | 777 | CG | HIS | 157 | 38.004 | 11.116 | 6.696 | 1.00 | 36.75 |
| ATOM | 778 | ND1 | HIS | 157 | 37.866 | 11.849 | 5.537 | 1.00 | 36.56 |
| ATOM | 779 | CD2 | HIS | 157 | 36.735 | 10.827 | 7.089 | 1.00 | 34.55 |
| ATOM | 781 | CE1 | HIS | 157 | 36.557 | 11.960 | 5.284 | 1.00 | 31.88 |
| ATOM | 780 | NE2 | HIS | 157 | 35.838 | 11.354 | 6.207 | 1.00 | 31.66 |
| ATOM | 782 | N | VAL | 158 | 38.186 | 9.258 | 9.559 | 1.00 | 34.03 |
| ATOM | 783 | CA | VAL | 158 | 37.058 | 8.911 | 10.434 | 1.00 | 30.28 |
| ATOM | 787 | C | VAL | 158 | 36.395 | 10.219 | 10.823 | 1.00 | 25.84 |
| ATOM | 788 | O | VAL | 158 | 37.081 | 11.185 | 11.182 | 1.00 | 23.69 |
| ATOM | 784 | CB | VAL | 158 | 37.441 | 8.114 | 11.731 | 1.00 | 31.15 |
| ATOM | 785 | CG1 | VAL | 158 | 36.168 | 7.750 | 12.475 | 1.00 | 31.88 |
| ATOM | 786 | CG2 | VAL | 158 | 38.151 | 6.814 | 11.410 | 1.00 | 22.16 |
| ATOM | 789 | N | ALA | 159 | 35.073 | 10.240 | 10.741 | 1.00 | 22.52 |
| ATOM | 790 | CA | ALA | 159 | 34.318 | 11.434 | 11.027 | 1.00 | 23.37 |
| ATOM | 792 | C | ALA | 159 | 33.428 | 11.278 | 12.244 | 1.00 | 25.14 |
| ATOM | 793 | O | ALA | 159 | 32.971 | 10.174 | 12.539 | 1.00 | 24.28 |
| ATOM | 791 | CB | ALA | 159 | 33.448 | 11.737 | 9.841 | 1.00 | 25.21 |
| ATOM | 794 | N | LEU | 160 | 33.199 | 12.380 | 12.954 | 1.00 | 26.27 |
| ATOM | 795 | CA | LEU | 160 | 32.311 | 12.404 | 14.121 | 1.00 | 23.20 |
| ATOM | 800 | C | LEU | 160 | 31.013 | 12.946 | 13.556 | 1.00 | 23.47 |
| ATOM | 801 | O | LEU | 160 | 31.009 | 14.018 | 12.979 | 1.00 | 20.58 |
| ATOM | 796 | CB | LEU | 160 | 32.808 | 13.360 | 15.198 | 1.00 | 27.37 |
| ATOM | 797 | CG | LEU | 160 | 34.203 | 13.205 | 15.810 | 1.00 | 31.90 |
| ATOM | 798 | CD1 | LEU | 160 | 34.298 | 14.188 | 17.009 | 1.00 | 33.23 |
| ATOM | 799 | CD2 | LEU | 160 | 34.462 | 11.745 | 16.248 | 1.00 | 26.75 |

Figure 21P

| ATOM | 802 | N | CYS | 161 | 29.916 | 12.237 | 13.777 | 1.00 | 23.74 |
| --- | --- | --- | --- | --- | --- | --- | --- | --- | --- |
| ATOM | 803 | CA | CYS | 161 | 28.631 | 12.615 | 13.223 | 1.00 | 26.80 |
| ATOM | 806 | C | CYS | 161 | 27.518 | 12.672 | 14.261 | 1.00 | 25.72 |
| ATOM | 807 | O | CYS | 161 | 27.665 | 12.141 | 15.362 | 1.00 | 30.63 |
| ATOM | 804 | CB | CYS | 161 | 28.229 | 11.576 | 12.177 | 1.00 | 31.50 |
| ATOM | 805 | SG | CYS | 161 | 29.544 | 11.000 | 11.196 | 1.00 | 35.88 |
| ATOM | 808 | N | SER | 162 | 26.366 | 13.206 | 13.868 | 1.00 | 24.30 |
| ATOM | 809 | CA | SER | 162 | 25.236 | 13.319 | 14.773 | 1.00 | 27.46 |
| ATOM | 812 | C | SER | 162 | 24.841 | 11.971 | 15.162 | 1.00 | 25.69 |
| ATOM | 813 | O | SER | 162 | 24.443 | 11.737 | 16.281 | 1.00 | 30.53 |
| ATOM | 810 | CB | SER | 162 | 24.037 | 13.949 | 14.098 | 1.00 | 29.54 |
| ATOM | 811 | OG | SER | 162 | 24.203 | 15.333 | 14.021 | 1.00 | 40.86 |
| ATOM | 814 | N | VAL | 163 | 24.894 | 11.109 | 14.174 | 1.00 | 26.40 |
| ATOM | 815 | CA | VAL | 163 | 24.533 | 9.720 | 14.310 | 1.00 | 30.19 |
| ATOM | 819 | C | VAL | 163 | 25.192 | 9.012 | 13.105 | 1.00 | 32.44 |
| ATOM | 820 | O | VAL | 163 | 25.279 | 9.593 | 12.013 | 1.00 | 37.05 |
| ATOM | 816 | CB | VAL | 163 | 22.981 | 9.574 | 14.346 | 1.00 | 24.63 |
| ATOM | 817 | CG1 | VAL | 163 | 22.349 | 10.183 | 13.084 | 1.00 | 26.16 |
| ATOM | 818 | CG2 | VAL | 163 | 22.601 | 8.131 | 14.532 | 1.00 | 19.95 |
| ATOM | 821 | N | GLY | 164 | 25.813 | 7.860 | 13.340 | 1.00 | 32.29 |
| ATOM | 822 | CA | GLY | 164 | 26.454 | 7.136 | 12.251 | 1.00 | 31.63 |
| ATOM | 823 | C | GLY | 164 | 25.442 | 6.526 | 11.307 | 1.00 | 33.63 |
| ATOM | 824 | O | GLY | 164 | 24.249 | 6.573 | 11.563 | 1.00 | 33.91 |
| ATOM | 825 | N | ARG | 165 | 25.889 | 5.958 | 10.199 | 1.00 | 38.58 |
| ATOM | 826 | CA | ARG | 165 | 24.933 | 5.344 | 9.268 | 1.00 | 42.05 |
| ATOM | 828 | C | ARG | 165 | 24.799 | 3.848 | 9.555 | 1.00 | 41.87 |
| ATOM | 829 | O | ARG | 165 | 23.693 | 3.301 | 9.630 | 1.00 | 45.87 |
| ATOM | 827 | CB | ARG | 165 | 25.351 | 5.595 | 7.809 | 1.00 | 43.59 |
| ATOM | 830 | N | ARG | 166 | 25.937 | 3.178 | 9.667 | 1.00 | 42.35 |
| ATOM | 831 | CA | ARG | 166 | 25.960 | 1.765 | 9.989 | 1.00 | 42.46 |
| ATOM | 839 | C | ARG | 166 | 25.579 | 1.750 | 11.467 | 1.00 | 41.38 |
| ATOM | 840 | O | ARG | 166 | 25.946 | 2.659 | 12.217 | 1.00 | 42.45 |
| ATOM | 832 | CB | ARG | 166 | 27.367 | 1.218 | 9.784 | 1.00 | 47.34 |
| ATOM | 833 | CG | ARG | 166 | 27.620 | 0.620 | 8.421 | 1.00 | 52.97 |
| ATOM | 834 | CD | ARG | 166 | 29.030 | 0.082 | 8.331 | 1.00 | 56.09 |
| ATOM | 835 | NE | ARG | 166 | 29.974 | 1.193 | 8.297 | 1.00 | 60.10 |
| ATOM | 836 | CZ | ARG | 166 | 30.849 | 1.394 | 7.307 | 1.00 | 65.05 |
| ATOM | 837 | NH1 | ARG | 166 | 30.922 | 0.527 | 6.286 | 1.00 | 66.02 |
| ATOM | 838 | NH2 | ARG | 166 | 31.671 | 2.447 | 7.335 | 1.00 | 62.96 |
| ATOM | 841 | N | ARG | 167 | 24.813 | 0.759 | 11.889 | 1.00 | 41.55 |
| ATOM | 842 | CA | ARG | 167 | 24.375 | 0.702 | 13.286 | 1.00 | 42.74 |
| ATOM | 844 | C | ARG | 167 | 25.433 | 0.164 | 14.269 | 1.00 | 40.29 |
| ATOM | 845 | O | ARG | 167 | 26.283 | -0.625 | 13.868 | 1.00 | 41.10 |
| ATOM | 843 | CB | ARG | 167 | 23.062 | -0.082 | 13.387 | 1.00 | 45.33 |
| ATOM | 846 | N | GLY | 168 | 25.461 | 0.714 | 15.488 | 1.00 | 35.52 |
| ATOM | 847 | CA | GLY | 168 | 26.408 | 0.281 | 16.515 | 1.00 | 33.40 |
| ATOM | 848 | C | GLY | 168 | 27.646 | 1.167 | 16.588 | 1.00 | 32.69 |
| ATOM | 849 | O | GLY | 168 | 28.575 | 0.949 | 17.371 | 1.00 | 36.01 |
| ATOM | 850 | N | THR | 169 | 27.629 | 2.208 | 15.769 | 1.00 | 30.93 |
| ATOM | 851 | CA | THR | 169 | 28.703 | 3.166 | 15.661 | 1.00 | 26.29 |
| ATOM | 855 | C | THR | 169 | 28.481 | 4.322 | 16.633 | 1.00 | 26.10 |
| ATOM | 856 | O | THR | 169 | 28.599 | 5.478 | 16.259 | 1.00 | 24.59 |
| ATOM | 852 | CB | THR | 169 | 28.731 | 3.726 | 14.247 | 1.00 | 28.83 |
| ATOM | 853 | OG1 | THR | 169 | 27.392 | 4.105 | 13.879 | 1.00 | 28.62 |

Figure 21Q

| ATOM | 854 | CG2 | THR | 169 | 29.260 | 2.693 | 13.253 | 1.00 | 27.89 |
| ATOM | 857 | N | LEU | 170 | 28.141 | 4.015 | 17.880 | 1.00 | 24.07 |
| ATOM | 858 | CA | LEU | 170 | 27.934 | 5.052 | 18.887 | 1.00 | 22.26 |
| ATOM | 863 | C | LEU | 170 | 29.286 | 5.582 | 19.351 | 1.00 | 23.34 |
| ATOM | 864 | O | LEU | 170 | 30.203 | 4.815 | 19.545 | 1.00 | 30.30 |
| ATOM | 859 | CB | LEU | 170 | 27.205 | 4.444 | 20.076 | 1.00 | 17.79 |
| ATOM | 860 | CG | LEU | 170 | 26.781 | 5.322 | 21.245 | 1.00 | 22.14 |
| ATOM | 861 | CD1 | LEU | 170 | 25.593 | 6.188 | 20.856 | 1.00 | 22.03 |
| ATOM | 862 | CD2 | LEU | 170 | 26.344 | 4.410 | 22.332 | 1.00 | 17.91 |
| ATOM | 865 | N | ALA | 171 | 29.458 | 6.880 | 19.501 | 1.00 | 22.71 |
| ATOM | 866 | CA | ALA | 171 | 30.738 | 7.359 | 19.999 | 1.00 | 18.39 |
| ATOM | 868 | C | ALA | 171 | 30.687 | 7.505 | 21.546 | 1.00 | 21.02 |
| ATOM | 869 | O | ALA | 171 | 29.669 | 7.937 | 22.113 | 1.00 | 24.45 |
| ATOM | 867 | CB | ALA | 171 | 31.107 | 8.673 | 19.325 | 1.00 | 19.01 |
| ATOM | 870 | N | VAL | 172 | 31.764 | 7.105 | 22.225 | 1.00 | 21.22 |
| ATOM | 871 | CA | VAL | 172 | 31.871 | 7.174 | 23.687 | 1.00 | 16.73 |
| ATOM | 875 | C | VAL | 172 | 33.089 | 8.042 | 23.944 | 1.00 | 16.31 |
| ATOM | 876 | O | VAL | 172 | 34.175 | 7.668 | 23.544 | 1.00 | 22.44 |
| ATOM | 872 | CB | VAL | 172 | 32.124 | 5.746 | 24.260 | 1.00 | 18.77 |
| ATOM | 873 | CG1 | VAL | 172 | 32.502 | 5.781 | 25.716 | 1.00 | 19.85 |
| ATOM | 874 | CG2 | VAL | 172 | 30.920 | 4.879 | 24.038 | 1.00 | 16.80 |
| ATOM | 877 | N | TYR | 173 | 32.916 | 9.229 | 24.515 | 1.00 | 14.11 |
| ATOM | 878 | CA | TYR | 173 | 34.047 | 10.104 | 24.754 | 1.00 | 12.78 |
| ATOM | 887 | C | TYR | 173 | 34.509 | 9.924 | 26.161 | 1.00 | 19.84 |
| ATOM | 888 | O | TYR | 173 | 33.749 | 9.519 | 27.027 | 1.00 | 20.82 |
| ATOM | 879 | CB | TYR | 173 | 33.672 | 11.563 | 24.533 | 1.00 | 15.57 |
| ATOM | 880 | CG | TYR | 173 | 33.296 | 11.895 | 23.101 | 1.00 | 17.92 |
| ATOM | 881 | CD1 | TYR | 173 | 32.074 | 11.481 | 22.575 | 1.00 | 18.64 |
| ATOM | 883 | CD2 | TYR | 173 | 34.176 | 12.567 | 22.257 | 1.00 | 17.47 |
| ATOM | 882 | CE1 | TYR | 173 | 31.738 | 11.726 | 21.252 | 1.00 | 17.54 |
| ATOM | 884 | CE2 | TYR | 173 | 33.850 | 12.803 | 20.932 | 1.00 | 17.35 |
| ATOM | 885 | CZ | TYR | 173 | 32.625 | 12.381 | 20.433 | 1.00 | 17.84 |
| ATOM | 886 | OH | TYR | 173 | 32.264 | 12.598 | 19.116 | 1.00 | 16.93 |
| ATOM | 889 | N | GLY | 174 | 35.757 | 10.257 | 26.417 | 1.00 | 22.64 |
| ATOM | 890 | CA | GLY | 174 | 36.290 | 10.079 | 27.741 | 1.00 | 23.42 |
| ATOM | 891 | C | GLY | 174 | 37.567 | 10.851 | 27.832 | 1.00 | 24.50 |
| ATOM | 892 | O | GLY | 174 | 37.989 | 11.411 | 26.851 | 1.00 | 29.56 |
| ATOM | 893 | N | ARG | 175 | 38.143 | 10.967 | 29.015 | 1.00 | 27.20 |
| ATOM | 894 | CA | ARG | 175 | 39.384 | 11.705 | 29.153 | 1.00 | 29.49 |
| ATOM | 902 | C | ARG | 175 | 40.534 | 10.730 | 29.228 | 1.00 | 31.91 |
| ATOM | 903 | O | ARG | 175 | 41.688 | 11.114 | 29.142 | 1.00 | 32.67 |
| ATOM | 895 | CB | ARG | 175 | 39.330 | 12.543 | 30.409 | 1.00 | 27.65 |
| ATOM | 896 | CG | ARG | 175 | 38.413 | 13.722 | 30.282 | 1.00 | 29.67 |
| ATOM | 897 | CD | ARG | 175 | 38.972 | 14.827 | 29.325 | 1.00 | 30.15 |
| ATOM | 898 | NE | ARG | 175 | 38.059 | 15.959 | 29.362 | 1.00 | 31.04 |
| ATOM | 899 | CZ | ARG | 175 | 38.234 | 17.120 | 28.755 | 1.00 | 34.65 |
| ATOM | 900 | NH1 | ARG | 175 | 39.338 | 17.370 | 28.046 | 1.00 | 30.78 |
| ATOM | 901 | NH2 | ARG | 175 | 37.282 | 18.040 | 28.888 | 1.00 | 37.65 |
| ATOM | 904 | N | ASP | 176 | 40.181 | 9.450 | 29.248 | 1.00 | 35.20 |
| ATOM | 905 | CA | ASP | 176 | 41.124 | 8.363 | 29.359 | 1.00 | 32.03 |
| ATOM | 910 | C | ASP | 176 | 40.893 | 7.233 | 28.315 | 1.00 | 30.86 |
| ATOM | 911 | O | ASP | 176 | 39.787 | 6.749 | 28.121 | 1.00 | 31.67 |
| ATOM | 906 | CB | ASP | 176 | 40.936 | 7.827 | 30.759 | 1.00 | 39.47 |
| ATOM | 907 | CG | ASP | 176 | 42.002 | 6.886 | 31.161 | 1.00 | 48.38 |

Figure 21R

| | | | | | | | | | |
|---|---|---|---|---|---|---|---|---|---|
| ATOM | 908 | OD1 | ASP | 176 | 41.984 | 5.705 | 30.744 | 1.00 | 50.80 |
| ATOM | 909 | OD2 | ASP | 176 | 42.863 | 7.338 | 31.928 | 1.00 | 58.97 |
| ATOM | 912 | N | PRO | 177 | 41.951 | 6.787 | 27.640 | 1.00 | 29.45 |
| ATOM | 914 | CA | PRO | 177 | 41.797 | 5.717 | 26.652 | 1.00 | 30.26 |
| ATOM | 917 | C | PRO | 177 | 41.423 | 4.366 | 27.241 | 1.00 | 30.24 |
| ATOM | 918 | O | PRO | 177 | 40.773 | 3.557 | 26.598 | 1.00 | 35.30 |
| ATOM | 915 | CB | PRO | 177 | 43.159 | 5.681 | 25.961 | 1.00 | 31.05 |
| ATOM | 916 | CG | PRO | 177 | 44.096 | 6.266 | 26.973 | 1.00 | 31.34 |
| ATOM | 913 | CD | PRO | 177 | 43.296 | 7.379 | 27.574 | 1.00 | 30.42 |
| ATOM | 919 | N | GLU | 178 | 41.883 | 4.067 | 28.439 | 1.00 | 30.89 |
| ATOM | 920 | CA | GLU | 178 | 41.501 | 2.803 | 29.038 | 1.00 | 28.04 |
| ATOM | 926 | C | GLU | 178 | 40.036 | 2.907 | 29.458 | 1.00 | 25.53 |
| ATOM | 927 | O | GLU | 178 | 39.242 | 2.048 | 29.157 | 1.00 | 28.11 |
| ATOM | 921 | CB | GLU | 178 | 42.349 | 2.501 | 30.268 | 1.00 | 30.41 |
| ATOM | 922 | CG | GLU | 178 | 42.096 | 1.118 | 30.858 | 1.00 | 32.44 |
| ATOM | 923 | CD | GLU | 178 | 42.790 | 0.050 | 30.058 | 1.00 | 37.09 |
| ATOM | 924 | OE1 | GLU | 178 | 43.951 | 0.283 | 29.671 | 1.00 | 41.06 |
| ATOM | 925 | OE2 | GLU | 178 | 42.204 | -1.024 | 29.823 | 1.00 | 40.37 |
| ATOM | 928 | N | TRP | 179 | 39.671 | 4.004 | 30.087 | 1.00 | 20.27 |
| ATOM | 929 | CA | TRP | 179 | 38.324 | 4.155 | 30.549 | 1.00 | 18.02 |
| ATOM | 940 | C | TRP | 179 | 37.368 | 4.024 | 29.387 | 1.00 | 24.92 |
| ATOM | 941 | O | TRP | 179 | 36.320 | 3.383 | 29.496 | 1.00 | 29.25 |
| ATOM | 930 | CB | TRP | 179 | 38.144 | 5.495 | 31.248 | 1.00 | 11.02 |
| ATOM | 931 | CG | TRP | 179 | 36.823 | 5.629 | 31.885 | 1.00 | 20.08 |
| ATOM | 935 | CD1 | TRP | 179 | 36.465 | 5.170 | 33.139 | 1.00 | 15.42 |
| ATOM | 932 | CD2 | TRP | 179 | 35.650 | 6.286 | 31.341 | 1.00 | 20.80 |
| ATOM | 936 | NE1 | TRP | 179 | 35.158 | 5.508 | 33.392 | 1.00 | 21.65 |
| ATOM | 933 | CE2 | TRP | 179 | 34.632 | 6.193 | 32.314 | 1.00 | 19.89 |
| ATOM | 934 | CE3 | TRP | 179 | 35.363 | 6.944 | 30.131 | 1.00 | 17.76 |
| ATOM | 937 | CZ2 | TRP | 179 | 33.332 | 6.743 | 32.114 | 1.00 | 21.72 |
| ATOM | 938 | CZ3 | TRP | 179 | 34.088 | 7.478 | 29.933 | 1.00 | 14.57 |
| ATOM | 939 | CH2 | TRP | 179 | 33.080 | 7.374 | 30.929 | 1.00 | 16.92 |
| ATOM | 942 | N | VAL | 180 | 37.735 | 4.585 | 28.247 | 1.00 | 24.63 |
| ATOM | 943 | CA | VAL | 180 | 36.856 | 4.494 | 27.095 | 1.00 | 24.07 |
| ATOM | 947 | C | VAL | 180 | 36.723 | 3.096 | 26.522 | 1.00 | 27.82 |
| ATOM | 948 | O | VAL | 180 | 35.628 | 2.668 | 26.159 | 1.00 | 30.00 |
| ATOM | 944 | CB | VAL | 180 | 37.320 | 5.411 | 25.990 | 1.00 | 23.26 |
| ATOM | 945 | CG1 | VAL | 180 | 36.454 | 5.201 | 24.706 | 1.00 | 15.40 |
| ATOM | 946 | CG2 | VAL | 180 | 37.321 | 6.832 | 26.513 | 1.00 | 22.46 |
| ATOM | 949 | N | THR | 181 | 37.837 | 2.383 | 26.415 | 1.00 | 30.50 |
| ATOM | 950 | CA | THR | 181 | 37.795 | 1.047 | 25.838 | 1.00 | 32.25 |
| ATOM | 954 | C | THR | 181 | 37.092 | 0.171 | 26.810 | 1.00 | 30.35 |
| ATOM | 955 | O | THR | 181 | 36.368 | -0.746 | 26.445 | 1.00 | 31.45 |
| ATOM | 951 | CB | THR | 181 | 39.208 | 0.499 | 25.525 | 1.00 | 34.34 |
| ATOM | 952 | OG1 | THR | 181 | 40.040 | 0.576 | 26.690 | 1.00 | 38.46 |
| ATOM | 953 | CG2 | THR | 181 | 39.851 | 1.350 | 24.410 | 1.00 | 38.81 |
| ATOM | 956 | N | GLN | 182 | 37.181 | 0.582 | 28.057 | 1.00 | 29.82 |
| ATOM | 957 | CA | GLN | 182 | 36.595 | -0.167 | 29.133 | 1.00 | 29.92 |
| ATOM | 963 | C | GLN | 182 | 35.066 | -0.110 | 29.197 | 1.00 | 29.67 |
| ATOM | 964 | O | GLN | 182 | 34.452 | -0.954 | 29.835 | 1.00 | 32.79 |
| ATOM | 958 | CB | GLN | 182 | 37.226 | 0.292 | 30.441 | 1.00 | 27.17 |
| ATOM | 959 | CG | GLN | 182 | 37.224 | -0.750 | 31.488 | 1.00 | 32.42 |
| ATOM | 960 | CD | GLN | 182 | 38.447 | -1.608 | 31.550 | 1.00 | 29.47 |
| ATOM | 961 | OE1 | GLN | 182 | 38.348 | -2.785 | 31.833 | 1.00 | 36.45 |

Figure 21S

| ATOM | 962 | NE2 | GLN | 182 | 39.603 | -1.022 | 31.372 | 1.00 | 33.03 |
|------|-----|-----|-----|-----|--------|--------|--------|------|-------|
| ATOM | 965 | N | ARG | 183 | 34.435 | 0.853 | 28.532 | 1.00 | 27.46 |
| ATOM | 966 | CA | ARG | 183 | 32.973 | 0.935 | 28.588 | 1.00 | 24.82 |
| ATOM | 974 | C | ARG | 183 | 32.275 | -0.096 | 27.725 | 1.00 | 23.34 |
| ATOM | 975 | O | ARG | 183 | 31.073 | -0.235 | 27.816 | 1.00 | 27.80 |
| ATOM | 967 | CB | ARG | 183 | 32.450 | 2.306 | 28.115 | 1.00 | 23.83 |
| ATOM | 968 | CG | ARG | 183 | 33.142 | 3.513 | 28.631 | 1.00 | 22.14 |
| ATOM | 969 | CD | ARG | 183 | 32.896 | 3.677 | 30.118 | 1.00 | 27.34 |
| ATOM | 970 | NE | ARG | 183 | 34.006 | 3.109 | 30.870 | 1.00 | 27.57 |
| ATOM | 971 | CZ | ARG | 183 | 33.956 | 2.723 | 32.136 | 1.00 | 24.93 |
| ATOM | 972 | NH1 | ARG | 183 | 32.841 | 2.809 | 32.848 | 1.00 | 25.63 |
| ATOM | 973 | NH2 | ARG | 183 | 35.040 | 2.222 | 32.676 | 1.00 | 26.19 |
| ATOM | 976 | N | PHE | 184 | 33.012 | -0.762 | 26.846 | 1.00 | 23.74 |
| ATOM | 977 | CA | PHE | 184 | 32.445 | -1.705 | 25.879 | 1.00 | 21.79 |
| ATOM | 985 | C | PHE | 184 | 32.474 | -3.168 | 26.272 | 1.00 | 25.02 |
| ATOM | 986 | O | PHE | 184 | 33.533 | -3.767 | 26.196 | 1.00 | 30.09 |
| ATOM | 978 | CB | PHE | 184 | 33.187 | -1.522 | 24.536 | 1.00 | 17.97 |
| ATOM | 979 | CG | PHE | 184 | 32.998 | -0.161 | 23.935 | 1.00 | 16.79 |
| ATOM | 980 | CD1 | PHE | 184 | 33.799 | 0.884 | 24.302 | 1.00 | 17.05 |
| ATOM | 981 | CD2 | PHE | 184 | 31.947 | 0.087 | 23.067 | 1.00 | 18.31 |
| ATOM | 982 | CE1 | PHE | 184 | 33.556 | 2.147 | 23.835 | 1.00 | 20.88 |
| ATOM | 983 | CE2 | PHE | 184 | 31.699 | 1.346 | 22.597 | 1.00 | 15.11 |
| ATOM | 984 | CZ | PHE | 184 | 32.503 | 2.382 | 22.977 | 1.00 | 18.91 |
| ATOM | 987 | N | PRO | 185 | 31.317 | -3.780 | 26.649 | 1.00 | 24.94 |
| ATOM | 989 | CA | PRO | 185 | 31.322 | -5.193 | 27.030 | 1.00 | 25.81 |
| ATOM | 992 | C | PRO | 185 | 31.696 | -6.230 | 25.951 | 1.00 | 29.32 |
| ATOM | 993 | O | PRO | 185 | 31.813 | -7.418 | 26.267 | 1.00 | 34.66 |
| ATOM | 990 | CB | PRO | 185 | 29.919 | -5.400 | 27.621 | 1.00 | 21.70 |
| ATOM | 991 | CG | PRO | 185 | 29.114 | -4.417 | 26.970 | 1.00 | 22.66 |
| ATOM | 988 | CD | PRO | 185 | 30.003 | -3.199 | 26.969 | 1.00 | 23.75 |
| ATOM | 994 | N | ASP | 186 | 31.866 | -5.816 | 24.692 | 1.00 | 30.88 |
| ATOM | 995 | CA | ASP | 186 | 32.298 | -6.762 | 23.629 | 1.00 | 33.49 |
| ATOM | 1000 | C | ASP | 186 | 33.833 | -6.863 | 23.706 | 1.00 | 35.14 |
| ATOM | 1001 | O | ASP | 186 | 34.437 | -7.773 | 23.144 | 1.00 | 37.18 |
| ATOM | 996 | CB | ASP | 186 | 31.995 | -6.276 | 22.190 | 1.00 | 29.65 |
| ATOM | 997 | CG | ASP | 186 | 30.738 | -5.487 | 22.078 | 1.00 | 34.74 |
| ATOM | 998 | OD1 | ASP | 186 | 30.761 | -4.272 | 22.431 | 1.00 | 43.46 |
| ATOM | 999 | OD2 | ASP | 186 | 29.725 | -6.058 | 21.618 | 1.00 | 33.67 |
| ATOM | 1002 | N | LEU | 187 | 34.453 | -5.834 | 24.284 | 1.00 | 33.94 |
| ATOM | 1003 | CA | LEU | 187 | 35.892 | -5.748 | 24.401 | 1.00 | 29.03 |
| ATOM | 1008 | C | LEU | 187 | 36.498 | -6.582 | 25.490 | 1.00 | 28.92 |
| ATOM | 1009 | O | LEU | 187 | 36.361 | -6.317 | 26.675 | 1.00 | 37.06 |
| ATOM | 1004 | CB | LEU | 187 | 36.307 | -4.296 | 24.542 | 1.00 | 29.47 |
| ATOM | 1005 | CG | LEU | 187 | 36.682 | -3.573 | 23.249 | 1.00 | 27.53 |
| ATOM | 1006 | CD1 | LEU | 187 | 35.599 | -3.735 | 22.192 | 1.00 | 25.99 |
| ATOM | 1007 | CD2 | LEU | 187 | 36.944 | -2.133 | 23.571 | 1.00 | 22.13 |
| ATOM | 1010 | N | THR | 188 | 37.106 | -7.652 | 25.051 | 1.00 | 27.92 |
| ATOM | 1011 | CA | THR | 188 | 37.803 | -8.615 | 25.861 | 1.00 | 27.24 |
| ATOM | 1015 | C | THR | 188 | 39.100 | -7.964 | 26.352 | 1.00 | 30.44 |
| ATOM | 1016 | O | THR | 188 | 39.565 | -6.986 | 25.751 | 1.00 | 30.56 |
| ATOM | 1012 | CB | THR | 188 | 38.059 | -9.822 | 24.940 | 1.00 | 24.35 |
| ATOM | 1013 | OG1 | THR | 188 | 37.076 | -10.819 | 25.204 | 1.00 | 30.69 |
| ATOM | 1014 | CG2 | THR | 188 | 39.436 | -10.381 | 25.027 | 1.00 | 28.27 |
| ATOM | 1017 | N | ALA | 189 | 39.686 | -8.506 | 27.431 | 1.00 | 34.52 |

Figure 21T

| ATOM | 1018 | CA | ALA | 189 | 40.944 | -7.990 | 28.009 | 1.00 | 35.65 |
|------|------|-----|-----|-----|--------|--------|--------|------|-------|
| ATOM | 1020 | C | ALA | 189 | 42.007 | -8.011 | 26.946 | 1.00 | 39.97 |
| ATOM | 1021 | O | ALA | 189 | 42.881 | -7.147 | 26.894 | 1.00 | 42.65 |
| ATOM | 1019 | CB | ALA | 189 | 41.375 | -8.839 | 29.121 | 1.00 | 35.31 |
| ATOM | 1022 | N | ALA | 190 | 41.948 | -9.064 | 26.139 | 1.00 | 40.80 |
| ATOM | 1023 | CA | ALA | 190 | 42.843 | -9.253 | 25.017 | 1.00 | 39.84 |
| ATOM | 1025 | C | ALA | 190 | 42.728 | -8.051 | 24.056 | 1.00 | 40.77 |
| ATOM | 1026 | O | ALA | 190 | 43.708 | -7.351 | 23.806 | 1.00 | 43.57 |
| ATOM | 1024 | CB | ALA | 190 | 42.462 | -10.519 | 24.310 | 1.00 | 38.24 |
| ATOM | 1027 | N | ASP | 191 | 41.519 | -7.803 | 23.549 | 1.00 | 38.93 |
| ATOM | 1028 | CA | ASP | 191 | 41.273 | -6.699 | 22.641 | 1.00 | 32.55 |
| ATOM | 1033 | C | ASP | 191 | 41.831 | -5.499 | 23.249 | 1.00 | 33.63 |
| ATOM | 1034 | O | ASP | 191 | 42.509 | -4.743 | 22.583 | 1.00 | 37.50 |
| ATOM | 1029 | CB | ASP | 191 | 39.799 | -6.433 | 22.502 | 1.00 | 29.76 |
| ATOM | 1030 | CG | ASP | 191 | 39.073 | -7.599 | 21.963 | 1.00 | 36.25 |
| ATOM | 1031 | OD1 | ASP | 191 | 39.714 | -8.479 | 21.341 | 1.00 | 41.09 |
| ATOM | 1032 | OD2 | ASP | 191 | 37.852 | -7.648 | 22.146 | 1.00 | 41.30 |
| ATOM | 1035 | N | ARG | 192 | 41.573 | -5.324 | 24.539 | 1.00 | 34.17 |
| ATOM | 1036 | CA | ARG | 192 | 42.049 | -4.126 | 25.195 | 1.00 | 37.71 |
| ATOM | 1044 | C | ARG | 192 | 43.566 | -4.008 | 25.211 | 1.00 | 42.33 |
| ATOM | 1045 | O | ARG | 192 | 44.090 | -2.895 | 25.317 | 1.00 | 43.93 |
| ATOM | 1037 | CB | ARG | 192 | 41.391 | -3.928 | 26.578 | 1.00 | 36.86 |
| ATOM | 1038 | CG | ARG | 192 | 39.861 | -3.690 | 26.511 | 1.00 | 27.25 |
| ATOM | 1039 | CD | ARG | 192 | 39.264 | -3.248 | 27.835 | 1.00 | 30.69 |
| ATOM | 1040 | NE | ARG | 192 | 39.714 | -4.055 | 28.972 | 1.00 | 35.90 |
| ATOM | 1041 | CZ | ARG | 192 | 39.097 | -5.143 | 29.446 | 1.00 | 39.05 |
| ATOM | 1042 | NH1 | ARG | 192 | 37.954 | -5.583 | 28.909 | 1.00 | 36.96 |
| ATOM | 1043 | NH2 | ARG | 192 | 39.628 | -5.794 | 30.476 | 1.00 | 32.71 |
| ATOM | 1046 | N | ASP | 193 | 44.259 | -5.139 | 25.013 | 1.00 | 45.77 |
| ATOM | 1047 | CA | ASP | 193 | 45.734 | -5.193 | 24.966 | 1.00 | 45.44 |
| ATOM | 1052 | C | ASP | 193 | 46.270 | -4.678 | 23.630 | 1.00 | 44.24 |
| ATOM | 1053 | O | ASP | 193 | 47.166 | -3.814 | 23.590 | 1.00 | 45.99 |
| ATOM | 1048 | CB | ASP | 193 | 46.251 | -6.625 | 25.186 | 1.00 | 48.79 |
| ATOM | 1049 | CG | ASP | 193 | 46.342 | -7.006 | 26.647 | 1.00 | 50.37 |
| ATOM | 1050 | OD1 | ASP | 193 | 46.423 | -6.089 | 27.491 | 1.00 | 51.03 |
| ATOM | 1051 | OD2 | ASP | 193 | 46.343 | -8.224 | 26.941 | 1.00 | 48.61 |
| ATOM | 1054 | N | GLY | 194 | 45.752 | -5.231 | 22.536 | 1.00 | 43.02 |
| ATOM | 1055 | CA | GLY | 194 | 46.187 | -4.787 | 21.220 | 1.00 | 42.74 |
| ATOM | 1056 | C | GLY | 194 | 45.952 | -3.300 | 21.026 | 1.00 | 39.80 |
| ATOM | 1057 | O | GLY | 194 | 46.736 | -2.603 | 20.407 | 1.00 | 45.17 |
| ATOM | 1058 | N | LEU | 195 | 44.852 | -2.823 | 21.577 | 1.00 | 38.61 |
| ATOM | 1059 | CA | LEU | 195 | 44.471 | -1.441 | 21.507 | 1.00 | 36.07 |
| ATOM | 1064 | C | LEU | 195 | 45.421 | -0.548 | 22.286 | 1.00 | 38.26 |
| ATOM | 1065 | O | LEU | 195 | 45.959 | 0.413 | 21.731 | 1.00 | 38.71 |
| ATOM | 1060 | CB | LEU | 195 | 43.068 | -1.311 | 22.061 | 1.00 | 35.04 |
| ATOM | 1061 | CG | LEU | 195 | 42.029 | -1.749 | 21.049 | 1.00 | 37.00 |
| ATOM | 1062 | CD1 | LEU | 195 | 40.612 | -1.784 | 21.636 | 1.00 | 32.88 |
| ATOM | 1063 | CD2 | LEU | 195 | 42.116 | -0.745 | 19.900 | 1.00 | 39.88 |
| ATOM | 1066 | N | ARG | 196 | 45.625 | -0.874 | 23.567 | 1.00 | 36.24 |
| ATOM | 1067 | CA | ARG | 196 | 46.484 | -0.112 | 24.466 | 1.00 | 33.52 |
| ATOM | 1075 | C | ARG | 196 | 47.887 | -0.024 | 23.965 | 1.00 | 37.30 |
| ATOM | 1076 | O | ARG | 196 | 48.540 | 1.012 | 24.128 | 1.00 | 38.25 |
| ATOM | 1068 | CB | ARG | 196 | 46.472 | -0.709 | 25.844 | 1.00 | 32.83 |
| ATOM | 1069 | CG | ARG | 196 | 47.459 | -0.101 | 26.800 | 1.00 | 39.70 |

Figure 21U

| ATOM | 1070 | CD | ARG | 196 | 46.917 | -0.087 | 28.214 | 1.00 | 48.58 |
|---|---|---|---|---|---|---|---|---|---|
| ATOM | 1071 | NE | ARG | 196 | 46.608 | -1.421 | 28.743 | 1.00 | 57.95 |
| ATOM | 1072 | CZ | ARG | 196 | 45.447 | -2.068 | 28.588 | 1.00 | 62.66 |
| ATOM | 1073 | NH1 | ARG | 196 | 44.448 | -1.520 | 27.897 | 1.00 | 66.54 |
| ATOM | 1074 | NH2 | ARG | 196 | 45.260 | -3.255 | 29.156 | 1.00 | 64.26 |
| ATOM | 1077 | N | ALA | 197 | 48.358 | -1.125 | 23.383 | 1.00 | 40.28 |
| ATOM | 1078 | CA | ALA | 197 | 49.694 | -1.214 | 22.783 | 1.00 | 43.97 |
| ATOM | 1080 | C | ALA | 197 | 49.869 | -0.097 | 21.719 | 1.00 | 46.74 |
| ATOM | 1081 | O | ALA | 197 | 50.943 | 0.499 | 21.564 | 1.00 | 45.42 |
| ATOM | 1079 | CB | ALA | 197 | 49.840 | -2.567 | 22.116 | 1.00 | 43.21 |
| ATOM | 1082 | N | GLN | 198 | 48.792 | 0.136 | 20.964 | 1.00 | 48.99 |
| ATOM | 1083 | CA | GLN | 198 | 48.749 | 1.145 | 19.915 | 1.00 | 45.12 |
| ATOM | 1089 | C | GLN | 198 | 48.585 | 2.547 | 20.514 | 1.00 | 44.49 |
| ATOM | 1090 | O | GLN | 198 | 49.435 | 3.400 | 20.303 | 1.00 | 47.79 |
| ATOM | 1084 | CB | GLN | 198 | 47.589 | 0.861 | 18.946 | 1.00 | 41.02 |
| ATOM | 1085 | CG | GLN | 198 | 47.516 | -0.536 | 18.349 | 1.00 | 36.69 |
| ATOM | 1086 | CD | GLN | 198 | 46.274 | -0.729 | 17.476 | 1.00 | 39.09 |
| ATOM | 1087 | OE1 | GLN | 198 | 45.968 | 0.104 | 16.639 | 1.00 | 36.72 |
| ATOM | 1088 | NE2 | GLN | 198 | 45.558 | -1.828 | 17.677 | 1.00 | 39.10 |
| ATOM | 1091 | N | TRP | 199 | 47.554 | 2.778 | 21.326 | 1.00 | 44.54 |
| ATOM | 1092 | CA | TRP | 199 | 47.365 | 4.118 | 21.864 | 1.00 | 46.88 |
| ATOM | 1103 | C | TRP | 199 | 48.603 | 4.609 | 22.579 | 1.00 | 49.80 |
| ATOM | 1104 | O | TRP | 199 | 48.813 | 5.814 | 22.754 | 1.00 | 50.10 |
| ATOM | 1093 | CB | TRP | 199 | 46.060 | 4.262 | 22.682 | 1.00 | 49.31 |
| ATOM | 1094 | CG | TRP | 199 | 45.970 | 3.813 | 24.184 | 1.00 | 53.69 |
| ATOM | 1098 | CD1 | TRP | 199 | 46.615 | 4.380 | 25.277 | 1.00 | 52.47 |
| ATOM | 1095 | CD2 | TRP | 199 | 45.043 | 2.849 | 24.746 | 1.00 | 50.35 |
| ATOM | 1099 | NE1 | TRP | 199 | 46.125 | 3.836 | 26.454 | 1.00 | 51.74 |
| ATOM | 1096 | CE2 | TRP | 199 | 45.170 | 2.899 | 26.151 | 1.00 | 49.04 |
| ATOM | 1097 | CE3 | TRP | 199 | 44.115 | 1.959 | 24.181 | 1.00 | 51.31 |
| ATOM | 1100 | CZ2 | TRP | 199 | 44.412 | 2.089 | 26.998 | 1.00 | 53.08 |
| ATOM | 1101 | CZ3 | TRP | 199 | 43.351 | 1.141 | 25.043 | 1.00 | 54.73 |
| ATOM | 1102 | CH2 | TRP | 199 | 43.507 | 1.217 | 26.426 | 1.00 | 54.74 |
| ATOM | 1105 | N | GLN | 200 | 49.499 | 3.674 | 22.866 | 1.00 | 53.97 |
| ATOM | 1106 | CA | GLN | 200 | 50.752 | 4.023 | 23.522 | 1.00 | 58.62 |
| ATOM | 1112 | C | GLN | 200 | 51.801 | 4.474 | 22.495 | 1.00 | 60.14 |
| ATOM | 1113 | O | GLN | 200 | 53.001 | 4.560 | 22.776 | 1.00 | 60.70 |
| ATOM | 1107 | CB | GLN | 200 | 51.229 | 2.873 | 24.411 | 1.00 | 54.54 |
| ATOM | 1108 | CG | GLN | 200 | 50.383 | 2.755 | 25.678 | 1.00 | 54.36 |
| ATOM | 1109 | CD | GLN | 200 | 50.813 | 1.627 | 26.583 | 1.00 | 55.82 |
| ATOM | 1110 | OE1 | GLN | 200 | 51.400 | 0.639 | 26.115 | 1.00 | 58.71 |
| ATOM | 1111 | NE2 | GLN | 200 | 50.543 | 1.764 | 27.894 | 1.00 | 51.10 |
| ATOM | 1114 | N | ARG | 201 | 51.300 | 4.863 | 21.330 | 1.00 | 59.79 |
| ATOM | 1115 | CA | ARG | 201 | 52.131 | 5.328 | 20.244 | 1.00 | 61.29 |
| ATOM | 1117 | C | ARG | 201 | 51.393 | 6.433 | 19.490 | 1.00 | 63.96 |
| ATOM | 1118 | O | ARG | 201 | 51.915 | 6.960 | 18.494 | 1.00 | 66.88 |
| ATOM | 1116 | CB | ARG | 201 | 52.453 | 4.167 | 19.293 | 1.00 | 62.46 |
| ATOM | 1119 | N | CYS | 202 | 50.187 | 6.779 | 19.945 | 1.00 | 62.41 |
| ATOM | 1120 | CA | CYS | 202 | 49.391 | 7.832 | 19.303 | 1.00 | 63.40 |
| ATOM | 1123 | C | CYS | 202 | 48.563 | 8.507 | 20.384 | 1.00 | 64.22 |
| ATOM | 1124 | O | CYS | 202 | 47.829 | 7.835 | 21.131 | 1.00 | 66.32 |
| ATOM | 1121 | CB | CYS | 202 | 48.450 | 7.239 | 18.257 | 1.00 | 61.39 |
| ATOM | 1122 | SG | CYS | 202 | 49.270 | 6.169 | 17.020 | 1.00 | 79.62 |
| ATOM | 1125 | N | GLY | 203 | 48.662 | 9.830 | 20.468 | 1.00 | 63.17 |

Figure 21V

| ATOM | 1126 | CA  | GLY | 203 | 47.921 | 10.566 | 21.486 | 1.00 | 62.01 |
| ---- | ---- | --- | --- | --- | ------ | ------ | ------ | ---- | ----- |
| ATOM | 1127 | C   | GLY | 203 | 48.289 | 12.027 | 21.367 | 1.00 | 62.07 |
| ATOM | 1128 | O   | GLY | 203 | 49.154 | 12.346 | 20.540 | 1.00 | 65.36 |
| ATOM | 1129 | N   | SER | 204 | 47.679 | 12.877 | 22.195 | 1.00 | 61.18 |
| ATOM | 1130 | CA  | SER | 204 | 47.888 | 14.332 | 22.192 | 1.00 | 62.35 |
| ATOM | 1133 | C   | SER | 204 | 48.903 | 14.935 | 21.177 | 1.00 | 65.46 |
| ATOM | 1134 | O   | SER | 204 | 48.651 | 14.827 | 19.936 | 1.00 | 68.87 |
| ATOM | 1131 | CB  | SER | 204 | 48.165 | 14.832 | 23.613 | 1.00 | 59.85 |
| ATOM | 1132 | OG  | SER | 204 | 47.912 | 16.230 | 23.680 | 1.00 | 61.90 |
| ATOM | 1139 | N   | ALA | 209 | 55.720 | 19.006 | 13.772 | 1.00 | 54.11 |
| ATOM | 1140 | CA  | ALA | 209 | 54.248 | 18.736 | 13.652 | 1.00 | 58.83 |
| ATOM | 1137 | C   | ALA | 209 | 53.674 | 19.827 | 12.786 | 1.00 | 60.31 |
| ATOM | 1138 | O   | ALA | 209 | 54.291 | 20.870 | 12.619 | 1.00 | 63.90 |
| ATOM | 1136 | CB  | ALA | 209 | 53.542 | 18.737 | 15.006 | 1.00 | 59.22 |
| ATOM | 1141 | N   | SER | 210 | 52.452 | 19.628 | 12.322 | 1.00 | 61.91 |
| ATOM | 1142 | CA  | SER | 210 | 51.781 | 20.579 | 11.429 | 1.00 | 61.68 |
| ATOM | 1145 | C   | SER | 210 | 50.896 | 21.633 | 12.162 | 1.00 | 60.77 |
| ATOM | 1146 | O   | SER | 210 | 50.137 | 22.401 | 11.532 | 1.00 | 60.26 |
| ATOM | 1143 | CB  | SER | 210 | 50.945 | 19.747 | 10.448 | 1.00 | 63.72 |
| ATOM | 1144 | OG  | SER | 210 | 51.606 | 18.515 | 10.124 | 1.00 | 63.43 |
| ATOM | 1147 | N   | GLY | 211 | 50.992 | 21.640 | 13.494 | 1.00 | 57.84 |
| ATOM | 1148 | CA  | GLY | 211 | 50.217 | 22.561 | 14.297 | 1.00 | 55.55 |
| ATOM | 1149 | C   | GLY | 211 | 48.778 | 22.100 | 14.486 | 1.00 | 54.23 |
| ATOM | 1150 | O   | GLY | 211 | 48.498 | 20.907 | 14.517 | 1.00 | 55.02 |
| ATOM | 1151 | N   | ASP | 212 | 47.863 | 23.050 | 14.630 | 1.00 | 50.53 |
| ATOM | 1152 | CA  | ASP | 212 | 46.449 | 22.745 | 14.827 | 1.00 | 47.14 |
| ATOM | 1157 | C   | ASP | 212 | 45.808 | 22.389 | 13.469 | 1.00 | 42.71 |
| ATOM | 1158 | O   | ASP | 212 | 45.754 | 23.219 | 12.549 | 1.00 | 45.37 |
| ATOM | 1153 | CB  | ASP | 212 | 45.759 | 23.954 | 15.478 | 1.00 | 45.05 |
| ATOM | 1154 | CG  | ASP | 212 | 44.460 | 23.599 | 16.139 | 1.00 | 45.14 |
| ATOM | 1155 | OD1 | ASP | 212 | 43.776 | 22.643 | 15.696 | 1.00 | 43.31 |
| ATOM | 1156 | OD2 | ASP | 212 | 44.117 | 24.303 | 17.103 | 1.00 | 43.04 |
| ATOM | 1159 | N   | PRO | 213 | 45.285 | 21.160 | 13.346 | 1.00 | 35.67 |
| ATOM | 1161 | CA  | PRO | 213 | 44.661 | 20.700 | 12.109 | 1.00 | 31.78 |
| ATOM | 1164 | C   | PRO | 213 | 43.277 | 21.259 | 11.818 | 1.00 | 32.46 |
| ATOM | 1165 | O   | PRO | 213 | 42.731 | 21.048 | 10.724 | 1.00 | 36.10 |
| ATOM | 1162 | CB  | PRO | 213 | 44.590 | 19.196 | 12.325 | 1.00 | 31.14 |
| ATOM | 1163 | CG  | PRO | 213 | 44.346 | 19.081 | 13.808 | 1.00 | 30.49 |
| ATOM | 1160 | CD  | PRO | 213 | 45.266 | 20.111 | 14.385 | 1.00 | 34.43 |
| ATOM | 1166 | N   | PHE | 214 | 42.701 | 21.972 | 12.779 | 1.00 | 32.02 |
| ATOM | 1167 | CA  | PHE | 214 | 41.338 | 22.476 | 12.622 | 1.00 | 28.90 |
| ATOM | 1175 | C   | PHE | 214 | 41.279 | 23.760 | 11.873 | 1.00 | 27.51 |
| ATOM | 1176 | O   | PHE | 214 | 41.722 | 24.780 | 12.368 | 1.00 | 27.26 |
| ATOM | 1168 | CB  | PHE | 214 | 40.656 | 22.625 | 13.984 | 1.00 | 25.19 |
| ATOM | 1169 | CG  | PHE | 214 | 39.175 | 22.917 | 13.912 | 1.00 | 18.12 |
| ATOM | 1170 | CD1 | PHE | 214 | 38.278 | 21.935 | 13.516 | 1.00 | 13.31 |
| ATOM | 1171 | CD2 | PHE | 214 | 38.677 | 24.172 | 14.304 | 1.00 | 18.16 |
| ATOM | 1172 | CE1 | PHE | 214 | 36.907 | 22.189 | 13.515 | 1.00 | 13.17 |
| ATOM | 1173 | CE2 | PHE | 214 | 37.291 | 24.439 | 14.304 | 1.00 | 16.89 |
| ATOM | 1174 | CZ  | PHE | 214 | 36.411 | 23.439 | 13.911 | 1.00 | 13.74 |
| ATOM | 1177 | N   | ARG | 215 | 40.634 | 23.723 | 10.721 | 1.00 | 29.52 |
| ATOM | 1178 | CA  | ARG | 215 | 40.534 | 24.914 | 9.902  | 1.00 | 33.36 |
| ATOM | 1186 | C   | ARG | 215 | 39.129 | 25.358 | 9.588  | 1.00 | 32.72 |
| ATOM | 1187 | O   | ARG | 215 | 38.899 | 26.130 | 8.665  | 1.00 | 37.25 |

Figure 21W

| ATOM | 1179 | CB | ARG | 215 | 41.384 | 24.757 | 8.643 | 1.00 | 34.33 |
|------|------|------|-----|-----|--------|--------|--------|------|-------|
| ATOM | 1180 | CG | ARG | 215 | 42.887 | 24.871 | 8.967 | 1.00 | 46.95 |
| ATOM | 1181 | CD | ARG | 215 | 43.771 | 24.409 | 7.843 | 1.00 | 53.60 |
| ATOM | 1182 | NE | ARG | 215 | 43.378 | 23.057 | 7.462 | 1.00 | 60.61 |
| ATOM | 1183 | CZ | ARG | 215 | 44.216 | 22.120 | 7.034 | 1.00 | 63.60 |
| ATOM | 1184 | NH1 | ARG | 215 | 45.519 | 22.380 | 6.941 | 1.00 | 63.33 |
| ATOM | 1185 | NH2 | ARG | 215 | 43.738 | 20.942 | 6.634 | 1.00 | 65.46 |
| ATOM | 1188 | N | SER | 216 | 38.170 | 24.830 | 10.319 | 1.00 | 30.58 |
| ATOM | 1189 | CA | SER | 216 | 36.788 | 25.247 | 10.128 | 1.00 | 27.44 |
| ATOM | 1192 | C | SER | 216 | 36.675 | 26.340 | 11.190 | 1.00 | 28.43 |
| ATOM | 1193 | O | SER | 216 | 37.695 | 26.884 | 11.654 | 1.00 | 25.95 |
| ATOM | 1190 | CB | SER | 216 | 35.824 | 24.093 | 10.435 | 1.00 | 26.03 |
| ATOM | 1191 | OG | SER | 216 | 34.455 | 24.469 | 10.369 | 1.00 | 31.02 |
| ATOM | 1194 | N | ASP | 217 | 35.453 | 26.597 | 11.640 | 1.00 | 30.09 |
| ATOM | 1195 | CA | ASP | 217 | 35.222 | 27.614 | 12.646 | 1.00 | 32.24 |
| ATOM | 1200 | C | ASP | 217 | 33.890 | 27.357 | 13.363 | 1.00 | 32.46 |
| ATOM | 1201 | O | ASP | 217 | 33.171 | 26.402 | 13.049 | 1.00 | 32.60 |
| ATOM | 1196 | CB | ASP | 217 | 35.248 | 29.036 | 12.012 | 1.00 | 29.83 |
| ATOM | 1197 | CG | ASP | 217 | 34.296 | 29.191 | 10.818 | 1.00 | 34.35 |
| ATOM | 1198 | OD1 | ASP | 217 | 33.152 | 28.702 | 10.860 | 1.00 | 38.57 |
| ATOM | 1199 | OD2 | ASP | 217 | 34.690 | 29.806 | 9.813 | 1.00 | 40.40 |
| ATOM | 1202 | N | SER | 218 | 33.530 | 28.306 | 14.218 | 1.00 | 30.22 |
| ATOM | 1203 | CA | SER | 218 | 32.311 | 28.271 | 14.996 | 1.00 | 28.39 |
| ATOM | 1206 | C | SER | 218 | 31.064 | 28.127 | 14.132 | 1.00 | 27.80 |
| ATOM | 1207 | O | SER | 218 | 30.148 | 27.366 | 14.463 | 1.00 | 25.20 |
| ATOM | 1204 | CB | SER | 218 | 32.227 | 29.562 | 15.799 | 1.00 | 28.12 |
| ATOM | 1205 | OG | SER | 218 | 31.321 | 29.381 | 16.855 | 1.00 | 32.39 |
| ATOM | 1208 | N | TYR | 219 | 31.053 | 28.853 | 13.018 | 1.00 | 25.85 |
| ATOM | 1209 | CA | TYR | 219 | 29.927 | 28.869 | 12.086 | 1.00 | 24.31 |
| ATOM | 1218 | C | TYR | 219 | 29.759 | 27.594 | 11.318 | 1.00 | 23.75 |
| ATOM | 1219 | O | TYR | 219 | 28.655 | 27.236 | 10.965 | 1.00 | 28.36 |
| ATOM | 1210 | CB | TYR | 219 | 30.079 | 30.003 | 11.100 | 1.00 | 25.49 |
| ATOM | 1211 | CG | TYR | 219 | 30.472 | 31.269 | 11.760 | 1.00 | 17.44 |
| ATOM | 1212 | CD1 | TYR | 219 | 29.527 | 32.050 | 12.359 | 1.00 | 20.39 |
| ATOM | 1214 | CD2 | TYR | 219 | 31.795 | 31.655 | 11.817 | 1.00 | 15.51 |
| ATOM | 1213 | CE1 | TYR | 219 | 29.868 | 33.183 | 13.003 | 1.00 | 21.63 |
| ATOM | 1215 | CE2 | TYR | 219 | 32.150 | 32.776 | 12.462 | 1.00 | 17.28 |
| ATOM | 1216 | CZ | TYR | 219 | 31.175 | 33.544 | 13.071 | 1.00 | 21.51 |
| ATOM | 1217 | OH | TYR | 219 | 31.503 | 34.633 | 13.851 | 1.00 | 25.64 |
| ATOM | 1220 | N | GLY | 220 | 30.844 | 26.900 | 11.058 | 1.00 | 21.69 |
| ATOM | 1221 | CA | GLY | 220 | 30.696 | 25.663 | 10.350 | 1.00 | 23.10 |
| ATOM | 1222 | C | GLY | 220 | 29.891 | 24.748 | 11.240 | 1.00 | 25.28 |
| ATOM | 1223 | O | GLY | 220 | 28.831 | 24.298 | 10.870 | 1.00 | 27.08 |
| ATOM | 1224 | N | LEU | 221 | 30.368 | 24.531 | 12.454 | 1.00 | 27.43 |
| ATOM | 1225 | CA | LEU | 221 | 29.687 | 23.663 | 13.400 | 1.00 | 23.85 |
| ATOM | 1230 | C | LEU | 221 | 28.232 | 24.050 | 13.574 | 1.00 | 24.86 |
| ATOM | 1231 | O | LEU | 221 | 27.379 | 23.188 | 13.646 | 1.00 | 28.26 |
| ATOM | 1226 | CB | LEU | 221 | 30.376 | 23.739 | 14.751 | 1.00 | 22.63 |
| ATOM | 1227 | CG | LEU | 221 | 31.629 | 22.918 | 15.039 | 1.00 | 23.32 |
| ATOM | 1228 | CD1 | LEU | 221 | 31.930 | 21.947 | 13.929 | 1.00 | 16.81 |
| ATOM | 1229 | CD2 | LEU | 221 | 32.786 | 23.839 | 15.343 | 1.00 | 25.13 |
| ATOM | 1232 | N | LEU | 222 | 27.942 | 25.338 | 13.703 | 1.00 | 24.44 |
| ATOM | 1233 | CA | LEU | 222 | 26.555 | 25.792 | 13.874 | 1.00 | 24.17 |
| ATOM | 1238 | C | LEU | 222 | 25.748 | 25.473 | 12.606 | 1.00 | 25.37 |

Figure 21X

| ATOM | 1239 | O   | LEU | 222 | 24.543 | 25.266 | 12.652 | 1.00 | 28.51 |
|------|------|-----|-----|-----|--------|--------|--------|------|-------|
| ATOM | 1234 | CB  | LEU | 222 | 26.530 | 27.294 | 14.158 | 1.00 | 18.10 |
| ATOM | 1235 | CG  | LEU | 222 | 25.413 | 28.055 | 14.861 | 1.00 | 19.64 |
| ATOM | 1236 | CD1 | LEU | 222 | 25.120 | 29.304 | 14.031 | 1.00 | 13.66 |
| ATOM | 1237 | CD2 | LEU | 222 | 24.181 | 27.215 | 15.130 | 1.00 | 10.70 |
| ATOM | 1240 | N   | GLY | 223 | 26.424 | 25.359 | 11.481 | 1.00 | 24.05 |
| ATOM | 1241 | CA  | GLY | 223 | 25.716 | 25.084 | 10.260 | 1.00 | 23.57 |
| ATOM | 1242 | C   | GLY | 223 | 25.230 | 23.673 | 10.187 | 1.00 | 24.92 |
| ATOM | 1243 | O   | GLY | 223 | 24.158 | 23.435 |  9.644 | 1.00 | 27.83 |
| ATOM | 1244 | N   | ASN | 224 | 26.024 | 22.721 | 10.668 | 1.00 | 26.40 |
| ATOM | 1245 | CA  | ASN | 224 | 25.595 | 21.345 | 10.581 | 1.00 | 30.28 |
| ATOM | 1250 | C   | ASN | 224 | 24.813 | 20.863 | 11.731 | 1.00 | 34.09 |
| ATOM | 1251 | O   | ASN | 224 | 24.192 | 19.807 | 11.649 | 1.00 | 38.67 |
| ATOM | 1246 | CB  | ASN | 224 | 26.680 | 20.343 | 10.150 | 1.00 | 37.71 |
| ATOM | 1247 | CG  | ASN | 224 | 27.829 | 20.218 | 11.112 | 1.00 | 44.96 |
| ATOM | 1248 | OD1 | ASN | 224 | 28.541 | 21.182 | 11.375 | 1.00 | 55.47 |
| ATOM | 1249 | ND2 | ASN | 224 | 28.108 | 18.991 | 11.541 | 1.00 | 50.17 |
| ATOM | 1252 | N   | SER | 225 | 24.703 | 21.710 | 12.750 | 1.00 | 37.86 |
| ATOM | 1253 | CA  | SER | 225 | 23.920 | 21.378 | 13.938 | 1.00 | 36.97 |
| ATOM | 1256 | C   | SER | 225 | 22.486 | 21.477 | 13.488 | 1.00 | 33.63 |
| ATOM | 1257 | O   | SER | 225 | 21.629 | 20.885 | 14.132 | 1.00 | 39.97 |
| ATOM | 1254 | CB  | SER | 225 | 24.125 | 22.387 | 15.059 | 1.00 | 39.46 |
| ATOM | 1255 | OG  | SER | 225 | 23.501 | 23.624 | 14.706 | 1.00 | 45.03 |
| ATOM | 1258 | N   | VAL | 226 | 22.221 | 22.300 | 12.459 | 1.00 | 27.68 |
| ATOM | 1259 | CA  | VAL | 226 | 20.866 | 22.449 | 11.906 | 1.00 | 24.84 |
| ATOM | 1263 | C   | VAL | 226 | 20.504 | 21.312 | 10.980 | 1.00 | 23.63 |
| ATOM | 1264 | O   | VAL | 226 | 19.317 | 20.947 | 10.848 | 1.00 | 26.16 |
| ATOM | 1260 | CB  | VAL | 226 | 20.650 | 23.752 | 11.146 | 1.00 | 26.42 |
| ATOM | 1261 | CG1 | VAL | 226 | 19.152 | 23.936 | 10.845 | 1.00 | 27.11 |
| ATOM | 1262 | CG2 | VAL | 226 | 21.122 | 24.897 | 11.997 | 1.00 | 34.71 |
| ATOM | 1265 | N   | ASP | 227 | 21.503 | 20.778 | 10.296 | 1.00 | 19.92 |
| ATOM | 1266 | CA  | ASP | 227 | 21.230 | 19.671 |  9.427 | 1.00 | 20.17 |
| ATOM | 1271 | C   | ASP | 227 | 20.823 | 18.524 | 10.327 | 1.00 | 23.27 |
| ATOM | 1272 | O   | ASP | 227 | 19.866 | 17.830 | 10.031 | 1.00 | 22.86 |
| ATOM | 1267 | CB  | ASP | 227 | 22.466 | 19.254 |  8.669 | 1.00 | 22.84 |
| ATOM | 1268 | CG  | ASP | 227 | 22.987 | 20.327 |  7.740 | 1.00 | 24.28 |
| ATOM | 1269 | OD1 | ASP | 227 | 22.253 | 21.268 |  7.367 | 1.00 | 26.78 |
| ATOM | 1270 | OD2 | ASP | 227 | 24.162 | 20.195 |  7.361 | 1.00 | 26.65 |
| ATOM | 1273 | N   | ALA | 228 | 21.548 | 18.321 | 11.429 | 1.00 | 22.68 |
| ATOM | 1274 | CA  | ALA | 228 | 21.238 | 17.214 | 12.331 | 1.00 | 22.37 |
| ATOM | 1276 | C   | ALA | 228 | 19.809 | 17.262 | 12.792 | 1.00 | 25.35 |
| ATOM | 1277 | O   | ALA | 228 | 19.206 | 16.231 | 13.044 | 1.00 | 28.84 |
| ATOM | 1275 | CB  | ALA | 228 | 22.119 | 17.223 | 13.512 | 1.00 | 20.24 |
| ATOM | 1278 | N   | LEU | 229 | 19.261 | 18.454 | 12.947 | 1.00 | 25.90 |
| ATOM | 1279 | CA  | LEU | 229 | 17.875 | 18.578 | 13.377 | 1.00 | 23.79 |
| ATOM | 1284 | C   | LEU | 229 | 16.930 | 17.923 | 12.351 | 1.00 | 25.05 |
| ATOM | 1285 | O   | LEU | 229 | 15.775 | 17.617 | 12.648 | 1.00 | 29.62 |
| ATOM | 1280 | CB  | LEU | 229 | 17.515 | 20.043 | 13.528 | 1.00 | 21.34 |
| ATOM | 1281 | CG  | LEU | 229 | 17.565 | 20.861 | 14.813 | 1.00 | 27.66 |
| ATOM | 1282 | CD1 | LEU | 229 | 18.840 | 20.742 | 15.550 | 1.00 | 32.14 |
| ATOM | 1283 | CD2 | LEU | 229 | 17.411 | 22.307 | 14.376 | 1.00 | 28.67 |
| ATOM | 1286 | N   | TYR | 230 | 17.415 | 17.675 | 11.152 | 1.00 | 24.44 |
| ATOM | 1287 | CA  | TYR | 230 | 16.565 | 17.106 | 10.152 | 1.00 | 24.41 |
| ATOM | 1296 | C   | TYR | 230 | 17.009 | 15.753 |  9.672 | 1.00 | 30.59 |

Figure 21Y

| ATOM | 1297 | O | TYR | 230 | 16.853 | 15.417 | 8.490 | 1.00 | 34.38 |
|------|------|-----|-----|-----|--------|--------|-------|------|-------|
| ATOM | 1288 | CB | TYR | 230 | 16.388 | 18.094 | 9.011 | 1.00 | 24.38 |
| ATOM | 1289 | CG | TYR | 230 | 15.606 | 19.291 | 9.453 | 1.00 | 22.41 |
| ATOM | 1290 | CD1 | TYR | 230 | 16.212 | 20.301 | 10.199 | 1.00 | 23.91 |
| ATOM | 1292 | CD2 | TYR | 230 | 14.224 | 19.363 | 9.227 | 1.00 | 18.72 |
| ATOM | 1291 | CE1 | TYR | 230 | 15.438 | 21.372 | 10.746 | 1.00 | 24.68 |
| ATOM | 1293 | CE2 | TYR | 230 | 13.462 | 20.403 | 9.753 | 1.00 | 24.11 |
| ATOM | 1294 | CZ | TYR | 230 | 14.072 | 21.397 | 10.522 | 1.00 | 23.61 |
| ATOM | 1295 | OH | TYR | 230 | 13.294 | 22.351 | 11.130 | 1.00 | 29.94 |
| ATOM | 1298 | N | ILE | 231 | 17.701 | 15.033 | 10.544 | 1.00 | 29.71 |
| ATOM | 1299 | CA | ILE | 231 | 18.066 | 13.672 | 10.234 | 1.00 | 31.94 |
| ATOM | 1304 | C | ILE | 231 | 16.915 | 12.951 | 10.960 | 1.00 | 37.44 |
| ATOM | 1305 | O | ILE | 231 | 16.638 | 13.218 | 12.141 | 1.00 | 35.38 |
| ATOM | 1300 | CB | ILE | 231 | 19.403 | 13.245 | 10.833 | 1.00 | 28.77 |
| ATOM | 1302 | CG1 | ILE | 231 | 20.535 | 14.093 | 10.298 | 1.00 | 29.35 |
| ATOM | 1301 | CG2 | ILE | 231 | 19.738 | 11.845 | 10.415 | 1.00 | 28.40 |
| ATOM | 1303 | CD1 | ILE | 231 | 21.878 | 13.562 | 10.737 | 1.00 | 30.62 |
| ATOM | 1306 | N | ARG | 232 | 16.157 | 12.147 | 10.211 | 1.00 | 44.59 |
| ATOM | 1307 | CA | ARG | 232 | 15.030 | 11.415 | 10.779 | 1.00 | 44.65 |
| ATOM | 1308 | C | ARG | 232 | 15.458 | 10.198 | 11.573 | 1.00 | 44.35 |
| ATOM | 1309 | O | ARG | 232 | 16.465 | 9.559 | 11.284 | 1.00 | 44.03 |
| ATOM | 1310 | N | GLU | 233 | 14.681 | 9.854 | 12.584 | 1.00 | 44.58 |
| ATOM | 1311 | CA | GLU | 233 | 15.037 | 8.696 | 13.390 | 1.00 | 46.58 |
| ATOM | 1312 | C | GLU | 233 | 16.459 | 8.746 | 13.917 | 1.00 | 43.35 |
| ATOM | 1313 | O | GLU | 233 | 17.191 | 7.763 | 13.819 | 1.00 | 40.83 |
| ATOM | 1314 | N | ARG | 234 | 16.852 | 9.922 | 14.412 | 1.00 | 42.22 |
| ATOM | 1315 | CA | ARG | 234 | 18.181 | 10.123 | 14.978 | 1.00 | 39.03 |
| ATOM | 1323 | C | ARG | 234 | 18.149 | 9.484 | 16.353 | 1.00 | 36.42 |
| ATOM | 1324 | O | ARG | 234 | 18.690 | 8.411 | 16.521 | 1.00 | 38.06 |
| ATOM | 1316 | CB | ARG | 234 | 18.539 | 11.619 | 15.081 | 1.00 | 39.42 |
| ATOM | 1317 | CG | ARG | 234 | 20.014 | 11.958 | 15.441 | 1.00 | 35.93 |
| ATOM | 1318 | CD | ARG | 234 | 20.165 | 13.417 | 15.921 | 1.00 | 35.07 |
| ATOM | 1319 | NE | ARG | 234 | 21.500 | 13.705 | 16.481 | 1.00 | 46.22 |
| ATOM | 1320 | CZ | ARG | 234 | 21.884 | 13.494 | 17.752 | 1.00 | 42.40 |
| ATOM | 1321 | NH1 | ARG | 234 | 21.056 | 12.956 | 18.635 | 1.00 | 40.75 |
| ATOM | 1322 | NH2 | ARG | 234 | 23.114 | 13.804 | 18.140 | 1.00 | 35.29 |
| ATOM | 1325 | N | LEU | 235 | 17.428 | 10.068 | 17.304 | 1.00 | 35.64 |
| ATOM | 1326 | CA | LEU | 235 | 17.393 | 9.491 | 18.645 | 1.00 | 38.17 |
| ATOM | 1331 | C | LEU | 235 | 17.132 | 7.996 | 18.587 | 1.00 | 38.36 |
| ATOM | 1332 | O | LEU | 235 | 17.886 | 7.219 | 19.160 | 1.00 | 42.99 |
| ATOM | 1327 | CB | LEU | 235 | 16.391 | 10.201 | 19.559 | 1.00 | 41.07 |
| ATOM | 1328 | CG | LEU | 235 | 16.829 | 11.466 | 20.306 | 1.00 | 40.52 |
| ATOM | 1329 | CD1 | LEU | 235 | 17.374 | 12.459 | 19.311 | 1.00 | 45.05 |
| ATOM | 1330 | CD2 | LEU | 235 | 15.635 | 12.095 | 21.045 | 1.00 | 39.89 |
| ATOM | 1333 | N | PRO | 236 | 16.088 | 7.565 | 17.858 | 1.00 | 39.21 |
| ATOM | 1335 | CA | PRO | 236 | 15.796 | 6.130 | 17.753 | 1.00 | 37.61 |
| ATOM | 1338 | C | PRO | 236 | 17.026 | 5.302 | 17.324 | 1.00 | 33.37 |
| ATOM | 1339 | O | PRO | 236 | 17.377 | 4.318 | 17.958 | 1.00 | 34.59 |
| ATOM | 1336 | CB | PRO | 236 | 14.696 | 6.107 | 16.694 | 1.00 | 35.13 |
| ATOM | 1337 | CG | PRO | 236 | 13.902 | 7.316 | 17.078 | 1.00 | 35.05 |
| ATOM | 1334 | CD | PRO | 236 | 15.008 | 8.342 | 17.220 | 1.00 | 40.99 |
| ATOM | 1340 | N | LYS | 237 | 17.697 | 5.718 | 16.270 | 1.00 | 30.03 |
| ATOM | 1341 | CA | LYS | 237 | 18.844 | 4.989 | 15.844 | 1.00 | 28.46 |
| ATOM | 1347 | C | LYS | 237 | 19.896 | 4.996 | 16.952 | 1.00 | 29.82 |

Figure 21Z

```
ATOM   1348  O    LYS  237      20.560   3.988  17.197  1.00  32.55
ATOM   1342  CB   LYS  237      19.403   5.613  14.588  1.00  26.78
ATOM   1343  CG   LYS  237      20.251   4.616  13.778  1.00  40.87
ATOM   1344  CD   LYS  237      21.781   4.899  13.724  1.00  36.29
ATOM   1345  CE   LYS  237      22.459   3.902  12.841  1.00  30.73
ATOM   1346  NZ   LYS  237      21.946   2.569  13.284  1.00  43.77
ATOM   1349  N    LEU  238      20.033   6.118  17.647  1.00  28.39
ATOM   1350  CA   LEU  238      21.037   6.217  18.690  1.00  28.54
ATOM   1355  C    LEU  238      20.697   5.370  19.899  1.00  31.28
ATOM   1356  O    LEU  238      21.589   4.778  20.534  1.00  33.98
ATOM   1351  CB   LEU  238      21.289   7.677  19.076  1.00  30.82
ATOM   1352  CG   LEU  238      22.233   8.539  18.208  1.00  27.93
ATOM   1353  CD1  LEU  238      22.006   9.987  18.605  1.00  26.37
ATOM   1354  CD2  LEU  238      23.718   8.133  18.350  1.00  20.29
ATOM   1357  N    ARG  239      19.409   5.255  20.195  1.00  29.28
ATOM   1358  CA   ARG  239      18.994   4.434  21.306  1.00  29.95
ATOM   1366  C    ARG  239      19.189   2.951  20.982  1.00  32.62
ATOM   1367  O    ARG  239      19.476   2.164  21.876  1.00  38.29
ATOM   1359  CB   ARG  239      17.564   4.748  21.693  1.00  33.28
ATOM   1360  CG   ARG  239      17.455   6.138  22.270  1.00  45.59
ATOM   1361  CD   ARG  239      16.230   6.334  23.133  1.00  50.39
ATOM   1362  NE   ARG  239      15.559   7.577  22.773  1.00  57.71
ATOM   1363  CZ   ARG  239      14.566   7.662  21.882  1.00  65.37
ATOM   1364  NH1  ARG  239      14.090   6.568  21.258  1.00  65.87
ATOM   1365  NH2  ARG  239      14.020   8.851  21.619  1.00  63.51
ATOM   1368  N    TYR  240      19.084   2.581  19.703  1.00  32.63
ATOM   1369  CA   TYR  240      19.256   1.204  19.230  1.00  31.79
ATOM   1378  C    TYR  240      20.719   0.807  19.325  1.00  30.50
ATOM   1379  O    TYR  240      21.052  -0.359  19.562  1.00  31.45
ATOM   1370  CB   TYR  240      18.788   1.113  17.769  1.00  35.95
ATOM   1371  CG   TYR  240      19.358  -0.053  16.982  1.00  38.78
ATOM   1372  CD1  TYR  240      20.653  -0.016  16.490  1.00  36.31
ATOM   1374  CD2  TYR  240      18.595  -1.204  16.738  1.00  42.29
ATOM   1373  CE1  TYR  240      21.179  -1.095  15.776  1.00  42.46
ATOM   1375  CE2  TYR  240      19.118  -2.302  16.011  1.00  37.93
ATOM   1376  CZ   TYR  240      20.409  -2.241  15.532  1.00  43.25
ATOM   1377  OH   TYR  240      20.938  -3.299  14.785  1.00  46.68
ATOM   1380  N    ASP  241      21.565   1.767  18.970  1.00  31.55
ATOM   1381  CA   ASP  241      23.022   1.659  19.014  1.00  31.08
ATOM   1386  C    ASP  241      23.595   1.432  20.430  1.00  32.84
ATOM   1387  O    ASP  241      24.339   0.471  20.651  1.00  33.81
ATOM   1382  CB   ASP  241      23.637   2.926  18.432  1.00  25.54
ATOM   1383  CG   ASP  241      23.556   2.981  16.936  1.00  26.72
ATOM   1384  OD1  ASP  241      23.377   1.938  16.280  1.00  29.52
ATOM   1385  OD2  ASP  241      23.703   4.083  16.393  1.00  28.20
ATOM   1388  N    LYS  242      23.280   2.309  21.382  1.00  30.91
ATOM   1389  CA   LYS  242      23.815   2.112  22.708  1.00  34.51
ATOM   1395  C    LYS  242      23.330   0.781  23.318  1.00  38.23
ATOM   1396  O    LYS  242      24.026   0.128  24.107  1.00  42.65
ATOM   1390  CB   LYS  242      23.508   3.316  23.606  1.00  34.78
ATOM   1391  CG   LYS  242      22.129   3.418  24.143  1.00  31.05
ATOM   1392  CD   LYS  242      22.094   4.487  25.164  1.00  35.26
ATOM   1393  CE   LYS  242      20.737   4.554  25.875  1.00  44.36
ATOM   1394  NZ   LYS  242      20.749   5.619  26.931  1.00  46.79
```

Figure 21AA

| | | | | | | | | | |
|---|---|---|---|---|---|---|---|---|---|
| ATOM | 1397 | N | GLN | 243 | 22.154 | 0.347 | 22.903 | 1.00 | 40.07 |
| ATOM | 1398 | CA | GLN | 243 | 21.572 | -0.915 | 23.372 | 1.00 | 43.12 |
| ATOM | 1404 | C | GLN | 243 | 22.263 | -2.132 | 22.708 | 1.00 | 41.18 |
| ATOM | 1405 | O | GLN | 243 | 22.500 | -3.157 | 23.356 | 1.00 | 42.71 |
| ATOM | 1399 | CB | GLN | 243 | 20.082 | -0.875 | 23.055 | 1.00 | 46.95 |
| ATOM | 1400 | CG | GLN | 243 | 19.288 | -2.114 | 23.250 | 1.00 | 52.35 |
| ATOM | 1401 | CD | GLN | 243 | 17.912 | -1.939 | 22.608 | 1.00 | 63.31 |
| ATOM | 1402 | OE1 | GLN | 243 | 17.715 | -2.178 | 21.381 | 1.00 | 65.44 |
| ATOM | 1403 | NE2 | GLN | 243 | 16.960 | -1.447 | 23.408 | 1.00 | 63.81 |
| ATOM | 1406 | N | LEU | 244 | 22.608 | -1.987 | 21.429 | 1.00 | 38.36 |
| ATOM | 1407 | CA | LEU | 244 | 23.284 | -3.013 | 20.642 | 1.00 | 34.79 |
| ATOM | 1412 | C | LEU | 244 | 24.717 | -3.231 | 21.163 | 1.00 | 38.42 |
| ATOM | 1413 | O | LEU | 244 | 25.131 | -4.357 | 21.451 | 1.00 | 42.12 |
| ATOM | 1408 | CB | LEU | 244 | 23.318 | -2.529 | 19.192 | 1.00 | 30.54 |
| ATOM | 1409 | CG | LEU | 244 | 23.842 | -3.341 | 18.001 | 1.00 | 31.10 |
| ATOM | 1410 | CD1 | LEU | 244 | 25.306 | -3.078 | 17.734 | 1.00 | 25.64 |
| ATOM | 1411 | CD2 | LEU | 244 | 23.555 | -4.829 | 18.225 | 1.00 | 34.08 |
| ATOM | 1414 | N | VAL | 245 | 25.432 | -2.116 | 21.335 | 1.00 | 37.64 |
| ATOM | 1415 | CA | VAL | 245 | 26.825 | -2.017 | 21.786 | 1.00 | 30.53 |
| ATOM | 1419 | C | VAL | 245 | 27.036 | -2.182 | 23.311 | 1.00 | 30.65 |
| ATOM | 1420 | O | VAL | 245 | 28.158 | -2.400 | 23.783 | 1.00 | 28.44 |
| ATOM | 1416 | CB | VAL | 245 | 27.367 | -0.681 | 21.240 | 1.00 | 29.97 |
| ATOM | 1417 | CG1 | VAL | 245 | 28.068 | 0.101 | 22.296 | 1.00 | 30.95 |
| ATOM | 1418 | CG2 | VAL | 245 | 28.229 | -0.930 | 20.018 | 1.00 | 27.26 |
| ATOM | 1421 | N | GLY | 246 | 25.954 | -2.037 | 24.080 | 1.00 | 32.34 |
| ATOM | 1422 | CA | GLY | 246 | 26.006 | -2.252 | 25.521 | 1.00 | 31.25 |
| ATOM | 1423 | C | GLY | 246 | 26.468 | -1.158 | 26.445 | 1.00 | 30.27 |
| ATOM | 1424 | O | GLY | 246 | 26.661 | -1.403 | 27.622 | 1.00 | 32.71 |
| ATOM | 1425 | N | VAL | 247 | 26.627 | 0.044 | 25.923 | 1.00 | 29.11 |
| ATOM | 1426 | CA | VAL | 247 | 27.055 | 1.193 | 26.692 | 1.00 | 26.91 |
| ATOM | 1430 | C | VAL | 247 | 25.840 | 1.944 | 27.200 | 1.00 | 31.04 |
| ATOM | 1431 | O | VAL | 247 | 25.047 | 2.453 | 26.419 | 1.00 | 32.46 |
| ATOM | 1427 | CB | VAL | 247 | 27.859 | 2.099 | 25.824 | 1.00 | 24.79 |
| ATOM | 1428 | CG1 | VAL | 247 | 28.121 | 3.418 | 26.529 | 1.00 | 24.35 |
| ATOM | 1429 | CG2 | VAL | 247 | 29.135 | 1.385 | 25.458 | 1.00 | 22.52 |
| ATOM | 1432 | N | THR | 248 | 25.755 | 2.070 | 28.517 | 1.00 | 31.59 |
| ATOM | 1433 | CA | THR | 248 | 24.640 | 2.705 | 29.191 | 1.00 | 31.52 |
| ATOM | 1437 | C | THR | 248 | 24.940 | 4.096 | 29.706 | 1.00 | 30.82 |
| ATOM | 1438 | O | THR | 248 | 26.072 | 4.433 | 29.978 | 1.00 | 27.71 |
| ATOM | 1434 | CB | THR | 248 | 24.112 | 1.772 | 30.367 | 1.00 | 39.88 |
| ATOM | 1435 | OG1 | THR | 248 | 25.123 | 1.511 | 31.381 | 1.00 | 37.28 |
| ATOM | 1436 | CG2 | THR | 248 | 23.718 | 0.439 | 29.778 | 1.00 | 43.33 |
| ATOM | 1439 | N | GLU | 249 | 23.917 | 4.918 | 29.854 | 1.00 | 35.18 |
| ATOM | 1440 | CA | GLU | 249 | 24.137 | 6.260 | 30.375 | 1.00 | 40.09 |
| ATOM | 1446 | C | GLU | 249 | 24.388 | 6.151 | 31.862 | 1.00 | 40.92 |
| ATOM | 1447 | O | GLU | 249 | 24.469 | 7.158 | 32.542 | 1.00 | 44.71 |
| ATOM | 1441 | CB | GLU | 249 | 22.954 | 7.198 | 30.127 | 1.00 | 40.60 |
| ATOM | 1442 | CG | GLU | 249 | 21.724 | 6.826 | 30.887 | 1.00 | 50.58 |
| ATOM | 1443 | CD | GLU | 249 | 21.291 | 5.376 | 30.636 | 1.00 | 59.02 |
| ATOM | 1444 | OE1 | GLU | 249 | 20.758 | 5.061 | 29.533 | 1.00 | 58.31 |
| ATOM | 1445 | OE2 | GLU | 249 | 21.532 | 4.543 | 31.548 | 1.00 | 64.12 |
| ATOM | 1448 | N | ARG | 250 | 24.467 | 4.930 | 32.376 | 1.00 | 38.91 |
| ATOM | 1449 | CA | ARG | 250 | 24.739 | 4.747 | 33.786 | 1.00 | 40.07 |
| ATOM | 1457 | C | ARG | 250 | 26.252 | 4.528 | 34.031 | 1.00 | 38.25 |

Figure 21BB

| ATOM | 1458 | O   | ARG | 250 | 26.748 | 4.725  | 35.146 | 1.00 | 32.79 |
|------|------|-----|-----|-----|--------|--------|--------|------|-------|
| ATOM | 1450 | CB  | ARG | 250 | 23.901 | 3.579  | 34.304 | 1.00 | 48.85 |
| ATOM | 1451 | CG  | ARG | 250 | 23.800 | 3.482  | 35.806 | 1.00 | 51.71 |
| ATOM | 1452 | CD  | ARG | 250 | 22.958 | 4.589  | 36.387 | 1.00 | 57.54 |
| ATOM | 1453 | NE  | ARG | 250 | 23.239 | 4.740  | 37.813 | 1.00 | 60.92 |
| ATOM | 1454 | CZ  | ARG | 250 | 24.274 | 5.427  | 38.313 | 1.00 | 64.84 |
| ATOM | 1455 | NH1 | ARG | 250 | 25.136 | 6.081  | 37.503 | 1.00 | 62.54 |
| ATOM | 1456 | NH2 | ARG | 250 | 24.428 | 5.489  | 39.639 | 1.00 | 61.35 |
| ATOM | 1459 | N   | GLU | 251 | 26.975 | 4.215  | 32.950 | 1.00 | 37.29 |
| ATOM | 1460 | CA  | GLU | 251 | 28.412 | 3.963  | 32.987 | 1.00 | 33.73 |
| ATOM | 1466 | C   | GLU | 251 | 29.221 | 4.849  | 32.047 | 1.00 | 33.52 |
| ATOM | 1467 | O   | GLU | 251 | 30.398 | 4.575  | 31.799 | 1.00 | 35.31 |
| ATOM | 1461 | CB  | GLU | 251 | 28.720 | 2.495  | 32.653 | 1.00 | 35.71 |
| ATOM | 1462 | CG  | GLU | 251 | 28.352 | 2.045  | 31.221 | 1.00 | 40.55 |
| ATOM | 1463 | CD  | GLU | 251 | 29.442 | 1.178  | 30.544 | 1.00 | 43.48 |
| ATOM | 1464 | OE1 | GLU | 251 | 30.384 | 0.720  | 31.240 | 1.00 | 42.46 |
| ATOM | 1465 | OE2 | GLU | 251 | 29.351 | 0.957  | 29.313 | 1.00 | 38.78 |
| ATOM | 1468 | N   | SER | 252 | 28.607 | 5.881  | 31.483 | 1.00 | 30.81 |
| ATOM | 1469 | CA  | SER | 252 | 29.341 | 6.775  | 30.590 | 1.00 | 29.66 |
| ATOM | 1472 | C   | SER | 252 | 28.526 | 8.036  | 30.411 | 1.00 | 25.67 |
| ATOM | 1473 | O   | SER | 252 | 27.457 | 8.137  | 30.973 | 1.00 | 22.60 |
| ATOM | 1470 | CB  | SER | 252 | 29.546 | 6.120  | 29.231 | 1.00 | 30.94 |
| ATOM | 1471 | OG  | SER | 252 | 28.296 | 5.962  | 28.571 | 1.00 | 34.82 |
| ATOM | 1474 | N   | TYR | 253 | 28.992 | 8.929  | 29.538 | 1.00 | 24.49 |
| ATOM | 1475 | CA  | TYR | 253 | 28.334 | 10.202 | 29.238 | 1.00 | 22.09 |
| ATOM | 1484 | C   | TYR | 253 | 27.370 | 10.233 | 28.055 | 1.00 | 20.73 |
| ATOM | 1485 | O   | TYR | 253 | 27.037 | 11.301 | 27.572 | 1.00 | 21.44 |
| ATOM | 1476 | CB  | TYR | 253 | 29.378 | 11.275 | 29.007 | 1.00 | 25.05 |
| ATOM | 1477 | CG  | TYR | 253 | 30.250 | 11.528 | 30.192 | 1.00 | 21.90 |
| ATOM | 1478 | CD1 | TYR | 253 | 31.421 | 10.822 | 30.377 | 1.00 | 25.70 |
| ATOM | 1480 | CD2 | TYR | 253 | 29.911 | 12.489 | 31.111 | 1.00 | 24.11 |
| ATOM | 1479 | CE1 | TYR | 253 | 32.221 | 11.069 | 31.432 | 1.00 | 25.12 |
| ATOM | 1481 | CE2 | TYR | 253 | 30.694 | 12.746 | 32.168 | 1.00 | 22.43 |
| ATOM | 1482 | CZ  | TYR | 253 | 31.839 | 12.039 | 32.327 | 1.00 | 25.62 |
| ATOM | 1483 | OH  | TYR | 253 | 32.589 | 12.321 | 33.420 | 1.00 | 32.22 |
| ATOM | 1486 | N   | VAL | 254 | 26.905 | 9.071  | 27.611 | 1.00 | 21.12 |
| ATOM | 1487 | CA  | VAL | 254 | 25.960 | 8.932  | 26.496 | 1.00 | 20.15 |
| ATOM | 1491 | C   | VAL | 254 | 24.739 | 9.786  | 26.768 | 1.00 | 23.00 |
| ATOM | 1492 | O   | VAL | 254 | 24.074 | 9.622  | 27.776 | 1.00 | 28.92 |
| ATOM | 1488 | CB  | VAL | 254 | 25.509 | 7.457  | 26.365 | 1.00 | 22.45 |
| ATOM | 1489 | CG1 | VAL | 254 | 24.408 | 7.301  | 25.349 | 1.00 | 24.89 |
| ATOM | 1490 | CG2 | VAL | 254 | 26.665 | 6.624  | 25.938 | 1.00 | 30.24 |
| ATOM | 1493 | N   | LYS | 255 | 24.417 | 10.672 | 25.852 | 1.00 | 27.30 |
| ATOM | 1494 | CA  | LYS | 255 | 23.275 | 11.538 | 26.022 | 1.00 | 30.38 |
| ATOM | 1500 | C   | LYS | 255 | 22.063 | 10.999 | 25.260 | 1.00 | 35.51 |
| ATOM | 1501 | O   | LYS | 255 | 20.934 | 11.434 | 25.474 | 1.00 | 40.15 |
| ATOM | 1495 | CB  | LYS | 255 | 23.642 | 12.955 | 25.556 | 1.00 | 24.85 |
| ATOM | 1496 | CG  | LYS | 255 | 24.794 | 13.563 | 26.334 | 1.00 | 23.95 |
| ATOM | 1497 | CD  | LYS | 255 | 24.327 | 13.823 | 27.732 | 1.00 | 21.71 |
| ATOM | 1498 | CE  | LYS | 255 | 25.409 | 14.193 | 28.711 | 1.00 | 23.83 |
| ATOM | 1499 | NZ  | LYS | 255 | 24.792 | 14.656 | 30.029 | 1.00 | 28.73 |
| ATOM | 1502 | N   | ALA | 256 | 22.291 | 10.044 | 24.379 | 1.00 | 39.90 |
| ATOM | 1503 | CA  | ALA | 256 | 21.204 | 9.497  | 23.580 | 1.00 | 44.20 |
| ATOM | 1505 | C   | ALA | 256 | 20.531 | 8.314  | 24.281 | 1.00 | 48.51 |

Figure 21CC

| | | | | | | | | | |
|---|---|---|---|---|---|---|---|---|---|
| ATOM | 1506 | O | ALA | 256 | 21.207 | 7.279 | 24.465 | 1.00 | 51.64 |
| ATOM | 1504 | CB | ALA | 256 | 21.739 | 9.077 | 22.200 | 1.00 | 45.14 |
| ATOM | 1507 | OXT | ALA | 256 | 19.333 | 8.422 | 24.621 | 1.00 | 49.50 |
| ATOM | 1508 | OH2 | TIP | 301 | 31.077 | 8.140 | 27.527 | 1.00 | 26.53 |
| ATOM | 1509 | OH2 | TIP | 302 | 28.508 | 19.427 | 33.073 | 1.00 | 44.65 |
| ATOM | 1510 | OH2 | TIP | 303 | 43.460 | -2.890 | 5.012 | 1.00 | 47.04 |
| ATOM | 1511 | OH2 | TIP | 304 | 34.353 | 1.990 | 5.346 | 1.00 | 60.54 |
| ATOM | 1512 | OH2 | TIP | 305 | 40.811 | -5.013 | 7.745 | 1.00 | 44.88 |
| ATOM | 1513 | OH2 | TIP | 306 | 36.406 | -9.018 | 7.810 | 1.00 | 45.38 |
| ATOM | 1514 | OH2 | TIP | 307 | 42.194 | -7.284 | 7.781 | 1.00 | 40.41 |
| ATOM | 1515 | OH2 | TIP | 308 | 41.962 | -3.068 | 10.961 | 1.00 | 43.60 |
| ATOM | 1516 | OH2 | TIP | 309 | 32.124 | -3.755 | 5.755 | 1.00 | 57.14 |
| ATOM | 1517 | OH2 | TIP | 310 | 45.283 | -4.742 | 8.388 | 1.00 | 66.05 |
| ATOM | 1518 | OH2 | TIP | 311 | 42.408 | 1.268 | 2.187 | 1.00 | 48.23 |
| ATOM | 1519 | OH2 | TIP | 312 | 33.724 | -9.694 | 7.964 | 1.00 | 31.21 |
| ATOM | 1520 | OH2 | TIP | 313 | 36.929 | 9.205 | 34.888 | 1.00 | 57.36 |
| ATOM | 1521 | OH2 | TIP | 314 | 36.951 | 10.140 | 31.663 | 1.00 | 28.65 |
| ATOM | 1522 | OH2 | TIP | 315 | 45.201 | 10.047 | 36.275 | 1.00 | 60.61 |
| ATOM | 1523 | OH2 | TIP | 316 | 33.982 | 7.104 | 37.021 | 1.00 | 37.87 |
| ATOM | 1524 | OH2 | TIP | 317 | 31.482 | 13.718 | 40.875 | 1.00 | 32.22 |
| ATOM | 1525 | OH2 | TIP | 318 | 28.066 | 20.405 | 14.687 | 1.00 | 28.25 |
| ATOM | 1526 | OH2 | TIP | 319 | 25.156 | 17.450 | 8.183 | 1.00 | 58.78 |
| ATOM | 1527 | OH2 | TIP | 320 | 24.965 | 17.970 | 15.523 | 1.00 | 38.76 |
| ATOM | 1528 | OH2 | TIP | 321 | 26.596 | 17.720 | 13.158 | 1.00 | 34.40 |
| ATOM | 1529 | OH2 | TIP | 322 | 24.695 | 16.736 | 10.779 | 1.00 | 46.64 |
| ATOM | 1530 | OH2 | TIP | 323 | 28.779 | 21.379 | 8.234 | 1.00 | 51.77 |
| ATOM | 1531 | OH2 | TIP | 324 | 27.672 | 9.637 | 22.884 | 1.00 | 26.42 |
| ATOM | 1532 | OH2 | TIP | 325 | 25.173 | 11.262 | 30.753 | 1.00 | 39.45 |
| ATOM | 1533 | OH2 | TIP | 326 | 29.730 | 9.819 | 25.094 | 1.00 | 16.06 |
| ATOM | 1534 | OH2 | TIP | 327 | 27.962 | 1.696 | 35.360 | 1.00 | 43.49 |
| ATOM | 1535 | OH2 | TIP | 328 | 47.125 | 9.642 | 8.720 | 1.00 | 62.32 |
| ATOM | 1536 | OH2 | TIP | 329 | 42.419 | 15.393 | 6.321 | 1.00 | 47.15 |
| ATOM | 1537 | OH2 | TIP | 330 | 46.244 | 15.052 | 16.322 | 1.00 | 31.89 |
| ATOM | 1538 | OH2 | TIP | 331 | 53.806 | 6.083 | 10.720 | 1.00 | 59.08 |
| ATOM | 1539 | OH2 | TIP | 332 | 46.628 | -11.519 | 15.104 | 1.00 | 59.71 |
| ATOM | 1540 | OH2 | TIP | 333 | 44.954 | 19.739 | 26.592 | 1.00 | 59.39 |
| ATOM | 1541 | OH2 | TIP | 334 | 12.217 | 15.492 | 8.254 | 1.00 | 49.78 |
| ATOM | 1542 | OH2 | TIP | 335 | 33.333 | 28.433 | 7.372 | 1.00 | 41.13 |
| ATOM | 1543 | OH2 | TIP | 336 | 31.448 | 3.643 | 9.698 | 1.00 | 27.38 |
| ATOM | 1544 | OH2 | TIP | 337 | 32.521 | 7.362 | 2.579 | 1.00 | 61.89 |
| ATOM | 1545 | OH2 | TIP | 338 | 13.938 | -1.160 | 24.723 | 1.00 | 59.26 |
| ATOM | 1546 | OH2 | TIP | 339 | 16.115 | 1.428 | 14.322 | 1.00 | 31.84 |
| ATOM | 1547 | OH2 | TIP | 340 | 52.974 | 1.048 | 19.319 | 1.00 | 59.43 |
| ATOM | 1548 | OH2 | TIP | 341 | 17.731 | -0.160 | 26.396 | 1.00 | 59.51 |
| ATOM | 1549 | OH2 | TIP | 342 | 25.870 | 6.267 | 15.266 | 1.00 | 28.55 |
| ATOM | 1550 | OH2 | TIP | 343 | 35.943 | -3.457 | 27.935 | 1.00 | 28.41 |
| ATOM | 1551 | OH2 | TIP | 344 | 41.943 | -11.451 | 27.321 | 1.00 | 48.13 |
| ATOM | 1552 | OH2 | TIP | 345 | 42.449 | 20.182 | 4.040 | 1.00 | 45.54 |
| ATOM | 1553 | OH2 | TIP | 346 | 38.786 | 9.933 | -2.493 | 1.00 | 45.94 |
| ATOM | 1554 | OH2 | TIP | 347 | 49.333 | 15.382 | 33.838 | 1.00 | 61.48 |
| ATOM | 1555 | OH2 | TIP | 348 | 46.147 | 25.427 | 24.597 | 1.00 | 59.02 |
| ATOM | 1556 | OH2 | TIP | 349 | 50.115 | 57.579 | 9.011 | 1.00 | 47.99 |
| ATOM | 1557 | OH2 | TIP | 350 | 15.511 | 3.002 | 23.488 | 1.00 | 55.01 |
| ATOM | 1558 | OH2 | TIP | 351 | 29.780 | 15.069 | 2.505 | 1.00 | 61.37 |

Figure 21DD

```
ATOM   1559  OH2 TIP   352      31.338  -11.352   21.807  1.00 46.71
ATOM   1560  OH2 TIP   353       2.522    0.611   13.871  1.00 44.63
ATOM   1561  OH2 TIP   354      43.141   22.961    4.410  1.00 48.86
ATOM   1562  OH2 TIP   355       5.521   10.199   15.309  1.00 49.92
ATOM   1563  OH2 TIP   356      53.638   12.036   19.109  1.00 65.19
ATOM   1564  OH2 TIP   357      46.005   14.980    8.384  1.00 56.73
ATOM   1565  OH2 TIP   358      32.766   22.125    9.759  1.00 44.57
ATOM   1566  OH2 TIP   359      41.156  -11.512   31.108  1.00 59.78
ATOM   1567  OH2 TIP   360      54.373    1.466    7.933  1.00 64.65
ATOM   1568  OH2 TIP   361      -0.133    6.947    3.004  1.00 58.66
ATOM   1569  OH2 TIP   362      40.287   17.373   32.363  1.00 59.68
ATOM   1570  OH2 TIP   363      14.084   11.697   13.980  1.00 62.14
ATOM   1571  OH2 TIP   364      11.142   54.359    5.085  1.00 57.08
ATOM   1572  OH2 TIP   365      22.432    3.979    5.522  1.00 62.25
ATOM   1573  OH2 TIP   366      30.748   30.157    5.660  1.00 46.26
ATOM   1574  OH2 TIP   367      47.936   -6.613   17.774  1.00 62.86
ATOM   1575  OH2 TIP   368      33.450   31.881    8.631  1.00 62.94
ATOM   1576  OH2 TIP   369      50.764    2.321   11.268  1.00 48.17
ATOM   1577  OH2 TIP   370      45.493    3.077   13.078  1.00 56.73
ATOM   1578  OH2 TIP   371      38.224  -10.673   15.493  1.00 54.69
ATOM   1579  OH2 TIP   372      36.265   20.816    1.443  1.00 61.72
ATOM   1580  OH2 TIP   373      44.933   30.624   15.656  1.00 60.55
```

Figure 22A

| CRYST1 | 90.0 | 90.0 | 117.4 | 90.0 | 90.0 | 120.0 | P6₄22 |
|---|---|---|---|---|---|---|---|

| Atom | | Residue AA | No | X | Y | Z | Occup'y | B Factor |
|---|---|---|---|---|---|---|---|---|
| ATOM | 295 | N | HIS | 52 | 60.710 | 19.064 | 34.809 | 1.00 | 25.00 |
| ATOM | 296 | CA | HIS | 52 | 61.673 | 18.368 | 33.923 | 1.00 | 25.00 |
| ATOM | 297 | C | HIS | 52 | 62.853 | 19.281 | 33.567 | 1.00 | 25.00 |
| ATOM | 298 | O | HIS | 52 | 63.644 | 18.965 | 32.685 | 1.00 | 25.00 |
| ATOM | 299 | CB | HIS | 52 | 61.040 | 17.836 | 32.638 | 1.00 | 25.00 |
| ATOM | 300 | CG | HIS | 52 | 60.095 | 16.703 | 32.846 | 1.00 | 25.00 |
| ATOM | 301 | ND1 | HIS | 52 | 60.477 | 15.394 | 33.018 | 1.00 | 25.00 |
| ATOM | 302 | CD2 | HIS | 52 | 58.739 | 16.690 | 32.866 | 1.00 | 25.00 |
| ATOM | 304 | CE1 | HIS | 52 | 59.365 | 14.648 | 33.133 | 1.00 | 25.00 |
| ATOM | 303 | NE2 | HIS | 52 | 58.277 | 15.389 | 33.047 | 1.00 | 25.00 |
| ATOM | 316 | N | LYS | 54 | 66.220 | 20.501 | 33.661 | 1.00 | 25.00 |
| ATOM | 317 | CA | LYS | 54 | 67.571 | 20.028 | 33.907 | 1.00 | 25.00 |
| ATOM | 323 | C | LYS | 54 | 68.314 | 21.061 | 34.724 | 1.00 | 25.00 |
| ATOM | 324 | O | LYS | 54 | 69.184 | 20.710 | 35.497 | 1.00 | 25.00 |
| ATOM | 318 | CB | LYS | 54 | 68.306 | 19.831 | 32.566 | 1.00 | 25.00 |
| ATOM | 319 | CG | LYS | 54 | 67.562 | 18.902 | 31.571 | 1.00 | 25.00 |
| ATOM | 320 | CD | LYS | 54 | 68.311 | 18.646 | 30.254 | 1.00 | 25.00 |
| ATOM | 321 | CE | LYS | 54 | 67.565 | 17.600 | 29.383 | 1.00 | 25.00 |
| ATOM | 322 | NZ | LYS | 54 | 67.361 | 16.272 | 30.087 | 1.00 | 25.00 |
| ATOM | 833 | N | SER | 120 | 56.783 | 12.750 | 37.744 | 1.00 | 25.00 |
| ATOM | 834 | CA | SER | 120 | 56.871 | 12.264 | 36.371 | 1.00 | 25.00 |
| ATOM | 837 | C | SER | 120 | 58.207 | 11.615 | 36.106 | 1.00 | 25.00 |
| ATOM | 838 | O | SER | 120 | 59.223 | 12.257 | 36.207 | 1.00 | 25.00 |
| ATOM | 835 | CB | SER | 120 | 56.654 | 13.416 | 35.393 | 1.00 | 25.00 |
| ATOM | 836 | OG | SER | 120 | 55.882 | 13.005 | 34.260 | 1.00 | 25.00 |
| ATOM | 847 | N | SER | 122 | 60.685 | 10.577 | 33.743 | 1.00 | 25.00 |

Figure 22B

| Atom | | Residue AA | No | X | Y | Z | Occup'y | B Factor |
|---|---|---|---|---|---|---|---|---|
| ATOM | 848 | CA | SER | 122 | 61.107 | 10.697 | 32.356 | 1.00 | 25.00 |
| ATOM | 851 | C | SER | 122 | 62.017 | 9.485 | 32.133 | 1.00 | 25.00 |
| ATOM | 852 | O | SER | 122 | 63.223 | 9.520 | 32.442 | 1.00 | 25.00 |
| ATOM | 849 | CB | SER | 122 | 61.864 | 12.007 | 32.113 | 1.00 | 25.00 |
| ATOM | 850 | OG | SER | 122 | 61.773 | 12.871 | 33.244 | 1.00 | 25.00 |
| ATOM | 897 | N | HIS | 139 | 65.401 | 11.038 | 34.964 | 1.00 | 25.00 |
| ATOM | 898 | CA | HIS | 139 | 65.038 | 11.906 | 36.075 | 1.00 | 25.00 |
| ATOM | 899 | C | HIS | 139 | 63.544 | 11.855 | 36.391 | 1.00 | 25.00 |
| ATOM | 900 | O | HIS | 139 | 62.740 | 11.480 | 35.530 | 1.00 | 25.00 |
| ATOM | 901 | CB | HIS | 139 | 65.484 | 13.338 | 35.810 | 1.00 | 25.00 |
| ATOM | 902 | CG | HIS | 139 | 64.651 | 14.035 | 34.794 | 1.00 | 25.00 |
| ATOM | 903 | ND1 | HIS | 139 | 63.791 | 15.068 | 35.084 | 1.00 | 25.00 |
| ATOM | 904 | CD2 | HIS | 139 | 64.485 | 13.778 | 33.477 | 1.00 | 25.00 |
| ATOM | 906 | CE1 | HIS | 139 | 63.141 | 15.388 | 33.977 | 1.00 | 25.00 |
| ATOM | 905 | NE2 | HIS | 139 | 63.529 | 14.632 | 32.974 | 1.00 | 25.00 |
| ATOM | 927 | N | CYS | 143 | 55.349 | 17.841 | 39.601 | 1.00 | 25.00 |
| ATOM | 928 | CA | CYS | 143 | 54.419 | 18.608 | 38.783 | 1.00 | 25.00 |
| ATOM | 931 | C | CYS | 143 | 53.004 | 18.555 | 39.358 | 1.00 | 25.00 |
| ATOM | 932 | O | CYS | 143 | 52.801 | 17.928 | 40.375 | 1.00 | 25.00 |
| ATOM | 929 | CB | CYS | 143 | 54.426 | 17.953 | 37.403 | 1.00 | 25.00 |
| ATOM | 930 | SG | CYS | 143 | 54.272 | 16.114 | 37.477 | 1.00 | 25.00 |
| ATOM | 951 | N | ARG | 147 | 51.312 | 12.231 | 33.512 | 1.00 | 25.00 |
| ATOM | 952 | CA | ARG | 147 | 50.733 | 11.463 | 32.422 | 1.00 | 25.00 |
| ATOM | 960 | C | ARG | 147 | 50.256 | 10.082 | 32.917 | 1.00 | 25.00 |
| ATOM | 961 | O | ARG | 147 | 49.302 | 9.523 | 32.355 | 1.00 | 25.00 |
| ATOM | 953 | CB | ARG | 147 | 51.807 | 11.235 | 31.366 | 1.00 | 25.00 |
| ATOM | 954 | CG | ARG | 147 | 52.970 | 12.230 | 31.429 | 1.00 | 25.00 |
| ATOM | 955 | CD | ARG | 147 | 52.760 | 13.360 | 30.428 | 1.00 | 25.00 |

Figure 22C

| | | Residue | | | | | | |
|---|---|---|---|---|---|---|---|---|
| Atom | | AA | No | X | Y | Z | Occup'y | B Factor |
| ATOM | 956 | NE | ARG | 147 | 52.455 | 12.799 | 29.116 | 1.00 | 25.00 |
| ATOM | 957 | CZ | ARG | 147 | 53.210 | 11.894 | 28.492 | 1.00 | 25.00 |
| ATOM | 958 | NH1 | ARG | 147 | 54.375 | 11.489 | 29.014 | 1.00 | 25.00 |
| ATOM | 959 | NH2 | ARG | 147 | 52.815 | 11.430 | 27.314 | 1.00 | 25.00 |
| ATOM | 962 | N | ARG | 148 | 50.936 | 9.527 | 33.937 | 1.00 | 25.00 |
| ATOM | 963 | CA | ARG | 148 | 50.619 | 8.200 | 34.492 | 1.00 | 25.00 |
| ATOM | 971 | C | ARG | 148 | 49.540 | 8.123 | 35.562 | 1.00 | 25.00 |
| ATOM | 972 | O | ARG | 148 | 49.295 | 9.085 | 36.276 | 1.00 | 25.00 |
| ATOM | 964 | CB | ARG | 148 | 51.899 | 7.483 | 34.904 | 1.00 | 25.00 |
| ATOM | 965 | CG | ARG | 148 | 52.654 | 7.052 | 33.662 | 1.00 | 25.00 |
| ATOM | 966 | CD | ARG | 148 | 54.099 | 6.580 | 33.847 | 1.00 | 25.00 |
| ATOM | 967 | NE | ARG | 148 | 54.697 | 6.425 | 32.515 | 1.00 | 25.00 |
| ATOM | 968 | CZ | ARG | 148 | 55.985 | 6.252 | 32.253 | 1.00 | 25.00 |
| ATOM | 969 | NH1 | ARG | 148 | 56.888 | 6.174 | 33.227 | 1.00 | 25.00 |
| ATOM | 970 | NH2 | ARG | 148 | 56.356 | 6.145 | 30.987 | 1.00 | 25.00 |

Figure 23A

| | | | | | | | | | |
|---|---|---|---|---|---|---|---|---|---|
| CRYST1 | 89.990 | | 89.990 | 117.420 | 90.00 | 90.00 | 120.00 | | P6422 |
| SCALE1 | | 0.01111 | 0.00642 | 0.00000 | | 0.00000 | | | |
| SCALE2 | | 0.00000 | 0.01283 | 0.00000 | | 0.00000 | | | |
| SCALE3 | | 0.00000 | 0.00000 | 0.00852 | | 0.00000 | | | |
| ATOM | 1 | CB | GLU | 11 | 64.652 | 21.405 | 57.653 | 1.00 | 25.00 |
| ATOM | 8 | N | GLU | 11 | 66.983 | 20.730 | 57.176 | 1.00 | 25.00 |
| ATOM | 9 | CA | GLU | 11 | 65.564 | 20.285 | 57.113 | 1.00 | 25.00 |
| ATOM | 6 | C | GLU | 11 | 65.166 | 19.833 | 55.677 | 1.00 | 25.00 |
| ATOM | 7 | O | GLU | 11 | 64.989 | 20.661 | 54.756 | 1.00 | 25.00 |
| ATOM | 1 | CB | GLU | 11 | 64.652 | 21.405 | 57.653 | 1.00 | 25.00 |
| ATOM | 2 | CG | GLU | 11 | 64.804 | 21.647 | 59.170 | 1.00 | 25.00 |
| ATOM | 3 | CD | GLU | 11 | 63.935 | 22.813 | 59.730 | 1.00 | 25.00 |
| ATOM | 4 | OE1 | GLU | 11 | 63.962 | 23.921 | 59.115 | 1.00 | 25.00 |
| ATOM | 5 | OE2 | GLU | 11 | 63.248 | 22.620 | 60.791 | 1.00 | 25.00 |
| ATOM | 10 | N | ALA | 12 | 65.051 | 18.518 | 55.488 | 1.00 | 25.00 |
| ATOM | 11 | CA | ALA | 12 | 64.697 | 17.975 | 54.179 | 1.00 | 25.00 |
| ATOM | 13 | C | ALA | 12 | 63.279 | 17.436 | 54.105 | 1.00 | 25.00 |
| ATOM | 14 | O | ALA | 12 | 62.554 | 17.388 | 55.088 | 1.00 | 25.00 |
| ATOM | 12 | CB | ALA | 12 | 65.686 | 16.883 | 53.766 | 1.00 | 25.00 |
| ATOM | 15 | N | LEU | 13 | 62.883 | 17.072 | 52.903 | 1.00 | 25.00 |
| ATOM | 16 | CA | LEU | 13 | 61.585 | 16.519 | 52.675 | 1.00 | 25.00 |
| ATOM | 21 | C | LEU | 13 | 61.864 | 15.223 | 51.980 | 1.00 | 25.00 |
| ATOM | 22 | O | LEU | 13 | 62.826 | 15.106 | 51.229 | 1.00 | 25.00 |
| ATOM | 17 | CB | LEU | 13 | 60.788 | 17.405 | 51.737 | 1.00 | 25.00 |
| ATOM | 18 | CG | LEU | 13 | 60.043 | 18.625 | 52.281 | 1.00 | 25.00 |
| ATOM | 19 | CD1 | LEU | 13 | 61.000 | 19.515 | 53.084 | 1.00 | 25.00 |
| ATOM | 20 | CD2 | LEU | 13 | 59.393 | 19.384 | 51.110 | 1.00 | 25.00 |
| ATOM | 23 | N | TYR | 14 | 61.065 | 14.223 | 52.290 | 1.00 | 25.00 |
| ATOM | 24 | CA | TYR | 14 | 61.202 | 12.941 | 51.658 | 1.00 | 25.00 |
| ATOM | 33 | C | TYR | 14 | 59.921 | 12.817 | 50.910 | 1.00 | 25.00 |
| ATOM | 34 | O | TYR | 14 | 58.871 | 13.223 | 51.408 | 1.00 | 25.00 |
| ATOM | 25 | CB | TYR | 14 | 61.322 | 11.846 | 52.697 | 1.00 | 25.00 |
| ATOM | 26 | CG | TYR | 14 | 62.613 | 11.952 | 53.420 | 1.00 | 25.00 |
| ATOM | 27 | CD1 | TYR | 14 | 62.769 | 12.862 | 54.459 | 1.00 | 25.00 |

Figure 23B

| ATOM | 29 | CD2 | TYR | 14 | 63.730 | 11.254 | 52.973 | 1.00 | 25.00 |
|------|----|----|-----|----|--------|--------|--------|------|-------|
| ATOM | 28 | CE1 | TYR | 14 | 63.993 | 13.092 | 55.018 | 1.00 | 25.00 |
| ATOM | 30 | CE2 | TYR | 14 | 64.975 | 11.480 | 53.535 | 1.00 | 25.00 |
| ATOM | 31 | CZ | TYR | 14 | 65.092 | 12.405 | 54.552 | 1.00 | 25.00 |
| ATOM | 32 | OH | TYR | 14 | 66.323 | 12.659 | 55.084 | 1.00 | 25.00 |
| ATOM | 35 | N | VAL | 15 | 60.030 | 12.353 | 49.676 | 1.00 | 25.00 |
| ATOM | 36 | CA | VAL | 15 | 58.886 | 12.157 | 48.807 | 1.00 | 25.00 |
| ATOM | 40 | C | VAL | 15 | 58.914 | 10.675 | 48.460 | 1.00 | 25.00 |
| ATOM | 41 | O | VAL | 15 | 59.998 | 10.114 | 48.276 | 1.00 | 25.00 |
| ATOM | 37 | CB | VAL | 15 | 59.064 | 12.948 | 47.511 | 1.00 | 25.00 |
| ATOM | 38 | CG1 | VAL | 15 | 57.788 | 12.963 | 46.725 | 1.00 | 25.00 |
| ATOM | 39 | CG2 | VAL | 15 | 59.519 | 14.337 | 47.809 | 1.00 | 25.00 |
| ATOM | 42 | N | ALA | 16 | 57.751 | 10.033 | 48.431 | 1.00 | 25.00 |
| ATOM | 43 | CA | ALA | 16 | 57.670 | 8.620 | 48.081 | 1.00 | 25.00 |
| ATOM | 45 | C | ALA | 16 | 56.377 | 8.391 | 47.299 | 1.00 | 25.00 |
| ATOM | 46 | O | ALA | 16 | 55.368 | 9.034 | 47.572 | 1.00 | 25.00 |
| ATOM | 44 | CB | ALA | 16 | 57.705 | 7.763 | 49.323 | 1.00 | 25.00 |
| ATOM | 47 | N | GLY | 17 | 56.417 | 7.527 | 46.291 | 1.00 | 25.00 |
| ATOM | 48 | CA | GLY | 17 | 55.240 | 7.254 | 45.489 | 1.00 | 25.00 |
| ATOM | 49 | C | GLY | 17 | 55.633 | 6.271 | 44.413 | 1.00 | 25.00 |
| ATOM | 50 | O | GLY | 17 | 56.784 | 5.847 | 44.365 | 1.00 | 25.00 |
| ATOM | 51 | N | TYR | 18 | 54.686 | 5.881 | 43.567 | 1.00 | 25.00 |
| ATOM | 52 | CA | TYR | 18 | 54.950 | 4.945 | 42.480 | 1.00 | 25.00 |
| ATOM | 61 | C | TYR | 18 | 55.305 | 5.694 | 41.223 | 1.00 | 25.00 |
| ATOM | 62 | O | TYR | 18 | 54.581 | 6.595 | 40.799 | 1.00 | 25.00 |
| ATOM | 53 | CB | TYR | 18 | 53.716 | 4.136 | 42.141 | 1.00 | 25.00 |
| ATOM | 54 | CG | TYR | 18 | 53.204 | 3.209 | 43.198 | 1.00 | 25.00 |
| ATOM | 55 | CD1 | TYR | 18 | 53.712 | 1.935 | 43.317 | 1.00 | 25.00 |
| ATOM | 57 | CD2 | TYR | 18 | 52.123 | 3.564 | 43.988 | 1.00 | 25.00 |
| ATOM | 56 | CE1 | TYR | 18 | 53.170 | 1.043 | 44.163 | 1.00 | 25.00 |
| ATOM | 58 | CE2 | TYR | 18 | 51.573 | 2.675 | 44.842 | 1.00 | 25.00 |
| ATOM | 59 | CZ | TYR | 18 | 52.099 | 1.408 | 44.922 | 1.00 | 25.00 |
| ATOM | 60 | OH | TYR | 18 | 51.517 | 0.472 | 45.743 | 1.00 | 25.00 |
| ATOM | 63 | N | LEU | 19 | 56.378 | 5.278 | 40.578 | 1.00 | 25.00 |
| ATOM | 64 | CA | LEU | 19 | 56.784 | 5.927 | 39.344 | 1.00 | 25.00 |
| ATOM | 69 | C | LEU | 19 | 55.732 | 5.619 | 38.284 | 1.00 | 25.00 |
| ATOM | 70 | O | LEU | 19 | 55.461 | 6.452 | 37.413 | 1.00 | 25.00 |

Figure 23C

| ATOM | 65 | CB | LEU | 19 | 58.146 | 5.392 | 38.897 | 1.00 | 25.00 |
| --- | --- | --- | --- | --- | --- | --- | --- | --- | --- |
| ATOM | 66 | CG | LEU | 19 | 59.417 | 6.149 | 39.272 | 1.00 | 25.00 |
| ATOM | 67 | CD1 | LEU | 19 | 59.159 | 7.068 | 40.422 | 1.00 | 25.00 |
| ATOM | 68 | CD2 | LEU | 19 | 60.550 | 5.181 | 39.574 | 1.00 | 25.00 |
| ATOM | 71 | N | ALA | 20 | 55.131 | 4.429 | 38.381 | 1.00 | 25.00 |
| ATOM | 72 | CA | ALA | 20 | 54.120 | 3.967 | 37.420 | 1.00 | 25.00 |
| ATOM | 74 | C | ALA | 20 | 53.390 | 2.696 | 37.880 | 1.00 | 25.00 |
| ATOM | 75 | O | ALA | 20 | 53.970 | 1.838 | 38.565 | 1.00 | 25.00 |
| ATOM | 73 | CB | ALA | 20 | 54.787 | 3.694 | 36.073 | 1.00 | 25.00 |
| ATOM | 76 | N | LEU | 21 | 52.118 | 2.565 | 37.518 | 1.00 | 25.00 |
| ATOM | 77 | CA | LEU | 21 | 51.403 | 1.361 | 37.903 | 1.00 | 25.00 |
| ATOM | 82 | C | LEU | 21 | 51.393 | 0.435 | 36.707 | 1.00 | 25.00 |
| ATOM | 83 | O | LEU | 21 | 51.003 | 0.847 | 35.601 | 1.00 | 25.00 |
| ATOM | 78 | CB | LEU | 21 | 49.984 | 1.659 | 38.388 | 1.00 | 25.00 |
| ATOM | 79 | CG | LEU | 21 | 49.814 | 2.274 | 39.784 | 1.00 | 25.00 |
| ATOM | 80 | CD1 | LEU | 21 | 48.358 | 2.185 | 40.179 | 1.00 | 25.00 |
| ATOM | 81 | CD2 | LEU | 21 | 50.660 | 1.548 | 40.796 | 1.00 | 25.00 |
| ATOM | 84 | N | TYR | 22 | 51.863 | -0.796 | 36.927 | 1.00 | 25.00 |
| ATOM | 85 | CA | TYR | 22 | 51.955 | -1.816 | 35.880 | 1.00 | 25.00 |
| ATOM | 94 | C | TYR | 22 | 50.657 | -1.941 | 35.107 | 1.00 | 25.00 |
| ATOM | 95 | O | TYR | 22 | 49.583 | -2.239 | 35.687 | 1.00 | 25.00 |
| ATOM | 86 | CB | TYR | 22 | 52.384 | -3.173 | 36.445 | 1.00 | 25.00 |
| ATOM | 87 | CG | TYR | 22 | 53.827 | -3.230 | 36.948 | 1.00 | 25.00 |
| ATOM | 88 | CD1 | TYR | 22 | 54.827 | -2.416 | 36.416 | 1.00 | 25.00 |
| ATOM | 90 | CD2 | TYR | 22 | 54.188 | -4.112 | 37.961 | 1.00 | 25.00 |
| ATOM | 89 | CE1 | TYR | 22 | 56.141 | -2.496 | 36.892 | 1.00 | 25.00 |
| ATOM | 91 | CE2 | TYR | 22 | 55.490 | -4.189 | 38.433 | 1.00 | 25.00 |
| ATOM | 92 | CZ | TYR | 22 | 56.451 | -3.387 | 37.903 | 1.00 | 25.00 |
| ATOM | 93 | OH | TYR | 22 | 57.708 | -3.482 | 38.422 | 1.00 | 25.00 |
| ATOM | 96 | N | SER | 23 | 50.773 | -1.593 | 33.816 | 1.00 | 25.00 |
| ATOM | 97 | CA | SER | 23 | 49.653 | -1.616 | 32.887 | 1.00 | 25.00 |
| ATOM | 98 | C | SER | 23 | 48.792 | -0.355 | 32.875 | 1.00 | 25.00 |
| ATOM | 99 | O | SER | 23 | 48.745 | 0.376 | 31.883 | 1.00 | 25.00 |
| ATOM | 100 | N | LYS | 24 | 48.143 | -0.088 | 34.001 | 1.00 | 25.00 |
| ATOM | 101 | CA | LYS | 24 | 47.243 | 1.054 | 34.177 | 1.00 | 25.00 |
| ATOM | 103 | C | LYS | 24 | 47.583 | 2.417 | 33.503 | 1.00 | 25.00 |
| ATOM | 104 | O | LYS | 24 | 46.681 | 3.073 | 32.914 | 1.00 | 25.00 |

Figure 23D

| ATOM | 102 | CB  | LYS | 24 | 46.959 | 1.244 | 35.672 | 1.00 | 25.00 |
|------|-----|-----|-----|----|--------|-------|--------|------|-------|
| ATOM | 105 | N   | ASP | 25 | 48.853 | 2.844 | 33.590 | 1.00 | 25.00 |
| ATOM | 106 | CA  | ASP | 25 | 49.292 | 4.112 | 32.993 | 1.00 | 25.00 |
| ATOM | 111 | C   | ASP | 25 | 48.991 | 4.227 | 31.492 | 1.00 | 25.00 |
| ATOM | 112 | O   | ASP | 25 | 48.985 | 5.340 | 30.964 | 1.00 | 25.00 |
| ATOM | 107 | CB  | ASP | 25 | 50.775 | 4.346 | 33.244 | 1.00 | 25.00 |
| ATOM | 108 | CG  | ASP | 25 | 51.659 | 3.274 | 32.623 | 1.00 | 25.00 |
| ATOM | 109 | OD1 | ASP | 25 | 51.148 | 2.256 | 32.088 | 1.00 | 25.00 |
| ATOM | 110 | OD2 | ASP | 25 | 52.898 | 3.450 | 32.697 | 1.00 | 25.00 |
| ATOM | 113 | N   | GLU | 26 | 48.773 | 3.080 | 30.823 | 1.00 | 25.00 |
| ATOM | 114 | CA  | GLU | 26 | 48.431 | 2.985 | 29.384 | 1.00 | 25.00 |
| ATOM | 116 | C   | GLU | 26 | 49.606 | 2.876 | 28.430 | 1.00 | 25.00 |
| ATOM | 117 | O   | GLU | 26 | 50.760 | 2.879 | 28.852 | 1.00 | 25.00 |
| ATOM | 115 | CB  | GLU | 26 | 47.516 | 4.146 | 28.946 | 1.00 | 25.00 |
| ATOM | 118 | N   | GLY | 27 | 49.288 | 2.753 | 27.142 | 1.00 | 25.00 |
| ATOM | 119 | CA  | GLY | 27 | 50.301 | 2.640 | 26.098 | 1.00 | 25.00 |
| ATOM | 120 | C   | GLY | 27 | 51.475 | 3.615 | 26.150 | 1.00 | 25.00 |
| ATOM | 121 | O   | GLY | 27 | 51.401 | 4.653 | 26.828 | 1.00 | 25.00 |
| ATOM | 122 | N   | GLU | 28 | 52.533 | 3.295 | 25.392 | 1.00 | 25.00 |
| ATOM | 123 | CA  | GLU | 28 | 53.771 | 4.087 | 25.351 | 1.00 | 25.00 |
| ATOM | 129 | C   | GLU | 28 | 54.317 | 4.289 | 26.767 | 1.00 | 25.00 |
| ATOM | 130 | O   | GLU | 28 | 55.269 | 3.619 | 27.176 | 1.00 | 25.00 |
| ATOM | 124 | CB  | GLU | 28 | 53.557 | 5.444 | 24.673 | 1.00 | 25.00 |
| ATOM | 125 | CG  | GLU | 28 | 53.502 | 5.391 | 23.144 | 1.00 | 25.00 |
| ATOM | 126 | CD  | GLU | 28 | 52.088 | 5.556 | 22.585 | 1.00 | 25.00 |
| ATOM | 127 | OE1 | GLU | 28 | 51.226 | 4.655 | 22.848 | 1.00 | 25.00 |
| ATOM | 128 | OE2 | GLU | 28 | 51.861 | 6.582 | 21.874 | 1.00 | 25.00 |
| ATOM | 131 | N   | LEU | 29 | 53.669 | 5.187 | 27.509 | 1.00 | 25.00 |
| ATOM | 132 | CA  | LEU | 29 | 53.999 | 5.497 | 28.892 | 1.00 | 25.00 |
| ATOM | 137 | C   | LEU | 29 | 54.172 | 4.218 | 29.684 | 1.00 | 25.00 |
| ATOM | 138 | O   | LEU | 29 | 54.892 | 4.204 | 30.685 | 1.00 | 25.00 |
| ATOM | 133 | CB  | LEU | 29 | 52.848 | 6.255 | 29.544 | 1.00 | 25.00 |
| ATOM | 134 | CG  | LEU | 29 | 52.537 | 7.687 | 29.124 | 1.00 | 25.00 |
| ATOM | 135 | CD1 | LEU | 29 | 53.753 | 8.537 | 29.390 | 1.00 | 25.00 |
| ATOM | 136 | CD2 | LEU | 29 | 52.112 | 7.765 | 27.662 | 1.00 | 25.00 |
| ATOM | 139 | N   | ASN | 30 | 53.446 | 3.172 | 29.277 | 1.00 | 25.00 |
| ATOM | 140 | CA  | ASN | 30 | 53.476 | 1.883 | 29.955 | 1.00 | 25.00 |

Figure 23E

| ATOM | 145 | C | ASN | 30 | 54.845 | 1.368 | 30.373 | 1.00 | 25.00 |
| --- | --- | --- | --- | --- | --- | --- | --- | --- | --- |
| ATOM | 146 | O | ASN | 30 | 55.776 | 1.317 | 29.575 | 1.00 | 25.00 |
| ATOM | 141 | CB | ASN | 30 | 52.728 | 0.810 | 29.155 | 1.00 | 25.00 |
| ATOM | 142 | CG | ASN | 30 | 51.554 | 0.202 | 29.953 | 1.00 | 25.00 |
| ATOM | 143 | OD1 | ASN | 30 | 51.752 | -0.393 | 31.028 | 1.00 | 25.00 |
| ATOM | 144 | ND2 | ASN | 30 | 50.329 | 0.364 | 29.439 | 1.00 | 25.00 |
| ATOM | 147 | N | ILE | 31 | 54.961 | 1.033 | 31.656 | 1.00 | 25.00 |
| ATOM | 148 | CA | ILE | 31 | 56.187 | 0.494 | 32.242 | 1.00 | 25.00 |
| ATOM | 153 | C | ILE | 31 | 55.901 | -0.976 | 32.612 | 1.00 | 25.00 |
| ATOM | 154 | O | ILE | 31 | 54.780 | -1.327 | 33.010 | 1.00 | 25.00 |
| ATOM | 149 | CB | ILE | 31 | 56.610 | 1.339 | 33.473 | 1.00 | 25.00 |
| ATOM | 151 | CG1 | ILE | 31 | 57.091 | 2.719 | 33.006 | 1.00 | 25.00 |
| ATOM | 150 | CG2 | ILE | 31 | 57.701 | 0.638 | 34.247 | 1.00 | 25.00 |
| ATOM | 152 | CD1 | ILE | 31 | 58.052 | 2.649 | 31.817 | 1.00 | 25.00 |
| ATOM | 155 | N | THR | 32 | 56.881 | -1.851 | 32.445 | 1.00 | 25.00 |
| ATOM | 156 | CA | THR | 32 | 56.638 | -3.256 | 32.731 | 1.00 | 25.00 |
| ATOM | 160 | C | THR | 32 | 57.860 | -3.886 | 33.383 | 1.00 | 25.00 |
| ATOM | 161 | O | THR | 32 | 58.980 | -3.347 | 33.261 | 1.00 | 25.00 |
| ATOM | 157 | CB | THR | 32 | 56.320 | -4.018 | 31.431 | 1.00 | 25.00 |
| ATOM | 158 | OG1 | THR | 32 | 57.539 | -4.216 | 30.694 | 1.00 | 25.00 |
| ATOM | 159 | CG2 | THR | 32 | 55.310 | -3.224 | 30.549 | 1.00 | 25.00 |
| ATOM | 162 | N | PRO | 33 | 57.682 | -5.064 | 34.034 | 1.00 | 25.00 |
| ATOM | 164 | CA | PRO | 33 | 58.763 | -5.794 | 34.722 | 1.00 | 25.00 |
| ATOM | 167 | C | PRO | 33 | 60.101 | -6.010 | 33.954 | 1.00 | 25.00 |
| ATOM | 168 | O | PRO | 33 | 61.182 | -5.770 | 34.515 | 1.00 | 25.00 |
| ATOM | 165 | CB | PRO | 33 | 58.069 | -7.093 | 35.157 | 1.00 | 25.00 |
| ATOM | 166 | CG | PRO | 33 | 56.674 | -6.634 | 35.446 | 1.00 | 25.00 |
| ATOM | 163 | CD | PRO | 33 | 56.392 | -5.749 | 34.236 | 1.00 | 25.00 |
| ATOM | 169 | N | GLU | 34 | 60.039 | -6.437 | 32.688 | 1.00 | 25.00 |
| ATOM | 170 | CA | GLU | 34 | 61.245 | -6.634 | 31.857 | 1.00 | 25.00 |
| ATOM | 176 | C | GLU | 34 | 62.063 | -5.346 | 31.882 | 1.00 | 25.00 |
| ATOM | 177 | O | GLU | 34 | 63.288 | -5.364 | 31.766 | 1.00 | 25.00 |
| ATOM | 171 | CB | GLU | 34 | 60.836 | -6.927 | 30.395 | 1.00 | 25.00 |
| ATOM | 172 | CG | GLU | 34 | 62.000 | -7.209 | 29.377 | 1.00 | 25.00 |
| ATOM | 173 | CD | GLU | 34 | 61.689 | -8.375 | 28.350 | 1.00 | 25.00 |
| ATOM | 174 | OE1 | GLU | 34 | 60.516 | -8.524 | 27.873 | 1.00 | 25.00 |
| ATOM | 175 | OE2 | GLU | 34 | 62.639 | -9.144 | 28.024 | 1.00 | 25.00 |

Figure 23F

| ATOM | 178 | N | ILE | 35 | 61.353 | -4.238 | 32.072 | 1.00 | 25.00 |
|---|---|---|---|---|---|---|---|---|---|
| ATOM | 179 | CA | ILE | 35 | 61.931 | -2.910 | 32.093 | 1.00 | 25.00 |
| ATOM | 184 | C | ILE | 35 | 62.427 | -2.524 | 33.464 | 1.00 | 25.00 |
| ATOM | 185 | O | ILE | 35 | 63.538 | -2.027 | 33.623 | 1.00 | 25.00 |
| ATOM | 180 | CB | ILE | 35 | 60.886 | -1.877 | 31.637 | 1.00 | 25.00 |
| ATOM | 182 | CG1 | ILE | 35 | 60.131 | -2.417 | 30.415 | 1.00 | 25.00 |
| ATOM | 181 | CG2 | ILE | 35 | 61.566 | -0.567 | 31.293 | 1.00 | 25.00 |
| ATOM | 183 | CD1 | ILE | 35 | 59.063 | -1.500 | 29.855 | 1.00 | 25.00 |
| ATOM | 186 | N | VAL | 36 | 61.584 | -2.739 | 34.457 | 1.00 | 25.00 |
| ATOM | 187 | CA | VAL | 36 | 61.930 | -2.391 | 35.831 | 1.00 | 25.00 |
| ATOM | 191 | C | VAL | 36 | 63.210 | -3.095 | 36.263 | 1.00 | 25.00 |
| ATOM | 192 | O | VAL | 36 | 64.262 | -2.475 | 36.453 | 1.00 | 25.00 |
| ATOM | 188 | CB | VAL | 36 | 60.824 | -2.826 | 36.807 | 1.00 | 25.00 |
| ATOM | 189 | CG1 | VAL | 36 | 60.849 | -1.952 | 38.030 | 1.00 | 25.00 |
| ATOM | 190 | CG2 | VAL | 36 | 59.483 | -2.787 | 36.142 | 1.00 | 25.00 |
| ATOM | 193 | N | ARG | 37 | 63.085 | -4.414 | 36.390 | 1.00 | 25.00 |
| ATOM | 194 | CA | ARG | 37 | 64.162 | -5.309 | 36.818 | 1.00 | 25.00 |
| ATOM | 196 | C | ARG | 37 | 65.469 | -5.054 | 36.065 | 1.00 | 25.00 |
| ATOM | 197 | O | ARG | 37 | 66.567 | -5.111 | 36.650 | 1.00 | 25.00 |
| ATOM | 195 | CB | ARG | 37 | 63.716 | -6.779 | 36.669 | 1.00 | 25.00 |
| ATOM | 198 | N | SER | 38 | 65.358 | -4.820 | 34.763 | 1.00 | 25.00 |
| ATOM | 199 | CA | SER | 38 | 66.551 | -4.526 | 34.001 | 1.00 | 25.00 |
| ATOM | 202 | C | SER | 38 | 67.092 | -3.191 | 34.532 | 1.00 | 25.00 |
| ATOM | 203 | O | SER | 38 | 68.214 | -3.130 | 35.026 | 1.00 | 25.00 |
| ATOM | 200 | CB | SER | 38 | 66.244 | -4.464 | 32.478 | 1.00 | 25.00 |
| ATOM | 201 | OG | SER | 38 | 65.138 | -3.623 | 32.113 | 1.00 | 25.00 |
| ATOM | 204 | N | ALA | 39 | 66.219 | -2.184 | 34.551 | 1.00 | 25.00 |
| ATOM | 205 | CA | ALA | 39 | 66.525 | -0.821 | 34.977 | 1.00 | 25.00 |
| ATOM | 207 | C | ALA | 39 | 67.130 | -0.599 | 36.392 | 1.00 | 25.00 |
| ATOM | 208 | O | ALA | 39 | 67.855 | 0.386 | 36.637 | 1.00 | 25.00 |
| ATOM | 206 | CB | ALA | 39 | 65.280 | 0.036 | 34.794 | 1.00 | 25.00 |
| ATOM | 209 | N | LEU | 40 | 66.815 | -1.470 | 37.341 | 1.00 | 25.00 |
| ATOM | 210 | CA | LEU | 40 | 67.358 | -1.284 | 38.690 | 1.00 | 25.00 |
| ATOM | 215 | C | LEU | 40 | 68.290 | -2.446 | 39.056 | 1.00 | 25.00 |
| ATOM | 216 | O | LEU | 40 | 68.205 | -3.530 | 38.472 | 1.00 | 25.00 |
| ATOM | 211 | CB | LEU | 40 | 66.226 | -1.127 | 39.722 | 1.00 | 25.00 |
| ATOM | 212 | CG | LEU | 40 | 64.816 | -0.832 | 39.178 | 1.00 | 25.00 |

Figure 23G

| ATOM | 213 | CD1 | LEU | 40 | 63.823 | -0.837 | 40.308 | 1.00 | 25.00 |
|------|-----|-----|-----|----|--------|--------|--------|------|-------|
| ATOM | 214 | CD2 | LEU | 40 | 64.774 | 0.493 | 38.422 | 1.00 | 25.00 |
| ATOM | 217 | N | PRO | 41 | 69.259 | -2.205 | 39.949 | 1.00 | 25.00 |
| ATOM | 219 | CA | PRO | 41 | 69.482 | -0.910 | 40.587 | 1.00 | 25.00 |
| ATOM | 222 | C | PRO | 41 | 70.020 | -0.005 | 39.485 | 1.00 | 25.00 |
| ATOM | 223 | O | PRO | 41 | 70.869 | -0.435 | 38.684 | 1.00 | 25.00 |
| ATOM | 220 | CB | PRO | 41 | 70.590 | -1.210 | 41.617 | 1.00 | 25.00 |
| ATOM | 221 | CG | PRO | 41 | 70.747 | -2.770 | 41.632 | 1.00 | 25.00 |
| ATOM | 218 | CD | PRO | 41 | 70.375 | -3.130 | 40.225 | 1.00 | 25.00 |
| ATOM | 224 | N | PRO | 42 | 69.476 | 1.223 | 39.371 | 1.00 | 25.00 |
| ATOM | 226 | CA | PRO | 42 | 69.891 | 2.217 | 38.351 | 1.00 | 25.00 |
| ATOM | 229 | C | PRO | 42 | 71.379 | 2.556 | 38.489 | 1.00 | 25.00 |
| ATOM | 230 | O | PRO | 42 | 71.867 | 2.756 | 39.615 | 1.00 | 25.00 |
| ATOM | 227 | CB | PRO | 42 | 69.016 | 3.435 | 38.675 | 1.00 | 25.00 |
| ATOM | 228 | CG | PRO | 42 | 67.755 | 2.795 | 39.308 | 1.00 | 25.00 |
| ATOM | 225 | CD | PRO | 42 | 68.369 | 1.731 | 40.211 | 1.00 | 25.00 |
| ATOM | 231 | N | THR | 43 | 72.100 | 2.618 | 37.366 | 1.00 | 25.00 |
| ATOM | 232 | CA | THR | 43 | 73.534 | 2.908 | 37.450 | 1.00 | 25.00 |
| ATOM | 236 | C | THR | 43 | 73.772 | 4.334 | 37.932 | 1.00 | 25.00 |
| ATOM | 237 | O | THR | 43 | 74.441 | 4.566 | 38.944 | 1.00 | 25.00 |
| ATOM | 233 | CB | THR | 43 | 74.297 | 2.675 | 36.097 | 1.00 | 25.00 |
| ATOM | 234 | OG1 | THR | 43 | 74.154 | 3.822 | 35.237 | 1.00 | 25.00 |
| ATOM | 235 | CG2 | THR | 43 | 73.770 | 1.406 | 35.379 | 1.00 | 25.00 |
| ATOM | 238 | N | SER | 44 | 73.158 | 5.280 | 37.234 | 1.00 | 25.00 |
| ATOM | 239 | CA | SER | 44 | 73.315 | 6.690 | 37.557 | 1.00 | 25.00 |
| ATOM | 241 | C | SER | 44 | 72.327 | 7.201 | 38.592 | 1.00 | 25.00 |
| ATOM | 242 | O | SER | 44 | 71.103 | 7.118 | 38.401 | 1.00 | 25.00 |
| ATOM | 240 | CB | SER | 44 | 73.229 | 7.531 | 36.278 | 1.00 | 25.00 |
| ATOM | 243 | N | LYS | 45 | 72.878 | 7.741 | 39.676 | 1.00 | 25.00 |
| ATOM | 244 | CA | LYS | 45 | 72.093 | 8.305 | 40.764 | 1.00 | 25.00 |
| ATOM | 246 | C | LYS | 45 | 71.058 | 9.285 | 40.193 | 1.00 | 25.00 |
| ATOM | 247 | O | LYS | 45 | 71.386 | 10.415 | 39.834 | 1.00 | 25.00 |
| ATOM | 245 | CB | LYS | 45 | 73.006 | 9.005 | 41.736 | 1.00 | 25.00 |
| ATOM | 248 | N | ILE | 46 | 69.818 | 8.809 | 40.113 | 1.00 | 25.00 |
| ATOM | 249 | CA | ILE | 46 | 68.681 | 9.534 | 39.567 | 1.00 | 25.00 |
| ATOM | 254 | C | ILE | 46 | 68.292 | 10.768 | 40.340 | 1.00 | 25.00 |
| ATOM | 255 | O | ILE | 46 | 68.077 | 10.703 | 41.549 | 1.00 | 25.00 |

Figure 23H

| ATOM | 250 | CB  | ILE | 46 | 67.480 | 8.617  | 39.497 | 1.00 | 25.00 |
|------|-----|-----|-----|----|--------|--------|--------|------|-------|
| ATOM | 252 | CG1 | ILE | 46 | 67.832 | 7.407  | 38.646 | 1.00 | 25.00 |
| ATOM | 251 | CG2 | ILE | 46 | 66.304 | 9.335  | 38.902 | 1.00 | 25.00 |
| ATOM | 253 | CD1 | ILE | 46 | 66.677 | 6.468  | 38.460 | 1.00 | 25.00 |
| ATOM | 256 | N   | PRO | 47 | 68.167 | 11.907 | 39.642 | 1.00 | 25.00 |
| ATOM | 258 | CA  | PRO | 47 | 67.803 | 13.197 | 40.219 | 1.00 | 25.00 |
| ATOM | 261 | C   | PRO | 47 | 66.334 | 13.605 | 40.104 | 1.00 | 25.00 |
| ATOM | 262 | O   | PRO | 47 | 65.599 | 13.164 | 39.223 | 1.00 | 25.00 |
| ATOM | 259 | CB  | PRO | 47 | 68.708 | 14.152 | 39.461 | 1.00 | 25.00 |
| ATOM | 260 | CG  | PRO | 47 | 68.638 | 13.600 | 38.081 | 1.00 | 25.00 |
| ATOM | 257 | CD  | PRO | 47 | 68.722 | 12.090 | 38.288 | 1.00 | 25.00 |
| ATOM | 263 | N   | ILE | 48 | 65.950 | 14.511 | 40.990 | 1.00 | 25.00 |
| ATOM | 264 | CA  | ILE | 48 | 64.603 | 15.035 | 41.070 | 1.00 | 25.00 |
| ATOM | 269 | C   | ILE | 48 | 64.613 | 16.526 | 40.742 | 1.00 | 25.00 |
| ATOM | 270 | O   | ILE | 48 | 65.226 | 17.328 | 41.436 | 1.00 | 25.00 |
| ATOM | 265 | CB  | ILE | 48 | 64.024 | 14.778 | 42.499 | 1.00 | 25.00 |
| ATOM | 267 | CG1 | ILE | 48 | 63.421 | 13.385 | 42.564 | 1.00 | 25.00 |
| ATOM | 266 | CG2 | ILE | 48 | 62.999 | 15.822 | 42.911 | 1.00 | 25.00 |
| ATOM | 268 | CD1 | ILE | 48 | 62.725 | 13.102 | 43.855 | 1.00 | 25.00 |
| ATOM | 271 | N   | ASN | 49 | 63.997 | 16.897 | 39.640 | 1.00 | 25.00 |
| ATOM | 272 | CA  | ASN | 49 | 63.940 | 18.302 | 39.306 | 1.00 | 25.00 |
| ATOM | 277 | C   | ASN | 49 | 62.477 | 18.674 | 39.152 | 1.00 | 25.00 |
| ATOM | 278 | O   | ASN | 49 | 61.608 | 17.807 | 39.219 | 1.00 | 25.00 |
| ATOM | 273 | CB  | ASN | 49 | 64.791 | 18.643 | 38.064 | 1.00 | 25.00 |
| ATOM | 274 | CG  | ASN | 49 | 64.249 | 18.060 | 36.775 | 1.00 | 25.00 |
| ATOM | 275 | OD1 | ASN | 49 | 63.041 | 17.877 | 36.617 | 1.00 | 25.00 |
| ATOM | 276 | ND2 | ASN | 49 | 65.147 | 17.795 | 35.822 | 1.00 | 25.00 |
| ATOM | 279 | N   | ILE | 50 | 62.205 | 19.952 | 38.949 | 1.00 | 25.00 |
| ATOM | 280 | CA  | ILE | 50 | 60.845 | 20.456 | 38.816 | 1.00 | 25.00 |
| ATOM | 285 | C   | ILE | 50 | 60.554 | 20.807 | 37.355 | 1.00 | 25.00 |
| ATOM | 286 | O   | ILE | 50 | 61.366 | 21.443 | 36.727 | 1.00 | 25.00 |
| ATOM | 281 | CB  | ILE | 50 | 60.707 | 21.745 | 39.670 | 1.00 | 25.00 |
| ATOM | 283 | CG1 | ILE | 50 | 60.974 | 21.459 | 41.145 | 1.00 | 25.00 |
| ATOM | 282 | CG2 | ILE | 50 | 59.367 | 22.430 | 39.417 | 1.00 | 25.00 |
| ATOM | 284 | CD1 | ILE | 50 | 61.054 | 22.697 | 41.962 | 1.00 | 25.00 |
| ATOM | 287 | N   | ASP | 51 | 59.416 | 20.383 | 36.817 | 1.00 | 25.00 |
| ATOM | 288 | CA  | ASP | 51 | 59.018 | 20.705 | 35.437 | 1.00 | 25.00 |

Figure 23I

| ATOM | 293 | C | ASP | 51 | 59.915 | 20.048 | 34.386 | 1.00 | 25.00 |
|------|-----|-----|-----|-----|--------|--------|--------|------|-------|
| ATOM | 294 | O | ASP | 51 | 59.833 | 20.381 | 33.194 | 1.00 | 25.00 |
| ATOM | 289 | CB | ASP | 51 | 59.010 | 22.251 | 35.251 | 1.00 | 25.00 |
| ATOM | 290 | CG | ASP | 51 | 58.470 | 22.728 | 33.852 | 1.00 | 25.00 |
| ATOM | 291 | OD1 | ASP | 51 | 57.376 | 22.260 | 33.453 | 1.00 | 25.00 |
| ATOM | 292 | OD2 | ASP | 51 | 59.111 | 23.607 | 33.183 | 1.00 | 25.00 |
| ATOM | 295 | N | HIS | 52 | 60.710 | 19.064 | 34.809 | 1.00 | 25.00 |
| ATOM | 296 | CA | HIS | 52 | 61.673 | 18.368 | 33.923 | 1.00 | 25.00 |
| ATOM | 297 | C | HIS | 52 | 62.853 | 19.281 | 33.567 | 1.00 | 25.00 |
| ATOM | 298 | O | HIS | 52 | 63.644 | 18.965 | 32.685 | 1.00 | 25.00 |
| ATOM | 299 | CB | HIS | 52 | 61.040 | 17.836 | 32.638 | 1.00 | 25.00 |
| ATOM | 300 | CG | HIS | 52 | 60.095 | 16.703 | 32.846 | 1.00 | 25.00 |
| ATOM | 301 | ND1 | HIS | 52 | 60.477 | 15.394 | 33.018 | 1.00 | 25.00 |
| ATOM | 302 | CD2 | HIS | 52 | 58.739 | 16.690 | 32.866 | 1.00 | 25.00 |
| ATOM | 304 | CE1 | HIS | 52 | 59.365 | 14.648 | 33.133 | 1.00 | 25.00 |
| ATOM | 303 | NE2 | HIS | 52 | 58.277 | 15.389 | 33.047 | 1.00 | 25.00 |
| ATOM | 305 | N | ARG | 53 | 62.972 | 20.396 | 34.290 | 1.00 | 25.00 |
| ATOM | 306 | CA | ARG | 53 | 64.033 | 21.369 | 34.117 | 1.00 | 25.00 |
| ATOM | 314 | C | ARG | 53 | 65.376 | 20.861 | 34.610 | 1.00 | 25.00 |
| ATOM | 315 | O | ARG | 53 | 65.645 | 20.811 | 35.799 | 1.00 | 25.00 |
| ATOM | 307 | CB | ARG | 53 | 63.690 | 22.672 | 34.839 | 1.00 | 25.00 |
| ATOM | 308 | CG | ARG | 53 | 62.664 | 23.523 | 34.126 | 1.00 | 25.00 |
| ATOM | 309 | CD | ARG | 53 | 63.218 | 24.057 | 32.816 | 1.00 | 25.00 |
| ATOM | 310 | NE | ARG | 53 | 63.931 | 25.325 | 32.972 | 1.00 | 25.00 |
| ATOM | 311 | CZ | ARG | 53 | 63.342 | 26.522 | 32.907 | 1.00 | 25.00 |
| ATOM | 312 | NH1 | ARG | 53 | 62.022 | 26.597 | 32.679 | 1.00 | 25.00 |
| ATOM | 313 | NH2 | ARG | 53 | 64.063 | 27.643 | 33.061 | 1.00 | 25.00 |
| ATOM | 316 | N | LYS | 54 | 66.220 | 20.501 | 33.661 | 1.00 | 25.00 |
| ATOM | 317 | CA | LYS | 54 | 67.571 | 20.028 | 33.907 | 1.00 | 25.00 |
| ATOM | 323 | C | LYS | 54 | 68.314 | 21.061 | 34.724 | 1.00 | 25.00 |
| ATOM | 324 | O | LYS | 54 | 69.184 | 20.710 | 35.497 | 1.00 | 25.00 |
| ATOM | 318 | CB | LYS | 54 | 68.306 | 19.831 | 32.566 | 1.00 | 25.00 |
| ATOM | 319 | CG | LYS | 54 | 67.562 | 18.902 | 31.571 | 1.00 | 25.00 |
| ATOM | 320 | CD | LYS | 54 | 68.311 | 18.646 | 30.254 | 1.00 | 25.00 |
| ATOM | 321 | CE | LYS | 54 | 67.565 | 17.600 | 29.383 | 1.00 | 25.00 |
| ATOM | 322 | NZ | LYS | 54 | 67.361 | 16.272 | 30.087 | 1.00 | 25.00 |
| ATOM | 325 | N | ASP | 55 | 67.979 | 22.334 | 34.535 | 1.00 | 25.00 |

Figure 23J

| ATOM | 326 | CA  | ASP | 55 | 68.618 | 23.436 | 35.261 | 1.00 | 25.00 |
| --- | --- | --- | --- | --- | --- | --- | --- | --- | --- |
| ATOM | 331 | C   | ASP | 55 | 67.939 | 23.679 | 36.575 | 1.00 | 25.00 |
| ATOM | 332 | O   | ASP | 55 | 68.259 | 24.648 | 37.267 | 1.00 | 25.00 |
| ATOM | 327 | CB  | ASP | 55 | 68.567 | 24.746 | 34.464 | 1.00 | 25.00 |
| ATOM | 328 | CG  | ASP | 55 | 67.144 | 25.164 | 34.100 | 1.00 | 25.00 |
| ATOM | 329 | OD1 | ASP | 55 | 66.229 | 24.318 | 34.100 | 1.00 | 25.00 |
| ATOM | 330 | OD2 | ASP | 55 | 66.934 | 26.353 | 33.792 | 1.00 | 25.00 |
| ATOM | 333 | N   | CYS | 56 | 66.952 | 22.846 | 36.887 | 1.00 | 25.00 |
| ATOM | 334 | CA  | CYS | 56 | 66.214 | 23.006 | 38.127 | 1.00 | 25.00 |
| ATOM | 337 | C   | CYS | 56 | 66.002 | 21.704 | 38.893 | 1.00 | 25.00 |
| ATOM | 338 | O   | CYS | 56 | 64.889 | 21.210 | 38.989 | 1.00 | 25.00 |
| ATOM | 335 | CB  | CYS | 56 | 64.885 | 23.704 | 37.864 | 1.00 | 25.00 |
| ATOM | 336 | SG  | CYS | 56 | 64.114 | 24.218 | 39.393 | 1.00 | 25.00 |
| ATOM | 339 | N   | VAL | 57 | 67.099 | 21.153 | 39.410 | 1.00 | 25.00 |
| ATOM | 340 | CA  | VAL | 57 | 67.127 | 19.908 | 40.182 | 1.00 | 25.00 |
| ATOM | 344 | C   | VAL | 57 | 67.134 | 20.364 | 41.619 | 1.00 | 25.00 |
| ATOM | 345 | O   | VAL | 57 | 67.836 | 21.312 | 41.955 | 1.00 | 25.00 |
| ATOM | 341 | CB  | VAL | 57 | 68.410 | 19.098 | 39.887 | 1.00 | 25.00 |
| ATOM | 342 | CG1 | VAL | 57 | 68.506 | 17.900 | 40.795 | 1.00 | 25.00 |
| ATOM | 343 | CG2 | VAL | 57 | 68.437 | 18.662 | 38.420 | 1.00 | 25.00 |
| ATOM | 346 | N   | VAL | 58 | 66.359 | 19.686 | 42.459 | 1.00 | 25.00 |
| ATOM | 347 | CA  | VAL | 58 | 66.219 | 20.055 | 43.870 | 1.00 | 25.00 |
| ATOM | 351 | C   | VAL | 58 | 66.341 | 18.905 | 44.868 | 1.00 | 25.00 |
| ATOM | 352 | O   | VAL | 58 | 65.980 | 19.065 | 46.042 | 1.00 | 25.00 |
| ATOM | 348 | CB  | VAL | 58 | 64.844 | 20.705 | 44.116 | 1.00 | 25.00 |
| ATOM | 349 | CG1 | VAL | 58 | 64.765 | 22.056 | 43.428 | 1.00 | 25.00 |
| ATOM | 350 | CG2 | VAL | 58 | 63.745 | 19.782 | 43.605 | 1.00 | 25.00 |
| ATOM | 353 | N   | GLY | 59 | 66.833 | 17.759 | 44.416 | 1.00 | 25.00 |
| ATOM | 354 | CA  | GLY | 59 | 66.963 | 16.622 | 45.298 | 1.00 | 25.00 |
| ATOM | 355 | C   | GLY | 59 | 67.369 | 15.450 | 44.449 | 1.00 | 25.00 |
| ATOM | 356 | O   | GLY | 59 | 67.750 | 15.646 | 43.286 | 1.00 | 25.00 |
| ATOM | 357 | N   | GLU | 60 | 67.322 | 14.243 | 45.012 | 1.00 | 25.00 |
| ATOM | 358 | CA  | GLU | 60 | 67.686 | 13.036 | 44.271 | 1.00 | 25.00 |
| ATOM | 364 | C   | GLU | 60 | 67.033 | 11.777 | 44.843 | 1.00 | 25.00 |
| ATOM | 365 | O   | GLU | 60 | 66.983 | 11.592 | 46.072 | 1.00 | 25.00 |
| ATOM | 359 | CB  | GLU | 60 | 69.212 | 12.848 | 44.234 | 1.00 | 25.00 |
| ATOM | 360 | CG  | GLU | 60 | 69.852 | 12.284 | 45.524 | 1.00 | 25.00 |

Figure 23K

| ATOM | 361 | CD | GLU | 60 | 71.256 | 11.712 | 45.294 | 1.00 | 25.00 |
|---|---|---|---|---|---|---|---|---|---|
| ATOM | 362 | OE1 | GLU | 60 | 71.446 | 10.930 | 44.343 | 1.00 | 25.00 |
| ATOM | 363 | OE2 | GLU | 60 | 72.171 | 12.048 | 46.065 | 1.00 | 25.00 |
| ATOM | 366 | N | VAL | 61 | 66.508 | 10.935 | 43.952 | 1.00 | 25.00 |
| ATOM | 367 | CA | VAL | 61 | 65.886 | 9.659 | 44.329 | 1.00 | 25.00 |
| ATOM | 371 | C | VAL | 61 | 66.937 | 8.836 | 45.099 | 1.00 | 25.00 |
| ATOM | 372 | O | VAL | 61 | 67.976 | 8.487 | 44.538 | 1.00 | 25.00 |
| ATOM | 368 | CB | VAL | 61 | 65.451 | 8.852 | 43.047 | 1.00 | 25.00 |
| ATOM | 369 | CG1 | VAL | 61 | 65.395 | 7.351 | 43.321 | 1.00 | 25.00 |
| ATOM | 370 | CG2 | VAL | 61 | 64.097 | 9.317 | 42.566 | 1.00 | 25.00 |
| ATOM | 373 | N | ILE | 62 | 66.679 | 8.529 | 46.367 | 1.00 | 25.00 |
| ATOM | 374 | CA | ILE | 62 | 67.647 | 7.750 | 47.123 | 1.00 | 25.00 |
| ATOM | 379 | C | ILE | 62 | 67.451 | 6.248 | 46.991 | 1.00 | 25.00 |
| ATOM | 380 | O | ILE | 62 | 68.322 | 5.497 | 47.396 | 1.00 | 25.00 |
| ATOM | 375 | CB | ILE | 62 | 67.737 | 8.168 | 48.624 | 1.00 | 25.00 |
| ATOM | 377 | CG1 | ILE | 62 | 66.593 | 7.592 | 49.433 | 1.00 | 25.00 |
| ATOM | 376 | CG2 | ILE | 62 | 67.738 | 9.688 | 48.762 | 1.00 | 25.00 |
| ATOM | 378 | CD1 | ILE | 62 | 66.488 | 8.209 | 50.816 | 1.00 | 25.00 |
| ATOM | 381 | N | ALA | 63 | 66.334 | 5.817 | 46.398 | 1.00 | 25.00 |
| ATOM | 382 | CA | ALA | 63 | 66.037 | 4.388 | 46.207 | 1.00 | 25.00 |
| ATOM | 384 | C | ALA | 63 | 64.724 | 4.115 | 45.473 | 1.00 | 25.00 |
| ATOM | 385 | O | ALA | 63 | 63.744 | 4.831 | 45.649 | 1.00 | 25.00 |
| ATOM | 383 | CB | ALA | 63 | 66.020 | 3.660 | 47.549 | 1.00 | 25.00 |
| ATOM | 386 | N | ILE | 64 | 64.712 | 3.042 | 44.685 | 1.00 | 25.00 |
| ATOM | 387 | CA | ILE | 64 | 63.537 | 2.613 | 43.905 | 1.00 | 25.00 |
| ATOM | 392 | C | ILE | 64 | 63.441 | 1.080 | 43.999 | 1.00 | 25.00 |
| ATOM | 393 | O | ILE | 64 | 64.432 | 0.390 | 43.766 | 1.00 | 25.00 |
| ATOM | 388 | CB | ILE | 64 | 63.676 | 2.934 | 42.362 | 1.00 | 25.00 |
| ATOM | 390 | CG1 | ILE | 64 | 64.256 | 4.330 | 42.118 | 1.00 | 25.00 |
| ATOM | 389 | CG2 | ILE | 64 | 62.313 | 2.841 | 41.680 | 1.00 | 25.00 |
| ATOM | 391 | CD1 | ILE | 64 | 64.319 | 4.721 | 40.652 | 1.00 | 25.00 |
| ATOM | 394 | N | ILE | 65 | 62.294 | 0.540 | 44.391 | 1.00 | 25.00 |
| ATOM | 395 | CA | ILE | 65 | 62.182 | -0.899 | 44.440 | 1.00 | 25.00 |
| ATOM | 400 | C | ILE | 65 | 61.117 | -1.269 | 43.481 | 1.00 | 25.00 |
| ATOM | 401 | O | ILE | 65 | 60.446 | -0.413 | 42.908 | 1.00 | 25.00 |
| ATOM | 396 | CB | ILE | 65 | 61.750 | -1.452 | 45.788 | 1.00 | 25.00 |
| ATOM | 398 | CG1 | ILE | 65 | 60.384 | -0.896 | 46.189 | 1.00 | 25.00 |

Figure 23L

| ATOM | 397 | CG2 | ILE | 65 | 62.819 | -1.200 | 46.825 | 1.00 | 25.00 |
| --- | --- | --- | --- | --- | --- | --- | --- | --- | --- |
| ATOM | 399 | CD1 | ILE | 65 | 59.638 | -1.796 | 47.154 | 1.00 | 25.00 |
| ATOM | 402 | N | GLU | 66 | 60.885 | -2.564 | 43.395 | 1.00 | 25.00 |
| ATOM | 403 | CA | GLU | 66 | 59.882 | -3.089 | 42.500 | 1.00 | 25.00 |
| ATOM | 409 | C | GLU | 66 | 58.789 | -3.706 | 43.336 | 1.00 | 25.00 |
| ATOM | 410 | O | GLU | 66 | 59.044 | -4.669 | 44.064 | 1.00 | 25.00 |
| ATOM | 404 | CB | GLU | 66 | 60.512 | -4.151 | 41.625 | 1.00 | 25.00 |
| ATOM | 405 | CG | GLU | 66 | 59.561 | -4.789 | 40.693 | 1.00 | 25.00 |
| ATOM | 406 | CD | GLU | 66 | 60.152 | -6.023 | 40.097 | 1.00 | 25.00 |
| ATOM | 407 | OE1 | GLU | 66 | 61.365 | -6.003 | 39.750 | 1.00 | 25.00 |
| ATOM | 408 | OE2 | GLU | 66 | 59.397 | -7.023 | 40.000 | 1.00 | 25.00 |
| ATOM | 411 | N | ASP | 67 | 57.607 | -3.096 | 43.291 | 1.00 | 25.00 |
| ATOM | 412 | CA | ASP | 67 | 56.445 | -3.571 | 44.039 | 1.00 | 25.00 |
| ATOM | 417 | C | ASP | 67 | 55.530 | -4.430 | 43.162 | 1.00 | 25.00 |
| ATOM | 418 | O | ASP | 67 | 55.565 | -4.351 | 41.928 | 1.00 | 25.00 |
| ATOM | 413 | CB | ASP | 67 | 55.665 | -2.388 | 44.633 | 1.00 | 25.00 |
| ATOM | 414 | CG | ASP | 67 | 54.319 | -2.801 | 45.221 | 1.00 | 25.00 |
| ATOM | 415 | OD1 | ASP | 67 | 54.250 | -3.859 | 45.876 | 1.00 | 25.00 |
| ATOM | 416 | OD2 | ASP | 67 | 53.321 | -2.069 | 45.034 | 1.00 | 25.00 |
| ATOM | 419 | N | ILE | 68 | 54.741 | -5.283 | 43.812 | 1.00 | 25.00 |
| ATOM | 420 | CA | ILE | 68 | 53.792 | -6.155 | 43.131 | 1.00 | 25.00 |
| ATOM | 425 | C | ILE | 68 | 52.962 | -5.288 | 42.155 | 1.00 | 25.00 |
| ATOM | 426 | O | ILE | 68 | 52.624 | -5.724 | 41.056 | 1.00 | 25.00 |
| ATOM | 421 | CB | ILE | 68 | 52.880 | -6.877 | 44.197 | 1.00 | 25.00 |
| ATOM | 423 | CG1 | ILE | 68 | 52.891 | -8.387 | 43.996 | 1.00 | 25.00 |
| ATOM | 422 | CG2 | ILE | 68 | 51.445 | -6.397 | 44.117 | 1.00 | 25.00 |
| ATOM | 424 | CD1 | ILE | 68 | 52.313 | -8.821 | 42.685 | 1.00 | 25.00 |
| ATOM | 427 | N | ARG | 69 | 52.698 | -4.044 | 42.572 | 1.00 | 25.00 |
| ATOM | 428 | CA | ARG | 69 | 51.919 | -3.072 | 41.808 | 1.00 | 25.00 |
| ATOM | 436 | C | ARG | 69 | 52.718 | -2.195 | 40.859 | 1.00 | 25.00 |
| ATOM | 437 | O | ARG | 69 | 52.160 | -1.698 | 39.900 | 1.00 | 25.00 |
| ATOM | 429 | CB | ARG | 69 | 51.124 | -2.158 | 42.751 | 1.00 | 25.00 |
| ATOM | 430 | CG | ARG | 69 | 49.915 | -2.788 | 43.450 | 1.00 | 25.00 |
| ATOM | 431 | CD | ARG | 69 | 49.025 | -1.716 | 44.155 | 1.00 | 25.00 |
| ATOM | 432 | NE | ARG | 69 | 48.399 | -0.768 | 43.222 | 1.00 | 25.00 |
| ATOM | 433 | CZ | ARG | 69 | 47.253 | -0.118 | 43.427 | 1.00 | 25.00 |
| ATOM | 434 | NH1 | ARG | 69 | 46.514 | -0.293 | 44.525 | 1.00 | 25.00 |

Figure 23M

| ATOM | 435 | NH2 | ARG | 69 | 46.826 | 0.703 | 42.493 | 1.00 | 25.00 |
| --- | --- | --- | --- | --- | --- | --- | --- | --- | --- |
| ATOM | 438 | N | GLY | 70 | 53.983 | -1.936 | 41.167 | 1.00 | 25.00 |
| ATOM | 439 | CA | GLY | 70 | 54.798 | -1.095 | 40.298 | 1.00 | 25.00 |
| ATOM | 440 | C | GLY | 70 | 56.075 | -0.545 | 40.920 | 1.00 | 25.00 |
| ATOM | 441 | O | GLY | 70 | 56.417 | -0.918 | 42.026 | 1.00 | 25.00 |
| ATOM | 442 | N | PRO | 71 | 56.843 | 0.289 | 40.215 | 1.00 | 25.00 |
| ATOM | 444 | CA | PRO | 71 | 58.057 | 0.809 | 40.836 | 1.00 | 25.00 |
| ATOM | 447 | C | PRO | 71 | 57.633 | 1.785 | 41.929 | 1.00 | 25.00 |
| ATOM | 448 | O | PRO | 71 | 56.783 | 2.649 | 41.669 | 1.00 | 25.00 |
| ATOM | 445 | CB | PRO | 71 | 58.719 | 1.582 | 39.689 | 1.00 | 25.00 |
| ATOM | 446 | CG | PRO | 71 | 58.175 | 0.965 | 38.472 | 1.00 | 25.00 |
| ATOM | 443 | CD | PRO | 71 | 56.746 | 0.743 | 38.824 | 1.00 | 25.00 |
| ATOM | 449 | N | PHE | 72 | 58.213 | 1.655 | 43.128 | 1.00 | 25.00 |
| ATOM | 450 | CA | PHE | 72 | 57.923 | 2.548 | 44.263 | 1.00 | 25.00 |
| ATOM | 458 | C | PHE | 72 | 59.233 | 3.224 | 44.646 | 1.00 | 25.00 |
| ATOM | 459 | O | PHE | 72 | 60.240 | 2.545 | 44.823 | 1.00 | 25.00 |
| ATOM | 451 | CB | PHE | 72 | 57.368 | 1.764 | 45.450 | 1.00 | 25.00 |
| ATOM | 452 | CG | PHE | 72 | 56.866 | 2.633 | 46.561 | 1.00 | 25.00 |
| ATOM | 453 | CD1 | PHE | 72 | 55.580 | 3.151 | 46.527 | 1.00 | 25.00 |
| ATOM | 454 | CD2 | PHE | 72 | 57.688 | 2.970 | 47.624 | 1.00 | 25.00 |
| ATOM | 455 | CE1 | PHE | 72 | 55.125 | 3.998 | 47.536 | 1.00 | 25.00 |
| ATOM | 456 | CE2 | PHE | 72 | 57.239 | 3.814 | 48.631 | 1.00 | 25.00 |
| ATOM | 457 | CZ | PHE | 72 | 55.961 | 4.329 | 48.586 | 1.00 | 25.00 |
| ATOM | 460 | N | PHE | 73 | 59.233 | 4.546 | 44.774 | 1.00 | 25.00 |
| ATOM | 461 | CA | PHE | 73 | 60.467 | 5.252 | 45.080 | 1.00 | 25.00 |
| ATOM | 469 | C | PHE | 73 | 60.412 | 6.130 | 46.277 | 1.00 | 25.00 |
| ATOM | 470 | O | PHE | 73 | 59.354 | 6.517 | 46.733 | 1.00 | 25.00 |
| ATOM | 462 | CB | PHE | 73 | 60.912 | 6.118 | 43.898 | 1.00 | 25.00 |
| ATOM | 463 | CG | PHE | 73 | 60.369 | 7.551 | 43.913 | 1.00 | 25.00 |
| ATOM | 464 | CD1 | PHE | 73 | 59.016 | 7.816 | 43.726 | 1.00 | 25.00 |
| ATOM | 465 | CD2 | PHE | 73 | 61.228 | 8.626 | 44.052 | 1.00 | 25.00 |
| ATOM | 466 | CE1 | PHE | 73 | 58.544 | 9.114 | 43.674 | 1.00 | 25.00 |
| ATOM | 467 | CE2 | PHE | 73 | 60.753 | 9.918 | 44.001 | 1.00 | 25.00 |
| ATOM | 468 | CZ | PHE | 73 | 59.414 | 10.160 | 43.812 | 1.00 | 25.00 |
| ATOM | 471 | N | LEU | 74 | 61.588 | 6.528 | 46.714 | 1.00 | 25.00 |
| ATOM | 472 | CA | LEU | 74 | 61.739 | 7.413 | 47.851 | 1.00 | 25.00 |
| ATOM | 477 | C | LEU | 74 | 62.815 | 8.398 | 47.396 | 1.00 | 25.00 |

Figure 23N

| ATOM | 478 | O | LEU | 74 | 63.735 | 8.034 | 46.663 | 1.00 | 25.00 |
|------|-----|-----|-----|----|--------|-------|--------|------|-------|
| ATOM | 473 | CB | LEU | 74 | 62.170 | 6.608 | 49.086 | 1.00 | 25.00 |
| ATOM | 474 | CG | LEU | 74 | 62.373 | 7.314 | 50.429 | 1.00 | 25.00 |
| ATOM | 475 | CD1 | LEU | 74 | 61.160 | 8.119 | 50.809 | 1.00 | 25.00 |
| ATOM | 476 | CD2 | LEU | 74 | 62.639 | 6.270 | 51.483 | 1.00 | 25.00 |
| ATOM | 479 | N | GLY | 75 | 62.675 | 9.656 | 47.744 | 1.00 | 25.00 |
| ATOM | 480 | CA | GLY | 75 | 63.681 | 10.579 | 47.301 | 1.00 | 25.00 |
| ATOM | 481 | C | GLY | 75 | 63.844 | 11.660 | 48.324 | 1.00 | 25.00 |
| ATOM | 482 | O | GLY | 75 | 63.045 | 11.771 | 49.265 | 1.00 | 25.00 |
| ATOM | 483 | N | ILE | 76 | 64.914 | 12.425 | 48.178 | 1.00 | 25.00 |
| ATOM | 484 | CA | ILE | 76 | 65.150 | 13.518 | 49.087 | 1.00 | 25.00 |
| ATOM | 489 | C | ILE | 76 | 65.138 | 14.855 | 48.317 | 1.00 | 25.00 |
| ATOM | 490 | O | ILE | 76 | 65.635 | 14.954 | 47.183 | 1.00 | 25.00 |
| ATOM | 485 | CB | ILE | 76 | 66.440 | 13.292 | 49.933 | 1.00 | 25.00 |
| ATOM | 487 | CG1 | ILE | 76 | 66.501 | 14.288 | 51.084 | 1.00 | 25.00 |
| ATOM | 486 | CG2 | ILE | 76 | 67.687 | 13.406 | 49.090 | 1.00 | 25.00 |
| ATOM | 488 | CD1 | ILE | 76 | 67.476 | 13.896 | 52.139 | 1.00 | 25.00 |
| ATOM | 491 | N | VAL | 77 | 64.407 | 15.817 | 48.875 | 1.00 | 25.00 |
| ATOM | 492 | CA | VAL | 77 | 64.291 | 17.156 | 48.319 | 1.00 | 25.00 |
| ATOM | 496 | C | VAL | 77 | 64.801 | 18.074 | 49.435 | 1.00 | 25.00 |
| ATOM | 497 | O | VAL | 77 | 64.118 | 18.362 | 50.418 | 1.00 | 25.00 |
| ATOM | 493 | CB | VAL | 77 | 62.818 | 17.482 | 47.865 | 1.00 | 25.00 |
| ATOM | 494 | CG1 | VAL | 77 | 62.675 | 18.941 | 47.430 | 1.00 | 25.00 |
| ATOM | 495 | CG2 | VAL | 77 | 62.417 | 16.561 | 46.715 | 1.00 | 25.00 |
| ATOM | 498 | N | ARG | 78 | 66.075 | 18.404 | 49.326 | 1.00 | 25.00 |
| ATOM | 499 | CA | ARG | 78 | 66.745 | 19.263 | 50.277 | 1.00 | 25.00 |
| ATOM | 507 | C | ARG | 78 | 67.311 | 20.433 | 49.464 | 1.00 | 25.00 |
| ATOM | 508 | O | ARG | 78 | 68.421 | 20.352 | 48.940 | 1.00 | 25.00 |
| ATOM | 500 | CB | ARG | 78 | 67.866 | 18.473 | 50.959 | 1.00 | 25.00 |
| ATOM | 501 | CG | ARG | 78 | 68.655 | 19.225 | 52.024 | 1.00 | 25.00 |
| ATOM | 502 | CD | ARG | 78 | 69.818 | 18.351 | 52.511 | 1.00 | 25.00 |
| ATOM | 503 | NE | ARG | 78 | 69.379 | 17.274 | 53.393 | 1.00 | 25.00 |
| ATOM | 504 | CZ | ARG | 78 | 69.600 | 17.263 | 54.710 | 1.00 | 25.00 |
| ATOM | 505 | NH1 | ARG | 78 | 70.350 | 18.222 | 55.267 | 1.00 | 25.00 |
| ATOM | 506 | NH2 | ARG | 78 | 69.135 | 16.255 | 55.466 | 1.00 | 25.00 |
| ATOM | 509 | N | CYS | 79 | 66.495 | 21.473 | 49.285 | 1.00 | 25.00 |
| ATOM | 510 | CA | CYS | 79 | 66.873 | 22.682 | 48.537 | 1.00 | 25.00 |

Figure 23O

| ATOM | 513 | C | CYS | 79 | 66.384 | 23.872 | 49.360 | 1.00 | 25.00 |
|------|-----|------|-----|----|--------|--------|--------|------|-------|
| ATOM | 514 | O | CYS | 79 | 65.192 | 24.121 | 49.475 | 1.00 | 25.00 |
| ATOM | 511 | CB | CYS | 79 | 66.240 | 22.689 | 47.122 | 1.00 | 25.00 |
| ATOM | 512 | SG | CYS | 79 | 66.357 | 24.292 | 46.237 | 1.00 | 25.00 |
| ATOM | 515 | N | PRO | 80 | 67.300 | 24.608 | 49.978 | 1.00 | 25.00 |
| ATOM | 517 | CA | PRO | 80 | 66.819 | 25.737 | 50.769 | 1.00 | 25.00 |
| ATOM | 520 | C | PRO | 80 | 66.026 | 26.759 | 49.987 | 1.00 | 25.00 |
| ATOM | 521 | O | PRO | 80 | 65.062 | 27.306 | 50.513 | 1.00 | 25.00 |
| ATOM | 518 | CB | PRO | 80 | 68.103 | 26.328 | 51.363 | 1.00 | 25.00 |
| ATOM | 519 | CG | PRO | 80 | 69.142 | 26.002 | 50.341 | 1.00 | 25.00 |
| ATOM | 516 | CD | PRO | 80 | 68.769 | 24.559 | 49.954 | 1.00 | 25.00 |
| ATOM | 522 | N | GLN | 81 | 66.374 | 26.987 | 48.728 | 1.00 | 25.00 |
| ATOM | 523 | CA | GLN | 81 | 65.643 | 27.985 | 47.953 | 1.00 | 25.00 |
| ATOM | 529 | C | GLN | 81 | 64.189 | 27.601 | 47.656 | 1.00 | 25.00 |
| ATOM | 530 | O | GLN | 81 | 63.296 | 28.455 | 47.693 | 1.00 | 25.00 |
| ATOM | 524 | CB | GLN | 81 | 66.386 | 28.340 | 46.661 | 1.00 | 25.00 |
| ATOM | 525 | CG | GLN | 81 | 67.700 | 29.107 | 46.868 | 1.00 | 25.00 |
| ATOM | 526 | CD | GLN | 81 | 68.774 | 28.254 | 47.500 | 1.00 | 25.00 |
| ATOM | 527 | OE1 | GLN | 81 | 68.818 | 27.045 | 47.284 | 1.00 | 25.00 |
| ATOM | 528 | NE2 | GLN | 81 | 69.619 | 28.863 | 48.315 | 1.00 | 25.00 |
| ATOM | 531 | N | LEU | 82 | 63.947 | 26.311 | 47.420 | 1.00 | 25.00 |
| ATOM | 532 | CA | LEU | 82 | 62.604 | 25.827 | 47.124 | 1.00 | 25.00 |
| ATOM | 537 | C | LEU | 82 | 61.583 | 26.245 | 48.168 | 1.00 | 25.00 |
| ATOM | 538 | O | LEU | 82 | 60.447 | 26.505 | 47.820 | 1.00 | 25.00 |
| ATOM | 533 | CB | LEU | 82 | 62.611 | 24.317 | 46.944 | 1.00 | 25.00 |
| ATOM | 534 | CG | LEU | 82 | 61.407 | 23.536 | 46.406 | 1.00 | 25.00 |
| ATOM | 535 | CD1 | LEU | 82 | 60.679 | 22.850 | 47.550 | 1.00 | 25.00 |
| ATOM | 536 | CD2 | LEU | 82 | 60.489 | 24.397 | 45.571 | 1.00 | 25.00 |
| ATOM | 539 | N | HIS | 83 | 61.979 | 26.340 | 49.438 | 1.00 | 25.00 |
| ATOM | 540 | CA | HIS | 83 | 61.049 | 26.759 | 50.496 | 1.00 | 25.00 |
| ATOM | 547 | C | HIS | 83 | 60.968 | 28.279 | 50.590 | 1.00 | 25.00 |
| ATOM | 548 | O | HIS | 83 | 59.910 | 28.839 | 50.890 | 1.00 | 25.00 |
| ATOM | 541 | CB | HIS | 83 | 61.462 | 26.249 | 51.868 | 1.00 | 25.00 |
| ATOM | 542 | CG | HIS | 83 | 61.604 | 24.767 | 51.960 | 1.00 | 25.00 |
| ATOM | 544 | ND1 | HIS | 83 | 61.658 | 24.106 | 53.171 | 1.00 | 25.00 |
| ATOM | 543 | CD2 | HIS | 83 | 61.806 | 23.826 | 51.006 | 1.00 | 25.00 |
| ATOM | 545 | CE1 | HIS | 83 | 61.902 | 22.824 | 52.960 | 1.00 | 25.00 |

Figure 23P

| ATOM | 546 | NE2 | HIS | 83 | 61.996 | 22.629 | 51.656 | 1.00 | 25.00 |
| --- | --- | --- | --- | --- | --- | --- | --- | --- | --- |
| ATOM | 549 | N | ALA | 84 | 62.087 | 28.948 | 50.367 | 1.00 | 25.00 |
| ATOM | 550 | CA | ALA | 84 | 62.104 | 30.389 | 50.465 | 1.00 | 25.00 |
| ATOM | 552 | C | ALA | 84 | 61.208 | 31.109 | 49.465 | 1.00 | 25.00 |
| ATOM | 553 | O | ALA | 84 | 60.433 | 31.966 | 49.873 | 1.00 | 25.00 |
| ATOM | 551 | CB | ALA | 84 | 63.512 | 30.897 | 50.369 | 1.00 | 25.00 |
| ATOM | 554 | N | VAL | 85 | 61.271 | 30.734 | 48.180 | 1.00 | 25.00 |
| ATOM | 555 | CA | VAL | 85 | 60.472 | 31.395 | 47.121 | 1.00 | 25.00 |
| ATOM | 559 | C | VAL | 85 | 58.948 | 31.205 | 47.241 | 1.00 | 25.00 |
| ATOM | 560 | O | VAL | 85 | 58.165 | 32.113 | 46.923 | 1.00 | 25.00 |
| ATOM | 556 | CB | VAL | 85 | 60.980 | 31.063 | 45.634 | 1.00 | 25.00 |
| ATOM | 557 | CG1 | VAL | 85 | 62.370 | 30.462 | 45.645 | 1.00 | 25.00 |
| ATOM | 558 | CG2 | VAL | 85 | 59.987 | 30.186 | 44.857 | 1.00 | 25.00 |
| ATOM | 561 | N | LEU | 86 | 58.563 | 30.021 | 47.709 | 1.00 | 25.00 |
| ATOM | 562 | CA | LEU | 86 | 57.184 | 29.623 | 47.921 | 1.00 | 25.00 |
| ATOM | 567 | C | LEU | 86 | 56.663 | 30.418 | 49.116 | 1.00 | 25.00 |
| ATOM | 568 | O | LEU | 86 | 55.654 | 31.094 | 49.034 | 1.00 | 25.00 |
| ATOM | 563 | CB | LEU | 86 | 57.163 | 28.117 | 48.197 | 1.00 | 25.00 |
| ATOM | 564 | CG | LEU | 86 | 56.290 | 27.177 | 47.365 | 1.00 | 25.00 |
| ATOM | 565 | CD1 | LEU | 86 | 56.116 | 27.695 | 45.983 | 1.00 | 25.00 |
| ATOM | 566 | CD2 | LEU | 86 | 56.901 | 25.791 | 47.331 | 1.00 | 25.00 |
| ATOM | 569 | N | PHE | 87 | 57.389 | 30.370 | 50.221 | 1.00 | 25.00 |
| ATOM | 570 | CA | PHE | 87 | 57.016 | 31.105 | 51.422 | 1.00 | 25.00 |
| ATOM | 578 | C | PHE | 87 | 56.751 | 32.579 | 51.089 | 1.00 | 25.00 |
| ATOM | 579 | O | PHE | 87 | 55.846 | 33.221 | 51.633 | 1.00 | 25.00 |
| ATOM | 571 | CB | PHE | 87 | 58.149 | 31.014 | 52.435 | 1.00 | 25.00 |
| ATOM | 572 | CG | PHE | 87 | 58.007 | 29.895 | 53.414 | 1.00 | 25.00 |
| ATOM | 573 | CD1 | PHE | 87 | 56.793 | 29.244 | 53.584 | 1.00 | 25.00 |
| ATOM | 574 | CD2 | PHE | 87 | 59.084 | 29.523 | 54.206 | 1.00 | 25.00 |
| ATOM | 575 | CE1 | PHE | 87 | 56.656 | 28.240 | 54.531 | 1.00 | 25.00 |
| ATOM | 576 | CE2 | PHE | 87 | 58.958 | 28.529 | 55.150 | 1.00 | 25.00 |
| ATOM | 577 | CZ | PHE | 87 | 57.743 | 27.883 | 55.318 | 1.00 | 25.00 |
| ATOM | 580 | N | GLU | 88 | 57.603 | 33.121 | 50.235 | 1.00 | 25.00 |
| ATOM | 581 | CA | GLU | 88 | 57.476 | 34.481 | 49.803 | 1.00 | 25.00 |
| ATOM | 587 | C | GLU | 88 | 56.176 | 34.597 | 49.040 | 1.00 | 25.00 |
| ATOM | 588 | O | GLU | 88 | 55.391 | 35.470 | 49.343 | 1.00 | 25.00 |
| ATOM | 582 | CB | GLU | 88 | 58.636 | 34.818 | 48.901 | 1.00 | 25.00 |

Figure 23Q

| ATOM | 583 | CG  | GLU | 88 | 58.746 | 36.262 | 48.501 | 1.00 | 25.00 |
| ---- | --- | --- | --- | -- | ------ | ------ | ------ | ---- | ----- |
| ATOM | 584 | CD  | GLU | 88 | 60.010 | 36.527 | 47.667 | 1.00 | 25.00 |
| ATOM | 585 | OE1 | GLU | 88 | 60.333 | 35.691 | 46.767 | 1.00 | 25.00 |
| ATOM | 586 | OE2 | GLU | 88 | 60.678 | 37.566 | 47.922 | 1.00 | 25.00 |
| ATOM | 589 | N   | ALA | 89 | 55.918 | 33.686 | 48.094 | 1.00 | 25.00 |
| ATOM | 590 | CA  | ALA | 89 | 54.686 | 33.705 | 47.253 | 1.00 | 25.00 |
| ATOM | 592 | C   | ALA | 89 | 53.341 | 33.663 | 48.002 | 1.00 | 25.00 |
| ATOM | 593 | O   | ALA | 89 | 52.361 | 34.303 | 47.578 | 1.00 | 25.00 |
| ATOM | 591 | CB  | ALA | 89 | 54.723 | 32.574 | 46.188 | 1.00 | 25.00 |
| ATOM | 594 | N   | ALA | 90 | 53.288 | 32.875 | 49.077 | 1.00 | 25.00 |
| ATOM | 595 | CA  | ALA | 90 | 52.082 | 32.741 | 49.874 | 1.00 | 25.00 |
| ATOM | 597 | C   | ALA | 90 | 51.714 | 34.106 | 50.464 | 1.00 | 25.00 |
| ATOM | 598 | O   | ALA | 90 | 52.585 | 34.880 | 50.855 | 1.00 | 25.00 |
| ATOM | 596 | CB  | ALA | 90 | 52.309 | 31.741 | 50.954 | 1.00 | 25.00 |
| ATOM | 599 | N   | HIS | 91 | 50.426 | 34.420 | 50.496 | 1.00 | 25.00 |
| ATOM | 600 | CA  | HIS | 91 | 49.969 | 35.703 | 51.021 | 1.00 | 25.00 |
| ATOM | 607 | C   | HIS | 91 | 50.205 | 35.729 | 52.517 | 1.00 | 25.00 |
| ATOM | 608 | O   | HIS | 91 | 50.284 | 34.665 | 53.161 | 1.00 | 25.00 |
| ATOM | 601 | CB  | HIS | 91 | 48.459 | 35.881 | 50.798 | 1.00 | 25.00 |
| ATOM | 602 | CG  | HIS | 91 | 48.078 | 36.359 | 49.431 | 1.00 | 25.00 |
| ATOM | 604 | ND1 | HIS | 91 | 46.794 | 36.245 | 48.939 | 1.00 | 25.00 |
| ATOM | 603 | CD2 | HIS | 91 | 48.794 | 36.987 | 48.468 | 1.00 | 25.00 |
| ATOM | 605 | CE1 | HIS | 91 | 46.736 | 36.785 | 47.734 | 1.00 | 25.00 |
| ATOM | 606 | NE2 | HIS | 91 | 47.938 | 37.241 | 47.425 | 1.00 | 25.00 |
| ATOM | 609 | N   | SER | 92 | 50.182 | 36.943 | 53.077 | 1.00 | 25.00 |
| ATOM | 610 | CA  | SER | 92 | 50.343 | 37.154 | 54.527 | 1.00 | 25.00 |
| ATOM | 613 | C   | SER | 92 | 49.399 | 36.278 | 55.373 | 1.00 | 25.00 |
| ATOM | 614 | O   | SER | 92 | 49.573 | 36.172 | 56.597 | 1.00 | 25.00 |
| ATOM | 611 | CB  | SER | 92 | 50.090 | 38.630 | 54.906 | 1.00 | 25.00 |
| ATOM | 612 | OG  | SER | 92 | 51.302 | 39.368 | 55.070 | 1.00 | 25.00 |
| ATOM | 615 | N   | ASN | 93 | 48.366 | 35.710 | 54.755 | 1.00 | 25.00 |
| ATOM | 616 | CA  | ASN | 93 | 47.474 | 34.879 | 55.525 | 1.00 | 25.00 |
| ATOM | 621 | C   | ASN | 93 | 47.243 | 33.446 | 55.082 | 1.00 | 25.00 |
| ATOM | 622 | O   | ASN | 93 | 46.230 | 32.799 | 55.400 | 1.00 | 25.00 |
| ATOM | 617 | CB  | ASN | 93 | 46.211 | 35.633 | 55.871 | 1.00 | 25.00 |
| ATOM | 618 | CG  | ASN | 93 | 46.481 | 36.729 | 56.875 | 1.00 | 25.00 |
| ATOM | 619 | OD1 | ASN | 93 | 47.000 | 37.803 | 56.512 | 1.00 | 25.00 |

Figure 23R

| ATOM | 620 | ND2 | ASN | 93 | 46.227 | 36.438 | 58.161 | 1.00 | 25.00 |
|------|-----|-----|-----|-----|--------|--------|--------|------|-------|
| ATOM | 623 | N   | PHE | 94 | 48.187 | 32.938 | 54.314 | 1.00 | 25.00 |
| ATOM | 624 | CA  | PHE | 94 | 48.094 | 31.549 | 53.968 | 1.00 | 25.00 |
| ATOM | 632 | C   | PHE | 94 | 48.509 | 31.036 | 55.358 | 1.00 | 25.00 |
| ATOM | 633 | O   | PHE | 94 | 49.521 | 31.493 | 55.918 | 1.00 | 25.00 |
| ATOM | 625 | CB  | PHE | 94 | 49.138 | 31.202 | 52.903 | 1.00 | 25.00 |
| ATOM | 626 | CG  | PHE | 94 | 48.881 | 29.899 | 52.223 | 1.00 | 25.00 |
| ATOM | 627 | CD1 | PHE | 94 | 49.285 | 28.710 | 52.809 | 1.00 | 25.00 |
| ATOM | 628 | CD2 | PHE | 94 | 48.173 | 29.856 | 51.030 | 1.00 | 25.00 |
| ATOM | 629 | CE1 | PHE | 94 | 48.984 | 27.506 | 52.226 | 1.00 | 25.00 |
| ATOM | 630 | CE2 | PHE | 94 | 47.868 | 28.656 | 50.440 | 1.00 | 25.00 |
| ATOM | 631 | CZ  | PHE | 94 | 48.273 | 27.473 | 51.039 | 1.00 | 25.00 |
| ATOM | 634 | N   | PHE | 95 | 47.677 | 30.203 | 55.962 | 1.00 | 25.00 |
| ATOM | 635 | CA  | PHE | 95 | 47.939 | 29.658 | 57.307 | 1.00 | 25.00 |
| ATOM | 643 | C   | PHE | 95 | 47.372 | 30.641 | 58.317 | 1.00 | 25.00 |
| ATOM | 644 | O   | PHE | 95 | 47.767 | 31.802 | 58.335 | 1.00 | 25.00 |
| ATOM | 636 | CB  | PHE | 95 | 49.438 | 29.469 | 57.631 | 1.00 | 25.00 |
| ATOM | 637 | CG  | PHE | 95 | 50.154 | 28.502 | 56.734 | 1.00 | 25.00 |
| ATOM | 638 | CD1 | PHE | 95 | 49.797 | 27.167 | 56.699 | 1.00 | 25.00 |
| ATOM | 639 | CD2 | PHE | 95 | 51.191 | 28.932 | 55.919 | 1.00 | 25.00 |
| ATOM | 640 | CE1 | PHE | 95 | 50.463 | 26.284 | 55.865 | 1.00 | 25.00 |
| ATOM | 641 | CE2 | PHE | 95 | 51.863 | 28.058 | 55.083 | 1.00 | 25.00 |
| ATOM | 642 | CZ  | PHE | 95 | 51.504 | 26.741 | 55.054 | 1.00 | 25.00 |
| ATOM | 645 | N   | GLY | 96 | 46.404 | 30.213 | 59.121 | 1.00 | 25.00 |
| ATOM | 646 | CA  | GLY | 96 | 45.871 | 31.140 | 60.103 | 1.00 | 25.00 |
| ATOM | 647 | C   | GLY | 96 | 46.804 | 31.220 | 61.300 | 1.00 | 25.00 |
| ATOM | 648 | O   | GLY | 96 | 47.991 | 30.885 | 61.200 | 1.00 | 25.00 |
| ATOM | 649 | N   | ASN | 97 | 46.273 | 31.640 | 62.447 | 1.00 | 25.00 |
| ATOM | 650 | CA  | ASN | 97 | 47.086 | 31.705 | 63.641 | 1.00 | 25.00 |
| ATOM | 655 | C   | ASN | 97 | 47.012 | 30.350 | 64.285 | 1.00 | 25.00 |
| ATOM | 656 | O   | ASN | 97 | 47.825 | 30.028 | 65.142 | 1.00 | 25.00 |
| ATOM | 651 | CB  | ASN | 97 | 46.611 | 32.805 | 64.567 | 1.00 | 25.00 |
| ATOM | 652 | CG  | ASN | 97 | 46.889 | 34.197 | 64.001 | 1.00 | 25.00 |
| ATOM | 653 | OD1 | ASN | 97 | 48.046 | 34.569 | 63.779 | 1.00 | 25.00 |
| ATOM | 654 | ND2 | ASN | 97 | 45.830 | 34.972 | 63.765 | 1.00 | 25.00 |
| ATOM | 657 | N   | ARG | 98 | 46.074 | 29.528 | 63.815 | 1.00 | 25.00 |
| ATOM | 658 | CA  | ARG | 98 | 45.920 | 28.169 | 64.328 | 1.00 | 25.00 |

Figure 23S

| ATOM | 666 | C | ARG | 98 | 47.120 | 27.347 | 63.912 | 1.00 | 25.00 |
|---|---|---|---|---|---|---|---|---|---|
| ATOM | 667 | O | ARG | 98 | 47.328 | 26.230 | 64.399 | 1.00 | 25.00 |
| ATOM | 659 | CB | ARG | 98 | 44.625 | 27.502 | 63.834 | 1.00 | 25.00 |
| ATOM | 660 | CG | ARG | 98 | 44.302 | 27.658 | 62.354 | 1.00 | 25.00 |
| ATOM | 661 | CD | ARG | 98 | 43.187 | 26.694 | 61.875 | 1.00 | 25.00 |
| ATOM | 662 | NE | ARG | 98 | 43.725 | 25.367 | 61.594 | 1.00 | 25.00 |
| ATOM | 663 | CZ | ARG | 98 | 43.514 | 24.678 | 60.479 | 1.00 | 25.00 |
| ATOM | 664 | NH1 | ARG | 98 | 42.730 | 25.170 | 59.537 | 1.00 | 25.00 |
| ATOM | 665 | NH2 | ARG | 98 | 44.068 | 23.476 | 60.324 | 1.00 | 25.00 |
| ATOM | 668 | N | ASP | 99 | 47.870 | 27.915 | 62.967 | 1.00 | 25.00 |
| ATOM | 669 | CA | ASP | 99 | 49.089 | 27.326 | 62.427 | 1.00 | 25.00 |
| ATOM | 674 | C | ASP | 99 | 50.267 | 27.962 | 63.147 | 1.00 | 25.00 |
| ATOM | 675 | O | ASP | 99 | 51.250 | 27.291 | 63.455 | 1.00 | 25.00 |
| ATOM | 670 | CB | ASP | 99 | 49.187 | 27.556 | 60.918 | 1.00 | 25.00 |
| ATOM | 671 | CG | ASP | 99 | 48.066 | 26.886 | 60.159 | 1.00 | 25.00 |
| ATOM | 672 | OD1 | ASP | 99 | 47.856 | 25.685 | 60.384 | 1.00 | 25.00 |
| ATOM | 673 | OD2 | ASP | 99 | 47.379 | 27.554 | 59.357 | 1.00 | 25.00 |
| ATOM | 676 | N | SER | 100 | 50.165 | 29.256 | 63.431 | 1.00 | 25.00 |
| ATOM | 677 | CA | SER | 100 | 51.224 | 29.946 | 64.165 | 1.00 | 25.00 |
| ATOM | 680 | C | SER | 100 | 51.527 | 29.031 | 65.335 | 1.00 | 25.00 |
| ATOM | 681 | O | SER | 100 | 52.618 | 28.447 | 65.482 | 1.00 | 25.00 |
| ATOM | 678 | CB | SER | 100 | 50.741 | 31.307 | 64.721 | 1.00 | 25.00 |
| ATOM | 679 | OG | SER | 100 | 50.565 | 32.285 | 63.700 | 1.00 | 25.00 |
| ATOM | 682 | N | VAL | 101 | 50.479 | 28.758 | 66.072 | 1.00 | 25.00 |
| ATOM | 683 | CA | VAL | 101 | 50.674 | 27.923 | 67.222 | 1.00 | 25.00 |
| ATOM | 687 | C | VAL | 101 | 50.777 | 26.417 | 66.900 | 1.00 | 25.00 |
| ATOM | 688 | O | VAL | 101 | 50.062 | 25.598 | 67.506 | 1.00 | 25.00 |
| ATOM | 684 | CB | VAL | 101 | 49.645 | 28.277 | 68.355 | 1.00 | 25.00 |
| ATOM | 685 | CG1 | VAL | 101 | 50.396 | 28.491 | 69.688 | 1.00 | 25.00 |
| ATOM | 686 | CG2 | VAL | 101 | 48.859 | 29.570 | 67.983 | 1.00 | 25.00 |
| ATOM | 689 | N | LEU | 102 | 51.622 | 26.070 | 65.918 | 1.00 | 25.00 |
| ATOM | 690 | CA | LEU | 102 | 51.849 | 24.668 | 65.595 | 1.00 | 25.00 |
| ATOM | 695 | C | LEU | 102 | 52.763 | 24.244 | 64.446 | 1.00 | 25.00 |
| ATOM | 696 | O | LEU | 102 | 53.401 | 23.192 | 64.550 | 1.00 | 25.00 |
| ATOM | 691 | CB | LEU | 102 | 50.538 | 23.858 | 65.550 | 1.00 | 25.00 |
| ATOM | 692 | CG | LEU | 102 | 50.710 | 22.549 | 66.361 | 1.00 | 25.00 |
| ATOM | 693 | CD1 | LEU | 102 | 51.013 | 22.854 | 67.857 | 1.00 | 25.00 |

Figure 23T

| ATOM | 694 | CD2 | LEU | 102 | 49.517 | 21.603 | 66.215 | 1.00 | 25.00 |
| --- | --- | --- | --- | --- | --- | --- | --- | --- | --- |
| ATOM | 697 | N | SER | 103 | 52.885 | 25.030 | 63.380 | 1.00 | 25.00 |
| ATOM | 698 | CA | SER | 103 | 53.717 | 24.611 | 62.242 | 1.00 | 25.00 |
| ATOM | 701 | C | SER | 103 | 55.014 | 25.434 | 62.112 | 1.00 | 25.00 |
| ATOM | 702 | O | SER | 103 | 55.002 | 26.622 | 62.399 | 1.00 | 25.00 |
| ATOM | 699 | CB | SER | 103 | 52.873 | 24.626 | 60.950 | 1.00 | 25.00 |
| ATOM | 700 | OG | SER | 103 | 51.778 | 23.711 | 61.012 | 1.00 | 25.00 |
| ATOM | 703 | N | PRO | 104 | 56.157 | 24.785 | 61.746 | 1.00 | 25.00 |
| ATOM | 705 | CA | PRO | 104 | 57.528 | 25.310 | 61.556 | 1.00 | 25.00 |
| ATOM | 708 | C | PRO | 104 | 58.286 | 25.311 | 60.201 | 1.00 | 25.00 |
| ATOM | 709 | O | PRO | 104 | 58.997 | 26.272 | 59.897 | 1.00 | 25.00 |
| ATOM | 706 | CB | PRO | 104 | 58.302 | 24.457 | 62.542 | 1.00 | 25.00 |
| ATOM | 707 | CG | PRO | 104 | 57.703 | 23.081 | 62.303 | 1.00 | 25.00 |
| ATOM | 704 | CD | PRO | 104 | 56.214 | 23.356 | 62.109 | 1.00 | 25.00 |
| ATOM | 710 | N | LEU | 105 | 58.340 | 24.113 | 59.593 | 1.00 | 25.00 |
| ATOM | 711 | CA | LEU | 105 | 58.967 | 23.714 | 58.307 | 1.00 | 25.00 |
| ATOM | 716 | C | LEU | 105 | 57.880 | 22.827 | 57.685 | 1.00 | 25.00 |
| ATOM | 717 | O | LEU | 105 | 57.965 | 22.402 | 56.532 | 1.00 | 25.00 |
| ATOM | 712 | CB | LEU | 105 | 60.191 | 22.812 | 58.567 | 1.00 | 25.00 |
| ATOM | 713 | CG | LEU | 105 | 60.481 | 21.572 | 57.686 | 1.00 | 25.00 |
| ATOM | 714 | CD1 | LEU | 105 | 61.539 | 21.918 | 56.706 | 1.00 | 25.00 |
| ATOM | 715 | CD2 | LEU | 105 | 60.965 | 20.370 | 58.457 | 1.00 | 25.00 |
| ATOM | 718 | N | GLU | 106 | 56.881 | 22.488 | 58.502 | 1.00 | 25.00 |
| ATOM | 719 | CA | GLU | 106 | 55.730 | 21.694 | 58.086 | 1.00 | 25.00 |
| ATOM | 725 | C | GLU | 106 | 54.897 | 22.621 | 57.220 | 1.00 | 25.00 |
| ATOM | 726 | O | GLU | 106 | 53.960 | 22.200 | 56.555 | 1.00 | 25.00 |
| ATOM | 720 | CB | GLU | 106 | 54.939 | 21.264 | 59.312 | 1.00 | 25.00 |
| ATOM | 721 | CG | GLU | 106 | 55.821 | 20.599 | 60.344 | 1.00 | 25.00 |
| ATOM | 722 | CD | GLU | 106 | 55.087 | 20.260 | 61.602 | 1.00 | 25.00 |
| ATOM | 723 | OE1 | GLU | 106 | 54.316 | 21.121 | 62.080 | 1.00 | 25.00 |
| ATOM | 724 | OE2 | GLU | 106 | 55.291 | 19.132 | 62.108 | 1.00 | 25.00 |
| ATOM | 727 | N | ARG | 107 | 55.224 | 23.904 | 57.294 | 1.00 | 25.00 |
| ATOM | 728 | CA | ARG | 107 | 54.579 | 24.904 | 56.500 | 1.00 | 25.00 |
| ATOM | 736 | C | ARG | 107 | 55.199 | 24.880 | 55.104 | 1.00 | 25.00 |
| ATOM | 737 | O | ARG | 107 | 54.539 | 25.224 | 54.129 | 1.00 | 25.00 |
| ATOM | 729 | CB | ARG | 107 | 54.722 | 26.260 | 57.162 | 1.00 | 25.00 |
| ATOM | 730 | CG | ARG | 107 | 53.923 | 26.337 | 58.441 | 1.00 | 25.00 |

Figure 23U

| ATOM | 731 | CD  | ARG | 107 | 53.468 | 27.742 | 58.744 | 1.00 | 25.00 |
| --- | --- | --- | --- | --- | --- | --- | --- | --- | --- |
| ATOM | 732 | NE  | ARG | 107 | 54.365 | 28.401 | 59.675 | 1.00 | 25.00 |
| ATOM | 733 | CZ  | ARG | 107 | 53.995 | 28.838 | 60.878 | 1.00 | 25.00 |
| ATOM | 734 | NH1 | ARG | 107 | 52.725 | 28.708 | 61.264 | 1.00 | 25.00 |
| ATOM | 735 | NH2 | ARG | 107 | 54.888 | 29.426 | 61.688 | 1.00 | 25.00 |
| ATOM | 738 | N   | ALA | 108 | 56.447 | 24.431 | 54.992 | 1.00 | 25.00 |
| ATOM | 739 | CA  | ALA | 108 | 57.105 | 24.339 | 53.690 | 1.00 | 25.00 |
| ATOM | 741 | C   | ALA | 108 | 56.434 | 23.172 | 53.071 | 1.00 | 25.00 |
| ATOM | 742 | O   | ALA | 108 | 55.887 | 23.264 | 51.994 | 1.00 | 25.00 |
| ATOM | 740 | CB  | ALA | 108 | 58.585 | 24.025 | 53.839 | 1.00 | 25.00 |
| ATOM | 743 | N   | LEU | 109 | 56.432 | 22.085 | 53.823 | 1.00 | 25.00 |
| ATOM | 744 | CA  | LEU | 109 | 55.831 | 20.839 | 53.399 | 1.00 | 25.00 |
| ATOM | 749 | C   | LEU | 109 | 54.389 | 20.992 | 52.955 | 1.00 | 25.00 |
| ATOM | 750 | O   | LEU | 109 | 53.976 | 20.346 | 52.019 | 1.00 | 25.00 |
| ATOM | 745 | CB  | LEU | 109 | 55.925 | 19.816 | 54.525 | 1.00 | 25.00 |
| ATOM | 746 | CG  | LEU | 109 | 55.682 | 18.345 | 54.210 | 1.00 | 25.00 |
| ATOM | 747 | CD1 | LEU | 109 | 56.666 | 17.856 | 53.193 | 1.00 | 25.00 |
| ATOM | 748 | CD2 | LEU | 109 | 55.854 | 17.572 | 55.470 | 1.00 | 25.00 |
| ATOM | 751 | N   | TYR | 110 | 53.620 | 21.838 | 53.626 | 1.00 | 25.00 |
| ATOM | 752 | CA  | TYR | 110 | 52.212 | 22.071 | 53.275 | 1.00 | 25.00 |
| ATOM | 761 | C   | TYR | 110 | 52.057 | 22.737 | 51.920 | 1.00 | 25.00 |
| ATOM | 762 | O   | TYR | 110 | 51.091 | 22.463 | 51.209 | 1.00 | 25.00 |
| ATOM | 753 | CB  | TYR | 110 | 51.511 | 22.940 | 54.333 | 1.00 | 25.00 |
| ATOM | 754 | CG  | TYR | 110 | 50.090 | 23.264 | 53.973 | 1.00 | 25.00 |
| ATOM | 755 | CD1 | TYR | 110 | 49.791 | 24.352 | 53.169 | 1.00 | 25.00 |
| ATOM | 757 | CD2 | TYR | 110 | 49.052 | 22.449 | 54.386 | 1.00 | 25.00 |
| ATOM | 756 | CE1 | TYR | 110 | 48.494 | 24.618 | 52.780 | 1.00 | 25.00 |
| ATOM | 758 | CE2 | TYR | 110 | 47.746 | 22.702 | 54.006 | 1.00 | 25.00 |
| ATOM | 759 | CZ  | TYR | 110 | 47.473 | 23.791 | 53.199 | 1.00 | 25.00 |
| ATOM | 760 | OH  | TYR | 110 | 46.176 | 24.054 | 52.810 | 1.00 | 25.00 |
| ATOM | 763 | N   | LEU | 111 | 52.951 | 23.690 | 51.633 | 1.00 | 25.00 |
| ATOM | 764 | CA  | LEU | 111 | 52.988 | 24.442 | 50.376 | 1.00 | 25.00 |
| ATOM | 769 | C   | LEU | 111 | 53.417 | 23.567 | 49.194 | 1.00 | 25.00 |
| ATOM | 770 | O   | LEU | 111 | 52.764 | 23.554 | 48.156 | 1.00 | 25.00 |
| ATOM | 765 | CB  | LEU | 111 | 53.974 | 25.609 | 50.491 | 1.00 | 25.00 |
| ATOM | 766 | CG  | LEU | 111 | 53.575 | 27.030 | 50.874 | 1.00 | 25.00 |
| ATOM | 767 | CD1 | LEU | 111 | 52.258 | 27.384 | 50.228 | 1.00 | 25.00 |

Figure 23V

| ATOM | 768 | CD2 | LEU | 111 | 53.484 | 27.175 | 52.340 | 1.00 | 25.00 |
|------|-----|-----|-----|-----|--------|--------|--------|------|-------|
| ATOM | 771 | N   | VAL | 112 | 54.528 | 22.852 | 49.365 | 1.00 | 25.00 |
| ATOM | 772 | CA  | VAL | 112 | 55.088 | 21.988 | 48.330 | 1.00 | 25.00 |
| ATOM | 776 | C   | VAL | 112 | 54.212 | 20.805 | 47.971 | 1.00 | 25.00 |
| ATOM | 777 | O   | VAL | 112 | 54.215 | 20.372 | 46.813 | 1.00 | 25.00 |
| ATOM | 773 | CB  | VAL | 112 | 56.512 | 21.489 | 48.678 | 1.00 | 25.00 |
| ATOM | 774 | CG1 | VAL | 112 | 56.489 | 20.680 | 49.912 | 1.00 | 25.00 |
| ATOM | 775 | CG2 | VAL | 112 | 57.067 | 20.659 | 47.563 | 1.00 | 25.00 |
| ATOM | 778 | N   | THR | 113 | 53.461 | 20.284 | 48.940 | 1.00 | 25.00 |
| ATOM | 779 | CA  | THR | 113 | 52.593 | 19.154 | 48.665 | 1.00 | 25.00 |
| ATOM | 783 | C   | THR | 113 | 51.431 | 19.606 | 47.819 | 1.00 | 25.00 |
| ATOM | 784 | O   | THR | 113 | 51.114 | 18.948 | 46.857 | 1.00 | 25.00 |
| ATOM | 780 | CB  | THR | 113 | 52.074 | 18.439 | 49.935 | 1.00 | 25.00 |
| ATOM | 781 | OG1 | THR | 113 | 53.166 | 17.858 | 50.638 | 1.00 | 25.00 |
| ATOM | 782 | CG2 | THR | 113 | 51.169 | 17.311 | 49.573 | 1.00 | 25.00 |
| ATOM | 785 | N   | ASN | 114 | 50.840 | 20.755 | 48.116 | 1.00 | 25.00 |
| ATOM | 786 | CA  | ASN | 114 | 49.699 | 21.197 | 47.326 | 1.00 | 25.00 |
| ATOM | 791 | C   | ASN | 114 | 50.020 | 21.818 | 45.961 | 1.00 | 25.00 |
| ATOM | 792 | O   | ASN | 114 | 49.209 | 21.734 | 45.032 | 1.00 | 25.00 |
| ATOM | 787 | CB  | ASN | 114 | 48.794 | 22.113 | 48.145 | 1.00 | 25.00 |
| ATOM | 788 | CG  | ASN | 114 | 47.927 | 21.352 | 49.131 | 1.00 | 25.00 |
| ATOM | 789 | OD1 | ASN | 114 | 46.785 | 21.007 | 48.841 | 1.00 | 25.00 |
| ATOM | 790 | ND2 | ASN | 114 | 48.458 | 21.109 | 50.307 | 1.00 | 25.00 |
| ATOM | 793 | N   | TYR | 115 | 51.197 | 22.427 | 45.831 | 1.00 | 25.00 |
| ATOM | 794 | CA  | TYR | 115 | 51.618 | 23.039 | 44.561 | 1.00 | 25.00 |
| ATOM | 803 | C   | TYR | 115 | 52.119 | 21.984 | 43.567 | 1.00 | 25.00 |
| ATOM | 804 | O   | TYR | 115 | 51.715 | 21.989 | 42.417 | 1.00 | 25.00 |
| ATOM | 795 | CB  | TYR | 115 | 52.729 | 24.077 | 44.792 | 1.00 | 25.00 |
| ATOM | 796 | CG  | TYR | 115 | 52.859 | 25.101 | 43.677 | 1.00 | 25.00 |
| ATOM | 797 | CD1 | TYR | 115 | 53.635 | 24.854 | 42.552 | 1.00 | 25.00 |
| ATOM | 799 | CD2 | TYR | 115 | 52.123 | 26.280 | 43.713 | 1.00 | 25.00 |
| ATOM | 798 | CE1 | TYR | 115 | 53.658 | 25.748 | 41.494 | 1.00 | 25.00 |
| ATOM | 800 | CE2 | TYR | 115 | 52.141 | 27.167 | 42.666 | 1.00 | 25.00 |
| ATOM | 801 | CZ  | TYR | 115 | 52.901 | 26.893 | 41.560 | 1.00 | 25.00 |
| ATOM | 802 | OH  | TYR | 115 | 52.844 | 27.764 | 40.513 | 1.00 | 25.00 |
| ATOM | 805 | N   | LEU | 116 | 52.985 | 21.082 | 44.033 | 1.00 | 25.00 |
| ATOM | 806 | CA  | LEU | 116 | 53.574 | 20.023 | 43.220 | 1.00 | 25.00 |

Figure 23W

| ATOM | 811 | C   | LEU | 116 | 53.167 | 18.605 | 43.661 | 1.00 | 25.00 |
|------|-----|-----|-----|-----|--------|--------|--------|------|-------|
| ATOM | 812 | O   | LEU | 116 | 54.016 | 17.803 | 44.029 | 1.00 | 25.00 |
| ATOM | 807 | CB  | LEU | 116 | 55.083 | 20.134 | 43.325 | 1.00 | 25.00 |
| ATOM | 808 | CG  | LEU | 116 | 55.741 | 21.400 | 42.807 | 1.00 | 25.00 |
| ATOM | 809 | CD1 | LEU | 116 | 57.235 | 21.350 | 43.086 | 1.00 | 25.00 |
| ATOM | 810 | CD2 | LEU | 116 | 55.469 | 21.513 | 41.324 | 1.00 | 25.00 |
| ATOM | 813 | N   | PRO | 117 | 51.884 | 18.245 | 43.530 | 1.00 | 25.00 |
| ATOM | 815 | CA  | PRO | 117 | 51.456 | 16.919 | 43.949 | 1.00 | 25.00 |
| ATOM | 818 | C   | PRO | 117 | 51.861 | 15.676 | 43.202 | 1.00 | 25.00 |
| ATOM | 819 | O   | PRO | 117 | 51.764 | 14.600 | 43.766 | 1.00 | 25.00 |
| ATOM | 816 | CB  | PRO | 117 | 49.938 | 17.056 | 44.026 | 1.00 | 25.00 |
| ATOM | 817 | CG  | PRO | 117 | 49.624 | 18.054 | 43.036 | 1.00 | 25.00 |
| ATOM | 814 | CD  | PRO | 117 | 50.716 | 19.075 | 43.198 | 1.00 | 25.00 |
| ATOM | 820 | N   | SER | 118 | 52.267 | 15.765 | 41.949 | 1.00 | 25.00 |
| ATOM | 821 | CA  | SER | 118 | 52.647 | 14.547 | 41.241 | 1.00 | 25.00 |
| ATOM | 824 | C   | SER | 118 | 54.125 | 14.431 | 40.822 | 1.00 | 25.00 |
| ATOM | 825 | O   | SER | 118 | 54.892 | 15.393 | 40.879 | 1.00 | 25.00 |
| ATOM | 822 | CB  | SER | 118 | 51.709 | 14.303 | 40.055 | 1.00 | 25.00 |
| ATOM | 823 | OG  | SER | 118 | 50.344 | 14.223 | 40.459 | 1.00 | 25.00 |
| ATOM | 826 | N   | VAL | 119 | 54.511 | 13.236 | 40.390 | 1.00 | 25.00 |
| ATOM | 827 | CA  | VAL | 119 | 55.880 | 12.925 | 39.984 | 1.00 | 25.00 |
| ATOM | 831 | C   | VAL | 119 | 55.861 | 12.316 | 38.608 | 1.00 | 25.00 |
| ATOM | 832 | O   | VAL | 119 | 55.075 | 11.411 | 38.369 | 1.00 | 25.00 |
| ATOM | 828 | CB  | VAL | 119 | 56.488 | 11.905 | 40.950 | 1.00 | 25.00 |
| ATOM | 829 | CG1 | VAL | 119 | 57.342 | 10.846 | 40.207 | 1.00 | 25.00 |
| ATOM | 830 | CG2 | VAL | 119 | 57.275 | 12.650 | 42.051 | 1.00 | 25.00 |
| ATOM | 833 | N   | SER | 120 | 56.783 | 12.750 | 37.744 | 1.00 | 25.00 |
| ATOM | 834 | CA  | SER | 120 | 56.871 | 12.264 | 36.371 | 1.00 | 25.00 |
| ATOM | 837 | C   | SER | 120 | 58.207 | 11.615 | 36.106 | 1.00 | 25.00 |
| ATOM | 838 | O   | SER | 120 | 59.223 | 12.257 | 36.207 | 1.00 | 25.00 |
| ATOM | 835 | CB  | SER | 120 | 56.654 | 13.416 | 35.393 | 1.00 | 25.00 |
| ATOM | 836 | OG  | SER | 120 | 55.882 | 13.005 | 34.260 | 1.00 | 25.00 |
| ATOM | 839 | N   | LEU | 121 | 58.187 | 10.328 | 35.782 | 1.00 | 25.00 |
| ATOM | 840 | CA  | LEU | 121 | 59.395 |  9.548 | 35.501 | 1.00 | 25.00 |
| ATOM | 845 | C   | LEU | 121 | 59.784 |  9.666 | 34.055 | 1.00 | 25.00 |
| ATOM | 846 | O   | LEU | 121 | 59.252 |  8.937 | 33.211 | 1.00 | 25.00 |
| ATOM | 841 | CB  | LEU | 121 | 59.149 |  8.062 | 35.769 | 1.00 | 25.00 |

Figure 23X

| ATOM | 842 | CG  | LEU | 121  | 60.287 | 7.140  | 35.336 | 1.00 | 25.00 |
| ---- | --- | --- | --- | ---- | ------ | ------ | ------ | ---- | ----- |
| ATOM | 843 | CD1 | LEU | 121  | 61.467 | 7.267  | 36.274 | 1.00 | 25.00 |
| ATOM | 844 | CD2 | LEU | 121  | 59.808 | 5.728  | 35.309 | 1.00 | 25.00 |
| ATOM | 847 | N   | SER | 122  | 60.685 | 10.577 | 33.743 | 1.00 | 25.00 |
| ATOM | 848 | CA  | SER | 122  | 61.107 | 10.697 | 32.356 | 1.00 | 25.00 |
| ATOM | 851 | C   | SER | 122  | 62.017 | 9.485  | 32.133 | 1.00 | 25.00 |
| ATOM | 852 | O   | SER | 122. | 63.223 | 9.520  | 32.442 | 1.00 | 25.00 |
| ATOM | 849 | CB  | SER | 122  | 61.864 | 12.007 | 32.113 | 1.00 | 25.00 |
| ATOM | 850 | OG  | SER | 122  | 61.773 | 12.871 | 33.244 | 1.00 | 25.00 |
| ATOM | 853 | N   | SER | 123  | 61.401 | 8.370  | 31.748 | 1.00 | 25.00 |
| ATOM | 854 | CA  | SER | 123  | 62.147 | 7.150  | 31.515 | 1.00 | 25.00 |
| ATOM | 857 | C   | SER | 123  | 62.965 | 7.427  | 30.296 | 1.00 | 25.00 |
| ATOM | 858 | O   | SER | 123  | 62.572 | 8.252  | 29.473 | 1.00 | 25.00 |
| ATOM | 855 | CB  | SER | 123  | 61.202 | 5.983  | 31.233 | 1.00 | 25.00 |
| ATOM | 856 | OG  | SER | 123  | 61.923 | 4.755  | 31.199 | 1.00 | 25.00 |
| ATOM | 859 | N   | LYS | 124  | 64.152 | 6.847  | 30.237 | 1.00 | 25.00 |
| ATOM | 860 | CA  | LYS | 124  | 65.000 | 7.032  | 29.061 | 1.00 | 25.00 |
| ATOM | 866 | C   | LYS | 124  | 64.725 | 5.781  | 28.237 | 1.00 | 25.00 |
| ATOM | 867 | O   | LYS | 124  | 64.801 | 5.774  | 26.992 | 1.00 | 25.00 |
| ATOM | 861 | CB  | LYS | 124  | 66.481 | 7.083  | 29.464 | 1.00 | 25.00 |
| ATOM | 862 | CG  | LYS | 124  | 67.400 | 7.815  | 28.484 | 1.00 | 25.00 |
| ATOM | 863 | CD  | LYS | 124  | 68.833 | 7.365  | 28.701 | 1.00 | 25.00 |
| ATOM | 864 | CE  | LYS | 124  | 68.925 | 5.848  | 28.543 | 1.00 | 25.00 |
| ATOM | 865 | NZ  | LYS | 124  | 68.304 | 5.370  | 27.255 | 1.00 | 25.00 |
| ATOM | 868 | N   | ARG | 125  | 64.314 | 4.774  | 29.004 | 1.00 | 25.00 |
| ATOM | 869 | CA  | ARG | 125  | 63.969 | 3.404  | 28.620 | 1.00 | 25.00 |
| ATOM | 871 | C   | ARG | 125  | 64.089 | 2.840  | 30.011 | 1.00 | 25.00 |
| ATOM | 872 | O   | ARG | 125  | 63.215 | 2.138  | 30.531 | 1.00 | 25.00 |
| ATOM | 870 | CB  | ARG | 125  | 65.053 | 2.799  | 27.745 | 1.00 | 25.00 |
| ATOM | 873 | N   | LEU | 126  | 65.161 | 3.329  | 30.616 | 1.00 | 25.00 |
| ATOM | 874 | CA  | LEU | 126  | 65.609 | 3.058  | 31.953 | 1.00 | 25.00 |
| ATOM | 876 | C   | LEU | 126  | 66.889 | 3.904  | 31.936 | 1.00 | 25.00 |
| ATOM | 877 | O   | LEU | 126  | 67.979 | 3.412  | 32.317 | 1.00 | 25.00 |
| ATOM | 875 | CB  | LEU | 126  | 65.934 | 1.578  | 32.123 | 1.00 | 25.00 |
| ATOM | 878 | OT  | LEU | 126  | 66.774 | 5.077  | 31.502 | 1.00 | 25.00 |
| ATOM | 888 | N   | PHE | 137  | 67.101 | 5.496  | 34.406 | 1.00 | 25.00 |
| ATOM | 889 | CA  | PHE | 137  | 65.776 | 6.051  | 34.080 | 1.00 | 25.00 |

Figure 23Y

| ATOM | 886 | C   | PHE | 137 | 65.966 | 7.381  | 33.389 | 1.00 | 25.00 |
|------|-----|-----|-----|-----|--------|--------|--------|------|-------|
| ATOM | 887 | O   | PHE | 137 | 65.563 | 7.531  | 32.239 | 1.00 | 25.00 |
| ATOM | 879 | CB  | PHE | 137 | 64.934 | 6.181  | 35.332 | 1.00 | 25.00 |
| ATOM | 880 | CG  | PHE | 137 | 64.182 | 4.925  | 35.682 | 1.00 | 25.00 |
| ATOM | 881 | CD1 | PHE | 137 | 63.514 | 4.199  | 34.693 | 1.00 | 25.00 |
| ATOM | 882 | CD2 | PHE | 137 | 64.123 | 4.467  | 36.999 | 1.00 | 25.00 |
| ATOM | 883 | CE1 | PHE | 137 | 62.796 | 3.035  | 35.017 | 1.00 | 25.00 |
| ATOM | 884 | CE2 | PHE | 137 | 63.413 | 3.314  | 37.320 | 1.00 | 25.00 |
| ATOM | 885 | CZ  | PHE | 137 | 62.748 | 2.599  | 36.326 | 1.00 | 25.00 |
| ATOM | 890 | N   | THR | 138 | 66.627 | 8.304  | 34.092 | 1.00 | 25.00 |
| ATOM | 891 | CA  | THR | 138 | 66.975 | 9.675  | 33.669 | 1.00 | 25.00 |
| ATOM | 895 | C   | THR | 138 | 66.660 | 10.618 | 34.832 | 1.00 | 25.00 |
| ATOM | 896 | O   | THR | 138 | 67.551 | 10.903 | 35.648 | 1.00 | 25.00 |
| ATOM | 892 | CB  | THR | 138 | 66.330 | 10.132 | 32.324 | 1.00 | 25.00 |
| ATOM | 893 | OG1 | THR | 138 | 66.990 | 9.472  | 31.241 | 1.00 | 25.00 |
| ATOM | 894 | CG2 | THR | 138 | 66.518 | 11.601 | 32.106 | 1.00 | 25.00 |
| ATOM | 897 | N   | HIS | 139 | 65.401 | 11.038 | 34.964 | 1.00 | 25.00 |
| ATOM | 898 | CA  | HIS | 139 | 65.038 | 11.906 | 36.075 | 1.00 | 25.00 |
| ATOM | 899 | C   | HIS | 139 | 63.544 | 11.855 | 36.391 | 1.00 | 25.00 |
| ATOM | 900 | O   | HIS | 139 | 62.740 | 11.480 | 35.530 | 1.00 | 25.00 |
| ATOM | 901 | CB  | HIS | 139 | 65.484 | 13.338 | 35.810 | 1.00 | 25.00 |
| ATOM | 902 | CG  | HIS | 139 | 64.651 | 14.035 | 34.794 | 1.00 | 25.00 |
| ATOM | 903 | ND1 | HIS | 139 | 63.791 | 15.068 | 35.084 | 1.00 | 25.00 |
| ATOM | 904 | CD2 | HIS | 139 | 64.485 | 13.778 | 33.477 | 1.00 | 25.00 |
| ATOM | 906 | CE1 | HIS | 139 | 63.141 | 15.388 | 33.977 | 1.00 | 25.00 |
| ATOM | 905 | NE2 | HIS | 139 | 63.529 | 14.632 | 32.974 | 1.00 | 25.00 |
| ATOM | 907 | N   | VAL | 140 | 63.221 | 12.183 | 37.648 | 1.00 | 25.00 |
| ATOM | 908 | CA  | VAL | 140 | 61.871 | 12.220 | 38.222 | 1.00 | 25.00 |
| ATOM | 912 | C   | VAL | 140 | 61.445 | 13.693 | 38.300 | 1.00 | 25.00 |
| ATOM | 913 | O   | VAL | 140 | 62.134 | 14.486 | 38.943 | 1.00 | 25.00 |
| ATOM | 909 | CB  | VAL | 140 | 61.906 | 11.666 | 39.684 | 1.00 | 25.00 |
| ATOM | 910 | CG1 | VAL | 140 | 60.629 | 12.001 | 40.424 | 1.00 | 25.00 |
| ATOM | 911 | CG2 | VAL | 140 | 62.174 | 10.151 | 39.681 | 1.00 | 25.00 |
| ATOM | 914 | N   | ALA | 141 | 60.318 | 14.066 | 37.692 | 1.00 | 25.00 |
| ATOM | 915 | CA  | ALA | 141 | 59.858 | 15.448 | 37.716 | 1.00 | 25.00 |
| ATOM | 917 | C   | ALA | 141 | 58.722 | 15.656 | 38.716 | 1.00 | 25.00 |
| ATOM | 918 | O   | ALA | 141 | 57.934 | 14.758 | 38.967 | 1.00 | 25.00 |

Figure 23Z

| ATOM | 916 | CB  | ALA | 141 | 59.413 | 15.840 | 36.364 | 1.00 | 25.00 |
| ATOM | 919 | N   | LEU | 142 | 58.688 | 16.810 | 39.359 | 1.00 | 25.00 |
| ATOM | 920 | CA  | LEU | 142 | 57.604 | 17.110 | 40.281 | 1.00 | 25.00 |
| ATOM | 925 | C   | LEU | 142 | 56.659 | 17.994 | 39.450 | 1.00 | 25.00 |
| ATOM | 926 | O   | LEU | 142 | 57.124 | 18.839 | 38.696 | 1.00 | 25.00 |
| ATOM | 921 | CB  | LEU | 142 | 58.125 | 17.851 | 41.528 | 1.00 | 25.00 |
| ATOM | 922 | CG  | LEU | 142 | 59.034 | 17.139 | 42.551 | 1.00 | 25.00 |
| ATOM | 923 | CD1 | LEU | 142 | 59.343 | 18.104 | 43.664 | 1.00 | 25.00 |
| ATOM | 924 | CD2 | LEU | 142 | 58.405 | 15.865 | 43.103 | 1.00 | 25.00 |
| ATOM | 927 | N   | CYS | 143 | 55.349 | 17.841 | 39.601 | 1.00 | 25.00 |
| ATOM | 928 | CA  | CYS | 143 | 54.419 | 18.608 | 38.783 | 1.00 | 25.00 |
| ATOM | 931 | C   | CYS | 143 | 53.004 | 18.555 | 39.358 | 1.00 | 25.00 |
| ATOM | 932 | O   | CYS | 143 | 52.801 | 17.928 | 40.375 | 1.00 | 25.00 |
| ATOM | 929 | CB  | CYS | 143 | 54.426 | 17.953 | 37.403 | 1.00 | 25.00 |
| ATOM | 930 | SG  | CYS | 143 | 54.272 | 16.114 | 37.477 | 1.00 | 25.00 |
| ATOM | 933 | N   | VAL | 144 | 52.026 | 19.207 | 38.723 | 1.00 | 25.00 |
| ATOM | 934 | CA  | VAL | 144 | 50.644 | 19.138 | 39.206 | 1.00 | 25.00 |
| ATOM | 938 | C   | VAL | 144 | 50.171 | 17.696 | 39.058 | 1.00 | 25.00 |
| ATOM | 939 | O   | VAL | 144 | 50.033 | 16.976 | 40.045 | 1.00 | 25.00 |
| ATOM | 935 | CB  | VAL | 144 | 49.712 | 20.056 | 38.431 | 1.00 | 25.00 |
| ATOM | 936 | CG1 | VAL | 144 | 48.256 | 19.803 | 38.800 | 1.00 | 25.00 |
| ATOM | 937 | CG2 | VAL | 144 | 50.053 | 21.459 | 38.754 | 1.00 | 25.00 |
| ATOM | 940 | N   | VAL | 145 | 49.916 | 17.257 | 37.833 | 1.00 | 25.00 |
| ATOM | 941 | CA  | VAL | 145 | 49.504 | 15.879 | 37.633 | 1.00 | 25.00 |
| ATOM | 945 | C   | VAL | 145 | 50.315 | 15.299 | 36.508 | 1.00 | 25.00 |
| ATOM | 946 | O   | VAL | 145 | 50.699 | 16.007 | 35.580 | 1.00 | 25.00 |
| ATOM | 942 | CB  | VAL | 145 | 48.029 | 15.746 | 37.337 | 1.00 | 25.00 |
| ATOM | 943 | CG1 | VAL | 145 | 47.246 | 16.718 | 38.216 | 1.00 | 25.00 |
| ATOM | 944 | CG2 | VAL | 145 | 47.752 | 15.906 | 35.850 | 1.00 | 25.00 |
| ATOM | 947 | N   | GLY | 146 | 50.620 | 14.017 | 36.618 | 1.00 | 25.00 |
| ATOM | 948 | CA  | GLY | 146 | 51.419 | 13.379 | 35.596 | 1.00 | 25.00 |
| ATOM | 949 | C   | GLY | 146 | 50.620 | 12.610 | 34.570 | 1.00 | 25.00 |
| ATOM | 950 | O   | GLY | 146 | 49.427 | 12.353 | 34.722 | 1.00 | 25.00 |
| ATOM | 951 | N   | ARG | 147 | 51.312 | 12.231 | 33.512 | 1.00 | 25.00 |
| ATOM | 952 | CA  | ARG | 147 | 50.733 | 11.463 | 32.422 | 1.00 | 25.00 |
| ATOM | 960 | C   | ARG | 147 | 50.256 | 10.082 | 32.917 | 1.00 | 25.00 |
| ATOM | 961 | O   | ARG | 147 | 49.302 |  9.523 | 32.355 | 1.00 | 25.00 |

Figure 23AA

| ATOM | 953 | CB | ARG | 147 | 51.807 | 11.235 | 31.366 | 1.00 | 25.00 |
|---|---|---|---|---|---|---|---|---|---|
| ATOM | 954 | CG | ARG | 147 | 52.970 | 12.230 | 31.429 | 1.00 | 25.00 |
| ATOM | 955 | CD | ARG | 147 | 52.760 | 13.360 | 30.428 | 1.00 | 25.00 |
| ATOM | 956 | NE | ARG | 147 | 52.455 | 12.799 | 29.116 | 1.00 | 25.00 |
| ATOM | 957 | CZ | ARG | 147 | 53.210 | 11.894 | 28.492 | 1.00 | 25.00 |
| ATOM | 958 | NH1 | ARG | 147 | 54.375 | 11.489 | 29.014 | 1.00 | 25.00 |
| ATOM | 959 | NH2 | ARG | 147 | 52.815 | 11.430 | 27.314 | 1.00 | 25.00 |
| ATOM | 962 | N | ARG | 148 | 50.936 | 9.527 | 33.937 | 1.00 | 25.00 |
| ATOM | 963 | CA | ARG | 148 | 50.619 | 8.200 | 34.492 | 1.00 | 25.00 |
| ATOM | 971 | C | ARG | 148 | 49.540 | 8.123 | 35.562 | 1.00 | 25.00 |
| ATOM | 972 | O | ARG | 148 | 49.295 | 9.085 | 36.276 | 1.00 | 25.00 |
| ATOM | 964 | CB | ARG | 148 | 51.899 | 7.483 | 34.904 | 1.00 | 25.00 |
| ATOM | 965 | CG | ARG | 148 | 52.654 | 7.052 | 33.662 | 1.00 | 25.00 |
| ATOM | 966 | CD | ARG | 148 | 54.099 | 6.580 | 33.847 | 1.00 | 25.00 |
| ATOM | 967 | NE | ARG | 148 | 54.697 | 6.425 | 32.515 | 1.00 | 25.00 |
| ATOM | 968 | CZ | ARG | 148 | 55.985 | 6.252 | 32.253 | 1.00 | 25.00 |
| ATOM | 969 | NH1 | ARG | 148 | 56.888 | 6.174 | 33.227 | 1.00 | 25.00 |
| ATOM | 970 | NH2 | ARG | 148 | 56.356 | 6.145 | 30.987 | 1.00 | 25.00 |
| ATOM | 973 | N | VAL | 149 | 48.965 | 6.939 | 35.731 | 1.00 | 25.00 |
| ATOM | 974 | CA | VAL | 149 | 47.837 | 6.753 | 36.644 | 1.00 | 25.00 |
| ATOM | 978 | C | VAL | 149 | 47.912 | 6.676 | 38.183 | 1.00 | 25.00 |
| ATOM | 979 | O | VAL | 149 | 46.872 | 6.800 | 38.838 | 1.00 | 25.00 |
| ATOM | 975 | CB | VAL | 149 | 46.903 | 5.615 | 36.126 | 1.00 | 25.00 |
| ATOM | 976 | CG1 | VAL | 149 | 46.581 | 5.836 | 34.653 | 1.00 | 25.00 |
| ATOM | 977 | CG2 | VAL | 149 | 47.541 | 4.250 | 36.351 | 1.00 | 25.00 |
| ATOM | 980 | N | GLY | 150 | 49.065 | 6.409 | 38.780 | 1.00 | 25.00 |
| ATOM | 981 | CA | GLY | 150 | 49.101 | 6.364 | 40.240 | 1.00 | 25.00 |
| ATOM | 982 | C | GLY | 150 | 50.180 | 7.311 | 40.742 | 1.00 | 25.00 |
| ATOM | 983 | O | GLY | 150 | 50.622 | 7.207 | 41.900 | 1.00 | 25.00 |
| ATOM | 984 | N | THR | 151 | 50.556 | 8.258 | 39.865 | 1.00 | 25.00 |
| ATOM | 985 | CA | THR | 151 | 51.633 | 9.217 | 40.098 | 1.00 | 25.00 |
| ATOM | 989 | C | THR | 151 | 51.434 | 10.313 | 41.121 | 1.00 | 25.00 |
| ATOM | 990 | O | THR | 151 | 52.115 | 11.327 | 41.056 | 1.00 | 25.00 |
| ATOM | 986 | CB | THR | 151 | 52.147 | 9.874 | 38.776 | 1.00 | 25.00 |
| ATOM | 987 | OG1 | THR | 151 | 51.071 | 10.519 | 38.077 | 1.00 | 25.00 |
| ATOM | 988 | CG2 | THR | 151 | 52.809 | 8.866 | 37.871 | 1.00 | 25.00 |
| ATOM | 991 | N | VAL | 152 | 50.487 | 10.166 | 42.038 | 1.00 | 25.00 |

Figure 23BB

| ATOM | 992 | CA | VAL | 152 | 50.334 | 11.182 | 43.072 | 1.00 | 25.00 |
| --- | --- | --- | --- | --- | --- | --- | --- | --- | --- |
| ATOM | 996 | C | VAL | 152 | 51.399 | 10.842 | 44.134 | 1.00 | 25.00 |
| ATOM | 997 | O | VAL | 152 | 51.763 | 9.670 | 44.302 | 1.00 | 25.00 |
| ATOM | 993 | CB | VAL | 152 | 48.916 | 11.189 | 43.628 | 1.00 | 25.00 |
| ATOM | 994 | CG1 | VAL | 152 | 48.928 | 11.304 | 45.114 | 1.00 | 25.00 |
| ATOM | 995 | CG2 | VAL | 152 | 48.159 | 12.342 | 43.036 | 1.00 | 25.00 |
| ATOM | 998 | N | VAL | 153 | 51.967 | 11.842 | 44.793 | 1.00 | 25.00 |
| ATOM | 999 | CA | VAL | 153 | 52.989 | 11.544 | 45.778 | 1.00 | 25.00 |
| ATOM | 1003 | C | VAL | 153 | 52.737 | 12.086 | 47.168 | 1.00 | 25.00 |
| ATOM | 1004 | O | VAL | 153 | 51.866 | 12.917 | 47.367 | 1.00 | 25.00 |
| ATOM | 1000 | CB | VAL | 153 | 54.382 | 11.975 | 45.306 | 1.00 | 25.00 |
| ATOM | 1001 | CG1 | VAL | 153 | 54.834 | 11.087 | 44.207 | 1.00 | 25.00 |
| ATOM | 1002 | CG2 | VAL | 153 | 54.377 | 13.397 | 44.871 | 1.00 | 25.00 |
| ATOM | 1005 | N | ASN | 154 | 53.473 | 11.551 | 48.135 | 1.00 | 25.00 |
| ATOM | 1006 | CA | ASN | 154 | 53.382 | 11.978 | 49.508 | 1.00 | 25.00 |
| ATOM | 1011 | C | ASN | 154 | 54.757 | 12.511 | 49.882 | 1.00 | 25.00 |
| ATOM | 1012 | O | ASN | 154 | 55.777 | 12.012 | 49.408 | 1.00 | 25.00 |
| ATOM | 1007 | CB | ASN | 154 | 52.972 | 10.815 | 50.406 | 1.00 | 25.00 |
| ATOM | 1008 | CG | ASN | 154 | 52.574 | 11.261 | 51.805 | 1.00 | 25.00 |
| ATOM | 1009 | OD1 | ASN | 154 | 51.682 | 12.084 | 51.980 | 1.00 | 25.00 |
| ATOM | 1010 | ND2 | ASN | 154 | 53.230 | 10.704 | 52.812 | 1.00 | 25.00 |
| ATOM | 1013 | N | TYR | 155 | 54.751 | 13.599 | 50.646 | 1.00 | 25.00 |
| ATOM | 1014 | CA | TYR | 155 | 55.943 | 14.294 | 51.140 | 1.00 | 25.00 |
| ATOM | 1023 | C | TYR | 155 | 55.826 | 14.353 | 52.664 | 1.00 | 25.00 |
| ATOM | 1024 | O | TYR | 155 | 54.714 | 14.502 | 53.184 | 1.00 | 25.00 |
| ATOM | 1015 | CB | TYR | 155 | 55.942 | 15.761 | 50.700 | 1.00 | 25.00 |
| ATOM | 1016 | CG | TYR | 155 | 56.046 | 16.082 | 49.237 | 1.00 | 25.00 |
| ATOM | 1017 | CD1 | TYR | 155 | 54.952 | 15.954 | 48.390 | 1.00 | 25.00 |
| ATOM | 1019 | CD2 | TYR | 155 | 57.222 | 16.604 | 48.722 | 1.00 | 25.00 |
| ATOM | 1018 | CE1 | TYR | 155 | 55.027 | 16.341 | 47.055 | 1.00 | 25.00 |
| ATOM | 1020 | CE2 | TYR | 155 | 57.316 | 16.997 | 47.398 | 1.00 | 25.00 |
| ATOM | 1021 | CZ | TYR | 155 | 56.218 | 16.865 | 46.555 | 1.00 | 25.00 |
| ATOM | 1022 | OH | TYR | 155 | 56.341 | 17.235 | 45.223 | 1.00 | 25.00 |
| ATOM | 1025 | N | ASP | 156 | 56.953 | 14.260 | 53.369 | 1.00 | 25.00 |
| ATOM | 1026 | CA | ASP | 156 | 56.976 | 14.369 | 54.841 | 1.00 | 25.00 |
| ATOM | 1031 | C | ASP | 156 | 58.388 | 14.641 | 55.289 | 1.00 | 25.00 |
| ATOM | 1032 | O | ASP | 156 | 59.268 | 14.776 | 54.444 | 1.00 | 25.00 |

Figure 23CC

| ATOM | 1027 | CB | ASP | 156 | 56.469 | 13.116 | 55.549 | 1.00 | 25.00 |
| --- | --- | --- | --- | --- | --- | --- | --- | --- | --- |
| ATOM | 1028 | CG | ASP | 156 | 55.697 | 13.439 | 56.813 | 1.00 | 25.00 |
| ATOM | 1029 | OD1 | ASP | 156 | 55.994 | 14.431 | 57.485 | 1.00 | 25.00 |
| ATOM | 1030 | OD2 | ASP | 156 | 54.757 | 12.709 | 57.127 | 1.00 | 25.00 |
| ATOM | 1033 | N | CYS | 157 | 58.642 | 14.668 | 56.591 | 1.00 | 25.00 |
| ATOM | 1034 | CA | CYS | 157 | 59.997 | 14.951 | 57.027 | 1.00 | 25.00 |
| ATOM | 1037 | C | CYS | 157 | 60.814 | 13.822 | 57.600 | 1.00 | 25.00 |
| ATOM | 1038 | O | CYS | 157 | 61.688 | 14.071 | 58.410 | 1.00 | 25.00 |
| ATOM | 1035 | CB | CYS | 157 | 60.042 | 16.145 | 57.964 | 1.00 | 25.00 |
| ATOM | 1036 | SG | CYS | 157 | 58.432 | 16.648 | 58.447 | 1.00 | 25.00 |
| ATOM | 1039 | N | THR | 158 | 60.552 | 12.595 | 57.174 | 1.00 | 25.00 |
| ATOM | 1040 | CA | THR | 158 | 61.305 | 11.433 | 57.621 | 1.00 | 25.00 |
| ATOM | 1044 | C | THR | 158 | 60.948 | 10.358 | 56.611 | 1.00 | 25.00 |
| ATOM | 1045 | O | THR | 158 | 59.770 | 10.180 | 56.296 | 1.00 | 25.00 |
| ATOM | 1041 | CB | THR | 158 | 60.813 | 10.918 | 58.957 | 1.00 | 25.00 |
| ATOM | 1042 | OG1 | THR | 158 | 59.453 | 10.518 | 58.808 | 1.00 | 25.00 |
| ATOM | 1043 | CG2 | THR | 158 | 60.912 | 11.961 | 60.040 | 1.00 | 25.00 |
| ATOM | 1046 | N | PRO | 159 | 61.929 | 9.585 | 56.134 | 1.00 | 25.00 |
| ATOM | 1048 | CA | PRO | 159 | 61.620 | 8.545 | 55.160 | 1.00 | 25.00 |
| ATOM | 1051 | C | PRO | 159 | 60.461 | 7.627 | 55.538 | 1.00 | 25.00 |
| ATOM | 1052 | O | PRO | 159 | 59.575 | 7.374 | 54.718 | 1.00 | 25.00 |
| ATOM | 1049 | CB | PRO | 159 | 62.927 | 7.780 | 55.063 | 1.00 | 25.00 |
| ATOM | 1050 | CG | PRO | 159 | 63.523 | 7.997 | 56.363 | 1.00 | 25.00 |
| ATOM | 1047 | CD | PRO | 159 | 63.311 | 9.452 | 56.578 | 1.00 | 25.00 |
| ATOM | 1053 | N | GLU | 160 | 60.416 | 7.179 | 56.790 | 1.00 | 25.00 |
| ATOM | 1054 | CA | GLU | 160 | 59.354 | 6.265 | 57.196 | 1.00 | 25.00 |
| ATOM | 1060 | C | GLU | 160 | 57.981 | 6.903 | 57.232 | 1.00 | 25.00 |
| ATOM | 1061 | O | GLU | 160 | 56.988 | 6.197 | 57.364 | 1.00 | 25.00 |
| ATOM | 1055 | CB | GLU | 160 | 59.663 | 5.583 | 58.524 | 1.00 | 25.00 |
| ATOM | 1056 | CG | GLU | 160 | 59.432 | 6.450 | 59.731 | 1.00 | 25.00 |
| ATOM | 1057 | CD | GLU | 160 | 60.662 | 7.233 | 60.149 | 1.00 | 25.00 |
| ATOM | 1058 | OE1 | GLU | 160 | 61.643 | 7.272 | 59.364 | 1.00 | 25.00 |
| ATOM | 1059 | OE2 | GLU | 160 | 60.643 | 7.793 | 61.280 | 1.00 | 25.00 |
| ATOM | 1062 | N | SER | 161 | 57.915 | 8.226 | 57.113 | 1.00 | 25.00 |
| ATOM | 1063 | CA | SER | 161 | 56.633 | 8.923 | 57.115 | 1.00 | 25.00 |
| ATOM | 1066 | C | SER | 161 | 56.107 | 9.213 | 55.716 | 1.00 | 25.00 |
| ATOM | 1067 | O | SER | 161 | 54.896 | 9.368 | 55.510 | 1.00 | 25.00 |

Figure 23DD

| ATOM | 1064 | CB  | SER | 161 | 56.739 | 10.211 | 57.887 | 1.00 | 25.00 |
|------|------|-----|-----|-----|--------|--------|--------|------|-------|
| ATOM | 1065 | OG  | SER | 161 | 57.021 | 9.902  | 59.222 | 1.00 | 25.00 |
| ATOM | 1068 | N   | SER | 162 | 57.011 | 9.313  | 54.756 | 1.00 | 25.00 |
| ATOM | 1069 | CA  | SER | 162 | 56.625 | 9.580  | 53.392 | 1.00 | 25.00 |
| ATOM | 1072 | C   | SER | 162 | 55.901 | 8.360  | 52.904 | 1.00 | 25.00 |
| ATOM | 1073 | O   | SER | 162 | 54.863 | 8.453  | 52.269 | 1.00 | 25.00 |
| ATOM | 1070 | CB  | SER | 162 | 57.879 | 9.781  | 52.600 | 1.00 | 25.00 |
| ATOM | 1071 | OG  | SER | 162 | 58.729 | 10.607 | 53.368 | 1.00 | 25.00 |
| ATOM | 1074 | N   | ILE | 163 | 56.416 | 7.209  | 53.305 | 1.00 | 25.00 |
| ATOM | 1075 | CA  | ILE | 163 | 55.856 | 5.931  | 52.915 | 1.00 | 25.00 |
| ATOM | 1080 | C   | ILE | 163 | 54.836 | 5.381  | 53.882 | 1.00 | 25.00 |
| ATOM | 1081 | O   | ILE | 163 | 54.152 | 4.414  | 53.570 | 1.00 | 25.00 |
| ATOM | 1076 | CB  | ILE | 163 | 56.945 | 4.861  | 52.775 | 1.00 | 25.00 |
| ATOM | 1078 | CG1 | ILE | 163 | 57.626 | 4.619  | 54.122 | 1.00 | 25.00 |
| ATOM | 1077 | CG2 | ILE | 163 | 57.962 | 5.276  | 51.725 | 1.00 | 25.00 |
| ATOM | 1079 | CD1 | ILE | 163 | 58.610 | 3.481  | 54.075 | 1.00 | 25.00 |
| ATOM | 1082 | N   | GLU | 164 | 54.723 | 5.978  | 55.052 | 1.00 | 25.00 |
| ATOM | 1083 | CA  | GLU | 164 | 53.777 | 5.470  | 56.017 | 1.00 | 25.00 |
| ATOM | 1089 | C   | GLU | 164 | 52.304 | 5.326  | 55.586 | 1.00 | 25.00 |
| ATOM | 1090 | O   | GLU | 164 | 51.645 | 4.360  | 56.004 | 1.00 | 25.00 |
| ATOM | 1084 | CB  | GLU | 164 | 53.864 | 6.264  | 57.292 | 1.00 | 25.00 |
| ATOM | 1085 | CG  | GLU | 164 | 53.019 | 5.667  | 58.342 | 1.00 | 25.00 |
| ATOM | 1086 | CD  | GLU | 164 | 52.542 | 6.682  | 59.328 | 1.00 | 25.00 |
| ATOM | 1087 | OE1 | GLU | 164 | 51.816 | 7.611  | 58.892 | 1.00 | 25.00 |
| ATOM | 1088 | OE2 | GLU | 164 | 52.880 | 6.541  | 60.531 | 1.00 | 25.00 |
| ATOM | 1091 | N   | PRO | 165 | 51.758 | 6.286  | 54.778 | 1.00 | 25.00 |
| ATOM | 1093 | CA  | PRO | 165 | 50.366 | 6.298  | 54.276 | 1.00 | 25.00 |
| ATOM | 1096 | C   | PRO | 165 | 49.918 | 5.425  | 53.107 | 1.00 | 25.00 |
| ATOM | 1097 | O   | PRO | 165 | 48.737 | 5.447  | 52.771 | 1.00 | 25.00 |
| ATOM | 1094 | CB  | PRO | 165 | 50.136 | 7.769  | 53.944 | 1.00 | 25.00 |
| ATOM | 1095 | CG  | PRO | 165 | 51.471 | 8.224  | 53.512 | 1.00 | 25.00 |
| ATOM | 1092 | CD  | PRO | 165 | 52.369 | 7.617  | 54.559 | 1.00 | 25.00 |
| ATOM | 1098 | N   | PHE | 166 | 50.832 | 4.731  | 52.436 | 1.00 | 25.00 |
| ATOM | 1099 | CA  | PHE | 166 | 50.454 | 3.855  | 51.324 | 1.00 | 25.00 |
| ATOM | 1107 | C   | PHE | 166 | 49.900 | 2.574  | 51.927 | 1.00 | 25.00 |
| ATOM | 1108 | O   | PHE | 166 | 50.667 | 1.677  | 52.240 | 1.00 | 25.00 |
| ATOM | 1100 | CB  | PHE | 166 | 51.677 | 3.542  | 50.478 | 1.00 | 25.00 |

Figure 23EE

| ATOM | 1101 | CG  | PHE | 166 | 52.235 | 4.741  | 49.783 | 1.00 | 25.00 |
| ---- | ---- | --- | --- | --- | ------ | ------ | ------ | ---- | ----- |
| ATOM | 1102 | CD1 | PHE | 166 | 51.735 | 5.136  | 48.552 | 1.00 | 25.00 |
| ATOM | 1103 | CD2 | PHE | 166 | 53.194 | 5.533  | 50.398 | 1.00 | 25.00 |
| ATOM | 1104 | CE1 | PHE | 166 | 52.164 | 6.290  | 47.961 | 1.00 | 25.00 |
| ATOM | 1105 | CE2 | PHE | 166 | 53.628 | 6.696  | 49.803 | 1.00 | 25.00 |
| ATOM | 1106 | CZ  | PHE | 166 | 53.109 | 7.074  | 48.584 | 1.00 | 25.00 |
| ATOM | 1109 | N   | ARG | 167 | 48.574 | 2.473  | 52.057 | 1.00 | 25.00 |
| ATOM | 1110 | CA  | ARG | 167 | 47.919 | 1.316  | 52.690 | 1.00 | 25.00 |
| ATOM | 1118 | C   | ARG | 167 | 48.110 | -0.065 | 52.107 | 1.00 | 25.00 |
| ATOM | 1119 | O   | ARG | 167 | 47.870 | -1.060 | 52.784 | 1.00 | 25.00 |
| ATOM | 1111 | CB  | ARG | 167 | 46.429 | 1.575  | 52.863 | 1.00 | 25.00 |
| ATOM | 1112 | CG  | ARG | 167 | 46.076 | 2.858  | 53.645 | 1.00 | 25.00 |
| ATOM | 1113 | CD  | ARG | 167 | 44.629 | 2.776  | 54.155 | 1.00 | 25.00 |
| ATOM | 1114 | NE  | ARG | 167 | 44.004 | 4.075  | 54.430 | 1.00 | 25.00 |
| ATOM | 1115 | CZ  | ARG | 167 | 42.778 | 4.221  | 54.942 | 1.00 | 25.00 |
| ATOM | 1116 | NH1 | ARG | 167 | 42.053 | 3.145  | 55.252 | 1.00 | 25.00 |
| ATOM | 1117 | NH2 | ARG | 167 | 42.273 | 5.435  | 55.155 | 1.00 | 25.00 |
| ATOM | 1120 | N   | VAL | 168 | 48.489 | -0.117 | 50.836 | 1.00 | 25.00 |
| ATOM | 1121 | CA  | VAL | 168 | 48.726 | -1.387 | 50.131 | 1.00 | 25.00 |
| ATOM | 1125 | C   | VAL | 168 | 50.198 | -1.862 | 50.180 | 1.00 | 25.00 |
| ATOM | 1126 | O   | VAL | 168 | 50.477 | -3.065 | 50.210 | 1.00 | 25.00 |
| ATOM | 1122 | CB  | VAL | 168 | 48.268 | -1.317 | 48.630 | 1.00 | 25.00 |
| ATOM | 1123 | CG1 | VAL | 168 | 46.749 | -1.167 | 48.539 | 1.00 | 25.00 |
| ATOM | 1124 | CG2 | VAL | 168 | 48.969 | -0.142 | 47.912 | 1.00 | 25.00 |
| ATOM | 1127 | N   | LEU | 169 | 51.127 | -0.913 | 50.189 | 1.00 | 25.00 |
| ATOM | 1128 | CA  | LEU | 169 | 52.543 | -1.221 | 50.220 | 1.00 | 25.00 |
| ATOM | 1133 | C   | LEU | 169 | 52.869 | -2.113 | 51.417 | 1.00 | 25.00 |
| ATOM | 1134 | O   | LEU | 169 | 52.660 | -1.746 | 52.561 | 1.00 | 25.00 |
| ATOM | 1129 | CB  | LEU | 169 | 53.350 | 0.077  | 50.264 | 1.00 | 25.00 |
| ATOM | 1130 | CG  | LEU | 169 | 54.850 | -0.097 | 50.078 | 1.00 | 25.00 |
| ATOM | 1131 | CD1 | LEU | 169 | 55.100 | -0.596 | 48.667 | 1.00 | 25.00 |
| ATOM | 1132 | CD2 | LEU | 169 | 55.604 | 1.192  | 50.366 | 1.00 | 25.00 |
| ATOM | 1135 | N   | SER | 170 | 53.372 | -3.299 | 51.127 | 1.00 | 25.00 |
| ATOM | 1136 | CA  | SER | 170 | 53.734 | -4.288 | 52.135 | 1.00 | 25.00 |
| ATOM | 1139 | C   | SER | 170 | 54.730 | -3.769 | 53.153 | 1.00 | 25.00 |
| ATOM | 1140 | O   | SER | 170 | 55.620 | -2.983 | 52.816 | 1.00 | 25.00 |
| ATOM | 1137 | CB  | SER | 170 | 54.378 | -5.486 | 51.448 | 1.00 | 25.00 |

Figure 23FF

| ATOM | 1138 | OG | SER | 170 | 55.558 | -5.087 | 50.768 | 1.00 | 25.00 |
|------|------|-----|-----|-----|--------|--------|--------|------|-------|
| ATOM | 1141 | N | MET | 171 | 54.622 | -4.260 | 54.386 | 1.00 | 25.00 |
| ATOM | 1142 | CA | MET | 171 | 55.555 | -3.858 | 55.434 | 1.00 | 25.00 |
| ATOM | 1147 | C | MET | 171 | 56.946 | -4.352 | 55.011 | 1.00 | 25.00 |
| ATOM | 1148 | O | MET | 171 | 57.949 | -3.697 | 55.287 | 1.00 | 25.00 |
| ATOM | 1143 | CB | MET | 171 | 55.151 | -4.471 | 56.777 | 1.00 | 25.00 |
| ATOM | 1144 | CG | MET | 171 | 55.960 | -3.990 | 57.994 | 1.00 | 25.00 |
| ATOM | 1145 | SD | MET | 171 | 55.705 | -2.255 | 58.485 | 1.00 | 25.00 |
| ATOM | 1146 | CE | MET | 171 | 57.425 | -1.813 | 58.948 | 1.00 | 25.00 |
| ATOM | 1149 | N | GLU | 172 | 56.971 | -5.470 | 54.277 | 1.00 | 25.00 |
| ATOM | 1150 | CA | GLU | 172 | 58.196 | -6.085 | 53.763 | 1.00 | 25.00 |
| ATOM | 1156 | C | GLU | 172 | 58.927 | -5.130 | 52.794 | 1.00 | 25.00 |
| ATOM | 1157 | O | GLU | 172 | 60.173 | -5.083 | 52.772 | 1.00 | 25.00 |
| ATOM | 1151 | CB | GLU | 172 | 57.828 | -7.393 | 53.054 | 1.00 | 25.00 |
| ATOM | 1152 | CG | GLU | 172 | 59.004 | -8.369 | 52.831 | 1.00 | 25.00 |
| ATOM | 1153 | CD | GLU | 172 | 58.652 | -9.571 | 51.929 | 1.00 | 25.00 |
| ATOM | 1154 | OE1 | GLU | 172 | 58.299 | -9.336 | 50.736 | 1.00 | 25.00 |
| ATOM | 1155 | OE2 | GLU | 172 | 58.754 | -10.738 | 52.415 | 1.00 | 25.00 |
| ATOM | 1158 | N | SER | 173 | 58.122 | -4.390 | 52.009 | 1.00 | 25.00 |
| ATOM | 1159 | CA | SER | 173 | 58.565 | -3.369 | 51.019 | 1.00 | 25.00 |
| ATOM | 1162 | C | SER | 173 | 58.953 | -2.072 | 51.735 | 1.00 | 25.00 |
| ATOM | 1163 | O | SER | 173 | 59.992 | -1.471 | 51.466 | 1.00 | 25.00 |
| ATOM | 1160 | CB | SER | 173 | 57.429 | -3.013 | 50.027 | 1.00 | 25.00 |
| ATOM | 1161 | OG | SER | 173 | 57.335 | -3.874 | 48.903 | 1.00 | 25.00 |
| ATOM | 1164 | N | LYS | 174 | 58.068 | -1.616 | 52.610 | 1.00 | 25.00 |
| ATOM | 1165 | CA | LYS | 174 | 58.311 | -0.408 | 53.351 | 1.00 | 25.00 |
| ATOM | 1171 | C | LYS | 174 | 59.646 | -0.578 | 54.033 | 1.00 | 25.00 |
| ATOM | 1172 | O | LYS | 174 | 60.519 | 0.265 | 53.913 | 1.00 | 25.00 |
| ATOM | 1166 | CB | LYS | 174 | 57.186 | -0.180 | 54.355 | 1.00 | 25.00 |
| ATOM | 1167 | CG | LYS | 174 | 55.872 | 0.145 | 53.672 | 1.00 | 25.00 |
| ATOM | 1168 | CD | LYS | 174 | 54.867 | 0.751 | 54.612 | 1.00 | 25.00 |
| ATOM | 1169 | CE | LYS | 174 | 53.574 | 1.054 | 53.890 | 1.00 | 25.00 |
| ATOM | 1170 | NZ | LYS | 174 | 52.441 | 1.382 | 54.812 | 1.00 | 25.00 |
| ATOM | 1173 | N | ALA | 175 | 59.850 | -1.758 | 54.600 | 1.00 | 25.00 |
| ATOM | 1174 | CA | ALA | 175 | 61.082 | -2.098 | 55.317 | 1.00 | 25.00 |
| ATOM | 1176 | C | ALA | 175 | 62.319 | -1.934 | 54.472 | 1.00 | 25.00 |
| ATOM | 1177 | O | ALA | 175 | 63.301 | -1.311 | 54.890 | 1.00 | 25.00 |

Figure 23GG

| ATOM | 1175 | CB | ALA | 175 | 61.012 | -3.538 | 55.810 | 1.00 | 25.00 |
| --- | --- | --- | --- | --- | --- | --- | --- | --- | --- |
| ATOM | 1178 | N | ARG | 176 | 62.266 | -2.559 | 53.299 | 1.00 | 25.00 |
| ATOM | 1179 | CA | ARG | 176 | 63.356 | -2.571 | 52.339 | 1.00 | 25.00 |
| ATOM | 1187 | C | ARG | 176 | 63.837 | -1.185 | 51.953 | 1.00 | 25.00 |
| ATOM | 1188 | O | ARG | 176 | 65.039 | -0.958 | 51.924 | 1.00 | 25.00 |
| ATOM | 1180 | CB | ARG | 176 | 62.942 | -3.385 | 51.114 | 1.00 | 25.00 |
| ATOM | 1181 | CG | ARG | 176 | 63.987 | -3.466 | 50.042 | 1.00 | 25.00 |
| ATOM | 1182 | CD | ARG | 176 | 65.256 | -4.188 | 50.509 | 1.00 | 25.00 |
| ATOM | 1183 | NE | ARG | 176 | 66.477 | -3.772 | 49.796 | 1.00 | 25.00 |
| ATOM | 1184 | CZ | ARG | 176 | 66.560 | -3.460 | 48.495 | 1.00 | 25.00 |
| ATOM | 1185 | NH1 | ARG | 176 | 65.487 | -3.492 | 47.698 | 1.00 | 25.00 |
| ATOM | 1186 | NH2 | ARG | 176 | 67.736 | -3.099 | 47.982 | 1.00 | 25.00 |
| ATOM | 1189 | N | LEU | 177 | 62.919 | -0.256 | 51.695 | 1.00 | 25.00 |
| ATOM | 1190 | CA | LEU | 177 | 63.294 | 1.102 | 51.321 | 1.00 | 25.00 |
| ATOM | 1195 | C | LEU | 177 | 64.023 | 1.754 | 52.476 | 1.00 | 25.00 |
| ATOM | 1196 | O | LEU | 177 | 65.106 | 2.310 | 52.323 | 1.00 | 25.00 |
| ATOM | 1191 | CB | LEU | 177 | 62.062 | 1.941 | 51.036 | 1.00 | 25.00 |
| ATOM | 1192 | CG | LEU | 177 | 61.005 | 1.421 | 50.083 | 1.00 | 25.00 |
| ATOM | 1193 | CD1 | LEU | 177 | 59.790 | 2.281 | 50.200 | 1.00 | 25.00 |
| ATOM | 1194 | CD2 | LEU | 177 | 61.516 | 1.480 | 48.694 | 1.00 | 25.00 |
| ATOM | 1197 | N | LEU | 178 | 63.407 | 1.676 | 53.647 | 1.00 | 25.00 |
| ATOM | 1198 | CA | LEU | 178 | 63.950 | 2.264 | 54.861 | 1.00 | 25.00 |
| ATOM | 1203 | C | LEU | 178 | 65.390 | 1.855 | 55.111 | 1.00 | 25.00 |
| ATOM | 1204 | O | LEU | 178 | 66.169 | 2.644 | 55.629 | 1.00 | 25.00 |
| ATOM | 1199 | CB | LEU | 178 | 63.067 | 1.907 | 56.056 | 1.00 | 25.00 |
| ATOM | 1200 | CG | LEU | 178 | 62.215 | 3.047 | 56.623 | 1.00 | 25.00 |
| ATOM | 1201 | CD1 | LEU | 178 | 61.738 | 3.956 | 55.509 | 1.00 | 25.00 |
| ATOM | 1202 | CD2 | LEU | 178 | 61.041 | 2.493 | 57.442 | 1.00 | 25.00 |
| ATOM | 1205 | N | SER | 179 | 65.758 | 0.638 | 54.732 | 1.00 | 25.00 |
| ATOM | 1206 | CA | SER | 179 | 67.125 | 0.187 | 54.938 | 1.00 | 25.00 |
| ATOM | 1209 | C | SER | 179 | 68.056 | 0.814 | 53.918 | 1.00 | 25.00 |
| ATOM | 1210 | O | SER | 179 | 69.118 | 1.343 | 54.258 | 1.00 | 25.00 |
| ATOM | 1207 | CB | SER | 179 | 67.212 | -1.332 | 54.845 | 1.00 | 25.00 |
| ATOM | 1208 | OG | SER | 179 | 68.571 | -1.749 | 54.923 | 1.00 | 25.00 |
| ATOM | 1211 | N | LEU | 180 | 67.653 | 0.730 | 52.658 | 1.00 | 25.00 |
| ATOM | 1212 | CA | LEU | 180 | 68.426 | 1.291 | 51.566 | 1.00 | 25.00 |
| ATOM | 1217 | C | LEU | 180 | 68.739 | 2.728 | 51.928 | 1.00 | 25.00 |

Figure 23HH

| | | | | | | | | | |
|---|---|---|---|---|---|---|---|---|---|
| ATOM | 1218 | O | LEU | 180 | 69.858 | 3.183 | 51.717 | 1.00 | 25.00 |
| ATOM | 1213 | CB | LEU | 180 | 67.628 | 1.229 | 50.261 | 1.00 | 25.00 |
| ATOM | 1214 | CG | LEU | 180 | 67.390 | -0.184 | 49.748 | 1.00 | 25.00 |
| ATOM | 1215 | CD1 | LEU | 180 | 66.227 | -0.205 | 48.762 | 1.00 | 25.00 |
| ATOM | 1216 | CD2 | LEU | 180 | 68.688 | -0.692 | 49.140 | 1.00 | 25.00 |
| ATOM | 1219 | N | VAL | 181 | 67.772 | 3.409 | 52.540 | 1.00 | 25.00 |
| ATOM | 1220 | CA | VAL | 181 | 67.956 | 4.797 | 52.937 | 1.00 | 25.00 |
| ATOM | 1224 | C | VAL | 181 | 69.083 | 4.910 | 53.958 | 1.00 | 25.00 |
| ATOM | 1225 | O | VAL | 181 | 69.940 | 5.792 | 53.872 | 1.00 | 25.00 |
| ATOM | 1221 | CB | VAL | 181 | 66.655 | 5.400 | 53.517 | 1.00 | 25.00 |
| ATOM | 1222 | CG1 | VAL | 181 | 66.863 | 6.853 | 53.906 | 1.00 | 25.00 |
| ATOM | 1223 | CG2 | VAL | 181 | 65.547 | 5.283 | 52.507 | 1.00 | 25.00 |
| ATOM | 1226 | N | LYS | 182 | 69.113 | 3.982 | 54.898 | 1.00 | 25.00 |
| ATOM | 1227 | CA | LYS | 182 | 70.139 | 4.011 | 55.920 | 1.00 | 25.00 |
| ATOM | 1233 | C | LYS | 182 | 71.538 | 3.988 | 55.279 | 1.00 | 25.00 |
| ATOM | 1234 | O | LYS | 182 | 72.459 | 4.649 | 55.765 | 1.00 | 25.00 |
| ATOM | 1228 | CB | LYS | 182 | 69.940 | 2.849 | 56.897 | 1.00 | 25.00 |
| ATOM | 1229 | CG | LYS | 182 | 70.951 | 2.818 | 58.022 | 1.00 | 25.00 |
| ATOM | 1230 | CD | LYS | 182 | 71.073 | 4.198 | 58.710 | 1.00 | 25.00 |
| ATOM | 1231 | CE | LYS | 182 | 72.230 | 4.232 | 59.754 | 1.00 | 25.00 |
| ATOM | 1232 | NZ | LYS | 182 | 72.420 | 5.568 | 60.424 | 1.00 | 25.00 |
| ATOM | 1235 | N | ASP | 183 | 71.700 | 3.238 | 54.191 | 1.00 | 25.00 |
| ATOM | 1236 | CA | ASP | 183 | 72.997 | 3.195 | 53.525 | 1.00 | 25.00 |
| ATOM | 1241 | C | ASP | 183 | 73.261 | 4.616 | 53.073 | 1.00 | 25.00 |
| ATOM | 1242 | O | ASP | 183 | 74.220 | 5.243 | 53.507 | 1.00 | 25.00 |
| ATOM | 1237 | CB | ASP | 183 | 72.995 | 2.339 | 52.233 | 1.00 | 25.00 |
| ATOM | 1238 | CG | ASP | 183 | 72.736 | 0.840 | 52.465 | 1.00 | 25.00 |
| ATOM | 1239 | OD1 | ASP | 183 | 72.636 | 0.362 | 53.629 | 1.00 | 25.00 |
| ATOM | 1240 | OD2 | ASP | 183 | 72.620 | 0.143 | 51.425 | 1.00 | 25.00 |
| ATOM | 1243 | N | TYR | 184 | 72.388 | 5.090 | 52.182 | 1.00 | 25.00 |
| ATOM | 1244 | CA | TYR | 184 | 72.453 | 6.415 | 51.552 | 1.00 | 25.00 |
| ATOM | 1253 | C | TYR | 184 | 73.152 | 7.519 | 52.332 | 1.00 | 25.00 |
| ATOM | 1254 | O | TYR | 184 | 72.572 | 8.134 | 53.257 | 1.00 | 25.00 |
| ATOM | 1245 | CB | TYR | 184 | 71.043 | 6.898 | 51.142 | 1.00 | 25.00 |
| ATOM | 1246 | CG | TYR | 184 | 71.016 | 8.245 | 50.439 | 1.00 | 25.00 |
| ATOM | 1247 | CD1 | TYR | 184 | 71.331 | 8.349 | 49.085 | 1.00 | 25.00 |
| ATOM | 1249 | CD2 | TYR | 184 | 70.725 | 9.418 | 51.140 | 1.00 | 25.00 |

Figure 23II

| ATOM | 1248 | CE1 | TYR | 184 | 71.368 | 9.589 | 48.438 | 1.00 | 25.00 |
| --- | --- | --- | --- | --- | --- | --- | --- | --- | --- |
| ATOM | 1250 | CE2 | TYR | 184 | 70.763 | 10.665 | 50.510 | 1.00 | 25.00 |
| ATOM | 1251 | CZ | TYR | 184 | 71.088 | 10.749 | 49.153 | 1.00 | 25.00 |
| ATOM | 1252 | OH | TYR | 184 | 71.153 | 11.983 | 48.513 | 1.00 | 25.00 |
| ATOM | 1255 | N | ALA | 185 | 74.402 | 7.771 | 51.961 | 1.00 | 25.00 |
| ATOM | 1256 | CA | ALA | 185 | 75.141 | 8.844 | 52.605 | 1.00 | 25.00 |
| ATOM | 1258 | C | ALA | 185 | 75.074 | 9.959 | 51.578 | 1.00 | 25.00 |
| ATOM | 1259 | O | ALA | 185 | 75.139 | 9.723 | 50.356 | 1.00 | 25.00 |
| ATOM | 1257 | CB | ALA | 185 | 76.570 | 8.445 | 52.903 | 1.00 | 25.00 |
| ATOM | 1260 | N | GLY | 186 | 74.941 | 11.175 | 52.083 | 1.00 | 25.00 |
| ATOM | 1261 | CA | GLY | 186 | 74.790 | 12.311 | 51.205 | 1.00 | 25.00 |
| ATOM | 1262 | C | GLY | 186 | 73.439 | 12.907 | 51.598 | 1.00 | 25.00 |
| ATOM | 1263 | O | GLY | 186 | 72.914 | 13.826 | 50.936 | 1.00 | 25.00 |
| ATOM | 1264 | N | LEU | 187 | 72.860 | 12.416 | 52.695 | 1.00 | 25.00 |
| ATOM | 1265 | CA | LEU | 187 | 71.589 | 12.963 | 53.126 | 1.00 | 25.00 |
| ATOM | 1270 | C | LEU | 187 | 71.814 | 14.358 | 53.748 | 1.00 | 25.00 |
| ATOM | 1271 | O | LEU | 187 | 71.018 | 14.801 | 54.565 | 1.00 | 25.00 |
| ATOM | 1266 | CB | LEU | 187 | 70.891 | 12.025 | 54.108 | 1.00 | 25.00 |
| ATOM | 1267 | CG | LEU | 187 | 71.591 | 11.897 | 55.468 | 1.00 | 25.00 |
| ATOM | 1268 | CD1 | LEU | 187 | 70.562 | 11.854 | 56.601 | 1.00 | 25.00 |
| ATOM | 1269 | CD2 | LEU | 187 | 72.544 | 10.674 | 55.494 | 1.00 | 25.00 |
| ATOM | 1272 | N | ASN | 188 | 72.919 | 15.017 | 53.378 | 1.00 | 25.00 |
| ATOM | 1273 | CA | ASN | 188 | 73.286 | 16.366 | 53.858 | 1.00 | 25.00 |
| ATOM | 1278 | C | ASN | 188 | 73.228 | 17.354 | 52.662 | 1.00 | 25.00 |
| ATOM | 1279 | O | ASN | 188 | 72.903 | 18.557 | 52.814 | 1.00 | 25.00 |
| ATOM | 1274 | CB | ASN | 188 | 74.726 | 16.360 | 54.431 | 1.00 | 25.00 |
| ATOM | 1275 | CG | ASN | 188 | 75.625 | 17.489 | 53.827 | 1.00 | 25.00 |
| ATOM | 1276 | OD1 | ASN | 188 | 76.086 | 17.397 | 52.669 | 1.00 | 25.00 |
| ATOM | 1277 | ND2 | ASN | 188 | 75.828 | 18.569 | 54.600 | 1.00 | 25.00 |
| ATOM | 1280 | N | LYS | 189 | 73.718 | 16.850 | 51.531 | 1.00 | 25.00 |
| ATOM | 1281 | CA | LYS | 189 | 73.773 | 17.542 | 50.259 | 1.00 | 25.00 |
| ATOM | 1287 | C | LYS | 189 | 72.633 | 18.551 | 50.142 | 1.00 | 25.00 |
| ATOM | 1288 | O | LYS | 189 | 71.487 | 18.144 | 50.172 | 1.00 | 25.00 |
| ATOM | 1282 | CB | LYS | 189 | 73.562 | 16.476 | 49.191 | 1.00 | 25.00 |
| ATOM | 1283 | CG | LYS | 189 | 74.464 | 16.503 | 48.014 | 1.00 | 25.00 |
| ATOM | 1284 | CD | LYS | 189 | 74.189 | 15.256 | 47.209 | 1.00 | 25.00 |
| ATOM | 1285 | CE | LYS | 189 | 75.188 | 15.083 | 46.064 | 1.00 | 25.00 |

Figure 23JJ

| ATOM | 1286 | NZ | LYS | 189 | 75.394 | 13.633 | 45.680 | 1.00 | 25.00 |
|------|------|-----|-----|-----|--------|--------|--------|------|-------|
| ATOM | 1289 | N | VAL | 190 | 72.909 | 19.848 | 50.084 | 1.00 | 25.00 |
| ATOM | 1290 | CA | VAL | 190 | 71.811 | 20.795 | 49.911 | 1.00 | 25.00 |
| ATOM | 1294 | C | VAL | 190 | 71.804 | 21.348 | 48.467 | 1.00 | 25.00 |
| ATOM | 1295 | O | VAL | 190 | 72.779 | 21.947 | 47.997 | 1.00 | 25.00 |
| ATOM | 1291 | CB | VAL | 190 | 71.755 | 21.929 | 51.012 | 1.00 | 25.00 |
| ATOM | 1292 | CG1 | VAL | 190 | 72.047 | 21.357 | 52.390 | 1.00 | 25.00 |
| ATOM | 1293 | CG2 | VAL | 190 | 72.671 | 23.088 | 50.700 | 1.00 | 25.00 |
| ATOM | 1296 | N | TRP | 191 | 70.746 | 21.024 | 47.728 | 1.00 | 25.00 |
| ATOM | 1297 | CA | TRP | 191 | 70.594 | 21.474 | 46.355 | 1.00 | 25.00 |
| ATOM | 1308 | C | TRP | 191 | 70.256 | 22.955 | 46.296 | 1.00 | 25.00 |
| ATOM | 1309 | O | TRP | 191 | 69.259 | 23.416 | 46.853 | 1.00 | 25.00 |
| ATOM | 1298 | CB | TRP | 191 | 69.532 | 20.642 | 45.641 | 1.00 | 25.00 |
| ATOM | 1299 | CG | TRP | 191 | 69.995 | 19.246 | 45.424 | 1.00 | 25.00 |
| ATOM | 1303 | CD1 | TRP | 191 | 70.581 | 18.741 | 44.292 | 1.00 | 25.00 |
| ATOM | 1300 | CD2 | TRP | 191 | 70.029 | 18.191 | 46.396 | 1.00 | 25.00 |
| ATOM | 1304 | NE1 | TRP | 191 | 70.995 | 17.444 | 44.508 | 1.00 | 25.00 |
| ATOM | 1301 | CE2 | TRP | 191 | 70.669 | 17.082 | 45.792 | 1.00 | 25.00 |
| ATOM | 1302 | CE3 | TRP | 191 | 69.582 | 18.073 | 47.717 | 1.00 | 25.00 |
| ATOM | 1305 | CZ2 | TRP | 191 | 70.878 | 15.873 | 46.474 | 1.00 | 25.00 |
| ATOM | 1306 | CZ3 | TRP | 191 | 69.786 | 16.870 | 48.391 | 1.00 | 25.00 |
| ATOM | 1307 | CH2 | TRP | 191 | 70.429 | 15.788 | 47.768 | 1.00 | 25.00 |
| ATOM | 1310 | N | LYS | 192 | 71.130 | 23.715 | 45.663 | 1.00 | 25.00 |
| ATOM | 1311 | CA | LYS | 192 | 70.910 | 25.136 | 45.542 | 1.00 | 25.00 |
| ATOM | 1317 | C | LYS | 192 | 70.531 | 25.511 | 44.128 | 1.00 | 25.00 |
| ATOM | 1318 | O | LYS | 192 | 71.239 | 25.127 | 43.183 | 1.00 | 25.00 |
| ATOM | 1312 | CB | LYS | 192 | 72.165 | 25.896 | 45.941 | 1.00 | 25.00 |
| ATOM | 1313 | CG | LYS | 192 | 72.369 | 25.927 | 47.428 | 1.00 | 25.00 |
| ATOM | 1314 | CD | LYS | 192 | 73.678 | 26.585 | 47.794 | 1.00 | 25.00 |
| ATOM | 1315 | CE | LYS | 192 | 73.662 | 27.012 | 49.254 | 1.00 | 25.00 |
| ATOM | 1316 | NZ | LYS | 192 | 72.722 | 28.163 | 49.484 | 1.00 | 25.00 |
| ATOM | 1319 | N | VAL | 193 | 69.367 | 26.154 | 43.974 | 1.00 | 25.00 |
| ATOM | 1320 | CA | VAL | 193 | 68.890 | 26.660 | 42.679 | 1.00 | 25.00 |
| ATOM | 1324 | C | VAL | 193 | 68.781 | 28.139 | 43.026 | 1.00 | 25.00 |
| ATOM | 1325 | O | VAL | 193 | 69.051 | 28.515 | 44.154 | 1.00 | 25.00 |
| ATOM | 1321 | CB | VAL | 193 | 67.522 | 26.045 | 42.228 | 1.00 | 25.00 |
| ATOM | 1322 | CG1 | VAL | 193 | 67.054 | 26.695 | 40.971 | 1.00 | 25.00 |

Figure 23KK

| ATOM | 1323 | CG2 | VAL | 193 | 67.664 | 24.561 | 41.939 | 1.00 | 25.00 |
|------|------|-----|-----|-----|--------|--------|--------|------|-------|
| ATOM | 1326 | N   | SER | 194 | 68.374 | 28.989 | 42.108 | 1.00 | 25.00 |
| ATOM | 1327 | CA  | SER | 194 | 68.339 | 30.408 | 42.420 | 1.00 | 25.00 |
| ATOM | 1330 | C   | SER | 194 | 66.974 | 31.056 | 42.336 | 1.00 | 25.00 |
| ATOM | 1331 | O   | SER | 194 | 66.445 | 31.214 | 41.250 | 1.00 | 25.00 |
| ATOM | 1328 | CB  | SER | 194 | 69.297 | 31.132 | 41.476 | 1.00 | 25.00 |
| ATOM | 1329 | OG  | SER | 194 | 70.278 | 30.220 | 40.973 | 1.00 | 25.00 |
| ATOM | 1332 | N   | GLU | 195 | 66.449 | 31.483 | 43.478 | 1.00 | 25.00 |
| ATOM | 1333 | CA  | GLU | 195 | 65.146 | 32.147 | 43.593 | 1.00 | 25.00 |
| ATOM | 1339 | C   | GLU | 195 | 64.589 | 32.746 | 42.290 | 1.00 | 25.00 |
| ATOM | 1340 | O   | GLU | 195 | 63.452 | 32.453 | 41.906 | 1.00 | 25.00 |
| ATOM | 1334 | CB  | GLU | 195 | 65.235 | 33.244 | 44.659 | 1.00 | 25.00 |
| ATOM | 1335 | CG  | GLU | 195 | 64.070 | 33.315 | 45.618 | 1.00 | 25.00 |
| ATOM | 1336 | CD  | GLU | 195 | 64.515 | 33.550 | 47.079 | 1.00 | 25.00 |
| ATOM | 1337 | OE1 | GLU | 195 | 65.724 | 33.359 | 47.386 | 1.00 | 25.00 |
| ATOM | 1338 | OE2 | GLU | 195 | 63.651 | 33.925 | 47.926 | 1.00 | 25.00 |
| ATOM | 1341 | N   | ASP | 196 | 65.410 | 33.539 | 41.595 | 1.00 | 25.00 |
| ATOM | 1342 | CA  | ASP | 196 | 65.015 | 34.194 | 40.343 | 1.00 | 25.00 |
| ATOM | 1347 | C   | ASP | 196 | 64.585 | 33.231 | 39.259 | 1.00 | 25.00 |
| ATOM | 1348 | O   | ASP | 196 | 63.647 | 33.529 | 38.538 | 1.00 | 25.00 |
| ATOM | 1343 | CB  | ASP | 196 | 66.132 | 35.106 | 39.811 | 1.00 | 25.00 |
| ATOM | 1344 | CG  | ASP | 196 | 66.162 | 36.485 | 40.494 | 1.00 | 25.00 |
| ATOM | 1345 | OD1 | ASP | 196 | 65.082 | 36.924 | 40.977 | 1.00 | 25.00 |
| ATOM | 1346 | OD2 | ASP | 196 | 67.256 | 37.138 | 40.525 | 1.00 | 25.00 |
| ATOM | 1349 | N   | LYS | 197 | 65.292 | 32.108 | 39.120 | 1.00 | 25.00 |
| ATOM | 1350 | CA  | LYS | 197 | 64.968 | 31.070 | 38.118 | 1.00 | 25.00 |
| ATOM | 1356 | C   | LYS | 197 | 63.995 | 30.021 | 38.677 | 1.00 | 25.00 |
| ATOM | 1357 | O   | LYS | 197 | 63.277 | 29.329 | 37.940 | 1.00 | 25.00 |
| ATOM | 1351 | CB  | LYS | 197 | 66.232 | 30.363 | 37.641 | 1.00 | 25.00 |
| ATOM | 1352 | CG  | LYS | 197 | 66.672 | 29.227 | 38.512 | 1.00 | 25.00 |
| ATOM | 1353 | CD  | LYS | 197 | 66.648 | 27.962 | 37.714 | 1.00 | 25.00 |
| ATOM | 1354 | CE  | LYS | 197 | 67.537 | 28.073 | 36.474 | 1.00 | 25.00 |
| ATOM | 1355 | NZ  | LYS | 197 | 68.988 | 28.283 | 36.784 | 1.00 | 25.00 |
| ATOM | 1358 | N   | LEU | 198 | 63.999 | 29.909 | 39.998 | 1.00 | 25.00 |
| ATOM | 1359 | CA  | LEU | 198 | 63.142 | 28.983 | 40.691 | 1.00 | 25.00 |
| ATOM | 1364 | C   | LEU | 198 | 61.737 | 29.531 | 40.577 | 1.00 | 25.00 |
| ATOM | 1365 | O   | LEU | 198 | 60.817 | 28.775 | 40.300 | 1.00 | 25.00 |

Figure 23LL

| ATOM | 1360 | CB | LEU | 198 | 63.570 | 28.874 | 42.150 | 1.00 | 25.00 |
|------|------|-----|-----|-----|--------|--------|--------|------|-------|
| ATOM | 1361 | CG | LEU | 198 | 63.115 | 27.632 | 42.917 | 1.00 | 25.00 |
| ATOM | 1362 | CD1 | LEU | 198 | 63.426 | 26.366 | 42.127 | 1.00 | 25.00 |
| ATOM | 1363 | CD2 | LEU | 198 | 63.788 | 27.606 | 44.272 | 1.00 | 25.00 |
| ATOM | 1366 | N | ALA | 199 | 61.590 | 30.850 | 40.706 | 1.00 | 25.00 |
| ATOM | 1367 | CA | ALA | 199 | 60.282 | 31.502 | 40.617 | 1.00 | 25.00 |
| ATOM | 1369 | C | ALA | 199 | 59.715 | 31.449 | 39.199 | 1.00 | 25.00 |
| ATOM | 1370 | O | ALA | 199 | 58.513 | 31.631 | 38.983 | 1.00 | 25.00 |
| ATOM | 1368 | CB | ALA | 199 | 60.368 | 32.923 | 41.096 | 1.00 | 25.00 |
| ATOM | 1371 | N | LYS | 200 | 60.596 | 31.170 | 38.242 | 1.00 | 25.00 |
| ATOM | 1372 | CA | LYS | 200 | 60.223 | 31.056 | 36.836 | 1.00 | 25.00 |
| ATOM | 1378 | C | LYS | 200 | 59.851 | 29.611 | 36.531 | 1.00 | 25.00 |
| ATOM | 1379 | O | LYS | 200 | 58.930 | 29.355 | 35.772 | 1.00 | 25.00 |
| ATOM | 1373 | CB | LYS | 200 | 61.371 | 31.521 | 35.915 | 1.00 | 25.00 |
| ATOM | 1374 | CG | LYS | 200 | 61.562 | 33.045 | 35.852 | 1.00 | 25.00 |
| ATOM | 1375 | CD | LYS | 200 | 62.792 | 33.459 | 35.054 | 1.00 | 25.00 |
| ATOM | 1376 | CE | LYS | 200 | 62.971 | 35.000 | 35.082 | 1.00 | 25.00 |
| ATOM | 1377 | NZ | LYS | 200 | 62.095 | 35.799 | 34.122 | 1.00 | 25.00 |
| ATOM | 1380 | N | VAL | 201 | 60.574 | 28.653 | 37.091 | 1.00 | 25.00 |
| ATOM | 1381 | CA | VAL | 201 | 60.195 | 27.281 | 36.824 | 1.00 | 25.00 |
| ATOM | 1385 | C | VAL | 201 | 58.855 | 27.022 | 37.518 | 1.00 | 25.00 |
| ATOM | 1386 | O | VAL | 201 | 57.984 | 26.370 | 36.963 | 1.00 | 25.00 |
| ATOM | 1382 | CB | VAL | 201 | 61.232 | 26.253 | 37.331 | 1.00 | 25.00 |
| ATOM | 1383 | CG1 | VAL | 201 | 60.849 | 24.858 | 36.858 | 1.00 | 25.00 |
| ATOM | 1384 | CG2 | VAL | 201 | 62.617 | 26.598 | 36.857 | 1.00 | 25.00 |
| ATOM | 1387 | N | LEU | 202 | 58.686 | 27.563 | 38.722 | 1.00 | 25.00 |
| ATOM | 1388 | CA | LEU | 202 | 57.458 | 27.369 | 39.490 | 1.00 | 25.00 |
| ATOM | 1393 | C | LEU | 202 | 56.308 | 28.161 | 38.909 | 1.00 | 25.00 |
| ATOM | 1394 | O | LEU | 202 | 55.158 | 27.825 | 39.138 | 1.00 | 25.00 |
| ATOM | 1389 | CB | LEU | 202 | 57.657 | 27.690 | 40.976 | 1.00 | 25.00 |
| ATOM | 1390 | CG | LEU | 202 | 58.604 | 26.830 | 41.827 | 1.00 | 25.00 |
| ATOM | 1391 | CD1 | LEU | 202 | 58.625 | 27.356 | 43.244 | 1.00 | 25.00 |
| ATOM | 1392 | CD2 | LEU | 202 | 58.176 | 25.399 | 41.833 | 1.00 | 25.00 |
| ATOM | 1395 | N | LEU | 203 | 56.609 | 29.246 | 38.205 | 1.00 | 25.00 |
| ATOM | 1396 | CA | LEU | 203 | 55.550 | 30.001 | 37.555 | 1.00 | 25.00 |
| ATOM | 1401 | C | LEU | 203 | 55.182 | 29.199 | 36.315 | 1.00 | 25.00 |
| ATOM | 1402 | O | LEU | 203 | 54.034 | 29.165 | 35.914 | 1.00 | 25.00 |

Figure 23MM

| ATOM | 1397 | CB  | LEU | 203 | 56.015 | 31.387 | 37.100 | 1.00 | 25.00 |
|------|------|-----|-----|-----|--------|--------|--------|------|-------|
| ATOM | 1398 | CG  | LEU | 203 | 55.030 | 32.024 | 36.105 | 1.00 | 25.00 |
| ATOM | 1399 | CD1 | LEU | 203 | 53.795 | 32.410 | 36.834 | 1.00 | 25.00 |
| ATOM | 1400 | CD2 | LEU | 203 | 55.588 | 33.219 | 35.418 | 1.00 | 25.00 |
| ATOM | 1403 | N   | SER | 204 | 56.164 | 28.547 | 35.704 | 1.00 | 25.00 |
| ATOM | 1404 | CA  | SER | 204 | 55.937 | 27.774 | 34.486 | 1.00 | 25.00 |
| ATOM | 1407 | C   | SER | 204 | 55.042 | 26.563 | 34.672 | 1.00 | 25.00 |
| ATOM | 1408 | O   | SER | 204 | 54.425 | 26.109 | 33.715 | 1.00 | 25.00 |
| ATOM | 1405 | CB  | SER | 204 | 57.269 | 27.352 | 33.863 | 1.00 | 25.00 |
| ATOM | 1406 | OG  | SER | 204 | 57.059 | 26.597 | 32.681 | 1.00 | 25.00 |
| ATOM | 1409 | N   | THR | 205 | 54.988 | 26.005 | 35.877 | 1.00 | 25.00 |
| ATOM | 1410 | CA  | THR | 205 | 54.127 | 24.863 | 36.064 | 1.00 | 25.00 |
| ATOM | 1414 | C   | THR | 205 | 52.680 | 25.327 | 36.211 | 1.00 | 25.00 |
| ATOM | 1415 | O   | THR | 205 | 51.778 | 24.578 | 35.886 | 1.00 | 25.00 |
| ATOM | 1411 | CB  | THR | 205 | 54.596 | 23.900 | 37.188 | 1.00 | 25.00 |
| ATOM | 1412 | OG1 | THR | 205 | 54.474 | 24.519 | 38.462 | 1.00 | 25.00 |
| ATOM | 1413 | CG2 | THR | 205 | 56.028 | 23.503 | 36.980 | 1.00 | 25.00 |
| ATOM | 1416 | N   | ALA | 206 | 52.467 | 26.587 | 36.601 | 1.00 | 25.00 |
| ATOM | 1417 | CA  | ALA | 206 | 51.120 | 27.164 | 36.741 | 1.00 | 25.00 |
| ATOM | 1419 | C   | ALA | 206 | 50.546 | 27.503 | 35.371 | 1.00 | 25.00 |
| ATOM | 1420 | O   | ALA | 206 | 49.462 | 27.055 | 35.005 | 1.00 | 25.00 |
| ATOM | 1418 | CB  | ALA | 206 | 51.155 | 28.418 | 37.594 | 1.00 | 25.00 |
| ATOM | 1421 | N   | VAL | 207 | 51.280 | 28.324 | 34.631 | 1.00 | 25.00 |
| ATOM | 1422 | CA  | VAL | 207 | 50.893 | 28.752 | 33.295 | 1.00 | 25.00 |
| ATOM | 1426 | C   | VAL | 207 | 50.524 | 27.536 | 32.443 | 1.00 | 25.00 |
| ATOM | 1427 | O   | VAL | 207 | 49.434 | 27.459 | 31.887 | 1.00 | 25.00 |
| ATOM | 1423 | CB  | VAL | 207 | 52.050 | 29.547 | 32.616 | 1.00 | 25.00 |
| ATOM | 1424 | CG1 | VAL | 207 | 51.859 | 29.569 | 31.111 | 1.00 | 25.00 |
| ATOM | 1425 | CG2 | VAL | 207 | 52.111 | 30.986 | 33.148 | 1.00 | 25.00 |
| ATOM | 1428 | N   | ASN | 208 | 51.422 | 26.562 | 32.402 | 1.00 | 25.00 |
| ATOM | 1429 | CA  | ASN | 208 | 51.233 | 25.331 | 31.648 | 1.00 | 25.00 |
| ATOM | 1434 | C   | ASN | 208 | 50.311 | 24.335 | 32.296 | 1.00 | 25.00 |
| ATOM | 1435 | O   | ASN | 208 | 50.538 | 23.141 | 32.160 | 1.00 | 25.00 |
| ATOM | 1430 | CB  | ASN | 208 | 52.562 | 24.637 | 31.500 | 1.00 | 25.00 |
| ATOM | 1431 | CG  | ASN | 208 | 53.429 | 25.310 | 30.532 | 1.00 | 25.00 |
| ATOM | 1432 | OD1 | ASN | 208 | 53.145 | 25.306 | 29.331 | 1.00 | 25.00 |
| ATOM | 1433 | ND2 | ASN | 208 | 54.520 | 25.887 | 31.015 | 1.00 | 25.00 |

Figure 23NN

| ATOM | 1436 | N | ASN | 209 | 49.306 | 24.795 | 33.033 | 1.00 | 25.00 |
| --- | --- | --- | --- | --- | --- | --- | --- | --- | --- |
| ATOM | 1437 | CA | ASN | 209 | 48.391 | 23.884 | 33.720 | 1.00 | 25.00 |
| ATOM | 1442 | C | ASN | 209 | 47.133 | 24.601 | 34.081 | 1.00 | 25.00 |
| ATOM | 1443 | O | ASN | 209 | 46.239 | 24.031 | 34.682 | 1.00 | 25.00 |
| ATOM | 1438 | CB | ASN | 209 | 49.025 | 23.350 | 35.002 | 1.00 | 25.00 |
| ATOM | 1439 | CG | ASN | 209 | 49.862 | 22.114 | 34.768 | 1.00 | 25.00 |
| ATOM | 1440 | OD1 | ASN | 209 | 49.322 | 21.024 | 34.693 | 1.00 | 25.00 |
| ATOM | 1441 | ND2 | ASN | 209 | 51.185 | 22.271 | 34.663 | 1.00 | 25.00 |
| ATOM | 1444 | N | MET | 210 | 47.050 | 25.855 | 33.685 | 1.00 | 25.00 |
| ATOM | 1445 | CA | MET | 210 | 45.887 | 26.650 | 33.996 | 1.00 | 25.00 |
| ATOM | 1450 | C | MET | 210 | 44.580 | 26.128 | 33.423 | 1.00 | 25.00 |
| ATOM | 1451 | O | MET | 210 | 43.536 | 26.277 | 34.039 | 1.00 | 25.00 |
| ATOM | 1446 | CB | MET | 210 | 46.110 | 28.084 | 33.542 | 1.00 | 25.00 |
| ATOM | 1447 | CG | MET | 210 | 46.471 | 28.212 | 32.099 | 1.00 | 25.00 |
| ATOM | 1448 | SD | MET | 210 | 46.890 | 29.872 | 31.686 | 1.00 | 25.00 |
| ATOM | 1449 | CE | MET | 210 | 46.941 | 29.769 | 29.920 | 1.00 | 25.00 |
| ATOM | 1452 | N | LEU | 211 | 44.643 | 25.484 | 32.265 | 1.00 | 25.00 |
| ATOM | 1453 | CA | LEU | 211 | 43.442 | 24.994 | 31.595 | 1.00 | 25.00 |
| ATOM | 1458 | C | LEU | 211 | 42.882 | 23.673 | 32.079 | 1.00 | 25.00 |
| ATOM | 1459 | O | LEU | 211 | 41.719 | 23.388 | 31.837 | 1.00 | 25.00 |
| ATOM | 1454 | CB | LEU | 211 | 43.651 | 24.963 | 30.077 | 1.00 | 25.00 |
| ATOM | 1455 | CG | LEU | 211 | 43.678 | 26.229 | 29.197 | 1.00 | 25.00 |
| ATOM | 1456 | CD1 | LEU | 211 | 43.898 | 27.517 | 29.960 | 1.00 | 25.00 |
| ATOM | 1457 | CD2 | LEU | 211 | 44.750 | 26.034 | 28.162 | 1.00 | 25.00 |
| ATOM | 1460 | N | LEU | 212 | 43.691 | 22.885 | 32.777 | 1.00 | 25.00 |
| ATOM | 1461 | CA | LEU | 212 | 43.271 | 21.585 | 33.321 | 1.00 | 25.00 |
| ATOM | 1466 | C | LEU | 212 | 42.067 | 21.675 | 34.274 | 1.00 | 25.00 |
| ATOM | 1467 | O | LEU | 212 | 42.030 | 22.500 | 35.187 | 1.00 | 25.00 |
| ATOM | 1462 | CB | LEU | 212 | 44.479 | 20.902 | 33.980 | 1.00 | 25.00 |
| ATOM | 1463 | CG | LEU | 212 | 44.459 | 20.006 | 35.214 | 1.00 | 25.00 |
| ATOM | 1464 | CD1 | LEU | 212 | 43.726 | 18.699 | 35.006 | 1.00 | 25.00 |
| ATOM | 1465 | CD2 | LEU | 212 | 45.900 | 19.739 | 35.587 | 1.00 | 25.00 |
| ATOM | 1468 | N | ARG | 213 | 41.059 | 20.845 | 34.035 | 1.00 | 25.00 |
| ATOM | 1469 | CA | ARG | 213 | 39.862 | 20.849 | 34.867 | 1.00 | 25.00 |
| ATOM | 1477 | C | ARG | 213 | 39.782 | 19.676 | 35.834 | 1.00 | 25.00 |
| ATOM | 1478 | O | ARG | 213 | 40.389 | 18.630 | 35.609 | 1.00 | 25.00 |
| ATOM | 1470 | CB | ARG | 213 | 38.622 | 20.947 | 33.994 | 1.00 | 25.00 |

Figure 23OO

| ATOM | 1471 | CG | ARG | 213 | 38.243 | 22.385 | 33.746 | 1.00 | 25.00 |
|------|------|------|-----|-----|--------|--------|--------|------|-------|
| ATOM | 1472 | CD | ARG | 213 | 37.771 | 22.613 | 32.343 | 1.00 | 25.00 |
| ATOM | 1473 | NE | ARG | 213 | 38.569 | 23.631 | 31.672 | 1.00 | 25.00 |
| ATOM | 1474 | CZ | ARG | 213 | 38.052 | 24.720 | 31.128 | 1.00 | 25.00 |
| ATOM | 1475 | NH1 | ARG | 213 | 36.740 | 24.922 | 31.213 | 1.00 | 25.00 |
| ATOM | 1476 | NH2 | ARG | 213 | 38.836 | 25.605 | 30.523 | 1.00 | 25.00 |
| ATOM | 1479 | N | ASP | 214 | 39.014 | 19.851 | 36.907 | 1.00 | 25.00 |
| ATOM | 1480 | CA | ASP | 214 | 38.893 | 18.842 | 37.959 | 1.00 | 25.00 |
| ATOM | 1485 | C | ASP | 214 | 40.295 | 18.416 | 38.407 | 1.00 | 25.00 |
| ATOM | 1486 | O | ASP | 214 | 40.599 | 17.238 | 38.583 | 1.00 | 25.00 |
| ATOM | 1481 | CB | ASP | 214 | 38.049 | 17.656 | 37.507 | 1.00 | 25.00 |
| ATOM | 1482 | CG | ASP | 214 | 36.612 | 18.046 | 37.203 | 1.00 | 25.00 |
| ATOM | 1483 | OD1 | ASP | 214 | 36.101 | 19.028 | 37.797 | 1.00 | 25.00 |
| ATOM | 1484 | OD2 | ASP | 214 | 35.997 | 17.357 | 36.358 | 1.00 | 25.00 |
| ATOM | 1487 | N | ARG | 215 | 41.133 | 19.431 | 38.587 | 1.00 | 25.00 |
| ATOM | 1488 | CA | ARG | 215 | 42.510 | 19.319 | 39.022 | 1.00 | 25.00 |
| ATOM | 1496 | C | ARG | 215 | 42.571 | 18.475 | 40.288 | 1.00 | 25.00 |
| ATOM | 1497 | O | ARG | 215 | 43.172 | 17.410 | 40.302 | 1.00 | 25.00 |
| ATOM | 1489 | CB | ARG | 215 | 42.996 | 20.731 | 39.298 | 1.00 | 25.00 |
| ATOM | 1490 | CG | ARG | 215 | 44.391 | 20.905 | 39.829 | 1.00 | 25.00 |
| ATOM | 1491 | CD | ARG | 215 | 44.606 | 22.396 | 40.184 | 1.00 | 25.00 |
| ATOM | 1492 | NE | ARG | 215 | 43.882 | 23.226 | 39.230 | 1.00 | 25.00 |
| ATOM | 1493 | CZ | ARG | 215 | 44.437 | 23.871 | 38.214 | 1.00 | 25.00 |
| ATOM | 1494 | NH1 | ARG | 215 | 45.759 | 23.891 | 38.093 | 1.00 | 25.00 |
| ATOM | 1495 | NH2 | ARG | 215 | 43.672 | 24.573 | 37.378 | 1.00 | 25.00 |
| ATOM | 1498 | N | TRP | 216 | 41.874 | 18.921 | 41.326 | 1.00 | 25.00 |
| ATOM | 1499 | CA | TRP | 216 | 41.868 | 18.219 | 42.599 | 1.00 | 25.00 |
| ATOM | 1510 | C | TRP | 216 | 41.113 | 16.934 | 42.574 | 1.00 | 25.00 |
| ATOM | 1511 | O | TRP | 216 | 41.299 | 16.124 | 43.472 | 1.00 | 25.00 |
| ATOM | 1500 | CB | TRP | 216 | 41.374 | 19.105 | 43.745 | 1.00 | 25.00 |
| ATOM | 1501 | CG | TRP | 216 | 42.306 | 20.248 | 44.009 | 1.00 | 25.00 |
| ATOM | 1505 | CD1 | TRP | 216 | 42.074 | 21.565 | 43.749 | 1.00 | 25.00 |
| ATOM | 1502 | CD2 | TRP | 216 | 43.679 | 20.152 | 44.383 | 1.00 | 25.00 |
| ATOM | 1506 | NE1 | TRP | 216 | 43.225 | 22.287 | 43.898 | 1.00 | 25.00 |
| ATOM | 1503 | CE2 | TRP | 216 | 44.228 | 21.447 | 44.286 | 1.00 | 25.00 |
| ATOM | 1504 | CE3 | TRP | 216 | 44.503 | 19.093 | 44.765 | 1.00 | 25.00 |
| ATOM | 1507 | CZ2 | TRP | 216 | 45.559 | 21.716 | 44.548 | 1.00 | 25.00 |

Figure 23PP

| ATOM | 1508 | CZ3 | TRP | 216 | 45.820 | 19.350 | 45.025 | 1.00 | 25.00 |
| --- | --- | --- | --- | --- | --- | --- | --- | --- | --- |
| ATOM | 1509 | CH2 | TRP | 216 | 46.344 | 20.664 | 44.913 | 1.00 | 25.00 |
| ATOM | 1512 | N | ASP | 217 | 40.267 | 16.734 | 41.563 | 1.00 | 25.00 |
| ATOM | 1513 | CA | ASP | 217 | 39.507 | 15.482 | 41.445 | 1.00 | 25.00 |
| ATOM | 1518 | C | ASP | 217 | 40.412 | 14.451 | 40.796 | 1.00 | 25.00 |
| ATOM | 1519 | O | ASP | 217 | 40.354 | 13.274 | 41.112 | 1.00 | 25.00 |
| ATOM | 1514 | CB | ASP | 217 | 38.239 | 15.658 | 40.614 | 1.00 | 25.00 |
| ATOM | 1515 | CG | ASP | 217 | 37.207 | 16.561 | 41.286 | 1.00 | 25.00 |
| ATOM | 1516 | OD1 | ASP | 217 | 37.026 | 16.476 | 42.531 | 1.00 | 25.00 |
| ATOM | 1517 | OD2 | ASP | 217 | 36.561 | 17.359 | 40.552 | 1.00 | 25.00 |
| ATOM | 1520 | N | VAL | 218 | 41.242 | 14.909 | 39.873 | 1.00 | 25.00 |
| ATOM | 1521 | CA | VAL | 218 | 42.196 | 14.052 | 39.213 | 1.00 | 25.00 |
| ATOM | 1525 | C | VAL | 218 | 43.137 | 13.603 | 40.314 | 1.00 | 25.00 |
| ATOM | 1526 | O | VAL | 218 | 43.286 | 12.425 | 40.540 | 1.00 | 25.00 |
| ATOM | 1522 | CB | VAL | 218 | 42.970 | 14.829 | 38.177 | 1.00 | 25.00 |
| ATOM | 1523 | CG1 | VAL | 218 | 44.153 | 14.024 | 37.699 | 1.00 | 25.00 |
| ATOM | 1524 | CG2 | VAL | 218 | 42.051 | 15.213 | 37.050 | 1.00 | 25.00 |
| ATOM | 1527 | N | VAL | 219 | 43.728 | 14.551 | 41.033 | 1.00 | 25.00 |
| ATOM | 1528 | CA | VAL | 219 | 44.621 | 14.229 | 42.134 | 1.00 | 25.00 |
| ATOM | 1532 | C | VAL | 219 | 43.884 | 13.449 | 43.216 | 1.00 | 25.00 |
| ATOM | 1533 | O | VAL | 219 | 44.493 | 12.723 | 43.993 | 1.00 | 25.00 |
| ATOM | 1529 | CB | VAL | 219 | 45.229 | 15.476 | 42.734 | 1.00 | 25.00 |
| ATOM | 1530 | CG1 | VAL | 219 | 46.113 | 15.143 | 43.886 | 1.00 | 25.00 |
| ATOM | 1531 | CG2 | VAL | 219 | 46.026 | 16.162 | 41.692 | 1.00 | 25.00 |
| ATOM | 1534 | N | ALA | 220 | 42.570 | 13.577 | 43.279 | 1.00 | 25.00 |
| ATOM | 1535 | CA | ALA | 220 | 41.827 | 12.821 | 44.270 | 1.00 | 25.00 |
| ATOM | 1537 | C | ALA | 220 | 41.940 | 11.350 | 43.921 | 1.00 | 25.00 |
| ATOM | 1538 | O | ALA | 220 | 42.381 | 10.566 | 44.735 | 1.00 | 25.00 |
| ATOM | 1536 | CB | ALA | 220 | 40.383 | 13.237 | 44.284 | 1.00 | 25.00 |
| ATOM | 1539 | N | LYS | 221 | 41.614 | 10.986 | 42.684 | 1.00 | 25.00 |
| ATOM | 1540 | CA | LYS | 221 | 41.667 | 9.584 | 42.290 | 1.00 | 25.00 |
| ATOM | 1546 | C | LYS | 221 | 43.048 | 8.963 | 42.085 | 1.00 | 25.00 |
| ATOM | 1547 | O | LYS | 221 | 43.196 | 7.761 | 42.328 | 1.00 | 25.00 |
| ATOM | 1541 | CB | LYS | 221 | 40.717 | 9.270 | 41.125 | 1.00 | 25.00 |
| ATOM | 1542 | CG | LYS | 221 | 41.118 | 9.824 | 39.784 | 1.00 | 25.00 |
| ATOM | 1543 | CD | LYS | 221 | 39.919 | 9.985 | 38.844 | 1.00 | 25.00 |
| ATOM | 1544 | CE | LYS | 221 | 39.059 | 11.207 | 39.242 | 1.00 | 25.00 |

Figure 23QQ

| ATOM | 1545 | NZ  | LYS | 221 | 38.729 | 11.325 | 40.729 | 1.00 | 25.00 |
| --- | --- | --- | --- | --- | --- | --- | --- | --- | --- |
| ATOM | 1548 | N   | ARG | 222 | 44.055 | 9.746  | 41.675 | 1.00 | 25.00 |
| ATOM | 1549 | CA  | ARG | 222 | 45.412 | 9.211  | 41.496 | 1.00 | 25.00 |
| ATOM | 1557 | C   | ARG | 222 | 45.899 | 8.813  | 42.887 | 1.00 | 25.00 |
| ATOM | 1558 | O   | ARG | 222 | 46.632 | 7.831  | 43.048 | 1.00 | 25.00 |
| ATOM | 1550 | CB  | ARG | 222 | 46.358 | 10.270 | 40.953 | 1.00 | 25.00 |
| ATOM | 1551 | CG  | ARG | 222 | 45.981 | 10.892 | 39.618 | 1.00 | 25.00 |
| ATOM | 1552 | CD  | ARG | 222 | 46.301 | 9.960  | 38.477 | 1.00 | 25.00 |
| ATOM | 1553 | NE  | ARG | 222 | 46.291 | 10.609 | 37.163 | 1.00 | 25.00 |
| ATOM | 1554 | CZ  | ARG | 222 | 47.148 | 11.553 | 36.764 | 1.00 | 25.00 |
| ATOM | 1555 | NH1 | ARG | 222 | 48.091 | 12.037 | 37.577 | 1.00 | 25.00 |
| ATOM | 1556 | NH2 | ARG | 222 | 47.034 | 12.039 | 35.538 | 1.00 | 25.00 |
| ATOM | 1559 | N   | ARG | 223 | 45.470 | 9.586  | 43.889 | 1.00 | 25.00 |
| ATOM | 1560 | CA  | ARG | 223 | 45.803 | 9.369  | 45.298 | 1.00 | 25.00 |
| ATOM | 1568 | C   | ARG | 223 | 45.230 | 8.020  | 45.757 | 1.00 | 25.00 |
| ATOM | 1569 | O   | ARG | 223 | 45.943 | 7.192  | 46.313 | 1.00 | 25.00 |
| ATOM | 1561 | CB  | ARG | 223 | 45.200 | 10.495 | 46.131 | 1.00 | 25.00 |
| ATOM | 1562 | CG  | ARG | 223 | 45.998 | 10.938 | 47.352 | 1.00 | 25.00 |
| ATOM | 1563 | CD  | ARG | 223 | 45.149 | 11.867 | 48.240 | 1.00 | 25.00 |
| ATOM | 1564 | NE  | ARG | 223 | 43.906 | 11.195 | 48.605 | 1.00 | 25.00 |
| ATOM | 1565 | CZ  | ARG | 223 | 43.747 | 10.453 | 49.699 | 1.00 | 25.00 |
| ATOM | 1566 | NH1 | ARG | 223 | 44.708 | 10.376 | 50.622 | 1.00 | 25.00 |
| ATOM | 1567 | NH2 | ARG | 223 | 42.588 | 9.846  | 49.913 | 1.00 | 25.00 |
| ATOM | 1570 | N   | ARG | 224 | 43.945 | 7.799  | 45.501 | 1.00 | 25.00 |
| ATOM | 1571 | CA  | ARG | 224 | 43.277 | 6.559  | 45.853 | 1.00 | 25.00 |
| ATOM | 1579 | C   | ARG | 224 | 43.915 | 5.375  | 45.132 | 1.00 | 25.00 |
| ATOM | 1580 | O   | ARG | 224 | 43.977 | 4.273  | 45.653 | 1.00 | 25.00 |
| ATOM | 1572 | CB  | ARG | 224 | 41.813 | 6.655  | 45.459 | 1.00 | 25.00 |
| ATOM | 1573 | CG  | ARG | 224 | 40.861 | 6.799  | 46.602 | 1.00 | 25.00 |
| ATOM | 1574 | CD  | ARG | 224 | 40.657 | 5.468  | 47.308 | 1.00 | 25.00 |
| ATOM | 1575 | NE  | ARG | 224 | 39.246 | 5.047  | 47.347 | 1.00 | 25.00 |
| ATOM | 1576 | CZ  | ARG | 224 | 38.295 | 5.622  | 48.092 | 1.00 | 25.00 |
| ATOM | 1577 | NH1 | ARG | 224 | 38.575 | 6.655  | 48.892 | 1.00 | 25.00 |
| ATOM | 1578 | NH2 | ARG | 224 | 37.054 | 5.151  | 48.042 | 1.00 | 25.00 |
| ATOM | 1581 | N   | GLU | 225 | 44.365 | 5.589  | 43.908 | 1.00 | 25.00 |
| ATOM | 1582 | CA  | GLU | 225 | 44.987 | 4.508  | 43.165 | 1.00 | 25.00 |
| ATOM | 1588 | C   | GLU | 225 | 46.335 | 4.132  | 43.780 | 1.00 | 25.00 |

Figure 23RR

| ATOM | 1589 | O | GLU | 225 | 46.682 | 2.954 | 43.841 | 1.00 | 25.00 |
|---|---|---|---|---|---|---|---|---|---|
| ATOM | 1583 | CB | GLU | 225 | 45.147 | 4.853 | 41.656 | 1.00 | 25.00 |
| ATOM | 1584 | CG | GLU | 225 | 44.012 | 4.373 | 40.698 | 1.00 | 25.00 |
| ATOM | 1585 | CD | GLU | 225 | 43.690 | 2.833 | 40.763 | 1.00 | 25.00 |
| ATOM | 1586 | OE1 | GLU | 225 | 44.349 | 2.063 | 41.502 | 1.00 | 25.00 |
| ATOM | 1587 | OE2 | GLU | 225 | 42.749 | 2.378 | 40.066 | 1.00 | 25.00 |
| ATOM | 1590 | N | ALA | 226 | 47.089 | 5.112 | 44.264 | 1.00 | 25.00 |
| ATOM | 1591 | CA | ALA | 226 | 48.395 | 4.799 | 44.845 | 1.00 | 25.00 |
| ATOM | 1593 | C | ALA | 226 | 48.293 | 4.076 | 46.189 | 1.00 | 25.00 |
| ATOM | 1594 | O | ALA | 226 | 49.260 | 3.483 | 46.677 | 1.00 | 25.00 |
| ATOM | 1592 | CB | ALA | 226 | 49.239 | 6.062 | 44.982 | 1.00 | 25.00 |
| ATOM | 1595 | N | GLY | 227 | 47.112 | 4.074 | 46.779 | 1.00 | 25.00 |
| ATOM | 1596 | CA | GLY | 227 | 46.983 | 3.425 | 48.061 | 1.00 | 25.00 |
| ATOM | 1597 | C | GLY | 227 | 47.088 | 4.454 | 49.167 | 1.00 | 25.00 |
| ATOM | 1598 | O | GLY | 227 | 47.102 | 4.087 | 50.343 | 1.00 | 25.00 |
| ATOM | 1599 | N | ILE | 228 | 47.214 | 5.734 | 48.811 | 1.00 | 25.00 |
| ATOM | 1600 | CA | ILE | 228 | 47.280 | 6.779 | 49.819 | 1.00 | 25.00 |
| ATOM | 1605 | C | ILE | 228 | 45.832 | 6.950 | 50.224 | 1.00 | 25.00 |
| ATOM | 1606 | O | ILE | 228 | 45.099 | 7.744 | 49.656 | 1.00 | 25.00 |
| ATOM | 1601 | CB | ILE | 228 | 47.791 | 8.118 | 49.266 | 1.00 | 25.00 |
| ATOM | 1603 | CG1 | ILE | 228 | 49.182 | 7.974 | 48.642 | 1.00 | 25.00 |
| ATOM | 1602 | CG2 | ILE | 228 | 47.840 | 9.137 | 50.376 | 1.00 | 25.00 |
| ATOM | 1604 | CD1 | ILE | 228 | 49.816 | 9.318 | 48.208 | 1.00 | 25.00 |
| ATOM | 1607 | N | MET | 229 | 45.390 | 6.099 | 51.128 | 1.00 | 25.00 |
| ATOM | 1608 | CA | MET | 229 | 44.012 | 6.157 | 51.597 | 1.00 | 25.00 |
| ATOM | 1613 | C | MET | 229 | 44.018 | 6.987 | 52.879 | 1.00 | 25.00 |
| ATOM | 1614 | O | MET | 229 | 43.072 | 7.746 | 53.142 | 1.00 | 25.00 |
| ATOM | 1609 | CB | MET | 229 | 43.486 | 4.727 | 51.839 | 1.00 | 25.00 |
| ATOM | 1610 | CG | MET | 229 | 42.031 | 4.457 | 51.474 | 1.00 | 25.00 |
| ATOM | 1611 | SD | MET | 229 | 40.858 | 4.995 | 52.693 | 1.00 | 25.00 |
| ATOM | 1612 | CE | MET | 229 | 40.597 | 6.691 | 52.168 | 1.00 | 25.00 |
| ATOM | 1615 | N | GLY | 230 | 45.147 | 6.898 | 53.596 | 1.00 | 25.00 |
| ATOM | 1616 | CA | GLY | 230 | 45.361 | 7.613 | 54.854 | 1.00 | 25.00 |
| ATOM | 1617 | C | GLY | 230 | 44.331 | 8.616 | 55.401 | 1.00 | 25.00 |
| ATOM | 1618 | O | GLY | 230 | 44.402 | 9.817 | 55.066 | 1.00 | 25.00 |
| ATOM | 1619 | N | ALA | 231 | 43.426 | 8.105 | 56.260 | 1.00 | 25.00 |

Figure 23SS

```
ATOM   1620  CA  ALA   231        42.335   8.836  56.938  1.00 25.00
ATOM   1622  C   ALA   231        41.172   7.899  57.268  1.00 25.00
ATOM   1623  O   ALA   231        40.438   7.572  56.296  1.00 25.00
ATOM   1621  CB  ALA   231        41.811   9.977  56.088  1.00 25.00
ATOM   1624  OT  ALA   231        40.983   7.537  58.470  1.00 25.00
```

Figure 24A

Distances that are less than 5Å for residues near active site

```
Angles of Atoms that are 4.0 Å or less apart
(Triad Atoms Only)

| | | | | |
|---|---|---|---|---|
| 52NE2 | 52ND1 | 139ND1 | A = | 146.98 |
| 52CB | 52ND1 | 139CE1 | A = | 81.02 |
| 52CB | 52ND1 | 139NE2 | A = | 90.90 |
| 52CB | 52ND1 | 139ND1 | A = | 88.36 |
| 139CE1 | 52ND1 | 139NE2 | A = | 24.69 |
| 139CE1 | 52ND1 | 52CA | A = | 64.66 |
| 139CE1 | 52ND1 | 139ND1 | A = | 12.99 |
| 139NE2 | 52ND1 | 52CA | A = | 82.63 |
| 139NE2 | 52ND1 | 139ND1 | A = | 33.57 |
| 52CA | 52ND1 | 139ND1 | A = | 68.12 |
| 52NE2 | 52CE1 | 120CB | A = | 68.06 |
| 52NE2 | 52CE1 | 120O | A = | 111.47 |
| 52NE2 | 52CE1 | 139CE1 | A = | 134.35 |
| 52ND1 | 52CE1 | 120CB | A = | 146.58 |
| 52ND1 | 52CE1 | 120O | A = | 115.99 |
| 52ND1 | 52CE1 | 139CE1 | A = | 28.47 |
| 52CD2 | 52CE1 | 120CB | A = | 100.18 |
| 52CD2 | 52CE1 | 120O | A = | 132.01 |
| 52CD2 | 52CE1 | 139CE1 | A = | 97.30 |
| 52CG | 52CE1 | 120CB | A = | 128.86 |
| 52CG | 52CE1 | 120O | A = | 133.49 |
| 52CG | 52CE1 | 139CE1 | A = | 62.25 |
| 52CB | 52CE1 | 120CB | A = | 134.87 |
| 52CB | 52CE1 | 120O | A = | 131.47 |
| 52CB | 52CE1 | 139CE1 | A = | 54.74 |
| 120CB | 52CE1 | 120O | A = | 45.13 |
| 120CB | 52CE1 | 139CE1 | A = | 128.87 |
| 120O | 52CE1 | 139CE1 | A = | 88.92 |
| 52CE1 | 52NE2 | 120CB | A = | 91.28 |
| 52CE1 | 52NE2 | 120OG | A = | 98.93 |
| 52CD2 | 52NE2 | 120CB | A = | 140.77 |
| 52CD2 | 52NE2 | 120OG | A = | 152.33 |
| 52ND1 | 52NE2 | 120CB | A = | 118.56 |
| 52ND1 | 52NE2 | 120OG | A = | 132.30 |
| 52CG | 52NE2 | 120CB | A = | 140.35 |
| 52CG | 52NE2 | 120OG | A = | 162.95 |
| 120CB | 52NE2 | 120OG | A = | 23.31 |
| 120C | 120O | 139O | A = | 132.85 |
| 120C | 120O | 52CE1 | A = | 106.93 |
| 120CA | 120O | 139O | A = | 166.12 |
| 120CA | 120O | 52CE1 | A = | 95.13 |
| 120N | 120O | 139O | A = | 158.93 |
| 120N | 120O | 52CE1 | A = | 109.96 |
| 120CB | 120O | 139O | A = | 150.80 |
| 120CB | 120O | 52CE1 | A = | 64.57 |
| 139O | 120O | 52CE1 | A = | 87.10 |
| 139O | 120O | 120OG | A = | 139.73 |
| 52CE1 | 120O | 120OG | A = | 61.60 |
| 120OG | 120CB | 52NE2 | A = | 83.13 |
| 120OG | 120CB | 52CE1 | A = | 90.41 |
| 120CA | 120CB | 52NE2 | A = | 142.75 |

| | | | |
|---|---|---|---|
| 52ND1 | 139CE1 | 52CB | A = 45.79 |
| 52ND1 | 139CE1 | 52CG | A = 21.92 |
| 52ND1 | 139CE1 | 139CB | A =141.56 |
| 52ND1 | 139CE1 | 52O | A = 90.42 |
| 52ND1 | 139CE1 | 52C | A = 83.89 |
| 52ND1 | 139CE1 | 52CE1 | A = 13.08 |
| 52CA | 139CE1 | 52CB | A = 25.76 |
| 52CA | 139CE1 | 52CG | A = 43.47 |
| 52CA | 139CE1 | 139CB | A =143.49 |
| 52CA | 139CE1 | 52O | A = 38.38 |
| 52CA | 139CE1 | 52C | A = 22.52 |
| 52CA | 139CE1 | 52CE1 | A = 75.02 |
| 52CB | 139CE1 | 52CG | A = 24.59 |
| 52CB | 139CE1 | 139CB | A =169.20 |
| 52CB | 139CE1 | 52O | A = 45.27 |
| 52CB | 139CE1 | 52C | A = 38.80 |
| 52CB | 139CE1 | 52CE1 | A = 58.19 |
| 52CG | 139CE1 | 139CB | A =160.08 |
| 52CG | 139CE1 | 52O | A = 69.85 |
| 52CG | 139CE1 | 52C | A = 61.99 |
| 52CG | 139CE1 | 52CE1 | A = 33.73 |
| | | | |
| 139CB | 139CE1 | 52O | A =127.95 |
| 139CB | 139CE1 | 52C | A =131.56 |
| 139CB | 139CE1 | 52CE1 | A =128.59 |
| 52O | 139CE1 | 52C | A = 18.13 |
| 52O | 139CE1 | 52CE1 | A =103.22 |
| 52C | 139CE1 | 52CE1 | A = 95.37 |
| | | | |
| 139CE1 | 139NE2 | 52ND1 | A = 64.13 |
| 139CD2 | 139NE2 | 52ND1 | A =144.94 |
| 139ND1 | 139NE2 | 52ND1 | A = 93.14 |
| 139CG | 139NE2 | 52ND1 | A =122.96 |
| 52ND1 | 139NE2 | 139CB | A =126.15 |

Figure 26

| | Phi<br>$C_{n-1}-N_n-C_{An}-C$ | Psi<br>$N-CA-C-N_{n+1}$ | Omega 1<br>$CA_{n-1}-C_{n-1}-N_n-CA_n$ | Omega 2<br>$CA_n-C_n-N_{n+1}-CA_{n+1}$ | Chi1<br>$N-CA-CB-CG$ | Chi2<br>$CA-CD-CG-XD$ |
|---|---|---|---|---|---|---|
| Ser120 | 120 | -120 | 118 | -179 | -180 | -141 |
| His52 | 71 | 13 | -178 | 179 | -69 | -81 |
| His139 | -158 | 155 | 178 | 180 | 74 | 111 |

VZV Protease

VZV Protease

VZVP Dimer

Figure 37

VZVP Active Site

D102

H57

S195

Light-VZV, Dark-Trypsin

| Data Set | Resol'n (Å) | Observed | Unique | Complet (%) | $R_{sym}$ | $R_{iso}$ | # sites | Phasing Power | $R_{cullis}$ |
|---|---|---|---|---|---|---|---|---|---|
| Native | 2.5 | 78502 | 15788 | 90.8 | 0.095 | --- | --- | --- | --- |
| KAuCN | 3.0 | 31511 | 10071 | 98.2 | 0.078 | 15.9 | 2 | 1.14 | 0.74 |
| $LuCl_3$ | 3.0 | 31104 | 9964 | 97.3 | 0.078 | 12.4 | 1 | 1.51 | 0.79 |
| $PrCl_3$ | 3.0 | 31645 | 10179 | 99.0 | 0.090 | 13.6 | 1 | 1.4 | 0.82 |
| $YbSO_4$ | 4.0 | 10495 | 3787 | 78.7 | 0.088 | 14.6 | 1 | 2.01 | 0.72 |
| $GdCl_3$ | 4.0 | 18308 | 4268 | 96.6 | 0.166 | 15.7 | 1 | 1.56 | 0.79 |
| $SmCl_3$ | 4.0 | 25172 | 4327 | 97.6 | 0.114 | 8.8 | 1 | 1.47 | 0.86 |

MIR Overall Mean Figure of Merit (15-3.0 ❹): 0.62 ❹

Overall Figure of Merit After Phase combination: 0.67 ❹

Mean Figure of Merit following density modification 100-3.0❹: 0.838 ❹

X-PLOR refinement: 10-2.5 ❹

No. Reflections Used (F>2s): 14605          No. Solvent Atoms: 43

R-factor: 20.5%                              Rms bond length: 0.016 ❹

No. Protein atoms (non-H): 3364              Rms bond angles: 1.919°

Figure 43

| Data Set | Resolu'n (Å) | Observed (>1σ) | Unique (>1σ) | Complete (%) | $R_m$ (%) | $R_{iso}$ (%) | # of sites | Phasing Power | $R_{Cullis}$ | $R_c$(ano) |
|---|---|---|---|---|---|---|---|---|---|---|
| Native | 2.5 | 22880 | 7644 | 90 | 6.0 | ----- | -- | --- | --- | -- |
| MeHgCl | 3.2 | 17566 | 3932 | 97 | 10.1 | 28.0 | 5 | 2.8 | 0.50 | 0.92 |
| MeHgCl | 3.5 | 3698 | 1958 | 76 | 19.8 | 36.5 | 3 | 1.4 | 0.75 | -- |
| $UO_2Ac_2$ | 3.8 | 9122 | 2330 | 99 | 23.2 | 27.5 | 2 | 1.1 | 0.83 | -- |
| $BakerHg_2$ | 3.2 | 14867 | 4425 | 97 | 9.8 | 30.7 | 4 | 1.9 | 0.68 | 0.97 |
| $LuCl_3$ | 3.2 | 9984 | 3734 | 95 | 10.8 | 23.4 | 3 | 2.0 | 0.63 | -- |
| $K_2PtCl_4$ | 4.1 | 3017 | 1673 | 79 | 13.1 | 25.9 | 2 | 1.4 | 0.77 | -- |
| $SmCl_3$ | 3.7 | 12708 | 2804 | 98 | 13.7 | 26.3 | 3 | 2.4 | 0.54 | 0.97 |

MIRAS Figure of Merit (30 - 3.2 Å): 0.70

XPLOR Refinement:

Resolution included  7.0 - 2.5 Å
of reflections used (>1σ)  7193
R-factor  0.185
of protein atoms (non-H)  1504
  (202 amino acids)

of solvent atoms (non-H)  73
Mean coordinates error  0.40 Å
Rms bond length  0.017 Å
Rms bond angle  2.2 degree Light-CMV, Dark-VZV, RMSCA 1.3A FIG. 45A [SEQ ID NO: 7]
H6(N)VZV:
  M<u>GHHHHHH</u> SSGHI<u>DDDDK</u> MAAEADEENC EALYVAGLYA LYSKDEGELN ITPEIVRSAL PPTSKIPINI DHRKDCVVGE VIAIIEDIRG PFFLGIVRCP QLHAVLFEAA HSNFFGNRDS VLSPLERALY LVTNYLPSVS LSSKRLSPNE IPDGNFFTHV ALCVVGRRVG TVVNYDCTPE SSIEPFRVLS MESKARLLSL VKDYAGLNKV WKVSEDKLAK VLLSTAVNNM LLRDRWDVVA KRRREAGIMG HVYLQA 254

FIG. 45B [SEQ ID NO: 8]
LQA-H6(C) VZV
MAAEADEENC EALYVAGLYA LYSKDEGELN ITPEIVRSAL PPTSKIPINI DHRKDCVVGE VIAIIEDIRG PFFLGIVRCP QLHAVLFEAA HSNFFGNRDS VLSPLERALY LVTNYLPSVS LSSKRLSPNE IPDGNFFTHV ALCVVGRRVG TVVNYDCTPE SSIEPFRVLS MESKARLLSL VKDYAGLNKV WKVSEDKLAK VLLSTAVNNM LLRDRWDVVA KRRREAGIMG HVYLQA<u>HHHH HH</u> 242

FIG. 45C [SEQ ID NO: 9]
LQAS-H6(C) VZV
MAAEADEENC EALYVAGLYA LYSKDEGELN ITPEIVRSAL PPTSKIPINI DHRKDCVVGE VIAIIEDIRG PFFLGIVRCP QLHAVLFEAA HSNFFGNRDS VLSPLERALY LVTNYLPSVS LSSKRLSPNE IPDGNFFTHV ALCVVGRRVG TVVNYDCTPE SSIEPFRVLS MESKARLLSL VKDYAGLNKV WKVSEDKLAK VLLSTAVNNM LLRDRWDVVA KRRREAGIMG HVYLQAS<u>HHH HHH</u> 243

FIG. 45D [SEQ ID NO: 10]
LQAS-12aa ext H6(C) VZV
MAAEADEENC EALYVAGLYA LYSKDEGELN ITPEIVRSAL PPTSKIPINI DHRKDCVVGE VIAIIEDIRG PFFLGIVRCP QLHAVLFEAA HSNFFGNRDS VLSPLERALY LVTNYLPSVS LSSKRLSPNE IPDGNFFTHV ALCVVGRRVG TVVNYDCTPE SSIEPFRVLS MESKARLLSL VKDYAGLNKV WKVSEDKLAK VLLSTAVNNM LLRDRWDVVA KRRREAGIMG HVYLQAS<u>TGY GLARITNVNH HHHH</u> 255

FIG. 45E [SEQ ID NO: 11]
Delta9 LQAS- 12 aa ext H6(C) VZV
M EALYVAGLYA LYSKDEGELN ITPEIVRSAL PPTSKIPINI DHRKDCVVGE VIAIIEDIRG PFFLGIVRCP QLHAVLFEAA HSNFFGNRDS VLSPLERALY LVTNYLPSVS LSSKRLSPNE IPDGNFFTHV ALCVVGRRVG TVVNYDCTPE SSIEPFRVLS MESKARLLSL VKDYAGLNKV WKVSEDKLAK VLLSTAVNNM LLRDRWDVVA KRRREAGIMG HVYLQAS<u>TGY GLARITNVNH HHHH</u> 246

PROTEASES COMPOSITIONS CAPABLE OF BINDING TO SAID SITE, AND METHODS OF USE THEREOF

This application claims the benefit of U.S. Provisional Application 60/018,616, filed May 15, 1996; U.S. Provisional Application 60/022,470, filed Jul. 26, 1996; U.S. Provisional Application 60/024,416, filed Aug. 21, 1996; U.S. Provisional Application 60/030,901, filed Nov. 14, 1996; U.S. Provisional Application 60/035,973 filed Jan. 21, 1997; and U.S. Provisional Application 60/039,191 filed Feb. 27, 1997.

TECHNICAL FIELD OF THE INVENTION

The invention relates to the identification of a novel protease catalytic active site and methods for enabling the design and selection of inhibitors of proteases, esterases, ligases and other hydrolases with that active site.

BACKGROUND OF THE INVENTION

Herpesviridae is a family of envelope DNA viruses comprising three subfamilies, alpha, beta and gamma herpesviridae. The alpha subfamily includes herpes simplex virus (HSV) 1 and 2, and varicella zoster virus (VZV). The beta subfamily includes cytomegalovirus (CMV) and human herpes virus 6 (HHV-6) and human herpes virus 7 (HHV-7). The gamma subfamily includes Epstein-Barr virus (EBV) and human herpes virus (HHV-8).

The human herpes viruses are responsible for a variety of disease states from subclinical infections to fatal disease states in the immunocompromised. As one example, VZV is known to cause a number of serious diseases: chickenpox, shingles and post-hepatic neuralgia [S. Straus, *Ann. Neurol.*, 35:S11–S12 (1994)]. As another example, HSV-1 is acquired in childhood when it causes a self-limiting gingivostomatitis. The virus remains latent in the dorsal root ganglia and is reactivated later in life as cold sores in about one third of the population. HSV-1 is also a cause of keratitis, resulting in more than 300,000 cases per year in the US. HSV-2 is usually acquired through sexual contact and gives rise to genital herpes. Human CMV is a ubiquitous opportunistic pathogen that can result in life threatening infections in congenitally infected infants, immunocompromised individuals and immunosuppressed cancer and transplant patients.

Each of these members of the herpes virus families encodes a serine protease that is essential for its replication [F. Liu, & B. Roizman, *J Virol,* 65: 5149–5156 (1991) (Liu I); F. Liu & B. Roizman, *Proc. Natl. Acad. Sci.* 89: 2076–2080 (1992) (Liu II); F. Liu & B. Roizman, *J. Virol,* 67: 1300–1309 (1993) (Liu III); A. R. Welch et al., *J Virol,* 67: 7360–7372 (1993) (Welch I); E. Z. Baum *et al., J. Virol,* 67: 497–506 (1993); J. T. Stevens *et al., Eur. J. Biochem.*, 226: 361–367 (1994); A. R. Welch et al., *J. Virol.,* 69: 341–347 (1993) (Welch II); D. L. Hall & P. L. Darke, *J. Biol. Chem.,* 270: 22697–22700 (1995); Weinheimer *et al., J. Virol.,* 67: 5813–5822 (1993); M. Gao *et al, J. Virol.,* 68: 3702–3712 (1994); C. L. DiIanni et al., *J. Biol. Chem.,* 268: 25449–25454 (1993) (DiIanni I); C. L. DiIanni *et al., J. Biol. Chem.* 269: 12672–12676 (1994) (DiIanni II); P. J. McCann III *et al., J. Virol.,* 68: 526–529 (1994)]. These proteases each provide a potential target for therapeutic intervention.

The proteases from these viruses are encoded as precursor proteins that catalyze their own cleavage to produce an N-terminal domain of approximately 28 kDa having full or increased catalytic activity. These protease domains show some degree of sequence homology –20% to 40% identity between members of different subfamilies and as high as 90% identity within each subfamily. They show little sequence homology to any other known protein, including the absence of the conserved G-X-S/C-G-G [SEQ ID NO: 12] for chymotrypsin-like and G-T-S-M/A[SEQ ID NO: 13] for subtilisin-like proteases. The known herpes virus proteases all cleave a peptide bond between an alanine and a serine, but their substrate specificity beyond the scissile bond are different [A. Welch et al., *J. Virol.* 69, 341–347 (1993)].

Each known serine protease has its characteristic set of functional amino acid residues arranged in a particular three dimensional configuration to form an active site. Knowledge of the active site of such proteases and their three dimensional structure permits the use of methods of structure-based drug design to identify and develop inhibitors of the proteases [C. Verlinde and W. Hol, *Structure,* 2:577–587 (July 1994); I. D. Kuntz, *Science,* 257:1078–1082 (August 1992)]. Because the proteolytic activity of the herpesvirus-encoded protease plays an essential role in virus capsid maturation, inhibitors of the protease would thus inhibit infectious virus particle formation and thereby exert an antiviral action. For serine proteases of which trypsin is a protype, the active site is formed by Ser, His and Asp [H. Neurath, *Science,* 224: 350–357 (April 1984)]. These three residues are known as the catalytic triad.

There is a need in the art for novel protease active sites and catalytic sequences to enable identification and structure-based design of protease inhibitors, which are useful in the treatment or prophylaxis of viral diseases caused by viruses of the herpes family, as well as other diseases in which the target enzyme may share catalytic domains with those of the herpes family.

SUMMARY OF THE INVENTION

The present invention provides novel herpes protease crystalline forms. In one aspect, the present invention provides liganded and unliganded herpes HSV-2 protease, HSV-1 protease, CMV protease, and VZV protease crystalline forms, each of which is characterized by a three dimensional catalytic site formed by the three amino acid residues Ser, His, and His.

In another aspect, the present invention provides novel HSV-1 and HSV-2 protease compositions characterized by a three dimensional catalytic site of the seven amino acid residues, Ser 129, His 61, His 148, Ser 131, Cys 152, Arg 156, and Arg 157 of SEQ ID NOS: 3 and 4.

In still another aspect, the present invention provides a novel unliganded HSV-2 protease composition characterized by a three dimensional catalytic site of the seven amino acids identified above, and further containing amino acid residues Leu 27, Val 128, and Leu 130 of SEQ ID NO: 4, and optionally two water molecules Wat1 and Wat2 which are present in the liganded form.

In yet another aspect, the present invention provides an HSV-2 protease having an active site characterized by the coordinates selected from the group consisting of the coordinates of FIGS. 2 and 3, the coordinates of FIGS. 8 and 9, and the coordinates of FIGS. 11 and 12. In another aspect, the present invention provides an HSV-2 protease having an active site characterized by the coordinates selected from the group consisting of the coordinates of FIGS. 4 and 5, the coordinates of FIGS. 8 and 9, the coordinates of FIGS. 11 and 12, and the coordinates of FIGS. 14 and 15.

In yet a further aspect, the present invention provides a novel HSV-1 protease composition characterized by a three dimensional catalytic site of Ser 129, His 61, His 148, Ala 131, Cys 152, Arg 156 and Arg 157 [SEQ ID NO: 3]. In one embodiment, this HSV-1 protease has an active site characterized by the coordinates selected from the group consisting of the coordinates of FIG. 6 or FIG. 7, the coordinates of FIG. 10, and the coordinates of FIG. 16.

In still another aspect, the present invention provides a novel CMV protease composition characterized by a three dimensional catalytic site of four amino acid residues, Ser, His, His, and Asp. In one embodiment, the CMV protease active site is formed by at least the amino acids Ser 132, His 63, His 157, Asp 65, Cys 161 and Ser 134. In another embodiment, the CMV protease active site further contains at least one amino acid selected the group consisting of Arg 165 and Arg 166. Desirably, the CMV protease active site is characterized by the coordinates selected from the group consisting of FIG. 17 or FIG. 21, the coordinates of FIG. 18 and the coordinates of FIG. 20.

In yet another aspect, the present invention provides a novel CMV protease composition characterized by a three dimensional catalytic site of nine amino acid residues, Ser 132, His 63, His 157, Asp 65, Ser 134, Cys 161, Arg 165, Arg 166 and Asn 60.

In yet another aspect, the present invention provides a novel VZV protease composition characterized by a three dimensional catalytic site of four amino acid residues of SEQ ID NO: 5: Ser 120, His 52, His 139, and Lys 54. In another aspect, the VZV protease has a catalytic site which includes the four amino acids aidentified above and Ser 122, Cys 143, Arg 147 and Arg 148. In one embodiment, the VZV protease active site is characterized by the coordinates selected from the group consisting of FIG. 22 or FIG. 23, the coordinates of FIG. 24 and the coordinates of FIG. 26.

In another aspect, the present invention provides a heavy atom derivative of a herpes virus protease crystal, where the herpes virus protease is HSV1, HSV2, CMV, or VZV.

In a further aspect, the invention provides a method for identifying inhibitors of the compositions described above which methods involve the steps of: providing the coordinates of a protease structure of the invention to a computerized modeling system; identifying compounds which will bind to this structure; and screening the compounds or analogs derived therefrom identified for protease inhibitory bioactivity. In one embodiment of this aspect, the inhibitor binds to the dimeric interface of the protease molecule, or fragment thereof, of the invention.

In yet a further aspect, the present invention provides for an inhibitor of the catalytic activity of any composition bearing a catalytic domain described above. Desirably, the inhibitor disrupts the ability of the protease molecule to form a dimer.

Another aspect of this invention includes machine readable media encoded with data representing the coordinates of the 3D structure of a protease crystal of the invention, or of a catalytic site domain thereof.

In yet another aspect, the invention provides a computer controlled method for designing a ligand capable of binding to the active site domain of a herpes protease involving the steps of providing a model of the crystal structure of the active site domain of a herpes protease, analyzing the model to design a ligand which binds to the active site domain, and determining the effect of the ligand on the active site.

Other aspects and advantages of the present invention are described further in the following detailed description of the preferred embodiments thereof.

BRIEF DESCRIPTION OF THE DRAWINGS

FIG. 1 provides an alignment of the amino acid sequences herpes proteases HHV-6 [SEQ ID NO: 2], CMV [SEQ ID NO: 1], EBV [SEQ ID NO: 6], HSV-1 [SEQ ID NO: 3], HSV-2 [SEQ ID NO: 4] and VZV [SEQ ID NO: 5]. Regions of α-helices and β-strands in the HSV-2 protease structure are indicated by A1 through A7, and B1 through B7, respectively.

FIG. 2A–2F provides the coordinates of the residues of the catalytic triad and other residues and water molecules in the active site of the diisopropyl phosphate (DIP)-liganded HSV-2 protease.

FIG. 3A–3E provides the coordinates of the residues of the catalytic triad and other residues and water molecules in the active site of unliganded HSV-2 protease.

FIG. 4A–4MMM provides the protein coordinates of the DIP-liganded HSV-2 protease crystalline structure of the invention. FIG. 2A–2F is included within FIG. 4A–4MMM.

FIG. 5A–5DDD provides the protein coordinates of the unliganded HSV-2 protease crystalline structure. FIG. 3A–3E is included in FIG. 5A–5DDD.

FIG. 6A–6B provides the coordinates of residues in the active site region of HSV-1 protease.

FIG. 7A–7DDD provides the protein coordinates of the HSV-1 protease crystalline structure of the invention. FIG. 6A–6B is included within FIG. 7A–7DDD.

FIG. 8A–8X provides the distances (in Angstrom) between any protein residue that has an atom within a 5.5 Å radius of any atom of Ser 129 covalently bonded to the DIP in the DIP-liganded HSV-2 protease [SEQ ID NO: 4].

FIG. 9A–9I provides the distances (in Angstroms) between every two atoms that are within 5.0 Å of the active site residues of the unliganded HSV-2 protease.

FIG. 10A–10B provides the distances (in Angstroms) between every two atoms that are less than 5 Å from the active site of HSV-1 protease.

FIG. 11A–11LLL provides the bond angles (in degrees) between any atom of HSV-2/DIP-modified Ser 129 and any two protein residue atoms that are within a 5.5 Å radius of the DIP modified Ser 129 [SEQ ID NO: 4].

FIG. 12A–12Q provides the bond angles (in degrees) between interresidue atoms in the active site region near Ser 129, His 61 and His 148 of the unliganded HSV-2 protease [SEQ ID NO: 4].

FIG. 13A–13D provides the bond angles between interresidue atoms in the active site region near Ser 129, His 61 and His 148 of the HSV-1 protease of this invention [SEQ ID NO: 3].

FIG. 14 provides the dihedral angles of the active site formed by Ser 129, His 61 and His 148 of the DIP-liganded HSV-2 protease [SEQ ID NO: 4].

FIG. 15 provides the dihedral angles of the active site formed by Ser 129, His 61 and His 148 of the unliganded HSV-2 protease [SEQ ID NO: 4].

FIG. 16 provides the dihedral angles of the active site formed by Ser 129, His 61 and His 148 of the HSV-1 protease [SEQ ID NO: 3].

FIG. 17A–17E provide the protein coordinates near the active site region (at amino acid residues Ser 132, His 63, Ser 134, Cys 161, Arg 165 and His 157, and including Arg 166) of the CMV protease [SEQ ID NO: 1] according to this invention.

FIG. 18A–18C provide the distances in Angstroms between every two atoms that are less than 5 Å from the active site for CMV protease.

FIG. 19A–19D illustrate the bond angles between interresidue atoms that are within four Å apart in the active site region near Ser 132, His 63, His 157 and Asp 65 of the CMV protease [SEQ ID NO: 1] according to this invention.

FIG. 20 provides the dihedral angles of the tetra active site formed by Ser 132, His 63, His 157 and Asp 65 of the CMV protease [SEQ ID NO: 1].

FIG. 21A–21DD provides the protein coordinates of the CMV protease crystalline structure of the invention. FIG. 17A–17E is included within FIG. 21A–21DD.

FIG. 22A–22C provide the protein coordinates near the active site region (at amino acid residues Ser 120, Ser 122, His 52, Lys 54, Cys 143, Arg 147 and Arg 148 of SEQ ID NO: 5) of the VZV protease according to this invention. The data is reported in Protein Data Bank (PDB) format as in FIGS. 3A–3E.

FIG. 23A–23SS provide the protein coordinates of the VZV protease crystalline structure of the invention, including the active site of FIG. 22A–22C.

FIG. 24A–24C provide the distances in Angstroms between every two atoms that are less than 5 Å from the active site for VZV protease.

FIG. 25A–25D illustrate the bond angles between inter-residue atoms that are within four Å apart in the active site region near Ser 120, His 52 and His 139 of the VZV protease [SEQ ID NO: 5] according to this invention.

FIG. 26 provides the dihedral angles of the tetra active site formed by Ser 120, His 52 and His 139 of the VZV protease [SEQ ID NO: 5].

FIG. 37 is a three dimensional diagram of the VZV protease dimer, viewing parallel to the two-fold axis, which was drawn using the MOLSCRIPT program, with each subunit in a different shade of grey.

FIG. 40B is the superposition between the active site of VZV protease and that of the classical serine protease trypsin. In light shading is the VZV protease in the identical orientation as in FIG. 40A, and in dark shading are the trypsin active site residues. Labels are those of trypsin. The proton transfer pathway in trypsin are depicted in dotted lines.

FIG. 42 provides the statistics of structure determination for HSV-2 protease.

FIG. 43 provides the data collection statistics for native and heavy atom derivatives of CMV protease.

FIG. 45A is the complete sequence of the VZV construct H6(N)VZV [SEQ ID NO: 7] containing an authentic protease domain preceded at the amino-terminus by six histidine residues (underlined) followed by an enterokinase cleavage site (bold, underlined).

FIG. 45B is the complete sequence of the VZV construct LQA-H6(C) VZV [SEQ ID NO: 8] containing an authentic protease domain followed by six histidine residues (underlined).

FIG. 45C is the complete sequence of the VZV construct LQAS-H6(C) VZV [SEQ ID NO: 9] containing an authentic protease domain followed by a serine residue and six histidine residues (underlined).

FIG. 45D is the complete sequence of the VZV construct LQAS-12*aa* ext H6(C) VZV [SEQ ID NO: 10] containing an authentic protease domain followed by a serine residue, 12 residues normally found after the LQAS R-site (bold underlined) and six histidine residues (underlined).

FIG. 45E is the complete sequence of the VZV construct Δ9 LQAS-12 aa ext H6(C) VZV [SEQ ID NO: 11] containing an authentic protease domain deleted at the amino-terminus (first nine natural residues removed and Cys 10 replaced by Met) and followed at the carboxyl-terminus by a serine residue, 12 residues normally found after the LQAS R-site (bold underlined) and six histidine residues (underlined).

DETAILED DESCRIPTION OF THE INVENTION

Figure 27A:
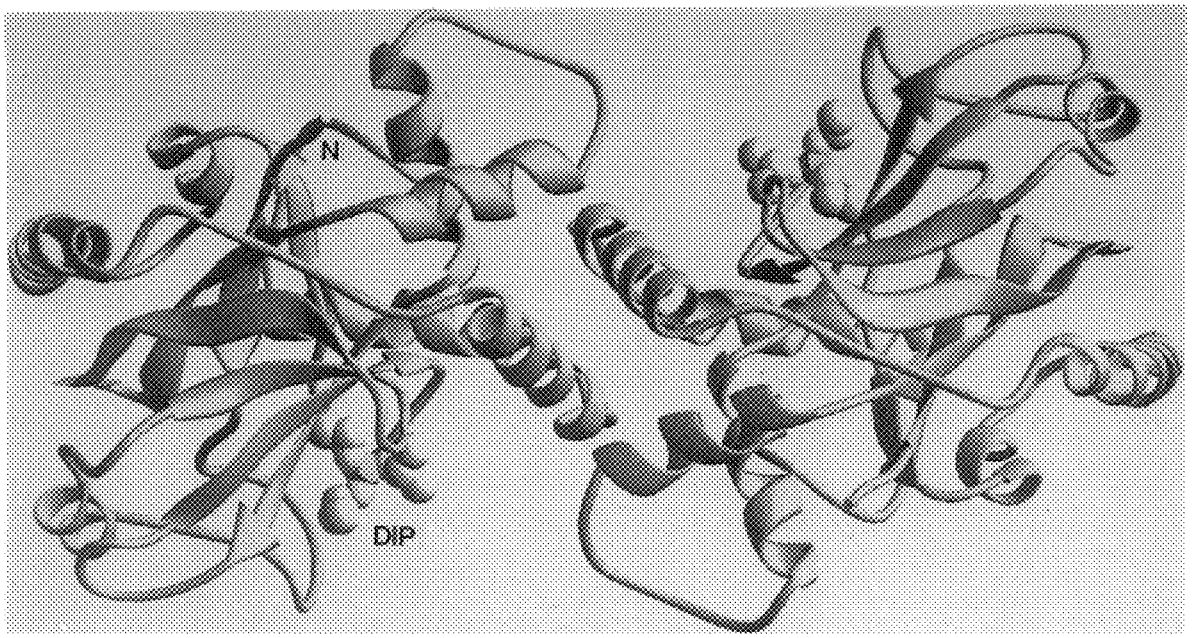
FIG. 27A is a three dimensional ribbon diagram of the DIP-liganded HSV-2 protease dimer. The ligand diusopropyl phosphate (DIP) is shown in the active site of each monomer rendered in space filling models. The amino terminus is indicated by N. The drawing was produced using the program RIBBONS [Carson, M. *J. Mol. Graphics* 5, 103–106 (1987)].
Figure 27B:
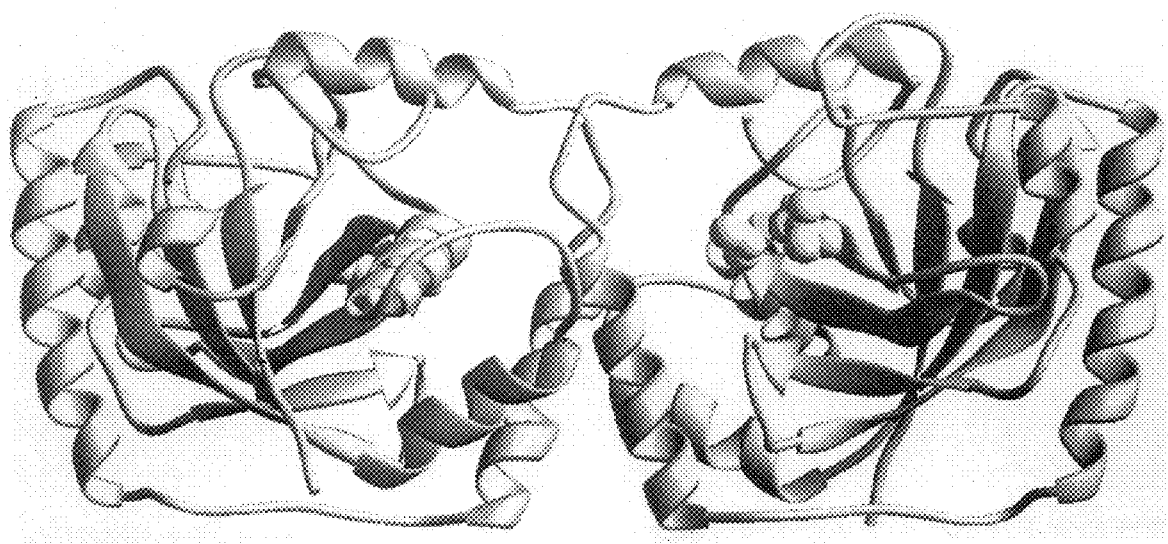
FIG. 27B is the same structure as in FIG. 27A, viewing from 90° away.
Figure 27C:
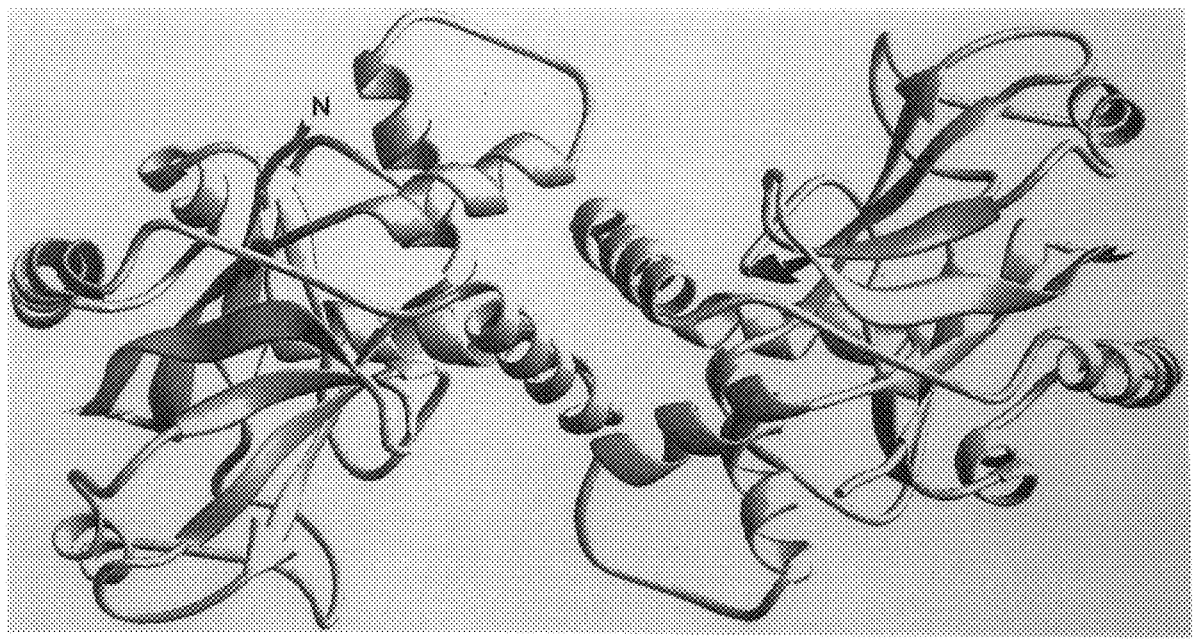
FIG. 27C is the unliganded dimer. The structure is essentially identical to that of the DIP-liganded HSV-2 protease structure.

The present invention provides novel herpes virus family protease crystalline structures, novel herpes virus protease active sites, and methods of use of the crystalline forms and active sites to identify protease inhibitor compounds (peptide, peptidomimetic or synthetic compositions) characterized by the ability to inhibit binding to the active site of herpes proteases. The herpes virus protease compositions of the invention are characterized by a three dimensional active catalytic site of conserved amino acid residues, Ser, His, and His.

For HSV-1 and HSV-2 proteases, these residues are located at aa Ser 129, His 61 and His 148 of SEQ ID NO: 3 and 4, respectively. For CMV protease, these residues are located at aa Ser 132, His 63 and His 157 of SEQ ID NO: 1. For VZV protease, these residues are located at *aa* Ser 120, His 52, and His 139 of SEQ ID NO: 5.

The present invention further provides a novel HSV-2 protease composition characterized by a three dimensional active catalytic site of three conserved amino acid residues, Ser 129, His 61, His 148, seven additional amino acid residues Ser 131, Cys 152, Arg 156, Arg 157, Leu 27, Val 128, Leu 130, and two water molecules Wat1 and Wat2 (present in only the DIP-liganded HSV-2 protease structure) as defined by position in FIG. 1 herein [SEQ ID NO: 4].

Also provided is a novel HSV-1 protease composition characterized by a three dimensional active catalytic site of three conserved amino acid residues, Ser 129, His 61, His 148, four additional amino acid residues Ala 131, Cys 152, Arg 156, and Arg 157, as defined by position in FIG. 1 herein [SEQ ID NO: 3].

In yet another aspect, the present invention provides a novel CMV protease composition characterized by a three dimensional active catalytic site of six conserved amino acid residues, Ser 132, His 63, His 157, Asp 65, Cys 161 and Ser 134. Additionally, the CMV catalytic site may also contain either or both Arg 165 and Arg 166, as defined by their position in FIG. 1 herein [SEQ ID NO: 1]. The CMV structure further reveals a novel active site tetra, formed by Ser 132-His 63-His 157-Asp 65 [SEQ ID NO: 1]. In still another aspect, the present invention provides a novel CMV protease composition characterized by a three dimensional active catalytic site of six conserved amino acid residues, Ser 132, His 63, His 157, Cys 161, Arg 165, and Arg 166 and three non-conserved amino acid residues Ser 134, Asp 65, and Asn 60, as defined by position in FIG. 1 herein [SEQ ID NO: 1].

The invention further provides a novel VZV protease composition characterized by a three dimensional active catalytic site of three conserved amino acid residues, Ser 120, His 52, His 139, and five additional amino acid residues Ser 122, Cys 143, Arg 147, Arg 148 and Lys 54, as defined by the amino acid positions in FIG. 1 [SEQ ID NO: 5].

I. The Novel Protease Crystalline Three-Dimensional Structure

The present invention provides novel protease crystalline structures based on the herpes proteases. The three dimensional (3D) structure of the HSV-1, HSV-2, CMV and VZV proteases provided herein reveal a unique fold that has not been reported for any serine protease, and a novel active site consisting of a novel catalytic triad formed by 3D interactions of the amino acids Ser, His and His. An unusual dimer interface that is important to protease activity was also found in the crystals for each of these proteases. In yet another aspect, the present invention provides for a novel herpes protease composition characterized by a dimer interface of two herpes protease molecules. Inhibition of this dimer interface by inhibitors which perturb interaction with these dimer interfaces. Inhibitors that perturb or interact with these dimer interfaces are yet another therapeutic target for the design and selection of therapeutic agents against herpes proteases.

Listed in FIG. 1 are known amino acid sequences for the herpes family proteases HHV-6, HSV-1, HSV-2, VZV, EBV and CMV, aligned to illustrate the homologies between them [SEQ ID NO: 1–6]. As seen in FIG. 1, when compared to members of the alpha subfamily, HSV-2, HSV-1, and VZV protease amino acid sequences are rather conserved (HSV-1 protease is 50% identical to VZV protease and 90% identical to HSV-2 protease; VZV protease is 26% identical to CMV protease); CMV protease differs in having a shorter N-terminus and two multi-residue insertions (at CMV protease amino acid residues 40–47 and 147–152, SEQ ID NO: 1).

According to the present invention, the crystal structure of human HSV-1, liganded and unliganded HSV-2, CMV and VZV proteases have been determined. These protease crystal structures reveal a fold and an active site that are distinct from other known, non-herpes serine proteases. Details of structure determination and refinement are presented in FIGS. 2–26 below.

Further refinement of the atomic coordinates will change the numbers in FIGS. 2–26, refinement of the crystal structure from another crystal form will result in a new set of coordinates, determination of the crystal structure of another herpes protease will also result in a different set of numbers for coordinates in these figures. However, distances and angles will remain the same within experimental error, and relative conformation of residues in the active site will remain the same within experimental error. Also for example, the amino acid sequence of the herpes proteases can be varied by mutation derivatization or by use of a different source of the protein, as described herein.

A. HSV-1 and HSV-2

The crystal structures of HSV-1 and HSV-2 have been determined, as described herein, and are discussed in tandem below.

The crystal structure of human HSV-1 protease has been determined at 3.5 Å resolution. The structure was determined using the method of molecular replacement (MR) and refined to an R-factor of 36.9% (10.0–3.5 Å, using |Fo|>2s |Fo| data).

The crystal structures of human DIP-liganded HSV-2 protease and the unliganded HSV-2 protease have been determined at 2.5 Å, and 2.8 Å resolution, respectively. The DIP-liganded HSV-2 protease structure was determined using the methods of multiple isomorphous replacement (MIR) and MR and refined to an R-factor of 20.5% (10.0–2.5 Å, using |Fo|>2s |Fo| data) with root-mean-square deviations on bond lengths and bond angles of 0.016 Å and 1.9°, respectively. The unliganded structure was determined using difference Fourier methods using the DIP-liganded HSV-2 protease structure and refined to an R factor of 22.4%. The root-mean-square deviations of bond lengths and bond angles are 0.017 Å and 2.1 Å.

Although human HSV-1 and HSV-2 proteases contain 247 amino acids, the models of these proteases are represented by 214 residues for HSV-1 protease and 217 residues for DIP-liganded HSV-2 protease. With respect to HSV-1 protease, residues 1–14 and residues in two surface loops 102–110, and 134–143 are disordered in the crystal [SEQ ID NO: 3]. With respect to HSV-2, residues 1–16 and residues in two surface loops 104–110, and 134–140 are disordered in the crystal [SEQ ID NO: 4]. The model of unliganded HSV-2 protease has 215 residues where 1–16, 104–112, and 134–140 are disordered in the crystal [SEQ ID NO: 4].

Figure 29A:
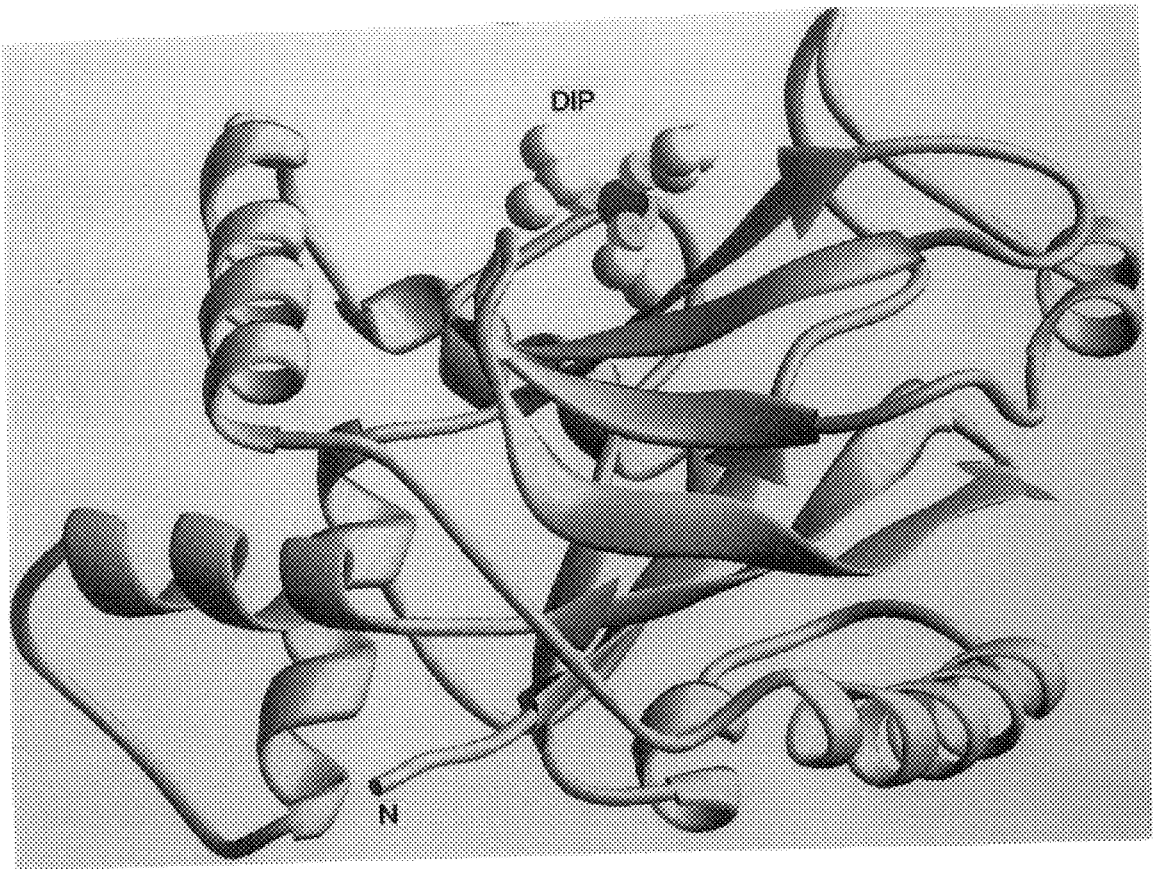
FIG. 29A is a three dimensional diagram of the HSV-2 protease monomer. The ligand DIP is shown in the active site rendered as a space filling model. The amino terminus is indicated by N. The drawing was produced using the program RIBBONS [Carson, M. *J. Mol. Graphics* 5, 103–106 (1987)].
Figure 29B:
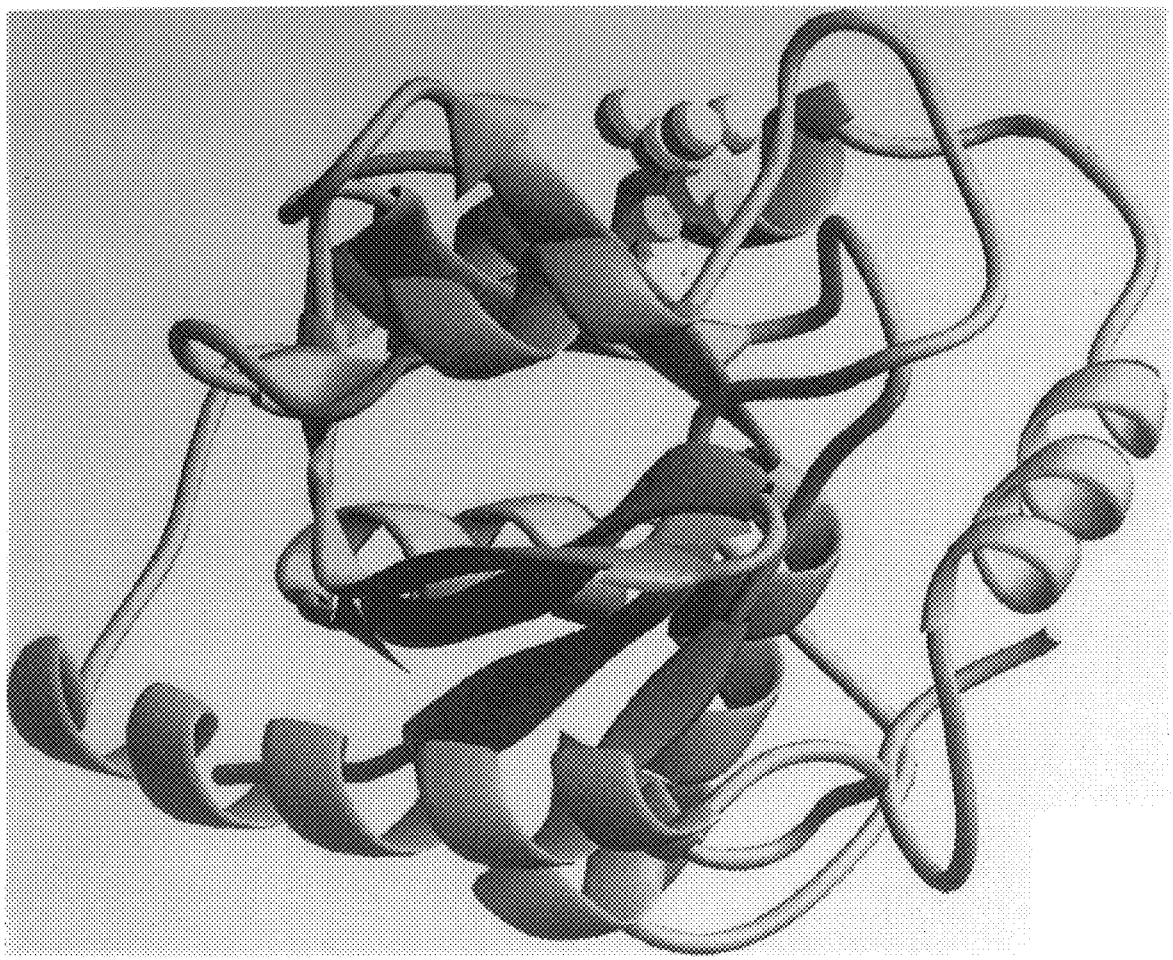
FIG. 29B is the same structure as in FIG. 29A, viewing from 90° away.
Figure 29C:
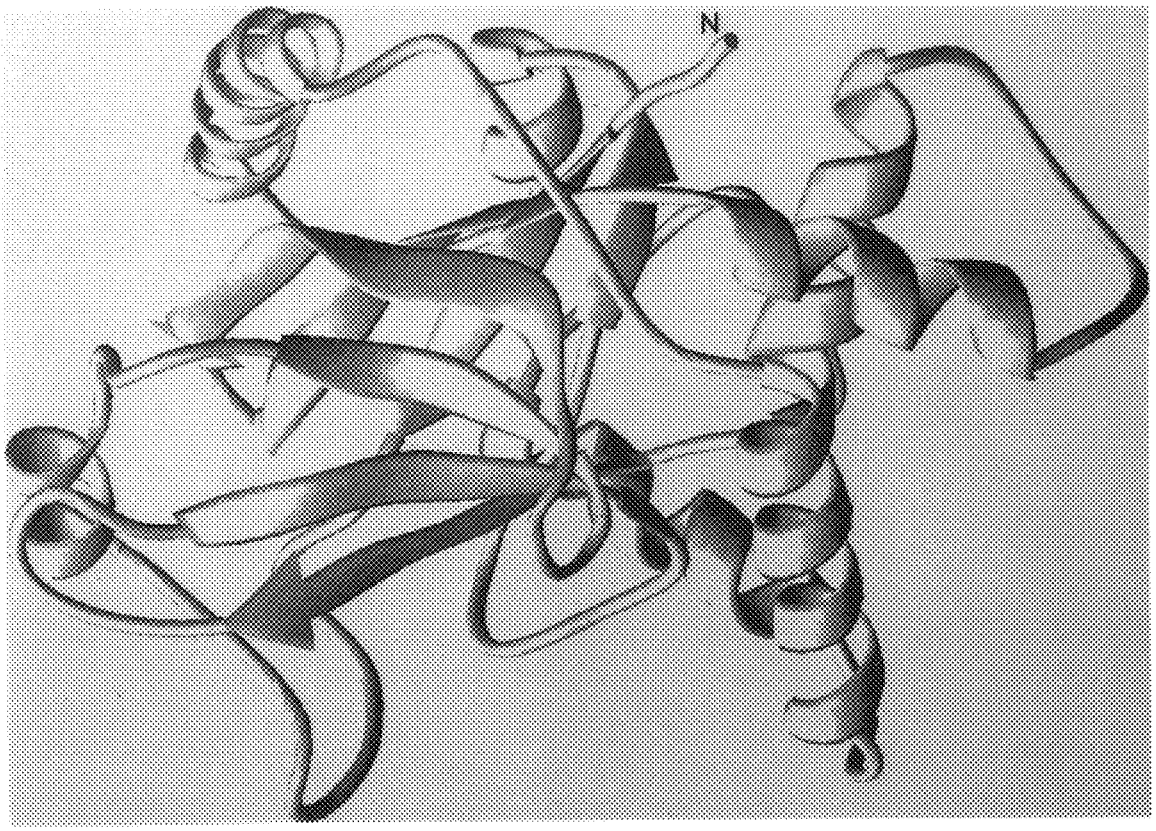
FIG. 29C is the unliganded HSV-2 monomer. The structure is the same as the DIP-liganded HSV-2 protease structure.

The fold in each of the HSV-1 and HSV-2 proteases is characterized by 7 b-strands and 7 a-helices as depicted in FIGS. 1, 29, and 30. As discussed herein, the loop containing residues 25–55 in the CMV protease [SEQ ID NO: 1] is disordered in the crystal, but the corresponding loop in the HSV-1 and HSV-2 protease crystals are observed.

FIG. 2A–2F disclose the coordinates of the residues of the novel HSV-2 catalytic triad and other residues and water molecules within 5.5 Å of the DIP modified Ser 129 (including the DIP ligand) in the active site. These include amino acid residues Ser 129, His 61, His 148, Ser 131, Cys 152, Arg 156, Arg 157, Leu 27, Val 128, Leu 130, and, water molecules Wat1 and Wat2 of the DIP-liganded HSV-2 protease [SEQ ID NO: 4] according to this invention. FIG. 3A–3E disclose the coordinates of residues of the novel catalytic triad and other residues in the active site of the unliganded HSV-2 protease. These include residues Ser 129, His 61, His 148, Ser 131, Cys 152, Arg 156, Arg 157, Leu 27, Val 128, and Leu 130. These data are reported for crystals with lattice constants of A=71.7 Å, B=87.4 Å, C=77.3 Å, α=90, β=90 and γ=90, with a space group=P2,2,2. The liganded and unliganded crystal forms have the same cell dimensions and space group. The data is reported in Protein Data Bank (PDB) format, illustrating the atom, i.e., nitrogen, oxygen, carbon (at α, β, δ or γ positions in the atom); the amino acid residue in which the atom is located with amino acid number, and the coordinates X, Y and Z in Angstroms (Å) within the crystal lattice. Also illustrated is the occupancy of the atom, noting that each atom in the active site has a unique position in the crystal. The data also report the B or Temperature Factor, which indicates the degree of thermal motion of the atom in volume measurements ($Å^2$). FIGS. 4A–4MMM and 5A–5DDD disclose the protein coordinates of the DIP-liganded HSV-2 and unliganded protease crystalline structure of the invention, respectively, including the active site.

FIG. 6A–6B disclose the coordinates of residues in the active site region (at amino acid residues Ser 129, His 61, His 148, Ala 131, Cys 152, Arg 156, Arg 157) of the HSV-1 protease [SEQ ID NO: 3] according to this invention. These data are reported for crystals with lattice constants of a=79.62 Å, b=81.18 Å, c=93.36 Å, α=115.49°, β=98.36° and γ=109.18°, with a space group=P1. The data is reported as described above for HSV-2 protease. FIG. 7A–7DDD illustrate the orthogonal three dimensional coordinates in Angstroms and B factors for HSV1 protease.

FIG. 8A–8X provide the distances (in Angstroms) between any protein residue that has an atom within a 5.5 Å radius of any atom of Ser 129 [SEQ ID NO: 4] covalently bonded to DIP in the DIP-liganded HSV-2 protease structure. FIG. 9A–9I provide distances (in Angstroms) between every two atoms that are within 5.0 Å of the active site residues of the unliganded HSV-2 protease. The atoms are indicated in this figure by the amino acid position number in which the atom appears, followed by the atom designation, ie., nitrogen, oxygen, etc. as described for FIGS. 2 and 3.

FIG. 10A–10B provide the distances (in Angstroms) between every two atoms that are less than 5 Å from the active site of HSV-1 protease. The atoms are indicated as described above for HSV-2 protease. FIG. 11A–11LLL provide the bond angles (in degrees) between any atom of HSV-2/DIP-modified Ser 129 and any two protein residue atoms that are within a 5.5 Å radius of the DIP modified Ser 129 (Overall Active Site Residues Only). FIG. 12A–12Q provide the bond angles (in degrees) between interresidue atoms that are within 5 Ångstroms apart in the active site region near Ser 129, His 61 and His 148 [SEQ ID NO: 4] of the unliganded HSV-2 protease. FIG. 13A–13D provide the bond angles between interresidue atoms that are within 5 Ångstroms apart in the active site region near Ser 129, His 61 and His 148 of the HSV-1 protease [SEQ ID NO: 3] of this invention. FIGS. 14 and 15 provide the dihedral angles of the active site formed by Ser 129, His 61 and His 148 [SEQ ID NO: 4] of the protease, for the DIP-liganded HSV-2 and unliganded proteases, respectively. FIG. 16 provides the dihedral angles of the active site formed by Ser 129, His 61 and His 148 of the HSV-1 protease [SEQ ID NO: 3].

The novel folds of the HSV-2 and HSV-1 protease crystal structures are discussed in part D. below; the novel active sites are discussed in part E.

B. CMV Protease

The crystal structure of human CMV protease has been determined at 2.5 Å resolution. As described in more detail in Example 3 below, a CMV protease sequence (CMV A143V) was employed in which the alanine residue at position 143 was replaced by a valine. This mutation had no effect on the enzyme activity, but was necessary to eliminate the nick after Ala 143 seen in preparations of the native enzyme [Welch I, and Baum et al, cited above]. The structure was determined using MIR, and refined to an R-factor of 18.5% (7.0–2.5 Å, using |Fo|>1s |Fo| data) with root-mean-square deviations on bond lengths and bond angles of 0.017 Å and 2.2°, respectively.

Although human CMV protease contains 256 amino acids, the model of the enzyme provided herein is represented by 202 residues. Residues 1–8 and residues in three surface loops (residues 25–55, 143–153 and 205–208 of SEQ ID NO: 1) are found disordered and are not present in FIG. 17A–17E. Details of structure determination and refinement are presented in FIGS. 17 through 21.

FIG. 17A–17E disclose the protein coordinates near the active site region (at amino acid residues Ser 132, His 63, Ser 134, Cys 161, Arg 165 and His 157, and including Arg 166 of SEQ ID NO: 1) of the CMV protease according to this invention. These data are reported for crystal lattice constants of a=58.7 Å, b=58.7 Å, c=131.0 Å, α=90, β=90 and γ=90, with a space group =$P4_322$. The data is reported in Protein Data Bank (PDB) format, as described above for HSV-2 and HSV-1. FIG. 18A–18C provide the distances in Angstroms between every two atoms that are less than 5 Å from the active site for CMV protease. FIG. 19A–19D illustrate the bond angles between interresidue atoms that are within four Å apart in the active site region near Ser 132, His 63, His 157 and Asp 65 of the CMV protease [SEQ ID NO: 1] according to this invention. FIG. 20 provides the dihedral angles of the tetra active site formed by Ser 132, His 63, His 157 and Asp 65 of the protease [SEQ ID NO: 1]. FIG. 21A–21DD disclose the protein coordinates of the CMV protease crystalline structure of the invention, including the active site. See D. below for discussion of the CMV crystal structure folds and part E. for further discussion of the active site.

C. VZV Protease

The crystal structure of human VZV protease has been determined at 3.0 Å resolution. As described in more detail in the Example 6 below, a VZV protease sequence was employed in which the mutant has the N-terminal nine (9) amino acids deleted. This mutation had little effect on the enzyme activity. The structure was determined using the methods of MR and single isomorphous replacement (SIR) and refined to an R-factor of 22.3% (7.0–3.0 Å, using |Fo|>1s |Fo| data) with root-mean-square deviations on bond lengths and bond angles of 0.014 Å and 2.1°, respectively.

Figure 35:
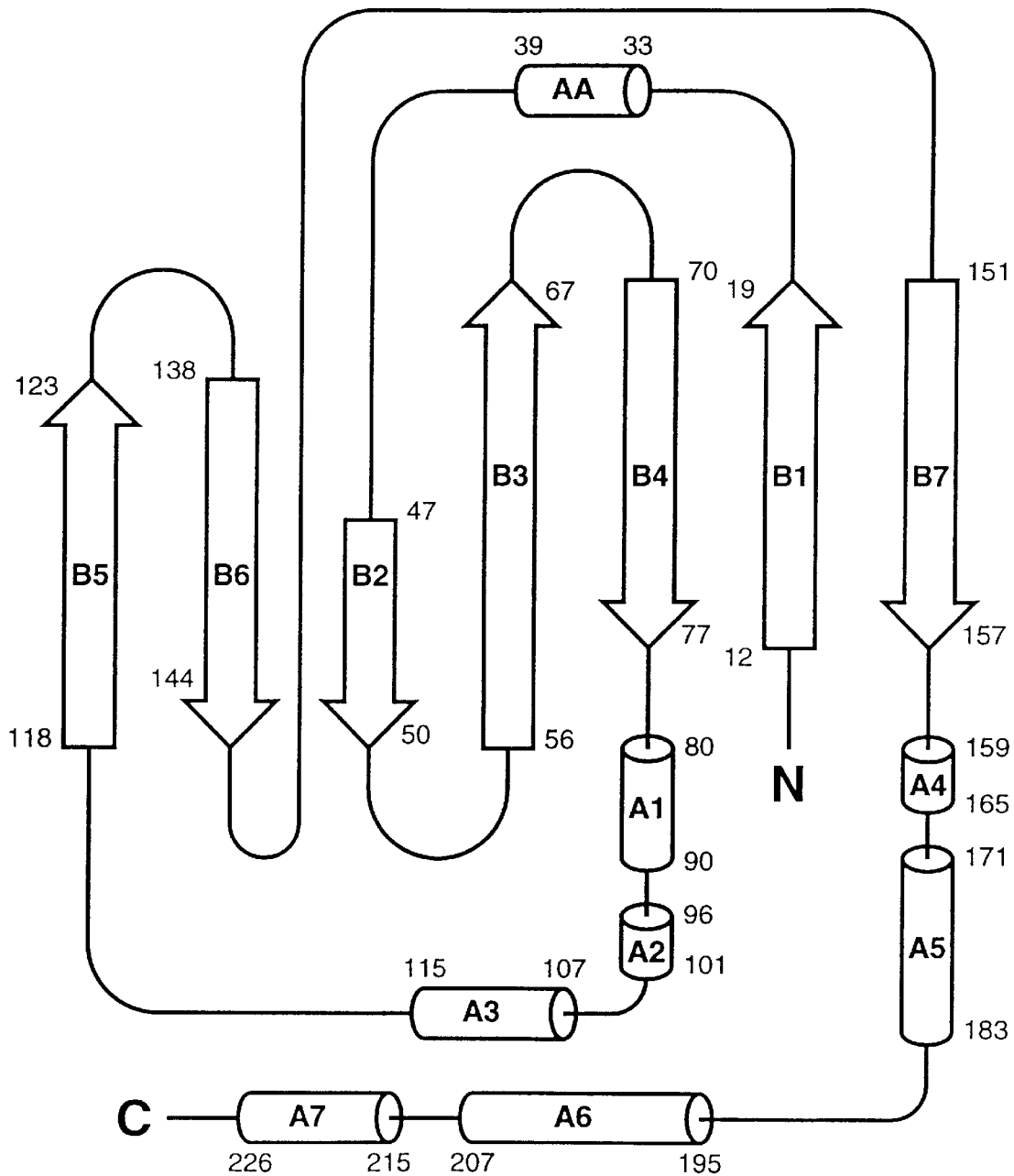
FIG. 35 is a topology diagram of the VZV monomer of FIG. 33A with helices (AA through A7) represented as cylinders, strands (B1 through B7) represented as arrows and termini as N or C. Strands B5 and B7 are next to each other. Amino acid positions are indicated.

The model of the VZV enzyme used in the crystal structure study consisted of residues 11–236 of SEQ ID NO: 5. The VZV structure model consists of 211 amino acids. A surface loop of aa 127–136 is disordered in the crystal, as are the last 5 amino acids at the C-terminal of VZV. In VZV, an additional helix has been observed in the region between residues 31–39 of SEQ ID NO: 5. The fold is characterized by 7β strand and 8 α-helices as depicted in FIGS. 1 and 35. The loop containing residues 22–55 in the CMV protease is disordered in the crystal, but as for HSV-1 and HSV-2 proteases, the corresponding loop in the VZV protease crystal is observed. This loop is situated near the active site and is proposed to enclose part of the substrate binding groove, the S subsites [I. Schechter and A. Berger, *Biochem. Biophys. Res. Commun.*, 27:157–162, (1967)].

FIG. 22A–22C disclose only the protein coordinates near the active site region (at amino acid residues Ser 120, Ser 122, His 52, Lys 54, Cys 143, Arg 147 and Arg 148 of SEQ ID NO: 5) of the VZV protease according to this invention. These data are reported for crystals with lattice constants of a=90.0 Å, b=90.0 Å, c=117.4 Å, α=90°, β=90° and γ=90°, with a space group=$P6_422$. FIG. 23A–23SS disclose protein coordinates of the VZV protease crystalline structure. FIG. 24A–24C provide the distances in Angstroms between every two atoms that are less than 5 Å from the active site for VZV protease. FIG. 25A–25D illustrate the bond angles between interresidue atoms that are within four Å apart in the active site region near Ser 120, His 52 and His 139 of the VZV protease [SEQ ID NO: 5] according to this invention. FIG. 26 provides the dihedral angles of the tetra active site formed by Ser 120, His 52 and His 139 of the protease [SEQ ID NO: 5].

The VZV protease crystal structure novel fold is discussed in more detail in D. below. The Novel active site is discussed in part E.

D. The novel fold

1. HSV-2 and HSV-1 Proteases

With reference to FIGS. 27A, B and C, the structures of the liganded and unliganded forms of HSV-2 are nearly identical. The binding of DIP to the HSV-2 protease structure does not alter the conformation of the enzyme. The root mean square deviation between the liganded and unliganded forms is 0.4 Å. The presence of the DIP changes interactions only within the active site of the enzyme but not the location of the active site or overall three dimensional structure of the enzyme.

Figure 28A:
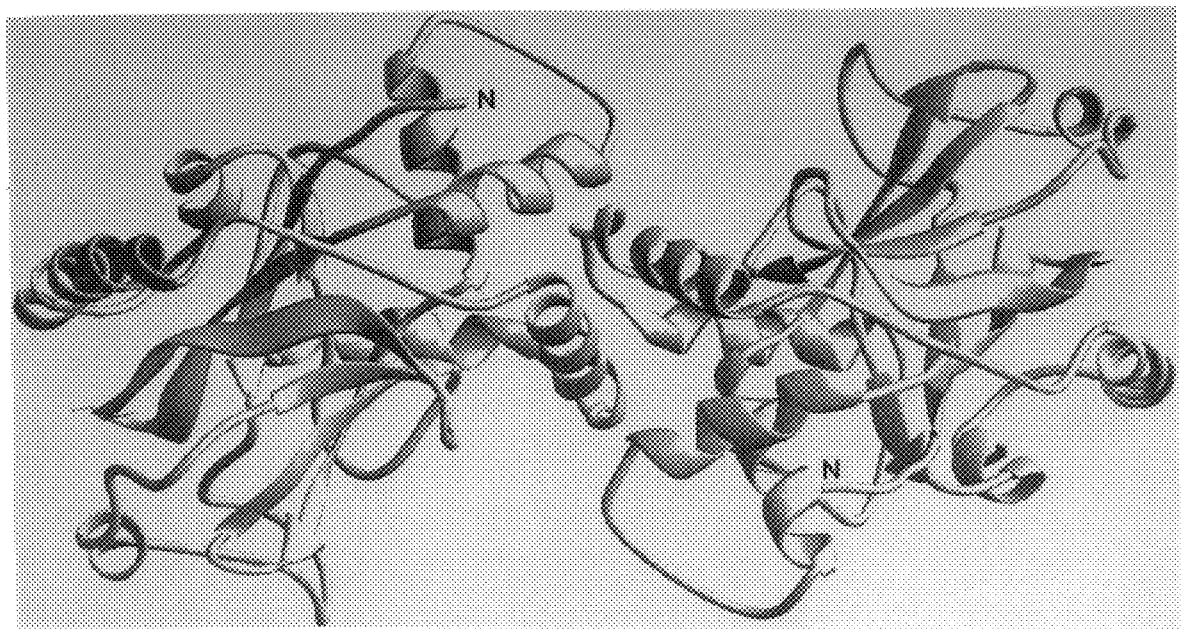
FIG. 28A is a three dimensional ribbon diagram of the HSV-1 protease dimer. The amino terminus is indicated by N. The drawing was produced using the program RIBBONS [Carson, M. *J. Mol. Graphics* 5, 103–106 (1987)].
Figure 28B:
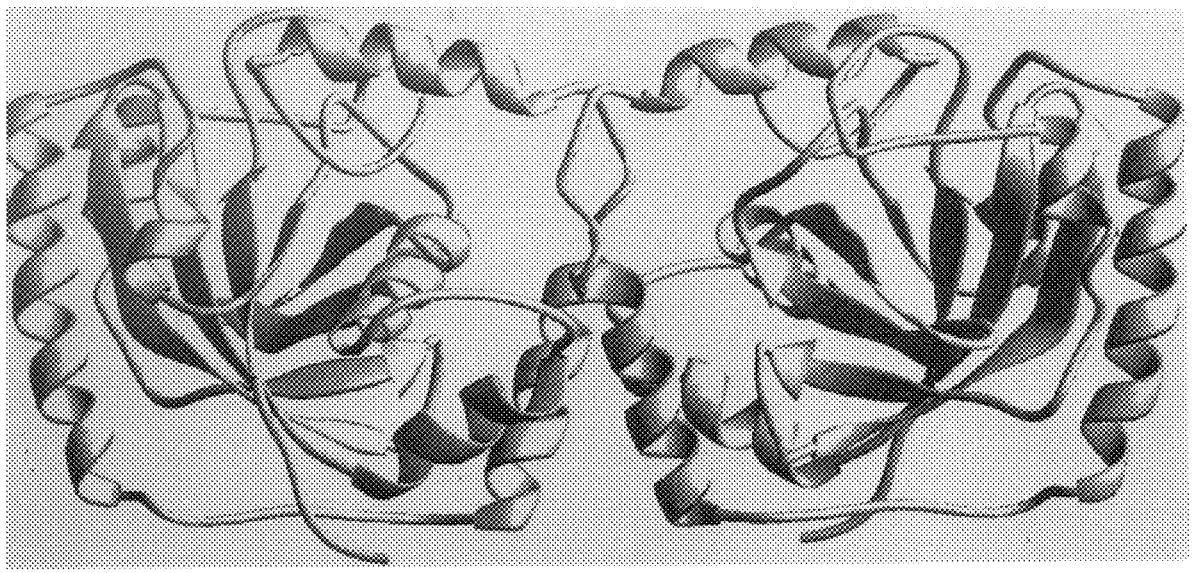
FIG. 28B is the same structure as in FIG. 28A, viewing from 90° away.
Figure 31:
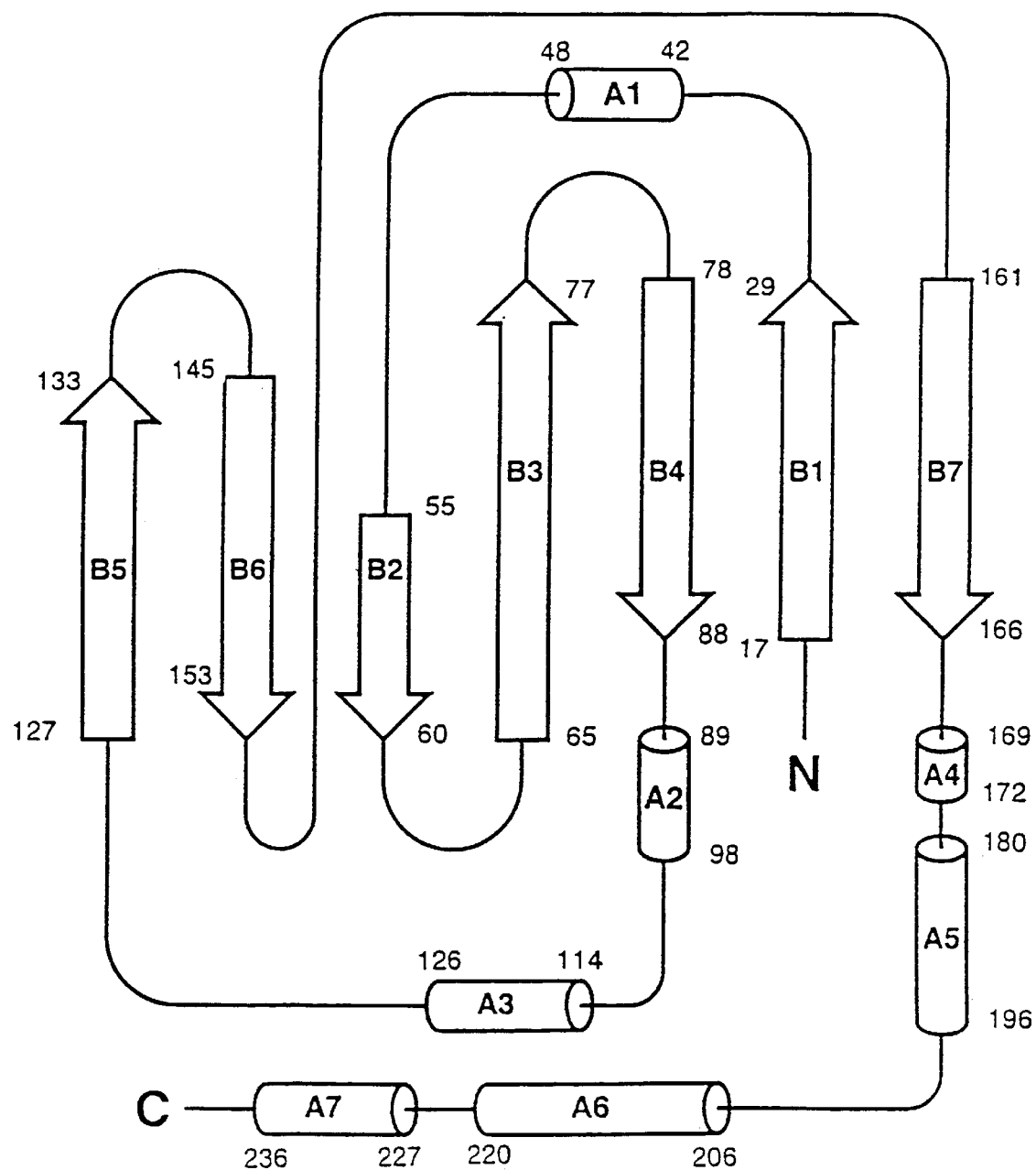
FIG. 31 is a topology diagram of the HSV-2 monomer of FIG. 29A and HSV-1 monomer of FIG. 30A with helices (A1 through A7) represented as cylinders, strands (B1 through B7) represented as arrows and termini as N or C. Strands B5 and B7 are next to each other. Amino acid positions are indicated.

The overall folds of the HSV-1 and HSV-2 protease dimers are comprised of two β-barrels. The folds of the HSV-2 protease are discussed above. The overall fold of the HSV-1 protease dimer is illustrated in FIGS. 28A and 28B. For each protease, seven b-strands form the core of each barrel (FIG. 29A,B,C for HSV-2 and 30A, 30B for HSV-1), each of which can be classified as an orthogonally packed β-barrel [(Chothia and Janin *Biochemistry*, 21: 3955–3965 (1982)], with the following exceptions: strands B6 and B7 are parallel, unlike most orthogonally packed b-barrels. Also, strand B3 (aa 65–77) is a β-bend that closes one corner of the barrel, but the other corner lacks this kind of classical closure and is maintained by only two hydrogen bonds between strand B5 (aa 127–133) and B7 (aa 161–166) [SEQ ID NO: 3 and 4]. Among well known serine proteases, the N-terminal domain of trypsin is also an orthogonally packed b-barrel, but superposition with the HSV-1 or HSV-2 protease barrel does not reveal any similarities and positions the active sites in different regions of the fold. Moreover, the β-strands (FIG. 31 for HSV-2 and HSV-1) are arranged differently in the two structures. For example, the first four strands of HSV-2 protease (B1, B2, B3 and B4) form a typical Greek Key motif, while those in trypsin do not. Therefore, it is reasonable to conclude that the HSV-2 and HSV-1 protease barrels are evolutionarily unrelated to other known non-herpes serine proteases.

The seven alpha helices of liganded and unliganded HSV-2 protease and HSV-1 do not surround the barrel but rather cluster towards the ends. Alpha helix A1 seals one end while helices A2, A3, A6 ,and A7 close the other. Of these, helices A6 and A2 with the corresponding helices of the dimer mate define a unique dimer interface that reveals an approximately 30 degree twist between the corresponding monomers. While four of the seven helices are at either end of the barrel the other two are on the same side of the structure, away from the active site.

For the DIP-liganded HSV-2 protease structure, the transition state analog inhibitor diisopropyl fluorophosphate was added to the enzyme in which the highly reactive (P-F) linkage undergoes displacement by the serine hydroxyl group. Once bound to the nucleophile (enzyme) the ligand is referred to as diisopropyl phosphate. The DIP-liganded HSV-2 protease has the inhibitor diisopropyl phosphate covalently bound to the active site serine (Ser 129).

Figure 30A:
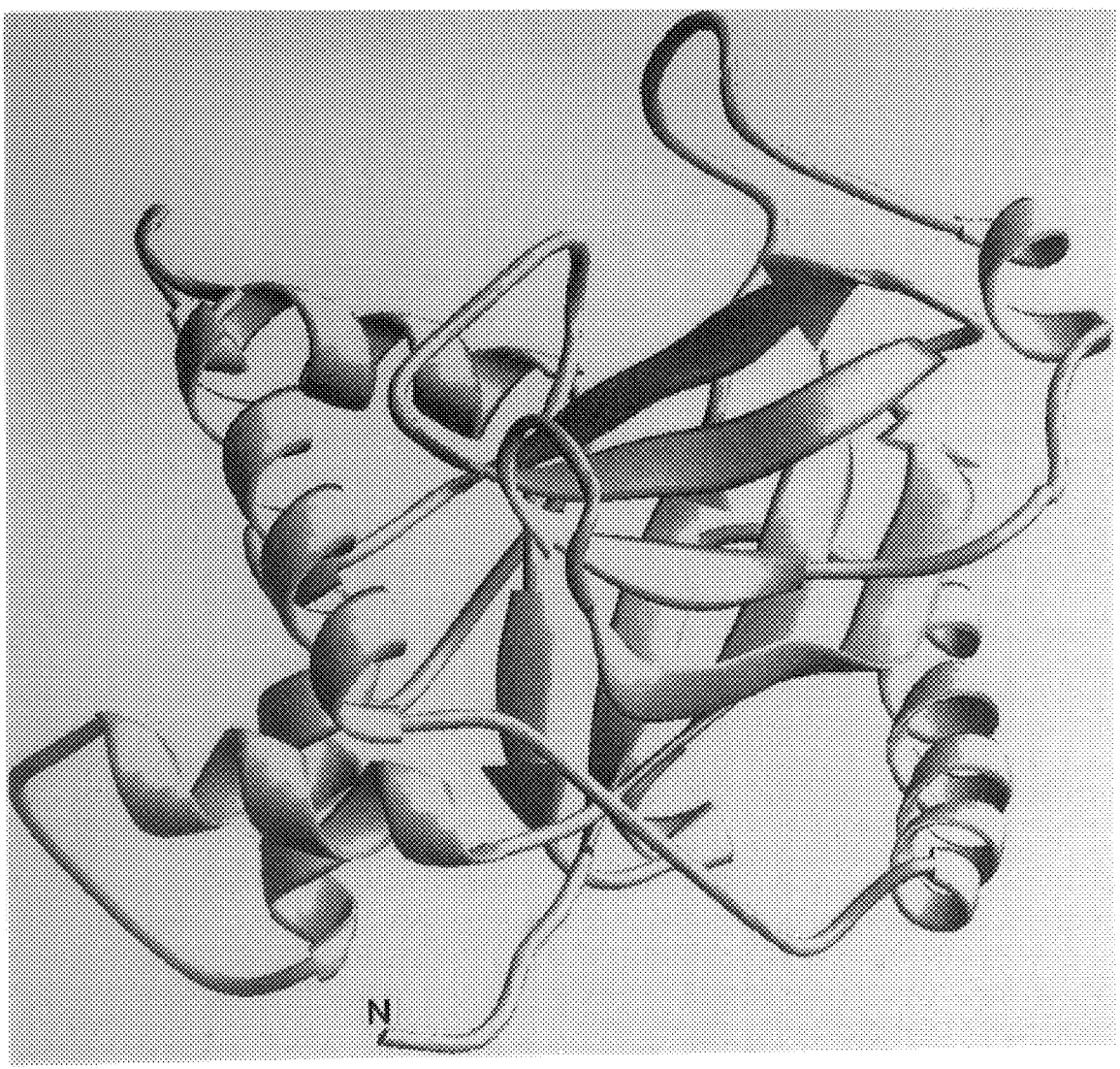
FIG. 30A is a three dimensional diagram of the HSV-1 protease monomer. The amino terminus is indicated by N. The drawing was produced using the program RIBBONS [Carson, M. *J. Mol. Graphics* 5, 103–106 (1987)].
Figure 30B:
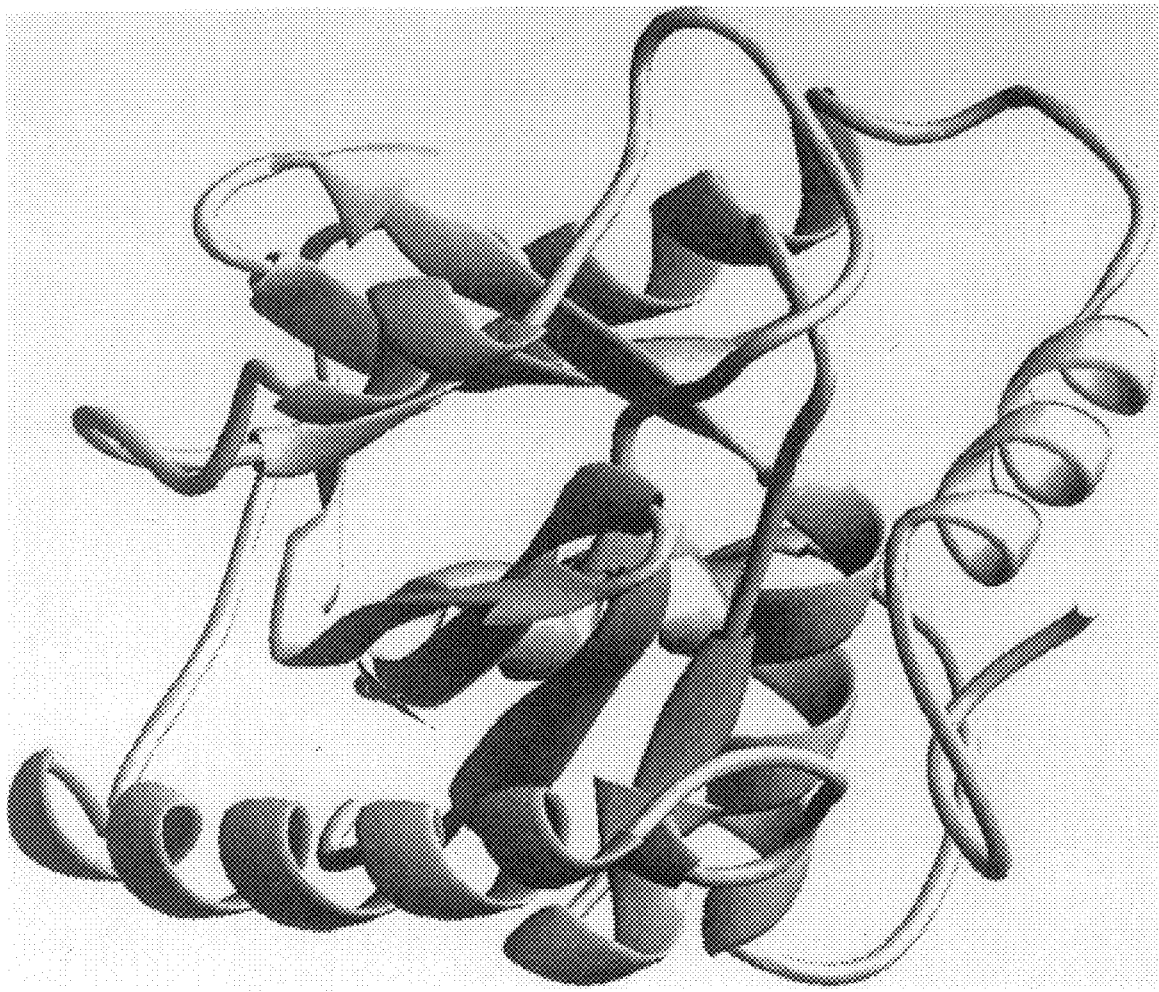
FIG. 30B is the same structure as in FIG. 30A, viewing from 90° away.

Unlike trypsin, the active sites of HSV-1 and HSV-2 proteases do not lie at the intersection of the two domains but rather bind in a cleft formed by one side of the barrel at strand B5 and a small loop between strands B6 and B7 made of residues 153–157 (FIGS. 27A,B,C and 29A,B,C for HSV-2 and FIGS. 28A, 28B and 30A. 30B for HSV-1). The DIP $C_\beta$ atom of the DIP-liganded HSV-2 protease is 17 Å from the closest point between the two monomers at helix A6. In each of the HSV-1 and HSV-2 protease structures, residues 34–38 [SEQ ID NO: 3 and 4] in the large loop between B1 and A1 approach the top of the cleft but do not completely cover it. The loop of residues 134–140 [SEQ ID NO: 3 and 4] is disordered in the HSV-1 and HSV-2 structures. This loop is a region of low homology among the herpes proteases (FIG. 1), and may suggest different conformations of the loop. Residues 104–110 and 104–112 are disordered in the DIP-liganded HSV-2 and unliganded HSV-2 protease structures, respectively [SEQ ID NO: 4]. Residues 102–110 of HSV-1 [SEQ ID NO: 3] are disordered in the structure. These regions represent regions of low homology among the herpes proteases; however, the corresponding regions are ordered in both the VZV and CMV proteases, where a small alpha helix is seen.

An intriguing non-crystallographic dimer interface in each of the HSV-1 and HSV-2 proteases is made up of the interactions between helices A6 and A2 with the corresponding helices in the dimer mate. The dimer interface is identical between the liganded and unliganded HSV-2 proteases. These same helices also interact in CMV but with a different orientation in relation to each other. In CMV protease the two A6 helices of each monomer are nearly co-axial. In the HSV-1 and HSV-2 proteases they are separated at the N-terminal ends by about 30 degrees, at a distance of nearly 14 Å. Because of the twist between the A6 helices in the HSV-1 and HSV-2 proteases, contacts can only be formed between the C-terminal ends of the helices. In both the liganded and unliganded HSV-2 proteases, a hydrogen bond (3.0 Å) is seen between the side chains of His 211 and Glu 207 [SEQ ID NO: 4]. When comparing the dimer interface of HSV-1, HSV-2 and CMV proteases, changes are also seen in the A2 helix position with respect to A6. In HSV-2 protease [SEQ ID NO: 4], hydrogen bonds are formed between Ala 98 on A2 to both Ser 215 -OH (2.7 Å) and Asn 219 (3.3 Å) on A6. These two interactions and that between 211 and 207 [SEQ ID NO: 4] do not occur in either CMV or VZV proteases. In CMV and VZV proteases the dimer interface is along a two-fold crystallographic axis, which could cause subtle changes in the interactions between the monomers.

There are other notable structural differences between HSV-2 and HSV-1 and those of the CMV and VZV proteases discussed below. One difference is in the segment between A2 and A3. In the structure of CMV protease, this segment assumed a "closed" conformation, making intra-molecular contacts and being part of the dimer interface. In the VZV protease structure, this segment adapts a completely "open" conformation, interacting only with another symmetry-related molecule to form a different dimer interface. In the liganded and unliganded HSV-2 protease structures, part of this loop is disordered but is a close distance (9 Å) to another symmetry-related molecule. This suggests that HSV-2 and VZV proteases may be capable of using this segment to form higher order oligomers.

It has been reported that CMV protease dimerization is important for maintaining the activity of the protease [Darke, et al., *J. Biol. Chem.*, 271, pp. 7445–7449 (1996)]. In fact, the Darke publication and S. Margosiak, et al. Biochemistry 35, 5300–5307 (1996) have shown that the CMV protease molecules self-associate to form dimers in solution with a monomerdimer equilibrium constant of approximately $10^{-6}$M and that the dimeric form of the protease is the only active species. There is now a similar report on the dimer formation of HSV-1 protease [Schmidt, U. and Darke, P. L., *J. Biol. Chem.*, 272, pp. 7732–7735 (1997)], but with a similar dimerization response in the presence of glycerol [Darke et al., *J. Biol. Chem.*, 270: 22697–22700 (1995)]. Furthermore, enzymatic assays are often reported in the presence of aggregation-promoting reagents such as glycerol or citrates [Burck et al., Hall et al., both cited above].

Based on the present structure it is difficult to determnine why the dimer is required for activity, since the interface is not near either active site. The addition of the covalent inhibitor DIP does not appear to alter the dimer interface. However, rearrangements of the helices at the interface in the absence of a dimer could have profound effects on the conformation in the active site region. Thus, dimerization is believed to stabilize the conformation of helix A6.

2. The CMV and VZV Proteases

Unlike the structures of other serine proteases having two distinct b-barrel domains, the structures of each of the herpes proteases herein have a single domain.

Figure 32A:
FIG. 32A is a three dimensional diagram of the structure of CMV protease with the core β-barrel highlighted. The amino and carboxyl-termini are indicated by N and C. Disordered portions of the structure are represented by dashed lines. The diagram was drawn with the program MOLSCRIPT [P. Kraulis, *J. Appl. Crystallogr.*, 24: 946–950 (1991)].
Figure 32B:
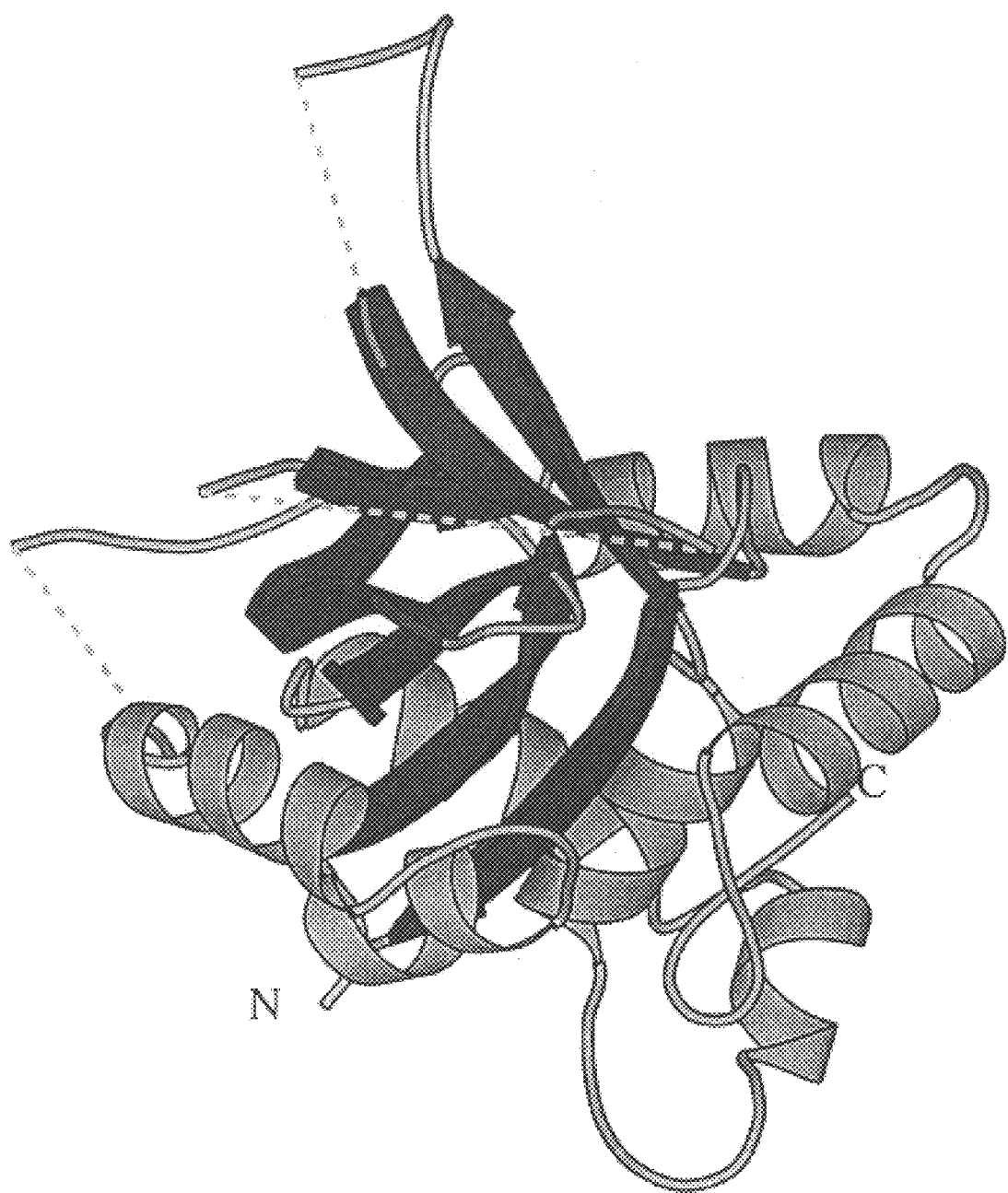
FIG. 32B is the same structure as in FIG. 32A, viewing from 90° away.
Figure 33A:
FIG. 33A is a three dimensional diagram of the structure of VZV protease with the core β-barrel highlighted in two shades of gray. The amino and carboxyl-termini are indicated by N and C. A disordered portion of the structure is represented by a dashed line. The diagram was drawn with the MOLSCRIPT program [P. Kraulis, *J. Appl. Crystallogr.*, 24:946–950 (1991)].
Figure 33B:
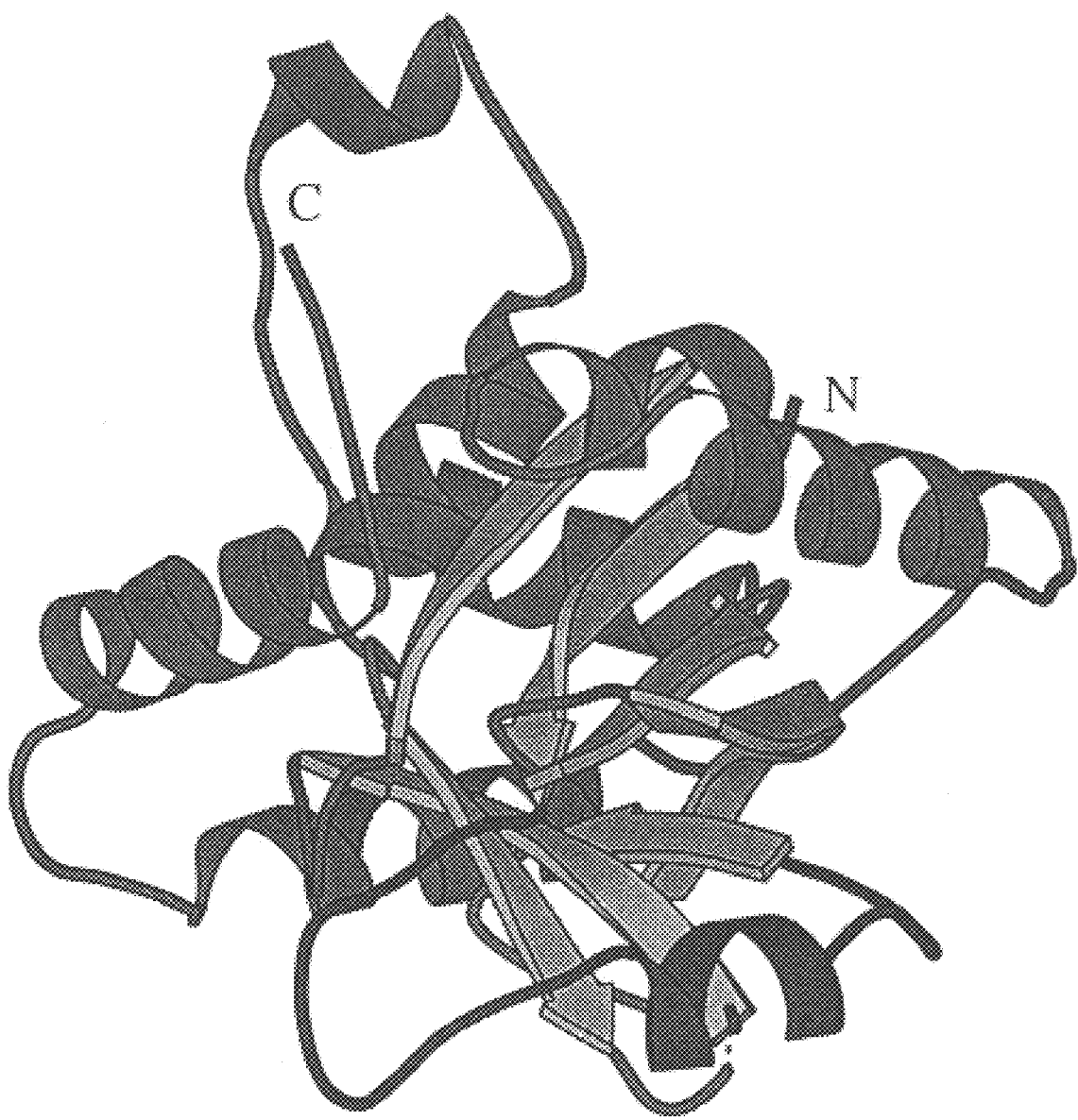
FIG. 33B is the same structure as in FIG. 33A, viewing from 90° away.
Figure 34:
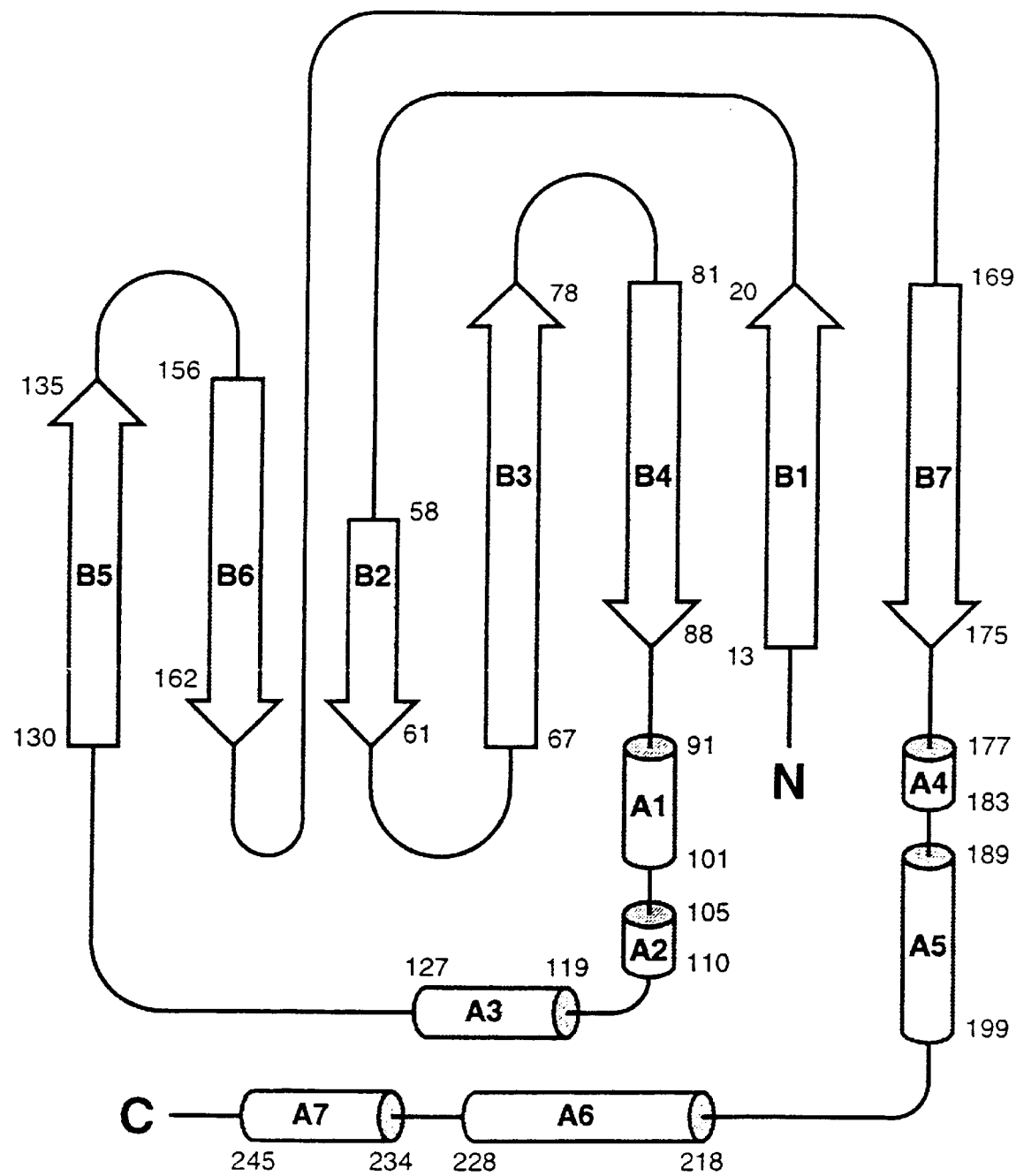
FIG. 34 is a topology diagram of the CMV monomer of FIG. 32A with helices (A1 through A7) represented as cylinders, strands (B1 through B7) represented as arrows and termini as N or C. Strands B5 and B7 are next to each other. Amino acid positions are indicated.

The overall fold of the CMV and VZV monomers can be best described as a 7-stranded β-barrel core which in CMV is decorated with seven α-helices on three sides (see FIGS. 32A and 32B) and in VZV is decorated with eight α-helices (FIGS. 33A and 33B). The core β-barrel can be classified as an orthogonal packed β-barrel as described in detail by C. Chothia & J. Janin, *Biochemistry*, 21: 3955–3965 (1982). Of the seven helices of CMV, three were found between strand β4 and β5, and four helices after strand β7 (FIG. 34).

Certain features of the CMV protease and VZV protease barrels are quite distinct. First, the CMV protease and VZV protease barrels contain two parallel strands (FIGS. 34 and 35) and thus are mixed β-barrels, while most of the orthogonal packed β-barrels are formed exclusively from anti-parallel strands. Second, strand β3 [aa67–78 of CMV (SEQ ID NO: 1) and aa57–67 of VZV (SEQ ID NO: )] are β-bends that close one comer of the barrel, but the other comer lacks this kind of classical closure and is maintained by only two hydrogen bonds between strand B5 [aa130–135 of CMV (SEQ ID NO: 1) and aa118–123 of VZV (SEQ ID NO: 5)] and B7 [aa169–175 of CMV (SEQ ID NO: 1) and aa151–157 of VZV (SEQ ID NO: 5)].

Interestingly, the N-terminal β-barrel of trypsin's prototype serine protease is an anti-parallel β-barrel that is also orthogonally packed. However, superposition of the CMV protease, VZV protease and trypsin barrels did not reveal any further resemblance, and show the enzyme active sites of the CMV and VZV proteases are at completely different regions of the fold than the active site of trypsin. Moreover, the CMV and VZV β-strands (FIG. 34 and FIG. 35) are arranged differently than in trypsin. For example, the first four strands of CMV and VZV proteases (B1, B2, B3 and B4) form a typical Greek Key motif, while those in trypsin do not. Therefore, it is reasonable to conclude that the CMV protease and VZV protease barrels are evolutionarily unrelated to other, non-herpes serine proteases. The overall fold is also unique to CMV, VZV and other herpes proteases.

Figure 36A:
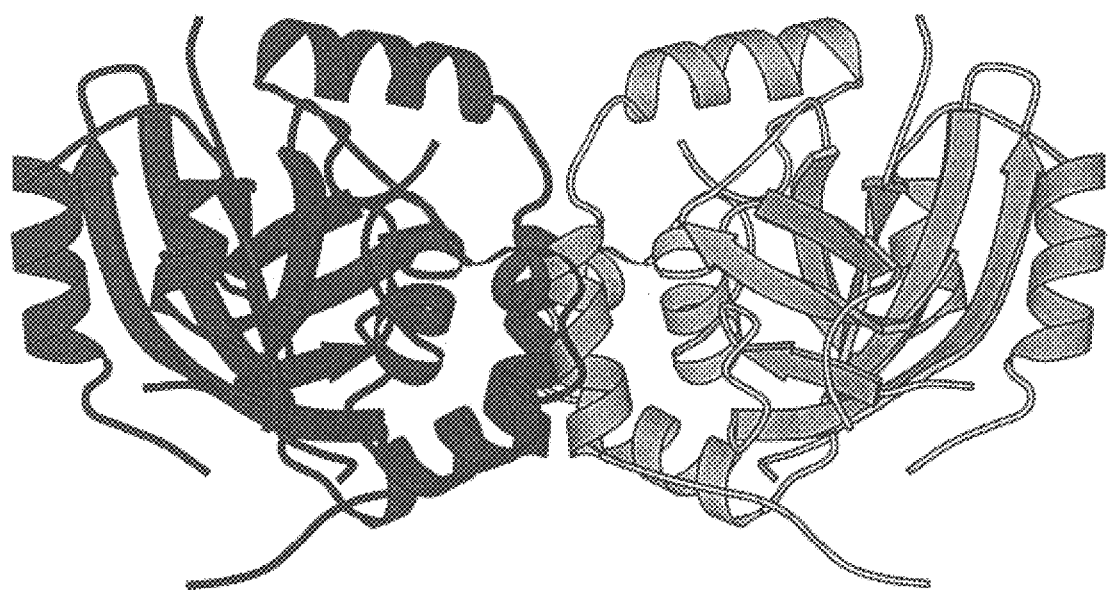
FIG. 36A is a three dimensional diagram of the CMV protease dimer, viewing perpendicular to the two-fold axis, which was drawn using the MOLSCRIPT program.
Figure 36B:
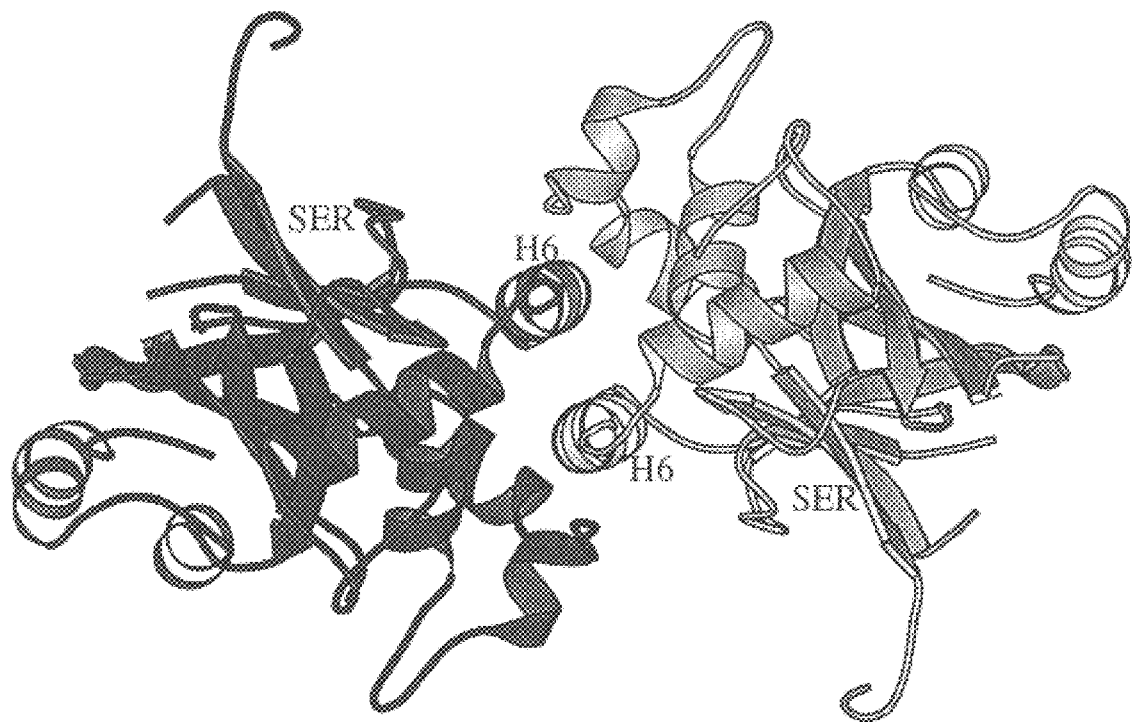
FIG. 36B is the dimer of FIG. 36A, viewing parallel to the two-fold axis. The two parallel helices are indicated by A6. The active site regions are represented by Ser at the Ser 132 positions [SEQ ID NO: 1].

An intriguing dimer interface in CMV and VZV proteases has been identified around two-fold crystallographic axes (FIGS. 36A and 36B, 37). The dimer interface is mainly made-up of a set of four helices (A1, A2, A3 and A6) of one monomer that surrounds helix A6 of the other monomer, where the two symmetry-related A6 helices are parallel (FIG. 37). The dimer interface is predominantly hydrophobic, involving many side chain van der Waals interactions for residues such as phenylalanines, leucines and valines. Despite the tight packing in the crystal, this dimer interface is much more significant than that of other inter-molecular interfaces within the crystal. The arrangements of the helices and the extent of the interface seem to suggest that this is not a simple coincidence of crystal packing.

The dimer interface is of importance in maintaining the activity of the proteases. The calculated interface area is between 850 (Connolly) to 1300 Å$^2$ (GRASP) from the crystal structures of CMV and VZV proteases. As for HSV-2 and HSV-1, from the crystal structures, it is noted that the dimer interface is not in the immediate vicinity of the active site. Also, the active sites of the two monomers are quite distant from each other (FIG. 36B and FIG. 37).

Although the dimer interfaces in VZV and CMV proteases are similar, there are notable differences in their structures. Helices A6 from both monomers were almost parallel in the structure of CMV protease, but helix A6 is twisted about 30° in the VZV protease structure (FIG. 37). The helix A6 in VZV protease has one more turn at the N-terminal, and the loops connecting A5 and A6 are quite different in the tnvo structures (FIG. 1). The biggest difference resides in the segment containing the small helix A2. In the structure of CMV protease, this segment assumed a "closed" conformation, making intra-molecular contacts and being part of the dimer interface. However, in the VZV protease structure, this segment adapts a completely "open" conformation, interacting only with another symmetry-related molecule to form a different dimer interface (FIG. 37). This suggests that VZV protease may be capable of using this segment to form higher order oligomers. By analogy with CMV protease, the VZV protease dimer is essential for enhanced catalytic activity. In the absence of a dimer, the rearrangements of helices involved in the interface may have profound effects on the conformation in the active site region. For example, the A6 helix may move toward the active site cavity and therefore affect the positioning of residues in the active site or it may simply block access to the substrate.

E. The novel active site

The catalytic mechanism of classical serine proteases involves an active site triad composed of a serine, histidine and an aspartic acid. However, although several prior art studies focused on mutagenesis of aspartic and glutamic acids of herpes proteases, none led to a correct identification of the third member of the herpes protease catalytic triad.

Figure 38A:
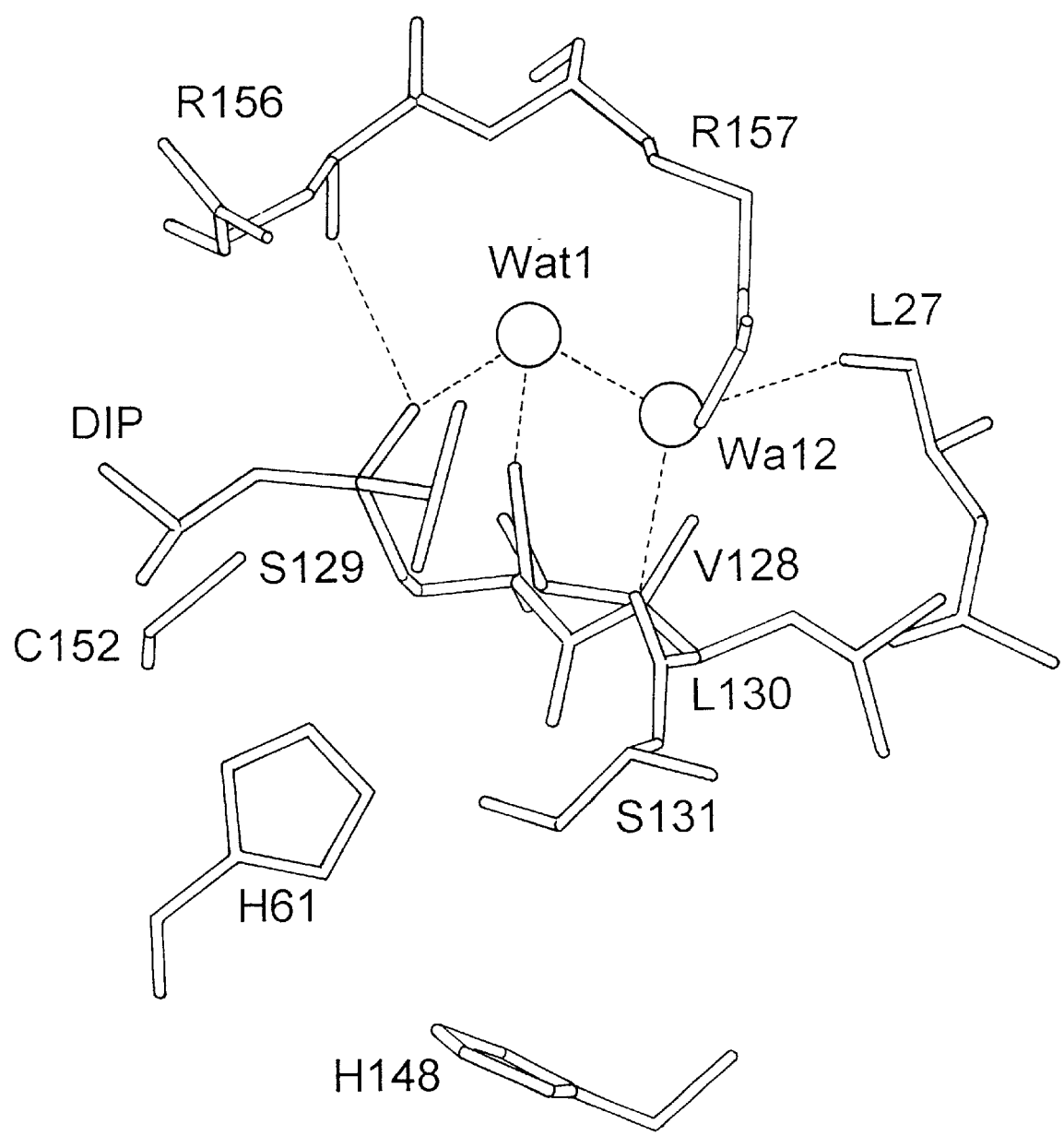
FIG. 38A is a model of the DIP-liganded HSV-2 protease active site in a thick stick representation. All carbon atoms are in light shading; nitrogen, oxygen and sulfur atoms in dark shading. The catalytic residues are Ser 129, His 61 and His 148. Other residues of importance are Arg 156, Arg 157 and possibly Ser 131, Cys 152, Leu 27, Val 128, Leu 130 [SEQ ID NO: 4] and the two water molecules Wat1 and Wat2 shown as spheres. Hydrogen bonds between the residues in this active site are shown with dotted lines.
Figure 38B:
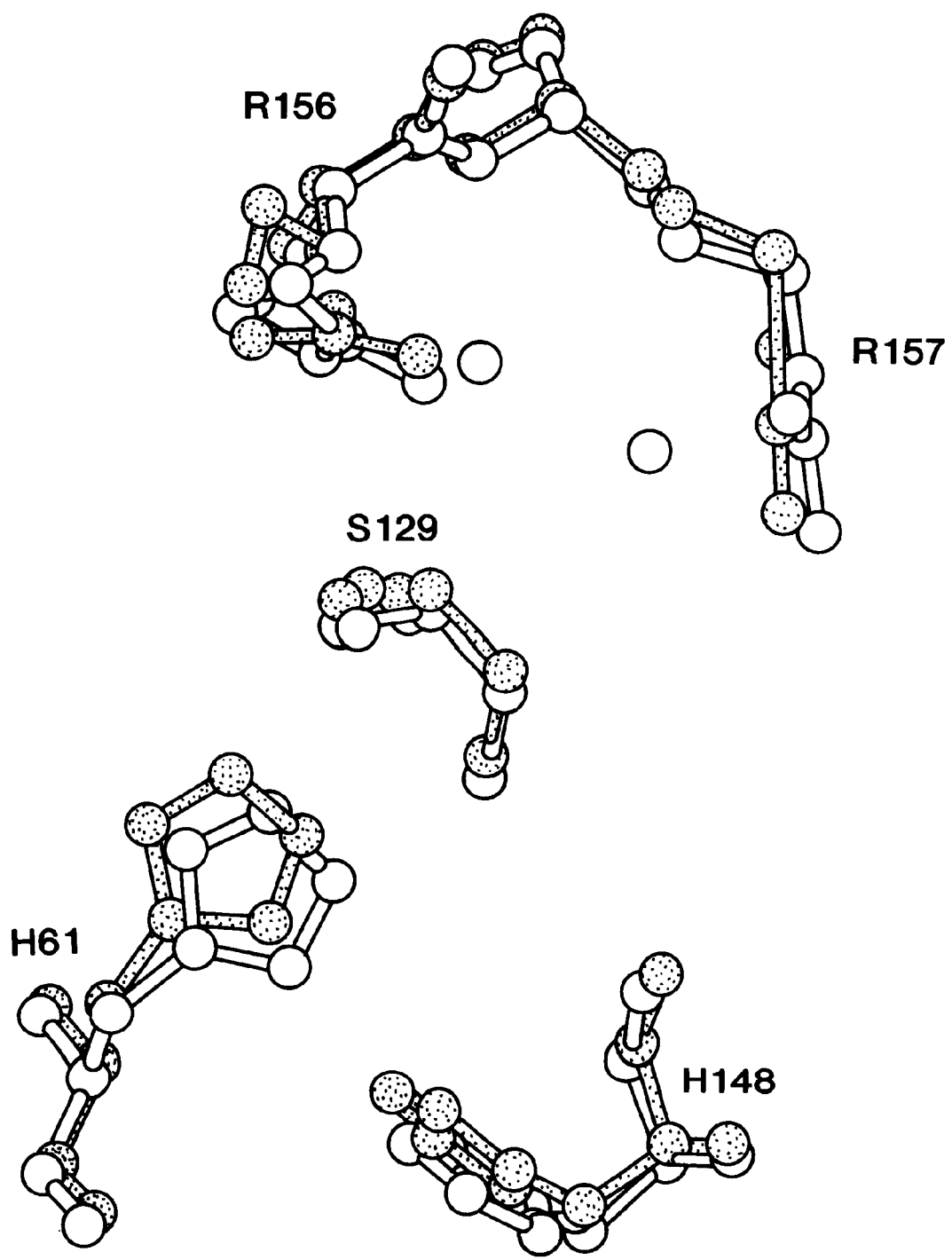
FIG. 38B is a superposition of the unliganded HSV-2 protease (dark) and the DIP-liganded HSV-2 protease (light) structures where the DIP ligand has been removed from the active site serine for clarity.
Figure 39A:
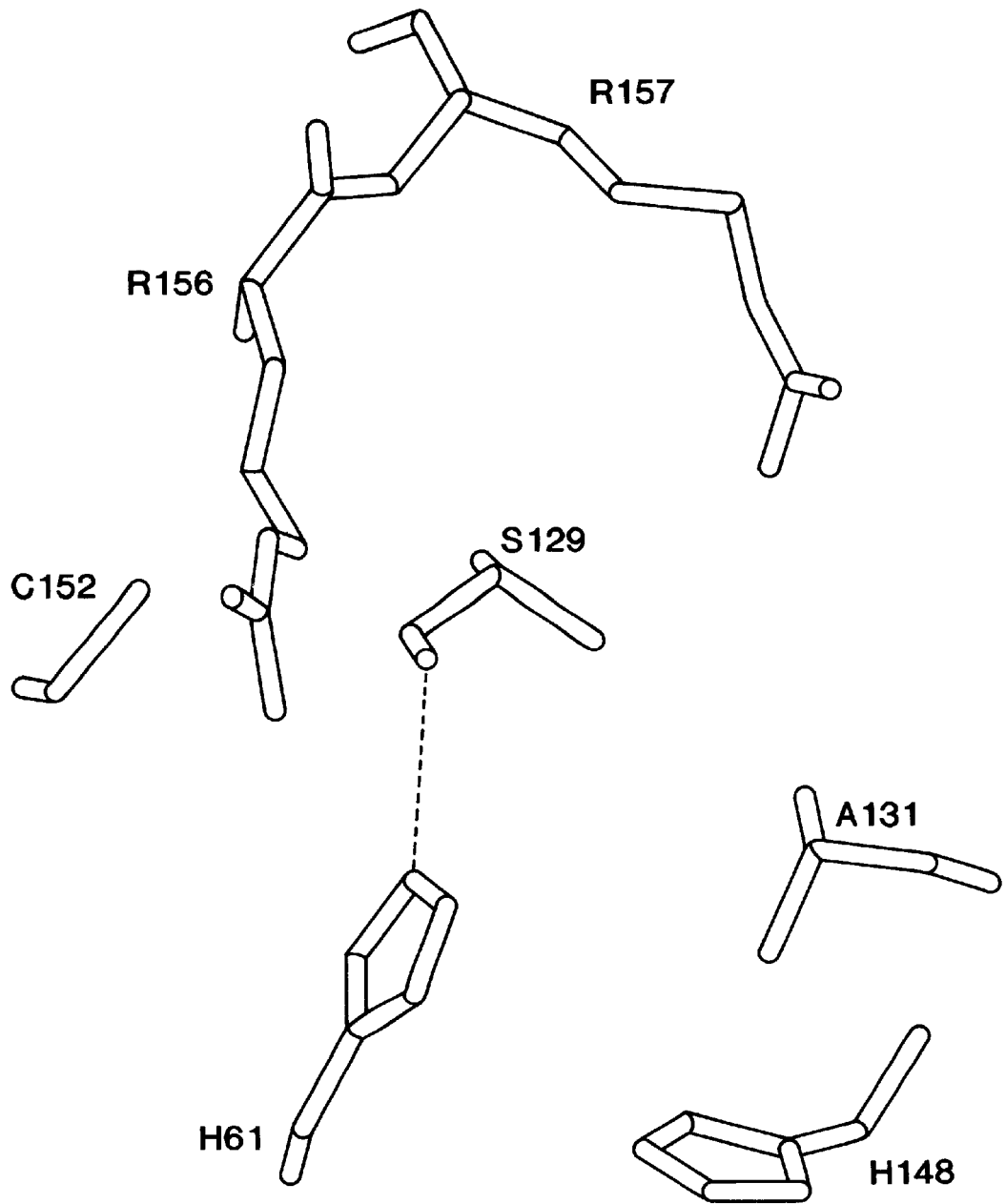
FIG. 39A is the HSV-1 protease active site in a thick stick representation. All carbon atoms are in light shading; nitrogen, oxygen and sulfur atoms in dark shading. The catalytic residues are Ser 129, His 61 and His 148 [SEQ ID NO: 3]. Other residues of importance are Arg 156, Arg 157 and possibly Ala 131 and Cys 152 [SEQ ID NO: 3]. Hydrogen bonds between the residues in this active site are shown with dotted lines.

The crystal structure of liganded and unliganded HSV-2 protease reveals an active site composed of a serine (Ser 129), a histidine (His 61), and a third residue also a histidine (His 148) (FIG. 38A,B), sequences which are conserved in all known herpes proteases (FIG. 1). The crystal structure of HSV-1 protease reveals an identical active site (FIG. 39A). The crystal structure is in agreement with early protease inhibition experiments on HSV-1 protease (sharing 90% sequence identity and identical numbering to HSV-2 protease) that identified HSV-1 as a serine protease and that substitution of His 148 and His 61 abolished [SEQ ID NO: 3] enzymatic activity (Liu & Roizman, DiIanni I). Similar studies on CMV protease had also demonstrated the homologous residues to His 61 and Ser 129 to be essential (Stevens, Welch I). Although several studies focused on mutagenesis of aspartic and glutamic acids of herpes proteases, none led to a correct identification of the third member of the catalytic triad. FIG. 38A shows the DIP molecule covalently bound to Ser 129 [SEQ ID NO: 4]. This is consistent with mutagenesis and chemical modification studies that identified Ser 129 as the active site nucleophile in HSV-1 protease [SEQ ID NO: 3] (DiIanni II).

As with HSV-2 and HSV-1 proteases, the crystal structure of the CMV and VZV proteases of the invention reveals a novel active site containing a serine [Ser 132 for CMV (SEQ ID NO: 1) and Ser 120 for VZV (SEQ ID NO: 5)] and a histidine [His 63 for CMV (SEQ ID NO: 1) and His 52 for VZV (SEQ ID NO: 5)], with the third member of the catalytic triad being a histidine [His 157 for CMV (SEQ ID NO: 1) and His 139 for VZV (SEQ ID NO: 5)] instead of aspartic acid. Mutagenesis and chemical modification studies had identified Ser 132/Ser 120 [SEQ ID NO: 1 and 5, respectively] and His 63/His 52 [SEQ ID NO: 1 and 5, respectively] as part of the catalytic triad [Welch I, Stevens et al., cited above]. Both residues are absolutely conserved in all herpes proteases (FIG. 1).

1. HSV-2 and HSV-1 Proteases

Figure 38C:
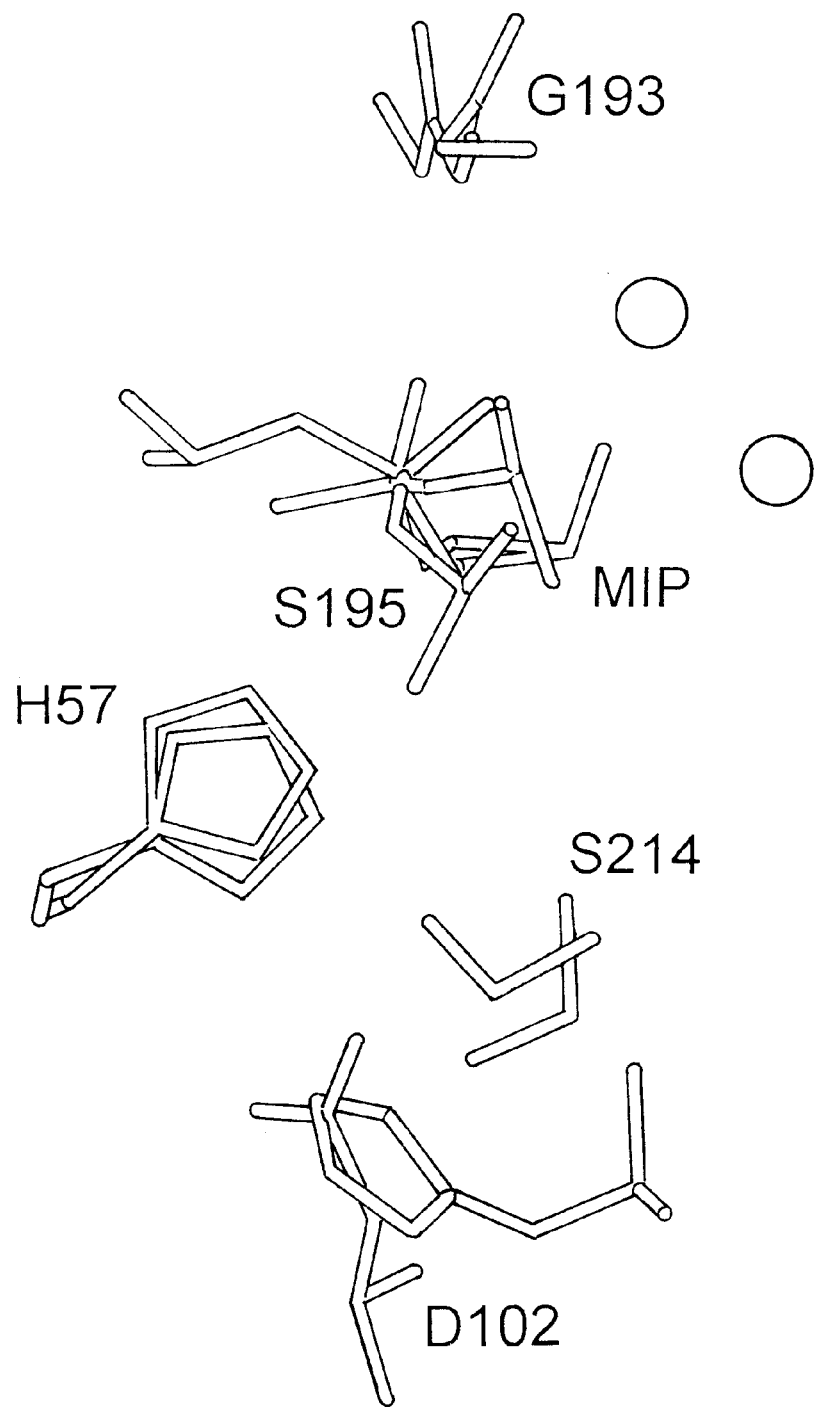
FIG. 38C is the superposition between the active site of DIP-liganded HSV-2 protease and that of the classical serine protease γ-chymotrypsin complexed with mono isopropyl phosphate (MIP). In light shading is the HSV-2 protease in the identical orientation as in FIG. 38A, and in dark shading are the γ-chymotrypsin active site residues. Labels are those of protease γ-chymotrypsin. Hydrogen bonding in the oxyanion hole of γ-chymotrypsin is shown.
Figure 39B:
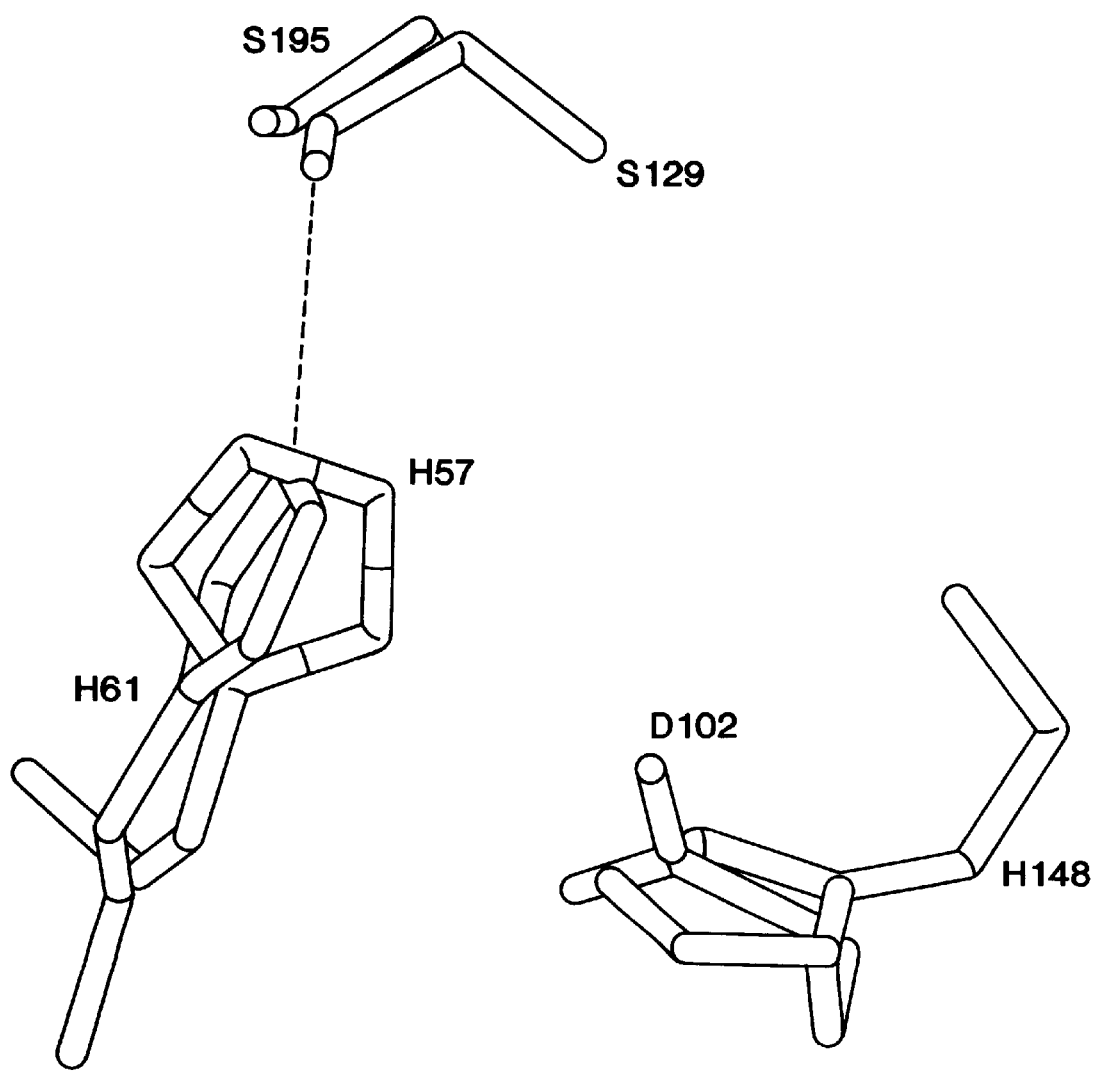
FIG. 39B is the superposition between the active site of HSV-1 protease and that of the classical serine protease trypsin. In light shading is the HSV-1 protease in the identical orientation as in FIG. 39A, and in dark shading are the trypsin active site residues. Labels are shown for both the active site of trypsin (Ser 195, His 57, Asp 102) and HSV-1 protease (Ser 129, His 61, and His 148).

The active site of DIP-liganded HSV-2 protease shows a network of hydrogen bonding between the enzyme active site, the ligand, and two central water molecules (Wat1 and Wat2 (FIG. 38A)). The crucial elements of the HSV-1 and HSV-2 active sites are strikingly similar to trypsin even though the two HSV enzymes share little sequence homology with trypsin and the overall tertiary structures are completely different to trypsin. An overlay of the catalytic triad of γ-chymotrypsin bound to mono-isopropyl phosphate (MIP) with that of the DIP-liganded HSV-2 structure (FIG. 38C), and an overlay of the catalytic triad of trypsin (BPD code ISGT) with that of the HSV-1 protease structure shows this similarity (FIG. 39B). In FIG. 38C, significant overlap is seen between the peptide backbone stabilizing the P=O oxygen of DIP, the catalytic serine residues, and His 61 and His 57 side chains of γ-chymotrypsin and DIP-liganded HSV-2 protease, respectively. FIG. 38C also reveals the overlap of Asp 102 and His 148 [SEQ ID NO: 4], supporting the role of this histidine in catalysis, despite its apparent lack of hydrogen bonds in this structure. Similar results are revealed in FIG. 39B. Not only does this confirm the role of His 148 [SEQ ID NO: 3 and 4] in catalysis, but it also suggests the possibility of converting the HSV-2 and HSV-1 enzymes into those having a normal catalytic triad by replacing His 148 [SEQ ID NO: 3 and 4] with an aspartic acid.

Figure 38D:
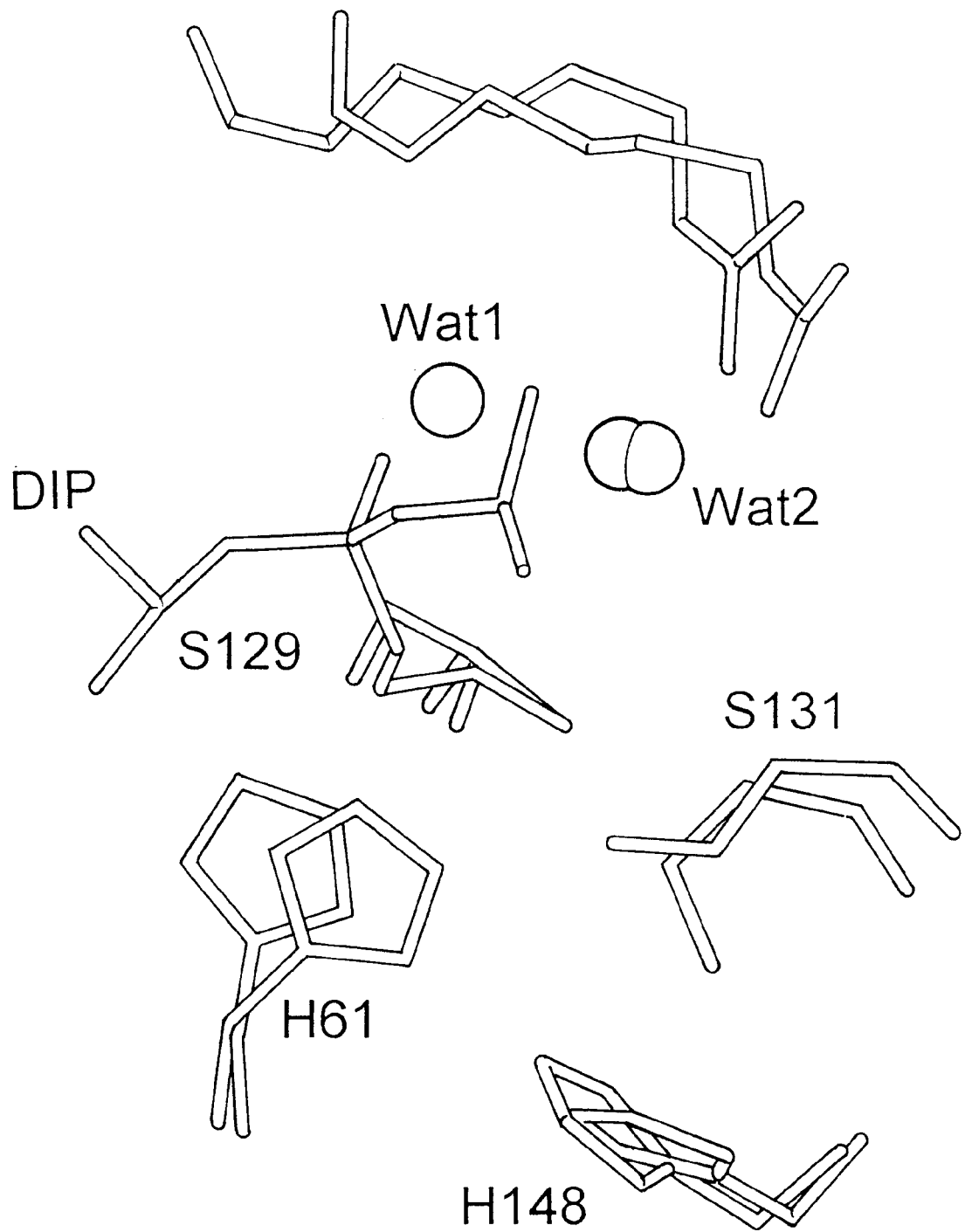
FIG. 38D is the superposition of DIP-liganded HSV-2 protease with CMV protease, illustrating the similarities and differences between the active sites of these two enzymes. Hydrogen bonding is shown for CMV protease but labels are for HSV-2 protease.

Because of the presence of the covalently bound inhibitor DIP, His 61 does not appear to hydrogen bond to Ser 129 [SEQ ID NO: 4] but instead maintains a close interaction with Ser 131 (2.5 Å). This can be compared to a slightly different hydrogen bonding network in apo CMV protease (FIG. 38D) where His 61 has hydrogen bonds to both Ser 129 and His 148 and Ser 131 clearly interacts with His 148 [SEQ ID NO: 1]. This is similar to the hydrogen bonding network in the γ-chymotrypsin/MIP structure where Ser 214 maintains a close hydrogen bond to Asp 102 (FIG. 38C) [SEQ ID NO: 3]. Despite its location in the active site, Ser 131 has been found to be non-essential for catalysis in CMV protease [SEQ ID NO: 1] (Welch I). This position is also an Ala residue in HSV-1 (FIG. 1). The average B factor of the side chain atoms of His 61 in the DIP-liganded HSV-2 protease [SEQ ID NO: 4] is 51 Å², more than twice the average B-factor of the structure, indicating that it is mobile. A rotation about the $C_\beta$–$C_\gamma$ bond could allow a hydrogen bond to Ser 129, and a subsequent rotation about the same bond in His 148 could allow a hydrogen bond between these two residues. These two rotations would present a hydrogen bond of 3.0 Å between His 148 and His 61, about the same distance as in the uncomplexed CMV structure, and thus an alternative set of hydrogen bonds.

Figure 39C:
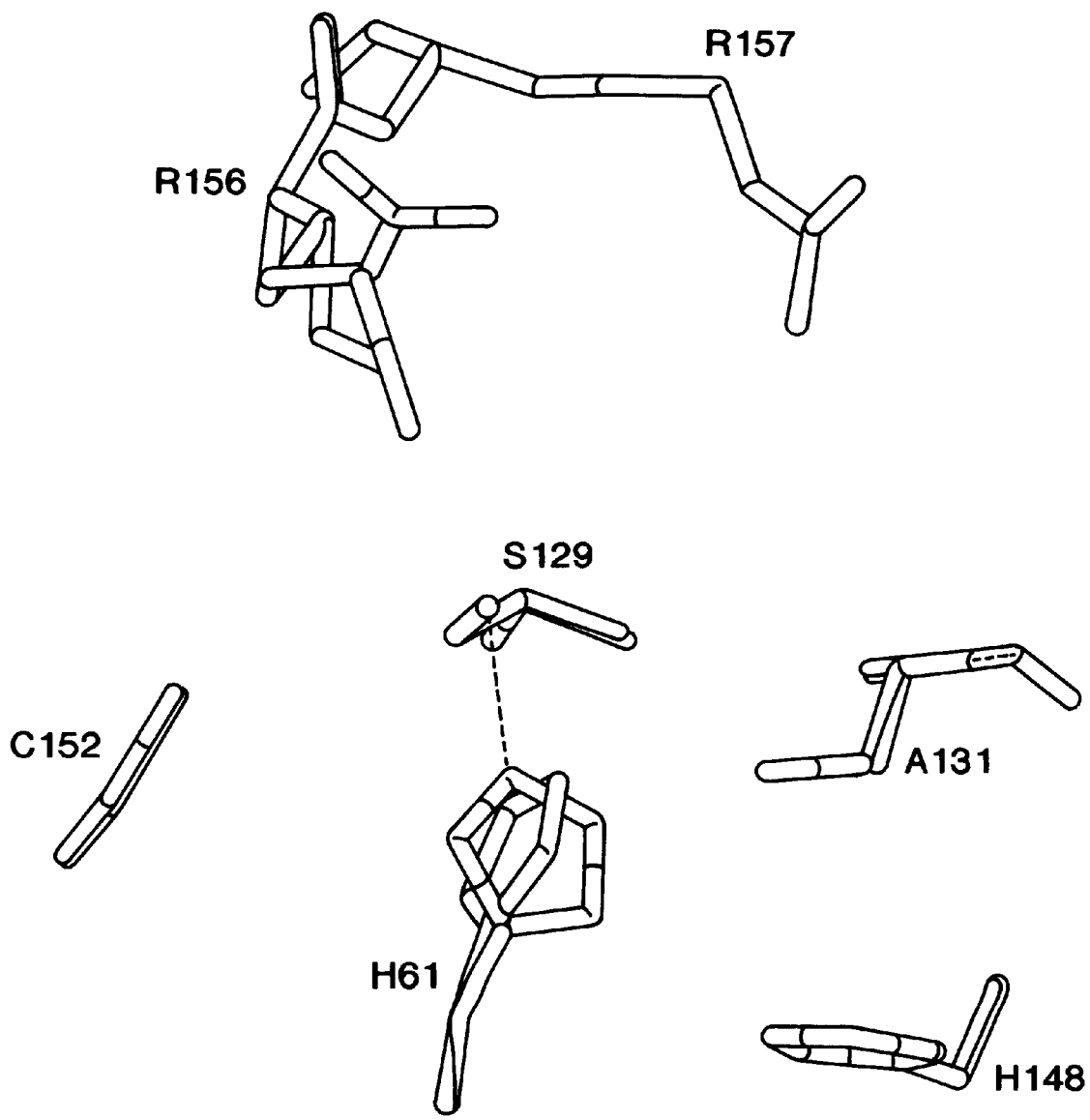
FIG. 39C is the superposition of HSV-1 protease with HSV-2 protease, illustrating the similarities and differences between the active sites of these two enzymes. In light shading is the HSV-1 protease in the identical orientation as in FIG. 39A, and in dark shading are the HSV-2 protease active site residues (numbering of the residues is identical between HSV-1 protease and HSV-2 protease).
Figure 39D:
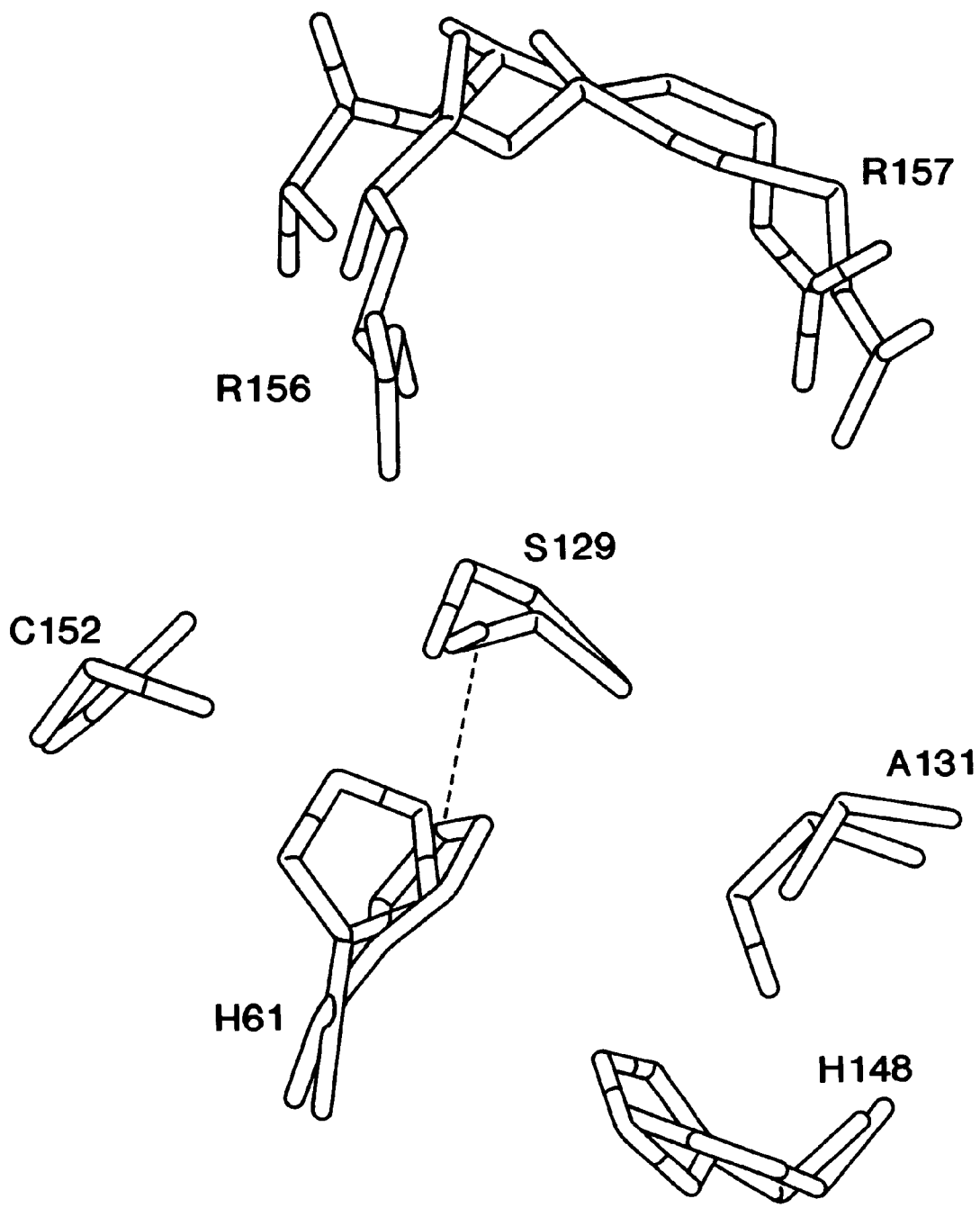
FIG. 39D is the superposition of HSV-1 protease with CMV protease, illustrating the similarities and differences between the active sites of these two enzymes. In light shading is the HSV-1 protease in the identical orientation as in FIG. 39A, and in dark shading are the CMV protease active site residues.

The active site of HSV-1 protease is very similar to that of HSV-2 protease with some minor differences (FIG. 39C). These differences are most likely because the HSV-2 protease had a covalently bound DIP inhibitor (not shown in the figure, for clarity) bound to the Ser 129 which prevented a hydrogen bond between Ser 129 and His 61 [SEQ ID NO: 4]. This hydrogen bond is present in the HSV-1 protease structure in which the imidazole ring has turned by about 90° to accommodate this hydrogen bond. Also, position 131 is an Alanine in HSV-1 protease [SEQ ID NO: 3] and thus cannot maintain any hydrogen bonds to either His 61 or His 148 as has been seen in HSV-2 [SEQ ID NO: 4] and the other herpes proteases. There is a slightly different hydrogen bonding network in the unliganded (or apo) CMV protease structure (FIG. 39D) where the equivalent residue of His 61 has hydrogen bonds to both Ser 129 and His 148 and Ser 131 clearly interacts with His 148 [SEQ ID NO: 1].

Another absolutely conserved residue in both HSV-1 and HSV-2 is Cys 152 [SEQ ID NO: 4] which is within the vicinity of the active site. It is also conserved and in an identical position in trypsin. However, it has limited contact with the DIP ligand (FIG. 38A): the C152 Cγ atom maintains a van der Waals contact (3.8 Å) to a Ser 129 methyl group. Thus, it is difficult to imagine it being a suitable proton acceptor because of its nature and position. Also, this cysteine is not essential for catalytic activity in HSV-1 protease (Liu & Roizman III), or CMV protease (Welch I).

An oxyanion hole for DIP-liganded HSV-2 protease can be identified in the present invention. Such an oxyanion hole for HSV-1 protease can also be identified based on its nearly identical structure to the HSV-2 proteases (FIG. 39C). An oxyanion hole is that portion of the protease which provides an environment for the stabilization of the tetrahedral intermediate. In DIP-liganded HSV-2 protease, the amide nitrogen of Arg 156 and Wat1 stabilize the P=O oxygen of the DIP and define the oxyanion hole of the enzyme (FIG. 38A). Wat1 is stabilized by hydrogen bonds to Wat2 (2.7 Å) and Val 128 (2.8 Å). Correspondingly, Wat2 is held by hydrogen bonds to backbone atoms of Leu 130 (2.9 Å) and Leu 127 (2.9 Å) and Arg 157$N_\epsilon$ (3.2 Å). The alignment with CMV protease (FIG. 38D) also shows a single water molecule in the active site region of this enzyme, closely overlapping with Wat2 in the HSV-2 protease structure. This water molecule maintains the same protein backbone hydrogen bonds as does Wat2 in HSV-2 and could help hold the side chain of Arg 157 in place. In HSV-1 protease, the backbone atoms at Arg 156 are the same as in DIP-liganded HSV-2 protease, making it likely this residue also helps define the oxyanion hole in HSV-1 protease. Arg 156 and Arg 157 are absolutely conserved in all herpes proteases and present an overall positive charge near the oxyanion hole. The stability of this region is reflected here where Arg 157 makes two hydrogen bonds to backbone atoms of Leu 130 and Leu 38 both absolutely conserved in all herpes proteases (FIG. 1). The alignment with γ-chymotrypsin shows how close the P=O oxygen of MIP is stabilized by a hydrogen bond to the amide nitrogen of Gly 193. In DIP-liganded HSV-2 protease, the amide nitrogen of Arg 156 closely corresponds to that of Gly 193 even though the overall structure of the two enzymes is completely different (FIG. 38C).

The active site of liganded and unliganded human HSV-2 protease and HSV-1 protease sit at a very shallow and mostly exposed region of the protease (FIGS. 27A,B,C; 29A,B,C; FIG. 28A, 28B, 30A, 30B). Shallowness of the active site cavity is not really surprising given that the scissile bond (the bond which gets cleaved) recognized by all herpes proteases is between two small amino acid residues (Ala-Ser). Missing around the active site cavity are amino acid residues 134–140 [SEQ ID NO: 3 and 4], that are part of a surface loop. Interestingly, a mutant with a five residue deletion in the corresponding loop in CMV protease residue was shown to be fully active, but with altered substrate specificity [Welch I, cited above]. Given this loop's proximity to the active site cavity, it may be a flexible flap that is involved in substrate recognition.

Since the CMV protease structure misses two large loops near the active site, it was difficult to speculate about the substrate binding mode of the enzyme. With the liganded and unliganded HSV-2 protease and HSV-1 protease structures, the missing loop containing residues 32–54 [SEQ ID NO: 3 and 4] becomes ordered, possibly having a role in substrate recognition (FIG. 27A, FIG. 28A). There are two grooves, or depressions near the active site. One of the grooves is deep and wide, found in a region that is reminiscent of the S' subsites of classical serine proteases. One side of the groove is delineated by the active site residues while the other is formed by a side of helix A6, a critical structural feature of the enzyme. The other groove is relatively narrow and is formed by B5, including the catalytic triad, on one side and the other made by the small loop of 154–160 [SEQ ID NO: 3 and 4] which includes the conserved GRR sequence (FIG. 1). This region is also in a position that is not very different from the unprimed (S) subsites in classical serine proteases. The substrate peptide (at least P2–P4) could be inserted into the groove with its main chain forming an antiparallel β-sheet with strand B5 and B6. Of course, structural studies of enzyme-substrate analog complexes are needed for proving this model.

2. CMV Protease and VZV Protease Active Sites

None of the aspartic or glutamic acids is absolutely conserved in all herpes proteases. Glu 122 was proposed as a member of the catalytic triad [Cox et al., cited above] for CMV protease. However, it is found to be distant from the catalytic site in the CMV protease crystal structure. This glutamic acid is buried near the C-terminus of the protein, making a salt bridge with Lys 255 of CMV protease (Glu 122 OE1-Lys 255 NZ, 2.7 Å) and a hydrogen bond with the backbone nitrogen of Asp 118 of CMV protease (Glu 122 OE2-Asp 118 N, 3.1 Å) [SEQ ID NO: 1]. Therefore, its importance to the protease can only be attributed to its role in maintaining the overall structure of the protease, rather than being directly involved in the catalytic machinery.

Although His 157 (for CMV, SEQ ID NO: 1) and His 139 (for VZV, SEQ ID NO: 5) are absolutely conserved among all herpes proteases, and mutagenesis of this histidine was show to abolish enzymatic activity in HSV-1 [Liu II, cited above] and CMV proteases in HSV-1 [Welch I, cited above], no one has suggested that it has a role as the third member of the catalytic triad. Abolition of enzymatic activity does not necessarily necessitate involvement in catalytic activity but could be a result of changes in protein conformation.

As expected, the Oγ atom of Ser 132 for CMV protease [SEQ ID NO: 1] (Ser 120 for VZV protease [SEQ ID NO: 5]) is found to be in the vicinity of His 63 for CMV protease (His 52 for VZV protease), with a distance of 3.3 Å from its Nε2 nitrogen for CMV protease (3.6 Å for VZV protease). Given the presence of about 0.4 Å coordinates error and the absence of a substrate in the active site, the 3.3 Å distance for CMV (3.6 Å for VZV) does not preclude these two residues from being the catalytic residues. Surprisingly, the conserved second histidine (His 157 for CMV protease [SEQ ID NO: 1] and His 139 for VZV protease [SEQ ID NO: 5]) is hydrogen bonded to the side chain of His 63 (His 63 Nδ1-His 157 Nε2, 3.2 Å) for CMV protease and His 52 (His 52 Nδ1-His 139 Nε2, 3.2 Å) for VZV protease, making it the third member of the catalytic triad. In CMV protease [SEQ ID NO: 1], the only acidic residue in the vicinity is Asp 65, with its Oδ1 atom 3.9 Å away from the Nδ1 nitrogen of His 157. In VZV protease [SEQ ID NO: 5], a basic residue Lys 54 replaces the Asp 65 of CMV protease, with its Oδ1 atom 5.1 Å away from the Nε2 nitrogen of His 139, too far to influence catalysis in VZV protease.

Figure 41A:
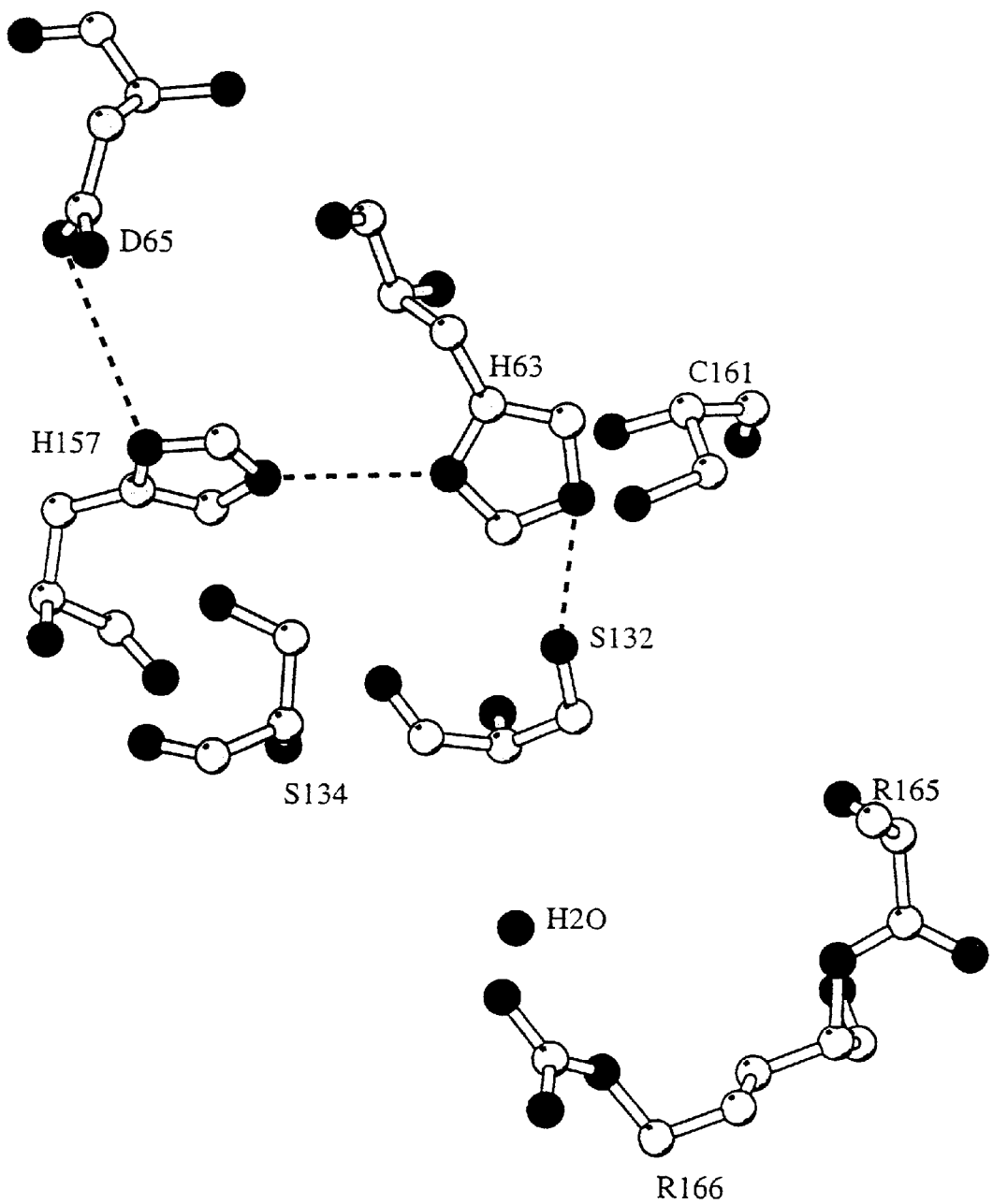
FIG. 41A is a drawing of the stereoview of the CMV protease active site in ball-and-stick representation drawn with MOLSCRIPT program. The catalytic residues are Ser 132, His 63, His 157 and optionally Asp 65 [SEQ ID NO: 1]. Other residues of importance are Arg 165, Arg 166 and possibly Ser 134 and Cys 161 [SEQ ID NO: 1]. The postulated proton transfer pathway is shown by dashed lines. The side chain of Arg 165 is disordered in the structure and hence omitted in the drawing, $H_2O$ is an ordered water molecule.

In the CMV protease crystal structure, Asp 65 forms a salt-bridge with Arg 109 of a neighboring, symmetry-related molecule other than the aforementioned dimer (Asp 65 Oδ2-Arg 109 NH1, 2.8 Å). Therefore, in the absence of this salt-bridge in solution, Asp 65 side chain could readily move to hydrogen-bond with His 157 and act as a proton acceptor in what can be described as a catalytic tetra. In the active site, Asn 60 is also found to interact with His 157 (Asn 60 Nδ2-His 157 Nδ1, 3.4 Å; Asn 60 Nδ2-His 157 Nε2, 3.7 Å), but it is difficult to imagine it being a suitable proton acceptor because of its nature and position. Therefore, the active site of CMV protease SEQ ID NO: 1) either consists of a novel triad of Ser 132, His 63 and His 157, or a unique tetra consisting of Ser 132, His 63, His 157 and Asp 65 that has also never been reported previously (FIG. 41A). In the "catalytic tetra", His 157 acts as an extra component in this novel "relay" proton transfer mechanism. However, the lack of sequence conservation for Asp 65 (FIG. 1) indicates that this tetra is not a general model for herpes proteases.

Figure 40A:
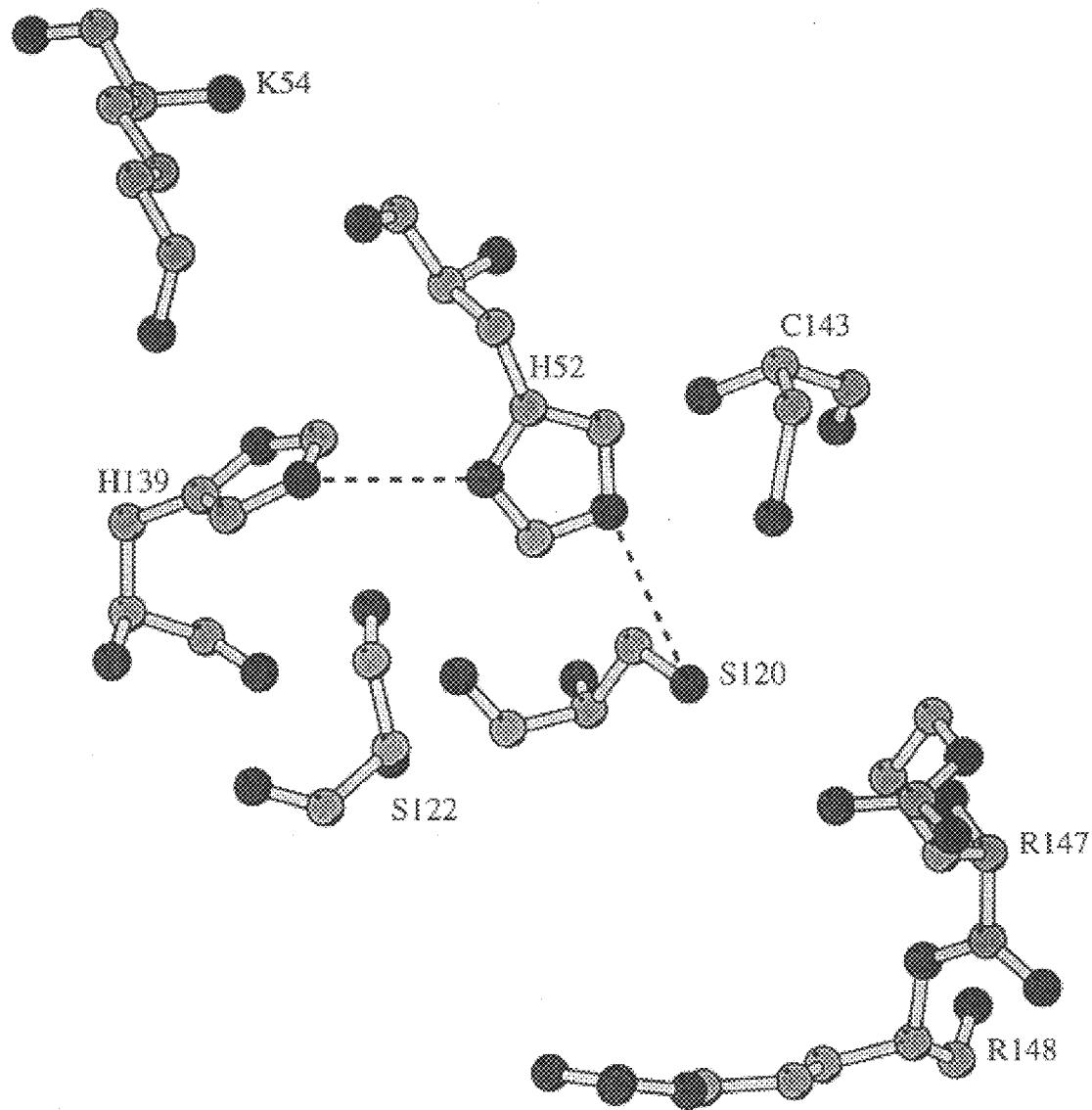
FIG. 40A is a drawing of the VZV protease active site in ball-and-stick representation drawn with MOLSCRIPT program. All carbon atoms are in light shading; nitrogen, oxygen and sulfur atoms in dark shading. The catalytic residues are Ser 120, His 52 and His 139 of SEQ ID NO: 5. Other residues of importance are Arg 147, Arg 148 and possibly Ser 122 and Cys 143 of SEQ ID NO: 5. The postulated proton transfer pathway is shown by dashed lines.

In the active site of the VZV protease [SEQ ID NO: 5] crystal structure, Cys 143 is also found to interact with Ser 120 (Cys 143 Sγ-Ser 120 Oγ 4.8 Å; Ser 122 Oγ-His 139 Cε1, 3.0 Å; Cys 143 Sγ-His 52 Nε2 6.0 Å; and Ser 122 Oγ-His 139 Nδ1 2.9 Å), but it is difficult to imagine it being a suitable proton acceptor because of its nature and position. Therefore, the active site of VZV protease consists of a novel triad of Ser 120, His 52 and His 139 of SEQ ID NO: 1 (FIG. 40A).

Figure 41B:
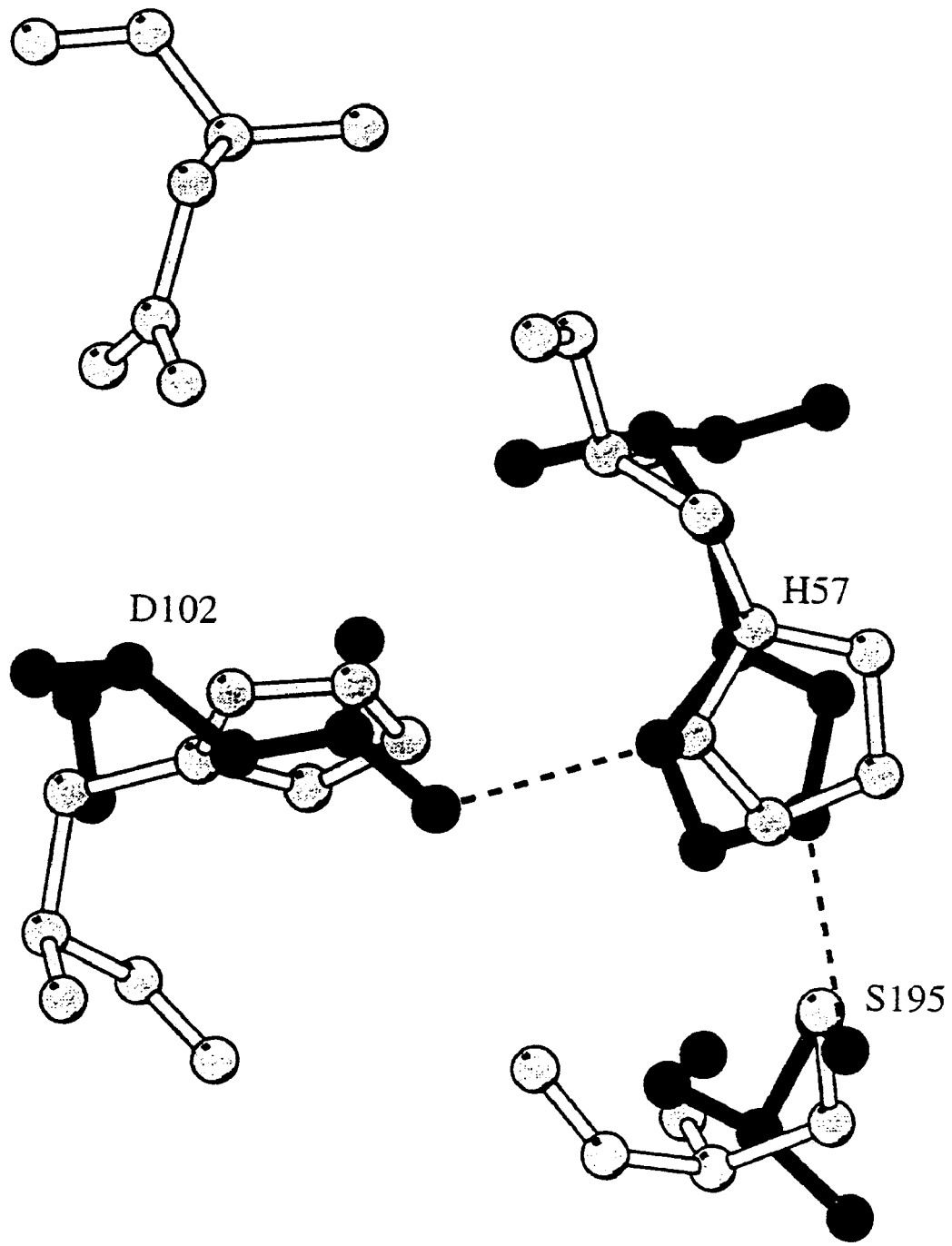
FIG. 41B is a stereoview of the superposition between the active site of CMV protease and that of the classical serine protease trypsin. The CMV protease is in the identical orientation as in FIG. 41A. Labels are those of trypsin. The proton transfer pathway in trypsin are depicted in dotted lines.
Figure 44:
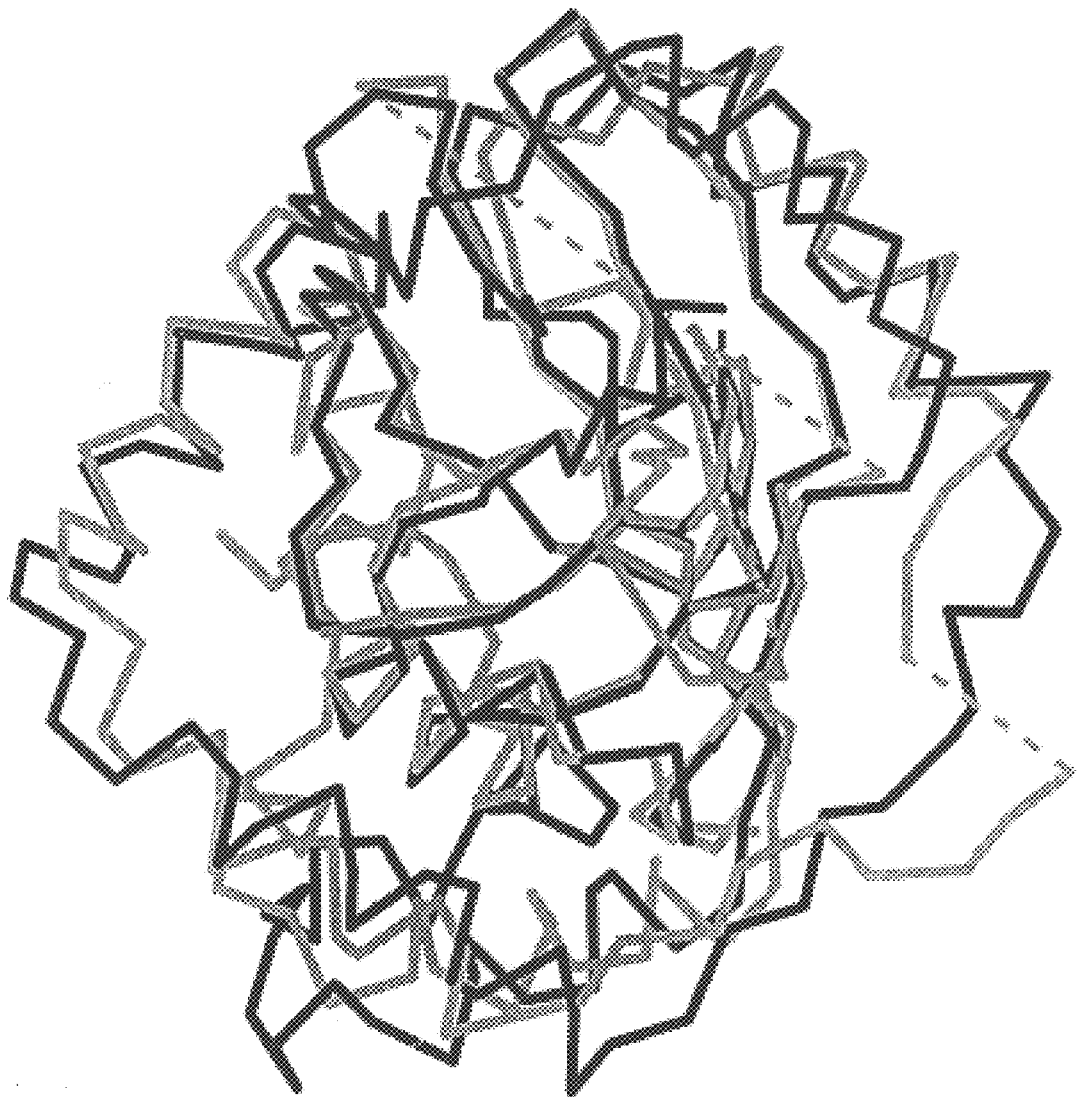
FIG. 44 is a stereoview of the superposition between the Ca trace of VZV protease and that of the CMV protease. The light color strand is the CMV protease and the dark color strand is the VZV protease. In spite of the limited sequence homology and apparent conformational differences in some helical or loop regions, the core b-barrel of the VZV protease superimposes quite well with that of the CMV protease. Excluding regions that are drastically different (>4 Å), the root-mean-square (rms) difference is only 1.3 Å between 142 (60%) Ca atoms from VZV and CMV.

Overlay of Ser 132 and His 63 of CMV protease (and Ser 120 and His 52 of VZV protease) on Ser 195 and His 57 of the classical serine protease triad in trypsin reveals that His 157 of CMV protease [SEQ ID NO: 1] and His 139 of VZV protease [SEQ ID NO: 5] can be superimposed almost perfectly onto Asp 102 of trypsin (FIG. 41B and FIG. 40B). Not only does this confirm the role of CMV protease His 157 and VZV protease His 139 in catalysis, but it also suggests the possibility of converting this enzyme into one having a normal catalytic triad by replacing His 157 in CMV protease or His 139 in VZV protease with an aspartic acid, which may also require substituting Asp 65 by a non-acidic residue.

In the same overlay, despite a totally different tertiary structure, many interesting conservations can be identified that seem to present a case of convergent evolution. First, Cys 161 for CMV protease and Cys 143 for VZV protease are at an identical position to Cys 42 of trypsin (FIG. 41B and FIG. 40B), making van der Waals interactions with the catalytic residues (Cys 161 Sγ-Ser 132 Oγ, 3.6 Å; Cys 161 Sγ-His 63 Nε2, 4.4 Å in CMV). This surprising conservation, as well as the fact that Cys 161 in CMV protease [SEQ ID NO: 1] and Cys 143 in VZV protease [SEQ ID NO: 5] are absolutely conserved in all herpes proteases, seems to suggest an important role for this amino acid, although mutagenesis studies had shown that it is not essential for the protease activity [Welch I, cited above]. Another similar scenario is found at Ser 134 in CMV protease and Ser 122 in VZV protease, which appear to be at identical positions to Ser 214 of trypsin (FIG. 41B and FIG. 40B).

In the CMV structure of the present invention, Ser 134 interacts strongly with His 157 (Ser 134 Oγ-His 157 Nε2, 2.6 Å; Ser 134 Oγ-His 157 Nε1, 3.0 Å) by forming a hydrogen bond. In the VZV structure of the invention, Ser 122 interacts strongly with His 139 (Ser 122 Oγ-His 139 Nε2, 2.5 Å) by forming a hydrogen bond. In both CMV and VZV structures, Ser 214 also interacts strongly with Asp 102 in trypsin by forming a hydrogen bond. However, the importance of Ser 134 in CMV protease to the catalytic activity has been undermined by mutagenesis studies [Welch I, cited above], and also the fact that it is an alanine in other herpes virus proteases.

A possible oxyanion hole for the CMV and VZV proteases also exists. In trypsin, the oxyanion is held by the backbone nitrogen atoms of Gly 193 and Ser 195. In the similar region of CMV protease, the construction of the oxyanion hole cannot be fully imitated by the G-X-S-G-G [SEQ ID NO: 14] motif because the backbone arrangements are completely different. However, the main chain nitrogen atom of Arg 165 in CMV protease and Arg 147 in VZV protease is at a nearly identical position as Gly 193 N in trypsin (FIGS. 41A and 41B and FIGS. 40A and 40B). Also found in the vicinity is a water molecule held by the side chain of Arg 166 and interacting with Leu 20 and Leu 133 ($H_2O$-Arg 166 NH1, 2.7 Å; $H_2O$-Arg 166, NZ, 3.2 Å; $H_2O$-Leu 20 O, 2.6 Å; $H_2O$-Leu 133 N 3.0 Å). The oxyanion in the structure defined herein may be held only by Arg 165 N, by Arg 165 N and the $H_2O$ molecule. Considering the fact that the two arginines (165 and 166) are absolutely conserved among all herpes proteases (FIG. 1), this general region is suitable for being the oxyanion pocket of CMV [SEQ ID NO: 1] and VZV [SEQ ID NO: 5] proteases.

The active sites of human CMV and VZV proteases sit at a very shallow and mostly exposed region of the protease (FIGS. 36B, 41A, 37, 40A). Shallowness of the active site cavity is not really surprising given that the scissile bond (the bond which gets cleaved) recognized by all herpes proteases is between two small amino acid residues (Ala-Ser). Missing around the active site cavity are amino acid residues 143–153 in CMV protease [SEQ ID NO: 1] and aa 139–154 in VZV protease [SEQ ID NO: 5], that are part of a surface loop. This loop contains the so called inactivation or internal (I) site, a cleavage site between Ala 143 and Ala 144 of native human CMV protease as described in Welch I, cited above.

Residue 143 [SEQ ID NO: 1] of the CMV protease of this invention has been mutated to valine to eliminate such processing. Also, it is not clear whether cleavage at the I site is a result of auto-processing or not. Interestingly, a mutant with a five residue deletion around residue 143 was shown to be fully active, but with altered substrate specificity [Welch I, cited above]. Given this loop's proximity to the active site cavity, it may be a flexible flap that is involved in substrate recognition and probably is ordered upon binding of ligands. Similarly, the missing loop containing residues 25–55 may also become ordered upon ligand binding. This is supported by the fact that a mutation of Glu22 in simian CMV protease (corresponding to Glu31 in the human enzyme), has shown altered substrate specificity [Welch I, cited above].

Since the CMV protease structure misses two large loops near the active site, it was difficult to speculate about the substrate binding mode of the enzyme. With the VZV protease structure, the missing loop containing residues 23–45 of SEQ ID NO: 5 becomes ordered, and the structure clearly defines two grooves near the active site that could be important for substrate recognition (FIG. 37). One of the grooves is deeper and wider, and is found in a region that is reminiscent of the S' subsites of classical serine proteases. One side of the groove is delineated by the active site residues, while the other is formed by a side of helix A6, which is also a critical structural feature of the enzyme and will be discussed later. The other groove is relatively narrow. The β-strand B5, including the catalytic triad, is on one side of the shallow depression. The other side is formed by the conserved GRR sequence (FIG. 1) as well as the loop immediately prior to helix AA. This region is also in a position that is not very different from the unprimed (S) subsites in classical serine proteases. Strand B5 being almost parallel to this groove suggests that the substrate peptide (at least P2–P4) could be inserted into the groove with its main chain forming an antiparallel b-sheet with strand B5 and B6. Moreover, several rather exposed hydrophobic residues in the AA loop could also make important interactions with the substrate protein. Of course, structural studies of enzyme-substrate analog complexes are needed for proving this model.

Given the conservation of amino acid sequence and substrate specificity between CMV, VZV, HSV-1, HSV-2 and other herpes proteases, the structures described herein represent that of the entire family of herpes proteases. These structures are clearly useful in the structure-based design of protease inhibitors, which may be used as therapeutic agents against viral disease. The discovery of the herpes protease catalytic triad, and the catalytic tetra, permits the design of potent highly selective protease inhibitors.

F. Mutants and Derivatives

The invention further provides homologues, co-complexes, mutants, derivatives and fragments of the herpes protease crystal structure of the invention.

The term "homologue" means a protein having at least 25% amino acid sequence identity with herpes protease or any functional domain of herpes protease. See, FIG. 1.

The term "co-complex" means herpes protease or a mutant or homologue of herpes protease in covalent or non-covalent association with a chemical entity or compound.

The term "mutant" refers to a herpes protease polypeptide, i.e., a polypeptide displaying the biological activity of wild-type protease activity, characterized by the replacement of at least one, or more, amino acids from the wild-type protease sequence. Such a mutant may be prepared, for example, by expression of herpes protease cDNA previously altered in its coding sequence by oligonucleotide-directed mutagenesis.

Herpes protease mutants may also be generated by site-specific incorporation of unnatural amino acids into herpes protease proteins using the general biosynthetic method of C. J. Noren et al, *Science*, 244:182–188 (1989).

In this method, the codon encoding the amino acid of interest in wild-type herpes protease is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant herpes protease enzyme with the site-specific incorporated unnatural amino acid.

Selenocysteine or selenomethionine may be incorporated into wild-type or mutant herpes protease by expression of herpes protease-encoding cDNAs in auxotrophic *E. coli* strains [W. A. Hendrickson et al, *EMBO J.*, 9(5): 1665–1672 (1990)]. In this method, the wild-type or mutagenized herpes protease cDNA may be expressed in a host organism on a growth medium depleted of either natural cysteine or methionine (or both) but enriched in selenocysteine or selenomethionine (or both).

The term "heavy atom derivative" refers to derivatives of herpes protease produced by chemically modifying a crystal of herpes protease. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by X-ray diffraction analysis of the soaked crystal. This information, in turn, is used to generate the phase information used to construct three-dimensional structure of the enzyme [T. L. Blundell and N. L. Johnson, *Protein Crystallography,* Academic Press (1976). See, Example 1.

The term "fragment", particularly as used in connection with protease fragments, refers to a protease of the invention which contains at least the catalytic active site of the protease, but less than the full length protease. Desirably, the fragment is characterized by a catalytic active site which has the same crystal structure as the active site in the full-length protease. However, a fragment of the invention is not so limited. Such a fragment may contain N-terminal, C-terminal or internal deletions of the protease. Particularly desirable are fragments which are N-terminally truncated proteases. It is currently anticipated that such fragments provide superior resolution or are more easily crystallized.

II. Methods of Identifying Inhibitors of the Novel Protease Crystalline Structure Another aspect of this invention involves a method for identifying inhibitors of a herpes protease characterized by the crystal structure and novel active site described herein, and the inhibitors themselves. The novel protease crystal structure of the invention permits the identification of inhibitors of protease activity. Such inhibitors may bind to all or a portion of the active site of the herpes protease, or even be competitive, non-competitive, or uncompetitive inhibitors; or interfere with dimerization by binding at the interface between the two monomers. Once identified and screened for biological activity, these inhibitors may be used therapeutically or prophylactically to block protease activity, and thus, herpes viral replication latency, reactivation and/or infection.

One design approach is to probe the herpes protease crystal of the invention with molecules composed of a variety of different chemical entities to determine optimal sites for interaction between candidate herpes protease inhibitors and the enzyme. For example, high resolution X-ray diffraction data collected from crystals soaked in or co-crystallized with other molecules allows the determination of where each type of solvent molecule sticks. Molecules that bind tightly to those sites can then be further modified and synthesized and tested for their herpes protease inhibitor activity [J. Travis, *Science,* 262:1374 (1993)].

This invention also enables the development of compounds that can isomerize to short-lived reaction intermediates in the chemical reaction of a substrate or other compound that binds to or with herpes protease. The time-dependent analysis of structural changes in herpes protease during its interaction with other molecules is permitted. The reaction intermediates of herpes protease can also be deduced from the reaction product in co-complex with herpes protease. Such information is useful to design improved analogues of known herpes protease inhibitors or to design novel classes of inhibitors based on the reaction intermediates of the herpes protease enzyme and herpes protease inhibitor co-complex. This provides a novel route for designing herpes protease inhibitors with both high specificity and stability.

Another approach made possible by this invention is to screen computationally small molecule data bases for chemical entities or compounds that can bind in whole, or in part, to the herpes protease enzyme. In this screening, the quality of fit of such entities or compounds to the binding site may be judged either by shape complementarity or by estimated interaction energy [E. C. Meng et al, *J. Comp. Chem.,* 13:505–524 (1992)].

Because herpes protease may crystallize in more than one crystal form, the structure coordinates of herpes protease, or portions thereof, as provided by this invention are particularly useful to solve the structure of those other crystal forms of herpes protease.

They may also be used to solve the structure of herpes protease mutants, herpes protease co-complexes, or of the crystalline form of any other protein with significant amino acid sequence homology to any functional domain of herpes protease.

One method that may be employed for this purpose is molecular replacement. In this method, the unknown crystal structure, whether it is another crystal form of herpes protease, a herpes protease mutant, or a herpes protease co-complex, or the crystal of some other protein with significant amino acid sequence homology to any functional domain of herpes protease, may be determined using the herpes protease structure coordinates of this invention as provided in FIGS. 1–26. This method will provide an accurate structural form for the unknown crystal more quickly and efficiently than attempting to determine such information ab initio.

Thus, the protease structure provided herein permits the screening of known molecules and/or the designing of new molecules which bind to the protease structure, particularly at the active site, via the use of computerized evaluation systems. For example, computer modelling systems are available in which the sequence of the protease, and/or the protease structure (i.e., atomic coordinates of CMV, VZV, HSV-2, or HSV-1 proteases and/or the atomic coordinates of the active site cavity, bond angles, dihedral angles, distances between atoms in the active site region, etc. as provided by FIGS. 1–26), may be input. Alternatively, the catalytic site domain crystal structure of a protease of the invention or another fragment of the protease may be input into computer readable form. Thus, for DIP-liganded HSV-2 protease, a machine readable medium may be encoded with data representing the coordinates of FIGS. 2, 3, 8, 9, 11, and 12; or FIGS. 2, 3, 8, 9, 14, and 15 (FIGS. 4 and 5 may be substituted for FIGS. 2 and 3 in the process). Similarly, for HSV-1 protease, a machine readable medium may be encoded with data representing the coordinates of FIGS. 6, 10 and 13; or FIGS. 6, 10 and 16 (as noted FIG. 7 may be substituted for FIG. 6 in this process). For CMV protease, a machine readable medium may be encoded with data representing the coordinates of FIGS. 17, 18 and 19; or FIGS. 17, 18 and 20 (FIG. 21 may be substituted for FIG. 17 in this process). For VZV protease, a machine readable medium may be encoded with data representing the coordinates of FIGS. 22, 24 and 25; or FIGS. 22, 24 and 26 (FIG. 23 may be substituted for FIG. 22 in this process). The computer then generates structural details of the site into which a test compound should bind, thereby, enabling the determination of the complementary structural details of said test compound.

More particularly, the design of compounds that bind to or inhibit herpes protease according to this invention generally involves consideration of two factors. First, the compound must be capable of physically and structurally associating with the herpes protease and, particularly, with the active site thereof. Non-covalent molecular interactions important in the association of herpes protease with its ligands include hydrogen bonding, van der Waals and hydrophobic interactions.

Second, the compound must be able to assume a conformation that allows it to associate with herpes protease. Although certain portions of the compound will not directly participate in this association with herpes protease, those portions may still influence the overall conformation of the molecule. This, in turn may have a significant impact on potency. Such conformational requirements include the overall three-dimensional structure and orientation of the chemical entity or compound in relation to all or a portion of the binding site, e.g., active site or accessory binding site of herpes protease, or the spacing between functional groups of a compound comprising several chemical entities that directly interact with herpes protease.

The potential inhibitory or binding effect of a chemical compound on herpes protease may be analyzed prior to its actual synthesis and testing by the use of computer modelling techniques. If the theoretical structure of the given compound suggests insufficient interaction and association between it and herpes protease, synthesis and testing of the compound is obviated. However, if computer modelling indicates a strong interaction, the molecule may then be synthesized and tested for its ability to bind to herpes protease and inhibit using a suitable assay. In this manner, synthesis of inoperative compounds may be avoided.

An inhibitory or other binding compound of herpes protease may be computationally evaluated and designed by means of a series of steps in which chemical entities or fragments are screened and selected for their ability to associate with the individual binding pockets or other areas of herpes protease.

One skilled in the art may use one of several methods to screen chemical entities or fragments for their ability to associate with herpes protease and more particularly with the individual binding pockets of the herpes protease active site or accessory binding site. This process may begin by visual inspection of, for example, the active site on the computer screen based on the herpes protease coordinates in FIGS. 2, 3, 6, 8–20, 22, and 24–26, Selected fragments or chemical entities may then be positioned in a variety of orientations, or docked, within a binding pocket of herpes protease. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include the GRID program available from Oxford University, Oxford, UK. [P. J. Goodford, "*A Computational Procedure for Determining Energetically Favorable Binding Sites on Biologically Important Macromolecules*", *J. Med. Chem.*, 28:849–857 (1985)]; the MCSS program available from Molecular Simulations, Burlington, Mass. [A. Miranker and M. Karplus, "*Functionality Maps of Binding Sites: A Multiple Copy Simultaneous Search Method*", *Proteins: Structure, Function and Genetics*, 11:29–34 (1991)]; the AUTODOCK program available from Scripps Research Institute, La Jolla, Calif. [D. S. Goodsell and A. J. Olsen, "*Automated Docking of Substrates to Proteins by Simulated Annealing*", *Proteins: Structure, Function, and Genetics*, 8: 195–202 (1990)]; and the DOCK program available from University of California, San Francisco, Calif. [I. D. Kuntz et al, "*A Geometric Approach to Macromoleczile-Ligand Interactions*", *J. Mol. Biol.*, 161:269–288 (1982)]. Additional commercially available computer databases for small molecular compounds include Cambridge Structural Database, Fine Chemical Database, and CONCORD database [for a review see Rusinko, A., *Chem. Des. Auto. News*, 8:44–47 (1993)].

Once suitable chemical entities or fragments have been selected, they can be assembled into a single compound or inhibitor. Assembly may proceed by visual inspection of the relationship of the fragments to each other on the three-dimensional image displayed on a computer screen in relation to the structure coordinates of herpes protease. This would be followed by manual model building using software such as Quanta or Sybyl.

Useful programs to aid one of skill in the art in connecting the individual chemical entities or fragments include the CAVEAT program [P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc. 78, pp. 182–196 (1989)], which is available from the University of California, Berkeley, Calif.; 3D Database systems such as MACCS-3D database (MDL Information Systems, San Leandro, Calif.) [see, e.g., Y. C. Martin, "3D Database Searching in Drug Design", *J. Med. Chem.*, 35:2145–2154 (1992)]; and the HOOK program, available from Molecular Simulations, Burlington, Mass.

Instead of proceeding to build a herpes protease inhibitor in a step-wise fashion one fragment or chemical entity at a time as described above, inhibitory or other herpes protease binding compounds may be designed as a whole or "de novo" using either an empty active site or optionally including some portion(s) of a known ligand(s). Suitable methods describing such methods include the LUDI program [H.-J. Bohm, "The Computer Program LUDI: A New Method for the De Novo Design of Enzyme Inhibitors", *J. Comp. Aid. Molec. Design*, 6:61–78 (1992)], available from Biosym Technologies, San Diego, Calif.; the LEGEND program [Y. Nishibata and A. Itai, *Tetrahedron*, 47:8985 (1991)], available from Molecular Simulations, Burlington, Mass.; and the LeapFrog program, available from Tripos Associates, St. Louis, Mo.

Other molecular modelling techniques may also be employed in accordance with this invention. See, e.g., N. C. Cohen et al, "Molecular Modeling Software and Methods for Medicinal Chemistry", *J. Med. Chem.*, 33:883–894 (1990). See also, M. A. Navia and M. A. Murcko, "The Use of Structural Information in Drug Design", *Current Opinions in Structural Biology*, 2:202–210 (1992). For example, where the structures of test compounds are known, a model of the test compound may be superimposed over the model of the structure of the invention. Numerous methods and techniques are known in the art for performing this step, any of which may be used. See, e.g., P. S. Farmer, *Drug Design*, Ariens, E. J., ed., Vol. 10, pp 119–143 (Academic Press, New York, 1980); U.S. Pat. No. 5,331,573; U.S. Pat. No. 5,500,807; C. Verlinde, *Structure*, 2:577–587 (1994); and I. D. Kuntz, *Science*, 257:1078–1082 (1992). The model building techniques and computer evaluation systems described herein are not a limitation on the present invention.

Thus, using these computer evaluation systems, a large number of compounds may be quickly and easily examined and expensive and lengthy biochemical testing avoided. Moreover, the need for actual synthesis of many compounds is effectively eliminated.

Once identified by the modelling techniques, the protease inhibitor may be tested for bioactivity using standard techniques. For example, structure of the invention may be used in binding assays using conventional formats to screen inhibitors. Suitable assays for use here include, but are not limited to, the enzyme-linked immunosorbent assay (ELISA), or a fluorescence quench assay. See, for example, the HSV-1, HSV-2, CMV, and VZV protease activity assays below. Other assay formats may be used; these assay formats are not a limitation on the present invention.

In another aspect, the protease stricture of the invention permits the design and identification of synthetic compounds and/or other molecules which have a shape complementary to the conformation of the protease active site of the invention. Using known computer systems, the coordinates of the protease structure of the invention may be provided in machine readable form, the test compounds designed and/or screened and their conformations superimposed on the structure of the protease of the invention. Subsequently, suitable candidates identified as above may be screened for the desired protease inhibitory bioactivity, stability, and the like.

Once identified and screened for biological activity, these inhibitors may be used therapeutically or prophylactically to block protease activity, and thus, herpes viral replication.

As used herein the term "natural product molecule" includes all non-synthetic products of nature and includes, but is not limited to, derivatives, extracts or homologs thereof, having, or containing, a bioactive component.

The following examples illustrate various aspects of this invention. These examples do not limit the scope of this invention which is defined by the appended claims.

EXAMPLE 1

Analysis of the Structure of the HSV-2 Protease

The HSV-2 protease (see FIG. 1, SEQ ID NO: 4) was cloned, expressed and purified as follows:

A. Expression, Purification and Crystallization

HSV-2 protease was expressed in *E. Coli* including a 19-residue addition beyond its C-terminal alanine residue [+SEKFKIWGAESAPHHHHHH (SEQ ID NO: 15)]. The hexa-His tag (the six H) allows the high-quality purification of the protein using a $Ni^{2+}$-NTA chromatographic column. The construct also allows the protease to self-process by cleaving the peptide bond between the C-terminal alanine and the first added residue (Ser), thus producing a protein that has the same length as the authentic protease. The protease was further purified using Superdex 75 size exclusion and, if necessary, Q-Sepharose anion exchange chromatography. For the DIP-liganded HSV-2 protease, dilsopropylfluorophosphate inhibitor (DFP) was added to the enzyme and incubated until >98% modification. Excess inhibitor was removed by Sephadex G-25 chromatography. The DIP-liganded HSV-2 protease was crystallized in 0.1M NaAcetate buffer pH 5.0 and 10% PEG 4000 (50% w/v). Large crystals are approximately 0.7 mm×0.3 mm×0.2 mm in size. The unliganded HSV-2 protease was crystallized in 0.1M phosphate/Citrate buffer at pH 4.5, 20% PEG 8000. The crystals were 0.3 mm×0.2 mm×0.2 mm in size.

B. X-ray Diffraction Characterization

For the liganded and unliganded HSV-2 proteases a crystal was mounted in a sealed glass capillary with a small amount of mother liquor in each end of the capillary. The $CuK_a$ x-ray, having a wavelength of 1.54 Å, was generated by a Siemens-RU200 rotating anode machine operating at 50 KV×95 mA electric power. The crystal was exposed to the $CuK_a$ x-ray, and the diffracted X-ray was collected by a Siemens multiwire area detector. The DIP-liganded HSV-2 protease crystal diffracted to 2.5 Å resolution. By registering the position and intensity of many tens of thousands of diffraction spots using the computer program XDS, [Kabsch, W., *J. AppL. Cryst.*, 21, pp. 916–924 (1988)] the crystal has been determined to be the orthorhombic space group $P2_12_12$, with a=71.7 Å, b=87.4 Å and c=77.3 Å. By established methods, an asymmetric unit was calculated to have two protein molecules. The crystal contains an estimated 45% solvent. The native data is 91% complete to 2.5 Å with an $R_{sym}$ ($\Sigma|I-<I>|/\Sigma<I>$) of 0.095. The unliganded HSV-2 protease crystal diffracted to 2.8 Å resolution with cell dimensions and space group identical to the DIP-liganded HSV-2 protease crystal. The native data is 94% complete to 2.8 Å with an Rsym of 0.095.

C Heavy Atom Derivative

Multiple isomorphous replacement (MIR) methods were used as one of the methods in order to obtain phase information of the diffraction data and to solve the three-dimensional atomic structure of the DIP-liganded HSV-2 protease. This involves the identification of derivative crystals containing specifically-bound heavy metal atoms. By testing various heavy metal compounds, the useful derivatives were prepared by soaking the native crystals with 0.1 mM KAuCN, 0.4 mM $LuCl_3$, 0.6 mM $PrCl_3$, 0.2 mM $YbS_4$, 0.5 mM $GdCl_3$, and 0.2 mM $SmCl_3$ for one to two days. The X-ray diffraction data of the derivative were then collected by the same methods described above. Data collection statistics for native and heavy atom derivatives are shown in FIG. 42. Heavy atom positions were identified by difference Patterson and difference Fourier methods using the programs in the XtalView software package [McRee. D. E. *Practical Protein Crystallography*, (San Diego, Academic Press 1993]. Heavy atom refinement and determination of an initial set of phases were carried out using the programs in the CCP4 suite [Collaborative Computational Project, Number 4, The CCP4 Suite: Programs for Protein Crystallography *Acta Crystallogr.* D50, 760–763 (1994)]. The program MLPHARE [Otwinowski, Z. *Isomorphous Replacement and Anomalous Scattering*, 80–86, Daresbury Laboratory, Warrington (1991)] was used for heavy atom phasing. Using the initial phases obtained through the MIR methods, a map of electron density within the crystal unit cell could be calculated. Because electrons are heavily distributed in the immediate vicinity of the centers of atoms, the positions of protein atoms are registered according to the electron density map. The resulting electron density map was interpretable but the phase information from MIR was improved with more phase information derived from molecular replacement.

D. Molecular Replacement

A molecular replacement solution of the DIP-liganded HSV-2 protease was also identified with the program XPLOR [Brünger, A. T. *X-PLOR Version 3.1 A System for X-ray Crystallography and NMR* (New Haven, Yale University Press; 1992)]. The model for these calculations was a subset of the crystallographic dimer structure of the homologous protease from the VZV alpha-herpes virus (see Example 6 below). Each monomer in the search model was derived from a total of 177 amino acid residues from the VZV protease structure with the sidechains truncated to alanine. The residues of the core secondary structure of the VZV protease were included in the model: residues 11–22, 46–91, 95–124, 137–183 and 189–230 of SEQ ID NO: 5. The rotation function calculation was carried out with data between 15 and 4.0 Å resolution with a maximum search vector length of 38 Å. The top peak in the rotation function from this dimer model was 4.9 s. The translation function was calculated with data between 8 and 4 Å resolution. The top solution was at 9.3 s. Rigid body refinement of the two monomers reduced the R factor to 0.48 for all data to 3.5 Å.

E. Phase Combination

Using difference Fourier methods, phases derived from the molecular replacement solution were consistent with those generated from MIR. The combination of these two sets of phases using the program SIGMAA [Read, R. J. Improved Fourier Coefficients for Maps Using Phases from Partial Structures with Errors *Acta Cryst*, A42, 140–149 (1986)] resulted in an overall figure of merit of 0.67. This was followed by one round of non-crystallographic symmetry averaging using the density modification program *dm* [Cowtan, K. Joint CCP4 and ESF-EACBM Newsletter on Protein Crystallography 31, 34–38 (1994)] resulting in an improved overall figure of merit of 0.83. Non-crystallographic symmetry is symmetry that exists locally within the asynimetric unit of the crystal. This information can be used to produce averaged electron density maps in which noise will cancel out and therefore can be used as a phase restriction to improve phasing. The calculated electron density map following this procedure showed side chain density, derived solely from the MIR phases, that was very well-defined and easily interpretable.

F. Model Building and Refinement

The electron density allowed placement of almost all of the side chains in the original model using the program Xfit (McRee). Remaining effort was focused on building the missing 27% of the structure that was not part of the molecular replacement model. Two more rounds of density modification with the combined MIR phases allowed placement of an additional alpha helix, several loops and the DIP ligand in the active site. The electron density map resolution was extended to 2.5 Å resolution using dm, more residues were added and the model refined using X-PLOR.

When building the model, each of the amino acid residues was manually positioned in its electron density, allowing for a unique position for each atom in the DIP-liganded HSV-2 protease in which each position is defined by a unique set of atomic coordinates (X,Y,Z) as shown in FIG. 2A–2F. Starting with these atomic coordinates, a diffraction pattern was calculated and compared to the experimental data. The difference between the calculated and experimentally determined diffraction patterns was monitored by the value of R-factors (R-factor=$\Sigma\|F_o|-|F_c\|/\Sigma F_o$). The refinement (using XPLOR) of the structural model neccesitates adjustments of atomic positions to minimize the R-factor, where a value of about 20% is typical for a good qualitv protein structure.

Cycles of model building with XTALVIEW and refinement with the computer program XPLOR produce a final model including 217 amino acids with 43 solvent molecules. Three segments of residues are found disordered in the crystal: 104–110, 134–140, and the first 16 residues of the N-terminus [SEQ ID NO: 4]. A total of 14605 reflections were included in the final refinement (10.0–2.5 Å), giving an R-factor ($\Sigma\|F_o|-|F_c\|/\Sigma F_o$) of 20.5%. The rms bond length is 0.016 Å and rms bond angle is 1.9°. The program PROCHECK [R. A. Laskowski et al., *J. Appl. Crystallogr.* 26: 283–291 (1993)] was used to check the stereochemical and geometrical outliers in the final structure, and the result is very satisfactory.

The statistics of structure determination arc reported in FIG. 42, where $R_{sym}=\Sigma|I-<I>|/\Sigma<I>$, I is the observed intensity and <I> is the average intensity of multiple observations; $R_{iso}=\Sigma|F_{PH}-F_P|/\Sigma F_P$ Phasing power=rms isomorphous difference/rms residual lack of closure; $R_{cullis}=\Sigma|FH_o-FH_c|/\Sigma|FH_o|$, $FH_o$ and $FH_c$ are the observed and calculated heavy atom structure factor amplitudes for centric reflections; R-factor=$\Sigma\|F_o|-|F_c\|/\Sigma F_o$. XPLOR refinement was performed according to A. F. Brunger et al, *Science*, 235: 458–460 (1987), from 10–2.5 Å. The number of reflections used (F>2s=14605), the R-factor was 20.5%; the number of protein atoms (non-H) was 3364; the number of solvent atoms was 43, the RMS bond length was 0.016 Å; and the RMS bond angles=1.919°. Mean coordinate error (0.3 Å) was performed according to P. V. Luzatti, *Acta Cryst*, 5: 802–810 (1952). MIR overall mean figure of merit (15–3.0 Å=0.62 Å; overall figure of merit after phase combination=0.67 Å; mean figure of merit following density modification 100–3.0 Å=0.838 Å.

Using the final atomic coordinates (FIGS. 2A–F) one can calculate distances between a pair of atoms, angles between any three atoms, and dihedral angles between any four atoms, such as listed in FIGS. 8A–X, 11A–LLL and 14.

The unliganded HSV-2 protease structure was solved using difference Fourier methods using the refined CIP-liganded HSV-2 protease structure. Since the cell dimensions and space group of the unliganded and liganded (DIP) structure were the same, the DIP-liganded HSV-2 protease structure could be used directly to determine the phases of the unliganded structure, without using heavy atom derivatives or molecular replacement. The unliganded HSV-2 protease model coordinates could then be determined and refined as described for the DIP-liganded HSV-2 protease structure. Three segments of residues were disordered in the unliganded HSV-2 protease structure: 1–16, 104–112, and 134–140 [SEQ ID NO: 4]. A total of 10127 reflections were included in the final refinement (7.0–2.8 Å) giving an R-factor ($\Sigma\|F_o|-|F_c\|/\Sigma F_o$) of 22.4%. The rms bond length is 0.017 Å and rms bond angle is 2.1°. The program PROCHECK [R. A. Laskowski *et al., J. Appl Crystallogr.,* 26: 283–291 (1993)] as used to check the stereochemical and geometrical outliers in the final structure, and the result is very satisfactory.

EXAMPLE 2

Analysis of the Structure of the HSV-1 Protease

The HSV-1 protease (see FIG. 1. SEQ ID NO: 3) was cloned, expressed and purified as follows:

A. Expression, Purification and Crystallization

HSV-1 protease was expressed and purified as described above in Example 1 for HSV-2. HSV-1 was crystallized in 45 mM Tris buffer pH 8.5, 88 mM $MgCl_2$ and 8.8% PEG 8000 at 4° C.

B. X-ray Diffraction Characterization

A HSV-1 protease crystal was subjected to X-ray diffraction using the techniques described in Example 1 above. The crystal diffracted to 3.5 Å resolution. By registering the position and intensity of many tens of thousands diffraction spots using the computer program XDS [Kabsch, W. *J. Appl Cryst.* 21, 916–924 (1988)], the crystal has been determined to be the orthorhombic space group P1, with a=79.62 b=81.18 Å and c=93.36 Å, α=115.49 β=98.36 γ=109.18. The native data is 78.4% complete to 3.5 Å with an $R_{sym}$ ($\Sigma|I-<I>|/\Sigma<I>$) of 0.059. By established methods, an asymmetric unit was calculated to have either six or eight protein molecules (three or four dimers).

C. Molecular Replacement

The HSV-1 protease structure was solved by the method of molecular replacement using the program AMoRe in the CCP4 Suite [Collaborative Computational Project, Number 4 *Acta Crystallogr.* D50, 760–763 (1994)]. The model for these calculations was the entire known crystallographic dimer structure of the highly homologous protease from the HSV-2 alpha-herpes virus complexed with the covalently bound inhibitor DFP. The model was defined as residues 17–103, 111–133, 141–247 [SEQ ID NO: 3] for each monomer with no inhibitor atoms included. The rotation function calculation was carried out with data between 8 and 4.0 Å resolution with a maximum search vector length of 31.3 Å. Only three pairs of peaks were found with peak height greater than 0.5 (maximum peak height). The pairs of peaks reflected the non-crystallographic symmetry of the dimer. Using data between 8 and 4 Å resolution, the translation function was calculated by fixing the top solution in the P1 cell and searching for a second molecule. This yielded a peak with a correlation coefficient of 41.0% and an R-factor of 38.5%. The top two solutions were then fixed to search for a third, yielding a peak of comparable height to the second solution. A search for a fourth solution showed smaller peaks of all about the same height. To see if there were three or four dimers in the cell, a rigid body fit was run to search for four dimers using the top three solutions with several of the similar peaks generated in the last translation function output. The fitting function yielded four peaks with a correlation coefficient of 45.6% and R-factor of 37.1%. Alternatively, when the top three dimer solutions were fit, the correlation coefficient rose to 55.9% With an R-factor of 33.1%. Several other combinations of peaks were tried as controls and none yielded satisfactory results as compared to the top three peaks. A packing diagram was determined and visually inspected using the program Xfit, [McRee, D. E. Practical Protein Crystallography, (San Diego, Academic Press, 1993)] showing no overlaps between symmetry related molecules.

D. Model Placement and Refinement

When the molecular replacement solution was placed into the P1 cell, the model was changed slightly in which residues that were different between the two sequences were truncated to alanine to reduce the bias of the HSV-2 protease phases in the calculation of the electron density map. Unfortunately, most of the significant differences between HSV-1 protease and HSV-2 protease in the sequence are present in regions missing in the HSV-2 protease structure [N-terminus and 134–140 of SEQ ID NO: 4], so that many of the changes in the new model, limited by the 3.5 Å resolution, would not be reflected in the electron density map. As a control, to ensure that the map revealed the contributions of the HSV-1 data, six phenylalanine or tyrosine residues were truncated to alanine on each monomer. Fourier coefficients were calculated using the program SIGMAA [Read, cited above (1986)]. This was followed by phase improvement by non-crystallographic symmetry averaging using the program dm [Cowtan, cited above (1994)]. Non-crystallographic symmetry is symmetry that exists locally within the asymmetric unit of the crystal. This information can be used to produce averaged electron density maps in which noise will cancel out and therefore can be used as a phase restriction to improve phasing.

The calculated electron density map following this procedure showed side chain density that reflected the HSV-1 sequence, within the limits of the resolution, and clearly showed density for the phenylalanine and tyrosine side chains that were omitted from the model, indicating the electron density did reflect the contributions from the HSV-1 protease data.

The residues unique to the HSV-1 protease sequence were built into the model using Xfit (McRee). When building and changing the model, each of the amino acid residues was manually positioned in its electron density allowing for a unique position for each atom in the HSV-1 protease in which each position is defined by a unique set of atomic coordinates (X, Y, Z) as shown in FIGS. 6A–B. Starting with these atomic coordinates, a diffraction pattern was calculated and compared to the experimental data. The difference between the calculated and experimentally determined diffraction patterns was monitored by the value of the R-factor (R-factor=$S\|F_o|-|F_c\|/SF_o$). The refinement of the structure was done by rigid body where the fit of the model could be refined by rotation and translation of the entire model. Further positional refinement was not possible because of lack of experimental data as compared to refinement parameters.

The final model has 214 amino acids. Three segments of residues are found disordered in the crystal: 102–110, 134–143, and the first 14 residues of the N-terminus of SEQ ID NO: 3. A total of 12346 reflections were included in the final refinement (10–3.5 Å), giving an R-factor ($\Sigma\||Fo|-|Fc\|/\Sigma Fo$)) of 36.9%.

Using the final atomic coordinates (FIG. 6) one can calculate distances between a pair of atoms, angles between any three atoms, and dihedral angles between any four atoms, such as listed in FIGS. 10A–B, 13A–D and 16.

EXAMPLE 3

Analysis of the Structure of the CMV Protease

The CMV protease (see FIG. 1, SEQ ID NO: 1) was cloned, expressed and purified as follows:

A. Expression, Purification and Crystallization

CMV A143V protease was expressed and purified as described for HSV-2 and HSV-1. After screening against about a thousand different conditions, the protein was finally crystallized in 30% PEG400 at pH4. Large crystals are approximately 0.4 mm×0.3 mm×0.3 mm in size.

B. X-ray Diffraction Characterization

The CMV protease crystal was subjected to x-ray diffraction using the techniques described above for HSV-2 and HSV-1 protease crystals, with the exception that the anode machine was operated at 50 KV×100 mA electrode power. The crystal diffracted to 3.0 Å resolution. By registering the position and intensity of many tens of thousands diffraction spots using the computer program XENGEN, the crystal has been determined to be tetragonal crystal system and P4$_3$22 space group. The unit cell dimensions are a=b=58.7 Å and c=131.0 Å. By established methods, an asymmetric unit was calculated to have one protein molecule. The crystal contains an estimated 40% solvent.

A higher resolution diffraction data set (2.5 Å) was collected at the Cornell Synchrotron Laboratory (CHESS) A-1 beamline using a CCD detector. The data was processed with the programs DENZO/SCALEPACK [Otwinowski, Z. in *Data Collection and Processing* (eds Sawyer, L., Isaacs, N. Bailey, S.) 56–62, Daresbury Laboratory, Warrington (1993)]. Others were collected with a Siemens multiwire detector on a Siemens CuK$_\alpha$ source and processed with XENGEN [A. J. Howard et al., *J. Appl. Crystallogr.* A47: 110–119 (1994)].

C. Heavy Atom Derivatives

Using the MIR methods described in Example 1, by testing various heavy metal compounds, the useful derivatives were prepared by soaking the native crystals with saturated MeHgCl (at pH4 or 5), saturated Baker's Dimercury, 1 mM UO$_2$Ac$_2$, 1 mM K$_2$PtCl$_4$, 0.5 mM LuCl$_3$ or SmCl$_3$ for one to four davs. The X-ray diffraction data of each of the derivatives were then collected by the same methods described above. Data collection statistics for native and heavy atom derivatives are shown in FIG. 43. Heavy atom positions were identified by difference Patterson and difference Fourier methods using the programs in the CCP4 suite [Collaborative Computational Project, Number 4 *Acta Crystallogr.* D50, 760–763 (1994)]. Anomalous signals from three of the derivatives allowed the determination of the chirality of space group and heavy atom coordinates. Heavy atom refinement and phasing were carried out using the program MLPHARE [Z. Otwinowski, cited above (1991)]. Using the initial phases obtained through the MIR methods, a map of electron density within the crystal unit cell was calculated. Because electrons are heavily distributed in the immediate vicinity of the centers of atoms, the positions of protein atoms are registered according to the electron density map. The clarity of the electron density map was improved with the methods of solvent flattening, histogram matching and skeletonization.

D. Model Building and Refinement

Using the three-dimensional electron density map obtained from above experiments, the polypeptide chain of the CMV protease can be traced without ambiguity. 193 residues (most with side chains) were built using the 3-D computer graphics program XTALVIEW [McRee, D. E., cited above (1993)]. XTALVIEW was used in building models of the CMV protease structure. Each of these 193 amino acids residues was manually positioned in its electron density, allowing for a unique position for each atom in the CMV protease in which each position is defined by a unique set of atomic coordinates (X, Y, Z) as shown in FIGS. 17A–E. Starting with these atomic coordinates, a diffraction pattern was calculated and compared to the experimental data. The difference between the calculated and experimentally determined diffraction patterns was monitored by the value of R-factors (R-factor=$\Sigma||F_o|-|F_c||/\Sigma F_o$). The refinement (using XPLOR) of the structural model neccesitates adjustments of atomic positions to minimize the R-factor, where a value of below 20% is typical for a good quality protein structure and a value of higher than 20% usually indicates the need of further refinement.

The initial model of CMV protease contains about 70% of the amino acids, having a starting R-factor of 43.8% using the diffraction data from 10 to 3.0 Å. The computer program XPLOR was used to carry out the refinements, and the models were improved gradually after many iteration cycles. The R-factor was decreased to 28.3% after 200 cycles of positional refinement with XPLOR. The final R-factor is 18.7% the CMV protease structure. The program PROCHECK [R. A. Laskowski et al., cited above (1993)] was used to check the stereochemical and geometrical outliers in the final structure, and the result is very satisfactory.

The statistics of structure determination data is reported in FIG. 43, where $R_m$, $R_{ISO}$, and $R_{Cullis}$, R-factor are as defined in Example 1 above. $R_c$(ano) is defined for anomalous amplitudes of non-centric reflections similar to the original $R_{Cullis}$ formula. As described in Example 1, XPLOR refinement was performed according to A. T. Brunger et al., cited above. More particularly, resolution included: 7.0–2.5 Å, No. reflections used (>1s):7193; R-factor: 0.185, No. protein atoms (non-H): 1604 (202 aa); No. of solvent atoms (non-H):73; MIR as figure of merit (30–3.2 Å):0.70, Mean coordinates error: 0.4 Å; RMS bond length: 0.017 Å; RMS bond angle (2.2 degrees). Mean coordinates error was performed according to the SIGMAA program [R. Read, *J. Appl. Crystallogr.*, A42: 140–149 (1986)].

Using the final atomic coordinates (FIGS. 17A–E) one can calculate distances between a pair of atoms, angles between any three atoms, and dihedral angles between any four atoms, such as listed in FIGS. 18A–C, 19A–D and 20.

EXAMPLE 4

Cloning and Expression of the VZV Protease

The VZV protease gene was located in the complete VZV genome by homology to the protease genes from the HSV-1 and CMV herpes viruses. The VZV genomic sequence used for this analysis was as published by A. Davison & J. Scott, *J. Gen. Virol.*, 67: 1759–1816 (1986). The open reading frame for the protease/capsid-encoding gene (equivalent to the HSV-1 UL26 gene) was found to start at base 62,138 and stop at base 60,324 encoding 605 amino acid residues. This open reading frame had been referred to as gene 33 in the above mentioned publication.

The 236 amino acid long protease catalytic domain [SEQ ID NO: 5] was located by identifying the R site that defines the carboxyl-terminal end of all known herpes virus proteases. An alignment of such known R sites is shown in Table I. These cleavage sites are highly conserved (as shown by underlined residues) with cleavage occurring between alanine and serine residues, as indicated by "*".

TABLE I

| Protease | R Site Sequence | Sequence ID No: |
| --- | --- | --- |
| HSV-1 | <u>Tyr</u>—Leu—Gln—<u>Ala*Ser</u> | 3 |
| HSV-2 | <u>Tyr</u>—Leu—Gln—<u>Ala*Ser</u> | 4 |
| CMV | <u>Tyr</u>—Val—Lys—<u>Ala*Ser</u> | 1 |
| EBV | <u>Tyr</u>—Leu—Lys—<u>Ala*Ser</u> | 6 |
| VZV | <u>Tyr</u>—Leu—Gln—<u>Ala*Ser</u> | 5 |

A. Design of VZV-Protease synthetic gene

In an effort to optimize bacterial expression of the VZV protease catalytic domain, a synthetic gene was constructed using codons that are found in proteins highly expressed in *E. coli*. In addition, a number of constructs were made with the goal of facilitating purification of the protein as an active enzyme. Most of the constructs were aimed at producing the authentic species believed to be made during viral infection.

The synthetic gene was designed as follows: A 788 bp VZV protease gene fragment was designed with an NcoI restriction site at the 5' end and XbaI site at the 3' end. These restriction sites are useful for subsequent cloning of the gene fragment in a suitable expression vector. A unique BstE2 restriction site was introduced in the middle of the gene fragment without altering the amino acid sequence. This restriction site was later used to ligate the two synthetic fragments together. It was decided to construct this gene in two portions for the ease of gene synthesis.

The 5' portion of the gene was about 370 bp long and the 3' portion was about 418 bp.

B. Design and synthesis of oligonucleotides

Four megaprimers (primers which are more than 100 bases long) with about 25 bp overlapping ends were designed using the Oligo 4.0 software from National Biosciences Inc. Care was taken to avoid mismatching of overlapping ends. All primers were synthesized on an Applied Biosystem DNA Synthesizer (Model 394) using 40 nM polystyrene columns. Crude oligonucleotide primers were used to assemble the gene fragments. For each portion of the gene, two PCR primers containing unique restriction sites were made using the same DNA synthesizer. These oligonucleotides were referred to as 'nested primers'.

C. Gene Synthesis

The gene synthesis was carried out using the procedure described by Rosen et al, *BioTechniques*, 9(3) (1990) with some modifications. For each portion of the gene, two megaprimers oligonucleotides were phosphorylated using the standard kinase procedure [Sambrook et al, *Molecular Cloning. A Laboratory Manual.*, 2nd edit., Cold Spring Laboratory, New York (1989)]. In the first polymerase chain reaction (PCR), 0.5 to 1 ug of each of the four megaprimers were mixed together and the PCR was carried out using dNTPs and a mixture of Taq and Vent DNA polymerases (6:1 v/v). Only about 15 cycles of PCR were carried out using the Perkin Elmer PCR 9600 thermocycler (94° C. for 30 seconds, 52° C. for 30 seconds, 72° C. for 45 seconds).

The product of this PCR reaction was used as a template in the second PCR reaction along with 5' and 3' gene specific primers containing unique restriction sites ('nested primers'). PCR reactions was carried out for 25–30 cycles using similar cycle times as above.

About 10 ul of reaction product was analyzed on a 1% agarose gel. PCR products showing a correct size band were then subcloned in the PCR II vector [Invitrogen, San Diego, Calif.]. The DNA sequence of the synthetic fragments was confirmed by automated DNA sequencing.

D. VZV protease constructs

Six constructs were prepared for the expression of the VZV protease catalytic domain and are illustrated as FIGS. 45A to 45E [SEQ ID NOS: 7 through 11, respectively]. Authentic VZV protease [SEQ ID NO: 5] contained a protease domain authentic at both amino and carboxyl termini.

H6(N)VZV protease [SEQ ID NO: 7] contained an authentic protease domain preceded at the amino-terminus by six histidine residues (underlined) followed by an enterokinase cleavage site (bold, underlined). The amino-terminal sequence of this construct is: MG<u>HHHHHH</u>SSGHI<u>DDDDK</u>-MAAE.

LQA-H6(C) VZV protease [SEQ ID NO: 8] contained an authentic protease domain followed by six histidine residues.

LQAS-H6(C) VZV protease [SEQ ID NO: 9] contained an authentic protease domain followed by a serine residue and six histidine residues (underlined).

LQAS-12aa ext H6(C) VZV protease [SEQ ID NO: 10] contains an authentic protease domain followed by a serine residue, 12 residues normally found after the LQAS R-site (bold underlined) and six histidine residues (underlined). The carboxyl-terminal sequence of this construct is: . . . LQAS-<u>TGYGLARITNVN</u>-<u>HHHHHH</u>.

Delta9 LQAS-12aa ext H6(C) VZV protease [SEQ ID NO: 11] contained an authentic protease domain deleted at the amino-terminus (first nine natural residues removed and Cys 10 replaced by Met) and followed at the carboxyl-terminus by a serine residue, 12 residues normally found after the LQAS R-site (bold underlined) and six histidine residues (underlined). The amino-terminus of this construct is MEALYV . . . ; and the carboxyl-terminal sequence of this construct is: . . . LQAS-<u>TGYGLARITNVN</u>-<u>HHHHHH</u>.

E. Expression of VZV protease constructs

All constructs were inserted in the E. coli expression vector pET 16b (Novagen, Madison, Wis.) in which the inserted gene is under the control of the inducible T7 promoter. The vectors were introduced in the BL21(DE3) *E. coli* strain (Novagen) by standard transformation techniques. The transformed cells were grown to $OD_{650}$=0.5 and then treated with IPTG at 10 mM to induce expression from the T7 promoter. The cells were then aerated for an additional 2 hours and collected by centrifugation. Cell extracts were analyzed for expression by SDS-PAGE followed by Coomassie staining or western blot analysis using a polyclonal antibody against HSV-1 protease, called Anti-95370.

Anti-95370 is a rabbit anti-HSV-1 protease polyclonal antiserum prepared by fusing the complete HSV1 UL26 gene to the C-terminus of a truncated GalK gene in the pOTSKF33 vector described in C. S. Chiang et al, *Clin. Chem.*, 35(6): 946–952 (1989). The fusion protein was expressed by conventional protocols and after cell lysis, the insoluble fraction was gel purified using preparative SDS-PAGE. The fusion protein was electroeluted and used to immunize rabbits by standard protocols. The resulting Anti-95370 antisera was shown to cross-react with the VZV protease.

EXAMPLE 5

Purification of VZV Protease Constructs

No purification work was done on the authentic VZV protease construct. The other constructs were purified as follows:

A. Purification of H6(N) VZV Protease [SEQ ID NO: 7]

Expression of this protease construct was examined by comparing two hour inductions at 25° C. and 37° C. Cells (2–3 g) were resuspended in 50 mM Tris pH8.0, 300 mM NaCl at a ratio of 10 ml/g cells and lysed by sonication on ice. Subsequent purification procedures were performed at 4° C. After centrifugation at 30,000 xg, the soluble fraction was further purified by a one hour batch incubation with NiNTA agarose (Qiagen) followed by column chromatography with imidazole washes and elution. Samples were analyzed by Coomassie stained SDS-PAGE and Western blot using Anti-95370 polyclonal antibody described above.

More protease was expressed at 37° C. but the majority of the protease was insoluble under both conditions. The soluble protease appeared divided between full length and truncated (identified as C-terminal desk30) forms. The majority of the product eluted at 50 mM imidazole rather than the expected 250 mM. The 50 mM eluate was 90% pure, ~90% truncated, active against the JM82 peptide substrate (Ac-HTYLQA*SEKFKMWG; * represents the cleavage site) [SEQ ID NO: 16] and had the correct N-terminal sequence. The activity was attributed to full length product.

B. Purification of LQA-H6(C) VZV Protease [SEQ ID NO: 8] and LQAS-H6(C) VZV Protease [SEQ ID NO: 9]

Cells (5–10 g) induced in shake flasks at 25° C. and 37° C. expressing these constructs were resuspended in 50 mM Tris pH8.0, 300 mM NaCl at a ratio of 10 ml/g cells and lysed with the Avestin homogenizer (~12,000 psi). The lysate was centrifuged and the soluble fraction was chromatographed on NiNTA agarose. More protease eluted with 50 mM imidazole than with 250 mM imidazole for both constructs induced at 37° C. The majority of product eluted at 250 mM imidazole for LQA-H6(C) VZV protease induced at 25° C. The relative elutions were consistent in RP-HPLC, Coomassie and Western analyses. All products appeared to be of equivalent size.

The products from both constructs had the predicted N-terminal (desMet). The 50 mM eluate from LQAS-H6(C) VZV protease [SEQ ID NO: 9] was concentrated to ~0.6 mg/ml, made 10 mM DTT, 1 mM EDTA and 10% glycerol and incubated at 4° C. Slight activity (<10% specific activity of fully processed protease) against the JM82 peptide substrate was detected 10 days later and confirmed after another 10 days. When the shake flask preparation was repeated and an additional Superdex 75 chromatography step was added, the final product still had only about 10% of the potential activity. Scale-up of LQAS-H6(C) VZV protease [SEQ ID NO: 9] using cells grown in a 10 liter fermentor and induced at OD 0.7 or OD 5.0 at 37° C. for 1 hour was unsuccessful.

Coomassie-stained SDS-PAGE gels indicated that lysis was successful but no protease could be detected in NiNTA eluates using RP-HPLC. Western blot detected the best expression with cells induced at OD 0.7 but the majority of the product was insoluble. The same levels of product were detected in the NiNTA agarose load and unbound for the 10 L fermented cells suggesting that product did not bind. Product was detected in the load from cells grown in shake flask but not in the unbound fraction suggesting complete capture by NiNTA agarose. The product from all samples had the same apparent molecular weight. The reason for the failure to bind to NiNTA agarose is unknown.

D. Purification of LQAS-12*aa* ext H6(C) VZV Protease [SEQ ID NO: 10] and delta9 LQAS-12*aa* ext H6(C) VZV Protease [SEQ ID NO: 11]

300 g of cells from LQAS-12*aa* ext H6(C) VZV protease [SEQ ID NO: 10] were resuspended in buffer A (50 mM Tris, pH8.0, 300 mM NaCl) to a final volume of 3 L and the cells were lysed with an Avestin homogenizer at ~12.000 psi. The homogenate was centrifuged for 1 hour, 4° C. at 14,000 rpm (30,000 g). The supernatant was collected and added to NiNTA agarose (Qiagen) at a ratio of 1 ml/10 g cells. After incubation with rotation at 4° C. for 1 hour, the resin was collected by centrifugation for 10 minutes at 3000 rpm. The supernatant was removed with a peristaltic pump and the resin was packed into a Pharmacia 2.6 cm XK column with a 25 ml pipette. The column was washed to baseline absorbance (0.5 mV) with buffer A at 2.5 ml/minute. After washing with 20% B (50 mM imidazole; buffer B is 50 mM Tris, pH8.0, 300 mM NaCl. 250 mM imidazole) the protease was eluted with 100% B (250 mM imidazole). Glycerol was added to the 250 mM eluate to 10%, DTT to 10 mM, and EDTA to 1 mM final concentrations. The sample was filtered with a STERWVEX 0.45 mm (Millipore) filter and transferred to an Amicon 50 ml stirred cell. After concentration to 5 ml, the sample was diluted to 50 ml with SEC buffer (25 mM HEPES, pH8.0, 50 mM NaCl, 1 mM EDTA, 5 mM DTT) and concentrated to <5 ml. After filtration the sample was stored overnight at 4° C.

The sample was chromatographed on a 2.6×60 cm Superdex column equilibrated in SEC buffer. Protease fractions determined by absorbance at 280 nm were pooled and concentrated in a 10 ml stirred cell. Precipitate was removed by centrifugation and the sample was filtered (Millipore ULTRAFREE MC 0.22 $\mu$m). The VZV protease product was concentrated to 2 mg/ml and diluted with an equal volume of glycerol before storage at −20° C. for protease assays. Alternately, protease was concentrated to ~10 mg/ml for crystallography.

The protease product from LQAS-12*aa* ext H6(C) VZV [SEQ ID NO: 10] was determined to be of the predicted mass by MALDI-MS without the N-terminal Met and with a carboxyl terminus corresponding to authentic protease (i.e., ending with LQA as a result of auto-processing of the 12 amino acid extension at the R site). In fact, it was determined that this construct, which contained a carboxy tail with a hexahistidine tail for binding to NiNTA, following 13 additional amino acids after the LQA mature protein carboxy terminal amino acids, permitted the production of a properly cleaved carboxy terminus for the protein. The protease from delta LQAS-12*aa* ext H6(C) VZV [SEQ ID NO: 11] had the predicted mass while retaining the N-terminal Met and also ending with LQA. Both proteases were active against the JM82 substrate. Purified protease was a single peak on RP-HPLC and SEC and 95% pure on RP-HPLC.

Protease from delta9 LQAS-12*aa* ext H6(C) VZV [SEQ ID NO: 11] was primarily prepared for crystallography (to eliminate structural disorder at the amino terminus) with atypical yield of 4 mg/300 g *E. coli* cells. Protease from LQAS-12*aa* ext H6(C) VZV SEQ ID NO: 10] yielded as much as 17 mg/300 g *E. coli* cells.

These modified VZV protein constructs are useful in the crystallization of VZV protease as described below in Example 6, as well as for other biophysical structural studies of VZV protease. The constructs are also useful in biochemical assays to identify compounds which inhibit and/or interact with VZV protease (see Examples 7 and 8 below).

EXAMPLE 6

Crystallization of the VZV Protease

Protease from delta9 LQAS-12*aa* ext H6(C) VZV [SEQ ID NO: 11] was crystallized in 0.1M phosphate buffer pH6.2 and 2.5M NaCl. Large crystals are approximately 0.5 mm×0.2 mm×0.2 mm in size.

A. X-ray Diffraction Characterization

A VZV protease crystal was subjected to x-ray diffraction characterization, using essentially the same methods as described for CMV. The crystal diffracted to 3.0 Å resolution. By registering the position and intensity of many tens of thousands diffraction spots using the computer program XENGEN, the crystal has been determined to be the hexagonal space group P6$_4$22, with a=b=90.0 Å and c=117.4 Å. By established methods, an asymmetric unit was calculated to have one protein molecule. The crystal contains an estimated 60% solvent. The native data is 90% complete to 3.0 Å with an $R_{merge}$ ($\Sigma|I-<I>|/\Sigma<I>$) of 0.07.

B. Heavy Atom Derivative

Single isomorphous replacement (SIR) methods were used. The useful derivatives were prepared by soaking the native crystals with 1 mM $KPt(CN)_2$ for one day. Using the initial phases obtained through the SIR methods, a map of electron density within the crystal unit cell could be calculated. Because electrons are heavily distributed in the intermediate vicinity of the centers of atoms, the positions of protein atoms are registered according to the electron density map. The clarity of the electron density map could be improved with the methods of solvent flattening, histogram matching and skeletonization. The derivative data is 81% complete to 4.5 Å with an $R_{merge}$ of 0.14 and $R_{iso}$ ($\Sigma|FPH-FP|/\Sigma FP$) of 0.19. This derivative gave a phasing power of 1.2 and $R_{Cullis}$ ($\Sigma|FH_o-FH_c|/\Sigma|FH_o|$) of 0.79. In this case, the phase information from SIR is not sufficient for structure solution.

C. Molecular Replacement

A molecular replacement (MR) solution using XPLOR [A. Brunger et al. Science 235, 458–460 (1987)] was successfully identified only after all the less conserved regions were excluded in the search model which originated from the CMV protease structure. The rotation solution (8.0–4.0 Å) is the highest peak and is 25s above the mean and 1s higher than the second highest peak. Translation searches were carried out in two possible spacegroups P6$_2$22 and P6$_4$22, and the latter gave a better solution of 5s in peak height and 52.6% in R-factor (8.0–3.0 Å). After rigid body refinement using 8.0–3.0 Å data, the R-factor dropped to 50.6%. When examining the crystal packing, a tight dimer interface was found that corresponds to the same interface in CMV protease. Using the calculated phases from the molecular replacement solution, a heavy atom position was identified using difference Fourier methods that is identical to the one found using difference Patterson methods. This position is in the vicinity of Cys 157, which further confirmed the correctness of these results.

D. Phase Combination

The crystal structure of VZV protease was determined using the combination of single isomorphous replacement (SIR) and molecular replacement methods. Neither the SIR map nor the MR map seemed to be interpretable. Combining the phases from both sources, the overall figure of merit was only 0.39 and the map is still quite noisy. Fortunately, there is 60% of solvent in the crystal. After solvent flattening and histogram matching, the electron density map became very clear.

E. Model Building and Refinement

The polypeptide chain of the VZV protease [SEQ ID NO: 5] can be traced without ambiguity using the three-dimensional electron density map obtained from the above-experiments and the methods described in Example 3 for CMV above, with the exception that 211 residues (most with side chains) were built.

Cycles of model building with XTALVIEW program and refinement with the XPLOR computer program produce a final model including 211 amino acids without any solvent molecules. Fifteen residues are found disordered in the crystal: 127–136 and 232–236 of SEQ ID NO: 5. A total of 4903 reflections were included in the final refinement (7.0–3.0 Å), giving an R-factor ($\Sigma\|F_o|-|F_c\|/\Sigma F_o$) of 22.3% without refining temperature factors. The rms bond length is 0.014 Å and rms bond angle is 2.1°. His 52 and His 139 were refined as carrying a single proton at the ND1 atom. The program PROCHECK [R. A. Laskowski et al., *J. Appl. Crystallogr.*, 26: 283–291 (1993)] was used to check the stereochemical and geometrical outliers in the final structure, and the result is very, satisfactory.

Using the final atomic coordinates (FIGS. 22A–C) one can calculate distances between a pair of atoms, angles between any three atoms, and dihedral angles between any four atoms, such as listed in FIGS. 24–26.

EXAMPLE 7

Protease Activity Assays

The biological function of the HSV-2, HSV-1, CMV, and VZV proteases in vivo is to specifically cleave the Ala-Ser peptide bonds within a large protein substrate molecule. For routine in vitro assay of the protease activity, use of a large protein substrate is inconvenient and very expensive.

A. HSV-2 Protease

For HSV-2 protease, a small peptide substrate having the sequence dabsyl-DNAVEA*SSKAPLK-(dansyl-II)-OH entitled FQ7 (based on VZV m site) [SEQ ID NO: 17] has been synthesized in place of large protein substrate. In the presence of the HSV-2 protease, the FQ7 peptide will be cleaved at the A*S peptide bond, and the product will be the two halves of the substrate. The peptide has been designed so that the cleaved molecules will give rise to strong fluorescence signals.

Therefore, the enzymatic activity of HSV-2 protease can be measured quantitatively by the intensity of the fluorescence signal. This is a very sensitive assay method called fluorescence quenching (FQ). For instance, see, "Principles of Fluorescence Spectroscopy", Lakowicz, J. R., Plenum Press, N.Y. 1983.

In experiments conducted on the HSV-2 protease, the optimized assay conditions call for the use of 520 nM of the HSV-2 protease, 30% of sucrose and 0.8M citrate. In the presence of added inhibitors, the decreased amount of activity also quantifies the potency of the inhibitors.

B. HSV-1 Protease

For HSV-1 protease, a small peptide substrate having the sequence Ac-HTYLQA*SEKFKMWG entitled JM82 [SEQ ID NO: 16] has been synthesized in place of large protein substrate. In the presence of the HSV-1 protease, the JM82 peptide will be cleaved at the A*S peptide bond, and the product will be the two halves of the substrate. Activity was measured by quantification of the two halves of the substrate using HPLC.

In experiments conducted on the HSV-1 protease, the optimized assay conditions call for the use of 0.3 mg/ml of the HSV-1 protease, 30% of sucrose and 0.8M citrate in a buffer of 25 mM Hepes (pH 8.0), 50 mM NaCl, 10 mM DTT, 1 mM EDTA and 10% Glycerol. In the presence of added inhibitors, the decreased amount of activity also quantifies the potency of the inhibitors.

C. CMV Protease

For CMV protease, a small peptide substrate having the sequence Dbs-RGVVNASSRLAKK-DNS(II) entitled FQ8 [SEQ ID NO: 18] has been synthesized in place of large protein substrate. In the presence of the CMV protease, the FQ8 peptide will be cleaved at the A*S peptide bond, and the product will be the two halves of the substrate. As for HSV-1 and HSV-2 proteases, the peptide substrate has been designed so that the cleaved molecules will give rise to strong fluorescence signals.

In experiments conducted on the CMV protease, the optimised assay conditions call for the use of 20 mM of the CMV protease and 30% of sucrose. In the presence of added inhibitors, the decreased amount of activity also quantifies the potency of the inhibitors.

D. VZV Protease

This assay was performed as described for the proteases above, making use of the FQ7 small peptide substrate. In experiments conducted on the VZV protease, the optimized assay conditions call for the use of 20 nM of the VZV protease, with buffer of 50 mM Hepes, pH8, 150 mM NaCl, 1 mM EDTA, 0.01% PEG with 0.8M citrate/30% sucrose. In the presence of added inhibitors, the decreased amount of activity also quantifies the potency of the inhibitors.

EXAMPLE 8

Method of Detecting Inhibitors

The three dimensional atomic structure can be readily used as a template for selecting potent inhibitors. Various computer programs and databases are available for the purpose. A good inhibitor should at least have excellent steric and electrostatic complementarity to the target, a fair amount of hydrophobic surface buried and sufficient conformational rigidity to minimize entropy loss upon binding.

There are generally several steps in employing the 3D structure as a template.

First, a target region is defined. In defining a region to target, one can choose the active site cavity of the herpes protease, or any place that is essential to the protease activity. As described above, for HSV-2, HSV-1, CMV and VZV proteases, the crystal structure is determined and therefore spatial and chemical properties of the target region are known.

Second, a small molecule is docked onto the target using one of a variety of methods. Computer databases of three-dimensional structures are available for screening millions of small molecular compounds. A negative image of these compounds is calculated and used to match the shape of the target cavity. The profiles of hydrogen bond donor-acceptor and lipophilic points of these compounds are also used to complement those of the target. One skilled in the art can readily identify many small molecules or fragments as hits.

Third, one may link and extend recognition fragments. Using the hits identified by above procedure, one can incorporate different functional groups or small molecules into a single, larger molecule. The resulting molecule is likely to be more potent and have higher specificity than a single hit. It is also possible to try to improve the "seed" inhibitor by adding more atoms or fragments that will interact with the target protein. The originally defined target region can be readily expanded to allow further necessary extension.

A limited number of promising compounds is selected via this process. The compounds are synthesized and assayed for their inhibitory properties. The success rate is sometimes as high as 20%, and it may still be higher with the rapid progresses in computing methods.

This invention is not to be limited in scope by the specific embodiments described herein. Indeed, various modifications of the invention in addition to those described herein will become apparent to those skilled in the art from the foregoing description. Such modifications are intended to fall within the scope of the appended claims.

The disclosures of the patents, patent applications and publications cited herein are incorporated by reference in their entireties.

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 256 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:1:

```
Met Thr Met Asp Glu Gln Gln Ser Gln Ala Val Ala Pro Val Tyr Val
 1               5                  10                  15

Gly Gly Phe Leu Ala Arg Tyr Asp Gln Ser Pro Asp Glu Ala Glu Leu
                20                  25                  30

Leu Leu Pro Arg Asp Val Val Glu His Trp Leu His Ala Gln Gly Gln
                35                  40                  45

Gly Gln Pro Ser Leu Ser Val Ala Leu Pro Leu Asn Ile Asn His Asp
        50                  55                  60

Asp Thr Ala Val Val Gly His Val Ala Ala Met Gln Ser Val Arg Asp
65                  70                  75                  80

Gly Leu Phe Cys Leu Gly Cys Val Thr Ser Pro Arg Phe Leu Glu Ile
                85                  90                  95

Val Arg Arg Ala Ser Glu Lys Ser Glu Leu Val Ser Arg Gly Pro Val
                100                 105                 110

Ser Pro Leu Gln Pro Asp Lys Val Val Glu Phe Leu Ser Gly Ser Tyr
            115                 120                 125

Ala Gly Leu Ser Leu Ser Ser Arg Arg Cys Asp Asp Val Glu Ala Ala
        130                 135                 140

Thr Ser Leu Ser Gly Ser Glu Thr Thr Pro Phe Lys His Val Ala Leu
145                 150                 155                 160

Cys Ser Val Gly Arg Arg Arg Gly Thr Leu Ala Val Tyr Gly Arg Asp
                165                 170                 175

Pro Glu Trp Val Thr Gln Arg Phe Pro Asp Leu Thr Ala Ala Asp Arg
                180                 185                 190

Asp Gly Leu Arg Ala Gln Trp Gln Arg Cys Gly Ser Thr Ala Val Asp
            195                 200                 205

Ala Ser Gly Asp Pro Phe Arg Ser Asp Ser Tyr Gly Leu Leu Gly Asn
        210                 215                 220

Ser Val Asp Ala Leu Tyr Ile Arg Glu Arg Leu Pro Lys Leu Arg Tyr
225                 230                 235                 240

Asp Lys Gln Leu Val Gly Val Thr Glu Arg Glu Ser Tyr Val Lys Ala
```

6,083,711

-continued

```
                  245                 250                 255

(2) INFORMATION FOR SEQ ID NO:2:

(i) SEQUENCE CHARACTERISTICS:
        (A) LENGTH: 230 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

Met Ser Lys Val Trp Val Gly Gly Phe Leu Cys Val Tyr Gly Glu Glu
    1               5                   10                  15

Pro Ser Glu Glu Cys Leu Ala Leu Pro Arg Asp Thr Val Gln Lys Glu
                20                  25                  30

Leu Gly Ser Gly Asn Ile Pro Leu Pro Leu Asn Ile Asn His Asn Glu
                35                  40                  45

Lys Ala Thr Ile Gly Met Val Arg Gly Leu Phe Asp Leu Glu His Gly
    50                  55                  60

Leu Phe Cys Val Ala Gln Ile Gln Ser Gln Thr Phe Met Asp Ile Ile
    65                  70                  75                  80

Arg Asn Ile Ala Gly Lys Ser Lys Leu Ile Thr Ala Gly Ser Val Ile
                85                  90                  95

Glu Pro Leu Pro Pro Asp Pro Glu Ile Glu Cys Leu Ser Ser Ser Phe
                100                 105                 110

Pro Gly Leu Ser Leu Ser Ser Lys Val Leu Gln Asp Glu Asn Leu Asp
                115                 120                 125

Gly Lys Pro Phe Phe His His Val Ser Val Cys Gly Val Gly Arg Arg
                130                 135                 140

Pro Gly Thr Ile Ala Ile Phe Gly Arg Glu Ile Ser Trp Ile Leu Asp
    145                 150                 155                 160

Arg Phe Ser Cys Ile Ser Glu Ser Glu Lys Arg Gln Val Leu Glu Gly
                165                 170                 175

Val Asn Val Tyr Ser Gln Gly Phe Asp Glu Asn Leu Phe Ser Ala Asp
                180                 185                 190

Leu Tyr Asp Leu Leu Ala Asp Ser Leu Asp Thr Ser Tyr Ile Arg Lys
                195                 200                 205

Arg Phe Pro Lys Leu Gln Leu Asp Lys Gln Leu Cys Gly Leu Ser Lys
                210                 215                 220

Cys Thr Tyr Ile Lys Ala
    225                 230

(2) INFORMATION FOR SEQ ID NO:3:

(i) SEQUENCE CHARACTERISTICS:
        (A) LENGTH: 247 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Met Ala Ala Asp Ala Pro Gly Asp Arg Met Glu Glu Pro Leu Pro Asp
    1               5                   10                  15

Arg Ala Val Pro Ile Tyr Val Ala Gly Phe Leu Ala Leu Tyr Asp Ser
                20                  25                  30

Gly Asp Ser Gly Glu Leu Ala Leu Asp Pro Asp Thr Val Arg Ala Ala
```

```
                    35                    40                     45
    Leu Pro Asp Asn Pro Leu Pro Ile Asn Val Asn His Arg Ala Gly
         50                      55                     60
    Cys Glu Val Gly Arg Val Leu Ala Val Val Asp Asp Pro Arg Gly Pro
    65                      70                     75                     80
    Phe Phe Val Gly Leu Ile Ala Cys Val Gln Leu Glu Arg Val Leu Glu
                        85                     90                     95
    Thr Ala Ala Ser Ala Ala Ile Phe Glu Arg Arg Gly Pro Pro Leu Ser
                       100                    105                    110
    Arg Glu Glu Arg Leu Leu Tyr Leu Ile Thr Asn Tyr Leu Pro Ser Val
                       115                    120                    125
    Ser Leu Ala Thr Lys Arg Leu Gly Gly Glu Ala His Pro Asp Arg Thr
                  130                    135                    140
    Leu Phe Ala His Val Ala Leu Cys Ala Ile Gly Arg Arg Leu Gly Thr
    145                    150                    155                    160
    Ile Val Thr Tyr Asp Thr Gly Leu Asp Ala Ala Ile Ala Pro Phe Arg
                       165                    170                    175
    His Leu Ser Pro Ala Ser Arg Glu Gly Ala Arg Arg Leu Ala Ala Glu
                       180                    185                    190
    Ala Glu Leu Ala Leu Ser Gly Arg Thr Trp Ala Pro Gly Val Glu Ala
                  195                    200                    205
    Leu Thr His Thr Leu Leu Ser Thr Ala Val Asn Asn Met Met Leu Arg
    210                    215                    220
    Asp Arg Trp Ser Leu Val Ala Glu Arg Arg Gln Ala Gly Ile Ala
    225                    230                    235                    240
    Gly His Thr Tyr Leu Gln Ala
                       245

(2) INFORMATION FOR SEQ ID NO:4:

(i) SEQUENCE CHARACTERISTICS:
        (A) LENGTH: 247 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Met Ala Ser Ala Glu Met Arg Glu Arg Leu Glu Ala Pro Leu Pro Asp
    1                   5                      10                     15
    Arg Ala Val Pro Ile Tyr Val Ala Gly Phe Leu Ala Leu Tyr Asp Ser
                        20                     25                     30
    Gly Asp Pro Gly Glu Leu Ala Leu Asp Pro Asp Thr Val Arg Ala Ala
                   35                     40                     45
    Leu Pro Pro Glu Asn Pro Leu Pro Ile Asn Val Asn His Arg Ala Arg
         50                      55                     60
    Cys Glu Val Gly Arg Val Leu Ala Val Val Asn Asp Pro Arg Gly Pro
    65                      70                     75                     80
    Phe Phe Val Gly Leu Ile Ala Cys Val Gln Leu Glu Arg Val Leu Glu
                        85                     90                     95
    Thr Ala Ala Ser Ala Ala Ile Phe Glu Arg Arg Gly Pro Ala Leu Ser
                       100                    105                    110
    Arg Glu Glu Arg Leu Leu Tyr Leu Ile Thr Asn Tyr Leu Pro Ser Val
                       115                    120                    125
    Ser Leu Ser Thr Lys Arg Gly Asp Glu Val Pro Pro Asp Arg Thr
                  130                    135                    140
```

```
Leu Phe Ala His Val Ala Leu Cys Ala Ile Gly Arg Arg Leu Gly Thr
145                 150                 155                 160

Ile Val Thr Tyr Asp Thr Ser Leu Asp Ala Ala Ile Ala Pro Phe Arg
                165                 170                 175

His Leu Asp Pro Ala Thr Arg Glu Gly Val Arg Arg Glu Ala Ala Glu
            180                 185                 190

Ala Glu Leu Ala Leu Ala Gly Arg Thr Trp Ala Pro Gly Val Glu Ala
        195                 200                 205

Leu Thr His Thr Leu Leu Ser Thr Ala Val Asn Asn Met Met Leu Arg
    210                 215                 220

Asp Arg Trp Ser Leu Val Ala Glu Arg Arg Gln Ala Gly Ile Ala
225                 230                 235                 240

Gly His Thr Tyr Leu Gln Ala
                245
```

(2) INFORMATION FOR SEQ ID NO:5:

(i) SEQUENCE CHARACTERISTICS:
        (A) LENGTH: 236 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Met Ala Ala Glu Ala Asp Glu Glu Asn Cys Glu Ala Leu Tyr Val Ala
1               5                   10                  15

Gly Leu Tyr Ala Leu Tyr Ser Lys Asp Glu Gly Glu Leu Asn Ile Thr
                20                  25                  30

Pro Glu Ile Val Arg Ser Ala Leu Pro Pro Thr Ser Lys Ile Pro Ile
            35                  40                  45

Asn Ile Asp His Arg Lys Asp Cys Val Val Gly Glu Val Ile Ala Ile
        50                  55                  60

Ile Glu Asp Ile Arg Gly Pro Phe Phe Leu Gly Ile Val Arg Cys Pro
65                  70                  75                  80

Gln Leu His Ala Val Leu Phe Glu Ala Ala His Ser Asn Phe Phe Gly
                85                  90                  95

Asn Arg Asp Ser Val Leu Ser Pro Leu Glu Arg Ala Leu Tyr Leu Val
            100                 105                 110

Thr Asn Tyr Leu Pro Ser Val Ser Leu Ser Ser Lys Arg Leu Ser Pro
        115                 120                 125

Asn Glu Ile Pro Asp Gly Asn Phe Phe Thr His Val Ala Leu Cys Val
    130                 135                 140

Val Gly Arg Arg Val Gly Thr Val Val Asn Tyr Asp Cys Thr Pro Glu
145                 150                 155                 160

Ser Ser Ile Glu Pro Phe Arg Val Leu Ser Met Glu Ser Lys Ala Arg
                165                 170                 175

Leu Leu Ser Leu Val Lys Asp Tyr Ala Gly Leu Asn Lys Val Trp Lys
            180                 185                 190

Val Ser Glu Asp Lys Leu Ala Lys Val Leu Leu Ser Thr Ala Val Asn
        195                 200                 205

Asn Met Leu Leu Arg Asp Arg Trp Asp Val Val Ala Lys Arg Arg Arg
    210                 215                 220

Glu Ala Gly Ile Met Gly His Val Tyr Leu Gln Ala
225                 230                 235
```

(2) INFORMATION FOR SEQ ID NO:6:

(i) SEQUENCE CHARACTERISTICS:
        (A) LENGTH: 235 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Val Gln Ala Pro Ser Val Tyr Val Cys Gly Phe Val Glu Arg Pro
 1               5                  10                  15

Asp Ala Pro Pro Lys Asp Ala Cys Leu His Leu Asp Pro Leu Thr Val
             20                  25                  30

Lys Ser Gln Leu Pro Leu Lys Lys Pro Leu Pro Leu Thr Val Glu His
         35                  40                  45

Leu Pro Asp Ala Pro Val Gly Ser Val Phe Gly Leu Tyr Gln Ser Arg
     50                  55                  60

Ala Gly Leu Phe Ser Ala Ala Ser Ile Thr Ser Gly Asp Phe Leu Ser
65                  70                  75                  80

Leu Leu Asp Ser Ile Tyr His Asp Cys Asp Ile Ala Gln Ser Gln Arg
                 85                  90                  95

Leu Pro Leu Pro Arg Glu Pro Lys Val Glu Ala Leu His Ala Trp Leu
            100                 105                 110

Pro Ser Leu Ser Leu Ala Ser Leu His Pro Asp Ile Pro Gln Thr Thr
        115                 120                 125

Ala Asp Gly Gly Lys Leu Ser Phe Phe Asp His Val Ser Ile Cys Ala
    130                 135                 140

Leu Gly Arg Arg Arg Gly Thr Thr Ala Val Tyr Gly Thr Asp Leu Ala
145                 150                 155                 160

Trp Val Leu Lys His Phe Ser Asp Leu Glu Pro Ser Ile Ala Ala Gln
                165                 170                 175

Ile Glu Asn Asp Ala Asn Ala Ala Lys Arg Glu Ser Gly Cys Pro Glu
            180                 185                 190

Asp His Pro Leu Pro Leu Thr Lys Leu Ile Ala Lys Ala Ile Asp Ala
        195                 200                 205

Gly Phe Leu Arg Asn Arg Val Glu Thr Leu Arg Gln Asp Arg Gly Val
    210                 215                 220

Ala Asn Ile Pro Ala Glu Ser Tyr Leu Lys Ala
225                 230                 235
```

(2) INFORMATION FOR SEQ ID NO:7:

(i) SEQUENCE CHARACTERISTICS:
        (A) LENGTH: 254 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Met Gly His His His His His His Ser Ser Gly His Ile Asp Asp Asp
 1               5                  10                  15

Asp Lys Met Ala Ala Glu Ala Asp Glu Glu Asn Cys Glu Ala Leu Tyr
             20                  25                  30

Val Ala Gly Leu Tyr Ala Leu Tyr Ser Lys Asp Glu Gly Glu Leu Asn
         35                  40                  45
```

```
Ile Thr Pro Glu Ile Val Arg Ser Ala Leu Pro Pro Thr Ser Lys Ile
 50                  55                  60

Pro Ile Asn Ile Asp His Arg Lys Asp Cys Val Val Gly Glu Val Ile
 65                  70                  75                  80

Ala Ile Ile Glu Asp Ile Arg Gly Pro Phe Phe Leu Gly Ile Val Arg
                 85                  90                  95

Cys Pro Gln Leu His Ala Val Leu Phe Glu Ala Ala His Ser Asn Phe
                100                 105                 110

Phe Gly Asn Arg Asp Ser Val Leu Ser Pro Leu Glu Arg Ala Leu Tyr
                115                 120                 125

Leu Val Thr Asn Tyr Leu Pro Ser Val Ser Leu Ser Ser Lys Arg Leu
130                 135                 140

Ser Pro Asn Glu Ile Pro Asp Gly Asn Phe Phe Thr His Val Ala Leu
145                 150                 155                 160

Cys Val Val Gly Arg Arg Val Gly Thr Val Val Asn Tyr Asp Cys Thr
                165                 170                 175

Pro Glu Ser Ser Ile Glu Pro Phe Arg Val Leu Ser Met Glu Ser Lys
                180                 185                 190

Ala Arg Leu Leu Ser Leu Val Lys Asp Tyr Ala Gly Leu Asn Lys Val
                195                 200                 205

Trp Lys Val Ser Glu Asp Lys Leu Ala Lys Val Leu Leu Ser Thr Ala
210                 215                 220

Val Asn Asn Met Leu Leu Arg Asp Arg Trp Asp Val Val Ala Lys Arg
225                 230                 235                 240

Arg Arg Glu Ala Gly Ile Met Gly His Val Tyr Leu Gln Ala
                245                 250
```

(2) INFORMATION FOR SEQ ID NO:8:

(i) SEQUENCE CHARACTERISTICS:
        (A) LENGTH: 242 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Met Ala Ala Glu Ala Asp Glu Glu Asn Cys Glu Ala Leu Tyr Val Ala
 1               5                  10                  15

Gly Leu Tyr Ala Leu Tyr Ser Lys Asp Glu Gly Glu Leu Asn Ile Thr
                 20                  25                  30

Pro Glu Ile Val Arg Ser Ala Leu Pro Pro Thr Ser Lys Ile Pro Ile
                 35                  40                  45

Asn Ile Asp His Arg Lys Asp Cys Val Val Gly Glu Val Ile Ala Ile
 50                  55                  60

Ile Glu Asp Ile Arg Gly Pro Phe Phe Leu Gly Ile Val Arg Cys Pro
 65                  70                  75                  80

Gln Leu His Ala Val Leu Phe Glu Ala Ala His Ser Asn Phe Gly
                 85                  90                  95

Asn Arg Asp Ser Val Leu Ser Pro Leu Glu Arg Ala Leu Tyr Leu Val
                100                 105                 110

Thr Asn Tyr Leu Pro Ser Val Ser Leu Ser Ser Lys Arg Leu Ser Pro
                115                 120                 125

Asn Glu Ile Pro Asp Gly Asn Phe Phe Thr His Val Ala Leu Cys Val
130                 135                 140

Val Gly Arg Arg Val Gly Thr Val Val Asn Tyr Asp Cys Thr Pro Glu
```

```
             145                 150                 155                 160

Ser Ser Ile Glu Pro Phe Arg Val Leu Ser Met Glu Ser Lys Ala Arg
                    165                 170                 175

Leu Leu Ser Leu Val Lys Asp Tyr Ala Gly Leu Asn Lys Val Trp Lys
                    180                 185                 190

Val Ser Glu Asp Lys Leu Ala Lys Val Leu Leu Ser Thr Ala Val Asn
                    195                 200                 205

Asn Met Leu Leu Arg Asp Arg Trp Asp Val Val Ala Lys Arg Arg Arg
            210                 215                 220

Glu Ala Gly Ile Met Gly His Val Tyr Leu Gln Ala His His His His
    225                 230                 235                 240

His His
```

(2) INFORMATION FOR SEQ ID NO:9:

(i) SEQUENCE CHARACTERISTICS:
        (A) LENGTH: 243 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
    Met Ala Ala Glu Ala Asp Glu Glu Asn Cys Glu Ala Leu Tyr Val Ala
    1               5                   10                  15

Gly Leu Tyr Ala Leu Tyr Ser Lys Asp Glu Gly Leu Asn Ile Thr
                    20                  25                  30

Pro Glu Ile Val Arg Ser Ala Leu Pro Pro Thr Ser Lys Ile Pro Ile
                35                  40                  45

Asn Ile Asp His Arg Lys Asp Cys Val Val Gly Glu Val Ile Ala Ile
            50                  55                  60

Ile Glu Asp Ile Arg Gly Pro Phe Phe Leu Gly Ile Val Arg Cys Pro
    65                  70                  75                  80

Gln Leu His Ala Val Leu Phe Glu Ala Ala His Ser Asn Phe Phe Gly
                    85                  90                  95

Asn Arg Asp Ser Val Leu Ser Pro Leu Glu Arg Ala Leu Tyr Leu Val
                    100                 105                 110

Thr Asn Tyr Leu Pro Ser Val Ser Leu Ser Ser Lys Arg Leu Ser Pro
                    115                 120                 125

Asn Glu Ile Pro Asp Gly Asn Phe Phe Thr His Val Ala Leu Cys Val
            130                 135                 140

Val Gly Arg Arg Val Gly Thr Val Val Asn Tyr Asp Cys Thr Pro Glu
    145                 150                 155                 160

Ser Ser Ile Glu Pro Phe Arg Val Leu Ser Met Glu Ser Lys Ala Arg
                    165                 170                 175

Leu Leu Ser Leu Val Lys Asp Tyr Ala Gly Leu Asn Lys Val Trp Lys
                    180                 185                 190

Val Ser Glu Asp Lys Leu Ala Lys Val Leu Leu Ser Thr Ala Val Asn
                    195                 200                 205

Asn Met Leu Leu Arg Asp Arg Trp Asp Val Val Ala Lys Arg Arg Arg
            210                 215                 220

Glu Ala Gly Ile Met Gly His Val Tyr Leu Gln Ala Ser His His His
    225                 230                 235                 240

His His His
```

(2) INFORMATION FOR SEQ ID NO:10:

(i) SEQUENCE CHARACTERISTICS:
       (A) LENGTH: 255 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:10:

Met Ala Glu Ala Asp Glu Glu Asn Cys Glu Ala Leu Tyr Val Ala
1               5                  10                  15

Gly Leu Tyr Ala Leu Tyr Ser Lys Asp Glu Gly Leu Asn Ile Thr
                20                  25                  30

Pro Glu Ile Val Arg Ser Ala Leu Pro Pro Thr Ser Lys Ile Pro Ile
                35                  40                  45

Asn Ile Asp His Arg Lys Asp Cys Val Val Gly Glu Val Ile Ala Ile
    50                  55                  60

Ile Glu Asp Ile Arg Gly Pro Phe Phe Leu Gly Ile Val Arg Cys Pro
65                  70                  75                  80

Gln Leu His Ala Val Leu Phe Glu Ala Ala His Ser Asn Phe Phe Gly
                85                  90                  95

Asn Arg Asp Ser Val Leu Ser Pro Leu Glu Arg Ala Leu Tyr Leu Val
                100                 105                 110

Thr Asn Tyr Leu Pro Ser Val Ser Leu Ser Ser Lys Arg Leu Ser Pro
    115                 120                 125

Asn Glu Ile Pro Asp Gly Asn Phe Phe Thr His Val Ala Leu Cys Val
    130                 135                 140

Val Gly Arg Arg Val Gly Thr Val Val Asn Tyr Asp Cys Thr Pro Glu
145                 150                 155                 160

Ser Ser Ile Glu Pro Phe Arg Val Leu Ser Met Glu Ser Lys Ala Arg
                165                 170                 175

Leu Leu Ser Leu Val Lys Asp Tyr Ala Gly Leu Asn Lys Val Trp Lys
                180                 185                 190

Val Ser Glu Asp Lys Leu Ala Lys Val Leu Leu Ser Thr Ala Val Asn
                195                 200                 205

Asn Met Leu Leu Arg Asp Arg Trp Asp Val Val Ala Lys Arg Arg Arg
    210                 215                 220

Glu Ala Gly Ile Met Gly His Val Tyr Leu Gln Ala Ser Thr Gly Tyr
225                 230                 235                 240

Gly Leu Ala Arg Ile Thr Asn Val Asn His His His His His
                245                 250                 255

(2) INFORMATION FOR SEQ ID NO:11:

(i) SEQUENCE CHARACTERISTICS:
       (A) LENGTH: 246 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:11:

Met Glu Ala Leu Tyr Val Ala Gly Leu Tyr Ala Leu Tyr Ser Lys Asp
1               5                   10                  15

Glu Gly Glu Leu Asn Ile Thr Pro Glu Ile Val Arg Ser Ala Leu Pro
                20                  25                  30

Pro Thr Ser Lys Ile Pro Ile Asn Ile Asp His Arg Lys Asp Cys Val

-continued

```
                35                  40                  45
    Val Gly Glu Val Ile Ala Ile Ile Glu Asp Ile Arg Gly Pro Phe Phe
        50                  55                  60
    Leu Gly Ile Val Arg Cys Pro Gln Leu His Ala Val Leu Phe Glu Ala
    65                  70                  75                  80
    Ala His Ser Asn Phe Phe Gly Asn Arg Asp Ser Val Leu Ser Pro Leu
                    85                  90                  95
    Glu Arg Ala Leu Tyr Leu Val Thr Asn Tyr Leu Pro Ser Val Ser Leu
                100                 105                 110
    Ser Ser Lys Arg Leu Ser Pro Asn Glu Ile Pro Asp Gly Asn Phe Phe
                115                 120                 125
    Thr His Val Ala Leu Cys Val Val Gly Arg Arg Val Gly Thr Val Val
    130                 135                 140
    Asn Tyr Asp Cys Thr Pro Glu Ser Ser Ile Glu Pro Phe Arg Val Leu
    145                 150                 155                 160
    Ser Met Glu Ser Lys Ala Arg Leu Leu Ser Leu Val Lys Asp Tyr Ala
                    165                 170                 175
    Gly Leu Asn Lys Val Trp Lys Val Ser Glu Asp Lys Leu Ala Lys Val
                180                 185                 190
    Leu Leu Ser Thr Ala Val Asn Asn Met Leu Leu Arg Asp Arg Trp Asp
                195                 200                 205
    Val Val Ala Lys Arg Arg Glu Ala Gly Ile Met Gly His Val Tyr
    210                 215                 220
    Leu Gln Ala Ser Thr Gly Tyr Gly Leu Ala Arg Ile Thr Asn Val Asn
    225                 230                 235                 240
    His His His His His His
                245
```

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Amino acid in position 3
                can be Cys or Ser"

(xi) SEQUENCE DESCRIPTION: SEQ ID NO:12:

```
Gly Xaa Xaa Gly Gly
1               5
```

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Amino acid in position 4
                can be Met or Ala"

(xi) SEQUENCE DESCRIPTION: SEQ ID NO:13:

Gly Thr Ser Xaa
1

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Gly Xaa Ser Gly Gly
1          5

(2) INFORMATION FOR SEQ ID NO:15:

(i) SEQUENCE CHARACTERISTICS:
        (A) LENGTH: 19 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:15:

Ser Glu Lys Phe Lys Ile Trp Gly Ala Glu Ser Ala Pro His His His
1          5                    10                   15

His His His (2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "His in amino acid position 1 is
                            modified to contain an acetyl group"

(xi) SEQUENCE DESCRIPTION: SEQ ID NO:16:

His Thr Tyr Leu Gln Ala Ser Glu Lys Phe Lys Met Trp Gly
1          5                    10

(2) INFORMATION FOR SEQ ID NO:17:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Asp Asn Ala Val Glu Ala Ser Ser Lys Ala Pro Leu Lys
1          5                    10

(2) INFORMATION FOR SEQ ID NO:18:

```
      (i) SEQUENCE CHARACTERISTICS:
          (A) LENGTH: 13 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Arg at amino acid position 1 is
                                 modified to contain a dabsyl group"

(ix) FEATURE:
          (A) NAME/KEY: Modified-site
          (B) LOCATION: 13
          (D) OTHER INFORMATION: /note= "Lys at amino acid position 13
                                 is modified to contain a dansyl-II
                                 g..."

(xi) SEQUENCE DESCRIPTION: SEQ ID NO:18:

Arg Gly Val Val Asn Ala Ser Ser Arg Leu Ala Lys Lys
     1               5                   10
```

What is claimed is:

1. A method of identifying a candidate inhibitor compound capable of binding to, and inhibiting the proteolytic activity of, an alpha, or beta herpes protease, said method comprising:
   a) introducing into a computer program information derived from atomic coordinate defining an active site conformation of a herpes protease molecule based upon three-dimensional structure determination comprising a catalytically active site formed by at least the interaction of three amino acids Serine, Histidine and Histidine, wherein said program utilizes or displays the three-dimensional structure thereof;
   b) generating a three dimensional representation of the active site cavity of said protease in said computer program;
   c) superimposing a model of the inhibitor test compound on the model of said active site of said protease;
   d) assessing whether said test compound model fits spatially into the active site of said protease;
   e) incorporating said test compound in a protease activity assay for a protease characterized by said active site of said protease, or an antiviral assay for an alpha or beta herpes virus; and
   f) determining whether said test compound inhibits proteolytic activity, or the herpes virus in said assay.

2. The method according to claim 1, wherein the protease is herpes simplex virus (HSV-2) protease, or an enzymatically active fragment thereof.

3. The method according to claim 2 wherein the protease is an HSV-2 protease molecule having a conformation comprising a catalytically active site formed by the interaceion of three amino acids Serine, Histidine and Histidine.

4. The method according to claim 2 wherein the protease is an enzymatically active fragment having a conformation comprising a catalytically active site formed by the interaction of three amino acids Serine, Histidine and Histidine.

5. The method according to claim 3 or 4 wherein the catalytically active site formed by the interaction of three amino acids Serine, Histidine, and Histidine is as shown in SEQ ID NO: 4, as Serine 129, Histidine 61, and Histidine 148.

6. The method according to claim 5 wherein the catalytically active site further comprises the interaction of the amino acids residues Arg 156, and Arg 157, as shown in SEQ ID NO: 4.

7. The method according to claim 6 wherein the catalytically active site further comprises the interaction of the amino acids residues Ser 131, Cys 152, Len 27, Val 128, and Leu 130, as shown in SEQ ID NO: 4.

8. The method according to claim 2 wherein said HSV-2 protease molecule is a monomer.

9. The method according to claim 2, wherein the atomic coordinates are of liganded or unliganded protease.

10. The method according to claim 9 wherein the active site of said protease is defined by the atomic coordinates of FIGS. 2 or 3.

11. The method according to claim 1, wherein the protease is herpes simplex virus (HSV-1) protease, or an enzymatically active, fragment thereof.

12. The method according to claim 11 wherein the protease is an HSV-1 protease molecule, having a conformation comprising a catalytically active site formed by the interaction of three amino acids Serine, Histidine and Histidine.

13. The method according to claim 11 wherein the protease is an enzymatically active fragment having a conformation comprising a catalytically active site formed by the interaction of three amino acids Serine, Histidine and Histidine.

14. The method according to claim 12 or 13 wherein the catalytically active site formed by the interaction of three amino acids Serine, Histidine, and Histidine is as shown in SEQ ID NO: 3, as Serine 129, Histidine 61, and Histidine 148.

15. The method according to claim 14 wherein the catalytically active site further comprises the interaction of the amino acids residues Arg 156, and Arg 157, as shown in SEQ ID NO: 3.

16. The method according to claim 15 wherein the catalytically active site further comprises the interaction of the amino acids residues Ala 131, and Cys 152, as shown in SEQ ID NO: 3.

17. The method according to claim 12 wherein said active site is defined by the atomic coordinates of FIG. 6.

18. The method according to claim 17 wherein said HSV-1 protease molecule is a monomer.

19. The method according to claim 1, wherein the protease is cytomegalovirus (CMV) protease, or an enzymatically active fragment thereof.

20. The method according to claim 19 wherein the protease is a CMV protease molecule having a conformation comprising a catalytically active site formed by the interaction of three ado acids Serine, Histidine and Histidine.

21. The method according to claim 19 wherein the protease is an enzymatically active fragment having a conformation comprising a catalytically active, site formed by the interaction of three amino acids Serine, Histidine and Histidine.

22. The method according to claim 20 or 21 wherein the catalytically active site formed by the interaction of three amino acids Serine, Histidine, and Histidine is as shown in SEQ ED NO: 1, as Serine 132, Histidine 63, and Histidine 157.

23. The method according to claim 22 wherein the catalytically active site further comprises the interaction of the amino acid reside Asp 65, as shown in SEQ ID NO: 1.

24. The method according to claim 23 wherein the catalytically active site further comprises the interaction of the amino acids residue Arg 165, and Arg 166, as shown in SEQ ID NO: 1.

25. The method according to claim 24 wherein the catalytically active site further comprises the interaction of the amino acids residues Ser 134, and Cys 161, as shown in SEQ ID NO: 1.

26. The method according to claim 20 wherein said active site is defined by the atomic coordinates of FIG. 17.

27. The method according to claim 19 wherein said CMV protease molecule is a monomer.

28. The method according to claim 1, wherein the protease is varicella zoster virus (VZV) protease, or an enzymatically active fragment thereof.

29. The method according to claim 28 wherein the protease is a VZV protease molecule having a conformation comprising a catalytically active site formed by the interaction of three amino acids Serine, Histidine, and Histidine.

30. The method according to claim 28 wherein the protease is an enzymatically active fragment having a conformation comprising a catalytically active site formed by the interaction of three amino acids Serine, Histidine and Histidine.

31. The method according to claim 29 or 30 wherein the catalytically active site formed by the interaction of three amino acids Serine, Histidine, and Histidine is as shown in SEQ ID NO: 5, as Serine 120, Histidine 52, and Histidine 139.

32. The method according to claim 31 wherein the catalytically active site further comprises the interaction of the amino acids residues Arg 147 and Arg 148, as shown in SEQ ID NO: 5.

33. The method according to claim 32 wherein the catalytically active site further comprises the interaction of the ano acids residues Ser 122 and Cys 143, as shown in SEQ ID NO: 5.

34. The method according to claim 29 wherein said active site as defined by the atomic coordinates of FIG. 22.

35. The method according to claim 28 wherein said VZV protease molecule is a monomer.

36. A method for identifying a candidate inhibitor compound which binds to, or interferes with, the dimer interface of an alpha or beta herpes virus protease molecule, which protease is characterized by a catalytically active site formed by the interaction of three amino acids Serine, Histidine and Histidine, said method comprising the steps of:

a) providing the atomic coordinates of the dimeric interface of at least one monomer of the protease to a computer program;

b) generating a three-dimensional representation of the dimeric interface of at least one monomer in the computer program;

c) superimposing a model of the inhibitor test compound on the model of the dimeric interface of the protease;

d) assessing whether said test compound interferes spatially with the dimeric interface of the protease;

e) incorporating said test compound in a protease activity assay for a protease characterized by said dimeric interface, or in an antiviral assay for an alpha or beta herpes virus; and f) determining whether said test compound will bind to, or interfere with, the dimeric interface; or inhibit the herpes virus in said assay.

37. The method according to claim 36 wherein the protease is a herpes simplex virus (HSV-2) protease.

38. The method according to claim 37 wherein the protease is an HSV-2 protease molecule having a conformation which comprises a catalytically active site formed by the interaction of three amino acids Serine, Histidine and Histidine.

39. The method according to claim 37 wherein the protease is an enzymatically active fragment having a conformation which comprises a catalytically active site formed by the interaction of three amino acids Serine, Histidine and Histidine.

40. The method according to claim 38 or 39 wherein the catalytically active site formed by the interaction of three acids Serine, Histidine, and Histidine is as shown in SEQ ID NO: 4, as Serine 129, Histidine 61, and Histidine 148.

41. The method according to claim 40 wherein the catalytically active site further comprises the interaction of the amino acids residues Arg 156, and Arg 157, as shown in SEQ ID NO: 4.

42. The method according to claim 41 wherein the catalytically active site further comprises the interaction of the amino acids residues Ser 131, Cys 152, Leu 27, Val 128, and Leu 130, as shown in SEQ ID NO: 4.

43. The method according to claim 37, wherein the atomic coordinates are of liganded or unliganded protease.

44. The method according to claim 43 wherein the active site of said protease is defined by the atomic coordinates of FIGS. 2 or 3.

45. The method according to claim 36 wherein the protease is a herpes simplex virus (HSV-1) protease.

46. The method according to claim 45 wherein the protease is an HSV-1 protease molecule having a conformation comprising a catalytically active site formed by the interaction of three amino acids Serine, Histidine, and Histidine.

47. The method according to claim 45 wherein the protease is an enzymatically active fragment having a conformation comprising a catalytically active site formed by the interaction of three amino acids Serine, Histidine, and Histidine.

48. The method according to claim 46 or 47 wherein the catalytically active site formed by the interaction of three amino acids Serine, Histidine, and Histidine is as shown in SEQ ID NO: 3, as Serine 129, Histidine 61, and Histidine 148.

49. The method according to claim 48 wherein the catalytically active site further comprises the interaction of the amino acids residues Arg 156, and Arg 157, as shown in SEQ ID NO: 3.

50. The method according to claim 49 wherein the catalytically active site further comprises the interaction of the amino acids residues Ala 131, and Cys 152, as shown in SEQ ID NO: 3.

51. The method according to claim 46 wherein said active site is defined by the atomic coordinates of FIG. 6.

52. The method according to claim 36 wherein the protease is a cytomegalovirus (CMV) protease.

53. The method according to claim 52 wherein the protease is a CMV protease molecule having a conformation comprising a catalytically active site formed by the interaction of three amino acids Serine, Histidine, and Histidine.

54. The method according to claim 52 wherein the protease is an enzymatically active fragment having a conformation comprising a catalytically active site formed by the interaction of three amino acids Serine, Histidine, and Histidine.

55. The method according to claim 53 or 54 wherein the catalytically active site formed by the interaction of three amino acids Serine, Histidine, and Histidine is as shown in SEQ ID NO: 1, as Serine 132, Histidine 63 and Histidine 157.

56. The method according to claim 55 wherein the catalytically active sire further comprises the interaction of the amino acid residue Asp 65, as shown in SEQ ID NO: 1.

57. The method according to claim 56 wherein the catalytically active site further comprises the interaction of the amino acids residue Arg 165, and Arg 166, as shown in SEQ ID NO: 1.

58. The method according to claim 57 wherein the catalytically active site further comprises the interaction of the amino acids residues Ser 134, and Cys 161, as shown in SEQ ID NO: 1.

59. The method according to claim 53 wherein said active site is defined by the atomic coordinates of FIG. 17.

60. The method according to claim 36, wherein the protease is a varicella zoster virus (VZV) protease.

61. The method according to claim 60 wherein the protease is a VZV protease molecule having a conformation comprising a catalytically active site formed by the interaction of three amino acids Serine, Histidine, and Histidine.

62. The method according to claim 60 wherein the protease is an enzymatically active fragment having a conformation comprising a catalytically active site formed by the interaction of three amino acids Serine, Histidine, and Histidine.

63. The method according to claim 61 or 62 wherein the catalytically active site formed by the interaction of three amino acids Serine, Histidine, and Histidine is as shown in SEQ ID NO: 5, as Serine 120, Histidine 52 and Histidine 139.

64. The method according to claim 63 wherein the catalytically active site further comprises the interaction of the amino acids residues Arg 147 and Arg 148, as shown in SEQ ID NO: 5.

65. The method according to claim 64 wherein the catalytically active site further comprises the interaction of the amino acids residues Ser 122 and Cys 143, as shown in SEQ ID NO: 5.

66. The method according to claim 60 wherein said active is defined by the atomic coordinates of FIG. 22.

* * * * *